(12) United States Patent
Ndubaku et al.

(10) Patent No.: US 11,858,915 B2
(45) Date of Patent: Jan. 2, 2024

(54) POLO LIKE KINASE 4 INHIBITORS

(71) Applicant: ORIC Pharmaceuticals, Inc., South San Francisco, CA (US)

(72) Inventors: Chudi Ndubaku, Montreal (CA); Jared Thomas Moore, San Rafael, CA (US); Paul Anthony Gibbons, San Francisco, CA (US); Jae Hyuk Chang, Alameda, CA (US); F. Anthony Romero, Redwood City, CA (US); Xiaohui Du, Belmont, CA (US); Hiroyuki Kawai, Pacifica, CA (US); Stephane Ciblat, Montreal (CA); Hong Wang, Montreal (CA); Vincent Albert, Montreal (CA); Lea Constantineau-Forget, Montreal (CA); Hugo De Almeida Silva, Montreal (CA); Dilan Emine Polat, Montreal (CA); Amit Nayyar, Montreal (CA); Daniel Gordon Michael Shore, San Mateo, CA (US); Kejia Wu, South San Francisco, CA (US); Joanne Tan, San Mateo, CA (US)

(73) Assignee: ORIC PHARMACEUTICALS, INC., South San Francisco, CA (US)

( * ) Notice: Subject to any disclaimer, the term of this patent is extended or adjusted under 35 U.S.C. 154(b) by 15 days.

(21) Appl. No.: 18/308,441

(22) Filed: Apr. 27, 2023

(65) Prior Publication Data
US 2023/0365537 A1 Nov. 16, 2023

Related U.S. Application Data

(63) Continuation of application No. PCT/US2022/028594, filed on May 10, 2022.

(60) Provisional application No. 63/337,445, filed on May 2, 2022, provisional application No. 63/317,174, filed on Mar. 7, 2022, provisional application No. 63/249,809, filed on Sep. 29, 2021, provisional application No. 63/187,049, filed on May 11, 2021.

(51) Int. Cl.
| | | |
|---|---|---|
| C07D 403/14 | (2006.01) | |
| C07D 413/14 | (2006.01) | |
| C07D 403/04 | (2006.01) | |
| C07D 401/14 | (2006.01) | |
| C07D 405/14 | (2006.01) | |

(52) U.S. Cl.
CPC ......... C07D 403/14 (2013.01); C07D 401/14 (2013.01); C07D 403/04 (2013.01); C07D 405/14 (2013.01); C07D 413/14 (2013.01)

(58) Field of Classification Search
CPC .. C07D 403/14; C07D 401/14; C07D 403/04; C07D 405/14; C07D 413/14

USPC .................................................... 514/210.21
See application file for complete search history.

(56) References Cited

U.S. PATENT DOCUMENTS

| | | | |
|---|---|---|---|
| 8,263,596 | B2 | 9/2012 | Sampson et al. |
| 8,481,525 | B2 | 7/2013 | Sampson et al. |
| 8,481,533 | B2 | 7/2013 | Sampson et al. |
| 8,921,545 | B2 | 12/2014 | Cumming et al. |
| 8,933,070 | B2 | 1/2015 | Pan et al. |
| 9,139,563 | B2 | 9/2015 | Sampson et al. |
| 9,402,828 | B2 | 8/2016 | Pan et al. |
| 9,579,327 | B2 | 2/2017 | Cumming et al. |
| 9,642,856 | B2 | 5/2017 | Hedley et al. |
| 9,796,703 | B2 | 10/2017 | Cumming et al. |
| 9,907,800 | B2 | 3/2018 | Sampson et al. |
| 10,077,255 | B2 | 9/2018 | Cumming et al. |

(Continued)

FOREIGN PATENT DOCUMENTS

| | | |
|---|---|---|
| CN | 112225729 A | 1/2021 |
| CN | 115677682 A | 2/2023 |

(Continued)

OTHER PUBLICATIONS

Bencsik et al. Discovery of dihydrothieno- and dihyrofuropyrimidines as potent pant Akt inhibitors. Bioor Med Chem Lett 10:7037-7041 (2010).

(Continued)

Primary Examiner — Kahsay Habte
(74) Attorney, Agent, or Firm — WILSON SONSINI GOODRICH & ROSATI

(57) ABSTRACT

Disclosed herein are compounds of Formula (I), or pharmaceutically acceptable salts thereof, that are inhibitors of Polo Like Kinase 4 (PLK4). Also disclosed herein are pharmaceutical compositions comprising the compounds of Formula (I), or pharmaceutically acceptable salts thereof, and one or more pharmaceutically acceptable excipients. Further disclosed herein are methods of treating cancer in a subject in need thereof, comprising administering to the subject an amount of a compound of Formula (I), or a pharmaceutically acceptable salt thereof.

Formula (I)

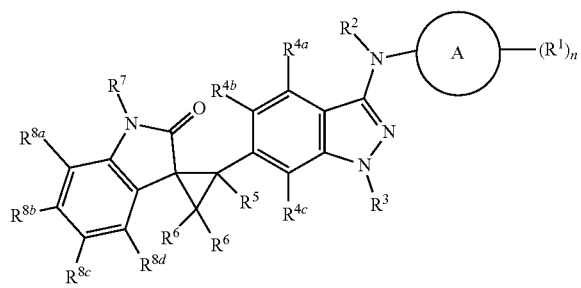

21 Claims, No Drawings

(56) References Cited

U.S. PATENT DOCUMENTS

| | | | |
|---|---|---|---|
| 10,358,436 | B2 | 7/2019 | Sampson et al. |
| RE47,731 | E | 11/2019 | Sampson et al. |
| 2018/0086739 | A1 | 3/2018 | Gahman et al. |
| 2018/0369214 | A1 | 12/2018 | Owonikoko |

FOREIGN PATENT DOCUMENTS

| | | |
|---|---|---|
| WO | WO-02057259 A2 | 7/2002 |
| WO | WO-2009079767 A1 | 7/2009 |
| WO | WO-2009079767 A9 | 10/2009 |
| WO | WO-2010115279 A1 | 10/2010 |
| WO | WO-2011123937 A1 | 10/2011 |
| WO | WO-2011123946 A1 | 10/2011 |
| WO | WO-2011123947 A1 | 10/2011 |
| WO | WO-2012000103 A1 | 1/2012 |
| WO | WO-2012048411 A1 | 4/2012 |
| WO | WO-2013050508 A1 | 4/2013 |
| WO | WO-2013053051 A1 | 4/2013 |
| WO | WO-2014056083 A1 | 4/2014 |
| WO | WO-2015054781 A1 | 4/2015 |
| WO | WO-2015054793 A1 | 4/2015 |
| WO | WO-2015066188 A1 | 5/2015 |
| WO | WO-2016166604 A1 | 10/2016 |
| WO | WO-2017028314 A1 | 2/2017 |
| WO | WO-2017075394 A1 | 5/2017 |
| WO | WO-2019046949 A1 | 3/2019 |
| WO | WO-2019113311 A1 | 6/2019 |
| WO | WO-2020215155 A1 | 10/2020 |
| WO | WO-2021108918 A1 | 6/2021 |
| WO | WO-2021203190 A1 | 10/2021 |
| WO | WO-2022184049 A1 | 9/2022 |
| WO | WO-2022240876 A1 | 11/2022 |

OTHER PUBLICATIONS

Cescon et al. A phase II study of CFI-400945 in patients with advance/metastatic HER2-negative breast cancer: Canadian Trials Group (CCTG) IND.237. Poser SABCS 2022.

Fancelli et al. 1,4,5,6-Tetrahydropyrrolo[3,4-c]pyrazoles: Identification of a Potent Aurora Kinase Inhibitor with a Favorable Antitumor Kinase Inhibition Profile. J Med Chem 49:7247-7251 (2006).

Ge et al. Pd-Catalyzed α-Arylation of α,α-Difluoroketones with Aryl Bromides and Chlorides. A Route to Difluoromethylarenes. J Am Chem Soc 136:4149-4152 (2014).

Hilton et al. CCTG IND.239: A Phase 2 Study of Combined CFI-400945 and Durvalumab in Patients with Advanced Triple Negative Breast Cancer (aTNBC). Poster SABCS 2022.

Laufer et al. The Discovery of PLK4 Inhibitors: (E)-3-((1H-Indazol-6-yl)methylene)indolin-2-ones as Novel Antiproliferative Agents. J Med Chem 56:6069-6087 (2013).

Lei et al. YLT-11, a novel PLK4 inhibitor, inhibits human breast cancer growth via inducing maladjusted centriole duplication and mitotic defect. Cell Death and Disease 9:1066 (2018).

Li et al., Design and optimization of (3-aryl-1H-indazol-6-yl)spiro[cyclopropane-1,3'-indolin]-2'- ones as potent PLK4 inhibitors with oral antitumor efficacy. Bioorg Med Chem Lett. 26(19):4625-4630 (2016).

Liu et al. Synthesis and biological evaluation of (E)-4-(3-arylvinyl-1H-indazol-6-yl)pyrimidin-2-amine derivatives as PLK4 inhibitors for the treatment of breast cancer. RSC Advanced 7(44):27737-27746 (2017).

Mason et al. Functional Characterization of CFI-400945, a Polo-like Kinase 4 Inhibitor, as a Potential Anticancer Agent. Cancer Cell 26:163-176 (2014).

Moody et al. Copper-catalysed approach to spirocyclic oxindole via a direct C—H, Ar—H functionalization. Tetrahedron Letters 53:1897-1899 (2012).

PCT/US2022/028594 International Search Report and Written Opinion dated Aug. 5, 2022.

Sampson et al., The discovery of Polo-like kinase 4 inhibitors: design and optimization of spiro [cyclopropane-1,3'[3H]indol]-2'(1'H).ones as orally bioavailable antitumor agents. J Med Chem. 58(1):130-146 (2015).

Sampson et al. The Discovery of Polo-Like Kinase 4 Inhibitors: Identification of (1R,2S)-2-(3-((E)-4-(((cis)-2,6-Dimethylmorpholino)methyl)styryl)-1H-indazol-6-yl)-5'-methoxyspiro[cyclopropane-1,3'-indolin]-2'-one (CFI-400945) as a Potent, Orally Active Antitumor Agent. J Med Chem 58:147-169 (2015).

Shi et al. Discovery of 3,3'-Spiro[Azetidine]-2-oxo-indoline Derivatives as Fusion Inhibitors for Treatment of RSV Infection. ACS Med Chem Lett 9:94-97 (2018).

Tan et al. Development of Selective Covalent Janus Kinase 3 Inhibitors. J Med Chem 58:6589-6606 (2015).

Veitch et al. Safety and tolerability of CFI-400945, a first-in-class, selective PLK4 inhibitor in advanced solid tumours: a phase 1 dose-escalation trial. Br J Cancer121(4):318-324 (2019).

Wang et al. Fragment-Based, Structure-Enabled Discovery of Novel Pyridones and Pyridone Macrocycles as Potent Bromodomain and Extra-Terminal Domain (BET) Family Bromodomain Inhibitors. J Med Chem 60:3828-3850 (2017).

Wu et al., FDA-approved small-molecule kinase inhibitors. Trends Pharmacol. Sci. 36:422-439 (2015).

Xing et al. Kinase hinge binding scaffolds and their hydrogen bond patterns. Bioorg Med Chem 23:6520-6527 (2015).

Xu et al. Green oxidation of indoles using halide catalysis. Nat Commun 10(1):4754 (2019).

Yu et al. Discovery of orally active anticancer candidate CFI-400945 derived from biologically promising spirooxindoles: Success and challenges. Eur J Med Chem Eur. 95:35e40 (2015) (with Corrigendum).

POLO LIKE KINASE 4 INHIBITORS

CROSS-REFERENCE

This application is a continuation of International Application No. PCT/US2022/028594, filed May 10, 2022, which claims the benefit of U.S. Provisional Application Ser. No. 63/187,049, filed May 11, 2021; U.S. Provisional Application Ser. No. 63/249,809, filed Sep. 29, 2021; U.S. Provisional Application Ser. No. 63/317,174, filed Mar. 7, 2022, and U.S. Provisional Application Ser. No. 63/337,445, filed May 2, 2022, which are hereby incorporated by reference in their entirety.

BACKGROUND OF THE INVENTION

The Polo-like kinases (PLKs) are a family of serine/threonine kinases that play a critical role in cell cycle regulation and cellular responses under stress (Helmke et al. 2016; Zitouni et al. 2014). Mammalian cells express five PLK family members (PLK1-5). All PLKs share a similar structure, with an N-terminal kinase catalytic domain and C-terminal Polo-box domains (PBDs) (Archambault et al. 2015). Polo-like kinase 4 (PLK4), also known as SAK, is a regulator of centriole duplication (Habedanck et al. 2005; Kleylein-Sohn et al. 2007). In proliferating tissues, PLK4 is expressed as a low-abundance enzyme under normal conditions and is required for centriole biogenesis via phosphorylation and interaction with centriolar proteins (Habedanck et al. 2005; Maniswami et al. 2018). Overexpression of PLK4 results in centriole amplification and further genomic instability and tumorigenesis (Holland et al. 2010). Aberrant PLK4 expression has been reported to be involved in several common human cancers (Marina and Saavedra 2014; Shinmura et al. 2014). Thus, strong evidence supports the critical role of PLK4 in carcinogenesis and therapeutic invention. Thus, there is a need for compounds that inhibit PLK4 in subjects having cancer for the treatment of those cancers.

SUMMARY OF THE INVENTION

Provided herein is a compound of Formula (I), or a pharmaceutically acceptable salt, solvate, or stereoisomer thereof:

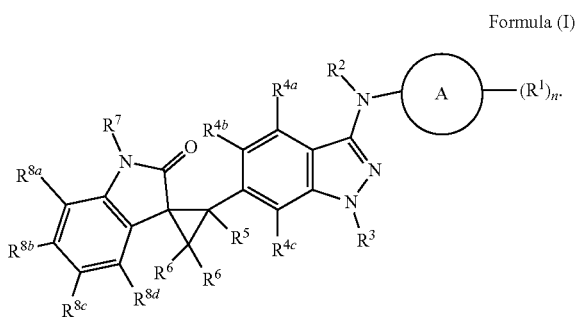

Formula (I)

wherein:
Ring A is $C_6$-$C_{10}$aryl, heteroaryl, $C_3$-$C_{10}$cycloalkyl, or heterocycloalkyl;
each $R^1$ is independently deuterium, halogen, —CN, oxo, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^a$, —$NR^bS(=O)_2R^a$, —C(=O)$R^a$, —C(=O)$OR^b$, —C(=O)$NR^cR^d$, —P(O)($R^a$), —P(O)$_2(R^a)_2$, $C_1$-$C_6$alkyl, $C_1$-$C_6$haloalkyl, —$OC_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_2$-$C_{10}$alkynyl, $C_3$-$C_{10}$cycloalkyl, heterocycloalkyl, $C_6$-$C_{10}$aryl, and heteroaryl is optionally and independently substituted with one or more $R^{1a}$;
or two $R^1$ on adjacent atoms are taken together to form a $C_3$-$C_{10}$cycloalkyl or heterocycloalkyl; each optionally substituted with one or more $R^{1b}$:
each $R^{1a}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^a$, —$NR^bS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;
or two $R^{1a}$ on the same atom are taken together to form an oxo;
each $R^{1b}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^a$, —$NR^hS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_1$-$C_6$alkynyl, $C_1$-$C_{10}$cycloalkyl, heterocycloalkyl, $C_6$-$C_{10}$aryl, or heteroaryl;
or two $R^{1b}$ on the same atom are taken together to form an oxo;
n is 0, 1, 2, 3, 4, 5, 6, 7, or 8;
$R^2$ is hydrogen, $C_1$-$C_6$alkyl, $C_1$-$C_6$haloalkyl, or $C_1$-$C_6$deuteroalkyl;
$R^3$ is hydrogen, $C_1$-$C_6$alkyl, $C_1$-$C_6$haloalkyl, or $C_1$-$C_6$deuteroalkyl;
each of $R^{4a}$, $R^{4b}$, and $R^{4c}$ is independently hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
$R^5$ is hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
each $R^6$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
$R^7$ is hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;
each of $R^{8a}$, $R^{8b}$, $R^{8c}$, and $R^{8d}$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_{10}$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_1$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$alkoxy, C$_1$-C$_6$aminoalkyl, C$_1$-C$_6$alkylamino, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl (heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$ aminoalkyl, or C$_1$-C$_6$heteroalkyl;

or R$^c$ and R$^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

In some embodiments of a compound of Formula (I), Ring A is C$_6$-C$_{10}$aryl or heteroaryl.

In some embodiments of a compound of Formula (I), Ring A is C$_6$-C$_{10}$aryl.

In some embodiments of a compound of Formula (I), Ring A is heteroaryl.

In some embodiments of a compound of Formula (I), Ring A is furanyl, pyrrolyl, thiophenyl, oxazolyl, imidazolyl, thiazolyl, pyrazolyl, isoxazolyl, isothiazolyl, triazolyl, pyridinyl, pyrazinyl, pyrimidinyl, or pyridazinyl.

In some embodiments of a compound of Formula (I), each R$^1$ is independently halogen, —CN, —OH, —OR$^a$, C$_1$-C$_6$alkyl, C$_1$-C$_6$haloalkyl, —OC$_1$-C$_6$haloalkyl, C$_1$-C$_6$hydroxyalkyl, C$_1$-C$_6$aminoalkyl, C$_1$-C$_6$heteroalkyl, C$_3$-C$_{10}$cycloalkyl, heterocycloalkyl, C$_6$-C$_{10}$aryl, or heteroaryl; wherein each of the C$_1$-C$_6$alkyl, C$_3$-C$_{10}$cycloalkyl, heterocycloalkyl, C$_6$-C$_{10}$aryl, and heteroaryl is optionally and independently substituted with one or more R$^{1a}$.

In some embodiments of a compound of Formula (I), n is 1, 2, or 3.

In some embodiments of a compound of Formula (I), R$^2$ is hydrogen.

In some embodiments of a compound of Formula (I), R$^3$ is hydrogen.

In some embodiments of a compound of Formula (I), R$^{4a}$, R$^{4b}$, and R$^{4c}$ are hydrogen.

In some embodiments of a compound of Formula (I), R$^5$ is hydrogen.

In some embodiments of a compound of Formula (I), each R$^6$ is hydrogen.

In some embodiments of a compound of Formula (I), R$^7$ is hydrogen or C$_1$-C$_6$alkyl.

In some embodiments of a compound of Formula (I), each of R$^{8a}$, R$^{8b}$, and R$^{8d}$ are hydrogen and R$^{8c}$ is hydrogen, halogen, or —OR$^a$.

In some embodiments of a compound of Formula (I), R$^{8c}$ is halogen or —OR$^a$.

In some embodiments of a compound of Formula (I), R$^{8c}$ is —OR$^a$.

In some embodiments of a compound of Formula (I), R$^a$ is C$_1$-C$_6$alkyl.

In some embodiments of a compound of Formula (I), R$^a$ is —CH$_3$.

Also disclosed herein is a pharmaceutical composition comprising an amount of a compound disclosed herein, or a pharmaceutically acceptable salt, solvate, or stereoisomer thereof, and one or more pharmaceutically acceptable excipients.

Also disclosed herein is a method of treating cancer in a subject in need thereof, comprising administering to the subject a therapeutically effective amount of a compound disclosed herein, or a pharmaceutically acceptable salt, solvate, or stereoisomer thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used in the specification and appended claims, unless specified to the contrary, the following terms have the meaning indicated below.

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

"Administering" when used in conjunction with a therapeutic means to administer a therapeutic systemically or locally, as directly into or onto a target tissue, or to administer a therapeutic to a subject whereby the therapeutic positively impacts the tissue to which it is targeted. Thus, as used herein, the term "administering", when used in conjunction with a composition described herein, can include, but is not limited to, providing a composition into or onto the target tissue; providing a composition systemically to a subject by, e.g., oral administration whereby the therapeutic reaches the target tissue or cells. "Administering" a composition may be accomplished by injection, topical administration, and oral administration or by other methods alone or in combination with other known techniques.

The term "$C_2$-$C_6$alkenyl" as used herein, means an alkyl moiety comprising 2 to 6 carbon atoms having at least one carbon-carbon double bond. The carbon-carbon double bond in such a group may be anywhere along the 2 to 6 carbon atom chain that will result in a stable compound. Examples of such groups include, but are not limited to, ethenyl, propenyl, butenyl, allyl, and pentenyl. The alkenyl may be in either the cis or trans conformation about the double bond(s), and should be understood to include both isomers. Examples of alkenyls include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl.

The term "$C_1$-$C_6$alkyl;" as used herein, refers to a straight or branched chain hydrocarbon monoradical, which may be fully saturated or unsaturated, having from one to about ten carbon atoms, or from one to six carbon atoms. Examples of saturated hydrocarbon monoradical include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "$C_2$-$C_6$alkynyl," as used herein, means an alkyl moiety comprising from 2 to 6 carbon atoms and having at least one carbon-carbon triple bond. The carbon-carbon triple bond in such a group may be anywhere along the 2 to 6 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne, ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "$C_6$-$C_{10}$aryl," as used herein, refers to a radical derived from a hydrocarbon ring system comprising hydrogen, 6 to 10 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl.

The term "$C_1$-$C_6$ aminoalkyl," as used herein, refers to a $C_1$-$C_6$alkyl radical, as defined above, that is substituted with one or more amino groups. The amino groups in such $C_1$-$C_6$ aminoalkyl groups may be unsubstituted, mono-substituted, or disubstituted. Examples of $C_1$-$C_6$ aminoalkyl groups include, but are not limited to, —$CH_2NH_2$, —$CH_2$N(H)$CH_3$, —$CH_2$N($CH_3$)$_2$, and the like.

The term "$C_3$-$C_{10}$cycloalkyl" refers to a partially or fully saturated, monocyclic, or polycyclic carbocyclic ring comprising from 3 to 10 carbon atoms, which may include fused (when fused with an aryl or a heteroaryl ring, the cycloalkyl is bonded through a non-aromatic ring atom) or bridged ring systems. Representative cycloalkyls include. In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1] heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl The term "$C_1$-$C_6$deuteroalkyl," as used herein, means a $C_1$-$C_6$alkyl group as defined herein wherein one or more hydrogen atoms in the $C_1$-$C_6$alkyl group is replaced with a deuterium atom.

The term "$C_1$-$C_6$ haloalkyl," as used herein, refers to a $C_1$-$C_6$alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

The term "$C_1$-$C_6$ hydroxyalkyl," as used herein, refers to a $C_1$-$C_6$alkyl radical, as defined above, that is substituted with one or more hydroxy groups.

The term "animal" as used herein includes, but is not limited to, humans and non-human vertebrates such as wild, domestic and farm animals. As used herein, the terms "subject," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the subject is a primate. In certain embodiments, the primate or subject is a human. In certain instances, the human is an adult. In certain instances, the human is child. In further instances, the human is under the age of 12 years. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with hypertensive pathology.

The term "Aurora kinase A," or "AurA," as used herein, means the human protein known to those of ordinary skill in the art as Aurora kinase A, and that is encoded by the AURKA gene.

The term "Aurora kinase B," or "AurB," as used herein, means the human protein known to those of ordinary skill in the art as Aurora kinase B, and that is encoded by the AURKB gene.

A "cyano" group refers to a —CN group.

The term "halo" or "halogen," as used herein, refers to bromo, chloro, fluoro or iodo. In some embodiments, halogen is fluoro or chloro. In some embodiments, halogen is fluoro.

The term "heterocycloalkyl," as used herein, refers to a 3- to 24-membered partially or fully saturated ring radical comprising 2 to 23 carbon atoms and from one to 8 heteroatoms selected from boron, nitrogen, oxygen, phosphorous, and sulfur. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenrofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "$C_1$-$C_6$heteroalkyl," as used herein, means an alkyl group in which one or more skeletal atoms of the alkyl are selected from an atom other than carbon, e.g., boron, oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl.

The term "heteroaryl," as used herein refers to a 5- to 14-membered ring system radical comprising hydrogen atoms, one to thirteen carbon atoms, one to six heteroatoms selected from boron, nitrogen, oxygen, phosphorous, and sulfur, and at least one aromatic ring. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, l-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl).

By "pharmaceutically acceptable," as used herein, is meant the carrier, diluent or excipient must be compatible with the other ingredients of the formulation and not deleterious to the recipient thereof.

The term "pharmaceutical composition" means a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "pharmaceutically acceptable salt," as used herein, means a salt of a compound of the present invention that retains the biological effectiveness of the free acids and bases of the specified derivative and that is not biologically or otherwise undesirable.

The term "PLK4," as used herein, means the human protein known to those of ordinary skill in the art as polo-like kinase 4, and that is encoded by the PLK4 gene The term "oxo," as used herein, refers to a carbonyl moiety such that alkyl substituted by oxo refers to a ketone group.

The term "solvate," as used herein, means a molecular complex between compounds of the present invention and solvent molecules. Examples of solvates include, but are not limited to, compounds of the invention in combination water, isopropanol, ethanol, methanol, dimethylsulfoxide (DMSO), ethyl acetate, acetic acid, ethanolamine, or mixtures thereof. The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

Where a compound of the invention contains an alkenyl group, geometric cis/trans (or Z/E) isomers are possible. Where the compound contains, for example, a keto or oxime group or an aromatic moiety, tautomeric isomerism ('tautomerism') can occur. Examples of tautomerism include keto and enol tautomers. A single compound may exhibit more than one type of isomerism. Included within the scope of the invention are all stereoisomers, geometric isomers, and tautomeric forms of the inventive compounds, including compounds exhibiting more than one type of isomerism, and mixtures of one or more thereof. Cis/trans isomers may be separated by conventional techniques well known to those skilled in the art, for example, chromatography and fractional crystallization.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. A mixture of racemates in which one racemate is present in a greater amount than the other racemate in such mixture may be described as "enantiomerically enriched." The term "diastereomers", on the other hand, refers to the relationship between a pair of stereoisomers that comprise two or more asymmetric centers and are not mirror images of one another. Designations that are conventional in the art may be used to describe stereoisomers of compounds, or the stereochemistry of a particular asymmetric carbon atom, of the compounds disclosed herein, or mixtures thereof. For example, a single racemate or stereocenter of a compound, may be described as of the (+), the (−), the (R)-, or the (S) configuration. A mixture of racemates may be described by use of the (±) symbol.

The compounds of the present invention may have asymmetric carbon atoms. The carbon-carbon bonds of the compounds of the present invention may be depicted herein using a solid line ( ), a solid wedge ( ) or a dotted wedge ( ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E L Eliel (Wiley, New York, 1994), the disclosure of which is incorporated herein by reference in its entirety.

The term "substituted," as used herein, means that the specified group or moiety bears one or more substituents. The term "unsubstituted" means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$aryl group, also called "phenyl" herein, is substituted with one additional substituent, one of ordinary skill in the art would understand that such a group has 4 open positions left on carbon atoms of the $C_6$aryl group (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$aryl group in the present compounds is said to be "disubstituted," one of ordinary skill in the art would understand it to mean that the $C_6$aryl group has 3 carbon atoms remaining that are unsubstituted. Those three unsubstituted carbon atoms are each bound to one hydrogen atom to fill their valencies.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group, and

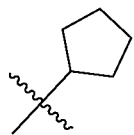 [SMILES: *C1CCCC1]

represents a cyclopentyl group, etc.

if a group, as for example, $(R^1)_n$ is depicted as "floating" Ring A in the formula:

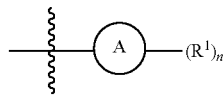

then, unless otherwise defined, the substituent $R^1$ may reside on any atom of the ring system, assuming replacement of a depicted, implied, or expressly defined hydrogen from one of the ring atoms, so long as a stable structure is formed. A ring system A may be, for example, but not limited to aryl, heteroaryl, cycloalkyl, cycloheteroalkyl, spirocyclyl or a fused ring system.

If a group "R" is depicted as "floating" on a ring system A as shown above, and Ring A contains saturated carbons, then "n" can be more than one, assuming each replaces a currently depicted, implied, or expressly defined hydrogen the ring A; then, unless otherwise defined, where the resulting structure is stable, two $R^1$ groups may reside on the same carbon. For example, when $R^1$ is a methyl group, there can exist a germinal dimethyl on a carbon of the ring A. In another example, two $R^1$ groups on the same carbon, including that carbon, may form a ring, thus creating a spirocyclic ring (a "spirocyclyl group"). It is to be understood that in the compounds of Formulae (I), (Ia), (Ib), (II), and (III) if n is less than the number of substitutable atoms on Ring A, the other substitutable positions on Ring A are bonded to a hydrogen atom.

As used herein, the term "therapeutic" means an agent utilized to treat, combat, ameliorate, prevent, or improve an unwanted condition or disease of a subject.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder, or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease, amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

The term "TRIM37," as used herein, means the human protein known those of ordinary skill in the art as tripartite motif-containing protein 37, an E3 ubiquitin ligase that is encoded by the TRIM37 gene.

The term "CFI-400495" means the compound having the Chemical Abstract Service Registry No. 1338806-73-7, and the structure shown below. The preparation of the compound is described in PCT Application Publication No. WO 2011/123946 and is commercially available for purchase.

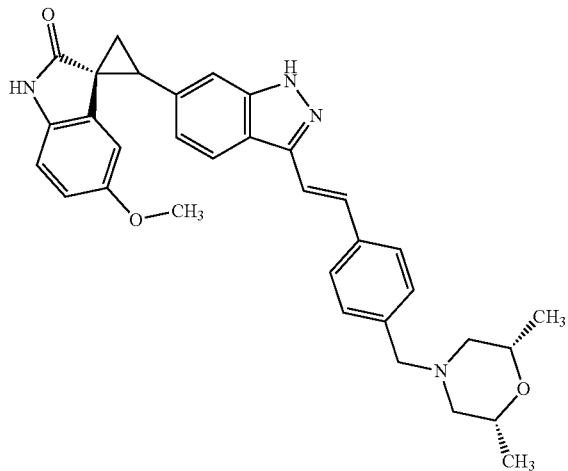 [SMILES: COc1ccc2c(c1)[C@]1(CC1c1ccc3c(/C=C/c4ccc(CN5C[C@@H](C)O[C@@H](C)C5)cc4)n[nH]c3c1)C(=O)N2]

PLK4 Inhibitor Compounds

Provided herein are compounds of Formula (I), or a pharmaceutically acceptable salt, solvate, or stereoisomer thereof:

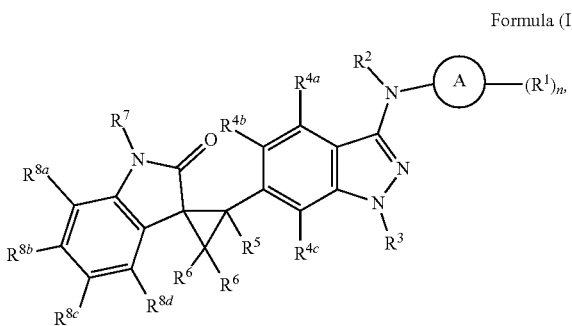

Formula (I)

wherein:

Ring A is $C_6$-$C_{10}$aryl, heteroaryl, $C_3$-$C_{10}$cycloalkyl, or heterocycloalkyl;

each $R^a$ is independently deuterium, halogen, —CN, oxo, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, —P(O)($R^a$)$_2$, —P(O)$_2$($R^a$)$_2$, $C_1$-$C_6$alkyl, $C_1$-$C_6$haloalkyl, —O$C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_2$-$C_{10}$alkynyl, $C_3$-$C_{10}$cycloalkyl, heterocycloalkyl, $C_6$-$C_{10}$aryl, and heteroaryl is optionally and independently substituted with one or more $R^{1a}$;

or two $R^a$ on adjacent atoms are taken together to form a $C_3$-$C_{10}$cycloalkyl or heterocycloalkyl; each optionally substituted with one or more $R^{1b}$;

each $R^{1a}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

or two $R^{1a}$ on the same atom are taken together to form an oxo;

each $R^{1b}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

or two $R^{1b}$ on the same atom are taken together to form an oxo;

n is 0, 1, 2, 3, 4, 5, 6, 7, or 8;

$R^2$ is hydrogen, $C_1$-$C_6$alkyl, $C_1$-$C_6$haloalkyl, or $C_1$-$C_6$deuteroalkyl;

$R^3$ is hydrogen, $C_1$-$C_6$alkyl, $C_1$-$C_6$haloalkyl, or $C_1$-$C_6$deuteroalkyl;

each of $R^{4a}$, $R^{4b}$, and $R^{4c}$ is independently hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^5$ is hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^6$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^7$ is hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

each of $R^{8a}$, $R^{8b}$, $R^{8c}$, and $R^{8d}$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_1$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O), NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$alkoxy, C$_1$-C$_6$aminoalkyl, C$_1$-C$_6$alkylamino, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$), —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or R$^c$ and R$^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)?N(CH$_3$)$_2$, —NH$_2$, —NHCH$_3$, —N(CH$_3$), —C(=O)CH$_3$, —C(=O)OH, —C(=O)OCH$_3$, C$_3$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

Provided herein are compounds of Formula (I), or a pharmaceutically acceptable salt, solvate, or stereoisomer thereof:

Formula (I)

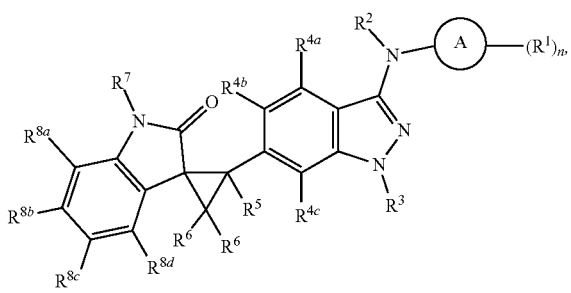

wherein:

Ring A is C$_6$-C$_{10}$aryl, heteroaryl, C$_3$-C$_{10}$cycloalkyl, or heterocycloalkyl;

each R$^1$ is independently deuterium, halogen, —CN, oxo, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, —OC$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl; wherein each of the C$_1$-C$_6$alkyl, C$_2$-C$_6$alkenyl, C$_2$-C$_{10}$alkynyl, C$_3$-C$_{10}$cycloalkyl, heterocycloalkyl, C$_6$-C$_{10}$aryl, and heteroaryl is optionally and independently substituted with one or more R$^{1a}$;

or two R$^1$ on adjacent atoms are taken together to form a C$_3$-C$_{10}$cycloalkyl or heterocycloalkyl; each optionally substituted with one or more R$^{1b}$;

each R$^{1a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

or two R$^{1a}$ on the same atom are taken together to form an oxo;

each R$^{1b}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

or two R$^{1b}$ on the same atom are taken together to form an oxo;

n is 0, 1, 2, 3, 4, 5, 6, 7, or 8;

R$^2$ is hydrogen, C$_1$-C$_6$alkyl, C$_1$-C$_6$haloalkyl, or C$_1$-C$_6$deuteroalkyl;

R$^3$ is hydrogen, C$_1$-C$_6$alkyl, C$_1$-C$_6$haloalkyl, or C$_1$-C$_6$deuteroalkyl;

each of R$^{4a}$, R$^{4b}$, and R$^{4c}$ is independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

R$^5$ is hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^6$ is independently hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

R⁷ is hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

each of $R^{8a}$, $R^{8b}$, $R^{8c}$, and $R^{8d}$ is independently hydrogen, deuterium, halogen, —CN, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

each R$^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH₃, —S(=O)CH₃, —S(=O)₂CH₃, —S(=O)₂NH₂, —S(=O)₂NHCH₃, —S(=O)₂N(CH₃)₂, —NH₂, —NHCH₃, —N(CH₃)₂, —C(=O)CH₃, —C(=O)OH, —C(=O)OCH₃, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each R$^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_1$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH₃, —S(=O)CH₃, —S(=O)₂CH₃, —S(=O)₂NH₂, —S(=O)₂NHCH₃, —S(=O)₂N(CH₃)₂, —NH₂, —NHCH₃, —N(CH₃)₂, —C(=O)CH₃, —C(=O)OH, —C(=O)OCH₃, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each R$^c$ and R$^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH₃, —S(=O)CH₃, —S(=O)₂CH₃, —S(=O)₂NH₂, —S(=O)₂NHCH₃, —S(=O)₂N(CH₃)₂, —NH₂, —NHCH₃, —N(CH₃)₂, —C(=O)CH₃, —C(=O)OH, —C(=O)OCH₃, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or R$^c$ and R$^d$ are taken together with the atom to which they are attached to form a heterocycloalkyl optionally substituted with one or more oxo, deuterium, halogen, —CN, —OH, —OCH₃, —S(=O)CH₃, —S(=O)CH₃, —S(=O)₂NH₂, —S(=O)₂NHCH₃, —S(=O)?N(CH₃)₂, —NH₂, —NHCH₃, —N(CH₃), —C(=O)CH₃, —C(=O) OH, —C(=O)OCH₃, $C_3$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In other embodiments are provided compounds of Formula (Ia), or a pharmaceutically acceptable salt, solvate, or stereoisomer thereof:

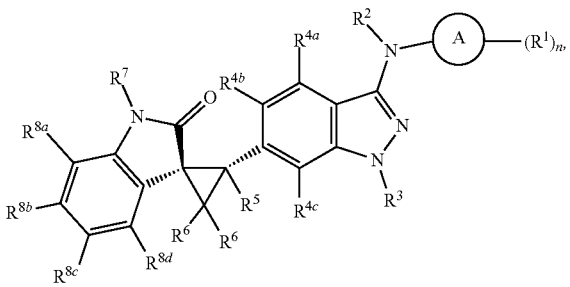

Formula (Ia)

wherein:

Ring A is $C_6$-$C_{10}$aryl, heteroaryl, $C_3$-$C_{10}$cycloalkyl, or heterocycloalkyl;

each R$^a$ is independently deuterium, halogen, —CN, oxo, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, —OC₁-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_1$-$C_6$alkynyl, $C_3$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_1$-$C_6$alkynyl, $C_3$-$C_{10}$cycloalkyl, heterocycloalkyl, $C_6$-$C_{10}$aryl, and heteroaryl is optionally and independently substituted with one or more R$^{1a}$;

or two R¹ on adjacent atoms are taken together to form a $C_3$-$C_{10}$cycloalkyl or heterocycloalkyl; each optionally substituted with one or more R$^{1b}$;

each R$^{1a}$ is independently deuterium, halogen, —CN, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

or two R$^{1a}$ on the same atom are taken together to form an oxo;

each R$^{1b}$ is independently deuterium, halogen, —CN, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$ alkenyl, $C_2$-$C_6$alkynyl, $C_3$-$C_{10}$cycloalkyl, heterocycloalkyl, $C_6$-$C_{10}$aryl, or heteroaryl;

or two $R^{1b}$ on the same atom are taken together to form an oxo;

n is 0, 1, 2, 3, 4, 5, 6, 7, or 8;

$R^2$ is hydrogen, $C_1$-$C_6$alkyl, $C_1$-$C_6$haloalkyl, or $C_1$-$C_6$deuteroalkyl;

$R^3$ is hydrogen, $C_1$-$C_6$alkyl, $C_1$-$C_6$haloalkyl, or $C_1$-$C_6$deuteroalkyl;

each of $R^{4a}$, $R^{4b}$, and $R^{4c}$ is independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^5$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^6$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^7$ is hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

each of $R^{8a}$, $R^{8b}$, $R^{8c}$, and $R^{8d}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_1$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In other embodiments are provided compounds of Formula (Ib), or a pharmaceutically acceptable salt, solvate, or stereoisomer thereof:

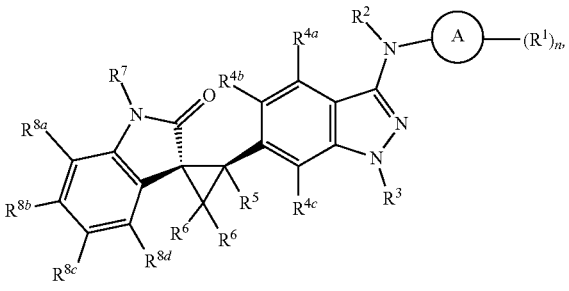

Formula (Ib)

wherein:

Ring A is $C_6$-$C_{10}$aryl, heteroaryl, $C_3$-$C_{10}$cycloalkyl, or heterocycloalkyl;

each $R^1$ is independently deuterium, halogen, —CN, oxo, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, —OC$_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is optionally and independently substituted with one or more $R^{1a}$;

or two $R^1$ on adjacent atoms are taken together to form a $C_3$-$C_{10}$cycloalkyl or heterocycloalkyl; each optionally substituted with one or more $R^{1b}$;

each $R^{1a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

or two $R^{1a}$ on the same atom are taken together to form an oxo;

each $R^{1b}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

or two $R^{1b}$ on the same atom are taken together to form an oxo;

n is 0, 1, 2, 3, 4, 5, 6, 7, or 8;

$R^2$ is hydrogen, $C_1$-$C_6$alkyl, $C_1$-$C_6$haloalkyl, or $C_1$-$C_6$deuteroalkyl;

$R^3$ is hydrogen, $C_1$-$C_6$alkyl, $C_1$-$C_6$haloalkyl, or $C_1$-$C_6$deuteroalkyl;

each of $R^{4a}$, $R^{4b}$, and $R^{4c}$ is independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^5$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^6$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^7$ is hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

each of $R^{8a}$, $R^{8b}$, $R^{8c}$, and $R^{8d}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_1$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Further provided herein are compounds of Formula (I), Formula (Ia), and Formula (Ib), or a pharmaceutically acceptable salt, solvate, or stereoisomer thereof, wherein Ring A is $C_6$-$C_{10}$aryl or heteroaryl. In some embodiments are provided compounds of Formula (I), Formula (Ia), and Formula (Ib), or a pharmaceutically acceptable salt, solvate, or stereoisomer thereof, wherein Ring A is $C_6$-$C_{10}$aryl. In some embodiments are provided compounds of Formula (I), Formula (Ia), and Formula (Ib), or a pharmaceutically acceptable salt, solvate, or stereoisomer thereof, wherein Ring A is phenyl. In some embodiments are provided compounds of Formula (I), Formula (Ia), and Formula (Ib), or a pharmaceutically acceptable salt, solvate, or stereoisomer thereof, wherein Ring A is heteroaryl. In some embodiments are provided compounds of Formula (I), Formula (Ia), and Formula (Ib), or a pharmaceutically acceptable salt, solvate, or stereoisomer thereof, wherein Ring A is furanyl, pyrrolyl, thiophenyl, oxazolyl, imidazolyl, thiazolyl, pyrazolyl, isoxazolyl, isothiazolyl, triazolyl, pyridinyl, pyrazinyl, pyrimidinyl, or pyridazinyl. In some embodiments are provided compounds of Formula (I), Formula (Ia), and Formula (Ib), or a pharmaceutically acceptable salt, solvate, or stereoisomer thereof, wherein Ring A is pyrazolyl, pyridinyl, pyrazinyl, pyrimidinyl, or pyridazinyl. In some embodiments are provided compounds of Formula (I), Formula (Ia), and Formula (Ib), or a pharmaceutically acceptable salt, solvate, or stereoisomer thereof, wherein Ring A is pyrazolyl, pyridinyl, pyrazinyl, or pyrimidinyl. In some embodiments are provided compounds of Formula (I). Formula (Ia), and Formula (Ib), or a pharmaceutically acceptable salt, solvate, or stereoisomer thereof, wherein Ring A is pyrazolyl. In some embodiments are provided compounds of Formula (I), Formula (Ia), and Formula (Ib), or a pharmaceutically acceptable salt, solvate, or stereoisomer thereof, wherein Ring A is 1-pyrazolyl, 3-pyrazolyl, 4-pyrazolyl, or 5-pyrazolyl. In some embodiments are provided compounds of Formula (I), Formula (Ia), and Formula (Ib), or a pharmaceutically acceptable salt, solvate, or stereoisomer thereof, wherein Ring A is 1-pyrazolyl. In some embodiments are provided compounds of Formula (I), Formula (Ia), and Formula (Ib), or a pharmaceutically acceptable salt, solvate, or stereoisomer thereof, wherein Ring A is 3-pyrazolyl. In some embodiments are provided compounds of Formula (I), Formula (Ia), and Formula (Ib), or a pharmaceutically acceptable salt, solvate, or stereoisomer thereof, wherein Ring A is 4-pyrazolyl. In some embodiments are provided compounds of Formula (I), Formula (Ia), and Formula (Ib), or a pharmaceutically acceptable salt, solvate, or stereoisomer thereof, wherein Ring A is 5-pyrazolyl. In some embodiments are provided compounds of Formula (I), Formula (Ia), and Formula (Ib), or a pharmaceutically acceptable salt, solvate, or stereoisomer thereof, wherein Ring A is pyridinyl. In some embodiments are provided compounds of Formula (I), Formula (Ia), and Formula (Ib), or a pharmaceutically acceptable salt, solvate, or stereoisomer thereof, wherein Ring A is 2-pyridinyl, 3-pyridinyl, 4-pyridinyl, 5-pyridinyl, or 6-pyridinyl. In some embodiments are provided compounds of Formula (I), Formula (Ia), and Formula (Ib), or a pharmaceutically acceptable salt, solvate, or stereoisomer thereof, wherein Ring A is 2-pyridinyl. In some embodiments are provided compounds of Formula (I), Formula (Ia), and Formula (Ib), or a pharmaceutically acceptable salt, solvate, or stereoisomer thereof, wherein Ring A is 3-pyridinyl. In some embodiments are provided compounds of Formula (I), Formula (Ia), and Formula (Ib), or a pharmaceutically acceptable salt, solvate, or stereoisomer thereof, wherein Ring A is 4-pyridinyl. In some embodiments are provided compounds of Formula (I), Formula (Ia), and Formula (Ib), or a pharmaceutically acceptable salt, solvate, or stereoisomer thereof, wherein Ring A is 5-pyridinyl. In some embodiments are provided compounds of Formula (I), Formula (Ia), and Formula (Ib), or a pharmaceutically acceptable salt, solvate, or stereoisomer thereof, wherein Ring A is 6-pyridinyl. In some embodiments are provided compounds of Formula (I), Formula (Ia), and Formula (Ib), or a pharmaceutically acceptable salt, solvate, or stereoisomer thereof, wherein Ring A is pyrazinyl. In some embodiments are provided compounds of Formula (I), Formula (Ia), and Formula (Ib), or a pharmaceutically acceptable salt, solvate, or stereoisomer thereof, wherein Ring A is 2-pyrazinyl, 3-pyrazinyl, 5-pyrazinyl, or 6-pyrazinyl. In some embodiments are provided compounds of Formula (I), Formula (Ia), and Formula (Ib), or a pharmaceutically acceptable salt, solvate, or stereoisomer thereof, wherein Ring A is 2-pyrazinyl. In some embodiments are provided compounds of Formula (I), Formula (Ia), and Formula (Ib), or a pharmaceutically acceptable salt, solvate, or stereoisomer thereof, wherein Ring A is 3-pyrazinyl. In some embodiments are provided compounds of Formula (I), Formula (Ia), and Formula (Ib), or a pharmaceutically acceptable salt, solvate, or stereoisomer thereof, wherein Ring A is 5-pyrazinyl. In some embodiments are provided compounds of Formula (I), Formula (Ia), and Formula (Ib), or a pharmaceutically acceptable salt, solvate, or stereoisomer thereof, wherein Ring A is 6-pyrazinyl. In some embodiments are provided compounds of Formula (I), Formula (Ia), and Formula (Ib), or a pharmaceutically acceptable salt, solvate, or stereoisomer thereof, wherein Ring A is pyrimidinyl. In some embodiments are provided compounds of Formula (I), Formula (Ia), and Formula (Ib), or a pharmaceutically acceptable salt, solvate, or stereoisomer thereof, wherein Ring A is 2-pyrimidinyl, 4-pyrimidinyl, 5-pyrimidinyl, or 6-pyrimidinyl. In some embodiments are provided compounds of Formula (I), Formula (Ia), and Formula (Ib), or a pharmaceutically acceptable salt, solvate, or stereoisomer thereof, wherein Ring A is 2-pyrimidinyl. In some embodiments are provided compounds of Formula (I), Formula (Ia), and Formula (Ib), or a pharmaceutically acceptable salt, solvate, or stereoisomer thereof, wherein Ring A is 4-pyrimidinyl. In some embodiments are provided compounds of Formula (I), Formula (Ia), and Formula (Ib), or a pharmaceutically acceptable salt, solvate, or stereoisomer thereof, wherein Ring A is 5-pyrimidinyl. In some embodiments are provided compounds of Formula (I), Formula (Ia), and Formula (Ib), or a pharmaceutically acceptable salt, solvate, or stereoisomer thereof, wherein Ring A is 6-pyrimidinyl. In some embodiments are provided compounds of Formula (I), Formula (Ia), and Formula (Ib), or a pharmaceutically acceptable salt, solvate, or stereoisomer thereof, wherein Ring A is pyridazinyl. In some embodiments are provided compounds of Formula (I), Formula (Ia), and Formula (Ib), or a pharmaceutically acceptable salt, solvate, or stereoisomer thereof, wherein Ring A is 3-pyridazinyl, 4-pyridazinyl, 5-pyridazinyl, or 6-pyridazinyl. In some embodiments are provided compounds of Formula (I), Formula (Ia), and Formula (Ib), or a pharmaceutically acceptable salt, solvate, or stereoisomer thereof, wherein Ring A is 3-pyridazinyl. In some embodiments are provided compounds of Formula (I), Formula (Ia), and Formula (Ib), or a pharmaceutically acceptable salt, solvate, or stereoisomer thereof, wherein Ring A is 4-pyridazinyl. In some embodiments are provided compounds of Formula (I), Formula (Ia), and Formula (Ib), or a pharmaceutically acceptable salt, solvate, or stereoisomer thereof, wherein Ring A is 5-pyridazinyl. In some embodiments are provided compounds of Formula (I), Formula (Ia), and Formula (Ib), or a pharmaceutically acceptable salt, solvate, or stereoisomer thereof, wherein Ring A is 6-pyridazinyl. In some embodiments are provided compounds of Formula (I), Formula (Ia), and Formula (Ib), or a pharmaceutically acceptable salt, solvate, or stereoisomer thereof, wherein Ring A is $C_3$-$C_{10}$cycloalkyl or heterocycloalkyl. In some embodiments are provided compounds of Formula (I), Formula (Ia), and Formula (Ib), or a pharmaceutically acceptable salt, solvate, or stereoisomer thereof, wherein Ring A is $C_3$-$C_{10}$cycloalkyl. In some embodiments are provided compounds of Formula (I), Formula (Ia), and Formula (Ib), or a pharmaceutically acceptable salt, solvate, or stereoisomer thereof, wherein Ring A is heterocycloalkyl.

Further provided herein are compounds of Formula (I). Formula (Ia), and Formula (Ib), or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$haloalkyl, —$OC_1$-$C_6$haloalkyl, $C_1$-$C_6$hydroxyalkyl, $C_1$-$C_6$aminoalkyl, $C_1$-$C_6$heteroalkyl, $C_3$-$C_{10}$cycloalkyl, heterocycloalkyl, $C_6$-$C_{10}$aryl, or heteroaryl; wherein each of the $C_1$-$C_6$alkyl, $C_3$-$C_{10}$cycloalkyl, heterocycloalkyl, $C_6$-$C_{10}$aryl, and heteroaryl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$haloalkyl, —$OC_1$-$C_6$haloalkyl, $C_1$-$C_6$hydroxyalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$haloalkyl, —$OC_1$-$C_6$haloalkyl, $C_3$-$C_{10}$cycloalkyl, or heterocycloalkyl; wherein each of the $C_1$-$C_6$alkyl, $C_1$-$C_{10}$cycloalkyl, and heterocycloalkyl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently halogen, —CN, —OH, —$OR^a$, $C_1$-$C_6$alkyl, —$OC_1$-$C_6$haloalkyl, —$CF_3$, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently fluoro, chloro, bromo, iodo, —CN, —OH, —$OR^a$, $C_1$-$C_6$alkyl, —$OC_1$-$C_6$haloalkyl, —$CF_3$, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently fluoro, chloro, bromo, —CN, —OH, —$OC_1$-$C_6$alkyl, —$OC_1$-$C_6$haloalkyl, $C_1$-$C_6$alkyl, —$CF_3$, $C_3$-$C_{10}$cycloalkyl, or heterocycloalkyl; wherein each of the —$OC_1$-$C_6$alkyl, $C_1$-$C_6$alkyl, $C_3$-$C_{10}$cycloalkyl, and heterocycloalkyl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^a$ is independently fluoro, chloro, —CN, —OH, —$OCH_3$, —$OCH_2CH_3$, —$C_1$-$C_6$alkyl($OR^{1a}$), —$CH_3$, —$CH_2CH_3$, iso-propyl, n-propyl, n-butyl, i-butyl, t-butyl, —$OCHF_2$, —$OC_1$-$C_6$hydroxyalkyl, —$CF_3$, cyclopropyl, azetidinyl, oxetanyl, piperidinyl, piperazinyl, morpholinyl, 1,4-oxazepanyl, or thiazinyl; wherein azetidinyl, oxetanyl, piperidinyl, piperazinyl, morpholinyl, thiazinyl, and 1,4-oxazepanyl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently chloro, —CN, —OH, —$OCH_3$, —$OCH_2CH_3$, —$CH_3$, iso-propyl, —$OCHF_2$, —$CF_3$, cyclopropyl, azetidinyl, oxetanyl, piperidinyl, piperazinyl, morpholinyl, or 1,4-oxazepanyl; wherein each of the azetidinyl, oxetanyl, piperidinyl, piperazinyl, morpholinyl, and 1,4-oxazepanyl is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, azetidinyl, piperidinyl, piperazinyl, or morpholinyl; wherein each of the azetidinyl, piperidinyl, piperazinyl, and morpholinyl, is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, azetidinyl, piperidinyl, piperazinyl, or morpholinyl; wherein each of the azetidinyl, piperidinyl, piperazinyl, and morpholinyl, is optionally and independently substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, piperidinyl, piperazinyl, or morpholinyl; wherein piperidinyl, piperazinyl, and morpholinyl are optionally substituted with one or more $R^{1a}$. In some embodiments are provided compounds of Formula (I), Formula (Ia), and Formula (Ib), or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, piperidinyl, piperazinyl, and morpholinyl are optionally substituted with one or more —$CH_3$, —$CH_2CH_3$, —$CH_2CH_2CH_3$, —OH, and —$OCH_3$. In some embodiments are provided compounds of Formula (I). Formula (Ia), and Formula (Ib), or a pharmaceutically acceptable salt, solvate, or stereoisomer thereof, wherein each $R^1$ is independently chloro, —CN, —$OCH_3$—$CH_3$, —$OCHF_2$, cyclopropyl, piperidinyl, piperazinyl, or morpholinyl; wherein piperidinyl, piperazinyl, and morpholinyl are optionally substituted with one or more —$CH_3$, —$CH_2CH_3$, —$CH_2CH_2CH_3$, —OH, and —$OCH_3$. In some embodiments are provided compounds of Formula (I), Formula (Ia), and Formula (Ib), or a pharmaceutically acceptable salt, solvate, or stereoisomer thereof, wherein each $R^1$ is independently chloro, —CN, —$OCH_3$—$CH_3$, —$OCHF_2$, cyclopropyl, or morpholinyl; wherein morpholinyl is optionally substituted with one or more —$CH_3$, —$CH_2CH_3$, —$CH_2CH_2CH_3$, —OH, and —$OCH_3$. In some embodiments are provided compounds of Formula (I), Formula (Ia), and Formula (Ib), or a pharmaceutically acceptable salt, solvate, or stereoisomer thereof, wherein each $R^1$ is independently chloro, —$OCH_3$—$CH_3$, —$OCHF_2$, cyclopropyl, or morpholinyl; wherein morpholinyl is optionally substituted with one or more —$CH_3$.

Further provided herein are compounds of Formula (I), Formula (Ia), and Formula (Ib), or a pharmaceutically acceptable salt, solvate, or stereoisomer thereof, wherein n is 1, 2, or 3. In some embodiments are provided compounds of Formula (I), Formula (Ia), and Formula (Ib), or a pharmaceutically acceptable salt, solvate, or stereoisomer thereof, wherein n is 1. In some embodiments are provided compounds of Formula (I), Formula (Ia), and Formula (Ib), or a pharmaceutically acceptable salt, solvate, or stereoisomer thereof, wherein n is 2. In some embodiments are provided compounds of Formula (I), Formula (Ia), and Formula (Ib), or a pharmaceutically acceptable salt, solvate, or stereoisomer thereof, wherein n is 3.

Further provided herein are compounds of Formula (I), Formula (Ia), and Formula (Ib), or a pharmaceutically acceptable salt, solvate, or stereoisomer thereof, wherein $R^2$ is hydrogen. Further provided herein are compounds of Formula (I), Formula (Ia), and Formula (Ib), or a pharmaceutically acceptable salt, solvate, or stereoisomer thereof, wherein $R^3$ is hydrogen.

Further provided herein are compounds of Formula (I), Formula (Ia), and Formula (Ib), or a pharmaceutically acceptable salt, solvate, or stereoisomer thereof, wherein $R^{4a}$, $R^{4b}$, and $R^{4c}$ are independently hydrogen or halogen. In some embodiments are provided compounds of Formula (I), Formula (Ia), and Formula (Ib), or a pharmaceutically acceptable salt, solvate, or stereoisomer thereof, wherein $R^{4a}$ is halogen and $R^{4b}$, and $R^{4c}$ are hydrogen. In some embodiments are provided compounds of Formula (I), Formula (Ia), and Formula (Ib), or a pharmaceutically acceptable salt, solvate, or stereoisomer thereof, wherein $R^{4a}$ and $R^{4b}$ are hydrogen and $R^{4b}$ is halogen. In some embodiments are provided compounds of Formula (I), Formula (Ia), and Formula (Ib), or a pharmaceutically acceptable salt, solvate, or stereoisomer thereof, wherein $R^{4a}$ and $R^{4b}$ are hydrogen and $R^{4c}$ is halogen. In some embodiments are provided compounds of Formula (I), Formula (Ia), and Formula (Ib), or a pharmaceutically acceptable salt, solvate, or stereoisomer thereof, wherein $R^{4a}$ and $R^{4b}$ are halogen and $R^{4c}$ is hydrogen. In some embodiments are provided compounds of Formula (I), Formula (Ia), and Formula (Ib), or a pharmaceutically acceptable salt, solvate, or stereoisomer thereof, wherein $R^{4a}$ and $R^{4b}$ are halogen and $R^{4c}$ is hydrogen. In some embodiments are provided compounds of Formula (I), Formula (Ia), and Formula (Ib), or a pharmaceutically acceptable salt, solvate, or stereoisomer thereof, wherein $R^{4a}$, $R^{4b}$ and $R^{4c}$ are halogen. In some embodiments are provided compounds of Formula (I), Formula (Ia), and Formula (Ib), or a pharmaceutically acceptable salt, solvate, or stereoisomer thereof, wherein $R^{4a}$, $R^{4b}$, and $R^{4c}$ are hydrogen. In some embodiments are provided compounds of Formula (I), Formula (Ia), and Formula (Ib), or a pharmaceutically acceptable salt, solvate, or stereoisomer thereof, wherein $R^5$ is hydrogen.

Further provided herein are compounds of Formula (I), Formula (Ia), and Formula (Ib), or a pharmaceutically acceptable salt, solvate, or stereoisomer thereof, wherein each $R^6$ is hydrogen.

Further provided herein are compounds of Formula (I), Formula (Ia), and Formula (Ib), or a pharmaceutically acceptable salt, solvate, or stereoisomer thereof, wherein $R^7$ is hydrogen or $C_1$-$C_6$alkyl. In some embodiments are provided compounds of Formula (I), Formula (Ia), and Formula (Ib), or a pharmaceutically acceptable salt, solvate, or stereoisomer thereof, wherein $R^7$ is hydrogen. In some embodiments are provided compounds of Formula (I), Formula (Ia), and Formula (Ib), or a pharmaceutically acceptable salt, solvate, or stereoisomer thereof, wherein $R^7$ is $C_1$-$C_6$alkyl.

Further provided herein are compounds of Formula (I), Formula (Ia), and Formula (Ib), or a pharmaceutically acceptable salt, solvate, or stereoisomer thereof, wherein each of $R^{8a}$, $R^{8b}$, $R^{8c}$, and $R^{8d}$ is independently hydrogen, halogen, or $-OR^a$. In some embodiments are provided compounds of Formula (I), Formula (Ia), and Formula (Ib), or a pharmaceutically acceptable salt, solvate, or stereoisomer thereof, wherein each of $R^{8a}$, $R^{8b}$, and $R^{8d}$ are hydrogen and $R^{8c}$ is hydrogen, halogen, or $-OR^a$. In some embodiments are provided compounds of Formula (I), Formula (Ia), and Formula (Ib), or a pharmaceutically acceptable salt, solvate, or stereoisomer thereof, wherein $R^{8c}$ is halogen or $-OR^a$. In some embodiments are provided compounds of Formula (I), Formula (Ia), and Formula (Ib), or a pharmaceutically acceptable salt, solvate, or stereoisomer thereof, wherein $R^{8c}$ is halogen. In some embodiments are provided compounds of Formula (I), Formula (Ia), and Formula (Ib), or a pharmaceutically acceptable salt, solvate, or stereoisomer thereof, wherein $R^{8c}$ is fluoro, chloro, bromo, or iodo. In some embodiments are provided compounds of Formula (I), Formula (Ia), and Formula (Ib), or a pharmaceutically acceptable salt, solvate, or stereoisomer thereof, wherein $R^{8c}$ is $-OR^a$.

Further provided herein are compounds of Formula (I), Formula (Ia), and Formula (Ib), or a pharmaceutically acceptable salt, solvate, or stereoisomer thereof, wherein $R^a$ is $C_1$-$C_6$alkyl. In some embodiments are provided compounds of Formula (I), Formula (Ia), and Formula (Ib), or a pharmaceutically acceptable salt, solvate, or stereoisomer thereof, wherein $R^a$ is $-CH_3$.

Further provided herein are compounds of Formula (II), or a pharmaceutically acceptable salt, solvate, or stereoisomer thereof:

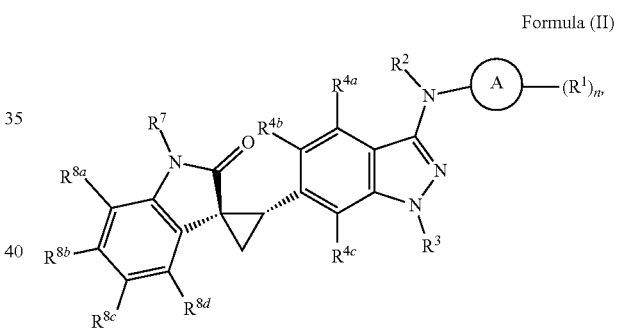

Formula (II)

wherein:
Ring A is $C_6$-$C_{10}$aryl or heteroaryl, $C_3$-$C_{10}$cycloalkyl, and heterocycloalkyl;
each $R^1$ is independently halogen, $-CN$, $-OH$, $-OR^a$, $C_1$-$C_6$alkyl, $C_1$-$C_6$haloalkyl, $-OC_1$-$C_6$haloalkyl, $C_1$-$C_6$hydroxyalkyl, $C_1$-$C_6$aminoalkyl, $C_1$-$C_6$heteroalkyl, $C_3$-$C_{10}$cycloalkyl, heterocycloalkyl, $C_6$-$C_{10}$aryl, or heteroaryl; wherein each of the $C_1$-$C_6$alkyl, $C_3$-$C_{10}$cycloalkyl, heterocycloalkyl, $C_6$-$C_{10}$aryl, and heteroaryl is optionally and independently substituted with one or more $R^{1a}$;
each $R^{1a}$ is independently deuterium, halogen, $-CN$, $-NO_2$, $-OH$, $-OR^a$, $-OC(=O)R^a$, $-OC(=O)OR^b$, $-OC(=O)NR^cR^d$, $-SH$, $-SR^a$, $-S(=O)R^a$, $-S(=O)R^a$, $-S(=O)_2NR^cR^d$, $-NR^cR^d$, $-NR^bC(=O)NR^cR^d$, $-NR^bC(=O)R^a$, $-NR^bC(=O)OR^a$, $-NR^bS(=O)_2R^a$, $-C(=O)R^a$, $-C(=O)OR^b$, $-C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;
n is 1, 2, 3, 4, 5, 6, 7, or 8;

$R^2$ is hydrogen or $C_1$-$C_6$alkyl;

$R^3$ is hydrogen or $C_1$-$C_6$alkyl;

$R^{4a}$, $R^{4b}$, and $R^{4c}$ are each independently hydrogen, deuterium, or halogen;

$R^7$ is hydrogen or $C_1$-$C_6$alkyl;

each of $R^{8a}$, $R^{8b}$, $R^{8c}$, and $R^{8d}$ is independently hydrogen, deuterium, halogen, or —$OR^a$;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_4$hydroxyalkyl, $C_1$-$C_6$aminoalkyl, $C_1$-$C_6$heteroalkyl, $C_1$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$ alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Further provided herein are compounds of Formula (II), or a pharmaceutically acceptable salt, solvate, or stereoisomer thereof, wherein Ring A is $C_6$-$C_{10}$aryl or heteroaryl. In some embodiments are provided compounds of Formula (II), or a pharmaceutically acceptable salt, solvate, or stereoisomer thereof, wherein Ring A is $C_6$-$C_{10}$aryl. In some embodiments are provided compounds of Formula (II), or a pharmaceutically acceptable salt, solvate, or stereoisomer thereof, wherein Ring A is phenyl. In some embodiments are provided compounds of Formula (II), or a pharmaceutically acceptable salt, solvate, or stereoisomer thereof, wherein Ring A is heteroaryl. In some embodiments are provided compounds of Formula (II), or a pharmaceutically acceptable salt, solvate, or stereoisomer thereof, wherein Ring A is furanyl, pyrrolyl, thiophenyl, oxazolyl, imidazolyl, thiazolyl, pyrazolyl, isoxazolyl, isothiazolyl, triazolyl, pyridinyl, pyrazinyl, pyrimidinyl, or pyridazinyl. In some embodiments are provided compounds of Formula (II), or a pharmaceutically acceptable salt, solvate, or stereoisomer thereof, wherein Ring A is pyrazolyl, pyridinyl, pyrazinyl, pyrimidinyl, or pyridazinyl. In some embodiments are provided compounds of Formula (II), or a pharmaceutically acceptable salt, solvate, or stereoisomer thereof, wherein Ring A is pyrazolyl, pyridinyl, pyrazinyl, or pyrimidinyl. In some embodiments are provided compounds of Formula (II), or a pharmaceutically acceptable salt, solvate, or stereoisomer thereof, wherein Ring A is pyrazolyl. In some embodiments are provided compounds of Formula (II), or a pharmaceutically acceptable salt, solvate, or stereoisomer thereof, wherein Ring A is 1-pyrazolyl, 3-pyrazolyl, 4-pyrazolyl, or 5-pyrazolyl. In some embodiments are provided compounds of Formula (II), or a pharmaceutically acceptable salt, solvate, or stereoisomer thereof, wherein Ring A is 1-pyrazolyl. In some embodiments are provided compounds of Formula (II), or a pharmaceutically acceptable salt, solvate, or stereoisomer thereof, wherein Ring A is 3-pyrazolyl. In some embodiments are provided compounds of Formula (II), or a pharmaceutically acceptable salt, solvate, or stereoisomer thereof, wherein Ring A is 4-pyrazolyl. In some embodiments are provided compounds of Formula (II), or a pharmaceutically acceptable salt, solvate, or stereoisomer thereof, wherein Ring A is 5-pyrazolyl. In some embodiments are provided compounds of Formula (II), or a pharmaceutically acceptable salt, solvate, or stereoisomer thereof, wherein Ring A is pyridinyl. In some embodiments are provided compounds of Formula (II), or a pharmaceutically acceptable salt, solvate, or stereoisomer thereof, wherein Ring A is 2-pyridinyl, 3-pyridinyl, 4-pyridinyl, 5-pyridinyl, or 6-pyridinyl. In some embodiments are provided compounds of Formula (II), or a pharmaceutically acceptable salt, solvate, or stereoisomer thereof, wherein Ring A is 2-pyridinyl. In some embodiments are provided compounds of Formula (II), or a pharmaceutically acceptable salt, solvate, or stereoisomer thereof, wherein Ring A is 3-pyridinyl. In some embodiments are provided compounds of Formula (II), or a pharmaceutically acceptable salt, solvate, or stereoisomer thereof, wherein Ring A is 4-pyridinyl. In some embodiments are provided compounds of Formula (II), or a pharmaceutically acceptable salt, solvate, or stereoisomer thereof, wherein Ring A is 5-pyridinyl. In some embodiments are provided compounds of Formula (II), or a pharmaceutically acceptable salt, solvate, or stereoisomer thereof, wherein Ring A is 6-pyridinyl. In some embodiments are provided compounds of Formula (II), or a pharmaceutically acceptable salt, solvate, or stereoisomer thereof, wherein Ring A is pyrazinyl. In some embodiments are provided compounds of Formula (II), or a pharmaceutically acceptable salt, solvate, or stereoisomer thereof, wherein Ring A is 2-pyrazinyl, 3-pyrazinyl, 5-pyrazinyl, or 6-pyrazinyl. In some embodiments are provided compounds of Formula (II), or a pharmaceutically acceptable salt, solvate, or stereoisomer thereof, wherein Ring A is 2-pyrazinyl. In some embodiments are provided compounds of Formula (II), or a pharmaceutically acceptable salt, solvate, or stereoisomer thereof, wherein Ring A is 3-pyrazinyl. In some embodiments are provided compounds of Formula (II), or a pharmaceutically acceptable salt, solvate, or stereoisomer thereof, wherein Ring A is 5-pyrazinyl. In some embodiments are provided compounds of Formula (II), or a pharmaceutically acceptable salt, solvate, or stereoisomer thereof, wherein Ring A is 6-pyrazinyl. In some embodiments are provided compounds of Formula (II), or a pharmaceutically acceptable salt, solvate, or stereoisomer thereof, wherein Ring A is pyrimidinyl. In some embodiments are provided compounds of Formula (II), or a pharmaceutically acceptable salt, solvate, or stereoisomer thereof, wherein Ring A is 2-pyrimidinyl, 4-pyrimidinyl, 5-pyrimidinyl, or 6-pyrimidinyl. In some embodiments are provided compounds of Formula (II), or a pharmaceutically acceptable salt, solvate, or stereoisomer thereof, wherein Ring A is 2-pyrimidinyl. In some embodiments are provided compounds of Formula (II), or a pharmaceutically acceptable salt, solvate, or stereoisomer thereof, wherein Ring A is 4-pyrimidinyl. In some embodiments are provided compounds of Formula (II), or a pharmaceutically acceptable salt, solvate, or stereoisomer thereof, wherein Ring A is 5-pyrimidinyl. In some embodiments are provided compounds of Formula (II), or a pharmaceutically acceptable salt, solvate, or stereoisomer thereof, wherein Ring A is 6-pyrimidinyl. In some embodiments are provided compounds of Formula (II), or a pharmaceutically acceptable salt, solvate, or stereoisomer thereof, wherein Ring A is pyridazinyl. In some embodiments are provided compounds of Formula (II), or a pharmaceutically acceptable salt, solvate, or stereoisomer thereof, wherein Ring A is 3-pyridazinyl, 4-pyridazinyl, 5-pyridazinyl, or 6-pyridazinyl. In some embodiments are provided compounds of Formula (II), or a pharmaceutically acceptable salt, solvate, or stereoisomer thereof, wherein Ring A is 3-pyridazinyl. In some embodiments are provided compounds of Formula (II), or a pharmaceutically acceptable salt, solvate, or stereoisomer thereof, wherein Ring A is 4-pyridazinyl. In some embodiments are provided compounds of Formula (II), or a pharmaceutically acceptable salt, solvate, or stereoisomer thereof, wherein Ring A is 5-pyridazinyl. In some embodiments are provided compounds of Formula (II), or a pharmaceutically acceptable salt, solvate, or stereoisomer thereof, wherein Ring A is 6-pyridazinyl. In some embodiments are provided compounds of Formula (II), or a pharmaceutically acceptable salt, solvate, or stereoisomer thereof, wherein Ring A is $C_3$-$C_{10}$cycloalkyl or heterocycloalkyl. In some embodiments are provided compounds of Formula (II), or a pharmaceutically acceptable salt, solvate, or stereoisomer thereof, wherein Ring A is $C_3$-$C_{10}$cycloalkyl. In some embodiments are provided compounds of Formula (II), or a pharmaceutically acceptable salt, solvate, or stereoisomer thereof, wherein Ring A is heterocycloalkyl.

Further provided herein are compounds of Formula (II), or a pharmaceutically acceptable salt, solvate, or stereoisomer thereof, wherein each $R^1$ is independently halogen, —CN, —OH, —OR$^a$, $C_1$-$C_6$alkyl, $C_1$-$C_6$haloalkyl, OC$_1$-$C_6$haloalkyl, $C_1$-$C_6$hydroxyalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$. In some embodiments are provided compounds of Formula (II), or a pharmaceutically acceptable salt, solvate, or stereoisomer thereof, wherein each $R^1$ is independently halogen, —CN, —OH, —OR$^a$, $C_1$-$C_6$alkyl, $C_1$-$C_6$haloalkyl, —OC$_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$. In some embodiments are provided compounds of Formula (II), or a pharmaceutically acceptable salt, solvate, or stereoisomer thereof, wherein each $R^1$ is independently fluoro, chloro, bromo, iodo, —CN, —OH, —OR$^a$, $C_1$-$C_6$alkyl, —CF$_3$, —OC$_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$. In some embodiments are provided compounds of Formula (II), or a pharmaceutically acceptable salt, solvate, or stereoisomer thereof, wherein each $R^1$ is independently fluoro, chloro, bromo, —CN, —OH, —OR$^a$, $C_1$-$C_6$alkyl, —CF$_3$, —OC$_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$. In some embodiments are provided compounds of Formula (II), or a pharmaceutically acceptable salt, solvate, or stereoisomer thereof, wherein each $R^1$ is independently fluoro, chloro, —CN, —OH, —OC$_1$-$C_6$alkyl, $C_1$-$C_6$alkyl, —CF$_3$, —OC$_1$-$C_6$haloalkyl, $C_3$-$C_{10}$cycloalkyl, or heterocycloalkyl; wherein each of the —OC$_1$-$C_6$alkyl, $C_1$-$C_6$alkyl, $C_3$-$C_{10}$cycloalkyl, and heterocycloalkyl is optionally and independently substituted with one or more $R^{1a}$. In some embodiments are provided compounds of Formula (II), or a pharmaceutically acceptable salt, solvate, or stereoisomer thereof, wherein each $R^1$ is independently fluoro, chloro, —CN, —OH, —OCH$_3$, —OCH$_2$CH$_3$, —C$_1$-$C_6$alkyl(OR$^{1a}$), —CH$_3$, —CH$_2$CH$_3$, iso-propyl, n-propyl, n-butyl, i-butyl, t-butyl, —OC$_1$-$C_6$hydroxyalkyl, —CF$_3$, —OCHF$_2$, cyclopropyl, azetidinyl, oxetanyl, piperidinyl, piperazinyl, morpholinyl, 1,4-oxazepanyl, or thiazinyl; wherein each of the azetidinyl, oxetanyl, piperidinyl, piperazinyl, morpholinyl, thiazinyl, and 1,4-oxazepanyl is optionally and independently substituted with one or more $R^{1a}$. In some embodiments are provided compounds of Formula (II), or a pharmaceutically acceptable salt, solvate, or stereoisomer thereof, wherein each $R^1$ is independently chloro, —CN, —OH, —OCH$_3$, —OCH$_2$CH$_3$, —CH$_3$, iso-propyl, —CF$_3$, —OCHF$_2$, cyclopropyl, azetidinyl, oxetanyl, piperidinyl, piperazinyl, morpholinyl, or 1,4-oxazepanyl; wherein each of the azetidinyl, oxetanyl, piperidinyl, piperazinyl, morpholinyl, and 1,4-oxazepanyl is optionally and independently substituted with one or more $R^{1a}$. In some embodiments are provided compounds of Formula (II), or a pharmaceutically acceptable salt, solvate, or stereoisomer thereof, wherein each $R^1$ is independently chloro, —CN, —OCH$_3$, —CH$_3$, iso-propyl, —CF$_3$, —OCHF$_2$, cyclopropyl, azetidinyl, piperidinyl, piperazinyl, or morpholinyl; wherein each of the azetidinyl, piperidinyl, piperazinyl, and morpholinyl, is optionally and independently substituted with one or more $R^{1a}$. In some embodiments are provided compounds of Formula (II), or a pharmaceutically acceptable salt, solvate, or stereoisomer thereof, wherein each $R^1$ is independently chloro, —CN, —OCH$_1$, —CH$_3$, iso-propyl, —CF$_3$, —OCHF$_2$, cyclopropyl, piperidinyl, piperazinyl, or morpholinyl; wherein each of the cyclopropyl, piperidinyl, piperazinyl, and morpholinyl, is optionally and independently substituted with one or more $R^{1a}$. In some embodiments are provided compounds of Formula (II), or a pharmaceutically acceptable salt, solvate, or stereoisomer thereof, wherein each $R^1$ is independently chloro, —OCH$_3$, —CH$_3$, iso-propyl, —CF$_3$, —OCHF$_2$, cyclopropyl, piperidinyl, piperazinyl, or morpholinyl; wherein piperidinyl, piperazinyl, and morpholinyl are optionally substituted with one or more $R^{1a}$. In some embodiments are provided compounds of Formula (II), or a pharmaceutically acceptable salt, solvate, or stereoisomer thereof, wherein each $R^1$ is independently chloro, —OCH$_3$, —CH$_3$, iso-propyl, —CF$_3$, —OCHF$_2$, cyclopropyl, piperidinyl, piperazinyl, or morpholinyl; wherein piperidinyl, piperazinyl, and morpholinyl are optionally substituted with one or more —CH$_3$, —CH$_2$CH$_3$, —CH$_2$CH$_2$CH$_3$, —OH, and —OCH$_3$. In some embodiments are provided compounds of Formula (II), or a pharmaceutically acceptable salt, solvate, or stereoisomer thereof, wherein each $R^1$ is independently chloro, —OCH$_3$, —CH$_3$, —OCHF$_2$, cyclopropyl, piperidinyl, piperazinyl, or morpholinyl; wherein piperidinyl, piperazinyl, and morpholinyl are optionally substituted with one or more —CH$_3$, —CH$_2$CH$_3$, —CH$_2$CH$_2$CH$_3$, —OH, and —OCH$_3$. In some embodiments are provided compounds of Formula (II), or a pharmaceutically acceptable salt, solvate, or stereoisomer thereof, wherein each $R^1$ is independently chloro, —OCH$_3$—CH$_3$, —OCHF$_2$, cyclopropyl, or morpholinyl; wherein morpholinyl is optionally substituted with one or more —CH$_3$, —CH$_2$CH$_3$, —CH$_2$CH$_2$CH$_3$, —OH, and —OCH$_3$. In some embodiments are provided compounds of Formula (II), or a pharmaceutically acceptable salt, solvate, or stereoisomer thereof, wherein each $R^1$ is independently chloro, —OCH$_3$, —CH$_3$, cyclopropyl, or morpholinyl; wherein morpholinyl is optionally substituted with one or more —CH$_3$.

Further provided herein are compounds of Formula (II), or a pharmaceutically acceptable salt, solvate, or stereoisomer thereof, wherein n is 1, 2, or 3. In some embodiments are provided compounds of Formula (II), or a pharmaceutically acceptable salt, solvate, or stereoisomer thereof, wherein n is 1. In some embodiments are provided compounds of Formula (II), or a pharmaceutically acceptable salt, solvate, or stereoisomer thereof, wherein n is 2. In some embodiments are provided compounds of Formula (II), or a pharmaceutically acceptable salt, solvate, or stereoisomer thereof, wherein n is 3.

Further provided herein are compounds of Formula (II), or a pharmaceutically acceptable salt, solvate, or stereoisomer thereof, wherein $R^2$ is hydrogen.

Further provided herein are compounds of Formula (II), or a pharmaceutically acceptable salt, solvate, or stereoisomer thereof, wherein $R^3$ is hydrogen.

Further provided herein are compounds of Formula (II), or a pharmaceutically acceptable salt, solvate, or stereoisomer thereof, wherein $R^{4a}$, $R^{4b}$, and $R^{4c}$ are independently hydrogen or halogen. In some embodiments are provided compounds of Formula (II), or a pharmaceutically acceptable salt, solvate, or stereoisomer thereof, wherein $R^{4a}$ is halogen and $R^{4b}$, and $R^{4c}$ are hydrogen. In some embodiments are provided compounds of Formula (II), or a pharmaceutically acceptable salt, solvate, or stereoisomer thereof, wherein $R^{4a}$ and $R^{4c}$ are hydrogen and $R^{4b}$ is halogen. In some embodiments are provided compounds of Formula (II), or a pharmaceutically acceptable salt, solvate, or stereoisomer thereof, wherein $R^{4a}$ and $R^{4b}$ are hydrogen and $R^{4c}$ is halogen. In some embodiments are provided compounds of Formula (II), or a pharmaceutically acceptable salt, solvate, or stereoisomer thereof, wherein $R^{4a}$ and $R^{4b}$ are halogen and $R^{4c}$ is hydrogen. In some embodiments are provided compounds of Formula (II), or a pharmaceutically acceptable salt, solvate, or stereoisomer thereof, wherein $R^{4a}$ and $R^{4c}$ are halogen and $R^{4b}$ is hydrogen. In some embodiments are provided compounds of Formula (II), or a pharmaceutically acceptable salt, solvate, or stereoisomer thereof, wherein $R^{4a}$ is halogen and $R^{4b}$ and $R^{4c}$ are hydrogen. In some embodiments are provided compounds of Formula (II), or a pharmaceutically acceptable salt, solvate, or stereoisomer thereof, wherein $R^{4a}$, $R^{4b}$, and $R^{4c}$ are hydrogen. In some embodiments are provided compounds of Formula (II), or a pharmaceutically acceptable salt, solvate, or stereoisomer thereof, wherein $R^{4a}$, $R^{4b}$, and $R^{4c}$ are halogen. In some embodiments are provided compounds of Formula (II), or a pharmaceutically acceptable salt, solvate, or stereoisomer thereof, wherein $R^{4a}$, $R^{4b}$, and $R^{4c}$ are fluoro.

Further provided herein are compounds of Formula (II), or a pharmaceutically acceptable salt, solvate, or stereoisomer thereof, wherein $R^7$ is hydrogen or $C_1$-$C_6$alkyl. In some embodiments are provided compounds of Formula (II), or a pharmaceutically acceptable salt, solvate, or stereoisomer thereof, wherein $R^7$ is hydrogen. In some embodiments are provided compounds of Formula (II), or a pharmaceutically acceptable salt, solvate, or stereoisomer thereof, wherein $R^7$ is $C_1$-$C_6$alkyl.

Further provided herein are compounds of Formula (II), or a pharmaceutically acceptable salt, solvate, or stereoisomer thereof, wherein each of $R^{8a}$, $R^{8b}$, $R^{8c}$, and $R^{8d}$ is independently hydrogen, deuterium, halogen, or —OR$^a$. In some embodiments are provided compounds of Formula (II), or a pharmaceutically acceptable salt, solvate, or stereoisomer thereof, wherein each of $R^{8a}$, $R^{8b}$, and $R^{8d}$ are hydrogen and $R^{8c}$ is hydrogen, halogen, or —OR$^a$. In some embodiments are provided compounds of Formula (II), or a pharmaceutically acceptable salt, solvate, or stereoisomer thereof, wherein $R^{8c}$ is halogen or —OR$^a$. In some embodiments are provided compounds of Formula (II), or a pharmaceutically acceptable salt, solvate, or stereoisomer thereof, wherein $R^{8c}$ is halogen. In some embodiments are provided compounds of Formula (II), or a pharmaceutically acceptable salt, solvate, or stereoisomer thereof, wherein $R^{8c}$ is fluoro, chloro, bromo, or iodo. In some embodiments are provided compounds of Formula (II), or a pharmaceutically acceptable salt, solvate, or stereoisomer thereof, wherein $R^{8c}$ is —OR$^a$.

Further provided herein are compounds of Formula (II), or a pharmaceutically acceptable salt, solvate, or stereoisomer thereof, wherein $R^a$ is $C_1$-$C_6$alkyl. In some embodiments are provided compounds of Formula (II), or a pharmaceutically acceptable salt, solvate, or stereoisomer thereof, wherein $R^a$ is —CH$_3$.

Further provided herein are compounds of Formula (III), or a pharmaceutically acceptable salt, solvate, or stereoisomer thereof:

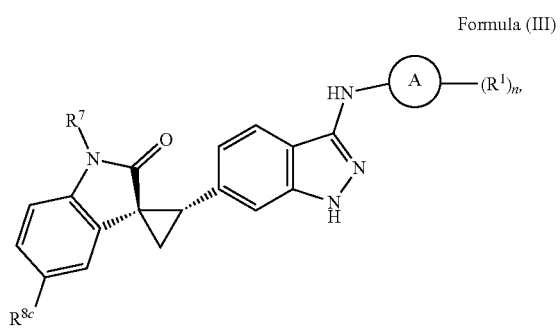

Formula (III)

wherein:

Ring A is heteroaryl;

each $R^1$ is independently halogen, —CN, —OH, —OR$^a$, $C_1$-$C_6$alkyl, $C_1$-$C_6$haloalkyl, —O$C_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;

each $R^{1a}$ is independently deuterium, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

n is 1, 2, 3, 4, 5, 6, 7, or 8;

$R^7$ is hydrogen or $C_1$-$C_6$alkyl;

$R^{8c}$ is halogen or —OR$^a$; and each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Further provided herein are compounds of Formula (III), or a pharmaceutically acceptable salt, solvate, or stereoisomer thereof, wherein Ring A is pyrazolyl, pyridinyl, pyrazinyl, pyrimidinyl, or pyridazinyl. In some embodiments are provided compounds of Formula (III), or a pharmaceutically acceptable salt, solvate, or stereoisomer thereof, wherein Ring A is pyrazolyl. In some embodiments are provided compounds of Formula (III), or a pharmaceutically acceptable salt, solvate, or stereoisomer thereof, wherein Ring A is 1-pyrazolyl, 3-pyrazolyl, 4-pyrazolyl, or 5-pyrazolyl. In some embodiments are provided compounds of Formula (III), or a pharmaceutically acceptable salt, solvate, or stereoisomer thereof, wherein Ring A is 1-pyrazolyl. In some embodiments are provided compounds of Formula (III), or a pharmaceutically acceptable salt, solvate, or stereoisomer thereof, wherein Ring A is 3-pyrazolyl. In some embodiments are provided compounds of Formula (III), or a pharmaceutically acceptable salt, solvate, or stereoisomer thereof, wherein Ring A is 4-pyrazolyl. In some embodiments are provided compounds of Formula (III), or a pharmaceutically acceptable salt, solvate, or stereoisomer thereof, wherein Ring A is 5-pyrazolyl. In some embodiments are provided compounds of Formula (III), or a pharmaceutically acceptable salt, solvate, or stereoisomer thereof, wherein Ring A is pyridinyl. In some embodiments are provided compounds of Formula (III), or a pharmaceutically acceptable salt, solvate, or stereoisomer thereof, wherein Ring A is 2-pyridinyl, 3-pyridinyl, 4-pyridinyl, 5-pyridinyl, or 6-pyridinyl. In some embodiments are provided compounds of Formula (III), or a pharmaceutically acceptable salt, solvate, or stereoisomer thereof, wherein Ring A is 2-pyridinyl. In some embodiments are provided compounds of Formula (III), or a pharmaceutically acceptable salt, solvate, or stereoisomer thereof, wherein Ring A is 3-pyridinyl. In some embodiments are provided compounds of Formula (III), or a pharmaceutically acceptable salt, solvate, or stereoisomer thereof, wherein Ring A is 4-pyridinyl. In some embodiments are provided compounds of Formula (III), or a pharmaceutically acceptable salt, solvate, or stereoisomer thereof, wherein Ring A is 5-pyridinyl. In some embodiments are provided compounds of Formula (III), or a pharmaceutically acceptable salt, solvate, or stereoisomer thereof, wherein Ring A is 6-pyridinyl. In some embodiments are provided compounds of Formula (III), or a pharmaceutically acceptable salt, solvate, or stereoisomer thereof, wherein Ring A is pyrazinyl. In some embodiments are provided compounds of Formula (III), or a pharmaceutically acceptable salt, solvate, or stereoisomer thereof, wherein Ring A is 2-pyrazinyl, 3-pyrazinyl, 5-pyrazinyl, or 6-pyrazinyl. In some embodiments are provided compounds of Formula (III), or a pharmaceutically acceptable salt, solvate, or stereoisomer thereof, wherein Ring A is 2-pyrazinyl. In some embodiments are provided compounds of Formula (III), or a pharmaceutically acceptable salt, solvate, or stereoisomer thereof, wherein Ring A is 3-pyrazinyl. In some embodiments are provided compounds of Formula (III), or a pharmaceutically acceptable salt, solvate, or stereoisomer thereof, wherein Ring A is 5-pyrazinyl. In some embodiments are provided compounds of Formula (III), or a pharmaceutically acceptable salt, solvate, or stereoisomer thereof, wherein Ring A is 6-pyrazinyl. In some embodiments are provided compounds of Formula (III), or a pharmaceutically acceptable salt, solvate, or stereoisomer thereof, wherein Ring A is pyrimidinyl. In some embodiments are provided compounds of Formula (III), or a pharmaceutically acceptable salt, solvate, or stereoisomer thereof, wherein Ring A is 2-pyrimidinyl, 4-pyrimidinyl, 5-pyrimidinyl, or 6-pyrimidinyl. In some embodiments are provided compounds of Formula (III), or a pharmaceutically acceptable salt, solvate, or stereoisomer thereof, wherein Ring A is 2-pyrimidinyl. In some embodiments are provided compounds of Formula (III), or a pharmaceutically acceptable salt, solvate, or stereoisomer thereof, wherein Ring A is 4-pyrimidinyl. In some embodiments are provided compounds of Formula (III), or a pharmaceutically acceptable salt, solvate, or stereoisomer thereof, wherein Ring A is 5-pyrimidinyl. In some embodiments are provided compounds of Formula (III), or a pharmaceutically acceptable salt, solvate, or stereoisomer thereof, wherein Ring A is 6-pyrimidinyl. In some embodiments are provided compounds of Formula (III), or a pharmaceutically acceptable salt, solvate, or stereoisomer thereof, wherein Ring A is pyridazinyl. In some embodiments are provided compounds of Formula (III), or a pharmaceutically acceptable salt, solvate, or stereoisomer thereof, wherein Ring A is 3-pyridazinyl, 4-pyridazinyl, 5-pyridazinyl, or 6-pyridazinyl. In some embodiments are provided compounds of Formula (III), or a pharmaceutically acceptable salt, solvate, or stereoisomer thereof, wherein Ring A is 3-pyridazinyl. In some embodiments are provided compounds of Formula (III), or a pharmaceutically acceptable salt, solvate, or stereoisomer thereof, wherein Ring A is 4-pyridazinyl. In some embodiments are provided compounds of Formula (III), or a pharmaceutically acceptable salt, solvate, or stereoisomer thereof, wherein Ring A is 5-pyridazinyl. In some embodiments are provided compounds of Formula (III), or a pharmaceutically acceptable salt, solvate, or stereoisomer thereof, wherein Ring A is 6-pyridazinyl.

Further provided herein are compounds of Formula (III), or a pharmaceutically acceptable salt, solvate, or stereoisomer thereof, wherein:
Ring A is pyrazolyl, pyridinyl, pyrazinyl, pyrimidinyl, or pyridazinyl;
each $R^1$ is independently halogen, —CN, —OH, —OR$^a$, $C_1$-$C_6$alkyl, $C_1$-$C_6$haloalkyl, —OC$_1$-$C_6$haloalkyl, $C_1$-$C_{10}$cycloalkyl, or heterocycloalkyl; wherein each of the $C_1$-$C_6$alkyl, $C_1$-$C_{10}$cycloalkyl, and heterocycloalkyl is optionally and independently substituted with one or more $R^{1a}$;
each $R^{1a}$ is independently —OH, —OR$^a$, $C_1$-$C_6$alkyl, $C_1$-$C_6$haloalkyl, $C_1$-$C_6$hydroxyalkyl, or $C_1$-$C_6$heteroalkyl;
n is 1, 2, or 3;
$R^7$ is hydrogen;
$R^{8c}$ is —OR$^a$; and
each $R^a$ is $C_1$-$C_6$alkyl. In some embodiments. Ring A is pyrimidinyl. In other embodiments, Ring A is 2-pyrimidinyl, 4-pyrimidinyl, 5-pyrimidinyl, or 6-pyrimidinyl. Instill further embodiments, Ring A is 2-pyrimidinyl. Further embodiments provide Ring A is 4-pyrimidinyl. In other embodiments, Ring A is 5-pyrimidinyl. In yet other embodiments, Ring A is 6-pyrimidinyl.

Further provided herein are compounds of Formula (III), or a pharmaceutically acceptable salt, solvate, or stereoisomer thereof, wherein:
Ring A is pyridinyl or pyrimidinyl;
each $R^1$ is independently fluoro, chloro, —CN, —OH, —OR$^a$, $C_1$-$C_6$alkyl, $C_1$-$C_6$haloalkyl, —OC$_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;
each $R^{1a}$ is independently —OH, —OR$^a$, $C_1$-$C_6$alkyl, $C_1$-$C_6$haloalkyl, $C_1$-$C_6$hydroxyalkyl, or $C_1$-$C_6$heteroalkyl;
n is 1, 2, or 3;
$R^7$ is hydrogen;
$R^{8c}$ is —OCH$_3$; and
each $R^a$ is $C_1$-$C_6$alkyl. In some embodiments, Ring A is pyridinyl. In other embodiments, Ring A is 2-pyridinyl, 3-pyridinyl, 4-pyridinyl, 5-pyridinyl, or 6-pyridinyl. In still further embodiments, Ring A is 2-pyridinyl. In some embodiments, Ring A is 3-pyridinyl. In some embodiments, Ring A is 4-pyridinyl. In some embodiments, Ring A is 5-pyridinyl. In some embodiments, Ring A is 6-pyridinyl. In some embodiments, Ring A is pyrimidinyl. In some embodiments, Ring A is 2-pyrimidinyl, 4-pyrimidinyl, 5-pyrimidinyl, or 6-pyrimidinyl. In some embodiments, Ring A is 2-pyrimidinyl. In some embodiments, Ring A is 4-pyrimindinyl. In some embodiments, Ring A is 5-pyrimindinyl. In some embodiments, Ring A is 6-pyrimindinyl.

Further provided herein are compounds of Formula (III), or a pharmaceutically acceptable salt, solvate, or stereoisomer thereof, wherein:
Ring A is pyridinyl or pyrimidinyl;
each $R^1$ is independently chloro, —CN, —OH, —OCH$_3$, —OCH$_2$CH$_3$, —CH$_3$, —CH$_2$CH$_3$, —CH(CH$_3$)$_2$, —CF$_3$, —OCHF$_2$, cyclopropyl, morpholinyl, piperidinyl, piperazinyl, azetidinyl, 1,1-dioxidothiomorpholinyl, or oxetanyl; wherein morpholinyl, piperidinyl, piperazinyl, azetidinyl, 1,1-dioxidothiomorpholinyl, and oxetanyl are each optionally and independently substituted with one or more $R^{1a}$;
each $R^{1a}$ is independently —OH, —OR$^a$, $C_1$-$C_6$alkyl, $C_1$-$C_6$haloalkyl, $C_1$-$C_6$hydroxyalkyl, or $C_1$-$C_6$heteroalkyl;
n is 1, 2, or 3;
$R^7$ is hydrogen;
$R^{8c}$ is —OCH$_3$; and
each $R^a$ is $C_1$-$C_6$alkyl.

Further provided herein are compounds of Formula (III), or a pharmaceutically acceptable salt, solvate, or stereoisomer thereof, wherein:
Ring A is heteroaryl;
each $R^1$ is independently halogen, —CN, —OR$^a$, —OC(=O)R$^a$, —OC(=O)OR$^b$, —OC(=O)NR$^c$R$^d$, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, —OC$_1$-$C_6$haloalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is optionally and independently substituted with one or more $R^{1a}$;
each $R^{1a}$ is independently deuterium, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;
n is 1, 2, or 3;
$R^7$ is hydrogen or $C_1$-$C_6$alkyl;
$R^{8c}$ is halogen or —OR$^a$;
each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_{10}$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$ alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CHs, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; or $R^c$ and $R^d$ are taken together with the atom to which they are attached to form a heterocycloalkyl optionally substituted with one or more oxo, deuterium, halogen, —CN, —OH, —OCH$_3$, —S(=O)CHs, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments, Ring A is pyrazolyl, pyridinyl, pyrazinyl, pyrimidinyl, or pyridazinyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl.

Further provided herein are compounds of Formula (III), or a pharmaceutically acceptable salt, solvate, or stereoisomer thereof, wherein:

Ring A is heteroaryl;

each $R^1$ is independently halogen, —OR$^3$, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$S(=O)$_2$R$^a$, —C(=O)R$^a$, —C(=O)NR$^c$R$^d$, $C_1$-$C_6$alkyl, $C_1$-$C_6$haloalkyl, —O$C_1$-$C_6$haloalkyl, $C_1$-$C_6$hydroxyalkyl, $C_1$-$C_6$aminoalkyl, $C_1$-$C_6$ heteroalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;

each $R^{1a}$ is independently deuterium, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_{10}$alkynyl, $C_3$-$C_{10}$cycloalkyl, heterocycloalkyl, $C_6$-$C_{10}$aryl, or heteroaryl;

n is 1, 2, or 3:

$R^7$ is hydrogen or $C_1$-$C_6$alkyl;

$R^{8c}$ is halogen or —OR$^a$;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_1$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl);

wherein each of the $C_1$-$C_6$alkyl, $C_2$-$C_6$alkenyl, $C_2$-$C_{10}$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments, Ring A is pyrazolyl, pyridinyl, pyrazinyl, pyrimidinyl, or pyridazinyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl Further provided herein are compounds of Formula (III), or a pharmaceutically acceptable salt, solvate, or stereoisomer thereof, wherein:

Ring A is heteroaryl;

each $R^1$ is independently halogen, —OR$^a$, —SR$^a$, —S(=O)R$^3$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$S(=O)$_2$R$^a$, —C(=O)R$^a$, —C(=O)NR$^c$R$^d$, $C_1$-$C_6$alkyl, $C_1$-$C_6$haloalkyl, —O$C_1$-$C_6$haloalkyl, $C_1$-$C_6$hydroxyalkyl, $C_1$-$C_6$aminoalkyl, $C_1$-$C_6$heteroalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;

each $R^{1a}$ is independently deuterium, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

n is 1, 2, or 3;

$R^7$ is hydrogen or $C_1$-$C_6$alkyl;

$R^{8c}$ is halogen or —$OR^a$;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_2$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_2$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments, Ring A is pyrazolyl, pyridinyl, pyrazinyl, pyrimidinyl, or pyridazinyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl.

Further provided herein are compounds of Formula (III), or a pharmaceutically acceptable salt, solvate, or stereoisomer thereof, wherein:

Ring A is phenyl, pyrazolyl, pyridinyl, pyrazinyl, pyrimidinyl, or pyridazinyl;

each $R^1$ is independently halogen, —S(=O)$_2(C_1$-$C_6$ alkyl), —S(=O)$_2N(C_1$-$C_6$ alkyl)$_2$, —$OC_1$-$C_6$ alkyl, —C(=O)N($C_1$-$C_6$ alkyl)$_2$, —C(=O)N(H)($C_1$-$C_6$ alkyl), —$OC_1$-$C_6$haloalkyl, $C_1$-$C_6$alkyl, —S($C_1$-$C_6$ alkyl), heterocycloalkyl, or —C(=O)(heterocycloalkyl);

n is 1, 2, or 3;

$R^7$ is hydrogen; and $R^{8c}$ is hydrogen, halogen, $CH_3$, or —$OCH_3$. In some embodiments, Ring A is phenyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl. In some embodiments, $R^{8c}$ is hydrogen. In some embodiments, $R^{8c}$ is halogen. In some embodiments, $R^{8c}$ is fluoro, chloro, bromo, or iodo. In some embodiments, $R^{8c}$ is fluoro. In some embodiments, $R^{8c}$ is $CH_3$. In some embodiments, $R^{8c}$ is or —$OCH_3$.

Further provided herein are compounds of Formula (III), or a pharmaceutically acceptable salt, solvate, or stereoisomer thereof, wherein:

Ring A is phenyl, pyrazolyl, pyridinyl, pyrazinyl, pyrimidinyl, or pyridazinyl;

each $R^1$ is independently halogen, —$CF_3$, —CN, —S(=O)$_2(CH_3)$, —S(=O)$_2(CH_2CH_3)$—S(=O)$_2N(CH_3)_2$, —$OCH_3$, —$CH_2CHF_2$, —C(=O)$N(CH_3)_2$, —C(=O)N(H)(CH$_3$), —$OC_1$$C_6$haloalkyl, —$CH_3$, —$CH_2CH_3$, iso-propyl, n-propyl, —$SCH_3$, azetidinyl, pyrrolidinyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;

n is 1, 2, or 3;

$R^7$ is hydrogen; and $R^{8c}$ is hydrogen, halogen, $CH_3$, or —$OCH_3$. In some embodiments, Ring A is phenyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl. In some embodiments, $R^{8c}$ is hydrogen. In some embodiments, $R^{8c}$ is halogen. In some embodiments, $R^{8c}$ is fluoro, chloro, bromo, or iodo. In some embodiments, $R^{8c}$ is fluoro. In some embodiments, $R^{8c}$ is $CH_3$. In some embodiments, $R^{8c}$ is or —$OCH_3$.

Further provided herein are compounds of Formula (III), or a pharmaceutically acceptable salt, solvate, or stereoisomer thereof, wherein:

Ring A is phenyl, pyrazolyl, pyridinyl, pyrazinyl, pyrimidinyl, or pyridazinyl;

each $R^1$ is independently halogen, —$CF_3$, —CN, —S(=O)$_2(CH_3)$, —S(=O)$_2(CH_2CH_3)$, —S(=O)$_2$(i-Pr), —S(=O)$_2$(cyclopropyl), —S(=O)$_2(C_1$$C_6$haloalkyl), —S(=O)$_2N(CH_3)_2$, —S(=O)$_2NH_2$, —S(=O)$_2N(CH_3)$(H), —$OCH_3$, —$OCH_3$, —$OCH_2CH_3$, —$CH_2CHF_2$, —C(=O)$N(CH_3)_2$, —C(=O)N(H)(CH$_3$), —$OC_1$-$C_6$haloalkyl, —$CH_3$, —$CH_2CH_3$, iso-propyl, n-propyl, —$SCH_3$, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;

n is 1, 2, or 3:

$R^7$ is hydrogen; and $R^{8c}$ is hydrogen, halogen, $CH_3$, or —$OCH_3$. In some embodiments, Ring A is phenyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl. In some embodiments, $R^{8c}$ is hydrogen. In some embodiments, $R^{8c}$ is halogen. In some embodiments, $R^{8c}$ is fluoro, chloro, bromo, or iodo. In some embodiments, $R^{8c}$ is fluoro. In some embodiments, $R^{8c}$ is CH. In some embodiments, $R^{8c}$ is or —OCH$_3$.

Further provided herein are compounds of Formula (III), or a pharmaceutically acceptable salt, solvate, or stereoisomer thereof, wherein:

Ring A is phenyl, pyrazolyl, pyridinyl, pyrazinyl, pyrimidinyl, or pyridazinyl;

each $R^1$ is independently halogen, —CF$_3$, —CN, —S(=O)$_2$(C$_1$-C$_6$alkyl), —S(=O)$_2$(C$_3$-C$_{10}$cycloalkyl), —S(=O)$_2$N(C$_1$-C$_6$alkyl)$_2$, —S(=O)?NH$_2$, —S(=O)$_2$N(C$_1$-C$_6$alkyl)(H), —OC$_1$-C$_6$alkyl, —CH$_2$CHF$_2$, —C(=O)N(C$_1$-C$_6$alkyl)$_2$, —C(=O)N(H)(C$_1$-C$_6$alkyl), —OC$_1$C$_6$haloalkyl, —C$_1$-C$_6$alkyl, —SC$_1$-C$_6$alkyl, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;

n is 1, 2, or 3:

$R^7$ is hydrogen; and $R^{8c}$ is hydrogen, halogen, CH$_3$, or —OCH$_3$. In some embodiments, Ring A is phenyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl. In some embodiments, $R^{8c}$ is hydrogen. In some embodiments, $R^{8c}$ is halogen. In some embodiments, $R^{8c}$ is fluoro, chloro, bromo, or iodo. In some embodiments, $R^{8c}$ is fluoro. In some embodiments, $R^{8c}$ is CH$_3$. In some embodiments, $R^{8c}$ is or —OCH$_3$.

Further provided herein are compounds of Formula (III), or a pharmaceutically acceptable salt, solvate, or stereoisomer thereof, wherein:

Ring A is phenyl, pyrazolyl, pyridinyl, pyrazinyl, pyrimidinyl, or pyridazinyl;

each $R^1$ is independently halogen, —CF$_3$, —CN, —S(=O)$_2$(C$_1$-C$_6$alkyl), —S(=O)$_2$(C$_3$-C$_{10}$cycloalkyl), —S(=O)$_2$N(C$_1$-C$_6$alkyl)$_2$, —S(=O)$_2$NH$_2$, —S(=O)$_2$N(C$_1$-C$_6$alkyl)(H), —OC$_1$-C$_6$alkyl, —CH$_2$CHF$_2$, —C(=O)N(C$_1$-C$_6$alkyl)$_2$, —C(=O)N(H)(C$_1$-C$_6$alkyl), —OC$_1$C$_6$haloalkyl, —C$_1$-C$_6$alkyl, —SC$_1$-C$_6$alkyl, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl, and wherein at least one of $R^1$ is —S(=O)$_2$(C$_1$-C$_6$alkyl), —S(=O)$_2$(C$_3$-C$_{10}$cycloalkyl), —S(=O)$_2$N(C$_1$-C$_6$alkyl)$_2$, —S(=O)$_2$NH$_2$, or —S(=O)$_2$N(C$_1$-C$_6$alkyl)(H);

n is 1, 2, or 3;

$R^7$ is hydrogen; and $R^{8c}$ is hydrogen, halogen, CH$_3$, or —OCH$_3$. In some embodiments, Ring A is phenyl. In some embodiments, Ring A is pyrazolyl. In some embodiments, Ring A is pyridinyl. In some embodiments, Ring A is pyrazinyl. In some embodiments, Ring A is pyrimidinyl. In some embodiments, Ring A is pyridazinyl. In some embodiments, $R^{8c}$ is hydrogen. In some embodiments, $R^{8c}$ is halogen. In some embodiments, $R^{8c}$ is fluoro, chloro, bromo, or iodo. In some embodiments, $R^{8c}$ is fluoro. In some embodiments, $R^{8c}$ is CH$_3$. In some embodiments, $R^{8c}$ is or —OCH$_3$.

Further provided herein are compounds of Formula (III), or a pharmaceutically acceptable salt, solvate, or stereoisomer thereof, wherein:

Ring A is heterocycloalkyl;

each $R^1$ is independently halogen, —CF$_3$, —CN, —S(=O)$_2$(C$_1$-C$_6$alkyl), —S(=O)$_2$(C$_3$-C$_{10}$cycloalkyl), —S(=O)$_2$N(C$_1$-C$_6$alkyl)$_2$, —S(=O)$_2$NH$_2$, —S(=O)$_2$N(C$_1$-C$_6$alkyl)(H), —OC$_1$-C$_6$alkyl, —CH$_2$CHF$_2$, —C(=O)N(C$_1$-C$_6$alkyl)$_2$, —C(=O)N(H)(C$_1$-C$_6$alkyl), —OC$_1$C$_6$haloalkyl, —C$_1$-C$_6$alkyl, —SC$_1$-C$_6$alkyl, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;

n is 1, 2, or 3:

$R^7$ is hydrogen; and $R^{8c}$ is hydrogen, halogen, CH$_3$, or —OCH$_3$. In some embodiments, Ring A is dihydropyridazinyl. In some embodiments, Ring A is 1,6-dihydropyridazin-3-yl. In some embodiments, $R^{8c}$ is hydrogen. In some embodiments, $R^{8c}$ is halogen. In some embodiments, $R^{8c}$ is fluoro, chloro, bromo, or iodo. In some embodiments, $R^{8c}$ is fluoro. In some embodiments, $R^c$ is CH$_3$. In some embodiments, $R^{8c}$ is or —OCH$_3$.

Further provided herein are compounds of Formula (III), or a pharmaceutically acceptable salt, solvate, or stereoisomer thereof, wherein:

Ring A is aryl;

each $R^1$ is independently halogen, —CN, —OR$^a$, —OC(=O)R$^a$, —OC(=O)OR$^b$, —OC(=O)NR$^c$R$^d$, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, —OC$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl; wherein each of the C$_1$-C$_6$alkyl, C$_2$-C$_6$alkenyl, C$_2$-C$_{10}$alkynyl, C$_1$-C$_{10}$cycloalkyl, heterocycloalkyl, C$_6$-C$_{10}$aryl, and heteroaryl is optionally and independently substituted with one or more $R^{1a}$;

each $R^{1a}$ is independently deuterium, —OH, —OR$^a$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

n is 1, 2, or 3:

$R^7$ is hydrogen or C$_1$-C$_6$alkyl;

$R^{8c}$ is hydrogen, C$_1$-C$_6$alkyl, halogen or —OR$^a$;

each $R^a$ is independently C$_1$-C$_6$alkyl, C$_1$-C$_6$haloalkyl, C$_1$-C$_6$deuteroalkyl, C$_1$-C$_6$ hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

Further provided herein are compounds of Formula (I) selected from (1R,2S)-5'-methoxy-2-{3-[(5-methoxypyrimidin-4-yl)amino]-1H-indazol-6-yl}spiro[cyclopropane-1,3'-indol]-2'(1'H)-one; (1R,2S)-5'-methoxy-2-{3-[(5-methylpyrimidin-4-yl)amino]-1H-indazol-6-yl}spiro[cyclopropane-1,3'-indol]-2'(1'H)-one; (1R,2S)-2-{3-[(5-chloropyrimidin-4-yl)amino]-1H-indazol-6-yl}-5'-methoxyspiro[cyclopropane-1,3'-indol]-2'(1'H)-one; (1R,2S)-5'-methoxy-2-{3-[(5-methoxypyrimidin-4-yl)amino]-1H-indazol-6-yl}spiro[cyclopropane-1,3'-indol]-2'(1'H)-one; (1R,2S)-2-{3-[(5-ethoxypyrimidin-4-yl)amino]-1H-indazol-6-yl}-5'-methoxyspiro[cyclopropane-1,3'-indol]-2'(1'H)-one; (1R,2S)-2-{3-[(5-cyclopropylpyrimidin-4-yl)amino]-1H-indazol-6-yl}-5'-methoxyspiro[cyclopropane-1,3'-indol]-2'(1'H)-one; (1R,2S)-2-{3-[(5-chloropyrimidin-4-yl)amino]-1H-indazol-6-yl}-5'-methoxyspiro[cyclopropane-1,3'-indol]-2'(1'H)-one; (1S,2R)-5'-methoxy-2-{3-[(5-methoxypyrimidin-4-yl)amino]-1H-indazol-6-yl}spiro[cyclopropane-1,3'-indol]-2'(1'H)-one; (1R,2S)-2-(3-{[5-chloro-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-{3-[(2-chloro-5-methoxypyrimidin-4-yl)amino]-1H-indazol-6-yl}-5'-methoxyspiro[cyclopropane-1,3'-indol]-2'(1'H)-one; (1R,2S)-5'-methoxy-2-(3-{[5-methoxy-6-(morpholin-4-yl)pyrimidin-4-yl]amino}-1H-indazol-6-yl)spiro[cyclopropane-1,3'-indol]-2'(1'H)-one; (1R,2S)-5'-methoxy-2-(3-{[5-methoxy-6-(piperidin-1-yl)pyrimidin-4-yl]amino}-1H-indazol-6-yl)spiro[cyclopropane-1,3'-indol]-2'(1'H)-one; (1R,2S)-5'-methoxy-2-{3-[(3-methoxypyrazin-2-yl)amino]-1H-indazol-6-yl}spiro[cyclopropane-1,3'-indol]-2'(1'H)-one; (1R,2S)-5'-methoxy-2-{3-[(6-methoxypyrimidin-4-yl)amino]-1H-indazol-6-yl}spiro[cyclopropane-1,3'-indol]-2'(1'H)-one; (1R,2S)-2-{3-[(6,7-dihydro-5H-cyclopenta[d]pyrimidin-4-yl)amino]-1H-indazol-6-yl}-5'-methoxyspiro[cyclopropane-1,3'-indol]-2'(1'H)-one; (1R,2S)-2-{3-[(2,3-dihydro-1-benzofuran-7-yl)amino]-1H-indazol-6-yl}-5'-methoxyspiro[cyclopropane-1,3'-indol]-2'(1'H)-one; (1R,2S)-5'-methoxy-2-{3-[(3-methoxypyridin-2-yl)amino]-1H-indazol-6-yl}spiro[cyclopropane-1,3'-indol]-2'(1'H)-one; (1R,2S)-5'-methoxy-2-{3-[(4-methoxypyridin-3-yl)amino]-1H-indazol-6-yl}spiro[cyclopropane-1,3'-indol]-2'(1'H)-one; (1R,2S)-5'-methoxy-2-{3-[(3-methoxypyridin-4-yl)amino]-1H-indazol-6-yl}spiro[cyclopropane-1,3'-indol]-2'(1'H)-one; (1R,2S)-2-(3-{[5-chloro-6-(4-methylpiperazin-1-yl)pyrimidin-4-yl]amino}-1H-indazol-6-yl)-5'-methoxyspiro[cyclopropane-1,3'-indol]-2'(1'H)-one; (1R,2S)-5'-methoxy-2-{3-[(1,3,5-trimethyl-1H-pyrazol-4-yl)amino]-1H-indazol-6-yl}spiro[cyclopropane-1,3'-indol]-2'(1'H)-one; (1R,2S)-5'-methoxy-2-(3-{[5-(trifluoromethyl)pyrimidin-4-yl]amino}-1H-indazol-6-yl)spiro[cyclopropane-1,3'-indol]-2'(1'H)-one; (1R,2S)-2-{3-[(5-chloro-2-methoxypyrimidin-4-yl)amino]-1H-indazol-6-yl}-5'-methoxyspiro[cyclopropane-1,3'-indol]-2'(1'H)-one; (1R,2S)-5'-methoxy-2-{3-[(2-methoxypyridin-3-yl)amino]-1H-indazol-6-yl}spiro[cyclopropane-1,3'-indol]-2'(1'H)-one; (1R,2S)-2-{3-[(1-benzofuran-7-yl)amino]-1H-indazol-6-yl}-5'-methoxyspiro[cyclopropane-1,3'-indol]-2'(1'H)-one; (1R,2S)-5'-methoxy-2-{3-[(3-methoxy-1-methyl-1H-pyrazol-4-yl)amino]-1H-indazol-6-yl}spiro[cyclopropane-1,3'-indol]-2'(1'H)-one; (1R,2S)-2-{3-[(3-hydroxy-2,3-dihydro-1-benzofuran-7-yl)amino]-1H-indazol-6-yl}-5'-methoxyspiro[cyclopropane-1,3'-indol]-2'(1'H)-one; (1R,2S)-2-(3-{[(3S)-3-hydroxy-2,3-dihydro-1-benzofuran-7-yl]amino}-1H-indazol-6-yl)-5'-methoxyspiro[cyclopropane-1,3'-indol]-2'(1'H)-one; (1R,2S)-2-(3-{[(3R)-3-hydroxy-2,3-dihydro-1-benzofuran-7-yl]amino}-1H-indazol-6-yl)-5'-methoxyspiro[cyclopropane-1,3'-indol]-2'(1'H)-one; (1R,2S)-2-{3-[(2,3-dihydropyrazolo[5,1-b][1,3]oxazol-7-yl)amino]-1H-indazol-6-yl}-5'-methoxyspiro[cyclopropane-1,3'-indol]-2'(1'H)-one; (1R,2S)-5'-methoxy-2-{3-[(3-oxo-2,3-dihydro-1-benzofuran-7-yl)amino]-1H-indazol-6-yl}spiro[cyclopropane-1,3'-indol]-2'(1'H)-one; (1R,2S)-2-{3-[(2,3-dihydrofuro[2,3-c]pyridin-7-yl)amino]-1H-indazol-6-yl}-5'-methoxyspiro[cyclopropane-1,3'-indol]-2'(1'H)-one; (1R,2S)-2-(3-{[(3S)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one; (1R,2S)-2-(3-{[(3R)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one; (1R,2S)-5'-methoxy-2-(3-{[6-(3-methoxyazetidin-1-yl)pyrimidin-4-yl]amino}-1H-indazol-6-yl)spiro[cyclopropane-1,3'-indol]-2'(1'H)-one; (1R,2S)-2-(3-{[6-(3-hydroxyazetidin-1-yl)pyrimidin-4-yl]amino}-1H-indazol-6-yl)-5'-methoxyspiro[cyclopropane-1,3'-indol]-2'(1'H)-one; (1R,2S)-2-(3-((6-(3-oxa-8-azabicyclo[3.2.1]octan-8-yl)-5-methoxypyrimidin-4-yl)amino)-1H-indazol-6-yl)-5'-methoxyspiro[cyclopropane-1,3'-indolin]-2'-one; (1R,2S)-2-(3-{[6-(2-hydroxyethoxy)pyrimidin-4-yl]amino}-1H-indazol-6-yl)-5'-methoxyspiro[cyclopropane-1,3'-indol]-2'(1'H)-one; (1R,2S)-2-(3-((6-(1,1-dioxidothiomorpholino)pyrimidin-4-yl)amino)-1H-indazol-6-yl)-5'-methoxyspiro[cyclopropane-1,3'-indolin]-2'-one); (1R,2S)-5'-methoxy-2-(3-{[6-(1,4-oxazepan-4-yl)pyrimidin-4-yl]amino}-1H-indazol-6-yl)spiro[cyclopropane-1,3'-indol]-2'(1'H)-one; (1R,2S)-5'-methoxy-2-(3-{[5-methoxy-2-methyl-6-(morpholin-4-yl)pyrimidin-4-yl]amino}-1H-indazol-6-yl)spiro[cyclopropane-1,3'-indol]-2'(1'H)-one; (1R,2S)-2-(3-{[6-(azetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-(3-{[6-(3-hydroxyazetidin- 1-yl)-5-methoxypyrimidin-4-yl]amino}-1H-indazol-6-yl)-5'-methoxyspiro[cyclopropane-1,3'-indol]-2'(1'H)-one; (1R,2S)-5'-methoxy-2-(3-{[5-methoxy-6-(1,4-oxazepan-4-yl)pyrimidin-4-yl]amino}-1H-indazol-6-yl)spiro[cyclopropane-1,3'-indol]-2'(1'H)-one; (1R,2S)-2-(3-{[6-(azetidin-1-yl)pyrimidin-4-yl]amino}-1H-indazol-6-yl)-5'-methoxyspiro[cyclopropane-1,3'-indol]-2'(1'H)-one; (1R,2S)-2-(3-{[5-chloro-6-(3-hydroxyazetidine-1-yl)pyrimidin-4-yl]amino}-1H-indazol-6-yl)-5'-methoxyspiro[cyclopropane-1,3'-indol]-2'(1'H)-one; (1R,2S)-2-(3-{[5-chloro-6-(3-methoxyazetidin-1-yl)pyrimidin-4-yl]amino}-1H-indazol-6-yl)-5'-methoxyspiro[cyclopropane-1,3'-indol]-2'(1'H)-one; (1R,2S)-2-(3-{[2-chloro-5-methoxy-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-{[4-chloro-5-methoxy-6-(morpholin-4-yl)pyrimidin-2-yl]amino}-1H-indazol-6-yl)-5'-methoxyspiro[cyclopropane-1,3'-indol]-2'(1'H)-one; (1R,2S)-2-(3-{[1-(2-hydroxyethyl)-3-methoxy-1H-pyrazol-4-yl]amino}-1H-indazol-6-yl)-5'-methoxyspiro[cyclopropane-1,3'-indol]-2'(1'H)-one; (1R,2S)-2-(3-{[2-cyclopropyl-5-methoxy-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-[3-({6-[(2R,6S)-2,6-dimethylmorpholin-4-yl]-5-methoxypyrimidin-4-yl}amino)-1H-indazol-6-yl]-5'-methoxyspiro[cyclopropane-1,3'-indol]-2'(1'H)-one; (1R,2S)-2-(3-((5-chloro-6-(1,1-dioxidothiomorpholino)pyrimidin-4-yl)amino)-1H-indazol-6-yl)-5'-methoxyspiro[cyclopropane-1,3'-indolin]-2'-one; (1R,2S)-2-(3-((6-(1,1-dioxidothiomorpholino)-5-methoxypyrimidin-4-yl)amino)-1H-indazol-6-yl)-5'-methoxyspiro[cyclopropane-1,3'-indolin]-2'-one; (R,2S)-2-(3-{[5-(2-hydroxyethyl)-3-methoxypyrazin-2-yl]amino}-1H-indazol-6-yl)-5'-methoxyspiro[cyclopropane-1,3'-indol]-2'(1'H)-one; (1R,2S)-2-(3-{[6-(2-hydroxyethyl)-3-methoxypyrazin-2-yl]amino}-1H-indazol-6-yl)-5'-methoxyspiro[cyclopropane-1,3'-indol]-2'(1'H)-one; (1R,2S)-2-(3-((6-(1,1-dioxidothiomorpholino)-5-methoxy-2-methylpyrimidin-4-yl)amino)-1H-indazol-6-yl)-5'-methoxyspiro[cyclopropane-1,3'-indolin]-2'-one; (1R,2S)-2-(3-((5-chloro-6-(1,1-dioxidothiomorpholino)-2-methylpyrimidin-4-yl)amino)-1H-indazol-6-yl)-5'-methoxyspiro[cyclopropane-1,3'-indolin]-2'-one; (1R,2S)-2-(3-((2-cyclopropyl-6-(1,1-dioxidothiomorpholino)pyrimidin-4-yl)amino)-1H-indazol-6-yl)-5'-methoxyspiro[cyclopropane-1,3'-indolin]-2'-one; (1R,2S)-2-(3-((6-(1,1-dioxidothiomorpholino)-2-methylpyrimidin-4-yl)amino)-1H-indazol-6-yl)-5'-methoxyspiro[cyclopropane-1,3'-indolin]-2'-one; 5-methoxy-4-({6-[(1R,2S)-5'-methoxy-2'-oxo-1',2'-dihydrospiro[cyclopropane-1,3'-indol]-2-yl]-1H-indazol-3-yl}amino)-6-(morpholin-4-yl)pyrimidine-2-carbonitrile; 4-(1,1-dioxidothiomorpholino)-5-methoxy-6-((6-(((1R,2S)-5'-methoxy-2'-oxospiro[cyclopropane-1,3'-indolin]-2-yl)-1H-indazol-3-yl)amino)pyrimidine-2-carbonitrile; (1R,2S)-2-{3-[(1,3-dimethyl-1H-pyrazol-4-yl)amino]-1H-indazol-6-yl}-5'-methoxyspiro[cyclopropane-1,3'-indol]-2'(1'H)-one; (1R,2S)-5'-methoxy-2-(3-{[1-methyl-3-(trifluoromethyl)-1H-pyrazol-4-yl]amino}-1H-indazol-6-yl)spiro[cyclopropane-1,3'-indol]-2'(1'H)-one; (1R,2S)-5'-methoxy-2-{3-[(1-methyl-1H-pyrazol-4-yl)amino]-1H-indazol-6-yl}spiro[cyclopropane-1,3'-indol]-2'(1'H)-one; 4-({6-[(1R,2S)-5'-methoxy-2'-oxo-1',2'-dihydrospiro[cyclopropane-1,3'-indol]-2-yl]-1H-indazol-3-yl}amino)-1-methyl-1H-pyrazole-3-carbonitrile; (1R,2S)-2-[3-({6-[(2R,6S)-2,6-dimethylmorpholin-4-yl]-5-methoxy-2-methylpyrimidin-4-yl}amino)-1H-indazol-6-yl]-5'-methoxyspiro[cyclopropane-1,3'-indol]-2'(1'H)-one; (1R,2S)-2-(3-{[2-(2-hydroxyethyl)-5-methoxy-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-((2-cyclopropyl-6-(1,1-dioxidothiomorpholino)-5-methoxypyrimidin-4-yl)amino)-1H-indazol-6-yl)-5'-methoxyspiro[cyclopropane-1,3'-indolin]-2'-one; (1R,2S)-2-(3-((5-chloro-2-cyclopropyl-6-(1,1-dioxidothiomorpholino)pyrimidin-4-yl)amino)-1H-indazol-6-yl)-5'-methoxyspiro[cyclopropane-1,3'-indolin]-2'-one; (1R,2S)-5'-methoxy-2-{3-[(3-methoxy-6-methylpyrazin-2-yl)amino]-1H-indazol-6-yl}spiro[cyclopropane-1,3'-indol]-2'(1'H)-one; (1R,2S)-2-(3-{[5-chloro-6-(3-hydroxyazetidin-1-yl)-2-methylpyrimidin-4-yl]amino}-1H-indazol-6-yl)-5'-methoxyspiro[cyclopropane-1,3'-indol]-2'(1'H)-one; (1R,2S)-2-(3-{[6-(3-hydroxyazetidin-1-yl)-5-methoxy-2-methylpyrimidin-4-yl]amino}-1H-indazol-6-yl)-5'-methoxyspiro[cyclopropane-1,3'-indol]-2'(1'H)-one; (1R,2S)-2-{3-[(1,3-dimethyl-1H-pyrazol-5-yl)amino]-1H-indazol-6-yl}-5'-methoxyspiro[cyclopropane-1,3'-indol]-2'(1'H)-one; (1R,2S)-5'-methoxy-2-{3-[(4-methoxy-1-methyl-1H-pyrazol-5-yl)amino]-1H-indazol-6-yl}spiro[cyclopropane-1,3'-indol]-2'(1'H)-one; (1R,2S)-2-(3-{[5-chloro-2-cyclopropyl-6-(3-hydroxyazetidin-1-yl)pyrimidin-4-yl]amino}-1H-indazol-6-yl)-5'-methoxyspiro[cyclopropane-1,3'-indol]-2'(1'H)-one; (1R,2S)-2-[3-({2-cyclopropyl-6-[(2R,6S)-2,6-dimethylmorpholin-4-yl]-5-methoxypyrimidin-4-yl}amino)-1H-indazol-6-yl]-5'-methoxyspiro[cyclopropane-1,3'-indol]-2'(1'H)-one; (1R,2S)-2-(3-((5-chloro-6-(1,1-dioxidothiomorpholino)-2-isopropylpyrimidin-4-yl)amino)-1H-indazol-6-yl)-5'-methoxyspiro[cyclopropane-1,3'-indolin]-2'-one; (1R,2S)-5'-methoxy-2-{3-[(4-methoxy-1-methyl-1H-pyrazol-3-yl)amino]-1H-indazol-6-yl}spiro[cyclopropane-1,3'-indol]-2'(1'H)-one; (1R,2S)-2-{3-[(6-cyclopropyl-3-methoxypyrazin-2-yl)amino]-1H-indazol-6-yl}-5'-methoxyspiro[cyclopropane-1,3'-indol]-2'(1'H)-one; (1R,2S)-2-(3-{[2-cyclopropyl-6-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-{3-[(3,6-dimethylpyrazin-2-yl)amino]-1H-indazol-6-yl}-5'-methoxyspiro[cyclopropane-1,3'-indol]-2'(1'H)-one; (1R,2S)-5'-methoxy-2-(3-{[3-methoxy-6-(propan-2-yl)pyrazin-2-yl]amino}-1H-indazol-6-yl)spiro[cyclopropane-1,3'-indol]-2'(1'H)-one; (1R,2S)-2-(3-((6-(1,1-dioxidothiomorpholino)-2-isopropyl-5-methoxypyrimidin-4-yl)amino)-1H-indazol-6-yl)-5'-methoxyspiro[cyclopropane-1,3'-indolin]-2'-one; (1R,2S)-5'-methoxy-2-(3-{[5-methoxy-6-(morpholin-4-yl)-2-(propan-2-yl)pyrimidin-4-yl]amino}-1H-indazol-6-yl)spiro[cyclopropane-1,3'-indol]-2'(1'H)-one; (1R,2S)-5'-methoxy-2-{3-[(5-methoxy-2-methylpyridin-4-yl)amino]-1H-indazol-6-yl}spiro[cyclopropane-1,3'-indol]-2'(1'H)-one; (1R,2S)-5'-methoxy-2-{3-[(5-methoxy-2-methylpyrimidin-4-yl)amino]-1H-indazol-6-yl}spiro[cyclopropane-1,3'-indol]-2'(1'H)-one; (1R,2S)-5'-methoxy-2-{3-[(3-methoxy-6-methylpyridin-2-yl)amino]-1H-indazol-6-yl}spiro[cyclopropane-1,3'-indol]-2'(1'H)-one; (1R,2S)-5'-methoxy-2-{3-[(2-methoxy-5-methylpyridin-3-yl)amino]-1H-indazol-6-yl}spiro[cyclopropane-1,3'-indol]-2'(1'H)-one; (1R,2S)-5'-methoxy-2-{3-[(4-methoxypyridazin-3-yl)amino]-1H-indazol-6-yl}spiro[cyclopropane-1,3'-indol]-2'(1'H)-one; (1R,2S)-2-{3-[(3-cyclopropyl-1-methyl-1H-pyrazol-5-yl)amino]-1H-indazol-6-yl}-5'-methoxyspiro[cyclopropane-1,3'-indol]-2'(1'H)-one; (1R,2S)-2-{3-[(3-cyclopropyl-1-ethyl-1H-pyrazol-5-yl)amino]-1H-indazol-6-yl}-5'-methoxyspiro[cyclopropane-1,3'-indol]-2'(1'H)-one; (1R,2S)-2-(3-{[2-(2-hydroxy-2-methylpropyl)-5-methoxy-6-(morpholin-4-yl)pyrimidin-4-yl]amino}-1H-indazol-6-yl)-5'-methoxyspiro

[cyclopropane-1,3'-indol]-2'(1'H)-one; (1R,2S)-5'-methoxy-2-(3-{[3-methoxy-5-(morpholin-4-yl)pyrazin-2-yl]amino}-1H-indazol-6-yl)spiro[cyclopropane-1,3'-indol]-2'(1'H)-one; (1R,2S)-5'-methoxy-2-(3-{[3-methoxy-2-(morpholin-4-yl)pyridin-4-yl]amino}-1H-indazol-6-yl)spiro[cyclopropane-1,3'-indol]-2'(1'H)-one; (1R,2S)-2-{3-[(5-chloro-2-methylpyridin-4-yl)amino]-1H-indazol-6-yl}-5'-methoxyspiro[cyclopropane-1,3'-indol]-2'(1'H)-one; (1R,2S)-5'-methoxy-2-(3-{[5-methoxy-2-(morpholin-4-yl)pyrimidin-4-yl]amino}-1H-indazol-6-yl)spiro[cyclopropane-1,3'-indol]-2'(1'H)-one; (1R,2S)-2-{3-[(5-chloro-2-methylpyrimidin-4-yl)amino]-1H-indazol-6-yl}-5'-methoxyspiro[cyclopropane-1,3'-indol]-2'(1'H)-one; (1R,2S)-5'-methoxy-2-(3-{[3-methoxy-6-(morpholin-4-yl)pyrazin-2-yl]amino}-1H-indazol-6-yl)spiro[cyclopropane-1,3'-indol]-2'(1'H)-one; (1R,2S)-5'-methoxy-2-(3-{[3-methoxy-6-(oxetan-3-yl)pyrazin-2-yl]amino}-1H-indazol-6-yl)spiro[cyclopropane-1,3'-indol]-2'(1'H)-one; (1R,2S)-5'-methoxy-2-(3-{[3-methoxy-6-(propan-2-yl)pyridazin-4-yl]amino}-1H-indazol-6-yl)spiro[cyclopropane-1,3'-indol]-2'(1'H)-one; (1R,2S)-5'-methoxy-2-(3-{[6-(morpholin-4-yl)-2-(propan-2-yl)pyrimidin-4-yl]amino}-1H-indazol-6-yl)spiro[cyclopropane-1,3'-indol]-2'(1'H)-one; (1R,2S)-2-(3-{[5-chloro-2-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-{[5-(3-hydroxyazetidin-1-yl)-3-methoxypyridin-2-yl]amino}-1H-indazol-6-yl)-5'-methoxyspiro[cyclopropane-1,3'-indol]-2'(1'H)-one; (1R,2S)-5'-methoxy-2-(3-{[3-methyl-6-(propan-2-yl)pyrazin-2-yl]amino}-1H-indazol-6-yl)spiro[cyclopropane-1,3'-indol]-2'(1'H)-one; (1R,2S)-5'-methoxy-2-(3-{[6-(propan-2-yl)pyrazin-2-yl]amino}-1H-indazol-6-yl)spiro[cyclopropane-1,3'-indol]-2'(1'H)-one; (1R,2S)-2-(3-{[5-chloro-6-(3-hydroxyazetidin-1-yl)pyrimidin-4-yl]amino}-1H-indazol-6-yl)-5'-methoxy-1'-methylspiro[cyclopropane-1,3'-indol]-2'(1'H)-one; (1R,2S)-2-(3-{[5-chloro-6-(3-hydroxyazetidin-1-yl)pyrimidin-4-yl]amino}-1H-indazol-6-yl)-1'-ethyl-5'-methoxyspiro[cyclopropane-1,3'-indol]-2'(1'H)-one; (1R,2S)-2-(3-{[5-(difluoromethoxy)-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-{[6-(azetidin-3-yl)-3-methoxypyrazin-2-yl]amino}-1H-indazol-6-yl)-5'-methoxyspiro[cyclopropane-1,3'-indol]-2'(1'H)-one; and (1R,2S)-2-(3-{[6-(3-hydroxyazetidin-1-yl)-2-(propan-2-yl)pyrimidin-4-yl]amino}-1H-indazol-6-yl)-5'-methoxyspiro[cyclopropane-1,3'-indol]-2'(1'H)-one, or a pharmaceutically acceptable salt, solvate, or stereoisomer thereof.

Further provided herein are compounds of Formula (I) selected from (1R,2S)-2-(3-{[1-(2,2-difluoroethyl)-3-methyl-1H-pyrazol-5-yl]amino}-1H-indazol-6-yl)-5'-methoxyspiro[cyclopropane-1,3'-indol]-2'(1'H)-one; (1R,2S)-5'-methoxy-2-(3-{[5-methoxy-6-(morpholin-4-yl)pyrimidin-4-yl]amino}-1H-indazol-6-yl)-1'-methylspiro[cyclopropane-1,3'-indol]-2'(1'H)-one; (1R,2S)-2-(3-{[2-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-5'-methoxy-2-(3-{[6-(oxetan-3-yl)pyrazin-2-yl]amino}-1H-indazol-6-yl)spiro[cyclopropane-1,3'-indol]-2'(1'H)-one; (1R,2S)-2-(3-{[5-chloro-2-(propan-2-yl)pyrimidin-4-yl]amino}-1H-indazol-6-yl)-5'-methoxyspiro[cyclopropane-1,3'-indol]-2'(1'H)-one; (1R,2S)-2-(3-{[5-chloro-2-(oxetan-3-yl)pyrimidin-4-yl]amino}-1H-indazol-6-yl)-5'-methoxyspiro[cyclopropane-1,3'-indol]-2'(1'H)-one; (1R,2S)-5'-methoxy-2-(3-{[5-methoxy-2-(oxetan-3-yl)pyrimidin-4-yl]amino}-1H-indazol-6-yl)spiro[cyclopropane-1,3'-indol]-2'(1'H)-one; (1R,2S)-2-(3-{[5-chloro-2-(3-hydroxyazetidin-1-yl)pyrimidin-4-yl]amino}-1H-indazol-6-yl)-5'-methoxyspiro[cyclopropane-1,3'-indol]-2'(1'H)-one; (1R,2S)-2-(3-{[5-(difluoromethoxy)-2-methylpyrimidin-4-yl]amino}-1H-indazol-6-yl)-5'-methoxyspiro[cyclopropane-1,3'-indol]-2'(1'H)-one; (1R,2S)-2-{3-[(5-methoxy-2-methylpyrimidin-4-yl)amino]-1H-indazol-6-yl}-1'-methylspiro[cyclopropane-1,3'-indol]-2'(1'H)-one; (1R,2R)-2-{7-fluoro-3-[(5-methoxy-2-methylpyrimidin-4-yl)amino]-1H-indazol-6-yl}-5'-methoxyspiro[cyclopropane-1,3'-indol]-2'(1'H)-one; (1R,2S)-2-{3-[(5-methoxy-2-methylpyrimidin-4-yl)amino]-1H-indazol-6-yl}spiro[cyclopropane-1,3'-indol]-2'(1'H)-one; (1R,2S)-5'-methoxy-2-(3-{[5-methoxy-2-(propan-2-yl)pyrimidin-4-yl]amino}-1H-indazol-6-yl)spiro[cyclopropane-1,3'-indol]-2'(1'H)-one; (1R,2S)-2-{3-[(5-methoxy-2-methylpyrimidin-4-yl)amino]-1H-indazol-6-yl}-5'-methylspiro[cyclopropane-1,3'-indol]-2'(1'H)-one; (1S,2S)-2-{3-[(5-methoxy-2-methylpyrimidin-4-yl)amino]-1H-indazol-6-yl}-5'-methylspiro[cyclopropane-1,3'-indol]-2'(1'H)-one; (1R,2S)-2-(3-{[5-(difluoromethoxy)-2-(propan-2-yl)pyrimidin-4-yl]amino}-1H-indazol-6-yl)-5'-methoxyspiro[cyclopropane-1,3'-indol]-2'(1'H)-one; (1R,2S)-4'-fluoro-2-{3-[(5-methoxy-2-methylpyrimidin-4-yl)amino]-1H-indazol-6-yl}spiro[cyclopropane-1,3'-indol]-2'(1'H)-one; (1S,2S)-4'-fluoro-2-{3-[(5-methoxy-2-methylpyrimidin-4-yl)amino]-1H-indazol-6-yl}spiro[cyclopropane-1,3'-indol]-2'(1'H)-one; (1R,2S)-6'-fluoro-2-{3-[(5-methoxy-2-methylpyrimidin-4-yl)amino]-1H-indazol-6-yl}spiro[cyclopropane-1,3'-indol]-2'(1'H)-one; (1R,2S)-2-(3-{[5-chloro-6-(2-oxa-6-azaspiro[3.3]heptan-6-yl)pyrimidin-4-yl]amino}-1H-indazol-6-yl)-5'-methoxyspiro[cyclopropane-1,3'-indol]-2'(1'H)-one; (1R,2S)-5'-fluoro-2-{3-[(5-methoxy-2-methylpyrimidin-4-yl)amino]-1H-indazol-6-yl}spiro[cyclopropane-1,3'-indol]-2'(1'H)-one; (1R,2S)-2-{3-[(5-ethoxy-2-methylpyrimidin-4-yl)amino]-1H-indazol-6-yl}-5'-methoxyspiro[cyclopropane-1,3'-indol]-2'(1'H)-one; (1R,2S)-2-(3-{[5-(difluoromethoxy)-2-methylpyrimidin-4-yl]amino}-1H-indazol-6-yl)-5'-fluorospiro[cyclopropane-1,3'-indol]-2'(1'H)-one; (1R,2S)-5'-methoxy-2-[3-({2-methyl-5-[(propan-2-yl)oxy]pyrimidin-4-yl}amino)-1H-indazol-6-yl]spiro[cyclopropane-1,3'-indol]-2'(1'H)-one; (1R,2S)-2-{3-[(5-methoxy-2-methylpyrimidin-4-yl)amino]-1H-indazol-6-yl}-5'-(trifluoromethyl)spiro[cyclopropane-1,3'-indol]-2'(1'H)-one; (1R,2S)-2-{3-[(5-methoxy-2-methylpyrimidin-4-yl)amino]-1H-indazol-6-yl}-5'-(trifluoromethoxy)spiro[cyclopropane-1,3'-indol]-2'(1'H)-one; (1S,2S)-2-{3-[(5-methoxy-2-methylpyrimidin-4-yl)amino]-1H-indazol-6-yl}-5'-(trifluoromethoxy)spiro[cyclopropane-1,3'-indol]-2'(1'H)-one; (1R,2S)-2-{3-[(5-cyclopropyl-2-methylpyrimidin-4-yl)amino]-1H-indazol-6-yl}-5'-methoxyspiro[cyclopropane-1,3'-indol]-2'(1'H)-one; (1R,2S)-2-(3-{[5-(difluoromethoxy)-2-(oxetan-3-yl)pyrimidin-4-yl]amino}-1H-indazol-6-yl)-5'-methoxyspiro[cyclopropane-1,3'-indol]-2'(1'H)-one; (1R,2R)-5'-fluoro-2-{7-fluoro-3-[(5-methoxy-2-methylpyrimidin-4-yl)amino]-1H-indazol-6-yl}spiro[cyclopropane-1,3'-indol]-2'(1'H)-one; and (1R,2R)-2-(3-{[5-(difluoromethoxy)-2-methylpyrimidin-4-yl]amino}-7-fluoro-1H-indazol-6-yl)-5'-fluorospiro[cyclopropane-1,3'-indol]-2'(1'H)-one, or a pharmaceutically acceptable salt, solvate, or stereoisomer thereof.

Further provided herein are compounds of Formula (I) selected from (R,2R)-2-{5-fluoro-3-[(5-methoxy-2-methylpyrimidin-4-yl)amino]-1H-indazol-6-yl}-5'-methoxyspiro[cyclopropane-1,3'-indol]-2'(1'H)-one; (1R,2S)-5'-methoxy-2-{3-[(3-methoxy-6-methylpyridazin-4-yl)amino]-1H- indazol-6-yl}spiro[cyclopropane-1,3'-indol]-2'(1'H)-one; (1R,2S)-2-(3-{[5-(cyclopropylmethoxy)-2-methylpyrimidin-4-yl]amino}-1H-indazol-6-yl)-5'-methoxyspiro[cyclopropane-1,3'-indol]-2'(1'H)-one; (1R,2S)-2-(3-{[5-(2,2-difluoroethoxy)-2-methylpyrimidin-4-yl]amino}-1H-indazol-6-yl)-5'-methoxyspiro[cyclopropane-1,3'-indol]-2'(1'H)-one; (1R,2S)-5'-methoxy-2-[3-(2-methoxy-5-methylanilino)-1H-indazol-6-yl]spiro[cyclopropane-1,3'-indol]-2'(1'H)-one; (1R,2S)-5'-methoxy-2-(3-{[2-methyl-5-(2,2,2-trifluoroethoxy)pyrimidin-4-yl]amino}-1H-indazol-6-yl)spiro[cyclopropane-1,3'-indol]-2'(1'H)-one; (1R,2S)-5'-methoxy-2-{3-[(2-methoxy-6-methylpyridin-3-yl)amino]-1H-indazol-6-yl}spiro[cyclopropane-1,3'-indol]-2'(1'H)-one; (1R,2S)-5'-methoxy-2-(3-{[2-methyl-6-(propan-2-yl)pyrimidin-4-yl]amino}-1H-indazol-6-yl)spiro[cyclopropane-1,3'-indol]-2'(1'H)-one; (1R,2S)-2-{3-[(5-ethyl-2-methylpyrimidin-4-yl)amino]-1H-indazol-6-yl}-5'-methoxyspiro[cyclopropane-1,3'-indol]-2'(1'H)-one; (1R,2S)-5'-methoxy-2-{3-[(2-methyl-6,7-dihydrofuro[3,2-d]pyrimidin-4-yl)amino]-1H-indazol-6-yl}spiro[cyclopropane-1,3'-indol]-2'(1'H)-one; (1R,2S)-5'-methoxy-2-(3-{[5-methoxy-2-(oxan-4-yl)pyrimidin-4-yl]amino}-1H-indazol-6-yl)spiro[cyclopropane-1,3'-indol]-2'(1'H)-one; (1R,2S)-5'-methoxy-2-(3-{[5-methoxy-2-(methylsulfanyl)pyrimidin-4-yl]amino}-1H-indazol-6-yl)spiro[cyclopropane-1,3'-indol]-2'(1'H)-one; (1R,2S)-2-{3-[(2,5-dimethoxypyrimidin-4-yl)amino]-1H-indazol-6-yl}-5'-methoxyspiro[cyclopropane-1,3'-indol]-2'(1'H)-one; (1R,2S)-2-(3-{[2-(azetidin-1-yl)-5-methoxypyrimidin-4-yl]amino}-1H-indazol-6-yl)-5'-methoxyspiro[cyclopropane-1,3'-indol]-2'(1'H)-one; (1R,2S)-5'-methoxy-2-(3-{[3-methoxy-5-(trifluoromethyl)pyridin-2-yl]amino}-1H-indazol-6-yl)spiro[cyclopropane-1,3'-indol]-2'(1'H)-one; (1R,2S)-5'-methoxy-2-{3-[(2-methyl-6,7-dihydro-5H-cyclopenta[d]pyrimidin-4-yl)amino]-1H-indazol-6-yl}spiro[cyclopropane-1,3'-indol]-2'(1'H)-one; (1R,2S)-2-{3-[(2-ethyl-5-methoxypyrimidin-4-yl)amino]-1H-indazol-6-yl}-5'-methoxyspiro[cyclopropane-1,3'-indol]-2'(1'H)-one; (1R,2S)-5'-methoxy-2-{3-[(7-methoxyquinolin-6-yl)amino]-1H-indazol-6-yl}spiro[cyclopropane-1,3'-indol]-2'(1'H)-one; (1R,2S)-5'-methoxy-2-(3-{[2-methyl-5-(methylsulfanyl)pyrimidin-4-yl]amino}-1H-indazol-6-yl)spiro[cyclopropane-1,3'-indol]-2'(1'H)-one; (1R,2S)-5'-methoxy-2-{3-[(3-methoxyquinolin-2-yl)amino]-1H-indazol-6-yl}spiro[cyclopropane-1,3'-indol]-2'(1'H)-one; (1R,2S)-2-{3-[(2,5-dimethoxypyridin-3-yl)amino]-1H-indazol-6-yl}-5'-methoxyspiro[cyclopropane-1,3'-indol]-2'(1'H)-one; (1R,2S)-2-{3-[(2-chlorofuro[3,2-d]pyrimidin-4-yl]amino}-1H-indazol-6-yl)-5'-methoxyspiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-5'-methoxy-2-(3-{[5-methoxy-2-(pyrrolidin-1-yl)pyrimidin-4-yl]amino}-1H-indazol-6-yl)spiro[cyclopropane-1,3'-indol]-2'(1'H)-one; (1R,2S)-2-(3-{[6-(methanesulfonyl)-2-methoxypyridin-3-yl]amino}-1H-indazol-6-yl)-5'-methoxyspiro[cyclopropane-1,3'-indol]-2'(1'H)-one; (1R,2S)-2-[3-({2-[(3R)-3-fluoropyrrolidin-1-yl]-5-methoxypyrimidin-4-yl}amino)-1H-indazol-6-yl]-5'-methoxyspiro[cyclopropane-1,3'-indol]-2'(1'H)-one; (1R,2S)-2-(3-{[2-(3,3-difluoropyrrolidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-{3-[(2-chloro-5-methyl-5H-pyrrolo[3,2-d]pyrimidin-4-yl)amino]-1H-indazol-6-yl}-5'-methoxyspiro[cyclopropane-1,3'-indol]-2'(1'H)-one; 5-methoxy-4-({6-[(1R,2S)-5'-methoxy-2'-oxo-1',2'-dihydrospiro[cyclopropane-1,3'-indol]-2-yl]-1H-indazol-3-yl}amino)pyrimidine-2-carbonitrile; (1R,2S)-2-(3-{[2-(3,3-difluoroazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-(3-{[2-(3-fluoroazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-{3-[5-(ethanesulfonyl)-2-methoxyanilino]-1H-indazol-6-yl}-5'-methoxyspiro[cyclopropane-1,3'-indol]-2'(1'H)-one; 4-methoxy-3-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzamide; 4-methoxy-3-({6-[(1R,2S)-5'-methoxy-2'-oxo-1',2'-dihydrospiro[cyclopropane-1,3'-indol]-2-yl]-1H-indazol-3-yl}amino)-N-methylbenzamide; (1R,2S)-5'-methoxy-2-{3-[2-methoxy-5-(propane-2-sulfonyl)anilino]-1H-indazol-6-yl}spiro[cyclopropane-1,3'-indol]-2'(1'H)-one; 4-methoxy-3-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzene-1-sulfonamide; (1R,2S)-5'-methoxy-2-{3-[2-methoxy-5-(morpholine-4-carbonyl)anilino]-1H-indazol-6-yl}spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide; (1R,2S)-2-(3-{[2-(dimethylamino)-5-methylpyrimidin-4-yl]amino}-1H-indazol-6-yl)-5'-methoxyspiro[cyclopropane-1,3'-indol]-2'(1'H)-one; (1R,2S)-5'-methoxy-2-(3-{[2-methoxy-6-(morpholine-4-carbonyl)pyridin-3-yl]amino}-1H-indazol-6-yl)spiro[cyclopropane-1,3'-indol]-2'(1'H)-one; (1R,2S)-2-(3-{[6-(3,3-difluoroazetidine-1-carbonyl)-2-methoxypyridin-3-yl]amino}-1H-indazol-6-yl)-5'-methoxyspiro[cyclopropane-1,3'-indol]-2'(1'H)-one; (1R,2S)-2-(3-{[6-(4,4-difluoropiperidine-1-carbonyl)-2-methoxypyridin-3-yl]amino}-1H-indazol-6-yl)-5'-methoxyspiro[cyclopropane-1,3'-indol]-2'(1'H)-one; (1R,2S)-2-(4-fluoro-3-{[5-methoxy-2-(methylsulfanyl)pyrimidin-4-yl]amino}-1H-indazol-6-yl)-5'-methoxyspiro[cyclopropane-1,3'-indol]-2'(1'H)-one; (1R,2S)-5'-methoxy-2-{3-[(2-methoxy-5-methylpyrimidin-4-yl)amino]-1H-indazol-6-yl}spiro[cyclopropane-1,3'-indol]-2'(1'H)-one; (1R,2S)-5'-methoxy-2-(3-{[2-methoxy-6-(2-oxa-6-azaspiro[3.3]heptane-6-carbonyl)pyridin-3-yl]amino}-1H-indazol-6-yl)spiro[cyclopropane-1,3'-indol]-2'(1'H)-one; (1R,2S)-2-(3-{[2-(4,4-difluoropiperidin-1-yl)-5-methoxypyrimidin-4-yl]amino}-1H-indazol-6-yl)-5'-methoxyspiro[cyclopropane-1,3'-indol]-2'(1'H)-one; 4-[5-methoxy-4-({6-[(1R,2S)-5'-methoxy-2'-oxo-1',2'-dihydrospiro[cyclopropane-1,3'-indol]-2-yl]-1H-indazol-3-yl}amino)pyrimidin-2-yl]-1λ6-thiomorpholine-1,1-dione; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methylpyridine-2-carboxamide; (1R,2S)-5'-methoxy-2-(3-{[5-methoxy-2-(2-oxa-6-azaspiro[3.3]heptan-6-yl)pyrimidin-4-yl]amino}-1H-indazol-6-yl)spiro[cyclopropane-1,3'-indol]-2'(1'H)-one; (1R,2S)-2-(3-{[5-(methanesulfonyl)-3-methoxypyridin-2-yl]amino}-1H-indazol-6-yl)-5'-methoxyspiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methyl-N-(propan-2-yl)pyridine-2-carboxamide; (1R,2S)-2-(3-{[5-ethoxy-2-(methylsulfanyl)pyrimidin-4-yl]amino}-1H-indazol-6-yl)-5'-methoxyspiro[cyclopropane-1,3'-indol]-2'(1'H)-one; (1R,2S)-2-(3-{[6-(methanesulfonyl)-3-methoxypyridin-2-yl]amino}-1H-indazol-6-yl)-5'-methoxyspiro[cyclopropane-1,3'-indol]-2'(1'H)-one; 5-methoxy-6-({6-[(1R,2S)-5'- methoxy-2'-oxo-1',2'-dihydrospiro[cyclopropane-1,3'-indol]-2-yl]-1H-indazol-3-yl}amino)-N,N-dimethylpyridine-3-carboxamide; 5-methoxy-4-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-5'-methoxy-2-{3-[2-methoxy-4-(morpholine-4-carbonyl)anilino]-1H-indazol-6-yl}spiro[cyclopropane-1,3'-indol]-2'(1'H)-one; Diastereomer 1: (1R,2S)-5'-methoxy-2-(3-{[5-methoxy-2-(oxolan-3-yl)pyrimidin-4-yl]amino}-1H-indazol-6-yl)spiro[cyclopropane-1,3'-indol]-2'(1'H)-one; Diastereomer 2: (1R,2S)-5'-methoxy-2-(3-{[5-methoxy-2-(oxolan-3-yl)pyrimidin-4-yl]amino}-1H-indazol-6-yl)spiro[cyclopropane-1,3'-indol]-2'(1'H)-one; (1R,2S)-2-(3-{[2-ethoxy-6-(methanesulfonyl)pyridin-3-yl]amino}-1H-indazol-6-yl)-5'-methoxyspiro[cyclopropane-1,3'-indol]-2'(1'H)-one; 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide; 5-methoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-sulfonamide; (1R,2S)-2-(3-{[6-(dimethylphosphoryl)-2-methoxypyridin-3-yl]amino}-1H-indazol-6-yl)-5'-methoxyspiro[cyclopropane-1,3'-indol]-2'(1'H)-one; 2-fluoro-5-methoxy-4-((6-[(1R,2S)-5'-methoxy-2'-oxo-1',2'-dihydrospiro[cyclopropane-1,3'-indol]-2-yl]-1H-indazol-3-yl)amino)-N,N-dimethylbenzamide; (1R,2S)-2-{3-[5-fluoro-2-methoxy-4-(morpholine-4-carbonyl)anilino]-1H-indazol-6-yl}-5'-methoxyspiro[cyclopropane-1,3'-indol]-2'(1'H)-one; and (1R,2S)-2-(3-{[3-ethoxy-5-(methanesulfonyl)pyridin-2-yl]amino}-1H-indazol-6-yl)-5'-methoxyspiro[cyclopropane-1,3'-indol]-2'(1'H)-one, or a pharmaceutically acceptable salt thereof.

Further provided herein are compounds of Formula (I) selected from (1R,2S)-2-(3-{[6-(ethanesulfonyl)-2-methoxypyridin-3-yl]amino}-1H-indazol-6-yl)-5'-methoxyspiro[cyclopropane-1,3'-indol]-2'(1'H)-one; 5-methoxy-4-({6-[(1R,2S)-5'-methoxy-2'-oxo-1',2'-dihydrospiro[cyclopropane-1,3'-indol]-2-yl]-1H-indazol-3-yl}amino)-N,2-dimethylbenzene-1-sulfonamide; (1R,2S)-2-{3-[(2,5-dimethyl-5,7-dihydrothieno[3,4-d]pyrimidin-4-yl)amino]-1H-indazol-6-yl}-5'-methoxyspiro[cyclopropane-1,3'-indol]-2'(1'H)-one; 2,5-dimethoxy-4-({6-[(1R,2S)-5'-methoxy-2'-oxo-1',2'-dihydrospiro[cyclopropane-1,3'-indol]-2-yl]-1H-indazol-3-yl}amino)benzene-1-sulfonamide; (1R,2S)-2-(3-{[24dimethylamino)-6,7-dihydro-5H-cyclopenta[d]pyrimidin-4-yl]amino}-1H-indazol-6-yl)-5'-methoxyspiro[cyclopropane-1,3'-indol]-2'(1'H)-one; 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-5'-methoxy-2-(3-{[2-methoxy-6-(2-oxopyrrolidin-1-yl)pyridin-3-yl]amino}-1H-indazol-6-yl)spiro[cyclopropane-1,3'-indol]-2'(1'H)-one; (1R,2S)-5'-methoxy-2-{3-[2-methoxy-5-(morpholine-4-sulfonyl)anilino]-1H-indazol-6-yl}spiro[cyclopropane-1,3'-indol]-2'(1'H)-one; (1R,2S)-5'-methoxy-2-{3-[(3-methoxy-1,5-naphthyridin-2-yl)amino]-1H-indazol-6-yl}spiro[cyclopropane-1,3'-indol]-2'(1'H)-one; N,6dimethoxy-5-({6-[(1R,2S)-5'-methoxy-2'-oxo-1',2'-dihydrospiro[cyclopropane-1,3'-indol]-2-yl]-1H-indazol-3-yl}amino)-N-methylpyridine-2-carboxamide; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N'-(propan-2-yl)pyridine-2-carbohydrazide; (1R,2S)-5'-methoxy-2-(3-{[2-methoxy-5-(2-oxopyrrolidin-1-yl)pyridin-3-yl]amino}-1H-indazol-6-yl)spiro[cyclopropane-1,3'-indol]-2'(1'H)-one; (1R,2S)-5'-methoxy-2-(3-{[2-methoxy-5-(3-methyl-2-oxoimidazolidin-1-yl)pyridin-3-yl]amino}-1H-indazol-6-yl)spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-sulfonamide; 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-sulfonamide; (1R,2S)-5'-methoxy-2-{3-[2-methoxy-5-(oxane-4-sulfonyl)anilino]-1H-indazol-6-yl}spiro[cyclopropane-1,3'-indol]-2'(1'H)-one; (1R,2S)-2-(3-{[5-(dimethylphosphoryl)-3-methoxypyridin-2-yl]amino}-1H-indazol-6-yl)-5'-methoxyspiro[cyclopropane-1,3'-indol]-2'(1'H)-one; (1R,2S)-2-(3-{[5-(2-hydroxypropan-2-yl)-2-methoxypyridin-3-yl]amino}-1H-indazol-6-yl)-5'-methoxyspiro[cyclopropane-1,3'-indol]-2'(1'H)-one; (0R,2S)-2-(3-{[6-(methanesulfonyl)-2-methoxy-5-methylpyridin-3-yl]amino}-1H-indazol-6-yl)-5'-methoxyspiro[cyclopropane-1,3'-indol]-2'(1'H)-one; (1R,2S)-2-(3-{[5-(ethanesulfonyl)-3-methoxypyridin-2-yl]amino}-1H-indazol-6-yl)-5'-methoxyspiro[cyclopropane-1,3'-indol]-2'(1'H)-one; (1R,2S)-2-(3-{[5-(dimethylphosphoryl)-3-methoxypyrazin-2-yl]amino}-1H-indazol-6-yl)-5'-methoxyspiro[cyclopropane-1,3'-indol]-2'(1'H)-one; N-(cyclopropylmethyl)-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-(propan-2-yl)pyridine-2-carboxamide; (1R,2S)-5'-methoxy-2-(3-{[2-methoxy-6-(3-oxa-8-azabicyclo[3.2.1]octane-8-carbonyl)pyridin-3-yl]amino}-1H-indazol-6-yl)spiro[cyclopropane-1,3'-indol]-2'(1'H)-one; (1R,2S)-5'-methoxy-2-{3-[(4-methoxy-1-methyl-6-oxo-1,6-dihydropyridazin-3-yl)amino]-1H-indazol-6-yl}spiro[cyclopropane-1,3'-indol]-2'(1'H)-one; (1R,2S)-5'-methoxy-2-(3-{[2-methoxy-5-(1,3-oxazol-2-yl)pyridin-3-yl]amino}-1H-indazol-6-yl)spiro[cyclopropane-1,3'-indol]-2'(1'H)-one; (1R,2S)-5'-methoxy-2-(3-{[3-methoxy-5-(3-methoxyazetidine-1-carbonyl)pyridin-2-yl]amino}-1H-indazol-6-yl)spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyrazine-2-carboxamide; 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyrazine-2-carboxamide; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N,3-trimethylpyridine-2-carboxamide; (1R,2S)-2-(3-{[6-(methanesulfinyl)-2-methoxypyridin-3-yl]amino}-1H-indazol-6-yl)-5'-methoxyspiro[cyclopropane-1,3'-indol]-2'(1'H)-one; (1R,2S)-2-(3-{[6-(methanesulfinyl)-2-methoxypyridin-3-yl]amino}-1H-indazol-6-yl)-5'-methoxyspiro[cyclopropane-1,3'-indol]-2'(1'H)-one; (1R,2S)-2-(3-{[6-(methanesulfonyl)-4-methoxypyridin-3-yl]amino}-1H-indazol-6-yl)-5'-methoxyspiro[cyclopropane-1,3'-indol]-2'(1'H)-one; (1R,2S)-2-(3-{[5-(methanesulfonyl)-3-methoxypyrazin-2-yl]amino}-1H-indazol-6-yl)-5'-methoxyspiro[cyclopropane-1,3'-indol]-2'(1'H)-one; N,N-dicyclopropyl-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide; N-(2,2-difluoroethyl)-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide; (1R,2S)-2-[3-({6-[(2R,6S)-2,6-dimethylpiperidine-1-carbonyl]-2-methoxypyridin-3-yl}amino)-1H-indazol-6-yl]-5'-methoxyspiro[cyclopropane-1,3'-indol]-2'(1'H)-one; (1R,2S)-5'-methoxy-2-(3-{[2-methoxy-6-(8-oxa-3-azabicyclo[3.2.1]octane-3-carbonyl)pyridin-3-yl]amino}-1H-indazol- 6-yl)spiro[cyclopropane-1,3'-indol]-2'(1'H)-one; (1R,2S)-2-(3-{[3-chloro-5-(methanesulfonyl)pyridin-2-yl]amino}-1H-indazol-6-yl)-5'-methoxyspiro[cyclopropane-1,3'-indol]-2'(1'H)-one; (1R,2S)-5'-methoxy-2-(3-{[3-methoxy-5-(propane-2-sulfonyl)pyridin-2-yl]amino}-1H-indazol-6-yl)spiro[cyclopropane-1,3'-indol]-2'(1'H)-one; (1R,2S)-2-(3-{[6-(dimethylphosphoryl)-4-methoxypyridin-3-yl]amino}-1H-indazol-6-yl)-5'-methoxyspiro[cyclopropane-1,3'-indol]-2'(1'H)-one; N-(1,3-difluoropropan-2-yl)-6-methoxy-5-({6-[(1R,2S)-5'-methoxy-2'-oxo-1',2'-dihydrospiro[cyclopropane-1,3'-indol]-2'-yl]-1H-indazol-3-yl}amino)pyridine-2-carboxamide; 6-chloro-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-2-{3-[(5-chloro-2-methyl-1,3-benzoxazol-6-yl)amino]-1H-indazol-6-yl}-5'-methoxyspiro[cyclopropane-1,3'-indol]-2'(1'H)-one; 4-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; 3-[6-methoxy-5-({6-[(1R,2S)-5'-methoxy-2'-oxo-1',2'-dihydrospiro[cyclopropane-1,3'-indol]-2-yl]-1H-indazol-3-yl}amino)pyrazin-2-yl]-1)₆-thietane-1,1-dione; (1R,2S)-5'-methoxy-2-(3-{[3-methoxy-5-(morpholine-4-sulfonyl)pyridin-2-yl]amino}-1H-indazol-6-yl)spiro[cyclopropane-1,3'-indol]-2'(1'H)-one; (1R,2S)-5'-methoxy-2-(3-{[3-methoxy-5-(8-oxa-3-azabicyclo[3.2.1]octane-3-sulfonyl)pyridin-2-yl]amino}-1H-indazol-6-yl)spiro[cyclopropane-1,3'-indol]-2'(1'H)-one; (1R,2S)-2-(3-{[6-(diethylphosphoryl)-2-methoxypyridin-3-yl]amino}-1H-indazol-6-yl)-5'-methoxyspiro[cyclopropane-1,3'-indol]-2'(1'H)-one; (1R,2S)-2-(3-{[5-(cyclopropanesulfonyl)-3-methoxypyridin-2-yl]amino}-1H-indazol-6-yl)-5'-methoxyspiro[cyclopropane-1,3'-indol]-2'(1'H)-one; (1R,2S)-5'-methoxy-2-(3-{[3-methoxy-5-(oxane-4-sulfonyl)pyridin-2-yl]amino}-1H-indazol-6-yl)spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carbonitrile; (1R,2S)-2-{3-[5-(diethylphosphoryl)-2-methoxyanilino]-1H-indazol-6-yl}-5'-methoxyspiro[cyclopropane-1,3'-indol]-2'(1'H)-one; (1R,2S)-2-(3-{[6-(ethanesulfonyl)-4-methoxypyridin-3-yl]amino}-1H-indazol-6-yl)-5'-methoxyspiro[cyclopropane-1,3'-indol]-2'(1'H)-one; (1R,2S)-2-(3-{[5-(azetidine-1-carbonyl)-3-methoxypyridin-2-yl]amino}-1H-indazol-6-yl)-5'-methoxyspiro[cyclopropane-1,3'-indol]-2'(1'H)-one; (1R,2S)-5'-methoxy-2-(3-{[3-methoxy-5-(morpholine-4-carbonyl)pyridin-2-yl]amino}-1H-indazol-6-yl)spiro[cyclopropane-1,3'-indol]-2'(1'H)-one; (1R,2S)-5'-methoxy-2-{3-[(6-methoxy-2-methyl-1-oxo-2,3-dihydro-1H-isoindol-5-yl)amino]-1H-indazol-6-yl}spiro[cyclopropane-1,3'-indol]-2'(1'H)-one; (1R,2S)-5'-methoxy-2-{3-[(4-methoxy-2-methyl-1-oxo-2,3-dihydro-1H-isoindol-5-yl)amino]-1H-indazol-6-yl}spiro[cyclopropane-1,3'-indol]-2'(1'H)-one; (1R,2S)-5'-methoxy-2-(3-{[3-methoxy-5-(1,2-oxazolidine-2-sulfonyl)pyridin-2-yl]amino}-1H-indazol-6-yl)spiro[cyclopropane-1,3'-indol]-2'(1'H)-one; (1R,2S)-2-(3-{[5-(azetidine-1-sulfonyl)-3-methoxypyridin-2-yl]amino}-1H-indazol-6-yl)-5'-methoxyspiro[cyclopropane-1,3'-indol]-2'(1'H)-one; 5-methoxy-6-({6-[(1R,2S)-5'-methoxy-2'-oxo-1',2'-dihydrospiro[cyclopropane-1,3'-indol]-2-yl]-1H-indazol-3-yl}amino)-N-(3-methyloxetan-3-yl)pyridine-3-sulfonamide; 5-methoxy-6-({6-[(1R,2S)-5'-methoxy-2'-oxo-1',2'-dihydrospiro[cyclopropane-1,3'-indol]-2-yl]-1H-indazol-3-yl}amino)-N-methyl-N-(3-methyloxetan-3-yl)pyridine-3-sulfonamide; (1R,2S)-2-(3-{[5-(1-hydroxyethyl)-2-methoxypyridin-3-yl]amino}-1H-indazol-6-yl)-5'-methoxyspiro[cyclopropane-1,3'-indol]-2'(1'H)-one; (1R,2S)-2-{3-[2-ethoxy-4-(methanesulfonyl)anilino]-1H-indazol-6-yl}-5'-methoxyspiro[cyclopropane-1,3'-indol]-2'(1'H)-one; (1R,2S)-2-(3-{[3-ethoxy-5-(4-methylpiperazine-1-sulfonyl)pyridin-2-yl]amino}-1H-indazol-6-yl)-5'-methoxyspiro[cyclopropane-1,3'-indol]-2'(1'H)-one; (1R,2S)-2-(3-{[5-(ethanesulfonyl)-3-ethoxypyridin-2-yl]amino}-1H-indazol-6-yl)-5'-methoxyspiro[cyclopropane-1,3'-indol]-2'(1'H)-one; 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N-methylpyridine-3-sulfonamide; (1R,2S)-5'-chloro-2-(3-{[3-ethoxy-5-(methanesulfonyl)pyridin-2-yl]amino}-1H-indazol-6-yl)spiro[cyclopropane-1,3'-indol]-2'(1'H)-one; (1R,2S)-2-{3-[(4-ethoxy-1-methyl-6-oxo-1,6-dihydropyridazin-3-yl)amino]-1H-indazol-6-yl}-5'-methoxyspiro[cyclopropane-1,3'-indol]-2'(1'H)-one; (1R,2S)-2-(3-{[6-(2-hydroxypropan-2-yl)-3-methoxypyridin-2-yl]amino}-1H-indazol-6-yl)-5'-methoxyspiro[cyclopropane-1,3'-indol]-2'(1'H)-one; (1R,2S)-2-(3-{[4-ethoxy-6-(methanesulfonyl)pyridin-3-yl]amino}-1H-indazol-6-yl)-5'-methoxyspiro[cyclopropane-1,3'-indol]-2'(1'H)-one; and (1R,2S)-2-(3-{[5-(difluoromethanesulfonyl)-3-methoxypyridin-2-yl]amino}-1H-indazol-6-yl)-5'-methoxyspiro[cyclopropane-1,3'-indol]-2'(1'H)-one, or a pharmaceutically acceptable salt thereof.

Further provided herein are compounds of Formula (I) selected from those set forth in Table 1A.

TABLE 1A

| Example No. | Structure | Name |
|---|---|---|
| 1 | 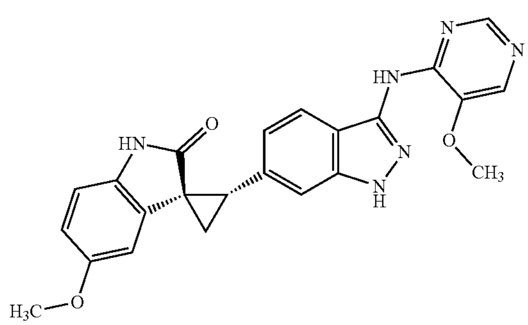 | ±-5'-methoxy-2-{3-[(5-methoxypyrimidin-4-yl)amino]-1H-indazol-6-yl}spiro[cyclopropane-1,3'-indol]-2'(1'H)-one (racemic mixture) |

TABLE 1A-continued

| Example No. | Structure | Name |
|---|---|---|
| 2 | 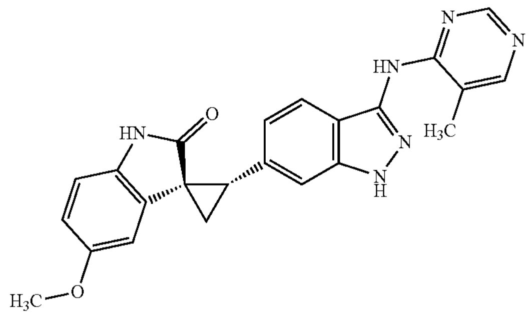 [SMILES: COc1ccc2c(c1)[C@]1(C[C@H]1c1ccc3c(Nc4ncncc4C)n[nH]c3c1)C(=O)N2] | ±-5'-methoxy-2-{3-[(5-methylpyrimidin-4-yl)amino]-1H-indazol-6-yl}spiro[cyclopropane-1,3'-indol]-2'(1'H)-one (racemic mixture) |
| 3 | 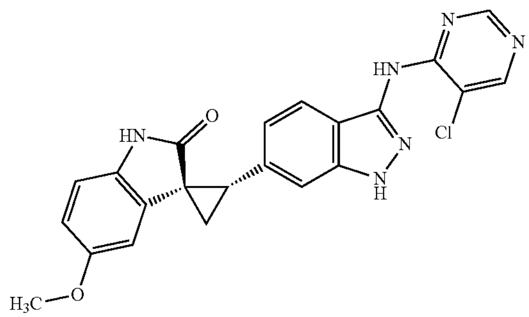 [SMILES: COc1ccc2c(c1)[C@]1(C[C@H]1c1ccc3c(Nc4ncncc4Cl)n[nH]c3c1)C(=O)N2] | ±-2-{3-[(5-chloropyrimidin-4-yl)amino]-1H-indazol-6-yl}-5'-methoxyspiro[cyclopropane-1,3'-indol]-2'(1'H)-one (racemic mixture) |
| 4 | 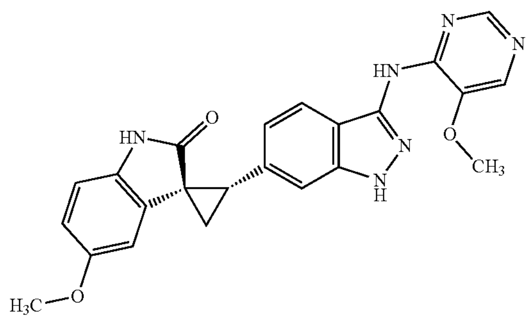 [SMILES: COc1ccc2c(c1)[C@]1(C[C@H]1c1ccc3c(Nc4ncncc4OC)n[nH]c3c1)C(=O)N2] | (1R,2S)-5'-methoxy-2-{3-[(5-methoxypyrimidin-4-yl)amino]-1H-indazol-6-yl}spiro[cyclopropane-1,3'-indol]-2'(1'H)-one |
| 5 | 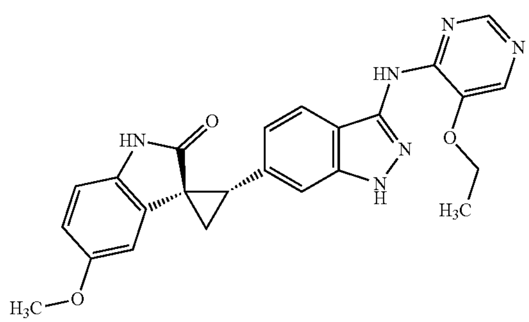 [SMILES: CCOc1cncnc1Nc1n[nH]c2cc([C@@H]3C[C@@]34C(=O)Nc3ccc(OC)cc34)ccc12] | (1R,2S)-2-{3-[(5-ethoxypyrimidin-4-yl)amino]-1H-indazol-6-yl}-5'-methoxyspiro[cyclopropane-1,3'-indol]-2'(1'H)-one |
| 6 | 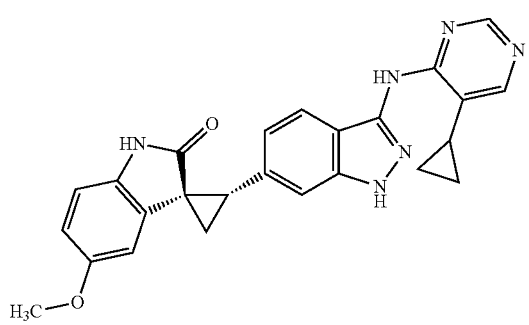 [SMILES: COc1ccc2c(c1)[C@]1(C[C@H]1c1ccc3c(Nc4ncncc4C4CC4)n[nH]c3c1)C(=O)N2] | (1R,2S)-2-{3-[(5-cyclopropylpyrimidin-4-yl)amino]-1H-indazol-6-yl}-5'-methoxyspiro[cyclopropane-1,3'-indol]-2'(1'H)-one |

TABLE 1A-continued

| Example No. | Structure | Name |
|---|---|---|
| 7 | 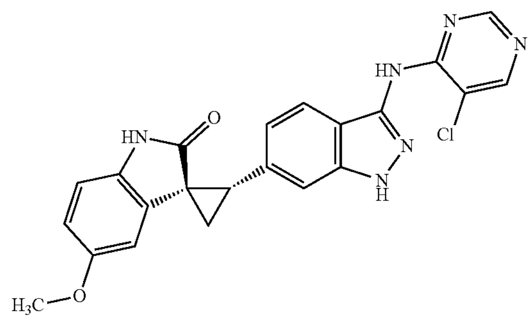 [SMILES: COc1ccc2c(c1)[C@]1(C[C@H]1c1ccc3c(Nc4ncncc4Cl)n[nH]c3c1)C(=O)N2] | (1R,2S)-2-{3-[(5-chloropyrimidin-4-yl)amino]-1H-indazol-6-yl}-5'-methoxyspiro[cyclopropane-1,3'-indol]-2'(1'H)-one |
| 8 | 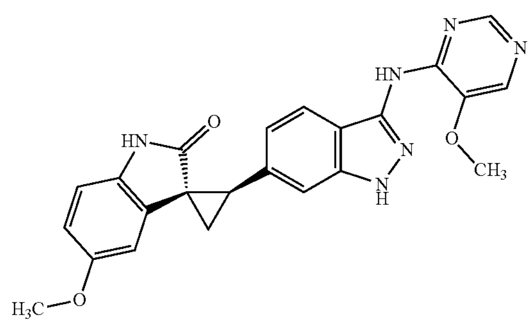 [SMILES: COc1ccc2c(c1)[C@@]1(C[C@@H]1c1ccc3c(Nc4ncncc4OC)n[nH]c3c1)C(=O)N2] | (1S,2R)-5'-methoxy-2-{3-[(5-methoxypyrimidin-4-yl)amino]-1H-indazol-6-yl}spiro[cyclopropane-1,3'-indol]-2'(1'H)-one |
| 9 | 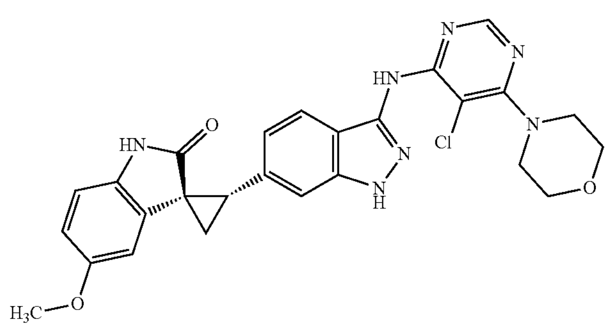 [SMILES: COc1ccc2c(c1)[C@]1(C[C@H]1c1ccc3c(Nc4ncnc(N5CCOCC5)c4Cl)n[nH]c3c1)C(=O)N2] | (1R,2S)-2-(3-{[5-chloro-6-(morpholin-4-yl)pyrimidin-4-yl]amino}-1H-indazol-6-yl)-5'-methoxyspiro[cyclopropane-1,3'-indol]-2'(1'H)-one |
| 10 | 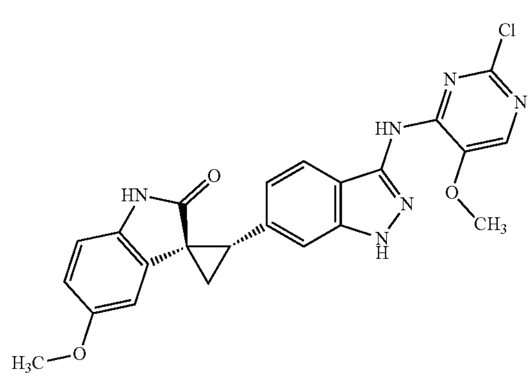 [SMILES: COc1ccc2c(c1)[C@]1(C[C@H]1c1ccc3c(Nc4nc(Cl)ncc4OC)n[nH]c3c1)C(=O)N2] | (1R,2S)-2-{3-[(2-chloro-5-methoxypyrimidin-4-yl)amino]-1H-indazol-6-yl}-5'-methoxyspiro[cyclopropane-1,3'-indol]-2'(1'H)-one |

TABLE 1A-continued

| Example No. | Structure | Name |
|---|---|---|
| 11 | 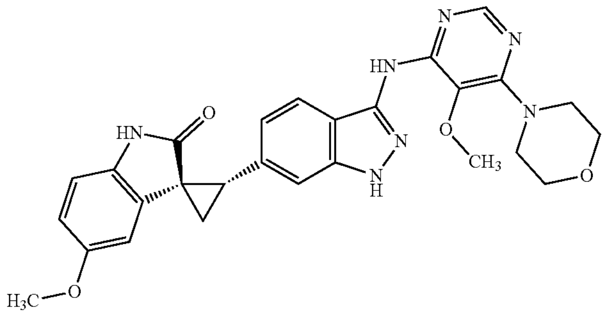 [SMILES: COc1ccc2c(c1)[C@]1(C[C@H]1c1ccc3c(Nc4ncnc(N5CCOCC5)c4OC)n[nH]c3c1)C(=O)N2] | (1R,2S)-5'-methoxy-2-(3-{[5-methoxy-6-(morpholin-4-yl)pyrimidin-4-yl]amino}-1H-indazol-6-yl)spiro[cyclopropane-1,3'-indol]-2'(1'H)-one |
| 12 | 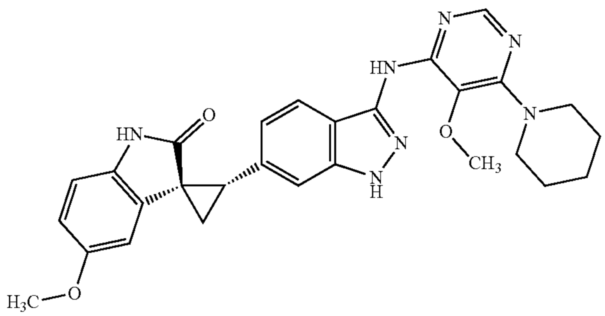 [SMILES: COc1ccc2c(c1)[C@]1(C[C@H]1c1ccc3c(Nc4ncnc(N5CCCCC5)c4OC)n[nH]c3c1)C(=O)N2] | (1R,2S)-5'-methoxy-2-(3-{[5-methoxy-6-(piperidin-1-yl)pyrimidin-4-yl]amino}-1H-indazol-6-yl)spiro[cyclopropane-1,3'-indol]-2'(1'H)-one |
| 13 | 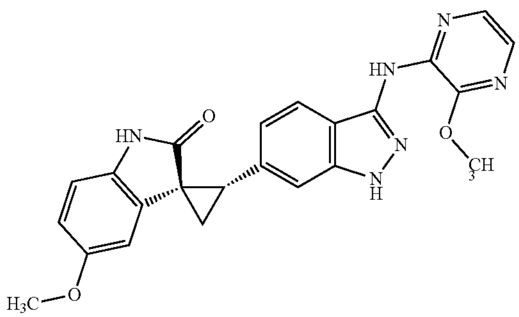 [SMILES: COc1ccc2c(c1)[C@]1(C[C@H]1c1ccc3c(Nc4nccnc4OC)n[nH]c3c1)C(=O)N2] | (1R,2S)-5'-methoxy-2-{3-[(3-methoxypyrazin-2-yl)amino]-1H-indazol-6-yl}spiro[cyclopropane-1,3'-indol]-2'(1'H)-one |
| 14 | 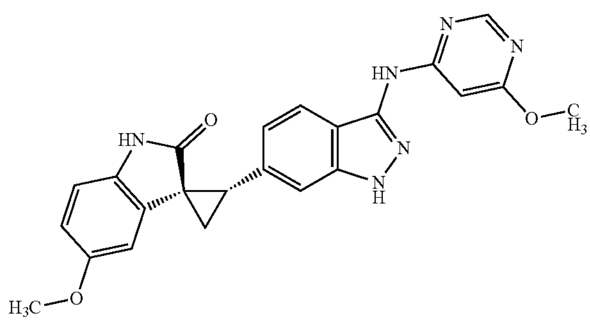 | (1R,2S)-5'-methoxy-2-{3-[(6-methoxypyrimidin-4-yl)amino]-1H-indazol-6-yl}spiro[cyclopropane-1,3'-indol]-2'(1'H)-one |
| 15 | 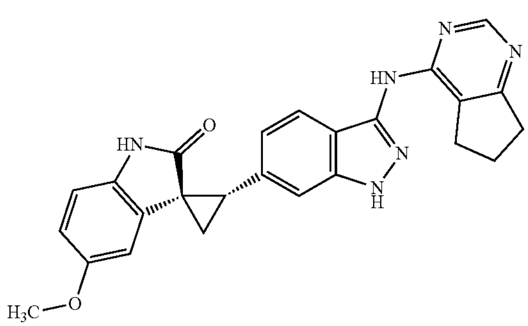 [SMILES: COc1ccc2c(c1)[C@]1(C[C@H]1c1ccc3c(Nc4ncnc5c4CCC5)n[nH]c3c1)C(=O)N2] | (1R,2S)-2-{3-[(6,7-dihydro-5H-cyclopenta[d]pyrimidin-4-yl)amino]-1H-indazol-6-yl}-5'-methoxyspiro[cyclopropane-1,3'-indol]-2'(1'H)-one |

TABLE 1A-continued

| Example No. | Structure | Name |
|---|---|---|
| 16 | 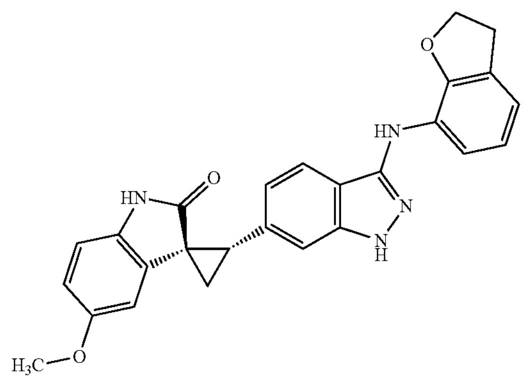 [SMILES: COc1ccc2c(c1)[C@]1(C[C@H]1c1ccc3c(Nc4cccc5c4OCC5)n[nH]c3c1)C(=O)N2] | (1R,2S)-2-{3-[(2,3-dihydro-1-benzofuran-7-yl)amino]-1H-indazol-6-yl}-5'-methoxyspiro[cyclopropane-1,3'-indol]-2'(1'H)-one |
| 17 | 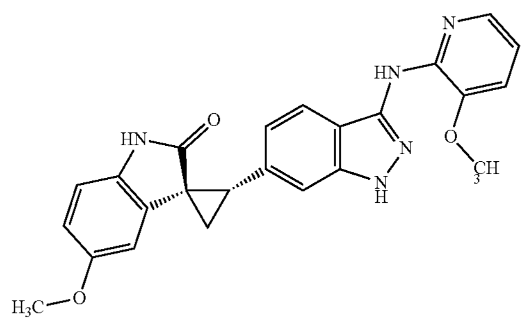 [SMILES: COc1ccc2c(c1)[C@]1(C[C@H]1c1ccc3c(Nc4ncccc4OC)n[nH]c3c1)C(=O)N2] | (1R,2S)-5'-methoxy-2-{3-[(3-methoxypyridin-2-yl)amino]-1H-indazol-6-yl}spiro[cyclopropane-1,3'-indol]-2'(1'H)-one |
| 18 | 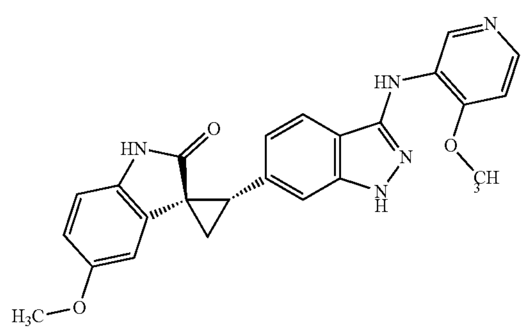 [SMILES: COc1ccc2c(c1)[C@]1(C[C@H]1c1ccc3c(Nc4cnccc4OC)n[nH]c3c1)C(=O)N2] | (1R,2S)-5'-methoxy-2-{3-[(4-methoxypyridin-3-yl)amino]-1H-indazol-6-yl}spiro[cyclopropane-1,3'-indol]-2'(1'H)-one |
| 19 | 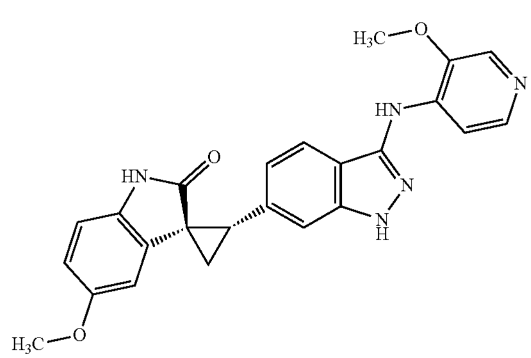 [SMILES: COc1ccc2c(c1)[C@]1(C[C@H]1c1ccc3c(Nc4ccncc4OC)n[nH]c3c1)C(=O)N2] | (1R,2S)-5'-methoxy-2-{3-[(3-methoxypyridin-4-yl)amino]-1H-indazol-6-yl}spiro[cyclopropane-1,3'-indol]-2'(1'H)-one |

TABLE 1A-continued

| Example No. | Structure | Name |
|---|---|---|
| 20 | 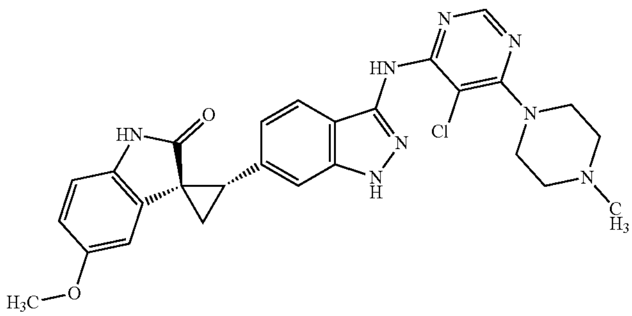 | (1R,2S)-2-(3-{[5-chloro-6-(4-methylpiperazin-1-yl)pyrimidin-4-yl]amino}-1H-indazol-6-yl)-5'-methoxyspiro[cyclopropane-1,3'-indol]-2'(1'H)-one |
| 21 | 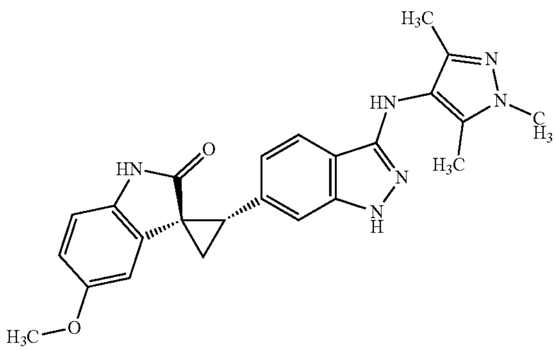 | (1R,2S)-5'-methoxy-2-{3-[(1,3,5-trimethyl-1H-pyrazol-4-yl)amino]-1H-indazol-6-yl}spiro[cyclopropane-1,3'-indol]-2'(1'H)-one |
| 22 | 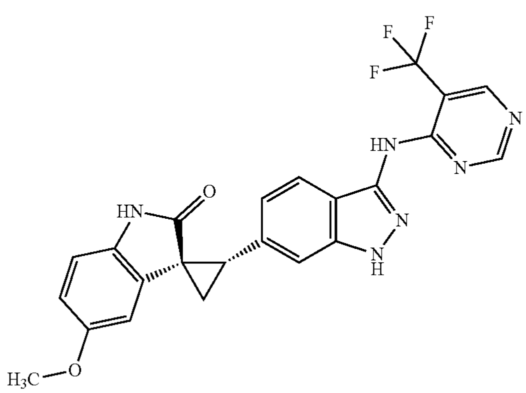 [SMILES: COc1ccc2c(c1)[C@]1(C[C@H]1c1ccc3c(Nc4ncncc4C(F)(F)F)n[nH]c3c1)C(=O)N2] | (1R,2S)-5'-methoxy-2-(3-{[5-(trifluoromethyl)pyrimidin-4-yl]amino}-1H-indazol-6-yl)spiro[cyclopropane-1,3'-indol]-2'(1'H)-one |
| 23 | 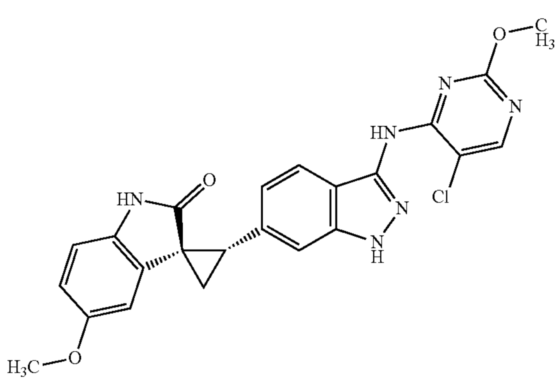 | (1R,2S)-2-{3-[(5-chloro-2-methoxypyrimidin-4-yl)amino]-1H-indazol-6-yl}-5'-methoxyspiro[cyclopropane-1,3'-indol]-2'(1'H)-one |

TABLE 1A-continued

| Example No. | Structure | Name |
|---|---|---|
| 24 | 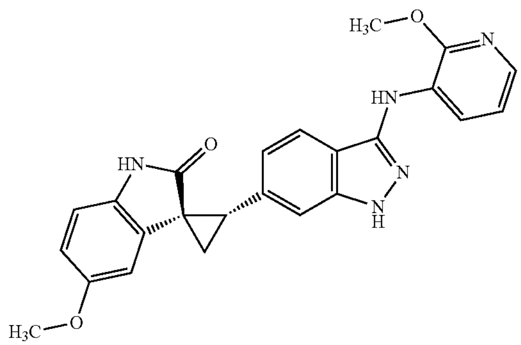 [SMILES: COc1ccc2c(c1)[C@]1(C[C@H]1c1ccc3c(Nc4cccnc4OC)n[nH]c3c1)C(=O)N2] | (1R,2S)-5'-methoxy-2-{3-[(2-methoxypyridin-3-yl)amino]-1H-indazol-6-yl}spiro[cyclopropane-1,3'-indol]-2'(1'H)-one |
| 25 | 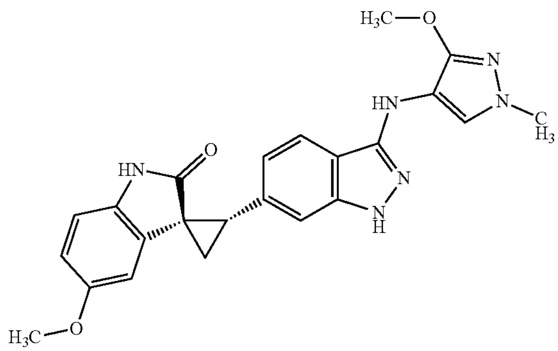 | (1R,2S)-5'-methoxy-2-{3-[(3-methoxy-1-methyl-1H-pyrazol-4-yl)amino]-1H-indazol-6-yl}spiro[cyclopropane-1,3'-indol]-2'(1'H)-one |
| 26 | 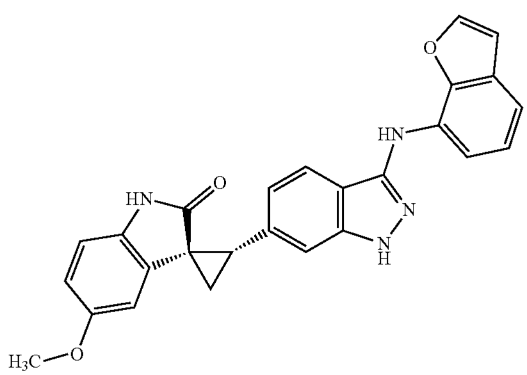 [SMILES: COc1ccc2c(c1)[C@]1(C[C@H]1c1ccc3c(Nc4cccc5ccoc45)n[nH]c3c1)C(=O)N2] | (1R,2S)-2-{3-[(1-benzofuran-7-yl)amino]-1H-indazol-6-yl}-5'-methoxyspiro[cyclopropane-1,3'-indol]-2'(1'H)-one |
| 27 | 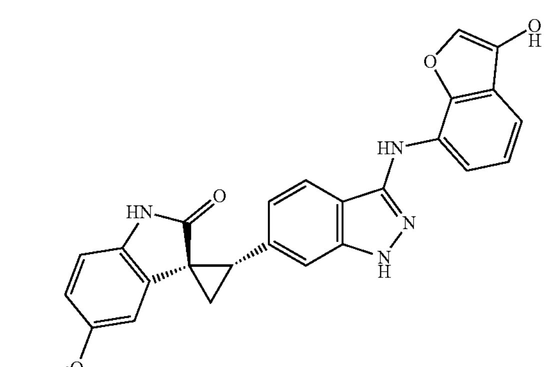 | (1R,2S)-2-{3-[(3-hydroxy-2,3-dihydro-1-benzofuran-7-yl)amino]-1H-indazol-6-yl}-5'-methoxyspiro[cyclopropane-1,3'-indol]-2'(1'H)-one (mixture of diastereomers) |

TABLE 1A-continued

| Example No. | Structure | Name |
|---|---|---|
| 28 | 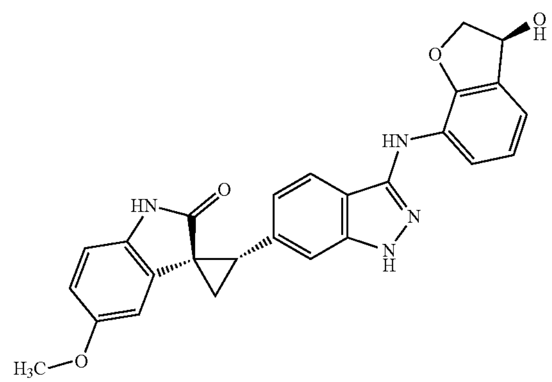 [SMILES: COc1ccc2c(c1)[C@]1(C[C@H]1c1ccc3c(Nc4cccc5c4OC[C@H]5O)n[nH]c3c1)C(=O)N2] | (1R,2S)-2-(3-{[(3S)-3-hydroxy-2,3-dihydro-1-benzofuran-7-yl]amino}-1H-indazol-6-yl)-5'-methoxyspiro[cyclopropane-1,3'-indol]-2'(1'H)-one |
| 29 | 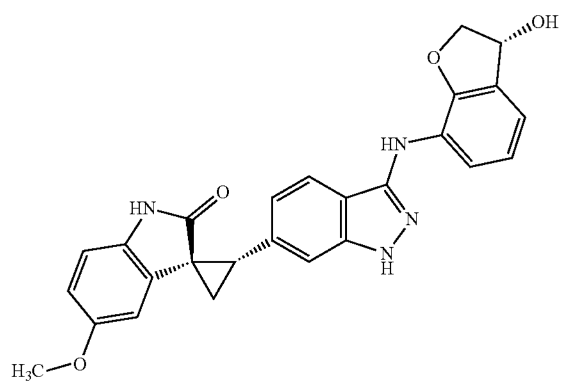 [SMILES: COc1ccc2c(c1)[C@]1(C[C@H]1c1ccc3c(Nc4cccc5c4OC[C@@H]5O)n[nH]c3c1)C(=O)N2] | (1R,2S)-2-(3-{[(3R)-3-hydroxy-2,3-dihydro-1-benzofuran-7-yl]amino}-1H-indazol-6-yl)-5'-methoxyspiro[cyclopropane-1,3'-indol]-2'(1'H)-one |
| 30 | 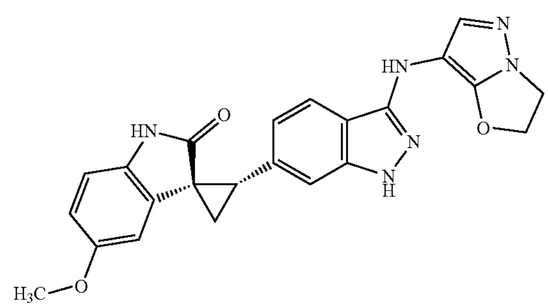 [SMILES: COc1ccc2c(c1)[C@]1(C[C@H]1c1ccc3c(Nc4cnn5c4OCC5)n[nH]c3c1)C(=O)N2] | (1R,2S)-2-{3-[(2,3-dihydropyrazolo[5,1-b][1,3]oxazol-7-yl)amino]-1H-indazol-6-yl}-5'-methoxyspiro[cyclopropane-1,3'-indol]-2'(1'H)-one |
| 31 | 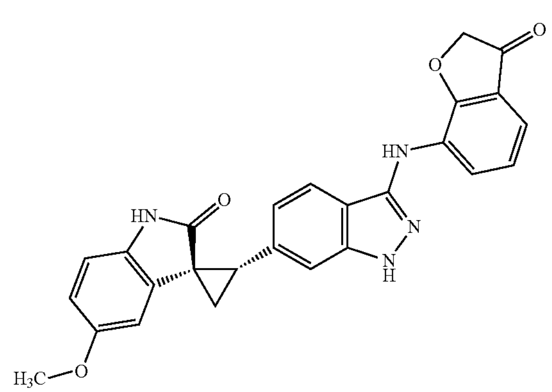 [SMILES: COc1ccc2c(c1)[C@]1(C[C@H]1c1ccc3c(Nc4cccc5c4OCC5=O)n[nH]c3c1)C(=O)N2] | (1R,2S)-5'-methoxy-2-{3-[(3-oxo-2,3-dihydro-1-benzofuran-7-yl)amino]-1H-indazol-6-yl}spiro[cyclopropane-1,3'-indol]-2'(1'H)-one |

TABLE 1A-continued

| Example No. | Structure | Name |
|---|---|---|
| 32 | 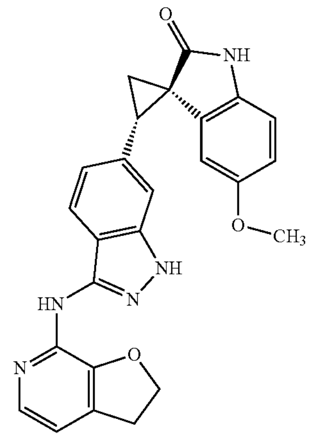 [SMILES: COc1ccc2c(c1)[C@]1(C[C@H]1c1ccc3c(Nc4nccc5c4OCC5)n[nH]c3c1)C(=O)N2] | (1R,2S)-2-{3-[(2,3-dihydrofuro[2,3-c]pyridin-7-yl)amino]-1H-indazol-6-yl}-5'-methoxyspiro[cyclopropane-1,3'-indol]-2'(1'H)-one |
| 33 | 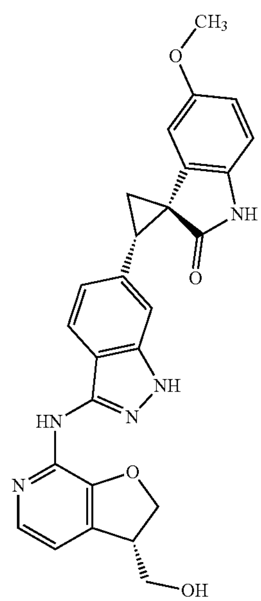 [SMILES: COc1ccc2c(c1)[C@]1(C[C@H]1c1ccc3c(Nc4nccc5c4OC[C@@H]5CO)n[nH]c3c1)C(=O)N2] | (1R,2S)-2-(3-{[(3S)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 34 | 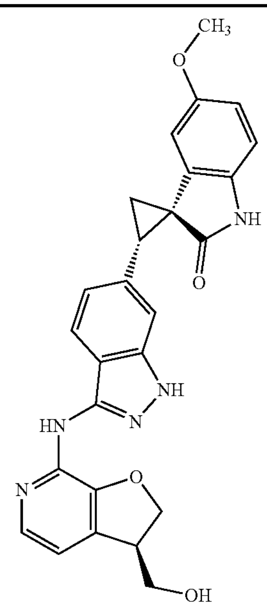 | (1R,2S)-2-(3-{[(3R)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one |
| 35 | 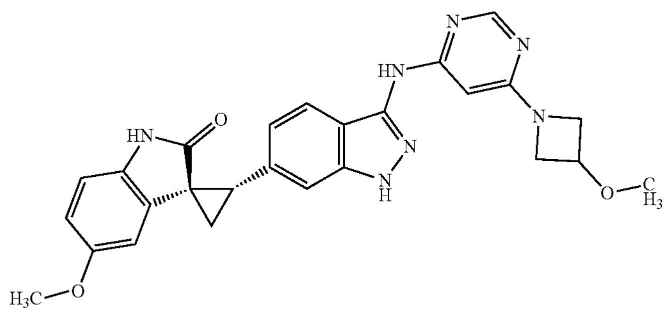 | (1R,2S)-5'-methoxy-2-(3-{[6-(3-methoxyazetidin-1-yl)pyrimidin-4-yl]amino}-1H-indazol-6-yl)spiro[cyclopropane-1,3'-indol]-2'(1'H)-one |
| 36 | 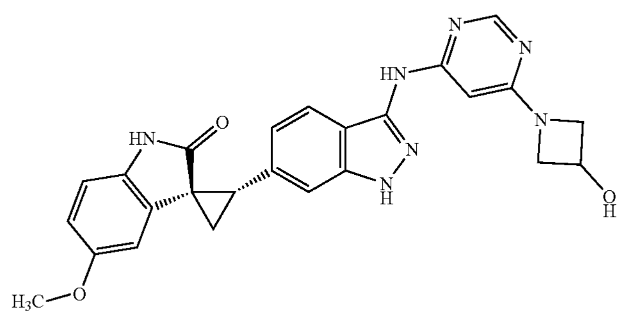 [SMILES: COc1ccc2c(c1)[C@]1(C[C@H]1c1ccc3c(Nc4cc(N5CC(O)C5)ncn4)n[nH]c3c1)C(=O)N2] | (1R,2S)-2-(3-{[6-(3-hydroxyazetidin-1-yl)pyrimidin-4-yl]amino}-1H-indazol-6-yl)-5'-methoxyspiro[cyclopropane-1,3'-indol]-2'(1'H)-one |
| 37 | 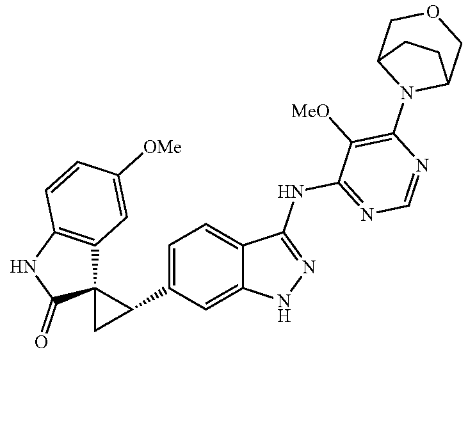 [SMILES: COc1ccc2c(c1)[C@]1(C[C@H]1c1ccc3c(Nc4ncnc(N5C6CCC5COC6)c4OC)n[nH]c3c1)C(=O)N2] | (1R,2S)-2-(3-((6-(3-oxa-8-azabicyclo[3.2.1]octan-8-yl)-5-methoxypyrimidin-4-yl)amino)-1H-indazol-6-yl)-5'-methoxyspiro[cyclopropane-1,3'-indolin]-2'-one |

TABLE 1A-continued

| Example No. | Structure | Name |
|---|---|---|
| 38 | 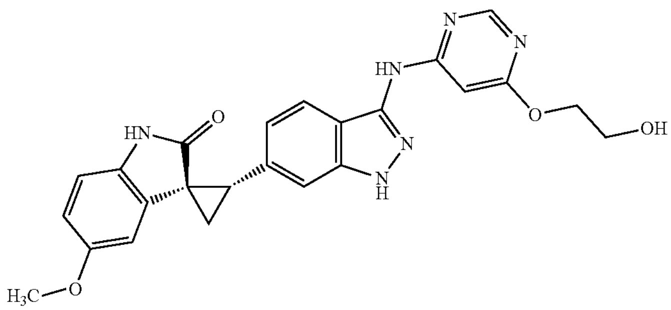 [SMILES: COc1ccc2c(c1)[C@]1(C[C@H]1c1ccc3c(Nc4cc(OCCO)ncn4)n[nH]c3c1)C(=O)N2] | (1R,2S)-2-(3-{[6-(2-hydroxyethoxy)pyrimidin-4-yl]amino}-1H-indazol-6-yl)-5'-methoxyspiro[cyclopropane-1,3'-indol]-2'(1'H)-one |
| 39 | 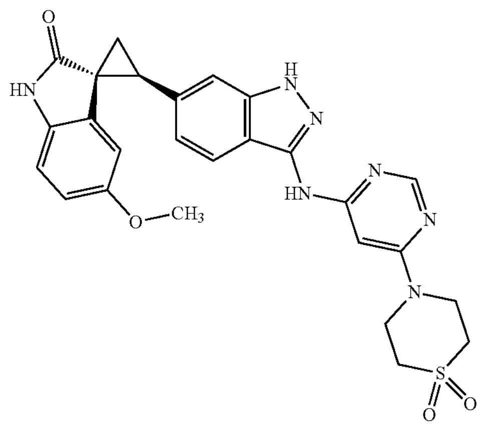 [SMILES: COc1ccc2c(c1)[C@]1(C[C@H]1c1ccc3c(Nc4cc(N5CCS(=O)(=O)CC5)ncn4)n[nH]c3c1)C(=O)N2] | (1R,2S)-2-(3-((6-(1,1-dioxidothiomorpholino)pyrimidin-4-yl)amino)-1H-indazol-6-yl)-5'-methoxyspiro[cyclopropane-1,3'-indolin]-2'-one) |
| 40 | 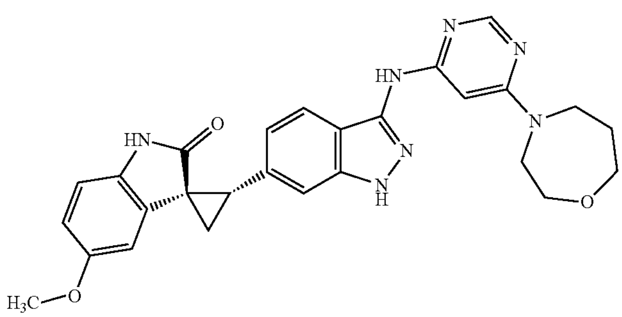 [SMILES: COc1ccc2c(c1)[C@]1(C[C@H]1c1ccc3c(Nc4cc(N5CCCOCC5)ncn4)n[nH]c3c1)C(=O)N2] | (1R,2S)-5'-methoxy-2-(3-{[6-(1,4-oxazepan-4-yl)pyrimidin-4-yl]amino}-1H-indazol-6-yl)spiro[cyclopropane-1,3'-indol]-2'(1'H)-one |
| 41 | 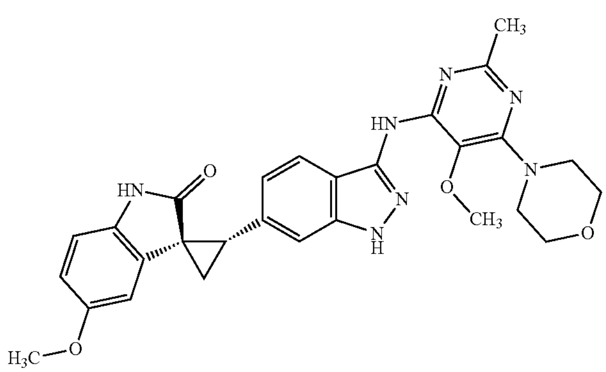 [SMILES: COc1ccc2c(c1)[C@]1(C[C@H]1c1ccc3c(Nc4nc(C)nc(N5CCOCC5)c4OC)n[nH]c3c1)C(=O)N2] | (1R,2S)-5'-methoxy-2-(3-{[5-methoxy-2-methyl-6-(morpholin-4-yl)pyrimidin-4-yl]amino}-1H-indazol-6-yl)spiro[cyclopropane-1,3'-indol]-2'(1'H)-one |

TABLE 1A-continued

| Example No. | Structure | Name |
|---|---|---|
| 42 | 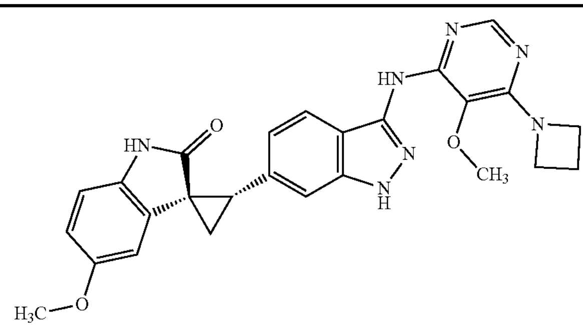 | (1R,2S)-2-(3-{[6-(azetidin-1-yl)-5-methoxypyrimidin-4-yl]amino}-1H-indazol-6-yl)-5'-methoxyspiro[cyclopropane-1,3'-indol]-2'(1'H)-one |
| 43 | 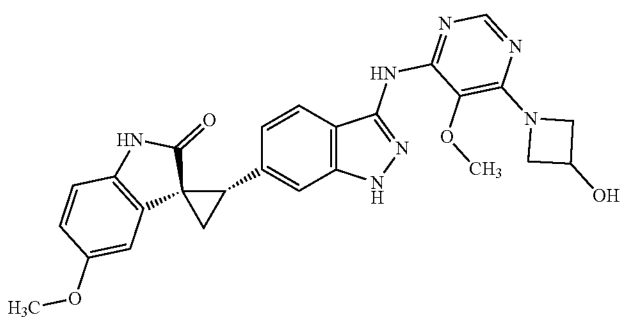 [SMILES: COc1ccc2c(c1)[C@]1(C[C@H]1c1ccc3c(Nc4ncnc(N5CC(O)C5)c4OC)n[nH]c3c1)C(=O)N2] | (1R,2S)-2-(3-{[6-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one |
| 44 | 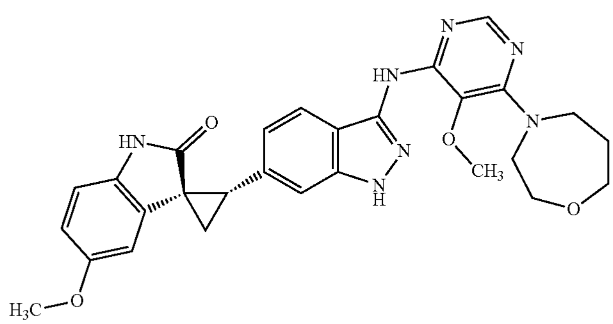 [SMILES: COc1ccc2c(c1)[C@]1(C[C@H]1c1ccc3c(Nc4ncnc(N5CCCOCC5)c4OC)n[nH]c3c1)C(=O)N2] | (1R,2S)-5'-methoxy-2-(3-{[5-methoxy-6-(1,4-oxazepan-4-yl)pyrimidin-4-yl]amino}-1H-indazol-6-yl)spiro[cyclopropane-1,3'-indol]-2'(1'H)-one |
| 45 | 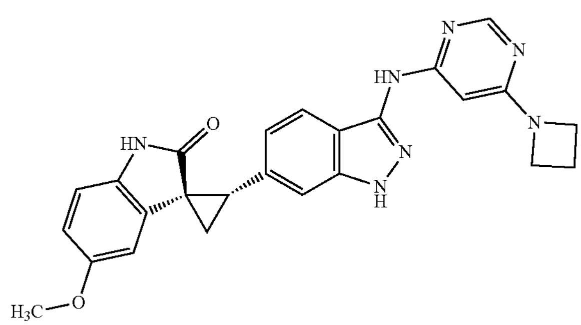 [SMILES: COc1ccc2c(c1)[C@]1(C[C@H]1c1ccc3c(Nc4cc(N5CCC5)ncn4)n[nH]c3c1)C(=O)N2] | (1R,2S)-2-(3-{[6-(azetidin-1-yl)pyrimidin-4-yl]amino}-1H-indazol-6-yl)-5'-methoxyspiro[cyclopropane-1,3'-indol]-2'(1'H)-one |
| 46 | 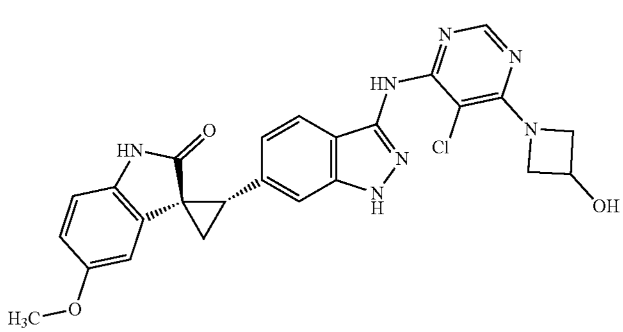 [SMILES: COc1ccc2c(c1)[C@]1(C[C@H]1c1ccc3c(Nc4ncnc(N5CC(O)C5)c4Cl)n[nH]c3c1)C(=O)N2] | (1R,2S)-2-(3-{[5-chloro-6-(3-hydroxyazetidin-1-yl)pyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 47 | 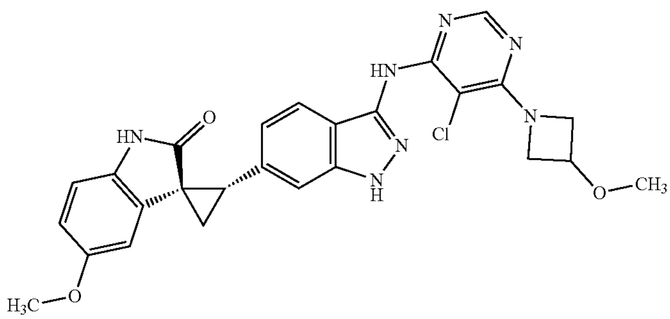 | (1R,2S)-2-(3-{[5-chloro-6-(3-methoxyazetidin-1-yl)pyrimidin-4-yl]amino}-1H-indazol-6-yl)-5'-methoxyspiro[cyclopropane-1,3'-indol]-2'(1'H)-one |
| 48 | 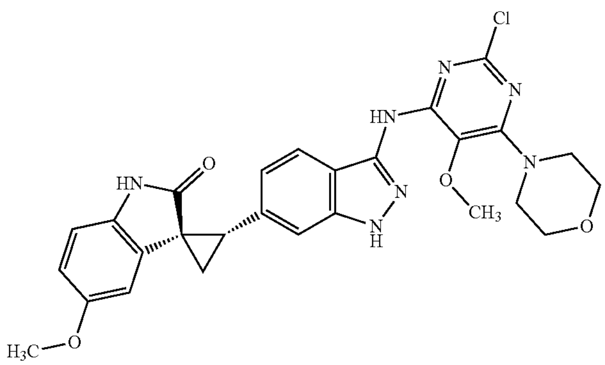 [SMILES: COc1ccc2c(c1)[C@]1(C[C@H]1c1ccc3c(Nc4nc(Cl)nc(N5CCOCC5)c4OC)n[nH]c3c1)C(=O)N2] | (1R,2S)-2-(3-{[2-chloro-5-methoxy-6-(morpholin-4-yl)pyrimidin-4-yl]amino}-1H-indazol-6-yl)-5'-methoxyspiro[cyclopropane-1,3'-indol]-2'(1'H)-one |
| 49 | 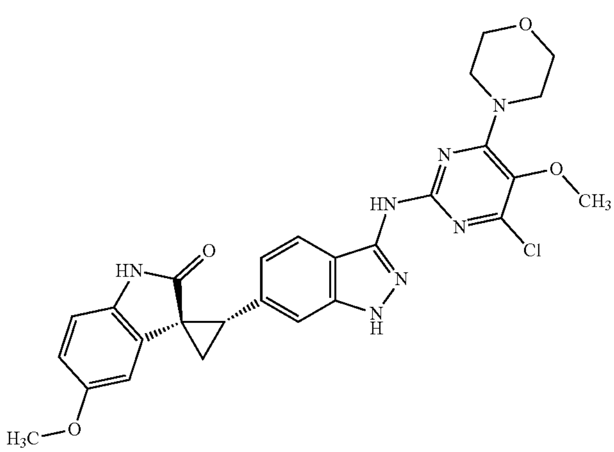 | (1R,2S)-2-(3-{[4-chloro-5-methoxy-6-(morpholin-4-yl)pyrimidin-2-yl]amino}-1H-indazol-6-yl)-5'-methoxyspiro[cyclopropane-1,3'-indol]-2'(1'H)-one |
| 50 | 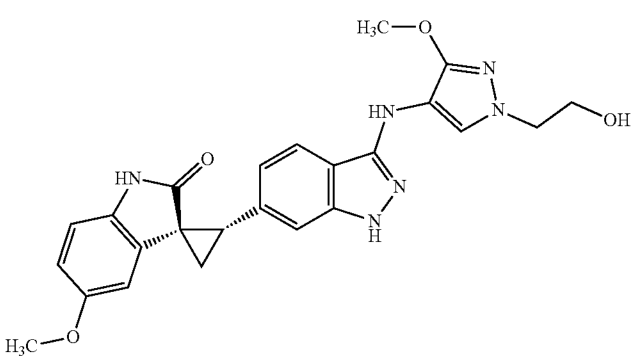 [SMILES: COc1ccc2c(c1)[C@]1(C[C@H]1c1ccc3c(Nc4cn(CCO)nc4OC)n[nH]c3c1)C(=O)N2] | (1R,2S)-2-(3-{[1-(2-hydroxyethyl)-3-methoxy-1H-pyrazol-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 51 | 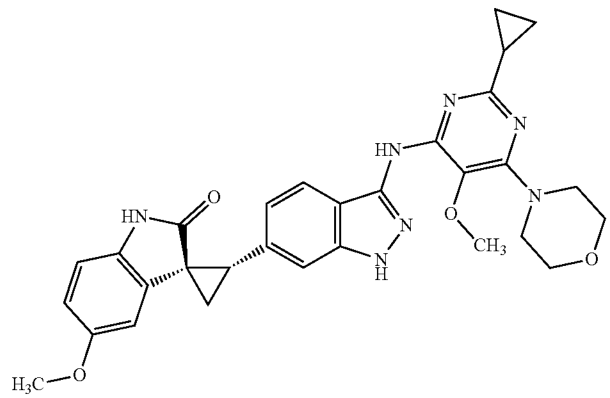 [SMILES: COc1ccc2c(c1)[C@]1(C[C@H]1c1ccc3c(Nc4nc(C5CC5)nc(N5CCOCC5)c4OC)n[nH]c3c1)C(=O)N2] | (1R,2S)-2-(3-{[2-cyclopropyl-5-methoxy-6-(morpholin-4-yl)pyrimidin-4-yl]amino}-1H-indazol-6-yl)-5'-methoxyspiro[cyclopropane-1,3'-indol]-2'(1'H)-one |
| 52 | 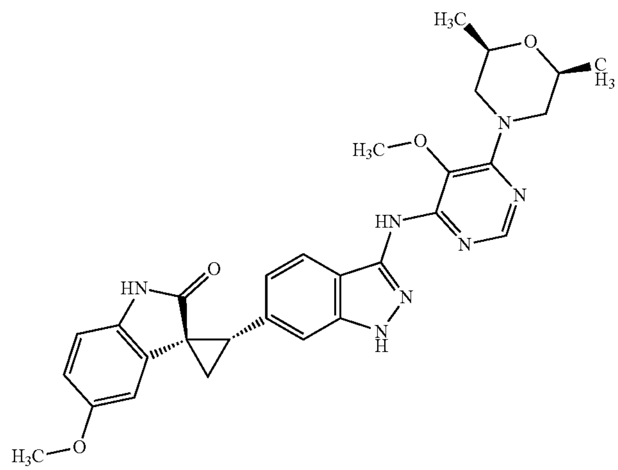 | (1R,2S)-2-[3-({6-[(2R,6S)-2,6-dimethylmorpholin-4-yl]-5-methoxypyrimidin-4-yl}amino)-1H-indazol-6-yl]-5'-methoxyspiro[cyclopropane-1,3'-indol]-2'(1'H)-one |
| 53 | 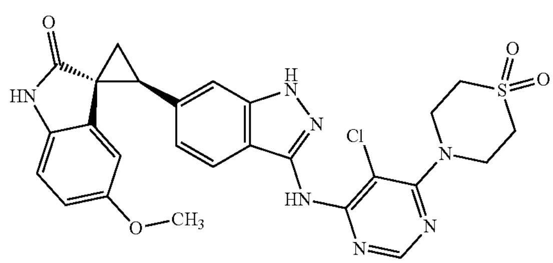 [SMILES: COc1ccc2c(c1)[C@]1(C[C@H]1c1ccc3c(Nc4ncnc(N5CCS(=O)(=O)CC5)c4Cl)n[nH]c3c1)C(=O)N2] | (1R,2S)-2-(3-((5-chloro-6-(1,1-dioxidothiomorpholino)pyrimidin-4-yl)amino)-1H-indazol-6-yl)-5'-methoxyspiro[cyclopropane-1,3'-indolin]-2'-one |
| 54 | 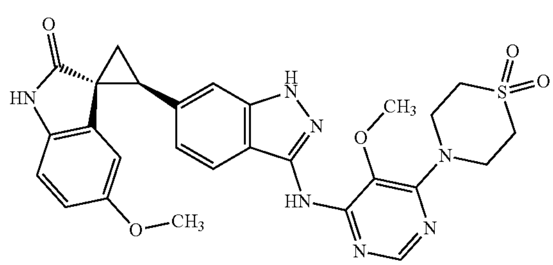 [SMILES: COc1ccc2c(c1)[C@]1(C[C@H]1c1ccc3c(Nc4ncnc(N5CCS(=O)(=O)CC5)c4OC)n[nH]c3c1)C(=O)N2] | (1R,2S)-2-(3-((6-(1,1-dioxidothiomorpholino)-5-methoxypyrimidin-4-yl)amino)-1H-indazol-6-yl)-5'-methoxyspiro[cyclopropane-1,3'-indolin]-2'-one |

TABLE 1A-continued

| Example No. | Structure | Name |
|---|---|---|
| 55 | 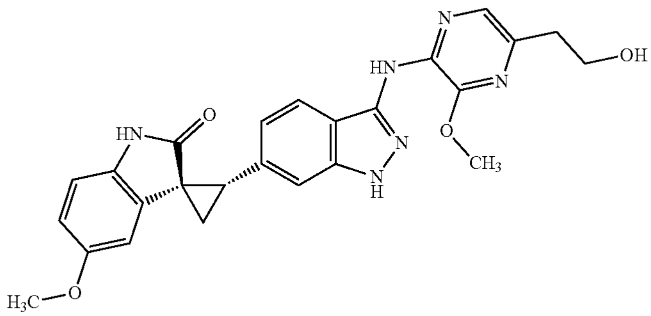 [SMILES: COc1ccc2c(c1)[C@]1(C[C@H]1c1ccc3c(Nc4ncc(CCO)nc4OC)n[nH]c3c1)C(=O)N2] | (1R,2S)-2-(3-{[5-(2-hydroxyethyl)-3-methoxypyrazin-2-yl]amino}-1H-indazol-6-yl)-5'-methoxyspiro[cyclopropane-1,3'-indol]-2'(1'H)-one |
| 56 | 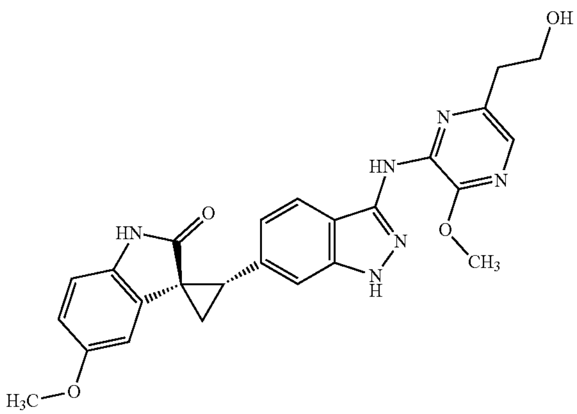 [SMILES: COc1ccc2c(c1)[C@]1(C[C@H]1c1ccc3c(Nc4nc(CCO)cnc4OC)n[nH]c3c1)C(=O)N2] | (1R,2S)-2-(3-{[6-(2-hydroxyethyl)-3-methoxypyrazin-2-yl]amino}-1H-indazol-6-yl)-5'-methoxyspiro[cyclopropane-1,3'-indol]-2'(1'H)-one |
| 57 | 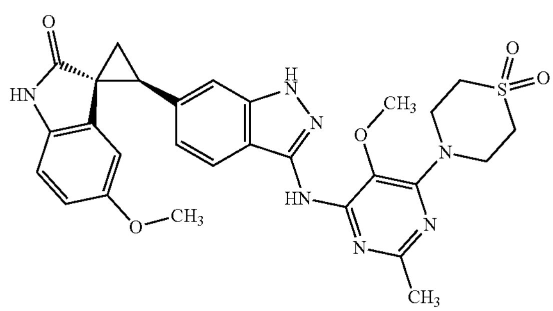 [SMILES: COc1ccc2c(c1)[C@]1(C[C@H]1c1ccc3c(Nc4nc(C)nc(N5CCS(=O)(=O)CC5)c4OC)n[nH]c3c1)C(=O)N2] | (1R,2S)-2-(3-((6-(1,1-dioxidothiomorpholino)-5-methoxy-2-methylpyrimidin-4-yl)amino)-1H-indazol-6-yl)-5'-methoxyspiro[cyclopropane-1,3'-indolin]-2'-one |
| 58 | 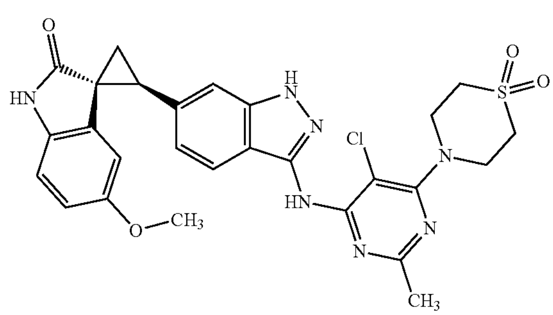 [SMILES: COc1ccc2c(c1)[C@]1(C[C@H]1c1ccc3c(Nc4nc(C)nc(N5CCS(=O)(=O)CC5)c4Cl)n[nH]c3c1)C(=O)N2] | (1R,2S)-2-(3-((5-chloro-6-(1,1-dioxidothiomorpholino)-2-methylpyrimidin-4-yl)amino)-1H-indazol-6-yl)-5'-methoxyspiro[cyclopropane-1,3'-indolin]-2'-one |

TABLE 1A-continued

| Example No. | Structure | Name |
| --- | --- | --- |
| 59 | 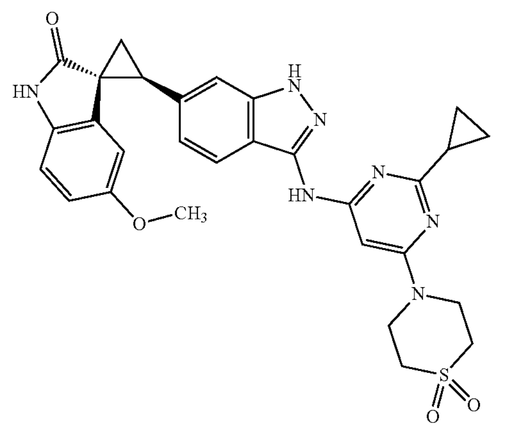 [SMILES: COc1ccc2c(c1)[C@]1(C[C@H]1c1ccc3c(Nc4cc(N5CCS(=O)(=O)CC5)nc(C5CC5)n4)n[nH]c3c1)C(=O)N2] | (1R,2S)-2-(3-((2-cyclopropyl-6-(1,1-dioxidothiomorpholino)pyrimidin-4-yl)amino)-1H-indazol-6-yl)-5'-methoxyspiro[cyclopropane-1,3'-indolin]-2'-one |
| 60 | 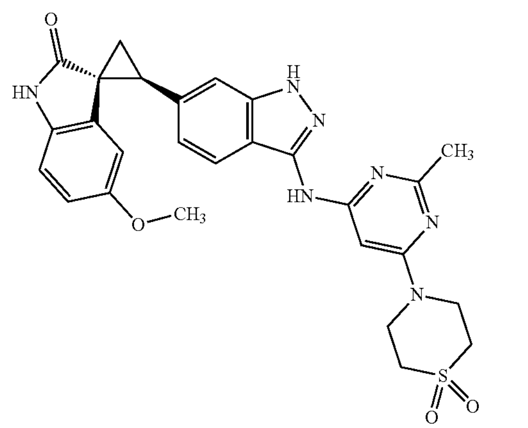 [SMILES: COc1ccc2c(c1)[C@]1(C[C@H]1c1ccc3c(Nc4cc(N5CCS(=O)(=O)CC5)nc(C)n4)n[nH]c3c1)C(=O)N2] | (1R,2S)-2-(3-((6-(1,1-dioxidothiomorpholino)-2-methylpyrimidin-4-yl)amino)-1H-indazol-6-yl)-5'-methoxyspiro[cyclopropane-1,3'-indolin]-2'-one |
| 61 | 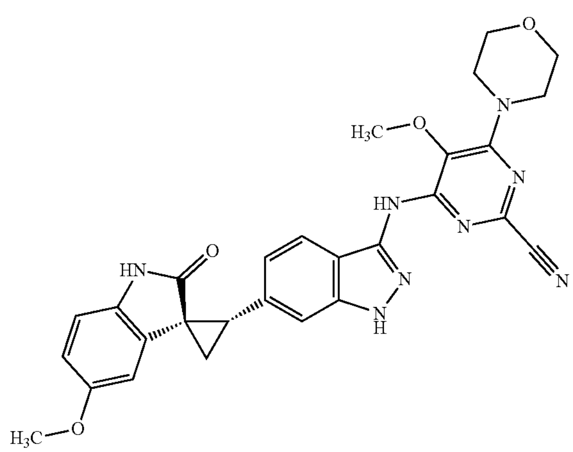 [SMILES: COc1ccc2c(c1)[C@]1(C[C@H]1c1ccc3c(Nc4nc(C#N)nc(N5CCOCC5)c4OC)n[nH]c3c1)C(=O)N2] | 5-methoxy-4-({6-[(1R,2S)-5'-methoxy-2'-oxo-1',2'-dihydrospiro[cyclopropane-1,3'-indol]-2-yl]-1H-indazol-3-yl}amino)-6-(morpholin-4-yl)pyrimidine-2-carbonitrile |

TABLE 1A-continued

| Example No. | Structure | Name |
|---|---|---|
| 62 | 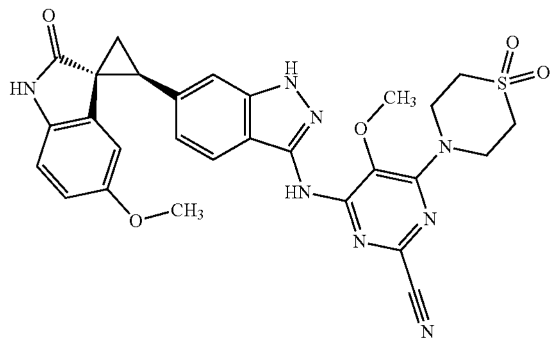 [SMILES: COc1ccc2c(c1)[C@]1(C[C@H]1c1ccc3c(Nc4nc(C#N)nc(N5CCS(=O)(=O)CC5)c4OC)n[nH]c3c1)C(=O)N2] | 4-(1,1-dioxidothiomorpholino)-5-methoxy-6-((6-((1R,2S)-5'-methoxy-2'-oxospiro[cyclopropane-1,3'-indolin]-2-yl)-1H-indazol-3-yl)amino)pyrimidine-2-carbonitrile |
| 63 | 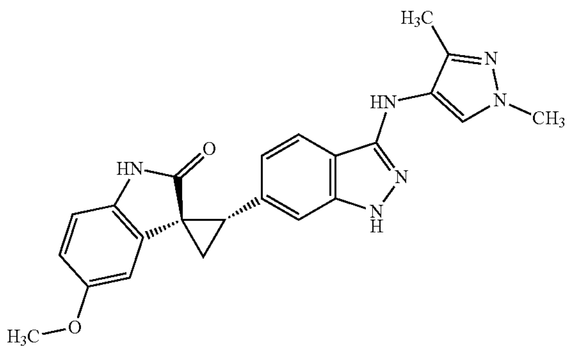 | (1R,2S)-2-{3-[(1,3-dimethyl-1H-pyrazol-4-yl)amino]-1H-indazol-6-yl}-5'-methoxyspiro[cyclopropane-1,3'-indol]-2'(1'H)-one |
| 64 | 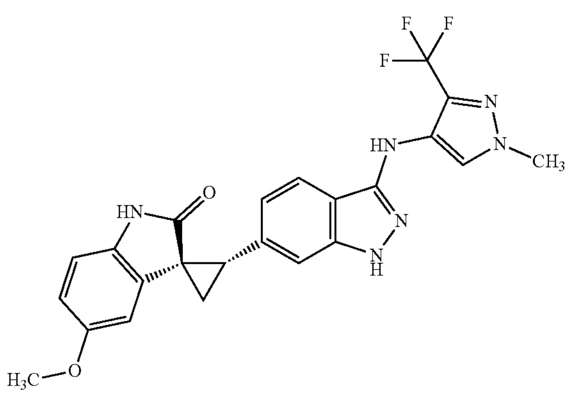 | (1R,2S)-5'-methoxy-2-(3-{[1-methyl-3-(trifluoromethyl)-1H-pyrazol-4-yl]amino}-1H-indazol-6-yl)spiro[cyclopropane-1,3'-indol]-2'(1'H)-one |
| 65 | 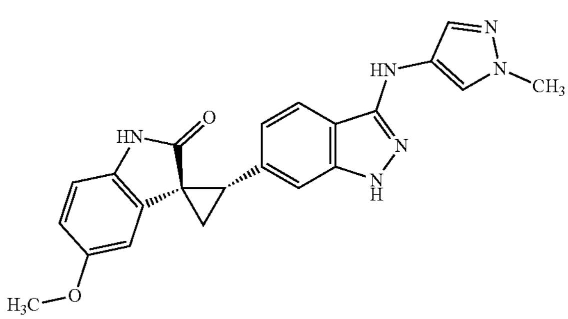 | (1R,2S)-5'-methoxy-2-{3-[(1-methyl-1H-pyrazol-4-yl)amino]-1H-indazol-6-yl}spiro[cyclopropane-1,3'-indol]-2'(1'H)-one |

TABLE 1A-continued

| Example No. | Structure | Name |
|---|---|---|
| 66 | 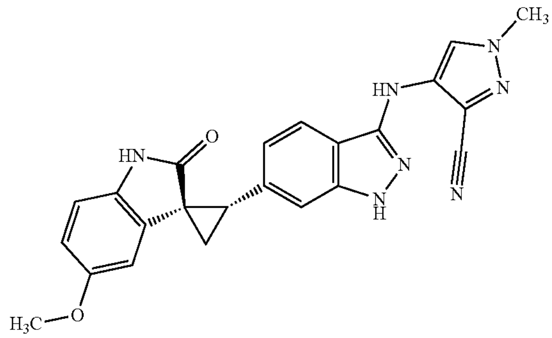 | 4-({6-[(1R,2S)-5'-methoxy-2'-oxo-1',2'-dihydrospiro[cyclopropane-1,3'-indol]-2-yl]-1H-indazol-3-yl}amino)-1-methyl-1H-pyrazole-3-carbonitrile |
| 67 | 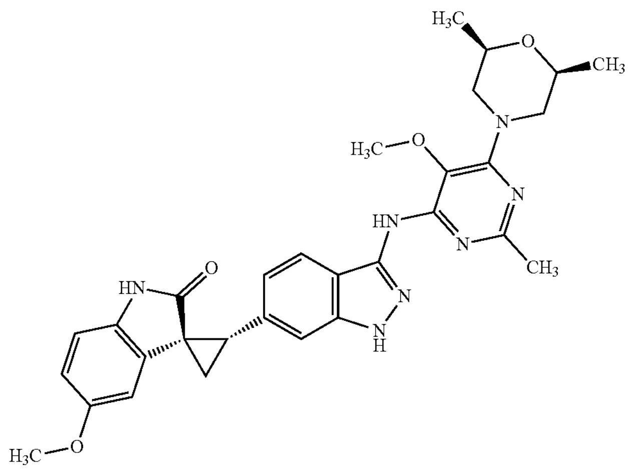 | (1R,2S)-2-[3-({6-[(2R,6S)-2,6-dimethylmorpholin-4-yl]-5-methoxy-2-methylpyrimidin-4-yl}amino)-1H-indazol-6-yl]-5'-methoxyspiro[cyclopropane-1,3'-indol]-2'(1'H)-one |
| 68 | 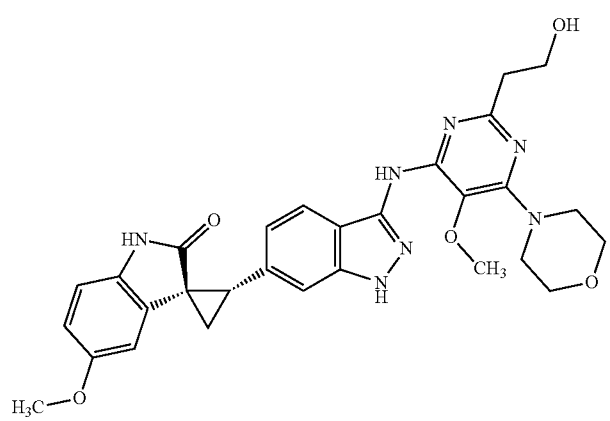 [SMILES: COc1ccc2c(c1)[C@]1(C[C@H]1c1ccc3c(Nc4nc(CCO)nc(N5CCOCC5)c4OC)n[nH]c3c1)C(=O)N2] | (1R,2S)-2-(3-{[2-(2-hydroxyethyl)-5-methoxy-6-(morpholin-4-yl)pyrimidin-4-yl]amino}-1H-indazol-6-yl)-5'-methoxyspiro[cyclopropane-1,3'-indol]-2'(1'H)-one |
| 69 | 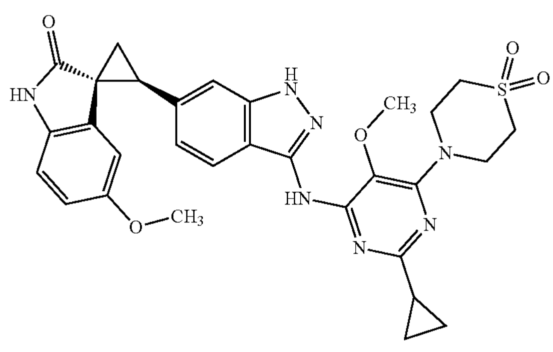 [SMILES: COc1ccc2c(c1)[C@]1(C[C@H]1c1ccc3c(Nc4nc(C5CC5)nc(N5CCS(=O)(=O)CC5)c4OC)n[nH]c3c1)C(=O)N2] | (1R,2S)-2-(3-((2-cyclopropyl-6-(1,1-dioxidothiomorpholino)-5-methoxypyrimidin-4-yl)amino)-1H-indazol-6-yl)-5'-methoxyspiro[cyclopropane-1,3'-indolin]-2'-one |

TABLE 1A-continued

| Example No. | Structure | Name |
|---|---|---|
| 70 | 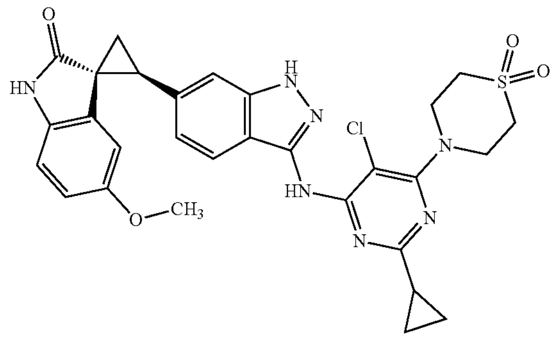 [SMILES: COc1ccc2c(c1)[C@]1(C[C@H]1c1ccc3c(Nc4nc(C5CC5)nc(N5CCS(=O)(=O)CC5)c4Cl)n[nH]c3c1)C(=O)N2] | (1R,2S)-2-(3-((5-chloro-2-cyclopropyl-6-(1,1-dioxidothiomorpholino)pyrimidin-4-yl)amino)-1H-indazol-6-yl)-5'-methoxyspiro[cyclopropane-1,3'-indolin]-2'-one |
| 71 | 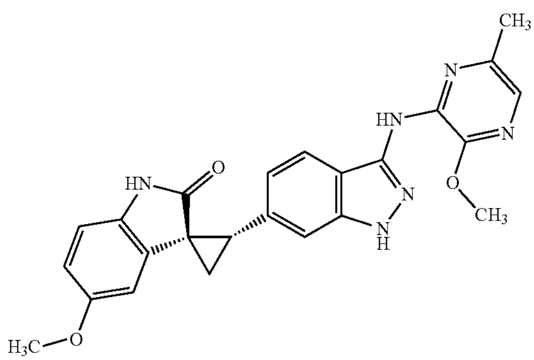 [SMILES: COc1ccc2c(c1)[C@]1(C[C@H]1c1ccc3c(Nc4nc(C)cnc4OC)n[nH]c3c1)C(=O)N2] | (1R,2S)-5'-methoxy-2-{3-[(3-methoxy-6-methylpyrazin-2-yl)amino]-1H-indazol-6-yl}spiro[cyclopropane-1,3'-indol]-2'(1'H)-one |
| 72 | 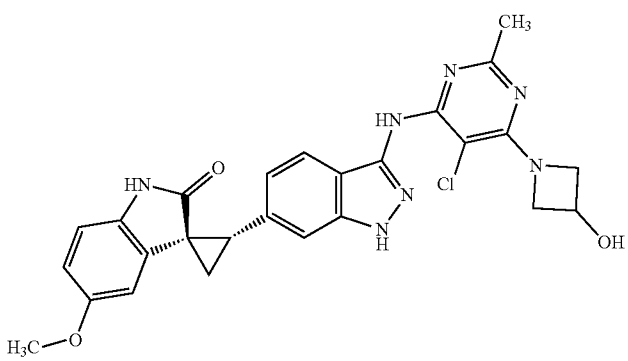 [SMILES: COc1ccc2c(c1)[C@]1(C[C@H]1c1ccc3c(Nc4nc(C)nc(N5CC(O)C5)c4Cl)n[nH]c3c1)C(=O)N2] | (1R,2S)-2-(3-{[5-chloro-6-(3-hydroxyazetidin-1-yl)-2-methylpyrimidin-4-yl]amino}-1H-indazol-6-yl)-5'-methoxyspiro[cyclopropane-1,3'-indol]-2'(1'H)-one |
| 73 | 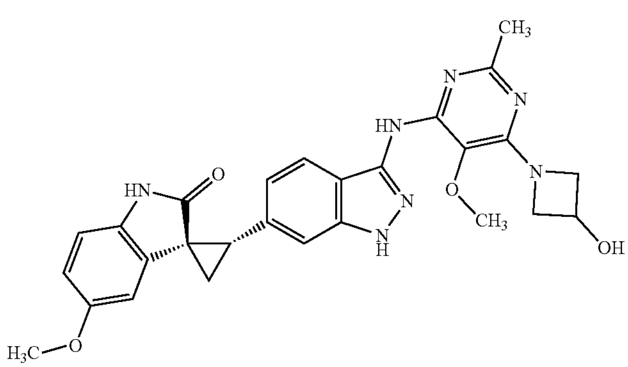 [SMILES: COc1ccc2c(c1)[C@]1(C[C@H]1c1ccc3c(Nc4nc(C)nc(N5CC(O)C5)c4OC)n[nH]c3c1)C(=O)N2] | (1R,2S)-2-(3-{[6-(3-hydroxyazetidin-1-yl)-5-methoxy-2-methylpyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 74 | 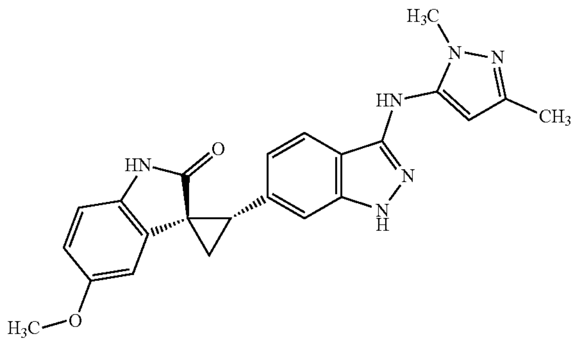 | (1R,2S)-2-{3-[(1,3-dimethyl-1H-pyrazol-5-yl)amino]-1H-indazol-6-yl}-5'-methoxyspiro[cyclopropane-1,3'-indol]-2'(1'H)-one |
| 75 | 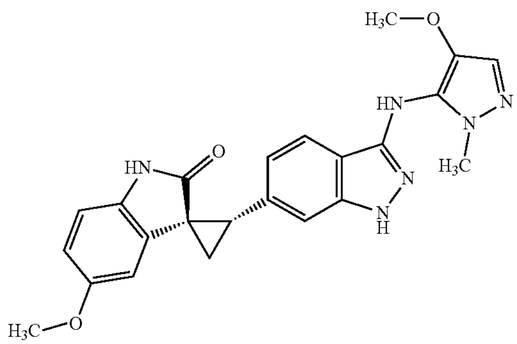 [SMILES: COc1ccc2c(c1)[C@]1(C[C@H]1c1ccc3c(Nc4c(OC)cnn4C)n[nH]c3c1)C(=O)N2] | (1R,2S)-5'-methoxy-2-{3-[(4-methoxy-1-methyl-1H-pyrazol-5-yl)amino]-1H-indazol-6-yl}spiro[cyclopropane-1,3'-indol]-2'(1'H)-one |
| 76 | 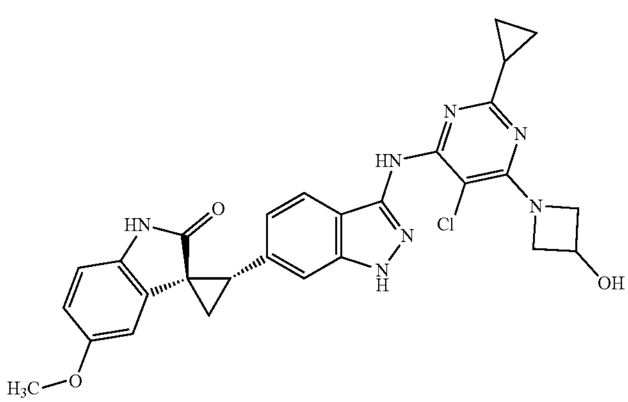 [SMILES: COc1ccc2c(c1)[C@]1(C[C@H]1c1ccc3c(Nc4nc(C5CC5)nc(N5CC(O)C5)c4Cl)n[nH]c3c1)C(=O)N2] | (1R,2S)-2-(3-{[5-chloro-2-cyclopropyl-6-(3-hydroxyazetidin-1-yl)pyrimidin-4-yl]amino}-1H-indazol-6-yl)-5'-methoxyspiro[cyclopropane-1,3'-indol]-2'(1'H)-one |
| 77 | 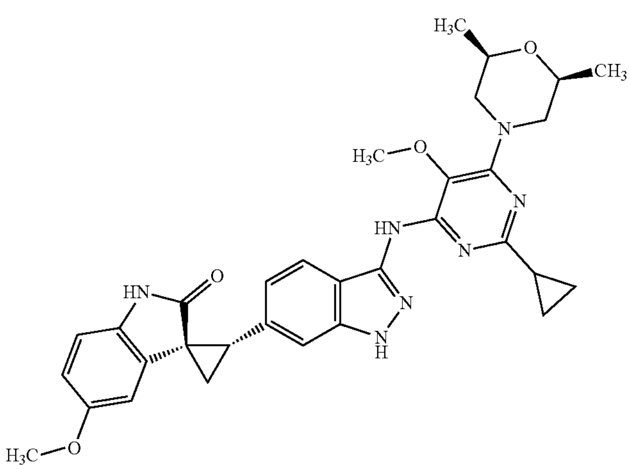 | (1R,2S)-2-[3-({2-cyclopropyl-6-[(2R,6S)-2,6-dimethylmorpholin-4-yl]-5-methoxypyrimidin-4-yl}amino)-1H-indazol-6-yl]-5'-methoxyspiro[cyclopropane-1,3'-indol]-2'(1'H)-one |

TABLE 1A-continued

| Example No. | Structure | Name |
|---|---|---|
| 78 | 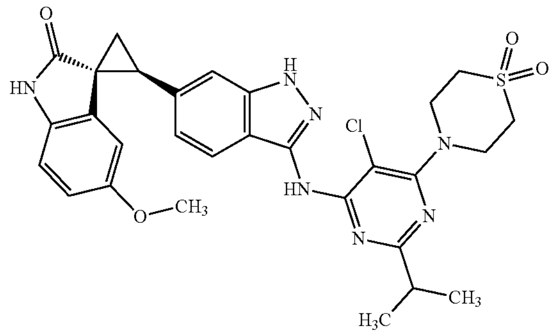 [SMILES: COc1ccc2c(c1)[C@]1(C[C@H]1c1ccc3c(Nc4nc(C(C)C)nc(N5CCS(=O)(=O)CC5)c4Cl)n[nH]c3c1)C(=O)N2] | (1R,2S)-2-(3-((5-chloro-6-(1,1-dioxidothiomorpholino)-2-isopropylpyrimidin-4-yl)amino)-1H-indazol-6-yl)-5'-methoxyspiro[cyclopropane-1,3'-indolin]-2'-one |
| 79 | 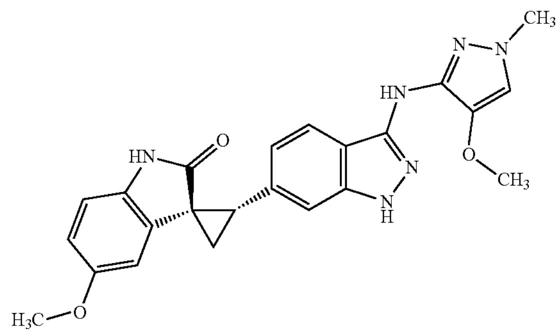 | (1R,2S)-5'-methoxy-2-{3-[(4-methoxy-1-methyl-1H-pyrazol-3-yl)amino]-1H-indazol-6-yl}spiro[cyclopropane-1,3'-indol]-2'(1'H)-one |
| 80 | 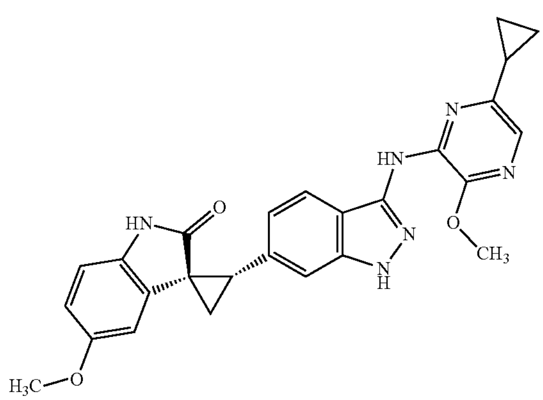 [SMILES: COc1ccc2c(c1)[C@]1(C[C@H]1c1ccc3c(Nc4nc(C5CC5)cnc4OC)n[nH]c3c1)C(=O)N2] | (1R,2S)-2-{3-[(6-cyclopropyl-3-methoxypyrazin-2-yl)amino]-1H-indazol-6-yl}-5'-methoxyspiro[cyclopropane-1,3'-indol]-2'(1'H)-one |
| 81 | 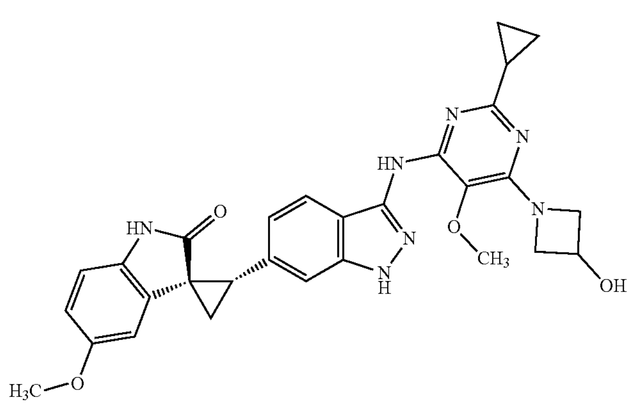 [SMILES: COc1ccc2c(c1)[C@]1(C[C@H]1c1ccc3c(Nc4nc(C5CC5)nc(N5CC(O)C5)c4OC)n[nH]c3c1)C(=O)N2] | (1R,2S)-2-(3-{[2-cyclopropyl-6-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 82 | 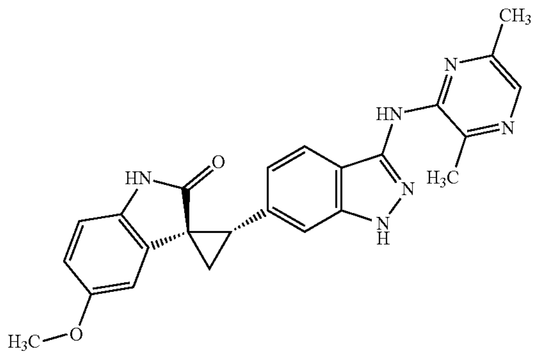 [SMILES: COc1ccc2c(c1)[C@]1(C[C@H]1c1ccc3c(Nc4nc(C)cnc4C)n[nH]c3c1)C(=O)N2] | (1R,2S)-2-{3-[(3,6-dimethylpyrazin-2-yl)amino]-1H-indazol-6-yl}-5'-methoxyspiro[cyclopropane-1,3'-indol]-2'(1'H)-one |
| 83 | 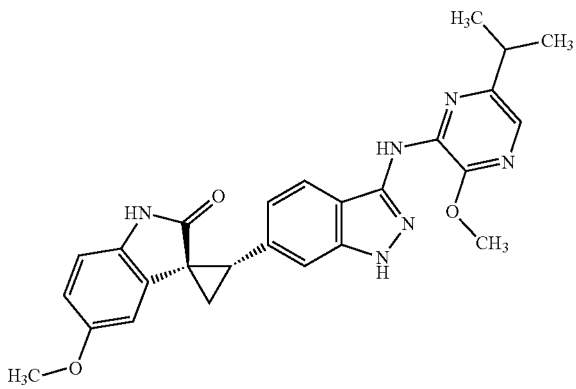 [SMILES: COc1ccc2c(c1)[C@]1(C[C@H]1c1ccc3c(Nc4nc(C(C)C)cnc4OC)n[nH]c3c1)C(=O)N2] | (1R,2S)-5'-methoxy-2-(3-{[3-methoxy-6-(propan-2-yl)pyrazin-2-yl]amino}-1H-indazol-6-yl)spiro[cyclopropane-1,3'-indol]-2'(1'H)-one |
| 84 | 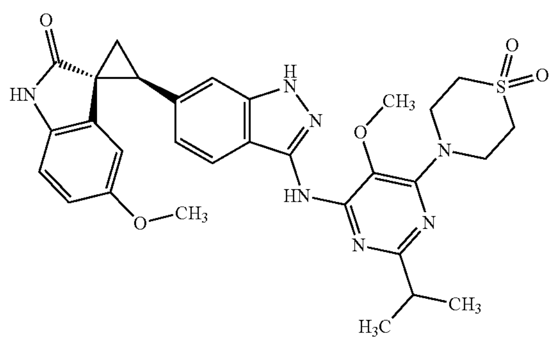 [SMILES: COc1ccc2c(c1)[C@]1(C[C@H]1c1ccc3c(Nc4nc(C(C)C)nc(N5CCS(=O)(=O)CC5)c4OC)n[nH]c3c1)C(=O)N2] | (1R,2S)-2-(3-((6-(1,1-dioxidothiomorpholino)-2-isopropyl-5-methoxypyrimidin-4-yl)amino)-1H-indazol-6-yl)-5'-methoxyspiro[cyclopropane-1,3'-indolin]-2'-one |
| 85 | 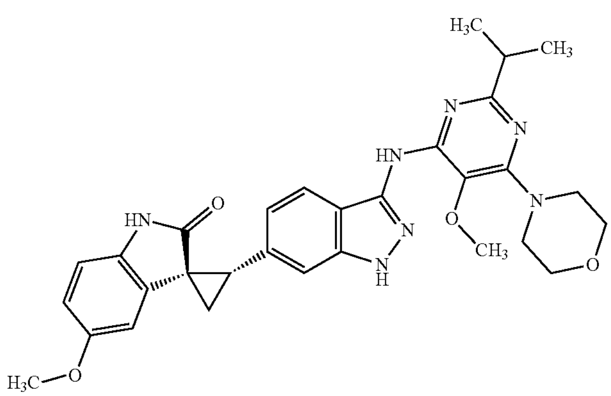 [SMILES: COc1ccc2c(c1)[C@]1(C[C@H]1c1ccc3c(Nc4nc(C(C)C)nc(N5CCOCC5)c4OC)n[nH]c3c1)C(=O)N2] | (1R,2S)-5'-methoxy-2-(3-{[5-methoxy-6-(morpholin-4-yl)-2-(propan-2-yl)pyrimidin-4-yl]amino}-1H-indazol-6-yl)spiro[cyclopropane-1,3'-indol]-2'(1'H)-one |

TABLE 1A-continued

| Example No. | Name |
|---|---|
| 86 | (1R,2S)-5'-methoxy-2-{3-[(5-methoxy-2-methylpyridin-4-yl)amino]-1H-indazol-6-yl}spiro[cyclopropane-1,3'-indol]-2'(1'H)-one |
| 87 | (1R,2S)-5'-methoxy-2-{3-[(5-methoxy-2-methylpyrimidin-4-yl)amino]-1H-indazol-6-yl}spiro[cyclopropane-1,3'-indol]-2'(1'H)-one |
| 88 | (1R,2S)-5'-methoxy-2-{3-[(3-methoxy-6-methylpyridin-2-yl)amino]-1H-indazol-6-yl}spiro[cyclopropane-1,3'-indol]-2'(1'H)-one |
| 89 | (1R,2S)-5'-methoxy-2-{3-[(2-methoxy-5-methylpyridin-3-yl)amino]-1H-indazol-6-yl}spiro[cyclopropane-1,3'-indol]-2'(1'H)-one |

TABLE 1A-continued

| Example No. | Structure | Name |
|---|---|---|
| 90 | 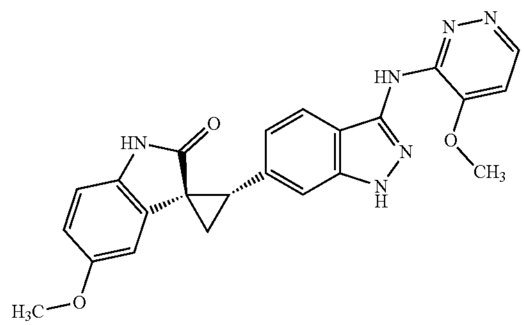 [SMILES: COc1ccc2c(c1)[C@]1(C[C@H]1c1ccc3c(Nc4nnccc4OC)n[nH]c3c1)C(=O)N2] | (1R,2S)-5'-methoxy-2-{3-[(4-methoxypyridazin-3-yl)amino]-1H-indazol-6-yl}spiro[cyclopropane-1,3'-indol]-2'(1'H)-one |
| 91 | 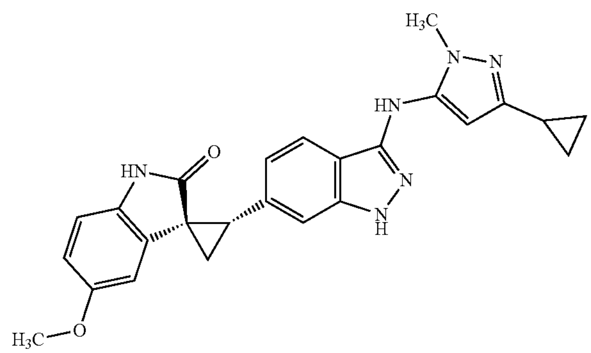 [SMILES: COc1ccc2c(c1)[C@]1(C[C@H]1c1ccc3c(Nc4cc(C5CC5)nn4C)n[nH]c3c1)C(=O)N2] | (1R,2S)-2-{3-[(3-cyclopropyl-1-methyl-1H-pyrazol-5-yl)amino]-1H-indazol-6-yl}-5'-methoxyspiro[cyclopropane-1,3'-indol]-2'(1'H)-one |
| 92 | 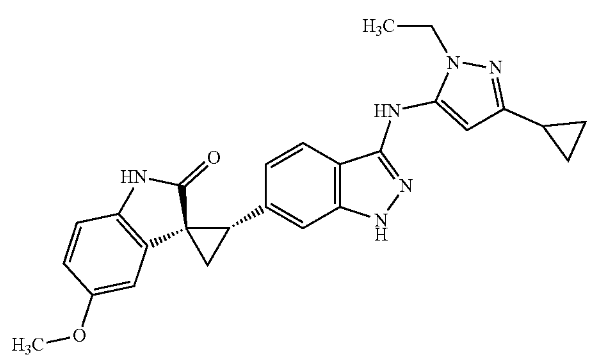 [SMILES: CCn1nc(C2CC2)cc1Nc1n[nH]c2cc([C@@H]3C[C@@]34C(=O)Nc3ccc(OC)cc34)ccc12] | (1R,2S)-2-{3-[(3-cyclopropyl-1-ethyl-1H-pyrazol-5-yl)amino]-1H-indazol-6-yl}-5'-methoxyspiro[cyclopropane-1,3'-indol]-2'(1'H)-one |
| 93 | 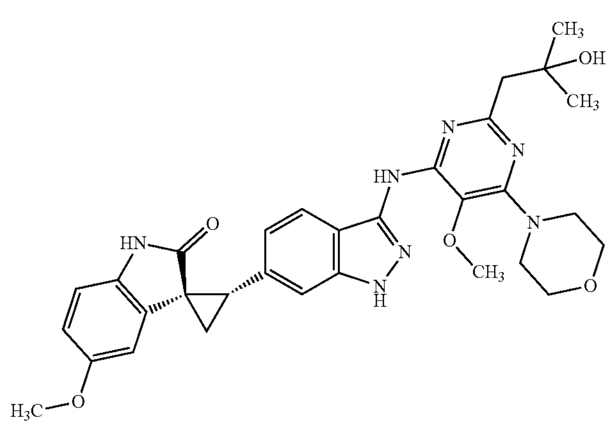 [SMILES: COc1ccc2c(c1)[C@]1(C[C@H]1c1ccc3c(Nc4nc(CC(C)(C)O)nc(N5CCOCC5)c4OC)n[nH]c3c1)C(=O)N2] | (1R,2S)-2-(3-{[2-(2-hydroxy-2-methylpropyl)-5-methoxy-6-(morpholin-4-yl)pyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 94 | 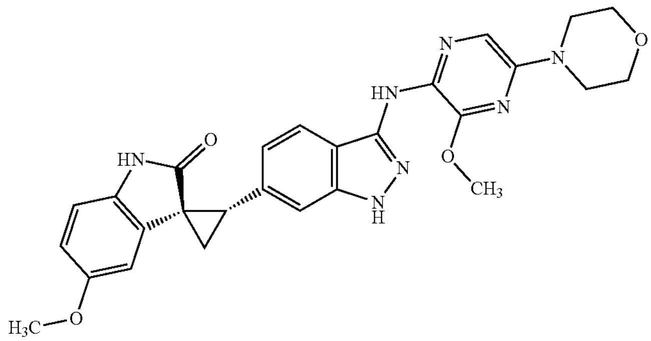 [SMILES: COc1ccc2c(c1)[C@]1(C[C@H]1c1ccc3c(Nc4ncc(N5CCOCC5)nc4OC)n[nH]c3c1)C(=O)N2] | (1R,2S)-5'-methoxy-2-(3-{[3-methoxy-5-(morpholin-4-yl)pyrazin-2-yl]amino}-1H-indazol-6-yl)spiro[cyclopropane-1,3'-indol]-2'(1'H)-one |
| 95 | 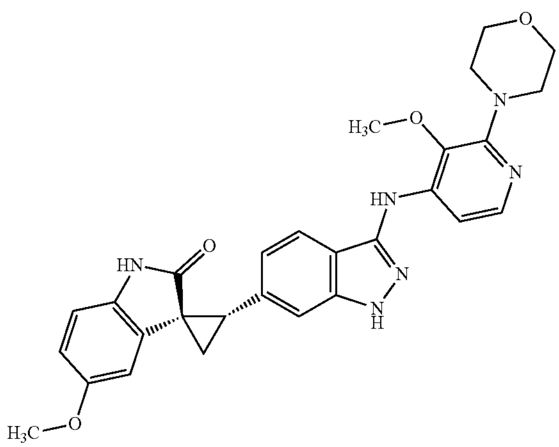 [SMILES: COc1ccc2c(c1)[C@]1(C[C@H]1c1ccc3c(Nc4ccnc(N5CCOCC5)c4OC)n[nH]c3c1)C(=O)N2] | (1R,2S)-5'-methoxy-2-(3-{[3-methoxy-2-(morpholin-4-yl)pyridin-4-yl]amino}-1H-indazol-6-yl)spiro[cyclopropane-1,3'-indol]-2'(1'H)-one |
| 96 | 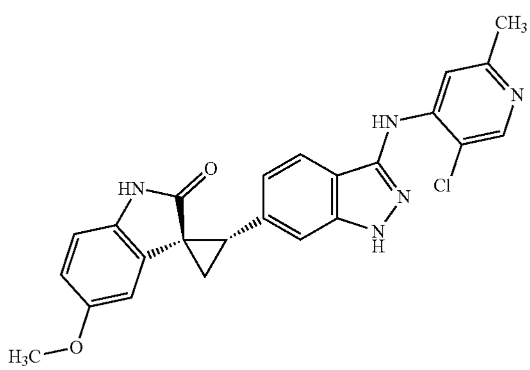 [SMILES: COc1ccc2c(c1)[C@]1(C[C@H]1c1ccc3c(Nc4cc(C)ncc4Cl)n[nH]c3c1)C(=O)N2] | (1R,2S)-2-{3-[(5-chloro-2-methylpyridin-4-yl)amino]-1H-indazol-6-yl}-5'-methoxyspiro[cyclopropane-1,3'-indol]-2'(1'H)-one |
| 97 | 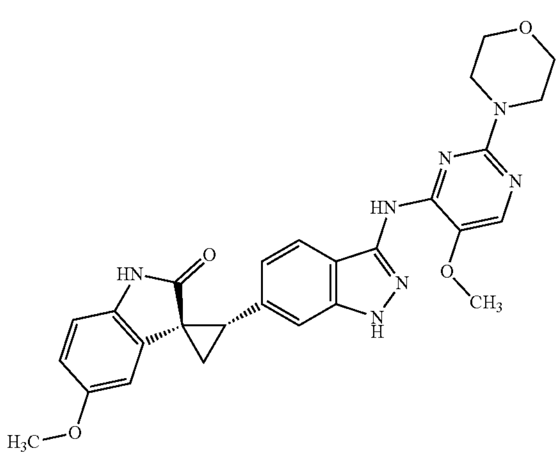 [SMILES: COc1ccc2c(c1)[C@]1(C[C@H]1c1ccc3c(Nc4nc(N5CCOCC5)ncc4OC)n[nH]c3c1)C(=O)N2] | (1R,2S)-5'-methoxy-2-(3-{[5-methoxy-2-(morpholin-4-yl)pyrimidin-4-yl]amino}-1H-indazol-6-yl)spiro[cyclopropane-1,3'-indol]-2'(1'H)-one |

TABLE 1A-continued

| Example No. | Structure | Name |
|---|---|---|
| 98 | 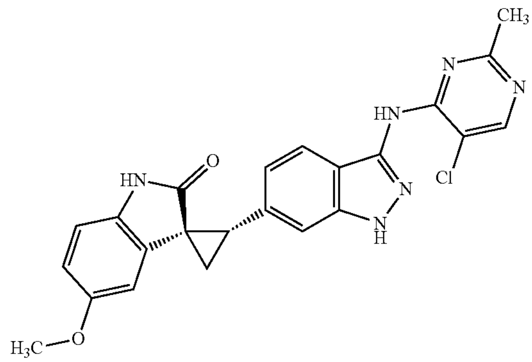 [SMILES: COc1ccc2c(c1)[C@]1(C[C@H]1c1ccc3c(Nc4nc(C)ncc4Cl)n[nH]c3c1)C(=O)N2] | (1R,2S)-2-{3-[(5-chloro-2-methylpyrimidin-4-yl)amino]-1H-indazol-6-yl}-5'-methoxyspiro[cyclopropane-1,3'-indol]-2'(1'H)-one |
| 99 | 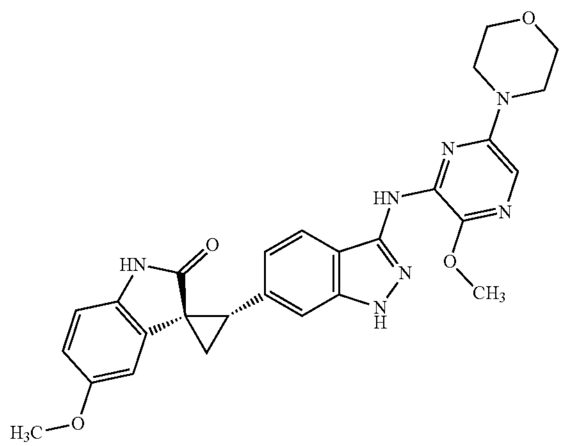 [SMILES: COc1ccc2c(c1)[C@]1(C[C@H]1c1ccc3c(Nc4nc(N5CCOCC5)cnc4OC)n[nH]c3c1)C(=O)N2] | (1R,2S)-5'-methoxy-2-(3-{[3-methoxy-6-(morpholin-4-yl)pyrazin-2-yl]amino}-1H-indazol-6-yl)spiro[cyclopropane-1,3'-indol]-2'(1'H)-one |
| 100 | 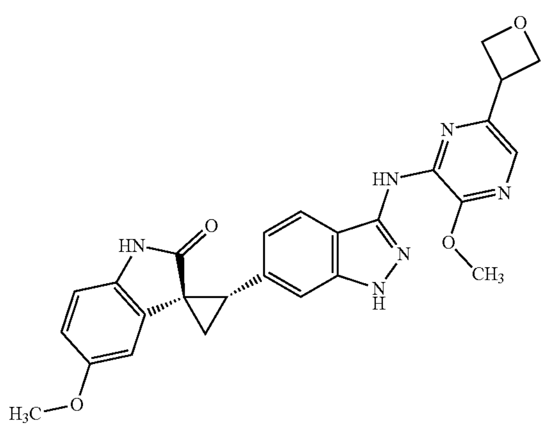 [SMILES: COc1ccc2c(c1)[C@]1(C[C@H]1c1ccc3c(Nc4nc(C5COC5)cnc4OC)n[nH]c3c1)C(=O)N2] | (1R,2S)-5'-methoxy-2-(3-{[3-methoxy-6-(oxetan-3-yl)pyrazin-2-yl]amino}-1H-indazol-6-yl)spiro[cyclopropane-1,3'-indol]-2'(1'H)-one |
| 101 | 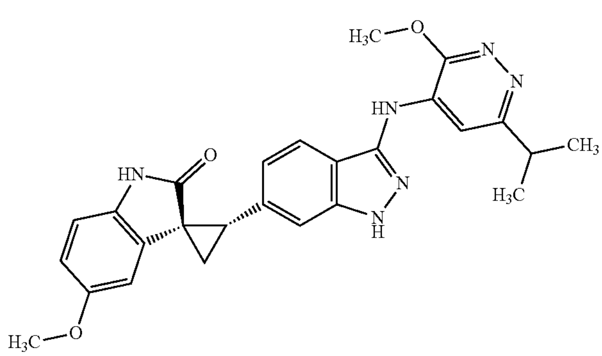 [SMILES: COc1ccc2c(c1)[C@]1(C[C@H]1c1ccc3c(Nc4cc(C(C)C)nnc4OC)n[nH]c3c1)C(=O)N2] | (1R,2S)-5'-methoxy-2-(3-{[3-methoxy-6-(propan-2-yl)pyridazin-4-yl]amino}-1H-indazol-6-yl)spiro[cyclopropane-1,3'-indol]-2'(1'H)-one |

TABLE 1A-continued

| Example No. | Structure | Name |
|---|---|---|
| 102 | 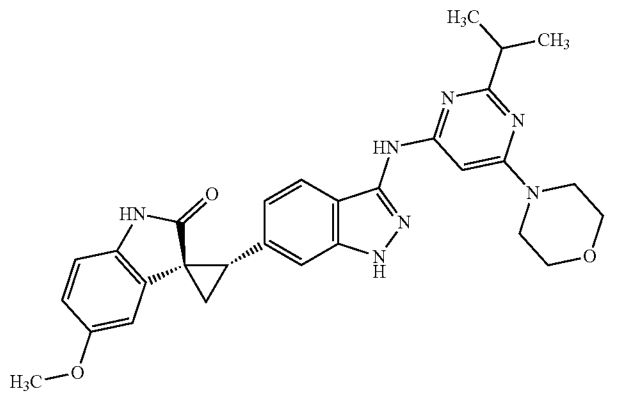 [SMILES: COc1ccc2c(c1)[C@]1(C[C@H]1c1ccc3c(Nc4cc(N5CCOCC5)nc(C(C)C)n4)n[nH]c3c1)C(=O)N2] | (1R,2S)-5'-methoxy-2-(3-{[6-(morpholin-4-yl)-2-(propan-2-yl)pyrimidin-4-yl]amino}-1H-indazol-6-yl)spiro[cyclopropane-1,3'-indol]-2'(1'H)-one |
| 103 | 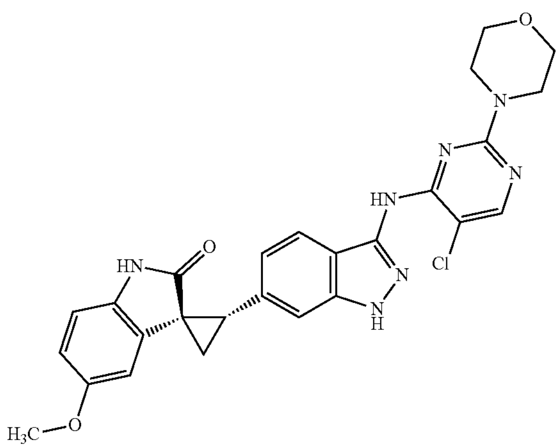 [SMILES: COc1ccc2c(c1)[C@]1(C[C@H]1c1ccc3c(Nc4nc(N5CCOCC5)ncc4Cl)n[nH]c3c1)C(=O)N2] | (1R,2S)-2-(3-{[5-chloro-2-(morpholin-4-yl)pyrimidin-4-yl]amino}-1H-indazol-6-yl)-5'-methoxyspiro[cyclopropane-1,3'-indol]-2'(1'H)-one |
| 104 | 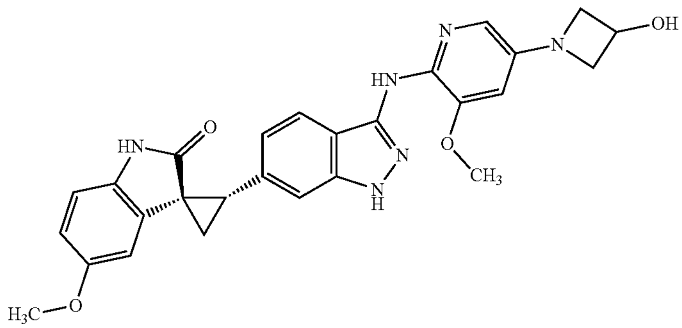 [SMILES: COc1ccc2c(c1)[C@]1(C[C@H]1c1ccc3c(Nc4ncc(N5CC(O)C5)cc4OC)n[nH]c3c1)C(=O)N2] | (1R,2S)-2-(3-{[5-(3-hydroxyazetidin-1-yl)-3-methoxypyridin-2-yl]amino}-1H-indazol-6-yl)-5'-methoxyspiro[cyclopropane-1,3'-indol]-2'(1'H)-one |
| 105 | 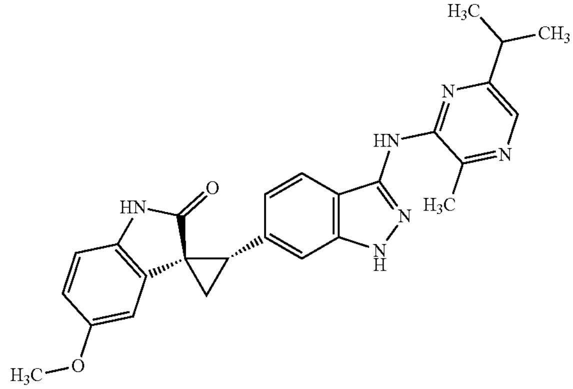 [SMILES: COc1ccc2c(c1)[C@]1(C[C@H]1c1ccc3c(Nc4nc(C(C)C)cnc4C)n[nH]c3c1)C(=O)N2] | (1R,2S)-5'-methoxy-2-(3-{[3-methyl-6-(propan-2-yl)pyrazin-2-yl]amino}-1H-indazol-6-yl)spiro[cyclopropane-1,3'-indol]-2'(1'H)-one |

TABLE 1A-continued

| Example No. | Structure | Name |
|---|---|---|
| 106 | 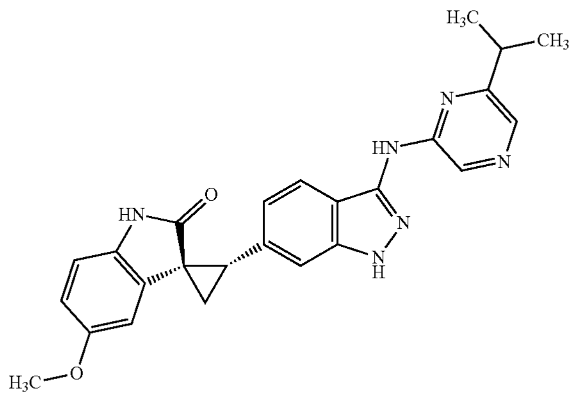 [SMILES: COc1ccc2c(c1)[C@]1(C[C@H]1c1ccc3c(Nc4cncc(C(C)C)n4)n[nH]c3c1)C(=O)N2] | (1R,2S)-5'-methoxy-2-(3-{[6-(propan-2-yl)pyrazin-2-yl]amino}-1H-indazol-6-yl)spiro[cyclopropane-1,3'-indol]-2'(1'H)-one |
| 107 | 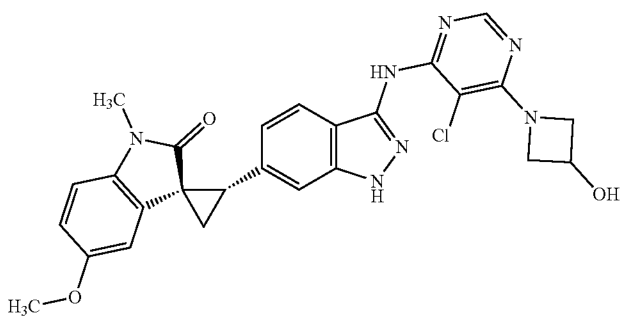 [SMILES: COc1ccc2c(c1)[C@]1(C[C@H]1c1ccc3c(Nc4ncnc(N5CC(O)C5)c4Cl)n[nH]c3c1)C(=O)N2C] | (1R,2S)-2-(3-{[5-chloro-6-(3-hydroxyazetidin-1-yl)pyrimidin-4-yl]amino}-1H-indazol-6-yl)-5'-methoxy-1'-methylspiro[cyclopropane-1,3'-indol]-2'(1'H)-one |
| 108 | 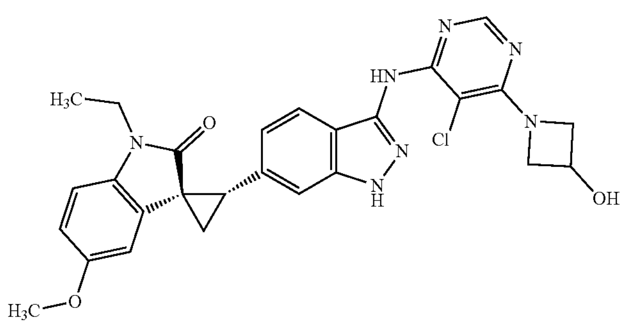 [SMILES: CCN1C(=O)[C@@]2(C[C@H]2c2ccc3c(Nc4ncnc(N5CC(O)C5)c4Cl)n[nH]c3c2)c2cc(OC)ccc21] | (1R,2S)-2-(3-{[5-chloro-6-(3-hydroxyazetidin-1-yl)pyrimidin-4-yl]amino}-1H-indazol-6-yl)-1'-ethyl-5'-methoxyspiro[cyclopropane-1,3'-indol]-2'(1'H)-one |
| 109 | 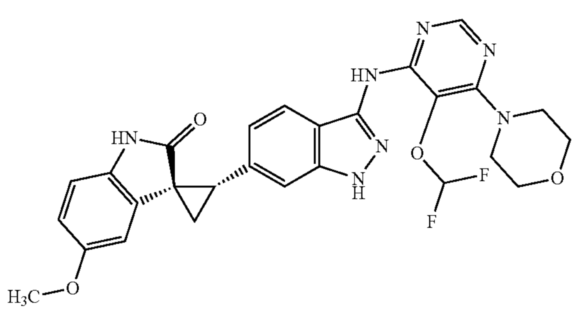 [SMILES: COc1ccc2c(c1)[C@]1(C[C@H]1c1ccc3c(Nc4ncnc(N5CCOCC5)c4OC(F)F)n[nH]c3c1)C(=O)N2] | (1R,2S)-2-(3-{[5-(difluoromethoxy)-6-(morpholin-4-yl)pyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 110 | 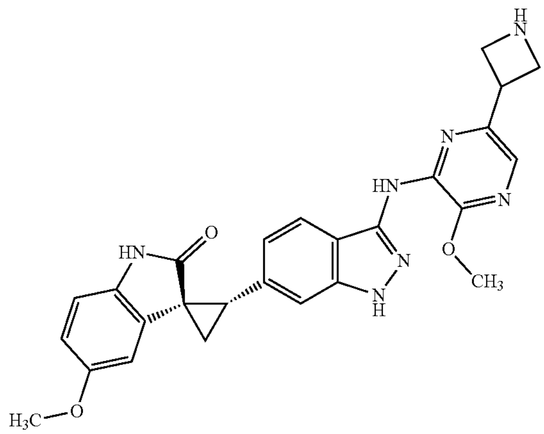 [SMILES: COc1ccc2c(c1)[C@]1(C[C@H]1c1ccc3c(Nc4nc(C5CNC5)cnc4OC)n[nH]c3c1)C(=O)N2] | (1R,2S)-2-(3-{[6-(azetidin-3-yl)-3-methoxypyrazin-2-yl]amino}-1H-indazol-6-yl)-5'-methoxyspiro[cyclopropane-1,3'-indol]-2'(1'H)-one |
| 111 | 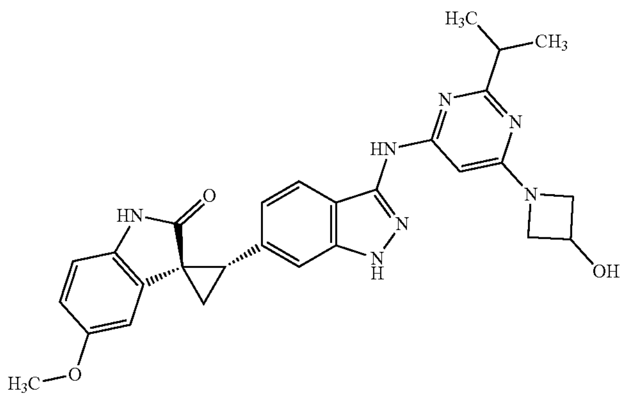 [SMILES: COc1ccc2c(c1)[C@]1(C[C@H]1c1ccc3c(Nc4cc(N5CC(O)C5)nc(C(C)C)n4)n[nH]c3c1)C(=O)N2] | (1R,2S)-2-(3-{[6-(3-hydroxyazetidin-1-yl)-2-(propan-2-yl)pyrimidin-4-yl]amino}-1H-indazol-6-yl)-5'-methoxyspiro[cyclopropane-1,3'-indol]-2'(1'H)-one |
| 112 | 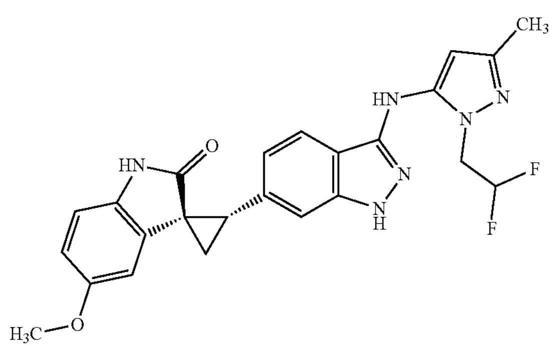 [SMILES: COc1ccc2c(c1)[C@]1(C[C@H]1c1ccc3c(Nc4cc(C)nn4CC(F)F)n[nH]c3c1)C(=O)N2] | (1R,2S)-2-(3-{[1-(2,2-difluoroethyl)-3-methyl-1H-pyrazol-5-yl]amino}-1H-indazol-6-yl)-5'-methoxyspiro[cyclopropane-1,3'-indol]-2'(1'H)-one |
| 113 | 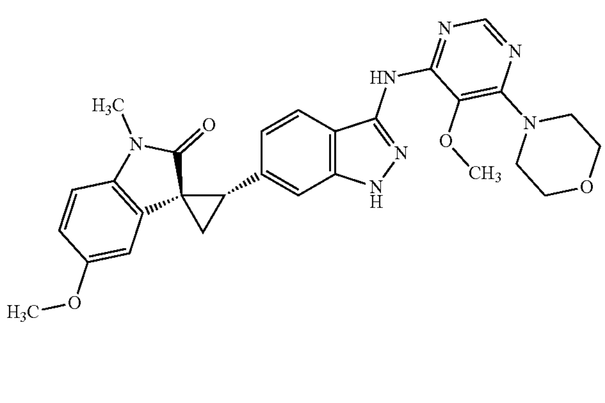 [SMILES: COc1ccc2c(c1)[C@]1(C[C@H]1c1ccc3c(Nc4ncnc(N5CCOCC5)c4OC)n[nH]c3c1)C(=O)N2C] | (1R,2S)-5'-methoxy-2-(3-{[5-methoxy-6-(morpholin-4-yl)pyrimidin-4-yl]amino}-1H-indazol-6-yl)-1'-methylspiro[cyclopropane-1,3'-indol]-2'(1'H)-one |

…
TABLE 1A-continued
| Example No. | Structure | Name |
|---|---|---|
| 114 | 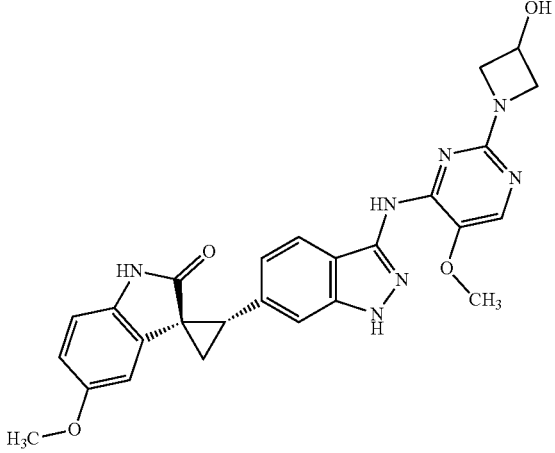 [SMILES: COc1ccc2c(c1)[C@]1(C[C@H]1c1ccc3c(Nc4nc(N5CC(O)C5)ncc4OC)n[nH]c3c1)C(=O)N2] | (1R,2S)-2-(3-{[2-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one |
| 115 | 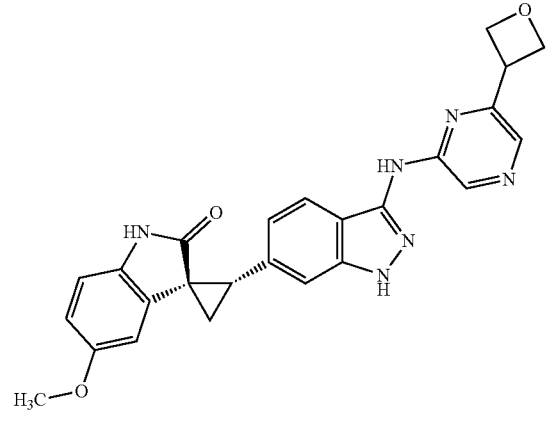 [SMILES: COc1ccc2c(c1)[C@]1(C[C@H]1c1ccc3c(Nc4cncc(C5COC5)n4)n[nH]c3c1)C(=O)N2] | (1R,2S)-5'-methoxy-2-(3-{[6-(oxetan-3-yl)pyrazin-2-yl]amino}-1H-indazol-6-yl)spiro[cyclopropane-1,3'-indol]-2'(1'H)-one |
| 116 | 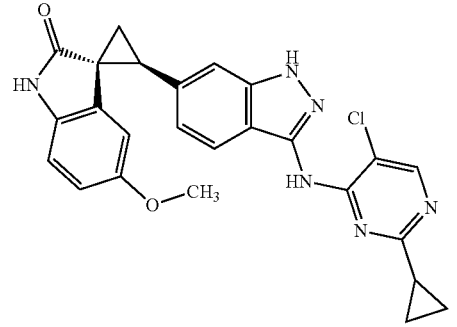 [SMILES: COc1ccc2c(c1)[C@]1(C[C@H]1c1ccc3c(Nc4nc(C5CC5)ncc4Cl)n[nH]c3c1)C(=O)N2] | (1R,2S)-2-(3-((5-chloro-2-cyclopropylpyrimidin-4-yl)amino)-1H-indazol-6-yl)-5'-methoxyspiro[cyclopropane-1,3'-indolin]-2'-one |

| Example No. | Structure | Name |
|---|---|---|
| 117 | 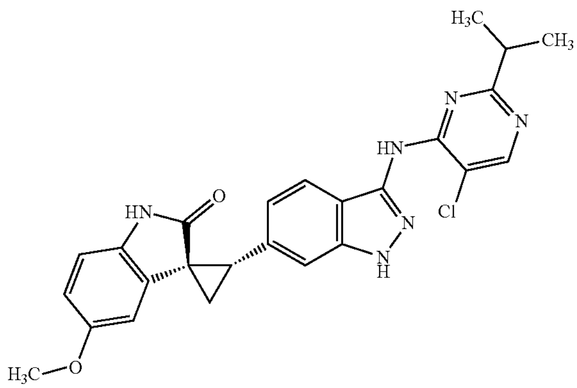 [SMILES: COc1ccc2c(c1)[C@]1(C[C@H]1c1ccc3c(Nc4nc(C(C)C)ncc4Cl)n[nH]c3c1)C(=O)N2] | (1R,2S)-2-(3-{[5-chloro-2-(propan-2-yl)pyrimidin-4-yl]amino}-1H-indazol-6-yl)-5'-methoxyspiro[cyclopropane-1,3'-indol]-2'(1'H)-one |
| 118 | 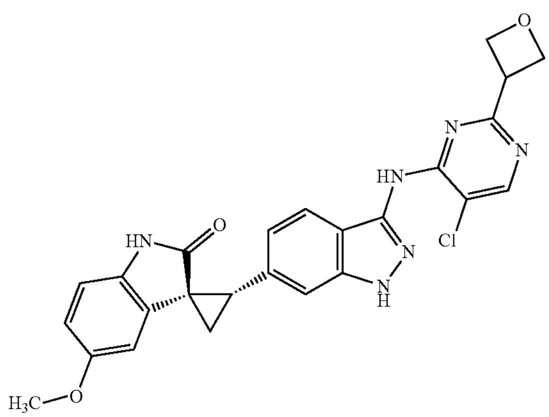 [SMILES: COc1ccc2c(c1)[C@]1(C[C@H]1c1ccc3c(Nc4nc(C5COC5)ncc4Cl)n[nH]c3c1)C(=O)N2] | (1R,2S)-2-(3-{[5-chloro-2-(oxetan-3-yl)pyrimidin-4-yl]amino}-1H-indazol-6-yl)-5'-methoxyspiro[cyclopropane-1,3'-indol]-2'(1'H)-one |
| 119 | 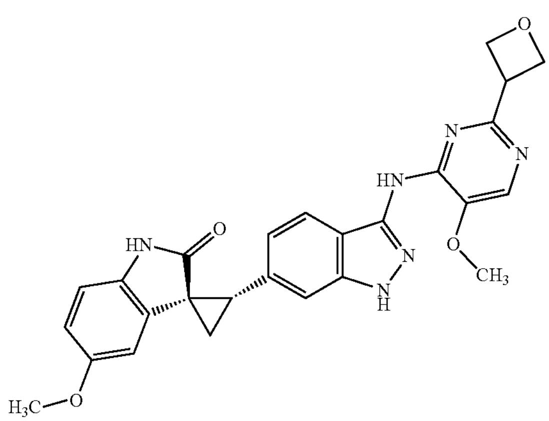 [SMILES: COc1ccc2c(c1)[C@]1(C[C@H]1c1ccc3c(Nc4nc(C5COC5)ncc4OC)n[nH]c3c1)C(=O)N2] | (1R,2S)-5'-methoxy-2-(3-{[5-methoxy-2-(oxetan-3-yl)pyrimidin-4-yl]amino}-1H-indazol-6-yl)spiro[cyclopropane-1,3'-indol]-2'(1'H)-one |

TABLE 1A-continued

| Example No. | Structure | Name |
|---|---|---|
| 120 | 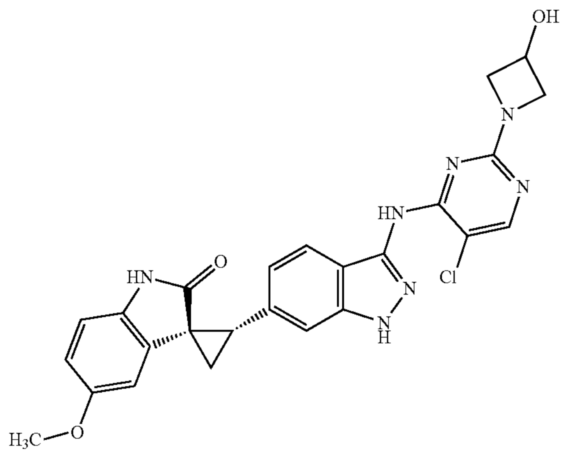 [SMILES: COc1ccc2c(c1)[C@]1(C[C@H]1c1ccc3c(Nc4nc(N5CC(O)C5)ncc4Cl)n[nH]c3c1)C(=O)N2] | (1R,2S)-2-(3-{[5-chloro-2-(3-hydroxyazetidin-1-yl)pyrimidin-4-yl]amino}-1H-indazol-6-yl)-5'-methoxyspiro[cyclopropane-1,3'-indol]-2'(1'H)-one |
| 121 | 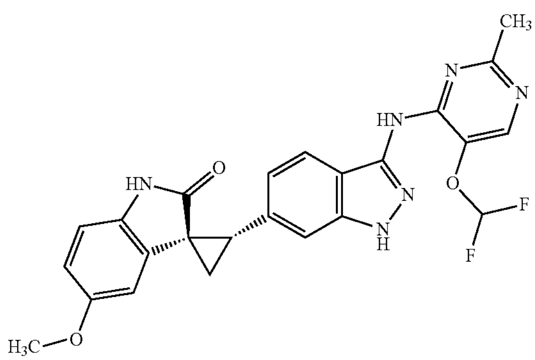 [SMILES: COc1ccc2c(c1)[C@]1(C[C@H]1c1ccc3c(Nc4nc(C)ncc4OC(F)F)n[nH]c3c1)C(=O)N2] | (1R,2S)-2-(3-{[5-(difluoromethoxy)-2-methylpyrimidin-4-yl]amino}-1H-indazol-6-yl)-5'-methoxyspiro[cyclopropane-1,3'-indol]-2'(1'H)-one |
| 122 | 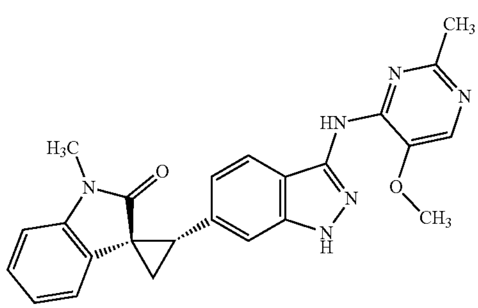 [SMILES: COc1cnc(C)nc1Nc1n[nH]c2cc([C@@H]3C[C@@]34C(=O)N(C)c3ccccc34)ccc12] | (1R,2S)-2-{3-[(5-methoxy-2-methylpyrimidin-4-yl)amino]-1H-indazol-6-yl}-1'-methylspiro[cyclopropane-1,3'-indol]-2'(1'H)-one |
| 123 | 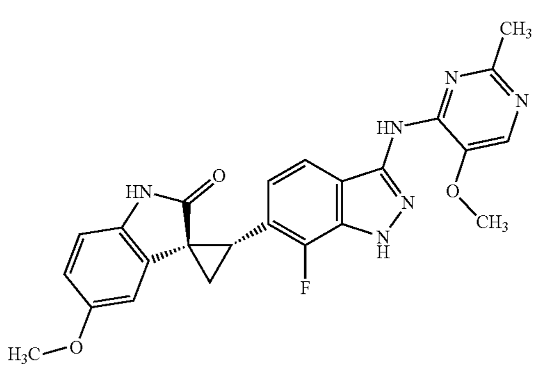 [SMILES: COc1ccc2c(c1)[C@]1(C[C@H]1c1ccc3c(Nc4nc(C)ncc4OC)n[nH]c3c1F)C(=O)N2] | (1R,2R)-2-{7-fluoro-3-[(5-methoxy-2-methylpyrimidin-4-yl)amino]-1H-indazol-6-yl}-5'-methoxyspiro[cyclopropane-1,3'-indol]-2'(1'H)-one |

TABLE 1A-continued

| Example No. | Structure | Name |
|---|---|---|
| 124 | 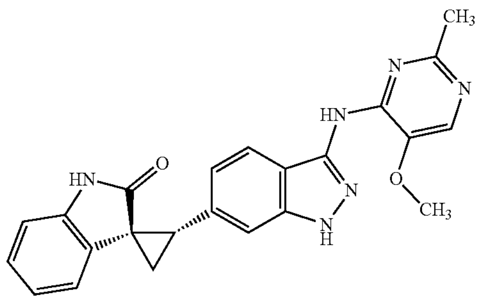 [SMILES: COc1cnc(C)nc1Nc1n[nH]c2cc([C@@H]3C[C@@]34C(=O)Nc3ccccc34)ccc12] | (1R,2S)-2-{3-[(5-methoxy-2-methylpyrimidin-4-yl)amino]-1H-indazol-6-yl}spiro[cyclopropane-1,3'-indol]-2'(1'H)-one |
| 125 | 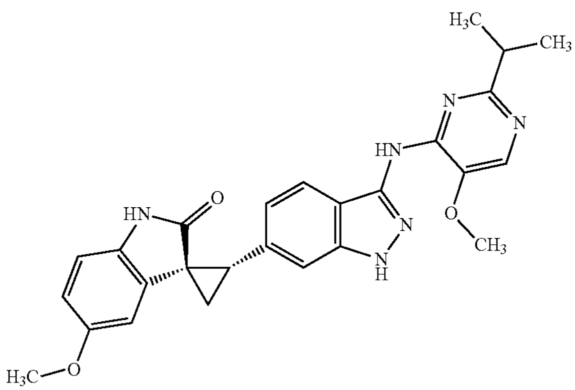 [SMILES: COc1ccc2c(c1)[C@]1(C[C@H]1c1ccc3c(Nc4nc(C(C)C)ncc4OC)n[nH]c3c1)C(=O)N2] | (1R,2S)-5'-methoxy-2-(3-{[5-methoxy-2-(propan-2-yl)pyrimidin-4-yl]amino}-1H-indazol-6-yl)spiro[cyclopropane-1,3'-indol]-2'(1'H)-one |
| 126 | 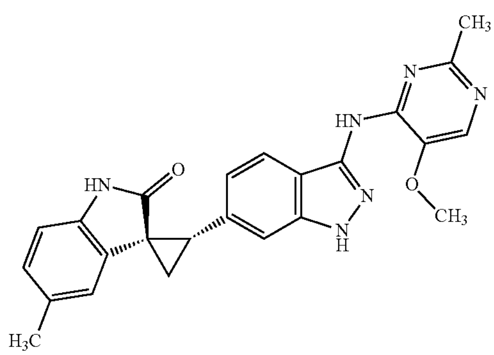 [SMILES: COc1cnc(C)nc1Nc1n[nH]c2cc([C@@H]3C[C@@]34C(=O)Nc3ccc(C)cc34)ccc12] | (1R,2S)-2-{3-[(5-methoxy-2-methylpyrimidin-4-yl)amino]-1H-indazol-6-yl}-5'-methylspiro[cyclopropane-1,3'-indol]-2'(1'H)-one |
| 127 | 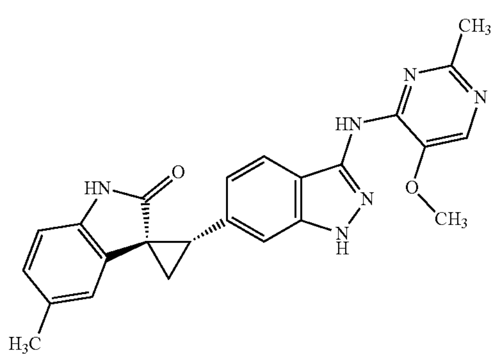 [SMILES: COc1cnc(C)nc1Nc1n[nH]c2cc([C@@H]3C[C@]34C(=O)Nc3ccc(C)cc34)ccc12] | (1S,2S)-2-{3-[(5-methoxy-2-methylpyrimidin-4-yl)amino]-1H-indazol-6-yl}-5'-methylspiro[cyclopropane-1,3'-indol]-2'(1'H)-one |

TABLE 1A-continued

| Example No. | Structure | Name |
|---|---|---|
| 128 | 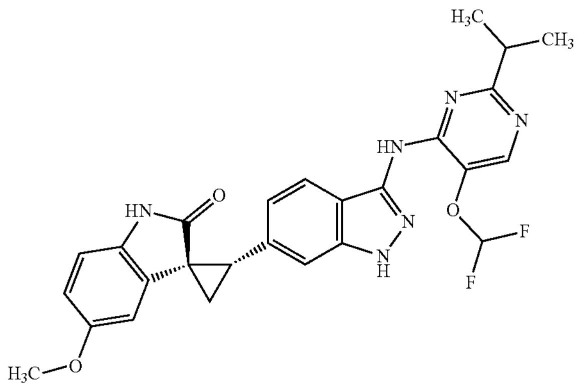 [SMILES: COc1ccc2c(c1)[C@]1(C[C@H]1c1ccc3c(Nc4nc(C(C)C)ncc4OC(F)F)n[nH]c3c1)C(=O)N2] | (1R,2S)-2-(3-{[5-(difluoromethoxy)-2-(propan-2-yl)pyrimidin-4-yl]amino}-1H-indazol-6-yl)-5'-methoxyspiro[cyclopropane-1,3'-indol]-2'(1'H)-one |
| 129 | 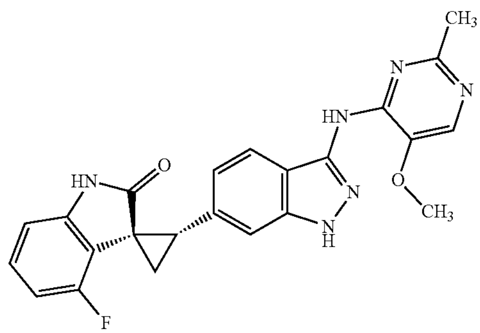 [SMILES: COc1cnc(C)nc1Nc1n[nH]c2cc([C@@H]3C[C@@]34C(=O)Nc3cccc(F)c34)ccc12] | (1R,2S)-4'-fluoro-2-{3-[(5-methoxy-2-methylpyrimidin-4-yl)amino]-1H-indazol-6-yl}spiro[cyclopropane-1,3'-indol]-2'(1'H)-one |
| 130 | 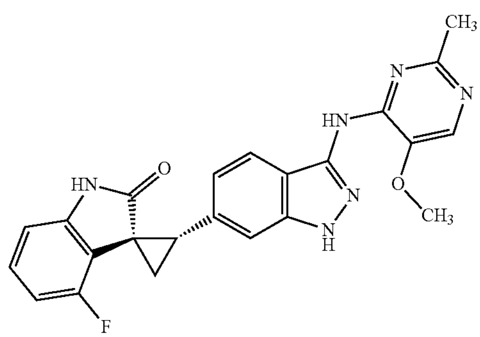 [SMILES: COc1cnc(C)nc1Nc1n[nH]c2cc([C@@H]3C[C@]34C(=O)Nc3cccc(F)c34)ccc12] | (1S,2S)-4'-fluoro-2-{3-[(5-methoxy-2-methylpyrimidin-4-yl)amino]-1H-indazol-6-yl}spiro[cyclopropane-1,3'-indol]-2'(1'H)-one |
| 131 | 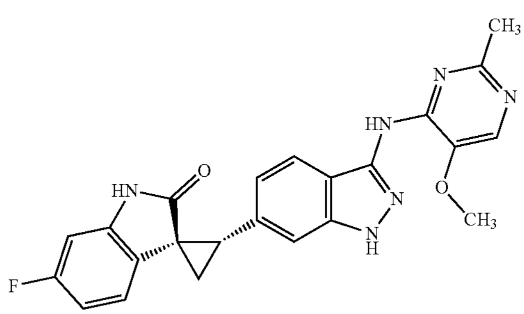 [SMILES: COc1cnc(C)nc1Nc1n[nH]c2cc([C@@H]3C[C@@]34C(=O)Nc3cc(F)ccc34)ccc12] | (1R,2S)-6'-fluoro-2-{3-[(5-methoxy-2-methylpyrimidin-4-yl)amino]-1H-indazol-6-yl}spiro[cyclopropane-1,3'-indol]-2'(1'H)-one |

TABLE 1A-continued

| Example No. | Structure | Name |
|---|---|---|
| 132 | 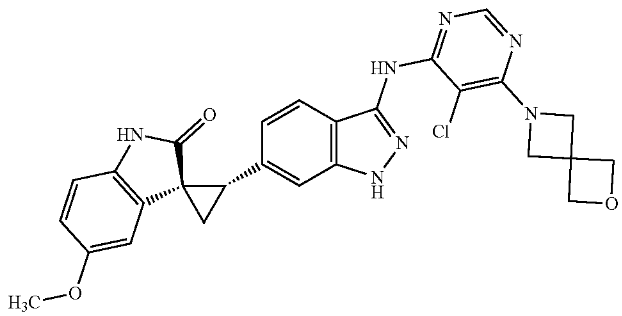 [SMILES: COc1ccc2c(c1)[C@]1(C[C@H]1c1ccc3c(Nc4ncnc(N5CC6(COC6)C5)c4Cl)n[nH]c3c1)C(=O)N2] | (1R,2S)-2-(3-{[5-chloro-6-(2-oxa-6-azaspiro[3.3]heptan-6-yl)pyrimidin-4-yl]amino}-1H-indazol-6-yl)-5'-methoxyspiro[cyclopropane-1,3'-indol]-2'(1'H)-one |
| 133 | 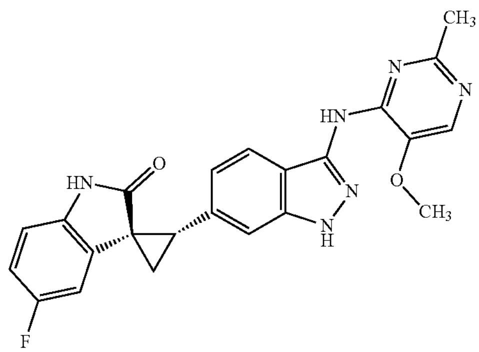 [SMILES: COc1cnc(C)nc1Nc1n[nH]c2cc([C@@H]3C[C@@]34C(=O)Nc3ccc(F)cc34)ccc12] | (1R,2S)-5'-fluoro-2-{3-[(5-methoxy-2-methylpyrimidin-4-yl)amino]-1H-indazol-6-yl}spiro[cyclopropane-1,3'-indol]-2'(1'H)-one |
| 134 | 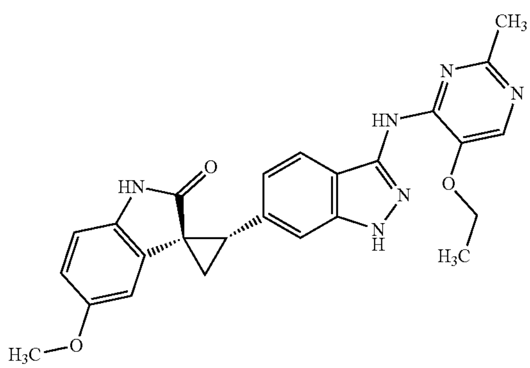 [SMILES: CCOc1cnc(C)nc1Nc1n[nH]c2cc([C@@H]3C[C@@]34C(=O)Nc3ccc(OC)cc34)ccc12] | (1R,2S)-2-{3-[(5-ethoxy-2-methylpyrimidin-4-yl)amino]-1H-indazol-6-yl}-5'-methoxyspiro[cyclopropane-1,3'-indol]-2'(1'H)-one |
| 135 | 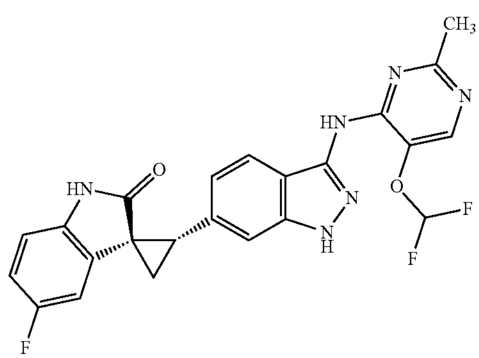 [SMILES: Cc1ncc(OC(F)F)c(Nc2n[nH]c3cc([C@@H]4C[C@@]45C(=O)Nc4ccc(F)cc45)ccc23)n1] | (1R,2S)-2-(3-{[5-(difluoromethoxy)-2-methylpyrimidin-4-yl]amino}-1H-indazol-6-yl)-5'-fluorospiro[cyclopropane-1,3'-indol]-2'(1'H)-one |

TABLE 1A-continued

| Example No. | Structure | Name |
|---|---|---|
| 136 | 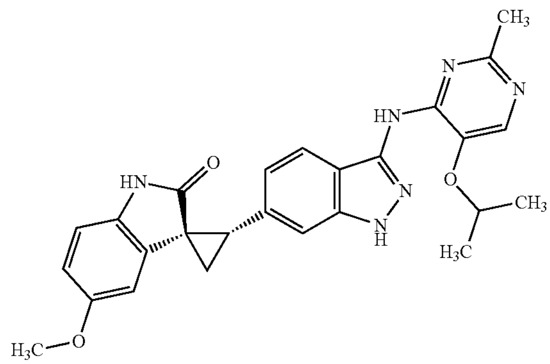 [SMILES: COc1ccc2c(c1)[C@]1(C[C@H]1c1ccc3c(Nc4nc(C)ncc4OC(C)C)n[nH]c3c1)C(=O)N2] | (1R,2S)-5'-methoxy-2-[3-({2-methyl-5-[(propan-2-yl)oxy]pyrimidin-4-yl}amino)-1H-indazol-6-yl]spiro[cyclopropane-1,3'-indol]-2'(1'H)-one |
| 137 | 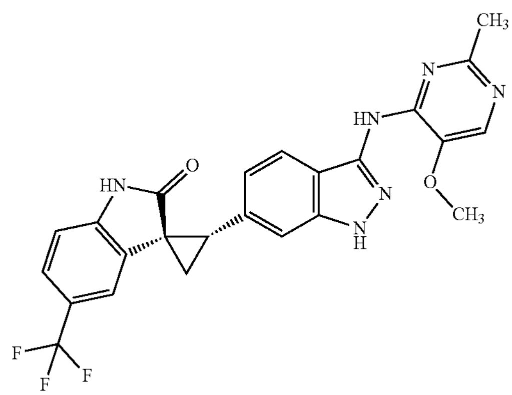 [SMILES: COc1cnc(C)nc1Nc1n[nH]c2cc([C@@H]3C[C@@]34C(=O)Nc3ccc(C(F)(F)F)cc34)ccc12] | (1R,2S)-2-{3-[(5-methoxy-2-methylpyrimidin-4-yl)amino]-1H-indazol-6-yl}-5'-(trifluoromethyl)spiro[cyclopropane-1,3'-indol]-2'(1'H)-one |
| 138 | 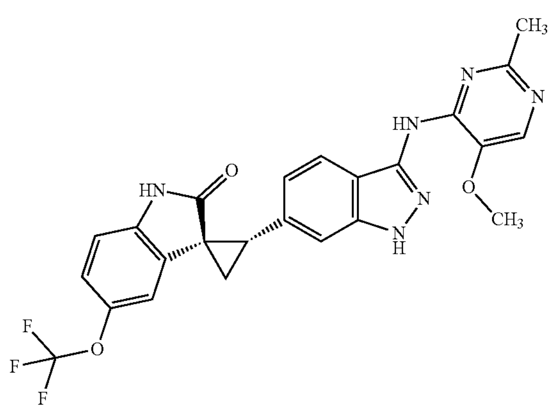 [SMILES: COc1cnc(C)nc1Nc1n[nH]c2cc([C@@H]3C[C@@]34C(=O)Nc3ccc(OC(F)(F)F)cc34)ccc12] | (1R,2S)-2-{3-[(5-methoxy-2-methylpyrimidin-4-yl)amino]-1H-indazol-6-yl}-5'-(trifluoromethoxy)spiro[cyclopropane-1,3'-indol]-2'(1'H)-one |
| 139 | 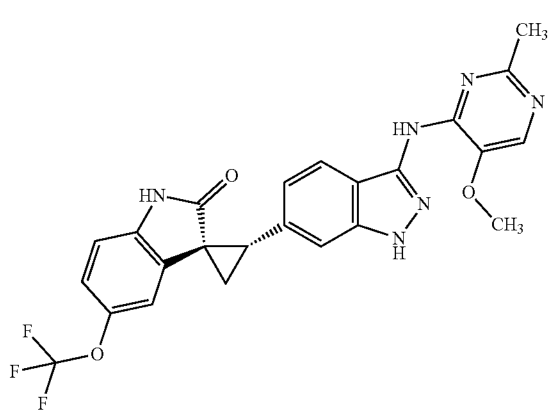 [SMILES: COc1cnc(C)nc1Nc1n[nH]c2cc([C@@H]3C[C@]34C(=O)Nc3ccc(OC(F)(F)F)cc34)ccc12] | (1S,2S)-2-{3-[(5-methoxy-2-methylpyrimidin-4-yl)amino]-1H-indazol-6-yl}-5'-(trifluoromethoxy)spiro[cyclopropane-1,3'-indol]-2'(1'H)-one |

TABLE 1A-continued

| Example No. | Structure | Name |
|---|---|---|
| 140 | 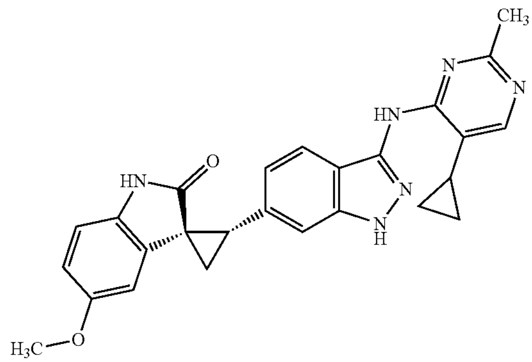 [SMILES: COc1ccc2c(c1)[C@]1(C[C@H]1c1ccc3c(Nc4nc(C)ncc4C4CC4)n[nH]c3c1)C(=O)N2] | (1R,2S)-2-{3-[(5-cyclopropyl-2-methylpyrimidin-4-yl)amino]-1H-indazol-6-yl}-5'-methoxyspiro[cyclopropane-1,3'-indol]-2'(1'H)-one |
| 141 | 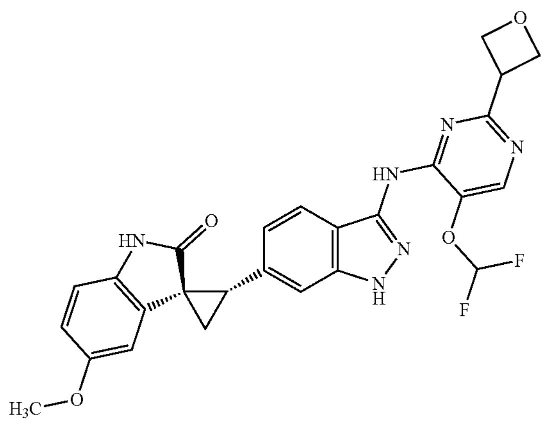 [SMILES: COc1ccc2c(c1)[C@]1(C[C@H]1c1ccc3c(Nc4nc(C5COC5)ncc4OC(F)F)n[nH]c3c1)C(=O)N2] | (1R,2S)-2-(3-{[5-(difluoromethoxy)-2-(oxetan-3-yl)pyrimidin-4-yl]amino}-1H-indazol-6-yl)-5'-methoxyspiro[cyclopropane-1,3'-indol]-2'(1'H)-one |
| 142 | 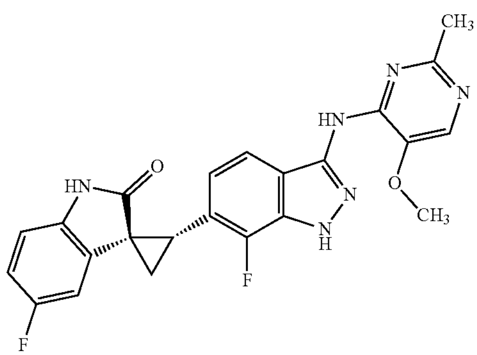 [SMILES: COc1cnc(C)nc1Nc1n[nH]c2c(F)c([C@@H]3C[C@@]34C(=O)Nc3ccc(F)cc34)ccc12] | (1R,2R)-5'-fluoro-2-{7-fluoro-3-[(5-methoxy-2-methylpyrimidin-4-yl)amino]-1H-indazol-6-yl}spiro[cyclopropane-1,3'-indol]-2'(1'H)-one |
| 143 | 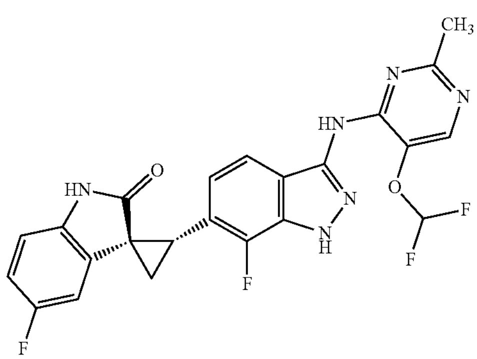 [SMILES: Cc1ncc(OC(F)F)c(Nc2n[nH]c3c(F)c([C@@H]4C[C@@]45C(=O)Nc4ccc(F)cc45)ccc23)n1] | (1R,2R)-2-(3-{[5-(difluoromethoxy)-2-methylpyrimidin-4-yl]amino}-7-fluoro-1H-indazol-6-yl)-5'-fluorospiro[cyclopropane-1,3'-indol]-2'(1'H)-one |

TABLE 1A-continued

| Example No. | Structure | Name |
|---|---|---|
| 144 | 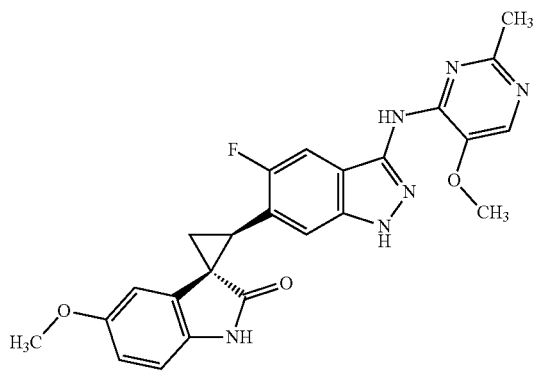 [SMILES: COc1ccc2c(c1)[C@]1(C[C@H]1c1cc3[nH]nc(Nc4nc(C)ncc4OC)c3cc1F)C(=O)N2] | (1R,2R)-2-{5-fluoro-3-[(5-methoxy-2-methylpyrimidin-4-yl)amino]-1H-indazol-6-yl}-5'-methoxyspiro[cyclopropane-1,3'-indol]-2'(1'H)-one |
| 145 | 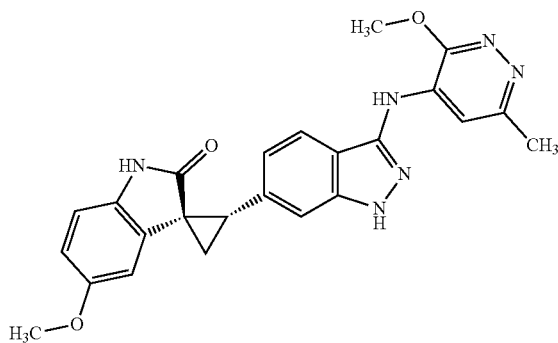 | (1R,2S)-5'-methoxy-2-{3-[(3-methoxy-6-methylpyridazin-4-yl)amino]-1H-indazol-6-yl}spiro[cyclopropane-1,3'-indol]-2'(1'H)-one |
| 146 | 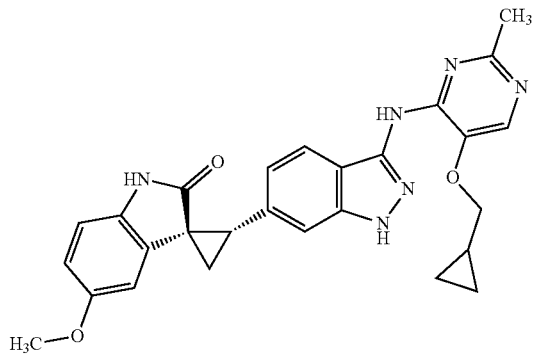 [SMILES: COc1ccc2c(c1)[C@]1(C[C@H]1c1ccc3c(Nc4nc(C)ncc4OCC4CC4)n[nH]c3c1)C(=O)N2] | (1R,2S)-2-(3-{[5-(cyclopropylmethoxy)-2-methylpyrimidin-4-yl]amino}-1H-indazol-6-yl)-5'-methoxyspiro[cyclopropane-1,3'-indol]-2'(1'H)-one |
| 147 | 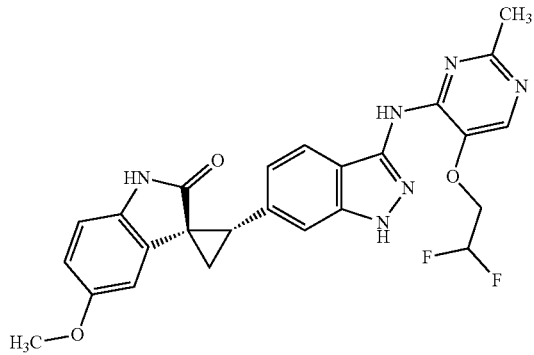 [SMILES: COc1ccc2c(c1)[C@]1(C[C@H]1c1ccc3c(Nc4nc(C)ncc4OCC(F)F)n[nH]c3c1)C(=O)N2] | (1R,2S)-2-(3-{[5-(2,2-difluoroethoxy)-2-methylpyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 148 | 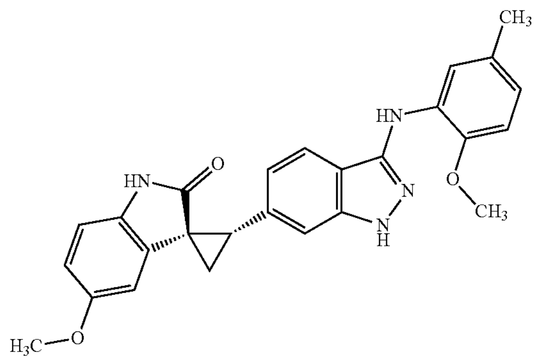 [SMILES: COc1ccc2c(c1)[C@]1(C[C@H]1c1ccc3c(Nc4cc(C)ccc4OC)n[nH]c3c1)C(=O)N2] | (1R,2S)-5'-methoxy-2-[3-(2-methoxy-5-methylanilino)-1H-indazol-6-yl]spiro[cyclopropane-1,3'-indol]-2'(1'H)-one |
| 149 | 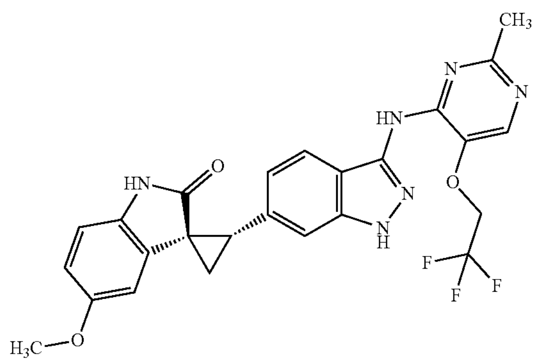 [SMILES: COc1ccc2c(c1)[C@]1(C[C@H]1c1ccc3c(Nc4nc(C)ncc4OCC(F)(F)F)n[nH]c3c1)C(=O)N2] | (1R,2S)-5'-methoxy-2-(3-{[2-methyl-5-(2,2,2-trifluoroethoxy)pyrimidin-4-yl]amino}-1H-indazol-6-yl)spiro[cyclopropane-1,3'-indol]-2'(1'H)-one |
| 150 | 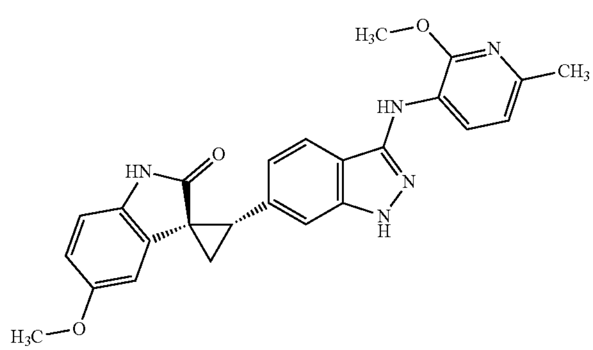 | (1R,2S)-5'-methoxy-2-{3-[(2-methoxy-6-methylpyridin-3-yl)amino]-1H-indazol-6-yl}spiro[cyclopropane-1,3'-indol]-2'(1'H)-one |
| 151 | 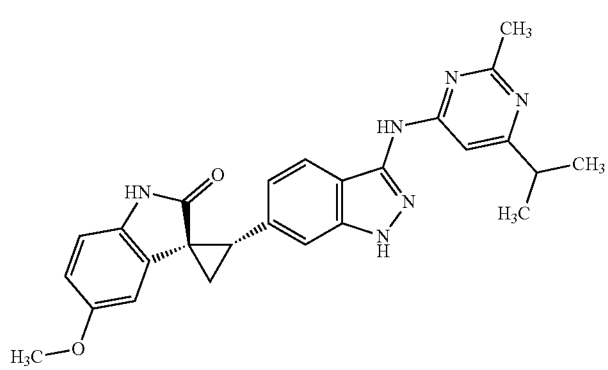 [SMILES: COc1ccc2c(c1)[C@]1(C[C@H]1c1ccc3c(Nc4cc(C(C)C)nc(C)n4)n[nH]c3c1)C(=O)N2] | (1R,2S)-5'-methoxy-2-(3-{[2-methyl-6-(propan-2-yl)pyrimidin-4-yl]amino}-1H-indazol-6-yl)spiro[cyclopropane-1,3'-indol]-2'(1'H)-one |

TABLE 1A-continued

| Example No. | Structure | Name |
|---|---|---|
| 152 | 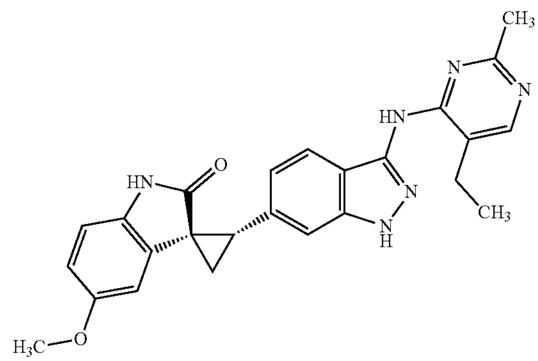 [SMILES: CCc1cnc(C)nc1Nc1n[nH]c2cc([C@@H]3C[C@@]34C(=O)Nc3ccc(OC)cc34)ccc12] | (1R,2S)-2-{3-[(5-ethyl-2-methylpyrimidin-4-yl)amino]-1H-indazol-6-yl}-5'-methoxyspiro[cyclopropane-1,3'-indol]-2'(1'H)-one |
| 153 | 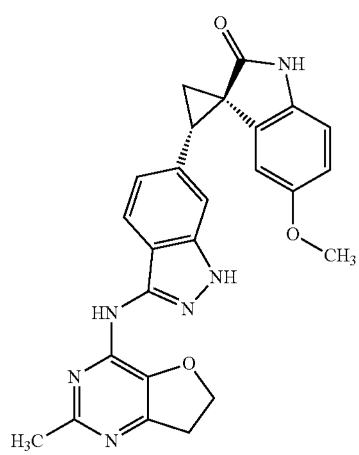 [SMILES: COc1ccc2c(c1)[C@]1(C[C@H]1c1ccc3c(Nc4nc(C)nc5c4OCC5)n[nH]c3c1)C(=O)N2] | (1R,2S)-5'-methoxy-2-{3-[(2-methyl-6,7-dihydrofuro[3,2-d]pyrimidin-4-yl)amino]-1H-indazol-6-yl}spiro[cyclopropane-1,3'-indol]-2'(1'H)-one |
| 154 | 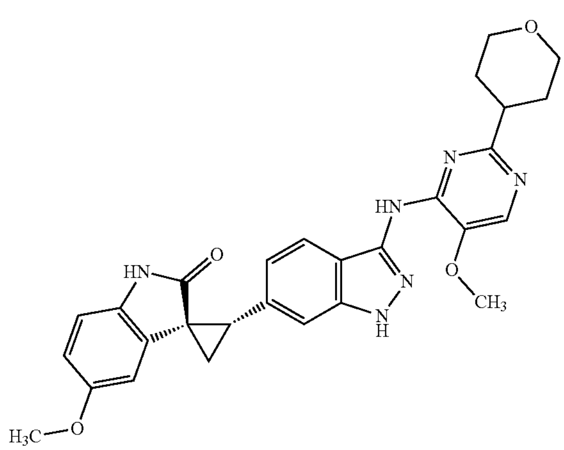 [SMILES: COc1ccc2c(c1)[C@]1(C[C@H]1c1ccc3c(Nc4nc(C5CCOCC5)ncc4OC)n[nH]c3c1)C(=O)N2] | (1R,2S)-5'-methoxy-2-(3-{[5-methoxy-2-(oxan-4-yl)pyrimidin-4-yl]amino}-1H-indazol-6-yl)spiro[cyclopropane-1,3'-indol]-2'(1'H)-one |

TABLE 1A-continued

| Example No. | Structure | Name |
|---|---|---|
| 155 | 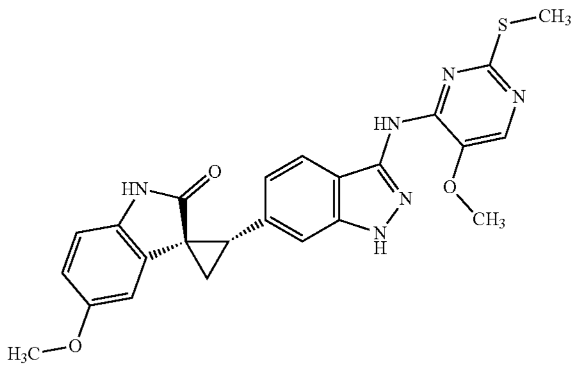 | (1R,2S)-5'-methoxy-2-(3-{[5-methoxy-2-(methylsulfanyl)pyrimidin-4-yl]amino}-1H-indazol-6-yl)spiro[cyclopropane-1,3'-indol]-2'(1'H)-one |
| 156 | 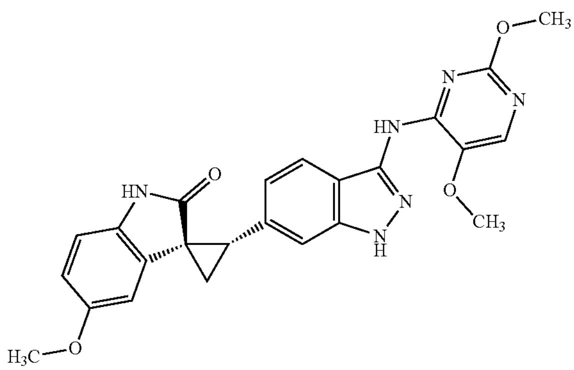 | (1R,2S)-2-{3-[(2,5-dimethoxypyrimidin-4-yl)amino]-1H-indazol-6-yl}-5'-methoxyspiro[cyclopropane-1,3'-indol]-2'(1'H)-one |
| 157 | 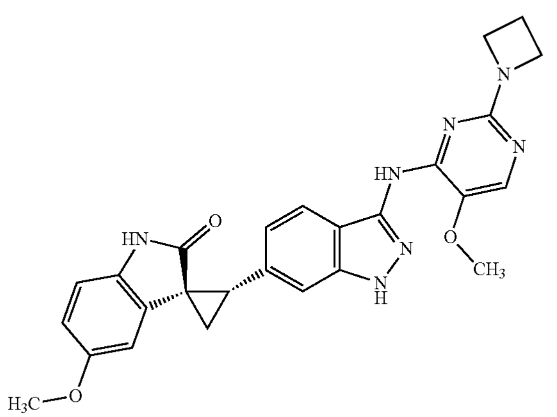 [SMILES: COc1ccc2c(c1)[C@]1(C[C@H]1c1ccc3c(Nc4nc(N5CCC5)ncc4OC)n[nH]c3c1)C(=O)N2] | (1R,2S)-2-(3-{[2-(azetidin-1-yl)-5-methoxypyrimidin-4-yl]amino}-1H-indazol-6-yl)-5'-methoxyspiro[cyclopropane-1,3'-indol]-2'(1'H)-one |
| 158 | 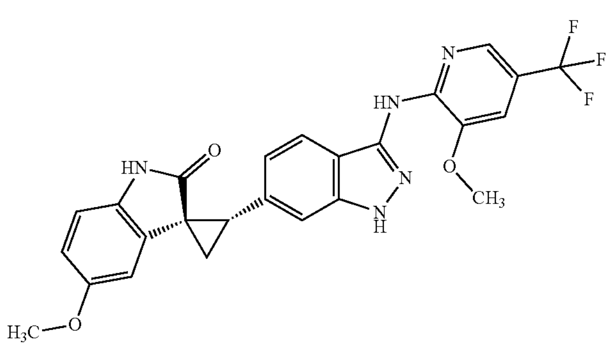 [SMILES: COc1ccc2c(c1)[C@]1(C[C@H]1c1ccc3c(Nc4ncc(C(F)(F)F)cc4OC)n[nH]c3c1)C(=O)N2] | (1R,2S)-5'-methoxy-2-(3-{[3-methoxy-5-(trifluoromethyl)pyridin-2-yl]amino}-1H-indazol-6-yl)spiro[cyclopropane-1,3'-indol]-2'(1'H)-one |

TABLE 1A-continued

| Example No. | Structure | Name |
|---|---|---|
| 159 | 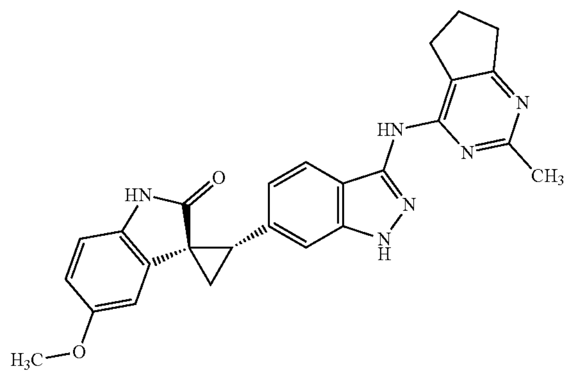 | (1R,2S)-5'-methoxy-2-{3-[(2-methyl-6,7-dihydro-5H-cyclopenta[d]pyrimidin-4-yl)amino]-1H-indazol-6-yl}spiro[cyclopropane-1,3'-indol]-2'(1'H)-one |
| 160 | 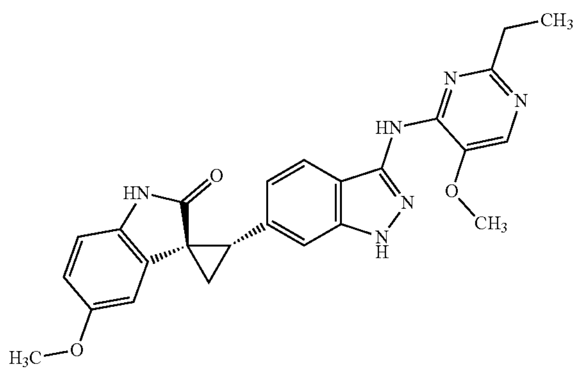 [SMILES: CCc1ncc(OC)c(Nc2n[nH]c3cc([C@@H]4C[C@@]45C(=O)Nc4ccc(OC)cc45)ccc23)n1] | (1R,2S)-2-{3-[(2-ethyl-5-methoxypyrimidin-4-yl)amino]-1H-indazol-6-yl}-5'-methoxyspiro[cyclopropane-1,3'-indol]-2'(1'H)-one |
| 161 | 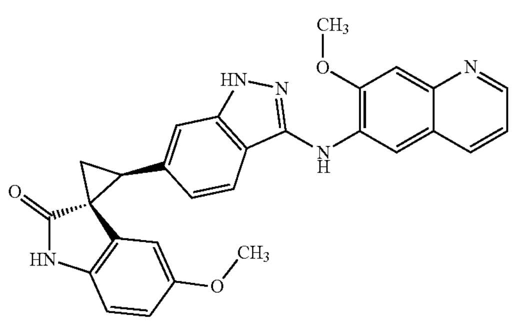 [SMILES: COc1ccc2c(c1)[C@]1(C[C@H]1c1ccc3c(Nc4cc5cccnc5cc4OC)n[nH]c3c1)C(=O)N2] | (1R,2S)-5'-methoxy-2-{3-[(7-methoxyquinolin-6-yl)amino]-1H-indazol-6-yl}spiro[cyclopropane-1,3'-indol]-2'(1'H)-one |
| 162 | 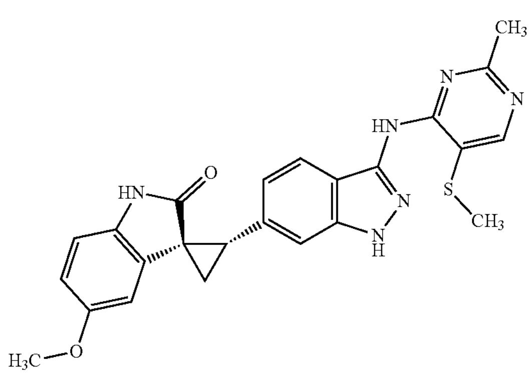 | (1R,2S)-5'-methoxy-2-(3-{[2-methyl-5-(methylsulfanyl)pyrimidin-4-yl]amino}-1H-indazol-6-yl)spiro[cyclopropane-1,3'-indol]-2'(1'H)-one |

TABLE 1A-continued

| Example No. | Structure | Name |
|---|---|---|
| 163 | 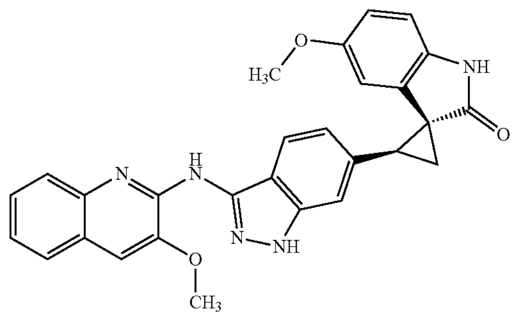 [SMILES: COc1ccc2c(c1)[C@]1(C[C@H]1c1ccc3c(Nc4nc5ccccc5cc4OC)n[nH]c3c1)C(=O)N2] | (1R,2S)-5'-methoxy-2-{3-[(3-methoxyquinolin-2-yl)amino]-1H-indazol-6-yl}spiro[cyclopropane-1,3'-indol]-2'(1'H)-one |
| 164 | 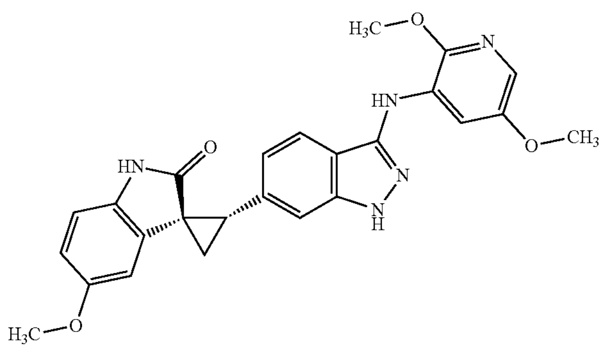 | (1R,2S)-2-{3-[(2,5-dimethoxypyridin-3-yl)amino]-1H-indazol-6-yl}-5'-methoxyspiro[cyclopropane-1,3'-indol]-2'(1'H)-one |
| 165 | 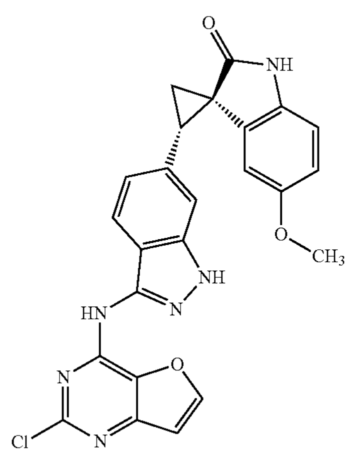 [SMILES: COc1ccc2c(c1)[C@]1(C[C@H]1c1ccc3c(Nc4nc(Cl)nc5ccoc45)n[nH]c3c1)C(=O)N2] | (1R,2S)-2-{3-[(2-chlorofuro[3,2-d]pyrimidin-4-yl)amino]-1H-indazol-6-yl}-5'-methoxyspiro[cyclopropane-1,3'-indol]-2'(1'H)-one |
| 166 | 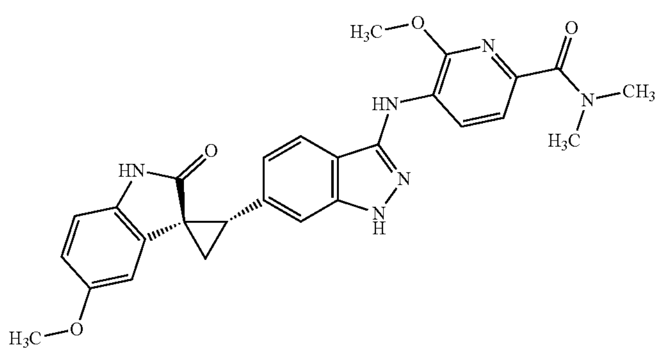 | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide |

TABLE 1A-continued

| Example No. | Structure | Name |
|---|---|---|
| 167 | 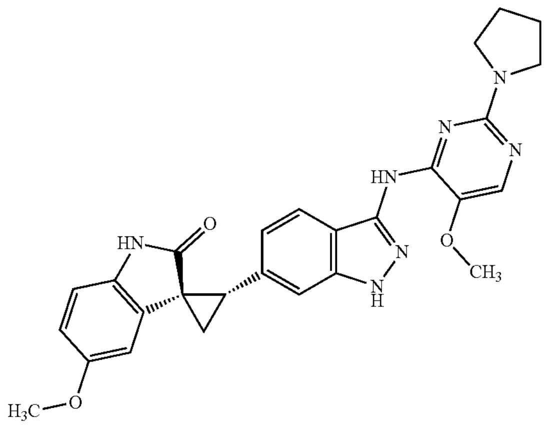 [SMILES: COc1ccc2c(c1)[C@]1(C[C@H]1c1ccc3c(Nc4nc(N5CCCC5)ncc4OC)n[nH]c3c1)C(=O)N2] | (1R,2S)-5'-methoxy-2-(3-{[5-methoxy-2-(pyrrolidin-1-yl)pyrimidin-4-yl]amino}-1H-indazol-6-yl)spiro[cyclopropane-1,3'-indol]-2'(1'H)-one |
| 168 | 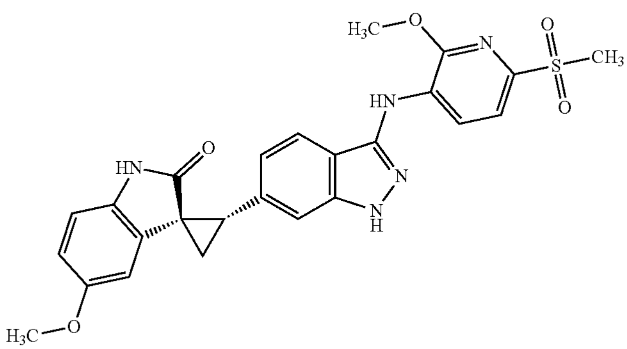 | (1R,2S)-2-(3-{[6-(methanesulfonyl)-2-methoxypyridin-3-yl]amino}-1H-indazol-6-yl)-5'-methoxyspiro[cyclopropane-1,3'-indol]-2'(1'H)-one |
| 169 | 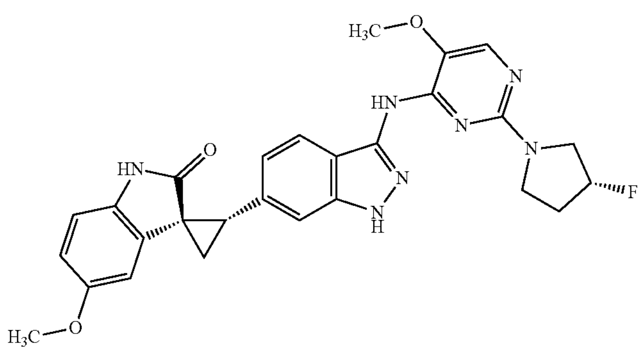 [SMILES: COc1ccc2c(c1)[C@]1(C[C@H]1c1ccc3c(Nc4nc(N5CC[C@@H](F)C5)ncc4OC)n[nH]c3c1)C(=O)N2] | (1R,2S)-2-[3-({2-[(3R)-3-fluoropyrrolidin-1-yl]-5-methoxypyrimidin-4-yl}amino)-1H-indazol-6-yl]-5'-methoxyspiro[cyclopropane-1,3'-indol]-2'(1'H)-one |
| 170 | 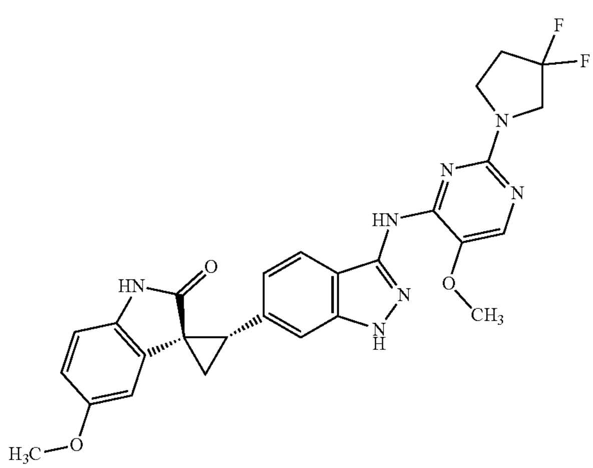 [SMILES: COc1ccc2c(c1)[C@]1(C[C@H]1c1ccc3c(Nc4nc(N5CCC(F)(F)C5)ncc4OC)n[nH]c3c1)C(=O)N2] | (1R,2S)-2-(3-{[2-(3,3-difluoropyrrolidin-1-yl)-5-methoxypyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 171 | 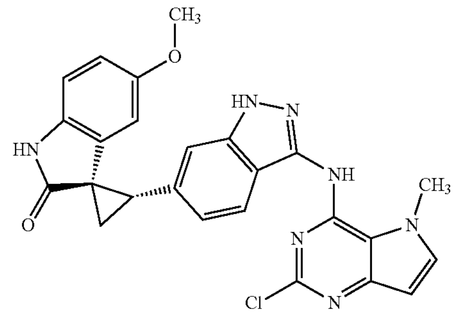 [SMILES: COc1ccc2c(c1)[C@]1(C[C@H]1c1ccc3c(Nc4nc(Cl)nc5ccn(C)c45)n[nH]c3c1)C(=O)N2] | (1R,2S)-2-{3-[(2-chloro-5-methyl-5H-pyrrolo[3,2-d]pyrimidin-4-yl)amino]-1H-indazol-6-yl}-5'-methoxyspiro[cyclopropane-1,3'-indol]-2'(1'H)-one |
| 172 | 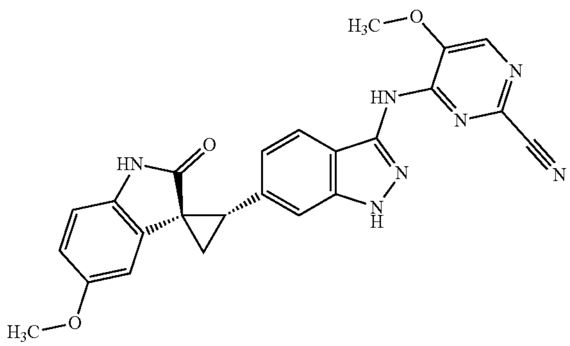 [SMILES: COc1ccc2c(c1)[C@]1(C[C@H]1c1ccc3c(Nc4nc(C#N)ncc4OC)n[nH]c3c1)C(=O)N2] | 5-methoxy-4-({6-[(1R,2S)-5'-methoxy-2'-oxo-1',2'-dihydrospiro[cyclopropane-1,3'-indol]-2-yl]-1H-indazol-3-yl}amino)pyrimidine-2-carbonitrile |
| 173 | 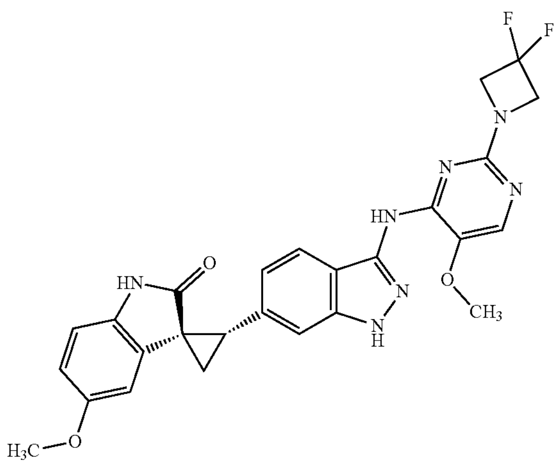 [SMILES: COc1ccc2c(c1)[C@]1(C[C@H]1c1ccc3c(Nc4nc(N5CC(F)(F)C5)ncc4OC)n[nH]c3c1)C(=O)N2] | (1R,2S)-2-(3-{[2-(3,3-difluoroazetidin-1-yl)-5-methoxypyrimidin-4-yl]amino}-1H-indazol-6-yl)-5'-methoxyspiro[cyclopropane-1,3'-indol]-2'(1'H)-one |
| 174 | 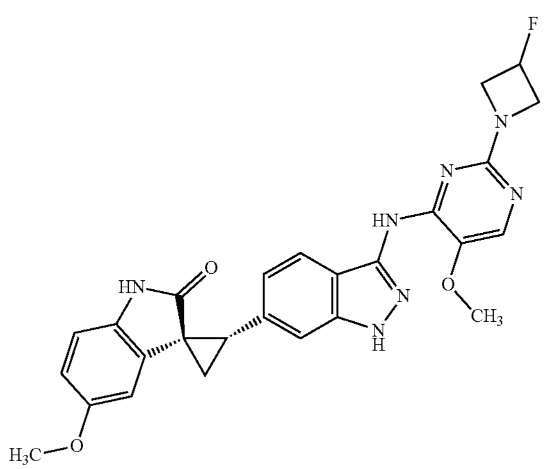 [SMILES: COc1ccc2c(c1)[C@]1(C[C@H]1c1ccc3c(Nc4nc(N5CC(F)C5)ncc4OC)n[nH]c3c1)C(=O)N2] | (1R,2S)-2-(3-{[2-(3-fluoroazetidin-1-yl)-5-methoxypyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 175 | 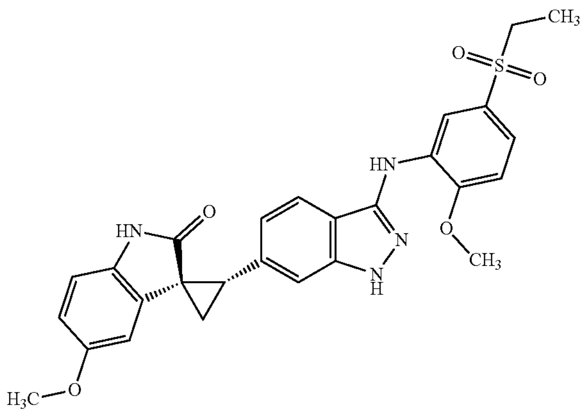 [SMILES: CCS(=O)(=O)c1ccc(OC)c(Nc2n[nH]c3cc([C@@H]4C[C@@]45C(=O)Nc4ccc(OC)cc45)ccc23)c1] | (1R,2S)-2-{3-[5-(ethanesulfonyl)-2-methoxyanilino]-1H-indazol-6-yl}-5'-methoxyspiro[cyclopropane-1,3'-indol]-2'(1'H)-one |
| 176 | 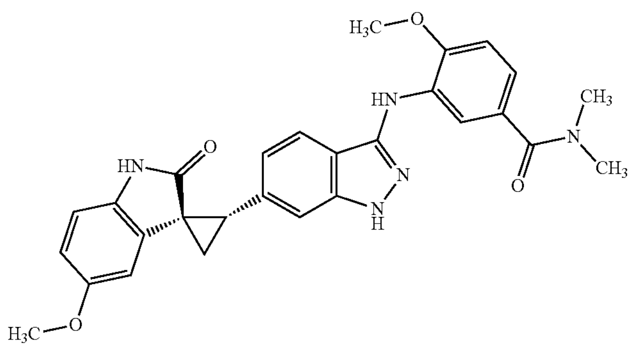 | 4-methoxy-3-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzamide |
| 177 | 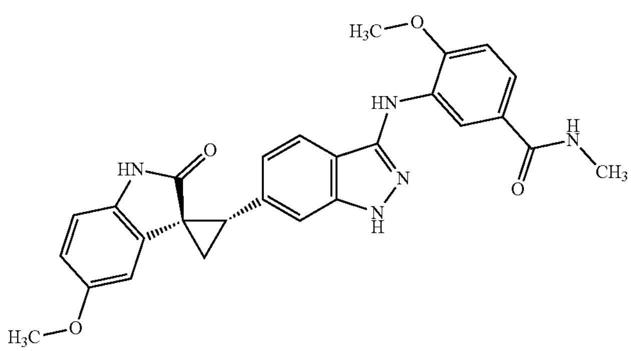 | 4-methoxy-3-({6-[(1R,2S)-5'-methoxy-2'-oxo-1',2'-dihydrospiro[cyclopropane-1,3'-indol]-2-yl]-1H-indazol-3-yl}amino)-N-methylbenzamide |
| 178 | 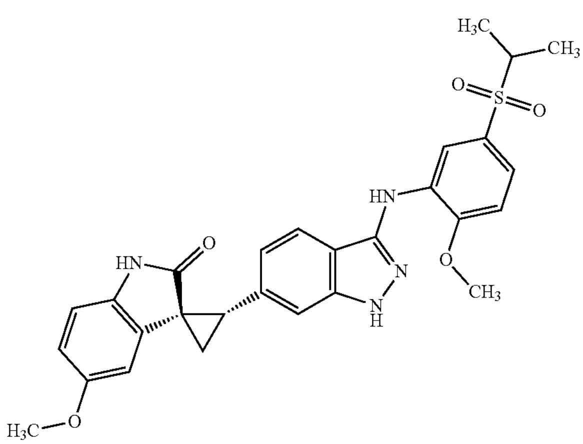 [SMILES: COc1ccc2c(c1)[C@]1(C[C@H]1c1ccc3c(Nc4cc(S(=O)(=O)C(C)C)ccc4OC)n[nH]c3c1)C(=O)N2] | (1R,2S)-5'-methoxy-2-{3-[2-methoxy-5-(propane-2-sulfonyl)anilino]-1H-indazol-6-yl}spiro[cyclopropane-1,3'-indol]-2'(1'H)-one |

TABLE 1A-continued

| Example No. | Structure | Name |
|---|---|---|
| 179 | 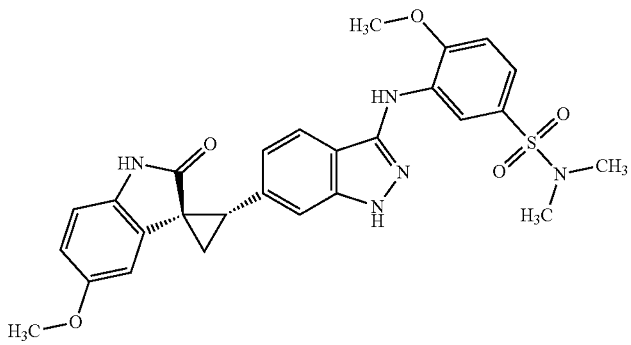 | 4-methoxy-3-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzene-1-sulfonamide |
| 180 | 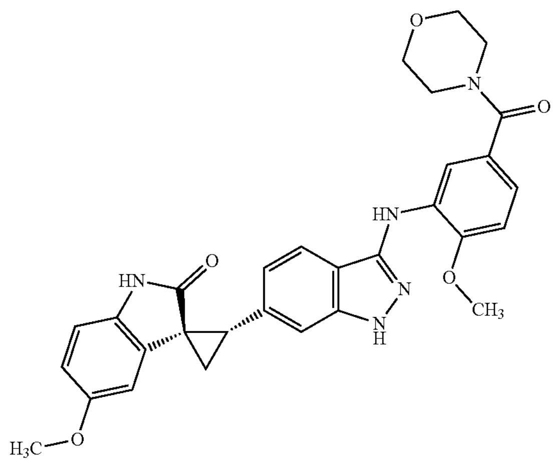 [SMILES: COc1ccc2c(c1)[C@]1(C[C@H]1c1ccc3c(Nc4cc(C(=O)N5CCOCC5)ccc4OC)n[nH]c3c1)C(=O)N2] | (1R,2S)-5'-methoxy-2-{3-[2-methoxy-5-(morpholine-4-carbonyl)anilino]-1H-indazol-6-yl}spiro[cyclopropane-1,3'-indol]-2'(1'H)-one |
| 181 | 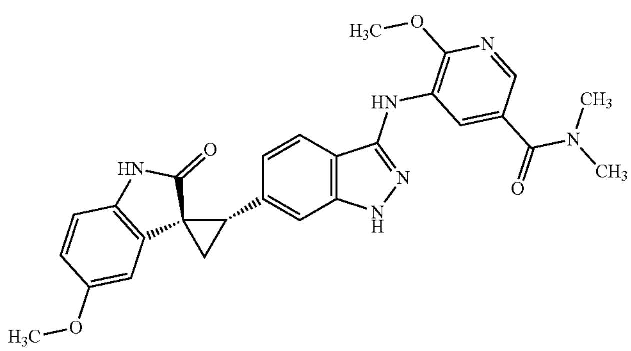 | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide |
| 182 | 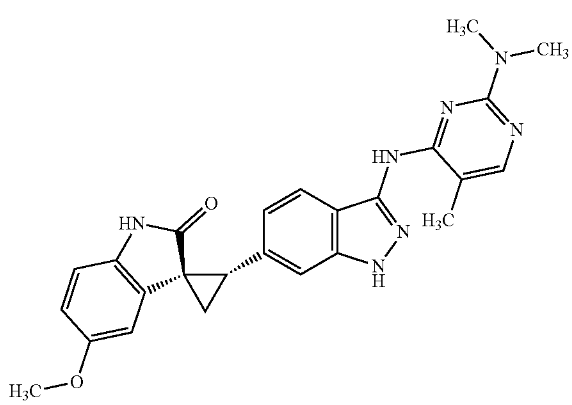 | (1R,2S)-2-(3-{[2-(dimethylamino)-5-methylpyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 183 | 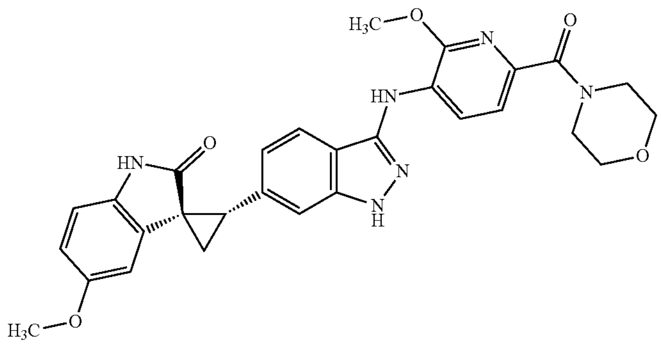 [SMILES: COc1ccc2c(c1)[C@]1(C[C@H]1c1ccc3c(Nc4ccc(C(=O)N5CCOCC5)nc4OC)n[nH]c3c1)C(=O)N2] | (1R,2S)-5'-methoxy-2-(3-{[2-methoxy-6-(morpholine-4-carbonyl)pyridin-3-yl]amino}-1H-indazol-6-yl)spiro[cyclopropane-1,3'-indol]-2'(1'H)-one |
| 184 | 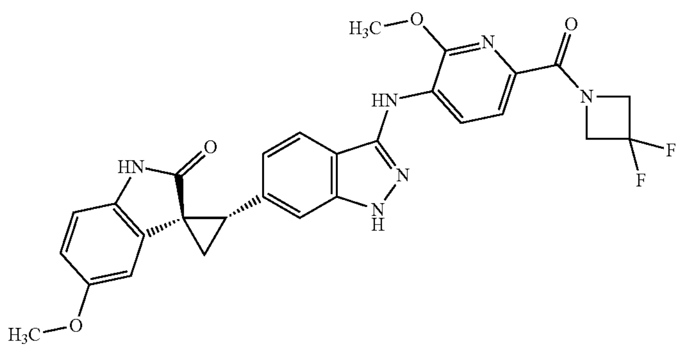 [SMILES: COc1ccc2c(c1)[C@]1(C[C@H]1c1ccc3c(Nc4ccc(C(=O)N5CC(F)(F)C5)nc4OC)n[nH]c3c1)C(=O)N2] | (1R,2S)-2-(3-{[6-(3,3-difluoroazetidine-1-carbonyl)-2-methoxypyridin-3-yl]amino}-1H-indazol-6-yl)-5'-methoxyspiro[cyclopropane-1,3'-indol]-2'(1'H)-one |
| 185 | 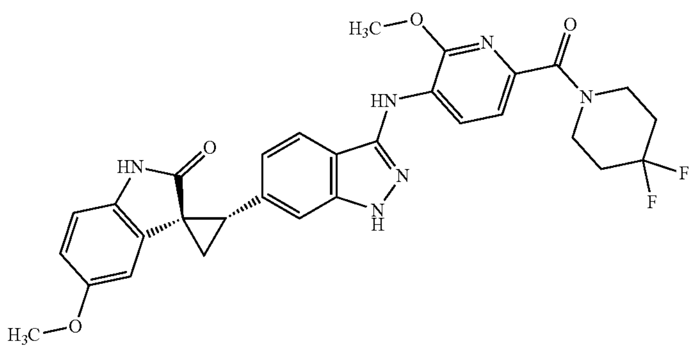 [SMILES: COc1ccc2c(c1)[C@]1(C[C@H]1c1ccc3c(Nc4ccc(C(=O)N5CCC(F)(F)CC5)nc4OC)n[nH]c3c1)C(=O)N2] | (1R,2S)-2-(3-{[6-(4,4-difluoropiperidine-1-carbonyl)-2-methoxypyridin-3-yl]amino}-1H-indazol-6-yl)-5'-methoxyspiro[cyclopropane-1,3'-indol]-2'(1'H)-one |
| 186 | 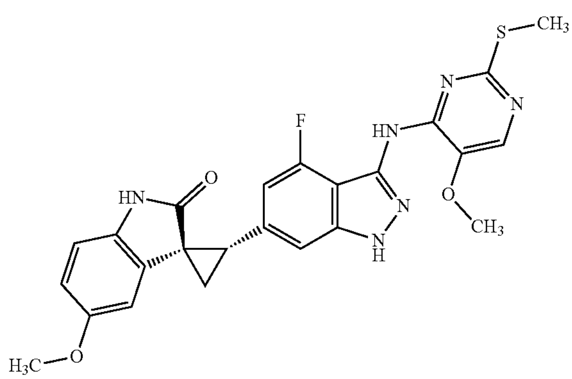 | (1R,2S)-2-(4-fluoro-3-{[5-methoxy-2-(methylsulfanyl)pyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 187 | 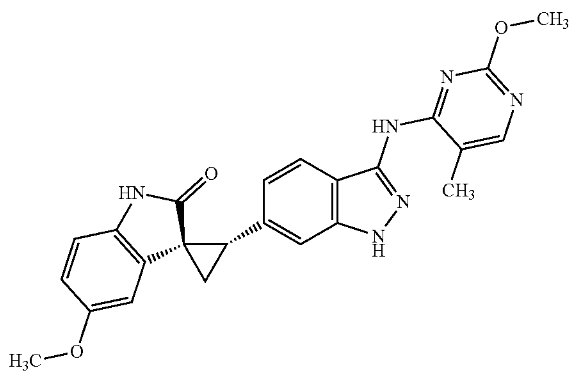 | (1R,2S)-5'-methoxy-2-{3-[(2-methoxy-5-methylpyrimidin-4-yl)amino]-1H-indazol-6-yl}spiro[cyclopropane-1,3'-indol]-2'(1'H)-one |
| 188 | 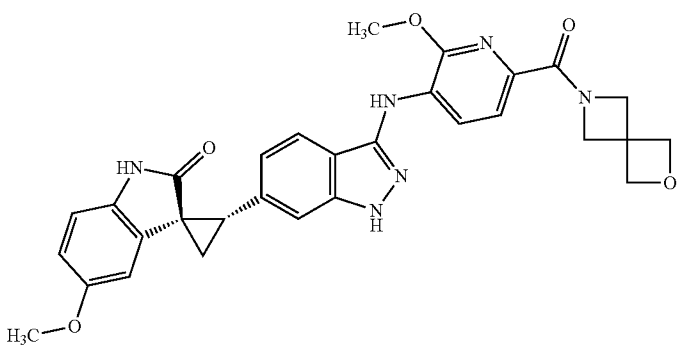 [SMILES: COc1ccc2c(c1)[C@]1(C[C@H]1c1ccc3c(Nc4ccc(C(=O)N5CC6(COC6)C5)nc4OC)n[nH]c3c1)C(=O)N2] | (1R,2S)-5'-methoxy-2-(3-{[2-methoxy-6-(2-oxa-6-azaspiro[3.3]heptane-6-carbonyl)pyridin-3-yl]amino}-1H-indazol-6-yl)spiro[cyclopropane-1,3'-indol]-2'(1'H)-one |
| 189 | 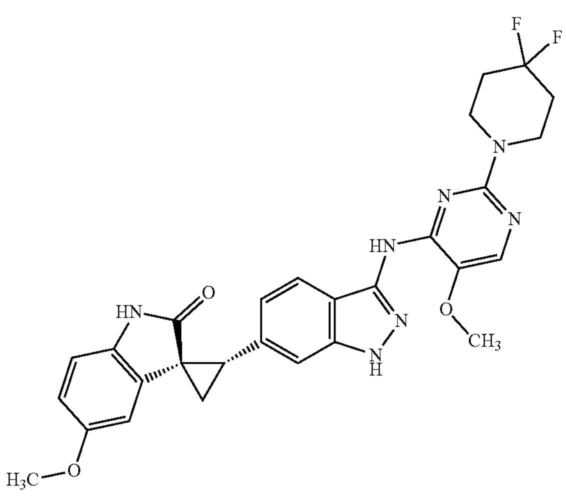 [SMILES: COc1ccc2c(c1)[C@]1(C[C@H]1c1ccc3c(Nc4nc(N5CCC(F)(F)CC5)ncc4OC)n[nH]c3c1)C(=O)N2] | (1R,2S)-2-(3-{[2-(4,4-difluoropiperidin-1-yl)-5-methoxypyrimidin-4-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 190 | 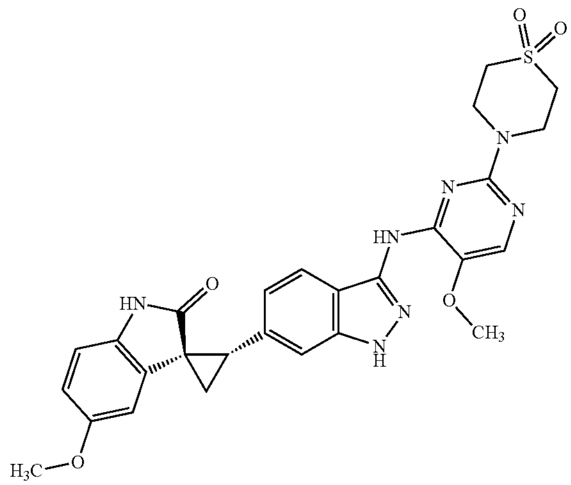 [SMILES: COc1ccc2c(c1)[C@]1(C[C@H]1c1ccc3c(Nc4nc(N5CCS(=O)(=O)CC5)ncc4OC)n[nH]c3c1)C(=O)N2] | 4-[5-methoxy-4-({6-[(1R,2S)-5'-methoxy-2'-oxo-1',2'-dihydrospiro[cyclopropane-1,3'-indol]-2-yl]-1H-indazol-3-yl}amino)pyrimidin-2-yl]-1λ6-thiomorpholine-1,1-dione |
| 191 | 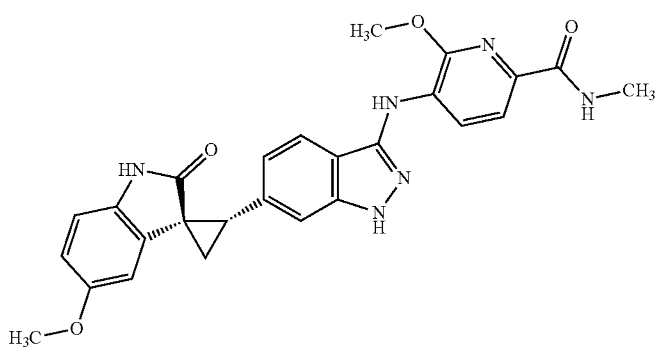 | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methylpyridine-2-carboxamide |
| 192 | 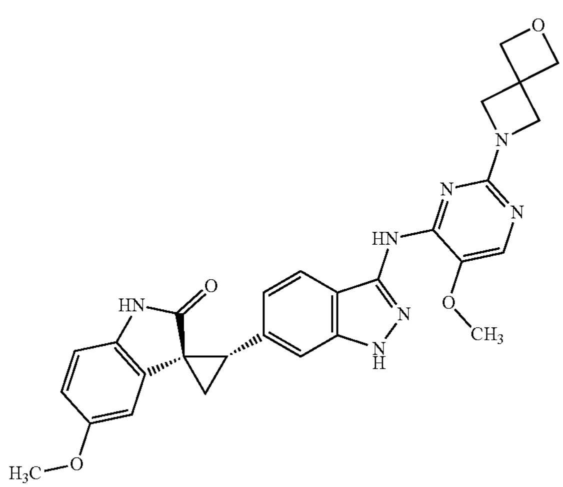 [SMILES: COc1ccc2c(c1)[C@]1(C[C@H]1c1ccc3c(Nc4nc(N5CC6(COC6)C5)ncc4OC)n[nH]c3c1)C(=O)N2] | (1R,2S)-5'-methoxy-2-(3-{[5-methoxy-2-(2-oxa-6-azaspiro[3.3]heptan-6-yl)pyrimidin-4-yl]amino}-1H-indazol-6-yl)spiro[cyclopropane-1,3'-indol]-2'(1'H)-one |

TABLE 1A-continued

| Example No. | Structure | Name |
|---|---|---|
| 193 | 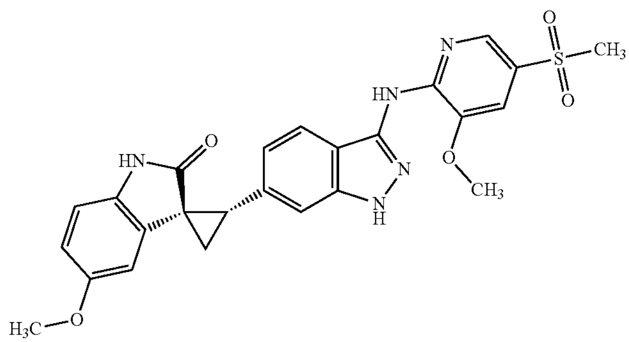 | (1R,2S)-2-(3-{[5-(methanesulfonyl)-3-methoxypyridin-2-yl]amino}-1H-indazol-6-yl)-5'-methoxyspiro[cyclopropane-1,3'-indol]-2'(1'H)-one |
| 194 | 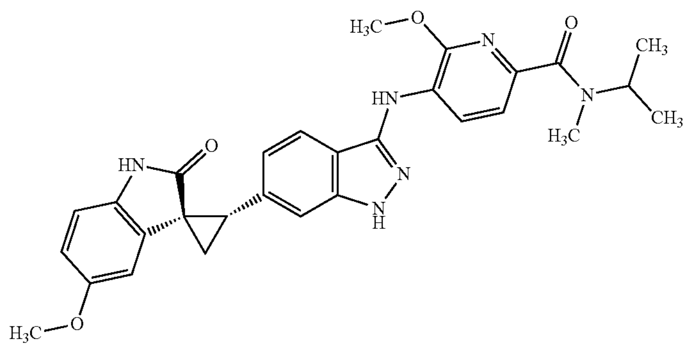 [SMILES: COc1ccc2c(c1)[C@]1(C[C@H]1c1ccc3c(Nc4ccc(C(=O)N(C)C(C)C)nc4OC)n[nH]c3c1)C(=O)N2] | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methyl-N-(propan-2-yl)pyridine-2-carboxamide |
| 195 | 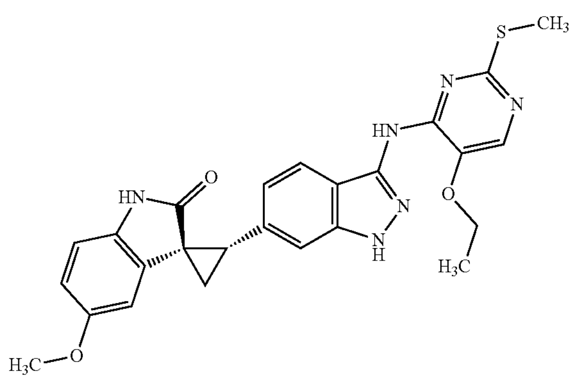 | (1R,2S)-2-(3-{[5-ethoxy-2-(methylsulfanyl)pyrimidin-4-yl]amino}-1H-indazol-6-yl)-5'-methoxyspiro[cyclopropane-1,3'-indol]-2'(1'H)-one |
| 196 | 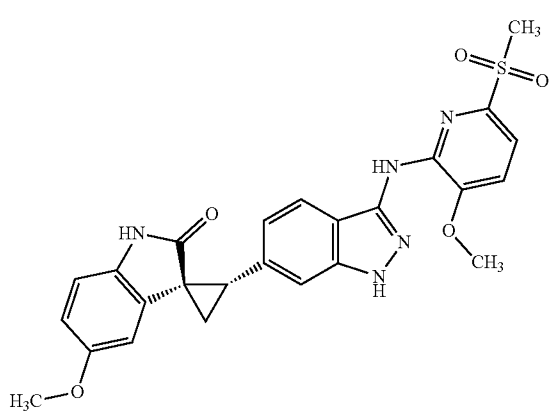 [SMILES: COc1ccc2c(c1)[C@]1(C[C@H]1c1ccc3c(Nc4nc(S(C)(=O)=O)ccc4OC)n[nH]c3c1)C(=O)N2] | (1R,2S)-2-(3-{[6-(methanesulfonyl)-3-methoxypyridin-2-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 197 | 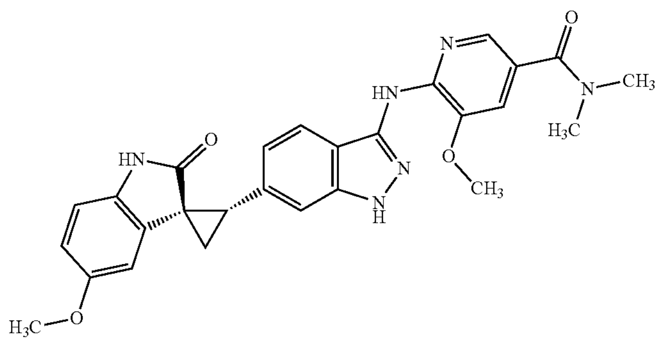 | 5-methoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide |
| 198 | 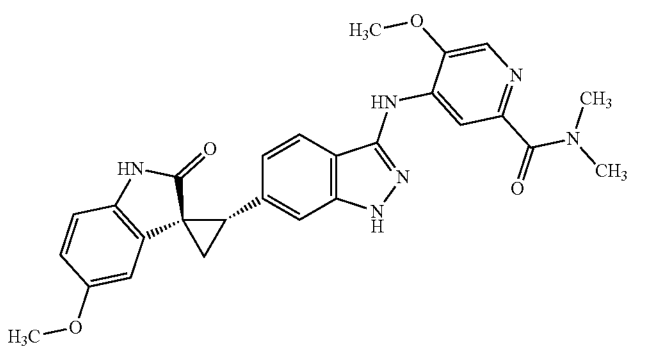 | 5-methoxy-4-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide |
| 199 | 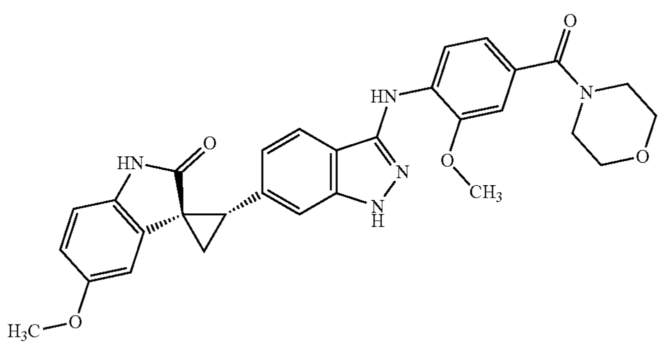 [SMILES: COc1ccc2c(c1)[C@]1(C[C@H]1c1ccc3c(Nc4ccc(C(=O)N5CCOCC5)cc4OC)n[nH]c3c1)C(=O)N2] | (1R,2S)-5'-methoxy-2-{3-[2-methoxy-4-(morpholine-4-carbonyl)anilino]-1H-indazol-6-yl}spiro[cyclopropane-1,3'-indol]-2'(1'H)-one |
| 200 | 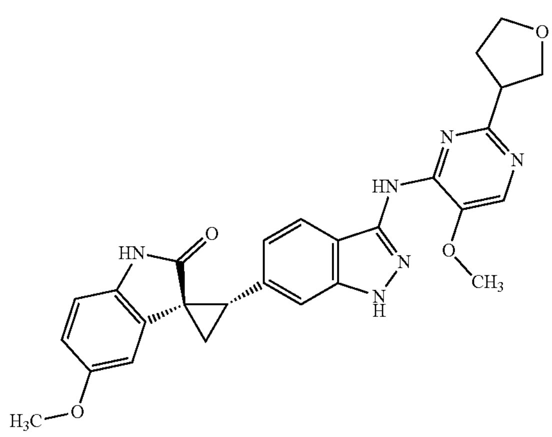 [SMILES: COc1ccc2c(c1)[C@]1(C[C@H]1c1ccc3c(Nc4nc(C5CCOC5)ncc4OC)n[nH]c3c1)C(=O)N2] | Diastereomer 1: (1R,2S)-5'-methoxy-2-(3-{[5-methoxy-2-(oxolan-3-yl)pyrimidin-4-yl]amino}-1H-indazol-6-yl)spiro[cyclopropane-1,3'-indol]-2'(1'H)-one |

| Example No. | Structure | Name |
|---|---|---|
| 201 | 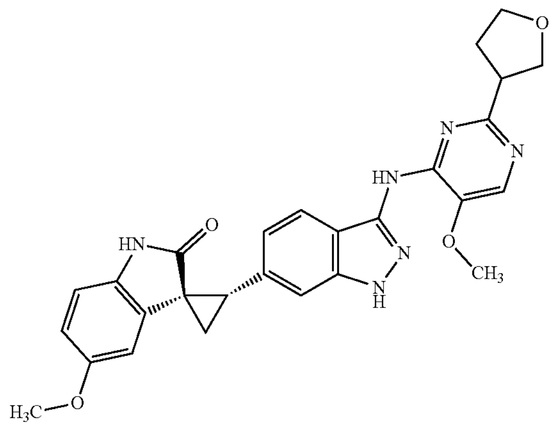 [SMILES: COc1ccc2c(c1)[C@]1(C[C@H]1c1ccc3c(Nc4nc(C5CCOC5)ncc4OC)n[nH]c3c1)C(=O)N2] | Diastereomer 2: (1R,2S)-5'-methoxy-2-(3-{[5-methoxy-2-(oxolan-3-yl)pyrimidin-4-yl]amino}-1H-indazol-6-yl)spiro[cyclopropane-1,3'-indol]-2'(1'H)-one |
| 202 | 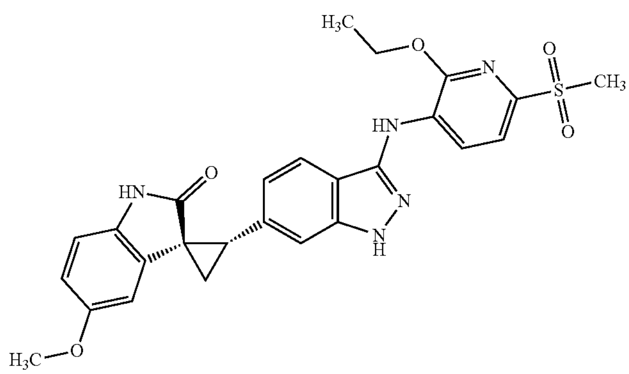 | (1R,2S)-2-(3-{[2-ethoxy-6-(methanesulfonyl)pyridin-3-yl]amino}-1H-indazol-6-yl)-5'-methoxyspiro[cyclopropane-1,3'-indol]-2'(1'H)-one |
| 203 | 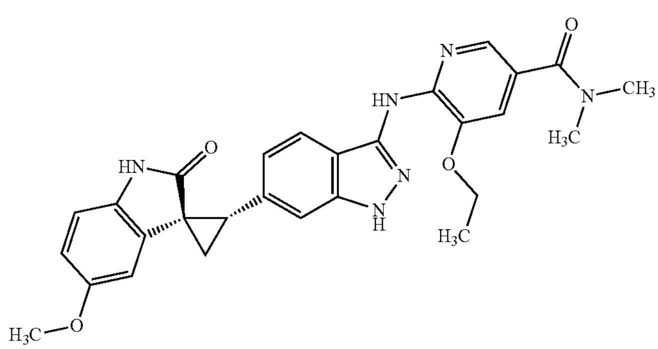 | 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide |
| 204 | 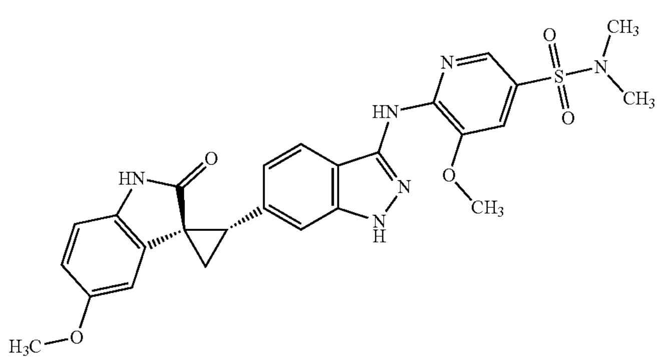 | 5-methoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-sulfonamide |

TABLE 1A-continued

| Example No. | Structure | Name |
|---|---|---|
| 205 | 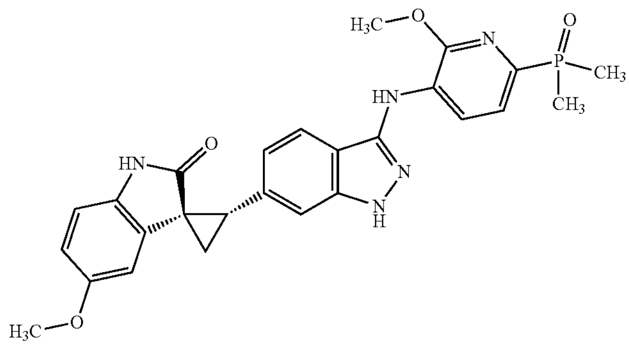 | (1R,2S)-2-(3-{[6-(dimethylphosphoryl)-2-methoxypyridin-3-yl]amino}-1H-indazol-6-yl)-5'-methoxyspiro[cyclopropane-1,3'-indol]-2'(1'H)-one |
| 206 | 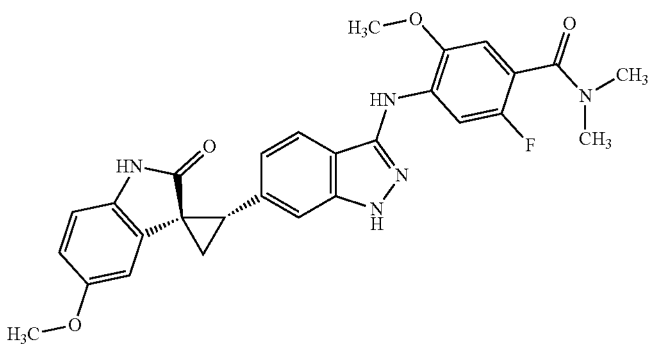 | 2-fluoro-5-methoxy-4-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzamide |
| 207 | 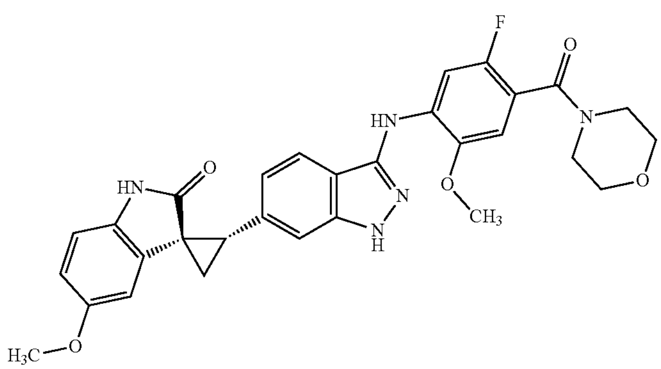 [SMILES: COc1ccc2c(c1)[C@]1(C[C@H]1c1ccc3c(Nc4cc(F)c(C(=O)N5CCOCC5)cc4OC)n[nH]c3c1)C(=O)N2] | (1R,2S)-2-{3-[5-fluoro-2-methoxy-4-(morpholine-4-carbonyl)anilino]-1H-indazol-6-yl}-5'-methoxyspiro[cyclopropane-1,3'-indol]-2'(1'H)-one |
| 208 | 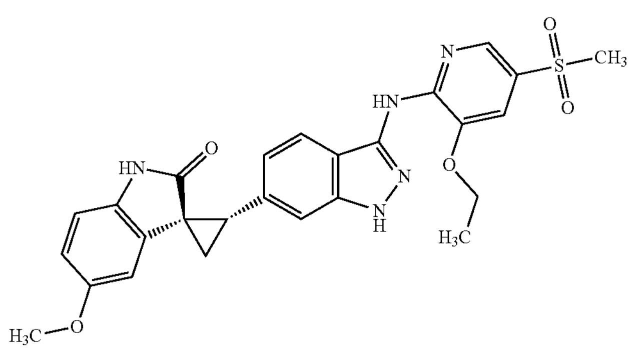 | (1R,2S)-2-{3-[5-fluoro-2-methoxy-4-(morpholine-4-carbonyl)anilino]-1H-indazol-6-yl}-5'-methoxyspiro[cyclopropane-1,3'-indol]-2'(1'H)-one |

TABLE 1A-continued

| Example No. | Structure | Name |
|---|---|---|
| 209 | 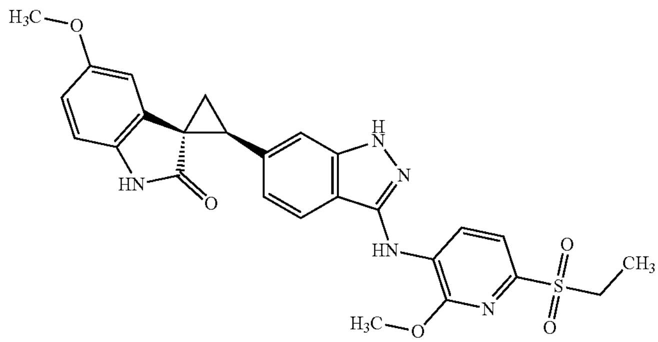 [SMILES: CCS(=O)(=O)c1ccc(Nc2n[nH]c3cc([C@@H]4C[C@@]45C(=O)Nc4ccc(OC)cc45)ccc23)c(OC)n1] | (1R,2S)-2-(3-{[6-(ethanesulfonyl)-2-methoxypyridin-3-yl]amino}-1H-indazol-6-yl)-5'-methoxyspiro[cyclopropane-1,3'-indol]-2'(1'H)-one |
| 210 | 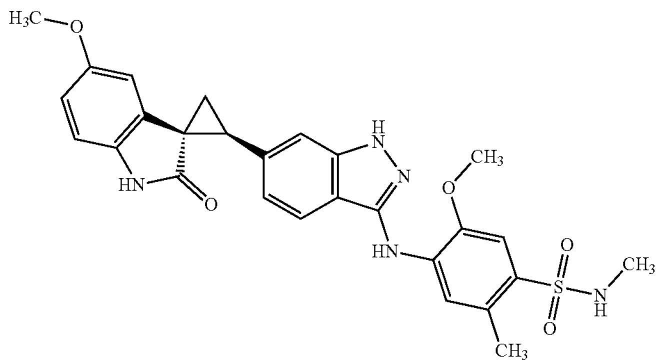 | 5-methoxy-4-({6-[(1R,2S)-5'-methoxy-2'-oxo-1',2'-dihydrospiro[cyclopropane-1,3'-indol]-2-yl]-1H-indazol-3-yl}amino)-N,2-dimethylbenzene-1-sulfonamide |
| 211 | 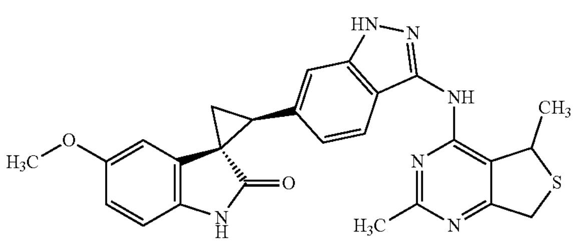 [SMILES: COc1ccc2c(c1)[C@]1(C[C@H]1c1ccc3c(Nc4nc(C)nc5c4C(C)SC5)n[nH]c3c1)C(=O)N2] | (1R,2S)-2-{3-[(2,5-dimethyl-5,7-dihydrothieno[3,4-d]pyrimidin-4-yl)amino]-1H-indazol-6-yl}-5'-methoxyspiro[cyclopropane-1,3'-indol]-2'(1'H)-one (single diastereomer of unknown absolute configuration) |
| 212 | 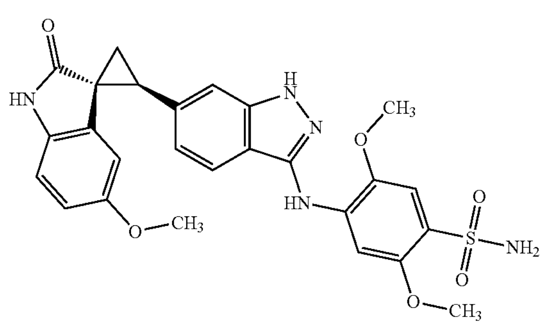 [SMILES: COc1ccc2c(c1)[C@]1(C[C@H]1c1ccc3c(Nc4cc(OC)c(S(N)(=O)=O)cc4OC)n[nH]c3c1)C(=O)N2] | 2,5-dimethoxy-4-({6-[(1R,2S)-5'-methoxy-2'-oxo-1',2'-dihydrospiro[cyclopropane-1,3'-indol]-2-yl]-1H-indazol-3-yl}amino)benzene-1-sulfonamide |

| Example No. | Structure | Name |
|---|---|---|
| 213 | 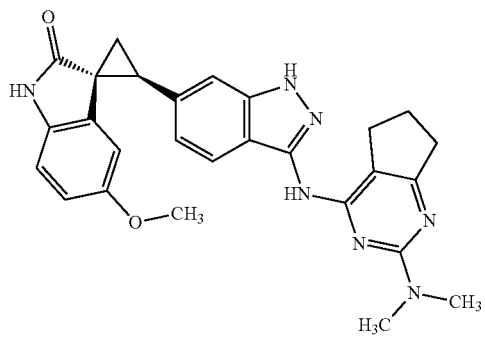 [SMILES: COc1ccc2c(c1)[C@]1(C[C@H]1c1ccc3c(Nc4nc(N(C)C)nc5c4CCC5)n[nH]c3c1)C(=O)N2] | (1R,2S)-2-(3-{[2-(dimethylamino)-6,7-dihydro-5H-cyclopenta[d]pyrimidin-4-yl]amino}-1H-indazol-6-yl)-5'-methoxyspiro[cyclopropane-1,3'-indol]-2'(1'H)-one |
| 214 | 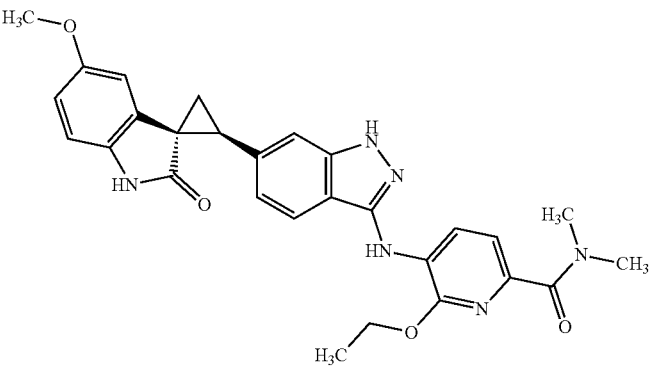 | 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide |
| 215 | 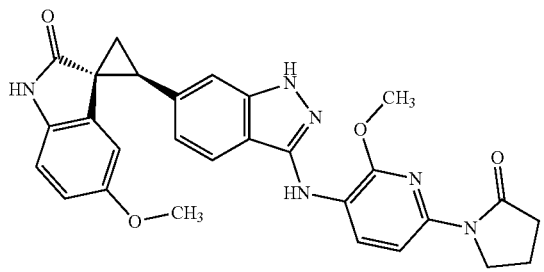 [SMILES: COc1ccc2c(c1)[C@]1(C[C@H]1c1ccc3c(Nc4ccc(N5CCCC5=O)nc4OC)n[nH]c3c1)C(=O)N2] | (1R,2S)-5'-methoxy-2-(3-{[2-methoxy-6-(2-oxopyrrolidin-1-yl)pyridin-3-yl]amino}-1H-indazol-6-yl)spiro[cyclopropane-1,3'-indol]-2'(1'H)-one |
| 216 | 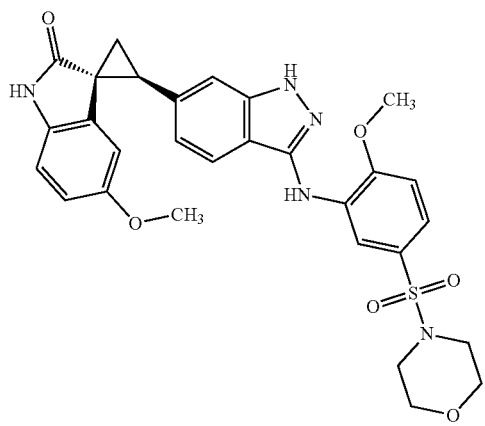 [SMILES: COc1ccc2c(c1)[C@]1(C[C@H]1c1ccc3c(Nc4cc(S(=O)(=O)N5CCOCC5)ccc4OC)n[nH]c3c1)C(=O)N2] | (1R,2S)-5'-methoxy-2-{3-[2-methoxy-5-(morpholine-4-sulfonyl)anilino]-1H-indazol-6-yl}spiro[cyclopropane-1,3'-indol]-2'(1'H)-one |

TABLE 1A-continued

| Example No. | Structure | Name |
|---|---|---|
| 217 | 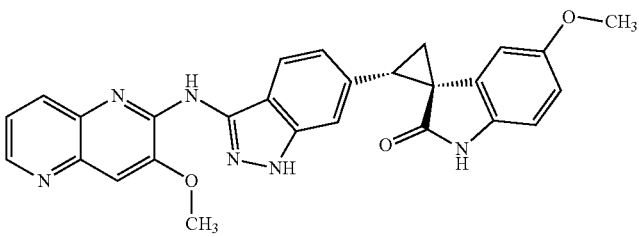 [SMILES: COc1ccc2c(c1)[C@]1(C[C@H]1c1ccc3c(Nc4nc5cccnc5cc4OC)n[nH]c3c1)C(=O)N2] | (1R,2S)-5'-methoxy-2-{3-[(3-methoxy-1,5-naphthyridin-2-yl)amino]-1H-indazol-6-yl}spiro[cyclopropane-1,3'-indol]-2'(1'H)-one |
| 218 | 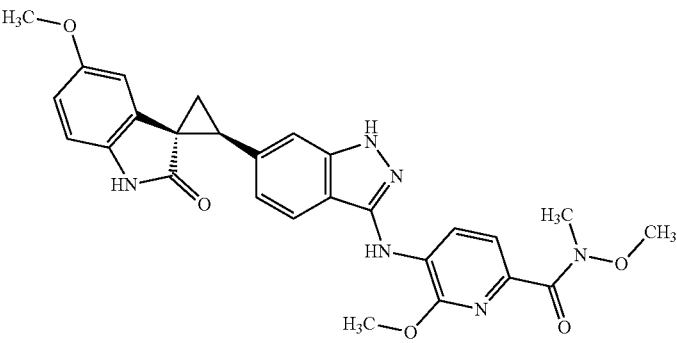 | N,6-dimethoxy-5-({6-[(1R,2S)-5'-methoxy-2'-oxo-1',2'-dihydrospiro[cyclopropane-1,3'-indol]-2-yl]-1H-indazol-3-yl}amino)-N-methylpyridine-2-carboxamide |
| 219 | 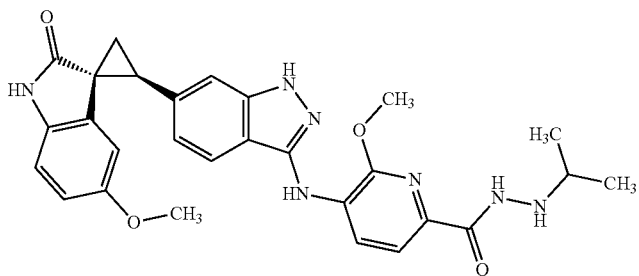 [SMILES: COc1ccc2c(c1)[C@]1(C[C@H]1c1ccc3c(Nc4ccc(C(=O)NNC(C)C)nc4OC)n[nH]c3c1)C(=O)N2] | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N'-(propan-2-yl)pyridine-2-carbohydrazide |
| 220 | 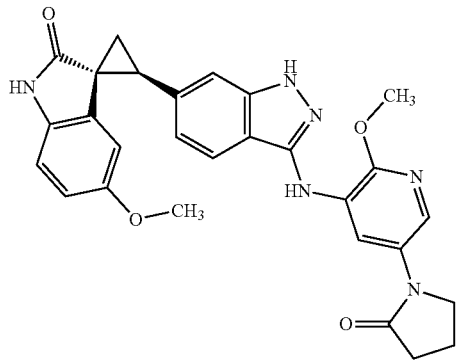 [SMILES: COc1ccc2c(c1)[C@]1(C[C@H]1c1ccc3c(Nc4cc(N5CCCC5=O)cnc4OC)n[nH]c3c1)C(=O)N2] | (1R,2S)-5'-methoxy-2-(3-{[2-methoxy-5-(2-oxopyrrolidin-1-yl)pyridin-3-yl]amino}-1H-indazol-6-yl)spiro[cyclopropane-1,3'-indol]-2'(1'H)-one |

TABLE 1A-continued

| Example No. | Structure | Name |
|---|---|---|
| 221 | 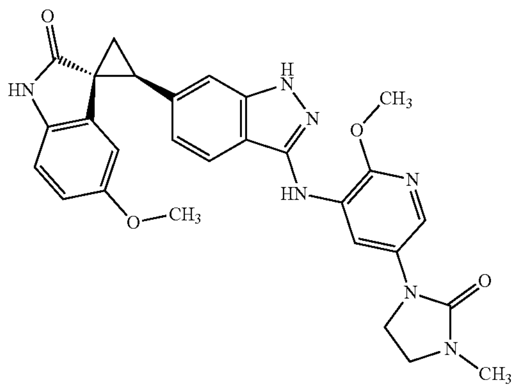 [SMILES: COc1ccc2c(c1)[C@]1(C[C@H]1c1ccc3c(Nc4cc(N5CCN(C)C5=O)cnc4OC)n[nH]c3c1)C(=O)N2] | (1R,2S)-5'-methoxy-2-(3-{[2-methoxy-5-(3-methyl-2-oxoimidazolidin-1-yl)pyridin-3-yl]amino}-1H-indazol-6-yl)spiro[cyclopropane-1,3'-indol]-2'(1'H)-one |
| 222 | 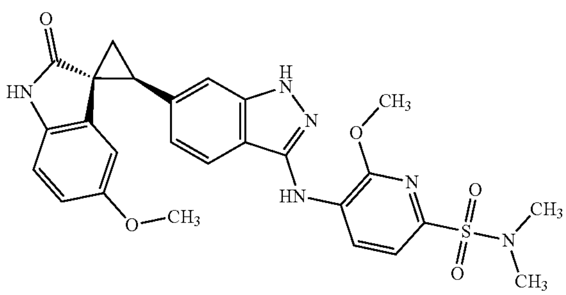 [SMILES: COc1ccc2c(c1)[C@]1(C[C@H]1c1ccc3c(Nc4ccc(S(=O)(=O)N(C)C)nc4OC)n[nH]c3c1)C(=O)N2] | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-sulfonamide |
| 223 | 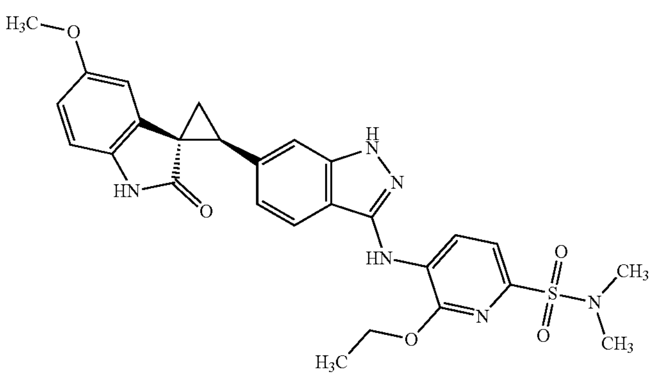 | 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-sulfonamide |
| 224 | 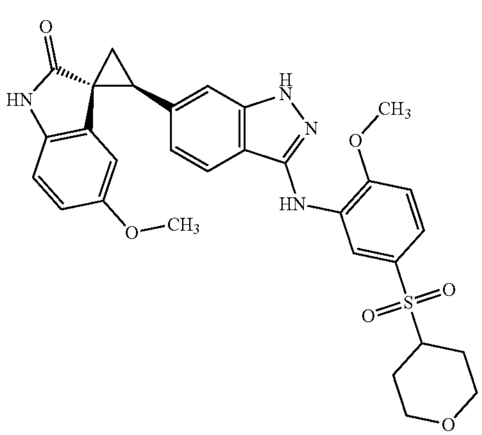 [SMILES: COc1ccc2c(c1)[C@]1(C[C@H]1c1ccc3c(Nc4cc(S(=O)(=O)C5CCOCC5)ccc4OC)n[nH]c3c1)C(=O)N2] | (1R,2S)-5'-methoxy-2-{3-[2-methoxy-5-(oxane-4-sulfonyl)anilino]-1H-indazol-6-yl}spiro[cyclopropane-1,3'-indol]-2'(1'H)-one |

TABLE 1A-continued

| Example No. | Structure | Name |
|---|---|---|
| 225 | 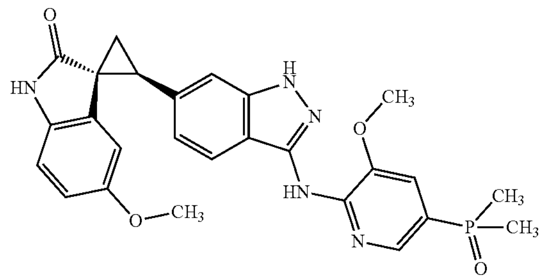 [SMILES: COc1ccc2c(c1)[C@]1(C[C@H]1c1ccc3c(Nc4ncc(P(C)(C)=O)cc4OC)n[nH]c3c1)C(=O)N2] | (1R,2S)-2-(3-{[5-(dimethylphosphoryl)-3-methoxypyridin-2-yl]amino}-1H-indazol-6-yl)-5'-methoxyspiro[cyclopropane-1,3'-indol]-2'(1'H)-one |
| 226 | 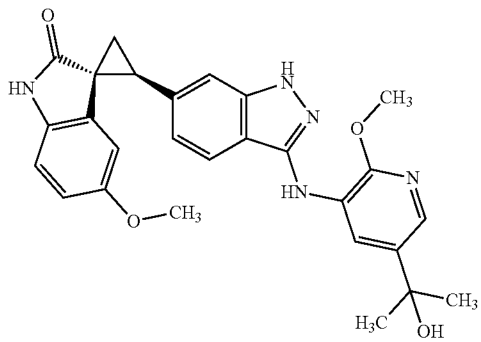 [SMILES: COc1ccc2c(c1)[C@]1(C[C@H]1c1ccc3c(Nc4cc(C(C)(C)O)cnc4OC)n[nH]c3c1)C(=O)N2] | (1R,2S)-2-(3-{[5-(2-hydroxypropan-2-yl)-2-methoxypyridin-3-yl]amino}-1H-indazol-6-yl)-5'-methoxyspiro[cyclopropane-1,3'-indol]-2'(1'H)-one |
| 227 | 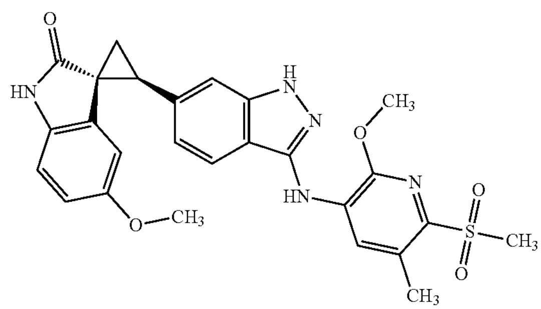 [SMILES: COc1ccc2c(c1)[C@]1(C[C@H]1c1ccc3c(Nc4cc(C)c(S(C)(=O)=O)nc4OC)n[nH]c3c1)C(=O)N2] | (1R,2S)-2-(3-{[6-(methanesulfonyl)-2-methoxy-5-methylpyridin-3-yl]amino}-1H-indazol-6-yl)-5'-methoxyspiro[cyclopropane-1,3'-indol]-2'(1'H)-one |
| 228 | 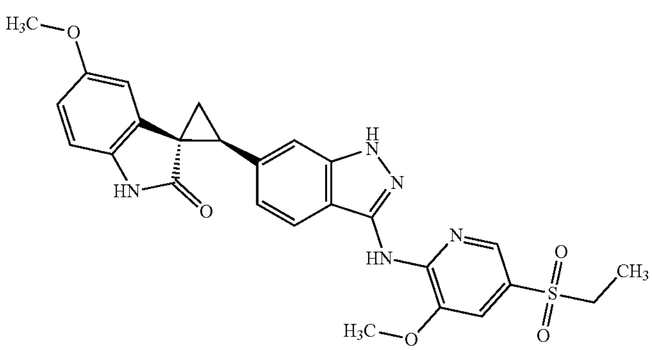 [SMILES: CCS(=O)(=O)c1cnc(Nc2n[nH]c3cc([C@@H]4C[C@@]45C(=O)Nc4ccc(OC)cc45)ccc23)c(OC)c1] | (1R,2S)-2-(3-{[5-(ethanesulfonyl)-3-methoxypyridin-2-yl]amino}-1H-indazol-6-yl)-5'-methoxyspiro[cyclopropane-1,3'-indol]-2'(1'H)-one |
| 229 | 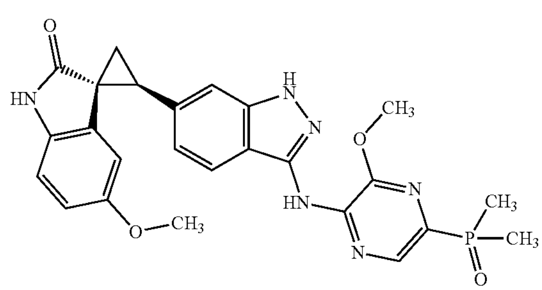 [SMILES: COc1ccc2c(c1)[C@]1(C[C@H]1c1ccc3c(Nc4ncc(P(C)(C)=O)nc4OC)n[nH]c3c1)C(=O)N2] | (1R,2S)-2-(3-{[5-(dimethylphosphoryl)-3-methoxypyrazin-2-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 230 | 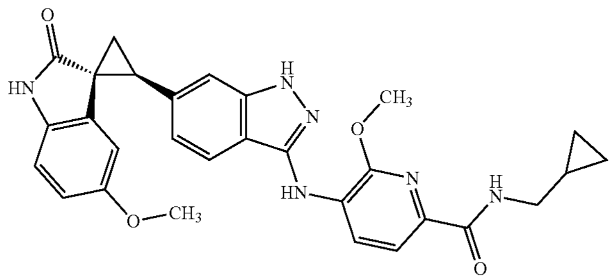 [SMILES: COc1ccc2c(c1)[C@]1(C[C@H]1c1ccc3c(Nc4ccc(C(=O)NCC5CC5)nc4OC)n[nH]c3c1)C(=O)N2] | N-(cyclopropylmethyl)-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide |
| 231 | 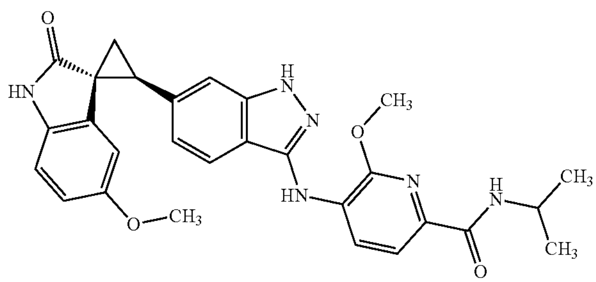 [SMILES: COc1ccc2c(c1)[C@]1(C[C@H]1c1ccc3c(Nc4ccc(C(=O)NC(C)C)nc4OC)n[nH]c3c1)C(=O)N2] | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-(propan-2-yl)pyridine-2-carboxamide |
| 232 | 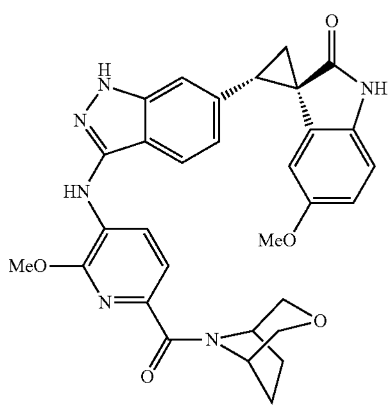 [SMILES: COc1ccc2c(c1)[C@]1(C[C@H]1c1ccc3c(Nc4ccc(C(=O)N5C6CCC5COC6)nc4OC)n[nH]c3c1)C(=O)N2] | (1R,2S)-5'-methoxy-2-(3-{[2-methoxy-6-(3-oxa-8-azabicyclo[3.2.1]octane-8-carbonyl)pyridin-3-yl]amino}-1H-indazol-6-yl)spiro[cyclopropane-1,3'-indol]-2'(1'H)-one |
| 233 | 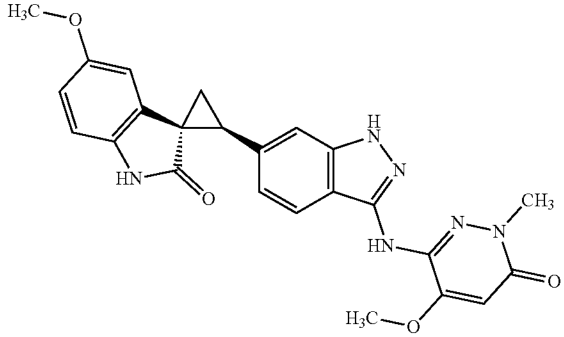 [SMILES: COc1ccc2c(c1)[C@]1(C[C@H]1c1ccc3c(Nc4nn(C)c(=O)cc4OC)n[nH]c3c1)C(=O)N2] | (1R,2S)-5'-methoxy-2-{3-[(4-methoxy-1-methyl-6-oxo-1,6-dihydropyridazin-3-yl)amino]-1H-indazol-6-yl}spiro[cyclopropane-1,3'-indol]-2'(1'H)-one |

TABLE 1A-continued

| Example No. | Structure | Name |
|---|---|---|
| 234 | 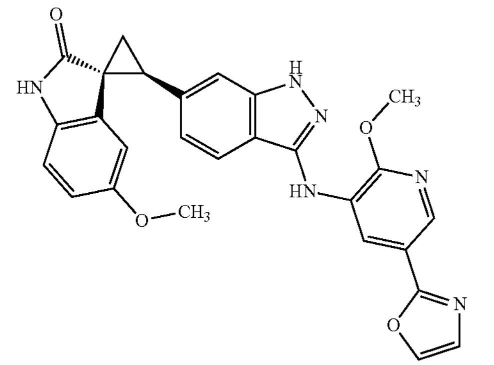 [SMILES: COc1ccc2c(c1)[C@]1(C[C@H]1c1ccc3c(Nc4cc(-c5ncco5)cnc4OC)n[nH]c3c1)C(=O)N2] | (1R,2S)-5'-methoxy-2-(3-{[2-methoxy-5-(1,3-oxazol-2-yl)pyridin-3-yl]amino}-1H-indazol-6-yl)spiro[cyclopropane-1,3'-indol]-2'(1'H)-one |
| 235 | 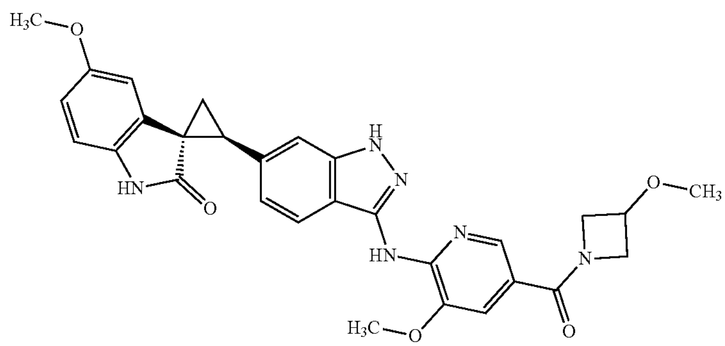 | (1R,2S)-5'-methoxy-2-(3-{[3-methoxy-5-(3-methoxyazetidine-1-carbonyl)pyridin-2-yl]amino}-1H-indazol-6-yl)spiro[cyclopropane-1,3'-indol]-2'(1'H)-one |
| 236 | 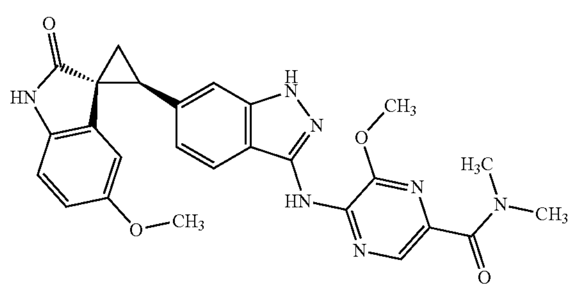 [SMILES: COc1ccc2c(c1)[C@]1(C[C@H]1c1ccc3c(Nc4ncc(C(=O)N(C)C)nc4OC)n[nH]c3c1)C(=O)N2] | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyrazine-2-carboxamide |
| 237 | 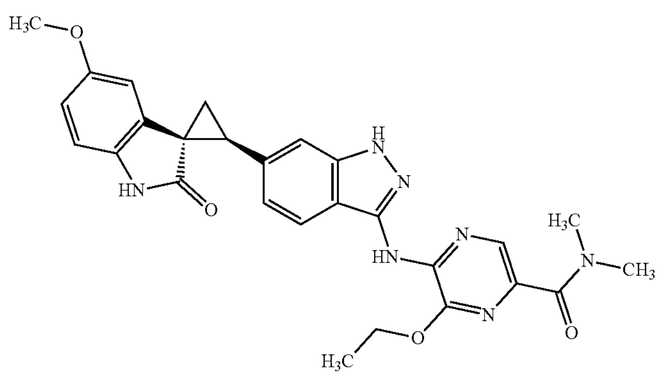 | 6-ethoxy-5-({6-[(1R,2S)-5'-methoxy-2'-oxo-1'2'-dihydrospiro[cyclopropane-1,3'-indol]-2-yl]-1H-indazol-3-yl}amino)-N,N-dimethylpyrazine-2-carboxamide |

TABLE 1A-continued

| Example No. | Structure | Name |
|---|---|---|
| 238 | 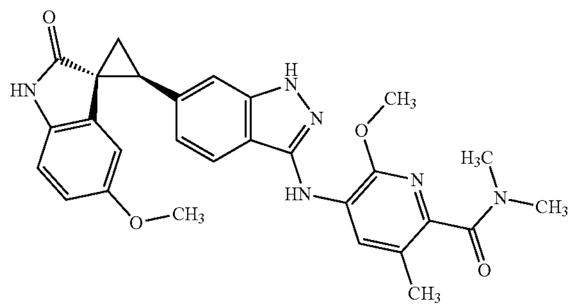 [SMILES: COc1ccc2c(c1)[C@]1(C[C@H]1c1ccc3c(Nc4cc(C)c(C(=O)N(C)C)nc4OC)n[nH]c3c1)C(=O)N2] | 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N,3-trimethylpyridine-2-carboxamide |
| 239 | 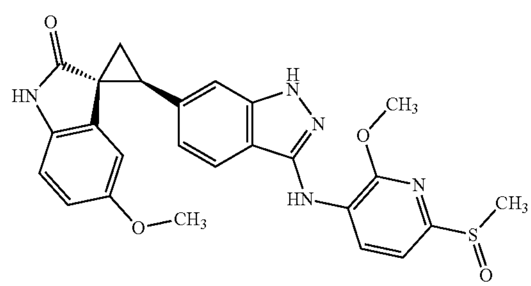 [SMILES: COc1ccc2c(c1)[C@]1(C[C@H]1c1ccc3c(Nc4ccc(S(C)=O)nc4OC)n[nH]c3c1)C(=O)N2] | Diastereomer 1: (1R,2S)-2-(3-{[6-(methanesulfinyl)-2-methoxypyridin-3-yl]amino}-1H-indazol-6-yl)-5'-methoxyspiro[cyclopropane-1,3'-indol]-2'(1'H)-one |
| 240 | 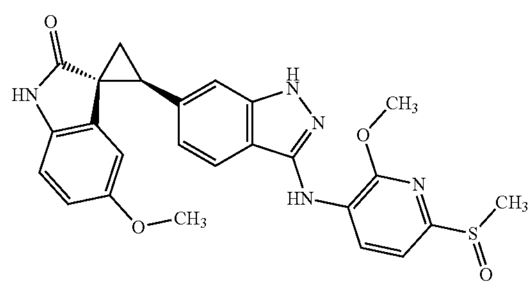 [SMILES: COc1ccc2c(c1)[C@]1(C[C@H]1c1ccc3c(Nc4ccc(S(C)=O)nc4OC)n[nH]c3c1)C(=O)N2] | Diastereomer 2: (1R,2S)-2-(3-{[6-(methanesulfinyl)-2-methoxypyridin-3-yl]amino}-1H-indazol-6-yl)-5'-methoxyspiro[cyclopropane-1,3'-indol]-2'(1'H)-one |
| 241 | 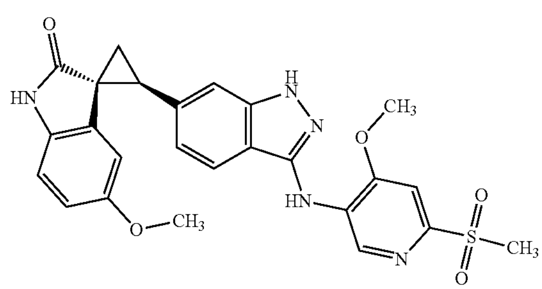 [SMILES: COc1ccc2c(c1)[C@]1(C[C@H]1c1ccc3c(Nc4cnc(S(C)(=O)=O)cc4OC)n[nH]c3c1)C(=O)N2] | (1R,2S)-2-(3-{[6-(methanesulfonyl)-4-methoxypyridin-3-yl]amino}-1H-indazol-6-yl)-5'-methoxyspiro[cyclopropane-1,3'-indol]-2'(1'H)-one |
| 242 | 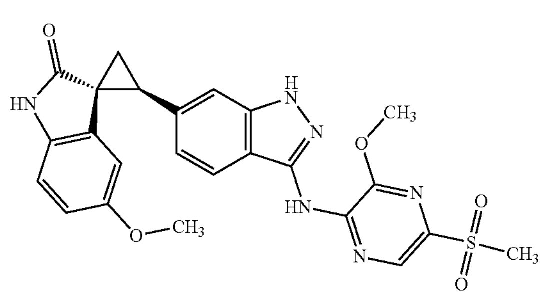 [SMILES: COc1ccc2c(c1)[C@]1(C[C@H]1c1ccc3c(Nc4ncc(S(C)(=O)=O)nc4OC)n[nH]c3c1)C(=O)N2] | (1R,2S)-2-(3-{[5-(methanesulfonyl)-3-methoxypyrazin-2-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 243 | 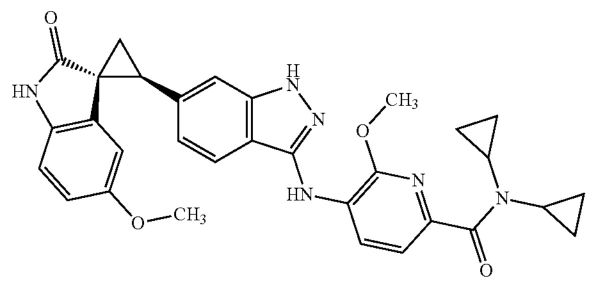 [SMILES: COc1ccc2c(c1)[C@]1(C[C@H]1c1ccc3c(Nc4ccc(C(=O)N(C5CC5)C5CC5)nc4OC)n[nH]c3c1)C(=O)N2] | N,N-dicyclopropyl-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide |
| 244 | 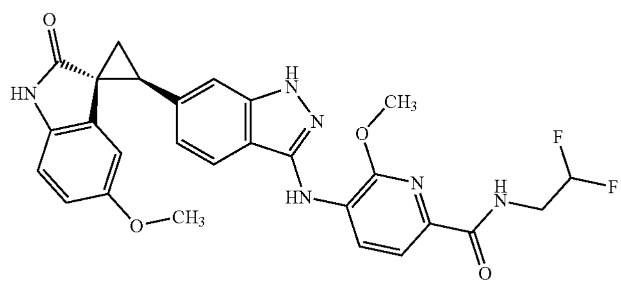 [SMILES: COc1ccc2c(c1)[C@]1(C[C@H]1c1ccc3c(Nc4ccc(C(=O)NCC(F)F)nc4OC)n[nH]c3c1)C(=O)N2] | N-(2,2-difluoroethyl)-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide |
| 245 | 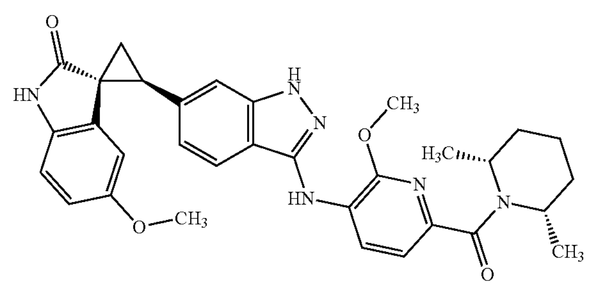 [SMILES: COc1ccc2c(c1)[C@]1(C[C@H]1c1ccc3c(Nc4ccc(C(=O)N5[C@H](C)CCC[C@@H]5C)nc4OC)n[nH]c3c1)C(=O)N2] | (1R,2S)-2-[3-({6-[(2R,6S)-2,6-dimethylpiperidine-1-carbonyl]-2-methoxypyridin-3-yl}amino)-1H-indazol-6-yl]-5'-methoxyspiro[cyclopropane-1,3'-indol]-2'(1'H)-one |
| 246 | 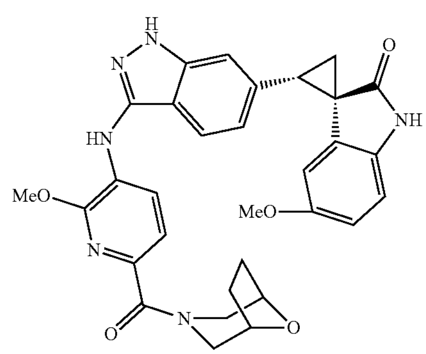 [SMILES: COc1ccc2c(c1)[C@]1(C[C@H]1c1ccc3c(Nc4ccc(C(=O)N5CC6CCC(C5)O6)nc4OC)n[nH]c3c1)C(=O)N2] | (1R,2S)-5'-methoxy-2-(3-{[2-methoxy-6-(8-oxa-3-azabicyclo[3.2.1]octane-3-carbonyl)pyridin-3-yl]amino}-1H-indazol-6-yl)spiro[cyclopropane-1,3'-indol]-2'(1'H)-one |
| 247 | 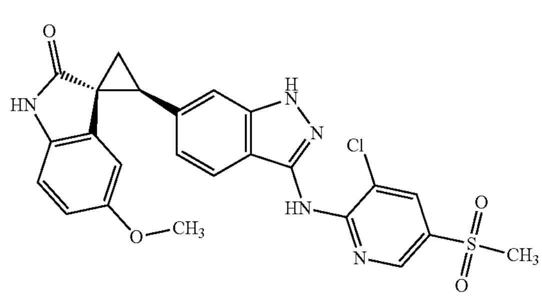 [SMILES: COc1ccc2c(c1)[C@]1(C[C@H]1c1ccc3c(Nc4ncc(S(C)(=O)=O)cc4Cl)n[nH]c3c1)C(=O)N2] | (1R,2S)-2-(3-{[3-chloro-5-(methanesulfonyl)pyridin-2-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 248 | 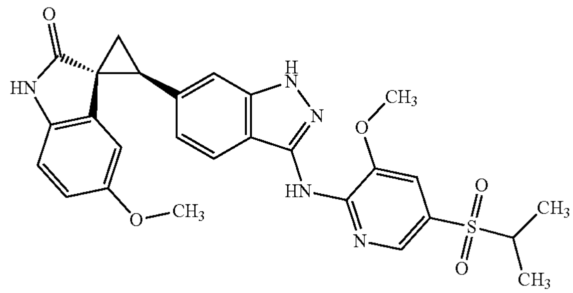 [SMILES: COc1ccc2c(c1)[C@]1(C[C@H]1c1ccc3c(Nc4ncc(S(=O)(=O)C(C)C)cc4OC)n[nH]c3c1)C(=O)N2] | (1R,2S)-5'-methoxy-2-(3-{[3-methoxy-5-(propane-2-sulfonyl)pyridin-2-yl]amino}-1H-indazol-6-yl)spiro[cyclopropane-1,3'-indol]-2'(1'H)-one |
| 249 | 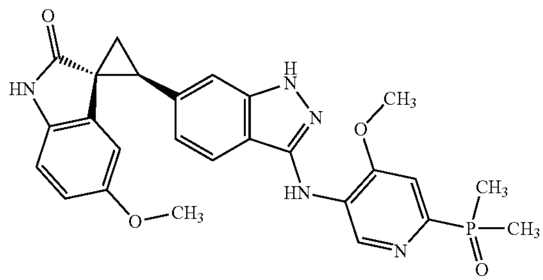 [SMILES: COc1ccc2c(c1)[C@]1(C[C@H]1c1ccc3c(Nc4cnc(P(C)(C)=O)cc4OC)n[nH]c3c1)C(=O)N2] | (1R,2S)-2-(3-{[6-(dimethylphosphoryl)-4-methoxypyridin-3-yl]amino}-1H-indazol-6-yl)-5'-methoxyspiro[cyclopropane-1,3'-indol]-2'(1'H)-one |
| 250 | 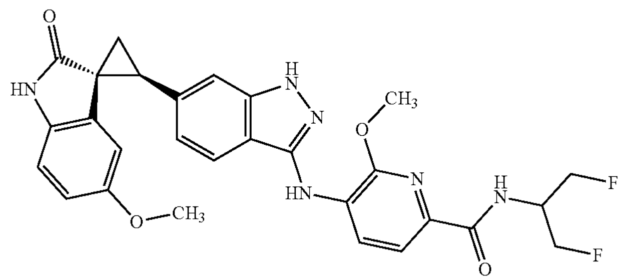 [SMILES: COc1ccc2c(c1)[C@]1(C[C@H]1c1ccc3c(Nc4ccc(C(=O)NC(CF)CF)nc4OC)n[nH]c3c1)C(=O)N2] | N-(1,3-difluoropropan-2-yl)-6-methoxy-5-(({6-[(1R,2S)-5'-methoxy-2'-oxo-1',2'-dihydrospiro[cyclopropane-1,3'-indol]-2-yl]-1H-indazol-3-yl}amino)pyridine-2-carboxamide |
| 251 | 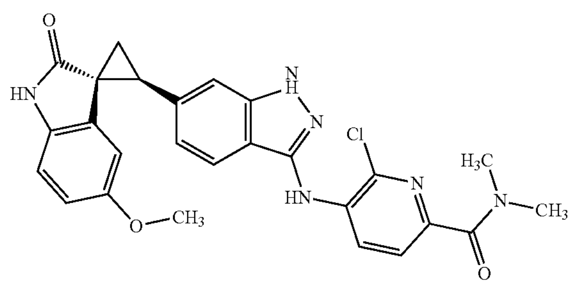 [SMILES: COc1ccc2c(c1)[C@]1(C[C@H]1c1ccc3c(Nc4ccc(C(=O)N(C)C)nc4Cl)n[nH]c3c1)C(=O)N2] | 6-chloro-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide |
| 252 | 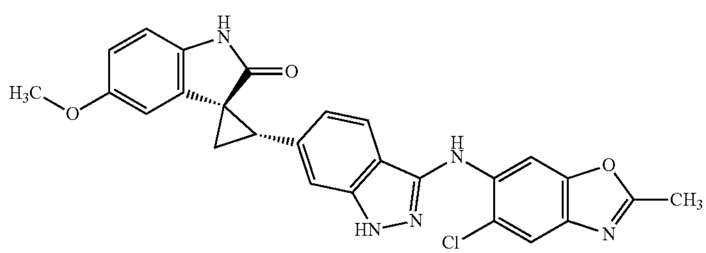 | (1R,2S)-2-{3-[(5-chloro-2-methyl-1,3-benzoxazol-6-yl)amino]-1H-indazol-6-yl}-5'-methoxyspiro[cyclopropane-1,3'-indol]-2'(1'H)-one |

TABLE 1A-continued

| Example No. | Structure | Name |
|---|---|---|
| 253 | 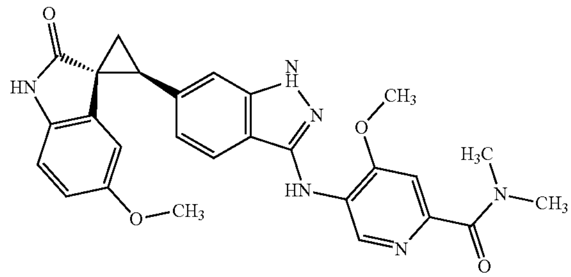 [SMILES: COc1ccc2c(c1)[C@]1(C[C@H]1c1ccc3c(Nc4cnc(C(=O)N(C)C)cc4OC)n[nH]c3c1)C(=O)N2] | 4-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide |
| 254 | 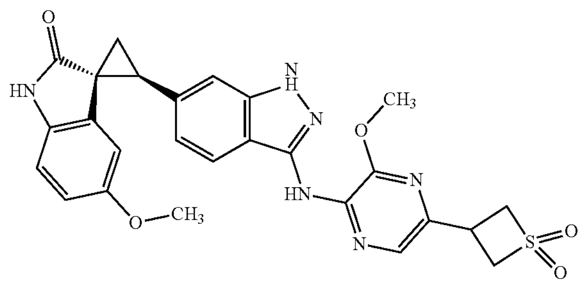 [SMILES: COc1ccc2c(c1)[C@]1(C[C@H]1c1ccc3c(Nc4ncc(C5CS(=O)(=O)C5)nc4OC)n[nH]c3c1)C(=O)N2] | 3-[6-methoxy-5-({6-[(1R,2S)-5'-methoxy-2'-oxo-1',2'-dihydrospiro[cyclopropane-1,3'-indol]-2-yl]-1H-indazol-3-yl}amino)pyrazin-2-yl]-1λ6-thietane-1,1-dione |
| 255 | 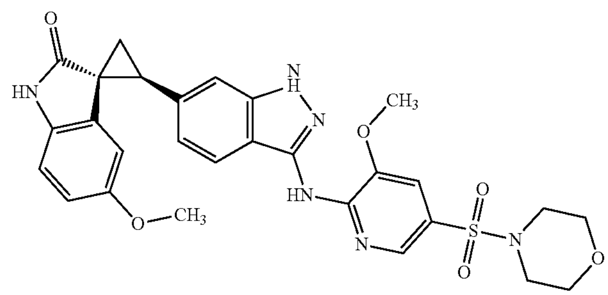 [SMILES: COc1ccc2c(c1)[C@]1(C[C@H]1c1ccc3c(Nc4ncc(S(=O)(=O)N5CCOCC5)cc4OC)n[nH]c3c1)C(=O)N2] | (1R,2S)-5'-methoxy-2-(3-{[3-methoxy-5-(morpholine-4-sulfonyl)pyridin-2-yl]amino}-1H-indazol-6-yl)spiro[cyclopropane-1,3'-indol]-2'(1'H)-one |
| 256 | 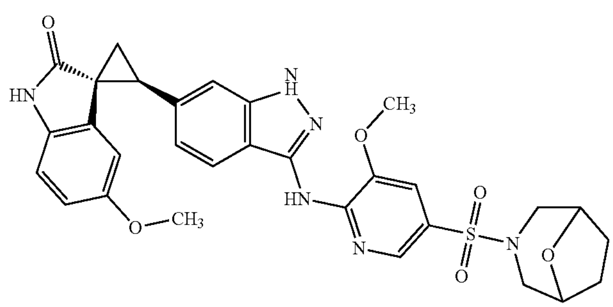 [SMILES: COc1ccc2c(c1)[C@]1(C[C@H]1c1ccc3c(Nc4ncc(S(=O)(=O)N5CC6CCC(C5)O6)cc4OC)n[nH]c3c1)C(=O)N2] | (1R,2S)-5'-methoxy-2-(3-{[3-methoxy-5-(8-oxa-3-azabicyclo[3.2.1]octane-3-sulfonyl)pyridin-2-yl]amino}-1H-indazol-6-yl)spiro[cyclopropane-1,3'-indol]-2'(1'H)-one |
| 257 | 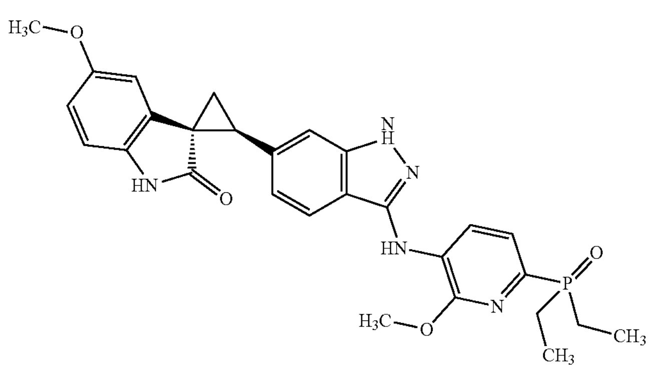 [SMILES: CCP(=O)(CC)c1ccc(Nc2n[nH]c3cc([C@@H]4C[C@@]45C(=O)Nc4ccc(OC)cc45)ccc23)c(OC)n1] | (1R,2S)-2-(3-{[6-(diethylphosphoryl)-2-methoxypyridin-3-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 258 | 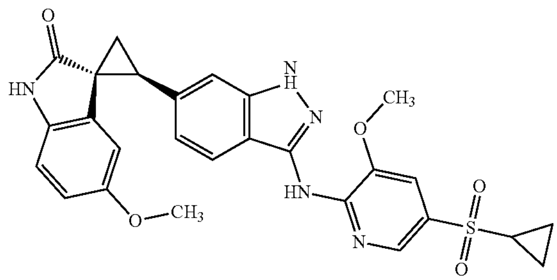 [SMILES: COc1ccc2c(c1)[C@]1(C[C@H]1c1ccc3c(Nc4ncc(S(=O)(=O)C5CC5)cc4OC)n[nH]c3c1)C(=O)N2] | (1R,2S)-2-(3-{[5-(cyclopropanesulfonyl)-3-methoxypyridin-2-yl]amino}-1H-indazol-6-yl)-5'-methoxyspiro[cyclopropane-1,3'-indol]-2'(1'H)-one |
| 259 | 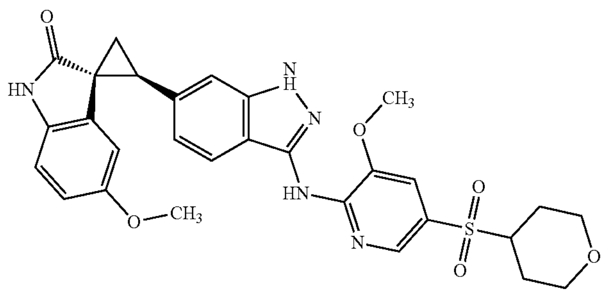 [SMILES: COc1ccc2c(c1)[C@]1(C[C@H]1c1ccc3c(Nc4ncc(S(=O)(=O)C5CCOCC5)cc4OC)n[nH]c3c1)C(=O)N2] | (1R,2S)-5'-methoxy-2-(3-{[3-methoxy-5-(oxane-4-sulfonyl)pyridin-2-yl]amino}-1H-indazol-6-yl)spiro[cyclopropane-1,3'-indol]-2'(1'H)-one |
| 260 | 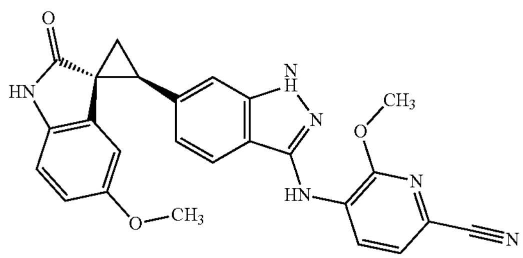 [SMILES: COc1ccc2c(c1)[C@]1(C[C@H]1c1ccc3c(Nc4ccc(C#N)nc4OC)n[nH]c3c1)C(=O)N2] | 6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carbonitrile |
| 261 | 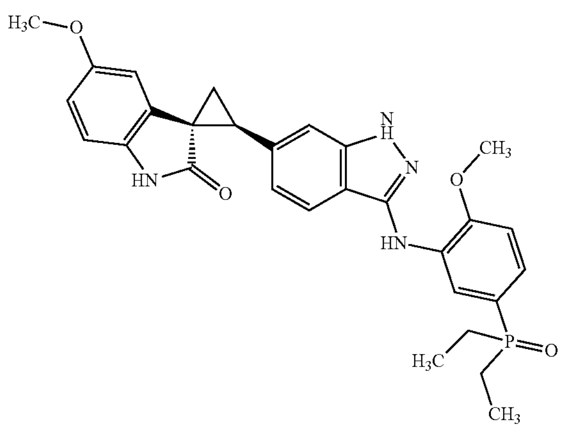 [SMILES: CCP(=O)(CC)c1ccc(OC)c(Nc2n[nH]c3cc([C@@H]4C[C@@]45C(=O)Nc4ccc(OC)cc45)ccc23)c1] | (1R,2S)-2-{3-[5-(diethylphosphoryl)-2-methoxyanilino]-1H-indazol-6-yl}-5'-methoxyspiro[cyclopropane-1,3'-indol]-2'(1'H)-one |
| 262 | 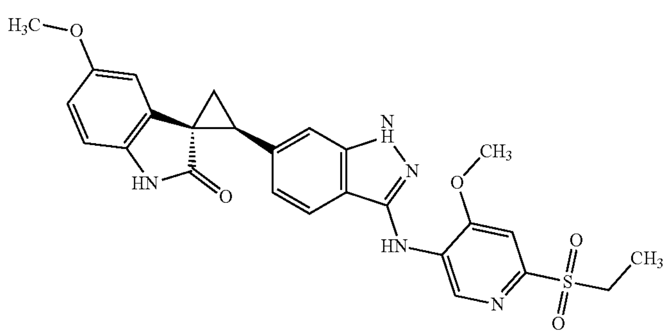 [SMILES: CCS(=O)(=O)c1cc(OC)c(Nc2n[nH]c3cc([C@@H]4C[C@@]45C(=O)Nc4ccc(OC)cc45)ccc23)cn1] | (1R,2S)-2-(3-{[6-(ethanesulfonyl)-4-methoxypyridin-3-yl]amino}-1H-indazol-6-yl)-5'-methoxyspiro[cyclopropane-1,3'-indol]-2'(1'H)-one |

TABLE 1A-continued

| Example No. | Structure | Name |
|---|---|---|
| 263 | 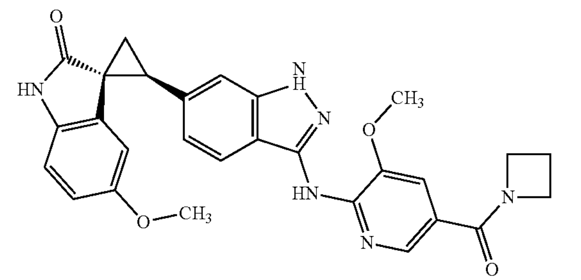 [SMILES: COc1ccc2c(c1)[C@]1(C[C@H]1c1ccc3c(Nc4ncc(C(=O)N5CCC5)cc4OC)n[nH]c3c1)C(=O)N2] | (1R,2S)-2-(3-{[5-(azetidine-1-carbonyl)-3-methoxypyridin-2-yl]amino}-1H-indazol-6-yl)-5'-methoxyspiro[cyclopropane-1,3'-indol]-2'(1'H)-one |
| 264 | 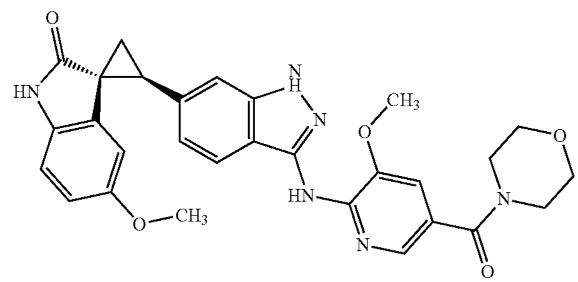 [SMILES: COc1ccc2c(c1)[C@]1(C[C@H]1c1ccc3c(Nc4ncc(C(=O)N5CCOCC5)cc4OC)n[nH]c3c1)C(=O)N2] | (1R,2S)-5'-methoxy-2-(3-{[3-methoxy-5-(morpholine-4-carbonyl)pyridin-2-yl]amino}-1H-indazol-6-yl)spiro[cyclopropane-1,3'-indol]-2'(1'H)-one |
| 265 | 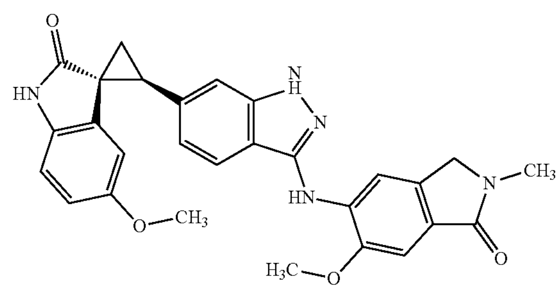 [SMILES: COc1ccc2c(c1)[C@]1(C[C@H]1c1ccc3c(Nc4cc5c(cc4OC)C(=O)N(C)C5)n[nH]c3c1)C(=O)N2] | (1R,2S)-5'-methoxy-2-{3-[(6-methoxy-2-methyl-1-oxo-2,3-dihydro-1H-isoindol-5-yl)amino]-1H-indazol-6-yl}spiro[cyclopropane-1,3'-indol]-2'(1'H)-one |
| 266 | 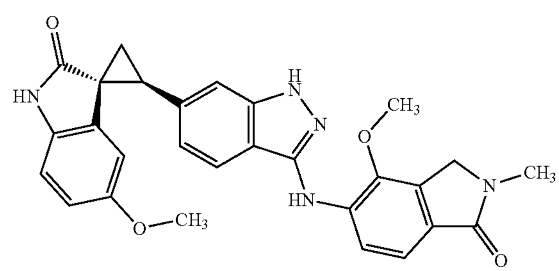 [SMILES: COc1ccc2c(c1)[C@]1(C[C@H]1c1ccc3c(Nc4ccc5c(c4OC)CN(C)C5=O)n[nH]c3c1)C(=O)N2] | (1R,2S)-5'-methoxy-2-{3-[(4-methoxy-2-methyl-1-oxo-2,3-dihydro-1H-isoindol-5-yl)amino]-1H-indazol-6-yl}spiro[cyclopropane-1,3'-indol]-2'(1'H)-one |
| 267 | 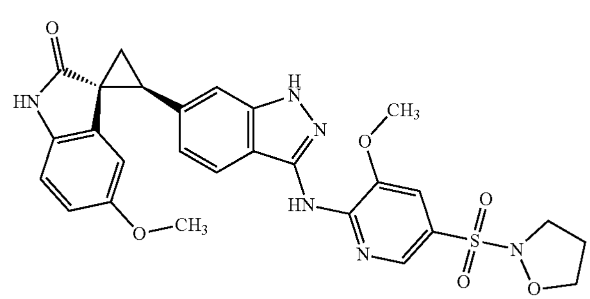 [SMILES: COc1ccc2c(c1)[C@]1(C[C@H]1c1ccc3c(Nc4ncc(S(=O)(=O)N5CCCO5)cc4OC)n[nH]c3c1)C(=O)N2] | (1R,2S)-5'-methoxy-2-(3-{[3-methoxy-5-(1,2-oxazolidine-2-sulfonyl)pyridin-2-yl]amino}-1H-indazol-6-yl)spiro[cyclopropane-1,3'-indol]-2'(1'H)-one |

TABLE 1A-continued

| Example No. | Structure | Name |
|---|---|---|
| 268 | 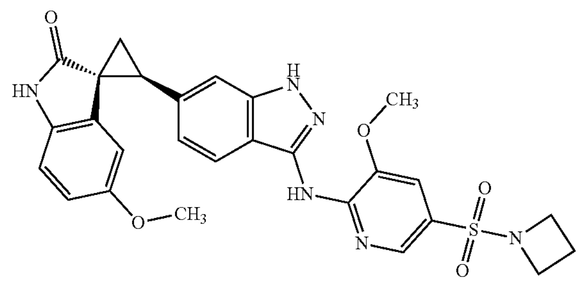 [SMILES: COc1ccc2c(c1)[C@]1(C[C@H]1c1ccc3c(Nc4ncc(S(=O)(=O)N5CCC5)cc4OC)n[nH]c3c1)C(=O)N2] | (1R,2S)-2-(3-{[5-(azetidine-1-sulfonyl)-3-methoxypyridin-2-yl]amino}-1H-indazol-6-yl)-5'-methoxyspiro[cyclopropane-1,3'-indol]-2'(1'H)-one |
| 269 | 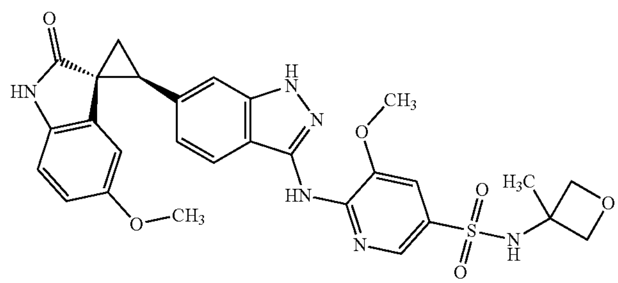 [SMILES: COc1ccc2c(c1)[C@]1(C[C@H]1c1ccc3c(Nc4ncc(S(=O)(=O)NC5(C)COC5)cc4OC)n[nH]c3c1)C(=O)N2] | 5-methoxy-6-({6-[(1R,2S)-5'-methoxy-2'-oxo-1',2'-dihydrospiro[cyclopropane-1,3'-indol]-2-yl]-1H-indazol-3-yl}amino)-N-(3-methyloxetan-3-yl)pyridine-3-sulfonamide |
| 270 | 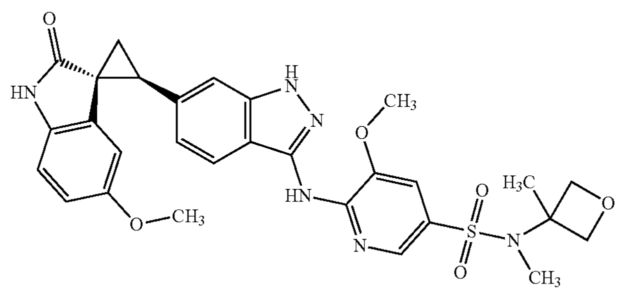 [SMILES: COc1ccc2c(c1)[C@]1(C[C@H]1c1ccc3c(Nc4ncc(S(=O)(=O)N(C)C5(C)COC5)cc4OC)n[nH]c3c1)C(=O)N2] | 5-methoxy-6-({6-[(1R,2S)-5'-methoxy-2'-oxo-1',2'-dihydrospiro[cyclopropane-1,3'-indol]-2-yl]-1H-indazol-3-yl}amino)-N-methyl-N-(3-methyloxetan-3-yl)pyridine-3-sulfonamide |
| 271 | 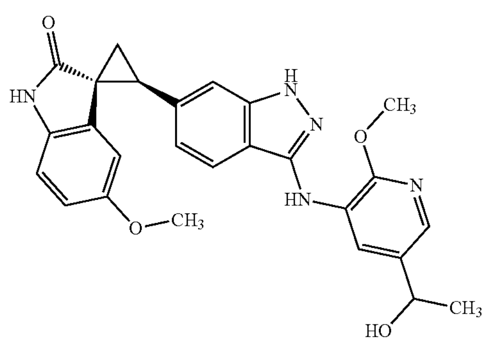 [SMILES: COc1ccc2c(c1)[C@]1(C[C@H]1c1ccc3c(Nc4cc(C(C)O)cnc4OC)n[nH]c3c1)C(=O)N2] | (1R,2S)-2-(3-{[5-(1-hydroxyethyl)-2-methoxypyridin-3-yl]amino}-1H-indazol-6-yl)-5'-methoxyspiro[cyclopropane-1,3'-indol]-2'(1'H)-one (mixture of diastereomers) |
| 272 | 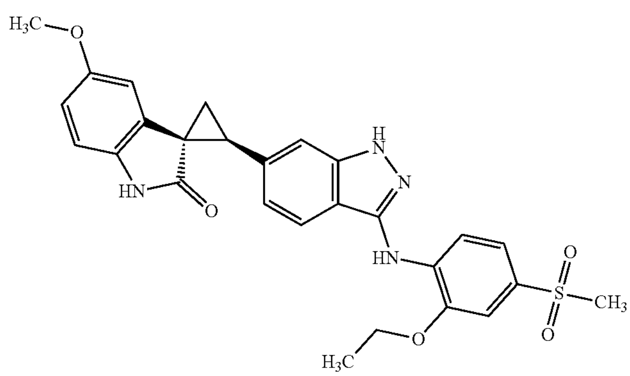 | (1R,2S)-2-{3-[2-ethoxy-4-(methanesulfonyl)anilino]-1H-indazol-6-yl}-5'-methoxyspiro[cyclopropane-1,3'-indol]-2'(1'H)-one |

TABLE 1A-continued

| Example No. | Structure | Name |
|---|---|---|
| 273 | 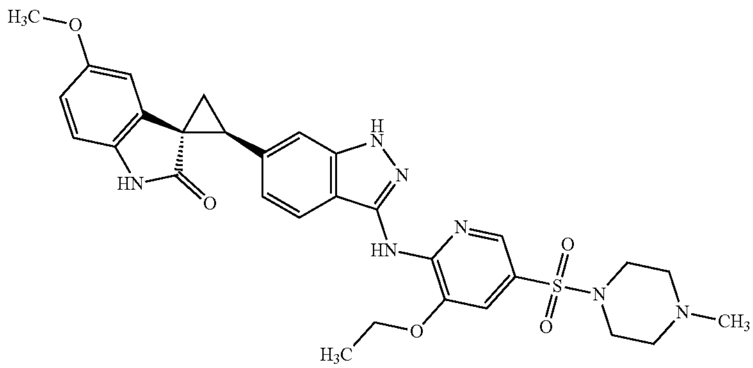 | (1R,2S)-2-(3-{[3-ethoxy-5-(4-methylpiperazine-1-sulfonyl)pyridin-2-yl]amino}-1H-indazol-6-yl)-5'-methoxyspiro[cyclopropane-1,3'-indol]-2'(1'H)-one |
| 274 | 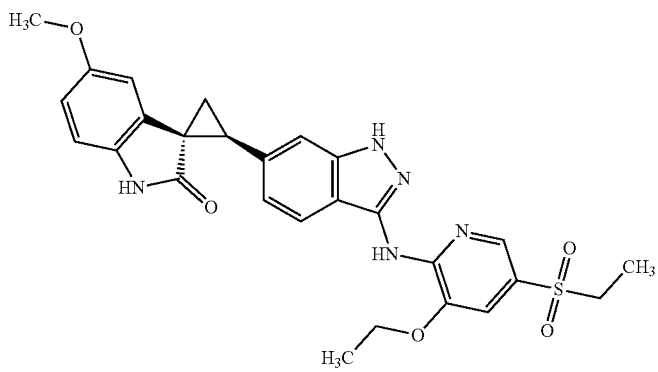 [SMILES: CCOc1cc(S(=O)(=O)CC)cnc1Nc1n[nH]c2cc([C@@H]3C[C@@]34C(=O)Nc3ccc(OC)cc34)ccc12] | (1R,2S)-2-(3-{[5-(ethanesulfonyl)-3-ethoxypyridin-2-yl]amino}-1H-indazol-6-yl)-5'-methoxyspiro[cyclopropane-1,3'-indol]-2'(1'H)-one |
| 275 | 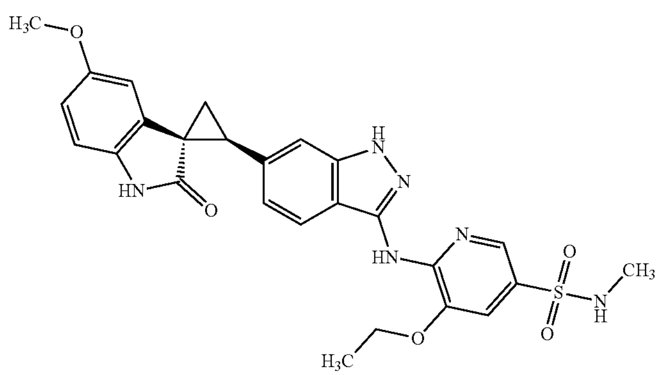 | 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N-methylpyridine-3-sulfonamide |
| 276 | 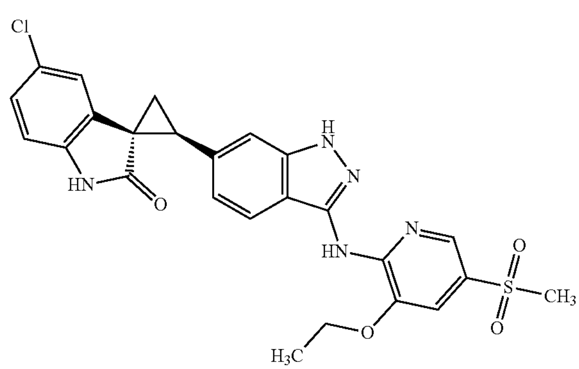 [SMILES: CCOc1cc(S(C)(=O)=O)cnc1Nc1n[nH]c2cc([C@@H]3C[C@@]34C(=O)Nc3ccc(Cl)cc34)ccc12] | (1R,2S)-5'-chloro-2-(3-{[3-ethoxy-5-(methanesulfonyl)pyridin-2-yl]amino}-1H-indazol-6-yl)spiro[cyclopropane-1,3'-indol]-2'(1'H)-one |

TABLE 1A-continued

| Example No. | Structure | Name |
|---|---|---|
| 277 | 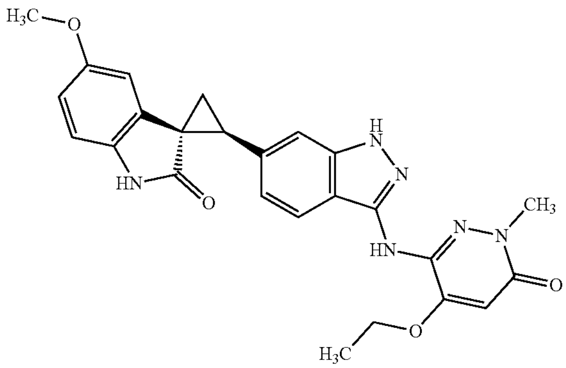 [SMILES: CCOc1cc(=O)n(C)nc1Nc1n[nH]c2cc([C@@H]3C[C@@]34C(=O)Nc3ccc(OC)cc34)ccc12] | (1R,2S)-2-{3-[(4-ethoxy-1-methyl-6-oxo-1,6-dihydropyridazin-3-yl)amino]-1H-indazol-6-yl}-5'-methoxyspiro[cyclopropane-1,3'-indol]-2'(1'H)-one |
| 278 | 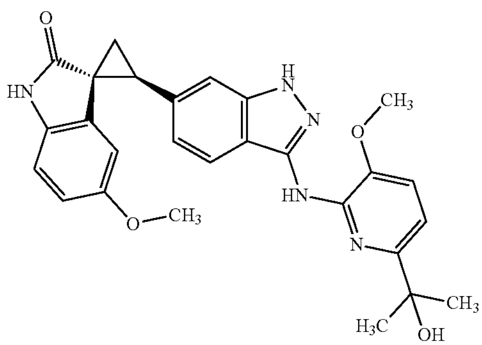 [SMILES: COc1ccc2c(c1)[C@]1(C[C@H]1c1ccc3c(Nc4nc(C(C)(C)O)ccc4OC)n[nH]c3c1)C(=O)N2] | (1R,2S)-2-(3-{[6-(2-hydroxypropan-2-yl)-3-methoxypyridin-2-yl]amino}-1H-indazol-6-yl)-5'-methoxyspiro[cyclopropane-1,3'-indol]-2'(1'H)-one |
| 279 | 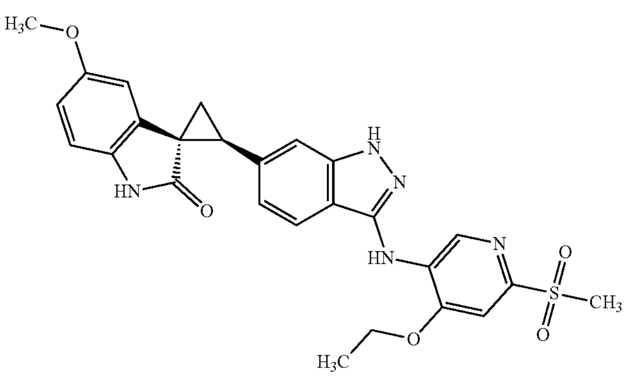 | (1R,2S)-2-(3-{[4-ethoxy-6-(methanesulfonyl)pyridin-3-yl]amino}-1H-indazol-6-yl)-5'-methoxyspiro[cyclopropane-1,3'-indol]-2'(1'H)-one |
| 280 | 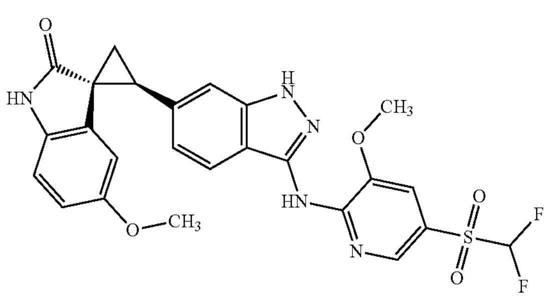 [SMILES: COc1ccc2c(c1)[C@]1(C[C@H]1c1ccc3c(Nc4ncc(S(=O)(=O)C(F)F)cc4OC)n[nH]c3c1)C(=O)N2] | (1R,2S)-2-(3-{[5-(difluoromethanesulfonyl)-3-methoxypyridin-2-yl]amino}-1H-indazol-6-yl)-5'-methoxyspiro[cyclopropane-1,3'-indol]-2'(1'H)-one |

Further provided herein are pharmaceutical compositions comprising an amount of a compound of Formulae (I), (Ia), (Ib), (II), or (III), or a pharmaceutically acceptable salt, solvate, or stereoisomer thereof, and one or more pharmaceutically acceptable excipients.

Methods of Treatment

Further provided herein are methods of treating cancer in a subject in need thereof, comprising administering to the subject a therapeutically effective amount of compound of Formulae (I), (Ia), (Ib), (II), or (III), or a pharmaceutically acceptable salt, solvate, or stereoisomer thereof, or a pharmaceutical composition disclosed herein comprising a compound of Formulae (I), (Ia), (Ib), (II), or (III), or a pharmaceutically acceptable salt, solvate, or stereoisomer thereof. Provided herein are such methods of treating cancer in a subject, wherein the cancer in the subject is a solid tumor. In some embodiments, the cancer is neuroblastoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. In some embodiments, the cancer in the subject expresses polo-like kinase 4 (PLK4). In some embodiments, the cancer in the subject has been determined to express polo-like kinase 4 (PLK4) prior to administering to the subject a compound of Formulae (I), (Ia), (Ib), (II), or (III), or a pharmaceutically acceptable salt, solvate, or stereoisomer thereof. In some embodiments, the cancer in the subject exhibits an overexpression of the E3 ubiquitin-protein ligase (TRIM37) protein. In some embodiments, the cancer in the subject exhibits an overexpression of the gene that encodes the tripartite motif-containing protein 37 (TRIM37). In some embodiments, the cancer in the subject exhibits an amplification of the gene that encodes the tripartite motif-containing protein 37 (TRIM37).

Further provided herein are methods of treating cancer in a subject in need thereof, comprising administering to the subject a therapeutically effective amount of compound of Formulae (I), (Ia), (Ib), (II), or (III), or a pharmaceutically acceptable salt, solvate, or stereoisomer thereof, wherein the cancer in the subject has been determined to overexpress the gene that encodes the tripartite motif-containing protein 37 (TRIM37) prior to administration of the compound to the subject.

Further provided herein are methods of treating cancer in a subject in need thereof, wherein the cancer in the subject has been determined to overexpress the gene that encodes the tripartite motif-containing protein 37 (TRIM37), comprising administering to the subject a therapeutically effective amount of compound of Formulae (I), (Ia), (Ib), (II), or (III), or a pharmaceutically acceptable salt, solvate, or stereoisomer thereof.

Further provided herein are methods of treating cancer in a subject, comprising:

a. obtaining a biological sample of the cancer from the subject;
b. determining whether the biological sample of the cancer overexpresses the gene that encodes the tripartite motif-containing protein 37 (TRIM37); and
c. administering to the subject a therapeutically effective amount of a compound of Formulae (I), (Ia), (Ib), (II), or (III), or a pharmaceutically acceptable salt, solvate, or stereoisomer thereof, if the biological sample of the cancer is determined to overexpress the gene that encodes the tripartite motif-containing protein 37 (TRIM37).

Further provided herein are methods of treating cancer in a subject described herein, wherein the cancer is neuroblastoma or breast cancer. Also provided herein are methods of treating cancer in a subject described herein, wherein the cancer is neuroblastoma. Also provided herein are methods of treating cancer in a subject described herein, wherein the cancer is breast cancer.

Further provided herein are methods of treating cancer in a subject described herein, wherein a compound of Formulae (I), (Ia), (Ib), (II), or (III), or a pharmaceutically acceptable salt, solvate, or stereoisomer thereof, is administered to the subject with one or more additional therapeutic agents. In some embodiments, the one or more additional therapeutic agents is selected from one or more mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, and immuno-oncology agents.

Further provided herein are methods of inhibiting polo-like kinase 4 (PLK4) in a subject in need thereof, comprising administering to the subject a therapeutically effective amount of a compound of Formulae (I), (Ia), (Ib), (II), or (III), or a pharmaceutically acceptable salt, solvate, or stereoisomer thereof, or a pharmaceutical composition comprising a compound of Formulae (I), (Ia), (Ib), (II), or (III), or a pharmaceutically acceptable salt, solvate, or stereoisomer thereof.

Further provided herein are methods of inhibiting polo-like kinase 4 (PLK4) in a subject having cancer, comprising administering to the subject a therapeutically effective amount of a compound of Formulae (I), (Ia), (Ib), (II), or (III), or a pharmaceutically acceptable salt, solvate, or stereoisomer thereof, or a pharmaceutical composition comprising a compound of Formulae (I), (Ia), (Ib), (II), or (III), or a pharmaceutically acceptable salt, solvate, or stereoisomer thereof, wherein the cancer in the subject has been determined to express polo-like kinase 4 (PLK4) prior to administering the compound or the pharmaceutical composition to the subject.

Further provided herein are methods of treating cancer in a subject in need thereof, comprising administering to the subject a therapeutically effective amount of compound of Formulae (I), (Ia), (Ib), (II), or (III), or a pharmaceutically acceptable salt, solvate, or stereoisomer thereof, wherein the cancer in the subject is acute myeloid leukemia, myelodysplastic syndromes, chronic myelomonocytic leukemia, triple negative breast cancer, advanced breast cancer, metastatic breast cancer, or prostate cancer. In some embodiments, the cancer in the subject is acute myeloid leukemia. In some embodiments, the cancer in the subject is myelodysplastic syndromes. In some embodiments, the cancer in the subject is chronic myelomonocytic leukemia. In some embodiments, the cancer in the subject is triple negative breast cancer. In some embodiments, the cancer in the subject is advanced breast cancer. In some embodiments, the cancer in the subject is metastatic breast cancer. In some embodiments, the cancer in the subject is prostate cancer.

Further provided herein are compounds of Formulae (I), (Ia), (Ib), (II), or (III), or a pharmaceutically acceptable salt, solvate, or stereoisomer thereof, or pharmaceutical compositions comprising a compound of Formulae (I), (Ia), (Ib), (II), or (III), or a pharmaceutically acceptable salt, solvate, or stereoisomer thereof, for use in methods of treating cancer in a subject in need thereof. In some embodiments are provided such compounds or pharmaceutical compositions for such use, wherein the cancer in the subject is a solid tumor. In some embodiments are provided such compounds or pharmaceutical compositions for such use, wherein the cancer is neuroblastoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. In some embodiments are provided such compounds or pharmaceutical compositions for such use, wherein the cancer in the subject expresses polo-like kinase 4 (PLK4). In some embodiments are provided such compounds or pharmaceutical compositions for such use, wherein the cancer in the subject has been determined to express polo-like kinase 4 (PLK4) prior to administering the compound or the pharmaceutical composition to the subject. In some embodiments are provided such compounds or pharmaceutical compositions for such use, wherein the cancer in the subject exhibits an overexpression of the E3 ubiquitin-protein ligase (TRIM37) protein. In some embodiments are provided such compounds or pharmaceutical compositions for such use, wherein the cancer in the subject exhibits an overexpression of the gene that encodes the tripartite motif-containing protein 37 (TRIM37). In some embodiments are provided such compounds or pharmaceutical compositions for such use, wherein the cancer in the subject exhibits an amplification of the gene that encodes the tripartite motif-containing protein 37 (TRIM37). In some embodiments are provided such compounds or pharmaceutical compositions for such use, wherein the cancer in the subject has been determined to overexpress the gene that encodes the tripartite motif-containing protein 37 (TRIM37) prior to administration of the compound or the pharmaceutical composition to the subject. In some embodiments are provided such compounds or pharmaceutical compositions for such use, wherein the cancer is neuroblastoma or breast cancer. In some embodiments are provided such compounds or pharmaceutical compositions for such use, wherein the cancer is neuroblastoma. In some embodiments are provided such compounds or pharmaceutical compositions for such use, wherein the cancer is breast cancer.

Further provided herein are compounds of Formulae (I), (Ia), (Ib), (II), or (III), or a pharmaceutically acceptable salt, solvate, or stereoisomer thereof, or pharmaceutical compositions comprising a compound of Formulae (I), (Ia), (Ib), (II), or (III), or a pharmaceutically acceptable salt, solvate, or stereoisomer thereof, for use in methods of treating cancer in a subject in need thereof wherein the cancer in the subject is acute myeloid leukemia, myelodysplastic syndromes, chronic myelomonocytic leukemia, triple negative breast cancer, advanced breast cancer, metastatic breast cancer, or prostate cancer. In some embodiments, the cancer in the subject is acute myeloid leukemia. In some embodiments, the cancer in the subject is myelodysplastic syndromes. In some embodiments, the cancer in the subject is chronic myelomonocytic leukemia. In some embodiments, the cancer in the subject is triple negative breast cancer. In some embodiments, the cancer in the subject is advanced breast cancer. In some embodiments, the cancer in the subject is metastatic breast cancer. In some embodiments, the cancer in the subject is prostate cancer.

Further provided herein are compounds of Formulae (I), (Ia), (Ib), (II), or (III), or a pharmaceutically acceptable salt, solvate, or stereoisomer thereof, or pharmaceutical compositions comprising a compound of Formulae (I), (Ia), (Ib), (II), or (III), or a pharmaceutically acceptable salt, solvate, or stereoisomer thereof, for use in methods of inhibiting polo-like kinase 4 (PLK4) in a subject having cancer.

Further provided herein are uses of a compound of Formulae (I), (Ia), (Ib), (II), or (III), or a pharmaceutically acceptable salt, solvate, or stereoisomer thereof, in the manufacture of a medicament for the treatment of cancer in a subject in need thereof. In some embodiments are provided such uses, wherein the cancer is neuroblastoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. In some embodiments the cancer in the subject expresses polo-like kinase 4 (PLK4). In some embodiments the cancer in the subject has been determined to express polo-like kinase 4 (PLK4) prior to administering the compound to the subject. In some embodiments the cancer in the subject exhibits an overexpression of the E3 ubiquitin-protein ligase (TRIM37) protein. In some embodiments the cancer in the subject exhibits an overexpression of the gene that encodes the tripartite motif-containing protein 37 (TRIM37). In some embodiments the cancer in the subject exhibits an amplification of the gene that encodes the tripartite motif-containing protein 37 (TRIM37). In some embodiments the cancer in the subject has been determined to overexpress the gene that encodes the tripartite motif-containing protein 37 (TRIM37) prior to administration of the compound to the subject. In some embodiments the cancer is neuroblastoma or breast cancer. In some embodiments the cancer is neuroblastoma. In some embodiments the cancer is breast cancer.

Further provided herein are uses of a compound of Formulae (I), (Ia), (Ib), (II), or (III), or a pharmaceutically acceptable salt, solvate, or stereoisomer thereof, in the manufacture of a medicament for the treatment of cancer in a subject in need thereof, wherein the cancer in the subject is acute myeloid leukemia, myelodysplastic syndromes, chronic myelomonocytic leukemia, triple negative breast cancer, advanced breast cancer, metastatic breast cancer, or prostate cancer. In some embodiments, the cancer in the subject is acute myeloid leukemia. In some embodiments, the cancer in the subject is myelodysplastic syndromes. In some embodiments, the cancer in the subject is chronic myelomonocytic leukemia. In some embodiments, the cancer in the subject is triple negative breast cancer. In some embodiments, the cancer in the subject is advanced breast cancer. In some embodiments, the cancer in the subject is metastatic breast cancer. In some embodiments, the cancer in the subject is prostate cancer.

In some embodiments, compound of Formulae (I), (Ia), (Ib), (II), or (III), or a pharmaceutically acceptable salt, solvate, or stereoisomer thereof, is used in combination with one or more additional anti-cancer agents. In some embodiments, the anti-cancer agent is mitoxantrone, estramustine, etoposide, vinblastine, carboplatin, vinorelbine, paclitaxel, daunomycin, darubicin, epirubicin, docetaxel, cabazitaxel, or doxorubicin. In some embodiments, the anti-cancer agent is paclitaxel, daunomycin, darubicin, epirubicin, docetaxel, cabazitaxel, or doxorubicin. In certain embodiments, the anti-cancer agent is docetaxel.

In some embodiments, one or more additional anti-cancer agents may include, without limitations, surgery, radiation, or chemotherapy. The chemotherapy may be an androgen receptor antagonist, a mitotic inhibitor, an antimetabolite, a platinum-based agent. Examples of androgen receptor antagonist include, without limitations, apalutamide, flutamide, nilutamide, bicalutamide, or enzalutamide. Examples of mitotic inhibitors include, without limitations, a taxane (e.g. paclitaxel, docetaxel, paclitaxel, docetaxel, cabazitaxel, tesetaxel, or nab-paclitaxel.

or nab-paclitaxel) or a vinca alkaloid (e.g., vinblastine, vincristine, vindesine, or vinorelbine). Examples of antimetabolites include, without limitations, 5-Fluorouracil, 6-mercaptopurine, capecitabine, cytarabine, floxuridine, fludarabine, gemcitabine, hydroxycarbamide, methotrexate, pemetrexed, or phototrexate. Examples of platinum-based agents include, without limitations, cisplatin, carboplatin, dicycloplatin, eptaplatin, lobaplatin, miriplatin, nedaplatin, oxaliplatin, picoplatin, satraplatin, or triplatin tetranitrate. The additional anti-cancer therapy may comprise an anti-PDL1 agent, an anti-PD1 agent or an anti CTLA-4 agent. The anti-PD-LI agent may comprise atezolizumab, avelumab, durvalumab, MPDL3280A (RG7446), MDX-1105 (BMS-936559) or BMS-935559, MSB0010718C, and MED14736. The anti-PD1 agent may comprise pembrolizumab, nivolumab, cemiplimab, partalizumab (PDR001), camrelizumab (SHR1210), sintilimab (IB1308), tislelizumab (BGB-A317), toripalimab (JS 001), dostarlimab (TSR-042, WBP-285), INCMGA00012 (MGA012), AMP-224, or AMP-514 (MEDI0680). The anti-CTLA agent may comprise ipilimumab, or tremelimumab.

Methods of Treatment in Conjunction with Biomarkers

Disclosed herein, in some embodiments, are methods of detecting the presence, absence, or level, of a biomarker. Such biomarkers may comprise genetic alterations in the gene encoding for certain proteins such as tripartite motif-containing protein 37 (TRIM37). The presence, absence, or level, of such biomarkers may be measured in a biological sample obtained from a subject, such as a sample of a solid tumor, such as a prostate cancer, or from a sample of a relevant biological fluid, such as a blood sample. In some instances, the methods of detection disclosed herein are useful for predicting a therapeutic response to a therapy described herein (e.g., a PLK4 inhibitor) in, monitor the treatment using the therapy of, and treating with the therapy, a proliferative disease or condition described herein in a subject. In some embodiments, the presence, or an absence, and/or a level of expression of the one or more biomarkers is detected in the sample obtained from a subject by analyzing the genetic material in the sample. In some embodiments, the genetic material is obtained from blood, serum, plasma, sweat, hair, tears, urine, and other techniques known by one of skill in the art. In some embodiments the sample comprises circulating tumor RNA (ctRNA). In some embodiments the sample comprises peripheral blood mononuclear cells (PBMCs). In some cases, the genetic material is obtained from a tumor biopsy or liquid biopsy. In some embodiments, a tumor biopsy comprises a formalin-fixed paraffin embedded biopsy, a fresh frozen biopsy, a fresh biopsy, or a frozen biopsy. In some embodiments, a liquid biopsy comprises PBMCs, circulating tumor RNA, plasma cell-free RNA, or circulating tumor cells (CTCs). Tumor biopsies can undergo additional analytic processing for sample dissociation, cell sorting, and enrichment of cell populations of interest.

In some embodiments, methods of detecting a presence, absence, or level of a biomarker in the sample obtained from the subject involve detecting a nucleic acid sequence. In some cases, the nucleic acid sequence comprises deoxyribonucleic acid (DNA), such as in the case of detecting complementary DNA (cDNA) of an mRNA transcript. In some instances, the nucleic acid sequence comprises a denatured DNA molecule or fragment thereof. In some instances, the nucleic acid sequence comprises DNA selected from: genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. The circular DNA may be cleaved or fragmented. In some instances, the nucleic acid sequence comprises ribonucleic acid (RNA). In some instances, the nucleic acid sequence comprises fragmented RNA. In some instances, the nucleic acid sequence comprises partially degraded RNA. In some instances, the nucleic acid sequence comprises a microRNA or portion thereof. In some instances, the nucleic acid sequence comprises an RNA molecule or a fragmented RNA molecule (RNA fragments) selected from: a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, an RNA transcript, a synthetic RNA, and combinations thereof.

Disclosed herein, in some embodiments, the biomarker is detected by subjecting a sample obtained from the subject to a nucleic acid-based detection assay. In some instances, the nucleic acid-based detection assay comprises quantitative polymerase chain reaction (qPCR), gel electrophoresis (including for e.g., Northern or Southern blot), immunochemistry, in situ hybridization such as fluorescent in situ hybridization (FISH), cytochemistry, microarray, or sequencing. In some embodiments, the sequencing technique comprises next generation sequencing. In some embodiments, the methods involve a hybridization assay such as fluorogenic qPCR (e.g., TaqMan™, SYBR green, SYBR green I, SYBR green II, SYBR gold, ethidium bromide, methylene blue, Pyronin Y, DAPI, acridine orange, Blue View or phycoerythrin), which involves a nucleic acid amplification reaction with a specific primer pair, and hybridization of the amplified nucleic acid probes comprising a detectable moiety or molecule that is specific to a target nucleic acid sequence. In some instances, a number of amplification cycles for detecting a target nucleic acid in a qPCR assay is about 5 to about 30 cycles. In some instances, the number of amplification cycles for detecting a target nucleic acid is at least about 5 cycles. In some instances, the number of amplification cycles for detecting a target nucleic acid is at most about 30 cycles. In some instances, the number of amplification cycles for detecting a target nucleic acid is about 5 to about 10, about 5 to about 15, about 5 to about 20, about 5 to about 25, about 5 to about 30, about 10 to about 15, about 10 to about 20, about 10 to about 25, about 10 to about 30, about 15 to about 20, about 15 to about 25, about 15 to about 30, about 20 to about 25, about 20 to about 30, or about 25 to about 30 cycles. For TaqMan™ methods, the probe may be a hydrolysable probe comprising a fluorophore and quencher that is hydrolyzed by DNA polymerase when hybridized to a target nucleic acid. In some cases, the presence of a target nucleic acid is determined when the number of amplification cycles to reach a threshold value is less than 30, 29, 28, 27, 26, 25, 24, 23, 22, 21, or 20 cycles. In some instances, hybridization may occur at standard hybridization temperatures, e.g., between about 35° C. and about 65° C. in a standard PCR buffer.

An additional exemplary nucleic acid-based detection assay comprises the use of nucleic acid probes conjugated or otherwise immobilized on a bead, multi-well plate, or other substrate, wherein the nucleic acid probes are configured to hybridize with a target nucleic acid sequence. In some instances, the nucleic acid probe is specific to one or more gene products described herein. In some instances, the nucleic acid probe specific to a biomarker comprises a nucleic acid probe sequence sufficiently complementary to the polynucleotide sequence of the biomarker. In some instances, the biomarker comprises a transcribed polynucleotide sequence (e.g., RNA, cDNA). In some embodiments, the nucleic acid probe can be, for example, a full-length cDNA, or a portion thereof, such as an oligonucleotide of at least about 7, 8, 9, 10, 11, 12, 13, 14, 15, 20, 25, 30, 35, 40, 45, or 50 nucleotides in length and sufficient to specifically hybridize under standard hybridization conditions to the target nucleic acid sequence. In some embodiments, the target nucleic acid sequence is immobilized on a solid surface and contacted with a probe, for example by running the isolated target nucleic acid sequence on an agarose gel and transferring the target nucleic acid sequence from the gel to a membrane, such as nitrocellulose. In some embodiments, the probe(s) are immobilized on a solid surface, for example, in an Affymetrix gene chip array, and the probe(s) are contacted with the target nucleic acid sequence.

In some embodiments, the term "probe" with regards to nucleic acids, refers to any nucleic acid molecule that is capable of selectively binding to a specifically intended target nucleic acid sequence. In some instances, probes are specifically designed to be labeled, for example, with a radioactive label, a fluorescent label, an enzyme, a chemiluminescent tag, a colorimetric tag, or other labels or tags that are known in the art. In some instances, the fluorescent label comprises a fluorophore. In some instances, the fluorophore is an aromatic or heteroaromatic compound. In some instances, the fluorophore is a pyrene, anthracene, naphthalene, acridine, stilbene, benzoxazole, indole, benzindole, oxazole, thiazole, benzothiazole, canine, carbocyanine, salicylate, anthranilate, xanthenes dye, coumarin. Exemplary xanthene dyes include, e.g., fluorescein and rhodamine dyes. Fluorescein and rhodamine dyes include, but are not limited to 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N, N; N'-tetramethyl-6-carboxyrhodamine (TAMRA), 6-carboxy-X-rhodamine (ROX). Suitable fluorescent probes also include the naphthylamine dyes that have an amino group in the alpha or beta position. For example, naphthylamino compounds include 1-dimethylaminonaphthyl-5-sulfonate, 1-anilino-8-naphthalene sulfonate, and 2-p-toluidinyl-6-naphthalene sulfonate, 5-(2'-aminoethyl) aminonaphthalene-1-sulfonic acid (EDANS). Exemplary coumarins include, e.g., 3-phenyl-7-isocyanatocoumarin; acridines, such as 9-isothiocyanatoacridine and acridine orange; N-(p-(2-benzoxazolyl)phenyl) maleimide; cyanines, such as, e.g., indodicarbocyanine 3 (Cy3), indodicarbocyanine 5 (Cy5), indodicarbocyanine 5.5 (Cy5.5), 3-(-carboxypentyl)-3'-ethyl-5,5'-dimethyloxacarbocyanine (CyA); 1H, 5H, 11H, 15H-Xantheno[2,3, 4-ij: 5,6, 7-i'j']diquinolizin-18-ium, 9-[2 (or 4)-[[[6-[2,5-dioxo-1-pyrrolidinyl)oxy]-6-oxohexyl]amino]sulfonyl]-4 (or 2)-sulfophenyl]-2,3, 6,7, 12,13, 16,17-octahydro-inner salt (TR or Texas Red); or BODIPY™ dyes. In some cases, the probe comprises FAM as the dye label.

In some embodiments, detecting the one or more biomarkers, such as gene products in a predictive response signature (PRS), comprises sequencing genetic material obtained from a sample from the subject. Sequencing can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. Sequencing methods also include next-generation sequencing, e.g., modern sequencing technologies such as Illumina sequencing (e.g., Solexa), Roche 454 sequencing, Ion torrent sequencing, and SOLiD sequencing. In some cases, next-generation sequencing involves high-throughput sequencing methods. Additional sequencing methods available to one of skill in the art may also be employed.

In some instances, a number of nucleotides that are sequenced are at least 5, 10, 15, 20, 25, 30, 35, 40, 45, 50, 100, 150, 200, 300, 400, 500, 2000, 4000, 6000, 8000, 10000, 20000, 50000, 100000, or more than 100000 nucleotides. In some instances, the number of nucleotides sequenced is in a range of about 1 to about 100000 nucleotides, about 1 to about 10000 nucleotides, about 1 to about 1000 nucleotides, about 1 to about 500 nucleotides, about 1 to about 300 nucleotides, about 1 to about 200 nucleotides, about 1 to about 100 nucleotides, about 5 to about 100000 nucleotides, about 5 to about 10000 nucleotides, about 5 to about 1000 nucleotides, about 5 to about 500 nucleotides, about 5 to about 300 nucleotides, about 5 to about 200 nucleotides, about 5 to about 100 nucleotides, about 10 to about 100000 nucleotides, about 10 to about 10000 nucleotides, about 10 to about 1000 nucleotides, about 10 to about 500 nucleotides, about 10 to about 300 nucleotides, about 10 to about 200 nucleotides, about 10 to about 100 nucleotides, about 20 to about 100000 nucleotides, about 20 to about 10000 nucleotides, about 20 to about 1000 nucleotides, about 20 to about 500 nucleotides, about 20 to about 300 nucleotides, about 20 to about 200 nucleotides, about 20 to about 100 nucleotides, about 30 to about 100000 nucleotides, about 30 to about 10000 nucleotides, about 30 to about 1000 nucleotides, about 30 to about 500 nucleotides, about 30 to about 300 nucleotides, about 30 to about 200 nucleotides, about 30 to about 100 nucleotides, about 50 to about 100000 nucleotides, about 50 to about 10000 nucleotides, about 50 to about 1000 nucleotides, about 50 to about 500 nucleotides, about 50 to about 300 nucleotides, about 50 to about 200 nucleotides, or about 50 to about 100 nucleotides.

Disclosed herein are methods comprising: (a) providing a sample obtained from a subject with a proliferative disease or condition (e.g., cancer); (b) assaying to detect in the sample obtained from the subject a presence or absence of the relevant biomarker; and (c) detecting the presence or absence of the biomarker in the sample using the methods described herein. In some cases, a hybridization assay, such as those described herein, is used to detect the biomarker in the sample. Exemplary probe sequences that are hybridizable to a target nucleic acid sequence (e.g., one or more genes in the biomarker, such as the PRS) comprise at least 10, but no more than 100 contiguous nucleotides comprising the relevant sequence. In some cases, RNA sequencing (RNAseq) is used to detect the one or more biomarkers.

Detection of the relevant biomarker, in some cases, involves amplification of the subject's nucleic acid by the polymerase chain reaction (PCR). In some embodiments, the PCR assay involves use of a pair of primers capable of amplifying at least about 10 contiguous nucleobases within a nucleic acid sequence, thereby amplifying the one or more gene products in the biomarker. In fluorogenic quantitative PCR, quantitation is based on amount of fluorescence signals (TaqMan and SYBR green). In some embodiments, the nucleic acid probe is conjugated to a detectable molecule. The detectable molecule may be a fluorophore. The nucleic acid probe may also be conjugated to a quencher.

In some embodiments, the assay for detecting the presence or absence of a relevant biomarker comprises reverse-transcribing the relevant mRNA molecule to produce a corresponding complementary DNA (cDNA) molecule). In some embodiments, the assay further comprises contacting the cDNA molecule with a nucleic acid probe comprising a nucleic acid sequence that is complementary to a nucleic acid sequence of the cDNA molecule. In some embodiments, the assay comprises detecting a double-stranded hybridization product between the nucleic acid probe and the cDNA molecule. In some embodiments, the hybridization product is further amplified using a pair of primers. In some embodiments, the primers comprises a first primer with a nucleic acid sequence comprising at least 10 but not more than 50 contiguous nucleic acids within a relevant nucleic acid sequence that binds to a top strand of the double-stranded hybridization product; and a second primer with a nucleic acid sequence comprising at least 10 but not more than 50 contiguous nucleic acids within a nucleic acid sequence that is reverse complement to the relevant nucleic acid sequence that binds to a bottom strand of the double-stranded hybridization product.

Disclosed herein, in some embodiments, are methods comprising preparing a complementary DNA (cDNA) library. In some embodiments, the cDNA library is sequenced using suitable sequence methodologies disclosed herein. In some embodiments, the cDNA library is labeled, a plurality of nucleic acid probes is generated, and fixed to an immobile surface (such as a microarray). In some embodiments, the plurality of nucleic acid probes is capable of hybridizing to at least about 10 contiguous nucleotides of the two or more genes in a sample obtained from the subject. In some embodiments, detecting the presence of or absence of a biomarker includes detecting a high or a low level of expression of the two or more genes as compared to a reference level.

Disclosed herein, in some embodiments, genetic material is extracted from a sample obtained from a subject, e.g., a sample of blood or serum. In certain embodiments where nucleic acids are extracted, the nucleic acids are extracted using any technique that does not interfere with subsequent analysis. In certain embodiments, this technique uses alcohol precipitation using ethanol, methanol, or isopropyl alcohol. In certain embodiments, this technique uses phenol, chloroform, or any combination thereof. In certain embodiments, this technique uses cesium chloride. In certain embodiments, this technique uses sodium, potassium or ammonium acetate or any other salt commonly used to precipitate DNA. In certain embodiments, this technique utilizes a column or resin based nucleic acid purification scheme such as those commonly sold commercially, one non-limiting example would be the GenElute Bacterial Genomic DNA Kit available from Sigma Aldrich. In certain embodiments, after extraction the nucleic acid is stored in water, Tris buffer, or Tris-EDTA buffer before subsequent analysis. In an exemplary embodiment, the nucleic acid material is extracted in water. In some cases, extraction does not comprise nucleic acid purification. In certain embodiments, RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland).

Circulating Tumor DNA (ctDNA) and RNA (ctRNA)

In some aspects, circulating tumor DNA (ctDNA) is used to assess the presence of certain DNA molecules and circulating tumor RNA (ctRNA) is used to assess the expression levels of RNA molecules, shed by the tumor into the blood stream.

In some embodiments, detection of ctDNA or ctRNA is useful, for example, for detecting and diagnosing a tumor. Because tumor DNA and RNA has acquired multiple genetic mutations, leading to tumor development, ctDNA and ctRNA are not an exact match to the individual's DNA and RNA, respectively. Finding DNA and RNA with genetic differences aids in tumor detection. Diagnosing the type of tumor using ctDNA or ctRNA can reduce the need for getting a sample of the tumor tissue (tumor biopsy), which can be challenging when a tumor is difficult to access, such as a tumor in the brain or lung.

In some embodiments, a decrease in the quantity of ctDNA or ctRNA suggests the solid tumor is shrinking and treatment with a compound of Formulae (I), (Ia), (Ib), (II), and (III), or a pharmaceutically acceptable salt thereof is effective. In some embodiments, a lack of ctDNA or ctRNA in the bloodstream indicates that the cancer has not returned after treatment with a compound of Formulae (I), (Ia), (Ib), (II), and (III), or a pharmaceutically acceptable salt thereof.

Described herein are methods of assessing genetic alterations by ctDNA or ctRNA genomic profiling. In some embodiments, the genomic profiling is performed after each treatment cycle with a compound of Formulae (I), (Ia), (Ib), (II), and (III), or a pharmaceutically acceptable salt thereof. In some embodiments, the gene mutations indicate that the cancer is becoming resistant to the treatment with a compound of Formulae (I), (Ia), (Ib), (II), and (III), or a pharmaceutically acceptable salt thereof. In some embodiments, the lack of gene mutations indicate that the cancer is not becoming resistant to the treatment with a compound of Formulae (I), (Ia), (Ib), (II), and (III), or a pharmaceutically acceptable salt thereof.

The compounds of Formulae (I), (Ia), (Ib), (II), and (III) may be administered as prodrugs. Thus certain derivatives of the compounds, which may have little or no pharmacological activity themselves can, when administered to a mammal, be converted into a compound having the desired activity, for example, by hydrolytic cleavage. Such derivatives are referred to as "prodrugs." Prodrugs can, for example, be produced by replacing appropriate functionalities present in the compound of Formulae (I), (Ia), (Ib), (II), and (III) with certain moieties known to those skilled in the art. See, e.g. "Pro-drugs as Novel Delivery Systems", Vol. 14, ACS Symposium Series (T Higuchi and W Stella) and "Bioreversible Carriers in Drug Design". Pergamon Press, 1987 (ed. E B Roche, American Pharmaceutical Association), the disclosures of which are incorporated herein by reference in their entireties. Some examples of such prodrugs include: an ester moiety in the place of a carboxylic acid functional group; an ether moiety or an amide moiety in place of an alcohol functional group; and an amide moiety in place of a primary or secondary amino functional group. Examples of replacement groups are known to those of skill in the art. See, e.g. "Design of Prodrugs" by H Bundgaard (Elsevier, 1985), the disclosure of which is incorporated herein by reference in its entirety.

Salts of the present invention can be prepared according to methods known to those of skill in the art. Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edisylate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, .gamma.-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phosphate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of Formulae (I), (Ia), (Ib), (II), and (III) that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The compounds of Formulae (I), (Ia), (Ib), (II), and (III) that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the compound of Formulae (I), (Ia), (Ib), (II), and (III) is a base, the desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formulae (I), (Ia), (Ib), (II), and (III) is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, and lithium.

If the compound of Formulae (I), (Ia), (Ib), (II), and (III) is a solid, it is understood by those skilled in the art that the compounds or salts thereof may exist in different crystal or polymorphic forms, all of which are intended to be within the scope of the present invention and specified formulas.

Also provided herein are isotopically-labeled compounds of Formulae (I), (Ia), (Ib), (II), and (III), wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^{2}$H and $^{3}$H, carbon, such as $^{11}$C, $^{12}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^{3}$H, and carbon-14, $^{14}$C, are particularly useful for this purpose in view of their ease of incorporation and ready means of detection. Substitution with heavier isotopes such as deuterium, $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formulae (I), (Ia), (Ib), (II), and (III) can generally be prepared by conventional techniques known to those skilled in the art or by processes analogous to those described herein, using an appropriate isotopically-labeled reagent in place of the non-labeled reagent otherwise employed.

In one aspect, the compositions of compounds of Formulae (I), (Ia), (Ib), (II), and (III), or a pharmaceutically acceptable salt, solvate, or stereoisomer thereof, described herein are used for the treatment of cancer in a subject. In one embodiment, such compositions are in the form of suitable dosage forms. Suitable dosage forms include, for example, liquids, suspensions, powders for reconstitution, tablets, pills, sachets, or capsules of hard or soft gelatin (See, e.g., Remington: The Science and Practice of Pharmacy (Gennaro, 21st Ed. Mack Pub. Co., Easton, PA (2005)).

The compounds of Formulae (I), (Ia), (Ib), (II), and (III), or a pharmaceutically acceptable salt, solvate, or stereoisomer thereof, may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

The pharmaceutical carriers employed may be either solid or liquid. Exemplary solid carriers are lactose, sucrose, talc, gelatin, agar, pectin, acacia, magnesium stearate, stearic acid, and the like. Exemplary liquid carriers are syrup, peanut oil, olive oil, water, and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol™, Gelucire™ or the like, or formulator, such as CMC (carboxymethylcellulose), PG (propyleneglycol), or PEG (polyethyleneglycol), may be added. Gelucire™, a semi-solid vehicle that protects active ingredients from light, moisture, and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions, and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5 W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide (DMSO) also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire™, Capryol™, Labrafil™, Labrasol™, Lauroglycol™, Plurol™, Peceol™, Transcutol™ and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal suffering from abnormal cell growth, such as a human, either alone or as part of a pharmaceutically acceptable formulation, once a day, twice a day, three times a day, or four times a day, or even more frequently.

Those of ordinary skill in the art will understand that with respect to the compounds Formulae (I), (Ia), (Ib), (II), or (III), or a pharmaceutically acceptable salt, solvate, or stereoisomer thereof, the particular pharmaceutical formulation, the dosage, and the number of doses given per day to a mammal requiring such treatment, are all choices within the knowledge of one of ordinary skill in the art and can be determined without undue experimentation.

Dosages of compositions described herein can be determined by any suitable method. Maximum tolerated doses (MTD) and maximum response doses (MRD) for the compounds of Formulae (I), (Ia), (Ib), (II), or (III), or a pharmaceutically acceptable salt, solvate, or stereoisomer thereof, can be determined via established animal and human experimental protocols as well as in the examples described herein. For example, toxicity and therapeutic efficacy of the compounds of Formulae (I), (Ia), (Ib), (II), or (III), or a pharmaceutically acceptable salt, solvate, or stereoisomer thereof, can be determined by standard pharmaceutical procedures in cell cultures or experimental animals, including, but not limited to, for determining the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of the compounds of Formulae (I), (Ia), (Ib), (II), or (III), or a pharmaceutically acceptable salt, solvate, or stereoisomer thereof, comprising a formulation to such an amount varies depending upon factors such as the particular salt or form, disease condition and its severity, the identity (e.g., age, weight, sex) of the subject or host in need of treatment, but can nevertheless be determined according to the particular circumstances surrounding the case, including. e.g., the specific agent being administered, the liquid formulation type, the condition being treated, and the subject or host being treated.

In some embodiments, a compound of Formulae (I), (Ia), (Ib), (II), or (III), or a pharmaceutically acceptable salt, solvate, or stereoisomer thereof, is administered in an amount between about 10 mg to 500 mg per day. In some embodiments, a compound of Formulae (I), (Ia), (Ib), (II), or (III), or a pharmaceutically acceptable salt, solvate, or stereoisomer thereof, or a pharmaceutically acceptable salt thereof) is administered in an amount between about 100 mg to about 400 mg per day. In some embodiments, a compound of Formulae (I), (Ia), (Ib), (II), or (III), or a pharmaceutically acceptable salt, solvate, or stereoisomer thereof is administered in an amount between about 150 mg to about 350 mg per day. In some embodiments, a compound of Formulae (I), (Ia), (Ib), (II), or (III), or a pharmaceutically acceptable salt, solvate, or stereoisomer thereof is administered in an amount between about 150 mg to about 300 mg per day. In some embodiments, a compound of Formulae (I), (Ia), (Ib), (II), or (III), or a pharmaceutically acceptable salt, solvate, or stereoisomer thereof, is administered in an amount between about 160 mg to about 300 mg per day. In some embodiments, a compound of Formulae (I), (Ia), (Ib), (II), or (III), or a pharmaceutically acceptable salt, solvate, or stereoisomer thereof, is administered in an amount of about 160 mg per day. In some embodiments, a compound of Formulae (I), (Ia), (Ib), (II), or (III), or a pharmaceutically acceptable salt, solvate, or stereoisomer thereof, is administered in an amount of about 200 mg per day. In some embodiments, a compound of Formulae (I), (Ia), (Ib), (II), or (III), or a pharmaceutically acceptable salt, solvate, or stereoisomer thereof, is administered in an amount of about 240 mg per day. In some embodiments, a compound of Formulae (I), (Ia), (Ib), (II), or (III), or a pharmaceutically acceptable salt, solvate, or stereoisomer thereof, is administered in an amount of about 280 mg per day. In some embodiments, a compound of Formulae (I), (Ia), (Ib), (II), or (III), or a pharmaceutically acceptable salt, solvate, or stereoisomer thereof, is administered in an amount of about 320 mg per day.

In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the subject. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the subject.

In certain embodiments wherein the subject's condition does not improve, upon the doctor's discretion the administration of a composition described herein are administered chronically, that is, for an extended period of time, including throughout the duration of the subject's life in order to ameliorate or otherwise control or limit the symptoms of the subject's disease. In other embodiments, administration of a composition continues until complete or partial response of a disease.

In some embodiments, a compound of Formulae (I), (Ia), (Ib), (II), or (III), or a pharmaceutically acceptable salt, solvate, or stereoisomer thereof, is administered to a subject in need thereof once a day. In some embodiments, a compound of Formulae (I), (Ia), (Ib), (II), or (III), or a pharmaceutically acceptable salt, solvate, or stereoisomer thereof, is administered to a subject in need thereof twice a day. In some embodiments, a compound of Formulae (I), (Ia), (Ib), (II), or (III), or a pharmaceutically acceptable salt, solvate, or stereoisomer thereof is administered to a subject in need thereof three times a day.

In some instances, the methods described herein comprise administering the compositions and formulations comprising the compounds of Formulae (I), (Ia), (Ib), (II), (III) in combination with one or more additional therapeutic agents, to the subject or subject in need thereof in multiple cycles repeated on a regular schedule with periods of rest in between each cycle. For example, in some instances, treatment given for one week followed by three weeks of rest is one treatment cycle.

The length of a treatment cycle depends on the treatment being given. In some embodiments, the length of a treatment cycle ranges from two to six weeks. In some embodiments, the length of a treatment cycle ranges from three to six weeks. In some embodiments, the length of a treatment cycle ranges from three to four weeks. In some embodiments, the length of a treatment cycle is three weeks (or 21 days). In some embodiments, the length of a treatment cycle is four weeks (28 days). In some embodiments, the length of a treatment cycle is 56 days. In some embodiments, a treatment cycle lasts one, two, three, or four weeks. In some embodiments, a treatment cycle lasts three weeks. In some embodiments, a treatment cycle lasts four weeks. The number of treatment doses scheduled within each cycle also varies depending on the drugs being given.

Kits and Articles of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded, or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Methods of Preparation

Compounds of Formulae (I), (Ia), (Ib), (II), or (III), or a pharmaceutically acceptable salt, solvate, or stereoisomer thereof, may be prepared using the reaction routes and synthetic schemes described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

The compounds of Formula (I) may be prepared from Compounds of Formula (IV), wherein $R^2$, $R^3$, $R^{4a}$, $R^{4b}$, $R^{4c}$, $R^5$, $R^6$, $R^7$, $R^{8a}$, $R^{8b}$, $R^{8c}$, and $R^{8d}$ are as defined herein, by allowing the compounds to react with compounds of Formula (V), wherein A, $R^1$, and n are as defined herein, and wherein LG is a leaving group. LG that may be used include halogens, such as chloro, bromo, and iodo. The reaction of the compounds of Formula (IV) with compounds of Formula (V) may be conducted using methods known to those of ordinary skill in the art. For example, the reaction of the compounds of Formula (IV) with compounds of Formula (V) may be conducted in aprotic solvents, such as acetonitrile, DMF, and the like, protic solvents, such as water or alcohols, mixtures of protic and aprotic solvents, such as mixtures of acetonitrile and water, at temperatures in the range from 25° C. to 200° C., and in the presence of an acid or a base. Compounds of Formula (V) may be prepared by methods disclosed herein and/or by methods known to those of ordinary skill in the art.

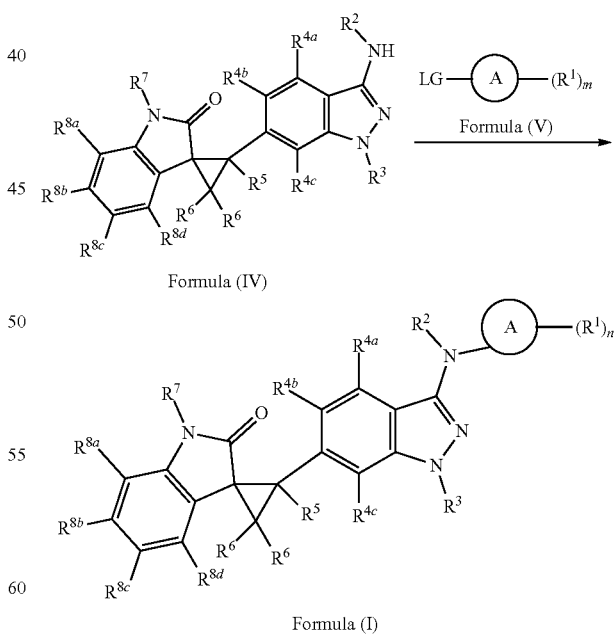

Formula (IV)

Formula (V)

Formula (I)

Alternatively, compounds of Formula (I) may be prepared by allowing compounds of Formula (VI), wherein $R^3$, $R^{4a}$, $R^{4b}$, $R^{4c}$, $R^5$, $R^6$, $R^7$, $R^{8a}$, $R^{8b}$, $R^{8c}$, and $R^{8d}$ are as defined herein, and Hal is a halogen, such as bromo or iodo, by allowing the compounds to react with compounds of Formula (VII), wherein A, $R^1$, $R^2$, and n are as defined herein. Such reactions may be performed in the presence of a catalytic amount of a palladium-containing compound, such as palladium(0) bis(dibenzylideneacetone) (also known as Pd(dba)$_2$), a phosphate ligand, such as 4,5-bis(diphenylphosphino)-9,9-dimethylxanthene (also known as Xantphos), a base, and in an aprotic solvent. The base may be selected from an organic base, such as a tertiary amine, for example triethyl amine, or an inorganic base, for example cesium carbonate. The aprotic solvent may be, for example, toluene. The reactions of the compounds of Formula (VI) with the compounds of Formula (VII) may be conducted at temperatures in the range from 25° C. to 200° C., for example such reactions may be conducted in toluene at a temperature of 100° C. The compounds of Formula (VII) are commercially available, or may be prepared by methods known to those having ordinary skill in the art, or by methods similar to those set forth herein.

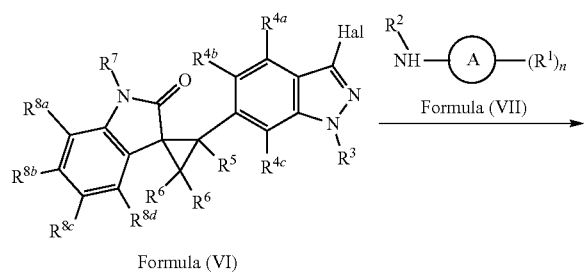

Formula (VI)

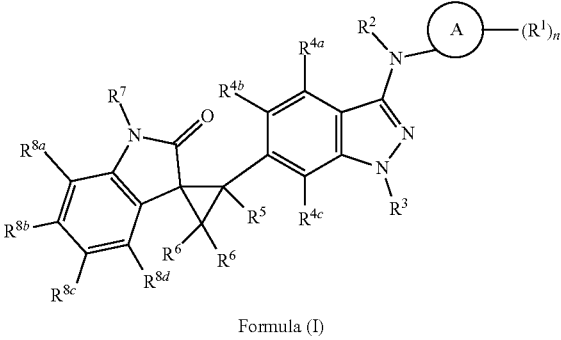

Formula (I)

Compounds of Formula (VI) may be prepared by methods known to those having ordinary skill in the art. For example, the compound of Formula (IV) (1R,2S)-2-(3-bromo-1H-indazol-6-yl)-5'-methoxyspiro[cyclopropane-1,3'-indolin]-2'-one may be prepared according to the scheme set forth below. Other compounds of Formula (VI) may be prepared by methods known to those of skill in the art by modifications apparent to those skilled in the art, e.g. by using different starting materials, appropriately protecting interfering groups, by changing to other suitable reagents known in the art, or by making routine modifications of reaction conditions.

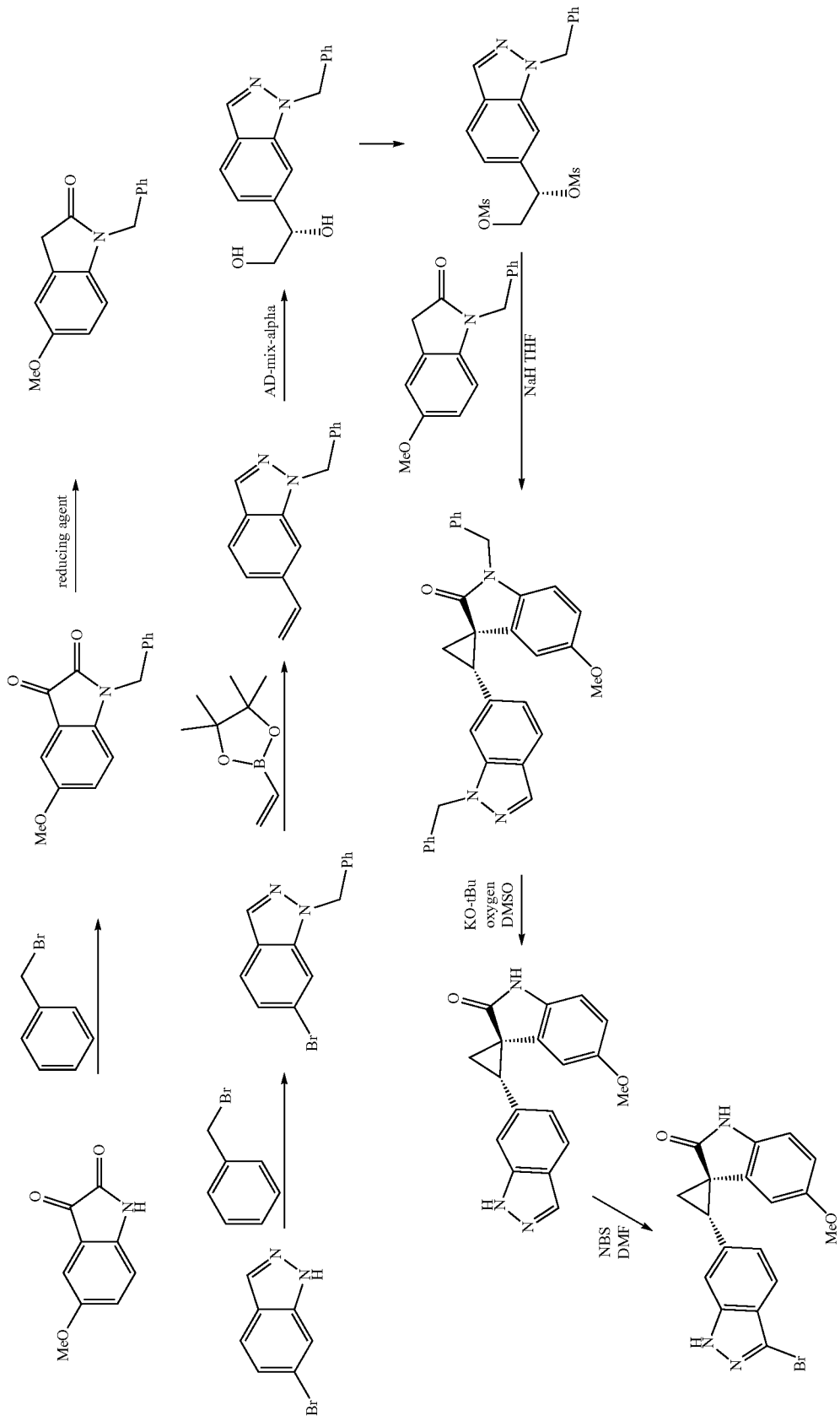

Similarly, (1R,2S)-2-(3-Iodo-1H-indazol-6-yl)-5'-methoxyspiro[cyclopropane-1,3'-indolin]-2'-one may be prepared by allowing (1R,2S)-2-(1H-indazol-6-yl)-5'-methoxyspiro[cyclopropane-1,3'-indolin]-2'-one to react with iodine in DMF and methanol in the presence of potassium carbonate as set forth below.

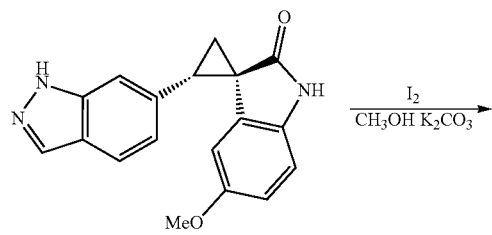

Compounds of Formula (IV) may be prepared from compounds of Formula (VI) by methods known to those having ordinary skill in the art. For example, tert-butyl (1R,2S)-2-(3-amino-1-(tert-butoxycarbonyl)-1H-indazol-6-yl)-5'-methoxy-2'-oxospiro[cyclopropane-1,3'-indoline]-1'-carboxylate may be prepared from (1R,2S)-2-(3-bromo-1H-indazol-6-yl)-5'-methoxyspiro[cyclopropane-1,3'-indolin]-2'-one as set forth below.

Compounds such as tert-butyl (1R,2S)-2-(3-amino-1-(tert-butoxycarbonyl)-1H-indazol-6-yl)-5'-methoxy-2'-oxospiro[cyclopropane-1,3'-indoline]-1'-carboxylate may be allowed to react with compounds of Formula (V) as described herein, followed by deprotection of the Boc groups using an acid, such as trifluoroacetic acid, to provide compounds of Formula (I). For example, tert-butyl (1R,2S)-2-(3-amino-1-(tert-butoxycarbonyl)-1H-indazol-6-yl)-5'-methoxy-2'-oxospiro[cyclopropane-1,3'-indoline]-1'-carboxylate may be allowed to react with 4-chloro-5-methoxypyrimidine to afford (1R,2S)-5'-methoxy-2-(3-((5-methoxypyrimidin-4-yl)amino)-1H-indazol-6-yl)spiro[cyclopropane-1,3'-indolin]-2'-one.

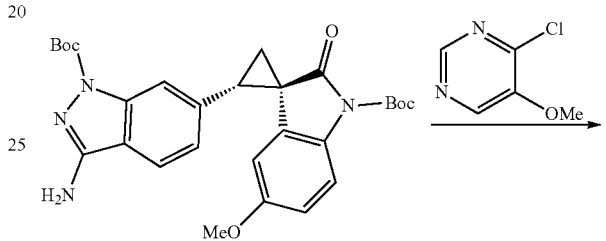

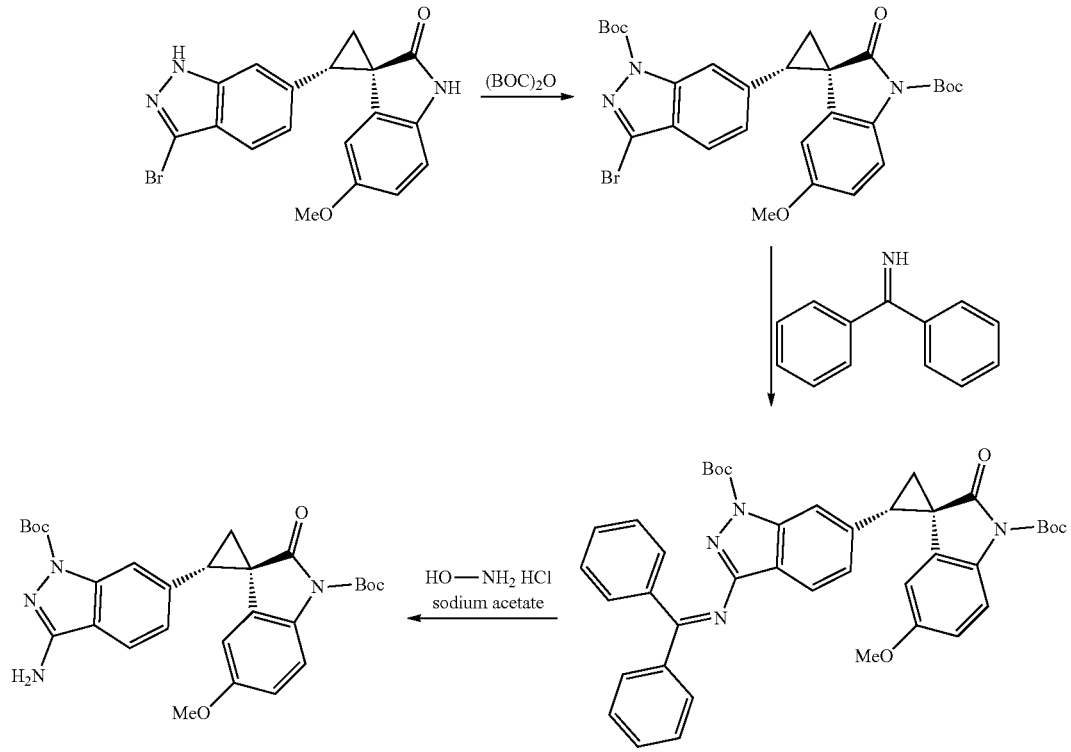

221

-continued

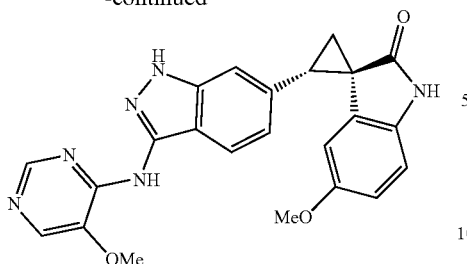

In the following Preparations and Examples, "Ac" means acetyl, "ACN" and "MeCN" mean acetonitrile, "Me" means methyl, "Et" means ethyl, "Ph" means phenyl, "BOC", "Boc" or "boc" means N-tert-butoxycarbonyl, "DCM" (CH$_2$Cl$_2$) means methylene chloride, "DIPEA" or "DIEA" means diisopropyl ethyl amine, "DMA" means N,N-dimethylacetamide, "DMF" means N—N-dimethyl formamide, "DMSO" means dimethylsulfoxide, "DPPP" means 1,3-bis(diphenylphosphino)propane, "HOAc" means acetic acid, "IPA" means isopropyl alcohol. "min" means minute. "NMP" means 1-methyl 2-pyrrolidinone, "TEA" means triethyl amine, "TFA" means trifluoroacetic acid, "DCM" means dichloromethane, "EtOAc" and "EA" mean ethyl acetate, "MgSO$_4$" means magnesium sulphate, "Na$_2$SO$_4$" means sodium sulphate, "MeOH" means methanol, "Et$_2$O" means diethyl ether, "EtOH" means ethanol, "H$_2$O" means water, "HCl" means hydrochloric acid, "K$_2$CO$_3$" means potassium carbonate, "THF" means tetrahydrofuran, "DBU" means 1,8-diazabicyclo[5.4.0]undec-7-ene, "LiHMDS" or "LHMDS" means lithium hexamethyldisilazide, "TBME" or "MTBE" means tert-butyl methyl ether, "LDA" means lithium diisopropylamide, "N" means Normal, "M" means molar, "mL" means milliliter, "mmol" means millimoles, "μmol" means micromoles, "eq." means equivalent, "° C." means degrees Celsius, "Pa" means pascals, "rt" or "RT" means room temperature, "h" means hours, "satd." means saturated, "aq" means aqueous, "anhyd." or "anh." means anhydrous, "MBTE" means methyl tert-butyl ether, "PE" means petroleum ether, and "TBSCl" means tert-butyldimethylsilyl chloride.

EXAMPLES

Intermediate 1. (1R,2S)-2-(3-Amino-1H-indazol-6-yl)-5'-methoxyspiro[cyclopropane-1,3'-indolin]-2'-one

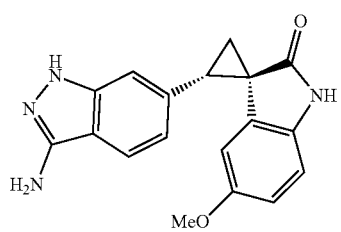 [SMILES: COc1ccc2c(c1)[C@]1(C[C@H]1c1ccc3c(N)n[nH]c3c1)C(=O)N2]

222

Step A. (E)-3-(3-Fluoro-4-isocyanobenzylidene)-5-methoxyindolin-2-one

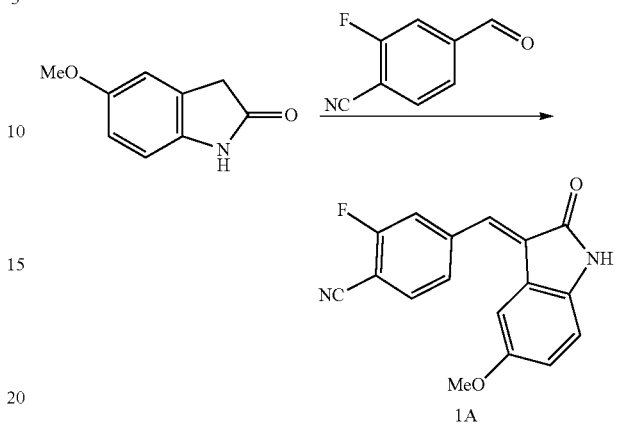

A round bottom flask was charged with 5-methoxyoxindole (5.00 g, 30.6 mmol), 4-cyano-3-fluorobenzaldehyde (4.57 g, 30.6 mmol), piperidine (835 μL, 8.40 mmol) and ethanol (120 mL). The reaction was refluxed for 4 h and was stirred for 16 h at rt. The reaction was cooled to 0° C. and the resulting precipitate was collected by filtration and dried to give the title compound (5.10 g, 57%) as a dark red solid. m/z (ESI, +ve ion)=295.0 [M+H]$^+$.

Step B. racemic-2-Fluoro-4-((1R,2S)-5'-methoxy-2'-oxospiro[cyclopropane-1,3'-indolin]-2-yl)benzonitrile

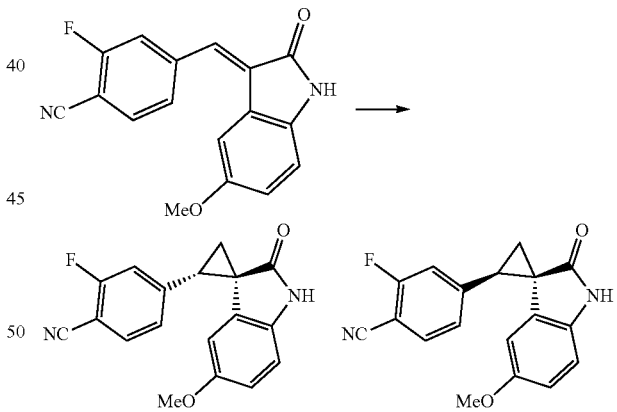

To a solution of trimethylsulfoxonium iodide (4.20 g, 19.1 mmol) in anhydrous DMF (173 mL) under nitrogen was added sodium hydride (60% dispersion in oil) (81.5 mg, 2.04 mmol) at 0° C. The mixture was stirred for 15 minutes after which (E)-3-(3-fluoro-4-isocyanobenzylidene)-5-methoxyindolin-2-one (5.10 g, 17.3 mmol) was added to the solution and the reaction was stirred for 1 h at rt. The solution was quench with satd. aq. ammonium chloride solution and extracted with EtOAc. The organic layer was then washed with brine, dried with anhyd. Na$_2$SO$_4$, filtered and concentrated under vacuum. The crude mixture was purified by column chromatography (10% to 65% EtOAc/heptanes, gradient elution), affording the title compound (1.50 g, 28%)

as an orange solid. NOESY NMR experiment confirmed relative stereochemistry. m/z (ESI, +ve ion)=309.0 [M+H]⁺. 1H NMR (400 MHz, CDCl₃) δ 8.14 (s, 1H), 7.63-7.54 (m, 1H), 7.13-7.08 (m, 2H), 6.85 (d, J=8.5 Hz, 1H), 6.67 (dd, J=8.5, 2.5 Hz, 1H), 5.55 (d, J=2.4 Hz, 1H), 3.55 (s, 3H), 3.29 (t, J=8.5 Hz, 1H), 2.26 (dd, J=9.0, 5.0 Hz, 1H), 1.94 (dd, J=8.0, 5.0 Hz, 1H). The corresponding diastereoisomer was found to be less polar and was first to elute in the given conditions. m/z (ESI, +ve ion)=309.0 [M+H]⁺. 1 H NMR (400 MHz, CDCl₃) δ 8.08 (s, 1H), 7.52 (dd, J=7.8, 6.9 Hz, 1H), 7.21 (s, 1H), 7.19 (s, 1H), 6.78 (d, J=1.5 Hz, 2H), 6.54 (s, 1H), 3.81 (s, 3H), 3.07 (t, J=8.7 Hz, 1H), 2.34 (dd, J=8.5, 5.3 Hz, 1H), 2.12 (dd, J=8.9, 5.3 Hz, 1H).

Step C. (1R,2S)-2-(3-Amino-1H-indazol-6-yl)-5'-methoxyspiro[cyclopropane-1,3'-indolin]-2'-one

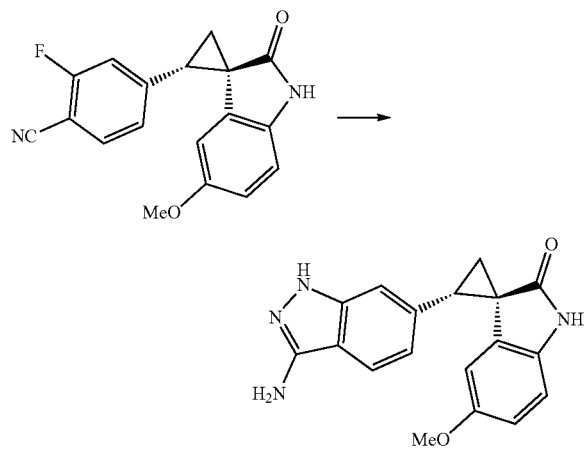

In a 20 mL vial was dissolved 2-fluoro-4-((1R,2S)-5'-methoxy-2'-oxospiro[cyclopropane-1,3'-indolin]-2-yl)benzonitrile (20.0 mg, 64.9 µmol) in tert-amyl alcohol (10.0 mL) and hydrazine hydrate solution (50.0 µL, 1.58 mmol) was subsequently added. The reaction was reflux for 16 h. The reaction was cooled to rt and silica was directly added to the mixture and concentrated. The product was purified by column chromatography (0 to 20% MeOH/DCM, gradient elution), affording the title compound (60.0 mg, 58%) as colorless oil. m/z (ESI, +ve ion)=321.1 [M+H]⁺.

Intermediate 2. (1R,2S)-2-(1H-Indazol-6-yl)-5'-methoxyspiro[cyclopropane-1,3'-indolin]-2'-one

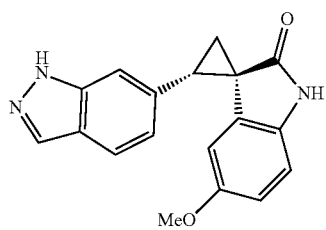 [SMILES: COc1ccc2c(c1)[C@]1(C[C@H]1c1ccc3cn[nH]c3c1)C(=O)N2]

Step A. 1-Benzyl-5-methoxyindoline-2,3-dione

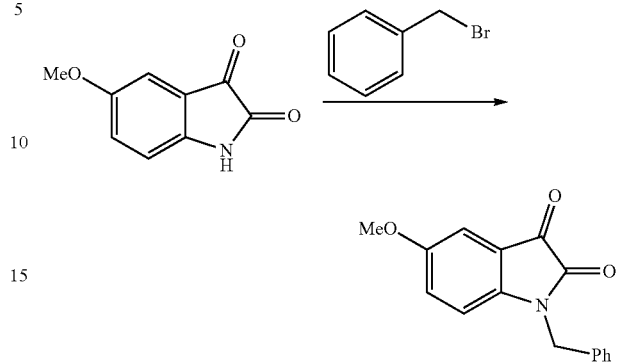

Benzyl bromide (9.65 mL, 79.7 mmol) was added to a mixture of 5-methoxyisatin (12.0 g, 66.4 mmol) and potassium carbonate (27.5 g, 199 mmol) in acetonitrile (250 mL). The mixture was stirred for 15 h at 80° C. then cooled to rt. The mixture was filtered and the filtrate concentrated. It was diluted with water (300 mL) and extracted with EtOAc (3×80 mL). The combined organic layers were washed with brine, then dried (Na₂SO₄), filtered and concentrated. The resulting solid was triturated with heptane, filtered, and washed with heptane, affording the title compound (18.2 g, quantitative yield) as a solid. m/z (ESI, +ve ion)=268.1 [M+H]⁺. 1H NMR (400 MHz, CDCl₃) δ 7.38-7.27 (m, 5H), 7.15 (d, J=2.7 Hz, 1H), 7.02 (dd, J=8.6, 2.7 Hz, 1H), 6.67 (d, J=8.6 Hz, 1H), 4.90 (s, 2H), 3.77 (s, 3H).

Step B. 1-Benzyl-5-methoxyindolin-2-one

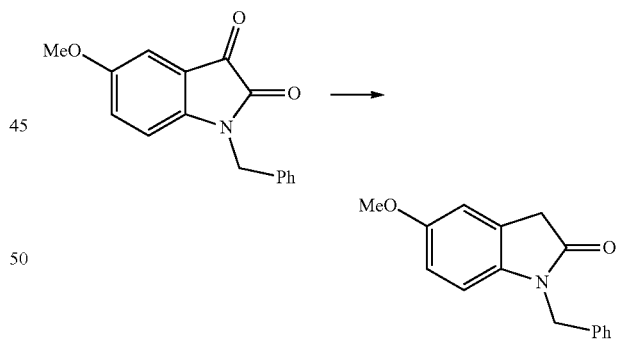

Hydrazine monohydrate (8.64 mL, 107 mmol) was added to a mixture of 1-benzyl-5-methoxyindoline-2,3-dione (18.2 g, 68.1 mmol) in DMSO (44.1 mL). The mixture was stirred for 5 h at 140° C. then cooled to rt. The mixture was diluted with water (300 mL) and extracted with EtOAc (3×200 mL). The combined organic layers were washed with 1 M H₂SO₄, brine (twice), then dried (Na₂SO₄), filtered and concentrated, affording the title compound (14.0 g, 81%) as a dark oil. m/z (ESI, +ve ion)=254.1 [M+H]⁺. 1 H NMR (400 MHz, CDCl₃) δ 7.38-7.22 (m, 5H), 6.90-6.86 (m, 1H), 6.68 (dd, J=8.5, 2.6 Hz, 1H), 6.60 (d, J=8.5 Hz, 1H), 4.89 (s, 2H), 3.75 (s, 3H), 3.61 (s, 2H).

Step C. 1-Benzyl-6-bromo-1H-indazole

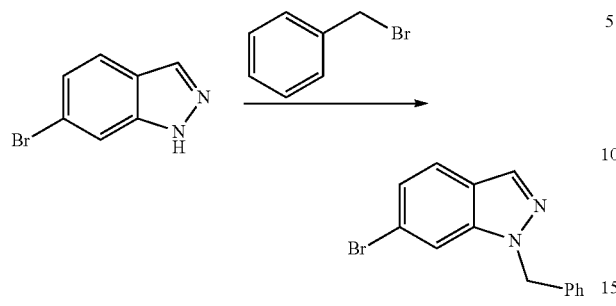

Potassium tert-butoxide (20.5 g, 179 mmol) was added to a mixture of 6-bromo-1H-indazole (30.0 g, 152 mmol) in DMSO (149 mL). The mixture was stirred for 10 min then benzyl chloride (20.8 mL, 179 mmol) was slowly added at 0° C. The mixture was stirred at rt for 3 h then diluted with saturated aqueous NH$_4$Cl (400 mL) and extracted with MTBE (3×200 mL). The combined organic layers were washed with brine twice, then dried (Na$_2$SO$_4$), filtered and concentrated to give crude material as a mixture of 1-benzyl-6-bromo-1H-indazole and 2-benzyl-6-bromo-2H-indazole. Benzyl bromide (37.7 mL, 311 mmol) was added to a mixture of 1-benzyl-6-bromo-1H-indazole and 2-benzyl-6-bromo-2H-indazole (31 g, 108 mmol). The mixture was stirred neat at 150° C. After 6 h, benzyl bromide was removed by distillation under high vacuum (vacuum pump) at 130° C. The residue was triturated in heptanes, then filtered and washed with heptanes. The crude material was put on the high vacuum overnight, affording the tittle compound (20.6 g, 67%) as a solid. m/z (ESI, +ve ion)=287.0 [M+H]$^+$.

Step D. 1-Benzyl-6-vinyl-1H-indazole

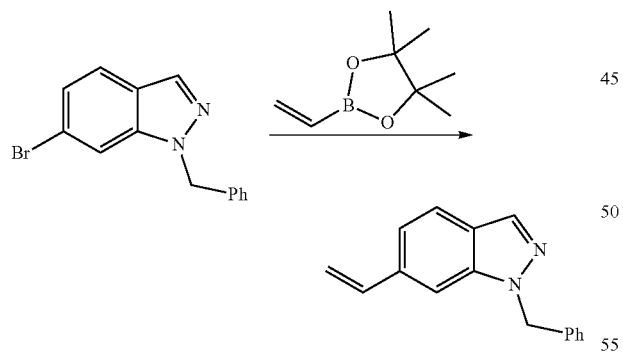

A mixture of 1-benzyl-6-bromo-1H-indazole (6.33 g, 22.0 mmol) and potassium carbonate (9.14 g, 66.1 mmol) in previously degassed (nitrogen bubbled through) DME/water (3:1) (70.0 mL) was purged with nitrogen and nitrogen was further bubbled through the reaction mixture. Vinylboronic acid pinacol ester (4.82 mL, 27.6 mmol) was added, followed by dichlorobis(triphenylphosphine)palladium (II) (774 mg, 1.10 mmol) and the mixture was heated to 80° C. overnight. The mixture was diluted with heptanes and washed with water (3×) and brine. The organic phase was dried with Na$_2$SO$_4$, filtered and concentrated. The crude product was purified by column chromatography (0 to 10% EtOAc/hexanes, gradient elution) to afford the title compound 4D (3.80 g, 74%). m/z (ESI, +ve ion)=235.4 [M+H]$^+$. 1H NMR (400 MHz, CDCl3) δ 8.01 (d, J=0.9 Hz, 1H), 7.73-7.64 (m, 1H), 7.36-7.23 (m, 5H), 7.23-7.16 (m, 2H), 6.80 (dd, J=17.6, 10.9 Hz, 1H), 5.80 (dd, J=17.5, 0.7 Hz, 1H), 5.60 (s, 2H), 5.30 (dd, J=10.9, 0.6 Hz, 1H).

Step E. (S)-1-(1-Benzyl-1H-indazol-1-yl)ethane-1,2-diol

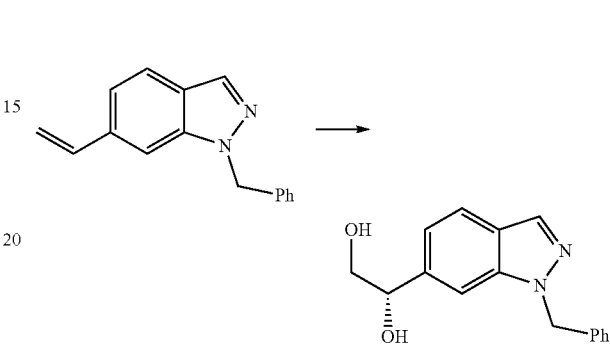

To a 500 mL flask was added AD-mix-alpha (83.7 g, 59.8 mmol) and t-BuOH/water (1:1) (598 mL) forming a clear biphasic mixture on stirring. The reaction mixture was cooled with an ice bath to 0° C. before adding 1-benzyl-6-vinyl-1H-indazole (14.0 g, 59.8 mmol). The resulting mixture was vigorously stirred at 0° C. and let warm to room temperature with the ice bath slowly warming up. The reaction mixture was stirred for 9 h. The reaction was quench by the portion-wise addition of 92 g of sodium sulfite. The reaction mixture was stirred overnight. The reaction mixture was diluted with brine and DCM and filtered through a pad of Celite. The filtrate was extracted with DCM (4×) and the combined organic layers were dried over MgSO$_4$, filtered and concentrated. The crude product was recrystallized from toluene (80 mL) to afford the title compound (12.2 g, 76%) as a white solid. m/z (ESI, +ve ion)=269.2 [M+H]$^+$. 99.1% ee.

Step F. (S)-1-(1-Benzyl-1H-indazol-6-yl)ethane-1,2-diyl dimethanesulfonate

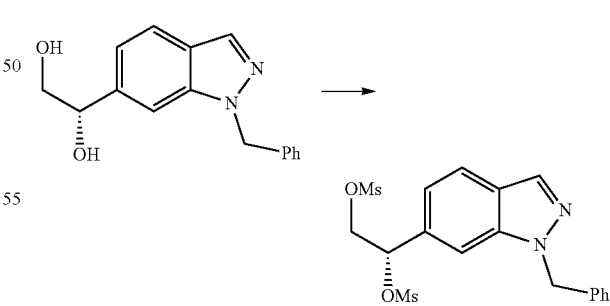

A solution of (S)-1-(1-Benzyl-1H-indazol-6-yl)ethane-1,2-diol (12.2 g, 45.5 mmol) and triethylamine (16.0 mL, 114 mmol) in DCM (227 mL) was cooled in an ice bath and treated by slow addition of methanesulfonyl chloride (7.77 mL, 100 mmol) over 15 minutes. The internal temperature increased to a maximum of 11° C. The resulting mixture was stirred at 0° C. After 6 h, LCMS showed 10% mono mesylated product. 0.400 mL of methanesulfonyl chloride and 0.600 mL of triethylamine were added. The mixture was stirred 1 h and upon completion, diluted with DCM (500 mL) and 1 M aqueous HCl (200 mL) at 0° C. The layers were separated and the organic layer was washed with saturated aqueous NaHCO₃ (2×200 mL), brine (200 mL), then dried (Na₂SO₄), filtered and concentrated. The crude material was passed through a small pad of Celite eluting with a mixture of DCM/Et₂O (1:1). Removal of the solvents gave a white solid. The solid was triturated in Et₂O (40 mL) and the precipitate was collected by filtration, affording the title compound (17.5 g, 91%) as white crystalline solid. m/z (ESI, +ve ion)=425.0 [M+H]⁺. 1H NMR (400 MHz, CDCl₃) δ 8.08 (s, 1H), 7.81 (d, J=8.3 Hz, 1H), 7.41 (s, 1H), 7.35-7.27 (m, 3H), 7.18 (dd, J=17.3, 7.5 Hz, 3H), 5.89 (dd, J=8.6.3.2 Hz, 1H), 5.66 (d, J=15.8 Hz, 1H), 5.60 (d, J=15.8 Hz, 1H), 4.53 (dd, J=11.9, 8.6 Hz, 1H), 4.40 (dd, J=11.9, 3.3 Hz, 1H), 3.05 (s, 3H), 2.75 (s, 3H).

Step G. (1R,2S)-1'-Benzyl-2-(1-benzyl-1H-indazol-6-yl)-5'-methoxyspiro[cyclopropane-1,3'-indolin]-2'-one

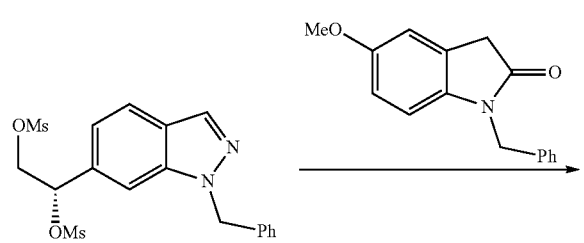

A solution of (S)-1-(1-benzyl-1H-indazol-6-yl)ethane-1,2-diyl dimethanesulfonate (2.03 g, 8.01 mmol) in dry THF (80 mL) under nitrogen was cooled in an ice bath. Sodium hydride (673 mg, 16.8 mmol) was added portion-wise and the mixture was stirred at 0° C. for 15 min. A solution of 1-benzyl-5-methoxyindolin-2-one (3.40 g, 8.01 mmol) in dry THF (50 mL) was added dropwise with an addition funnel. The reaction mixture was stirred for 3 h at 0° C. The reaction was quench with satd. NH₄Cl solution, diluted with water, and extracted with EtOAc (3×). The organic layer was dried with anhyd. MgSO₄ and concentrated to a crude product. The crude product was triturated with 3:1 hexanes/EtOAc, affording the title compound (2.10 g, 54%) as an orange solid. m/z (ESI, +ve ion)=486.2 [M+H]⁺.

Step H. (1R,2S)-2-(1H-Indazol-6-yl)-5'-methoxyspiro[cyclopropane-1,3'-indolin]-2'-one

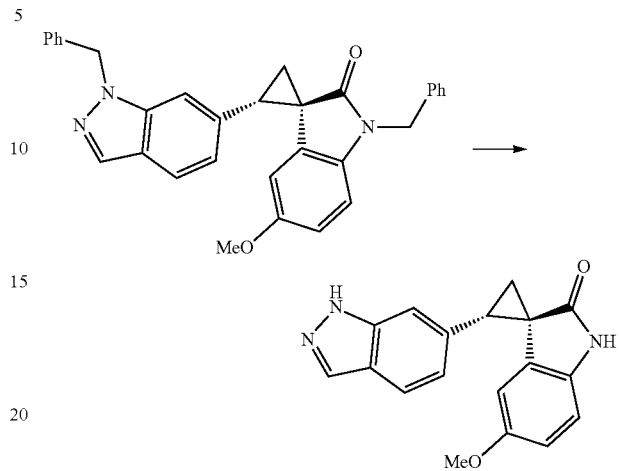

To a round-bottom flask charged with a stir bar was added (1R,2S)-1'-Benzyl-2-(1-benzyl-1H-indazol-6-yl)-5'-methoxyspiro[cyclopropane-1,3'-indolin]-2-one (4.00 g, 8.24 mmol) in THF (118 mL). The solution was cooled to 0° C. and potassium tert-butoxide (23.0 mL, 165 mmol) was added portion wise over 20 min and then DMSO (10.7 mL) was added. Oxygen was bubbled through the solution at 0° C. for 1 h. The reaction was quenched with satd. aqueous NH₄Cl at 0° C. and diluted with EtOAc (50 mL). The mixture was washed with satd. aqueous NH₄Cl (1×) and extracted with EtOAc (2×). The organic phase was dried over Na₂SO₄, filtered, and concentrated under vacuum. The crude was triturated in Et₂O and recrystallized from ethanol, affording the title compound (2.56 g, 56%). m/z (ESI, +ve ion)=306.4 [M+H]⁺.

Intermediate 3: (1R,2S)-2-(3-Bromo-1H-indazol-6-yl)-5'-methoxyspiro[cyclopropane-1,3'-indolin]-2'-one

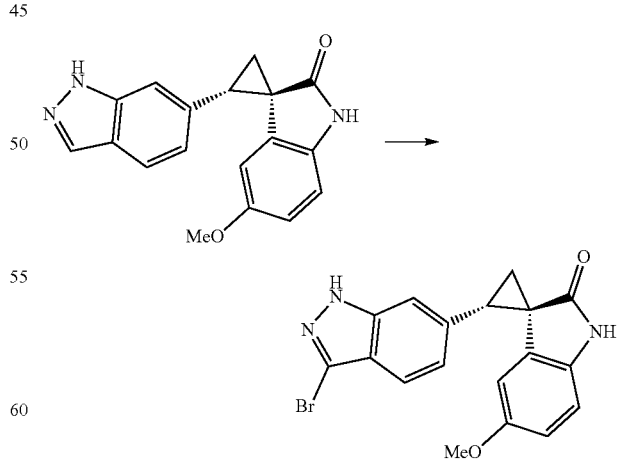

In a flask. (1R,2S)-2-(1H-indazol-6-yl)-5'-methoxyspiro[cyclopropane-1,3'-indolin]-2'-one (4.49 g, 12.5 mmol) was dissolved in DMF (16.7 mL) and NBS (2.70 g, 15.0 mmol) dissolved in DMF (8.33 mL) was added dropwise at 0° C.

The reaction was stirred for 2 h at rt. The reaction was quenched with an aqueous solution of Na$_2$S$_2$O$_3$ and extracted with EtOAc (3×100 mL). The combined organic layers were washed with brine, dried (Na$_2$SO$_4$), filtered and concentrated. The crude was purified by column chromatography (40 to 100% EtOAc/hexanes, gradient elution), affording the title compound (3.12 g, 65%). m/z (ESI, +ve ion)=384.0, 386.0 [M+H]$^+$.

Intermediate 4: Tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate

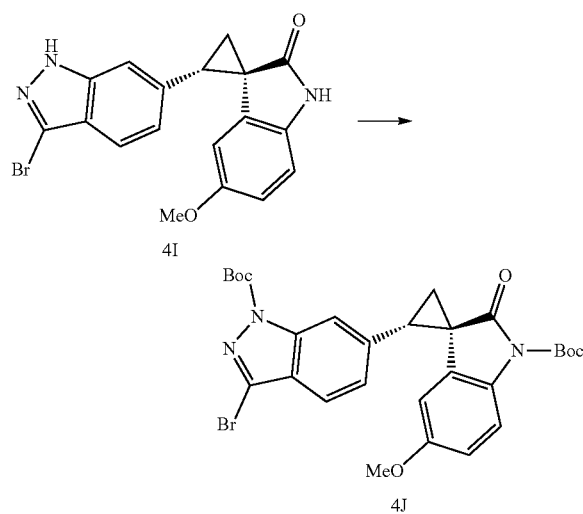

4-Dimethylaminopyridine (79.8 mg, 640 μmol) was added to a solution of triethylamine (3.61 mL, 25.6 mmol), di-tert-butyl dicarbonate (4.0 mL, 17.3 mmol) and (1R,2S)-2-(3-bromo-1H-indazol-6-yl)-5'-methoxyspiro[cyclopropane-1,3'-indolin]-2'-one (2.46 g, 6.40 mmol) in DCM (24 mL). The solution was stirred at room temperature for 16 h. LCMS showed incomplete conversion. Di-tert-butyl dicarbonate (0.75 mL, 3.2 mmol, 0.5 equiv.) was added and the reaction was stirred another hour. The crude product was purified by column chromatography (0 to 20% EtOAc/heptanes, gradient elution), affording the title compound (3.06 g, 82%) as a yellow foamy solid. m/z (EST, +ve ion)=384.0, 386.0 [M+H-boc]$^+$.

Intermediate 5: Tert-butyl 3-amino-6-((1R,2S)-1'-(tert-butoxycarbonyl)-5'-methoxy-2'-oxospiro[cyclopropane-1,3'-indolin]-2-yl)-1H-indazole-1-carboxylate

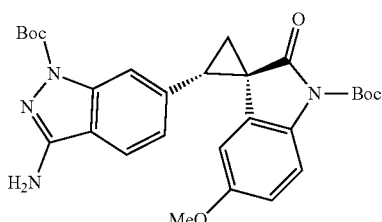

Step A. Tert-butyl 6-((1R,2S)-1'-(tert-butoxycarbonyl)-5'-methoxy-2'-oxospiro[cyclopropane-1,3'-indolin]-2-yl-3-((diphenylmethylene)amino)-1H-indazole-1-carboxylate

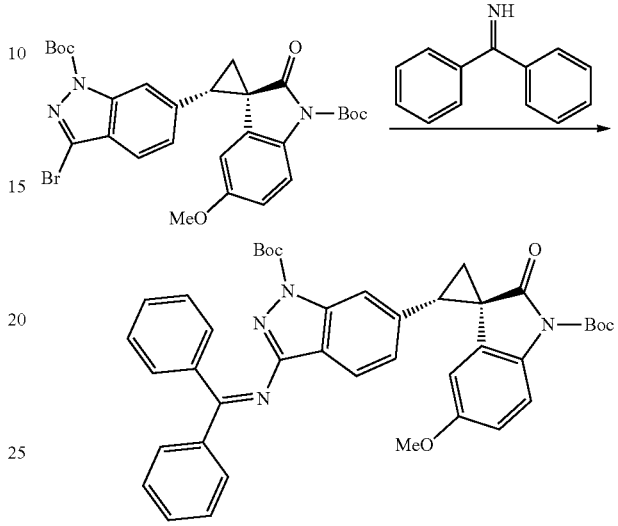

A microwave vial was charged with tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (1.00 g, 1.71 mmol), cesium carbonate (1.14 g, 3.42 mmol), Pd$_2$(dba)$_3$ (157 mg, 171 μmol) and XantPhos (101 mg, 171 μmol). Dry dioxane (17.1 mL) followed by benzophenone imine (310 μL, 1.83 mmol) were added and nitrogen was bubbled through the reaction mixture for 5 min. The vial was sealed, and the reaction mixture was heated to 90° C. for 2 h in an oil bath. A satd. aqueous solution of NaHCO$_3$ was added and the reaction mixture was extracted with EtOAc (3×). The combined extracts were then washed with brine, dried with anhyd. Na$_2$SO$_4$, filtered and concentrated under vacuum. The crude product was purified by column chromatography (0 to 30% EtOAc/heptanes, gradient elution), affording the title compound (1.03 g, 88%) as yellow oil. m/z (ESI, +ve ion)=685.4 [M+H]$^+$.

Step B. Tert-butyl 3-amino-6-((1R,2S)-1'-(tert-butoxycarbonyl)-5'-methoxy-2'-oxospiro[cyclopropane-1,3'-indolin]-2-yl)-1H-indazole-1-carboxylate

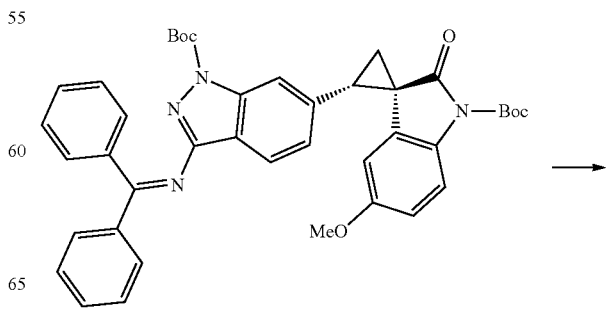

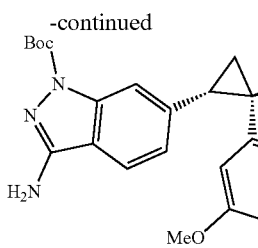

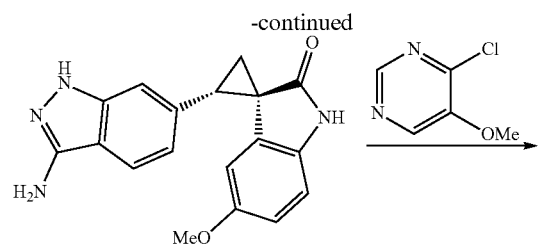

Hydroxylamine hydrochloride (101 mg, 1.46 mmol) and sodium acetate (120 mg, 1.46 mmol) were added to tert-butyl 6-((1R,2S)-1'-(tert-butoxycarbonyl)-5'-methoxy-2'-oxospiro[cyclopropane-1,3'-indolin]-2-yl)-3-((diphenylmethylene)amino)-1H-indazole-1-carboxylate (1.00 g, 1.46 mmol) in dry MeOH (14.6 mL) at room temperature and the reaction was stirred for 16 h. The solvent was removed under reduced pressure. The crude product was purified by column chromatography (0 to 60% EtOAc/heptanes, gradient elution), affording the title compound (640 mg, 84%) as yellow solid. m/z (EST, +ve ion)=521.0 [M+H]+. 1H NMR (400 MHz, CDCl3) δ8.06 (s, 1H), 7.78 (d, J=8.9 Hz, 1H), 7.41 (d, J=8.2 Hz, 1H), 7.01 (d, J=8.2 Hz, 1H), 6.66 (dd, J=8.9, 2.6 Hz, 1H), 5.55 (d, J=2.3 Hz, 1H), 4.44 (s, 2H), 3.49 (t, J=8.6 Hz, 1H), 3.37 (s, 3H), 2.34 (dd, J=9.2, 4.8 Hz, 1H), 2.14-2.06 (m, 1H), 1.67 (d, J=2.4 Hz, 18H).

Example 1. racemic-5'-Methoxy-2-{3-[(5-methoxypyrimidin-4-yl)amino]-1H-indazol-6-yl}spiro[cyclopropane-1,3'-indol]-2'(1'H)-one

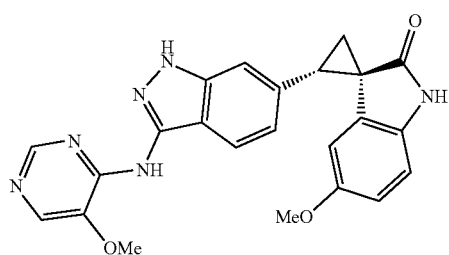

In a 4 mL vial was dissolved (1R,2S)-2-(3-amino-1H-indazol-6-yl)-5'-methoxyspiro[cyclopropane-1,3'-indolin]-2'-one (54.0 mg, 169 µmol) and 4-chloro-5-methoxypyrimidine (29.8 mg, 202 µmol) in acetic acid/water (1:1) (1.00 mL). The reaction was heated to 100° C. for 1 h. The reaction mixture was poured into 5 mL of a solution of aq. NaOH 2 M. The aqueous layer was extracted with EtOAc (3×). The combined organic layers were washed with brine, dried over anhyd. sodium sulfate and concentrated. The product was purified by column chromatography (0 to 10% MeOH/DCM, gradient elution), affording Example 1 (22.9 mg, 32%) as white solid after lyophilization. m/z (EST, +ve ion)=429.2 [M+H]+. 1H NMR (400 MHz, DMSO) δ 12.68 (s, 1H), 10.42 (s, 1H), 9.12 (s, 1H), 8.04 (d, J=3.0 Hz, 2H), 7.40 (d, J=7.9 Hz, 2H), 6.89 (d, J=9.4 Hz, 1H), 6.74 (d, J=8.4 Hz, 1H), 6.58 (dd, J=8.5, 2.6 Hz, 1H), 5.72 (d, J=2.5 Hz, 1H), 3.94 (s, 3H), 3.33 (s, 3H under water peak), 3.18 (t, J=8.5 Hz, 1H), 2.33 (dd, J=7.8, 4.7 Hz, 1H), 1.98 (dd, J=9.0, 4.7 Hz, 1H).

Example 2. racemic-5'-Methoxy-2-{3-[(5-methylpyrimidin-4-yl)amino]-1H-indazol-6-yl}spiro[cyclopropane-1,3'-indol]-2'(1'H)-one

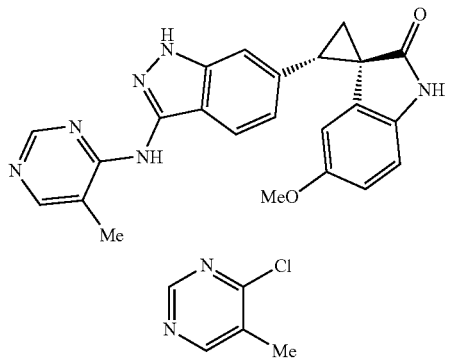

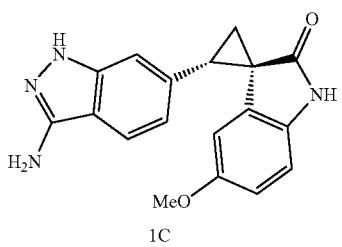

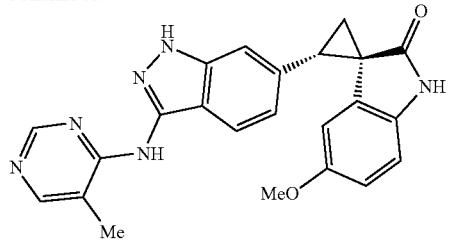

Example 2 was prepared using the procedure described in Example 1 from (1R,2S)-2-(3-amino-1H-indazol-6-yl)-5'-methoxyspiro[cyclopropane-1,3'-indolin]-2'-one (60.0 mg, 187 μmol) and 4-chloro-5-methylpyrimidine (27 mg, 206 μmol). The product was purified by column chromatography (0 to 10/o MeOH/DCM, gradient elution), concentrated, and then lyophilized from MeCN and water to afford Example 2 (7.7 mg, 10%) as white solid. m/z (ESI, +ve ion)=413.2 [M+H]$^+$. 1 H NMR (400 MHz, DMSO) δ12.69 (s, 1H), 10.43 (s, 1H), 9.02 (s, 1H), 8.24 (s, 1H), 8.13 (s, 1H), 7.41 (s, 1H), 7.34 (d, J=8.5 Hz, 1H), 6.89 (dd, J=8.5, 1.0 Hz, 1H), 6.74 (d, J=8.4 Hz, 1H), 6.58 (dd, J=8.5, 2.6 Hz, 1H), 5.71 (d, J=2.6 Hz, 1H), 3.33 (s, 3H, under water peak), 3.18 (t, J=8.4 Hz, 1H), 2.33 (dd, J=7.9.4.7 Hz, 1H), 2.21 (s, 3H), 1.98 (dd, J=9.0, 4.7 Hz, 1H).

Example 3. racemic-2-{3-[(5-Chloropyrimidin-4-yl)amino]-1H-indazol-6-yl}-5'-methoxyspiro[cyclopropane-1,3'-indol]-2'(1'H)-one

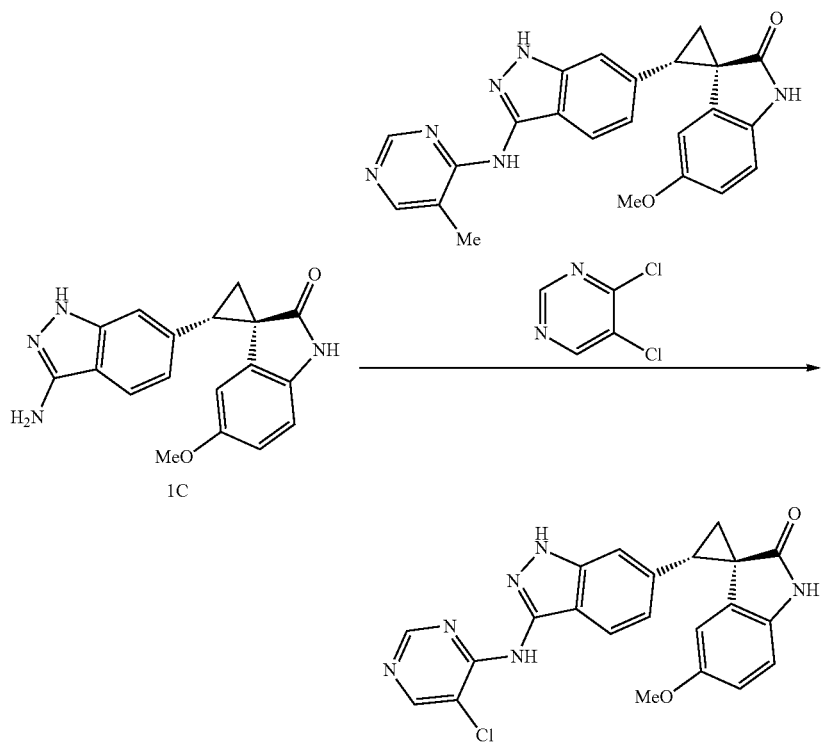

Example 3 was prepared using the procedure described in Example 1 from (1R,2S)-2-(3-Amino-1H-indazol-6-yl)-5'-methoxyspiro[cyclopropane-1,3'-indolin]-2'-one (60.0 mg, 187 μmol) and 4,5-dichloropyrimidine (31.3 mg, 206 μmol). The product was purified by C18 column chromatography (5 to 40% MeCN/aq. ammonium formate buffer, gradient elution), affording Example 3 (4.8 mg, 6%) as white solid after lyophilization. m/z (EST, +ve ion)=433.1 [M+H]$^+$. 1H NMR (40 MHz, DMSO) δ 12.85 (s, 1H), 10.43 (s, 1H), 9.58 (s, 1H), 8.46 (s, 1H), 8.31 (s, 1H), 7.44 (s, 1H), 7.37 (d, J=8.3 Hz, 1H), 6.95-6.87 (m, 1H), 6.74 (d, J=8.4 Hz, 1H), 6.58 (dd, J=8.5, 2.6 Hz, 1H), 5.70 (d, J=2.5 Hz, 1H), 3.33 (s, 3H), 3.19 (t, J=8.4 Hz, 1H), 2.34 (dd, J=8.0, 4.7 Hz, 1H), 1.98 (dd, J=9.0, 4.6 Hz, 1H).

Example 4. (1R,2S)-5'-Methoxy-2-{3-[(5-methoxy-pyrimidin-4-yl)amino]-1H-indazol-6-yl}spiro[cyclopropane-1,3'-indol]-2'(1'H)-one

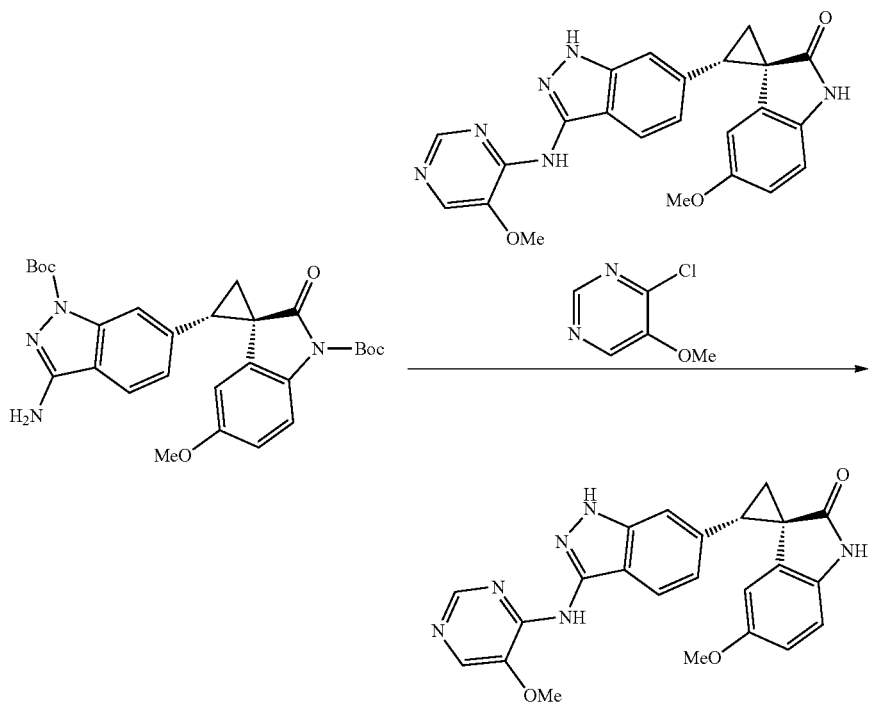

This compound was prepared using the procedure described in Example 1, from tert-butyl 3-amino-6-((1R,2S)-1'-(tert-butoxycarbonyl)-5'-methoxy-2'-oxospiro[cyclopropane-1,3'-indolin]-2-yl)-1H-indazole-1-carboxylate (108 mg, 207 μmol) and 4-chloro-5-methoxypyrimidine (36.7 mg, 249 μmol). The Boc groups are cleaved in situ during the reaction conditions. The product was purified by C18 column chromatography (10% to 30% MeCN/aq. ammonium formate buffer, gradient elution), affording Example 4 (9.6 mg, 11%) as white solid after lyophilization. m/z (ESI, +ve ion)=429.2 [M+H]⁺. 1H NMR (400 MHz, DMSO) δ 12.68 (s, 1H), 10.43 (s, 1H), 9.12 (s, 1H), 8.04 (d, J=3.1 Hz, 2H), 7.44-7.35 (m, 2H), 6.89 (d, J=9.4 Hz, 1H), 6.74 (d, J=8.4 Hz, 1H), 6.58 (dd, J=8.5, 2.6 Hz, 1H), 5.72 (d, J=2.5 Hz, 1H), 3.94 (s, 3H), 3.33 (s, 3H under water peak), 3.18 (t, J=8.6 Hz, 1H), 2.33 (dd, J=7.9, 4.7 Hz, 1H), 1.98 (dd, J=9.0, 4.6 Hz, 1H).

Example 5. (1R,2S)-5'-Methoxy-2-{3-[(5-methoxy-pyrimidin-4-yl)amino]-1H-indazol-6-yl}spiro[cyclopropane-1,3'-indol]-2'(1'H)-one

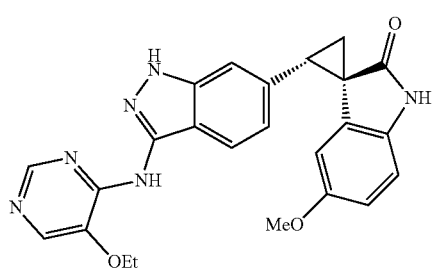

Step A. (1R,2S)-2-(3-Iodo-1H-indazol-6-yl)-5'-methoxyspiro[cyclopropane-1,3'-indolin]-2'-one

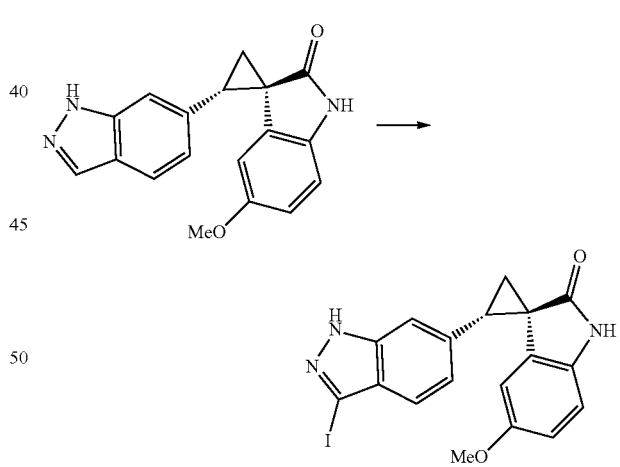

To an oven-dried flask was added (1R,2S)-2-(1H-indazol-6-yl)-5'-methoxyspiro[cyclopropane-1,3'-indolin]-2'-one (4.00 g, 13.1 mmol) followed by DMF (8 mL and Methanol (8 mL. To this suspension was added K₂CO₃ (3.62 g, 26.2 mmol). Finally, molecular iodine (4.32 g, 17.0 mmol) dissolved in DMF (8 mL) and was added dropwise and allowed to stir at rt. After 4 h, the reaction was complete. The mixture was quenched with Na₂S₂O₃ in water and stirred for 2 h. Solid was collected by filtration and washed with water. Wet solid was frozen and lyophilized, affording the title compound (4.4 g, 78% yield.

Step B. Tert-butyl (1R,2S)-2-(1-(tert-butoxycarbonyl)-3-iodo-1H-indazol-6-yl)-5'-methoxy-2'-oxospiro[cyclopropane-1,3'-indoline]-1'-carboxylate

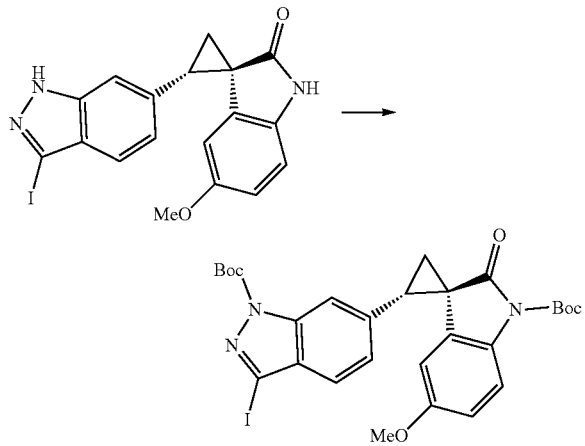

To an oven-dried flask was added 4-dimethylaminopyridine (9.0 mg, 0.07 mmol) followed by (1R,2S)-2-(3-iodo-1H-indazol-6-yl)-5'-methoxyspiro[cyclopropane-1,3'-indolin]-2'-one (637 mg, 1.48 mmol), N-ethyl-N-isopropylpropan-2-amine (1.0 mL, 5.9 mmol) and MeCN (5.0 mL). The mixture was stirred at room temperature and di-tert-butyl dicarbonate (967 mg, 4.43 mmol) was added, resulted in light yellow homogeneous solution. After 2 h, the reaction mixture was concentrated and the resulting residue was purified by column chromatography (0% to 25%, EtOAc/hexanes, gradient elution) to afford the product as a white foam (51) (822 mg, 88%).

Step C. Tert-butyl (1R,2S)-2-[1-tert-butoxycarbonyl-3-[(5-ethoxypyrimidin-4-yl)amino]indazol-6-yl]-5'-methoxy-2'-oxo-spiro[cyclopropane-1,3'-indoline]-1'-carboxylate

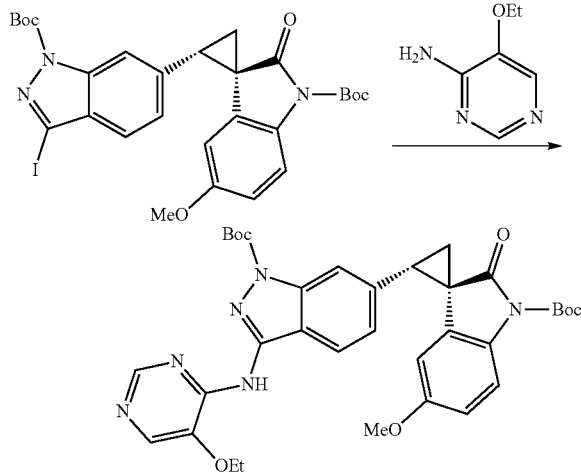

To a 50 ml round bottom flask were added cesium carbonate (41.3 mg, 0.130 mmol), 5-ethoxypyrimidin-4-amine (9.3 mg, 0.070 mmol), Pd₂(dba)₃ (5.8 mg, 0.010 mmol), tert-butyl (1R,2S)-2-(1-(tert-butoxycarbonyl)-3-iodo-1H-indazol-6-yl)-5'-methoxy-2'-oxospiro[cyclopropane-1,3'-indoline]-1'-carboxylate (40.0 mg, 0.0600 mmol), XantPhos (3.7 mg, 0.010 mmol) and dry toluene (4.2 mL). The reaction mixture was stirred and purged with argon (in balloon) for 10 min to form a green suspension, and then heated to 120° C., resulting in a yellow suspension. The reaction was monitored by LCMS and TLC until the full conversion of the starting materials (approx. 70 min), cooled down to rt, diluted with EtOAc, washed with sat. aq. NaHCO₃ and dried over Na₂SO₄. The residue was purified by column chromatography (0% to 90% ethyl acetate/hexane, gradient elution) to provide the title compound (24.0 mg, 59%) as a yellow oil.

Step D. (1R,2S)-2-[3-[(5-ethoxypyrimidin-4-yl)amino]-1H-indazol-6-yl]-5'-methoxy-spiro[cyclopropane-1,3'-indoline]-2'-one

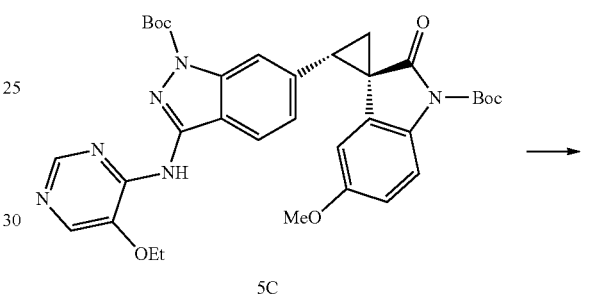

5C

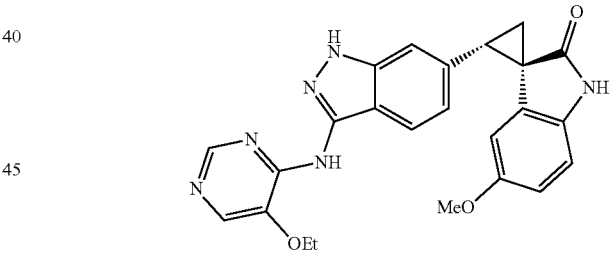

To a 50 ml round bottom flask containing tert-butyl (1R,2S)-2-[1-tert-butoxycarbonyl-3-[(5-ethoxypyrimidin-4-yl)amino]indazol-6-yl]-5'-methoxy-2'-oxo-spiro[cyclopropane-1,3'-indoline]-1'-carboxylate (24.0 mg, 0.0400 mmol) in DCM (1.9 mL) was added trifluoroacetic acid (0.15 mL, 1.9 mmol). The reaction mixture was stirred and monitored by LCMS until the full conversion of the starting materials (approx. 3 hrs), diluted with acetonitrile. The resulting brown solution was purified by Prep. HPLC (Gemini C18, 30 to 80% (0.1% TFA in water)/(0.1% TFA in Acetonitrile)) to provide the desired product Example 5 (12.4 mg, 75%) as a yellow film. m/z (ESI, +ve ion) 443.2 (M+H)⁺. ¹H NMR (400 MHz, METHANOL-d₄) δ ppm 1.58 (t, J=6.94 Hz, 3H) 2.10-2.32 (m, 2H) 3.26-3.30 (m, 3H) 3.32-3.39 (m, 1H) 4.27-4.44 (m, 2H) 5.50-5.61 (m, 1H) 6.55-6.67 (m, 1H) 6.76-6.89 (m, 1H) 6.91-7.04 (m, 1H) 7.44-7.62 (m, 2H) 8.03-8.18 (m, 1H) 8.36-8.49 (m, 1H).

Example 6. (1R,2S)-2-{3-[(5-cyclopropylpyrimidin-4-yl)amino]-1H-indazol-6-yl}-5'-methoxyspiro[cyclopropane-1,3'-indol]-2'(1'H)-one

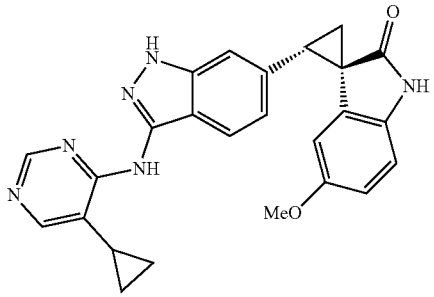

Step A. Tert-butyl (1R,2S)-2-[1-tert-butoxycarbonyl-3-[(5-cyclopropylpyrimidin-4-yl)amino]indazol-6-yl]-5'-methoxy-2'-oxo-spiro[cyclopropane-1,3'-indoline]-1'-carboxylate

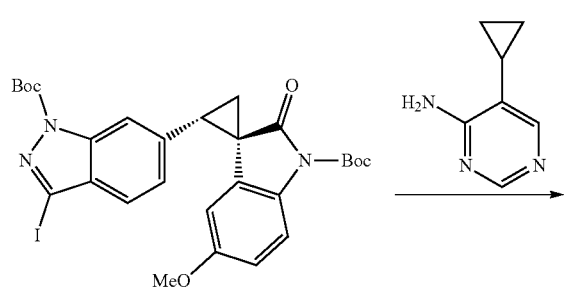

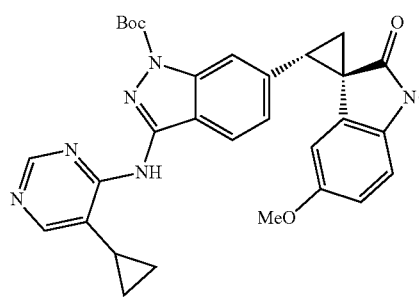

This compound was prepared using the procedure described in Example 5 from tert-butyl (1R,2S)-2-(1-(tert-butoxycarbonyl)-3-iodo-1H-indazol-6-yl)-5'-methoxy-2'-oxospiro[cyclopropane-1,3'-indoline]-1'-carboxylate (40.0 mg, 0.0600 mmol) and 5-cyclopropylpyrimidin-4-amine (9.0 mg, 0.070 mmol). The residue was purified by column chromatography (ethyl acetate/hexane=0~90%) to provide the title compound (17.0 mg, 42%) as a yellow oil.

Step B. (1R,2S)-2-[3-[(5-Cyclopropylpyrimidin-4-yl)amino]-1H-indazol-6-yl]-5'-methoxy-spiro[cyclopropane-1,3'-indoline]-2'-one

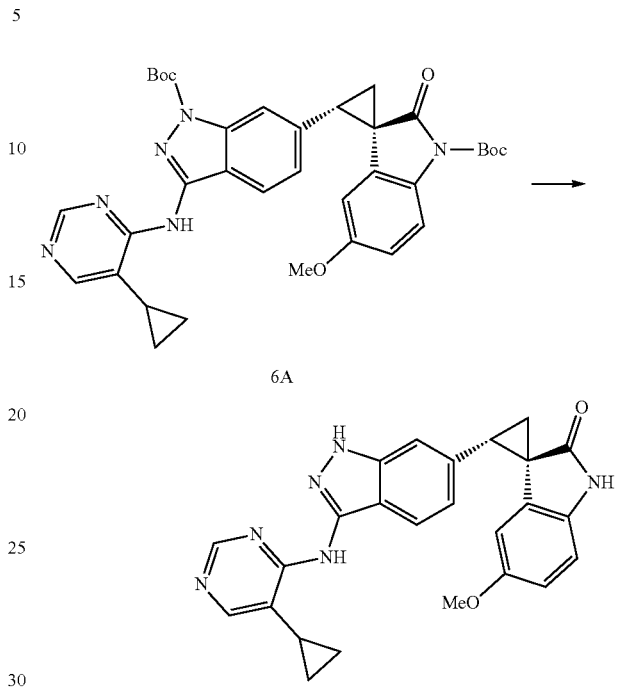

6A

This compound was prepared using the procedure described in Example 5 from tert-butyl (1R,2S)-2-[1-tert-butoxycarbonyl-3-[(5-cyclopropylpyrimidin-4-yl)amino]indazol-6-yl]-5'-methoxy-2'-oxo-spiro[cyclopropane-1,3'-indoline]-1'-carboxylate (17.0 mg, 0.0400 mmol) and trifluoroacetic acid (0.10 mL, 1.3 mmol). The resulting brown solution was purified by Prep. HPLC (Gemini C18, 10 to 90% (0.1% TFA in water)/(0.1% TFA in Acetonitrile)) to provide the desired product Example 6 (6.2 mg, 53%) as a colorless film. m/z (ESI, +ve ion) 439.2 (M+H)+. $^1$H NMR (400 MHz, METHANOL-$d_4$) δ ppm 0.85-0.97 (m, 2H) 1.16-1.31 (m, 2H) 1.87-2.04 (m, 1H) 2.16-2.32 (m, 2H) 5.53-5.63 (m, 1H) 6.58-6.69 (m, 1H) 6.79-6.90 (m, 1H) 6.96-7.06 (m, 1H) 7.48-7.63 (m, 2H) 8.15-8.30 (m, 1H) 8.52-8.63 (m, 1H).

Example 7. (1R,2S)-2-{3-[(5-Chloropyrimidin-4-yl)amino]-1H-indazol-6-yl}-5'-methoxyspiro[cyclopropane-1,3'-indol]-2'(1'H)-one

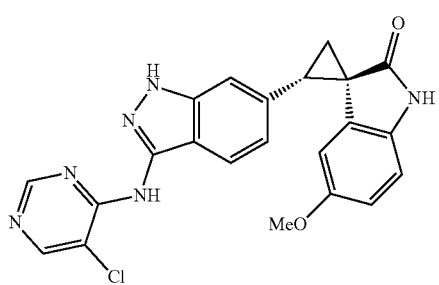 [SMILES: COc1ccc2c(c1)[C@]1(C[C@H]1c1ccc3c(Nc4ncncc4Cl)n[nH]c3c1)C(=O)N2]

Step A. Tert-butyl 6-((1R,2S)-1'-(tert-butoxycarbonyl)-5'-methoxy-2'-oxospiro[cyclopropane-1,3'-indolin]-2-yl)-3-((5-chloropyrimidin-4-yl)amino)-1H-indazole-1-carboxylate

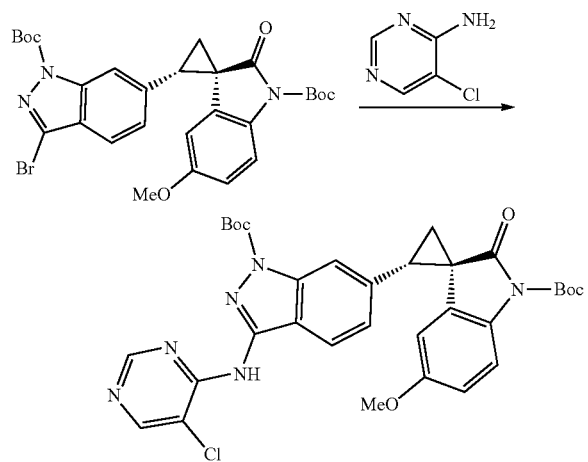

This compound was prepared using the procedure described in Example 5 from tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (110 mg, 188 μmol) and 4-amino-5-chloropyrimidine (29.3 mg, 215 μmol). The product was purified by column chromatography (20 to 100/o EtOAc/heptanes, gradient elution), affording the title compound (18.0 mg, 15%). m/z (ESI, +e ion)=633.3 [M+H]⁺.

Step B. (1R,2S)-2-(3-((5-Chloropyrimidin-4-yl)amino)-1H-indazol-6-yl)-5'-methoxyspiro[cyclopropane-1,3'-indolin]-2'-one

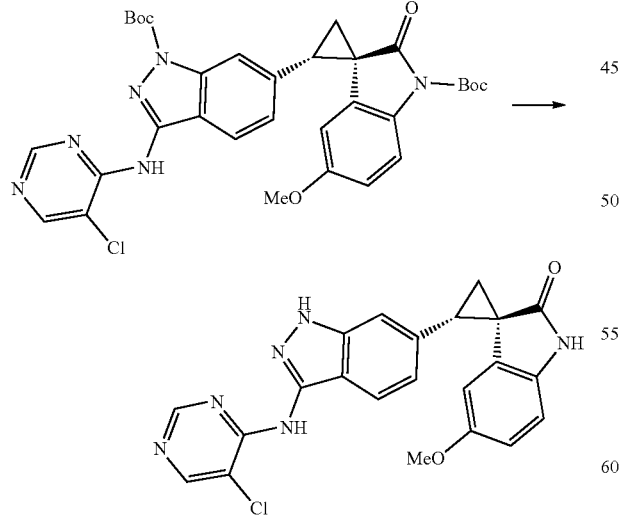

This compound was prepared using the procedure described in Example 5 from tert-butyl 6-((1R,2S)-1'-(tert-butoxycarbonyl)-5'-methoxy-2'-oxospiro[cyclopropane-1,3'-indolin]-2-yl)-3-((5-chloropyrimidin-4-yl)amino)-1H-indazole-1-carboxylate (18 mg, 28.4 μmol). The product was purified by C18 column chromatography (10 to 40% MeCN in aq. ammonium formate buffer), affording Example 7 (3.0 mg, 24%) as white solid after lyophilization. m/z (ESI, +ve ion)=433.1 [M+H]⁺. 1H NMR (400 MHz, DMSO) δ 12.85 (s, 1H), 10.43 (s, 1H), 9.58 (s, 1H), 8.46 (s, 1H), 8.31 (s, 1H), 7.44 (s, 1H), 7.37 (d, J=8.4 Hz, 1H), 6.91 (d, J=8.4 Hz, 1H), 6.74 (d, J=8.4 Hz, 1H), 6.58 (dd, J=8.4, 2.4 Hz, 1H), 5.70 (d, J=2.3 Hz, 1H), 3.33 under water (s, 3H), 3.19 (t, J=8.4 Hz, 1H), 2.34 (dd, J=7.9, 4.6 Hz, 1H), 1.98 (dd, J=9.0, 4.6 Hz, 1H).

Example 8. (1S,2R)-5'-Methoxy-2-{3-[(5-methoxypyrimidin-4-yl)amino]-1H-indazol-6-yl}spiro[cyclopropane-1,3'-indol]-2'(1'H)-one

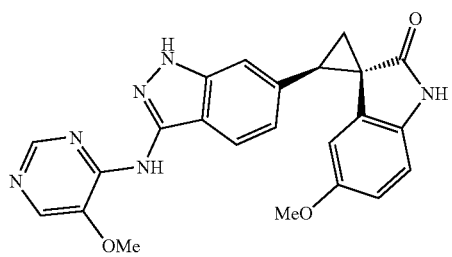 [SMILES: COc1ccc2c(c1)[C@@]1(C[C@@H]1c1ccc3c(Nc4ncncc4OC)n[nH]c3c1)C(=O)N2]

Step A. (1S,2R)-5'-methoxy-2-(3-((5-methoxypyrimidin-4-yl)amino)-1H-indazol-6-yl)spiro[cyclopropane-1,3'-indolin]-2'-one (8A)

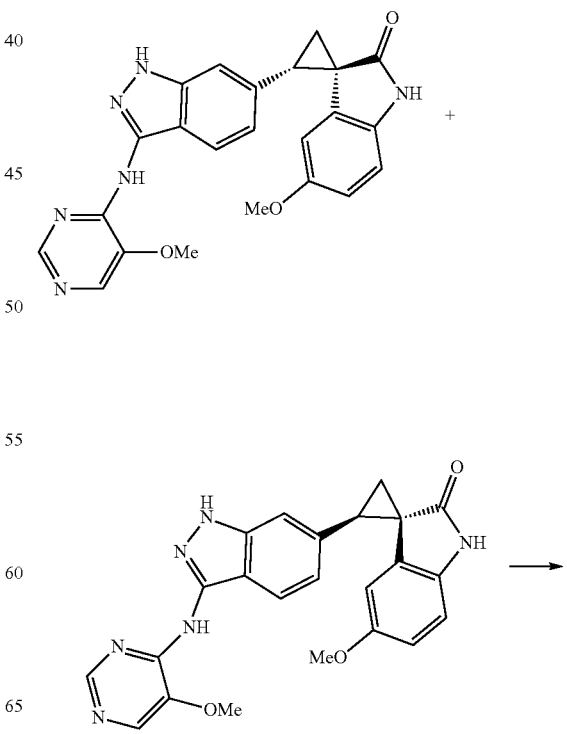

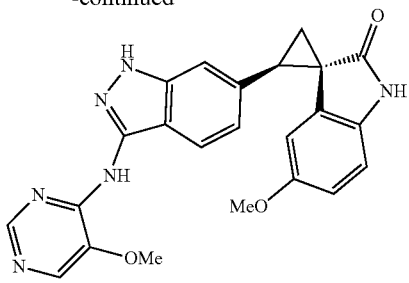

A vial containing Example 1 (17.0 mg, 39.7 μmol) was submitted to chiral HPLC separation. Separation conditions are: Column: AS-H, 10×250 mm 5 um, Mode: Isocratic, Mobile phase: 60% MeOH-0.1% ammonium hydroxide, 40% supercritical $CO_2$, Flow rate: 10 mL/min, Back pressure: 120 bar, Column Temperature: 40° C., Run time (min): 16). The second peak to elute corresponds to title product while the first peak is the corresponding enantiomer (1R,2S). The solution is concentrated and lyophilized from MeCN and water, affording the title compound (15a) (6.7 mg, 39%) as white solid. m/z (ESI, +ve ion)=429.3 [M+H]$^+$. 1H NMR (400 MHz, DMSO) δ 12.67 (s, 1H), 10.41 (s, 1H), 9.10 (s, 1H), 8.04 (d, J=2.1 Hz, 2H), 7.42-7.37 (m, 2H), 6.89 (d, J=9.5 Hz, 1H), 6.74 (d, J=8.4 Hz, 1H), 6.58 (dd, J=8.5, 2.6 Hz, 1H), 5.72 (d, J=2.5 Hz, 1H), 3.94 (s, 3H), 3.18 (t, J=8.5 Hz, 1H), 2.32 (dd, J=7.9, 4.6 Hz, 1H), 1.98 (dd, J=9.0, 4.7 Hz, 1H).

Example 9. (1R,2S)-2-(3-{[5-Chloro-6-(morpholin-4-yl)pyrimidin-4-yl]amino}-1H-indazol-6-yl)-5'-methoxyspiro[cyclopropane-1,3'-indol]-2'(1'H)-one

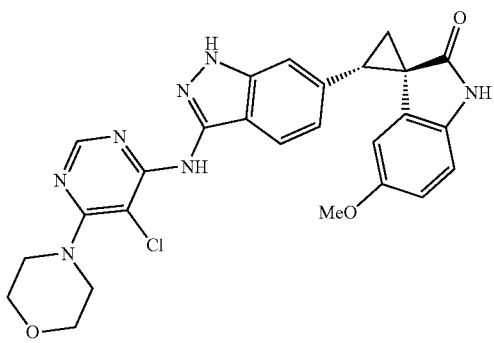 [SMILES: COc1ccc2c(c1)[C@]1(C[C@H]1c1ccc3c(Nc4ncnc(N5CCOCC5)c4Cl)n[nH]c3c1)C(=O)N2]

Step A. 5-Chloro-6-morpholinopyrimidin-4-amine (9A)

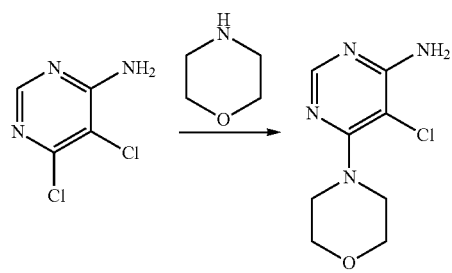

A reaction vial was charged with 4-amino-5,6-dichloropyrimidine (300 mg, 1.83 mmol) and morpholine (145 μL, 1.65 mmol) in DMSO (3.66 mL). The reaction mixture was heated to 60° C. for 16 h. The reaction mixture was partially concentrated and directly purified by column chromatography (40% to 100% EtOAc/heptanes, gradient elution), affording the title compound (9A) (318 mg, 81%) as white crystals. m/z (ESI, +ve ion)=215.0 [M+H]$^+$.

Step B. tert-butyl (1R,2S)-2-(1-(tert-butoxycarbonyl)-3-((5-chloro-6-morpholinopyrimidin-4-yl)amino)-1H-indazol-6-yl)-5'-methoxy-2'-oxospiro[cyclopropane-1,3'-indoline]-1'-carboxylate

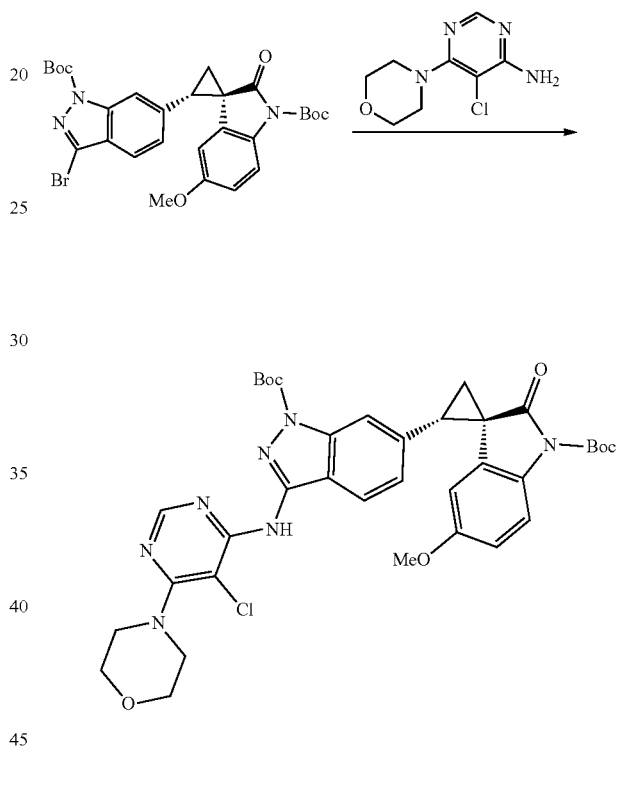

A microwave vial was charged with tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (60.0 mg, 103 μmol), 5-chloro-6-morpholinopyrimidin-4-amine (24.2 mg, 113 μmol), cesium carbonate (68.3 mg, 205 μmol), Pd$_2$(dba)$_3$ (9.4 mg, 10.3 μmol) and XantPhos (6.0 mg, 10.3 μmol) and was purged with nitrogen. Previously degassed toluene (2.0 mL) was added and nitrogen was bubbled through the reaction mixture for 2 min. The vial was sealed and the reaction mixture was heated to 100° C. for 2 h in an oil bath. The reaction mixture was filtered on a pad of celite using EtOAc and concentrated. The crude product was purified by column chromatography (0% to 10% MeOH/DCM, gradient elution), affording the title compound (49.5 mg, 67%). m/z (ESI, +ve ion)=718.0 [M+H]$^+$.

245

Step C

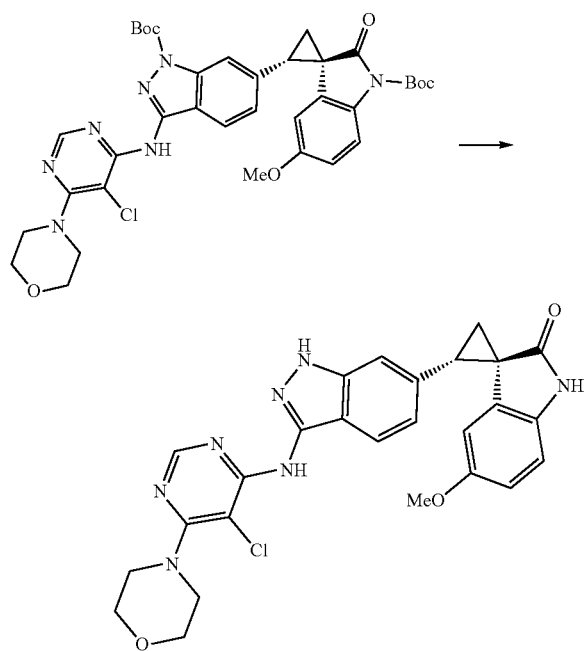

246

In a flask, tert-butyl (1R,2S)-2-(1-(tert-butoxycarbonyl)-3-((5-chloro-6-morpholinopyrimidin-4-yl)amino)-1H-indazol-6-yl)-5'-methoxy-2'-oxospiro[cyclopropane-1,3'-indoline]-1'-carboxylate (49.5 mg, 60.7 μmol) was dissolved in DCM (4.40 mL) and trifluoroacetic acid (440 μL, 5.69 mmol) was added. The reaction was stirred at rt for 5 h and then concentrated to dryness. The crude residue was directly purified by C18 column chromatography (10 to 40% MeCN/aq. ammonium formate buffer, gradient elution). The desired fractions were combined and lyophilized, affording Example 9 (12.3 mg, 39%) as white solid. m/z (ESI, +ve ion)=518.2 [M+H]$^+$. 1 H NMR (400 MHz, DMSO) δ 12.72 (s, 1H), 10.43 (s, 1H), 9.16 (s, 1H), 7.98 (s, 1H), 7.41 (s, 1H), 7.35 (d, J=8.3 Hz, 1H), 6.94-6.83 (m, 1H), 6.74 (d, J=8.4 Hz, 1H), 6.58 (dd, J=8.5, 2.5 Hz, 1H), 5.71 (d, J=2.6 Hz, 1H), 3.74-3.67 (m, 4H), 3.51-3.44 (m, 4H), 3.33 (with water peak) (s, 3H), 3.18 (t, J=8.4 Hz, 1H), 2.33 (dd, J=8.0, 4.8 Hz, 1H), 1.98 (dd, J=9.0, 4.7 Hz, 1H).

Example 10. (1R,2S)-2-{3-[(2-Chloro-5-methoxypyrimidin-4-yl)amino]-1H-indazol-6-yl}-5'-methoxyspiro[cyclopropane-1,3'-indol]-2'(1'H)-one

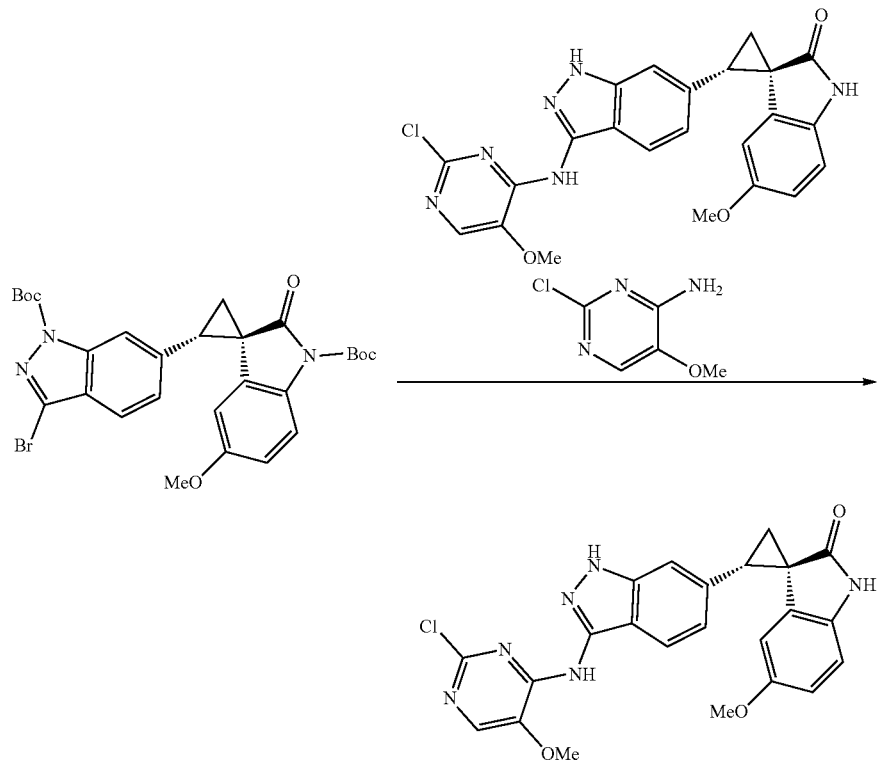

A microwave vial was charged with tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (75.0 mg, 128 µmol), 2-chloro-5-methoxypyrimidin-4-amine (22.6 mg, 137 µmol), cesium carbonate (85.3 mg, 257 µmol). Pd$_2$(dba)$_3$ (11.8 mg, 12.8 µmol) and XantPhos (7.6 mg, 12.8 µmol) and was purged with nitrogen. Previously degassed toluene (2.6 mL) was added, and nitrogen was bubbled through the reaction mixture for 2 min. The vial was sealed, and the reaction mixture was heated to 100° C. for 2 h in an oil bath. The reaction mixture was then filtered on a pad of Celite using EtOAc and the crude product was concentrated. The residue was dissolved in DCM (5.00 mL) and trifluoroacetic acid (1.00 mL, 13.0 mmol) was added. The reaction was stirred at rt for 1.5 h. A saturated aqueous solution of sodium bicarbonate was slowly added, and the reaction mixture was transferred to an extraction funnel. The layers were separated, and the aqueous layer was extracted with DCM (3×10 mL). The organic layer was dried with anhyd. Na$_2$SO$_4$, filtered and concentrated under vacuum. The product was purified by C18 column chromatography (10% to 40% MeCN/aq. ammonium formate buffer, gradient elution). The desired fractions were combined and lyophilized, affording Example 10 (4.8 mg, 8.0%) as white solid. m/z (ESI, +ve ion)=463.2 [M+H]$^+$. 1 H NMR (400 MHz, DMSO) δ 12.80 (s, 1H), 10.43 (s, 1H), 9.61 (br s, 1H), 7.94 (s, 1H), 7.46-7.40 (m, 2H), 6.97-6.91 (m, 1H), 6.74 (d, J=8.4 Hz, 1H), 6.57 (dd, J=8.5, 2.6 Hz, 1H), 5.70 (d, J=2.5 Hz, 1H), 3.94 (s, 3H), 3.30 (s, 3H), 3.19 (t, J=8.3 Hz, 1H), 2.33 (dd, J=7.9, 4.6 Hz, 1H), 1.98 (dd, J=9.1, 4.7 Hz, 1H).

Example 11. (1R,2S)-5'-Methoxy-2-(3-{[5-methoxy-6-(morpholin-4-yl)pyrimidin-4-yl]amino}-1H-indazol-6-yl)spiro[cyclopropane-1,3'-indol]-2'(1'H)-one

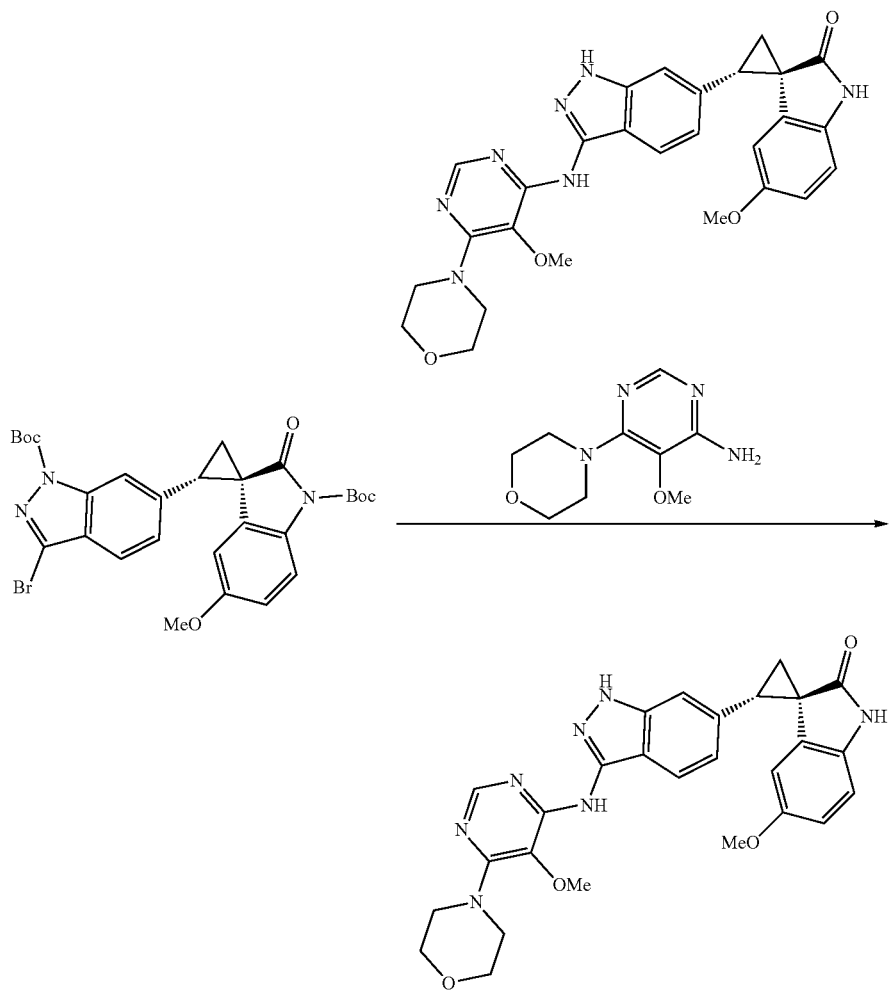

A microwave vial was charged with tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (75.0 mg, 128 µmol), 5-chloro-6-morpholinopyrimidin-4-amine (29.7 mg, 141 µmol), cesium carbonate (85.3 mg, 257 µmol), Pd$_2$(dba)$_3$ (11.8 mg, 12.8 µmol) and XantPhos (7.6 mg, 12.8 µmol) and was purged with nitrogen. Previously degassed toluene (2.57 mL) was added and nitrogen was bubbled through the reaction mixture for 2 min. The vial was sealed and the reaction mixture was heated to 100° C. for 2 h in an oil bath. The reaction mixture was filtered on a pad of Celite using EtOAc and the crude product was concentrated. The residue was then dissolved in DCM (5.00 mL) and trifluoroacetic acid (1.00 mL, 13.0 mmol) was added. The reaction was stirred at rt for 1.5 h. A saturated aqueous solution of sodium bicarbonate was slowly added and the reaction mixture was transferred to an extraction funnel. The layers were separated and the aqueous layer was extracted with DCM (3×10 mL). The combined extracts were dried with anhyd. Na$_2$SO$_4$, filtered and concentrated under vacuum. The crude was purified by C18 column chromatography (10% to 40% MeCN/aq. ammonium formate buffer, gradient elution). The desired fractions were combined and lyophilized, affording Example 11 (23.2 mg, 35%) as white solid. m/z (ESI, +ve ion)=514.3 [M+H]+. 1H NMR (400 MHz, DMSO) δ 12.58 (s, 1H), 10.42 (s, 1H), 8.88 (s, 1H), 7.80 (s, 1H), 7.47-7.32 (m, 2H), 6.87 (d, J=8.4 Hz, 1H), 6.74 (d, J=8.4 Hz, 1H), 6.58 (dd, J=8.4, 2.3 Hz, 1H), 5.72 (d, J=2.2 Hz, 1H), 379-3.68 (m, 4H), 3.67 (s, 3H), 3.62-3.53 (m, 4H), 3.33 (s, 3H), 3.18 (t, J=8.4 Hz, 1H), 2.32 (dd, J=7.7, 4.7 Hz, 1H), 1.98 (dd, J=8.9, 4.6 Hz, 1H).

Example 12. (1R,2S)-5'-Methoxy-2-(3-{[5-methoxy-6-(piperidin-1-yl)pyrimidin-4-yl]amino}-1H-indazol-6-yl)spiro[cyclopropane-1,3'-indol]-2'(1'H)-one

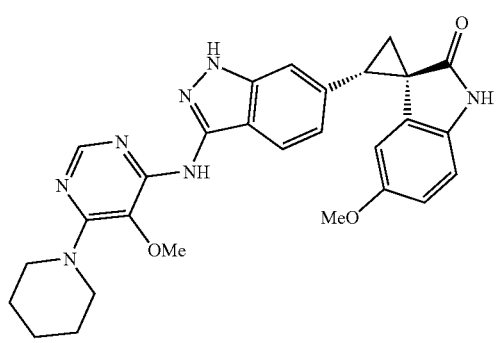 [SMILES: COc1ccc2c(c1)[C@]1(C[C@H]1c1ccc3c(Nc4ncnc(N5CCCCC5)c4OC)n[nH]c3c1)C(=O)N2]

Step A. 5-Methoxy-6-(piperidin-1-yl)pyrimidin-4-amine (12A)

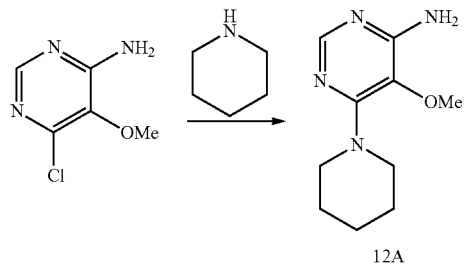

A reaction vial was charged with 4-amino-6-chloro-5-methoxypyrimidine (100 mg, 595 µmol) and piperidine (120 µL, 1.19 mmol) in toluene (1.2 mL). The reaction mixture was heated to 105° C. for 16 h. The solution was then concentrated to dryness. The product was purified by column chromatography (50% to 100% EtOAc/heptanes, gradient elution), affording the title compound (87.8 mg, 71%) as white crystals. m/z (ESI, +ve ion)=209.0 [M+H]$^+$.

Step B. (1R,2S)-5'-methoxy-2-(3-((5-methoxy-6-(piperidin-1-yl)pyrimidin-4-yl)amino)-1H-indazol-6-yl)spiro[cyclopropane-1,3'-indolin]-2'-one

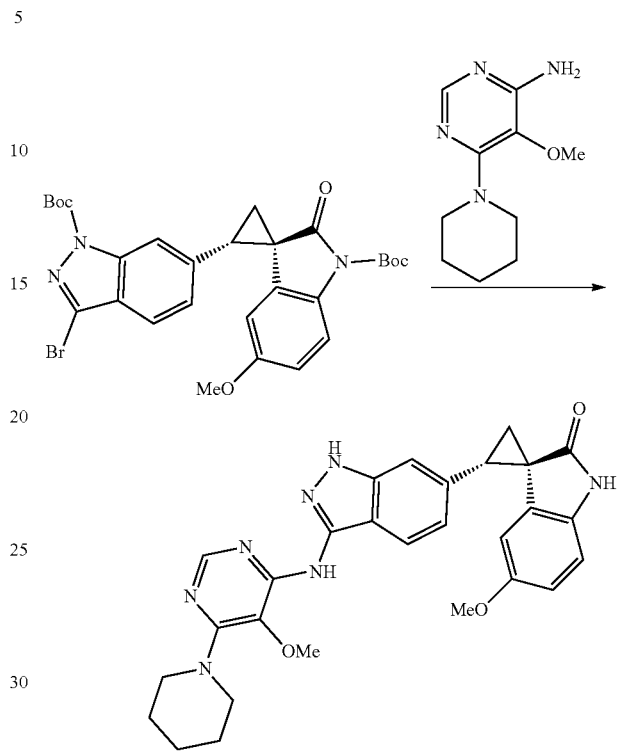

A microwave vial was charged with tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (75.0 mg, 128 µmol), 5-methoxy-6-(piperidin-1-yl)pyrimidin-4-amine (29.4 mg, 141 µmol), cesium carbonate (85.3 mg, 257 µmol), Pd$_2$(dba)$_3$ (11.8 mg, 12.8 µmol) and XantPhos (7.6 mg, 12.8 µmol) and was purged with nitrogen. Previously degassed toluene (2.57 mL) was added and nitrogen was bubbled through the reaction mixture for 2 min. The vial was sealed and the reaction mixture was heated to 100° C. for 2 h in an oil bath. The reaction mixture was filtered on a pad of Celite using EtOAc and the crude product was concentrated. The residue was dissolved in DCM (5.00 mL) and trifluoroacetic acid (1.00 mL, 13.0 mmol) was added. The reaction was stirred at rt for 1.5 h. A satd. aq. solution of bicarbonate was added and the reaction mixture was transferred to an extraction funnel. The layers were separated, and the aqueous layer was extracted with DCM (3×10 mL). The combined organic extracts were dried with anhyd. Na$_2$SO$_4$, filtered and concentrated under vacuum. The product was purified by C18 column chromatography (20 to 40% MeCN in aq. ammonium formate buffer). The desired fractions were combined and lyophilized, affording the title compound (23.2 mg, 35%) as white solid. m/z (ESI, +ve ion)=512.3 [M+H]+. 1H NMR (400 MHz, DMSO) δ 12.53 (s, 1H), 10.41 (s, 1H), 8.76 (1Hs), 7.76 (s, 1H), 7.42 (d, J=8.4 Hz, 1H), 7.37 (s, 1H), 6.87 (d, J=8.4 Hz, 1H), 6.74 (d, J=8.4 Hz, 1H), 6.58 (dd, J=8.4, 2.4 Hz, 11H), 5.72 (d, J=2.3 Hz, 1H), 3.65 (s, 3H), 3.62-3.53 (m, 4H), 3.33 (s, 3H under water peak), 3.17 (t, J=8.5 Hz, 1H), 2.31 (dd, J=7.8, 4.7 Hz, 1H), 1.97 (dd, J=8.9, 4.6 Hz, 1H), 1.67-1.54 (m, 6H).

Example 13. (1R,2S)-5'-methoxy-2-{3-[(3-methoxy-pyrazin-2-yl)amino]-1H-indazol-6-yl}spiro[cyclopropane-1,3'-indol]-2'(1'H)-one

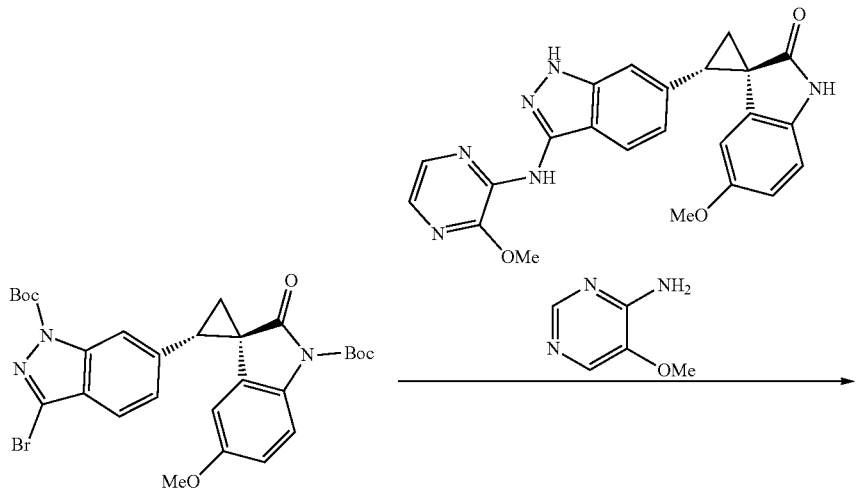

This compound was prepared using the procedure described in Example 5, from tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (50.0 mg, 85.5 μmol) and 3-methoxypyrazine-2-amine (18.6 mg, 145 μmol). The product was purified by C18 column chromatography (0 to 50% MeCN in water), affording the title compound (13) (9.3 mg, 20%) as yellow solid after lyophilization. m/z (ESI, +ve ion)=429.4 [M+H]+. 1H NMR (500 MHz, DMSO) δ 12.56 (s, 1H), 10.40 (s, 1H), 8.80 (s, 1H), 7.48 (d, J=3.0 Hz, 1H), 7.46 (d, J=3.0 Hz, 1H), 7.42-7.37 (m, 2H), 6.87 (d, J=8.4 Hz, 1H), 6.74 (d, J=8.4 Hz, 1H), 6.58 (dd, J=8.4, 2.6 Hz, 1H), 5.72 (d, J=2.5 Hz, 1H), 3.98 (s, 3H), 3.33 (s, J=0.9 Hz, 3H), 3.17 (t, J=8.5 Hz, 1H), 2.31 (dd, J=7.9, 4.7 Hz, 1H), 1.98 (dd, J=9.0, 4.7 Hz, 1H).

Example 14. (1R,2S)-5'-methoxy-2-{3-[(6-methoxy-pyrimidin-4-yl)amino]-1H-indazol-6-yl}spiro[cyclopropane-1,3'-indol]-2'(1'H)-one

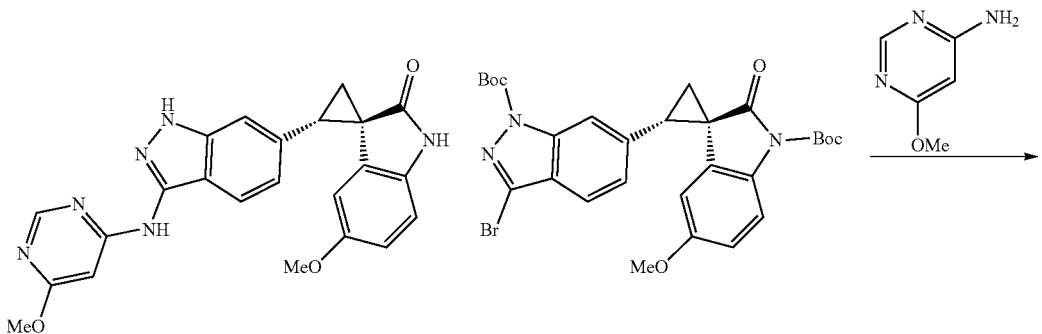

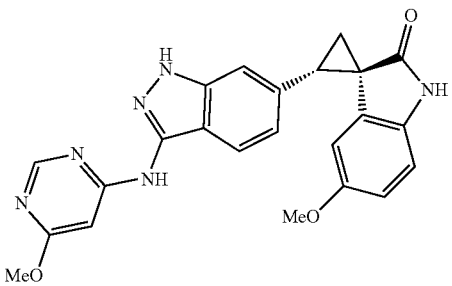

This compound was prepared according to the procedure described in Example 5, from tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (50.0 mg, 85.5 μmol) and 6-methoxypyrimidine-4-amine (16.4 mg, 128 μmol). The product was purified by C18 column chromatography (0 to 50% MeCN in aq. ammonium formate buffer), affording the title compound (19.6 mg, 43%) as white solid after lyophilization. m/z (EST, +ve ion)=429.3 [M+H]+. 1H NMR (500 MHz, DMSO) δ 12.43 (s, 1H), 10.41 (s, 1H), 10.17 (s, 1H), 8.38 (d, J=0.9 Hz, 1H), 7.93 (d, J=8.4 Hz, 1H), 7.35 (s, 1H), 7.20 (s, 1H), 6.91 (dd, J=8.5, 1.0 Hz, 1H), 6.74 (d, J=8.4 Hz, 1H), 6.58 (dd, J=8.5, 2.6 Hz, 1H), 5.68 (d, J=2.6 Hz, 1H), 3.87 (s, 3H), 3.31 (s, 3H), 3.17 (t, J=8.4 Hz, 1H), 2.32 (dd, J=7.9, 4.7 Hz, 1H), 1.97 (dd, J=9.0, 4.7 Hz, 1H).

Example 15. (1R,2S)-2-{3-[(6,7-dihydro-5H-cyclopenta[d]pyrimidin-4-yl)amino]-1H-indazol-6-yl}-5'-methoxyspiro[cyclopropane-1,3'-indol]-2'(1'H)-one

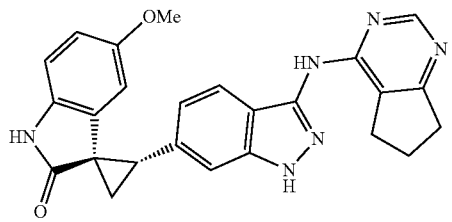 [SMILES: COc1ccc2c(c1)[C@]1(C[C@H]1c1ccc3c(Nc4ncnc5c4CCC5)n[nH]c3c1)C(=O)N2]

Step A. tert-butyl (1R,2S)-2-[1-(tert-butoxycarbonyl)-3-[5H,6H,7H-cyclopenta[d]pyrimidin-4-ylamino]indazol-6-yl]-5'-methoxy-2'-oxospiro[cyclopropane-1,3'-indole]-1'-carboxylate

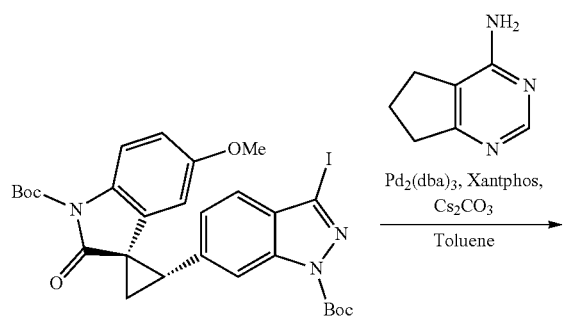

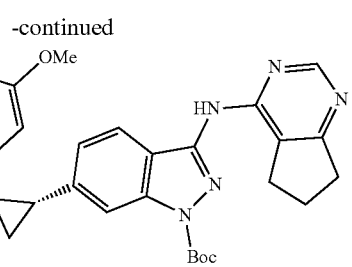

To a mixture of tert-butyl (R,2S)-2-[1-(tert-butoxycarbonyl)-3-iodoindazol-6-yl]-5'-methoxy-2'-oxospiro[cyclopropane-1,3'-indole]-1'-carboxylate (240.00 mg, 0.380 mmol, 1.00 equiv) and 5H,6H,7H-cyclopenta[d]pyrimidin-4-amine (61.65 mg, 0.456 mmol, 1.2 equiv) in dry toluene (20.00 mL) were added Cs₂CO₃ (247.67 mg, 0.760 mmol, 2.00 equiv). Pd₂(dba)₃ (34.80 mg, 0.038 mmol, 0.10 equiv) and XantPhos (21.99 mg, 0.038 mmol, 0.10 equiv) under argon atmosphere. The mixture was stirred at 90° C. for 2 h. The solvent was filtered and washed with EtOAc (10 mL). The filtrate was concentrated under reduced pressure and the residue was purified by silica gel column chromatography, eluted with 0-50% EtOAc in PE to give the title compound (80 mg, 31.31%) as light yellow oil. m/z (ESI, +ve ion)=639.35 [M+H]+. ¹H NMR (400 MHz, Chloroform-d) δ 8.57 (s, 1H), 8.12 (s, 1H), 7.89 (d, J=8.4 Hz, 1H), 7.82 (d, J=8.8 Hz, 1H), 7.12 (d, J=8.4 Hz, 1H), 6.72-6.69 (m, 1H), 5.62 (d, J=2.8 Hz, 1H), 4.17-4.12 (m, 1H), 3.53 (t, J=8.4 Hz, 1H), 3.42 (s, 3H), 3.12 (t, J=8.0 Hz, 2H), 2.94 (t, =7.6 Hz, 2H), 2.41-2.37 (m, 1H), 2.28-2.21 (m, 2H), 2.13-2.10 (m, 1H), 1.70 (s, 18H).

Step B. (1R,2S)-2-(3-[5H,6H,7H-cyclopenta[d]pyrimidin-4-ylamino]-1H-indazol-6-yl)-5'-methoxy-1'H-spiro[cyclopropane-1,3'-indol]-2'-one

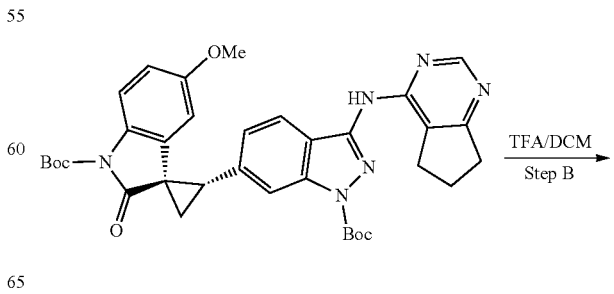

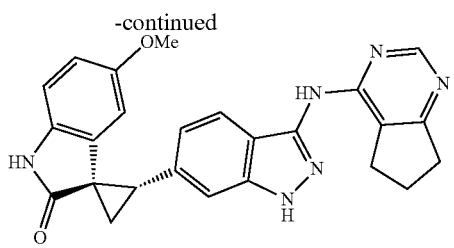

To a mixture of the compound from Step A (60.00 mg, 0.094 mmol, 1.00 equiv) in DCM (1.00 mL) was added TFA (0.20 mL). The mixture was stirred at 25° C. for 12 h, then diluted with DCM (20 mL) and washed with saturated NaHCO$_3$ (20 mL). The aqueous layer was extracted with DCM (2×10 mL). The combined organic layers were washed with brine (20 mL), dried over anhydrous Na$_2$SO$_4$, filtered and concentrated in vacuum. The residue (two batches combined, total 0.125 mmol) was purified by prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 13% B to 40% B in 8 min; 254/220 nm; RT1: 7.35 min to give Example 15 (30 mg, 72.10%) as a white solid. m/z (ESI+ve ion)=439.20 [M+H]$^+$. $^1$H NMR (400 MHz, DMSO-d$_6$) δ 12.65 (s, 1H), 10.42 (s, 1H), 9.22 (s, 1H), 8.24 (s, 1H), 7.43-7.41 (m, 2H), 6.92-6.89 (m, 1H), 6.75 (d, J=8.4 Hz, 1H), 6.60-6.58 (m, 1H), 5.72 (d, J=2.4 Hz, 1H), 3.35 (s, 3H), 3.19 (t, J=8.4 Hz, 1H), 2.80 (t, J=7.6 Hz, 2H), 2.73-2.68 (m, 2H), 2.35-2.32 (m, 1H), 2.04-1.96 (m, 3H).

Example 16. (1R,2S)-2-{3-[(2,3-dihydro-1-benzofuran-7-yl)amino]-1H-indazol-6-yl}-5'-methoxyspiro[cyclopropane-1,3'-indol]-2' 1'H one

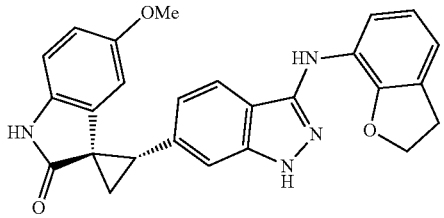 [SMILES: COc1ccc2c(c1)[C@]1(C[C@H]1c1ccc3c(Nc4cccc5c4OCC5)n[nH]c3c1)C(=O)N2]

Step A. tert-butyl (1R,2S)-2-[1-(tert-butoxycarbonyl)-3-(2,3-dihydro-1-benzofuran-7-ylamino)indazol-6-yl]-5'-methoxy-2'-oxospiro[cyclopropane-1,3'-indole]-1'-carboxylate

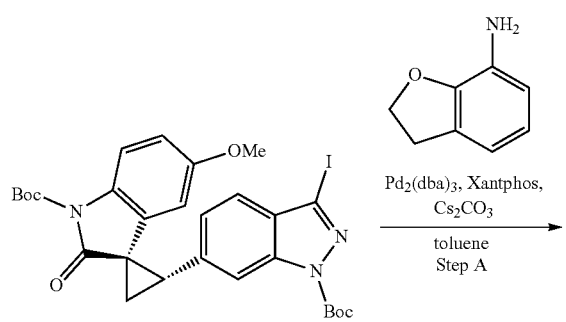

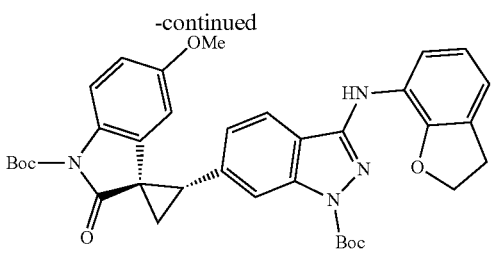

To a mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (200.00 mg, 0.317 mmol, 1.00 equiv) and 2,3-dihydro-1-benzofuran-7-amine (51.37 mg, 0.380 mmol, 1.20 equiv) in dry toluene (5.0 mL) were added Cs$_2$CO$_3$ (206.39 mg, 0.634 mmol, 2.00 equiv), Pd$_2$(dba)$_3$ (29.00 mg, 0.032 mmol, 0.10 equiv) and XantPhos (18.33 mg, 0.032 mmol, 0.10 equiv) under argon atmosphere. The mixture was stirred at 90° C. for 2 h. The solvent was removed under reduced pressure. The residue was purified by prep-TLC (rinsed with PE/EA=2/1) to give the title compound (200 mg, 97.88%) as yellow oil. m/z (ESI+ve ion)=639.20 [M+H]$^+$. $^1$H NMR (400 MHz, Chloroform-d) δ 8.16 (d, J=8.0 Hz, 1H), 7.82-7.80 (m, 1H), 7.56-7.52 (m, 1H), 7.06 (d, J=8.4 Hz, 1H), 6.96-6.88 (m, 2H), 6.70-6.66 (m, 2H), 5.57 (d, J=2.8 Hz, 1H), 4.69-4.65 (m, 2H), 3.56-3.50 (m, 1H), 3.38 (s, 3H), 3.31 (t, J=8.4 Hz, 2H), 2.39-2.36 (m, 1H), 2.14-2.10 (m, 1H), 1.71 (d, J=5.6 Hz, 18H).

Step B. (1R,2S)-2-[3-(2,3-dihydro-1-benzofuran-7-ylamino)-1H-indazol-6-yl]-5'-methoxy-1'H-spiro[cyclopropane-1,3'-indol]-2'-one

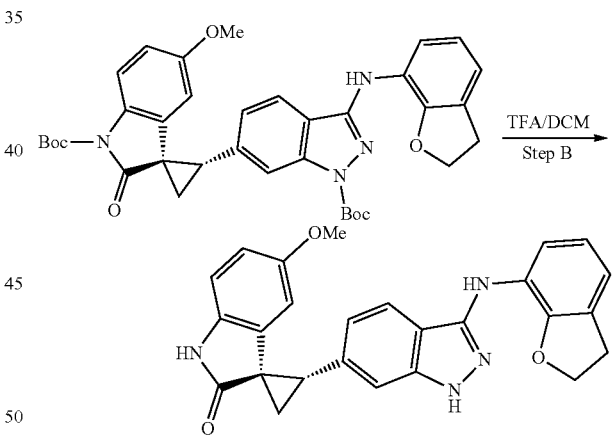

To the mixture of the compound from Step A (215 mg, 0.336 mmol) in DCM (5 mL) was added TFA (0.5 mL). The mixture was stirred at 25° C. for 12 h, then diluted with DCM (20 mL) and washed with saturated NaHCO$_3$ (20 mL) and brine (20 mL), dried over anhydrous Na$_2$SO$_4$, filtered and concentrated in vacuum. The residue was purified by prep-HPLC with the following conditions: Column: XBridge Shield RP18 OBD Column, 19×250 mm, 10 μm; Mobile Phase A: Water (10 mmol/L NH$_4$HCO$_3$+0.1% NH$_3$·H$_2$O). Mobile Phase B: ACN; Flow rate: 60 mL/min; Gradient: 42% B to 52% B in 8 min; 254 nm; RT1: 7.15 min to give Example 2 (80 mg, 54%) as a white solid. m/z (ESI+ve ion)=439.15 [M+H]$^+$. $^1$H NMR (400 MHz, DMSO-d$_6$) δ 11.95 (s, 1H), 10.41 (s, 1H), 7.89 (d, J=8.8 Hz, 2H), 7.82 (t, J=4.4 Hz, 1H), 7.28 (s, 1H), 6.86-6.83 (m, 1H), 6.76-6.74 (m, 3H), 6.60-6.57 (m, 1H), 5.71 (d, J=2.4 Hz, 1H), 4.60 (t, J=8.8 Hz, 2H), 3.33 (s, 3H), 3.33-3.15 (m, 3H), 2.33-2.30 (m, 1H), 1.99-1.97 (m, 1H).

Example 17. (1R,2S)-5'-methoxy-2-{3-[(3-methoxy-pyridin-2-yl)amino]-1H-indazol-6-yl}spiro[cyclo-propane-1,3'-indol]-2'(1'H)-one

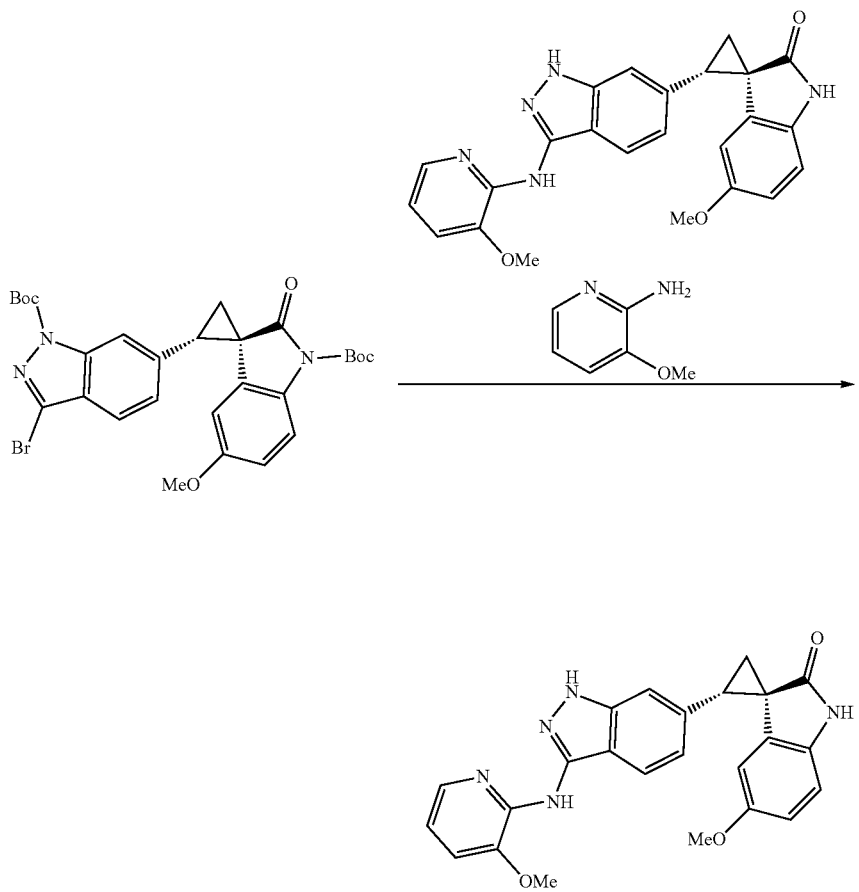

This compound was prepared using the procedure described in Example 5, from tert-butyl 3-bromo-6-((1R,2S)-1'-(tert-butoxycarbonyl)-5'-methoxy-2'-oxospiro[cyclo-propane-1,3'-indolin]-2-yl)-1H-indazole-1-carboxylate (75.0 mg, 128 µmol) and 3-methoxypyridin-2-amine (17.9 mg, 141 µmol). The product was purified by C18 column chromatography (10 to 30% MeCN in aq. ammonium formate buffer), affording the title compound (16.1 mg, 29%) as white solid after lyophilization. m/z (ESI, +ve ion)=428.3 [M+H]+. 1H NMR (400 MHz, DMSO) δ 12.42 (s, 1H), 10.42 (s, 1H), 8.16 (s, 1H), 7.51 (dd, J=5.0, 1.3 Hz, 1H), 7.44 (d, J=8.4 Hz, 1H), 7.35 (s, 1H), 7.19 (dd, J=7.9, 1.3 Hz, 1H), 6.85 (d, J=8.7 Hz, 1H), 6.76-6.66 (m, 2H), 6.58 (dd, J=8.5, 2.6 Hz, 1H), 5.74 (d, J=2.6 Hz, 1H), 3.87 (s, 3H), 3.30 (s, 3H, peak under water), 3.17 (t, J=8.4 Hz, 1H), 2.35-2.29 (m, 1H), 1.97 (dd, J=9.0, 4.6 Hz, 1H).

Example 18. (1R,2S)-5'-methoxy-2-{3-[(4-methoxy-pyridin-3-yl)amino]-1H-indazol-6-yl}spiro[cyclo-propane-1,3'-indol]-2'(1'H)-one

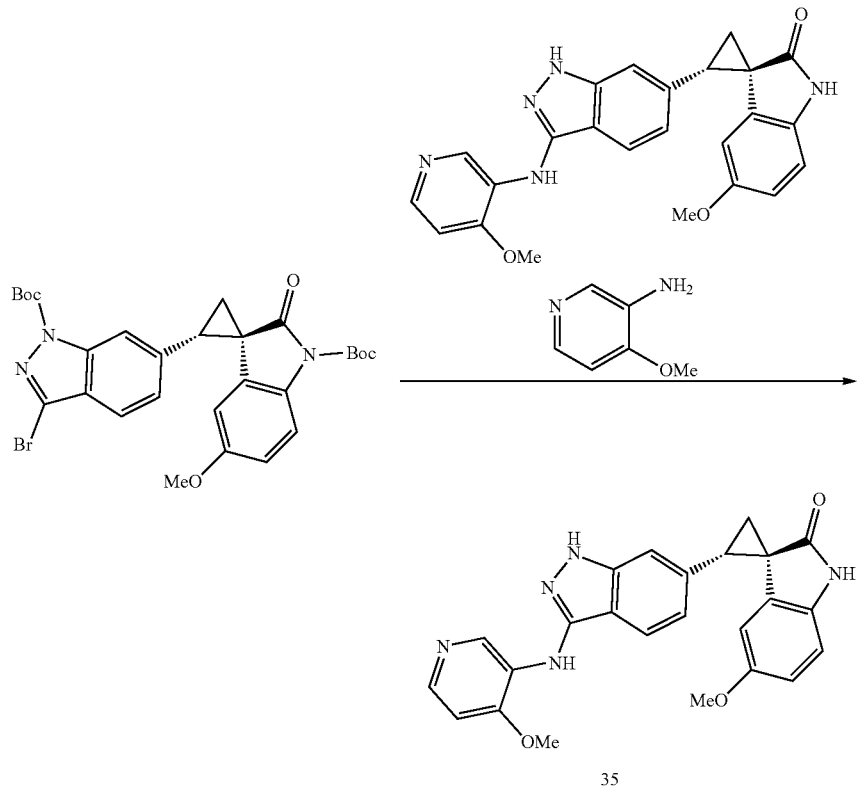

This compound was prepared using the procedure described in Example 5, from tert-butyl 3-bromo-6-((1R, 2S)-1'-(tert-butoxycarbonyl)-5'-methoxy-2'-oxospiro[cyclo-propane-1,3'-indolin]-2-yl)-1H-indazole-1-carboxylate (75.0 mg, 128 μmol) and 4-methoxypyridin-3-amine (18.4 mg, 141 μmol). The product was purified by C18 column chromatography (10 to 40% MeCN in aq. ammonium formate buffer), affording the title compound (9.5 mg, 17%) as white solid after lyophilization. m/z (ESI, +ve ion)=428.2 [M+H]+. 1H NMR (400 MHz, DMSO) δ 12.13 (s, 1H), 10.43 (s, 1H), 9.18 (s, 1H), 8.02 (d, J=5.3 Hz, 1H), 7.90-7.81 (m, 2H), 7.31 (s, 1H), 7.03 (d, J=5.4 Hz, 1H), 6.87 (d, J=8.4 Hz, 1H), 6.74 (d, J=8.4 Hz, 1H), 6.58 (dd, J=8.4, 2.5 Hz, 1H), 5.70 (d, J=2.4 Hz, 1H), 3.94 (s, 3H), 3.32 (s, 3H), 3.17 (t, J=8.5 Hz, 1H), 2.32 (dd, J=7.8, 4.8 Hz, 1H), 1.97 (dd, J=9.0, 4.7 Hz, 1H).

Example 19. (1R,2S)-5'-methoxy-2-{3-[(3-methoxy-pyridin-4-yl)amino]-1H-indazol-6-yl}spiro[cyclo-propane-1,3'-indol]-2'(1'H)-one

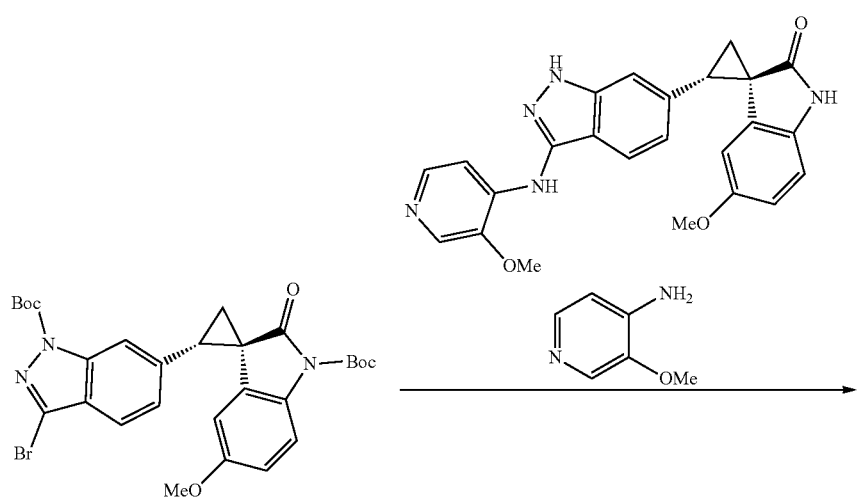

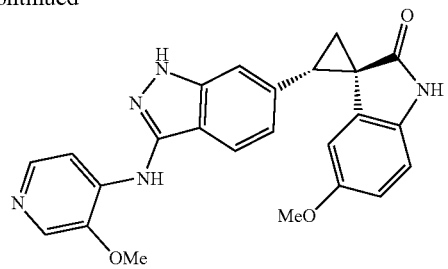

This compound was prepared according to the procedure described in Example 5, from tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (50.0 mg, 85.5 μmol) and 3-methoxypyridin-4-amine (16.1 mg, 126 μmol). The product was purified by C18 column chromatography (0 to 30/o MeCN in water), affording the title compound (6.5 mg, 14%) as white solid after lyophilization. m/z (ESI, +ve ion)=428.3 [M+H]+. 1H NMR (500 MHz, DMSO) δ 12.95 (s, 1H), 10.43 (s, 1H), 9.97 (s, 1H), 8.28 (s, 1H), 8.20 (d, J=6.6 Hz, 1H), 7.82 (d, J=6.6 Hz, 1H), 7.77 (d, J=8.4 Hz, 1H), 7.48 (s, 1H), 7.00 (d, J=8.5 Hz, 1H), 6.75 (d, J=8.4 Hz, 1H), 6.59 (dd, J=8.5, 2.6 Hz, 1H), 5.70 (d, J=2.6 Hz, 1H), 4.07 (s, 3H), 3.20 (t, J=8.4 Hz, 1H), 2.35 (dd, J=8.0, 4.9 Hz, 1H), 2.00 (dd, J=9.1, 4.7 Hz, 1H).

Example 20. (1R,2S)-2-(3-{[5-chloro-6-(4-methylpiperazin-1-yl)pyrimidin-4-yl]amino}-1H-indazol-6-yl)-5'-methoxyspiro[cyclopropane-1,3'-indol]-2'(1'H)-one 1-Methylpiperazine (200 μL, 1.77 mmol) was added to a mixture of 4,5,6-trichloropyrimidine (336 mg, 1.77 mmol) and N,N-diisopropylethylamine (930 μL, 5.32 mmol) in NMP (7.0 mL). The reaction was stirred at 80° C. for 15 h. EtOAc and water were added and the reaction mixture was transferred to an extraction funnel. The layers were separated and the aqueous layer was extracted with EtOAc. The combined organic layers were then washed with brine, dried with anh. Na₂SO₄, filtered and concentrated under vacuum. The product was purified by column chromatography (0 to 5% MeOH in DCM), affording the title compound (312 mg, 71%) as red oil. m/z (ESI, +ve ion)=247.0 [M+H]+.

Step B. (1R,2S)-2-(3-((5-chloro-6-(4-methylpiperazin-1-yl)pyrimidin-4-yl)amino)-1H-indazol-6-yl)-5'-methoxyspiro[cyclopropane-1,3'-indolin]-2'-one

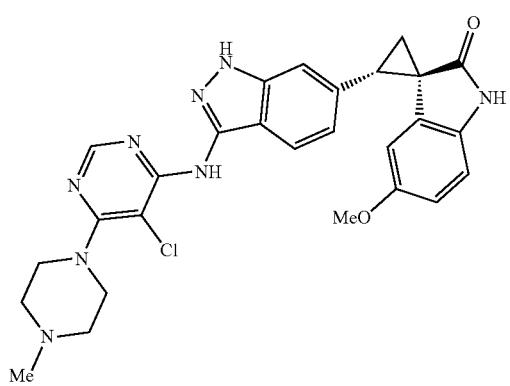 [SMILES: COc1ccc2c(c1)[C@]1(C[C@H]1c1ccc3c(Nc4ncnc(N5CCN(C)CC5)c4Cl)n[nH]c3c1)C(=O)N2]

Step A.
4,5-dichloro-6-(4-methylpiperazin-1-yl)pyrimidine

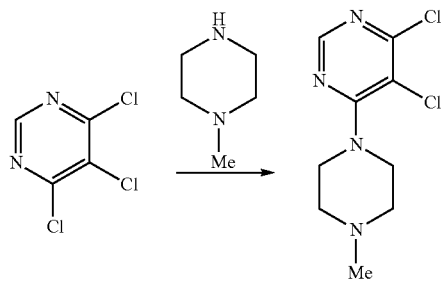

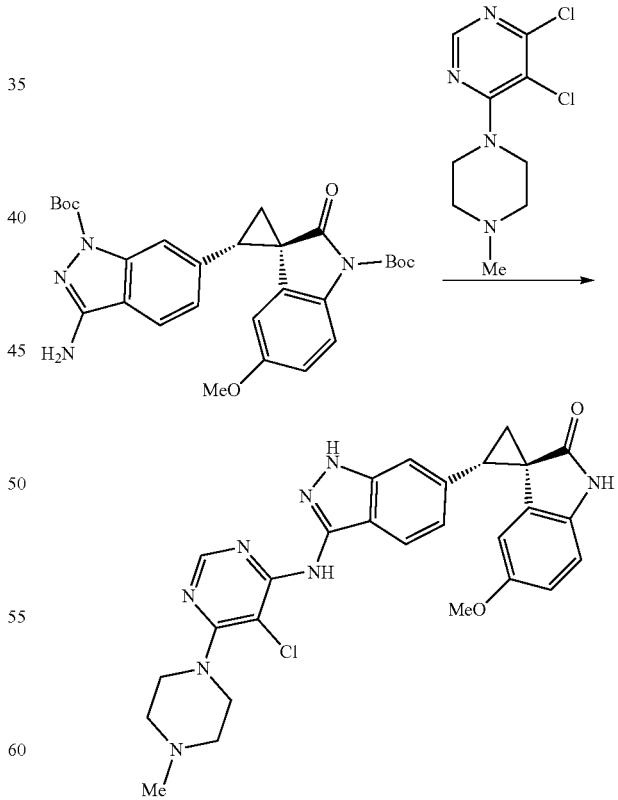

A microwave vial was charged with tert-butyl (1R,2S)-2-(3-amino-1-4tert-butoxycarbonyl)-1H-indazol-6-yl)-5'-methoxy-2'-oxospiro[cyclopropane-1,3'-indoline]-1'-carboxylate (75.0 mg, 144 μmol), 4,5-dichloro-6-(4- methylpiperazin-1-yl)pyrimidine (39.2 mg, 158 µmol), cesium carbonate (95.8 mg, 288 µmol), Pd$_2$(dba)$_3$ (13.2 mg, 14.4 µmol) and XantPhos (8.5 mg, 14.4 µmol) and was purged with nitrogen. Previously degassed toluene (3.0 mL) was added and nitrogen was bubbled through the reaction mixture for 2 min. The vial was sealed and the reaction mixture was heated to 100° C. for 1.5 h in an oil bath. The reaction mixture was filtered on a pad of Celite using EtOAc and the crude product was concentrated. The residue was dissolved in DCM (5.00 mL) and trifluoroacetic acid (1.00 mL, 13.0 mmol) was added. The reaction was stirred at rt for 1.5 h. A satd. aqueous solution of sodium bicarbonate was added and the reaction mixture was transferred to an extraction funnel. The layers were separated and the aqueous layer was extracted with DCM (3×10 mL). The combined extracts were dried with anhyd. Na$_2$SO$_4$, filtered and concentrated under vacuum. The product was purified by C18 column chromatography (5 to 30% MeCN in aq. ammonium formate buffer). The desired fraction were combined and lyophilized, affording the title compound (37.1 mg, 55%) as yellow solid identified as a formate salt. m/z (ESI, +ve ion)=531.3 [M+H]+. 1H NMR (400 MHz, DMSO) δ 12.71 (s, 1H), 10.43 (s, 1H), 9.11 (s, 1H), 7.95 (s, 1H), 7.41 (s, 1H), 7.35 (d, J=8.4 Hz, 1H), 6.89 (d, J=8.4 Hz, 1H), 6.74 (d, J=8.4 Hz, 1H), 6.58 (dd, J=8.4, 2.2 Hz, 1H), 5.71 (d, J=2.0 Hz, 1H), 3.54-3.45 (m, 4H), 3.33 (s, 3H under water), 3.18 (t, J=8.4 Hz, 1H), 2.47-2.39 (m, 4H), 2.33 (dd, J=7.5, 4.9 Hz, 1H), 2.22 (s, 3H), 1.98 (dd, J=8.9, 4.6 Hz, 1H).

Example 21. (1R,2S)-5'-methoxy-2-{3-[(1,3,5-trimethyl-1H-pyrazol-4-yl)amino]-1H-indazol-6-yl}spiro[cyclopropane-1,3'-indol]-2'(1'H)-one

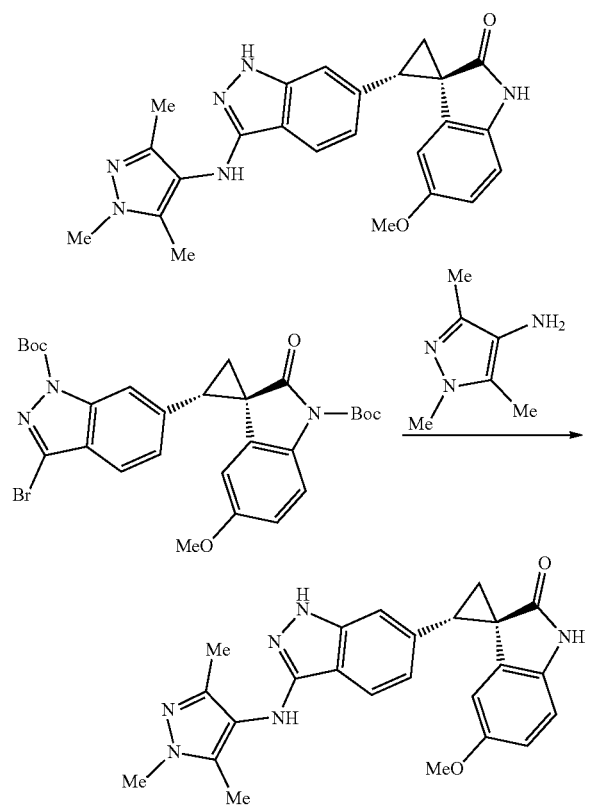

This compound was prepared according to the procedure described in Example 5, from tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (50.0 mg, 85.5 µmol) and 1,3,5-trimethyl-1H-pyrazol-4-amine (7.3 mg, 58.2 µmol). The product was purified by C18 column chromatography (0 to 30% MeCN in aq. ammonium formate buffer), affording the title compound (8.2 mg, 33%) as white solid after lyophilization. m/z (ESI, +ve ion)=429.1 [M+H]+. 1H NMR (400 MHz, DMSO) δ 11.35 (s, 1H), 10.39 (s, 1H), 7.41 (d, J=8.1 Hz, 1H), 7.22 (s, 1H), 7.14 (s, 1H), 6.75 (s, 1H), 6.73 (s, 1H), 6.58 (dd, J=8.5, 2.6 Hz, 1H), 5.67 (d, J=2.6 Hz, 1H), 3.64 (s, 3H), 3.12 (t, J=8.5 Hz, 1H), 2.25 (dd, J=7.9,4.6 Hz, 1H), 2.06 (d, J=5.9 Hz, 3H), 1.98-1.89 (m, 4H).

Example 22. (1R,2S)-5'-methoxy-2-(3-{[5-(trifluoromethyl)pyrimidin-4-yl]amino}-1H-indazol-6-yl)spiro[cyclopropane-1,3'-indol]-2'(1'H)-one

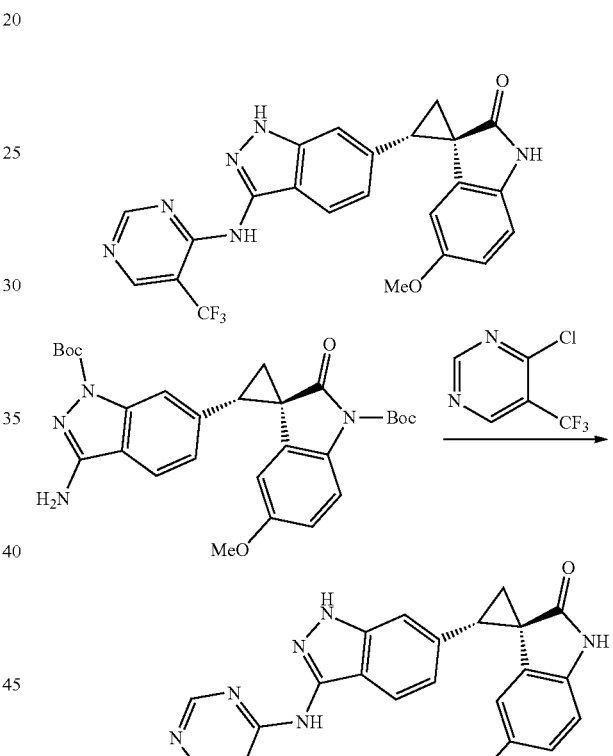

This compound was prepared according to the procedure described in Example 1, from tert-butyl 3-amino-6-((1R,2S)-1'-(tert-butoxycarbonyl)-5'-methoxy-2'-oxospiro[cyclopropane-1,3'-indolin]-2-yl)-1H-indazole-1-carboxylate (30.9 mg, 59.4 µmol) and 4-chloro-5-(trifluoromethyl)pyrimidine (11.9 mg, 65.3 µmol). The product was purified by C18 column chromatography (15 to 40% MeCN in aq. ammonium formate buffer), affording the title compound (6.9 mg, 25%) as yellow solid after lyophilization. m/z (ESI, +ve ion)=467.1 [M+H]+. 1H NMR (500 MHz, DMSO) δ 12.89 (s, 1H), 10.42 (s, 1H), 8.68 (s, 1H), 8.54 (s, 1H), 7.46 (s, 1H), 7.32 (d, J=8.4 Hz, 1H), 6.92 (dd, J=8.4, 1.0 Hz, 1H), 6.74 (d, J=8.4 Hz, 1H), 6.58 (dd, J=8.5, 2.6 Hz, 1H), 5.69 (d, J=2.6 Hz, 1H), 3.19 (t, J=8.4 Hz, 1H), 2.33 (dd, J=8.0, 4.7 Hz, 1H), 1.99 (dd, J=9.0, 4.7 Hz, 1H). CH3O signal is in water peak.

Example 23. (1R,2S)-2-{3-[(5-chloro-2-methoxypyrimidin-4-yl)amino]-1H-indazol-6-yl}-5'-methoxyspiro[cyclopropane-1,3'-indol]-2'(1'H)-one

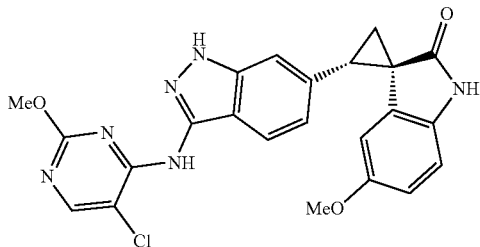 [SMILES: COc1ccc2c(c1)[C@]1(C[C@H]1c1ccc3c(Nc4nc(OC)ncc4Cl)n[nH]c3c1)C(=O)N2]

Step A. 5-chloro-2-methoxypyrimidin-4-amine

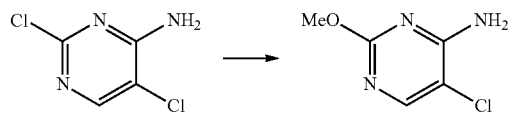 [SMILES: Nc1nc(Cl)ncc1Cl ; COc1ncc(Cl)c(N)n1]

In a flask was dissolved 2,5-dichloropyrimidin-4-amine (300 mg, 1.74 mmol) in MeOH (8.7 mL) to which was added a sodium methoxide solution (30 wt. % in MeOH, 150 μL, 2.09 mmol) and the solution was heated at 70° C. for 2 h (reflux) and cooled back to rt. Some conversion was observed by LCMS but reaction was not complete. Another 0.5 equiv of sodium methoxide solution (60 μL, 869 μmol) was added and the reaction was stirred further at reflux for another 2 h, when it was then quenched with water and extracted with EtOAc. The organic layer was washed with water, dried (Na₂SO₄) and concentrated. Crude white solid material (6a) was used such as in next step. m/z (ESI, +ve ion)=159.7 [M+H]+. 1H NMR (500 MHz, DMSO) δ 8.19 (s, 1H), 8.13-7.38 (m, 2H), 3.86 (s, 3H).

Step B. (1R,2S)-2-(3-((5-chloro-2-methoxypyrimidin-4-yl)amino)-1H-indazol-6-yl)-5'-methoxyspiro[cyclopropane-1,3'-indolin]-2'-one

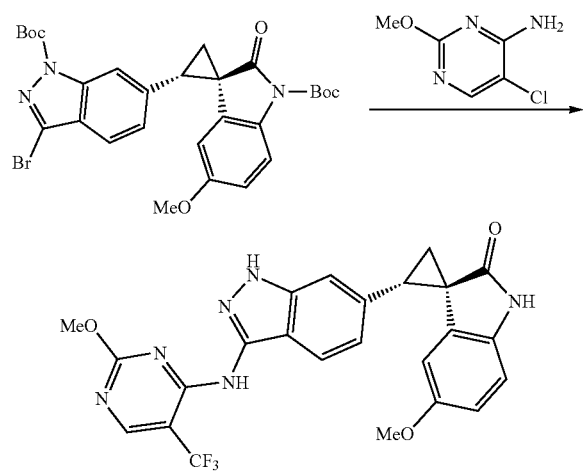

In a vial were added tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (50.0 mg, 85.5 μmol), cesium carbonate (70.4 mg, 216 μmol), Pd₂(dba)₃ (9.8 mg, 10.7 μmol), XantPhos (6.31 mg, 10.9 μmol), 5-chloro-2-methoxypyrimidin-4-amine (41.0 mg, 128 μmol) and toluene (2.50 mL) and the vial degassed (nitrogen bubbled through solvent for 5 min), and sealed and stirred at 100° C. for 2 h in an oil bath. The reaction was then transferred to a flask and concentrated to dryness. The residue was dissolved in DCM (2.50 mL) and trifluoroacetic acid (1.7 mL) and stirred at rt for 1 h when it was subsequently concentrated to dryness. The product was purified by C18 column chromatography (15 to 40% MeCN in aq. ammonium formate buffer). The desired fraction were combined and lyophilized, affording the title compound (9.0 mg, 18%) as white solid. m/z (ESI, +ve ion)=463.1 [M+H]+. 1H NMR (500 MHz, DMSO) δ 12.81 (s, 1H), 10.41 (s, 1H), 9.57 (s, 1H), 8.23 (s, 1H), 7.44-7.40 (m, 2H), 6.91 (d, J=8.4 Hz, 1H), 6.74 (d, J=8.4 Hz, 1H), 6.58 (dd, J=8.5, 2.6 Hz, 1H), 5.65 (d, J=2.6 Hz, 1H), 3.48 (s, 3H), 3.19 (t, J=8.5 Hz, 1H), 2.32 (dd, J=8.0, 4.7 Hz, 1H), 1.98 (dd, J=9.0, 4.7 Hz, 1H); (Extra MeO signal unseparated from water peak).

Example 24. (1R,2S)-5'-methoxy-2-{3-[(2-methoxypyridin-3-yl)amino]-1H-indazol-6-yl}spiro[cyclopropane-1,3'-indol]-2'(1'H)-one

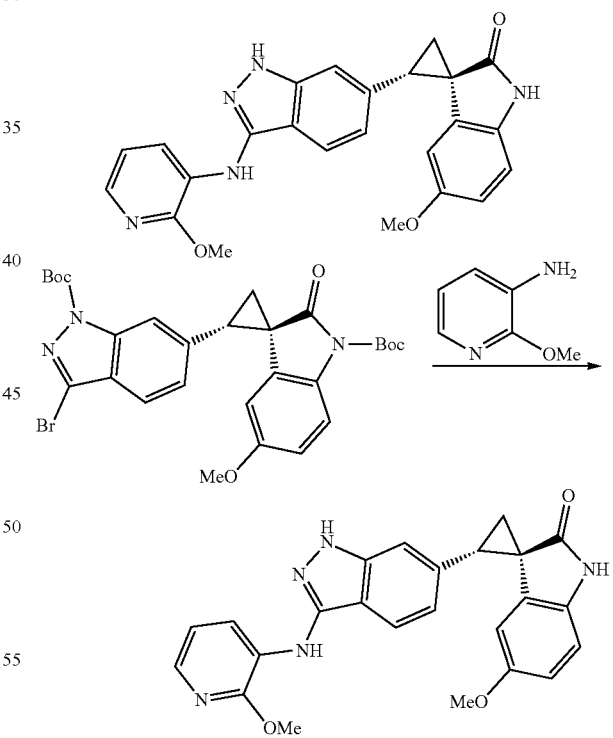

This compound was prepared using the procedure described in Example 5, from tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (75.0 mg, 128 μmol) and 2-methoxypyridin-3-amine (18.6 mg, 145 μmol). The product was purified by C18 column chromatography (10 to 50% MeCN in aq. ammonium formate buffer), affording the title compound (28.0 mg, 51%) as white solid after lyophilization. m/z (ESI, +ve ion)=428.2 [M+H]+. 1H NMR (400 MHz, DMSO) δ 12.16 (s, 1H), 10.43 (s, 1H), 8.37 (dd, J=7.8, 1.4 Hz, 1H), 8.02 (s, 1H), 7.91 (d, J=8.4 Hz, 1H), 7.61 (dd, J=4.9, 1.4 Hz, 1H), 7.31 (s, 1H), 6.97-6.85 (m, 2H), 6.74 (d, J=8.4 Hz, 1H), 6.58 (dd, J=8.4, 2.5 Hz, 1H), 5.70 (d, J=2.3 Hz, 1H), 3.98 (s, 3H), 3.32 (s, 3H), 3.17 (t, J=8.4 Hz, 1H), 2.32 (dd, J=7.7, 4.8 Hz, 1H), 1.97 (dd, J=8.9, 4.6 Hz, 1H).

Example 25. (1R,2S)-5'-methoxy-2-{3-[(3-methoxy-1-methyl-1H-pyrazol-4-yl)amino]-1H-indazol-6-yl}spiro[cyclopropane-1,3'-indol]-2'(1'H)-one

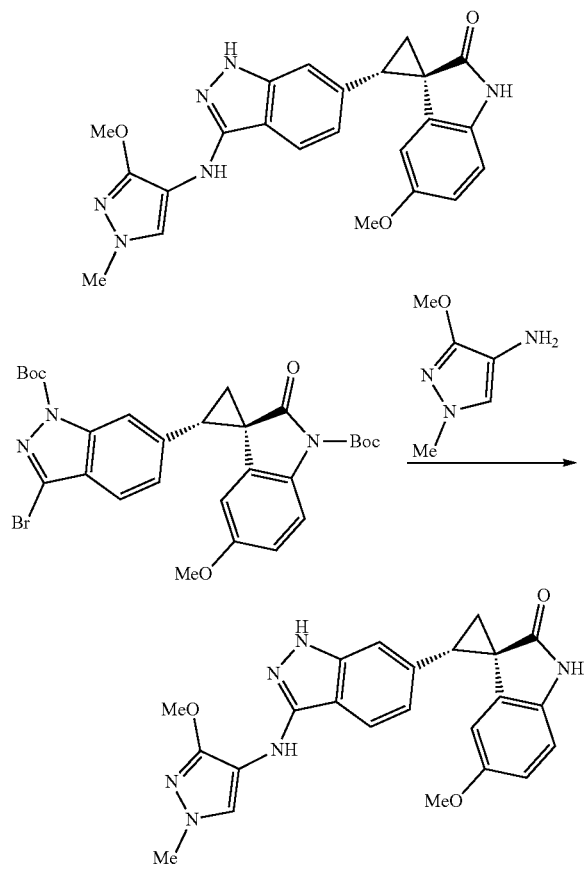

This compound was prepared according to the procedure described in Example 5, from tert-butyl 3-bromo-6-((1R,2S)-1'-(tert-butoxycarbonyl)-5'-methoxy-2'-oxospiro[cyclopropane-1,3'-indolin]-2-yl)-1H-indazole-1-carboxylate (50.0 mg, 85.5 μmol) and 3-methoxy-1-methyl-1H-pyrazol-4-amine hydrochloride (15.4 mg, 94.1 μmol). The product was purified by C18 column chromatography (20 to 40% MeCN in aq. ammonium formate buffer), affording the title compound (7.4 mg, 20%) as white solid after lyophilization. m/z (ESI, +ve ion)=431.4 [M+H]+. 1H NMR (500 MHz, DMSO) δ 11.54 (s, 1H), 10.39 (s, 1H), 7.88 (s, 1H), 7.85 (d, J=8.4 Hz, 1H), 7.82 (s, 1H), 7.17 (s, 1H), 6.77 (d, J=8.5 Hz, 1H), 6.74 (d, J=8.4 Hz, 1H), 6.57 (dd, J=8.5, 2.6 Hz, 1H), 5.68 (d, J=2.5 Hz, 1H), 3.84 (s, 3H), 3.66 (s, 3H), 3.33 (s, 3H), 3.14 (t, J=8.5 Hz, 1H), 2.27 (dd, J=8.0, 4.6 Hz, 1H), 1.95 (dd, J=9.0.4.7 Hz, 1H).

Example 26. (1R,2S)-2-{3-[(1-benzofuran-7-yl)amino]-1H-indazol-6-yl}-5'-methoxyspiro[cyclopropane-1,3'-indol]-2'(1'H)-one

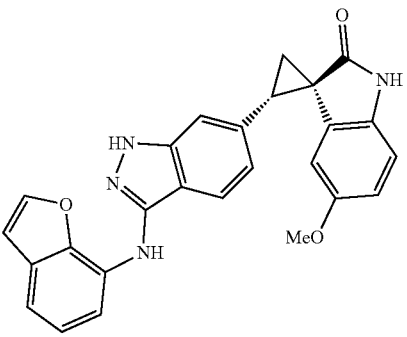 [SMILES: COc1ccc2c(c1)[C@]1(C[C@H]1c1ccc3c(Nc4cccc5ccoc45)n[nH]c3c1)C(=O)N2]

Step A. 7-bromo-2,3-dihydro-1-benzofuran-3-ol

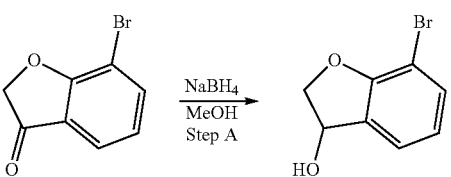

NaBH₄ (23.09 mg, 0.610 mmol, 1.3 equiv) was added to a mixture of 7-bromo-2H-1-benzofuran-3-one (100.00 mg, 0.469 mmol, 1.00 equiv) in MeOH (1.00 mL) at 0° C. The mixture was stirred at 0° C. for 1 h.

The solvent was concentrated in vacuo. The residue was diluted with water (20 mL), extracted with EA (3×10 mL). The combined organic layers were dried over anhydrous Na₂SO₄, filtered and the filtrate was concentrated in vacuo to give the title compound (100 mg, 97%) as a light yellow solid. The product showed no signal in LCMS. ¹H NMR (400 MHz, Chloroform-d) δ 7.48-7.38 (m, 2H), 6.90-6.86 (m, 1H), 5.50-5.48 (m, 1H), 4.70-4.67 (m, 1H), 4.59-4.56 (m, 1H).

Step B: [(7-bromo-2,3-dihydro-1-benzofuran-3-yl)oxy](tert-butyl)diphenylsilane

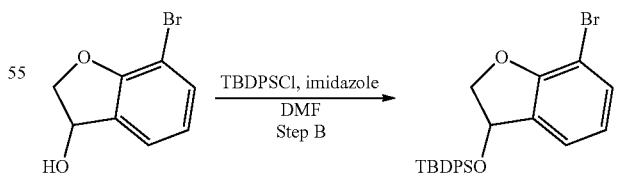

To the mixture of 7-bromo-2,3-dihydro-1-benzofuran-3-ol (100.00 mg, 0.465 mmol, 1.00 equiv) and imidazole (63.31 mg, 0.930 mmol, 2 equiv) in DMF (1.00 mL) was added TBDPS-Cl (153.38 mg, 0.558 mmol, 1.2 equiv) at 0° C. under nitrogen atmosphere. The resulting mixture was stirred at 25° C. for 3 h. The reaction was diluted with water (10 mL) and extracted with EA (3×10 mL). The combined Step D. (1R,2S)-2-[3-([3-[(tert-butyldiphenylsilyl)oxy]-2,3-dihydro-1-benzofuran-7-yl]amino)-1H-indazol-6-yl]-5'-methoxy-1'H-spiro[cyclopropane-1,3'-indol]-2'-one

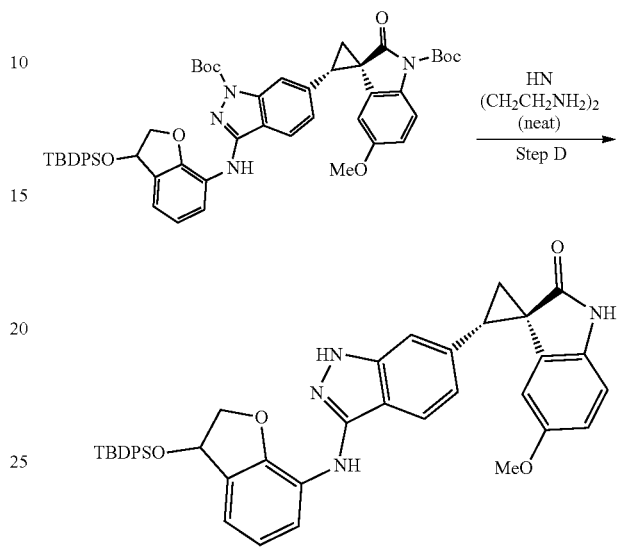

Step C. tert-butyl (1R,2S)-2-[1-(tert-butoxycarbonyl)-3-([3-[(tert-butyldiphenylsilyl)oxy]-2,3-dihydro-1-benzofuran-7-yl]amino)indazol-6-yl]-5'-methoxy-2'-oxospiro[cyclopropane-1,3'-indole]-1'-carboxylate

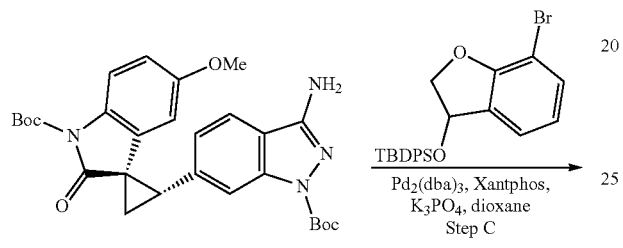

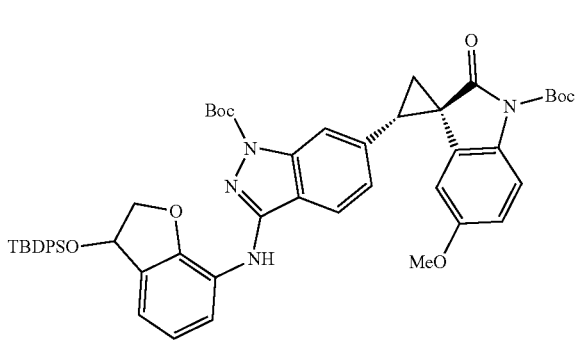

To the mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (130.00 mg, 0.250 mmol, 1.00 equiv) and [(7-bromo-2,3-dihydro-1-benzofuran-3-yl)oxy](tert-butyl)diphenylsilane (147.21 mg, 0.325 mmol, 1.30 equiv) in dry Dioxane (4 mL) were added $K_3PO_4$ (106.01 mg, 0.499 mmol, 2 equiv), $Pd_2(dba)_3$ (22.87 mg, 0.025 mmol, 0.1 equiv) and XantPhos (14.45 mg, 0.025 mmol, 0.1 equiv) under argon atmosphere. The mixture was stirred at 90° C. for 2 h. The solvent was removed under reduced pressure. The residue was purified by prep-TLC (rinsed with PE/EA=3/1) to give the title compound (120 mg, 51.11%) as yellow solid. m/z (ESI, +ve ion)=893.25 [M+H]$^+$. $^1$H NMR (400 MHz, Chloroform-d) δ 8.24 (d, J=8.0 Hz, 1H), 8.13-8.10 (m, 1H), 7.83-7.80 (m, 1H), 7.73-7.68 (m, 4H), 7.53-7.40 (m, 6H), 7.06 (d, J=8.0 Hz, 1H), 6.92-6.88 (m, 1H), 6.71-6.66 (m, 3H), 5.57-5.52 (m, 2H), 4.51-4.47 (m, 1H), 4.38-4.34 (m, 1H), 3.53 (t, J=8.4 Hz, 1H), 3.38 (d, J=6.8 Hz, 3H), 2.40-2.36 (m, 1H), 2.12 (s, 1H), 1.73-1.70 (m, 18H), 1.09 (s, 9H)

The mixture of tert-butyl (1R,2S)-2-[1-(tert-butoxycarbonyl)-3-([3-[(tert-butyldiphenylsilyl)oxy]-2,3-dihydro-1-benzofuran-7-yl]amino)indazol-6-yl]-5'-methoxy-2'-oxospiro[cyclopropane-1,3'-indole]-1'-carboxylate (68.00 mg, 0.076 mmol, 1.00 equiv) in bis(2-aminoethyl)amine (0.50 mL) was stirred at 25° C. for 16 h. The resulting mixture was diluted with EA (20 mL) and washed with brine (20 mL). The organic layer was dried over anhydrous $Na_2SO_4$ and filtered. The filtrate was concentrated in vacuo. The residue was purified by prep-TLC (rinsed with EA/PE=2/1) to give the title compound (50 mg, 90.04%) as a yellow solid. m/z (ESI, +ve ion)=693.15 [M+H]. $^1$H NMR (400 MHz, Chloroform-d) δ 7.81-7.79 (m, 1H), 7.75-7.66 (m, 5H), 7.56-7.54 (m, 1H), 7.49-7.40 (m, 8H), 6.95-6.80 (m, 2H), 6.70-6.61 (m, 1H), 5.58-5.52 (m, 2H), 4.49-4.45 (m, 1H), 4.38-4.32 (m, 1H), 3.47-3.42 (m, 1H), 3.37 (d, J=1.6 Hz 3H), 2.30-2.26 (m, 1H), 2.06-2.04 (m, 1H), 1.10-1.09 (m, 9H).

Step E. (1R,2S)-2-[3-(1-benzofuran-7-ylamino)-1H-indazol-6-yl]-5'-methoxy-1'H-spiro[cyclopropane-1,3'-indol]-2'-one

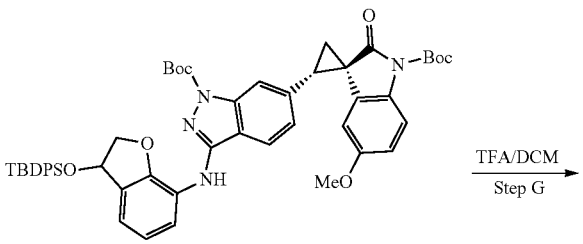

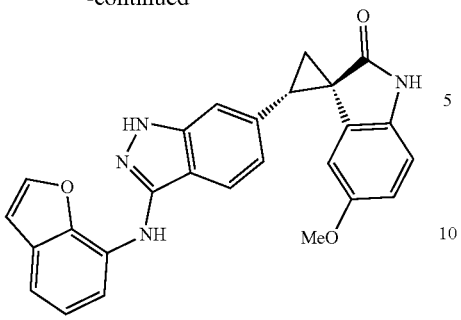

To the mixture of (1R,2S)-2-[3-([3-[(tert-butyldiphenyl-silyl)oxy]-2,3-dihydro-1-benzofuran-7-yl]amino)-1H-indazol-6-yl]-5'-methoxy-1'H-spiro[cyclopropane-1,3'-indol]-2'-one (9.00 mg, 0.010 mmol, 1.00 equiv) in DCM (0.50 mL, 0.006 mmol, 0.58 equiv) was added TFA (0.05 mL). The mixture was stirred at 25° C. for 12 h. The mixture was diluted with DCM (20 ml) and washed with sat. aq. NaHCO$_3$ (20 mL). The organic layer was washed with brine (20 mL), dried over anhydrous Na$_2$SO$_4$, filtered and concentrated in vacuo. The residue was purified by prep-HPLC with the following conditions: Column: XBridge Shield RP18 OBD Column, 30×150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 35% B to 65% B in 8 min; 254 nm; RT1: 6.73 min. The product-containing fractions were concentrated to give the title compound as a white solid (2.2 mg, 49.52%). m/z (ESI, +ve ion)=437.15 [M+H]$^+$. $^1$H NMR (400 MHz, Methanol-d$_4$) δ 7.76 (d, J=2.0 Hz, 1H), 7.71 (d, J=8.4 Hz, 1H), 7.57-7.55 (m, 1H), 7.37 (s, 1H), 7.16-7.10 (m, 2H), 6.91-6.87 (m, 1H), 6.85-6.83 (m, 2H), 6.65-6.62 (m, 1H), 5.63 (d, J=2.4 Hz, 1H), 3.39-3.37 (m, 1H), 3.32 (s, 3H), 2.26-2.23 (m, 1H), 2.20-2.17 (m, 1H).

Example 27. 2-{3-[(3-hydroxy-2,3-dihydro-1-benzofuran-7-yl)amino]-1H-indazol-6-yl}-5'-methoxyspiro[cyclopropane-1,3'-indol]-2'(1'H)-one (Mixture of Diastereomers)

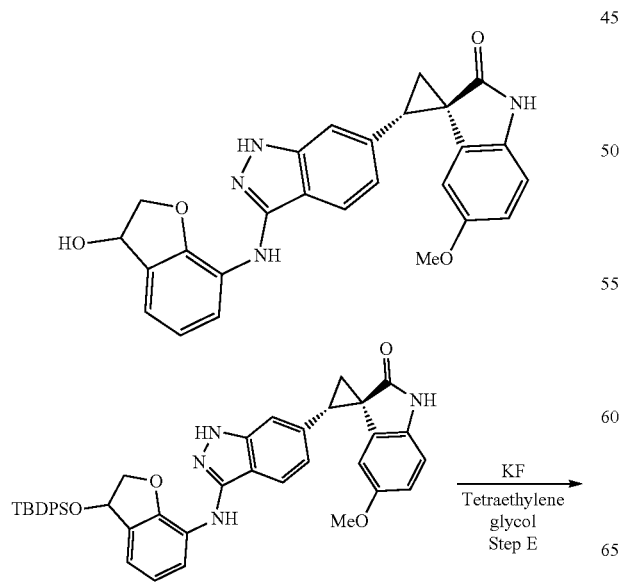

To the mixture of (1R,2S)-2-[3-([3-[(tert-butyldiphenyl-silyl)oxy]-2,3-dihydro-1-benzofuran-7-yl]amino)-1H-indazol-6-yl]-5'-methoxy-1'H-spiro[cyclopropane-1,3'-indol]-2'-one (50.00 mg, 0.069 mmol, 1.00 equiv) in tetraethylene glycol (1.00 mL) was added KF (5.97 mg, 0.104 mmol, 1.50 equiv). The resulting mixture was stirred at 80° C. for 12 h. The mixture was purified by prep-HPLC with the following conditions: Column: XBridge Prep OBD C18 Column, 30×150 mm 5 μm; Mobile Phase A: Water (10 mmol/L NH$_4$HCO$_3$), Mobile Phase B: ACN; Flow rate: 60 mL/min; Gradient: 20% B to 38% B in 8 min; 254/220 nm; RT1: 7.63 min. The product-containing fractions were concentrated to give the title compound (15 mg, 45.7%) as a white solid. m/z (ESI, +ve ion)=455.10 [M+H]$^+$. $^1$H NMR (400 MHz, Methanol-d$_4$) δ 7.66-7.64 (m, 2H), 7.34 (s, 1H), 6.99 (d, J=7.2 Hz, 1H), 6.89-6.83 (m, 3H), 6.64-6.61 (m, 1H), 5.61 (s, 1H), 5.39-5.38 (m, 1H), 4.65-4.60 (m, 1H), 4.47-4.44 (m, 1H), 3.38-3.35 (m, 1H), 3.30 (s, 3H), 2.25-2.21 (m, 1H), 2.20-2.16 (m, 1H).

Example 28. (1R,2S)-2-(3-{[(3S)-3-hydroxy-2,3-dihydro-1-benzofuran-7-yl]amino}-1H-indazol-6-yl)-5'-methoxyspiro[cyclopropane-1,3'-indol]-2'(1'H)-one

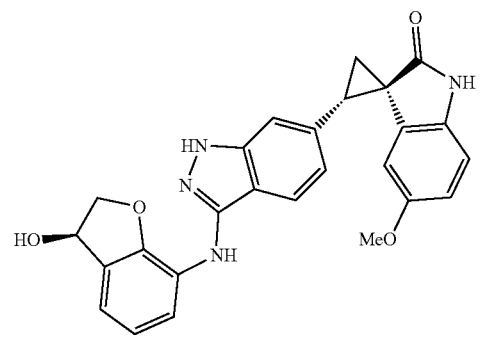 [SMILES: COc1ccc2c(c1)[C@]1(C[C@H]1c1ccc3c(Nc4cccc5c4OC[C@@H]5O)n[nH]c3c1)C(=O)N2]

Example 29. (1R,2S)-2-(3-{[(3R)-3-hydroxy-2,3-dihydro-1-benzofuran-7-yl]amino}-1H-indazol-6-yl)-5'-methoxyspiro[cyclopropane-1,3'-indol]-2'(1'H)-one

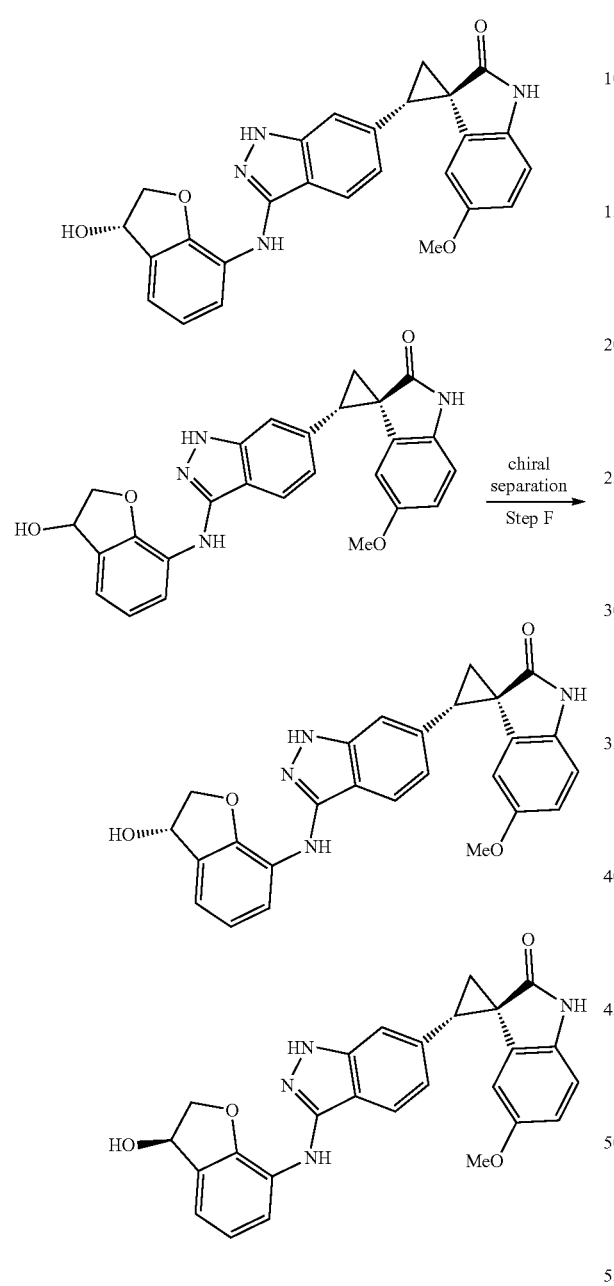

The racemic mixture was separated by PREP-Chiral-HPLC with the following conditions: CHIRALPAK IF, 2×25 cm, 5 µm; Mobile Phase A: HEX:DCM=3:1 (0.1% DEA)-HPLC, Mobile Phase B: IPA-HPLC; Flow rate: 20 mL/min; Gradient: 20% B to 20% B in 15.5 min; 220/254 nm; RT1: 9.797 min; RT2: 13.157 min. The first product-containing fractions were collected and roto-evaporated in vacuo and lyophilized overnight to give Example 4 (5 mg) as a white solid. m/z (EST, +ve ion)=455.35 [M+H]+. 1H NMR (400 MHz, Methanol-d4) δ 7.66-7.64 (m, 2H), 7.34 (s, 1H), 6.99 (d, J=6.8 Hz, 1H), 6.89-6.83 (m, 3H), 6.64-6.61 (m, 1H), 5.61 (d, J=2.4 Hz, 1H), 5.40-5.38 (m, 1H), 4.64- 4.60 (m, 1H), 4.48-4.44 (m, 1H), 3.35-3.33 (m, 1H), 3.30 (s, 3H), 2.25-2.22 (m, 1H), 2.20-2.16 (m, 1H). The second product-containing fractions were collected and roto-evaporated in vacuo and lyophilized overnight to give Example 5 (3.9 mg) as a white solid. m/z (ESI, +ve ion)=455.30 [M+H]+. 1H NMR (400 MHz, Methanol-d4) δ 7.67-7.65 (m, 2H), 7.34 (s, 1H), 6.99 (d, J=7.2 Hz, 1H), 6.89-6.83 (m, 3H), 6.64-6.61 (m, 1H), 5.61 (d, J=2.4 Hz, 1H), 5.40-5.38 (m, 1H), 4.65-4.61 (m, 1H), 4.48-4.44 (m, 1H), 3.35-3.33 (m, 1H), 3.30 (s, 3H), 2.24-2.22 (m, 1H), 2.20-2.17 (in, 1H).

Example 30. (1R,2S)-2-{3-[(2,3-dihydropyrazolo[5,1-b][1,3]oxazol-7-yl)amino]-1H-indazol-6-yl}-5'-methoxyspiro[cyclopropane-1,3'-indol]-2'(1'H)-one

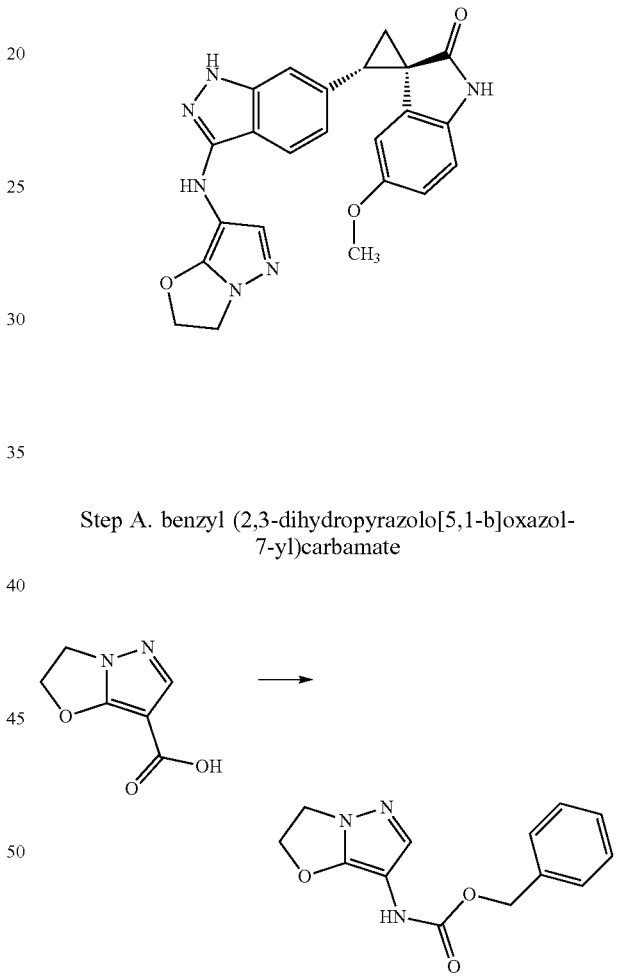

Step A. benzyl (2,3-dihydropyrazolo[5,1-b]oxazol-7-yl)carbamate

To an oven-dried flask was added 2,3-dihydropyrazolo[5,1-b]oxazole-7-carboxylic acid (250 mg, 1.62 mmol) followed by 1,4-dioxane (7.0 mL). diisopropylethylamine (0.57 mL, 3.2 mmol), benzyl alcohol (0.84 mL, 8.1 mmol) and diphenyl phosphorazidate (0.42 mL, 1.9 mmol). The mixture was heated at 90° C. overnight during which time the solution turned dark brown. The mixture was concentrated purified by column chromatography (20% to 30% acetone/hexanes, gradient elution) to afford the title compound (220 mg, 52%) as an off-white solid. m/z (ESI, +ve ion)=260.2 [M+H]+.

Step B. 2,3-dihydropyrazolo[5,1-b]oxazol-7-amine

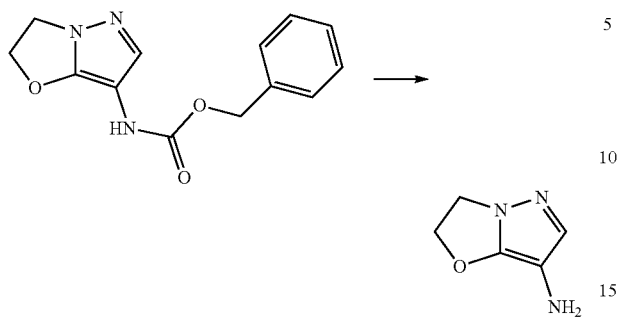

To a suspension of benzyl (2,3-dihydropyrazolo[5,1-b]oxazol-7-yl)carbamate (220 mg, 0.849 mmol) in ethanol (9.0 mL) was added 10% Pd/C (44 mg). The atmosphere was replaced with argon and then replaced with hydrogen. The reaction mixture was stirred at under a hydrogen atmosphere for 2.5 h. The catalyst was removed by filtering over a pad of celite and rinsed with ethanol. The filtrate was concentrated and purified by column chromatography (0% to 10% methanol/DCM, gradient elution) to afford the title compound (90 mg, 85%) as a red purple solid. m/z (ESI, +ve ion)=126.3 [M+H]$^+$.

Step C. tert-butyl (1R,2S)-2-(1-(tert-butoxycarbonyl)-3-((2,3-dihydropyrazolo[5,1-b]oxazol-7-yl)amino)-1H-indazol-6-yl)-5'-methoxy-2'-oxospiro[cyclopropane-1,3'-indoline]-1'-carboxylate

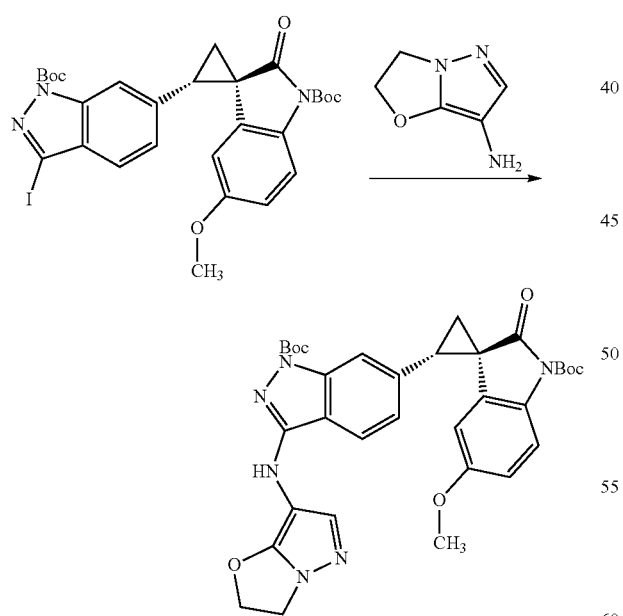

To an oven-dried flask was added tert-butyl (1R,2S)-2-(1-(tert-butoxycarbonyl)-3-iodo-1H-indazol-6-yl)-5'-methoxy-2'-oxospiro[cyclopropane-1,3'-indoline]-1'-carboxylate (63.1 mg, 0.100 mmol), 2,3-dihydropyrazolo[5,1-b]oxazol-7-amine (13.8 mg, 0.110 mmol), xantphos (5.8 mg, 0.010 mmol), Pd$_2$dba$_3$ (9.2 mg, 0.010 mmol), and toluene (2.0 mL). The mixture was degassed with bubbling argon for 10 min. At this time, Cs$_2$CO$_3$ (65.2 mg, 0.200 mmol) was added and the reaction mixture was heated to 100° C. for 2 h. The reaction mixture was cooled was cooled to room temperature and diluted with EtOAc and washed with sat. aqueous NaHCO$_3$. The aqueous layer was extracted an additional three times with EtOAc. Combined organic layers were washed with brine, dried with MgSO$_4$, filtered, and concentrated. The residue was purified by column chromatography (0.5% to 7% methanol/DCM, a gradient elution) to provide the title compound (10 mg, 16%) as a yellow foam. m/z (ESI, +ve ion)=629.2 [M+H]$^+$.

Step D

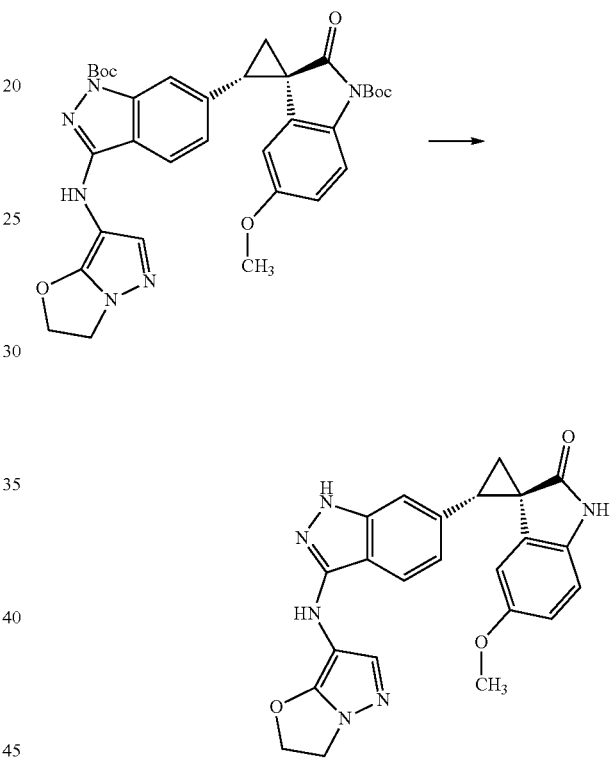

To an oven-dried flask was added tert-butyl (1R,2S)-2-(1-(tert-butoxycarbonyl)-3-((2,3-dihydropyrazolo[5,1-b]oxazol-7-yl)amino)-1H-indazol-6-yl)-5'-methoxy-2'-oxospiro[cyclopropane-1,3'-indoline]-1'-carboxylate (10 mg, 0.016 mmol) followed DCM (0.4 mL) and trifluoroacetic acid (0.12 mL, 1.5 mmol). The reaction mixture was stirred at room temperature for 2.5 h. At this time, the mixture was concentrated and purified by prep HPLC (15% to 45% ACN/H$_2$O, 0.1% TFA modifier, gradient elution) to afford the Example 30 (5.7 mg, 66%) as a white amorphous solid after lyophilization. m/z (ESI, +ve ion)=429.1 [M+H]$^+$. $^1$H NMR (400 MHz, MeOD) δ=7.81 (d, J=8.6 Hz, 1H), 7.52 (s, 1H), 7.38 (d, J=0.8 Hz, 1H), 7.06 (dd, J=1.0, 8.6 Hz, 1H), 6.86 (d, J=8.1 Hz, 1H), 6.67 (dd, J=2.5, 8.6 Hz, 1H), 5.65 (d, J=2.5 Hz, 1H), 5.23-5.17 (m, 2H), 4.38 (t, J=8.0 Hz, 2H), 3.41 (s, 3H), 3.35-3.34 (m, 1H), 2.29-2.16 (m, 2H). Did not observe exchangeable protons.

Example 31. (1R,2S)-5'-methoxy-2-{3-[(3-oxo-2,3-dihydro-1-benzofuran-7-yl)amino]-1H-indazol-6-yl}spiro[cyclopropane-1,3'-indol]-2'(1'H)-one

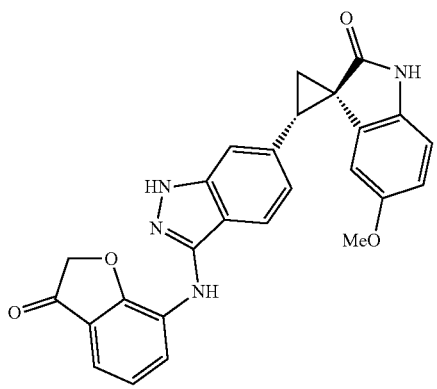 [SMILES: COc1ccc2c(c1)[C@]1(C[C@H]1c1ccc3c(Nc4cccc5c4OCC5=O)n[nH]c3c1)C(=O)N2]

Step A. tert-butyl (1R,2S)-2-[1-(tert-butoxycarbonyl)-3-[(3-hydroxy-2,3-dihydro-1-benzofuran-7-yl)amino]indazol-6-yl]-5'-methoxy-2'-oxospiro[cyclopropane-1,3'-indole]-1'-carboxylate

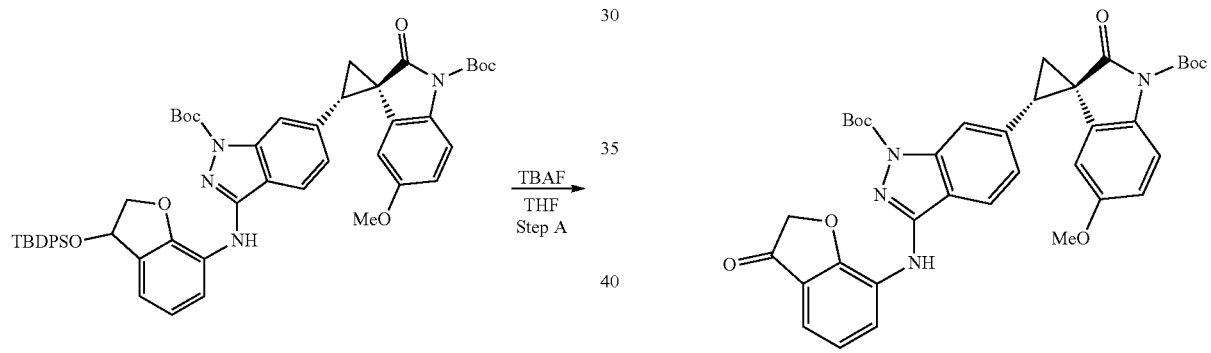

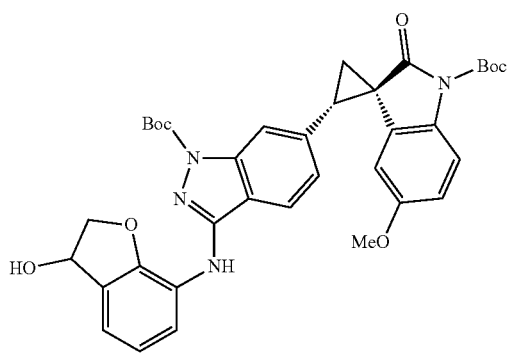

To the mixture of tert-butyl (1R,2S)-2-(1-(tert-butoxycarbonyl)-3-((3-((tert-butyldiphenylsilyl)oxy)-2,3-dihydrobenzofuran-7-yl)amino)-1H-indazol-6-yl)-5'-methoxy-2'-oxospiro[cyclopropane-1,3'-indoline]-1'-carboxylate (300.00 mg, 0.336 mmol, 1.00 equiv) in THF (5.00 mL) was added TBAF (131.74 mg, 0.504 mmol, 1.50 equiv). After stirred at 25° C. for 2 h. the solvent was removed under reduced pressure. The residue was purified by prep-TLC (rinsed with EA/PE=1/1) to give the title compound (7a) (200 mg, 90.94%) as a light yellow solid. m/z (EST, +ve ion)=655.30 [M+H]+.

Step B. tert-butyl (1R,2S)-2-[1-(tert-butoxycarbonyl)-3-[(3-oxo-2H-1-benzofuran-7-yl)amino]indazol-6-yl]-5'-methoxy-2'-oxospiro[cyclopropane-1,3'-indole]-1'-carboxylate

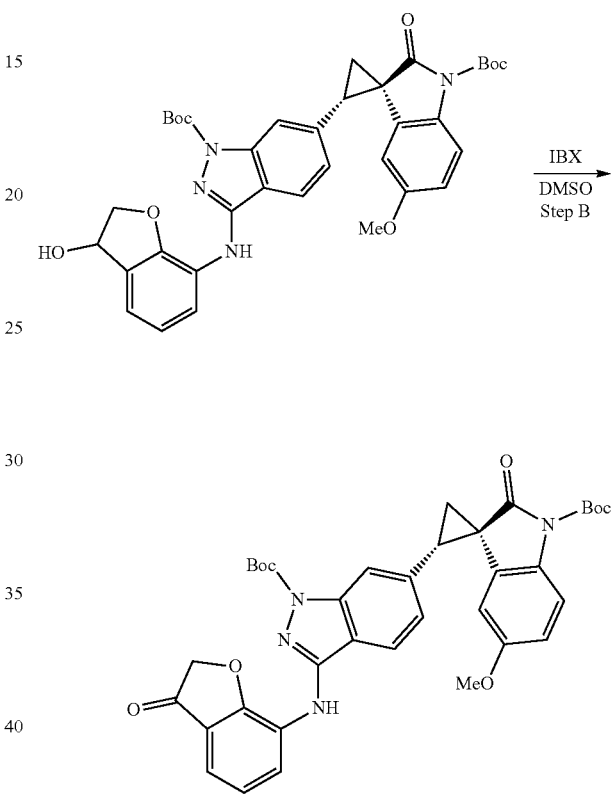

To the mixture of tert-butyl (1R,2S)-2-[1-(tert-butoxycarbonyl)-3-[(3-hydroxy-2,3-dihydro-1-benzofuran-7-yl)amino]indazol-6-yl]-5'-methoxy-2'-oxospiro[cyclopropane-1,3'-indole]-1'-carboxylate (50.00 mg, 0.076 mmol, 1.00 equiv) in DMSO (1.00 mL) was added IBX (42.77 mg, 0.152 mmol, 2.00 equiv). The resulting mixture was stirred at 25° C. for 12 h. The mixture was diluted with EA (50 mL) and washed with brine (30 mL×3). The organic layers were dried over anhydrous Na$_2$SO$_4$, filtered and concentrated in vacuo. The residue was purified by prep-TLC (rinsed with EA/PE=1/1) to give the title compound (35 mg, 66.71%) as a light yellow solid. m/z (ESI, +ve ion)=653.30 [M+H]+. $^1$H NMR (400 MHz, Chloroform-d) δ 8.71 (d, J=8.0 Hz, 1H), 8.11 (s, 1H), 7.84-7.82 (m, 1H), 7.58 (d, J=8.4 Hz, 1H), 7.33-7.31 (m, 1H), 7.22-7.19 (m, 1H), 7.12 (d, J=8.4 Hz, 1H), 6.86 (s, 1H), 6.71-6.68 (m, 1H), 5.58 (d, J=2.8 Hz, 1H), 4.77 (s, 2H), 3.59-3.52 (m, 1H), 3.41 (s, 3H), 2.41-2.38 (m, 1H), 2.12 (s, 1H), 1.72 (d, J=9.2 Hz, 18H).

Step C. (1R,2S)-5'-methoxy-2-[3-[(3-oxo-2H-1-benzofuran-7-yl)amino]-1H-indazol-6-yl]-1'H-spiro[cyclopropane-1,3'-indol]-2'-one Example 32. (1R,2S)-2-{3-[(2,3-dihydrofuro[2,3-c]pyridin-7-yl)amino]-1H-indazol-6-yl}-5'-methoxyspiro[cyclopropane-1,3'-indol]-2'(1'H)-one

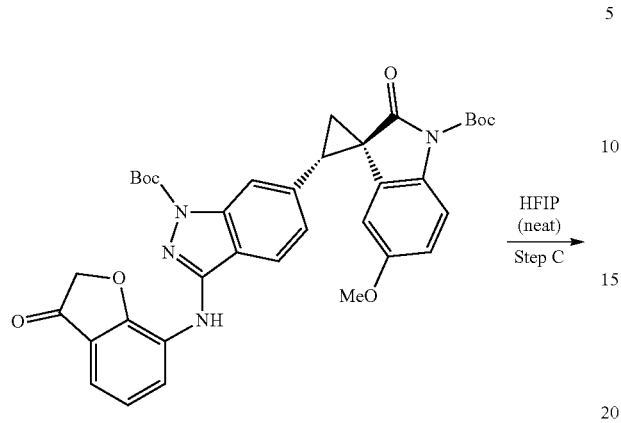

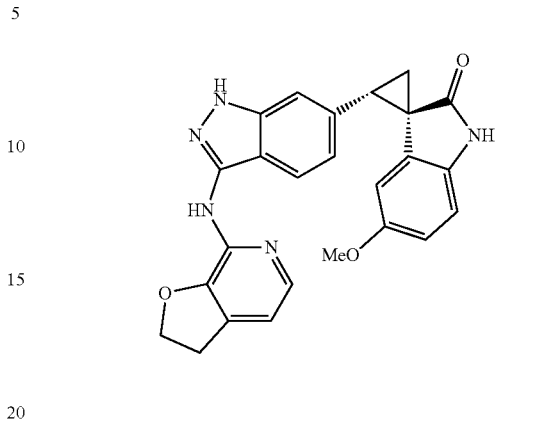

Step A. 2H,3H-furo[2,3-c]pyridin-7-amine

To a mixture of furo[2,3-c]pyridin-7-amine (400.00 mg, 2.982 mmol, 1.00 equiv) in AcOH (8 mL) was added 10% Pd/C (400.00 mg, 0.376 mmol, 0.13 equiv). The reaction mixture was stirred for 16 h at 1 atm H₂ atmosphere. The reaction mixture was concentrated under reduced pressure. The residue was dissolved with EA (50 mL) and washed with saturated NaHCO₃ (3×20 mL). The organic layers were dried over anhydrous Na₂SO₄, filtered. The filtrate was concentrated under reduced pressure to give the title compound (400 mg, 98.52%) as a yellow oil. m/z (EST, +ve ion)=137.00 [M+H]⁺. ¹H NMR (400 MHz, DMSO-d₆) δ 7.46 (d, J=5.2 Hz, 1H), 6.53 (d, J=5.2 Hz, 1H), 5.53 (s, 2H), 4.50 (t, J=8.8 Hz, 2H), 3.18-3.08 (m, 2H).

Step B. tert-butyl (1R,2S)-2-[1-tert-butoxycarbonyl)-3-[2H,3H-furo[2,3-c]pyridin-7-ylamino]indazol-6-yl]-5'-methoxy-2'-oxospiro[cyclopropane-1,3'-indole]-1'-carboxylate

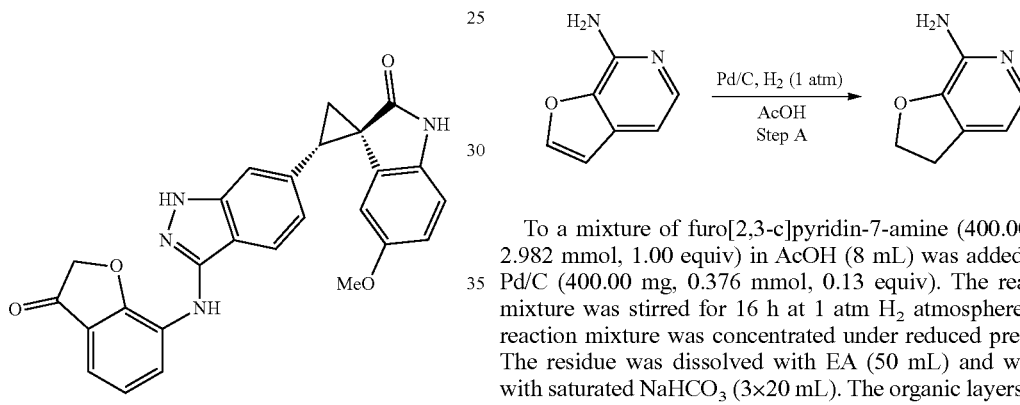

The mixture of tert-butyl (1R,2S)-2-[1-(tert-butoxycarbonyl)-3-[(3-oxo-2H-1-benzofuran-7-yl)amino]indazol-6-yl]-5'-methoxy-2'-oxospiro[cyclopropane-1,3'-indole]-1'-carboxylate (25.00 mg, 0.038 mmol, 1.00 equiv) in 1,1,1,3,3,3-hexafluoropropan-2-ol (1.00 mL) was stirred at 50° C. for 12 h. The solvent was removed under reduced pressure and the residue was purified with the following conditions: Column: XBridge Prep OBD C18 Column, 30 Å, 150 mm 5 μm; Mobile Phase A: Water (10 mmol/L NH₄HCO₃), Mobile Phase B: ACN; Flow rate: 60 mL/min; Gradient: 28% B to 42% B in 8 min; Detector: 254/220 nm; RT1: 7.27 min. The product-containing fractions was concentrated in vacuo to give Example 31 (3.3 mg, 18.85%) as a light yellow solid. m/z (ESI, +ve ion)=453.30 [M+H]⁺. ¹H NMR (400 MHz, Methanol-d₄) δ 8.16-8.14 (m, 1H), 7.74 (d, J=8.0 Hz, 1H), 7.38 (s, 1H), 7.16-7.14 (m, 1H), 7.08-7.04 (m, 1H), 6.92 (d, J=8.4 Hz, 1H), 6.84 (d, J=8.8 Hz, 1H), 6.64-6.62 (m, 1H), 5.62 (d, J=2.4 Hz, 1H), 4.82 (s, 2H), 3.39-3.37 (m, 1H), 3.31 (s, 3H), 2.26-2.23 (m, 1H), 2.20-2.17 (m, 1H).

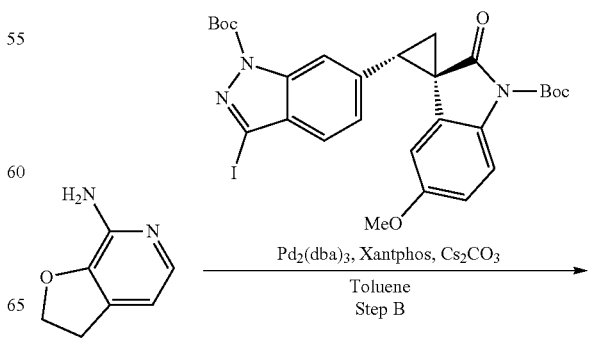

-continued

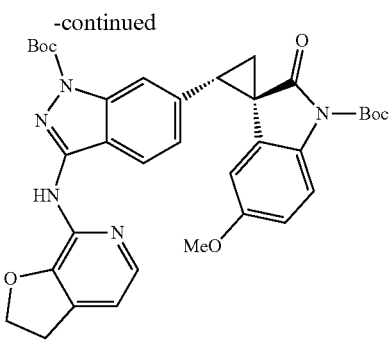

To a mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (190.00 mg, 0.301 mmol, 1.00 equiv), 2H,3H-furo[2,3-c]pyridin-7-amine (49.16 mg, 0.361 mmol, 1.2 equiv) and $Cs_2CO_3$ (196.07 mg, 0.602 mmol, 2.00 equiv) in toluene (6.00 mL) were added $Pd_2(dba)_3$ (27.55 mg, 0.030 mmol, 0.1 equiv) and XantPhos (17.41 mg, 0.030 mmol, 0.10 equiv) under $N_2$ atmosphere. The resulting mixture was stirred for 2 h at 90° C. The reaction mixture was filtered. The filtrate was concentrated under reduced pressure. The residue was purified with silica gel chromatography, eluted with 7/o MeOH in DCM to afford the title compound (160 mg, 83.13%) as a yellow oil. m/z (EST, +ve ion)=(40.40 [M+H]$^+$.

Step C. (1R,2S)-2-(3-[2H,3H-furo[2,3-c]pyridin-7-ylamino]-1H-indazol-6-yl)-5'-methoxy-1'H-spiro[cyclopropane-1,3'-indol]-2'-one

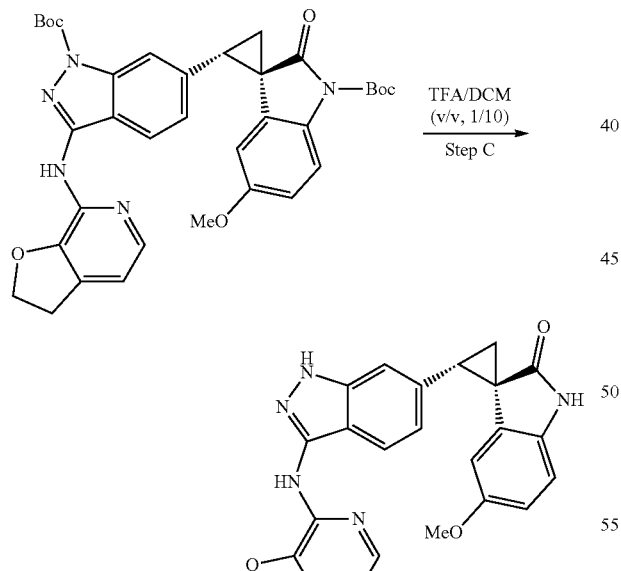

TFA/DCM (v/v, 1/10)
Step C

To a mixture of tert-butyl (1R,2S)-2-[1-(tert-butoxycarbonyl)-3-[2H,3H-furo[2,3-c] pyridin-7-ylamino]indazol-6-yl]-5'-methoxy-2-oxospiro[cyclopropane-1,3'-indole]-1'-carboxylate (160.00 mg, 0.250 mmol, 1.00 equiv) in DCM (5.00 mL) was added TFA (0.50 mL, 6.732 mmol, 26.91 equiv). The resulting mixture was stirred for 16 h at room temperature. The reaction mixture was concentrated under reduced pressure. The residue was purified by RP flash, eluted with 45% ACN in water (10 mM $NH_4HCO_3$) to afford Example 32 (40 mg, 36.39%) as an off-white solid. m/z (ESI, +ve ion)=440.05 [M+H]$^+$. $^1$H NMR (400 MHz, DMSO-$d_6$) δ 12.32 (s, 1H), 10.42 (s, 1H), 8.42 (s, 1H), 7.52 (d, J=5.0 Hz, 1H), 7.42 (d, J=8.4 Hz, 1H), 7.34 (s, 1H), 6.84 (d, J=8.4 Hz, 1H), 6.77-6.73 (m, 2H), 6.59 (dd, J=8.5, 2.6 Hz, 1H), 5.74 (d, J=2.6 Hz, 1H), 4.59 (t, J=8.9 Hz, 2H), 3.3 (s, 3H), 3.22 (t, J=8.9 Hz, 2H), 3.17 (t, J=8.4 Hz, 1H), 2.32 (dd, J=8.0, 4.7 Hz, 1H), 1.98 (dd, J=9.1, 4.6 Hz, 1H).

Example 33. (1R,2S)-2-(3-{[(3S)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one

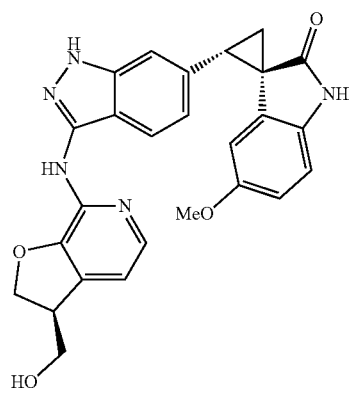 [SMILES: COc1ccc2c(c1)[C@]1(C[C@H]1c1ccc3c(Nc4nccc5c4OC[C@@H]5CO)n[nH]c3c1)C(=O)N2]

Example 34. (1R,2S)-2-(3-{[(3R)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one

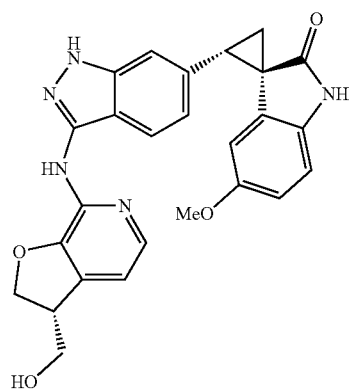 [SMILES: COc1ccc2c(c1)[C@]1(C[C@H]1c1ccc3c(Nc4nccc5c4OC[C@H]5CO)n[nH]c3c1)C(=O)N2]

Step A. 3-[[(tert-butyldimethylsilyl)oxy]methyl]-7-chloro-2H,3H-furo[2,3-c] pyridine

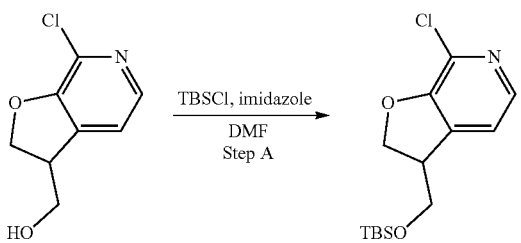 [SMILES: OCC1COc2c1ccnc2Cl ; CC(C)(C)[Si](C)(C)OCC1COc2c1ccnc2Cl]

To a stirred mixture of [7-chloro-2H,3H-furo[2,3-c]pyridin-3-yl]methanol (500.00 mg, 2.694 mmol, 1.00 equiv) and Imidazole (220.07 mg, 3.233 mmol, 1.20 equiv) in DMF (4.00 mL, 0.055 mmol) were added t-butyldimethylchlorosilane (487.22 mg, 3.233 mmol, 1.20 equiv) at room temperature under nitrogen atmosphere. The resulting mixture was stirred for 2 h at room temperature under nitrogen atmosphere. The resulting mixture was extracted with EtOAc (3×40 mL). The combined organic layers were washed with brine (3×40 mL), dried over anhydrous Na$_2$SO$_4$. After filtration, the filtrate was concentrated under reduced pressure to afford the crude title product (1.0 g). m/z (ESI, +ve ion)=300.15 [M+H]$^+$.

Step B. N-(3-[[(tert-butyldimethylsilyl)oxy]methyl]-2H,3H-furo[2,3-c]pyridin-7-yl)-1,1-diphenylmethanimine

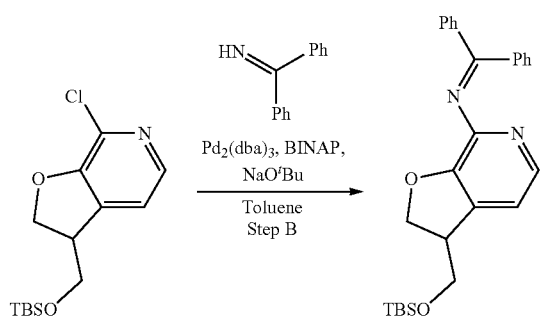 [SMILES: CC(C)(C)[Si](C)(C)OCC1COc2c1ccnc2Cl ; N=C(c1ccccc1)c1ccccc1 ; CC(C)(C)[Si](C)(C)OCC1COc2c1ccnc2N=C(c1ccccc1)c1ccccc1]

To a stirred mixture of 3-[[(tert-butyldimethylsilyl)oxy]methyl]-7-chloro-2H,3H-furo[2,3-c] pyridine (300.00 mg, 1.000 mmol, 1.00 equiv), diphenylmethanimine (36.26 mg, 0.200 mmol, 1.20 equiv) in toluene (5.00 mL, 4.699 mmol, 28.18 equiv) were added t-BuONa (134.60 mg, 1.400 mmol, 1.40 equiv), BINAP (12.46 mg, 0.020 mmol, 0.12 equiv) and Pd$_2$(dba)$_3$ (36.64 mg, 0.040 mmol, 0.04 equiv) at room temperature under nitrogen atmosphere. The resulting mixture was stirred overnight at 90° C. under nitrogen atmosphere. The resulting mixture was extracted with EtOAc (3×40 mL). The combined organic layers were washed with brine (60 mL), dried over anhydrous Na$_2$SO$_4$. After filtration, the filtrate was concentrated under reduced pressure to give 400 mg crude title compound. m/z (ESI, +ve ion)=445.15 [M+H]$^+$.

Step C. 3-[[(tert-butyldimethylsilyl)oxy]methyl]-2H,3H-furo[2,3-c]pyridin-7-amine

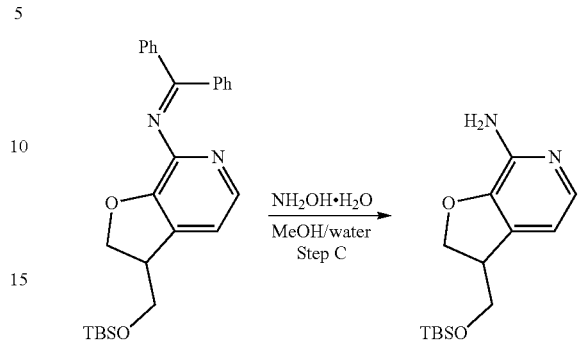

A mixture of N-(3-[[(tert-butyldimethylsilyl)oxy]methyl]-2H,3H-furo[2,3-c]pyridin-7-yl)-1,1-diphenylmethanimine (400.00 mg, 0.900 mmol, 1.00 equiv) and NH$_2$OH (50% in water, 0.50 mL) in MeOH (0.50 mL) and H$_2$O (0.50 mL) was stirred for 1 h at room temperature under nitrogen atmosphere. The resulting mixture was extracted with EtOAc (3×40 mL). The combined organic layers were washed with brine (60 mL), dried over anhydrous Na$_2$SO$_4$. After filtration, the filtrate was concentrated under reduced pressure. The residue was purified by silica gel column chromatography, eluted with DCM/MeOH (10/1) to afford the title compound (177 mg, 70.16%) as a white solid. m/z (ESI, +ve ion)=281.25 [M+H]$^+$. $^1$H NMR (400 MHz, DMSO-d) δ 7.47 (d, J=4.8 Hz, 1H), 6.56 (d, J=5.2 Hz, 1H), 5.55 (s, 2H), 4.61-4.51 (m, 1H), 4.35-4.26 (m, 1H), 3.81-3.73 (m, 1H), 3.72-3.64 (m, 11H), 3.63-3.52 (m, 1H), 0.84 (s, 9H), 0 (s, 6H).

Step D. tert-butyl(1R,2S)-2-[1-(tert-butoxycarbonyl)-3-[(3-[[(tert-butyldimethylsilyl)oxy]methyl]-2H,3H-furo[2,3-c]pyridin-7-yl)amino]indazol-6-yl]-5'-methoxy-2'-oxospiro[cyclopropane-1,3'-indole]-1'-carboxylate

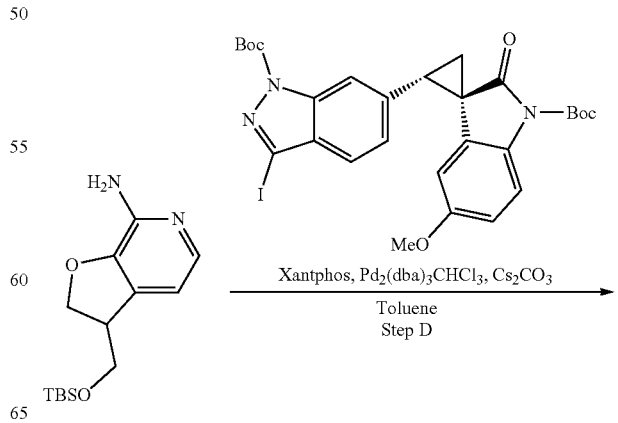

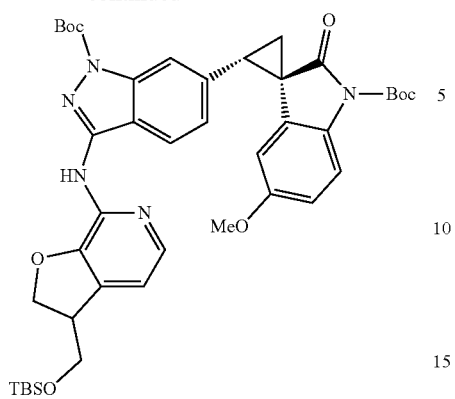

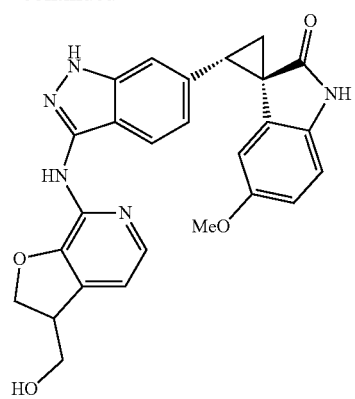

To a stirred mixture of tert-butyl (1R,2S)-2-[1-(tert-butoxycarbonyl)-3-iodoindazol-6-yl]-5-methoxy-2-oxospiro[cyclopropane-1,3-indole]-1-carboxylate (150.00 mg, 0.238 mmol, 1.00 equiv) and 3-[[(tert-butyldimethylsilyl)oxy]methyl]-2H,3H-furo[2,3-c]pyridin-7-amine (79.94 mg, 0.286 mmol, 1.20 equiv) in toluene (2.30 mL) were added $Cs_2CO_3$ (154.79 mg, 0.476 mmol, 2.00 equiv), XantPhos (13.74 mg, 0.024 mmol, 0.10 equiv) and $Pd_2(dba)_3 \cdot CHCl_3$ (24.59 mg, 0.024 mmol, 0.10 equiv) at room temperature under nitrogen atmosphere. The resulting mixture was stirred for 2 h at 85° C. under nitrogen atmosphere then concentrated under vacuum. The resulting mixture was extracted with EtOAc (3×40 mL). The combined organic layers were washed with brine (3×10 mL), dried over anhydrous $Na_2SO_4$. After filtration, the filtrate was concentrated under reduced pressure to give 100 mg of the crude title compound. The crude resulting mixture was used for the next step directly without further purification. m/z (ESI, +ve ion)=784.50 $[M+H]^+$.

Step E. (1R,2S)-2-(3-[[3-(hydroxymethyl)-2H,3H-furo[2,3-c]pyridin-7-yl] amino]-1H-indazol-6-yl)-5'-methoxy-1'H-spiro[cyclopropane-1,3'-indol]-2'-one To a stirred mixture of the crude tert-butyl(1R,2S)-2-[1-(tert-butoxycarbonyl)-3-[(3-[[(tert-butyldimethylsilyl)oxy]methyl]-2H,3H-furo[2,3-c]pyridin-7-yl)amino]indazol-6-yl]-5'-methoxy-2'-oxospiro[cyclopropane-1,3'-indole]-1'-carboxylate (100.00 mg, 1 equiv) were added DCM (3.00 mL) and TFA (1.50 mL) at room temperature. The resulting mixture was stirred for 6 h at room temperature, then concentrated under vacuum. The residue was purified by prep-HPLC with the following conditions: Column: Sunfire prep C18 column, 30×150, 5 μm; Mobile Phase A: Water (0.1% FA), Mobile Phase B: ACN; Flow rate: 60 mL/min; Gradient: 5% B to 40% B in 8 min 220 nm; RT1: 7.12 m in to afford the title compound (55 mg, 91.84%) as a white solid. m/z (EST, +ve ion)=470.15 $[M+H]^+$. $^1$H NMR (400 MHz, DMSO-$d_6$) δ 12.53 (s, 1H), 10.42 (s, 1H), 8.91 (s, 1H), 7.66-7.46 (m, 2H), 7.36 (s, 1H), 6.94-6.79 (m, 2H), 6.75 (d, J=8.4 Hz, 1H), 6.61-6.54 (m, 1H), 5.73 (d, J=2.6 Hz, 1H), 5.04 (s, 1H), 4.77-4.65 (m, 1H), 4.55-4.42 (m, 1H), 3.74-3.53 (m, 3H), 3.22-3.13 (m, 1H), 2.51 (s, 3H), 2.38-2.26 (m, 1H), 2.04-1.92 (m, 1H).

Step F: (1R,2S)-2-(3-[[(3S)-3-(hydroxymethyl)-2H,3H-furo[2,3-c] pyridin-7-yl]amino]-1H-indazol-6-yl)-5'-methoxy-1'H-spiro[cyclopropane-1,3'-indol]-2'-one and (1R,2S)-2-(3-[[(3R)-3-(hydroxymethyl)-2H,3H-furo[2,3-c]pyridin-7-yl]amino]-1H-indazol-6-yl)-5'-methoxy-1'H-spiro[cyclopropane-1,3'-indol]-2'-one

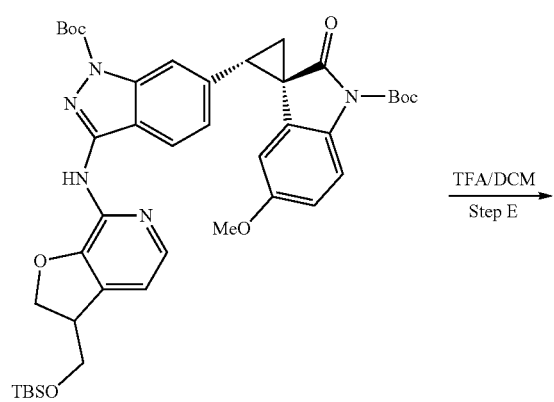

TFA/DCM
Step E

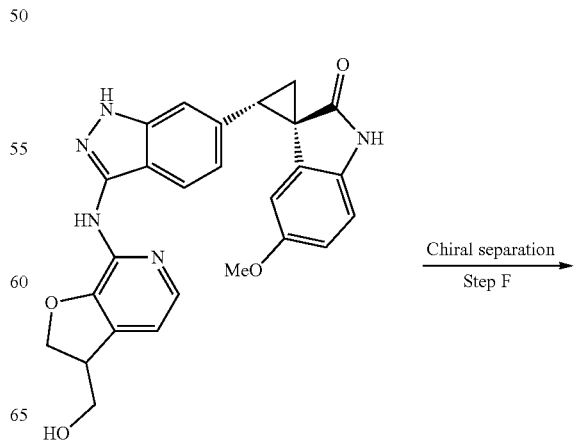

Chiral separation
Step F

-continued

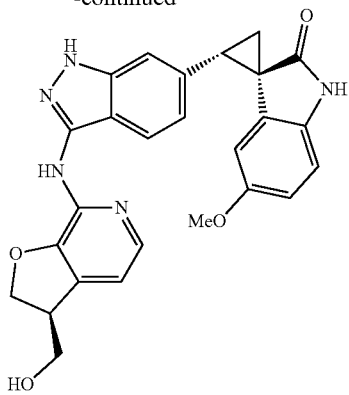

and

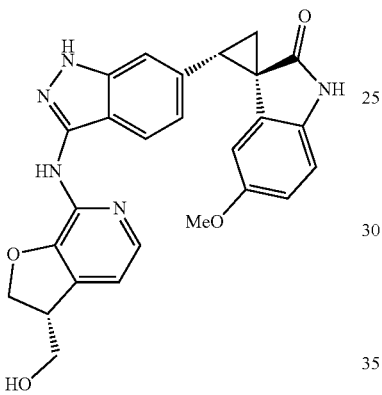

Racemic (1R,2S)-2-(3-[[3-(hydroxymethyl)-2H,3H-furo[2,3-c]pyridin-7-yl] amino]-1H-indazol-6-yl)-5'-methoxy-1'H-spiro[cyclopropane-1,3'-indol]-2'-one was separated by prep-Chiral-HPLC with the following conditions: Column: Column: CHIRALPAK IG, 2×25 cm, 5 un; Mobile Phase A: Hex (0.2% DEA)-HPLC, Mobile Phase B: EtOH:DCM=1:1-HPLC; Flow rate: 20 mL/min; Gradient: 60% B to 60% B in 12 min; Wavelength: 220/254 nm; RT1(min): 6.603: RT2 (min): 8.571 to afford (first peak) Example 34 (13.9 mg) as a white solid. m/z (EST, +ve ion)=470.15 [M+H]$^+$. $^1$H NMR (400 MHz, Methanol-$d_4$) δ 7.63 (d, J=8.4 Hz, 2H), 7.40 (s, 1H), 6.92 (d, J=7.6 Hz, 2H), 6.83 (d, J=8.4 Hz, 1H), 6.63 (d, J=2.8 Hz, 1H), 6.61 (d, J=2.4 Hz, 1H), 5.66 (d, J=2.4 Hz, 1H), 4.89 (s, 3H), 4.82-4.78 (m, 1H), 4.65-4.63 (m, 1H), 3.85-3.71 (m, 3H), 3.36-3.34 (s, 1H), 2.26-2.22 (m, 1H), 2.19-2.16 (m, 1H). And to afford second peak, the other diastereomer (11.3 mg) as a white solid. m/z (ESI, +ve ion)=470.15 [M+H]+. 1H NMR (400 MHz, Methanol-d4) δ 7.63 (d, J=8.4 Hz, 2H), 7.40 (s, 1H), 6.92 (d, J=7.6 Hz, 2H), 6.83 (d, J=8.4 Hz, 1H), 6.63 (d, J=2.8 Hz, 1H), 6.61 (d, J=2.4 Hz, 1H), 5.66 (d, J=2.4 Hz, 1H), 4.89 (s, 3H), 4.82-4.78 (m, 1H), 4.65-4.63 (m, 1H), 3.85-3.71 (m, 3H), 3.36-3.34 (s, 1H), 2.26-2.22 (m, 1H), 2.19-2.16 (m, 1H).

Example 35. (1R,2S)-5'-methoxy-2-(3-{[6-(3-methoxyazetidin-1-yl)pyrimidin-4-yl]amino}-1H-indazol-6-yl)spiro[cyclopropane-1,3'-indol]-2'(1'H)-one

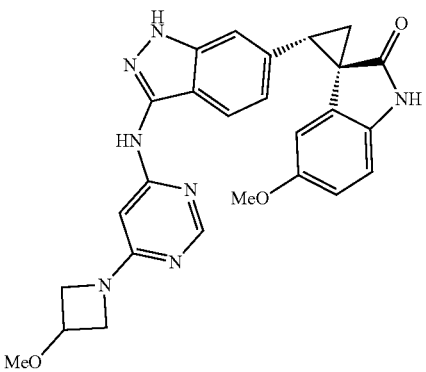 [SMILES: COc1ccc2c(c1)[C@]1(C[C@H]1c1ccc3c(Nc4cc(N5CC(OC)C5)ncn4)n[nH]c3c1)C(=O)N2]

Step A.
6-(3-methoxyazetidin-1-yl)pyrimidin-4-amine)

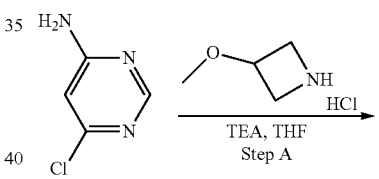

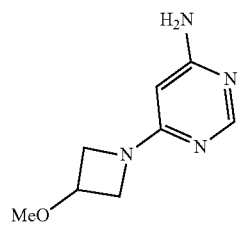

To a mixture of 6-chloropyrimidin-4-amine (516.00 mg, 3.983 mmol, 1.00 equiv) and 3-methoxyazetidine hydrochloride (590.67 mg, 4.800 mmol, 1.20 equiv) in THF (20.00 mL) was added TEA (806.08 mg, 7.966 mmol, 2.00 equiv). The resulting mixture was stirred for 16 h at 60° C. The reaction was concentrated under reduced pressure. The residue was purified by RP flash, eluted with 10% ACN in water (10 mM NH$_4$HCO$_3$) to afford the title compound (200 mg, 27.86%) as a white solid. m/z (ESI, +ve ion)=181.15 [M+H]$^+$. $^1$H NMR (400 MHz, DMSO-$d_6$) δ 7.91 (d, J=1.0 Hz, 1H), 6.23 (s, 2H), 5.23 (d, J=1.0 Hz, 1H), 4.30-4.26 (m, 1H), 4.08-4.04 (m, 2H), 3.69-3.66 (m, 2H), 3.23 (s, 3H).

289

Step B. tert-butyl (1R,2S)-2-[1-(tert-butoxycarbonyl)-3-[[6-(3-methoxyazetidin-1-yl)pyrimidin-4-yl]amino]indazol-6-yl]-5'-methoxy-2'-oxospiro[cyclopropane-1,3'-indole]-1'-carboxylate

290

Step C. (1R,2S)-5'-methoxy-2-(3-[[6-(3-methoxyazetidin-1-yl)pyrimidin-4-yl] amino]-1H-indazol-6-yl)-1'H-spiro[cyclopropane-1,3'-indol]-2'-one

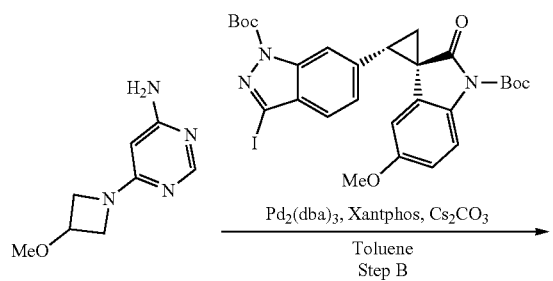

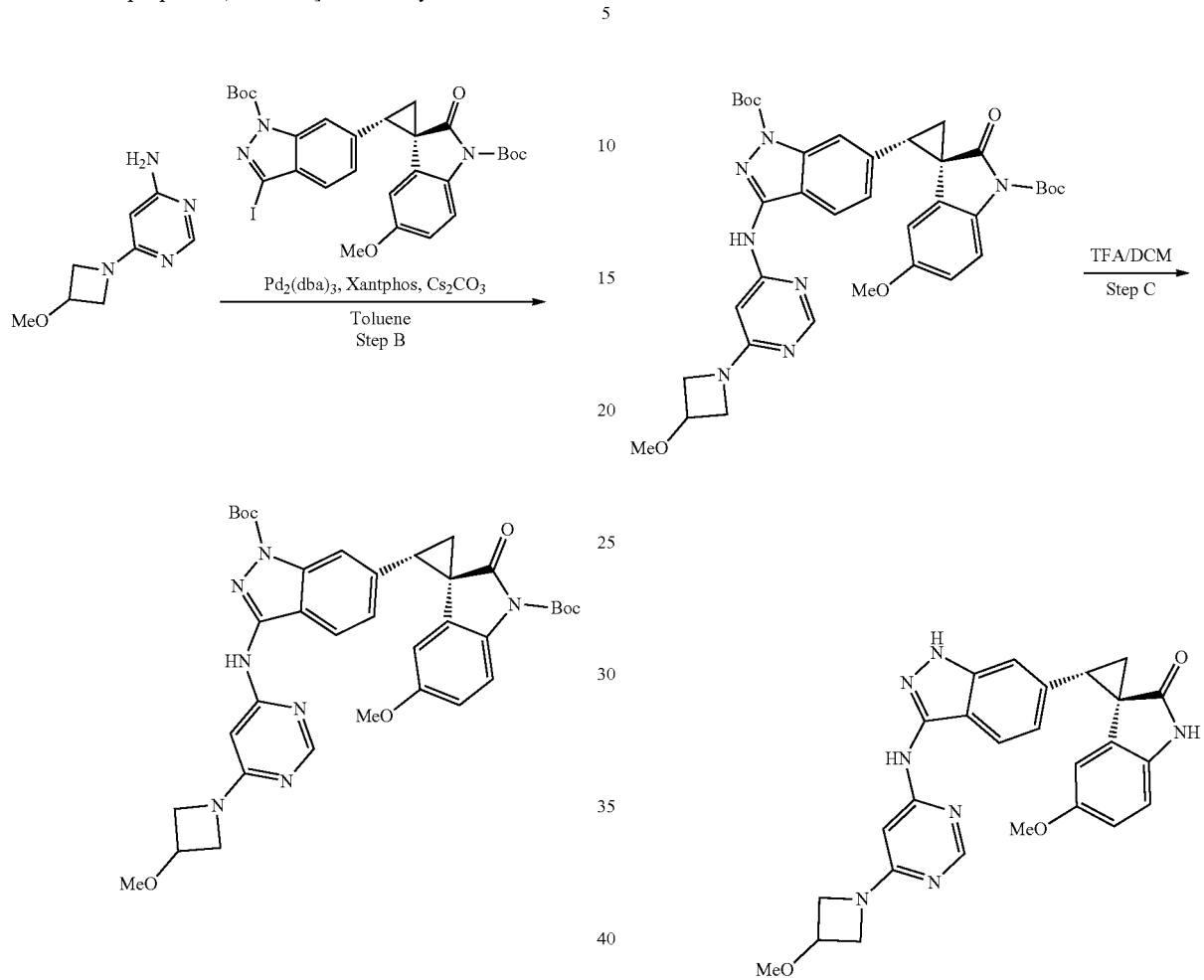

To the mixture of 6-(3-methoxyazetidin-1-yl)pyrimidin-4-amine) (35.00 mg, 0.194 mmol, 1.00 equiv) and tert-butyl (1R,2S)-2-[I-(tert-butoxycarbonyl)-3-iodoindazol-6-yl]-5'-methoxy-2'-oxospiro[cyclopropane-1,3'-indole]-1'-carboxylate (134.91 mg, 0.214 mmol, 1.1 equiv) in toluene (3.00 mL) were added $Cs_2CO_3$ (126.56 mg, 0.388 mmol, 2 equiv). $Pd_2(dba)_3$ (17.78 mg, 0.019 mmol, 0.1 equiv) and XantPhos (11.24 mg, 0.019 mmol, 0.1 equiv) under argon atmosphere. The mixture was stirred at 90° C. for 2 h. The mixture was filtered and washed with EA (3×10 mL). The filtrate was removed under reduced pressure and the residue was purified by prep-TLC (rinsed with EA/PE=1/1) to give the title compound (88 mg, 62.95%) as a yellow solid. m/z (ESI, +ve ion)=684.45 [M+H]$^+$. $^1$H NMR (400 MHz, Chloroform-d) δ 8.29 (d, J=1.2 Hz, 1H), 8.13 (s, 1H), 7.81 (d, J=8.8 Hz, 1H), 7.75-7.73 (m, 1H), 7.56-7.54 (m, 1H), 7.13 (d, J=8.4 Hz, 1H), 6.70-6.67 (m, 1H), 5.55 (d, J=2.4 Hz, 1H), 4.41-4.38 (m, 3H), 4.11 (d, J=8.0 Hz, 2H), 3.52 (t, J=8.8 Hz, 1H), 3.40 (d, J=8.8 Hz, 6H), 2.39-2.36 (m, 1H), 2.12 (s, 1H), 1.71 (d, J=4.4 Hz, 18H).

The mixture of tert-butyl (1R,2S)-2-[1-(tert-butoxycarbonyl)-3-[[6-(3-methoxyazetidin-1-yl)pyrimidin-4-yl]amino]indazol-6-yl]-5'-methoxy-2'-oxospiro[cyclopropane-1,3'-indole]-1'-carboxylate (100 mg, 0.146 mmol, 1.00 equiv) in TFA (0.50 mL) and DCM (5.00 mL) was stirred at 25° C. for 2 h. The mixture was quenched with saturated aqueous of $NaHCO_2$ (20 mL) and extracted with EA (3×20 mL). The combined organic was dried over anhydrous $Na_2SO_4$ and filtered. The filtrate was concentrated in vacuo. The product was purified with the following conditions: Column: Column: XBridge Prep OBD C18 Column, 30×150 mm, 5 μm; Mobile Phase A: Water (10 mmol/L $NH_4HCO_3$). Mobile Phase B: ACN; Flow rate: 60 mL/min; Gradient: 18% B to 35% B in 8 min; Detector: 254 and 220 nm; RT1: 7.43 min. The product-containing fractions were combined and concentrated to give Example 35 (32.3 mg, 45.7%) as a white solid. m/z (ESI, +ve ion)=484.20 [M+H]. $^1$H NMR (400 MHz, DMSO-4) δ 12.37 (s, 1H), 10.42 (s, 1H), 9.82 (s, 1H), 8.15 (d, J=0.8 Hz, 1H), 7.95 (d, J=8.4 Hz, 1H), 7.33 (s, 1H), 6.90-6.88 (m, 1H), 6.78-6.74 (m, 2H), 6.60-6.57 (m, 1H), 5.69 (d, J=2.8 Hz, 1H), 4.37-4.31 (m, 1H), 4.19-4.15 (m, 2H), 3.80-3.76 (m, 2H), 3.33 (s, 3H), 3.26 (s, 3H), 3.17 (t, J=8.4 Hz, 1H), 2.35-2.32 (m, 1H), 1.99-1.95 (m, 1H).

Example 36. (1R,2S)-2-(3-{[6-(3-hydroxyazetidin-1-yl)pyrimidin-4-yl]amino}-1H-indazol-6-yl)-5'-methoxyspiro[cyclopropane-1,3'-indol]-2'(1'H)-one

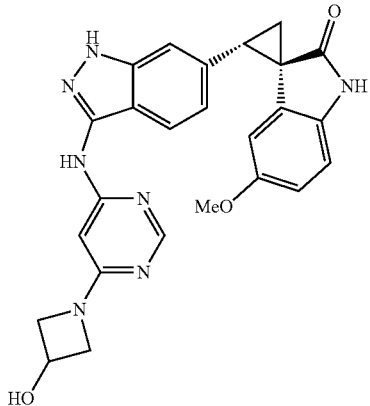 [SMILES: COc1ccc2c(c1)[C@]1(C[C@H]1c1ccc3c(Nc4cc(N5CC(O)C5)ncn4)n[nH]c3c1)C(=O)N2]

Step A. 3-[(tert-butyldimethylsilyl)oxy]azetidine

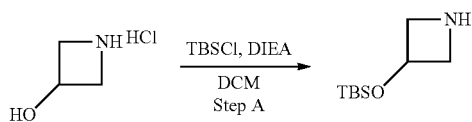

To a stirred solution of azetidin-3-ol (1.09 g, 14.912 mmol, 1.00 equiv) and t-butyldimethylchlorosilane (2.25 g, 14.912 mmol, 1.00 equiv) in DCM (10.00 mL) was added DIEA (4.82 g, 37.280 mmol, 2.50 equiv) dropwise at room temperature under nitrogen atmosphere. The resulting mixture was stirred for overnight at room temperature under nitrogen atmosphere, then concentrated under vacuum. The residue was neutralized to pH 8 with saturated NaHCO$_3$. The resulting mixture was extracted with EtOAc (2×100 mL). The combined organic layers were washed with brine (3×40 mL), dried over anhydrous Na$_2$SO$_4$. After filtration, the filtrate was concentrated under reduced pressure to give the title compound (12a) (1.5 g, 53.69%) as a yellow oil. $^1$H NMR (400 MHz, Chloroform-d) δ 4.50-4.53 (m, 1H), 3.47-3.44 (m, 2H), 2.50-2.52 (s, 2H), 0.85-0.87 (m, 9H), 0.02-0.04 (m, 6H).

Step B. 6-[3-[(tert-butyldimethylsilyl)oxy]azetidin-1-yl]pyrimidin-4-amine

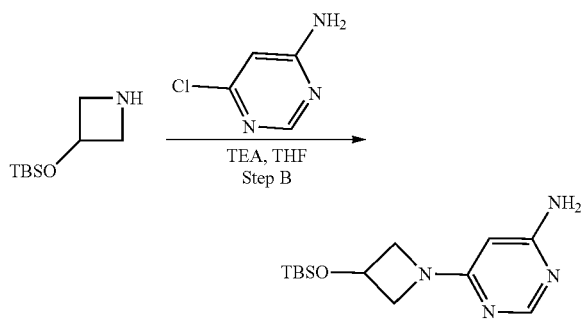

To a stirred mixture of 3-[(tert-butyldimethylsilyl)oxy]azetidine (299.37 mg, 1.598 mmol, 1.50 equiv) and 6-chloropyrimidin-4-amine (138.00 mg, 1.065 mmol, 1.00 equiv) in THF (0.50 mL) was added TEA (161.40 mg, 1.598 mmol, 1.50 equiv) at room temperature under nitrogen atmosphere. The resulting mixture was stirred overnight at 60° C., then cooled down to room temperature. The resulting mixture was concentrated under vacuum. The residue was purified by silica gel column chromatography, eluted with PE/EtOAc (3/1) to afford the title compound (256 mg, 85.69%) as a yellow solid. m/z (ESI, +ve ion)=281.20 [M+H]$^+$.

Step C. (1R,2S)-5'-methoxy-2-(3-[[5-methoxy-6-(morpholin-4-yl)pyrimidin-4-yl](methyl)amino]-1H-indazol-6-yl)-1'H-spiro[cyclopropane-1,3'-indol]-2'-one

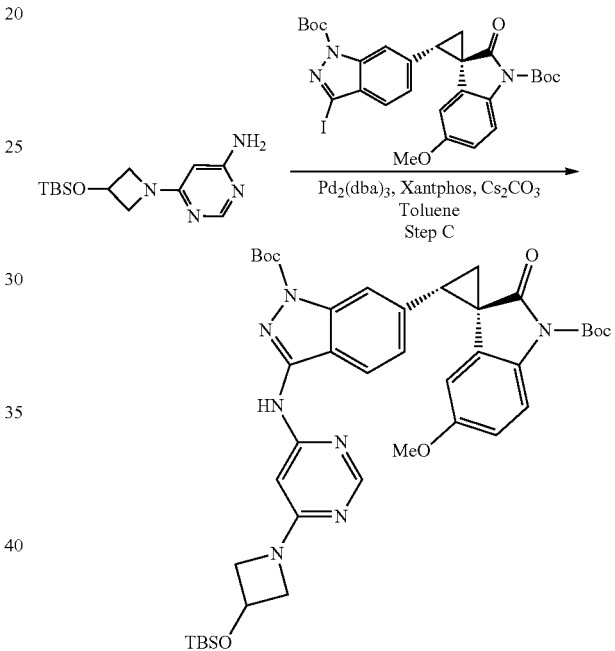

To the mixture of 6-[3-[(tert-butyldimethylsilyl)oxy]azetidin-1-yl]pyrimidin-4-amine (60.00 mg, 0.214 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (135.10 mg, 0.214 mmol, 1 equiv) in toluene (2.50 mL) were added Cs$_2$CO$_3$ (139.41 mg, 0.428 mmol, 2 equiv), Pd$_2$(dba)$_3$ (19.59 mg, 0.021 mmol, 0.1 equiv) and XantPhos (12.38 mg, 0.021 mmol, 0.1 equiv) under argon atmosphere. The mixture was stirred at 90° C. for 2 h. The mixture was filtered and washed with EA (3×10 mL). The filtrate was removed under reduced pressure and the residue was purified by silica gel column eluted with EA/PE=1/1 to give the title compound (100 mg, 56.64%) as an off-white solid. m/z (ESI, +ve ion)=784.25 [M+H]$^+$. $^1$H NMR (400 MHz, DMSO-d$_6$) δ 10.45 (s, 1H), 8.28-8.24 (m, 2H), 8.04 (s, 1H), 7.68 (d, J=8.8 Hz, 1H), 7.36-7.34 (m, 1H), 7.26 (d, J=1.2 Hz, 1H), 6.74-6.71 (m, 1H), 5.71 (d, J=2.8 Hz, 1H), 4.85-4.80 (m, 1H), 4.31-4.28 (m, 2H), 3.80-3.74 (m, 2H), 3.44-3.40 (m, 1H), 3.35 (s, 3H), 2.48-2.45 (m, 1H), 2.21-2.17 (m, 1H), 1.60 (d, J=6.4 Hz, 18H), 0.88 (s, 9H), 0.08 (s, 6H).

Step D. (1R,2S)-2-(3-[[6-(3-hydroxyazetidin-1-yl)pyrimidin-4-yl]amino]-1H-indazol-6-yl)-5'-methoxy-1'H-spiro[cyclopropane-1,3'-indol]-2'-one

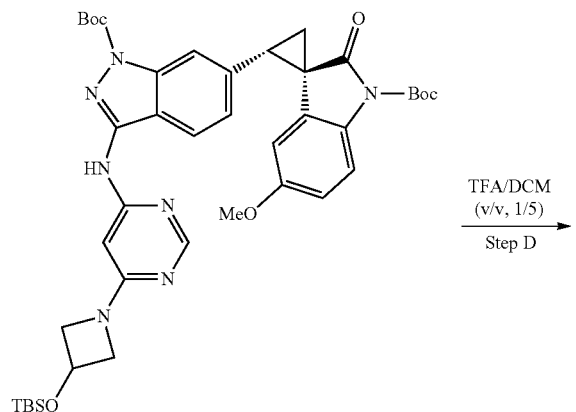

The mixture of (1R,2S)-5'-methoxy-2-(3-[[5-methoxy-6-(morpholin-4-yl)pyrimidin-4-yl](methyl)amino]-1H-indazol-6-yl)-1'H-spiro[cyclopropane-1,3'-indol]-2'-one (100.00 mg, 0.128 mmol, 1.00 equiv) in TFA (0.50 mL) and DCM (2.50 mL) was stirred at 25° C. for 12 h. The solvent was removed under reduced pressure. The residue was further purified with the following conditions: Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 10% B to 40% B in 7 min; Detector: 254 & 220 nm; RT1: 7.27 min. The product-containing fractions were combined and concentrated to give Example 36 (33.4 mg, 58.12%) as a white solid. m/z (ESI, +ve ion)=470.35 [M+H]. $^1$H NMR (400 MHz, DMSO-$d_6$) δ 12.38 (s, 1H), 10.43 (s, 1H), 9.81 (s, 1H), 8.14 (d, J=0.8 Hz, 1H), 7.94 (d, J=8.4 Hz, 1H), 7.33 (s, 1H), 6.90-6.87 (m, 1H), 6.77-6.73 (m, 2H), 6.59-6.56 (m, 1H), 5.75 (d, J=6.8 Hz, 1H), 5.68 (d, J=2.4 Hz, 1H), 4.58 (s, 1H), 4.20-4.16 (m, 2H), 3.72-3.69 (m, 2H), 3.32 (s, 3H), 3.17 (t, J=8.4 Hz, 1H), 2.35-2.32 (m, 1H), 1.98-1.95 (m, 1H).

Example 37. (1R,2S)-2-(3-((6-(3-oxa-8-azabicyclo[3.2.1]octan-8-yl)-5-methoxypyrimidin-4-yl)amino)-1H-indazol-6-yl)-5'-methoxyspiro[cyclopropane-1,3'-indolin]-2'-one

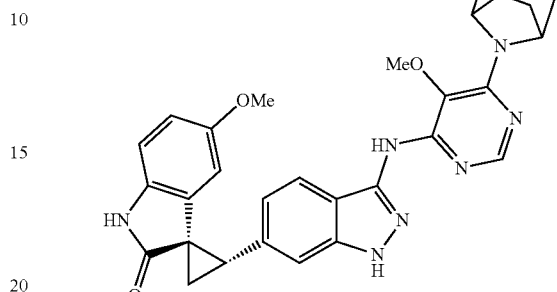

Step A. 5-(6-chloro-5-methoxy-pyrimidin-4-yl)-2-oxa-5-azabicyclo[2.2.2]octane

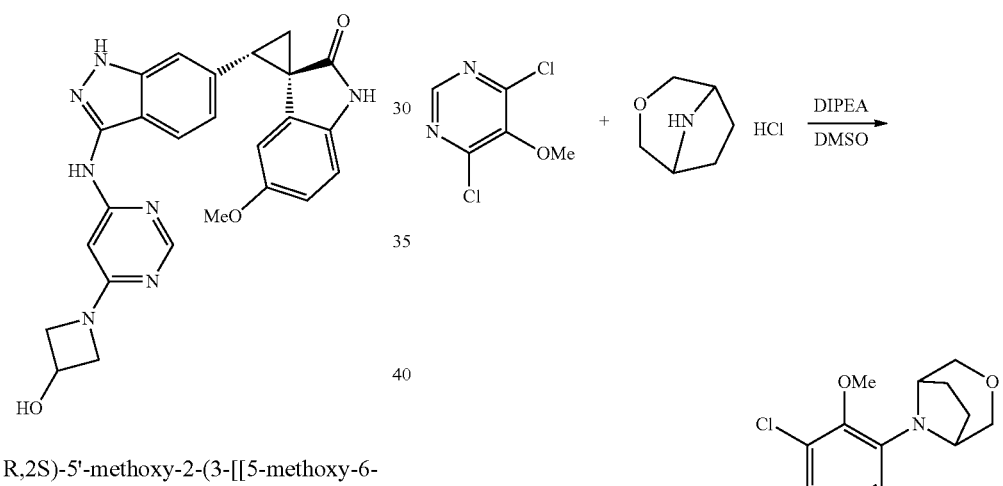

To a 50 ml round bottom flask containing 4,6-Dichloro-5-methoxypyrimidine (200.0 mg, 1.120 mmol) in DMSO (3.7 mL) were added (1R,5S)-3-Oxa-8-azabicyclo[3.2.1]octane hydrochloride (1:1) (167.2 mg, 1.120 mmol) and N-ethyl-N-isopropylpropan-2-amine (0.50 mL, 2.8 mmol). The reaction mixture was heated to 60° C. and stirred, monitored by LCMS until the full conversion of the starting materials (approx. 80 min). Then the reaction mixture was cooled down to rt, diluted with EtOAc and water, extracted with EtOAc for 3 times. The organic layer was then dried over $Na_2SO_4$. The residue was purified by column chromatography (ethyl acetate/hexane=0~50%) to provide the title compound (228.0 mg, 80%) as a white solid.

295

Step B. tert-butyl (1R,2S)-2-[1-tert-butoxycarbonyl-3-[[5-methoxy-6-(2-oxa-5-azabicyclo[2.2.2]octan-5-yl)pyrimidin-4-yl]amino]indazol-6-yl]-5'-methoxy-2'-oxo-spiro[cyclopropane-1,3'-indoline]-1'-carboxylate

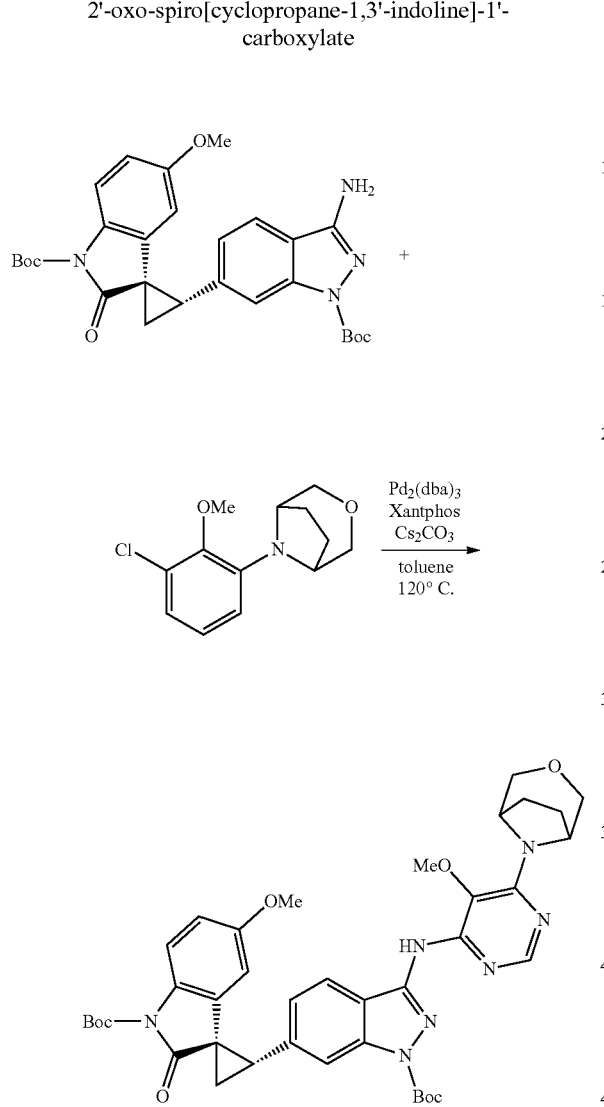

To a 50 ml round bottom flask were added cesium carbonate (37.6 mg, 0.115 mmol), tert-butyl (1R,2S)-2-(3-amino-1-tert-butoxycarbonyl-indazol-6-yl)-5'-methoxy-2'-oxo-spiro[cyclopropane-1,3'-indoline]-1'-carboxylate (30.0 mg, 0.0600 mmol), Tris(dibenzylideneacetone)dipalladium (0) (5.3 mg, 0.010 mmol), 5-(6-chloro-5-methoxy-pyrimidin-4-yl)-2-oxa-5-azabicyclo[2.2.2]octane (15.4 mg, 0.0605 mmol), Xantphos (3.3 mg, 0.010 mmol) and dry toluene (2.9 mL). The reaction mixture was stirred and purged with argon (in balloon) for 10 min to form a green suspension, and then heated to 120° C., resulting in a yellow suspension. The reaction was monitored by LCMS and TLC until the full conversion of the starting materials (approx. 5 hrs), cooled down to rt, diluted with EtOAc, washed with sat. aq. NaHCO₃ and dried over Na₂SO₄. The residue was purified by column chromatography (ethyl acetate/hexane=0~50%) to provide the title compound (16.0 mg, 38%) as a yellow oil.

296

Step C

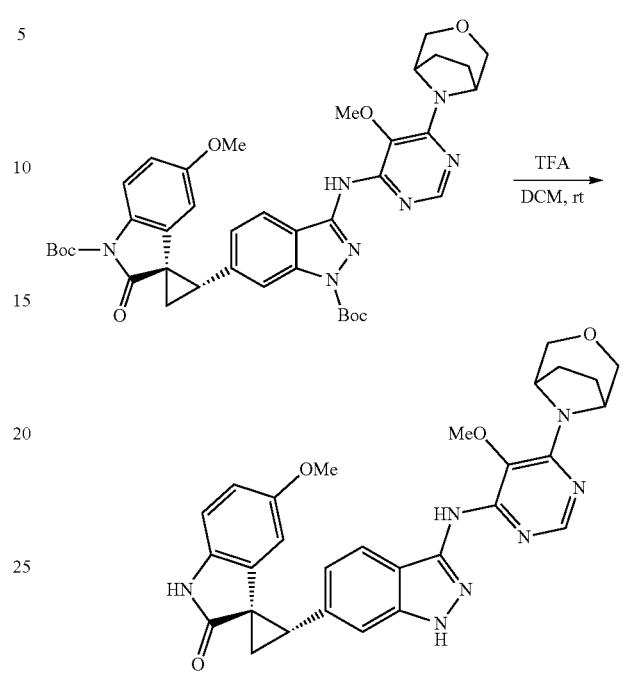

This compound was prepared from tert-butyl (1R,2S)-2-[1-tert-butoxycarbonyl-3-[[5-methoxy-6-(2-oxa-5-azabicyclo[2.2.2]octan-5-yl)pyrimidin-4-yl]amino]indazol-6-yl]-5'-methoxy-2'-oxo-spiro[cyclopropane-1,3'-indoline]-1'-carboxylate (16.0 mg, 0.0200 mmol) and trifluoroacetic acid (0.17 mL, 2.2 mmol). The resulting brown solution was purified by Prep. HPLC (Gemini C18, 10 to 90% (0.1% TFA in water)/(0.1% TFA in Acetonitrile)) to provide Example 37 (7.8 mg, 67%) as a colorless film. $^1$H NMR (400 MHz, METHANOL-$d_4$) δ ppm 2.08-2.14 (m, 2H) 2.15-2.27 (m, 5H) 3.34-3.36 (m, 3H) 3.70-3.75 (m, 2H) 3.79-3.84 (m, 5H) 4.98-5.03 (m, 2H) 5.61 (d, J=2.27 Hz, 1H) 6.62 (dd, J=8.59, 2.53 Hz, 1H) 6.83 (d, J=8.84 Hz, 1H) 7.03 (dd, J=8.46, 0.88 Hz, 1H) 7.48-7.51 (m, 1H) 7.87-7.91 (m, 1H) 8.22 (s, 1H); m/z (ESI, +ve ion) 540.2 (M+H)+.

Example 38. (1R,2S)-2-(3-{[6-(2-hydroxyethoxy)pyrimidin-4-yl]amino}-1H-indazol-4-yl)-5'-methoxyspiro[cyclopropane-1,3'-indol]-2'(1'H)-one

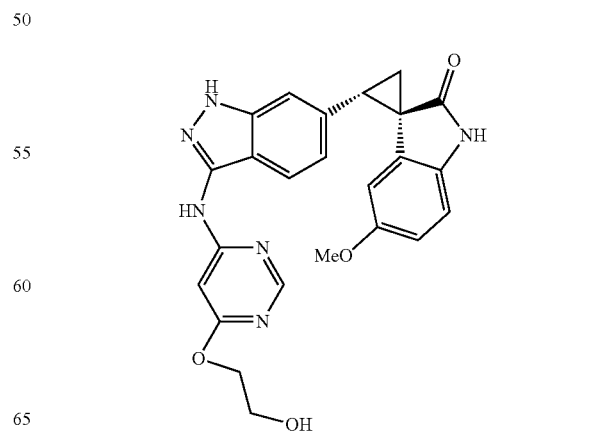

Step A. 6-[2-[(tert-butyldimethylsilyl)oxy]ethoxy] pyrimidin-4-amine

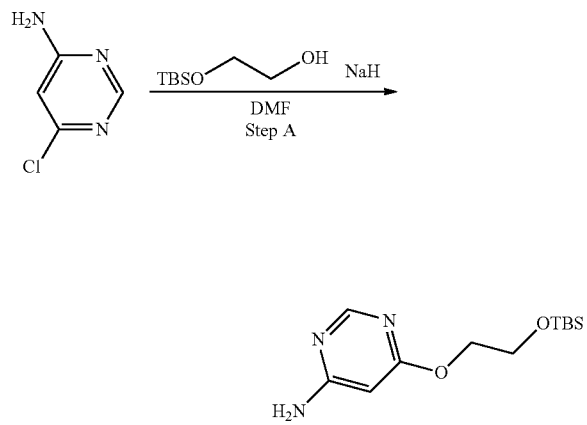

To a stirred mixture of 6-chloropyrimidin-4-amine (600.00 mg, 4.631 mmol, 1.00 equiv) and 2-[(tert-butyldimethylsilyl)oxy]ethanol (1224.99 mg, 0.000 mmol, 1.50 equiv) in THF (15.00 mL) was added NaH (222.29 mg, 9.262 mmol, 2.00 equiv, 60/o in mineral oil) in portions at 0° C. under nitrogen atmosphere. The resulting mixture was stirred for 2 h at 100° C. under nitrogen atmosphere, then cooled down to room temperature. The reaction was quenched with sat. NH$_4$Cl (30 mL) at room temperature. The resulting mixture was extracted with DCM (3×20 mL). The combined organic layers were washed with brine (30 mL), dried over anhydrous Na$_2$SO$_4$. After filtration, the filtrate was concentrated under reduced pressure. The residue was purified by reverse flash chromatography with the following conditions: column, C18 silica gel; mobile phase. ACN in water, 30% to 70% gradient in 60 min-; detector, UV 254 nm to give the title compound (164 mg, 13.14%) as a pink solid. m/z (ESI, +ve ion)=270.25 [M+H]$^+$. $^1$H NMR (400 MHz, DMSO-d$_6$) δ 8.08 (d, J=1.0 Hz, 1H), 6.60 (s, 2H), 5.68 (d, J=1.1 Hz, 1H), 4.58-4.07 (m, 2H), 3.86 (m, 2H), 0.86 (d, J=1.4 Hz, 9H), 0.12-0.03 (m, 6H).

Step B. tert-butyl(1R,2S)-2-[1-(tert-butoxycarbonyl)-3-[(6-[2-[(tert-butyldimethylsilyl)oxy]ethoxy] pyrimidin-4-yl)amino]indazol-6-yl]-5-methoxy-2-oxospiro[cyclopropane-1,3-indole]-1-carboxylate

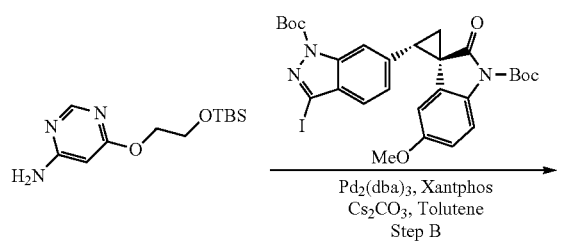

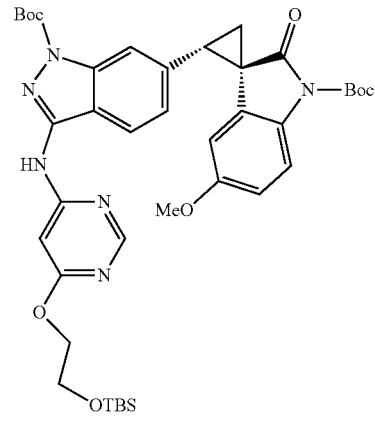

To a stirred solution of 6-[2-[(tert-butyldimethylsilyl)oxy] ethoxy] pyrimidin-4-amine (51.15 mg, 1.2 equiv) and tert-butyl (1R,2S)-2-[I-(tert-butoxycarbonyl)-3-iodoindazol-6-yl]-5-methoxy-2-oxospiro[cyclopropane-1,3-indole]-1-carboxylate (100 mg, 1.00 equiv) in toluene (3 mL) were added Pd$_2$(dba), (14.50 mg, 0.1 equiv), XantPhos (9.16 mg, 0.1 equiv) and Cs$_2$CO$_3$ (103.26 mg, 2 equiv) at room temperature under nitrogen atmosphere. The resulting mixture was stirred for 2 h at 90° C. under nitrogen atmosphere. The resulting mixture was cooled down and filtered, the filter cake was washed with MeOH (2×10 mL). The filtrate was concentrated under reduced pressure. The residue was purified by silica gel column chromatography, eluted with PE/EtOAc (2/1) to afford the title compound (110 mg, 89.86%) as a yellow solid. m/z [ESI+ve ion]=773.35 [M+H]$^+$.

Step C. (1R,2S)-2-(3-[[6-(2-hydroxyethoxy)pyrimidin-4-yl]amino]-1H-indazol-6-yl)-5-methoxy-1H-spiro[cyclopropane-1,3-indol]-2-one

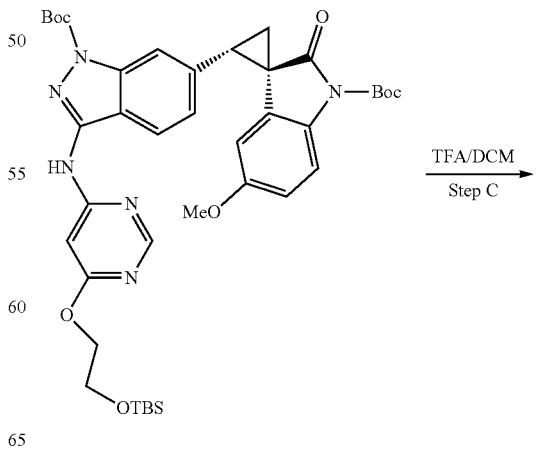

299

-continued

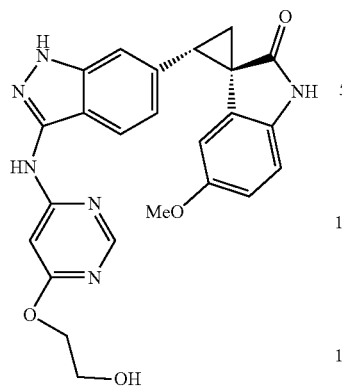

A mixture of tert-butyl(1R,2S)-2-[1-(tert-butoxycarbonyl)-3-[(6-[2-[(tert-butyldimethylsilyl)oxy]ethoxy]pyrimidin-4-yl)amino]indazol-6-yl]-5-methoxy-2-oxospiro[cyclopropane-1,3-indole]-1-carboxylate (130.00 mg, 0.168 mmol, 1.00 equiv) and TFA (2.00 mL, 0.018 mmol, 0.10 equiv) in DCM (10.00 m L) was stirred for 4 h at room temperature. The mixture was neutralized to pH 7 with saturated NaHCO$_3$. The resulting mixture was extracted with DCM (3×10 mL). The combined organic layers were washed with brine (15 mL), dried over anhydrous Na$_2$SO$_4$. After filtration, the filtrate was concentrated under reduced pressure. The residue was purified by prep-HPLC with the following conditions Column: YMC-Actus Triart C18 ExRS, 30×150 mm, 5 µm; Mobile Phase A: Water (10 mmol/L NH$_4$HCO$_3$), Mobile Phase B: ACN; Flow rate: 60 mL/min; Gradient: 15% B to 30% B in 10 min, 30% B; Wavelength: 254 nm; RT1: 8.5 min to afford Example 38 (8.2 mg, 25.94%) as a white solid. m/z (ESI+ve ion)=459.10 [M+H]$^+$. $^1$H NMR (400 MHz, DMSO-d$_6$) δ 12.42 (s, 1H), 10.42 (s, 1H), 10.19 (s, 1H), 8.36 (d, J=0.8 Hz, 1H), 7.95 (d, J=8.4 Hz, 1H), 7.36 (s, 1H), 7.24 (s, 1H), 6.92 (d, J=8.4 Hz, 1H), 6.75 (d, J=8.4 Hz, 1H), 6.59 (m, 1H), 5.69 (d, J=2.4 Hz, 1H), 4.88 (s, 1H), 4.30 (t, J=4.8 Hz, 2H), 3.70 (d, J=4.4 Hz, 2H), 3.30 (s, 3H), 3.20 (s, 1H), 2.33 (s, 1H), 1.98 (m, 1H).

Example 39. (1R,2S)-2-(3-((6-(1,1-dioxidothiomorpholino)pyrimidin-4-yl)amino)-1H-indazol-6-yl)-5'-methoxyspiro[cyclopropane-1,3'-indolin]-2'-one

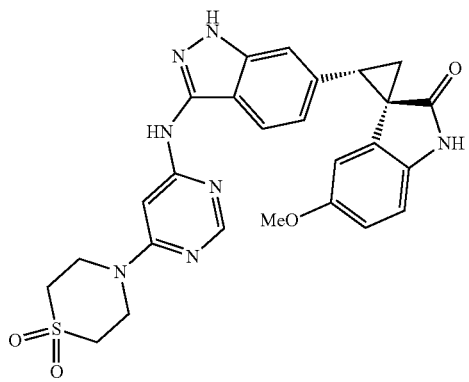 [SMILES: COc1ccc2c(c1)[C@]1(C[C@H]1c1ccc3c(Nc4cc(N5CCS(=O)(=O)CC5)ncn4)n[nH]c3c1)C(=O)N2]

300

Step A. 4-(6-aminopyrimidin-4-yl)-1lambda6-thiomorpholine-1,1-dione

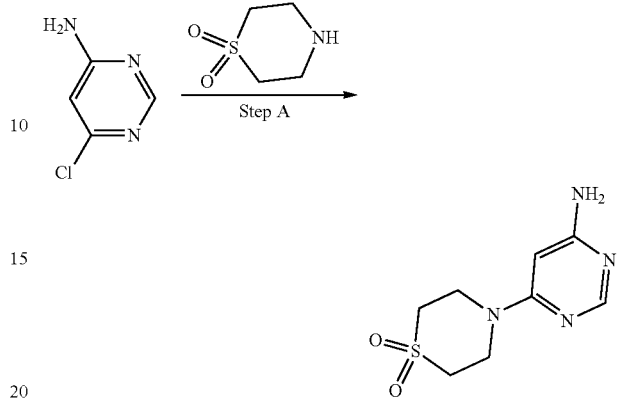

Into a 20 mL vial were added 6-chloropyrimidin-4-amine (300.00 mg, 2.316 mmol, 1.00 equiv) and 1lambda 6-thiomorpholine-1,1-dione (939.11 mg, 6.947 mmol, 3.00 equiv) at room temperature. The resulting mixture was stirred overnight at 80° C. under nitrogen atmosphere. After cooled down to room temperature, the residue was purified by silica gel column chromatography, eluted with PE/EtOAc (3/1) to afford the title compound (110 mg, 19.21%) as a yellow solid. m/z (ESI, +ve ion)=229.10 [M+H]$^+$. $^1$H NMR (400 MHz, DMSO-d$_6$) δ 8.01 (d, J=0.9 Hz, 1H), 6.34 (s, 2H), 5.75 (d, J=1.1 Hz, 1H), 4.00-3.88 (m, 4H), 3.15-3.06 (m, 4H).

Step B. tert-butyl (1R,2S)-2-[1-(tert-butoxycarbonyl)-3-[[6-(1,1-dioxo-1lambda6-thiomorpholin-4-yl)pyrimidin-4-yl]amino]indazol-6-yl]-5'-methoxy-2'-oxospiro[cyclopropane-1,3'-indole]-1'-carboxylate

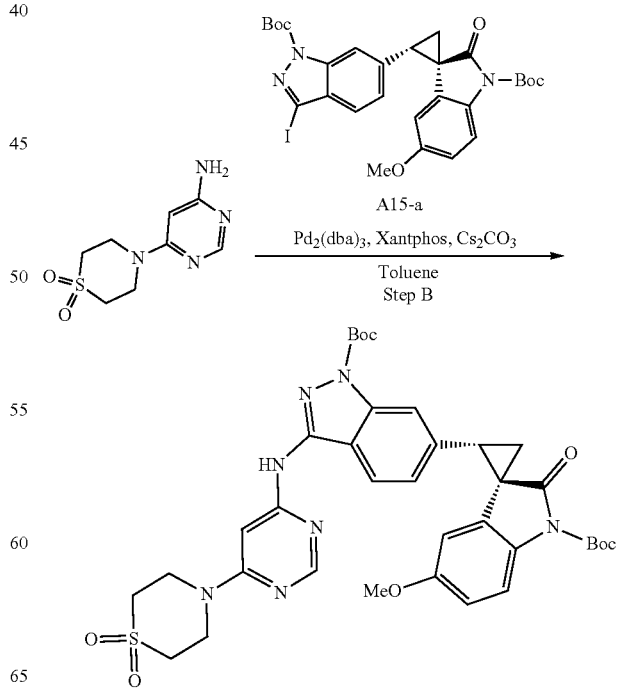

To a stirred mixture of tert-butyl (1R,2S)-2-[1-(tert-butoxycarbonyl)-3-iodoindazol-6-yl]-5-methoxy-2-oxospiro[cyclopropane-1,3-indole]-1-carboxylate (100.00 mg, 0.158 mmol, 1.00 equiv) and 4-(6-aminopyrimidin-4-yl)-1lambda6-thiomorpholine-1,1-dione (43.38 mg, 0.190 mmol, 1.20 equiv) in toluene (1.00 mL) were added Cs₂CO₃ (103.19 mg, 0.316 mmol, 2.00 equiv), Pd₂(dba)₃ (14.50 mg, 0.016 mmol, 0.10 equiv) and XantPhos (9.16 mg, 0.016 mmol, 0.10 equiv) at room temperature under nitrogen atmosphere. The resulting mixture was stirred for 2 h at 90° C. under nitrogen atmosphere and then cooled down to room temperature. The resulting mixture was diluted with water (20 mL), extracted with EtOAc (3×40 mL). The combined organic layers were washed with brine (40 mL), dried over anhydrous Na₂SO₄. After filtration, the filtrate was concentrated under reduced pressure. The residue was purified by silica gel column chromatography, eluted with PE/EA (1/1) to afford the title compound (100 mg, 86.29%) as an off-white solid. m/z (ESI, +ve ion)=732.25 [M+H]⁺. ¹H NMR (400 MHz, DMSO-d₆) δ 10.57 (s, 1H), 8.36 (d, J=0.9 Hz, 1H), 8.27 (d, J=8.3 Hz, 1H), 8.05 (d, J=14.3 Hz, 1H), 7.77 (s, 1H), 7.68 (d, J=8.9 Hz, 1H), 7.40-7.33 (m, 1H), 6.74-6.69 (m, 1H), 5.70 (d, J=2.7 Hz, 1H), 4.20-3.99 (m, 4H), 3.27-3.08 (m, 8H), 1.60 (d, J=5.2 Hz, 18H), 1.23 (s, 2H).

Step C. 4-[6-([6-[(1R,2S)-5'-methoxy-2'-oxo-1'H-spiro[cyclopropane-1,3'-indol]-2-yl]-1H-indazol-3-yl]amino)pyrimidin-4-yl]-1lambda6-thiomorpholine-1,1-dione

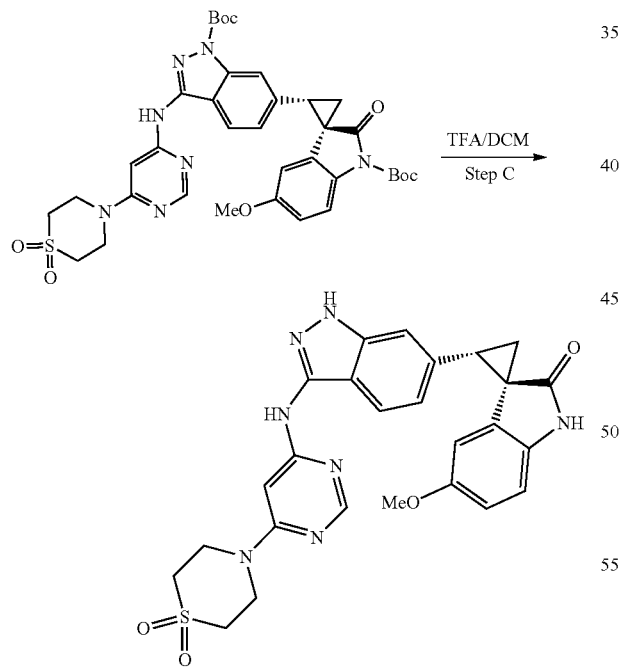

A mixture of tert-butyl (1R,2S)-2-[1-(tert-butoxycarbonyl)-3-[[6-(1,1-dioxo-1lambda6-thiomorpholin-4-yl)pyrimidin-4-yl]amino]indazol-6-yl]-5'-methoxy-2'-oxospiro[cyclopropane-1,3'-indole]-1'-carboxylate (100.00 mg) in DCM (0.80 mL) and TFA (0.20 mL) was stirred for 2 h at room temperature. The resulting mixture was concentrated under reduced pressure. The residue was purified by prep-HPLC with the following conditions: Column: XBridge Prep OBD C18 Column, 30×150 mm 5 μm; Mobile Phase A: Water (10 mmol/L NH₄HCO₃), Mobile Phase B: ACN; Flow rate: 60 mL/min; Gradient: 20% B to 32% B in 8 min, 254/220 nm; RT1: 7.05 min to afford Example 39 (15.1 mg) as a white solid m/z (ESI, +ve ion)=532.10 [M+H]⁺. ¹H NMR (400 MHz, DMSO-d₆) δ 12.41 (s, 1H), 10.42 (s, 1H), 9.93 (s, 1H), 8.26 (s, 1H), 7.94 (d, J=8.4 Hz, 1H), 7.34 (s, 1H), 7.27 (s, 1H), 6.90 (d, J=7.6 Hz, 1H), 6.75 (d, J=8.4 Hz, 1H), 6.60-6.57 (m, 1H), 5.69 (d, J=2.8 Hz, 1H), 4.04 (s, 4H), 3.33 (s, 3H), 3.19-3.16 (m, 5H), 2.35-2.32 (m, 1H), 1.99-1.96 (m, 1H).

Example 40. (1R,2S)-5'-methoxy-2-(3-{[6-(1,4-oxazepan-4-yl)pyrimidin-4-yl]amino}-1H-indazol-6-yl)spiro[cyclopropane-1,3'-indol]-2'(1'H)-one

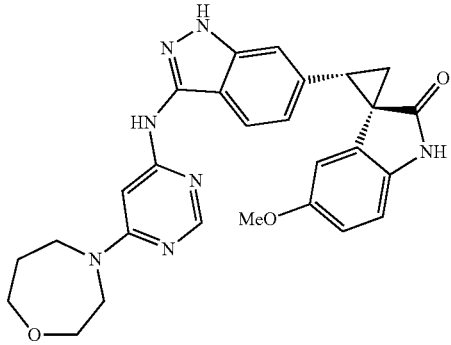 [SMILES: COc1ccc2c(c1)[C@]1(C[C@H]1c1ccc3c(Nc4cc(N5CCCOCC5)ncn4)n[nH]c3c1)C(=O)N2]

Step A. 6-(1,4-oxazepan-4-yl)pyrimidin-4-amine

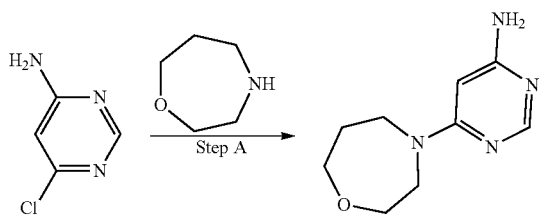

A mixture of 6-chloropyrimidin-4-amine (516.00 mg, 1 equiv) in 1,4-oxazepane (3.00 mL) was stirred for 16 h at 60° C. The mixture was purified with RP flash, eluted with RP flash, eluted with 10% ACN in water (10 mM NH₄HCO₃) to afford the title compound (300 mg, 38.78%) as a white solid. m/z (ESI+ve ion)=195.10 [M+H]⁺. ¹H NMR (400 MHz, DMSO-d₆) δ 7.92 (d, J=1.0 Hz, 1H), 6.12 (s, 2H), 5.50 (d, J=1.0 Hz, 1H), 3.66 (s, 4H), 3.63-3.55 (m, 4H), 1.88-1.78 (m, 2H).

Step B. tert-butyl (1R,2S)-2-[1-tert-butoxycarbonyl)-3-[[6-(1,4-oxazepan-4-yl)pyrimidin-4-yl]amino]indazol-6-yl]-5'-methoxy-2'-oxospiro[cyclopropane-1,3'-indole]-1'-carboxylate

Step C. (1R,2S)-5'-methoxy-2-(3-[[6-(1,4-oxazepan-4-yl)pyrimidin-4-yl]amino]-1H-indazol-6-yl)-1'H-spiro[cyclopropane-1,3'-indol]-2'-one

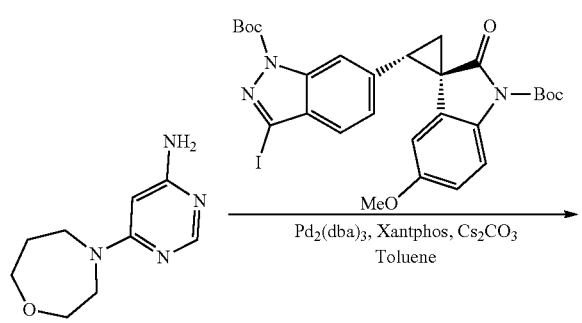

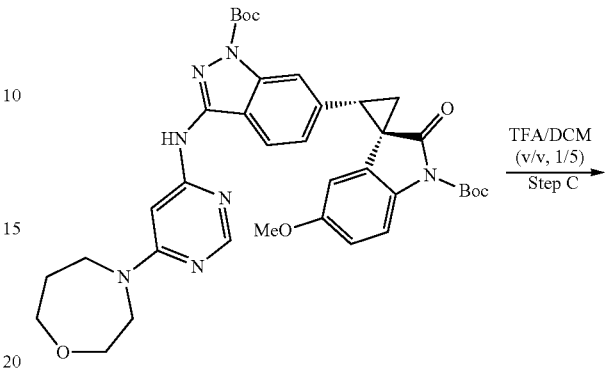

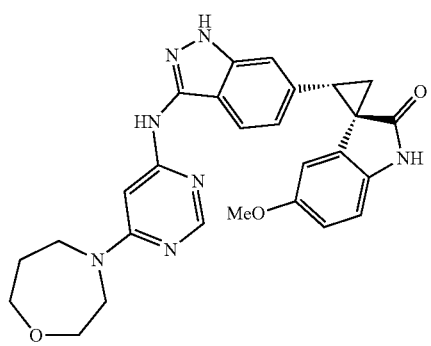

To the mixture of tert-butyl (1R,2S)-2-(1-(tert-butoxycarbonyl)-3-iodo-1H-indazol-6-yl)-5'-methoxy-2'-oxospiro[cyclopropane-1,3'-indoline]-1'-carboxylate (200.00 mg, 0.317 mmol, 1.00 equiv) and 6-(1,4-oxazepan-4-yl)pyrimidin-4-amine (73.82 mg, 0.380 mmol, 1.2 equiv) in toluene (5.00 mL) were added Cs₂CO₃ (206.39 mg, 0.633 mmol, 2 equiv), Pd₂(dba)₃ (29.00 mg, 0.032 mmol, 0.1 equiv) and XantPhos (18.33 mg, 0.032 mmol, 0.1 equiv) under argon atmosphere. The mixture was stirred at 90° C. for 2 h. The mixture was filtered and washed with EA (3×10 mL). The filtrate was removed under reduced pressure and the residue was purified by silica gel column eluted with EA/PE=1/1 to give the title compound (80 mg, 34.39%) as a yellow solid. m/z (ESI, +ve ion)=698.50 [M+H]. ¹H NMR (400 MHz, DMSO-d₆) δ 10.40 (s, 1H), 8.31-8.27 (m, 2H), 8.04 (s, 1H), 7.72-7.68 (m, 1H), 7.60 (s, 1H), 7.36 (d, J=8.8 Hz, 1H), 6.73 (d, J=9.6 Hz, 1H), 5.71 (s, 1H), 3.89-3.71 (m, 6H), 3.66-3.62 (m, 2H), 3.45-3.43 (m, 1H), 3.35 (s, 3H), 2.34 (s, 1H), 2.22-2.18 (m, 1H), 1.92 (s, 2H), 1.60 (s, 18H).

A mixture of tert-butyl (1R,2S)-2-[1-(tert-butoxycarbonyl)-3-[[6-(1,4-oxazepan-4-yl)pyrimidin-4-yl]amino]indazol-6-yl]-5'-methoxy-2'-oxospiro[cyclopropane-1,3'-indole]-1'-carboxylate (80.00 mg, 0.115 mmol, 1.00 equiv) in TFA (0.50 mL) and DCM (5.00 mL) was stirred at 25° C. for 2 h. The mixture was quenched with saturated aqueous of NaHCO₃ (20 mL) and extracted with EA (3×20 mL). The combined organics were dried over anhydrous Na₂SO₄, filtered and concentrated in vacuo. The product was purified with the following conditions: Column: XBridge Prep OBD C18 Column, 30×150 mm 5 μm; Mobile Phase A: Water (10 mmol/L NH₄HCO₃), Mobile Phase B: ACN; Flow rate: 60 mL/min; Gradient: 20/o B to 45% B in 8 min; Detector: 254&220 nm; RT1: 5.73 min. The product-containing fractions were combined and concentrated to give Example 40 (19.3 mg, 33.50%) as a white solid. m/z (ESI, +ve ion)=498.20 [M+H]⁺. ¹H NMR (400 MHz, DMSO-d₆) δ 12.37 (s, 1H), 10.43 (s, 1H), 9.75 (s, 1H), 8.17 (s, 1H), 7.96 (d, J=8.4 Hz, 1H), 7.33 (s, 1H), 7.12 (s, 1H), 6.90-6.88 (m, 1H), 6.75 (d, J=8.6 Hz, 1H), 6.60-6.57 (m, 1H), 5.69 (d, J=2.4 Hz, 1H), 3.78-3.68 (m, 6H), 3.63 (t, J=5.6 Hz, 2H), 3.33 (s, 3H), 3.18 (t, J=8.0 Hz, 1H), 2.35-2.32 (m, 1H), 1.99-1.96 (m, 1H), 1.90-1.88 (m, 2H).

Example 41. (1R,2S)-5'-methoxy-2-(3-{[5-methoxy-2-methyl-6-(morpholin-4-yl)pyrimidin-4-yl]amino}-1H-indazol-6-yl)spiro[cyclopropane-1,3'-indol]-2'(1'H)-one

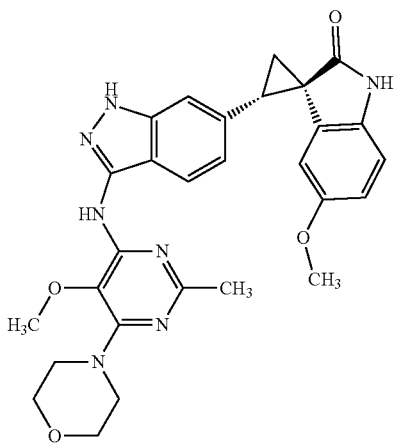 [SMILES: COc1ccc2c(c1)[C@]1(C[C@H]1c1ccc3c(Nc4nc(C)nc(N5CCOCC5)c4OC)n[nH]c3c1)C(=O)N2]

Step A. 6-Hydroxy-5-methoxy-2-methylpyrimidin-4(3H)-one

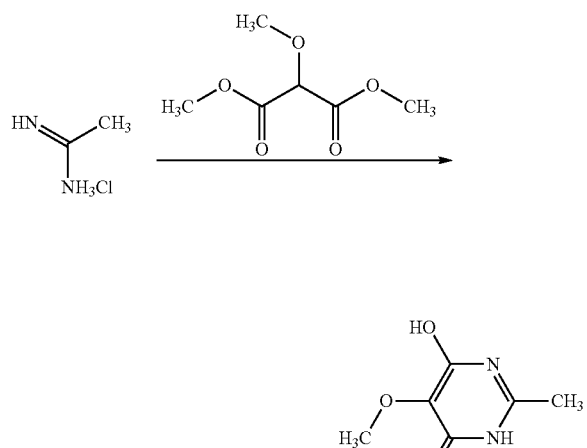

To an oven-dried flask containing methanol (100 mL) at 0° C. was added sodium tert-butoxide (12.2 g, 127 mmol) in four-portions over 20 minutes. To this solution was added acetimidamide hydrochloride (4.5 g, 50.9 mmol) and dimethyl methoxymalonate (7.0 mL, 51 mmol). The mixture was heated to reflux for 2 h and then cooled to 0° C. The reaction mixture was made acidic with concentrated HCl and the resulting solid was collected by vacuum filtration. The wet material was frozen and lyophilized to afford the title compound (2.4 g, 30%) as a beige solid. m/z (ESI, +ve ion)=157.1 [M+H]+.

Step B.
4,6-Dichloro-5-methoxy-2-methylpyrimidine

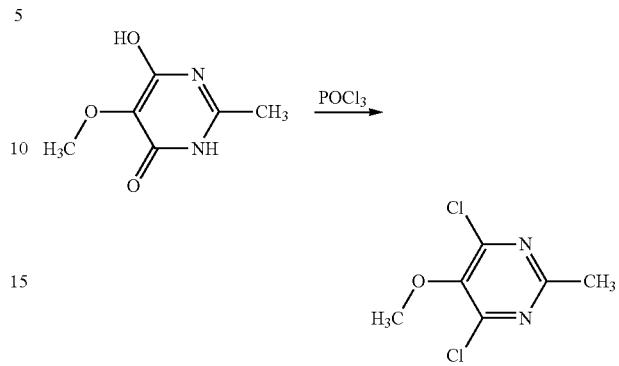

To a microwave tube was added 6-hydroxy-5-methoxy-2-methylpyrimidin-4 (3H)-one (2.40 g, 15.4 mmol), N,N-dimethylaniline (1.94 mL, 15.4 mmol), and phosphoryl chloride (12.7 mL, 135 mmol) and the mixture was heated to 100° C. in a microwave reactor for 1 h. The reaction mixture was filtered and concentrated. The resulting material was purified by column chromatography (0% to 25% EtOAc/hexanes, gradient elution) to afford the title compound (2.6 g, 87%) as a white solid.

Step C. 4-(6-Chloro-5-methoxy-2-methylpyrimidin-4-yl)morpholine

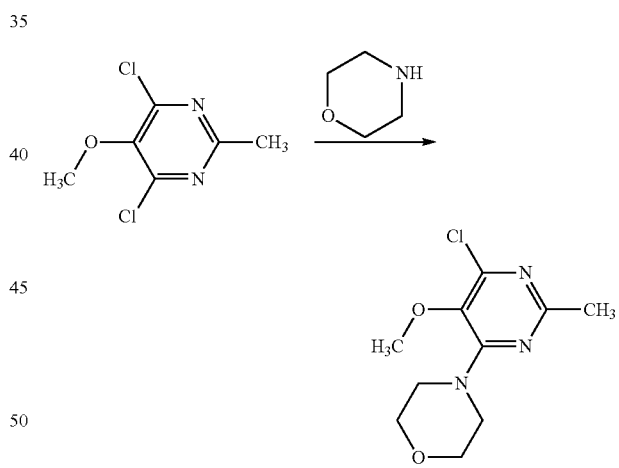

To an oven-dried flask was added 4,6-Dichloro-5-methoxy-2-methylpyrimidine (1.0 g, 5.18 mmol) followed by ethanol (30 mL). The mixture was cooled to 0° C. morpholine (0.54 mL, 6.2 mmol) was added followed by TEA (1.0 mL, 7.3 mmol), dropwise. The reaction mixture was stirred at room temperature for 1 h and concentrated. The residue was purified by column chromatography (0% to 30% EtOAc/hexanes, gradient elution) to provide the title compound (909 mg, 72%) as a white crystalline solid. m/z (ESI, +ve ion)=244.1 [M+H]+.

Step D. Tert-butyl (1R,2S)-2-(1-(tert-butoxycarbonyl)-3-((5-methoxy-2-methyl-6-morpholinopyrimidin-4-yl)amino)-1H-indazol-6-yl)-5'-methoxy-2'-oxospiro[cyclopropane-1,3'-indoline]-1'-carboxylate

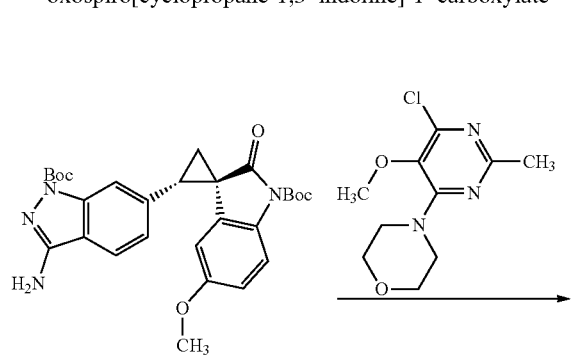

Step E

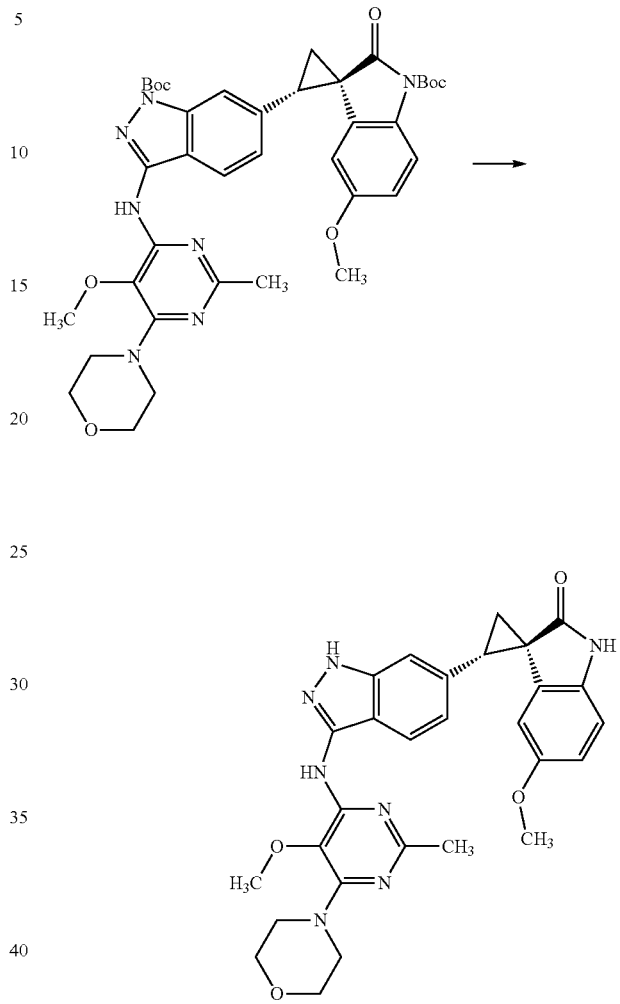

To an oven-dried flask was added 4-(6-Chloro-5-methoxy-2-methylpyrimidin-4-yl)morpholine (28.1 mg, 0.115 mmol), tert-butyl (1R,2S)-2-(3-amino-1-(tert-butoxycarbonyl)-1H-indazol-6-yl)-5'-methoxy-2'-oxospiro[cyclopropane-1,3'-indoline]-1'-carboxylate (30.0 mg, 0.0576 mmol), Xantphos Pd G4 (5.6 mg, 0.0058 mmol), and 1,4-dioxane (0.6 mL). The mixture was degassed with bubbling argon for 10 min. At this time, $Cs_2CO_3$ (37.6 mg, 0.115 mmol) was added and the reaction mixture was heated to 100° C. for 2 h. The reaction mixture was cooled was cooled to room temperature and diluted with EtOAc and washed with sat. aqueous $NaHCO_3$. The aqueous layer was extracted an additional three times with EtOAc. Combined organic layers were washed with brine, dried with $MgSO_4$, filtered, and concentrated. The residue was purified by column chromatography (0% to 50% acetone/hexanes, a gradient elution) to provide the title compound (25 mg, 59%) as a white foam. m/z (ESI, +ve ion)=728.3 [M+H]$^+$.

To an oven-dried flask was added tert-butyl (1R,2S)-2-(1-(tert-butoxycarbonyl)-3-((5-methoxy-2-methyl-6-morpholinopyrimidin-4-yl)amino)-1H-indazol-6-yl)-5'-methoxy-2'-oxospiro[cyclopropane-1,3'-indoline]-1'-carboxylate (25 mg, 0.034 mmol) followed DCM (1.7 mL) and trifluoroacetic acid (0.13 mL, 1.7 mmol). The reaction mixture was stirred at room temperature for 2 h. At this time, the mixture was concentrated and purified by prep HPLC (20% to 40% ACN/$H_2O$, 0.1% TFA modifier, gradient elution) to afford Example 41 (8.1 mg, 45%) as a white amorphous solid after lyophilization. m/z (ESI, +ve ion)=528.2 [M+H]$^+$. $^1$H NMR (400 MHz, DMSO-d)=12.88 (br s, 1H), 10.45 (s, 1H), 9.90 (br s, 1H), 7.66 (d, J=8.3 Hz, 1H), 7.45 (s, 1H), 6.97 (d, J=8.6 Hz, 1H), 6.75 (d, J=8.3 Hz, 1H), 6.59 (dd, J=2.7, 8.5 Hz, 1H), 5.74 (d, J=2.5 Hz, 1H), 3.81-3.70 (m, 8H), 3.67 (s, 3H), 3.35 (s, 3H), 3.19 (t, J=8.5 Hz, 1H), 2.35 (dd, J=4.7, 8.0 Hz, 1H), 2.27 (s, 3H), 1.99 (dd, J=4.7, 9.0 Hz, 1H).

Example 42. (1R,2S)-2-(3-{[6-(azetidin-1-yl)-5-methoxypyrimidin-4-yl]amino}-1H-indazol-6-yl)-5'-methoxyspiro[cyclopropane-1,3'-indol]-2'(1'H)-one

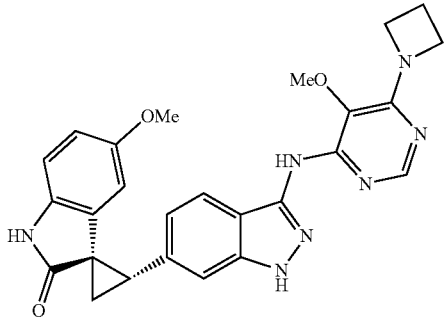 [SMILES: COc1ccc2c(c1)[C@]1(C[C@H]1c1ccc3c(Nc4ncnc(N5CCC5)c4OC)n[nH]c3c1)C(=O)N2]

Step A. 5-(6-chloro-5-methoxy-pyrimidin-4-yl)-2-oxa-5-azabicyclo[2.2.2]octane

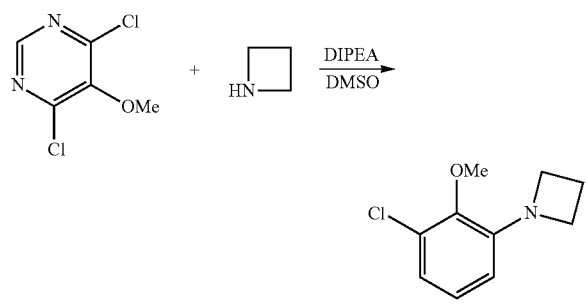

This compound was prepared from 4,6-dichloro-5-methoxypyrimidine (200.0 mg, 1.120 mmol) and azetidine (63.4 mg, 0.08 mL, 1.12 mmol). The residue was purified by column chromatography (ethyl acetate/hexane=0~50%) to provide the title compound (179.0 mg, 80%) as a white solid.

Step B. tert-butyl (1R,2S)-2-[3-[[6-(azetidin-1-yl)-5-methoxy-pyrimidin-4-yl]amino]-1-tert-butoxycarbonyl-indazol-6-yl]-5'-methoxy-2'-oxo-spiro[cyclopropane-1,3'-indoline]-1'-carboxylate

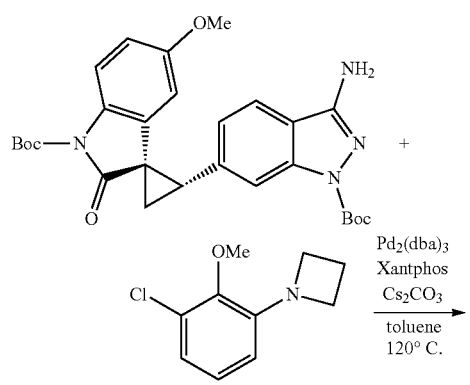

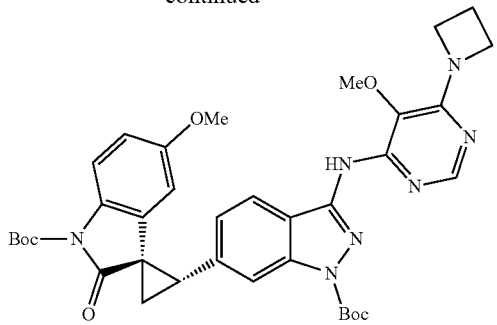

This compound was prepared using the procedure described in Example 5 from tert-butyl (1R,2S)-2-(3-amino-1-tert-butoxycarbonyl-indazol-6-yl)-5'-methoxy-2'-oxo-spiro[cyclopropane-1,3'-indoline]-1'-carboxylate (30.0 mg, 0.0600 mmol) and 5-(6-chloro-5-methoxy-pyrimidin-4-yl)-2-oxa-5-azabicyclo[2.2.2]octane (12.1 mg, 0.0605 mmol). The residue was purified by column chromatography (ethyl acetate/hexane=0~80%) to provide the title compound (3.0 mg, 7.6%) as a yellow oil.

Step C. (1R,2S)-2-[3-[[6-(azetidin-1-yl)-5-methoxy-pyrimidin-4-yl]amino]-1H-indazol-6-yl]-5'-methoxy-spiro[cyclopropane-1,3'-indoline]-2'-one

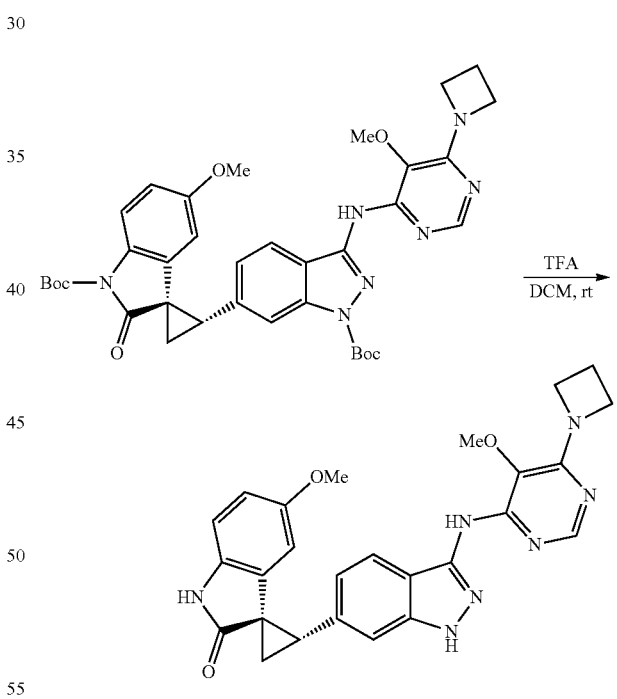

This compound was prepared using the procedure described in Example 5 from tert-butyl (1R,2S)-2-[3-[[6-(azetidin-1-yl)-5-methoxy-pyrimidin-4-yl]amino]-1-tert-butoxycarbonyl-indazol-6-yl]-5'-methoxy-2'-oxo-spiro[cyclopropane-1,3'-indoline]-1'-carboxylate (3.0 mg, 0.0044 mmol) and trifluoroacetic acid (0.03 mL, 0.4 mmol). The resulting brown solution was purified by Prep. HPLC (Gemini C18, 10 to 90% (0.1% TFA in water)/(0.1% TFA in Acetonitrile)) to provide the desired product Example 42 (1.7 mg, 81%) as a colorless film. $^1$H NMR (400 MHz, METHANOL-$d_4$) δ ppm 2.15-2.22 (m, 1H) 2.24 (dd, J=7.83, 4.80 Hz, 1H) 2.53 (quin, J=7.71 Hz, 2H) 3.33 (s, 3H) 3.33-3.38 (m, 1H) 3.83 (s, 3H) 4.42-4.59 (m, 4H) 5.55-5.63 (m, 1H) 6.58-6.66 (m, 1H) 6.78-6.89 (m, 1H) 6.96-7.08 (m, 1H) 7.42-7.50 (m, 1H) 7.80-7.91 (m, 1H) 8.11-8.19 (m, 1H); m/z (ESI, +ve ion) 484.3 (M+H)+.

Example 43. (1R,2S)-2-(3-{[6-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one

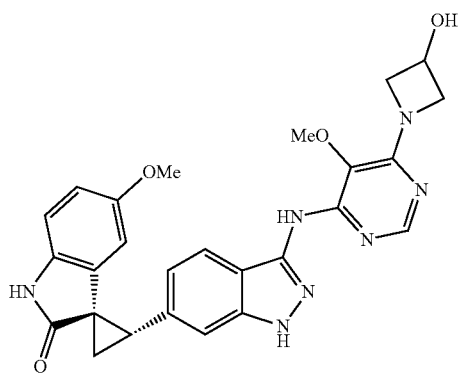 [SMILES: COc1ccc2c(c1)[C@]1(C[C@H]1c1ccc3c(Nc4ncnc(N5CC(O)C5)c4OC)n[nH]c3c1)C(=O)N2]

Step A. 1-(6-chloro-5-methoxy-pyrimidin-4-yl)azetidin-3-ol

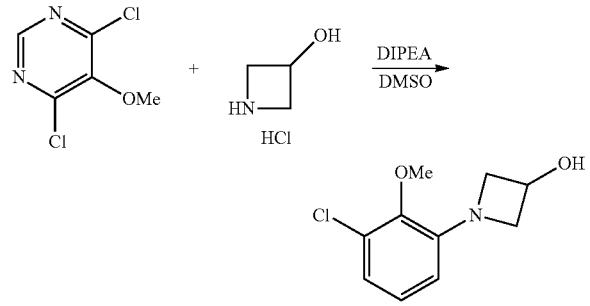

This compound was prepared using 4,6-dichloro-5-methoxypyrimidine (200.0 mg, 1.120 mmol) and azetidin-3-ol Hydrochloride (122.4 mg, 1.120 mmol). The residue was purified by column chromatography (ethyl acetate/hexane=0~100%) to provide the title compound (216.0 mg, 90%) as a white solid.

Step B. tert-butyl-[1-(6-chloro-5-methoxy-pyrimidin-4-yl)azetidin-3-yl]oxy-dimethyl-silane

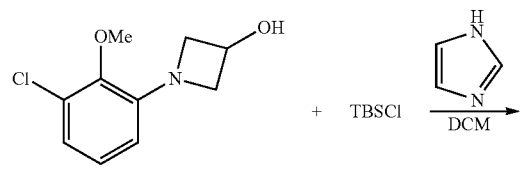

-continued

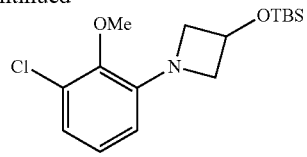

To a 50 ml round bottom flask containing 1-(6-chloro-5-methoxy-pyrimidin-4-yl)azetidin-3-ol (143.0 mg, 0.6600 mmol) in DCM (3.3 mL) were added tert-butylchlorodimethylsilane (119.9 mg, 0.8000 mmol) and Imidazole (112.9 mg, 1.660 mmol). The reaction mixture was stirred at rt and monitored by LCMS until the full conversion of the starting materials (approx. 80 min), cooled down to it, diluted with EtOAc and water, extracted with EtOAc for 3 times. The organic layer was then dried over Na$_2$SO$_4$. The residue was purified by column chromatography (ethyl acetate/hexane=0~50%) to provide the title compound (180.0 mg, 82%) as a colorless oil.

Step C. tert-butyl (1R,2S)-2-[1-tert-butoxycarbonyl-3-[[6-[3-[tert-butyl(dimethyl)silyl]oxyazetidin-1-yl]-5-methoxy-pyrimidin-4-yl]amino]indazol-6-yl]-5'-methoxy-2'-oxo-spiro[cyclopropane-1,3'-indoline]-1'-carboxylate (5c)

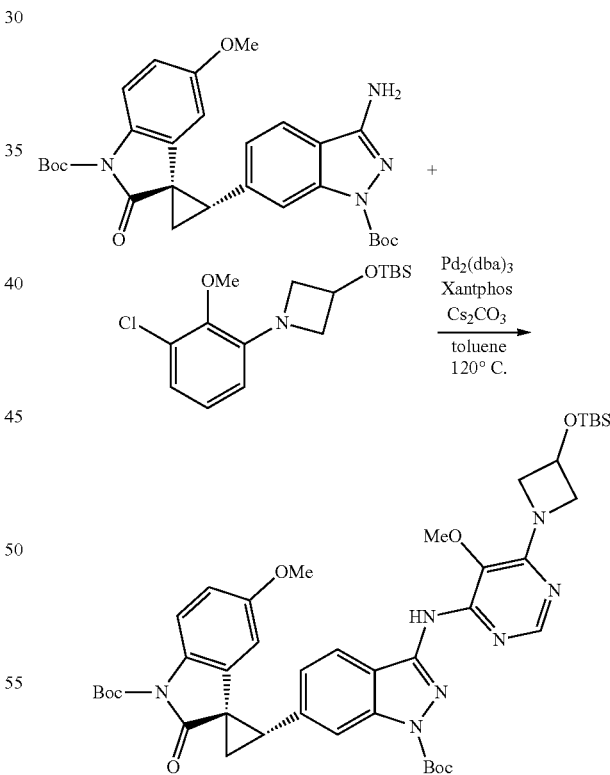

This compound was prepared using the procedure described in Example 5 from tert-butyl (1R,2S)-2-(3-amino-1-tert-butoxycarbonyl-indazol-6-yl)-5'-methoxy-2'-oxo-spiro[cyclopropane-1,3'-indoline]-1'-carboxylate (30.0 mg, 0.0600 mmol) and tert-butyl-[1-(6-chloro-5-methoxy-pyrimidin-4-yl)azetidin-3-yl]oxy-dimethyl-silane (20.9 mg, 0.0605 mmol). The residue was purified by column chromatography (ethyl acetate/hexane=0˜50%) to provide the title compound (6.0 mg, 13%) as a yellow oil.

Step D. (1R,2S)-2-[3-[[6-(3-hydroxyazetidin-1-yl)-5-methoxy-pyrimidin-4-yl]amino]-1H-indazol-6-yl]-5'-methoxy-spiro[cyclopropane-1,3'-indoline]-2'-one

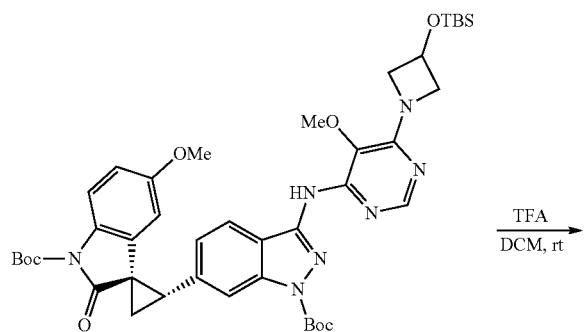

Example 44. (1R,2S)-5'-methoxy-2-(3-{[5-methoxy-6-(1,4-oxazepan-4-yl)pyrimidin-4-yl]amino}-1H-indazol-6-yl)spiro[cyclopropane-1,3'-indol]-2'(1'H)-one

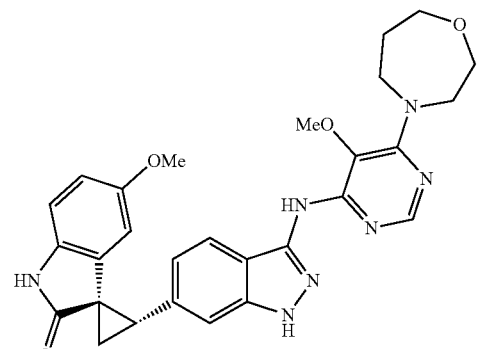

Step A. 4-(6-chloro-5-methoxy-pyrimidin-4-yl)-1,4-oxazepane

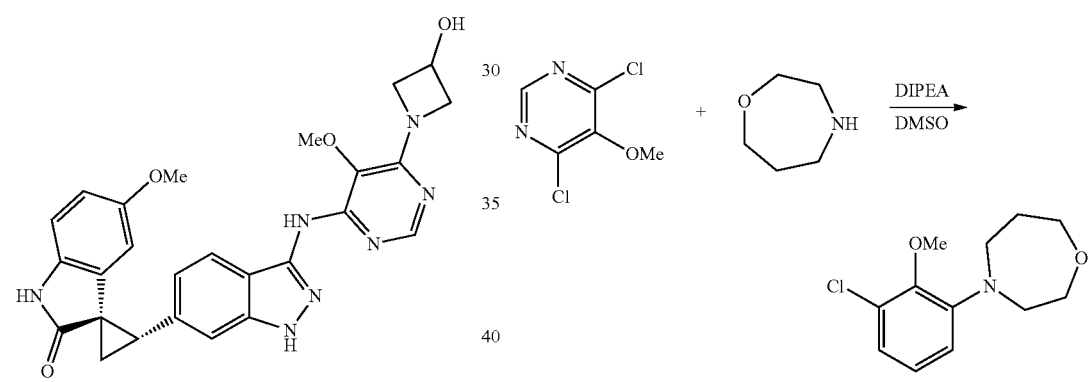

This compound was prepared using 4,6-Dichloro-5-methoxypyrimidine (200.0 mg, 1.120 mmol) and 1,4-Oxazepane (113.0 mg, 1.120 mmol). The residue was purified by column chromatography (ethyl acetate/hexane=0~50%) to provide the title compound (203.0 mg, 75%) as a colorless oil.

Step B. tert-butyl (1R,2S)-2-[1-tert-butoxycarbonyl-3-[[5-methoxy-6-(1,4-oxazepan-4-yl)pyrimidin-4-yl]amino]indazol-6-yl]-5'-methoxy-2'-oxo-spiro[cyclopropane-1,3'-indoline]-1'-carboxylate

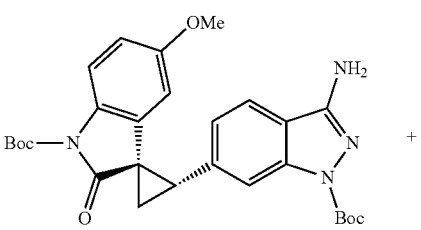

This compound was prepared using the procedure described in Example 5 from tert-butyl (1R,2S)-2-[1-tert-butoxycarbonyl-3-[[6-[3-[tert-butyl(dimethyl)silyl]oxyazetidin-1-yl]-5-methoxy-pyrimidin-4-yl]amino]indazol-6-yl]-5'-methoxy-2'-oxo-spiro[cyclopropane-1,3'-indoline]-1'-carboxylate (6.0 mg, 0.010 mmol) and trifluoroacetic acid (0.06 mL, 0.7 mmol). The resulting brown solution was purified by Prep. HPLC (Gemini C18, 20 to 40% (0.1% TFA in water)/(0.1% TFA in Acetonitrile)) to provide the desired product Example 43 (2.3 mg, 62%) as a colorless film. $^1$H NMR (400 MHz, METHANOL-$d_4$) δ ppm 2.16-2.21 (m, 1H) 2.25 (dd, J=7.96, 4.93 Hz, 1H) 3.33 (s, 3H) 3.33-3.38 (m, 1H) 3.83 (s, 3H) 4.16-4.27 (m, 2H) 4.61-4.86 (m, 3H) 5.60 (d, J=2.27 Hz, 1H) 6.62 (dd, J=8.59, 2.53 Hz, 1H) 6.83 (d, J=8.08 Hz, 1H) 7.03 (dd, J=8.59, 1.01 Hz, 1H) 7.48 (d, J=1.01 Hz, 1H) 7.87 (d, J=8.34 Hz, 1H) 8.17 (s, 1H); m/z (ESI, +ve ion) 500.1 (M+H)+.

-continued

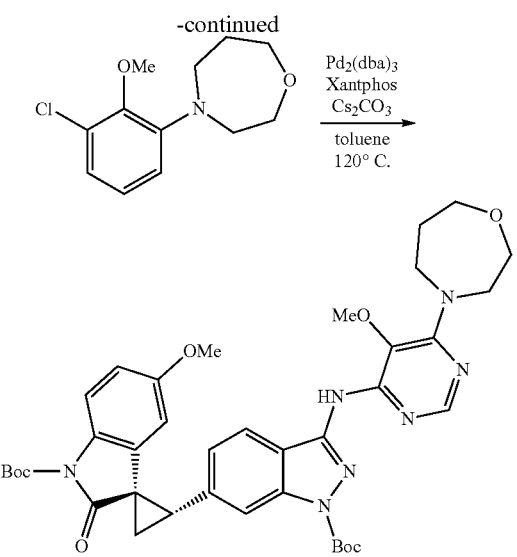

This compound was prepared using the procedure described in Example 5 from tert-butyl (1R,2S)-2-(3-amino-1-tert-butoxycarbonyl-indazol-6-yl)-5'-methoxy-2'-oxo-spiro[cyclopropane-1,3'-indoline]-1'-carboxylate (30.0 mg, 0.0600 mmol) and 4-(6-chloro-5-methoxy-pyrimidin-4-yl)-1,4-oxazepane (14.7 mg, 0.0605 mmol). The residue was purified by column chromatography (ethyl acetate/hexane=0~60%) to provide the title compound (13.0 mg, 31%) as a yellow oil.

Step C. (1R,2S)-5'-methoxy-2-[3-[[5-methoxy-6-(1,4-oxazepan-4-yl)pyrimidin-4-yl]amino]-1H-indazol-6-yl]spiro[cyclopropane-1,3'-indoline]-2'-one

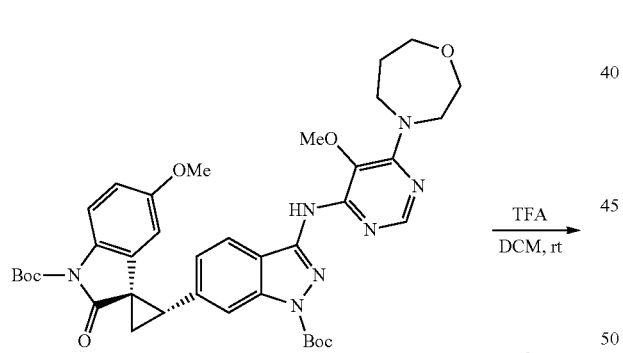

This compound was prepared using the procedure described in Example 5 from tert-butyl (1R,2S)-2-[1-tert-butoxycarbonyl-3-[[5-methoxy-6-(1,4-oxazepan-4-yl)pyrimidin-4-yl]amino]indazol-6-yl]-5'-methoxy-2'-oxo-spiro[cyclopropane-1,3'-indoline]-1'-carboxylate (13.0 mg, 0.0179 mmol) and trifluoroacetic acid (0.14 mL, 1.8 mmol). The resulting brown solution was purified by Prep. HPLC (Gemini C18, 10 to 90% (0.1% TFA in water)/(0.1% TFA in Acetonitrile)) to provide Example 44 (6.8 mg, 72%) as a colorless film. $^1$H NMR (400 MHz, METHANOL-$d_4$) δ ppm 1.98-2.05 (m, 2H) 2.16-2.21 (m, 1H) 2.25 (dd, J=7.96, 4.93 Hz, 1H) 3.33 (s, 3H) 3.34-3.38 (m, 1H) 3.77-3.81 (m, 2H) 3.82 (s, 3H) 3.87 (t, J=5.31 Hz, 2H) 4.04-4.17 (m, 4H) 5.60 (d, J=2.53 Hz, 1H) 6.62 (dd, J=8.59, 2.53 Hz, 1H) 6.83 (d, J=8.34 Hz, 1H) 7.04 (dd, J=8.59, 1.01 Hz, 1H) 7.50 (d, J=1.01 Hz, 1H) 7.91 (dd, J=8.59, 0.76 Hz, 1H) 8.24 (s, 1H); m/z (ESI, +ve ion) 528.2 (M+H)+.

Example 45. (1R,2S)-2-(3-{[6-(azetidin-1-yl)pyrimidin-4-yl]amino}-1H-indazol-6-yl)-5'-methoxyspiro[cyclopropane-1,3'-indol]-2'(1'H)-one

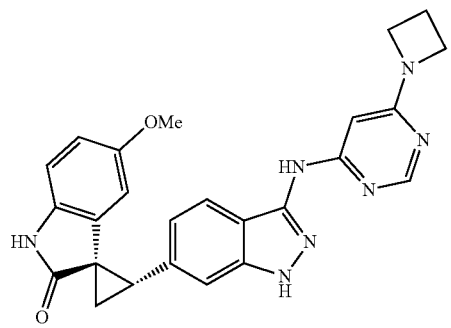 [SMILES: COc1ccc2c(c1)[C@]1(C[C@H]1c1ccc3c(Nc4cc(N5CCC5)ncn4)n[nH]c3c1)C(=O)N2]

Step A. 4-(azetidin-1-yl)-6-chloro-pyrimidine

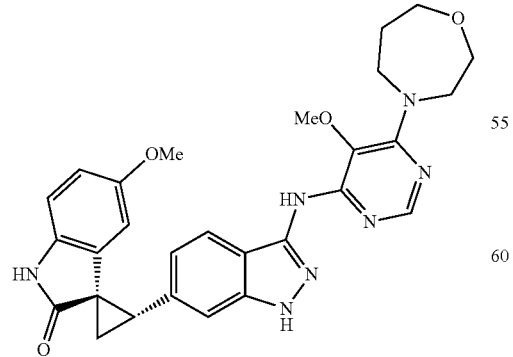

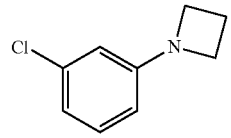

This compound was prepared from 4,6-dichloropyrimidine (200.0 mg, 1.340 mmol) and azetidine (76.6 mg, 0.09 mL, 1.34 mmol). The residue was purified by column chromatography (ethyl acetate/hexane=0-50%) to provide the title compound (148.0 mg, 65%) as a white solid.

Step B. tert-butyl (1R,2S)-2-[3-[[6-(azetidin-1-yl)pyrimidin-4-yl]amino]-1-tert-butoxycarbonyl-indazol-6-yl]-5'-methoxy-2'-oxo-spiro[cyclopropane-1,3'-indoline]-1'-carboxylate

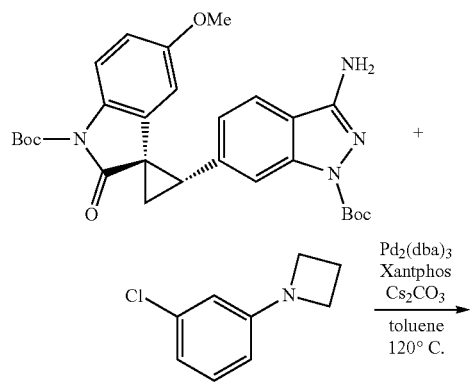

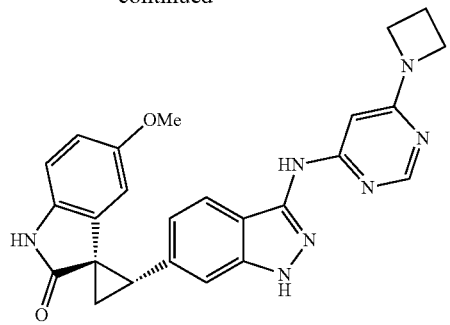

This compound was prepared using the procedure described in Example 5 from tert-butyl (1R,2S)-2-(3-amino-1-tert-butoxycarbonyl-indazol-6-yl)-5'-methoxy-2'-oxo-spiro[cyclopropane-1,3'-indoline]-1'-carboxylate (36.0 mg, 0.0700 mmol) and 4-(azetidin-1-yl)-6-chloro-pyrimidine (12.3 mg, 0.0700 mmol). The residue was purified by column chromatography (ethyl acetate/hexane=0~90%) to provide the title compound (5.0 mg, 11%) as a yellow oil.

Step C. (1R,2S)-2-[3-[[6-(azetidin-1-yl)pyrimidin-4-yl]amino]-1H-indazol-6-yl]-5'-methoxy-spiro[cyclopropane-1,3'-indoline]-2'-one

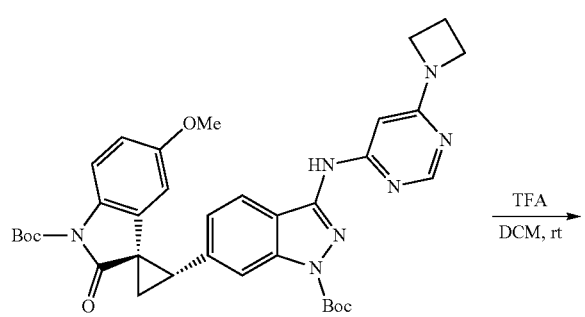

TFA
DCM, rt

This compound was prepared using the procedure described in Example 5 from tert-butyl (1R,2S)-2-[3-[[6-(azetidin-1-yl)pyrimidin-4-yl]amino]-1-tert-butoxycarbonyl-indazol-6-yl]-5'-methoxy-2'-oxo-spiro[cyclopropane-1,3'-indoline]-1'-carboxylate (5.0 mg, 0.0044 mmol) and trifluoroacetic acid (0.06 mL, 0.8 mmol). The resulting brown solution was purified by Prep. HPLC (Gemini C18, 10 to 90/o (0.1% TFA in water)/(0.1% TFA in Acetonitrile)) to provide the desired product Example 45 (1.4 mg, 40%) as a colorless film. $^1$H NMR (400 MHz, METHANOL-d$_4$) δ ppm 2.15-2.20 (m, 1H) 2.24 (dd, J=7.96, 4.93 Hz, 1H) 2.49-2.59 (m, 2H) 3.32 (s, 3H) 3.33-3.37 (m, 1H) 4.16-4.44 (m, 4H) 5.58 (d, J=2.53 Hz, 1H) 5.82-6.34 (m, 1H) 6.62 (dd, J=8.59, 2.53 Hz, 1H) 6.83 (d, J=8.34 Hz, 1H) 7.01 (dd, J=8.72, 0.88 Hz, 1H) 7.45 (d, J=0.76 Hz, 1H) 7.77 (d, J=8.59 Hz, 1H) 8.35 (s, 1H); m/z (ESI, +ve ion) 454.3 (M+H)+.

Example 46. (1R,2S)-2-(3-{[5-chloro-6-(3-hydroxyazetidin-1-yl)pyrimidin-4-yl]amino}-1H-indazol-6-yl)-5'-methoxyspiro[cyclopropane-1,3'-indol]-2'(1'H)-one

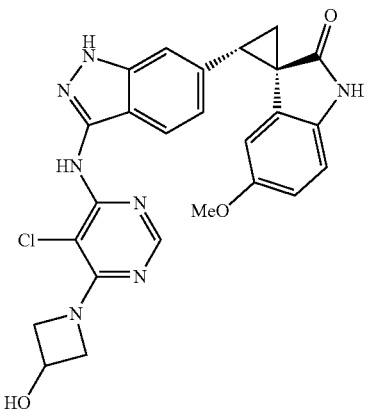 [SMILES: COc1ccc2c(c1)[C@]1(C[C@H]1c1ccc3c(Nc4ncnc(N5CC(O)C5)c4Cl)n[nH]c3c1)C(=O)N2]

Step A. 6-[3-[(tert-butyldimethylsilyl)oxy]azetidin-1-yl]-5-chloropyrimidin 4-amine

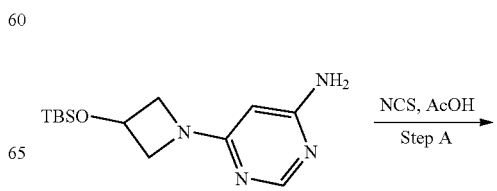

NCS, AcOH
Step A

319

-continued

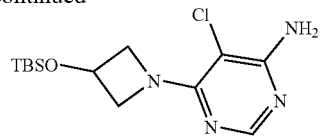

A mixture of 6-(3-((tert-butyldimethylsilyl)oxy)azetidin-1-yl)pyrimidin-4-amine (110.00 mg, 0.392 mmol, 1.00 equiv) and NCS (62.85 mg, 0.470 mmol, 1.20 equiv) in AcOH (0.60 mL) was stirred for 2 h at room temperature under nitrogen atmosphere. The resulting mixture was concentrated under vacuum. The residue was purified by silica gel column chromatography, eluted with DCM/MeOH (10/1) to afford the title compound (70 mg, 56.68%) as a yellow solid. m/z (ESI, +ve ion)=315.10 [M+H]$^+$. $^1$H NMR (400 MHz, DMSO-d$_6$) δ 7.91 (d, J=1.0 Hz, 1H), 6.22 (s, 2H), 4.72-4.77 (m, 1H), 4.11-4.15 (m, 2H), 3.58-3.61 (m, 2H), 0.88 (s, 9H), 0.08 (s, 6H).

Step B

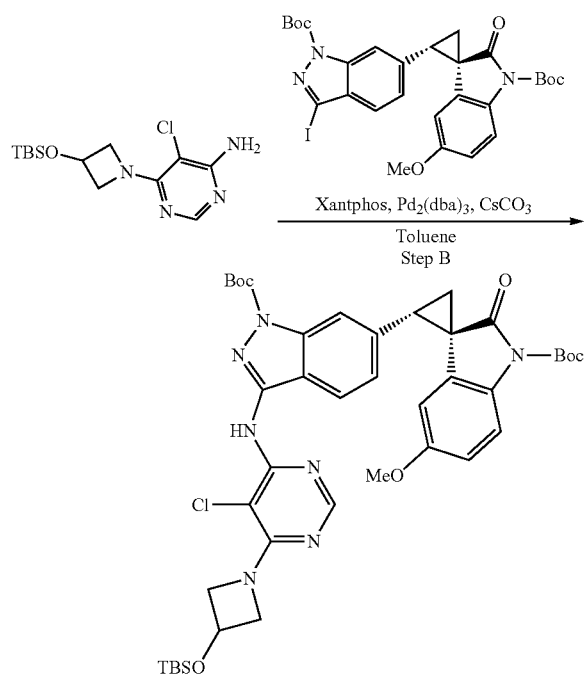

To a stirred mixture of 6-[3-[(tert-butyldimethylsilyl)oxy] azetidin-1-yl]-5-chloropyrimidin 4-amine (47.77 mg, 0.152 mmol, 1.20 equiv) and tert-butyl (1R,2S)-2-[1-(tert-butoxycarbonyl)-3-iodoindazol-6-yl]-5-methoxy-2-oxospiro[cyclopropane-1,3-indole]-1-carboxylate (80.00 mg, 0.127 mmol, 1.00 equiv) in toluene (5.00 mL) were added XantPhos (7.34 mg, 0.013 mmol, 0.10 equiv), Pd$_2$(dba)$_3$ (11.61 mg, 0.013 mmol, 0.1 equiv) and Cs$_2$CO$_3$ (82.62 mg, 0.254 mmol, 2.00 equiv) at room temperature under nitrogen atmosphere. The resulting mixture was stirred overnight at 90° C. under nitrogen atmosphere. The product was diluted by water (10 mL), extracted with EtOAc (3×10 mL). The combined organic layers were washed with brine (3×5 mL), dried over anhydrous Na$_2$SO$_4$. After filtration, the filtrate was concentrated under reduced pressure. The residue was purified by silica gel column chromatography, eluted with DCM/MeOH (10/1) to afford the title compound (15 mg, 14.96%) as a white solid. m/z (ESI, +ve ion)=818.45 [M+H]$^+$.

320

Step C. (1R,2S)-2-(3-[[5-chloro-6-(3-hydroxyazetidin-1-yl)pyrimidin-4-yl] amino]-1H-indazol-6-yl)-5'-methoxy-1'H-spiro[cyclopropane-1,3'-indol]-2'-one

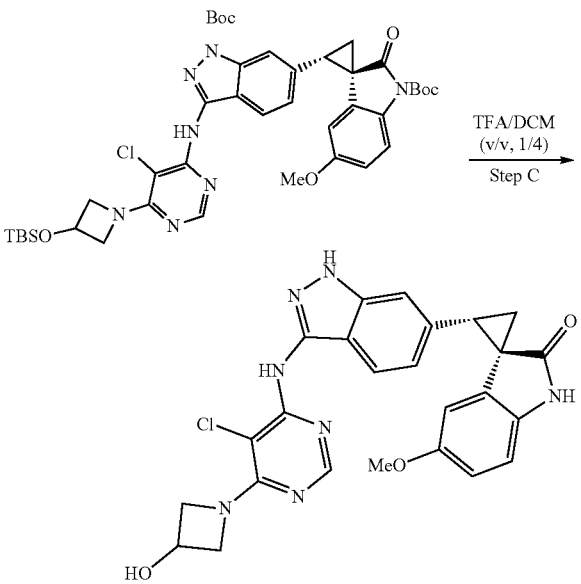

A mixture of the compound from Step B (80.00 mg, 0.098 mmol, 1.00 equiv) and TFA (0.20 mL) in DCM (1 mL) was stirred overnight at room temperature. The mixture was concentrated under reduced pressure. The residue was purified by reverse flash chromatography with the following conditions: column, C18 silica gel; mobile phase, ACN in water (5 mM, NH$_4$HCO$_3$), gradient: 10% to 50% in 60 min to afford Example 46 (5.03 mg, 10%) as a white solid. m/z (ESI, +ve ion)=504.10 [M+H]$^+$. $^1$H NMR (400 MHz, DMSO-d$_6$) δ 12.68 (s, 1H), 10.43 (s, 1H), 8.91 (s, 1H), 7.83 (d, J=4 Hz, 1H), 7.40 (s, 1H), 7.35 (d, J=8.4 Hz, 1H), 6.90 (d, J=8.4 Hz, 1H), 6.75 (d, J=8.4 Hz, 1H), 6.59-6.57 (m, 1H), 5.72-5.68 (m, 2H), 4.52-4.43 (m, 3H), 3.99-3.96 (m, 2H), 3.18-3.16 (m, 1H), 3.34 (s, 3H), 2.53-2.50 (m, 1H), 1.99-1.95 (m, 1H).

Example 47. (1R,2S)-2-(3-{[5-chloro-6-(3-methoxyazetidin-1-yl)pyrimidin-4-yl]amino}-1H-indazol-6-yl)-5'-methoxyspiro[cyclopropane-1,3'-indol]-2'(1'H)-one

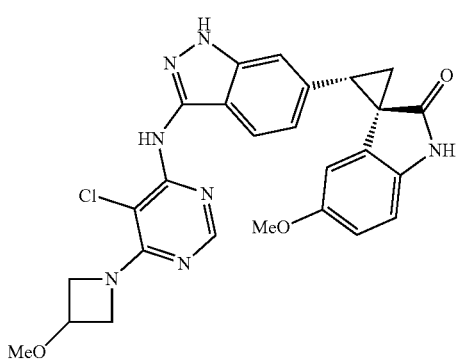 [SMILES: COc1ccc2c(c1)[C@]1(C[C@H]1c1ccc3c(Nc4ncnc(N5CC(OC)C5)c4Cl)n[nH]c3c1)C(=O)N2]

Step A. 5-chloro-6-(3-methoxyazetidin-1-yl)pyrimidin-4-amine

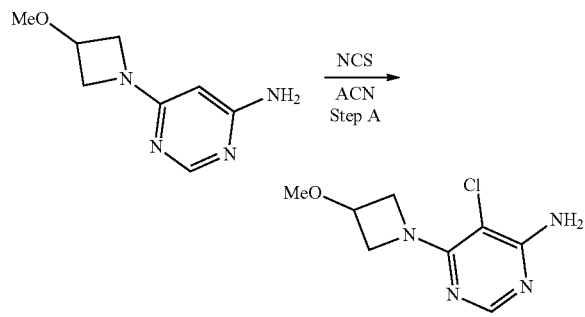

A mixture of 6-(3-methoxyazetidin-1-yl)pyrimidin-4-amine (200.00 mg, 1.110 mmol, 1.00 equiv) and NCS (177.84 mg, 1.332 mmol, 1.2 equiv) in ACN (10.00 mL) was stirred for 16 h at room temperature under nitrogen atmosphere. The reaction was quenched by the addition of Water (10 mL) at room temperature. The resulting mixture was extracted with DCM (3×10 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with DCM/MeOH (10/1) to the title compound (220 mg, 92.35%) as a white solid. m/z (ESI+ve ion)=215.10 [M+H]$^+$. $^1$H NMR (400 MHz, Chloroform-d) δ 8.02 (s, 1H), 5.08 (s, 2H), 4.52 (d, J=5.7 Hz, 1H), 4.35-4.17 (m, 4H), 3.35 (s, 3H).

Step B. tert-butyl (1R,2S)-2-[1-(tert-butoxycarbonyl)-3-[[5-chloro-6-(3-methoxyazetidin-1-yl)pyrimidin-4-yl] amino] indazol-6-yl]-5-methoxy-2-oxospiro[cyclopropane-1,3-indole]-1-carboxylate

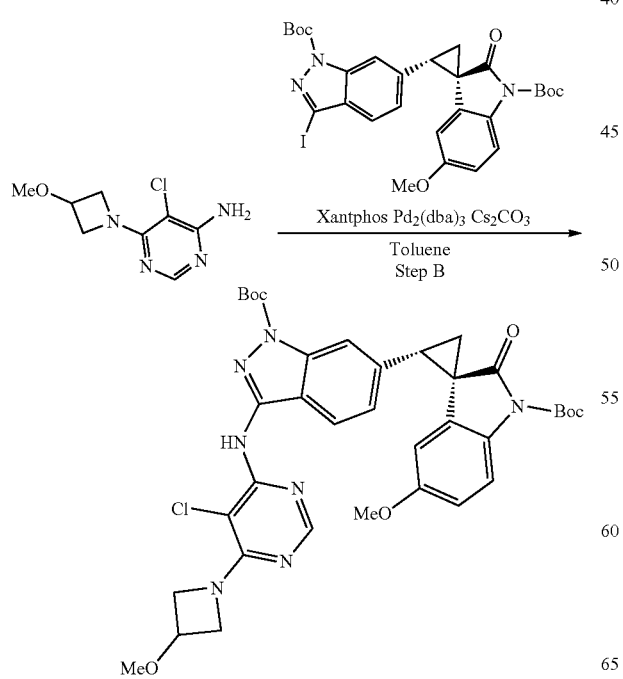

To a stirred mixture of tert-butyl (1R,2S)-2-[1-(tert-butoxycarbonyl)-3-iodoindazol-6-yl]-5-methoxy-2-oxospiro[cyclopropane-1,3-indole]-1-carboxylate (100.00 mg, 0.158 mmol, 1.00 equiv) and 5-chloro-6-(3-methoxyazetidin-1-yl)pyrimidin-4-amine (40.79 mg, 0.190 mmol, 1.2 equiv) in toluene (2.50 mL) were added Pd$_2$(dba)$_3$ (14.50 mg, 0.016 mmol, 0.1 equiv) and XantPhos (9.16 mg, 0.016 mmol, 0.1 equiv) and Cs$_2$CO$_3$ (103.19 mg, 0.317 mmol, 2 equiv) at room temperature under nitrogen atmosphere. The resulting mixture was stirred for 2 h at 90° C. under nitrogen atmosphere. The mixture was cooled down to room temperature. The reaction was quenched by the addition of Water (10 mL). The resulting mixture was extracted with DCM (3×15 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with DCM/MeOH (10/1) to afford the title compound (62 mg, 54.51%) as a yellow solid. m/z=718.25 [M+H]. $^1$H NMR (400 MHz, Chloroform-d) δ 8.10 (d, J=11.5 Hz, 1H), 7.87-7.70 (m, 2H), 7.62 (s, 1H), 7.55 (m, 1H), 7.08 (d, J=8.5 Hz, 1H), 6.70 (m, 1H), 5.62 (d, J=2.7 Hz, 1H), 4.63-4.58 (m, 1H), 4.37-4.26 (m, 3H), 3.52 (t, J=8.7 Hz, 1H), 3.38 (d, J=10.9 Hz, 4H), 3.35 (s, 3H), 2.38 (m, 1H), 2.13 (m, 1H), 1.70 (d, J=2.6 Hz, 18H)

Step C. (1R,2S)-2-(3-[[5-chloro-6-(3-methoxyazetidin-1-yl)pyrimidin-4-yl]amino]-1H-indazol-6-yl)-5-methoxy-1H-spiro[cyclopropane-1,3-indol]-2-one

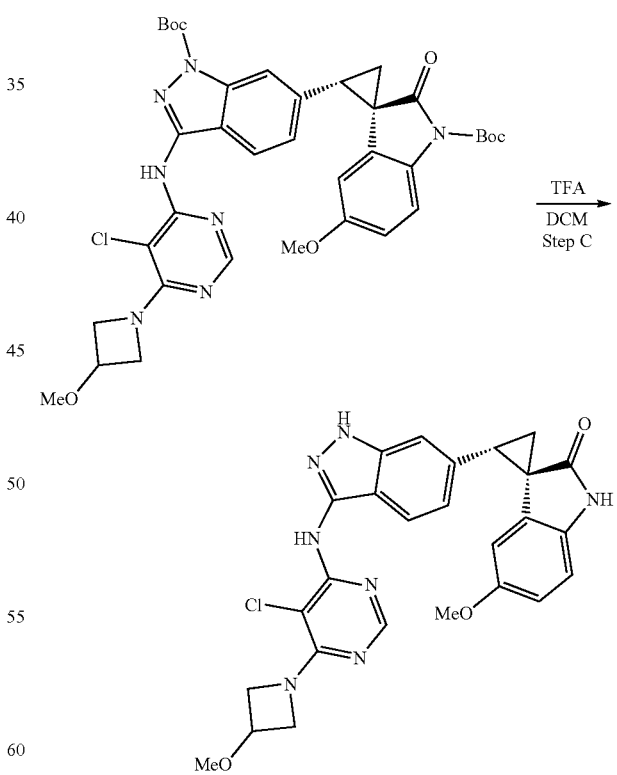

A mixture of tert-butyl (1R,2S)-2-[1-(tert-butoxycarbonyl)-3-[[5-chloro-6-(3-methoxyazetidin-1-yl) pyrimidin-4-yl] amino] indazol-6-yl]-5-methoxy-2-oxospiro[cyclopropane-1,3-indole]-1-carboxylate (62.00 mg, 0.086 mmol, 1.00 equiv) and TFA (2.00 mL, 0.018 mmol, 0.20 equiv) in DCM (4.00 mL) was stirred for 1 h at room temperature under nitrogen atmosphere. The resulting mixture was concentrated under reduced pressure. The residue was purified by Prep-HPLC with the following conditions: Column: YMC-Actus Triart C18 ExRS, 30 mm×150 mm, 5 μm; Mobile Phase A: Water (10 mmol/L NH$_4$HCO$_3$), Mobile Phase B: ACN; Flow rate: 60 mL/min. Gradient: 25% B to 48% B in 8 min, 254 nm; RT1: 7.28 min to afford Example 47 (25.0 mg, 55.91%) as a white solid. m/z (ESI, +ve ion)=518.20 [M+H]$^+$. $^1$H NMR (400 MHz, DMSO-d$_6$) δ 12.68 (s, 1H), 10.42 (s, 1H), 8.93 (s, 1H), 7.83 (s, 1H), 7.53-7.22 (m, 2H), 6.90 (d, J=8.8 Hz, 1H), 6.75 (d, J=8.4 Hz, 1H), 6.58 (m, 1H), 5.71 (d, J=2.7 Hz, 1H), 4.44 (m, 2H), 4.25 (s, 1H), 4.05 (m, 2H), 3.17 (m, 7H), 2.32 (d, J=7.5 Hz, 1H), 1.98 (m, 1H).

Example 48. (1R,2S)-2-(3-{[2-chloro-5-methoxy-6-(morpholin-4-yl)pyrimidin-4-yl]amino}-1H-indazol-6-yl)-5'-methoxyspiro[cyclopropane-1,3'-indol]-2'(1'H)-one

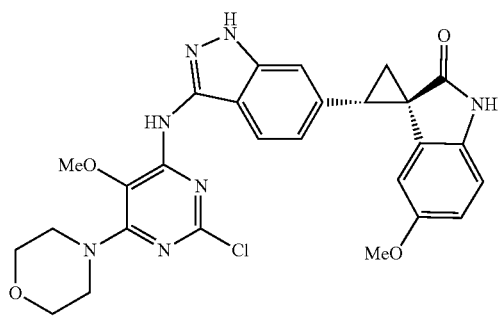 [SMILES: COc1ccc2c(c1)[C@]1(C[C@H]1c1ccc3c(Nc4nc(Cl)nc(N5CCOCC5)c4OC)n[nH]c3c1)C(=O)N2]

Example 49. (1R,2S)-2-(3-{[4-chloro-5-methoxy-6-(morpholin-4-yl)pyrimidin-2-yl]amino}-1H-indazol-6-yl)-5'-methoxyspiro[cyclopropane-1,3'-indol]-2'(1'H)-one

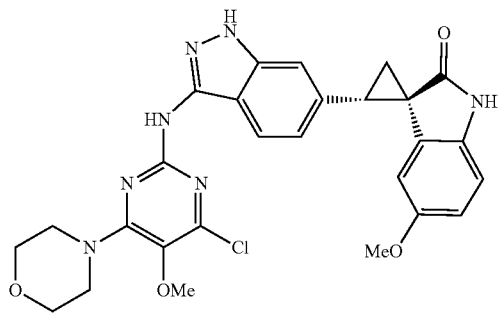 [SMILES: COc1ccc2c(c1)[C@]1(C[C@H]1c1ccc3c(Nc4nc(Cl)c(OC)c(N5CCOCC5)n4)n[nH]c3c1)C(=O)N2]

Step A. 4-(2,6-dichloro-5-methoxypyrimidin-4-yl)morpholine

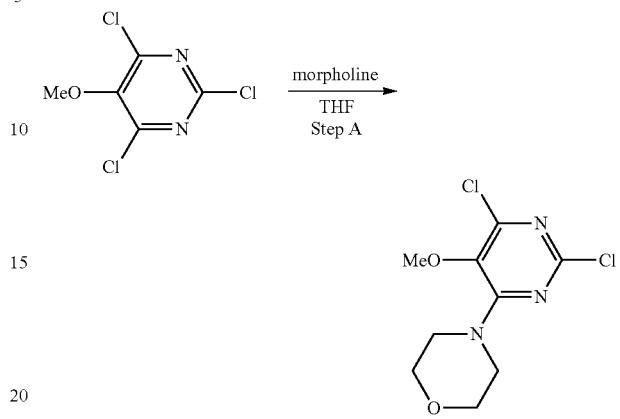

A mixture of 2,4,6-trichloro-5-methoxypyrimidine (200.00 mg, 0.937 mmol, 1.00 equiv) and morpholine (97.96 mg, 1.124 mmol, 1.2 equiv) in THF (5 mL) was stirred for 2 h at room temperature under nitrogen atmosphere. The reaction was quenched by the addition of Water (10 mL) at room temperature. The resulting mixture was extracted with DCM (3×10 mL). The combined organic layers were washed with brine (2×20 mL), dried over anhydrous Na$_2$SO$_4$. After filtration, the filtrate was concentrated under reduced pressure. The residue was purified by reverse phase flash chromatography with the following conditions: Column: Spherical C18, 20-40 μm, 80 g; Mobile Phase A: Water (plus 5 mM NH$_4$HCO$_3$); Mobile Phase B: ACN; Flow rate: 40 mL/min; Gradient: 40% B-60% B in 20 min; Detector: 254 nm. The fractions containing desired product were collected at 54% B and concentrated under reduced pressure to afford the title compound (130 mg, 52.53%) as an off-white solid. m/z (ESI+ve ion)=263.95 [M+H]$^+$. $^1$H NMR (400 MHz, Chloroform-d) δ 3.94-3.87 (m, 4H), 3.83-3.77 (m, 4H), 3.75 (s, 3H).

Step B. The mixture of tert-butyl (1R,2S)-2-[1-(tert-butoxycarbonyl)-3-[[2-chloro-5-methoxy-6-(morpholin-4-yl) pyrimidin-4-yl]amino]indazol-6-yl]-5'-methoxy-2'-oxospiro[cyclopropane-1,3'-indole]-1'-carboxylate (16b) and tert-butyl (1R,2S)-2-(1-(tert-butoxycarbonyl)-3-((4-chloro-5-methoxy-6-morpholinopyrimidin-2-yl)amino)-1H-indazol-6-yl)-5'-methoxy-2'-oxospiro[cyclopropane-1,3'-indoline]-1'-carboxylate

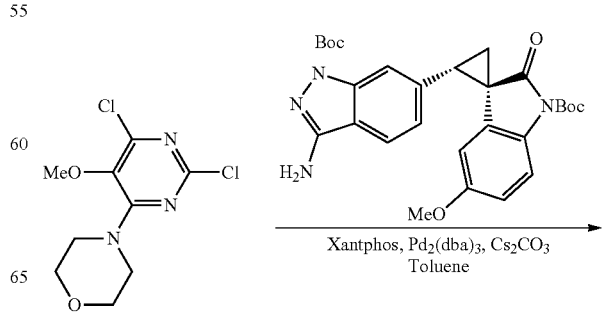

325
-continued

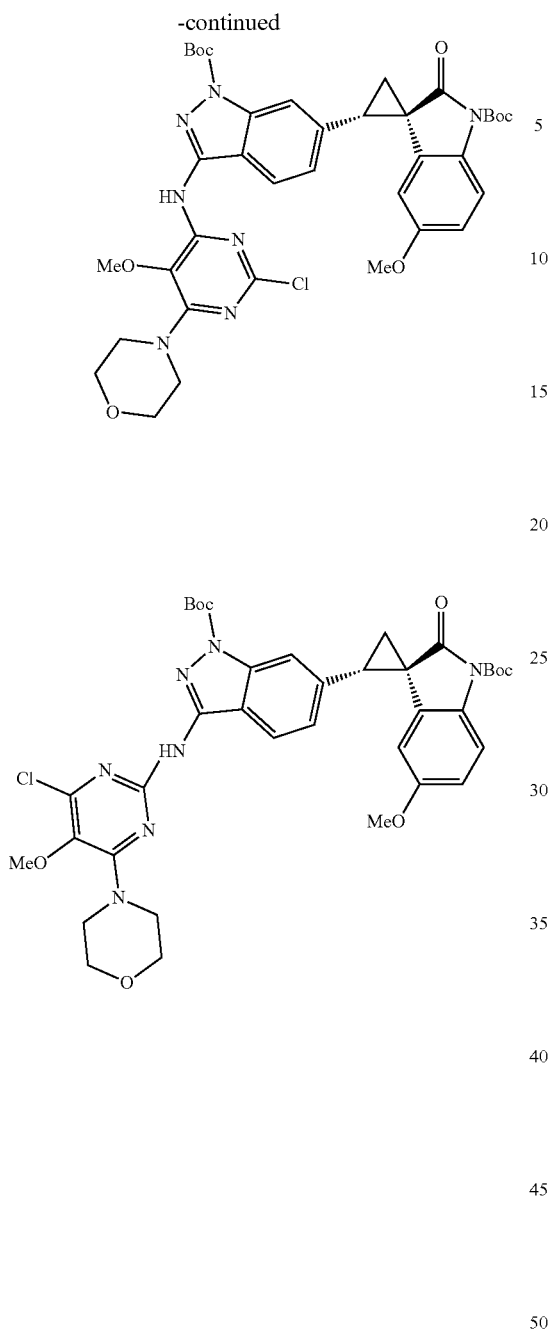

326

Step C. (1R,2)-2-(3-((2-chloro-5-methoxy-6-morpholinopyrimidin-4-yl)amino)-1H-indazol-6-yl)-5'-methoxyspiro[cyclopropane-1,3'-indolin]-2'-one and (1R,2S)-2-(3-[[4-chloro-5-methoxy-6-(morpholin-4-yl)pyrimidin-2-yl]amino]-1H-indazol-6-yl)-5'-methoxy-1'H-spiro[cyclopropane-1,3'-indol]-2'-one

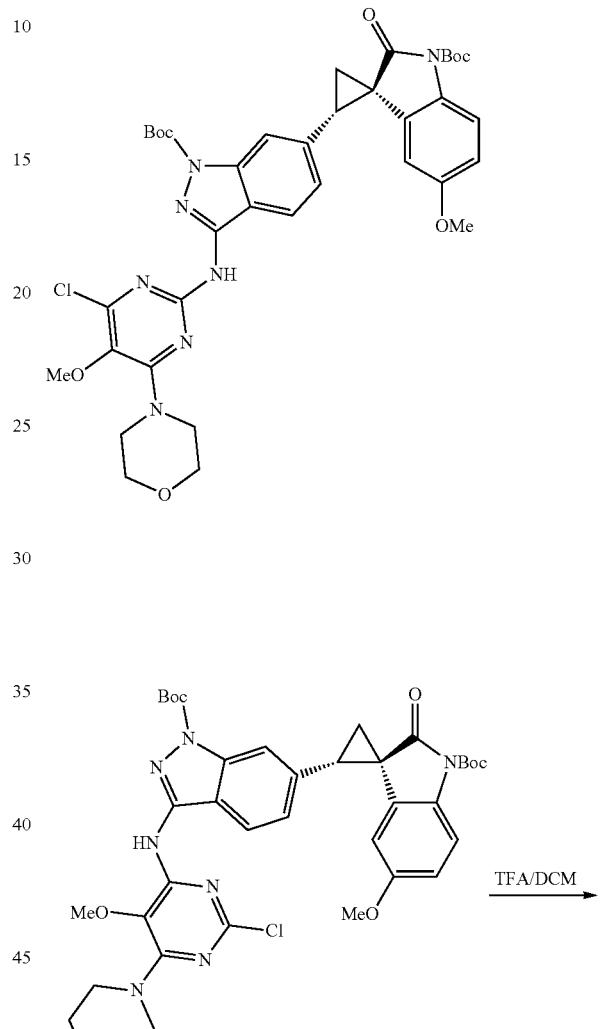

To a stirred mixture of 4-(2,6-dichloro-5-methoxypyrimidin-4-yl) morpholine (30.34 mg, 1.20 equiv) and tert-butyl (1R,2S)-2-[3-amino-1-(tert-butoxycarbonyl) indazol-6-yl]-5-methoxy-2-oxospiro[cyclopropane-1,3-indole]-1-carboxylate (50.00 mg, 1.00 equiv) in toluene (1.25 mL) were added Pd$_2$(dba)$_3$ (8.79 mg, 0.10 equiv) and XantPhos (5.56 mg, 0.10 equiv) and Cs$_2$CO$_3$ (62.65 mg, 2.00 equiv) at room temperature under nitrogen atmosphere. The resulting mixture was stirred for 2 h at 90° C. under nitrogen atmosphere. The reaction mixture was concentrated under reduced pressure. The residue was purified by prep-TLC (PE/EA 1/1) to afford a mixture of the title compounds (50 mg, 70%) as a yellow oil. m/z (ESI +ve ion)=748.35 [M+H]$^+$.

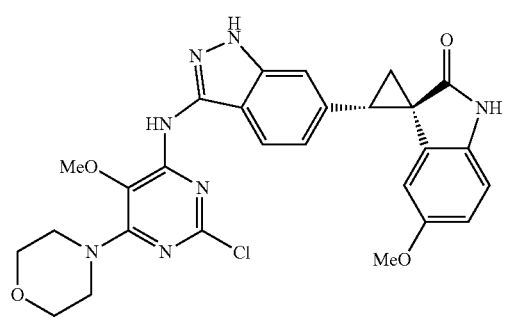

327
-continued

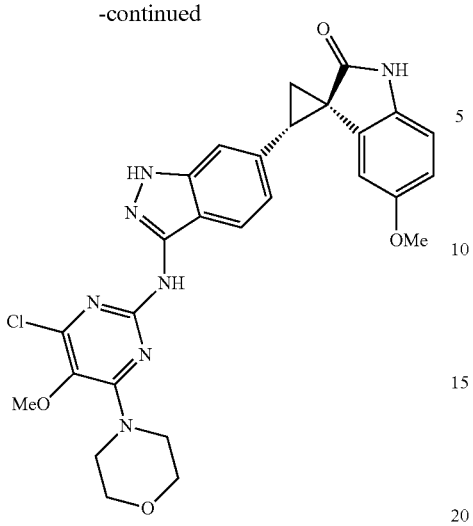

The mixture of compounds from Step B (50.00 mg) in TFA (2.00 mL) and DCM (4.00 mL) was stirred for 1 h at room temperature under nitrogen atmosphere. The resulting mixture was concentrated under vacuum. The residue was purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 20% B to 50% B in 8 min, 220 nm; RT1:7.30 min; RT2: 7.75 min) to afford Example 48 (8.1 mg) as an off-white solid. m/z (ESI+ve ion)=548.20 [M+H]. $^1$H NMR (400 MHz, DMSO-$d_6$) δ 12.67 (s, 1H), 10.41 (s, 1H), 9.21 (s, 1H), 7.61-7.26 (m, 2H), 6.93 (d, J=8.4 Hz, 1H), 6.75 (d, J=8.4 Hz, 1H), 6.58 (m, 1H), 5.70 (d, J=1.6 Hz, 1H), 3.71 (t, J=4.5 Hz, 4H), 3.65 (s, 3H), 3.62 (t, J=4.6 Hz, 4H), 3.19 (t, J=8.5 Hz, 3H), 3.18 (m, 1H), 2.32 (m, 1H), 1.99 (m, 1H). Compound Example 49 (8.2 mg) was also obtained as an off-white solid from the collection of fractions from the HPLC. m/z (ESI+ve ion)=548.20 [M+H]$^+$. $^1$H NMR (400 MHz, DMSO-$d_6$) δ 12.46 (s, 1H), 10.41 (s, 1H), 9.43 (s, 1H), 7.49 (d, J=8.4 Hz, 1H), 7.38 (s, 1H), 6.83 (d, J=8.4 Hz, 1H), 6.75 (d, J=8.4 Hz, 1H), 6.59 (m, 1H), 5.64 (d, J=2.0 Hz, 1H), 3.59 (s, 3H), 3.52 (m, 6H), 3.37 (s, 2H), 3.31 (m, 3H) 3.17 (t, J=7.2 Hz, 1H), 2.31 (m, 1H), 1.97 (m, 1H).

Example 50. (1R,2S)-2-(3-{[1-(2-hydroxyethyl)-3-methoxy-1H-pyrazol-4-yl]amino}-1H-indazol-6-yl)-5'-methoxyspiro[cyclopropane-1,3'-indol]-2'(1'H)-one

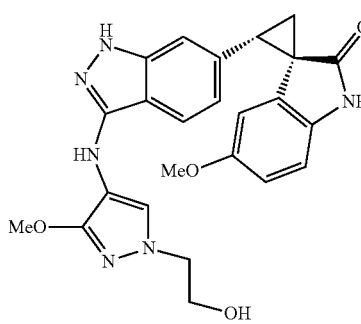

328
Step A. 4-bromo-3-methoxy-1-[2-(oxan-2-yloxy)ethyl]pyrazole

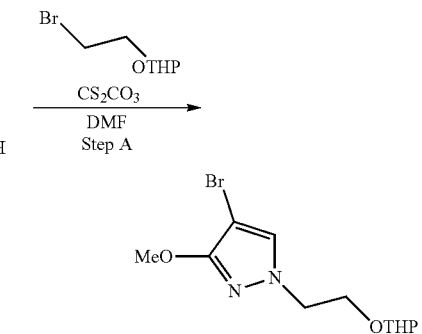

To the mixture of 4-bromo-3-methoxy-1H-pyrazole (500.00 mg, 2.825 mmol, 1.00 equiv) in DMF (5.00 mL) was added $Cs_2CO_3$ (1104.47 mg, 3.390 mmol, 1.2 equiv) at 25° C. After stirred for 30 min, 2-(2-bromoethoxy)oxane (708.75 mg, 3.390 mmol, 1.2 equiv) was added. The mixture was stirred for 3 h. The reaction was diluted with water (50 mL) and extracted with EA (20 mL×3). The combined organic layer was washed with brine (50 mL×2), dried over anhydrous $Na_2SO_4$ and filtered. The filtrate was concentrated in vacuo. The residue was purified by silica gel column eluted with 0-50% EA in PE to give the title compound (750 mg, 82.65%) as a colorless oil. m/z (ESI+ve ion)=305.00 [M+H]$^+$. $^1$H NMR (300 MHz, Chloroform-d) δ 7.35 (s, 1H), 4.55 (t, J=3.3 Hz, 1H), 4.16-4.10 (m, 2H), 4.05-3.97 (m, 1H), 3.96 (s, 3H), 3.75-3.65 (m, 2H), 3.52-3.45 (m, 1H), 1.85-1.52 (m, 6H).

Step B. tert-butyl (1R,2S)-2-[1-(tert-butoxycarbonyl)-3-([3-methoxy-1-[2-(oxan-2-yloxy)ethyl]pyrazol-4-yl]amino)indazol-6-yl]-5'-methoxy-2'-oxospiro[cyclopropane-1,3'-indole]-1'-carboxylate

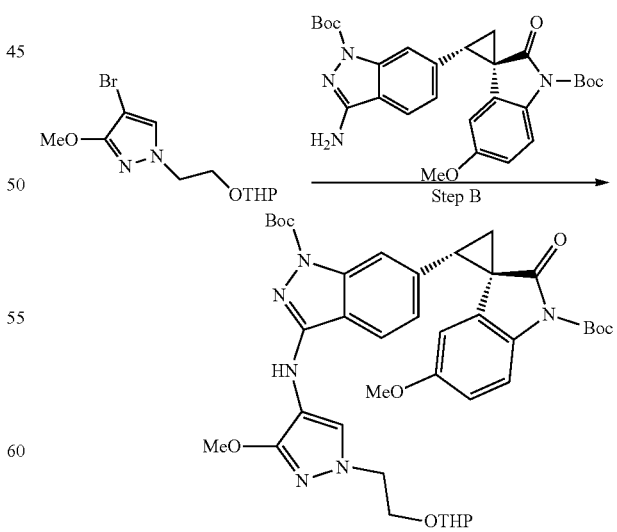

To the mixture tert-butyl (1R,2S)-2-[3-amino-1-(tert-butoxycarbonyl)indazol-6-yl]-5'-methoxy-2'-oxospiro[cyclopropane-1,3'-indole]-1-carboxylate (110.00 mg, 0.211 mmol, 1.00 equiv) and 4-bromo-3-methoxy-1-[2-(oxan-2-yloxy)ethyl]pyrazole (77.38 mg, 0.253 mmol, 1.20 equiv) in a dry dioxane (2.00 mL) were added Cs$_2$CO$_3$ (137.69 mg, 0.422 mmol, 2.00 equiv), EPhos (22.60 mg, 0.042 mmol, 0.20 equiv) and EPhos Pd G$_4$ (38.82 mg, 0.042 mmol, 0.20 equiv) under argon atmosphere. The mixture was stirred at 90° C. for 12 h. The solvent was removed under reduced pressure. The residue was purified by Prep-TLC (rinsed with PE/EA=2/1) to give the title compound (15 mg, 9.05%) as yellow oil. m/z (ESI+ve ion)=745.55 [M+H]$^+$.

Step C. (1R,2S)-2-(3-[[1-(2-hydroxyethyl)-3-methoxypyrazol-4-yl]amino]-1H-indazol-6-yl)-5'-methoxy-1'H-spiro[cyclopropane-1,3'-indol]-2'-one

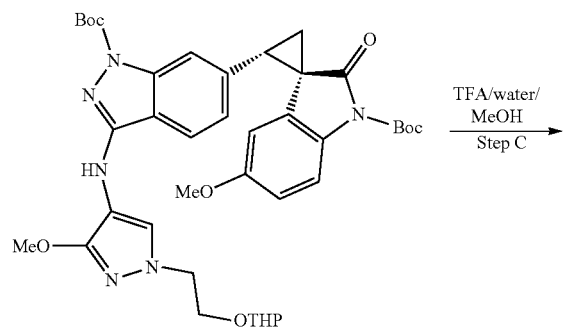

To a mixture solution of TFA (0.40 mL), H$_2$O (0.20 mL) and THF (0.40 mL) was added tert-butyl (1R,2S)-2-[1-(tert-butoxycarbonyl)-3-([3-methoxy-1-[2-(oxan-2-yloxy)ethyl]pyrazol-4-yl]amino)indazol-6-yl]-5'-methoxy-2'-oxospiro[cyclopropane-1,3'-indole]-1'-carboxylate (14.00 mg, 0.019 mmol, 1.00 equiv). The mixture was stirred at 50° C. for 12 h. The solvent was removed under reduced pressure. The residue was purified with the following conditions: Column: XBridge Prep OBD C18 Column, 19×250 mm, 5 μm; Mobile Phase A: Water (10 mmol/L NH$_4$HCO$_3$), Mobile Phase B: ACN; Flow rate: 25 mL/min; Gradient: 15% B to 35% B in 10 min; Detector: 254 & 220 nm; RT1: 8.62 min. The product-containing fractions was combined and concentrated to give Example 50 (2.7 mg) as a white solid. m/z (ESI+ve ion)=461.30 [M+H]$^+$. $^1$H NMR (400 MHz, Methanol-d$_4$) δ 7.73 (s, 1H), 7.66 (d, J=8.0 Hz, 1H), 7.24 (s, 1H), 6.82 (t, J=8.4 Hz, 2H), 6.64-6.61 (m, 1H), 5.61 (d, J=2.4 Hz, 1H), 4.07-4.04 (m, 2H), 3.93 (s, 3H), 3.88-3.86 (m, 2H), 3.35 (s, 1H), 3.30 (s, 3H), 2.23-2.14 (m, 2H).

Example 51. (1R,2S)-2-(3-{[2-cyclopropyl-5-methoxy-6-(morpholin-4-yl)pyrimidin-4-yl]amino}-1H-indazol-6-yl)-5'-methoxyspiro[cyclopropane-1,3'-indol]-2'(1'H)-one

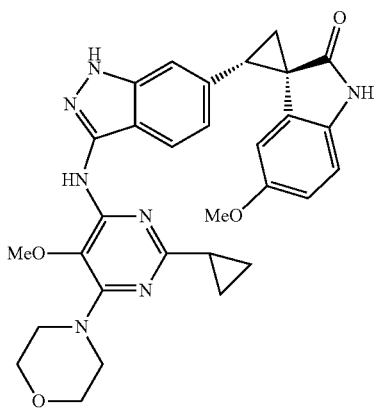 [SMILES: COc1ccc2c(c1)[C@]1(C[C@H]1c1ccc3c(Nc4nc(C5CC5)nc(N5CCOCC5)c4OC)n[nH]c3c1)C(=O)N2]

Step A. 2-cyclopropyl-6-hydroxy-5-methoxy-3H-pyrimidin-4-one

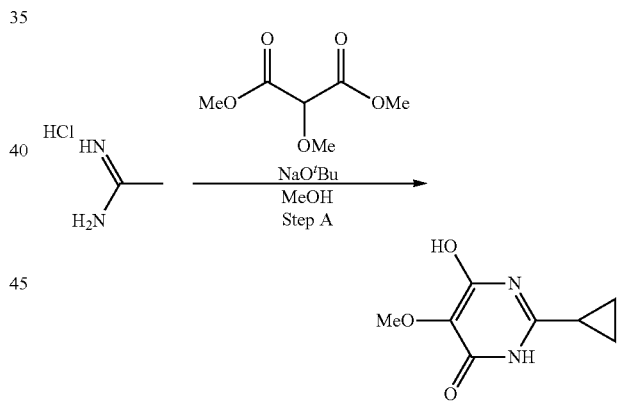

Sodium 2-methylpropan-2-olate (1.48 g, 15.419 mmol, 2.50 equiv) was added to MeOH (10.00 mL) in portions over 20 min at 0° C. To this solution were added 1,3-dimethyl 2-methoxypropanedioate (0.10 g, 0.617 mmol, 1.00 equiv) 1,3-dimethyl 2-methoxypropanedioate (1.00 g, 6.167 mmol, 1.00 equiv) and cyclopropanecarboximidamide (0.52 g, 6.167 mmol, 1.00 equiv). The mixture was heated to reflux for 12 h and then cooled to 0° C. The PH was adjusted to ~4 with Conc. HCl and filtered. The solid was collected and lyophilized to give crude the title compound (500 mg, crude) as a white solid. m/z (ESI+ve ion)=183.10 [M+H]$^+$.

Step B.
4,6-dichloro-2-cyclopropyl-5-methoxypyrimidine

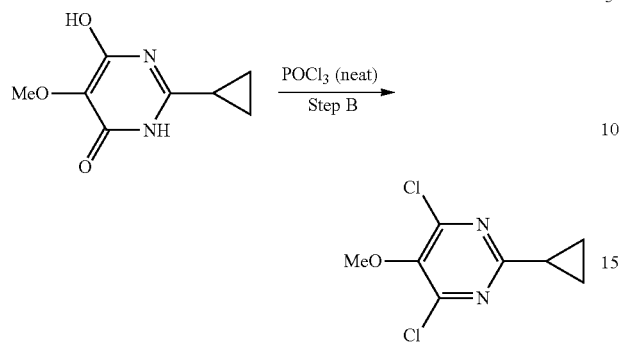

A mixture of crude 2-cyclopropyl-6-hydroxy-5-methoxy-3H-pyrimidin-4-one (500.00 mg) in POCl$_3$ (5.00 mL) was stirred for 3 h at 100° C. After cooled to room temperature, the mixture solution was added dropwise to cooled sat. aq. NaHCO$_3$ (150 mL). The mixture was extracted with EA (3×20 mL). The combined organic layers were washed with brine (30 mL), dried over anhydrous Na$_2$SO$_4$ and filtered. The filtrate was concentrated in vacuo. The residue was purified by silica gel column eluted with 0-20% EA in PE to give the title compound (370 mg) as a colorless oil. m/z (ESI+ve ion)=219.00 [M+H]$^+$. $^1$H NMR (400 MHz, Chloroform-d) δ 3.93 (s, 3H), 2.23-2.17 (m, 1H), 1.18-1.09 (m, 4H).

Step C. 4-(6-chloro-2-cyclopropyl-5-methoxypyrimidin-4-yl)morpholine

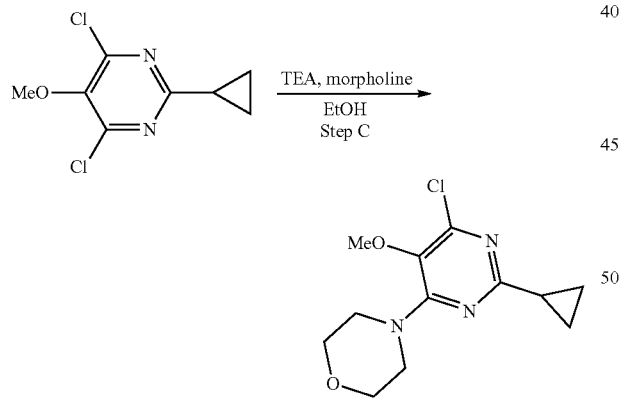

To the mixture of 4,6-dichloro-2-cyclopropyl-5-methoxypyrimidine (370.00 mg, 1.689 mmol, 1.00 equiv) and TEA (205.09 mg, 2.027 mmol, 1.20 equiv) in EtOH (5.00 mL) was added morpholine (176.57 mg, 2.027 mmol, 1.20 equiv). The mixture was stirred at 25° C. for 12 h. The solvent was moved and the residue was purified by silica gel column, eluted with 0-50% EA in PE to give the title compound (280 mg, 58.39%) as colorless oil. m/z (ESI+ve ion)=270.15 [M+H]$^+$. $^1$H NMR (400 MHz, Chloroform-d) 3.82-3.73 (m, 8H), 3.72 (s, 3H), 2.08-2.01 (m, 1H), 1.04-0.94 (m, 4H).

Step D. tert-butyl (1R,2S)-2-[1-(tert-butoxycarbonyl)-3-{[2-cyclopropyl-5-methoxy-6-(morpholin-4-yl)pyrimidin-4-yl]amino}indazol-6-yl]-5'-methoxy-2'-oxospiro[cyclopropane-1,3'-indole]-1'-carboxylate

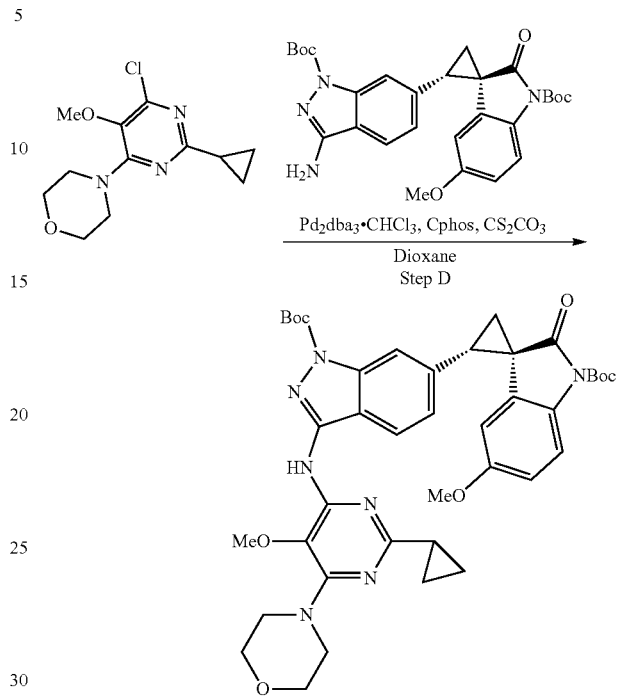

To the mixture tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (80 mg, 0.154 mmol, 1.00 equiv) and 4-(6-chloro-2-cyclopropyl-5-methoxypyrimidin-4-yl)morpholine (49.74 mg, 0.185 mmol, 1.2 equiv) in a dry dioxane (2 mL) were added Cs$_2$CO$_3$ (100.14 mg, 0.308 mmol, 2 equiv), CPhos (13.42 mg, 0.031 mmol, 0.2 equiv) and Pd$_2$(dba)$_3$·CHCl$_3$ (31.81 mg, 0.031 mmol, 0.2 equiv) under argon atmosphere. The mixture was stirred at 90° C. for 2 h. The solvent was removed under reduced pressure. The residue was purified by silica gel column eluted with 0-100% of EA in PE to give crude the title compound (60 mg, 51.79%) as a white solid. m/z (ESI +ve ion)=754.55 [M+H]$^+$.

Step E. (1R,2S)-2-(3-[[1-(2-hydroxyethyl)-3-methoxypyrazol-4-yl]amino]-1H-indazol-6-yl)-5'-methoxy-1'H-spiro[cyclopropane-1,3'-indol]-2'-one

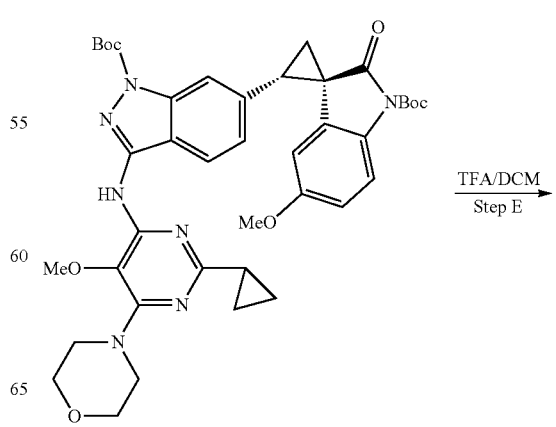

333
-continued

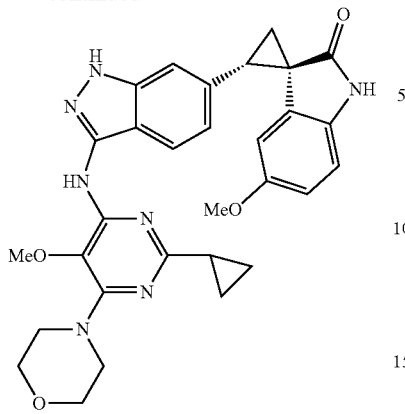

334
Step A. (2S,6R)-4-(6-Chloro-5-methoxypyrimidin-4-yl)-2,6-dimethylmorpholine

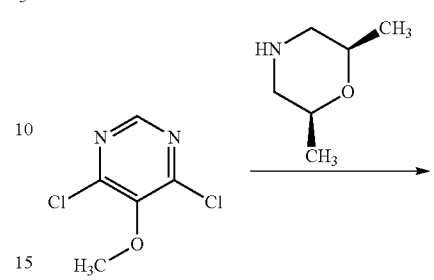

The mixture of tert-butyl (1R,2S)-2-[1-(tert-butoxycarbonyl)-3-{[2-cyclopropyl-5-methoxy-6-(morpholin-4-yl)pyrimidin-4-yl]amino}indazol-6-yl]-5'-methoxy-2'-oxospiro[cyclopropane-1,3'-indole]-1'-carboxylate (60.00 mg, 0.060 mmol, 1.00 equiv) in DCM (3.00 mL) and TFA (0.30 mL) was stirred for 4 h. The solvent was removed under reduced pressure and the residue was purified with the following conditions: Column: XBridge Prep OBD C18 Column, 19×250 mm 5 μm; Mobile Phase A: Water (10 mmol/L NH$_4$HCO$_3$), Mobile Phase B: ACN; Flow rate: 25 mL/min; Gradient: 35% B to 55% B in 10 min; Detector: 254&220 nm; RT1:8.62 min. The product-containing fractions was combined and concentrated to give Example 51 (27.1 mg, 77.28%) as a white solid. m/z (ESI+ve ion)=554.40 [M+H]$^+$. $^1$H NMR (400 MHz, Methanol-d$_4$) δ 7.59 (d, J=8.4 Hz, 1H), 7.41 (s, 1H), 6.92-6.89 (m, 1H), 6.84 (d, J=8.4 Hz, 1H), 6.63-6.61 (m, 1H), 5.65 (d, J=2.8 Hz, 1H), 3.84-3.79 (m, 4H), 3.74 (s, 3H), 3.67-3.64 (m, 4H), 3.38-3.36 (m, 1H), 3.32 (s, 3H), 2.25-2.23 (m, 1H), 2.20-2.17 (m, 1H), 1.78-1.73 (m, 1H), 0.79-0.77 (m, 2H), 0.74-0.68 (m, 2H).

Example 52. (1R,2S)-2-[3-({6-[(2R,6S)-2,6-dimethylmorpholin-4-yl]-5-methoxypyrimidin-4-yl}amino)-1H-indazol-6-yl]-5'-methoxyspiro[cyclopropane-1,3'-indol]-2'(1'H)-one To an oven-dried flask was added 4,6-dichloro-5-methoxypyrimidine (1.00 g, 5.59 mmol) followed by DMSO (19 mL), K$_2$CO$_3$ (1.16 g, 8.34 mmol), and cis-2,6-dimethylmorpholine (0.64 mL, 5.9 mmol). The reaction mixture was stirred at room temperature for 1 h at which time it was quenched with sat. aqueous NH$_4$Cl. The mixture was extracted three times with EtOAc. The combined organic layers were washed with water and brine, dried with MgSO$_4$, filtered, and concentrated. The residue was purified by column chromatography (5% to 30% EtOAc/hexanes, gradient elution) to afford the title compound (1.30 g, 90%) as a white solid. m/z (ESI, +ve ion)=258.2 [M+H]$^+$.

Step B. Tert-butyl (1R,2S)-2-(1-(tert-butoxycarbonyl)-3-((6-((2S,6R)-2,6-dimethylmorpholino)-5-methoxypyrimidin-4-yl)amino)-1H-indazol-6-yl)-5'-methoxy-2'-oxospiro[cyclopropane-1,3'-indoline]-1'-carboxylate

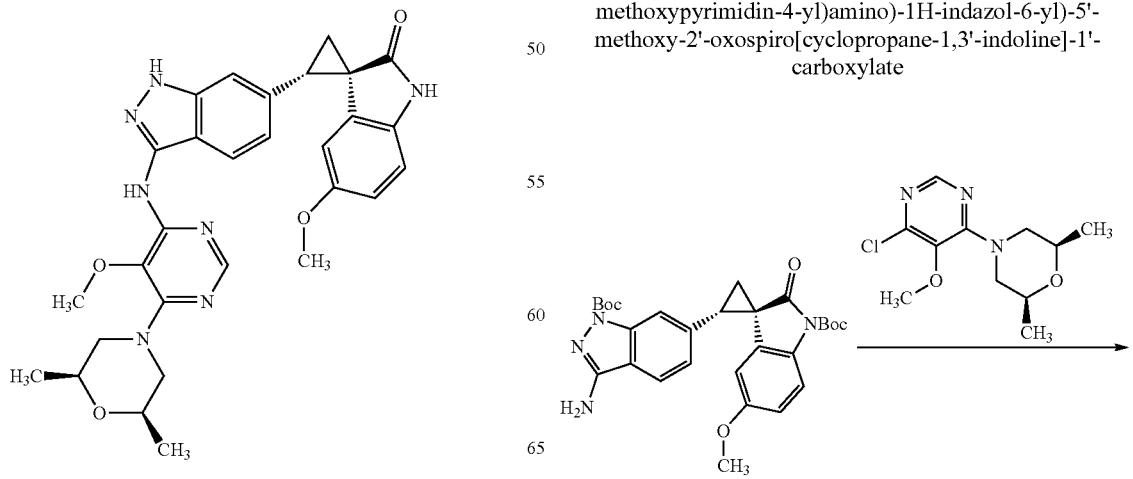

-continued

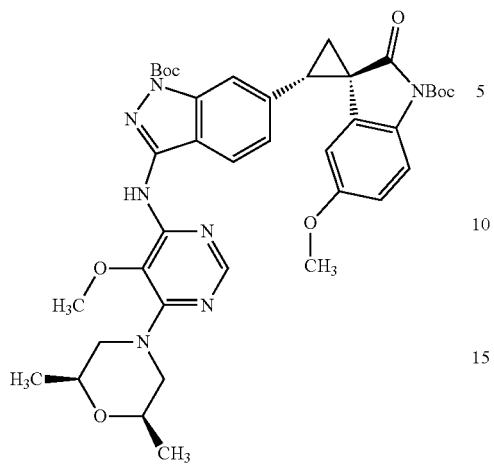

To an oven-dried flask was added (2S,6R)-4-(6-Chloro-5-methoxypyrimidin-4-yl)-2,6-dimethylmorpholine (36.4 mg, 0.141 mmol), tert-butyl (R,2S)-2-(3-amino-1-(tert-butoxycarbonyl)-1H-indazol-6-yl)-5'-methoxy-2'-oxospiro[cyclopropane-1,3'-indoline]-1'-carboxylate (70.0 mg, 0.135 mmol), rac-binap Pd G4 (13.5 mg, 0.0134 mmol), BINAP (8.40 mg, 0.0134 mmol), Tripotassium phosphate (57.0 mg, 0.270 mmol) and 1,4-dioxane (3.4 mL). The mixture was degassed with bubbling argon for 10 min. At this time, the reaction mixture was heated to 70° C. for 2 h. The reaction mixture was cooled was cooled to room temperature and diluted with EtOAc and washed with sat. aqueous NaHCO$_3$. The aqueous layer was extracted an additional three times with EtOAc. Combined organic layers were washed with brine, dried with MgSO$_4$, filtered, and concentrated. The residue was purified by column chromatography (0% to 80% EtOAc/hexanes, a gradient elution) to provide the title compound (30 mg, 30%) as a white foam. m/z (ESI, +ve ion)=742.3 [M+H]$^+$.

Step C

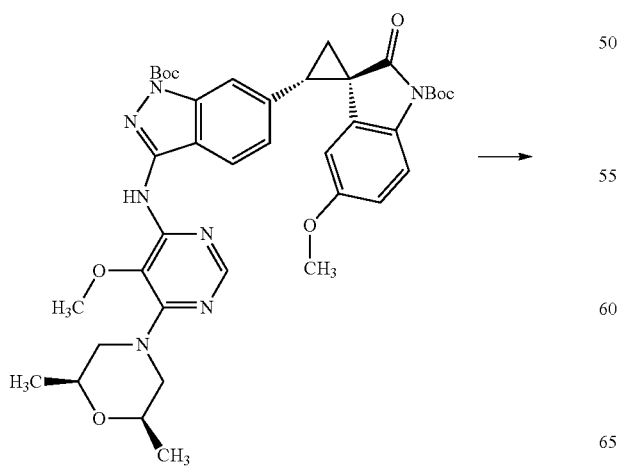

-continued

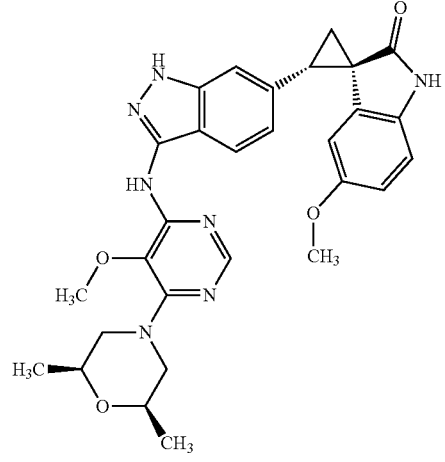 [SMILES: COc1ccc2c(c1)[C@]1(C[C@H]1c1ccc3c(Nc4ncnc(N5C[C@@H](C)O[C@@H](C)C5)c4OC)n[nH]c3c1)C(=O)N2]

To an oven-dried flask was added tert-butyl (1R,2S)-2-(1-(tert-butoxycarbonyl)-3-((6-((2S,6R)-2,6-dimethylmorpholino)-5-methoxypyrimidin-4-yl)amino)-1H-indazol-6-yl)-5'-methoxy-2'-oxospiro[cyclopropane-1,3'-indoline]-1'-carboxylate (30 mg, 0.040 mmol) followed DCM (2.0 mL) and trifluoroacetic acid (0.15 mL, 2.0 mmol). The reaction mixture was stirred at room temperature for 2 h. At this time, the mixture was concentrated and purified by prep HPLC (20% to 40% ACN/H$_2$O, 0.1% TFA modifier, gradient elution) to afford Example 52 (8.0 mg, 37%) as a white amorphous solid after lyophilization. m/z (ESI, +ve ion)=542.3 [M+H]$^+$. $^1$H NMR (400 MHz, DMSO-d) δ=12.99-12.60 (m, 1H), 10.45 (s, 1H), 9.81 (br s, 1H), 8.03 (s, 1H), 7.62 (d, J=8.3 Hz, 1H), 7.44 (s, 1H), 6.96 (d, J=8.3 Hz, 1H), 6.75 (d, J=8.6 Hz, 1H), 6.59 (dd, J=2.5, 8.6 Hz, 1H), 5.76-5.69 (m, 1H), 4.40 (br d, J=12.9 Hz, 2H), 3.69 (s, 3H), 3.68-3.59 (m, 2H), 3.34 (s, 3H), 3.19 (t, J=8.5 Hz, 1H), 2.72 (dd, J=10.9, 12.9 Hz, 2H), 2.34 (dd, J=4.7, 8.0 Hz, 1H), 1.99 (dd, J=4.7.9.0 Hz, 1H), 1.14 (d, J=6.3 Hz, 6H).

Example 53. (1R,2S)-2-(3-((5-chloro-6-(1,1-dioxidothiomorpholino)pyrimidin-4-yl)amino)-1H-indazol-6-yl)-5'-methoxyspiro[cyclopropane-1,3'-indolin]-2'-one

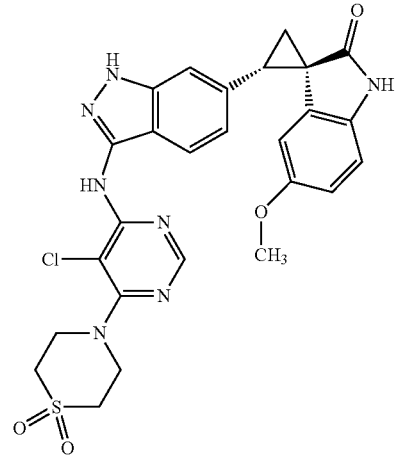 [SMILES: COc1ccc2c(c1)[C@]1(C[C@H]1c1ccc3c(Nc4ncnc(N5CCS(=O)(=O)CC5)c4Cl)n[nH]c3c1)C(=O)N2]

Step A.
4-(6-Amino-5-chloropyrimidin-4-yl)thiomorpholine 1,1-dioxide

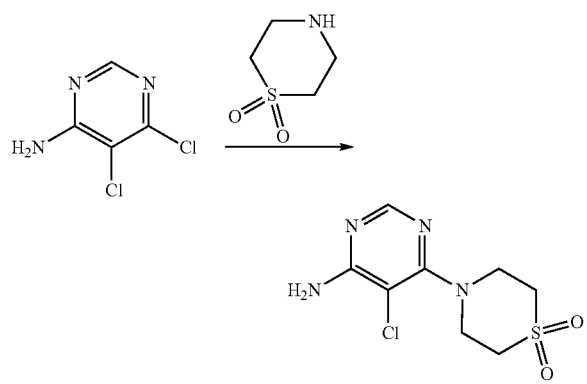

To an oven-dried flask was added 5,6-dichloro-4-pyrimidinamine (1.0) g, 6.10 mmol) followed by toluene (9.0 mL) and thiomorpholine dioxide (0.850 mL, 6.31 mmol). The reaction mixture was heated to 80° C. for 16 hours and then cooled to room temperature. The reaction was then concentrated to a white solid to give the title compound (700 mg, 44%) as a white amorphous solid.

Step B. Tert-butyl (1R,2S)-2-(1-(tert-butoxycarbonyl)-3-((5-chloro-6-(1,1-dioxidothiomorpholino) pyrimidin-4-yl)amino)-1H-indazol-6-yl)-5'-methoxy-2'-oxospiro[cyclopropane-1,3'-indoline]-1'-carboxylate To an oven-dried flask was added tert-butyl (1R,2S)-2-(1-(tert-butoxycarbonyl)-3-iodo-1H-indazol-6-yl)-5'-methoxy-2'-oxospiro[cyclopropane-1,3'-indoline]-1'-carboxylate (102 mg, 0.162 mmol), 4-(6-amino-5-chloropyrimidin-4-yl)thiomorpholine 1,1-dioxide (45 mg, 0.167 mmol), Xantphos Pd G4 (15.6 mg, 0.0162 mmol), and 1,4-dioxane (1.6 mL). The mixture was degassed with bubbling argon for 10 min. At this time, Cs$_2$CO$_3$ (105 mg, 0.323 mmol) was added and the reaction mixture was heated to 100° C. for 1 h. The reaction mixture was cooled was cooled to room temperature and diluted with EtOAc and washed with sat. aqueous NaHCO$_3$. The aqueous layer was extracted an additional three times with EtOAc. Combined organic layers were washed with brine, dried with MgSO$_4$, filtered, and concentrated. The residue was purified by column chromatography (0% to 50% acetone/hexanes, a gradient elution) to provide the title compound (30 mg, 24%) as a white foam. m/z (ESI, +ve ion)=767.2 [M+H]$^+$.

Step C

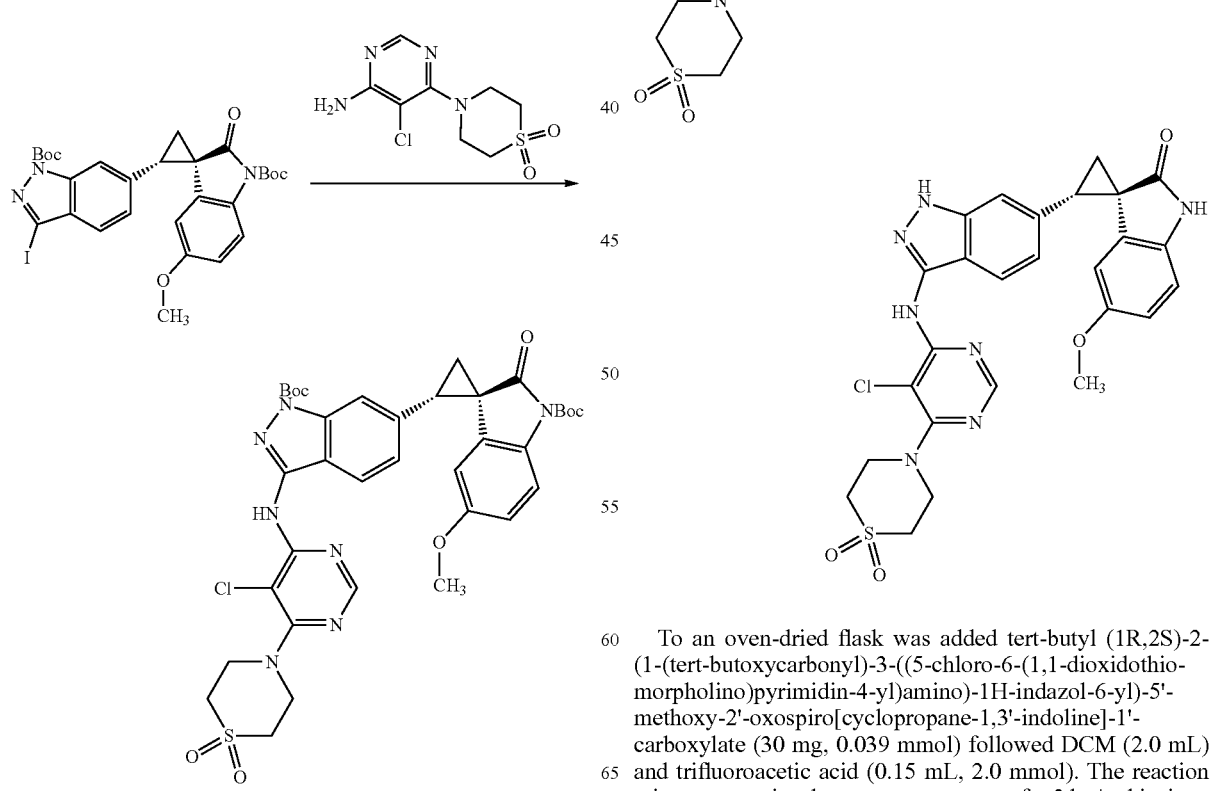

To an oven-dried flask was added tert-butyl (1R,2S)-2-(1-(tert-butoxycarbonyl)-3-((5-chloro-6-(1,1-dioxidothiomorpholino)pyrimidin-4-yl)amino)-1H-indazol-6-yl)-5'-methoxy-2'-oxospiro[cyclopropane-1,3'-indoline]-1'-carboxylate (30 mg, 0.039 mmol) followed DCM (2.0 mL) and trifluoroacetic acid (0.15 mL, 2.0 mmol). The reaction mixture was stirred at room temperature for 2 h. At this time, the mixture was concentrated and purified by prep HPLC (20% to 40% ACN/H$_2$O, 0.1% TFA modifier, gradient elution) to afford Example 53 (5.0 mg, 23%) as a white amorphous solid after lyophilization. m/z (ESI, +ve ion) =566.0 [M+H]$^+$. $^1$H NMR (400 MHz, DMSO-d6) δ=12.75 (br s, 1H), 10.43 (s, 1H), 9.29 (s, 1H), 8.01 (s, 1H), 7.42 (s, 1H), 7.35 (d, J=8.3 Hz, 1H), 6.90 (dd, J=1.1, 8.5 Hz, 1H), 6.74 (d, J=8.3 Hz, 1H), 6.60-6.55 (m, 1H), 5.71 (d, J=2.8 Hz, 1H), 3.94 (br s, 4H), 3.33 (s, 3H), 3.32-3.26 (m, 4H), 3.21-3.15 (m, 1H), 2.33 (dd, J=4.7, 8.0 Hz, 1H), 2.01-1.95 (m, 1H).

Example 54. (1R,2S)-2-(3-((6-(1,1-dioxidothiomorpholino)-5-methoxypyrimidin-4-yl)amino)-1H-indazol-6-yl)-5'-methoxyspiro[cyclopropane-1,3'-indolin]-2'-one

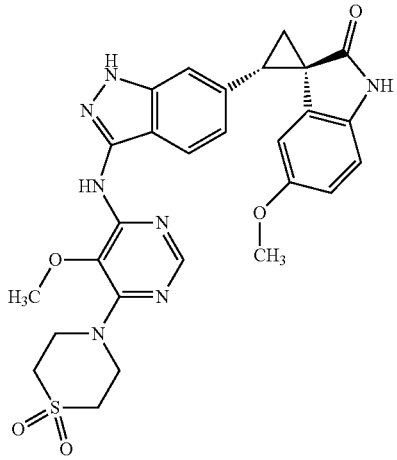 [SMILES: COc1ccc2c(c1)[C@]1(C[C@H]1c1ccc3c(Nc4ncnc(N5CCS(=O)(=O)CC5)c4OC)n[nH]c3c1)C(=O)N2]

Step A.
4-(6-Chloro-5-methoxypyrimidin-4-yl)thiomorpholine 1,1-dioxide

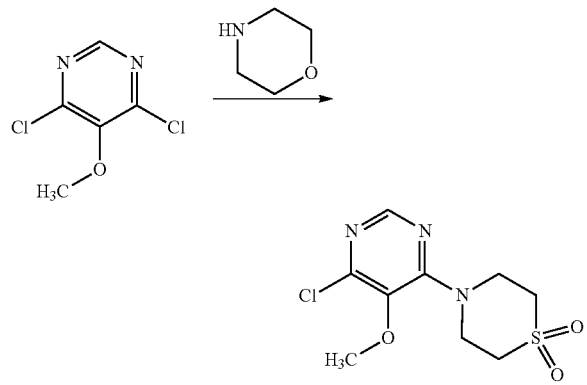

To an oven-dried flask was added 4,6-dichloro-5-methoxypyrimidine (1.00 g, 5.59 mmol) followed by DMSO (19 mL), K$_2$CO$_3$ (1.16 g, 8.34 mmol), and thiomorpholine dioxide (0.75 mL, 5.6 mmol). The reaction mixture was stirred at room temperature for overnight at which time it was quenched with sat. aqueous NH$_4$Cl. The mixture was extracted three times with EtOAc. The combined organic layers were washed with water and brine, dried with MgSO$_4$, filtered, and concentrated. The residue was purified by column chromatography (5% to 30% EtOAc/hexanes, gradient elution) to afford the title compound (973 mg, 63%) as a white solid. m/z (ESI, +ve ion)=278.0 [M+H]$^+$.

Step B. Tert-butyl (1R,2S)-2-(1-(tert-butoxycarbonyl)-3-((6-(1,1-dioxidothiomorpholino)-5-methoxypyrimidin-4-yl)amino)-1H-indazol-6-yl)-5'-methoxy-2'-oxospiro[cyclopropane-1,3'-indoline]-1'-carboxylate

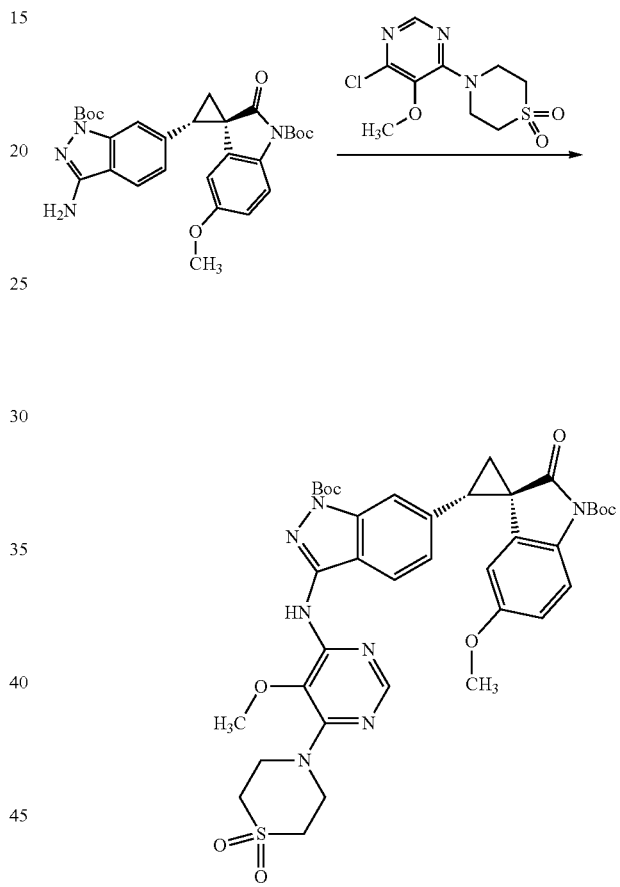

To an oven-dried flask was added 4-(6-Chloro-5-methoxypyrimidin-4-yl)thiomorpholine 1,1-dioxide (74.7 mg, 0.2689 mmol), tert-butyl (1R,2S)-2-(3-amino-1-(tert-butoxycarbonyl)-1H-indazol-6-yl)-5'-methoxy-2'-oxospiro [cyclopropane-1,3'-indoline]-1'-carboxylate (70.0 mg, 0.135 mmol), Xantphos Pd G4 (13.0 mg, 0.134 mmol), and 1,4-dioxane (1.3 mL). The mixture was degassed with bubbling argon for 10 min. At this time, Cs$_2$CO$_3$ (87.6 mg, 0.269 mmol) was added and the reaction mixture was heated to 100° C. for 2 h. The reaction mixture was cooled was cooled to room temperature and diluted with EtOAc and washed with sat. aqueous NaHCO$_3$. The aqueous layer was extracted an additional three times with EtOAc. Combined organic layers were washed with brine, dried with MgSO$_4$, filtered, and concentrated. The residue was purified by column chromatography (0% to 80% EtOAc/hexanes, a gradient elution) to provide the title compound (19 mg, 19%) as a white foam. m/z (ESI, +ve ion)=762.2 [M+H]$^+$.

Step C

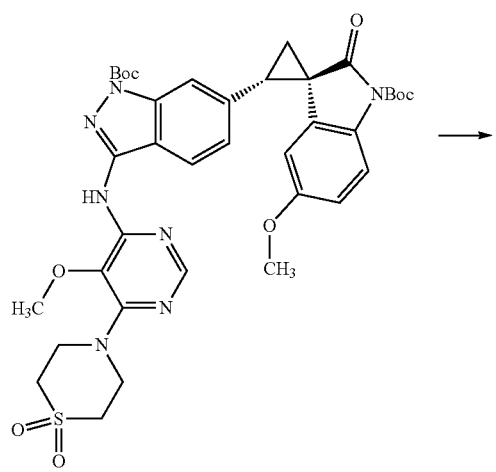

To an oven-dried flask was added tert-butyl (1R,2S)-2-(1-(tert-butoxycarbonyl)-3-((6-(1,1-dioxidothiomorpholino)-5-methoxypyrimidin-4-yl)amino)-1H-indazol-6-yl)-5'-methoxy-2'-oxospiro[cyclopropane-1,3'-indoline]-1'-carboxylate (19 mg, 0.025 mmol) followed DCM (1.25 mL) and trifluoroacetic acid (0.10 mL, 1.3 mmol). The reaction mixture was stirred at room temperature for 3 h. At this time, the mixture was concentrated and purified by prep HPLC (20% to 40% ACN/H$_2$O, 0.1% TFA modifier, gradient elution) to afford Example 54 (10 mg, 71%) as a white amorphous solid after lyophilization. m/z (ESI, +ve ion) =562.3 [M+H]$^+$. $^1$H NMR (400 MHz, DMSO-d$_6$) δ=12.78 (br s, 1H), 10.45 (s, 1H), 9.57 (br s, 1H), 7.99 (s, 1H), 7.54 (d, J=8.3 Hz, 1H), 7.43 (s, 1H), 6.93 (d, J=8.3 Hz, 1H), 6.75 (d, J=8.3 Hz, 1H), 6.59 (dd, J=2.7, 8.5 Hz, 1H), 5.73 (d, J=2.5 Hz, 1H), 4.15 (br s, 4H), 3.71 (s, 3H), 3.34 (s, 3H), 3.30-3.24 (m, 4H), 3.22-3.16 (m, 1H), 2.34 (dd, J=4.7, 8.0 Hz, 1H), 1.99 (dd, J=4.7, 9.0 Hz, 1H).

Example 55. (1R,2S)-2-(3-{[5-(2-hydroxyethyl)-3-methoxypyrazin-2-yl]amino}-1H-indazol-6-yl)-5'-methoxyspiro[cyclopropane-1,3'-indol]-2'(1'H)-one

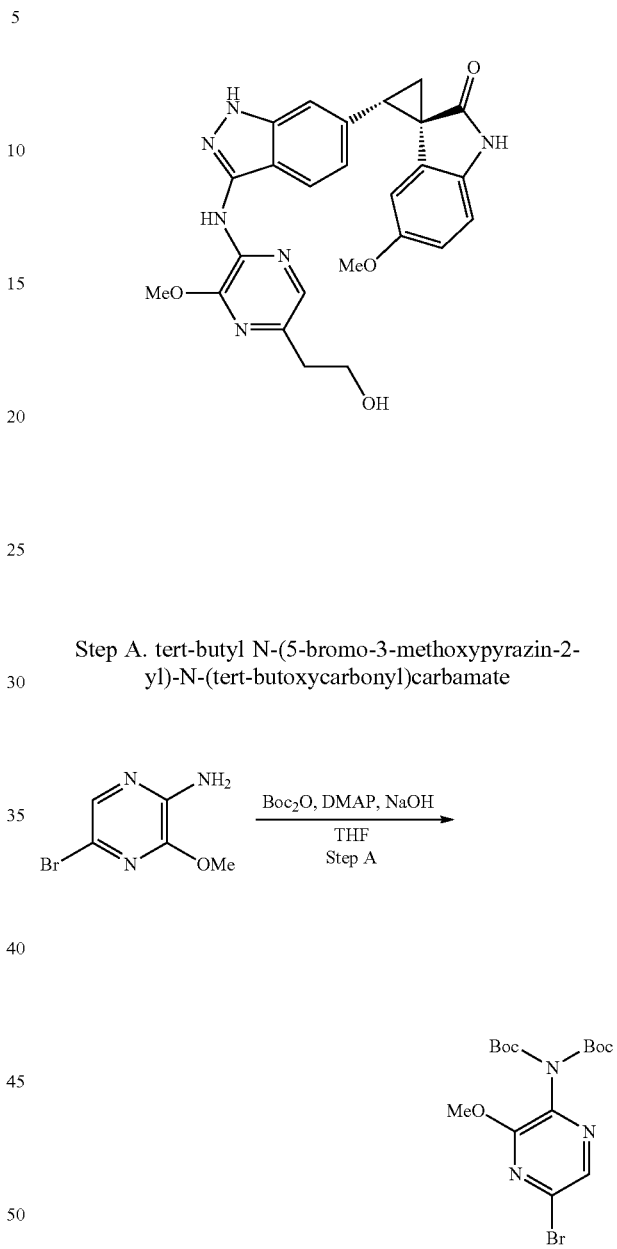

Step A. tert-butyl N-(5-bromo-3-methoxypyrazin-2-yl)-N-(tert-butoxycarbonyl)carbamate To a stirred mixture of 5-bromo-3-methoxypyrazin-2-amine (2000.00 mg, 9.803 mmol, 1.00 equiv) and Boc$_2$O (3209.09 mg, 14.705 mmol, 1.50 equiv) in THF (5.00 mL) were added DMAP (119.76 mg, 0.980 mmol, 0.10 equiv) and NaOH (784.15 mg, 19.606 mmol, 2.00 equiv). The resulting mixture was stirred for 2 hours at RT under N$_2$ atmosphere. The resulting mixture was extracted with EA (3×60 mL). The combined organic layers were washed with sat. brine (3×25 mL), dried over anhydrous Na$_2$SO$_4$. After filtration, the filtrate was concentrated under reduced pressure. The residue was purified by silica gel column chromatography, eluted with PE:EA (3:1) to afford the title compound (1.7 g, 42.5%) as white solid. m/z (ESI+ve ion-100)=403.85 [M+H−100]$^+$.

Step B. tert-butyl N-(tert-butoxycarbonyl)-N-{5-[(E)-2-ethoxyethenyl]-3-methoxypyrazin-2-yl}carbamate

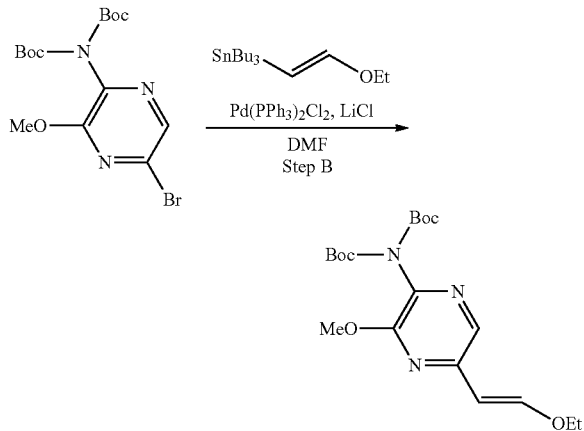

To a stirred mixture of tert-butyl N-(5-bromo-3-methoxypyrazin-2-yl)-N-(tert-butoxycarbonyl)carbamate (990 mg, 2.449 mmol, 1.00 equiv) and tributyl[(E)-2-ethoxyethenyl]stannane (1768.85 mg, 4.898 mmol, 2 equiv) in DMF (15 mL, 193.826 mmol, 79.15 equiv) were added LiCl (363.37 mg, 8.572 mmol, 3.5 equiv) and Pd(PPh$_3$)$_2$Cl$_2$ (171.89 mg, 0.245 mmol, 0.1 equiv) at room temperature under nitrogen atmosphere. The resulting mixture was stirred for 1.5 h at 80° C. under nitrogen atmosphere. The mixture was cooled down to room temperature. The reaction was quenched by the addition of Water (15 mL) at room temperature. The resulting mixture was extracted with DCM (3×15 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EA (1/1) to afford the title compound (730 mg, 75.38%) as a white solid. m/z (ESI+ve ion)=396.10 [M+H]$^+$. $^1$H NMR (400 MHz, Chloroform-d) δ 8.66 (s, 1H), 6.53 (d, J=7.1 Hz, 1H), 5.40 (d, J=7.1 Hz, 1H), 4.11 (m, 2H), 3.97 (s, 3H), 1.42 (s, 21H).

Step C. tert-butyl N-(tert-butoxycarbonyl)-N-[5-(2-hydroxyethyl)-3-methoxypyrazin-2-yl] carbamate

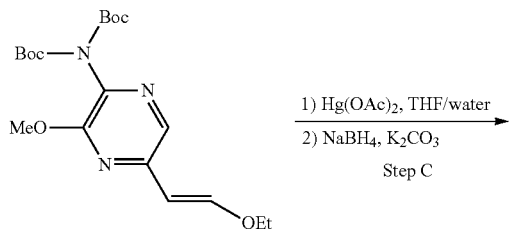

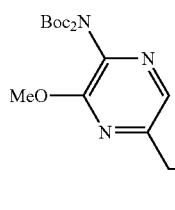

To a stirred mixture of tert-butyl N-(tert-butoxycarbonyl)-N-{5-[(E)-2-ethoxyethenyl]-3-methoxypyrazin-2-yl} carbamate (720.00 mg, 1.821 mmol, 1.00 equiv) in THF (5.50 mL) were added mercuric acetate (696.26 mg, 2.18 mmol, 1.20 equiv) in water (6.55 mL) dropwise at 0° C. under nitrogen atmosphere. The resulting mixture was stirred for 15 min at 0° C. under nitrogen atmosphere. To the above mixture was added NaBH$_4$ (275.53 mg, 7.284 mmol, 4.00 equiv) in saturated K$_2$CO$_3$ (aq.) (5.44 mL) dropwise at room temperature. The resulting mixture was stirred for additional 20 min at room temperature. The reaction was quenched by the addition of Water (10 mL). The resulting mixture was extracted with DCM (3×15 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with PE/EtOAc (1/1) to afford the title compound (600 mg, 89.21%) as a colorless solid. m/z (ESI+ve ion)=370.20 [M+H]$^+$. $^1$H NMR (400 MHz, Chloroform-d) δ 7.93 (s, 1H), 4.07-3.98 (m, 6H), 3.01 (t, J=5.8 Hz, 2H), 1.44 (s, 18H).

Step D. tert-butyl N-(tert-butoxycarbonyl)-N-(6-[2-[(tert-butyldimethylsilyl) oxy]ethyl]-3-methoxypyrazin-2-yl)carbamate

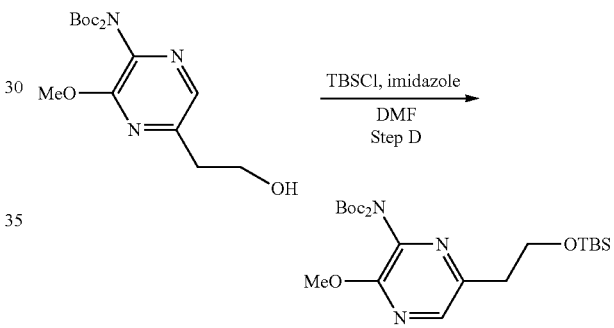

To a stirred mixture of tert-butyl N-(tert-butoxycarbonyl)-N-[5-(2-hydroxyethyl)-3-methoxypyrazin-2-yl] carbamate (166.00 mg, 0.449 mmol, 1.00 equiv) in DMF (4.00 mL) were added 1H-imidazole (73.42 mg, 0.000 mmol, 2.40 equiv) and TBDMS-Cl (81.27 mg, 0.539 mmol, 1.20 equiv) at 0° C. under nitrogen atmosphere. The resulting mixture was stirred for 2 h at room temperature under nitrogen atmosphere. The reaction was quenched by the addition of water (15 mL) at room temperature. The resulting mixture was extracted with DCM (3×10 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with PE/EtOAc (6/1) to afford the title compound (105 mg, 48.31%) as a yellow oil. m/z (ESI+ve ion)=484.30 [M+H]$^+$.

Step E. 6-[2-[(tert-butyl dimethylsilyl)oxy]ethyl]-3-methoxypyrazin-2-amine

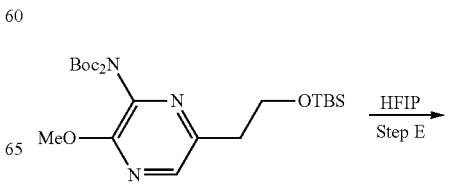

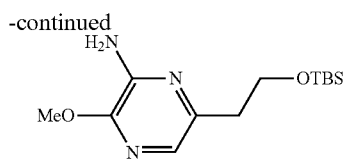

Into a 50 mL round-bottom flask were added tert-butyl N-tert-butoxycarbonyl)-N-(6-[2-[(tert-butyldimethylsilyl)oxy]ethyl]-3-methoxypyrazin-2-yl)carbamate (560.00 mg, 1 equiv) and 1,1,1,3,3,3-hexafluoropropan-2-ol (20.00 mL) at room temperature. The resulting mixture was stirred for 16 h at 60° C. under nitrogen atmosphere. The resulting mixture was concentrated under reduced pressure. The residue was purified by silica gel column chromatography, eluted with PE/EtOAc (2/1) to afford the title compound (237 mg, 72.22%) as a white solid. m/z (ESI+ve ion)=284.20 [M+H]$^+$. $^1$H NMR (400 MHz, DMSO-d$_6$) δ 7.33 (s, 1H), 5.98 (s, 2H), 3.85 (d, J=15.4 Hz, 5H), 2.63 (m, 2H), 0.81 (s, 9H), 0.06 (s, 6H).

Step F. tert-butyl (1R,2S)-2-(1-tert-butoxycarbonyl)-3-((5-(2-((tert-butyldimethylsilyl)oxy)ethyl)-3-methoxypyrazin-2-yl)amino)-1H-indazol-6-yl)-5'-methoxy-2'-oxospiro[cyclopropane-1,3'-indoline]-1'-carboxylate

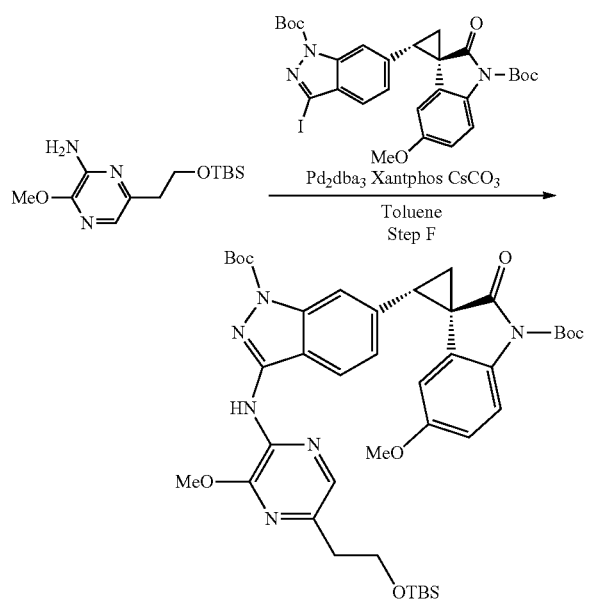

To a stirred mixture of tert-butyl (1R,2S)-2-(1-(tert-butoxycarbonyl)-3-iodo-1H-indazol-6-yl)-5'-methoxy-2'-oxospiro[cyclopropane-1,3'-indoline]-1'-carboxylate (100.00 mg, 0.158 mmol, 1.00 equiv) and 6-[2-[(tert-butyldimethylsilyl)oxy]ethyl]-3-methoxypyrazin-2-amine (53.86 mg, 0.190 mmol, 1.20 equiv) in toluene (2.50 mL) were added Pd$_2$(dba)$_3$ (14.50 mg, 0.016 mmol, 0.1 equiv) and XantPhos (9.16 mg, 0.016 mmol, 0.1 equiv) and Cs$_2$CO$_3$ (103.19 mg, 0.317 mmol, 2 equiv) at room temperature under nitrogen atmosphere. The resulting mixture was stirred for 2 h at 90° C. under nitrogen atmosphere and cooled down to room temperature. The reaction was quenched by the addition of water (5 mL) at room temperature. The resulting mixture was extracted with DCM (3×10 mL). The combined organic layers were washed with brine (15 mL), dried over anhydrous Na$_2$SO$_4$. After filtration, the filtrate was concentrated under reduced pressure. The residue was purified by silica gel column chromatography, eluted with PE/EtOAc (3/1) to afford the title compound (84 mg, 67.40%) as a yellow solid. m/z (ESI+ve ion)=787.60 [M+H]$^+$.

Step G: (1R,2S)-2-(3-((5-(2-hydroxyethyl)-3-methoxypyrazin-2-yl)amino)-1H-indazol-6-yl)-5'-methoxyspiro[cyclopropane-1,3'-indolin]-2'-one

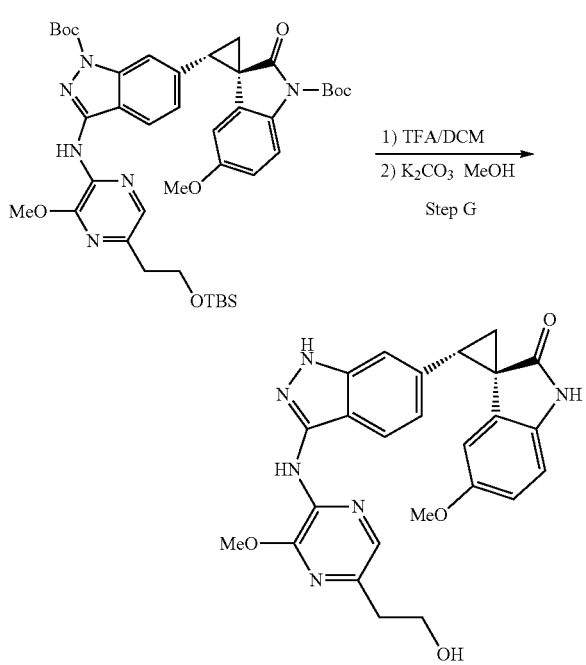

A mixture of tert-butyl (1R,2S)-2-(1-(tert-butoxycarbonyl)-3-((5-(2-((tert-butyldimethylsilyl)oxy)ethyl)-3-methoxypyrazin-2-yl)amino)-1H-indazol-6-yl)-5'-methoxy-2'-oxospiro[cyclopropane-1,3'-indoline]-1'-carboxylate (84.00 mg, 0.107 mmol, 1.00 equiv) and TFA (2.0) mL, 26.926 mmol, 252.27 equiv) in DCM (4.00 mL) was stirred for 2 h at room temperature under nitrogen atmosphere. The resulting mixture was concentrated under reduced pressure. The resulting mixture was diluted with MeOH (5.00 mL). To the above mixture was added K$_2$CO$_3$ (50.00 mg, 0.362 mmol, 3.39 equiv) in portions at room temperature. The resulting mixture was stirred for additional 2 h at room temperature then concentrated under reduced pressure. The residue was purified by Prep-HPLC with the following conditions (Column: YMC-Actus Triart C18 ExRS, 30 mm×150 mm, 5 μm; Mobile Phase A: Water (10 mmol/L NH$_4$HCO$_3$), Mobile Phase B: ACN; Flow rate: 60 mL/min; Gradient: 20% B to 45% B in 8 min, 254 nm; RT1: 6.58 min to afford Example 55 (21.5 mg, 42.63%) as a white solid. m/z (ESI+ve ion)=473.30 [M+H]$^+$. $^1$H NMR (400 MHz, DMSO-d$_6$) δ 12.51 (s, 1H), 10.43 (s, 1H), 8.63 (s, 1H), 7.39 (m, 3H), 6.87 (d, J=9.2 Hz, 1H), 6.75 (d, J=8.4 Hz, 1H), 6.59 (m, 1H), 5.72 (d, J=2.4 Hz, 1H), 4.60 (m, 1H), 3.97 (s, 3H), 3.68 (q, J=6.5 Hz, 2H), 3.33 (s, 3H), 3.35 (d, J=15.2 Hz, 2H), 2.51 (d, J=1.6 Hz, 2H), 1.98 (m, 1H).

347

Example 56. (1R,2S)-2-(3-{[6-(2-hydroxyethyl)-3-methoxypyrazin-2-yl]amino}-1H-indazol-6-yl)-5'-methoxyspiro[cyclopropane-1,3'-indol]-2'(1'H)-one

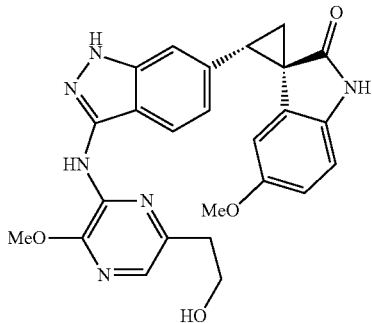 [SMILES: COc1ccc2c(c1)[C@]1(C[C@H]1c1ccc3c(Nc4nc(CCO)cnc4OC)n[nH]c3c1)C(=O)N2]

Step A. tert-butyl N-(tert-butoxycarbonyl)-N-(6-chloro-3-methoxypyrazin-2-yl)carbamate

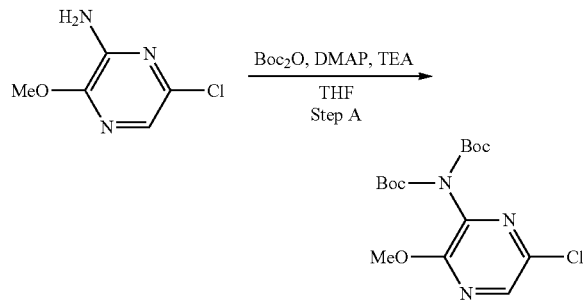

To a stirred mixture of 6-chloro-3-methoxypyrazin-2-amine (1500.00 mg, 9.400 mmol, 1.00 equiv) and Boc$_2$O (3077.37 mg, 14.100 mmol, 1.5 equiv) in THF (10 mL) were added DMAP (114.84 mg, 0.940 mmol, 0.1 equiv) and Et$_3$N (1902.43 mg, 18.801 mmol, 2 equiv). The resulting mixture was stirred for 2 hours at room temperature under N$_2$ atmosphere. The resulting mixture was extracted with EA (3×20 mL). The combined organic layers were washed with brine (3×15 mL), dried over anhydrous Na$_2$SO$_4$. After filtration, the filtrate was concentrated under reduced pressure. The residue was purified by silica gel column chromatography, eluted with PE:EA (4:1) to afford the title compound (2.8 g, 82%) as a white solid. m/z (ESI, +ve ion)=204.1 [M+H−100−56]$^+$.

Step B. tert-butyl N-(tert-butoxycarbonyl)-N-[6-[(E)-2-ethoxyethenyl]-3-methoxypyrazin-2-yl]carbamate

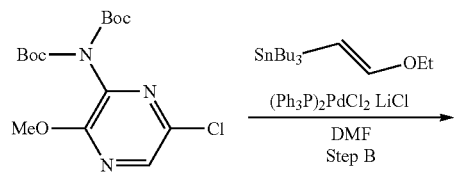

348

-continued

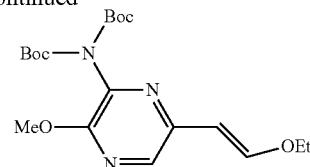

To a stirred mixture of tert-butyl N-(tert-butoxycarbonyl)-N-(6-chloro-3-methoxypyrazin-2-yl)carbamate (410.00 mg, 1.139 mmol, 1.00 equiv) and Pd(PPh$_3$)$_2$Cl$_2$ (79.98 mg, 0.114 mmol, 0.10 equiv) in DMF (10.00 mL) were added tributyl [(E)-2-ethoxyethenyl]stannane (823.05 mg, 2.278 mmol, 2.00 equiv) and LiCl (169.08 mg, 3.987 mmol, 3.50 equiv) at room temperature under nitrogen atmosphere. The resulting mixture was stirred for 1.5 h at 80° C. under nitrogen atmosphere. The mixture was cooled down to room temperature. The reaction was quenched by the addition of water (15 mL) at room temperature. The resulting mixture was extracted with DCM (3×15 mL). The combined organic layers were washed with brine (2×25 mL), dried over anhydrous Na$_2$SO$_4$. After filtration, the filtrate was concentrated under reduced pressure. The residue was purified by reverse phase flash chromatography with the following conditions: Column: Spherical C18, 20-40 μm, 120 g; Mobile Phase A: Water (plus 5 mM NH$_4$HCO$_3$); Mobile Phase B: ACN; Flow rate: 50 mL/min; Gradient: 50% B-60% B in 15 min; Detector: 254 nm. The fractions containing desired product were collected at 61% B and concentrated under reduced pressure to afford the title compound (400 mg, 88.77%) as a yellow oil. m/z=396.30 [M+H]$^+$. $^1$H NMR (400 MHz, Chloroform-d) δ 8.76 (s, 1H), 6.41 (d, J=7.0 Hz, 1H), 5.38 (d, J=7.0 Hz, 1H), 4.12-3.92 (m, 5H), 1.39 (d, J=3.2 Hz, 21H).

Step C. tert-butyl N-(tert-butoxycarbonyl)-N-[6-(2-hydroxyethyl)-3-methoxypyrazin-2-yl] carbamate

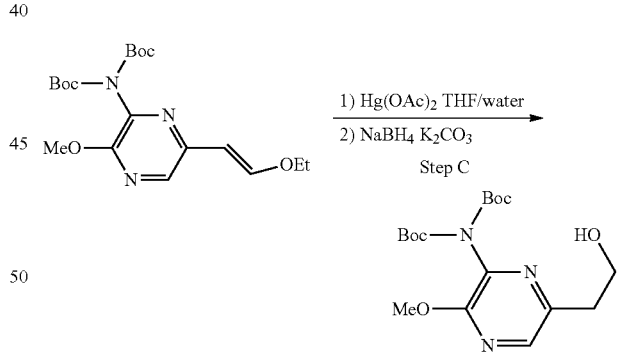

To a stirred mixture of tert-butyl N-(tert-butoxycarbonyl)-N-[6-[(E)-2-ethoxyethenyl]-3-methoxypyrazin-2-yl] carbamate (333.00 mg, 0.842 mmol, 1.00 equiv) in THF (2.53 mg) was added mercuric acetate (322.02 mg, 1.010 mmol, 1.20 equiv) in water (3.03 m L) dropwise at 0° C. under nitrogen atmosphere. The resulting mixture was stirred for 15 min at 0° C. under nitrogen atmosphere. To the above mixture was added NaBH$_4$ (127.43 mg, 3.368 mmol, 4.00 equiv) in saturated K$_2$CO$_3$, aq. (3.00 mL) dropwise at room temperature. The resulting mixture was stirred for additional 1 h at room temperature. The reaction was quenched by the addition of water (10 mL) at room temperature. The resulting mixture was extracted with DCM (3×10 mL). The combined organic layers were washed with brine (2×15 mL), dried over anhydrous Na$_2$SO$_4$. After filtration, the filtrate was concentrated under reduced pressure. The residue was purified by reverse phase flash chromatography with the following conditions: Column: Spherical C18, 20-40 μm, 80 g; Mobile Phase A: Water (plus 5 mM NH$_4$HCO); Mobile Phase B: ACN; Flow rate: 80 mL/min; Gradient: 40% B-60% B in 20 min; Detector: 254 nm. The fractions containing desired product were collected at 55% B and concentrated under reduced pressure to afford the title compound (217 mg, 69.76%) as an off-white solid. m/z=370.30 [M+H]$^+$. $^1$H NMR (400 MHz, DMSO-d) δ 8.11 (s, 1H), 4.68 (t, J=5.2 Hz, 1H), 3.93 (s, 3H), 3.68 (m, 2H), 2.83 (t, J=6.7 Hz, 2H), 1.35 (s, 18H).

Step D. tert-butyl N-(tert-butoxycarbonyl)-N-(6-[2-[(tert-butyldimethylsilyl) oxy]ethyl]-3-methoxy-pyrazin-2-yl)carbamate

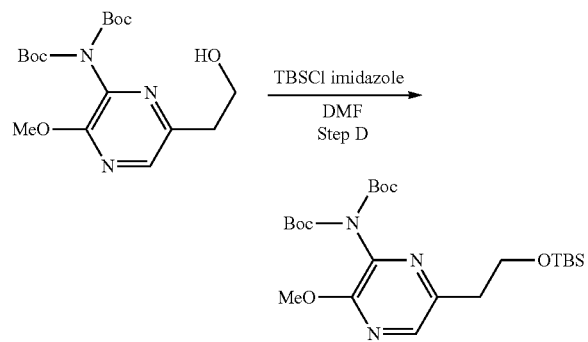

To a stirred mixture of tert-butyl N-(tert-butoxycarbonyl)-N-[6-[(E)-2-ethoxyethenyl]-3-methoxypyrazin-2-yl] carbamate (182.00 mg, 0.493 mmol, 1.00 equiv) in DMF (4.55 mL) was added 1H-imidazole (80.49 mg, 0.000 mmol, 2.40 equiv) at room temperature under nitrogen atmosphere. To the above mixture was added TBS-Cl (89.11 mg, 0.592 mmol, 1.20 equiv) at 0° C. The resulting mixture was stirred for additional 2 h at room temperature. The reaction was quenched with water at room temperature. The resulting mixture was extracted with DCM (3×10 mL). The combined organic layers were washed with brine (2×15 mL), dried over anhydrous Na$_2$SO$_4$. After filtration, the filtrate was concentrated under reduced pressure. The residue was purified by silica gel column chromatography, eluted with PE/EtOAc (4:1) to afford the title compound (238 mg, 99.88%) as a dark yellow oil. m/z (ESI+ve ion)=484.25 [M+H]$^+$.

Step E. 6-[2-[(tert-butyldimethylsilyl) oxy]ethyl]-3-methoxypyrazin-2-amine

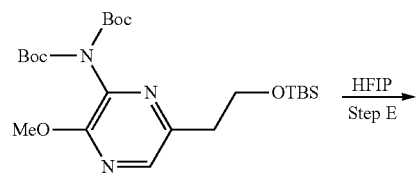

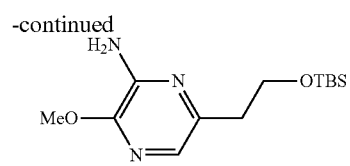

Into a 50 mL round-bottom flask were added tert-butyl N-(tert-butoxycarbonyl)-N-[6-[(E)-2-ethoxyethenyl]-3-methoxypyrazin-2-yl] carbamate (218.00 mg, 0.450 mmol) and 1,1,1,3,3,3-hexafluoropropan-2-ol (5.50 mL) at room temperature. The resulting mixture was stirred for 16 h at 60° C. under nitrogen atmosphere. The mixture was allowed to cool down to room temperature. The reaction was quenched with water (10 mL) at room temperature. The resulting mixture was extracted with DCM (3×10 mL). The combined organic layers were washed with brine (2×15 mL), dried over anhydrous Na$_2$SO$_4$. After filtration, the filtrate was concentrated under reduced pressure. The residue was purified by silica gel column chromatography, eluted with PE/EtOAc (3/1) to afford the title compound (122 mg, 94%) as an off-white solid. m/z (ESI, +ve ion)=284.10 [M+H]$^+$. $^1$H NMR (400 MHz, Chloroform-d) δ 7.50-7.11 (m, 3H), 4.05-3.75 (m, 5H), 2.76 (t, J=6.6 Hz, 2H), 1.01-0.75 (m, 9H), 0.01 (d, J=0.7 Hz, 6H).

Step F. tert-butyl(1R,2S)-2-[1-(tert-butoxycarbonyl)-3-[(6-[2-[(tert-butyldimethylsilyl) oxy]ethyl]-3-methoxypyrazin-2-yl)amino]indazol-6-yl]-5-methoxy-2-oxospiro[cyclopropane-1,3-indole]-1-carboxylate

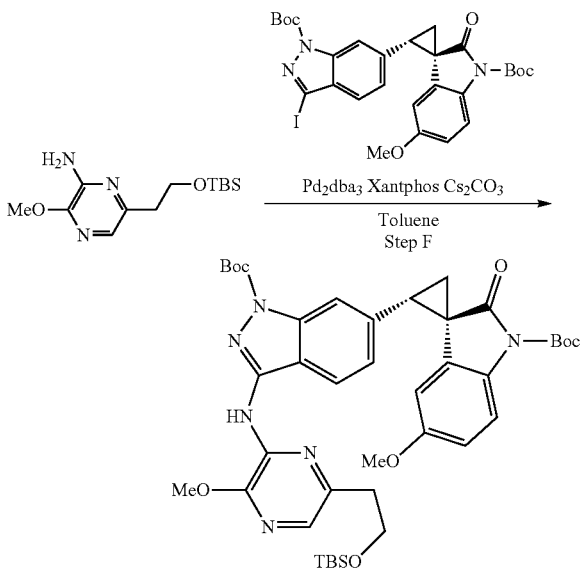

To a stirred mixture of 6-[2-[(tert-butyldimethylsilyl) oxy]ethyl]-3-methoxypyrazin-2-amine (53.80 mg, 1.20 equiv) and tert-butyl (1R,2S)-2-[1-(tert-butoxycarbonyl)-3-iodoindazol-6-yl]-5-methoxy-2-oxospiro[cyclopropane-1,3-indole]-1-carboxylate (100.00 mg, 1.00 equiv) in toluene (2.5 mL) were added Pd$_2$(dba)$_3$ (14.5 mg, 0.1 equiv) and XantPhos (9.15 mg, 0.1 equiv) and Cs$_2$CO$_3$ (103.25 mg, 2 equiv) at room temperature under nitrogen atmosphere. The resulting mixture was stirred for 2 h at 90° C. under nitrogen atmosphere. The mixture was cooled down to room temperature. The reaction was quenched with Water at room temperature. The resulting mixture was extracted with DCM (3×10 mL). The combined organic layers were washed with brine (2×15 mL), dried over anhydrous Na₂SO₄. After filtration, the filtrate was concentrated under reduced pressure. The residue was purified by silica gel column chromatography, eluted with PE/EtOAc (3/I) to afford the title compound (84.1 mg, 67.48%) as a dark yellow solid. m/z (ESI, +ve ion)=787.30 [M+H]⁺.

Step G. (1R,2S)-2-(3-[[6-(2-hydroxyethyl)-3-methoxypyrazin-2-yl]amino]-1H-indazol-6-yl)-5-methoxy-1H-spiro[cyclopropane-1,3-indol]-2-one

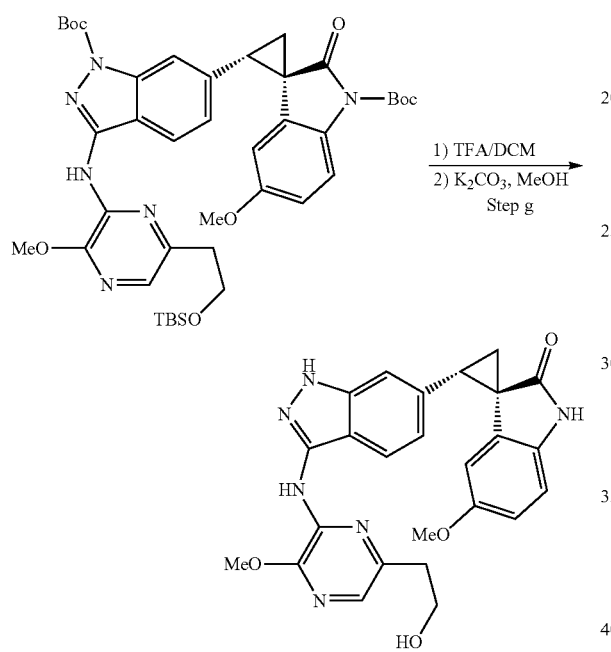

A mixture of tert-butyl(1R,2S)-2-[1-(tert-butoxycarbonyl)-3-[(6-[2-[(tert-butyldimethylsilyl)oxy]ethyl]-3-methoxypyrazin-2-yl)amino]indazol-6-yl]-5-methoxy-2-oxospiro[cyclopropane-1,3-indole]-1-carboxylate (84.00 mg, 0.107 mmol, 1.00 equiv) and TFA (2.00 mL, 0.018 mmol, 0.16 equiv) in DCM (4.00 mL) was stirred for 2 h at room temperature under nitrogen atmosphere. The resulting mixture was concentrated under reduced pressure. To the above mixture was added K₂CO₃ (50.00 mg, 0.362 mmol, 3.39 equiv) in MeOH (5.00 mL) at room temperature. The resulting mixture was stirred for additional 2 h at room temperature. The resulting mixture was concentrated under reduced pressure. The residue was purified by Prep-HPLC with the following conditions: Column: YMC-Actus Triart C18 ExRS, 30 mm×150 mm, 5 μm; Mobile Phase A: Water (10 mmol/L NH₄HCO₃), Mobile Phase B: ACN; Flow rate: 60 mL/min; Gradient: 20% B to 43% B in 8 min, 254 nm; RT1: 7.22 min to afford Example 56 (24.5 mg, 48.09%) as a white solid. m/z (ESI, +ve ion)=473.20 [M+H]⁺, ¹H NMR (400 MHz, DMSO-d₆) δ 12.50 (s, 1H), 10.40 (s, 1H), 8.75 (s, 1H), 7.50 (d, J=8.0 Hz, 1H), 7.35 (d, J=6.0 Hz, 2H), 6.86 (d, J=8.0 Hz, 1H), 6.75 (d, J=8.4 Hz, 1H), 6.58 (m, 1H), 5.67 (d, J=2.0 Hz, 1H), 4.48 (m, 1H), 3.96 (s, 3H), 3.52 (d, J=6.2 Hz, 2H), 3.49 (m, 4H), 3.19 (m, 2H), 2.29 (m, 1H), 1.98 (m, 1H).

Example 57. 4-[5-methoxy-6-({6-[(1R,2S)-5'-methoxy-2'-oxo-1',2'-dihydrospiro[cyclopropane-1,3'-indol]-2-yl]-1H-indazol-3-yl}amino)-2-methylpyrimidin-4-yl]-1λ6-thiomorpholine-1,1-dione

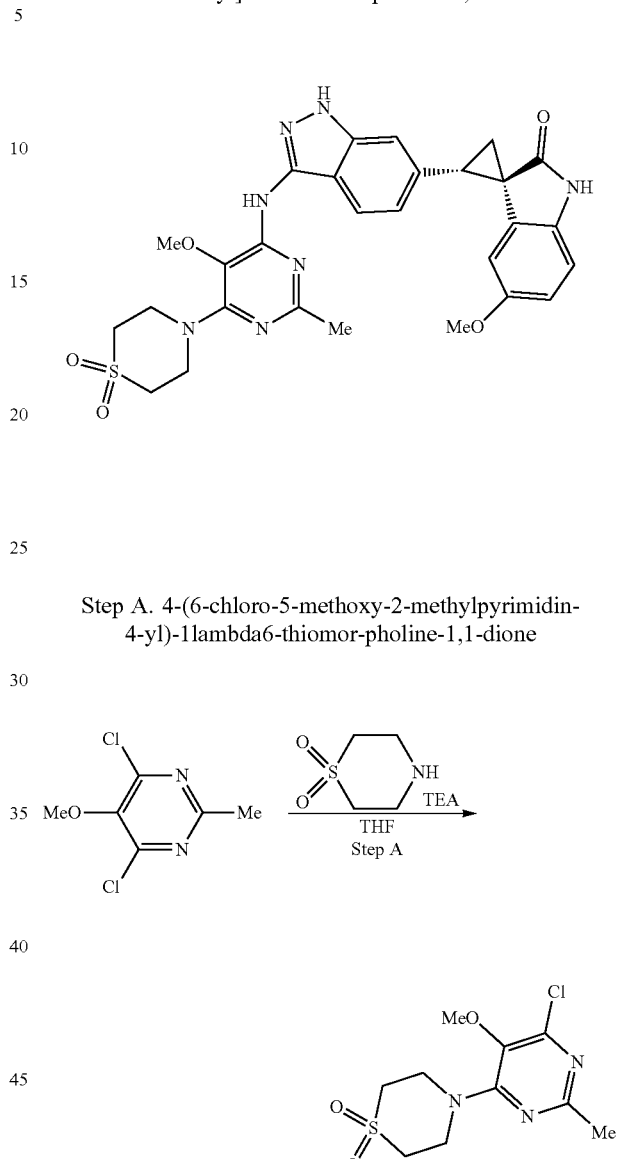

Step A. 4-(6-chloro-5-methoxy-2-methylpyrimidin-4-yl)-1lambda6-thiomor-pholine-1,1-dione To a stirred solution of 4,6-dichloro-5-methoxy-2-methylpyrimidine (400.0 mg, 1.0 equiv) and 1lambda6-thiomorpholine-1,1-dione (308.0 mg, 1.1 equiv) in THF (12.0 mL) was added TEA (420.0 mg, 2.0 equiv) at room temperature. The resulting mixture was stirred for 20 h at 70° C. The resulting mixture was concentrated under vacuum. The residue was purified by silica gel column chromatography, eluted with 0-50% EtOAc in PE to afford the title compound (400.0 mg, 65.7% yield) as a white solid. m/z (ESI, +ve ion)=292.00 [M+H]⁺. ¹H NMR (400 MHz, Chloroform-d) δ 4.35-4.33 (m, 4H), 3.78 (s, 3H), 3.15-3.12 (m, 4H), 2.53 (s, 3H).

353

Step B. tert-butyl (1R,2S)-2-[1-(tert-butoxycarbonyl)-3-{[6-(1,1-dioxo-1lambda6-thiomorpholin-4-yl)-5-methoxy-2-methylpyrimidin-4-yl]amino}indazol-6-yl]-5'-methoxy-2'-oxospiro[cyclopropane-1,3'-indole]-1'-carboxylate

354

Step C. 4-[5-methoxy-6-({6-[(1R,2S)-5'-methoxy-2'-oxo-1'H-spiro[cyc-lopropane-1,3'-indol]-2-yl]-1H-indazol-3-yl}amino)-2-methylpyrimidin-4-yl]-1lambda6-thiomorpholine-1,1-dione

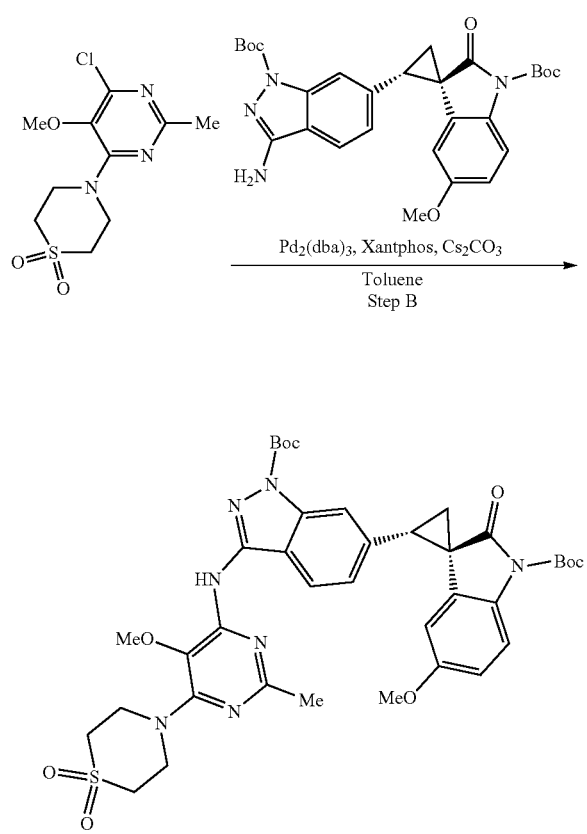

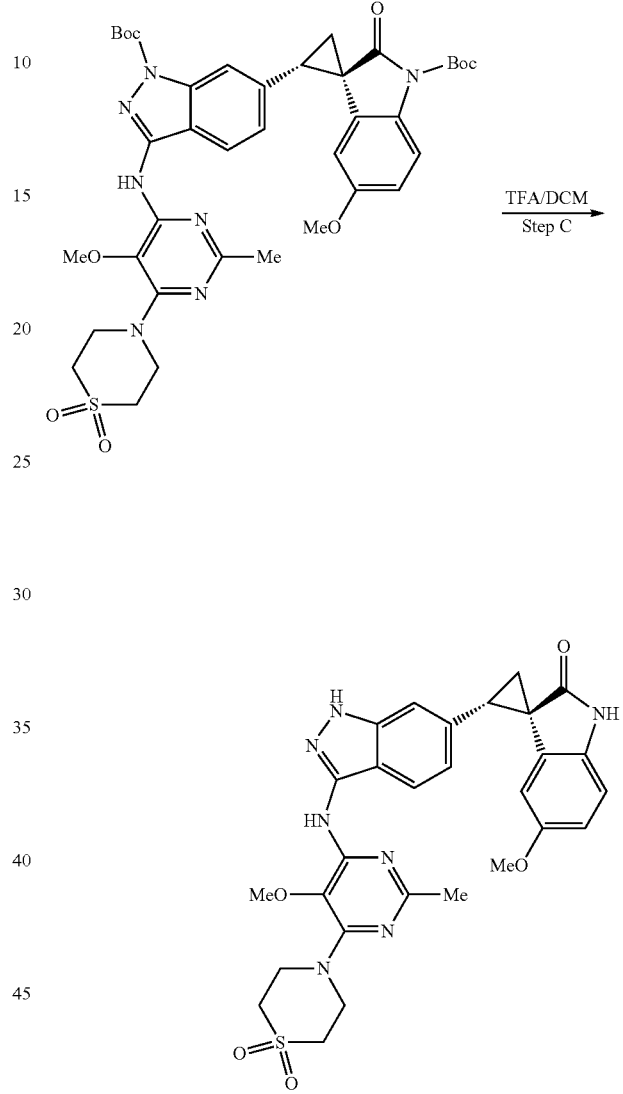

To a stirred solution of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (100.0 mg, 1.0 equiv) and 4-(6-chloro-5-methoxy-2-methylpyrimidin-4-yl)-1lambda6-thiomor-pholine-1,1-dione (72.9 mg, 1.3 equiv) in toluene (2.5 mL) were added $Cs_2CO_3$ (125.1 mg, 2.0 equiv), XantPhos (19.9 mg, 0.2 equiv) and $Pd_2(dba)_3$ (35.1 mg, 0.2 equiv) at room temperature under nitrogen atmosphere. The resulting mixture was stirred for 2 h at 90° C. under nitrogen atmosphere. The resulting mixture was filtered, the filter cake was washed with EtOAc (3×7 mL). The filtrate was concentrated under reduced pressure. The residue was purified by silica gel column chromatography, eluted with 0-50% EtOAc in PE to afford the title compound (80.0 mg, 53.7%) as a yellow solid. m/z (ESI, +ve ion)=776.40 [M+H]$^+$. $^1$H NMR (400 MHz, Chloroform-d) δ 8.13 (s, 1H), 8.04 (s, 1H), 7.82 (d, J=8.0 Hz, 1H), 7.07 (d, J=8.0 Hz, 1H), 6.72-6.69 (m, 1H), 5.62 (d, J=0.0 Hz, 1H), 4.35-4.31 (m, 1H), 4.25 (s, 4H), 3.75 (s, 3H), 3.56-3.52 (m, 1H), 3.39 (s, 3H), 3.15 (s, 4H), 2.41-2.37 (m, 1H), 2.34 (s, 3H), 2.15-2.12 (m, 1H), 1.73-1.69 (m, 181-1).

To a stirred solution of tert-butyl (1R,2S)-2-[1-(tert-butoxycarbonyl)-3-{[6-(1,1-dioxo-1lambda6-thiomorpholin-4-yl)-5-methoxy-2-methylpyrimidin-4-yl]amino}indazol-6-yl]-5'-methoxy-2'-oxospiro[cyclopropane-1,3'-indole]-1'-carboxylate (80.0 mg) in DCM (4.0 mL) was added TFA (0.7 mL) dropwise at room temperature. The resulting mixture was stirred for 2 h at mom temperature. The resulting mixture was concentrated under vacuum. The crude product (50 mg) was purified by RP flash, eluted with ACN in water (5 mM NH$_4$HCO$_3$), 10% to 50% gradient in 30 min to afford Example 39 (22.0 mg, 37.0%) as a white solid. m/z (ESI, +ve ion)=576.30 [M+H]$^+$. $^1$H NMR (400 MHz, Methanol-d$_4$) δ 7.59 (d, J=8.0 Hz, 1H), 7.43 (s, 1H), 6.92 (d, J=8.0 Hz, 1H), 6.84 (d, J=8.0 Hz, 1H), 6.64-6.61 (m, 1H), 5.66 (d, J=4.0 Hz, 1H), 4.23 (s, 4H), 3.76 (s, 3H), 3.37 (d, J=8.0 Hz, 1H), 3.35-3.30 (m, 3H), 3.21-3.15 (m, 4H), 3.01 (s, 1H), 2.88 (s, 1H), 2.26-2.20 (m, 4H), 2.19-2.17 (m, 1H).

Example 58. 4-[5-chloro-6-({6-[(1R,2S)-5'-methoxy-2'-oxo-1',2'-dihydrospiro[cyclopropane-1,3'-indol]-2-yl]-1H-indazol-3-yl}amino)-2-methylpyrimidin-4-yl]-1λ6-thiomorpholine-1,1-dione

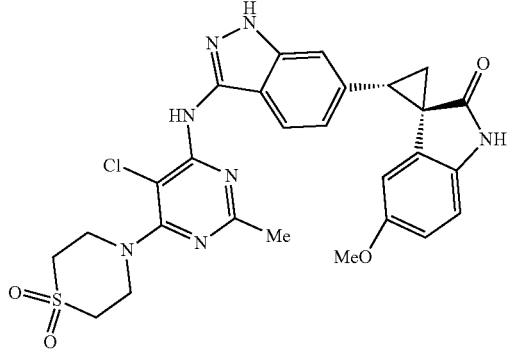 [SMILES: COc1ccc2c(c1)[C@]1(C[C@H]1c1ccc3c(Nc4nc(C)nc(N5CCS(=O)(=O)CC5)c4Cl)n[nH]c3c1)C(=O)N2]

Step A. 4-(6-amino-2-methylpyrimidin-4-yl)-lambda6-thiomorpholine-1,1-dione

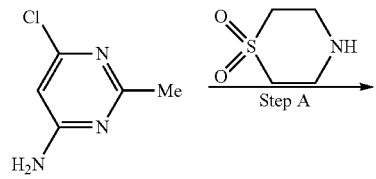

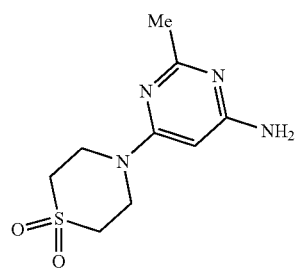

The mixture of 6-chloro-2-methylpyrimidin-4-amine (1 g, 6.965 mmol, 1.00 equiv) and 1lambda6-thiomorpholine-1,1-dione (2.82 g, 20.895 mmol, 3 equiv) was stirred for 80° C. for 12 h. The reaction mixture was turned out to be white solid. The solid was triturated with EA (20 mL) for 2 h and filtered. The filter cake was collected and dried in vacuo to give the title compound (500 mg, 29.33%) as a white solid. m/z (ESI+ve ion)=243.05 [M+H]$^+$. $^1$H NMR (400 MHz, DMSO-4) δ 6.74 (s, 2H), 5.70 (s, 1H), 4.00-3.98 (m, 4H), 3.16-3.13 (m, 4H), 2.27 (s, 3H).

Step B. 4-(6-amino-5-chloro-2-methylpyrimidin-4-yl)-1lambda6-thiomorpholine-1,1-dione

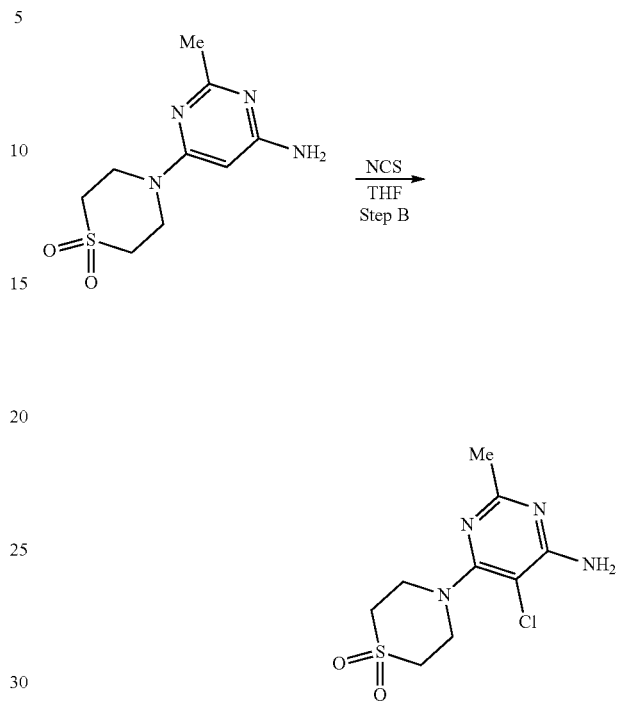

To a stirred mixture of 4-(6-amino-2-methylpyrimidin-4-yl)-1lambda6-thiomorpholine-1,1-dione (500 mg, 2.064 mmol, 1.00 equiv) in THF (5 mL) was added NCS (220.44 mg, 1.651 mmol, 0.8 equiv) under nitrogen atmosphere. The mixture was stirred at 25° C. for 12 h. The solvent was removed under reduced pressure. The residue was purified by silica gel column chromatography, eluted with 0-100% of EA in PE to give the title compound (250 mg, 43.78%) as a colorless oil. m/z (ESI+ve ion)=277.15 [M+H]. $^1$H NMR (400 MHz, DMSO-d$_6$) δ 6.89 (s, 2H), 3.85-3.83 (m, 4H), 3.24-3.21 (m, 4H), 2.25 (s, 3H).

Step C. tert-butyl (1R,2S)-2-[1-(tert-butoxycarbonyl)-3-{[5-chloro-6-(1,1-dioxo-1lambda6-thiomorpholin-4-yl)-2-methylpyrimidin-4-yl]amino}indazol-6-yl]-5'-methoxy-2'-oxospiro[cyclopropane-1,3'-indole]-1'-carboxylate

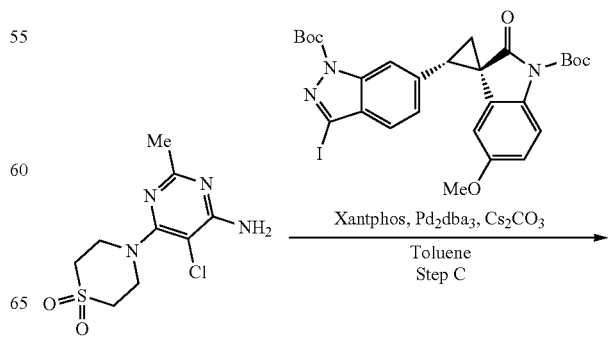

357

-continued

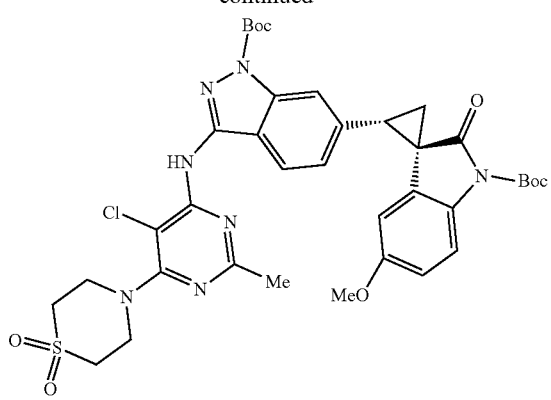

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 4-(6-amino-5-chloro-2-methylpyrimidin-4-yl)-1lambda6-thiomorpholine-1,1-dione (52.59 mg, 0.190 mmol, 1.2 equiv) in toluene (2.5 mL) were added $Cs_2CO_3$ (103.19 mg, 0.316 mmol, 2 equiv), XantPhos (18.33 mg, 0.032 mmol, 0.2 equiv) and $Pd_2(dba)_3$ (29.00 mg, 0.032 mmol, 0.2 equiv) under argon atmosphere. The mixture was stirred at 90° C. for 2 h. The reaction mixture was filtered and washed with EA (5 mL×3). The filtrate was concentrated in vacuo and the residue was purified by silica gel column eluted with 0-50% EA in PE to give the title compound (90 mg, 72.83%) as a yellow solid. m/z (ESI+ve ion)=780.35 [M+H]. $^1$H NMR (400 MHz, Chloroform-d) δ 8.15 (s, 1H), 7.84-7.80 (m, 2H), 7.07-7.02 (m, 1H), 6.71-6.68 (m, 1H), 5.59 (d, J=2.8 Hz, 1H), 4.15-4.12 (m, 4H), 3.53 (t, J=8.4 Hz, 1H), 3.40 (s, 3H), 3.23 (s, 4H), 2.41-2.37 (m, 4H), 2.14-2.11 (m, 1H), 1.71 (d, J=5.2 Hz, 18H).

Step D. 4-[5-chloro-6-({6-[(1R,2S)-5'-methoxy-2'-oxo-1'H-spiro[cyclopropane-1,3'-indol]-2-yl]-1H-indazol-3-yl}amino)-2-methylpyrimidin-4-yl]-1lambda6-thiomorpholine-1,1-dione

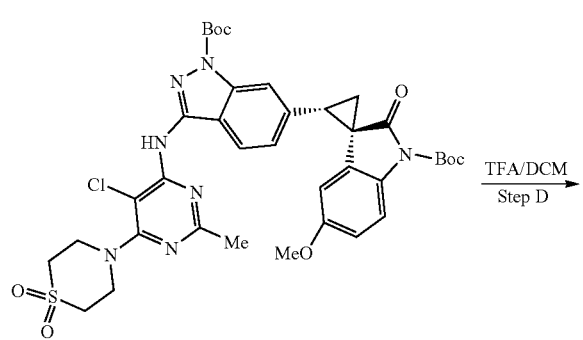

358

-continued

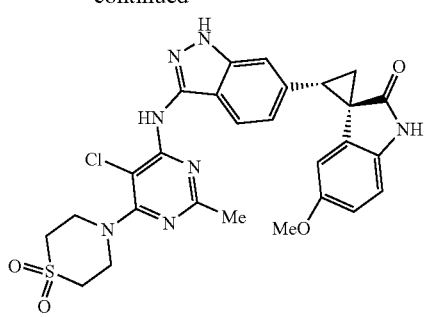

To the mixture of tert-butyl (1R,2S)-2-[1-(tert-butoxycarbonyl)-3-{[5-chloro-6-(1,1-dioxo-1lambda6-thiomorpholin-4-yl)-2-methylpyrimidin-4-yl]amino}indazol-6-yl]-5'-methoxy-2'-oxospiro[cyclopropane-1,3'-indole]-1'-carboxylate (80 mg, 0.103 mmol, 1.00 eq) in DCM (1 mL) was added TFA (0.1 mL). The mixture was stirred for 6 h. The solvent was removed under reduced pressure. The residue was purified by prep-HPLC with the following conditions: Column: XBridge Shield RP18 OBD Column, 30×150 mm, 5 μm; Mobile Phase A: water (10 mmol/L $NH_4HCO_3$), Mobile Phase B: ACN; Flow rate: 60 mL/min; Gradient: 27% B to 42% B in 8 min; wavelength: 254 nm; RT1(min): 7.5. The product-containing fractions were collected and concentrated in vacuo to give Example 58 (35 mg, 58.26%) as a white solid. m/z (ESI+ve ion)=580.25 [M+H]$^+$. $^1$H NMR (400 MHz, DMSO-$d_6$) δ 12.68 (s, 1H), 10.42 (s, 1H), 9.16 (s, 1H), 7.40-7.37 (m, 2H), 6.91-6.88 (m, 1H), 6.75 (d, J=8.4 Hz, 1H), 6.60-6.57 (m, 1H), 5.69 (d, J=2.4 Hz, 1H), 3.92 (s, 4H), 3.32 (s, 3H), 3.29-3.26 (m, 4H), 3.20 (t, J=8.4 Hz, 1H), 2.34-2.30 (m, 1H), 2.13 (s, 3H), 2.00-1.97 (m, 1H).

Example 59. (1R,2S)-2-(3-((2-cyclopropyl-&(1,1-dioxidothiomorpholino)pyrimidin-4-yl)amino)-1H-indazol-6-yl)-5'-methoxyspiro[cyclopropane-1,3'-indolin]-2'-one

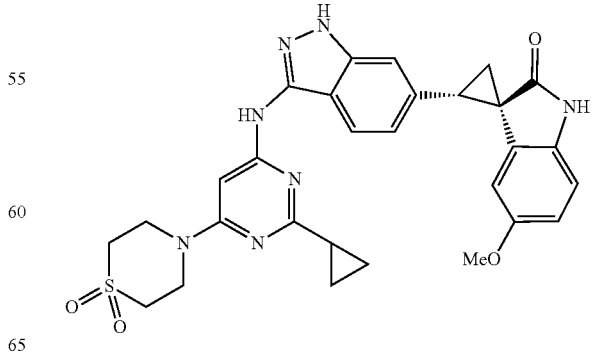

Step A. 6-chloro-2-cyclopropylpyrimidin-4-amine

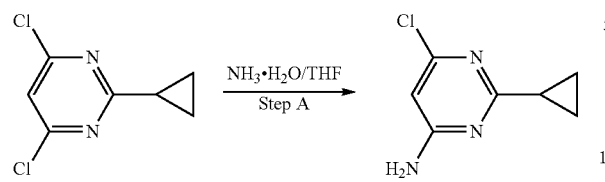

A mixture of 4,6-dichloro-2-cyclopropylpyrimidine (1.00 g, 5.290 mmol, 1.00 equiv) and $NH_3 \cdot H_2O$ (13.00 mL, 0.371 mmol, 0.07 equiv) in THF (6.50 mL) was stirred for 6 h at 70° C. under nitrogen atmosphere and then cooled down to room temperature. The reaction was quenched with Water at room temperature. The resulting mixture was extracted with DCM (3×20 mL). The combined organic layers were washed with brine (2×30 mL), dried over anhydrous $Na_2SO_4$. After filtration, the filtrate was concentrated under reduced pressure. The residue was purified by silica gel column chromatography, eluted with PE/EA (1/1) to afford the title compound (860 mg, 95.85%) as an off-white solid. m/z=169.95 [M+H]$^+$. $^1$H NMR (400 MHz, Chloroform-d) δ 6.24 (s, 1H), 4.88 (s, 2H), 2.03 (m, 1H), 1.11 (m, 2H), 1.00 (m, 2H).

Step B. 4-(6-amino-2-cyclopropylpyrimidin-4-yl)-1lambda6-thiomorpholine-1,1-dione

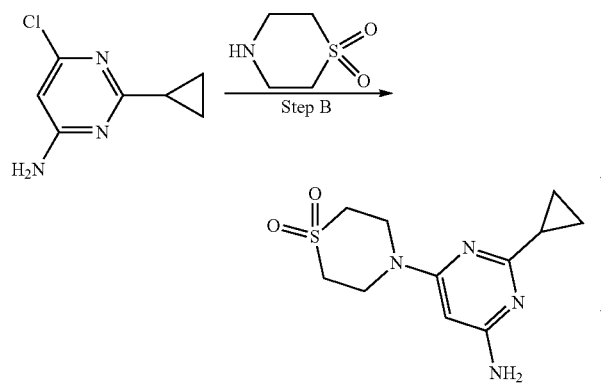

Into a 25 mL round-bottom flask were added 6-chloro-2-cyclopropylpyrimidin-4-amine (725.00 mg, 4.275 mmol, 1.00 equiv) and thiomorpholine 1,1-dioxide (2890.00 mg, 21.385 mmol, 5.00 equiv) at room temperature. The resulting mixture was stirred for 16 h at 100° C. under nitrogen atmosphere and cooled down to room temperature. The resulting mixture was diluted with MeOH (5 mL). The residue was purified by reverse phase flash chromatography with the following conditions: Column: Spherical C18, 20-40 um, 120 g; Mobile Phase A: Water (plus 5 mM $NH_4HCO$); Mobile Phase B: ACN; Flow rate: 60 mL/min; Gradient: 20% B-40% B in 20 min; Detector: 254 nm. The fractions containing desired product were collected at 22% B and concentrated under reduced pressure to afford the title compound (1.07 g, 93.28%) as a white solid. m/z (ESI+ve ion)=269.05 [M+H]$^+$. $^1$H NMR (400 MHz, DMSO-d$_6$) δ 6.17 (s, 2H), 5.56 (s, 1H), 3.93 (t, J=5.1 Hz, 4H), 3.07 (t, J=5.1 Hz, 4H), 1.77 (m, 1H), 0.92-0.74 (m, 4H).

Step C. tert-butyl(1R,2S)-2-[1-(tert-butoxycarbonyl)-3-{[2-cyclopropyl-6-(1,1-dioxo-1lambda6-thiomorpholin-4-yl)pyrimidin-4-yl]amino}indazol-6-yl]-5'-methoxy-2'-oxospiro[cyclopropane-1,3'-indole]-1'-carboxylate

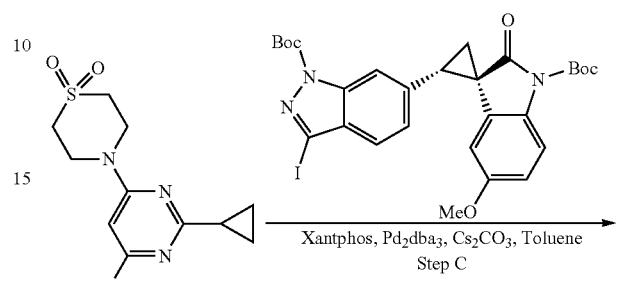

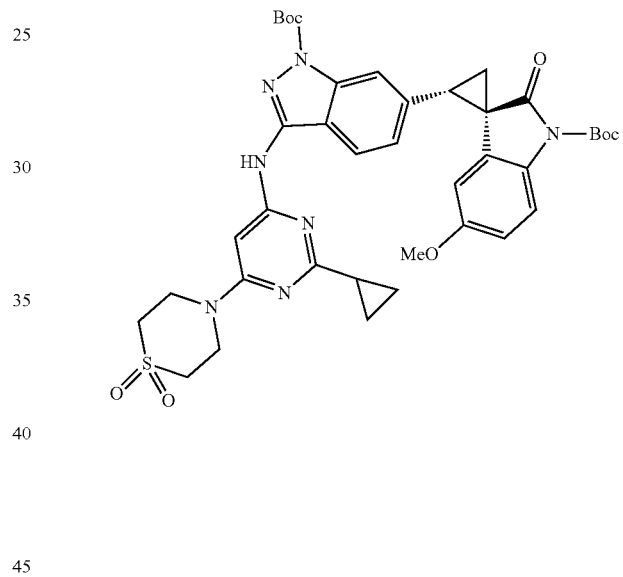

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 4-(6-amino-2-cyclopropylpyrimidin-4-yl)-1lambda6-thiomorpholine-1,1-dione (50.99 mg, 0.190 mmol, 1.2 equiv) in toluene (2.5 mL) were added Pd$_2$(dba)$_3$ (14.50 mg, 0.016 mmol, 0.1 equiv) and XantPhos (9.16 mg, 0.016 mmol, 0.1 equiv) and Cs$_2$C$_{O3}$ (103.19 mg, 0.316 mmol, 2 equiv) at room temperature under nitrogen atmosphere. The resulting mixture was stirred for 2 h at 90° C. under nitrogen atmosphere. The reaction was monitored by LCMS. The mixture was allowed to cool down to room temperature. The reaction was quenched by the addition of Water (10 mL) at room temperature. The resulting mixture was extracted with DCM (3×8 mL). The combined organic layers were washed with brine (1×15 mL), dried over anhydrous Na$_2$SO$_4$. After filtration, the filtrate was concentrated under reduced pressure. The residue was purified by silica gel column chromatography, eluted with PE/EA (1/1) to afford the title compound (96 mg, 78.54%) as a yellow solid. m/z (ESI+ve ion)=772.50 [M+H]$^+$ Step D. 4-[2-cyclopropyl-6-({6-[(1R,2S)-5'-methoxy-2'-oxo-1'H-spiro[cyclopropane-1,3'-indol]-2-yl]-1H-indazol-3-yl}amino)pyrimidin-4-yl]-1lambda6-thiomorpholine-1,1-dione

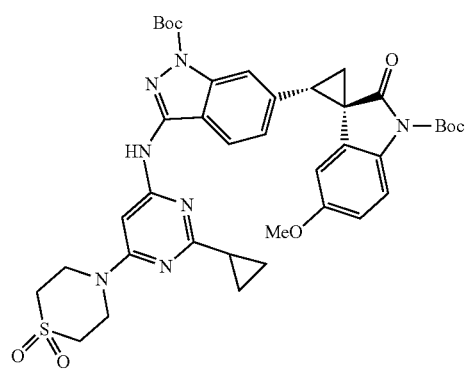

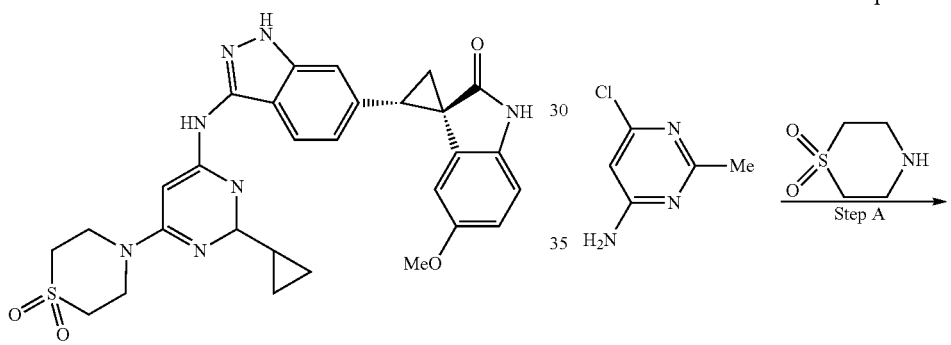

A mixture of tert-butyl(1R,2S)-2-[1-(tert-butoxycarbonyl)-3-{[2-cyclopropyl-6-(1,1-dioxo-1lambda6-thiomorpholin-4-yl)pyrimidin-4-yl]amino}indazol-6-yl]-5'-methoxy-2'-oxospiro[cyclopropane-1,3'-indole]-1'-carboxylate (20.00 mg, 0.026 mmol, 1.00 equiv) and TFA (2.00 mL) in DCM (4.00 mL) was stirred for 2 h at room temperature under nitrogen atmosphere. The resulting mixture was concentrated under vacuum. The residue was purified by Prep-HPLC with the following conditions (Column: XBridge Shield RP18 OBD Column, 30×150 mm, 5 μm; Mobile Phase A: Water (10 mmol/L NH₄HCO₃), Mobile Phase B: ACN; Flow rate: 60 mL/min; Gradient: 32% B to 45% B in 8 min, 45% B: wavelength: 254 nm; RT1 (min): 6.88 to afford Example 59 (46.1 mg, 64.84%) as a white solid. m/z (ESI+ve ion)=572.25 [M+H]⁺. ¹H NMR (400 MHz, DMSO-d₆) δ 12.36 (s, 1H), 10.42 (s, 1H), 9.74 (s, 1H), 7.96 (d, J=8.4 Hz, 1H), 7.33 (s, 1H), 7.08 (s, 1H), 6.92-6.85 (m, 1H), 6.75 (d, J=8.4 Hz, 1H), 6.58 (m, 1H), 5.69 (d, J=2.8 Hz, 1H), 4.00 (d, J=6.5 Hz, 4H), 3.33 (s, 3H), 3.17 (m, 5H), 1.97 (m, 1H), 1.90 (m, 1H), 1.24 (s, 1H), 0.99-0.93 (m, 2H), 0.87 (m, 2H).

Example 60. (1R,2S)-2-(3-((6-(1,1-dioxidothiomorpholino)-2-methylpyrimidin-4-yl)amino)-1H-indazol-6-yl)-5'-methoxyspiro[cyclopropane-1,3'-indolin]-2'-one

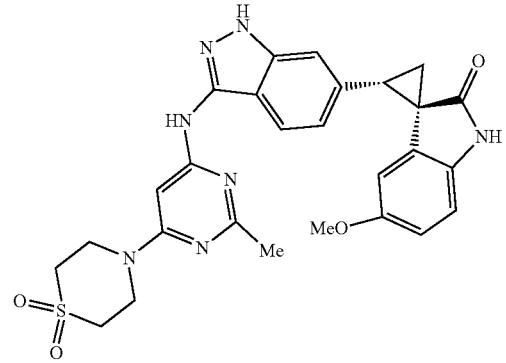 [SMILES: COc1ccc2c(c1)[C@]1(C[C@H]1c1ccc3c(Nc4cc(N5CCS(=O)(=O)CC5)nc(C)n4)n[nH]c3c1)C(=O)N2]

Step A. 4-(6-amino-2-methylpyrimidin-4-yl)-1lambda6-thiomorpholine-1,1-dione

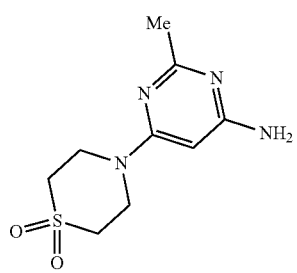

The mixture of 6-chloro-2-methylpyrimidin-4-amine (1 g, 6.965 mmol, 1.00 equiv) and 1lambda6-thiomorpholine-1,1-dione (2.82 g, 20.895 mmol, 3 equiv) was stirred at 80° C. for 12 h. The reaction mixture was turned out to be white solid. The solid was triturated with EA (20 mL) for 2 h and filtered. The filter cake was collected and dried in vacuo to give title compound (500 mg, 29.33%) as a white solid. m/z (ESI+ve ion)=243.05 [M+H]. ¹H NMR (400 MHz, DMSO-d₆) δ 6.74 (s, 2H), 5.70 (s, 1H), 4.00-3.98 (m, 4H), 3.16-3.13 (m, 4H), 2.27 (s, 3H).

Step B. tert-butyl (1R,2S)-2-[1-(tert-butoxycarbonyl)-3-{[6-(1,1-dioxo-1lambda6-thiomorpholin-4-yl)-2-methylpyrimidin-4-yl]amino}indazol-6-yl]-5'-methoxy-2'-oxospiro[cyclopropane-1,3'-indole]-1'-carboxylate Step C. 4-[6-({6-[(1R,2S)-5'-methoxy-2'-oxo-1'H-spiro[cyclopropane-1,3'-indol]-2-yl]-1H-indazol-3-yl}amino)-2-methylpyrimidin-4-yl]-1lambda6-thiomorpholine-1,1

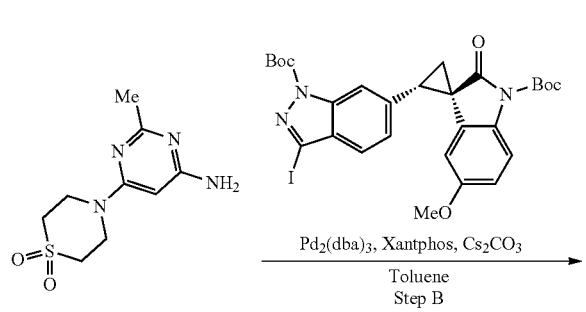

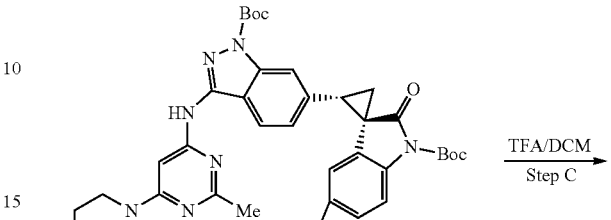

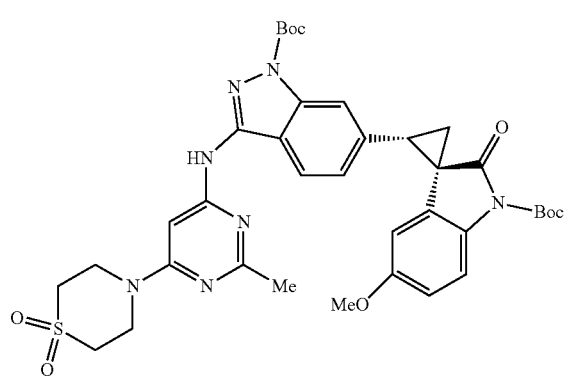

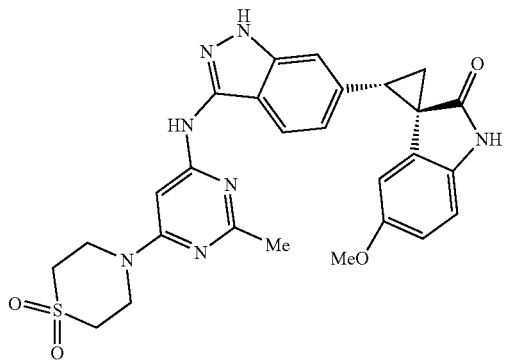

To a stirred solution of 4-(6-amino-2-methylpyrimidin-4-yl)-1lambda6-thiomorpholine-1,1-dione (49.9 mg, 1.3 equiv) and tert-butyl (1R,2S)-2-[1-(tert-butoxycarbo-nyl)-3-iodoindazol-6-yl]-5'-methoxy-2'-oxospiro[cyclopropane-1, 3'-indole]-1'-carboxylate (100.0 mg, 1.0 equiv) in toluene (2.5 mL) were added Cs$_2$CO$_3$ (103.3 mg, 2.0 equiv) and XantPhos (16.5 mg, 0.2 equiv) and Pd$_2$(dba)$_3$ (29.0 mg, 0.2 equiv) at room temperature under nitrogen atmosphere. The resulting mixture was stirred for 2 h at 90° C. under nitrogen atmosphere. The resulting mixture was filtered, the filter cake was washed with EtOAc (3×6 mL). The filtrate was concentrated under reduced pressure. The residue was purified by silica gel column chromatography, eluted with 0-50% of EtOAc in PE to afford the title compound (100.0 mg, 84.7%) as a yellow solid. m/z (ESI, +ve ion)=746.40 [M+H]$^+$. $^1$H NMR (400 MHz, Chloroform-d) δ 8.16 (s, 1H), 7.82 (d, J=12.0 Hz, 1H), 7.75 (s, 1H), 7.61 (d, J=8.0 Hz, 1H), 7.13 (d, J=8.0 Hz, 1H), 6.71-6.68 (m, 1H), 5.57 (d, J=4.0 Hz, 1H), 4.35-4.31 (m, 4H), 4.17-4.12 (m, 1H), 3.55-3.50 (m, 1H), 3.42 (s, 3H), 3.17-3.11 (m, 4H), 2.49 (s, 3H), 2.40-2.37 (m, 1H), 2.14-2.11 (m, 1H), 1.70 (s, 18H).

To a stirred solution of tert-butyl (1R,2S)-2-[1-(tert-butoxycarbonyl)-3-{[6-(1,1-dioxo-1lambda6-thiomorpholin-4-yl)-2-methylpyrimidin-4-yl]amino}indazol-6-yl]-5'-methoxy-2'-oxospiro[cyclopropane-1,3'-indole]-1'-carboxylate (90.0 mg) in DCM (4.0 mL) was added TFA (0.5 mL) dropwise at room temperature under air atmosphere. The resulting mixture was stirred for 5 h at room temperature. The resulting mixture was concentrated under vacuum. The crude product (50.0 mg) was purified by Prep-HPLC with the following conditions: Column: XBridge Prep OBD C18 Column, 30×150 mm, 5 μm; Mobile Phase A: Water (10 mmol/L NH$_4$HCO$_3$). Mobile Phase B: ACN; Flow rate: 60 mL/min; Gradient: 20% B to 40% B in 8 min, 40% B; wavelength: 254 nm; RT1(min): 6.6 to afford Example 60 (23.0 mg, 35.0% yield) as a white solid. m/z (ESI, +ve ion)=546.15 [M+H]$^+$. $^1$H NMR (400 MHz, DMSO-d$_6$) δ 12.37 (s, 1H), 10.42 (s, 1H), 9.89 (s, 1H), 7.98 (d, J=4.0 Hz, 1H), 7.33 (s, 1H), 7.20 (s, 1H), 6.89 (d, J=4.0 Hz, 1H), 6.75 (d, J=8.0 Hz, 1H), 6.60-6.57 (m, 1H), 5.69 (d, J=0.0 Hz, 1H), 4.04 (d, J=5.6 Hz, 4H), 3.17 (s, 5H), 2.50 (s, 3H), 2.33 (d, J=8.0 Hz, 4H), 1.99-1.95 (m, 1H).

Example 61. 5-methoxy-4-({6-[(1R,2S)-5'-methoxy-2'-oxo-1',2'-dihydrospiro[cyclopropane-1,3'-indol]-2-yl]-1H-indazol-3-yl}amino)-6-(morpholin-4-yl)pyrimidine-2-carbonitrile

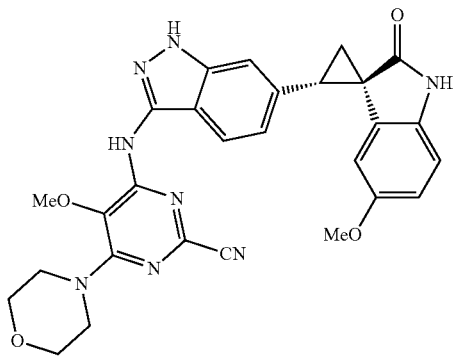 [SMILES: COc1ccc2c(c1)[C@]1(C[C@H]1c1ccc3c(Nc4nc(C#N)nc(N5CCOCC5)c4OC)n[nH]c3c1)C(=O)N2]

Step A.
6-hydroxy-5-methoxy-2-sulfanyl-3H-pyrimidin-4-one

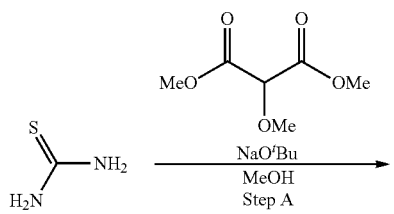

To a stirred mixture of thiourea (3.00 g, 39.411 mmol, 1.00 equiv) and 1,3-dimethyl 2-methoxypropanedioate (6.39 g, 39.411 mmol, 1.00 equiv) in MeOH (80.00 mL) was added sodium 2-methylpropan-2-olate (7.58 g, 78.822 mmol, 2.00 equiv) in portions at room temperature under nitrogen atmosphere. The resulting mixture was stirred for 7 h at 50° C. under nitrogen atmosphere. The mixture was allowed to cool down to room temperature. The resulting mixture was concentrated under reduced pressure. The resulting mixture was diluted with water (50 mL). The resulting mixture was extracted with EtOAc (2×40 mL). The aqueous layer was acidified to pH 1 with conc. HCl. The precipitated solids were collected by filtration and washed with water (2×10 mL) and dried to afford the title compound (4 g, 58.27%) as a yellow solid. m/z (ESI, +ve ion)=175.05 [M+H]+.

Step B. 2-(ethylsulfanyl)6-hydroxy-5-methoxy-3H-pyrimidin-4-one

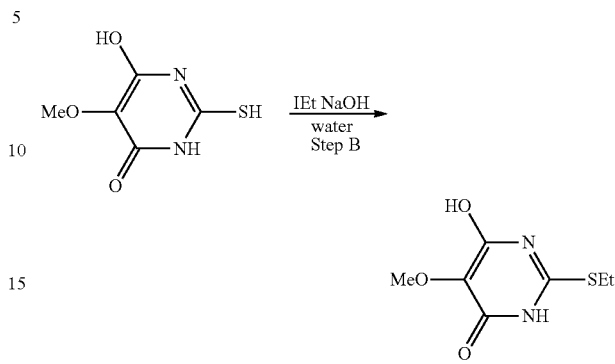

To a stirred mixture of 6-hydroxy-5-methoxy-2-sulfanyl-3H-pyrimidin-4-one (4.00 g, 22.966 mmol, 1.00 equiv) and iodoethane (7.16 g, 0.000 mmol, 2.00 equiv) in water (120 mL) was added NaOH (1.84 g, 0.046 mmol, 2.00 equiv) at room temperature under nitrogen atmosphere. The resulting mixture was stirred for 3 h at room temperature under nitrogen atmosphere. The resulting mixture was filtered, the filter cake was washed with water (2×20 mL). The filtrate was acidified to pH 1 with HCl (aq.). The precipitated solids were collected by filtration and washed with water (2×30 mL) and dried to afford the title compound (2.27 g, 48.88%) as a yellow solid. m/z (ESI, +ve ion)=203.10 [M+H]+. 1H NMR (400 MHz, DMSO-d6) δ 12.23 (s, 1H), 11.25 (s, 1H), 3.59 (d, J=6.0 Hz, 3H), 3.07 (q, J=7.3 Hz, 2H), 1.28 (t, J=7.3 Hz, 3H).

Step C.
4,6-dichloro-2-(ethylsulfanyl)-5-methoxypyrimidine

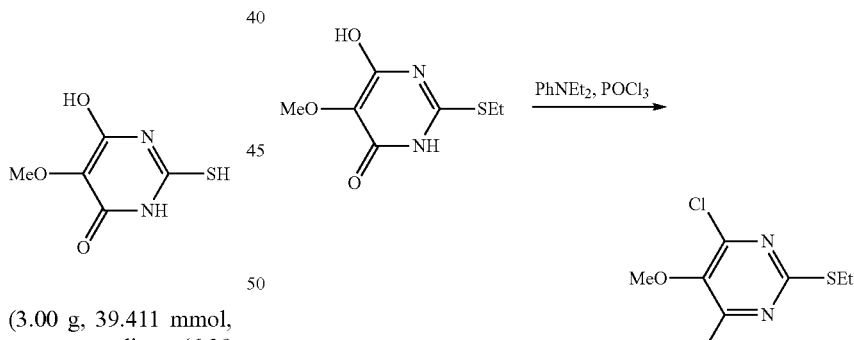

A mixture of 2-(ethylsulfanyl)-6-hydroxy-5-methoxy-3H-pyrimidin-4-one (2.27 g, 11.225 mmol, 1.00 equiv) and PhNEt2 (5.03 g, 0.034 mmol, 3.00 equiv) in POCl3 (38.00 mL) was stirred for 3 h at 100° C. under nitrogen atmosphere. The mixture was cooled down to room temperature. The reaction was quenched with sat. NaHCO3 (aq. 30 mL) at 0° C. The resulting mixture was extracted with EtOAc (3×30 mL). The combined organic layers were washed with brine (2×50 mL), dried over anhydrous Na2SO4. After filtration, the filtrate was concentrated under reduced pressure. The residue was purified by reverse phase flash chromatography with the following conditions: Column: Spherical C18, 20-40 um, 120 g; Mobile Phase A: Water (plus 0.05% TFA); Mobile Phase B: ACN; Flow rate: 80 mL/min; Gradient: 60% B-70% B in 15 min: Detector: 254 nm. The fractions containing desired product were collected at 64% B and concentrated under reduced pressure to afford the title compound (2.5 g, 93.15%) as a dark green oil. m/z=238.95 [M+H]+. 1H NMR (400 MHz, DMSO-$d_6$) δ 3.87 (s, 3H), 3.13-3.09 (m, 2H), 1.71-1.46 (m, 3H).

Step D. 4-[6-chloro-2-(ethylsulfanyl)-5-methoxypyrimidin-4-yl] morpholine

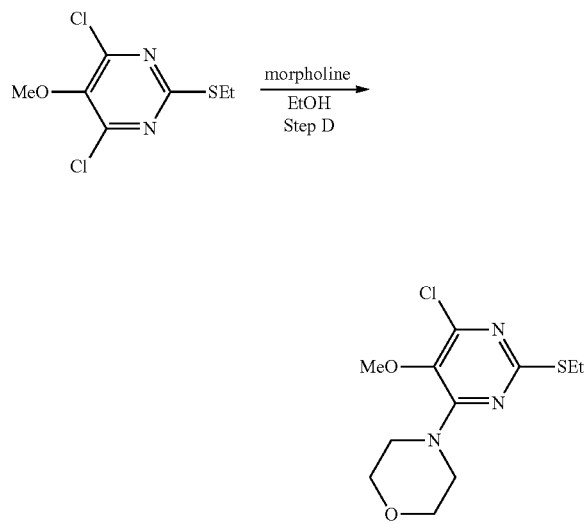

A mixture of 4,6-dichloro-2-(ethylsulfanyl)-5-methoxypyrimidine (400.00 mg, 1.673 mmol, 1.00 equiv) and morpholine (174.89 mg, 0.000 mmol, 1.20 equiv) in EtOH (10.00 mL) was stirred for 2 h at 85° C. under nitrogen atmosphere. The mixture was cooled down to room temperature. The reaction was quenched with Water at room temperature. The resulting mixture was extracted with DCM (3×15 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EtOAc (3/1) to afford the title compound (230 mg, 47.45%) as a white solid. m/z (ESI, +ve ion)=290.15 [M+H]+.

Step E. 4-[6-chloro-2-(ethanesulfonyl)-5-methoxypyrimidin-4-yl] morpholine

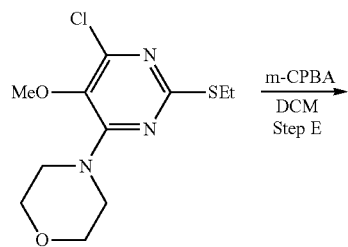

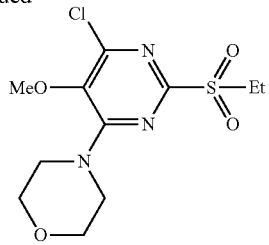

A mixture of 4-[6-chloro-2-(ethylsulfanyl)-5-methoxypyrimidin-4-yl] morpholine (430.00 mg, 1.484 mmol, 1.00 equiv) and m-CPBA (896.24 mg, 5.194 mmol, 3.5 equiv) in DCM (10.75 mL) were stirred for 3 h at room temperature under nitrogen atmosphere. The reaction was quenched with sat. $Na_2S_2O_3$ (aq., 15 mL) at room temperature. The resulting mixture was extracted with DCM (2×15 mL). The combined organic layers were washed with sat. $NaHCO_3$ (aq. 20 mL), dried over anhydrous $Na_2SO_4$. After filtration, the filtrate was concentrated under reduced pressure. The residue was purified by silica gel column chromatography, eluted with PE/EA (2/1) to afford the title compound (450 mg, 94.24%) as an off-white solid. m/z (ESI, +ve ion)=322.00 [M+H]+.

Step F. 4-chloro-5-methoxy-6-(morpholin-4-yl)pyrimidine-2-carbonitrile

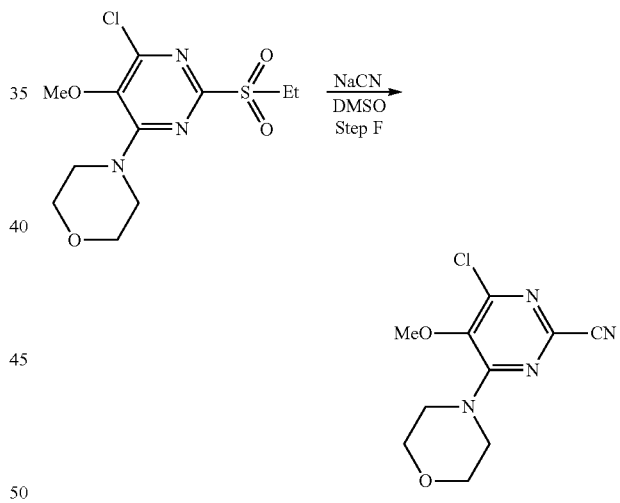

Into a 50 mL round-bottom flask were added 4-[6-chloro-2-(ethanesulfonyl)-5-methoxypyrimidin-4-yl] morpholine (465.00 mg, 1.445 mmol, 1.00 equiv) and DMSO (11.62 mL) at room temperature. To the above mixture was added NaCN (106.23 mg, 2.168 mmol, 1.5 equiv) in portions at room temperature. The resulting mixture was stirred for additional 2 h at room temperature. The reaction was quenched with Water (15 mL) at room temperature. The resulting mixture was extracted with DCM (3×20 mL). The combined organic layers were washed with brine (2×30 mL), dried over anhydrous $Na_2SO_4$. After filtration, the filtrate was concentrated under reduced pressure. The residue was purified by silica gel column chromatography, eluted with PE/EtOAc (2/1) to afford the title compound (122 mg, 33.15%) as an off-white solid. m/z (ESI, +ve ion)=255.15 [M+H]+.

Step G. tert-butyl (1R,2S)-2-(1-(tert-butoxycarbonyl)-3-((2-cyano-5-methoxy-6-morpholinopyrimidin-4-yl)amino)-1H-indazol-6-yl 5'-methoxy-2'-oxospiro[cyclopropane-1'-indoline]-1'-carboxylate Step H

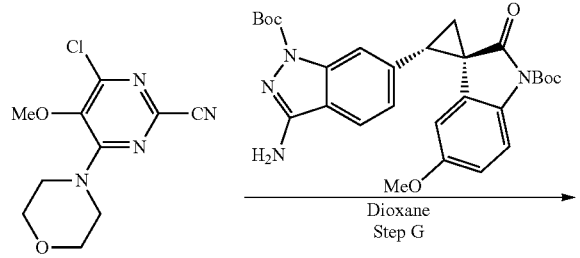

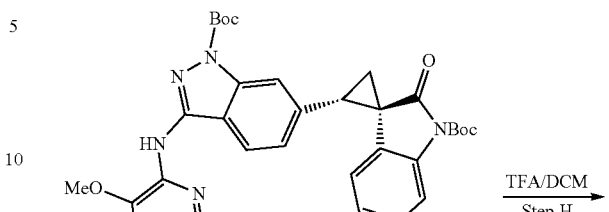

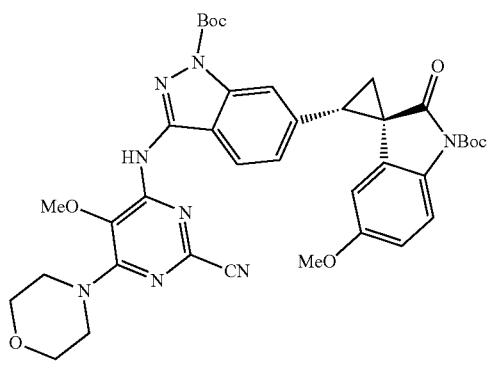

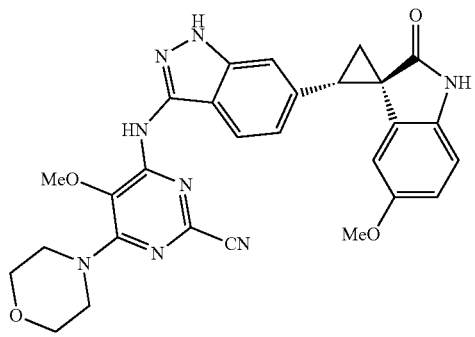

To a stirred mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (70 mg, 0.134 mmol, 1.00 equiv) and 4-chloro-5-methoxy-6-(morpholin-4-yl) pyrimidine-2-carbonitrile (34.24 mg, 0.134 mmol, 1 equiv) in dioxane (2 mL) were added Methanesulfonato(2-bis(3,5-di(trifluoromethyl)phenylphosphino)-3,6-dimethoxy-2',6'-bis(dimethylamino)-1,1'-biphenyl)(2'-methylamino-1,1'-biphenyl-2-yl)palladium (II (15.35 mg, 0.013 mmol, 0.1 equiv) and 2'-(Bis(3,5-bis(trifluoromethyl)phenyl)phosphino)-3',6'-dimethoxy-$N_2,N_2,N_6,N_6$-tetramethyl-[1,1'-biphenyl]-2,6-diamine (10.17 mg, 0.013 mmol, 0.1 equiv) and $Cs_2CO_3$ (87.62 mg, 0.268 mmol, 2 equiv) at room temperature under nitrogen atmosphere. The resulting mixture was stirred for 2 h at 90° C. under nitrogen atmosphere. The mixture was cooled down to room temperature. The reaction was quenched by the addition of Water (8 mL) at room temperature. The resulting mixture was extracted with DCM (3×5 mL). The combined organic layers were washed with brine (2×10 mL), dried over anhydrous $Na_2SO_4$. After filtration, the filtrate was concentrated under reduced pressure. The residue was purified by silica gel column chromatography, eluted with PE/EA (1/1) to afford the title compound (89 mg, 89.59%) as a brown yellow solid. m/z (ESI, +ve ion)=739.25 [M+H]$^+$.

A mixture of tert-butyl (1R,2S)-2-(1-(tert-butoxycarbonyl)-3-((2-cyano-5-methoxy-6-morpholinopyrimidin-4-yl)amino)-1H-indazol-6-yl)-5'-methoxy-2'-oxospiro[cyclopropane-1,3'-indoline]-1'-carboxylate (89 mg, 0.120 mmol, 1.00 equiv) and TFA (2 mL, 26.926 mmol, 223.52 equiv) in DCM (4 mL) was stirred for 2 h at room temperature under nitrogen atmosphere. The reaction was monitored by LCMS. The resulting mixture was concentrated under reduced pressure. The residue was purified by Prep-HPLC with the following conditions: Column: XBridge Prep OBD C18 Column, 19×250 mm, 5 un; Mobile Phase A: water (10 mmol/L $NH_4HCO_3$), Mobile Phase B: MeOH-HPLC; Flow rate: 25 mL/min; Gradient: 50% B to 60% B in 10 min, 60% B to 60% B in 15 min, 60% B; wavelength: 254 nm; RT1(min): 9 to afford Example 61 (17.6 mg, 27.13%) as a pink solid. m/z (ESI, +ve ion)=539.25 [M+H]$^+$. $^1$H NMR (400 MHz, DMSO-d) S 12.72 (s, 1H), 10.42 (s, 1H), 9.40 (s, 1H), 7.47-7.39 (m, 2H), 6.96-6.91 (m, 1H), 6.75 (d, J=8.4 Hz, 1H), 6.69-6.55 (m, 1H), 5.68 (d, J=2.4 Hz, 1H), 3.72 (d, J=7.2 Hz, 7H), 3.68-3.62 (m, 4H), 3.31 (s, 3H), 3.24-3.15 (m, 2H), 2.34-2.32 (m, 1H), 2.01-1.97 (m, 1H).

Example 62. 4-(1,1-dioxidothiomorpholino)-5-methoxy-6-((6-((1R,2S)-5'-methoxy-2'-oxospiro[cyclopropane-1,3'-indolin]-2-yl)-1H-indazol-3-yl)amino)pyrimidine-2-carbonitrile

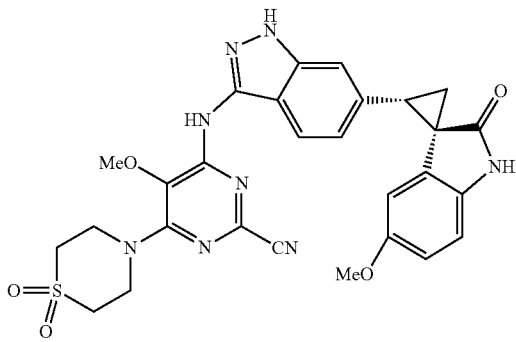 [SMILES: COc1ccc2c(c1)[C@]1(C[C@H]1c1ccc3c(Nc4nc(C#N)nc(N5CCS(=O)(=O)CC5)c4OC)n[nH]c3c1)C(=O)N2]

Step A. 4-[6-chloro-2-(ethylsulfanyl)-5-methoxypyrimidin-4-yl]-1lambda6-thiomorpholine-1,1-dione

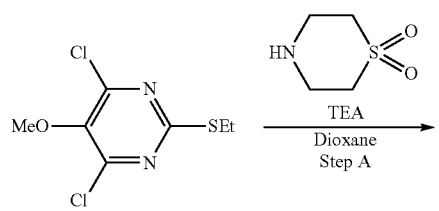

To a stirred mixture of 4,6-dichloro-2-(ethylsulfanyl)-5-methoxypyrimidine (800.00 mg, 3.346 mmol, 1.00 equiv) and 1lambda6-thiomorpholine-1,1-dione (452.28 mg, 3.346 mmol, 1.00 equiv) in dioxane (20.00 mL) were added TEA (1354.22 mg, 13.383 mmol, 4 equiv) dropwise at room temperature under nitrogen atmosphere. The resulting mixture was stirred for 16 h at 100° C. under nitrogen atmosphere. The mixture was cooled down to room temperature. The reaction was quenched by the addition of Water (20 mL) at room temperature. The residue was purified by silica gel column chromatography, eluted with PE/EA (3/1) to afford the title compound (443 mg, 39.19%) as a white solid. m/z (ESI, +ve ion)=338.15 [M+H]$^+$. $^1$H NMR (400 MHz, Chloroform-d) δ 4.36-4.29 (m, 4H), 3.76 (s, 3H), 3.17-3.12 (m, 4H), 3.08 (q, J=7.3 Hz, 2H), 1.40 (t, J=7.3 Hz, 3H).

Step B. 4-[6-chloro-2-(ethanesulfonyl)-5-methoxypyrimidin-4-yl]-1lambda6-thiomorpholine-1,1-dione

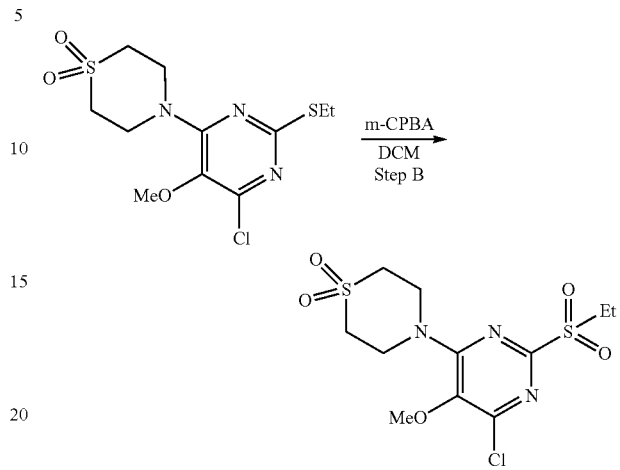

A mixture of 4-[6-chloro-2-(ethylsulfanyl)-5-methoxypyrimidin-4-yl]-1lambda6-thiomorpholine-1,1-dione (417.00 mg, 1.234 mmol, 1.00 equiv) and m-CPBA (745.50 mg, 4.320 mmol, 3.50 equiv) in DCM (10.00 mL) was stirred for 3 h at room temperature under nitrogen atmosphere. The reaction was quenched with Na$_2$S$_2$O$_3$ (aq. 10 mL) at room temperature. The resulting mixture was extracted with DCM (2×15 mL). The combined organic layers were washed with NaHCO$_3$ (aq., 25 mL), dried over anhydrous Na$_2$SO$_4$. After filtration, the filtrate was concentrated under reduced pressure. The residue was purified by silica gel column chromatography, eluted with PE/EtOAc (3/1) to afford the title compound (400 mg, 87.62%) as an off-white solid. m/z (ESI, +ve ion)=370.00 [M+H]$^+$. $^1$H NMR (400 MHz, DMSO-d$_6$) δ 4.27 (t, J=5.1 Hz, 4H), 3.81 (s, 3H), 3.56-3.48 (m, 2H), 3.34 (t, J=5.1 Hz, 4H), 1.29-1.25 (m, 3H).

Step C. 4-chloro-6-(1,1-dioxo-1lambda6-thiomorpholin-4-yl)-5-methoxypyrimidine-2-carbonitrile

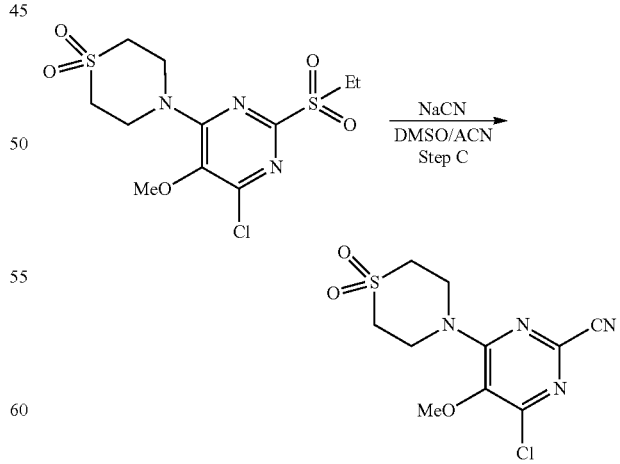

To a stirred mixture of 4-[6-chloro-2-(ethanesulfonyl)-5-methoxypyrimidin-4-yl]-1lambda6-thiomorpholine-1,1-dione (460 mg, 1.244 mmol, 1.00 equiv) and ACN (4.6 mL) in DMSO (11.5 mL) was added NaCN (91.43 mg, 1.866 mmol, 1.5 equiv) at 0° C. under nitrogen atmosphere. The resulting mixture was stirred for 2 h at 0° C. under nitrogen atmosphere. The reaction was quenched by the addition of Water (10 mL) at room temperature. The resulting mixture was extracted with DCM (3×10 mL). The combined organic layers were washed with brine (20 mL), dried over anhydrous Na₂SO₄. After filtration, the filtrate was concentrated under reduced pressure. The residue was purified by silica gel column chromatography, eluted with PE/EA (1/1) to afford the title compound (158 mg, 41.96%) as an off-white solid. m/z (ESI, +ve ion)=302.90 [M+H]⁺.

Step D. tert-butyl (1R,2S)-2-[1-(tert-butoxycarbonyl)-3-{[2-cyano-6-(1,1-dioxo-1lambda6-thiomorpholin-4-yl)-5-methoxypyrimidin-4-yl]amino}indazol-6-yl]-5'-methoxy-2'-oxospiro[cyclopropane-1,3'-indole]-1'-carboxylate

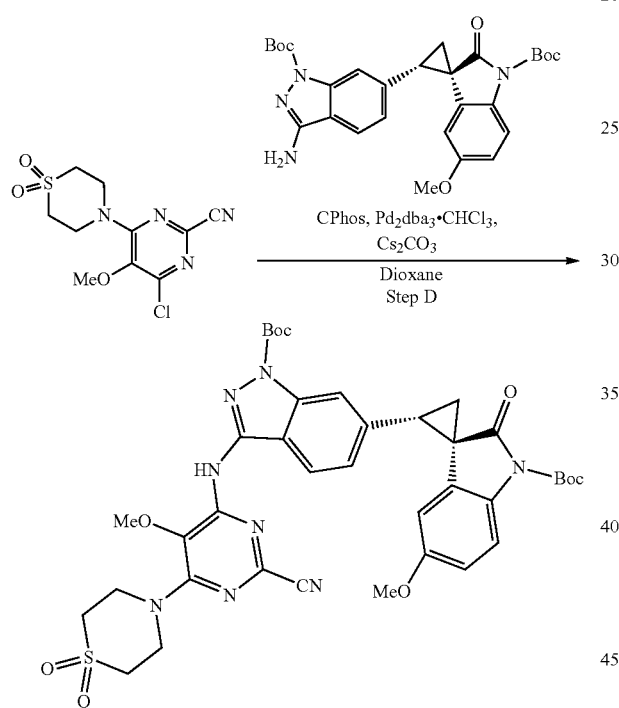

To a stirred mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (100 mg, 0.192 mmol, 1.00 equiv) and 4-chloro-6-(1,1-dioxo-1lambda6-thiomorpholin-4-yl)-5-methoxypyrimidine-2-carbonitrile (69.78 mg, 0.230 mmol, 1.2 equiv) in dioxane (5.00 mL, 58.992 mmol, 307.25 equiv) were added CPhos (8.39 mg, 0.019 mmol, 0.1 equiv) and Pd₂(dba)₃·CHCl₃ (19.88 mg, 0.019 mmol, 0.1 equiv) and Cs₂CO₃ (125.17 mg, 0.384 mmol, 2 equiv) at room temperature under nitrogen atmosphere. The resulting mixture was stirred for 2 h at 90° C. under nitrogen atmosphere. The mixture was cooled down to room temperature. The reaction was quenched by the addition of Water (10 mL) at room temperature. The residue was purified by reverse phase flash chromatography with the following conditions: Column: Spherical C18, 20-40 μm, 80 g; Mobile Phase A: Water (plus 5 mM NH₄HCO₃); Mobile Phase B: ACN; Flow rate: 40 mL/min; Gradient: 60% B-80% B in 20 min; Detector: 254 nm. The fractions containing desired product were collected at 70% B and concentrated under reduced pressure to afford the title compound (54 mg, 35.73%) as an off-white solid. m/z (ESI, +ve ion)=787.25 [M+H]⁺.

Step E. 4-(1,1-dioxo-1lambda6-thiomorpholin-4-yl)-5-methoxy-6-{(6-[(1R,2S)-5'-methoxy-2'-oxo-1'H-spiro[cyclopropane-1,3'-indol]-2-yl]-1H-indazol-3-yl} amino) pyrimidine-2-carbonitrile

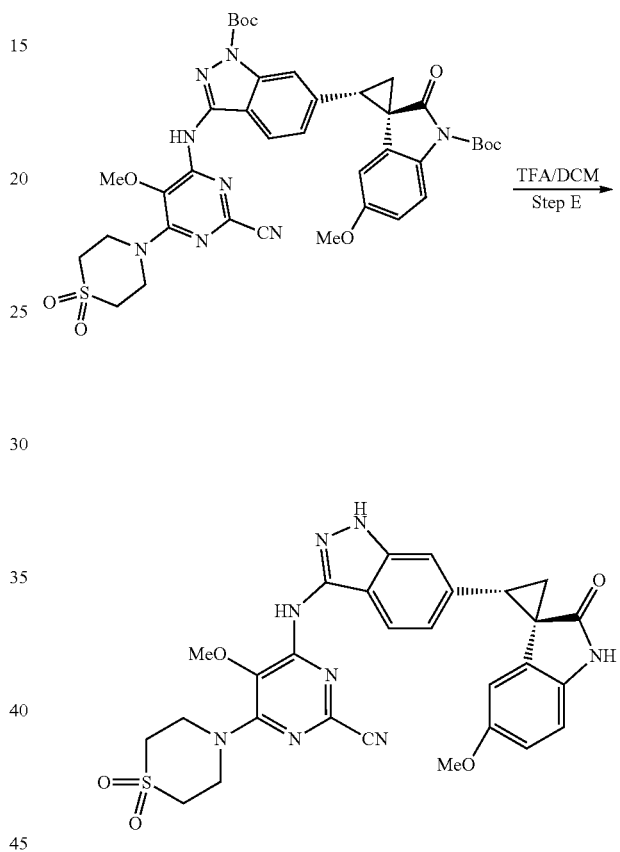

A mixture of tert-butyl (1R,2S)-2-[1-(tert-butoxycarbonyl)-3-{[2-cyano-6-(1,1-dioxo-1lambda6-thiomorpholin-4-yl)-5-methoxypyrimidin-4-yl]amino}indazol-6-yl]-5'-methoxy-2'-oxospiro[cyclopropane-1,3'-indole]-1'-carboxylate (54 mg, 0.069 mmol, 1.00 equiv) and TFA (2 mL, 26.926 mmol, 392.35 equiv) in DCM (4 mL) was stirred for 2 h at room temperature under nitrogen atmosphere. The resulting mixture was concentrated under reduced pressure. The residue was purified by Prep-HPLC with the following conditions: Column: XBridge Prep OBD C18 Column, 19×250 mm, 5 μm; Mobile Phase A: Water (10 mmol/L NH₄HCO₃), Mobile Phase B: MeOH-HPLC; Flow rate: 25 mL/min; Gradient: 50% B to 60% B in 10 min, 60% B to 60% B in 15 min, 60% B; Wavelength: 254 nm; RT1(min): 9 to afford Example 62 (10.7 mg, 26.31%) as a white solid. MS: m/z=587.25 [M+H]⁺. ¹H NMR (400 MHz, Methanol-d₄) δ 7.59 (d, J=8.4 Hz, 1H), 7.43 (s, 1H), 6.98 (d, J=8.4 Hz, 1H), 6.84 (d, J=8.4 Hz, 1H), 6.62 (m, 1H), 5.58 (d, J=2.4 Hz, 1H), 4.26 (d, J=5.9 Hz, 4H), 3.83 (s, 3H), 3.42 (m, 1H), 3.37 (s, 3H), 3.24 (t, J=4.8 Hz, 4H), 2.25 (m, 1H), 2.19 (m, 1H).

Example 63. (1R,2S)-2-{3-[(1,3-dimethyl-1H-pyrazol-4-yl)amino]-1H-indazol-6-yl}-5'-methoxyspiro[cyclopropane-1,3'-indol]-2'(1'H)-one

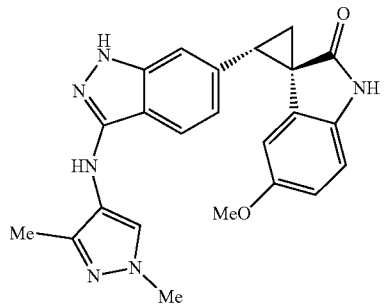 [SMILES: COc1ccc2c(c1)[C@]1(C[C@H]1c1ccc3c(Nc4cn(C)nc4C)n[nH]c3c1)C(=O)N2]

Step A. tert-butyl (1R,2S)-2-[1-(tert-butoxycarbonyl)-3-[(1,3-dimethylpyrazol-4-yl)amino]indazol-6-yl]-5'-methoxy-2'-oxospiro[cyclopropane-1,3'-indole]-1'-carboxylate

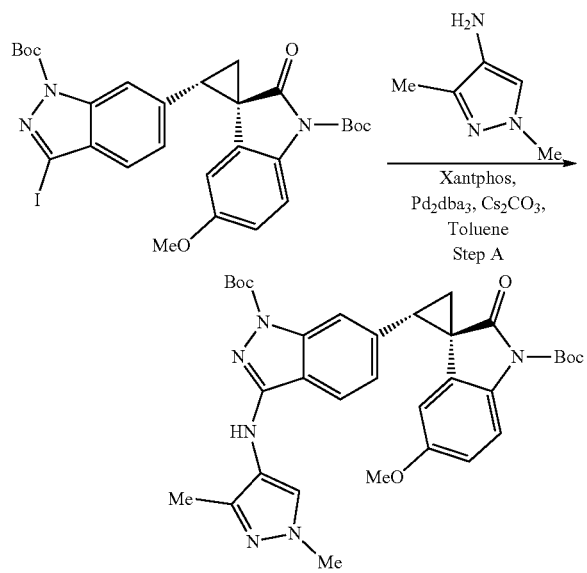

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 1,3-dimethylpyrazol-4-amine (21.12 mg, 0.190 mmol, 1.2 equiv) in toluene (2.5 mL) were added $Cs_2CO_3$ (103.19 mg, 0.316 mmol, 2 equiv), XantPhos (18.33 mg, 0.032 mmol, 0.2 equiv) and $Pd_2(dba)_3$ (29.00 mg, 0.032 mmol, 0.2 equiv) under argon atmosphere. The mixture was stirred at 90° C. for 2 h, then filtered and washed with EA (5 mL×3). The filtrate was concentrated in vacuo. The residue was purified by Prep-TLC (rinsed with EA/PE=1/1) to afford the title compound (60 mg, 58.55%) as a yellow solid. m/z (ESI+ve ion)=615.50 [M+H]$^+$. $^1$H NMR (400 MHz, DMSO-$d_6$) δ 8.05 (s, 1H), 7.89 (s, 1H), 7.81 (d, J=8.8 Hz, 1H), 6.99 (d, J=8.4 Hz, 1H), 6.69 (d, J=9.2 Hz, 1H), 5.92 (s, 1H), 5.57 (d, J=1.6 Hz, 1H), 3.89 (s, 3H), 3.52-3.48 (m, 1H), 3.40 (d, J=1.2 Hz, 3H), 2.38-2.34 (m, 1H), 2.27 (s, 3H), 2.11-2.05 (m, 1H), 1.70 (s, 18H).

Step B. (1R,2S)-2-{3-[(1,3-dimethylpyrazol-4-yl)amino]-1H-indazol-6-yl}-5'-methoxy-1'H-spiro[cyclopropane-1,3'-indol]-2'-one

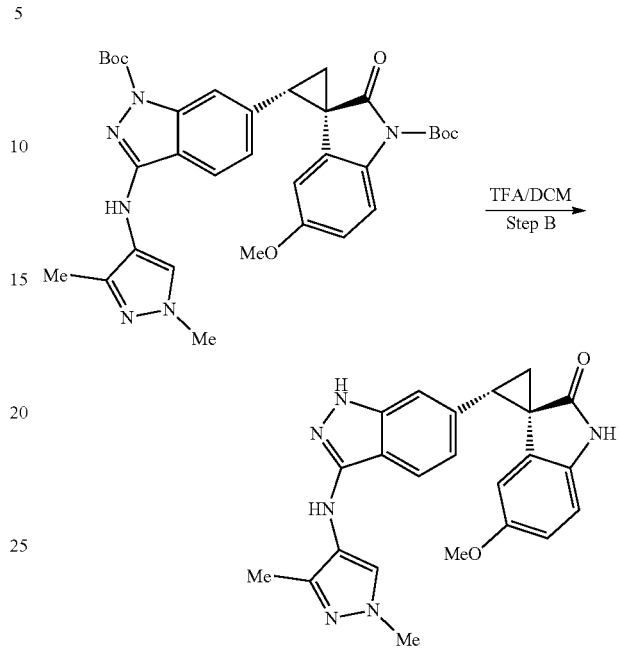

The mixture of tert-butyl (1R,2S)-2-[1-(tert-butoxycarbonyl)-3-[(1,3-dimethylpyrazol-4-yl)amino]indazol-6-yl]-5'-methoxy-2'-oxospiro[cyclopropane-1,3'-indole]-1'-carboxylate (55 mg, 0.089 mmol, 1.00 equiv) in TFA (0.5 mL) and DCM (5 mL) was stirred at 25° C. for 4 h. The solvent was removed under reduced pressure and the residue was purified by Prep-HPLC with the following conditions: Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 25% B to 35% B in 8 min; Wavelength: 254 nm; RT1(min): 6.6. The product-containing fractions was collected and concentrated in vacuo to give Example 63 (8.8 mg, 22.54%) as an off-white solid. m/z (ESI+ve ion)=415.35 [M+H]. $^1$H NMR (400 MHz, Methanol-$d_4$) δ 7.76 (s, 1H), 7.65 (d, J=8.4 Hz, 1H), 7.25 (s, 1H), 6.85-6.80 (m, 2H), 6.64-6.61 (m, 1H), 5.61 (d, J=2.4 Hz, 1H), 3.82 (s, 4H), 3.31 (s, 3H), 2.22 (s, 3H), 2.18-2.15 (m, 1H).

Example 64. (1R,2S)-5'-methoxy-2-(3-{[1-methyl-3-(trifluoromethyl)-1H-pyrazol-4-yl]amino}-1H-indazol-6-yl)spiro[cyclopropane-1,3'-indol]-2'(1'H)-one

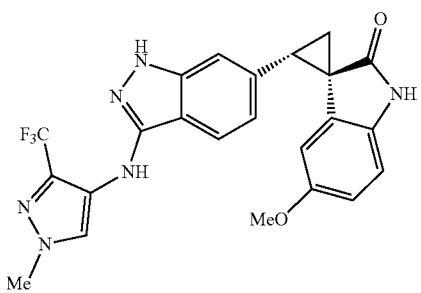 [SMILES: COc1ccc2c(c1)[C@]1(C[C@H]1c1ccc3c(Nc4cn(C)nc4C(F)(F)F)n[nH]c3c1)C(=O)N2]

377

Step A. tert-butyl (1R,2S)-2-[1-(tert-butoxycarbonyl)-3-{[1-methyl-3-(trifluoromethyl)pyrazol-4-yl]amino}indazol-6-yl]-5'-methoxy-2'-oxospiro[cyclopropane-1,3'-indole]-1'-carboxylate

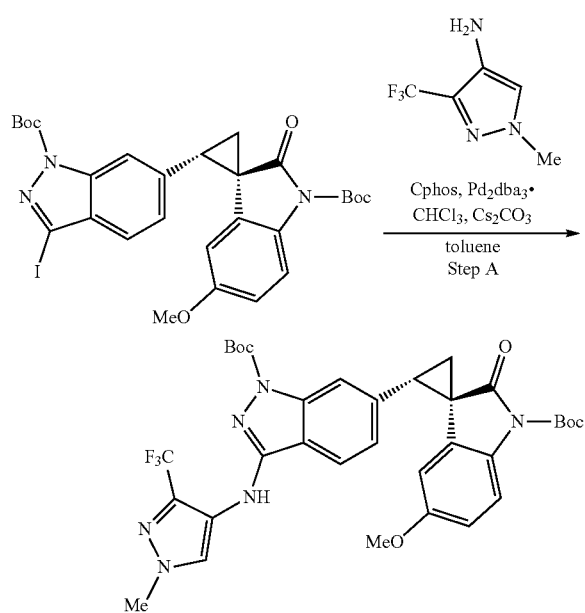

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 1-methyl-3-(trifluoromethyl)pyrazol-4-amine (31.38 mg, 0.190 mmol, 1.2 equiv) in toluene (2.5 mL) were added Cs$_2$CO$_3$ (103.19 mg, 0.316 mmol, 2 equiv), CPhos (13.83 mg, 0.032 mmol, 0.2 equiv) and Pd$_2$(dba)$_3$·CHCl$_3$ (32.78 mg, 0.032 mmol, 0.2 equiv) under argon atmosphere. The mixture was stirred at 90° C. for 2 h. The reaction mixture was filtered and washed with EA (5 mL×3). The filtrate was concentrated in vacuo. The residue was purified by Prep-TLC (rinsed with EA/PE=1/2) to afford crude the title compound (23a) (80 mg, 75%) as a yellow solid. m/z (ESI+ve ion)=669.50 [M+H]$^+$.

Step B. (1R,2S)-5'-methoxy-2-(3-{[1-methyl-3-(trifluoromethyl)pyrazol-4-yl]amino}-1H-indazol-6-yl)-1'H-spiro[cyclopropane-1,3'-indol]-2'-one

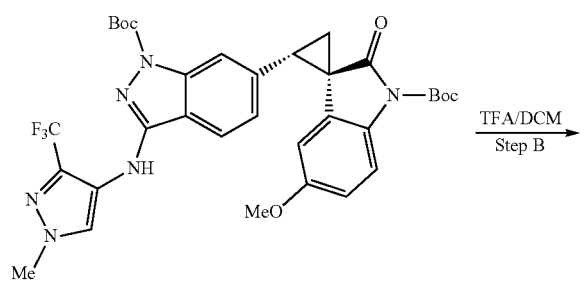

378

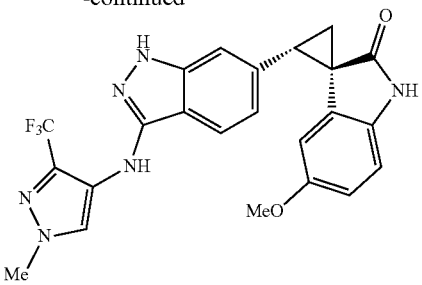

The mixture of crude tert-butyl (1R,2S)-2-[1-(tert-butoxycarbonyl)-3-{[1-methyl-3-(trifluoromethyl)pyrazol-4-yl]amino}indazol-6-yl]-5'-methoxy-2'-oxospiro[cyclopropane-1,3'-indole]-1'-carboxylate (75 mg) in TFA (0.5 mL) and DCM (3 mL) was stirred for 4 h at 25° C. The solvent was removed under reduced pressure. The residue was purified by prep-HPLC with the following conditions: Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 30% B to 50% B in 8 min, 50% B; wavelength: 254 nm; RT1: 7 min. The product-containing fractions was concentrated in vacuo to give Example 64 (29.8 mg, 40.01% over two steps) as a white solid. m/z (ESI +ve ion)=469.20 [M+H]$^+$. $^1$H NMR (400 MHz, DMSO-d$_6$) δ 11.81 (s, 1H), 10.40 (s, 1H), 8.26 (s, 1H), 8.04 (s, 1H), 7.83 (d, J=8.4 Hz, 1H), 7.24 (s, 1H), 6.86-6.84 (m, 1H), 6.75 (d, J=8.4 Hz, 1H), 6.60-6.57 (m, 1H), 5.70 (d, J=2.4 Hz, 1H), 3.91 (s, 3H), 3.33 (s, 3H), 3.17 (t, J=8.4 Hz, 1H), 2.31-2.27 (m, 1H), 2.00-1.98 (m, 1H). $^{19}$F NMR (376 MHz, DMSO-d$_6$) δ −58.60 (s, 3F).

Example 65. (1R,2S)-5'-methoxy-2-{3-[(1-methyl-1H-pyrazol-4-yl)amino]-1H-indazol-6-yl}spiro[cyclopropane-1,3'-indol]-2'(1'H)-one

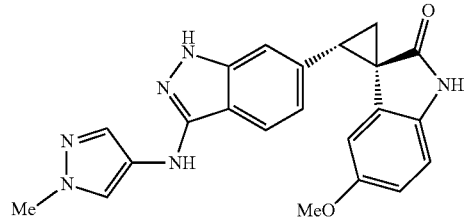 [SMILES: COc1ccc2c(c1)[C@]1(C[C@H]1c1ccc3c(Nc4cnn(C)c4)n[nH]c3c1)C(=O)N2]

Step A. tert-butyl (1R,2S)-2-[1-(tert-butoxycarbonyl)-3-[(1-methylpyrazol-4-yl)amino]indazol-6-yl]-5'-methoxy-2'-oxospiro[cyclopropane-1,3'-indole]-1'-carboxylate

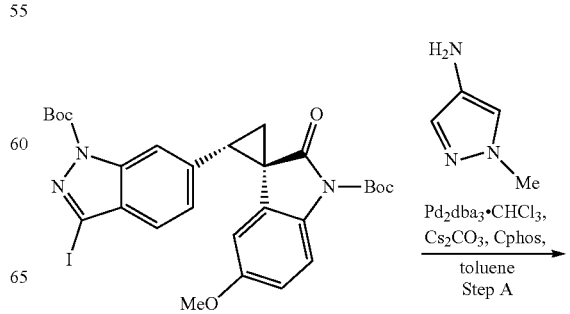

-continued

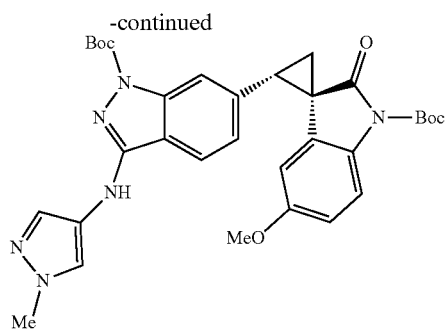

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 1-methylpyrazol-4-amine (18.46 mg, 0.190 mmol, 1.2 equiv) in toluene (2.5 mL) were added $Cs_2CO_3$ (103.19 mg, 0.316 mmol, 2 equiv), CPhos (13.83 mg, 0.032 mmol, 0.2 equiv) and $Pd_2(dba)_3 \cdot CHCl_3$ (32.78 mg, 0.032 mmol, 0.2 equiv) under argon atmosphere. After the mixture was stirred at 90° C. for 2 h, it was cooled down to room temperature, filtered and washed with EA (5 mL×3). The filtrate was concentrated in vacuo. The residue was purified by Prep-TLC (rinsed with EA/PE=1/2) to afford the title compound (30 mg, 31.54%) as a yellow solid. m/z (ESI+ve ion)=601.50 [M+H]$^+$.

Step B. (1R,2S)-5'-methoxy-2-{3-[(1-methylpyrazol-4-yl)amino]-1H-indazol-6-yl}-1'H-spiro[cyclopropane-1,3'-indol]-2'-one

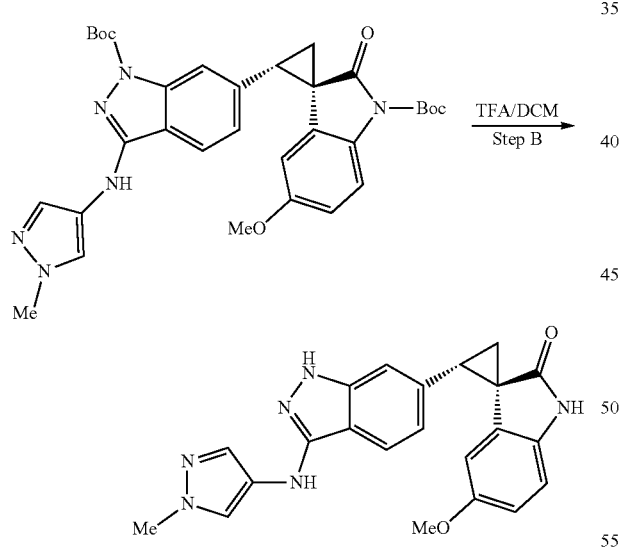

The mixture of tert-butyl (1R,2S)-2-[1-(tert-butoxycarbonyl)-3-[(1-methylpyrazol-4-yl)amino]indazol-6-yl]-5'-methoxy-2'-oxospiro[cyclopropane-1,3'-indole]-1'-carboxylate (30 mg, 0.050 mmol, 1.00 equiv) in TFA (0.2 mL) and DCM (2 mL) was stirred for 5 h. The solvent was removed under reduced pressure. The residue was purified by Prep-HPLC with the following conditions: Column: XBridge Shield RP18 OBD Column, 30×150 mm, 5 µm; Mobile Phase A: Water (10 mmol/L $NH_4HCO_3$), Mobile Phase B: ACN; Flow rate: 60 mL/min; Gradient: 20% B to 45% B in 8 min; Wavelength: 254 nm; RT1(min): 6.5. The product-containing fractions were collected and concentrated in vacuo to give Example 65 (9.3 mg, 46.27%) as a white solid. m/z (ESI+ve ion)=401.30 [M+H]$^+$. $^1$H NMR (400 MHz, Methanol-d$_4$) δ 7.87 (s, 1H), 7.67 (d, J=8.4 Hz, 1H), 7.52 (s, 1H), 7.26 (s, 1H), 6.83 (d, J=8.4 Hz, 2H), 6.64-6.61 (m, 1H), 5.61 (d, J=2.4 Hz, 1H), 3.88 (s, 3H), 3.36-3.33 (s, 1H), 3.29 (s, 3H), 2.22-2.15 (m, 2H).

Example 66. 4-({6-[(1R,2S)-5'-methoxy-2'-oxo-1',2'-dihydrospiro[cyclopropane-1,3'-indol]-2-yl]-1H-indazol-3-yl}amino)-1-methyl-1H-pyrazole-3-carbonitrile

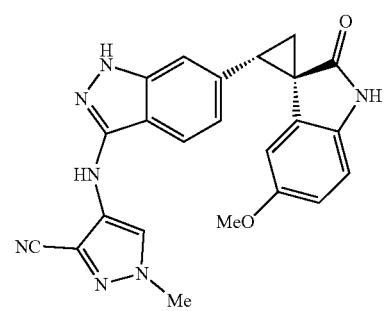 [SMILES: COc1ccc2c(c1)[C@]1(C[C@H]1c1ccc3c(Nc4cn(C)nc4C#N)n[nH]c3c1)C(=O)N2]

Step A. tert-butyl (1R,2S)-2-[1-(tert-butoxycarbonyl)-3-[(1-methylpyrazol-4-yl)amino]indazol-6-yl]-5'-methoxy-2'-oxospiro[cyclopropane-1,3'-indole]-1'-carboxylate

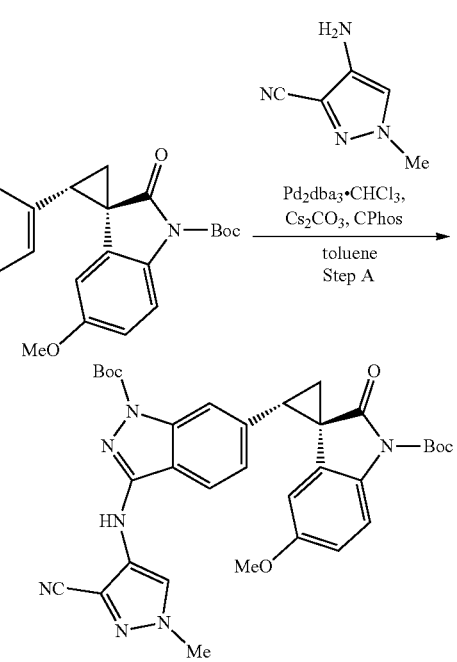

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 4-amino-1-methylpyrazole-3-carbonitrile (23.21 mg, 0.190 mmol, 1.2 equiv) in toluene (2.5 mL) were added $Cs_2CO_3$ (103.19 mg, 0.316 mmol, 2 equiv), CPhos (13.83 mg, 0.032 mmol, 0.2 equiv) and Pd₂(dba)₃·CHCl₃ (32.78 mg, 0.032 mmol, 0.2 equiv) under argon atmosphere. The mixture was stirred at 90° C. for 2 h and then cooled down to room temperature. The reaction mixture was filtered and washed with EA (5 mL×3). The filtrate was concentrated in vacuo. The residue was purified by Prep-TLC (rinsed with EA/PE=1/2) to afford crude title compound (25a) (28 mg, 22.61%) as a yellow solid. m/z (ESI+ve ion)=526.35 [M+H–100]⁺.

Step B. 4-({6-[(1R,2S)-5'-methoxy-2'-oxo-1'H-spiro[cyclopropane-1,3'-indol]-2-yl]-1H-indazol-3-yl}amino)-1-methylpyrazole-3-carbonitrile

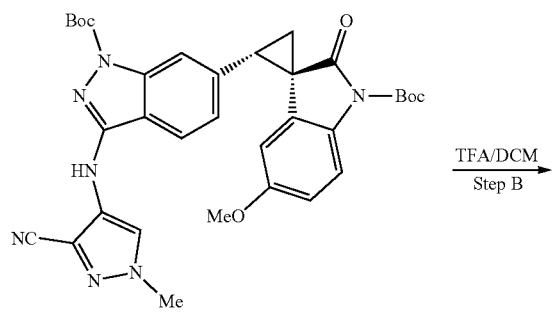

The mixture of tert-butyl (1R,2S)-2-[1-(tert-butoxycarbonyl)-3-[(1-methylpyrazol-4-yl)amino]indazol-6-yl]-5'-methoxy-2'-oxospiro[cyclopropane-1,3'-indole]-1'-carboxylate (26 mg, 0.033 mmol, 1.00 equiv) in TFA (0.5 mL) and DCM (2.5 mL) was stirred at 25° C. for 5 h. The solvent was removed under reduced pressure. The residue was purified by Prep-HPLC with the following conditions: Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 18% B to 28% B in 8 min; wavelength: 254 nm; RT1(min): 7. The product containing fractions were collected and concentrated in vacuo to give Example 66 (4.0 mg, 28.00%) as a yellow solid. m/z (ESI+ve ion)=426.35 [M+H]⁺. ¹H NMR (400 MHz, Methanol-d₄) δ 8.36 (s, 1H), 8.04 (d, J=8.4 Hz, 1H), 7.44 (s, 1H), 6.85-6.79 (m, 2H), 6.62-6.60 (m, 1H), 5.76 (d, J=2.0 Hz, 1H), 4.37 (s, 3H), 3.40-3.38 (m, 1H), 3.25 (s, 3H), 2.31-2.28 (m, 1H), 2.22-2.18 (m, 1H).

Example 67. (1R,2S)-2-[3-({6-[(2R,6S)-2,6-dimethylmorpholin-4-yl]-5-methoxy-2-methylpyrimidin-4-yl}amino)-1H-indazol-6-yl]-5'-methoxyspiro[cyclopropane-1,3'-indol]-2'(1'H)-one

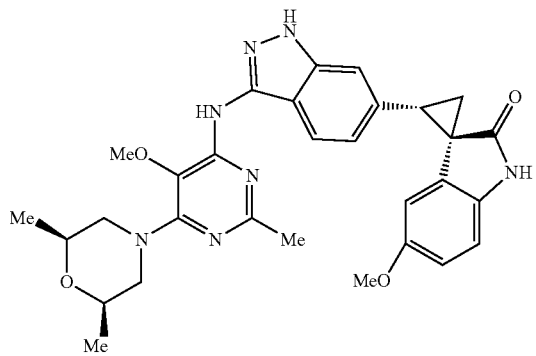 [SMILES: COc1ccc2c(c1)[C@]1(C[C@H]1c1ccc3c(Nc4nc(C)nc(N5C[C@@H](C)O[C@@H](C)C5)c4OC)n[nH]c3c1)C(=O)N2]

Step A. (2R,6S)-4-(6-chloro-5-methoxy-2-methylpyrimidin-4-yl)-2,6-dimethylmorpholine

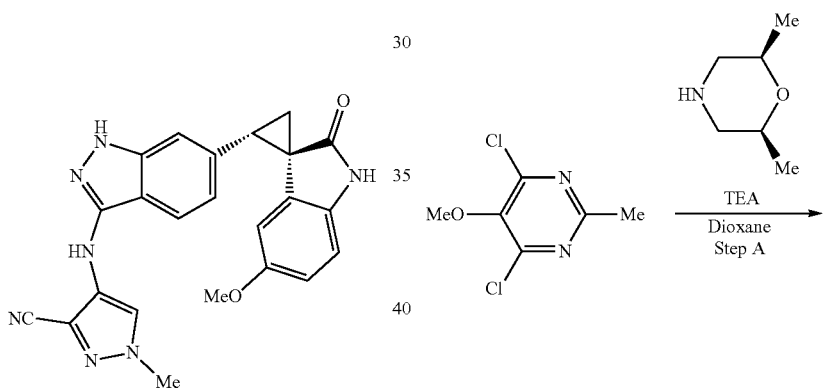

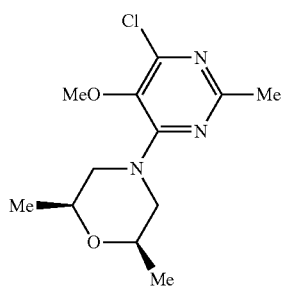

A mixture of 4,6-dichloro-5-methoxy-2-methylpyrimidine (300 mg, 1.554 mmol, 1.00 equiv) and (2R,6S)-2,6-dimethylmorpholine (179.00 mg, 1.554 mmol, 1 equiv) in THF (7.5 mL) was stirred for 2 h at room temperature under nitrogen atmosphere. The resulting mixture was concentrated under vacuum. The residue was purified by silica gel column chromatography, eluted with PE/EA (5/1) to afford the title compound (211 mg, 49.96%) as a colorless oil. m/z=272.00 [M+H]⁺.

Step B. tert-butyl (1R,2S)-2-[1-(tert-butoxycarbonyl)-3-({6-[(2R,6S)-2,6-dimethylmorpholin-4-yl]-5-methoxy-2-methylpyrimidin-4-yl} amino)indazol-6-yl]-5'-methoxy-2'-oxospiro[cyclopropane-1,3'-indole]-1'-carboxylate Step C. (1R,2S)-2-[3-({6-[(2R,6S)-2,6-dimethylmorpholin-4-yl]-5-methoxy-2-methylpyrimidin-4-yl}amino)-1H-indazol-6-yl]-5'-methoxy-1'H-spiro[cyclopropane-1,3'-indol]-2'-one

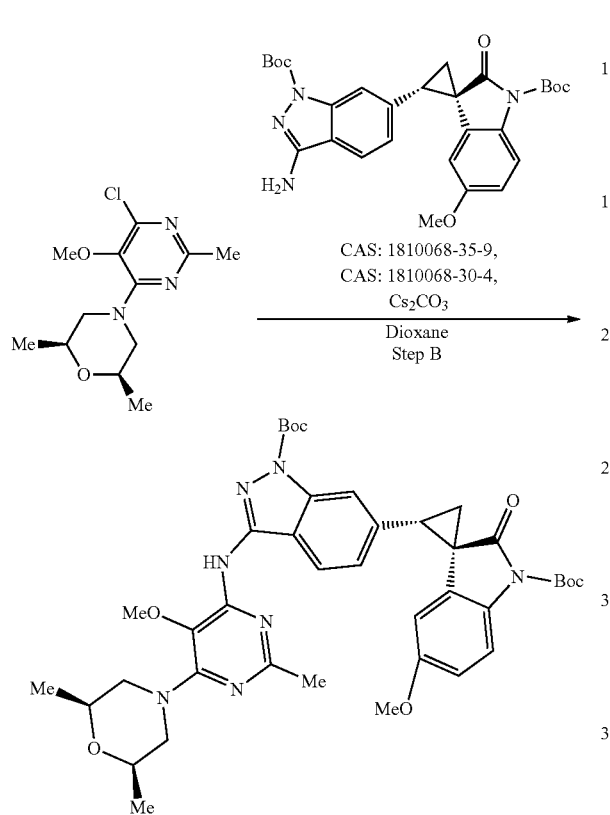

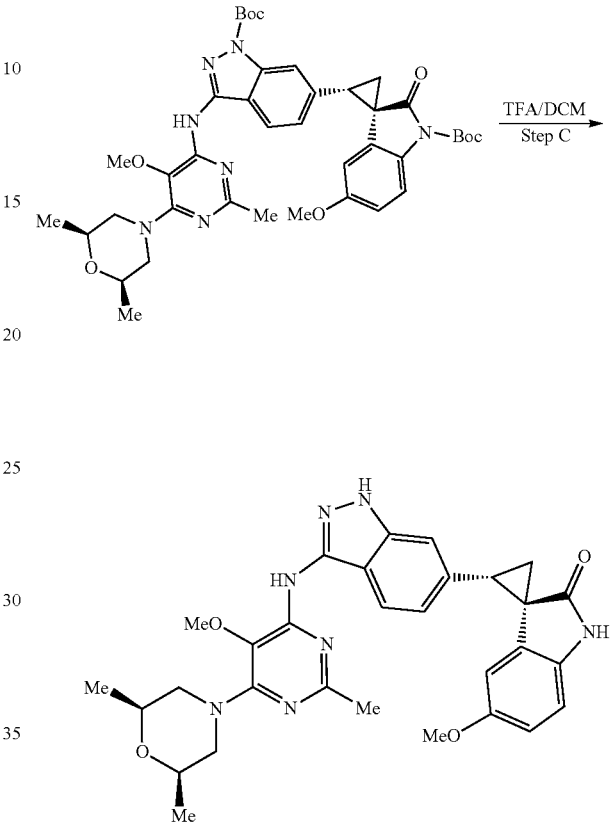

To a stirred mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (80 mg, 0.154 mmol, 1.00 equiv) and (2R,6S)-4-(6-chloro-5-methoxy-2-methylpyrimidin-4-yl)-2,6-dimethylmorpholine (41.76 mg, 0.154 mmol, 1 equiv) in dioxane (4 mL, 47.216 mmol, 307.25 equiv) were added methanesulfonato(2-bis(3,5-di(trifluoromethyl)phenylphosphino)-3,6-dimethoxy-2',6'-bis(dimethylamino)-1,1'-biphenyl)(2'-methylamino-1,1'-biphenyl-2-yl)palladium (II) (17.54 mg, 0.015 mmol, 0.1 equiv) and 2'-(Bis(3,5-bis(trifluoromethyl)phenyl)phosphino)-3',6'-dimethoxy-$N_2,N_2,N_6,N_6$-tetramethyl-[1,1'-biphenyl]-2,6-diamine (11.63 mg, 0.015 mmol, 0.1 equiv) and $Cs_2CO_3$ (100.14 mg, 0.308 mmol, 2 equiv) at room temperature under nitrogen atmosphere. The resulting mixture was stirred for 2 h at 90° C. under nitrogen atmosphere. The reaction was quenched by the addition of Water (8 mL) at room temperature. The resulting mixture was extracted with DCM (3×8 mL). The combined organic layers were washed with brine (15 mL), dried over anhydrous $Na_2SO_4$. After filtration, the filtrate was concentrated under reduced pressure. The residue was purified by silica gel column chromatography, eluted with PE/EA (5/1) to afford the title compound (74.5 mg, 64.14%) as a yellow solid. m/z (ESI, +ve ion)=756.30 $[M+H]^+$.

A mixture of tert-butyl (1R,2S)-2-[1-(tert-butoxycarbonyl)-3-({6-[(2R,6S)-2,6-dimethylmorpholin-4-yl]-5-methoxy-2-methylpyrimidin-4-yl} amino)indazol-6-yl]-5'-methoxy-2'-oxospiro[cyclopropane-1,3'-indole]-1'-carboxylate (74.5 mg, 0.099 mmol, 1.00 equiv) and TFA (2 mL, 26.926 mmol) in DCM (4 mL) was stirred for 2 h at room temperature under nitrogen atmosphere. The resulting mixture was concentrated under reduced pressure. The residue was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 35% B to 45% B in 8 min, 45% B; wavelength: 254 nm; RT1(min): 7.2 to afford Example 67 (28.1 mg, 50.80%) as a white solid. m/z (ESI, +ve ion)=556.25 $[M+H]^+$. $^1$H NMR (400 MHz, DMSO-$d_6$) δ 12.53 (s, 1H), 10.43 (s, 1H), 8.75 (s, 1H), 7.36 (d, J=8.3 Hz, 1H), 7.37 (s, 1H), 6.88 (d, J=8.4 Hz, 1H), 6.74 (d, J=8.4 Hz, 1H), 6.58 (m, 1H), 5.71 (d, J=2.4 Hz, 1H), 4.23 (d, J=12.8 Hz, 2H), 3.67 (t, J=8.6 Hz, 2H), 3.62 (s, 3H), 3.30 (s, 4H), 3.18-3.16 (m, 2H), 2.35-2.28 (m, 1H), 2.07 (s, 3H), 1.98 (m, 1H), 1.13 (d, J=6.4 Hz, 6H).

Example 68. (1R,2S)-2-(3-{[2-(2-hydroxyethyl)-5-methoxy-6-(morpholin-4-yl)pyrimidin-4-yl]amino}-1H-indazol-6-yl)-5'-methoxyspiro[cyclopropane-1,3'-indol]-2'(1'H)-one

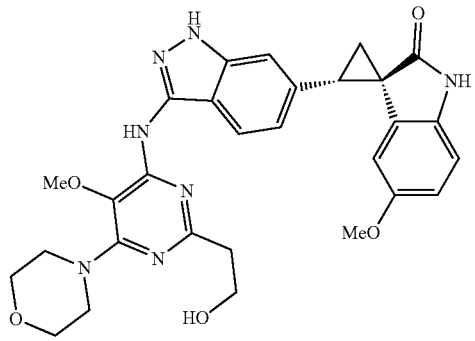 [SMILES: COc1ccc2c(c1)[C@]1(C[C@H]1c1ccc3c(Nc4nc(CCO)nc(N5CCOCC5)c4OC)n[nH]c3c1)C(=O)N2]

Step A. methyl 2-(4-hydroxy-5-methoxy-6-oxo-1H-pyrimidin-2-yl)acetate

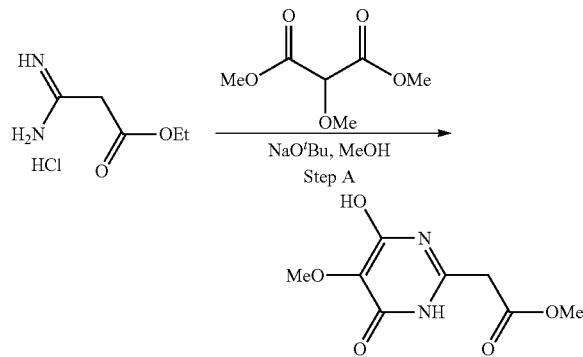

To a mixture of t-BuONa (12.01 g, 124.992 mmol, 2.5 equiv) in MeOH (100 mL) were added ethyl 2-carbamimidoylacetate hydrochloride (8.33 g, 49.997 mmol, 1.00 equiv) and 1,3-dimethyl 2-methoxypropanedioate (8.11 g, 49.997 mmol, 1 equiv). The mixture was stirred for 3 h at 70° C. The mixture was quenched with water (50 mL) and then MeOH was evacuated under reduced pressure and then extracted with CHCl₃ (3×30 mL). The combined organic layers were dried over anhydrous Na₂SO₄ and then concentrated under reduced pressure to afford the title compound (6 g, 56.03%) as a yellow oil. m/z (ESI, +ve ion)=215.05 [M+H]⁺

Step B. methyl 2-(4,6-dichloro-5-methoxypyrimidin-2-yl)acetate

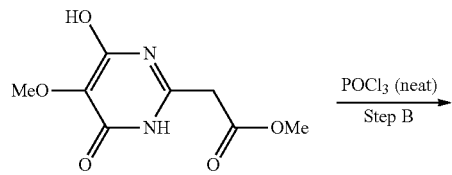

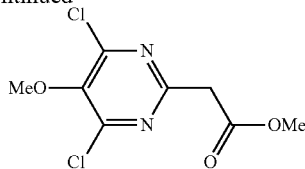

A mixture of methyl 2-(4-hydroxy-5-methoxy-6-oxo-1H-pyrimidin-2-yl)acetate (400.00 mg, 1 equiv) in POCl₃ (5.00 mL) was stirred for 3 h at 100° C. The mixture was concentrated under reduced pressure. The residue was purified with silica gel chromatography, eluted with 20% EA in PE to afford the title compound (70 mg, 14.93%) as a yellow solid. m/z (ESI, +ve ion)=250.95 [M+H]⁺. ¹H NMR (400 MHz, DMSO-d₆) δ 3.97 (s, 3H), 3.94 (s, 2H), 3.75 (s, 3H).

Step C. methyl 2-[4-chloro-5-methoxy-6-(morpholin-4-yl)pyrimidin-2-yl]acetate

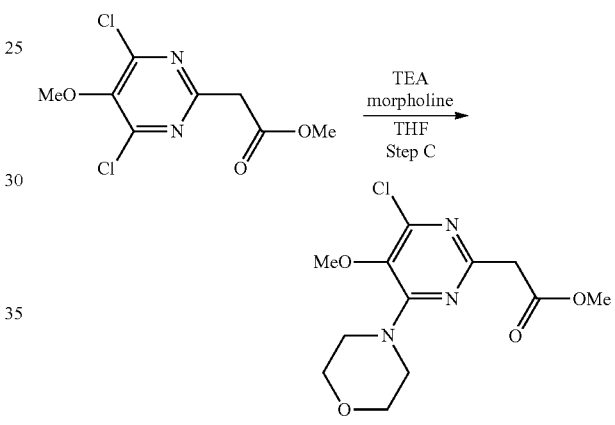

To a mixture of methyl 2-(4,6-dichloro-5-methoxypyrimidin-2-yl)acetate (500 mg, 1.992 mmol, 1.00 equiv) and TEA (403.05 mg, 3.984 mmol, 2 equiv) in THF (10 mL, 123.430 mmol, 61.98 equiv) was added morpholine (190.86 mg, 2.191 mmol, 1.1 equiv) at 0° C. The resulting mixture was stirred for 16 h at room temperature. The reaction was concentrated under reduced pressure to afford the title compound (600 mg, 99.85%) as a yellow oil. m/z (ESI, +ve ion)=302.15 [M+H]⁺. ¹H NMR (400 MHz, DMSO-d₆) δ 3.79-3.87 (m, 4H), 3.77 (d, J=4.4 Hz, 7H), 3.73 (d, J=2.1 Hz, 6H).

Step D. 2-[4-chloro-5-methoxy-6-(morpholin-4-yl)pyrimidin-2-yl]ethanol

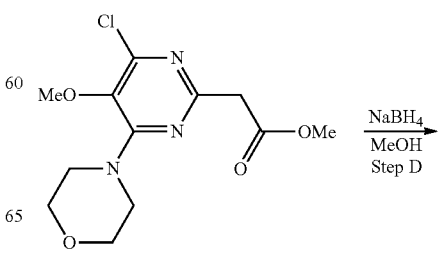

387

-continued

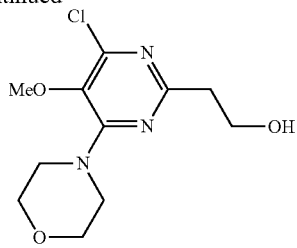

To a mixture of methyl 2-[4-chloro-5-methoxy-6-(morpholin-4-yl)pyrimidin-2-yl]acetate (1500 mg, 4.97 mmol, 1.00 equiv) in MeOH (50 mL) was added NaBH$_4$ (1128.5 mg, 29.82 mmol, 6 equiv) at 0° C. The resulting mixture was stirred for 3 h at room temperature. The reaction was quenched with water (50 mL), extracted with EA (3×100 mL). The combined organic layers were dried over anhydrous Na$_2$SO$_4$ and then concentrated under reduced pressure. The residue was purified with silica gel chromatography, eluted with PE:EA=1:1 to afforded the title compound (800 mg, 58.79%) as a yellow oil. m/z (ESI, +ve ion)=274.15 [M+H]$^+$. $^1$H NMR (400 MHz, Chloroform-d) δ 4.01 (s, 2H), 3.80 (s, 8H), 3.74 (s, 3H), 2.96 (t, J=5.4 Hz, 2H).

Step E. 4-(2-{2-[(tert-butyldimethylsilyl)oxy]ethyl}-6-chloro-5-methoxypyrimidin-4-yl)morpholine

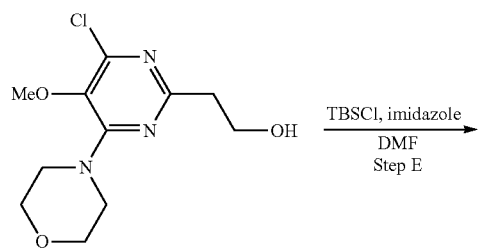

To a mixture of 2-[4-chloro-5-methoxy-6-(morpholin-4-yl)pyrimidin-2-yl]ethanol (700 mg, 0.256 mmol, 1.00 equiv) and Imidazole (348.2 mg, 5.12 mmol, 2 equiv) in DMF (5 mL) was added TBSCl (578.2 mg, 3.84 mmol, 1.5 equiv). The resulting mixture was stirred for 16 h at room temperature. The mixture was concentrated under reduced pressure. The residue was purified with silica gel chromatography, eluted with PE/EA 4/1 to afford the title compound (860 mg, 86.68%) as a colorless oil. m/z (ESI, +ve ion)=388.15 [M+H]$^+$.

388

Step F. tert-butyl (1R,2S)-2-[1-(tert-butoxycarbonyl)-3-[(2-{2-[(tert-butyldimethylsilyl)oxy]ethyl}-5-methoxy-6-(morpholin-4-yl)pyrimidin-4-yl)amino] indazol-6-yl]-5'-methoxy-2'-oxospiro[cyclopropane-1,3'-indole]-1'-carboxylate

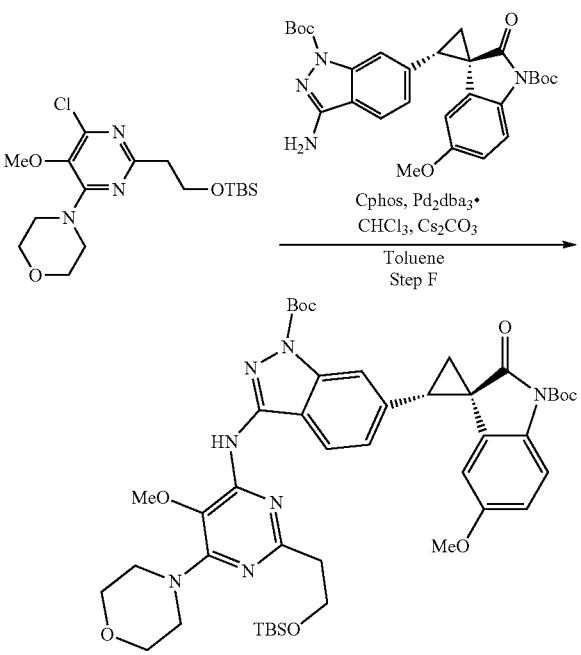

To a mixture of 4-(2-{2-[(tert-butyldimethylsilyl)oxy]ethyl}-6-chloro-5-methoxypyrimidin-4-yl)morpholine (58 mg, 0.149 mmol, 1.00 equiv), tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (77.82 mg, 0.149 mmol, 1 equiv) and Cs$_2$CO$_3$ (97.42 mg, 0.298 mmol, 2 equiv) in dioxane (5 mL) were added CPhos (6.53 mg, 0.015 mmol, 0.1 equiv) and Pd$_2$(dba)$_3$·CHCl$_3$ (15.47 mg, 0.015 mmol, 0.1 equiv) under N$_2$ atmosphere. The resulting mixture was stirred for 90° C. for 4 h. The mixture was concentrated under reduced pressure. The residue was purified with prep-TLC, eluted with PE/EA 1/1 to afford the title compound (20 mg, 15.34%) as a yellow oil. m/z (ESI, +ve ion)=872.40 [M+H]$^+$ Step G. (1R,2S)-2-(3-{[2-(2-hydroxyethyl)-5-methoxy-6-(morpholin-4-yl)pyrimidin-4-yl]amino}-1H-indazol-6-yl)-5'-methoxy-1'H-spiro[cyclopropane-1,3'-indol]-2'-one

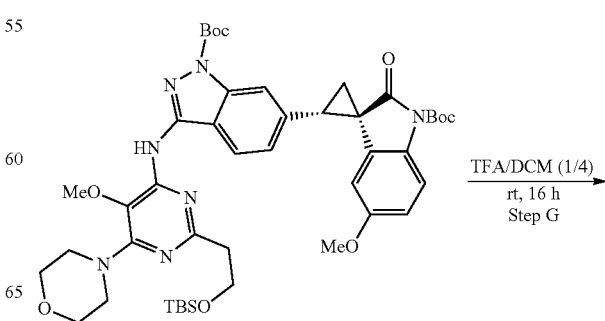

-continued

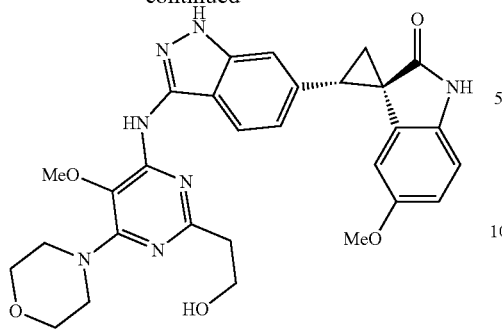

To a mixture of tert-butyl (1R,2S)-2-[1-(tert-butoxycarbonyl)-3-[(2-{2-[(tert-butyldimethylsilyl)oxy]ethyl}-5-methoxy-6-(morpholin-4-yl)pyrimidin-4-yl)amino]indazol-6-yl]-5'-methoxy-2'-oxospiro[cyclopropane-1,3'-indole]-1'-carboxylate (100 mg, 0.115 mmol, 1.00 equiv) in DCM (2 mL) was added TFA (1 mL). The resulting mixture was stirred for 16 h at room temperature. The mixture was concentrated under reduced pressure. The residue was purified with prep-HPLC with following conditions: Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 25% B to 40% B in 8 min, 40% B; wavelength: 254 nm to afford Example 68 (26 mg, 40.66%) as a white solid. m/z (ESI, +ve ion)=558.50 [M+H]$^+$, $^1$H NMR (400 MHz, Methanol-d$_4$) δ 7.64 (d, J=8.4 Hz, 1H), 7.41 (d, J=1.2 Hz, 1H), 6.93 (dd, J=8.4, 1.4 Hz, 1H), 6.84 (d, J=8.5 Hz, 1H), 6.63 (dd, J=8.5, 2.5 Hz, 1H), 5.65 (d, J=2.5 Hz, 1H), 3.75-3.85 (m, 9H), 3.73-3.71 (m, 4H), 3.38-3.37 (m, 1H), 3.30 (s, 3H), 2.71 (t, J=6.2 Hz, 2H), 2.24-2.18 (m, 2H).

Example 69. 4-[2-cyclopropyl-5-methoxy-6-({6-[(1R,2S)-5'-methoxy-2'-oxo-1',2'-dihydrospiro[cyclopropane-1,3'-indol]-2-yl]-1H-indazol-3-yl}amino)pyrimidin-4-yl]-1 λ6-thiomorpholine-1,1-dione Step A. 4-(6-chloro-2-cyclopropyl-5-methoxypyrimidin-4-yl)-1lambda6-thiomorpholine-1,1-dione

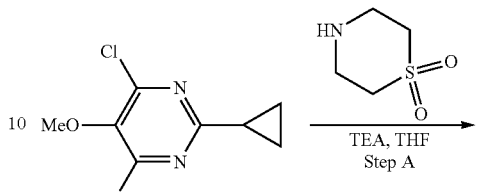

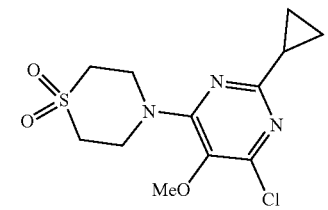

To a stirred solution of 4,6-dichloro-2-cyclopropyl-5-methoxypyrimidine (400.0 mg, 1.0 equiv) and 1lambda6-thiomorpholine-1,1-dione (271.5 mg, 1.1 equiv) in THF (8.0 mL) was added TEA (369.5 mg, 2.0 equiv) at room temperature under nitrogen atmosphere. The resulting mixture was stirred for 2 h at 70° C. The resulting mixture was concentrated under vacuum. The residue was purified by silica gel column chromatography, eluted with 0-50% of EA in PE to the title compound (300.0 mg, 51.8% yield) as a white solid. m/z (ESI+ve ion)=318.05 [M+H]$^+$.

Step B. tert-butyl (1R,2S)-2-[1-(tert-butoxycarbonyl)-3-{[2-cyclopropyl-6-(1,1-dioxo-1lambda6-thiomorpholin-4-yl)-5-methoxypyrimidin-4-yl]amino}indazol-6-yl]-5'-methoxy-2'-oxospiro[cyclopropane-1,3'-indole]-1'-carboxylate

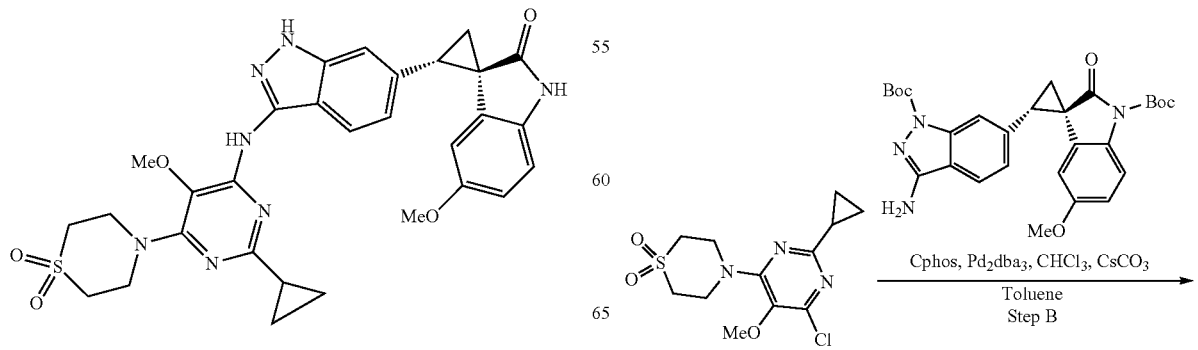

391

-continued

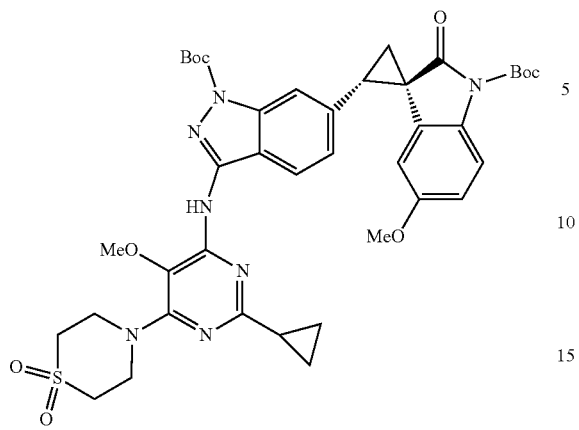

To the mixture of tert-butyl (1R,2S)-2-[3-amino-1-tert-butoxycarbonyl)indazol-6-yl]-5'-methoxy-2'-oxospiro[cyclopropane-1,3'-indole]-1'-carboxylate (100 mg, 0.192 mmol, 1.00 equiv) and 4-(6-chloro-2-cyclopropyl-5-methoxypyrimidin-4-yl)-1lambda6-thiomorpholine-1,1-dione (73.25 mg, 0.230 mmol, 1.2 equiv) in toluene (2.5 mL) were added Cs₂CO₃ (125.17 mg, 0.384 mmol, 2 equiv), CPhos (16.77 mg, 0.038 mmol, 0.2 equiv) and Pd₂(dba)₃·CHCl₃ (39.77 mg, 0.038 mmol, 0.2 equiv) under nitrogen atmosphere. The resulting mixture was stirred at 90° C. for 2 h. The mixture was filtered and washed with EA (5 mL×3). The filtrate was concentrated and the residue was purified by prep-TLC (rinsed with EA/PE=1/1) to give crude the title compound (50 mg, 25.97%) as a light yellow solid. m/z (ESI+ve ion)=802.65 [M+H]⁺.

Step C. 4-[2-cyclopropyl-5-methoxy-6-({6-[(1R,2S)-5'-methoxy-2'-oxo-1'H-spiro[cyclopropane-1,3'-indol]-2-yl]-1H-indazol-3-yl}amino)pyrimidin-4-yl]-1lambda6-thiomorpholine-1,1-dione

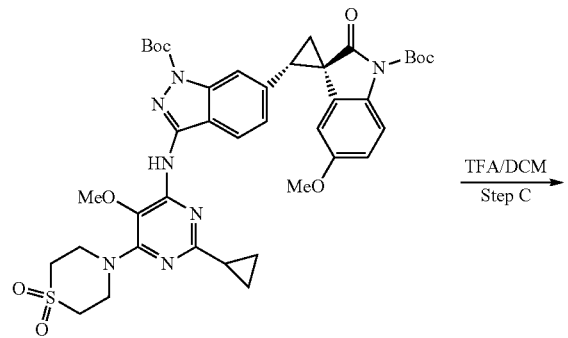

392

-continued

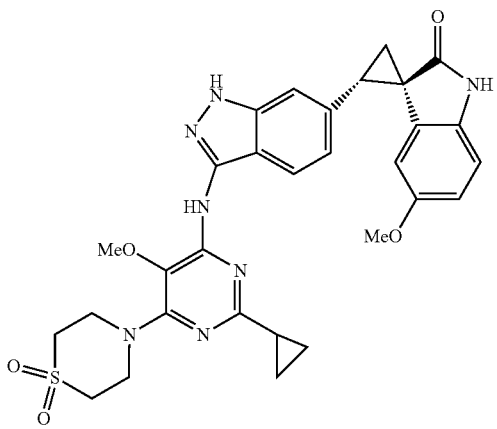

The mixture of tert-butyl (1R,2S)-2-[1-(tert-butoxycarbonyl)-3-{[2-cyclopropyl-6-(1,1-dioxo-1lambda6-thiomorpholin-4-yl)-5-methoxypyrimidin-4-yl]amino}indazol-6-yl]-5'-methoxy-2'-oxospiro[cyclopropane-1,3'-indole]-1'-carboxylate (50 mg, 0.062 mmol, 1.00 equiv) in TFA (0.10 mL) and DCM (1.00 mL) was stirred at 25° C. for 12 h. The solvent was removed under reduced pressure. The residue was purified by Prep-HPLC with the following conditions: Column: XBridge Prep OBD C18 Column, 30×150 mm, 5 μm. Mobile Phase A: Water (10 mmol/L NH₄HCO₃), Mobile Phase B: ACN; Flow rate: 60 mL/min; Gradient: 25% B to 45% B in 8 min; wavelength: 254/220 nm; RT1 (min): 6. The product-containing fractions was collected and concentrated in vacuo to give Example 69 (36 mg, 95.48%) as a white solid. m/z (ESI+ve ion)=602.40 [M+H]⁺. ¹H NMR (400 MHz, DMSO-d₆) δ 12.54 (s, 1H), 10.43 (s, 1H), 8.88 (s, 1H), 7.43 (d, J=8.4 Hz, 1H), 7.37 (s, 1H), 6.88 (d, J=8.0 Hz, 1H), 6.75 (d, J=8.4 Hz, 1H), 6.59-6.57 (m, 1H), 5.69 (d, J=2.4 Hz, 1H), 4.07-4.05 (m, 4H), 3.63 (s, 3H), 3.32 (s, 3H), 3.23-3.17 (m, 5H), 2.34-2.30 (m, 1H), 2.00-1.97 (m, 1H), 1.64-1.60 (m, 1H), 0.66-0.64 (m, 4H).

Example 70. 4-[5-chloro-2-cyclopropyl-6-({6-[(1R,2S)-5'-methoxy-2'-oxo-1',2'-dihydrospiro[cyclopropane-1,3'-indol]-2-yl]-1H-indazol-3-yl}amino)pyrimidin-4-yl]-1λ6-thiomorpholine-1,1-dione

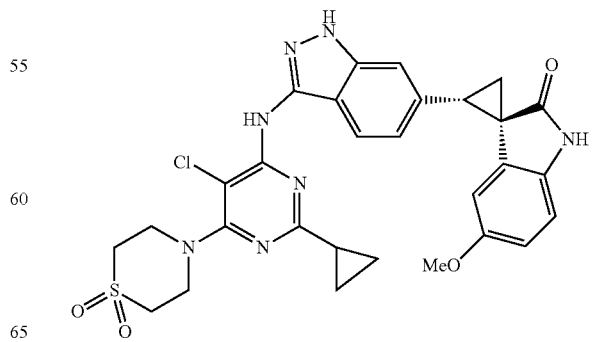

Step A. 4-(6-amino-5-chloro-2-cyclopropylpyrimidin-4-yl)-1lambda6-thiomorpholine-1,1-dione

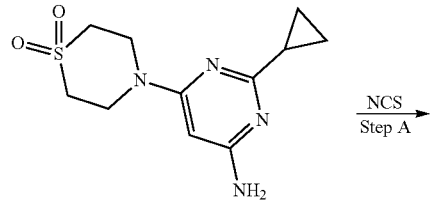

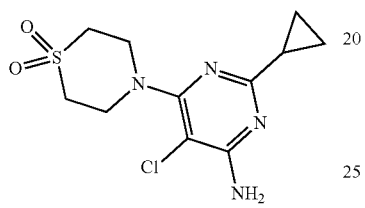

A mixture of 4-(6-amino-2-cyclopropylpyrimidin-4-yl)thiomorpholine 1,1-dioxide (400 mg, 1.491 mmol, 1.00 equiv) and NCS (238.86 mg, 1.789 mmol, 1.2 equiv) in THF (20 mL) was stirred for 5 h at 50° C. under nitrogen atmosphere. The mixture was cooled down to room temperature. The resulting mixture was concentrated under vacuum. The residue was purified by silica gel column chromatography, eluted with PE/EA (1/1) to afford the title compound (420 mg, 93.06%) as an off-white solid. m/z (ESI, +ve ion)=302.90 [M+H]$^+$. $^1$H NMR (400 MHz, DMSO-d$_6$) δ 6.81 (s, 2H), 3.87-3.80 (m, 4H), 3.24-3.17 (m, 4H), 1.82 (m, 1H), 0.87 (d, J=6.4 Hz, 4H).

Step B. tert-butyl (1R,2S)-2-[1-(tert-butoxycarbonyl)-3-{[5-chloro-2-cyclopropyl-6-(1,1-dioxo-1lambda6-thiomorpholin-4-yl)pyrimidin-4-yl]amino}indazol-6-yl]-5'-methoxy-2'-oxospiro[cyclopropane-1,3'-indole]-1'-carboxylate

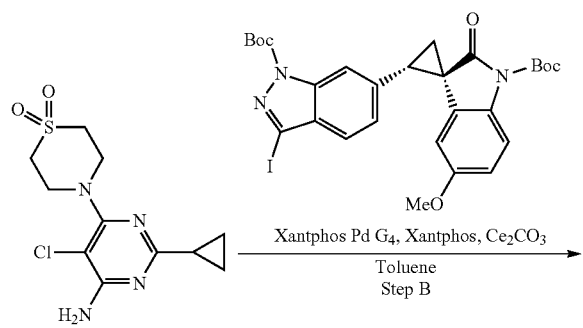

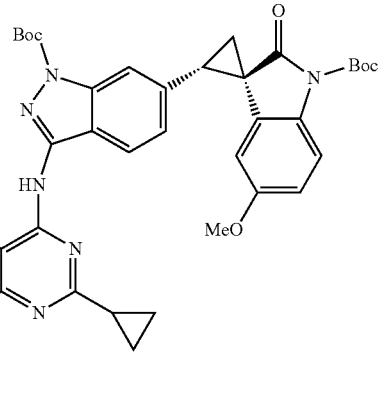

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-F-carboxylate (80 mg, 0.127 mmol, 1.00 equiv) and 4-(6-amino-5-chloro-2-cyclopropylpyrimidin-4-yl)-1lambda6-thiomorpholine-1,1-dione (46.03 mg, 0.152 mmol, 1.2 equiv) in toluene (4 mL) were added Xantphos Pd G$_4$ (12.19 mg, 0.013 mmol, 0.1 equiv) and XantPhos (7.33 mg, 0.013 mmol, 0.1 equiv) and Cs$_2$CO$_3$ (82.56 mg, 0.254 mmol, 2 equiv) at room temperature under nitrogen atmosphere. The resulting mixture was stirred for 9 h at 90° C. under nitrogen atmosphere. The mixture was cooled down to room temperature. The reaction was quenched by the addition of Water (10 mL) at room temperature. The resulting mixture was extracted with DCM (3×10 mL). The combined organic layers were washed with brine (15 mL), dried over anhydrous Na$_2$SO$_4$. After filtration, the filtrate was concentrated under reduced pressure. The residue was purified by silica gel column chromatography, eluted with PE/EA (1/1) to afford the title compound (46b) (50 mg, 48.95%) as a brown yellow solid. m/z=806.35 [M+H]$^+$.

Step C. 4-[5-chloro-2-cyclopropyl-6-({6-[(1R,2S)-5'-methoxy-2'-oxo-1'H-spiro[cyclopropane-1,3'-indol]-2-yl]-1H-indazol-3-yl}amino)pyrimidin-4-yl]-1lambda6-thiomorpholine-1,1-dione

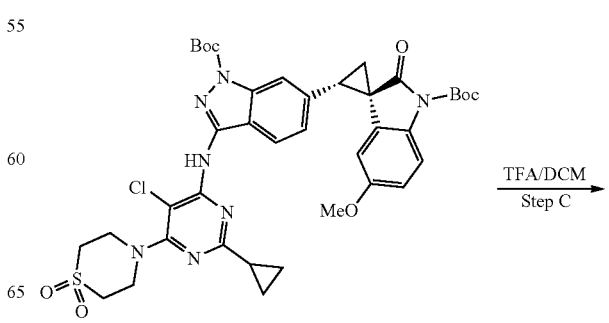

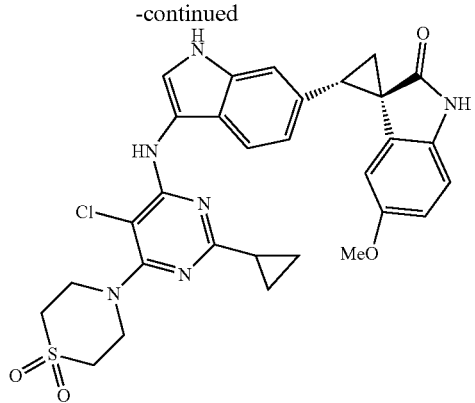

A mixture of tert-butyl (1R,2S)-2-[1-(tert-butoxycarbonyl)-3-{[5-chloro-2-cyclopropyl-6-(1,1-dioxo-1lambda6-thiomorpholin-4-yl)pyrimidin-4-yl]amino}indazol-6-yl]-5'-methoxy-2'-oxospiro[cyclopropane-1,3'-indole]-1'-carboxylate (50 mg, 0.062 mmol, 1.00 equiv) and TFA (2 mL, 26.926 mmol, 434.23 equiv) in DCM (4 mL) was stirred for 2 h at mom temperature under nitrogen atmosphere. The resulting mixture was concentrated under reduced pressure. The residue was purified by Prep-HPLC with the following conditions: Column: XBridge Prep OBD C18 Column, 30×150 mm, 5 μm; Mobile Phase A: Water (10 m mol/L NH$_4$HCO$_3$), Mobile Phase B: ACN; Flow rate: 60 mL/min; Gradient: 30% B to 40% B in 8 min, 40% B: wavelength: 254 nm; RT1(min): 7.63 to afford Example 70 (16.1 mg, 42.24%) as a white solid. m/z (ESI, +ve ion)=606.25 [M+H]$^+$. $^1$H NMR (400 MHz, DMSO-d$_6$) δ 12.67 (s, 1H), 10.42 (s, 1H), 9.13 (s, 1H), 7.40 (s, 1H), 7.35 (d, J=8.4 Hz, 1H), 6.90 (d, J=8.6 Hz, 1H), 6.75 (d, J=8.4 Hz, 1H), 6.58 (m, 1H), 5.68 (d, J=2.4 Hz, 1H), 3.91 (s, 4H), 3.27 (s, 4H), 3.20 (t, J=8.4 Hz, 1H), 2.50 (s, 3H), 2.35-2.28 (m, 1H), 1.99 (m, 1H), 1.63 (m, 1H), 0.66 (m, 4H).

Example 71. (1R,2S)-5'-methoxy-2-{3-[(3-methoxy-6-methylpyrazin-2-yl)amino]-1H-indazol-6-yl}spiro[cyclopropane-1,3'-indol]-2'(1'H)-one

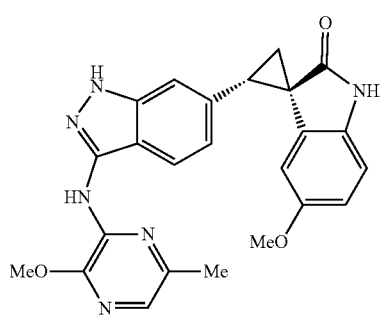

Step A. 3-methoxy-6-methylpyrazin-2-amine

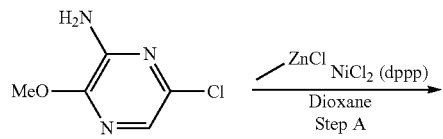

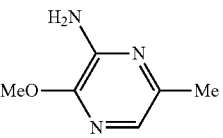

A solution of 6-chloro-3-methoxypyrazin-2-amine (200 mg, 1.253 mmol, 1.00 equiv) and Ni(dppp)Cl$_2$ (67.94 mg, 0.125 mmol, 0.1 equiv) in dioxane (3 mL) was stirred for 5 min at room temperature under nitrogen atmosphere. To the above mixture was added 1 M MeZnCl (5.01 mL, 5.012 mmol, 4 equiv) at room temperature. The resulting mixture was stirred for additional 3 min at room temperature. The resulting mixture was stirred for 4 h at 100° C. under nitrogen atmosphere then cooled down to room temperature. The reaction was quenched by the addition of Water (8 mL) at room temperature. The resulting mixture was extracted with EtOAc (3×8 mL). The combined organic layers were washed with brine (2×10 mL), dried over anhydrous Na$_2$SO$_4$. After filtration, the filtrate was concentrated under reduced pressure. The residue was purified by Prep-TLC (DCM/MeOH 20/1) to afford the title compound as a white solid. m/z (ESI+ve ion)=140.10 [M+H]$^+$. $^1$H NMR (400 MHz, DMSO-d$_6$) δ 7.11-7.10 (m, 1H), 6.15 (s, 2H), 3.83 (s, 3H), 2.14 (d, J=0.84 Hz, 3H).

Step B. tert-butyl(1R,2S)-2-[1-(tert-butoxycarbonyl)-3-[(3-methoxy-6-methylpyrazin-2-yl) amino]indazol-6-yl]-5'-methoxy-2'-oxospiro[cyclopropane-1,3'-indole]-1'-carboxylate

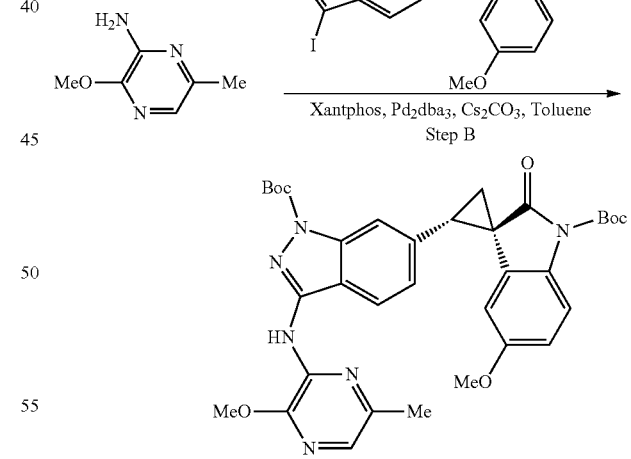

To a stirred solution of 3-methoxy-6-methylpyrazin-2-amine (21.16 mg, 0.152 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80 mg, 0.127 mmol, 1.00 equiv) in toluene (1.5 mL) were added XantPhos (7.33 mg, 0.013 mmol, 0.1 equiv) and Pd$_2$(dba). (23.20 mg, 0.025 mmol, 0.2 equiv) and Cs$_2$CO$_3$ (82.56 mg, 0.254 mmol, 2 equiv) at room temperature under nitrogen atmosphere. The resulting mixture was stirred for 4 h at room temperature under nitrogen atmosphere then quenched by the addition of Water (5 mL) at room temperature. The resulting mixture was extracted with EtOAc (3×5 mL). The combined organic layers were washed with brine (2×10 mL), dried over anhydrous $Na_2SO_4$. After filtration, the filtrate was concentrated under reduced pressure. The residue was purified by silica gel column chromatography, eluted with PE/EA (2/1) to afford the title compound (70 mg, 85.97%) as a yellow oil. m/z (ESI+ve ion)=643.50 $[M+H]^+$. $^1$H NMR (400 MHz, Chloroform-d) 8.16 (s, 1H), 7.93 (d, J=8.4 Hz, 1H), 7.81 (d, J=8.9 Hz, 1H), 7.66 (s, 1H), 7.46 (s, 1H), 7.04 (d, J=8.3 Hz, 1H), 6.71-6.69 (m, 1H), 4.05 (s, 3H), 3.56-3.51 (m, 1H), 3.37 (s, 3H), 2.39-2.36 (m, 1H), 2.30 (s, 3H), 2.15-2.12 (m, 1H), 1.29 (s, 18H).

Step C. (1R,2S)-5'-methoxy-2-{3-[(3-methoxy-6-methylpyrazin-2-yl) amino]-1H-indazol-6-yl}-1'H-spiro[cyclopropane-1,3'-indol]-2'-one

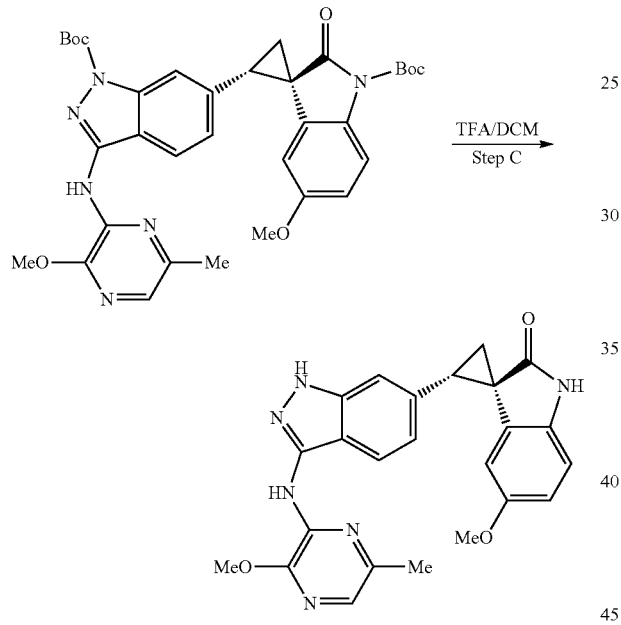

To a stirred mixture of tert-butyl(1R,2S)-2-[1-(tert-butoxycarbonyl)-3-[(3-methoxy-6-methylpyrazin-2-yl)amino]indazol-6-yl]-5'-methoxy-2'-oxospiro[cyclopropane-1,3'-indole]-1'-carboxylate (65 mg, 0.101 mmol, 1.00 equiv) was added TFA (1 mL, 13.463 mmol, 133.12 equiv) and DCM (2 mL, 31.460 mmol, 311.07 equiv) dropwise at room temperature under nitrogen atmosphere. The resulting mixture was stirred for 4 h at room temperature under nitrogen atmosphere. The residue was purified by Prep-HPLC with the following conditions (Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 25% B to 50% B in 8 min, 50% B; wavelength: 254 nm; RT1(min): 6.5 to afford Example 71 (13.5 mg, 30.17%) as a white solid. m/z (ESI+ve ion)=443.25 $[M+H]^+$. $^1$H NMR (400 MHz, DMSO-$d_6$) δ 12.52 (s, 1H), 10.41 (s, 1H), 8.71 (s, 1H), 7.44 (d, J=8.4 Hz, 1H), 7.37 (s, 1H), 7.31 (s, 1H), 6.87 (d, J=9.2 Hz, 1H), 6.74 (d, J=8.4 Hz, 1H), 6.59-6.57 (m, 1H), 5.71 (d, J=2.4 Hz, 1H), 3.94 (s, 3H), 3.32 (s, 3H), 3.21-3.16 (m, 1H), 2.34-2.28 (m, 1H), 2.07 (s, 3H), 2.00-1.97 (m, 1H).

Example 72. (1R,2S)-2-(3-{[5-chloro-6-(3-hydroxyazetidin-1-yl)-2-methylpyrimidin-4-yl]amino}-1H-indazol-6-yl)-5'-methoxyspiro[cyclopropane-1,3'-indol]-2'(1'H)-one

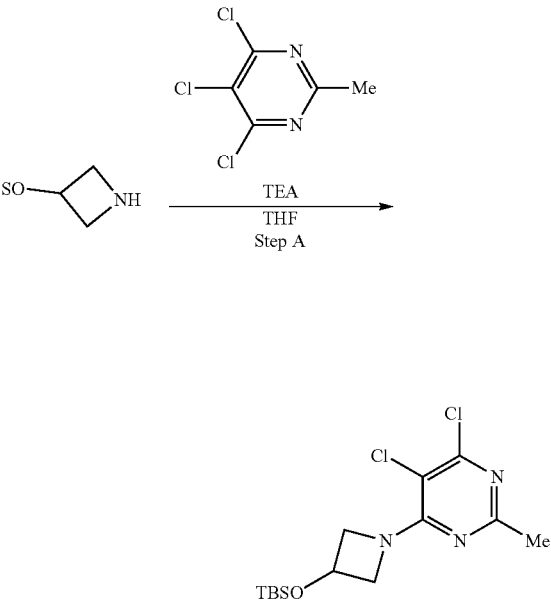

Step A. 4-{3-[(tert-butyldimethylsilyl)oxy]azetidin-1-yl}-5,6-dichloro-2-methylpyrimidine

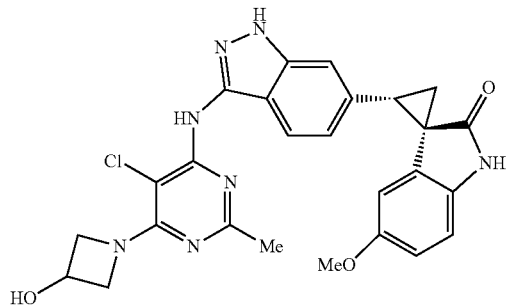 [SMILES: COc1ccc2c(c1)[C@]1(C[C@H]1c1ccc3c(Nc4nc(C)nc(N5CC(O)C5)c4Cl)n[nH]c3c1)C(=O)N2]

To a stirred solution of 3-((tert-butyldimethylsilyl)oxy) azetidine (200.0 mg, 1.0 equiv) and 4,5,6-trichloro-2-methylpyrimidine (210.7 mg, 1.0 equiv) in THF (5.0 mL) were added TEA (324.0 mg, 3.0 equiv) dropwise at room temperature under air atmosphere. The resulting mixture was stirred for 2 h at room temperature. The resulting mixture was concentrated under vacuum. The residue was purified by silica gel column chromatography, eluted with 0-50% EA in PE to afford the title compound (80.0 mg, 21.5%) as a white solid. m/z (ESI, +ve ion)=348.15 $[M+H]^+$.

399

Step B. tert-butyl (1R,2S)-2-[1-(tert-butoxycarbonyl)-3-[(6-{3-[(tert-butyldimeth-ylsilyl)oxy]azetidin-1-yl}-5-chloro-2-methylpyrimidin-4-yl)amino]indazol-6-yl]-5'-methoxy-2'-oxospiro[cyclopropane-1,3'-indole]-1'-carboxylate

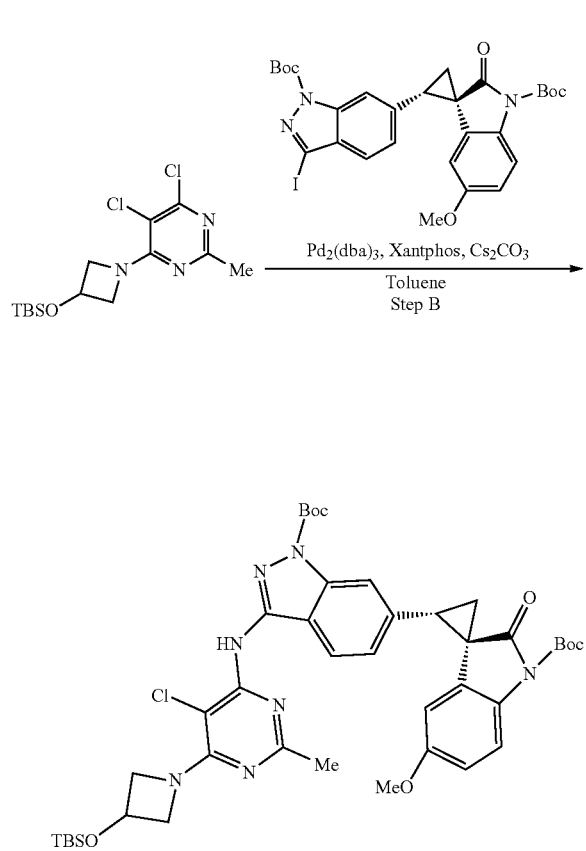

To a stirred solution of 4-{3-[(tert-butyldimethylsilyl)oxy]azetidin-1-yl}-5,6-dichloro-2-methylpyrimidine (80.4 mg, 1.2 equiv) and tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (100.0 mg, 1.0 equiv) in toluene (2.5 mL) were added Cs₂CO₃ (126.0 mg, 2.0 equiv) and XantPhos (40.0 mg, 0.2 equiv) and Pd₂(dba)₃ (70.0 mg, 0.2 equiv) at room temperature under nitrogen atmosphere. The resulting mixture was stirred for 2 h at 90° C. under nitrogen atmosphere. The resulting mixture was filtered, the filter cake was washed with EtOAc (3×7 mL). The filtrate was concentrated under reduced pressure. The residue was purified by silica gel column chromatography, eluted with 0-50% of EtOAc in PE to afford the title compound (100.0 mg, 62.5%) as a yellow solid. m/z (ESI, +ve ion)=832.40 [M+H]⁺. ¹H NMR (400 MHz, Chloroform-d) δ 8.12 (s, 1H), 7.82 (s, 1H), 7.80 (s, 1H), 7.04 (d, J=8.0 Hz, 1H), 6.70 (d, J=4.0 Hz, 1H), 6.68 (d, J=4.0 Hz, 1H), 5.59 (d, J=4.0 Hz, 1H), 4.71-4.68 (m, 1H), 4.61 (s, 2H), 4.20 (s, 2H), 3.55-3.50 (m, 1H), 3.38 (s, 3H), 2.39-2.36 (m, 1H), 2.31 (s, 3H), 2.14-2.11 (m, 1H), 1.70 (d, J=4.0 Hz, 18H), 0.93 (s, 9H), 0.11 (s, 6H).

400

Step D. (1R,2S)-2-(3-{[5-chloro-6-(3-hydroxyazetidin-1-yl)-2-methylp-yrimidin-4-yl]amino}-1H-indazol-6-yl)-5'-methoxy-1'H-spiro[cyclopropane-1,3'-indol]-2'-one

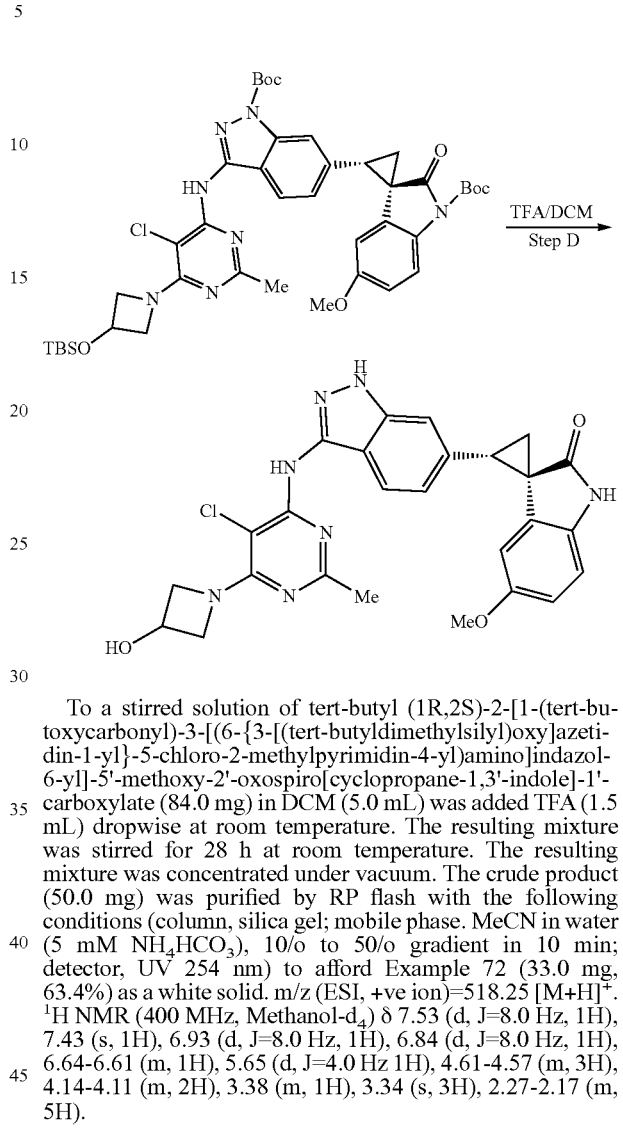

To a stirred solution of tert-butyl (1R,2S)-2-[1-(tert-butoxycarbonyl)-3-[(6-{3-[(tert-butyldimethylsilyl)oxy]azetidin-1-yl}-5-chloro-2-methylpyrimidin-4-yl)amino]indazol-6-yl]-5'-methoxy-2'-oxospiro[cyclopropane-1,3'-indole]-1'-carboxylate (84.0 mg) in DCM (5.0 mL) was added TFA (1.5 mL) dropwise at room temperature. The resulting mixture was stirred for 28 h at room temperature. The resulting mixture was concentrated under vacuum. The crude product (50.0 mg) was purified by RP flash with the following conditions (column, silica gel; mobile phase. MeCN in water (5 mM NH₄HCO₃), 10/o to 50/o gradient in 10 min; detector, UV 254 nm) to afford Example 72 (33.0 mg, 63.4%) as a white solid. m/z (ESI, +ve ion)=518.25 [M+H]⁺. ¹H NMR (400 MHz, Methanol-d₄) δ 7.53 (d, J=8.0 Hz, 1H), 7.43 (s, 1H), 6.93 (d, J=8.0 Hz, 1H), 6.84 (d, J=8.0 Hz, 1H), 6.64-6.61 (m, 1H), 5.65 (d, J=4.0 Hz 1H), 4.61-4.57 (m, 3H), 4.14-4.11 (m, 2H), 3.38 (m, 1H), 3.34 (s, 3H), 2.27-2.17 (m, 5H).

Example 73. (1R,2S)-2-(3-{[6-(3-hydroxyazetidin-1-yl)-5-methoxy-2-methylpyrimidin-4-yl]amino}-1H-indazol-6-yl)-5'-methoxyspiro[cyclopropane-1,3'-indol]-2'(1'H)-one

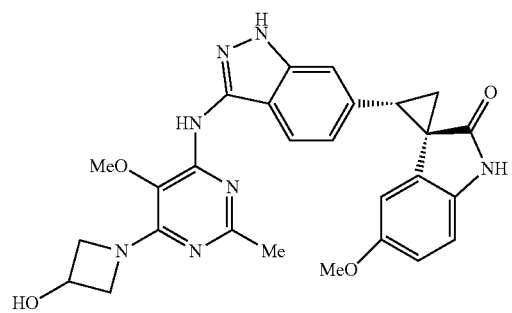 [SMILES: COc1ccc2c(c1)[C@]1(C[C@H]1c1ccc3c(Nc4nc(C)nc(N5CC(O)C5)c4OC)n[nH]c3c1)C(=O)N2]

Step A. 4-{3-[(tert-butyldimethylsilyl)oxy]azetidin-1-yl}-6-chloro-5-methoxy-2-methylpyrimidine

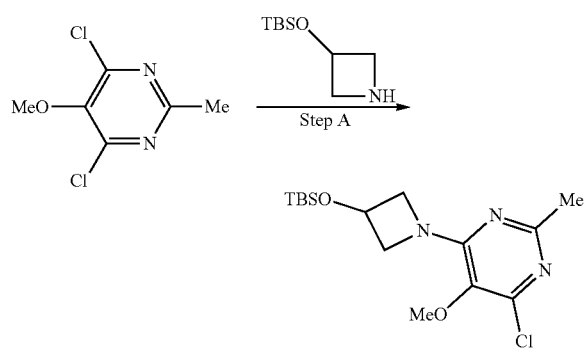

To a stirred mixture of 4,6-dichloro-5-methoxy-2-methylpyrimidine (300 mg, 1.554 mmol, 1.00 equiv) and 3-((tert-butyldimethylsilyl)oxy)azetidine (436.78 mg, 2.331 mmol, 1.5 equiv) in THE (7.5 mL) was added TEA (471.80 mg, 4.662 mmol, 3 equiv) at room temperature under nitrogen atmosphere. The resulting mixture was stirred for 16 h at 60° C. under nitrogen atmosphere. The resulting mixture was concentrated under vacuum. The residue was purified by silica gel column chromatography, eluted with PE/EA (5/1) to afford the title compound (510 mg, 95.41%) as a white solid. m/z (ESI, +ve ion)=344.05 [M+H]$^+$.

Step B. tert-butyl(1R,2S)-2-[1-(tert-butoxycarbonyl)-3-[(6-{3-[(tert-butyldimethylsilyl) oxy] azetidin-1-yl}-5-methoxy-2-methylpyrimidin-4-yl)amino]indazol-6-yl]-5'-methoxy-2'-oxospiro[cyclopropane-1,3'-indole]-1'-carboxylate

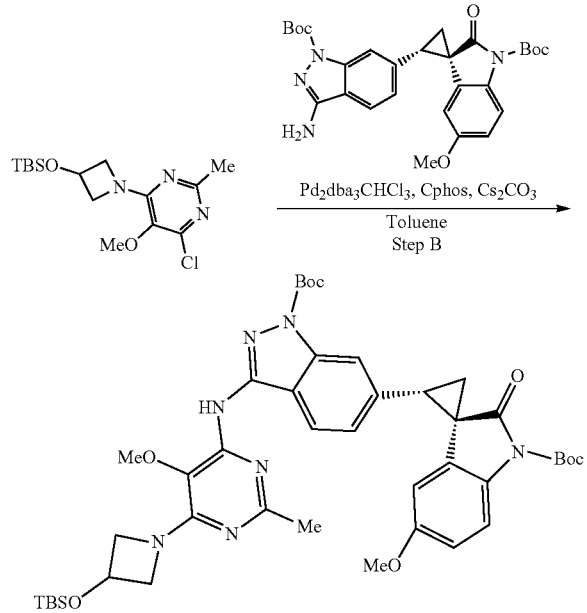

To a stirred mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (80 mg, 0.154 mmol, 1.00 equiv) and 4-{3-[(tert-butyldimethylsilyl)oxy]azetidin-1-yl}-6-chloro-5-methoxy-2-methylpyrimidine (63.42 mg, 0.185 mmol, 1.2 equiv) in toluene (4 mL) were added CPhos (6.71 mg, 0.015 mmol, 0.1 equiv) and Pd$_2$(dba)$_3$·CHCl$_3$ (15.91 mg, 0.015 mmol, 0.1 equiv) and Cs$_2$CO$_3$ (100.14 mg, 0.308 mmol, 2 equiv) at room temperature under nitrogen atmosphere. The resulting mixture was stirred for 2 h at 90° C. under nitrogen atmosphere. The mixture was cooled down to room temperature. The reaction was quenched by the addition of Water (10 mL) at room temperature. The resulting mixture was extracted with DCM (3×10 mL). The combined organic layers were washed with brine (15 mL), dried over anhydrous Na$_2$SO$_4$. After filtration, the filtrate was concentrated under reduced pressure. The residue was purified by silica gel column chromatography, eluted with PE/EA (5/1) to afford the title compound (85 mg, 59.45%) as a yellow solid. m/z (ESI, +ve ion)=828.70 [M+H]$^+$.

Step C. (1R,2S)-2-(3-{[6-(3-hydroxyazetidin-1-yl)-5-methoxy-2-methylpyrimidin-4-yl] amino}-1H-indazol-6-yl 5'-methoxy-1'H-spiro[cyclopropane-1,3'-indol]-2'-one

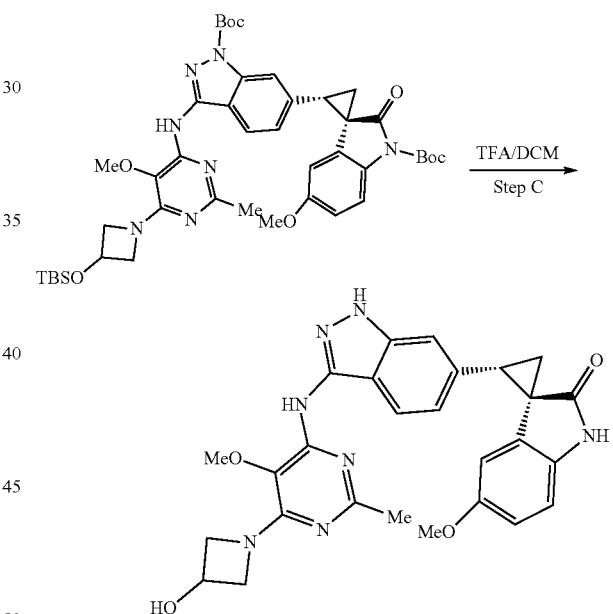

A mixture of tert-butyl(1R,2S)-2-[1-tert-butoxycarbonyl)-3-[(6-{3-[(tert-butyldimethylsilyl) oxy]azetidin-1-yl}-5-methoxy-2-methylpyrimidin-4-yl)amino]indazol-6-yl]-5'-methoxy-2'-oxospiro[cyclopropane-1,3'-indole]-1'-carboxylate (85 mg, 0.103 mmol, 1.00 equiv) and TFA (2 mL, 26.926 mmol, 262.31 equiv) in DCM (4 mL) was stirred for 16 h at room temperature under nitrogen atmosphere. The resulting mixture was concentrated under reduced pressure. The residue was purified by Prep-HPLC with the following conditions: Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 20% B to 30% B in 8 min, 30% B; wavelength: 254 nm; RT1(min): 7.8 to afford Example 73 (34.2 mg, 62.67%) as a white solid. m/z (ESI, +ve ion)=514.45 [M+H]$^+$. $^1$H NMR (400 MHz, DMSO-d$_6$)

δ 12.48 (s, 1H), 10.40 (s, 1H), 8.63 (s, 1H), 7.46 (d, J=8.4 Hz, 1H), 7.36 (s, 1H), 6.91-6.84 (m, 1H), 6.75 (d, J=8.4 Hz, 1H), 6.58 (m, 1H), 5.71 (d, J=2.8 Hz, 1H), 5.60 (d, J=6.4 Hz, 1H), 4.53 (m, 1H), 4.31-4.23 (m, 2H), 4.09 (m, 1H), 3.82 (m, 2H), 3.58 (s, 3H), 3.18 (d, J=5.2 Hz, 3H), 2.31 (m, 1H), 2.04 (s, 3H), 1.98 (m, 1H).

Example 74. (1R,2S)-2-{3-[(1,3-dimethyl-1H-pyrazol-5-yl)amino]-1H-indazol-6-yl}-5'-methoxyspiro[cyclopropane-1,3'-indol]-2'(1'H)-one

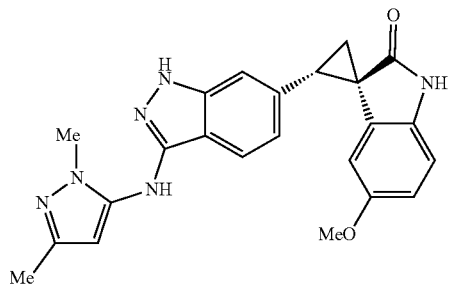 [SMILES: COc1ccc2c(c1)[C@]1(C[C@H]1c1ccc3c(Nc4cc(C)nn4C)n[nH]c3c1)C(=O)N2]

Step A. tert-butyl (1R,2S)-2-[1-(tert-butoxycarbonyl)-3-[(2,5-dimethylpyrazol-3-yl)amino]indazol-6-yl]-5'-methoxy-2'-oxospiro[cyclopropane-1,3'-indole]-1'-carboxylate

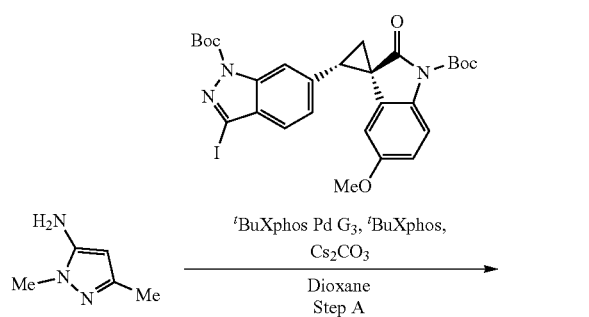

To a mixture of 2,5-dimethylpyrazol-3-amine (120 mg, 1.080 mmol, 1.00 equiv), tBuXPhos Pd G3 (171.53 mg, 0.216 mmol, 0.2 equiv), tert-butyl(1R,2S)-2-[1-(tert-butoxycarbonyl)-3-iodoindazol-6-yl]-5'-methoxy-2'-oxospiro[cyclopropane-1,3'-indole]-1'-carboxylate (68.18 mg, 0.1080 mmol, 1 equiv) and di-tert-butyl([2-[2,4,6-tris(propan-2-yl)phenyl]phenyl])phosphane (9.17 mg, 0.022 mmol, 0.2 equiv) in dioxane (6 mL) was added Cs$_2$CO$_3$ (703.54 mg, 2.160 mmol, 2 equiv). The resulting mixture was stirred for 1 h at 90° C. then concentrated under reduced pressure. The residue was purified with silica gel chromatography, eluted with 8% MeOH in DCM to afford the title compound (50 mg, 7.53%) as a yellow solid. m/z (ESI+ve ion)=615.40 [M+H]+

Step B. (1R,2S)-2-{3-[(2,5-dimethylpyrazol-3-yl)amino]-1H-indazol-6-yl}-5'-methoxy-1'H-spiro[cyclopropane-1,3'-indol]-2'-one; trifluoroacetic acid

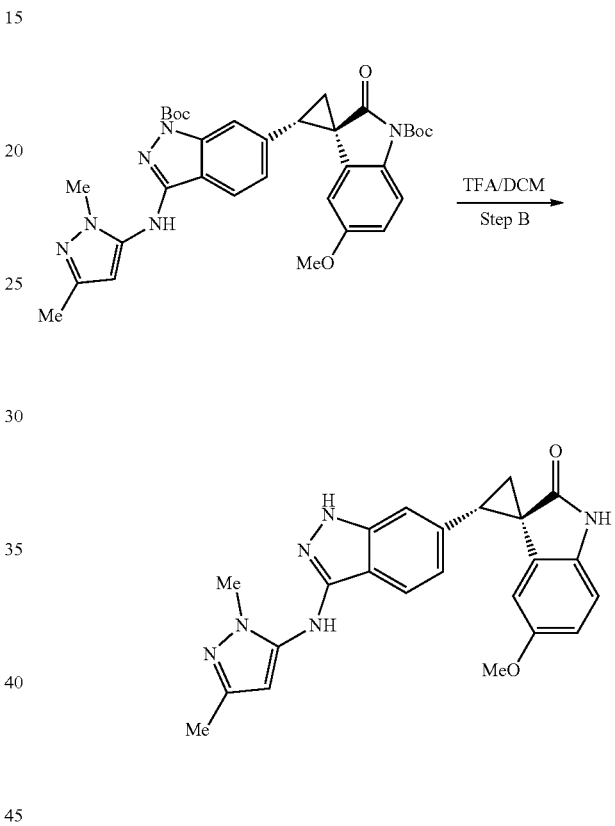

To a mixture of tert-butyl (1R,2S)-2-[1-(tert-butoxycarbonyl)-3-[(2,5-dimethylpyrazol-3-yl)amino]indazol-6-yl]-5'-methoxy-2'-oxospiro[cyclopropane-1,3'-indole]-1'-carboxylate (30 mg, 0.049 mmol, 1.00 equiv) in DCM (0.8 mL, 12.584 mmol, 257.85 equiv) was added TFA (0.2 mL, 2.693 mmol, 55.17 equiv). The resulting mixture was stirred for 2 h at room temperature and then concentrated under reduced pressure. The crude product (30 mg) was purified by Prep-HPLC with the following conditions (Column: XBridge Prep Phenyl OBD Column, 19×250 mm, 5 µm; Mobile Phase A: Water (0.05% TFA), Mobile Phase B: ACN; Flow rate: 25 mL/min; Gradient: 28% B to 33% B in 10 min, 33% B; wavelength: 254 nm; RT1(min): 6 to afford Example 74 (9 mg, 34.89%) as an off-white solid. m/z (ESI, +ve ion)=415.05 [M+H]+. $^1$H NMR (400 MHz, Methanol-d$_4$) δ 7.68 (d, J=8.4 Hz, 1H), 7.40-7.39 (m, 1H), 6.93 (dd, J=8.5, 1.4 Hz, 1H), 6.85 (d, J=8.5 Hz, 1H), 6.63 (dd, J=8.5, 2.5 Hz, 1H), 5.60 (d, J=2.5 Hz, 1H), 4.85 (s, 2H), 3.86 (s, 3H), 3.34-3.4 (m, 1H), 3.32 (s, 3H), 2.32 (s, 3H), 2.25-2.17 (m, 2H).

Example 75. (1R,2S)-5'-methoxy-2-{3-[(4-methoxy-1-methyl-1H-pyrazol-5-yl)amino]-1H-indazol-6-yl}spiro[cyclopropane-1,3'-indol]-2'(1'H)-one Step B. (1R,2S)-5'-methoxy-2-{3-[(4-methoxy-2-methylpyrazol-3-yl)amino]-1H-indazol-6-yl}-1'H-spiro[cyclopropane-1,3'-indol]-2'-one

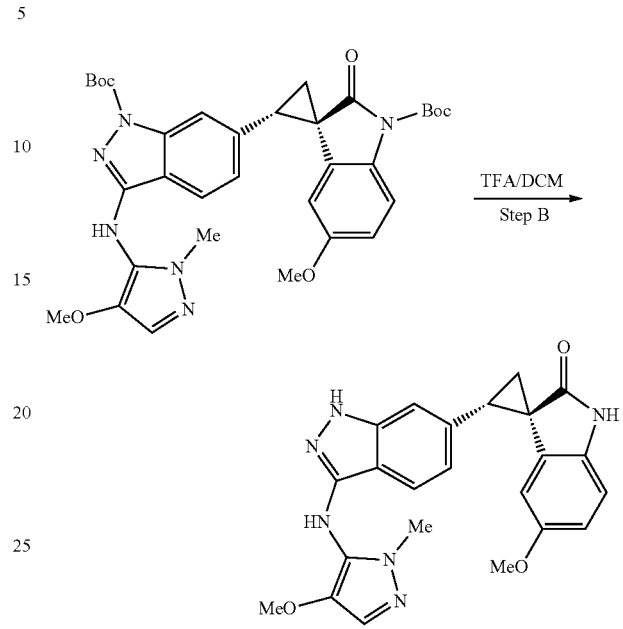

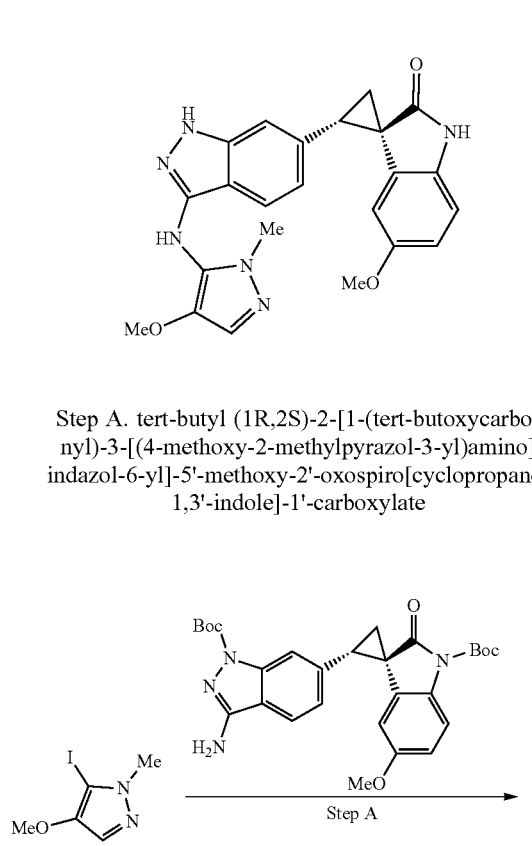

Step A. tert-butyl (1R,2S)-2-[1-(tert-butoxycarbonyl)-3-[(4-methoxy-2-methylpyrazol-3-yl)amino]indazol-6-yl]-5'-methoxy-2'-oxospiro[cyclopropane-1,3'-indole]-1'-carboxylate The mixture of tert-butyl (1R,2S)-2-[1-(tert-butoxycarbonyl)-3-[(4-methoxy-2-methylpyrazol-3-yl)amino]indazol-6-yl]-5'-methoxy-2'-oxospiro[cyclopropane-1,3'-indole]-1'-carboxylate (30 mg, 0.048 mmol, 1.00 equiv) in TFA (0.5 mL) and DCM (5 mL) was stirred at 25° C. for 8 h. The solvent was removed under reduced pressure. The residue was purified by Prep-HPLC with the following conditions: Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 20% B to 35% B in 8 min; wavelength: 254 nm; RT1 (min): 6.2. The product-containing fractions were concentrated in vacuo to give Example 75 (10.7 mg, 50.27%) as a white solid. m/z (ESI+ve ion)=431.15 [M+H]$^+$. $^1$H NMR (400 MHz, Methanol-d$_4$) δ 7.35-7.28 (m, 3H), 6.85-6.79 (m, 2H), 6.64-6.62 (m, 1H), 5.59 (d, J=2.4 Hz, 1H), 3.71 (s, 3H), 3.67 (s, 3H), 3.31 (s, 4H), 2.12-2.14 (m, 2H).

Example 76. (R,2S)-2-(3-{[5-chloro-2-cyclopropyl-(3-hydroxyazetidin-1-yl)pyrimidin-4-yl]amino}-1H-indazol-6-yl)-5'-methoxyspiro[cyclopropane-1,3'-indol]-2'(1'H)-one To the mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (90 mg, 0.173 mmol, 1.00 equiv) and 5-iodo-4-methoxy-1-methylpyrazole (45.27 mg, 0.190 mmol, 1.1 equiv) in toluene (2.0 mL) were added Cs$_2$CO$_3$ (112.66 mg, 0.346 mmol, 2 equiv) and Pd-PEPPSI-IPentCl 2-methylpyridine (o-picoline (29.08 mg, 0.035 mmol, 0.2 equiv) under nitrogen atmosphere. The mixture was stirred at 90° C. for 2 h. The mixture was filtered and washed with EA (3×5 mL). The filtrate was concentrated under reduced pressure. The residue was purified by prep-TLC (rinsed with EA) to give the title compound (30 mg, 24.76%) as a light yellow oil. m/z (ESI+ve ion)=631.60 [M+H]$^+$.

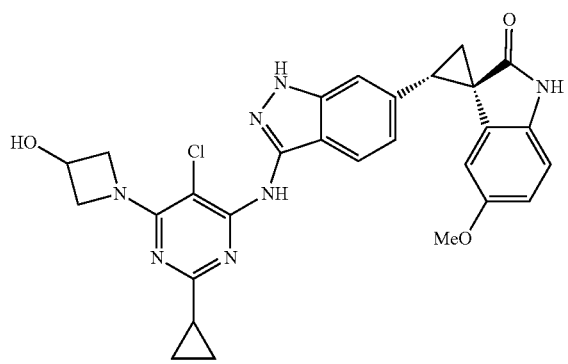 [SMILES: COc1ccc2c(c1)[C@]1(C[C@H]1c1ccc3c(Nc4nc(C5CC5)nc(N5CC(O)C5)c4Cl)n[nH]c3c1)C(=O)N2]

Step A. 6-{3-[(tert-butyldimethylsilyl)oxy]azetidin-1-yl}-2-cyclopropylpyrimidin-4-amine

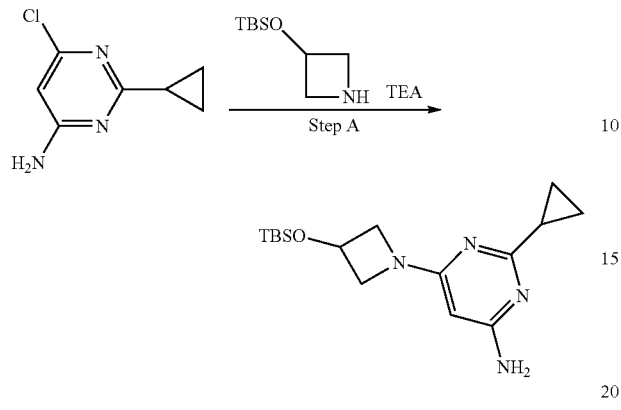

Into a 25 mL round-bottom flask were added 6-chloro-2-cyclopropylpyrimidin-4-amine (400 mg, 2.358 mmol, 1.00 equiv) and 3-[(tert-butyldimethylsilyl)oxy]azetidine (883.71 mg, 4.716 mmol, 2 equiv) at room temperature. The resulting mixture was stirred for 16 h at 100° C. under nitrogen atmosphere. The mixture was cooled down to room temperature. The resulting mixture was diluted with DCM (3 mL). The residue was purified by silica gel column chromatography, eluted with PE/EA (1/1) to afford the title compound (260 mg, 34.40%) as an off-white solid. m/z (ESI, +ve ion)=321.20 [M+H]$^+$. $^1$H NMR (400 MHz, Chloroform-d) δ 5.32 (s, 2H), 5.07 (s, 1H), 4.73 (m, 1H), 4.27-4.19 (m, 2H), 3.85 (m, 2H), 1.99 (m, 1H), 1.13 (p, J=4.0 Hz, 2H), 1.00 (m, 2H), 0.92 (s, 9H), 0.10 (s, 6H).

Step B. 6-{3-[(tert-butyldimethylsilyl)oxy]azetidin-1-yl}-5-chloro-2-cyclopropylpyrimidin-4-amine

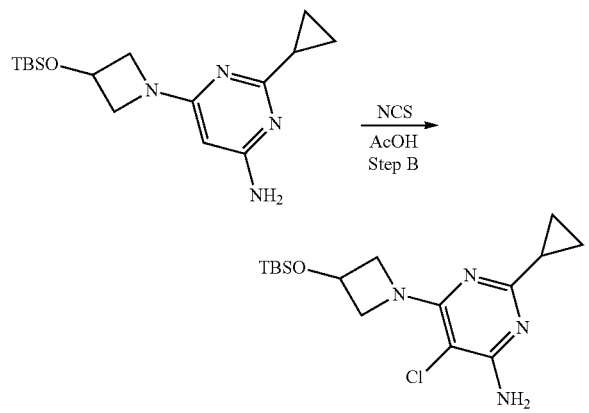

A mixture of 6-{3-[(tert-butyldimethylsilyl)oxy]azetidin-1-yl}-2-cyclopropylpyrimidin-4-amine (200 mg, 0.624 mmol, 1.00 equiv) and NCS (99.99 mg, 0.749 mmol, 1.2 equiv) in AcOH (10 mL) was stirred for 2 h at room temperature under nitrogen atmosphere. The resulting mixture was concentrated under vacuum. The residue was purified by silica gel column chromatography, eluted with PE/EA (3/1) to afford the title compound (65 mg, 29.35%) as a white solid. m/z=355.15 [M+H]$^+$. $^1$H NMR (400 MHz, DMSO-d$_6$) δ 6.45 (s, 2H), 4.64 (m, 1H), 4.38 (m, 2H), 3.84 (m, 2H), 1.73 (m, 1H), 0.87 (s, 9H), 0.81 (m, 4H), 0.06 (s, 6H).

Step C. tert-butyl (1R,2S)-2-[1-(tert-butoxycarbonyl)-3-[(6-{3-[(tert-butyldimethylsilyl)oxy]azetidin-1-yl}-5-chloro-2-cyclopropylpyrimidin-4-yl)amino]indazol-6-yl]-5'-methoxy-2'-oxospiro[cyclopropane-1,3'-indole]-1'-carboxylate

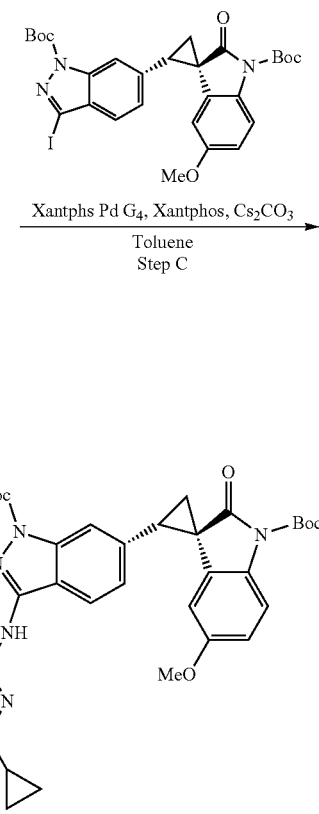

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80 mg, 0.127 mmol, 1.00 equiv) and 6-{3-[(tert-butyldimethylsilyl)oxy]azetidin-1-yl}-5-chloro-2-cyclopropylpyrimidin-4-amine (53.96 mg, 0.152 mmol, 1.2 equiv) in toluene (4 mL) were added Xantphos Pd G$_4$ (12.19 mg, 0.013 mmol, 0.1 equiv) and XantPhos (7.33 mg, 0.013 mmol, 0.1 equiv) and Cs$_2$CO$_3$ (82.56 mg, 0.254 mmol, 2 equiv) at room temperature under nitrogen atmosphere. The resulting mixture was stirred for 2 h at 90° C. under nitrogen atmosphere. The mixture was cooled down to room temperature. The reaction was quenched by the addition of Water (8 mL) at room temperature. The resulting mixture was extracted with DCM (3×8 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EA (4/1) to afford the title compound (83 mg, 76.31%) as a white solid. m/z (ESI, +ve ion)=858.35 [M+H]$^+$.

409

Step D. (1R,2S)-2-(3-{[5-chloro-2-cyclopropyl-6-(3-hydroxyazetidin-1-yl)pyrimidin-4-yl]amino}-1H-indazol-6-yl)-5'-methoxy-1'H-spiro[cyclopropane-1,3'-indol]-2'-one

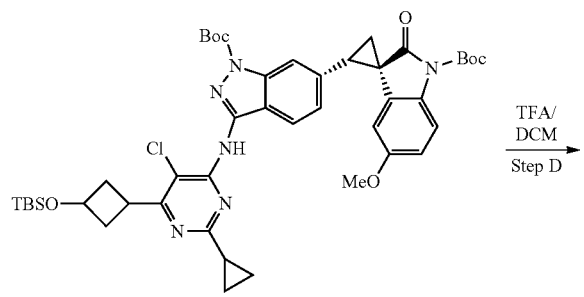

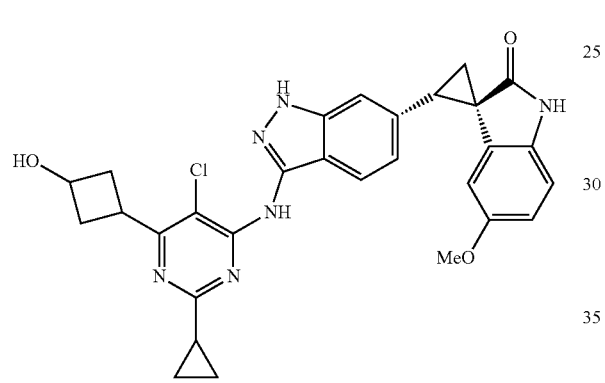

A mixture of tert-butyl (1R,2S)-2-[1-(tert-butoxycarbonyl)-3-[(6-{3-[(tert-butyldimethylsilyl)oxy]azetidin-1-yl}-5-chloro-2-cyclopropylpyrimidin-4-yl)amino]indazol-6-yl]-5'-methoxy-2'-oxospiro[cyclopropane-1,3'-indole]-1'-carboxylate (83 mg, 0.097 mmol, 1.00 equiv) and TFA (2 mL, 26.926 mmol, 278.51 equiv) in DCM (4 mL) was stirred for 16 h at room temperature under nitrogen atmosphere. The reaction was monitored by LCMS. The resulting mixture was concentrated under vacuum. The residue was purified by Prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 15% B to 45% B in 8 min, 45% B; wavelength: 254 nm; RT1(min): 7 to afford Example 76 (36.9 mg, 70.16%) as a white solid. m/z (ESI, +ve ion)=544.45 [M+H]$^+$. $^1$H NMR (400 MHz, DMSO-d$_6$) δ 12.57 (s, 1H), 10.40 (s, 1H), 8.72 (s, 1H), 7.33-7.37 (m, 2H), 6.89 (d, J=8.4 Hz, 1H), 6.75 (d, J=8.4 Hz, 1H), 6.54-6.61 (m, 1H), 5.62 (m, 2H), 4.42-4.47 (m, 3H), 4.41 (m, 2H), 3.94 (m, 2H), 3.19 (m, 2H), 2.30 (s, 1H), 1.95-2.02 (m, 1H), 2.50-2.73 (m, 1H), 0.59 (d, J=16.0 Hz, 4H).

410

Example 77. (1R,2S)-2-[3-({2-cyclopropyl-6-[(2R,6S)-2,6-dimethylmorpholin-4-yl]-5-methoxypyrimidin-4-yl}amino)-1H-indazol-6-yl]-5'-methoxyspiro[cyclopropane-1,3'-indol]-2'(1'H)-one

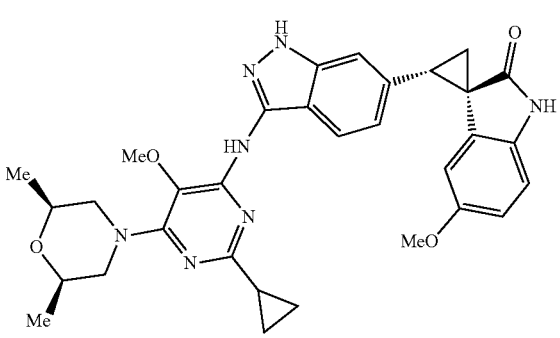 [SMILES: COc1ccc2c(c1)[C@]1(C[C@H]1c1ccc3c(Nc4nc(C5CC5)nc(N5C[C@@H](C)O[C@@H](C)C5)c4OC)n[nH]c3c1)C(=O)N2]

Step A. (2R,6S)-4-(6-chloro-2-cyclopropyl-5-methoxypyrimidin-4-yl)-2,6-dimethylmorpholine

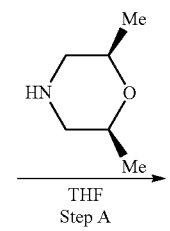

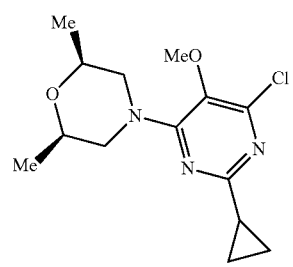

The mixture of 4,6-dichloro-2-cyclopropyl-5-methoxypyrimidine (200 mg, 0.913 mmol, 1.00 equiv), (2R,6S)-2,6-dimethylmorpholine (105.15 mg, 0.913 mmol, 1 equiv) and TEA (184.76 mg, 1.826 mmol, 2 equiv) in THF (2 mL) was stirred at 60° C. for 12 h. The solvent was removed under reduced pressure. The residue was purified by silica gel column eluted with 0-50% of EA in PE to give the title compound (250 mg, 91.04%) as a colorless oil. m/z (ESI, +ve ion)=298.25 [M+H]$^+$. $^1$H NMR (400 MHz, Chloroform-d S 4.47 (d, J=13.2 Hz, 2H), 3.71-3.64 (m, 5H), 2.69-2.63 (m, 2H), 2.07-2.01 (m, 1H), 1.25 (s, 3H), 1.23 (s, 3H), 1.24-0.94 (m, 4H).

411

Step B. 2-cyclopropyl-6-[(2R,6S)-2,6-dimethylmorpholin-4-yl]-5-methoxypyrimidin-4-amine

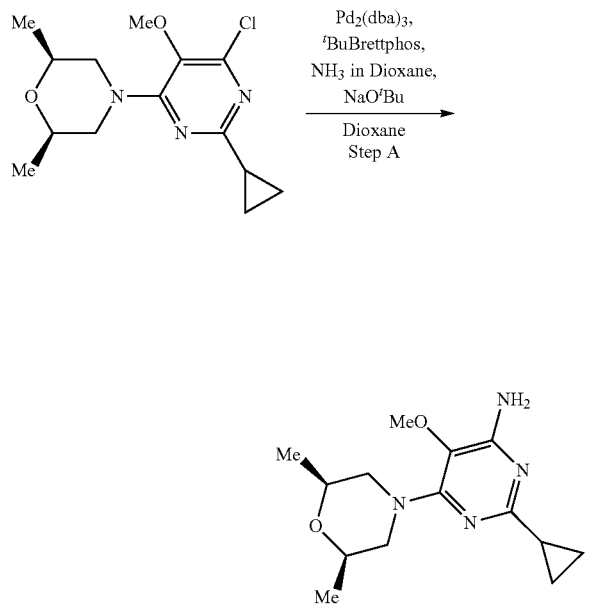

To the mixture of (2R,6S)-4-(6-chloro-2-cyclopropyl-5-methoxypyrimidin-4-yl)-2,6-dimethylmorpholine (200 mg, 0.672 mmol, 1.00 equiv) and $NH_3$ 0.5 M in dioxane (4.03 mL, 2.016 mmol, 3 equiv) in dioxane (2.0 mL) were added sodium 2-methylpropan-2-olate (90.37 mg, 0.941 mmol, 1.4 equiv), $Pd_2(dba)_3$ (12.30 mg, 0.013 mmol, 0.02 equiv) and t-BuBrettphos (32.55 mg, 0.067 mmol, 0.1 equiv) under nitrogen atmosphere. The mixture was stirred at 80° C. for 12 h. The mixture was filtered and washed with EA (5 mL×3). The filtrate was removed under reduced pressure. The residue was purified by silica gel column eluted with 0-100% of EA in PE to give the title compound (150 mg, 79.83%) as a light yellow solid. m/z (ESI, +ve ion)=279.10 [M+H]$^+$. $^1$H NMR (400 MHz, Chloroform-d) δ 4.89 (s, 2H), 4.31-4.27 (m, 2H), 3.72-3.66 (m, 2H), 3.62 (s, 3H), 2.62-2.56 (m, 2H), 1.93-1.87 (m, 1H), 1.24-1.22 (m, 6H), 1.01-0.87 (m, 4H).

Step C. tert-butyl (1R,2S)-2-[1-(tert-butoxycarbonyl)-3-({2-cyclopropyl-6-[(2R,6S)-2,6-dimethylmorpholin-4-yl]-5-methoxypyrimidin-4-yl}amino)indazol-6-yl]-5'-methoxy-2'-oxospiro[cyclopropane-1,3'-indole]-1'-carboxylate

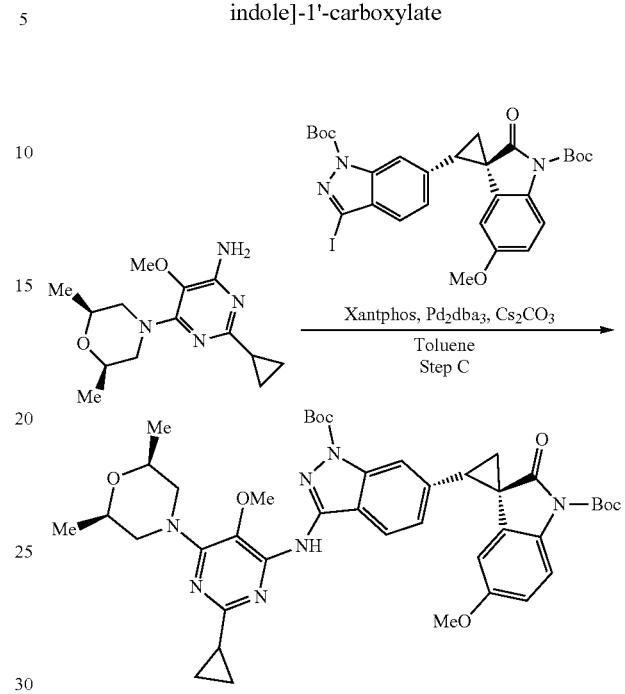

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 2-cyclopropyl-6-[(2R,6S)-2,6-dimethylmorpholin-4-yl]-5-methoxypyrimidin-4-amine (52.90 mg, 0.190 mmol, 1.2 equiv) in toluene (2.5 mL) were added $Cs_2CO_3$ (103.19 mg, 0.316 mmol, 2 equiv), XantPhos (18.33 mg, 0.032 mmol, 0.2 equiv) and $Pd_2(dba)_3$ (29.00 mg, 0.032 mmol, 0.2 equiv) under nitrogen atmosphere. The mixture was stirred at 90° C. for 2 h. The resulting mixture was filtered and washed with EA (5 mL×3). The filtrate was concentrated in vacuo. The residue was purified by silica gel column eluted with 0-50% EA in PE to give crude the title compound (70 mg, 50.88%) as a light yellow solid. m/z (ESI, +ve ion)=782.40 [M+H]$^+$.

Step D. (1R,2S)-2-[3-({2-cyclopropyl-6-[(2R,6S)-2,6-dimethylmorpholin-4-yl]-5-methoxypyrimidin-4-yl}amino)-1H-indazol-6-yl]-5'-methoxy-1'H-spiro[cyclopropane-1,3'-indol]-2'-one

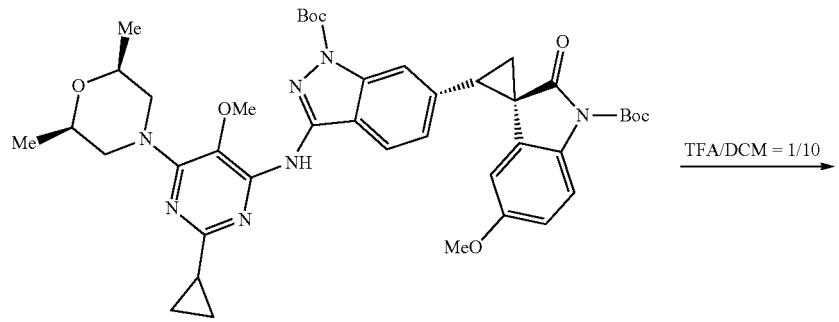

-continued

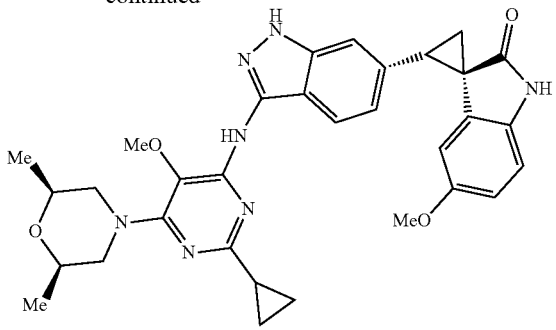

The mixture of tert-butyl (1R,2S)-2-[1-(tert-butoxycarbonyl)-3-({2-cyclopropyl-6-[(2R,6S)-2,6-dimethylmorpholin-4-yl]-5-methoxypyrimidin-4-yl}amino)indazol-6-yl]-5'-methoxy-2'-oxospiro[cyclopropane-1,3'-indole]-1'-carboxylate (55 mg, 0.070 mmol, 1.00 equiv) in TFA (0.5 mL) and DCM (3 mL) was stirred at 25° C. for 5 h. The solvent was removed under reduced pressure. The residue was purified by Prep-HPLC with the following conditions: Column: XBridge Prep OBD C18 Column, 30×150 mm, 5 µm; Mobile Phase A: Water (10 mmol/L $NH_4HCO_3$), Mobile Phase B: ACN; Flow rate: 60 mL/min; Gradient: 39% B to 55% B in 8 min; wavelength: 254 nm; RT1(min): 7.65. The product-containing fractions were concentrated in vacuo to give Example 77 (33.4 mg, 81.31%) as a white solid. m/z (ESI, +ve ion)=582.45 [M+H]$^+$. $^1$H NMR (400 MHz, DMSO-4) δ 12.50 (s, 1H), 10.42 (s, 1H), 8.72 (s, 1H), 7.43 (d, J=8.4 Hz, 1H), 7.36 (s, 1H), 6.88 (d, J=8.4 Hz, 1H), 6.75 (d, J=8.4 Hz, 1H), 6.59-6.57 (m, 1H), 5.70 (d, J=2.4 Hz, 1H), 4.23 (d, J=12.8 Hz, 2H), 3.68-3.63 (m, 2H), 3.61 (s, 3H), 3.33 (s, 3H), 3.19 (t, J=8.0 Hz, 1H), 2.68 (s, 1H), 2.53 (s, 1H), 2.33-2.29 (m, 1H), 2.00-1.97 (m, 1H), 1.65-1.58 (m, 1H), 1.13 (d, J=6.4 Hz, 6H), 0.63-0.60 (m, 4H).

Example 78. (1R,2S)-2-(3-((5-chloro-6-(1,1-dioxidothiomorpholino)-2-isopropylpyrimidin-4-yl)amino)-1H-indazol-6-yl)-5'-methoxyspiro[cyclopropane-1,3'-indolin]-2'-one

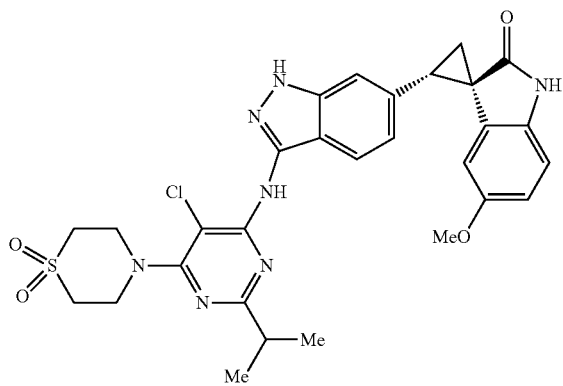 [SMILES: COc1ccc2c(c1)[C@]1(C[C@H]1c1ccc3c(Nc4nc(C(C)C)nc(N5CCS(=O)(=O)CC5)c4Cl)n[nH]c3c1)C(=O)N2]

Step A.
5-chloro-6-hydroxy-2-isopropyl-3H-pyrimidin-4-one

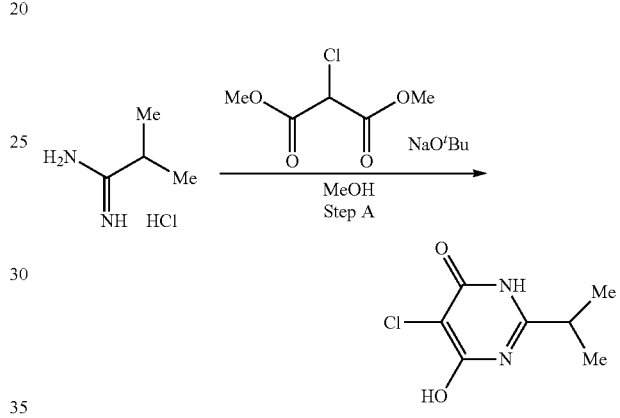

To a stirred mixture of 2-methylpropanimidamide hydrochloride (3 g, 24.470 mmol, 1.00 equiv) and 1,3-dimethyl 2-chloropropanedioate (4.08 g, 24.470 mmol, 1 equiv) in MeOH (60 mL) was added sodium 2-methylpropan-2-olate (4.70 g, 48.940 mmol, 2 equiv) in portions at 0° C. under nitrogen atmosphere. The resulting mixture was stirred for 2 h at 80° C. under nitrogen atmosphere. The mixture was allowed to cool down to room temperature. The reaction was quenched by the addition of 2N HCl (aq., 20 mL) at room temperature. The resulting mixture was extracted with EtOAc (3×20 mL). The combined organic layers were washed with brine (45 mL), dried over anhydrous $Na_2SO_4$. After filtration, the filtrate was concentrated under reduced pressure to afford the title compound (2 g, 43.33%) as an off-white solid. m/z (ESI, +ve ion)=189.00 [M+H]$^+$. $^1$H NMR (400 MHz, DMSO-d$_6$) δ 12.40 (s, 2H), 2.72-2.89 (m, 1H), 1.20 (d, J=6.8 Hz, 6H).

Step B. 4,5,6-trichloro-2-isopropylpyrimidine

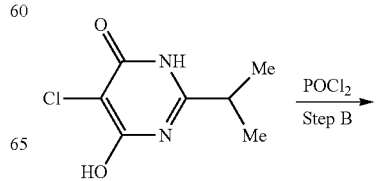

-continued

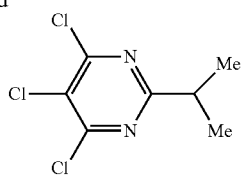

Into a 50 mL 3-necked round-bottom flask were added 5-chloro-6-hydroxy-2-isopropyl-3H-pyrimidin-4-one (200 mg, 1.060 mmol, 1.00 equiv) and POCl₃ (7 mL, 75.098 mmol, 70.82 equiv) at room temperature. The resulting mixture was stirred for 16 h at 100° C. under nitrogen atmosphere. The mixture was allowed to cool down to room temperature. The reaction was quenched by the addition of sat. NaHCO₃ (aq., 50 mL) at 0° C. The resulting mixture was extracted with EtOAc (3×15 mL). The combined organic layers were washed with brine (20 mL), dried over anhydrous Na₂SO₄. After filtration, the filtrate was concentrated under reduced pressure. The residue was purified by silica gel column chromatography, eluted with PE/EA (1/1) to afford the title compound. m/z (ESI, +ve ion)=227.05 [M+H]⁺. ¹H NMR (400 MHz, Chloroform-d) δ 3.18 (m, 1H), 1.35 (d, J=6.8 Hz, 6H).

Step C. 4-(5,6-dichloro-2-isopropylpyrimidin-4-yl)-1lambda6-thiomorpholine-1,1-dione

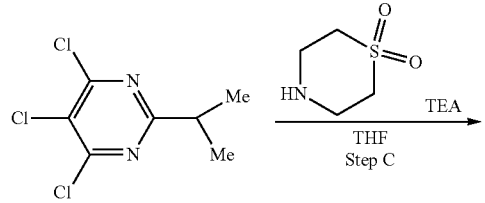

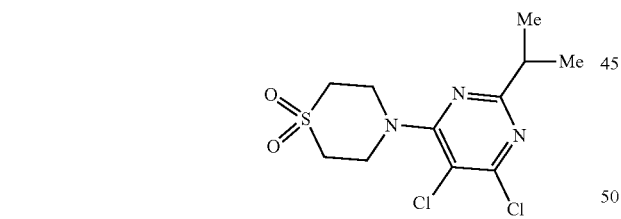

To a stirred mixture of 4,5,6-trichloro-2-isopropylpyrimidine (130 mg, 0.576 mmol, 1.00 equiv) and 1lambda6-thiomorpholine-1,1-dione (187.03 mg, 1.382 mmol, 2.4 equiv) in THF (3.25 mL, 40.115 mmol, 69.58 equiv) was added TEA (233.34 mg, 2.304 mmol, 4 equiv) dropwise at room temperature under nitrogen atmosphere. The resulting mixture was stirred for 16 h at room temperature under nitrogen atmosphere. The reaction was quenched by the addition of Water (10 mL) at room temperature. The resulting mixture was extracted with DCM (3×10 mL). The combined organic layers were washed with brine (15 mL), dried over anhydrous Na₂SO₄. After filtration, the filtrate was concentrated under reduced pressure. The residue was purified by silica gel column chromatography, eluted with PE/EA (1/1) to afford the title compound (150 mg, 80.25%) as a white solid. m/z (ESI, +ve ion)=323.95 [M+H]⁺.

Step D. tert-butyl (1R,2S)-2-[1-(tert-butoxycarbonyl)-3-{[5-chloro-6-(1,1-dioxo-1lambda6-thiomorpholin-4-yl)-2-isopropylpyrimidin-4-yl]amino}indazol-6-yl]-5'-methoxy-2'-oxospiro[cyclopropane-1,3'-indole]-1'-carboxylate

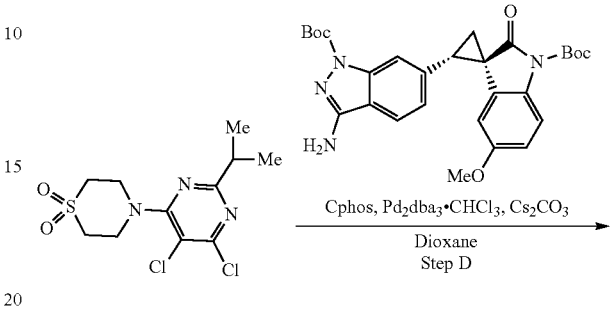

To a stirred mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (80 mg, 0.154 mmol, 1.00 equiv) and 4-(5,6-dichloro-2-isopropylpyrimidin-4-yl)-1lambda6-thiomorpholine-1,1-dione (59.79 mg, 0.185 mmol, 1.2 equiv) in toluene (4 mL) were added CPhos (6.71 mg, 0.015 mmol, 0.1 equiv) and Pd₂(dba)₃·CHCl₃ (15.91 mg, 0.015 mmol, 0.1 equiv) and Cs₂CO₃ (100.14 mg, 0.308 mmol, 2 equiv) at room temperature under nitrogen atmosphere. The resulting mixture was stirred for 2 h at 90° C. under nitrogen atmosphere. The mixture was allowed to cool down to room temperature. The reaction was quenched by the addition of Water (8 mL) at room temperature. The resulting mixture was extracted with DCM (3×5 mL). The combined organic layers were washed with brine (10 mL), dried over anhydrous Na₂SO₄. After filtration, the filtrate was concentrated under reduced pressure. The residue was purified by silica gel column chromatography, eluted with PE/EA (2/1) to afford the title compound (29 mg, 23.35%) as a brown solid. m/z (ESI, +ve ion)=808.20 [M+H]⁺.

Step E. 4-[5-chloro-2-isopropyl-6-({6-[(1R,2S)-5'-methoxy-2'-oxo-1'H-spiro[cyclopropane-1,3'-indol]-2-yl]-1H-indazol-3-yl}amino)pyrimidin-4-yl]-1lambda6-thiomorpholine-1,1-dione

Example 79. (1R,2S)-5'-methoxy-2-{3-[(4-methoxy-1-methyl-1H-pyrazol-3-yl)amino]-1H-indazol-6-yl}spiro[cyclopropane-1,3'-indol]-2'(1'H)-one

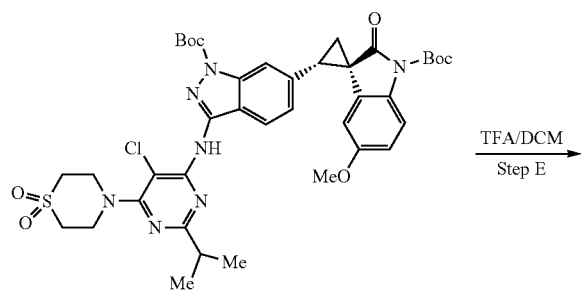

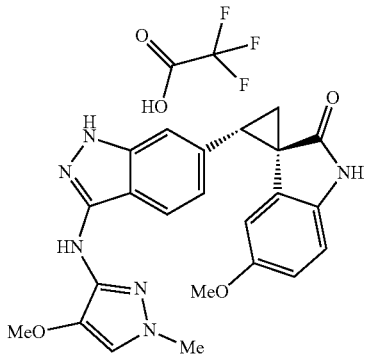

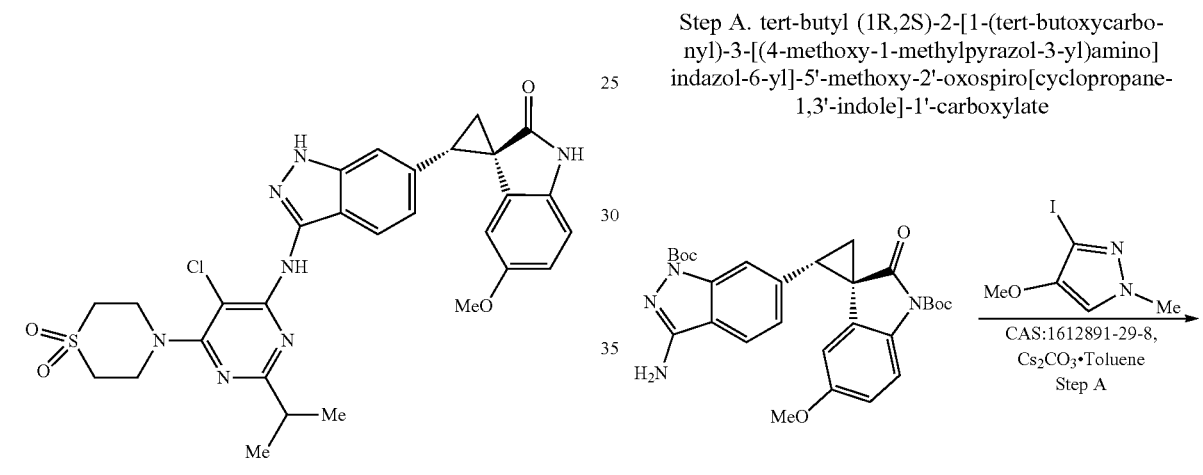

Step A. tert-butyl (1R,2S)-2-[1-(tert-butoxycarbonyl)-3-[(4-methoxy-1-methylpyrazol-3-yl)amino]indazol-6-yl]-5'-methoxy-2'-oxospiro[cyclopropane-1,3'-indole]-1'-carboxylate

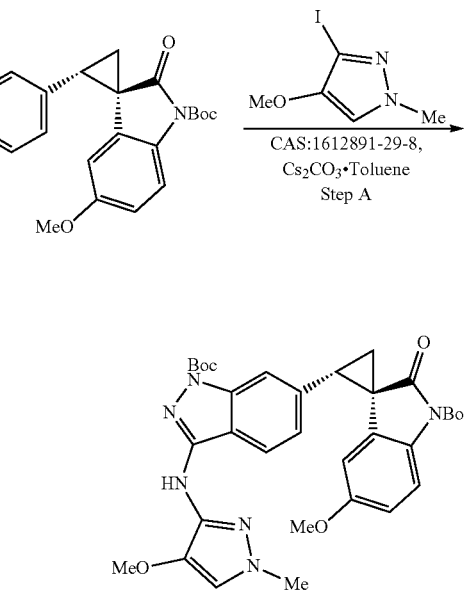

A mixture of tert-butyl (1R,2S)-2-[1-(tert-butoxycarbonyl)-3-{[5-chloro-6-(1,1-dioxo-1lambda6-thiomorpholin-4-yl)-2-isopropylpyrimidin-4-yl]amino}indazol-6-yl]-5'-methoxy-2'-oxospiro[cyclopropane-1,3'-indole]-1'-carboxylate (29 mg, 0.036 mmol, 1.00 equiv) and TFA (1.5 mL, 20.195 mmol, 562.91 equiv) in DCM (3 mL) was stirred for 2 h at room temperature under nitrogen atmosphere. The resulting mixture was concentrated under vacuum. The residue was purified by Prep-HPLC with the following conditions: Column: Xselect CSH OBD Column 30×150 mm 5 um, n: Mobile Phase A: Water (0.1% FA), Mobile Phase B: MeOH-HPLC; Flow rate: 60 mL/min; Gradient: 55% B to 70% B in 8 min, 70% B: wavelength: 220 nm; RT1(min): 6.47 to afford Example 78 (14 mg, 63.79%) as a white solid. m/z (ESI, +ve ion)=608.15 [M+H]$^+$. $^1$H NMR (400 MHz, Methanol-$d_4$) δ 7.50 (d, J=8.4 Hz, 1H), 7.44 (s, 1H), 6.81-6.92 (m, 2H), 6.62 (m, 1H), 5.62 (d, J=2.4 Hz, 1H), 4.09 (s, 4H), 3.29 (d, J=12.0 Hz, 8H), 2.72-2.67 (m, 1H), 2.25 (m, 1H), 2.18 (m, 1H), 1.06 (m, 6H).

To the mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (100 mg, 0.192 mmol, 1.00 equiv) and 3-iodo-4-methoxy-1-methylpyrazole (45.72 mg, 0.192 mmol, 1.00 equiv) in toluene (2.5 mL) were added Cs$_2$CO$_3$ (125.17 mg, 0.384 mmol, 2 equiv) and Pd-PEPPSI-IPentCl 2-methylpyridine (o-picoline (16.16 mg, 0.019 mmol, 0.1 equiv) under nitrogen atmosphere. The mixture was stirred at 90° C. for 2 h. The mixture was filtered and washed with EA (5 mL×3). The filtrate was concentrated under reduced pressure. The residue was purified by prep-TLC (rinsed with EA) to give the title compound (40 mg, 26.41%) as a light-yellow oil. m/z (ESI, +ve ion)=631.55 [M+H]+.

419

Step B. (1R,2S)-5'-methoxy-2-{3-[(4-methoxy-1-methylpyrazol-3-yl)amino]-1H-indazol-6-yl}-1'H-spiro[cyclopropane-1,3'-indol]-2'-one; trifluoroacetic acid

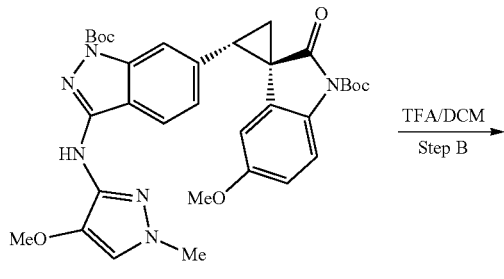

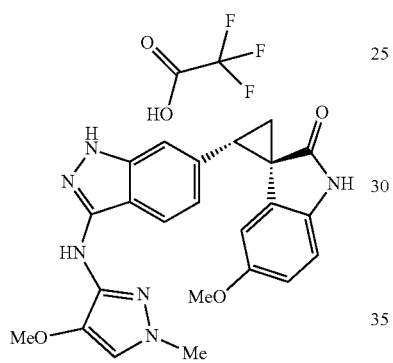

The mixture of tert-butyl (1R,2S)-2-[1-(tert-butoxycarbonyl)-3-[(4-methoxy-1-methylpyrazol-3-yl)amino]indazol-6-yl]-5'-methoxy-2'-oxospiro[cyclopropane-1,3'-indole]-1'-carboxylate (35 mg, 0.055 mmol, 1.00 equiv) in TFA (0.5 mL) and DCM (3 mL) was stirred at 25° C. for 5 h. The solvent was removed under reduced pressure. The residue was purified by Prep-HPLC with the following conditions: Column: Xselect CSH OBD Column 30×150 mm 5 µm; Mobile Phase A: ACN, Mobile Phase B: Water (0.05% TFA); Flow rate: 60 mL/min; Gradient: 8% B to 25% B in 10 min; wavelength: 254 nm; RT1(min): 9.5. The product-containing fractions were concentrated in vacuo to give Example 79 (9.2 mg, 30.33%) as a white solid. m/z (ESI, +ve ion)=431.15 [M+H]+. $^1$H NMR (400 MHz, Methanol-$d_4$) δ 7.94-7.92 (m, 1H), 7.42 (d, J=23.2 Hz, 2H), 7.05 (d, J=8.4 Hz, 1H), 6.85 (d, J=8.4 Hz, 1H), 6.67-6.64 (m, 1H), 5.65 (d, J=2.0 Hz, 1H), 3.83 (d, J=7.2 Hz, 6H), 3.37 (s, 3H), 3.32 (s, 1H), 2.26-2.18 (m, 2H). $^{19}$F NMR (376 MHz, MeOD) δ −77.05 (s, 3F).

420

Example 80. (1R,2S)-2-{3-[(6-cyclopropyl-3-methoxypyrazin-2-yl)amino]-1H-indazol-6-yl}-5'-methoxyspiro[cyclopropane-1,3'-indol]-2'(1'H)-one

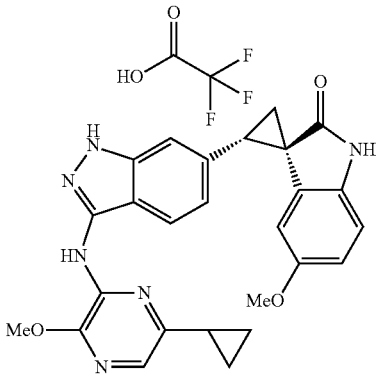

Step A. 6-cyclopropyl-3-methoxypyrazin-2-amine

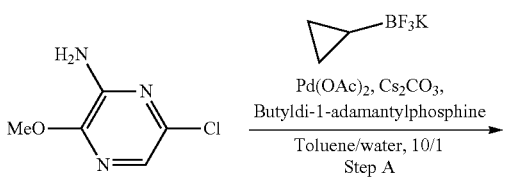

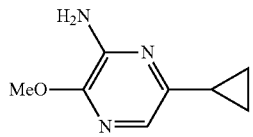

To a stirred solution of 6-chloro-3-methoxypyrazin-2-amine (200.0 mg, 1.253 mmol, 1.00 equiv) in toluene (4.0 mL) and water (0.4 mL) were added cyclopropyltrifluoro-lambda4-borane potassium (278.21 mg, 1.5 equiv) and bis(adamantan-1-yl) (butyl)phosphane (89.88 mg, 0.2 equiv) and Pd(OAc)$_2$ (28.14 mg, 0.1 equiv) and Cs$_2$CO$_3$ (1225.12 mg, 3.0 equiv) at room temperature under nitrogen atmosphere. The resulting mixture was stirred for 5 h at 100° C. under nitrogen atmosphere. The mixture was cooled down to room temperature. The reaction was quenched by the addition of sat. NH$_4$Cl (aq., 20 mL) at room temperature. The resulting mixture was extracted with EtOAc (3×20 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with 0-50% EA in PE to afford the title compound (150.0 mg, 72.45%) as a yellow solid. m/z (ESI, +ve ion)=166.05[M+H]+. $^1$H NMR (400 MHz, DMSO-$d_6$) δ 7.19 (s, 1H), 6.11 (s, 2H), 3.83 (s, 3H), 1.81-1.87 (m, 5.0 Hz, 1H), 0.82-0.68 (m, 4H).

421

Step B. tert-butyl (1R,2S)-2-[1-(tert-butoxycarbonyl)-3-[(6-cyclopropyl-3-methoxypyrazin-2-yl)amino]indazol-6-yl]-5'-methoxy-2'-oxospiro[cyclopropane-1,3'-indole]-1'-carboxylate

422

Step C. (1R,2S)-2-{3-[(6-cyclopropyl-3-methoxypyrazin-2-yl)amino]-1H-indazol-1-yl}-5'-methoxy-1'H-spiro[cyclopropane-1,3'-indol]-2'-one; trifluoroacetic acid

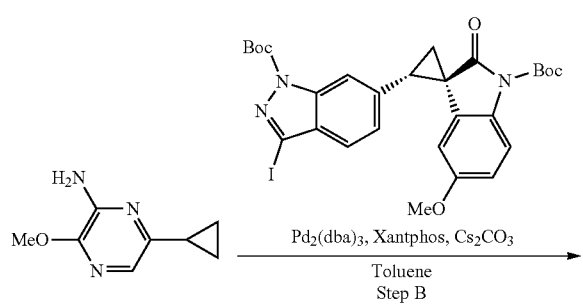

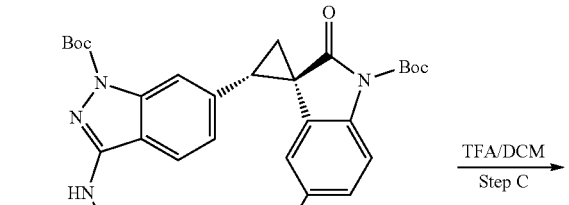

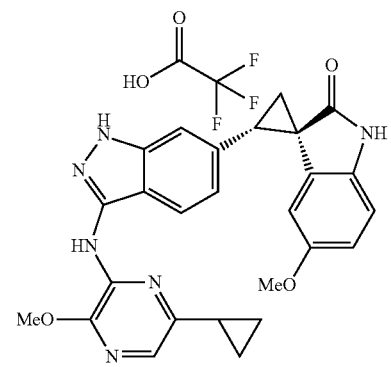

To a stirred solution of 6-cyclopropyl-3-methoxypyrazin-2-amine (26.0 mg, 0.157 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (99.39 mg, 1.0 equiv) in toluene (5.0 mL) were added Cs$_2$CO$_3$ (102.56 mg, 0.314 mmol, 2.0 equiv) and XantPhos (18.21 mg, 0.031 mmol, 0.2 equiv) and Pd$_2$(dba)$_3$ (28.82 mg, 0.2 equiv) at room temperature under nitrogen atmosphere. The resulting mixture was stirred for 2.0 h at 90° C. under nitrogen atmosphere. The mixture was cooled down to room temperature. The resulting mixture was filtered, the filter cake was washed with EA (4×10 mL). The filtrate was concentrated under reduced pressure. The residue was purified by silica gel column chromatography, eluted with 0-50% of EA in PE to afford the title compound (80.0 mg, 76.01% yield) as a yellow solid. m/z (ESI, +ve ion)=669.45 [M+H]$^+$. $^1$H NMR (400 MHz, Chloroform-d) 8.13 (s, 1H), 7.90 (s, 1H), 7.82 (d, J=8.0 Hz, 1H), 7.54 (s, 1H), 7.06 (d, J=8.0 Hz, 1H), 6.72-6.66 (m, 1H), 5.58 (d, J=4.0 Hz, 1H), 4.07 (s, 3H), 3.50-3.45 (m, 1H), 3.38 (s, 3H), 2.38-2.35 (m, 1H), 2.15-2.13 (m, 1H), 1.51 (s, 18H), 0.89-0.79 (m, 4H).

To a stirred solution of tert-butyl (1R,2S)-2-[I-(tert-butoxycarbonyl)-3-[(6-cyclopropyl-3-methoxypyrazin-2-yl)amino]indazol-6-yl]-5'-methoxy-2'-oxospiro[cyclopropane-1,3'-indole]-1'-carboxylate (80.0 mg) in DCM (5.0 mL) was added TFA (1.0 mL) dropwise at room temperature. The resulting mixture was stirred for 5.0 h at room temperature. The resulting mixture was concentrated under reduced pressure. The crude product (40 mg) was purified by Prep-HPLC with the following conditions: Column: XSelect CSH Prep C18 OBD Column, 19×250 mm, 5 μm; Mobile Phase A: Water (0.05% TFA), Mobile Phase B: ACN; Flow rate: 25 mL/min; Gradient: 43% B to 43% B in 10 min, 43% B; wavelength: 254 nm; RT1(min): 9 to afford Example 80 (27.8 mg, 48.9%) as a yellow solid. m/z (ESI, +ve ion)=469.40 [M+H]$^+$. $^1$H NMR (400 MHz, Methanol-d$_4$) δ 7.76 (d, J=8.0 Hz, 1H), 7.52 (s, 1H), 7.46 (s, 1H), 6.98 (d, J=8.6 Hz, 1H), 6.85 (d, J=8.4 Hz, 1H), 6.63 (d, J=8.0 Hz, 1H), 5.63 (d, J=4.0 Hz, 1H), 4.12 (s, 3H), 3.32 (s, 4H), 2.26 (d, J=8.0 Hz, 1H), 2.20 (d, J=8.0 Hz, 1H), 1.99 (s, 1H), 0.91-0.82 (m, 2H), 0.80-0.77 (m, 2H). $^{19}$F NMR (376 MHz, Methanol-d$_4$) δ −77.42

423

Example 81. (1R,2S)-2-(3-{[2-cyclopropyl-6-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one

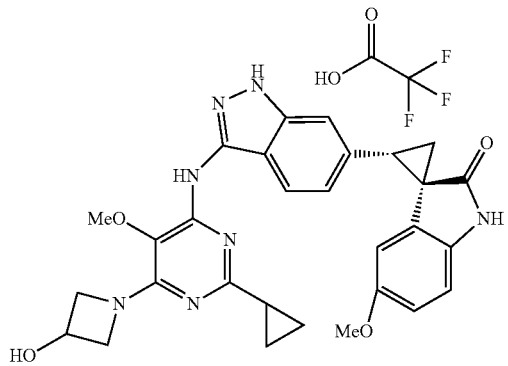

Step A. 4-{3-[(tert-butyldimethylsilyl)oxy]azetidin-1-yl}-6-chloro-2-cyclopropyl-5-methoxypyrimidine

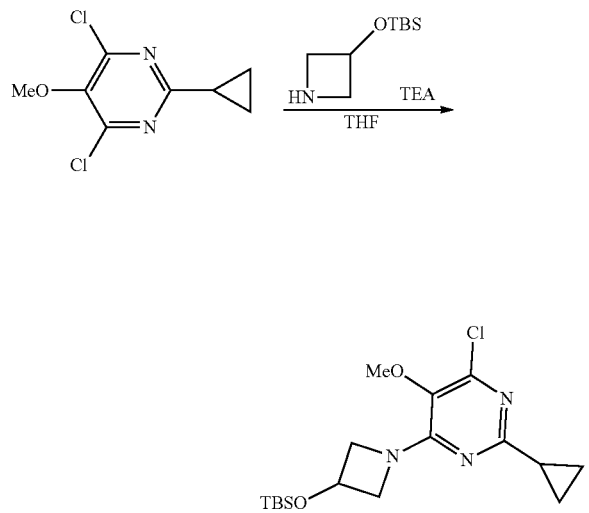

The mixture of 4,6-dichloro-2-cyclopropyl-5-methoxypyrimidine (200 mg, 0.913 mmol, 1.00 equiv), 3-((tert-butyldimethylsilyl)oxy)azetidine (205.26 mg, 1.096 mmol, 1.2 equiv) and TEA (184.76 mg, 1.826 mmol, 2 equiv) in THF (2 mL, 24.686 mmol, 27.04 equiv) was stirred at 60° C. for 8 h. The solvent was removed under reduced pressure. The residue was purified by silica gel column eluted with 0-50% EA in PE to give the title compound (300 mg, 84.38%) as a light yellow solid. m/z (ESI+ve ion)=370.20 [M+H]$^+$. $^1$H NMR (400 MHz, Chloroform-d) δ 4.75-4.70 (m, 1H), 4.44-4.40 (m, 2H), 4.06-4.02 (m, 2H), 3.72 (s, 3H), 2.03 (s, 1H), 1.05-1.02 (m, 2H), 0.92 (s, 11H), 0.10 (s, 6H).

424

Step B. tert-butyl (1R,2S)-2-[1-(tert-butoxycarbonyl)-3-[(6-{3-[(tert-butyldimethylsilyl)oxy]azetidin-1-yl}-2-cyclopropyl-5-methoxypyrimidin-4-yl)amino]indazol-6-yl]-5'-methoxy-2'-oxospiro[cyclopropane-1,3'-indole]-1'-carboxylate

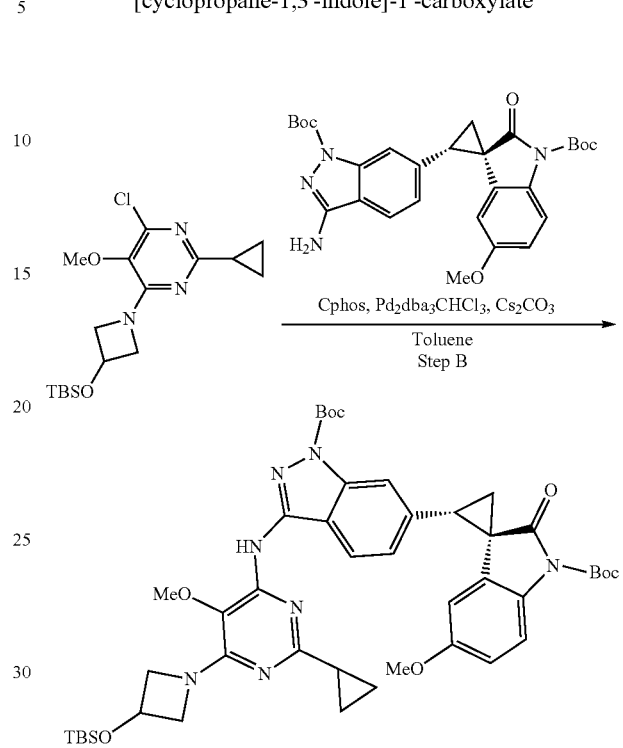

To the mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (100 mg, 0.192 mmol, 1.00 equiv) and 4-{3-[(tert-butyldimethylsilyl)oxy]azetidin-1-yl}-6-chloro-2-cyclopropyl-5-methoxypyrimidine (92.39 mg, 0.250 mmol, 1.3 equiv) in dry toluene (2.5 mL) were added Cs$_2$CO$_3$ (125.17 mg, 0.384 mmol, 2 equiv), CPhos (16.77 mg, 0.038 mmol, 0.2 equiv) and Pd$_2$(dba)$_3$·CHCl$_3$ (39.77 mg, 0.038 mmol, 0.2 equiv) under nitrogen atmosphere. The mixture was stirred at 90° C. for 2 h. The mixture was filtered and washed with EA (5 mL×3). The filtrate was removed under reduced pressure. The residue was purified by silica gel column eluted with 0-50% of EA in PE to give crude the title compound (70 mg, 36.27%) as a yellow solid. m/z (ESI+ve ion)=854.40 [M+H]$^+$.

Step C. (1R,2S)-2-(3-{[2-cyclopropyl-6-(3-hydroxyazetidin-1-yl)-5-methoxypyrimidin-4-yl]amino}-1H-indazol-6-yl)-5'-methoxy-1'H-spiro[cyclopropane-1,3'-indol]-2'-one; trifluoroacetic acid

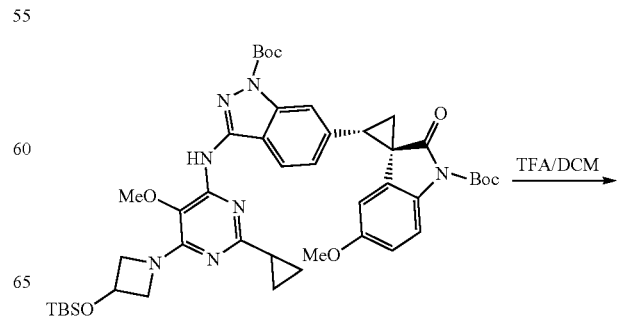

-continued

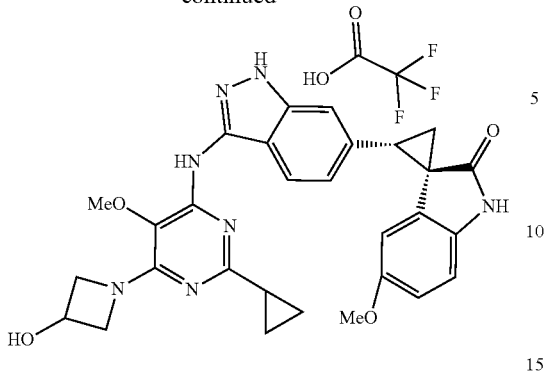

The mixture of tert-butyl (1R,2S)-2-[1-(tert-butoxycarbonyl)-3-[(6-{3-[(tert-butyldimethylsilyl)oxy]azetidin-1-yl}-2-cyclopropyl-5-methoxypyrimidin-4-yl)amino]indazol-6-yl]-5'-methoxy-2'-oxospiro[cyclopropane-1,3'-indole]-1'-carboxylate (70 mg, 0.082 mmol, 1.00 equiv) in TFA (0.5 mL) and DCM (3 mL) was stirred at 25° C. for 8 h. The solvent was removed under reduced pressure. The residue was purified by Prep-HPLC with the following conditions: Column: Xselect CSH OBD Column 30×150 mm 5 μm, Mobile Phase A: ACN, Mobile Phase B: Water (0.05% TFA); Flow rate: 60 mL/min; Gradient: 10% B to 35% B in 8 min; wavelength: 254 nm; RT1(min): 7. The product-containing fractions were collected and concentrated in vacuo to give Example 81 (46.1 mg, 86.06%) as a white solid. m/z (ESI +ve ion)=540.25 [M+H]$^+$. $^1$H NMR (400 MHz, DMSO-d$_6$) δ 12.82 (s, 1H), 10.44 (s, 1H), 9.86 (s, 1H), 7.60 (s, 1H), 7.44 (s, 1H), 6.96 (d, J=8.4 Hz, 1H), 6.76 (d, J=8.4 Hz, 1H), 6.61-6.58 (m, 1H), 5.72 (m, 1H), 4.62-4.59 (m, 1H), 4.48 (s, 2H), 4.02 (s, 2H), 3.65 (s, 3H), 3.34 (s, 3H), 3.20 (t, J=8.4 Hz, 1H), 2.35-2.32 (m, 1H), 2.00-1.98 (m, 2H), 0.89-0.80 (m, 4H). $^{19}$F NMR (376 MHz, DMSO-d$_6$) δ −74.10 (s, 3F).

Example 82. (1R,2S)-2-{3-[(3,6-dimethylpyrazin-2-yl)amino]-1H-indazol-6-yl}-5'-methoxyspiro[cyclopropane-1,3'-indol]-2'(1'H)-one

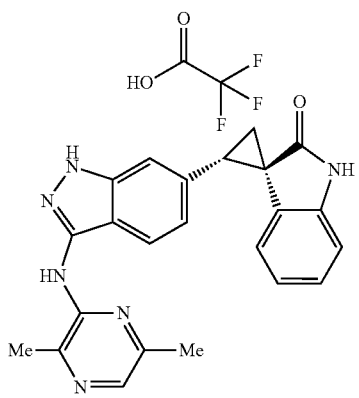

Step A. tert-butyl (1R,2S)-2-[1-(tert-butoxycarbonyl)-3-[(3,6-dimethylpyrazin-2-yl)amino] indazol-6-yl]-5'-methoxy-2'-oxospiro[cyclopropane-1,3'-indole]-1'-carboxylate

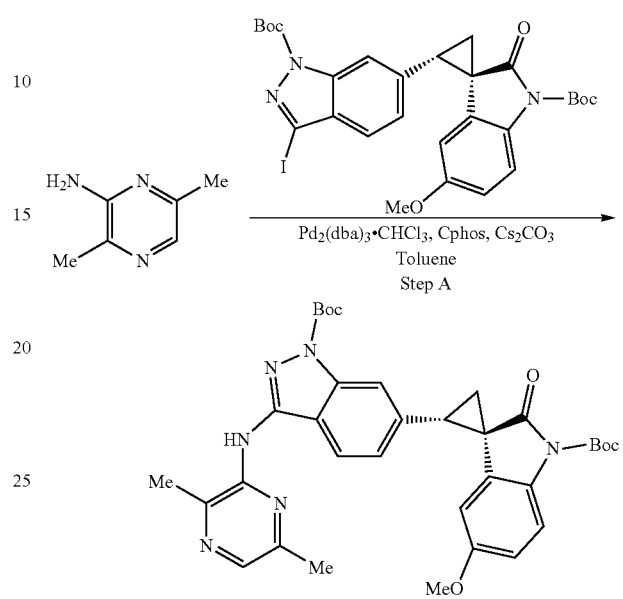

To a stirred solution of 3,6-dimethylpyrazin-2-amine (20.0 mg, 0.162 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (102.55 mg, 1.0 equiv) in toluene (5.0 mL) were added Cs$_2$CO$_3$ (105.82 mg, 0.324 mmol, 2.0 equiv) and CPhos (14.18 mg, 0.032 mmol, 0.2 equiv) and Pd$_2$(dba)$_3$·CHCl$_3$ (33.62 mg, 0.2 equiv) at room temperature under nitrogen atmosphere. The resulting mixture was stirred for 2.0 h at 90.0° C. under nitrogen atmosphere. The mixture was cooled down to room temperature and then filtered, the filter cake was washed with EtOAc (4×5 mL). The filtrate was concentrated under reduced pressure. The residue was purified by silica gel column chromatography, eluted with PE/EA (5/1) to afford the title compound (40.0 mg, 39.3% yield) as a yellow solid. m/z (ESI, +ve ion)=627.30 [M+H]$^+$.

Step B. tert-butyl (1R,2S)-2-[1-(tert-butoxycarbonyl)-3-[(3,6-dimethylpyrazin-2-yl)amino] indazol-6-yl]-5'-methoxy-2'-oxospiro[cyclopropane-1,3'-indole]-1'-carboxylate; trifluoroacetic acid

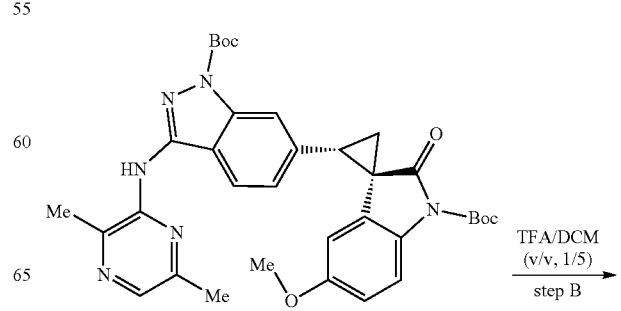

427
-continued

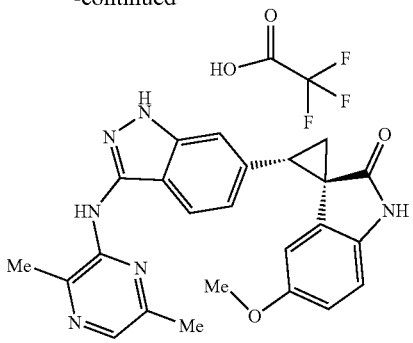

To a stirred solution of tert-butyl (1R,2S)-2-[1-(tert-butoxycarbonyl)-3-[(3,6-dimethylpyrazin-2-yl)amino] indazol-6-yl]-5'-methoxy-2'-oxospiro[cyclopropane-1,3'-indole]-1'-carboxylate (50.0 mg) in DCM (5.0 mL) was added TFA (1.0 mL) dropwise at room temperature. The resulting mixture was stirred for 4 h at room temperature. The reaction was monitored by LCMS. The resulting mixture was concentrated under reduced pressure. The crude product (30.0 mg) was purified by Prep-HPLC with the following conditions: (Column: Xselect CSH C18 OBD Column 30×150 mm 5 μm, Mobile Phase A: ACN, Mobile Phase B: Water (0.05% TFA); Flow rate: 60 mL/min; Gradient: 6% B to 30% B in 8 min. 30% B to 30% B in 11 min. 30% B; wavelength: 254 nm; RT1(min): 9.0-10.4 to afford Example 82 (14.5 mg, 41.4% yield) as a yellow solid. m/z (ESI, +ve ion)=427.30 [M+H]$^+$. $^1$H NMR (400 MHz, Methanol-d$_4$) δ 7.85 (s, 1H), 7.61 (d, J=8.5 Hz, 1H), 7.48 (s, 1H), 6.95 (d, J=8.0 Hz, 1H), 6.85 (d, J=8.4 Hz, 1H), 6.63 (dd, J=8.5, 2.6 Hz, 1H), 5.62 (d, J=2.5 Hz, 1H), 3.42-3.33 (m, 4H), 2.64 (s, 3H), 2.35 (s, 3H), 2.27-2.15 (m, 2H).

Example 83. (1R,2S)-5'-methoxy-2-(3-{[3-methoxy-6-(propan-2-yl)pyrazin-2-yl]amino}-1H-indazol-6-yl)spiro[cyclopropane-1,3'-indol]-2'(1'H)-one

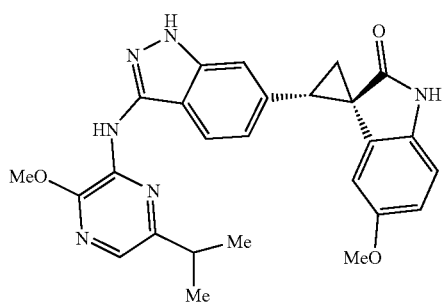 [SMILES: COc1ccc2c(c1)[C@]1(C[C@H]1c1ccc3c(Nc4nc(C(C)C)cnc4OC)n[nH]c3c1)C(=O)N2]

Step A. 3-methoxy-6-(prop-1-en-2-yl)pyrazin-2-amine

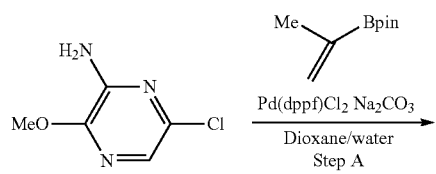

428
-continued

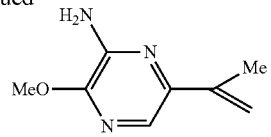

To a stirred mixture of 6-chloro-3-methoxypyrazin-2-amine (400 mg, 2.507 mmol, 1.00 equiv) and 4,4,5,5-tetramethyl-2-(prop-1-en-2-yl)-1,3,2-dioxaborolane (842.47 mg, 5.014 mmol, 2 equiv) in dioxane (20 mL) and water (10 mL) were added Pd(dppf)Cl$_2$ (204.20 mg, 0.251 mmol, 0.1 equiv) and Na$_2$CO$_3$ (797.06 mg, 7.521 mmol, 3 equiv) at room temperature under nitrogen atmosphere. The resulting mixture was stirred for 16 h at 110° C. under nitrogen atmosphere. The mixture was cooled down to room temperature. The reaction was quenched by the addition of Water (10 mL) at room temperature. The resulting mixture was extracted with DCM (3×10 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EA (1/1) to afford the title compound (163 mg, 39.36%) as a white solid. m/z (ESI, +ve ion)=166.20 [M+H]$^+$.

Step B. 6-isopropyl-3-methoxypyrazin-2-amine

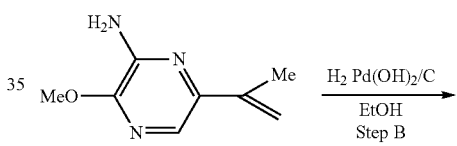

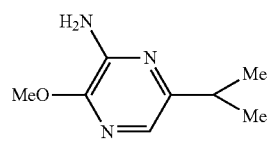

A mixture of 3-methoxy-6-(prop-1-en-2-yl)pyrazin-2-amine (132 mg, 0.799 mmol, 1.00 equiv) and Pd(OH)$_2$/C (112.21 mg, 0.799 mmol, 1 equiv) in EtOH (6.5 mL) was stirred for 16 h at room temperature under hydrogen atmosphere. The resulting mixture was filtered, the filter cake was washed with EtOH (2×5 mL). The filtrate was concentrated under reduced pressure. The residue was purified by silica gel column chromatography, eluted with PE/EA (2/1) to afford the title compound (74 mg, 55.38%) as a colorless oil. m/z (ESI+ve ion)=168.00 [M+H]$^+$. $^1$H NMR (400 MHz, chloroform-d) δ 7.30 (s, 1H), 4.80 (s, 2H), 3.98 (s, 3H), 2.85 (m, 1H), 1.26 (d, J=6.8 Hz, 6H).

429

Step C. tert-butyl (1R,2S)-2-[1-(tert-butoxycarbonyl)-3-[(6-isopropyl-3-methoxypyrazin-2-yl)amino]indazol-6-yl]-5'-methoxy-2'-oxospiro[cyclopropane-1,3'-indole]-1'-carboxylate

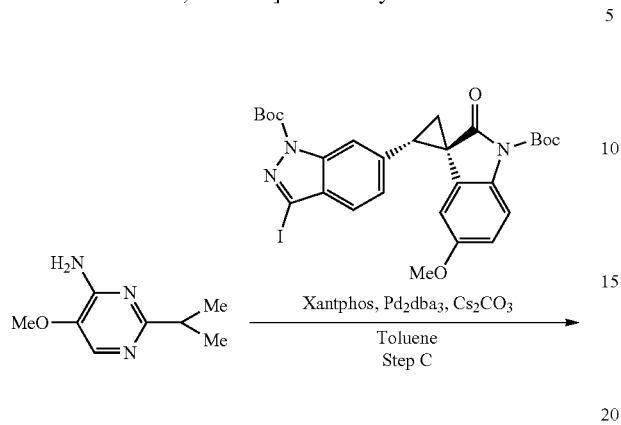
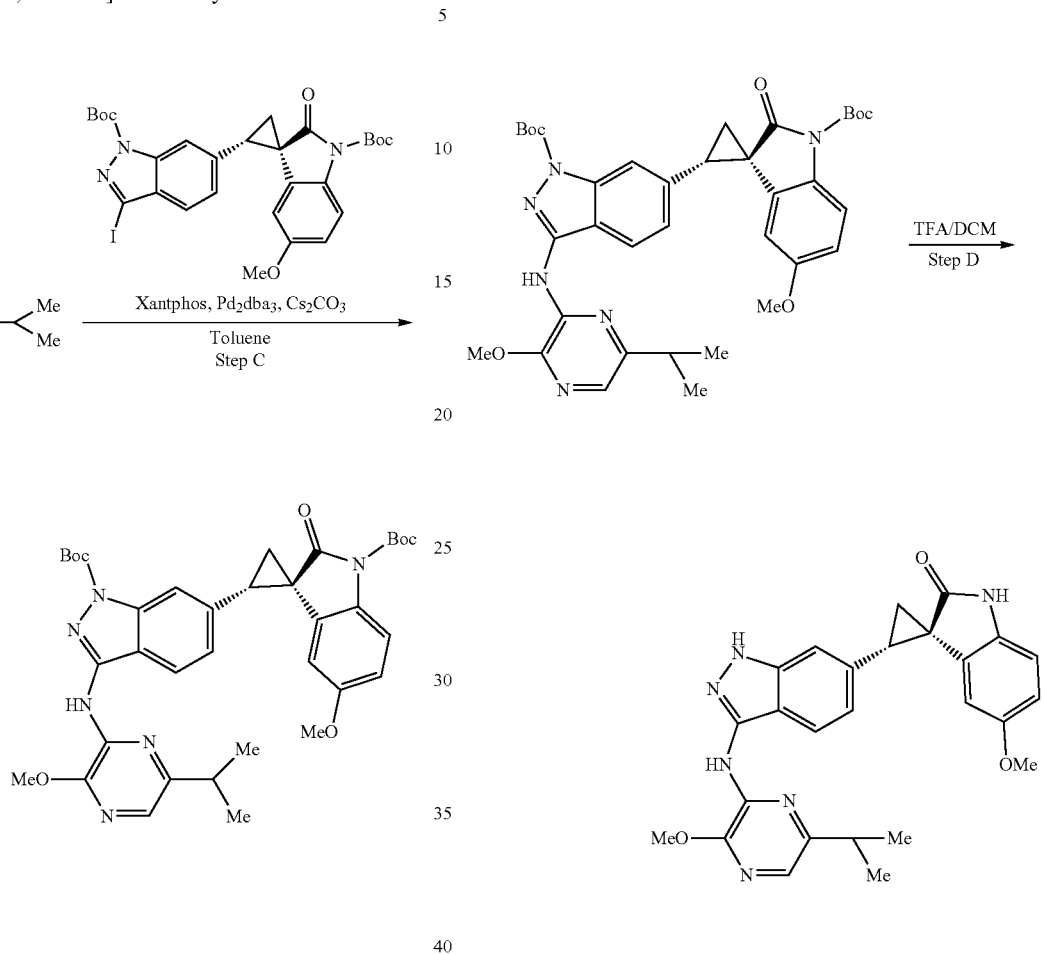

430

Step D. tert-butyl (1R,2S)-2-[1-(tert-butoxycarbonyl)-3-[(6-isopropyl-3-methoxypyrazin-2-yl)amino]indazol-6-yl]-5'-methoxy-2'-oxospiro[cyclopropane-1,3'-indole]-1'-carboxylate To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80 mg, 0.127 mmol, 1.00 equiv) and 6-isopropyl-3-methoxypyrazin-2-amine (25.42 mg, 0.152 mmol, 1.2 equiv) in toluene (4 mL) were added $Pd_2(dba)_3$ (11.60 mg, 0.013 mmol, 0.1 equiv), XantPhos (7.33 mg, 0.013 mmol, 0.1 equiv) and $Cs_2CO_3$ (82.56 mg, 0.254 mmol, 2 equiv) at room temperature under nitrogen atmosphere. The resulting mixture was stirred for 2 h at 90° C. under nitrogen atmosphere. The mixture was cooled down to room temperature. The reaction was quenched by the addition of Water (10 mL) at room temperature. The resulting mixture was extracted with DCM (3×8 mL). The combined organic layers were washed with brine (15 mL), dried over anhydrous $Na_2SO_4$. After filtration, the filtrate was concentrated under reduced pressure. The residue was purified by silica gel column chromatography, eluted with PE/EA (2/1) to afford the title compound (84.7 mg, 99.67%) as a brown yellow solid. m/z (ESI, +ve ion)=671.45 [M+H]$^+$. $^1$H NMR (400 MHz, Chloroform-d) δ 8.16 (s, 1H), 7.93 (d, J=8.4 Hz, 1H), 7.82 (d, J=8.9 Hz, 1H), 7.64 (s, 1H), 7.47 (s, 1H), 7.01 (d, J=8.2 Hz, 1H), 6.69 (m, 1H), 5.57 (d, J=2.8 Hz, 1H), 4.06 (s, 3H), 3.56-3.54 (m, 1H), 3.36 (s, 3H), 2.87-2.84 (m, 1H), 1.71 (d, J=6.6 Hz, 18H), 1.28 (t, J=7.2 Hz, 2H), 1.15 (t, J=6.4 Hz, 6H).

A mixture of tert-butyl (1R,2S)-2-[1-(tert-butoxycarbonyl)-3-[(6-isopropyl-3-methoxypyrazin-2-yl)amino]indazol-6-yl]-5'-methoxy-2'-oxospiro[cyclopropane-1,3'-indole]-1'-carboxylate (84.7 mg, 0.126 mmol, 1.00 equiv) and TFA (2 mL, 26.926 mmol, 213.24 equiv) in DCM (4 mL, 62.920 mmol, 498.29 equiv) was stirred for 2 h at room temperature under nitrogen atmosphere. The resulting mixture was concentrated under vacuum. The residue was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 30% B to 60% Vo B in 8 min, 60% B; wavelength: 254 nm; RT1(min): 7 to afford Example 83 (33.6 mg, 56.49%) as a white solid. m/z=471.35 [M+H]$^+$. $^1$H NMR (400 MHz, DMSO-$d_6$) δ 12.48 (s, 1H), 10.38 (s, 1H), 8.69 (s, 1H), 7.45 (d, J=8.4 Hz, 1H), 7.35 (d, J=4.4 Hz, 2H), 6.83 (d, J=8.5 Hz, 1H), 6.75 (d, J=8.4 Hz, 1H), 6.58 (m, 1H), 5.67 (d, J=2.4 Hz, 1H), 3.96 (s, 3H), 3.31 (s, 2H), 3.15-3.22 (m, 2H), 2.70-2.65 (m, 1H), 2.29 (m, 1H), 1.98 (m, 1H), 1.00 (m, 6H).

Example 84. (1R,2S)-2-(3-((6-(1,1-dioxidothiomorpholino)-2-isopropyl-5-methoxypyrimidin-4-yl)amino)-1H-indazol-6-yl)-5'-methoxyspiro[cyclopropane-1,3'-indolin]-2'-one

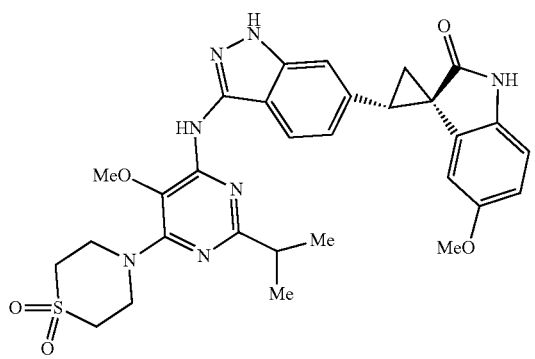 [SMILES: COc1ccc2c(c1)[C@]1(C[C@H]1c1ccc3c(Nc4nc(C(C)C)nc(N5CCS(=O)(=O)CC5)c4OC)n[nH]c3c1)C(=O)N2]

Step A.
6-hydroxy-2-isopropyl-5-methoxy-3H-pyrimidin-4-one

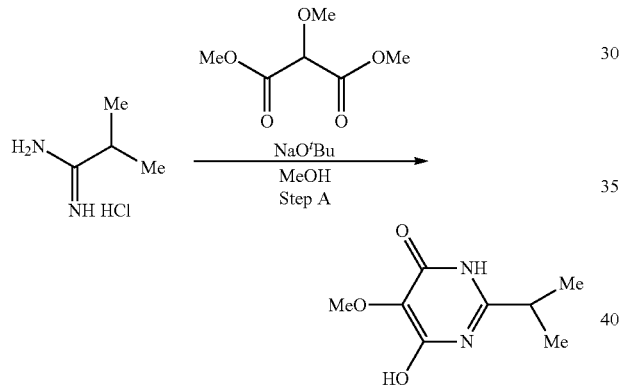

To a stirred solution of Sodium t-butoxide (1.96 g, 2.5 equiv) in MeOH (10.0 mL) were added 2-methylpropanimidamide hydrochloride (1.0 g, 1.0 equiv) and 1,3-dimethyl 2-methoxypropanedioate (1.32 g, 1.0 equiv) at 0° C. under nitrogen atmosphere. The resulting mixture was stirred for 12 h at 80° C. under nitrogen atmosphere. The mixture was cooled down to room temperature. The resulting mixture was filtered. The filtrate was concentrated under reduced pressure to afford the title compound (1.0 g, 66.56%) as a yellow solid. m/z (ESI, +ve ion)=185.00 [M+H]$^+$.

Step B.
4,6-dichloro-2-isopropyl-5-methoxypyrimidine

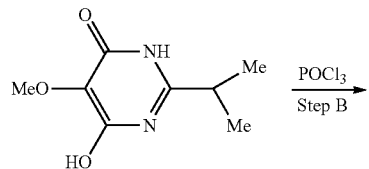

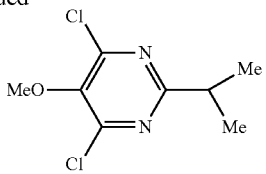

The mixture of crude 6-hydroxy-2-isopropyl-5-methoxy-3H-pyrimidin-4-one (1 g, 5.429 mmol, 1.00 equiv) in POCl$_3$ (10.00 mL) was stirred for 3 h at 100° C. After cooled to room temperature, the mixture solution was added dropwise to cooled sat·aq·NaHCO$_3$ (150 mL). The mixture was extracted with EA (50 mL×3). The combined organic layer was washed with brine (30 mL), dried over anhydrous Na$_2$SO$_4$ and filtered. The filtrate was concentrated in vacuo. The residue was purified by silica gel column eluted with 0-30% EA in PE to give the title compound (600 mg, 47.49%) as a colorless oil. m/z (ESI, +ve ion)=220.95 [M+H]$^+$. $^1$H NMR (400 MHz, Chloroform-d) δ 3.97 (s, 3H), 3.22-3.11 (m, 1H), 1.35 (s, 3H), 1.33 (s, 3H).

Step C. 4-(6-chloro-2-isopropyl-5-methoxypyrimidin-4-yl)-1lambda6-thiomorpholine-1,1-dione

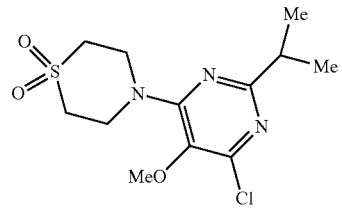

The mixture of 4,6-dichloro-2-isopropyl-5-methoxypyrimidine (200 mg, 0.905 mmol, 1.00 equiv) and 1lambda6-thiomorpholine-1,1-dione (122.29 mg, 0.905 mmol, 1 equiv) and TEA (183.08 mg, 1.810 mmol, 2 equiv) in THF (2 mL, 24.686 mmol, 27.29 equiv) was stirred at 60° C. for 12 h. The solvent was removed under reduced pressure. The residue was purified by silica gel column eluted with 0-50% of EA in PE to give the title compound (150 mg, 51.85%) as a white solid. m/z (ESI, +ve ion)=320.05 [M+H]$^+$. $^1$H NMR (400 MHz, Chloroform-d) δ 4.36-4.34 (m, 4H), 3.78 (s, 3H), 3.15-3.12 (m, 4H), 3.06-2.99 (m, 1H), 1.29 (s, 3H), 1.28 (s, 3H).

Step D. tert-butyl (1R,2S)-2-[1-(tert-butoxycarbonyl)-3-{[6-(1,1-dioxo-1lambda6-thiomorpholin-4-yl)-2-isopropyl-5-methoxypyrimidin-4-yl]amino}indazol-6-yl]-5'-methoxy-2'-oxospiro[cyclopropane-1,3'-indole]-1'-carboxylate Step E

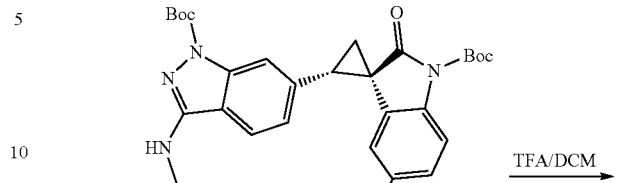

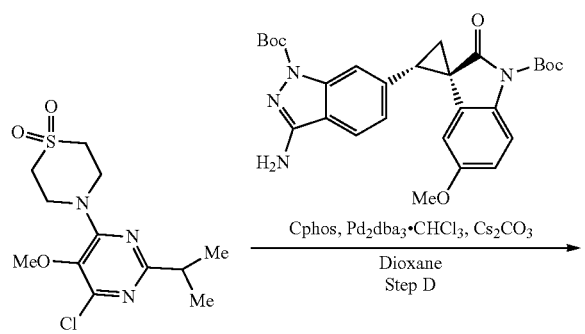

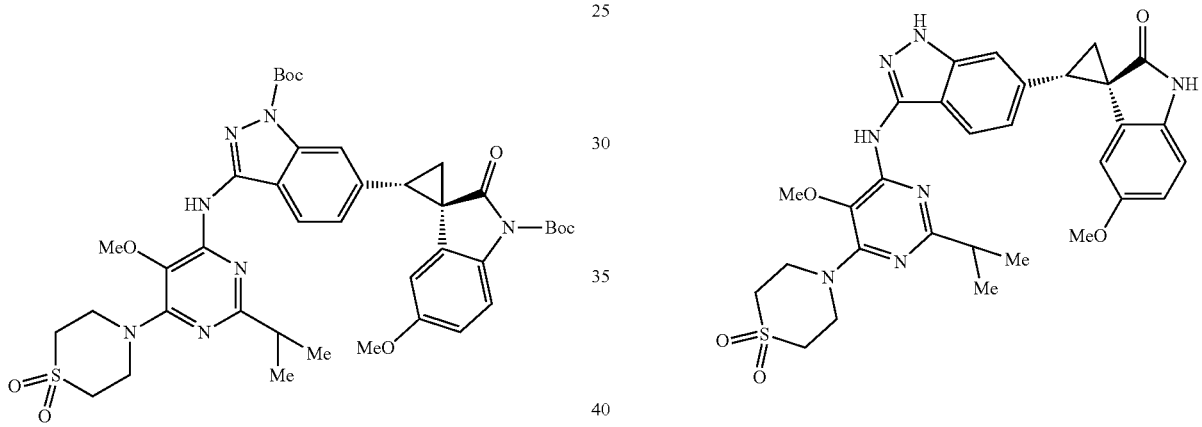

To the mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (90 mg, 0.173 mmol, 1.00 equiv) and 4-(6-chloro-2-isopropyl-5-methoxypyrimidin-4-yl)-1lambda6-thiomorpholine-1,1dione (66.35 mg, 0.208 mmol, 1.2 equiv) in dry toluene (2.5 mL) were added Cs$_2$CO$_3$ (112.66 mg, 0.346 mmol, 2 equiv), CPhos (15.10 mg, 0.035 mmol, 0.2 equiv) and Pd$_2$(dba)$_3$·CHCl$_3$ (35.79 mg, 0.035 mmol, 0.2 equiv) under nitrogen atmosphere. The mixture was stirred at 90° C. for 2 h. The mixture was filtered and washed with EA (3×5 mL). The filtrate was removed under reduced pressure. The residue was purified by silica gel column eluted with 0-100% of EA in PE to give the title compound (70 mg, 45.33%) as a yellow solid. m/z (ESI, +ve ion)=804.30 [M+H]$^+$.

The mixture of tert-butyl (1R,2S)-2-[1-(tert-butoxycarbonyl)-3-{[6-(1,1-dioxo-1lambda6-thiomorpholin-4-yl)-2-isopropyl-5-methoxypyrimidin-4-yl]amino}indazol-6-yl]-5'-methoxy-2'-oxospiro[cyclopropane-1,3'-indole]-1'-carboxylate (70 mg, 0.087 mmol, 1.00 equiv) in TFA (0.5 mL) and DCM (5 mL) was stirred at 25° C. for 5 h. The solvent was removed under reduced pressure. The residue was purified by Prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 33% B to 43% B in 8 min; wavelength: 254 nm; RT1(min): 7.45. The product-containing fractions was collected and concentrated in vacuo to give Example 84 (31.9 mg, 60.26%) as a white solid. m/z (ESI, +ve ion)=604.25 [M+H]$^+$. $^1$H NMR (400 MHz, DMSO-d$_6$) δ 12.52 (s, 1H), 10.41 (s, 1H), 8.93 (s, 1H), 7.46 (d, J=8.4 Hz, 1H), 7.36 (s, 1H), 6.84 (d, J=8.4 Hz, 1H), 6.74 (d, J=8.4 Hz, 1H), 6.59-6.57 (m, 1H), 5.67 (s, 1H), 4.09 (s, 4H), 3.65 (s, 3H), 3.32 (s, 3H), 3.24-3.21 (m, 5H), 2.61-2.56 (m, 1H), 2.32-2.28 (m, 1H), 1.99-1.96 (m, 1H), 1.00 (d, J=6.8 Hz, 6H).

Example 85. (1R,2S)-5'-methoxy-2-(3-{[5-methoxy-6-(morpholin-4-yl)-2-(propan-2-yl)pyrimidin-4-yl]amino}-1H-indazol-6-yl)spiro[cyclopropane-1,3'-indol]-2'(1'H)-one

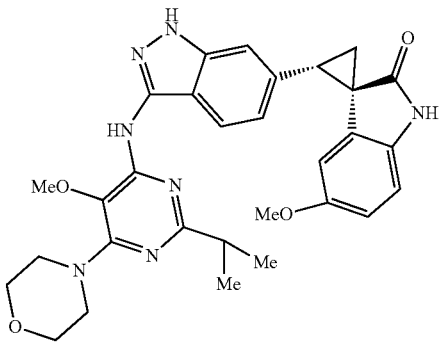 [SMILES: COc1ccc2c(c1)[C@]1(C[C@H]1c1ccc3c(Nc4nc(C(C)C)nc(N5CCOCC5)c4OC)n[nH]c3c1)C(=O)N2]

Step A. 4-(6-chloro-2-isopropyl-5-methoxypyrimidin-4-yl)morpholine

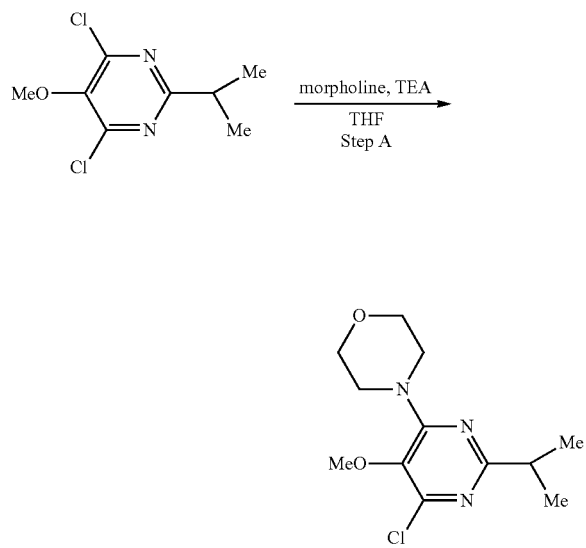

The mixture of 4-(6-chloro-2-isopropyl-5-methoxypyrimidin-4-yl)-1lambda6-thiomorpholine-1,1-dione (100 mg, 0.452 mmol, 1.00 equiv), morpholine (39.41 mg, 0.452 mmol, 1 equiv) and TEA (91.54 mg, 0.904 mmol, 2 equiv) in THF (2 mL) was stirred at 60° C. for 12 h. The solvent was removed under reduced pressure. The residue was purified by silica gel column eluted with 0-50% of EA in PE to give the title compound (100 mg, 81.35%) as a white solid. m/z (ESI+ve ion)=272.00 [M+H]$^+$. $^1$H NMR (400 MHz, Chloroform-d) δ 4.36-4.34 (m, 4H), 3.78 (s, 3H), 3.15-3.12 (m, 4H), 3.06-3.00 (m, 1H), 1.30 (s, 3H), 1.28 (s, 3H).

Step B. tert-butyl (1R,2S)-2-[1-(tert-butoxycarbonyl)-3-{[2-isopropyl-5-methoxy-6-(morpholin-4-yl)pyrimidin-4-yl]amino}indazol-6-yl]-5'-methoxy-2'-oxospiro[cyclopropane-1,3'-indole]-1'-carboxylate

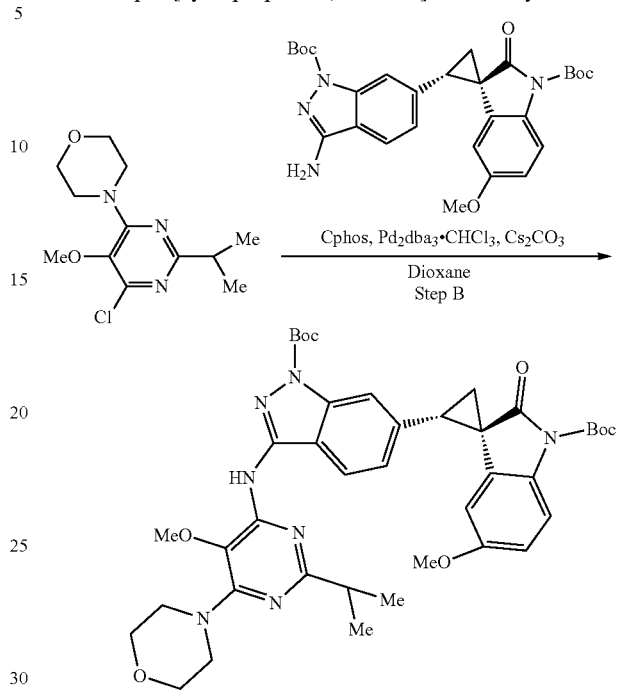

To the mixture of tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (80 mg, 0.154 mmol, 1.00 equiv) and 56a (50.11 mg, 0.185 mmol, 1.2 equiv) in dry toluene (2.0 mL) were added Cs$_2$CO$_3$ (100.14 mg, 0.308 mmol, 2 equiv), CPhos (13.42 mg, 0.031 mmol, 0.2 equiv) and Pd$_2$(dba)$_3$·CHCl$_3$ (31.81 mg, 0.031 mmol, 0.2 equiv) under nitrogen atmosphere. The mixture was stirred at 90° C. for 2 h. The mixture was filtered and washed with EA (5 mL×3). The filtrate was removed under reduced pressure. The residue was purified by silica gel column eluted with 0-100% of EA in PE to give crude the title compound (56b) (70 mg, 48.21%) as a light yellow solid. m/z (ESI+ve ion)=756.35 [M+H]$^+$.

Step C. (1R,2S)-2-(3-{[2-isopropyl-5-methoxy-6-(morpholin-4-yl)pyrimidin-4-yl]amino}-1H-indazol-6-yl)-5'-methoxy-1'H-spiro[cyclopropane-1,3'-indol]-2'-one

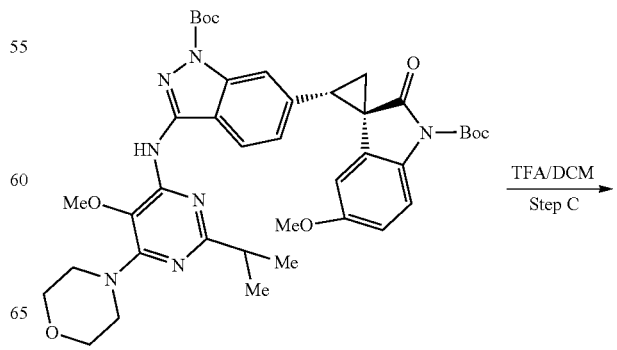

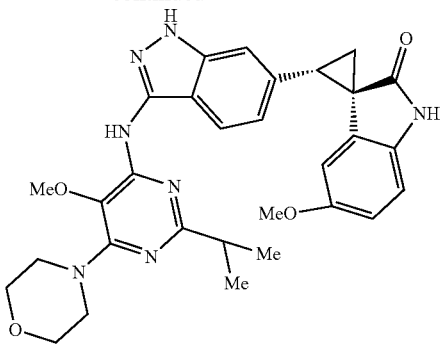

The mixture of 4-(6-chloro-2-isopropyl-5-methoxypyrimidin-4-yl)morpholine (70 mg, 0.093 mmol, 1.00 equiv) in TFA (0.5 mL) and DCM (5 mL) was stirred at 25° C. for 5 h. The solvent was removed under reduced pressure. The residue was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 38% B to 48% B in 8 min; wavelength: 254 nm; RT1(min): 7.33. The product-containing fractions were collected and concentrated in vacuo to give Example 85 (30.7 mg, 59.42%) as a white solid. m/z (ESI+ve ion)=556.30 [M+H]$^+$. $^1$H NMR (400 MHz, DMSO-$d_6$) δ 12.48 (s, 1H), 10.41 (s, 1H), 8.78 (s, 1H), 7.46 (d, J=8.4 Hz, 1H), 7.35 (s, 1H), 6.84 (d, J=8.8 Hz, 1H), 6.75 (d, J=8.4 Hz, 1H), 6.60-6.57 (m, 1H), 5.68 (d, J=2.4 Hz, 1H), 3.73-3.71 (m, 4H), 3.64 (s, 3H), 3.61-3.58 (m, 4H), 3.32 (s, 3H), 3.18 (t, J=8.0 Hz, 1H), 2.60-2.55 (m, 1H), 2.31-2.28 (m, 1H), 1.99-1.96 (m, 1H), 0.98 (d, J=6.8 Hz, 6H).

Example 86. (1R,2S)-5'-methoxy-2-{3-[(5-methoxy-2-methylpyridin-4-yl)amino]-1H-indazol-6-yl}spiro[cyclopropane-1,3'-indol]-2'(1'H)-one Step A. tert-butyl (1R,2S)-2-[1-(tert-butoxycarbonyl)-3-[(5-methoxy-2-methylpyridin-4-yl) amino] indazol-6-yl]-5'-methoxy-2'-oxospiro[cyclopropane-1,3'-indole]-1'-carboxylate

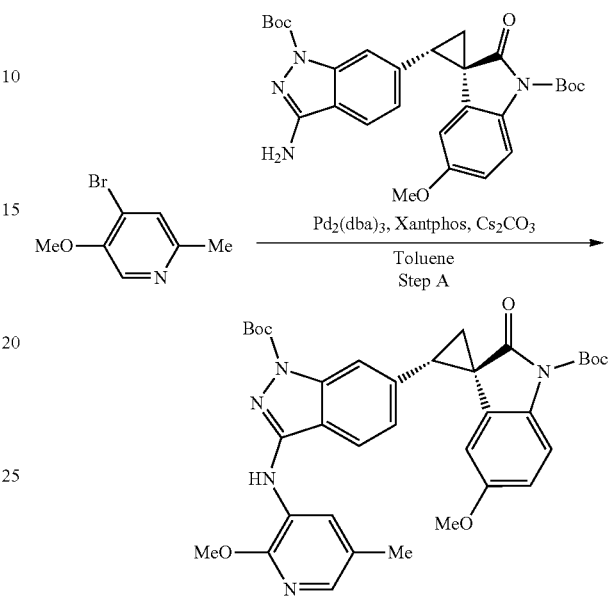

To a stirred solution of 4-bromo-5-methoxy-2-methylpyridine (38.81 mg, 0.192 mmol, 1.0 equiv) and tert-butyl (1R,2S)-2-[3-amino-1-(tert-butoxycarbonyl)indazol-6-yl]-5'-methoxy-2'-oxospiro[cyclopropane-1,3-indole]-1'-carboxylate (100.0 mg, 1.0 equiv) in toluene (5.0 mL) were added $Cs_2CO3$ (125.17 mg, 0.384 mmol, 2.0 equiv) and XantPhos (22.23 mg, 0.038 mmol, 0.2 equiv) and $Pd_2(dba)_3$ (35.18 mg, 0.2 equiv) at room temperature under nitrogen atmosphere. The resulting mixture was stirred for 2 h at 90° C. under nitrogen atmosphere. The mixture was cooled down to room temperature. The resulting mixture was filtered, the filter cake was washed with EtOAc (3×6 mL). The filtrate was concentrated under reduced pressure. The residue was purified by silica gel column chromatography, eluted with DCM/MeOH (9/1) to afford the title compound (80.0 mg, 64.90%) as a yellow solid. m/z (ESI, +ve ion)=642.40 [M+H]$^+$.

Step B. (1R,2S)-5'-methoxy-2-{3-[(5-methoxy-2-methylpyridin-4-yl)amino]-1H-indazol-6-yl}-1'H-spiro[cyclopropane-1,3'-indol]-2'-one

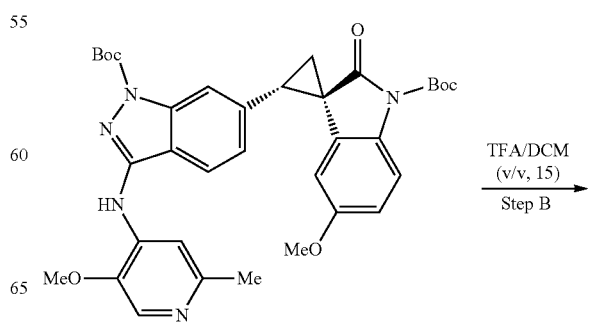

-continued

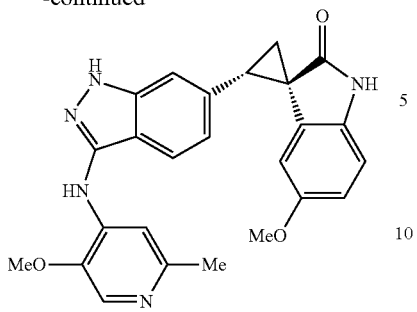

To a stirred solution of tert-butyl (1R,2S)-2-[1-(tert-butoxycarbonyl)-3-[(5-methoxy-2-methylpyridin-4-yl)amino]indazol-6-yl]-5'-methoxy-2'-oxospiro[cyclopropane-1,3'-indole]-1'-carboxylate (60.0 mg) in DCM (5.0 mL) was added TFA (1.0 mL) dropwise at room temperature. The resulting mixture was stirred for 5 h at room temperature then concentrated under reduced pressure. The crude product (30 mg) was purified by Prep-HPLC with the following conditions: Column: XBridge Shield RP18 OBD Column, 30×150 mm, 5 μm; Mobile Phase A: Water (10 mmol/L NH₄HCO₃), Mobile Phase B: ACN; Flow rate: 60 mL/min; Gradient: 25% B to 45% B in 8 min, 45% B; wavelength: 254 nm; RT1(min): 6.12 to afford Example 86 (19.2 mg, 46.51%) as a white solid. m/z (ESI, +ve ion)=442.25 [M+H]⁺. ¹H NMR (400 MHz, Methanol-d₄) δ 7.90 (s, 1H), 7.66 (d, J=8.0 Hz, 1H), 7.51 (s, 1H), 7.43 (s, 1H), 6.95 (d, J=8.0 Hz, 1H), 6.84 (d, J=8.0 Hz, 1H), 6.63 (d, J=8.0 Hz, 1H), 5.61 (d, J=4.0 Hz, 1H), 4.03 (s, 3H), 3.31 (s, 4H), 2.37 (s, 3H), 2.37-2.27 (m, 1H), 2.25-2.19 (m, 1H).

Example 87. (1R,2S)-5'-methoxy-2-{3-[(5-methoxy-2-methylpyrimidin-4-yl)amino]-1H-indazol-6-yl}spiro[cyclopropane-1,3'-indol]-2'(1'H)-one

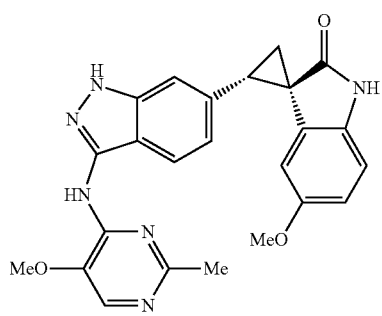

Step A. 6-chloro-5-methoxy-2-methylpyrimidin-4-amine

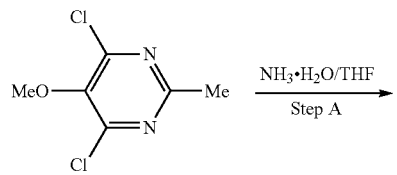

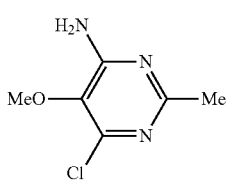

A mixture of 4,6-dichloro-5-methoxy-2-methylpyrimidine (500 mg, 2.590 mmol, 1.00 equiv) and 30% NH₃·H₂O (8 mL) in THF (4 mL) was stirred for 16 h at 70° C. under nitrogen atmosphere. The reaction was monitored by LCMS. The resulting mixture was concentrated under vacuum. The residue was purified by silica gel column chromatography, eluted with PE/EA (1/1) to afford the title compound (288 mg, 64.05%) as a white solid. m/z (ESI, +ve ion)=174.00 [M+H]⁺.

Step B. 5-methoxy-2-methylpyrimidin-4-amine

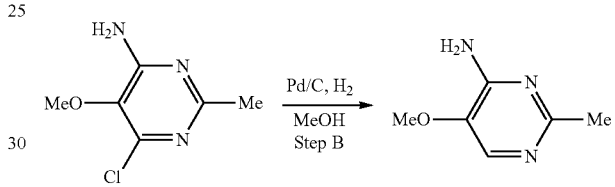

A mixture of 6-chloro-5-methoxy-2-methylpyrimidin-4-amine (250 mg, 1.440 mmol, 1.00 equiv) and Pd/C (229.88 mg, 2.160 mmol, 1.5 equiv) in MeOH (8.5 mL, 209.941 mmol, 145.78 equiv) was stirred for 16 h at room temperature under hydrogen atmosphere. The resulting mixture was filtered, the filter cake was washed with MeOH (3×5 mL). The filtrate was concentrated under reduced pressure to give the title compound (158 mg, 78.84%) as a white solid. m/z (ESI, +ve ion)=140.05 [M+H]⁺. ¹H NMR (400 MHz, DMSO-d₆) δ 8.93 (s, 1H), 8.43 (s, 1H), 7.92 (s, 1H), 3.89 (s, 3H), 2.47 (s, 3H).

Step C. tert-butyl (1R,2S)-2-[1-(tert-butoxycarbonyl)-3-[(5-methoxy-2-methylpyrimidin-4-yl)amino]indazol-6-yl]-5'-methoxy-2'-oxospiro[cyclopropane-1,3'-indole]-1'-carboxylate

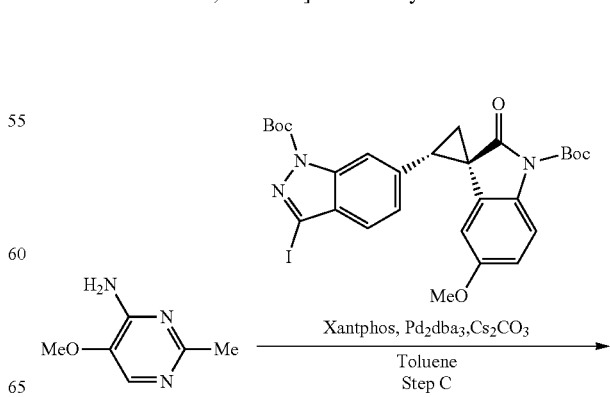

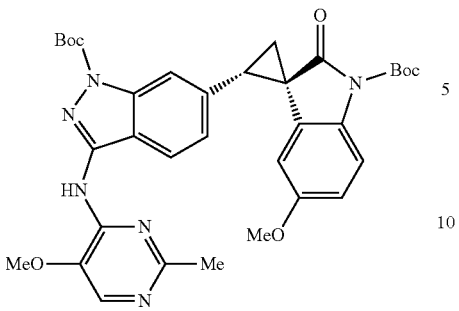

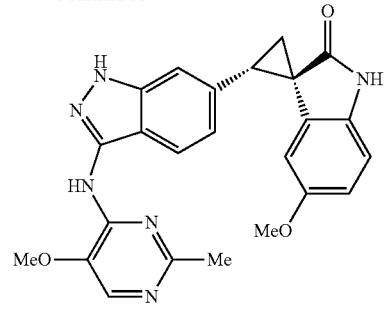 [SMILES: COc1ccc2c(c1)[C@]1(C[C@H]1c1ccc3c(Nc4nc(C)ncc4OC)n[nH]c3c1)C(=O)N2]

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80 mg, 0.127 mmol, 1.00 equiv) and 5-methoxy-2-methylpyrimidin-4-amine (21.16 mg, 0.152 mmol, 1.2 equiv) in toluene (4 mL) were added $Pd_2(dba)_3$ (11.60 mg, 0.013 mmol, 0.1 equiv), XantPhos (7.33 mg, 0.013 mmol, 0.1 equiv) and $Cs_2CO_3$ (82.56 mg, 0.254 mmol, 2 equiv) at room temperature under nitrogen atmosphere. The resulting mixture was stirred for 2 h at 90° C. under nitrogen atmosphere. The mixture was cooled down to room temperature. The reaction was quenched by the addition of Water (5 mL) at room temperature. The resulting mixture was extracted with DCM (3×5 mL). The combined organic layers were washed with brine (10 mL), dried over anhydrous $Na_2SO_4$. After filtration, the filtrate was concentrated under reduced pressure. The residue was purified by silica gel column chromatography, eluted with PE/EA (1/1) to afford the title compound (80 mg, 98.25%) as a brown yellow solid. m/z (ESI, +ve ion)=643.20 [M+H]$^+$. 1H NMR (400 MHz, Chloroform-d) δ 8.16 (s, 1H), 7.91-8.00 (m, 2H), 7.82 (d, J=8.8 Hz, 1H), 7.08 (d, J=8.4 Hz, 1H), 6.70 (m, 1H), 5.61 (d, J=2.4 Hz, 1H), 5.32 (s, 1H), 4.00 (s, 3H), 3.56-3.52 (m, 1H), 3.39 (s, 3H), 2.52 (s, 3H), 2.41-2.37 (m, 1H), 2.15-2.12 (m, 1H), 1.71 (d, J=5.6 Hz, 18H).

Step D. (1R,2S)-5'-methoxy-2-{3-[(5-methoxy-2-methylpyrimidin-4-yl)amino]-1H-indazol-6-yl}-1'H-spiro[cyclopropane-1,3'-indol]-2'-one A mixture of tert-butyl (1R,2S)-2-[1-(tert-butoxycarbonyl)-3-[(5-methoxy-2-methylpyrimidin-4-yl)amino]indazol-6-yl]-5'-methoxy-2'-oxospiro[cyclopropane-1,3'-indole]-1'-carboxylate (87.5 mg, 0.136 mmol, 1.00 equiv) and TFA (2 mL, 26.926 mmol, 197.78 equiv) in DCM (4 mL, 62.920 mmol, 462.17 equiv) was stirred for 2 h at room temperature under nitrogen atmosphere. The resulting mixture was concentrated under vacuum. The crude product was purified by Prep-HPLC with the following conditions: Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 20% B to 40% B in 8 min. 40% B: wavelength: 254 nm; RT1(min): 6.4 to afford Example 87 (23.3 mg, 38.60%) as a white solid. m/z (ESI, +ve ion)=443.30 [M+H]$^+$. $^1$H NMR (400 MHz, DMSO-$d_6$) δ 12.62 (s, 1H), 10.42 (s, 1H), 8.98 (s, 1H), 7.92 (s, 1H), 7.45 (d, J=8.4 Hz, 1H), 7.39 (s, 1H), 6.90 (d, J=8.4 Hz, 1H), 6.75 (d, J=8.4 Hz, 1H), 6.59 (m, 1H), 5.71 (d, J=2.4 Hz, 1H), 3.90 (s, 3H), 3.32 (s, 3H), 3.19 (t, J=8.4 Hz, 1H), 2.32 (m, 1H), 2.18 (s, 3H), 1.99 (m, 1H).

Example 88. (1R,2S)-5'-methoxy-2-{3-[(3-methoxy-6-methylpyridin-2-yl)amino]-1H-indazol-6-yl}spiro[cyclopropane-1,3'-indol]-2'(1'H)-one

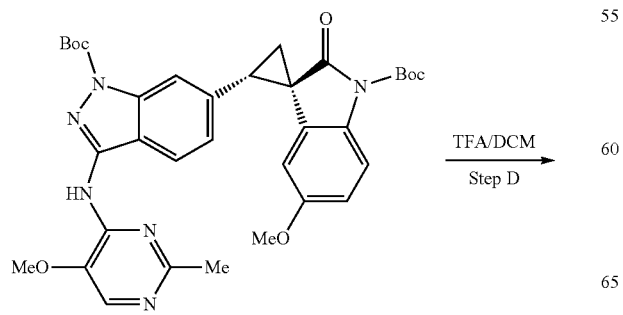

TFA/DCM
Step D

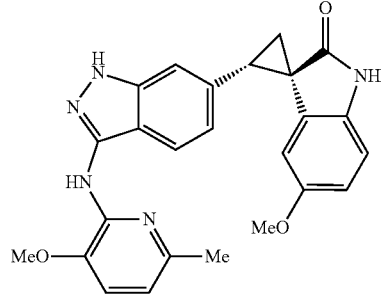 [SMILES: COc1ccc2c(c1)[C@]1(C[C@H]1c1ccc3c(Nc4nc(C)ccc4OC)n[nH]c3c1)C(=O)N2]

443

Step A. tert-butyl (1R,2S)-2-[1-(tert-butoxycarbonyl)-3-[(3-methoxy-6-methylpyridin-2-yl)amino]indazol-6-yl]-5'-methoxy-2'-oxospiro[cyclopropane-1,3'-indole]-1'-carboxylate

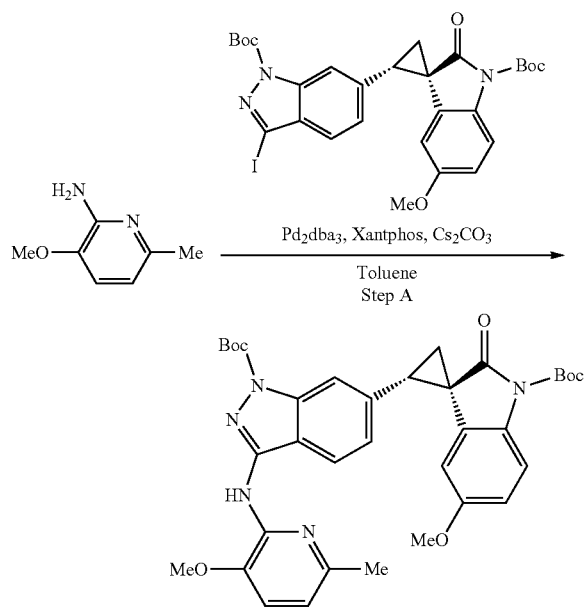

To a stirred mixture of 3-methoxy-6-methylpyridin-2-amine (24 mg, 1.3 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80 mg, 1 equiv) in 1,4-dioxane (4 mL) and Cs$_2$CO$_3$ (80 mg, 2 equiv) were added XantPhos (24 mg, 0.2 equiv) and Pd$_2$(dba)$_3$ (16 mg, 0.2 equiv) at 25° C. under nitrogen atmosphere. The mixture was warmed up to 90° C. and stirred for 2 h. The mixture was concentrated under reduced pressure. The crude product 200 mg was purified by Prep-HPLC with PE:EA=1:1 to afford the title compound (59 mg, 70%) as an off-white solid. m/z (ESI+ve ion)=642.25 [M+H]$^+$. $^1$H NMR (400 MHz, Chloroform-d) δ 8.41 (s, 1H), 8.10 (s, 1H), 7.81 (d, J=8.9 Hz, 1H), 7.08 (dd, J=14.3, 8.2 Hz, 2H), 6.76-6.65 (m, 2H), 5.61 (d, J=2.6 Hz, 1H), 4.15 (q, J=7.1 Hz, 1H), 3.97 (s, 3H), 3.37 (s, 3H), 2.44-2.34 (m, 3H), 1.86-1.70 (m, 18H), 1.58-1.50 (m, 1H), 0.92-0.86 (m, 1H).

Step B. (1R,2S)-5'-methoxy-2-{3-[(3-methoxy-6-methylpyridin-2-yl)amino]-1H-indazol-6-yl}-1'H-spiro[cyclopropane-1,3'-indol]-2'-one

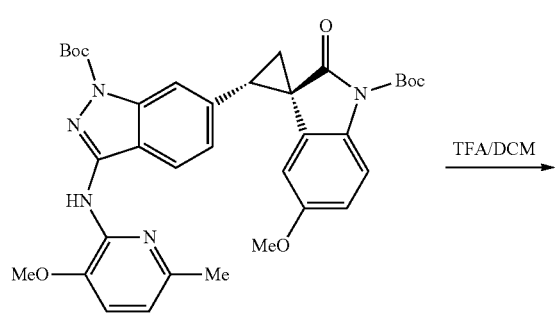

444

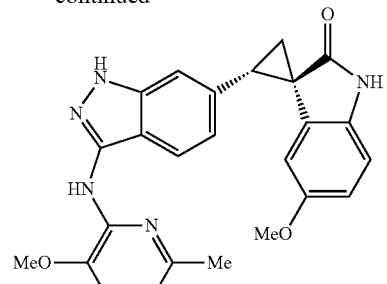

To a stirred mixture of tert-butyl (1R,2S)-2-[1-(tert-butoxycarbonyl)-3-[(3-methoxy-6-methylpyridin-2-yl)amino]indazol-6-yl]-5'-methoxy-2'-oxospiro[cyclopropane-1,3'-indole]-1'-carboxylate (59 mg, 1 equiv) in DCM (5 mL) was added TFA (1 mL) at 25° C. The solution was stirred for 2 hours. The mixture was concentrated under reduced pressure. The residue was purified by C18 silica gel; mobile phase, MeCN in water (5 mM NH$_4$HCO), 30% to 40/o gradient in 10 min; detector, UV 254 nm to afford Example 88 (20 mg, 49%) as an off-white solid. m/z (ESI+ve ion)=442.25 [M+H]$^+$. $^1$H NMR (400 MHz, DMSO-d$_6$) δ 12.35 (s, 1H), 10.41 (s, 1H), 8.04 (s, 1H), 7.55 (d, J=8.4 Hz, 1H), 7.33 (s, 1H), 7.10 (d, J=7.9 Hz, 1H), 6.89-6.82 (m, 1H), 6.75 (d, J=8.4 Hz, 1H), 6.62-6.53 (m, 2H), 5.73 (d, J=2.5 Hz, 1H), 3.84 (s, 3H), 3.33 (s, 3H), 3.18 (t, J=8.4 Hz, 1H), 2.31 (dd, J=7.9, 4.7 Hz, 1H), 2.12 (s, 3H), 1.98 (dd, J=9.0, 4.7 Hz, 1H).

Example 89. (1R,2S)-5'-methoxy-2-{3-[(2-methoxy-5-methylpyridin-3-yl)amino]-1H-indazol-6-yl}spiro[cyclopropane-1,3'-indol]-2'(1'H)-one

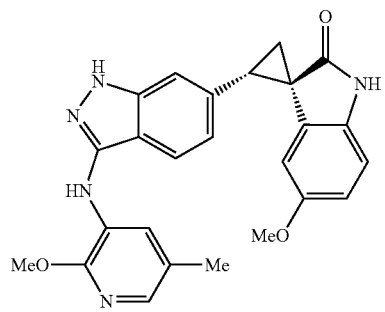 [SMILES: COc1ccc2c(c1)[C@]1(C[C@H]1c1ccc3c(Nc4cc(C)cnc4OC)n[nH]c3c1)C(=O)N2]

Step A. 2-methoxy-5-methylpyridin-3-amine

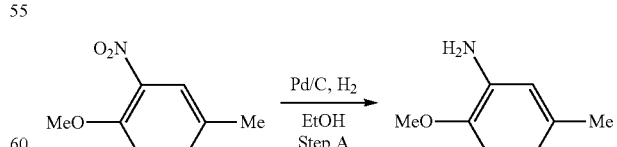

To a solution of 2-methoxy-5-methyl-3-nitropyridine (100.0 mg, 0.595 mmol, 1.00 equiv) in EtOH (4.0 mL) was added Pd/C (10%, 50.0 mg) under nitrogen atmosphere in a 50 mL round-bottom flask. The mixture was hydrogenated at room temperature for overnight under hydrogen atmosphere using a hydrogen balloon, filtered through a Celite pad, and concentrated under reduced pressure to afford the title compound (70.0 mg, 85.19%) as a white solid. m/z (ESI, +ve ion)=139.05 [M+H]⁺. ¹H NMR (400 MHz, Chloroform-d) δ 7.41 (d, J=4.0 Hz, 1H), 6.77 (d, J=4.0 Hz, 1H), 4.00 (s, 3H), 2.20 (s, 3H).

Step B tert-butyl (1R,2S)-2-[1-(tert-butoxycarbonyl)-3-[(2-methoxy-5-methylpyridin-3-yl)amino]indazol-6-yl]-5'-methoxy-2'-oxospiro[cyclopropane-1,3'-indole]-1'-carboxylate

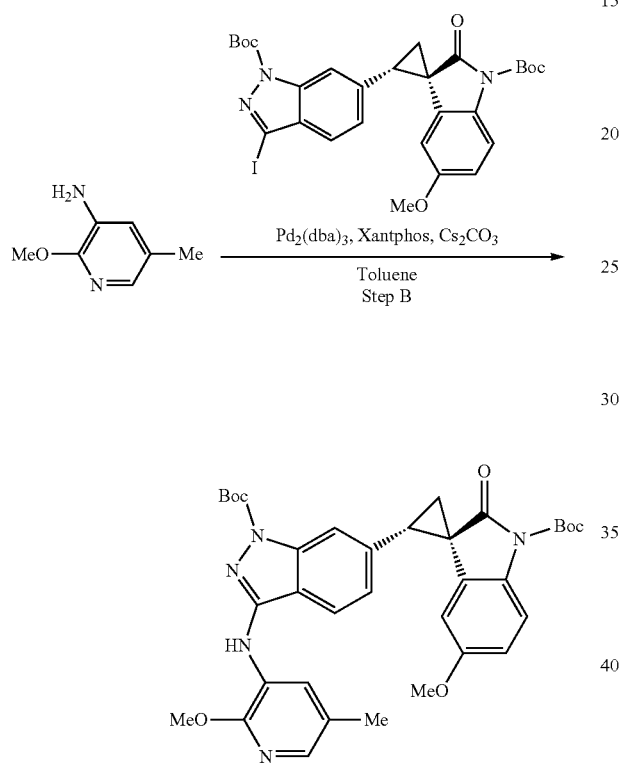

To a stirred solution of 2-methoxy-5-methylpyridin-3-amine (17.50 mg, 0.127 mmol, 1.0 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80.0 mg, 1.0 equiv) in toluene (4.0 mL) were added Cs₂CO₃ (82.56 mg, 0.254 mmol, 2.0 equiv) and XantPhos (14.66 mg, 0.025 mmol, 0.2 equiv) and Pd₂(dba)₃ (23.2 mg, 0.2 equiv) at room temperature under nitrogen atmosphere. The resulting mixture was stirred for 2 h at 90° C. under nitrogen atmosphere. The mixture was cooled down to room temperature. The resulting mixture was filtered, the filter cake was washed with EA (3×10 mL). The filtrate was concentrated under reduced pressure. The crude product was purified by prep-TLC (EA/PE=1/1) to afford the title compound (45.0 mg, 55.35%) as a yellow solid. m/z (ESI, +ve ion)=642.60 [M+H]⁺. ¹H NMR (400 MHz, Chloroform-d) δ 8.73 (s, 1H), 8.14 (s, 1H), 7.82 (d, J=8.0 Hz, 1H), 7.63 (s, 1H), 7.59 (d, J=8.0 Hz, 1H), 7.09 (s, 1H), 6.69 (d, J=8.0 Hz, 1H), 5.57 (s, 1H), 4.18 (s, 3H), 3.54 (d, J=8.0 Hz, 1H), 3.39 (s, 3H), 2.42-2.33 (m, 4H), 2.15-2.12 (m, 1H), 1.73 (s, 9H), 1.71 (s, 9H).

Step C. (1R,2S)-5'-methoxy-2-{3-[(2-methoxy-5-methylpyridin-3-yl)amino]-1H-indazol-6-yl}-1'H-spiro[cyclopropane-1,3'-indol]-2'-one

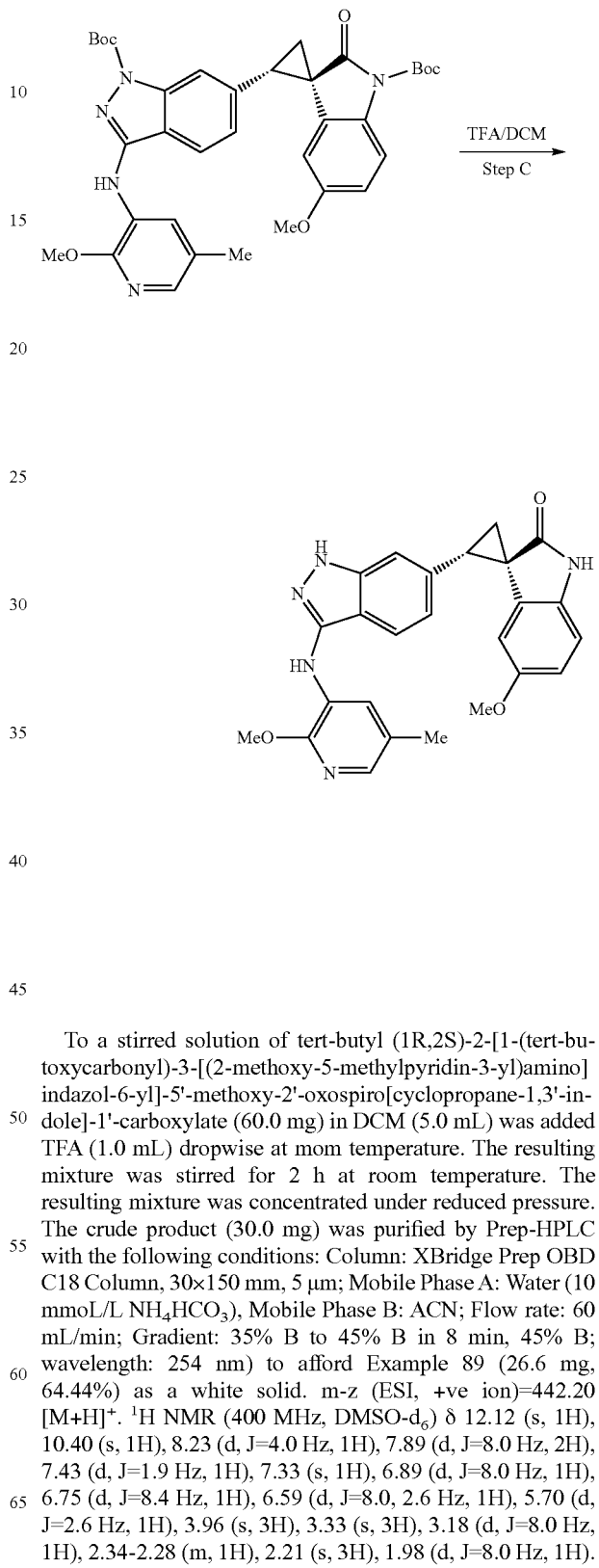

To a stirred solution of tert-butyl (1R,2S)-2-[1-(tert-butoxycarbonyl)-3-[(2-methoxy-5-methylpyridin-3-yl)amino]indazol-6-yl]-5'-methoxy-2'-oxospiro[cyclopropane-1,3'-indole]-1'-carboxylate (60.0 mg) in DCM (5.0 mL) was added TFA (1.0 mL) dropwise at mom temperature. The resulting mixture was stirred for 2 h at room temperature. The resulting mixture was concentrated under reduced pressure. The crude product (30.0 mg) was purified by Prep-HPLC with the following conditions: Column: XBridge Prep OBD C18 Column, 30×150 mm, 5 μm; Mobile Phase A: Water (10 mmoL/L NH₄HCO₃), Mobile Phase B: ACN; Flow rate: 60 mL/min; Gradient: 35% B to 45% B in 8 min, 45% B; wavelength: 254 nm) to afford Example 89 (26.6 mg, 64.44%) as a white solid. m-z (ESI, +ve ion)=442.20 [M+H]⁺. ¹H NMR (400 MHz, DMSO-d₆) δ 12.12 (s, 1H), 10.40 (s, 1H), 8.23 (d, J=4.0 Hz, 1H), 7.89 (d, J=8.0 Hz, 2H), 7.43 (d, J=1.9 Hz, 1H), 7.33 (s, 1H), 6.89 (d, J=8.0 Hz, 1H), 6.75 (d, J=8.4 Hz, 1H), 6.59 (d, J=8.0, 2.6 Hz, 1H), 5.70 (d, J=2.6 Hz, 1H), 3.96 (s, 3H), 3.33 (s, 3H), 3.18 (d, J=8.0 Hz, 1H), 2.34-2.28 (m, 1H), 2.21 (s, 3H), 1.98 (d, J=8.0 Hz, 1H).

Example 90. (1R,2S)-5'-methoxy-2-{3-[(4-methoxypyridazin-3-yl)amino]-1H-indazol-6-yl}spiro[cyclopropane-1,3'-indol]-2'(1'H)-one

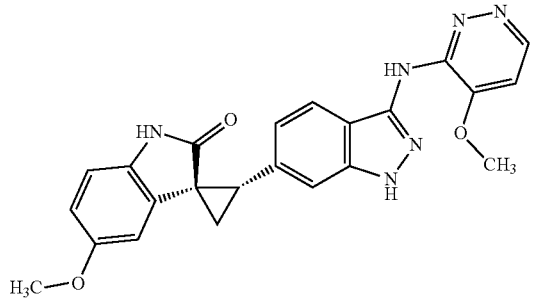 [SMILES: COc1ccc2c(c1)[C@]1(C[C@H]1c1ccc3c(Nc4nnccc4OC)n[nH]c3c1)C(=O)N2]

Example 90 was prepared using similar procedures as other examples, but using a 4-methoxypyridazinyl starting material.

Example 91. (1R,2S)-2-{3-[(3-cyclopropyl-1-methyl-1H-pyrazol-5-yl)amino]-1H-indazol-6-yl}-5'-methoxyspiro[cyclopropane-1,3'-indol]-2'(1'H)-one

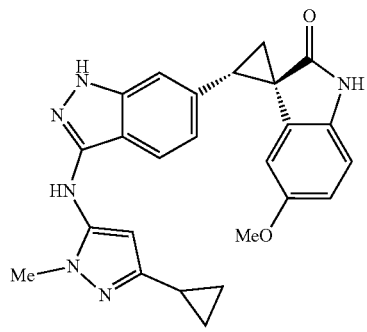 [SMILES: COc1ccc2c(c1)[C@]1(C[C@H]1c1ccc3c(Nc4cc(C5CC5)nn4C)n[nH]c3c1)C(=O)N2]

Step A. tert-butyl (1R,2S)-2-[1-(tert-butoxycarbonyl)-3-[(5-cyclopropyl-2-methylpyrazol-3-yl)amino]indazol-6-yl]-5'-methoxy-2'-oxospiro[cyclopropane-1,3'-indole]-1'-carboxylate

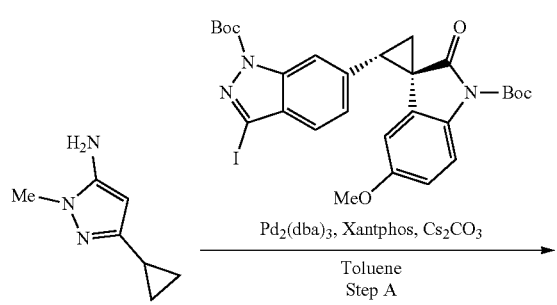

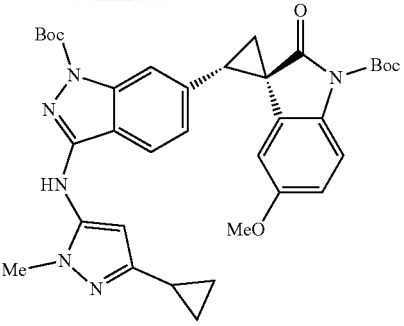

To a stirred solution of 5-cyclopropyl-2-methylpyrazol-3-amine (17.38 mg, 0.127 mmol, 1.0 equiv) and tert-butyl (R,2S)-2-[1-(tert-butoxycarbonyl)-3-iodoindazol-6-yl]-5'-methoxy-2'-oxospiro[cyclopropane-1,3'-indole]-1'-carboxylate (80.0 mg, 0.127 mmol, 1.00 equiv) in toluene (4.0 mL) were added Pd$_2$(dba)$_3$ (23.20 mg, 0.025 mmol, 0.2 equiv) and XantPhos (14.66 mg, 0.025 mmol, 0.2 equiv) and Cs$_2$CO$_3$ (82.56 mg, 0.254 mmol, 2.0 equiv) at room temperature under nitrogen atmosphere. The resulting mixture was stirred for 2 h at 90° C. under nitrogen atmosphere. The mixture was cooled down to room temperature. The resulting mixture was filtered, the filter cake was washed with EA (3×9 mL). The filtrate was concentrated under reduced pressure. The crude product was purified by prep-TLC (EA/PE=1/1) to afford the title compound (50.0 mg, 61.60%) as a yellow solid. m/z (ESI, +ve ion)=641.25 [M+H]$^+$.

Step B. (1R,2S)-2-{3-[(5-cyclopropyl-2-methylpyrazol-3-yl)amino]-1H-indazol-6-yl}-5'-methoxy-1'H-spiro[cyclopropane-1,3'-indol]-2'-one

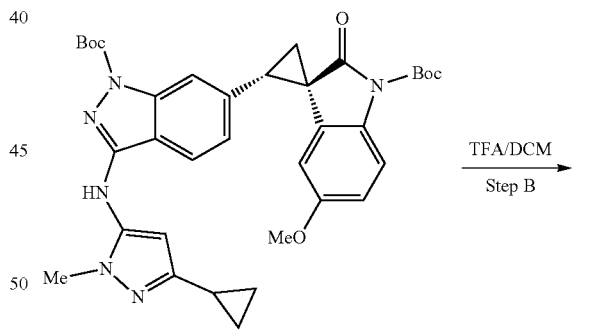

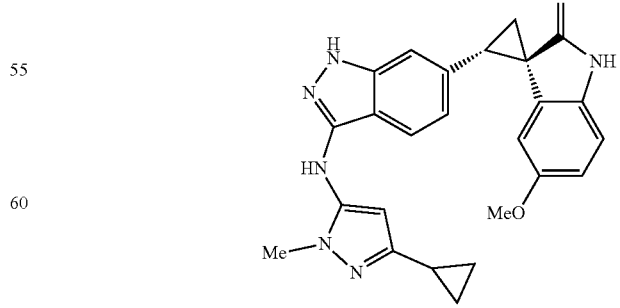

To a stirred solution of tert-butyl (1R,2S)-2-[1-(tert-butoxycarbonyl)-3-[(5-cyclopropyl-2-methylpyrazol-3-yl)

amino]indazol-6-yl]-5'-methoxy-2'-oxospiro[cyclopropane-1,3'-indole]-1'-carboxylate (50.0 mg, 0.078 mmol, 1.00 equiv) in DCM (5.0 mL) was added TFA (0.5 mL) dropwise at room temperature. The resulting mixture was stirred for 2 h at room temperature. The resulting mixture was concentrated under vacuum. The crude product (30 mg) was purified by Prep-HPLC with the following conditions (Column: Atlantis HILIC OBD Column, 19×150 mm, 5 μm; Mobile Phase A: Water (10 mmol/L NH$_4$HCO$_3$), Mobile Phase B: ACN; Flow rate: 60 mL/min; Gradient: 26% B to 34% B in 8 min, 34% B; wavelength: 254 nm; RT1(min): 6.95 to afford Example 91 (18.7 mg, 54.40%) as a white solid. m/z (ESI, +ve ion)=441.20 [M+H]$^+$. $^1$H NMR (400 MHz, Methanol-d$_4$) δ 7.55 (d, J=8.0 Hz, 1H), 7.32 (s, 1H), 6.81-6.89 (m, 2H), 6.63 (d, J=8.0, 4.0 Hz, 1H), 5.81 (s, 1H), 5.60 (d, J=4.0 Hz, 1H), 3.69 (s, 3H), 3.31 (s, 4H), 2.2-2.25 (m, 1H), 2.17 (d, J=8.0 Hz, 1H), 1.84 (d, J=8.0 Hz, 1H), 0.84-0.92 (m, 2H), 0.68 (s, 2H).

Example 92. (1R,2S)-2-{3-[(3-cyclopropyl-1-ethyl-1H-pyrazol-5-yl)amino]-1H-indazol-6-yl}-5'-methoxyspiro[cyclopropane-1,3'-indol]-2'(1'H)-one

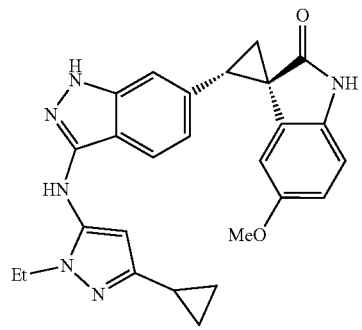 [SMILES: CCn1nc(C2CC2)cc1Nc1n[nH]c2cc([C@@H]3C[C@@]34C(=O)Nc3ccc(OC)cc34)ccc12]

Step A. tert-butyl (1R,2S)-2-[1-(tert-butoxycarbonyl)-3-[(5-cyclopropyl-2-ethylpyrazol-3-yl)amino]indazol-6-yl]-5'-methoxy-2'-oxospiro[cyclopropane-1,3'-indole]-1'-carboxylate

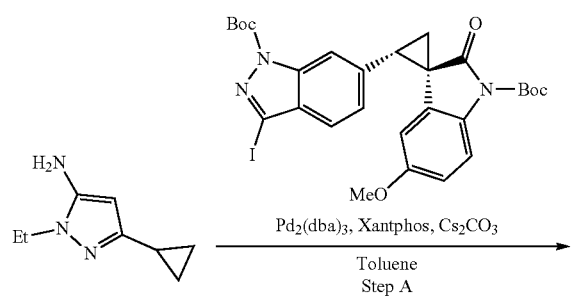

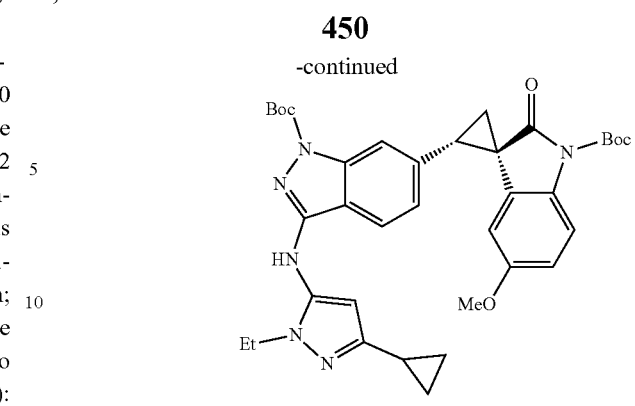

To a stirred solution of 5-cyclopropyl-2-ethylpyrazol-3-amine (16.76 mg, 0.111 mmol, 1.0 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (70.0 mg, 0.111 mmol, 1.00 equiv) in toluene (3.0 mL) were added Pd(dba), (10.15 mg, 0.011 mmol, 0.1 equiv) and XantPhos (6.41 mg, 0.011 mmol, 0.1 equiv) and Cs$_2$CO$_3$ (72.24 mg, 0.222 mmol, 2.0 equiv) at mom temperature under nitrogen atmosphere. The resulting mixture was stirred for 2 h at 90° C. under nitrogen atmosphere. The mixture was cooled down to room temperature. The resulting mixture was filtered, the filter cake was washed with EA (3×8 mL). The filtrate was concentrated under reduced pressure. The residue was purified by silica gel column chromatography, eluted with PE/EA (1/1) to afford the title compound (40.0 mg, 55.11%) as a yellow solid. m/z (ESI, +ve ion)=655.55 [M+H]$^+$.

Step B. (1R,2S)-2-{3-[(5-cyclopropyl-2-ethylpyrazol-3-yl)amino]-1H-indazol-6-yl}-5'-methoxy-1'H-spiro[cyclopropane-1,3'-indol]-2'-one

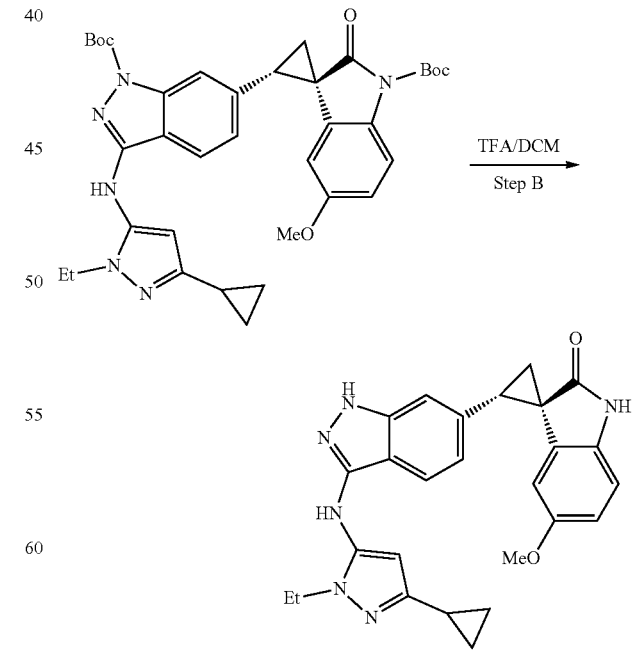

To a stirred solution of tert-butyl (1R,2S)-2-[1-(tert-butoxycarbonyl)-3-[(5-cyclopropyl-2-ethylpyrazol-3-yl)

amino]indazol-6-yl]-5'-methoxy-2'-oxospiro[cyclopropane-1,3'-indole]-1'-carboxylate (35.0 mg, 0.053 mmol, 1.0) equiv) in DCM (5.0 mL) was added TFA (0.5 mL, 6.732 mmol, 125.93 equiv) dropwise at room temperature. The resulting mixture was stirred for 4 h at room temperature. The resulting mixture was concentrated under vacuum. The crude product (20.0 mg) was purified by Prep-HPLC with the following conditions: Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 25% B to 50% B in 8 min, 50% B; wavelength: 254 nm; RT1(min): 6 to afford Example 92 (9.1 mg, 37.45%) as a pink solid. m/z (ESI, +ve ion)=455.15 [M+H]$^+$. $^1$H NMR (400 MHz, Methanol-d$_4$) δ 7.52 (d, J=8.0 Hz, 1H), 7.32 (s, 1H), 6.84 (d, J=8.0 Hz, 2H), 6.63 (d, J=8.0 Hz, 1H), 5.76 (s, 1H), 5.59 (d, J=4.0 Hz, 1H), 4.10-4.04 (m, 2H), 3.31 (s, 4H), 2.20 (d, J=8.0, Hz, 2H), 1.88-1.84 (t, J=8.0 Hz, 1H), 1.36 (t, J=4.0 Hz, 3H), 0.91-0.87 (m, 2H), 0.63-0.71 (m, 2H), 1.90-1.82 (m, 1H).

Example 93. (1R,2S)-2-(3-{[2-(2-hydroxy-2-methylpropyl)-5-methoxy-6-(morpholin-4-yl)pyrimidin-4-yl]amino}-1H-indazol-6-yl)-5'-methoxyspiro[cyclopropane-1,3'-indol]-2'(1'H)-one

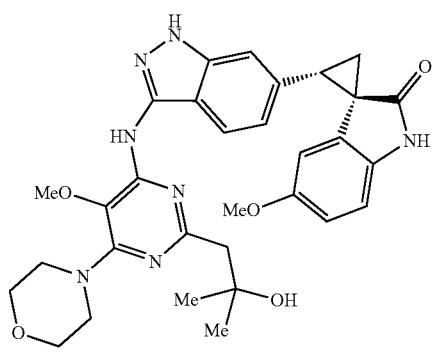 [SMILES: COc1ccc2c(c1)[C@]1(C[C@H]1c1ccc3c(Nc4nc(CC(C)(C)O)nc(N5CCOCC5)c4OC)n[nH]c3c1)C(=O)N2]

Step A. 1-[4-chloro-5-methoxy-6-(morpholin-4-yl)pyrimidin-2-yl]-2-methylpropan-2-ol

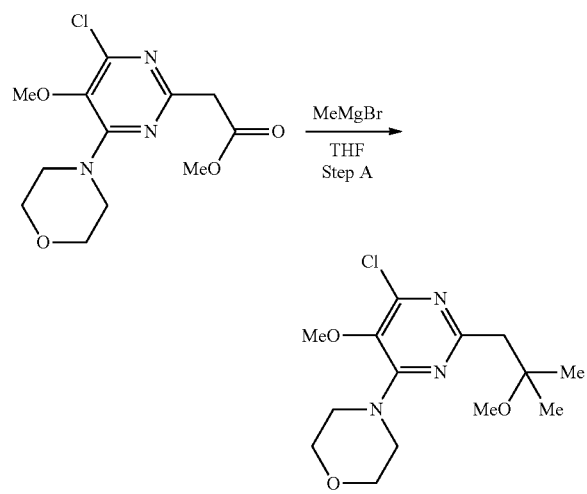

To a stirred solution of methyl 2-[4-chloro-5-methoxy-6-(morpholin-4-yl)pyrimidin-2-yl]acetate (150.0 mg, 0.497 mmol, 1.00 equiv) in THF (5.0 mL) were added MeMgBr (2.4 mg, 2.485 mmol, 5.0 equiv, 1M in THF) and LaCl$_3$·2LiCl (0.5 mL, 3 mmol, 0.6 M in THF) dropwise at 0° C. under nitrogen atmosphere. The resulting mixture was stirred for 2 h at room temperature under nitrogen atmosphere. The reaction was quenched by the addition of sat. NH$_4$Cl (aq., 20 mL) at room temperature. The aqueous layer was extracted with EtOAc (3×8 mL). The combined organic layer was concentrated under vacuum. The residue was purified by silica gel column chromatography, eluted with PE/EA (1/1) to afford the title compound (100.0 mg, 66.66%) as a white oil. m/z (ESI, +ve ion)=315.10 [M+H]$^+$. $^1$H NMR (400 MHz, DMSO-d$_6$) δ 3.65-3.76 (m, 11H), 2.72 (s, 2H), 1.16 (s, 6H).

Step B. tert-butyl (1R,2S)-2-[1-(tert-butoxycarbonyl)-3-{[2-(2-hydroxy-2-methylpropyl)-5-methoxy-6-(morpholin-4-yl)pyrimidin-4-yl]amino}indazol-6-yl]-5'-methoxy-2'-oxospiro[cyclopropane-1,3'-indole]-1'-carboxylate

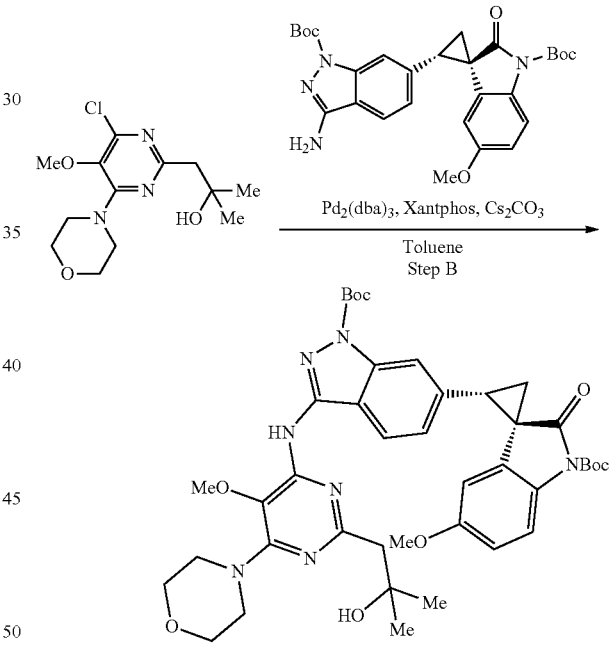

To a stirred solution of 1-[4-chloro-5-methoxy-6-(morpholin-4-yl)pyrimidin-2-yl]-2-methylpropan-2-el (57.97 mg, 0.192 mmol, 1.0 equiv) and tert-butyl (1R,2S)-2-[3-amino-1-(tert-butoxycarbonyl)indazol-6-yl]-5'-methoxy-2'-oxospiro[cyclopropane-1,3'-indole]-1'-carboxylate (100.0 mg, 1.0 equiv) in toluene (5.0 mL) were added Cs$_2$CO$_3$ (125.17 mg, 0.384 mmol, 2.0 equiv) and XantPhos (44.46 mg, 0.077 mmol, 0.4 equiv) and Pd$_2$(dba)$_3$ (70.36 mg, 0.4 equiv) at room temperature under nitrogen atmosphere. The resulting mixture was stirred for 3 h at 100° C. under nitrogen atmosphere. The mixture was cooled down to room temperature. The resulting mixture was filtered; the filter cake was washed with EtOAc (3×10 mL). The filtrate was concentrated under reduced pressure. The residue was purified by silica gel column chromatography, eluted with PE/EA (1/2) to afford the title compound (30.0 mg, 20.00% yield) as a yellow solid. m/z (ESI, +ve ion)=786.40 [M+H]+.

Step C. (1R,2S)-2-(3-{[2-(2-hydroxy-2-methylpropyl)-5-methoxy-6-(morpholin-4-yl)pyrimidin-4-yl]amino}-1H-indazol-6-yl)-5'-methoxy-1'H-spiro[cyclopropane-1,3'-indol]-2'-one

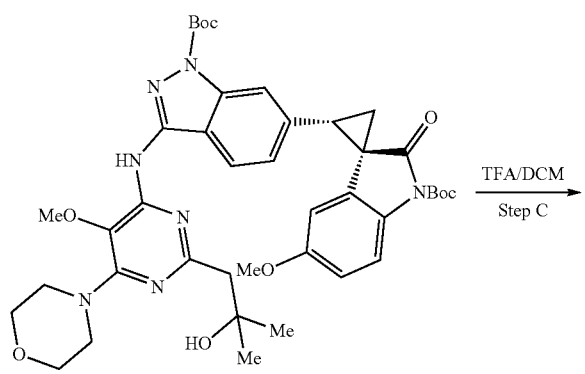

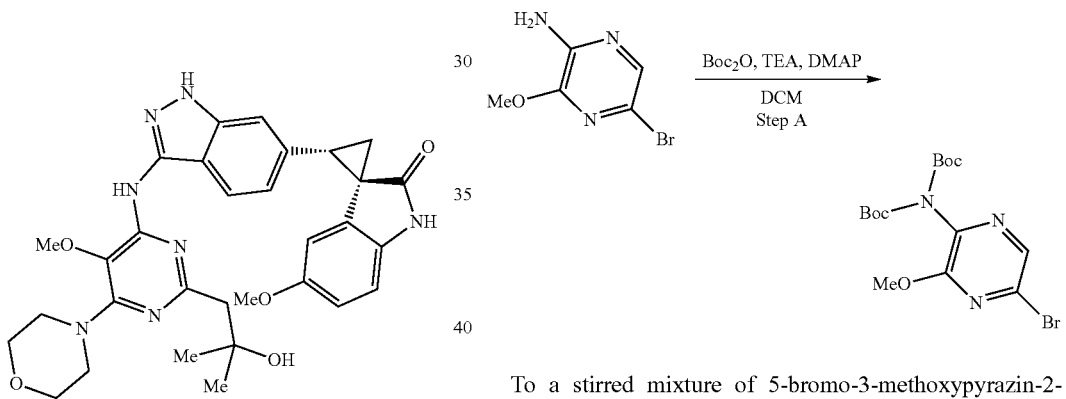

To a stirred solution of tert-butyl (1R,2S)-2-[1-(tert-butoxycarbonyl)-3-{[2-(2-hydroxy-2-methylpropyl)-5-methoxy-6-(morpholin-4-yl)pyrimidin-4-yl]amino}indazol-6-yl]-5'-methoxy-2'-oxospiro[cyclopropane-1,3'-indole]-1'-carboxylate (30.0 mg) in DCM (5.0 mL) was added TFA (0.5 mL) dropwise at room temperature under air atmosphere. The resulting mixture was stirred for 2 h at room temperature under air atmosphere. The resulting mixture was concentrated under reduced pressure. The crude product (25 mg) was purified by Prep-HPLC with the following conditions: Column: XBridge Prep OBD C18 Column, 30×150 mm, 5 μm; Mobile Phase A: Water (10 mmol/L NH4HCO3), Mobile Phase B: ACN; Flow rate: 60 mL/min; Gradient: 28% B to 38% B in 8 min, 38% B: wavelength: 254 nm to afford Example 93 (13.8 mg, 61.54%) as a white solid. m/z (ESI, +ve ion)=586.50 [M+H]+. 1H NMR (400 MHz, Methanol-d4) δ 7.59 (d, J=8.0 Hz, 1H), 7.44 (s, 1H), 6.91 (d, J=8.0 Hz, 1H), 6.84 (d, J=8.0 Hz, 1H), 6.63 (d, J=8.0 Hz, 1H), 5.63 (d, J=4.0 Hz, 1H), 3.77-3.86 (m, 7H), 3.68 (d, J=4.0 Hz, 4H), 3.50 (s, 1H), 3.36-3.39 (m, 3H), 2.64 (s, 2H), 2.27-2.23 (m, 1H), 2.19-2.17 (m, 1H), 1.13 (d, J=4.0 Hz, 6H).

Example 94. (1R,2S)-5'-methoxy-2-(3-{[3-methoxy-5-(morpholin-4-yl)pyrazin-2-yl]amino}-1H-indazol-6-yl)spiro[cyclopropane-1,3'-indol]-2'(1'H)-one

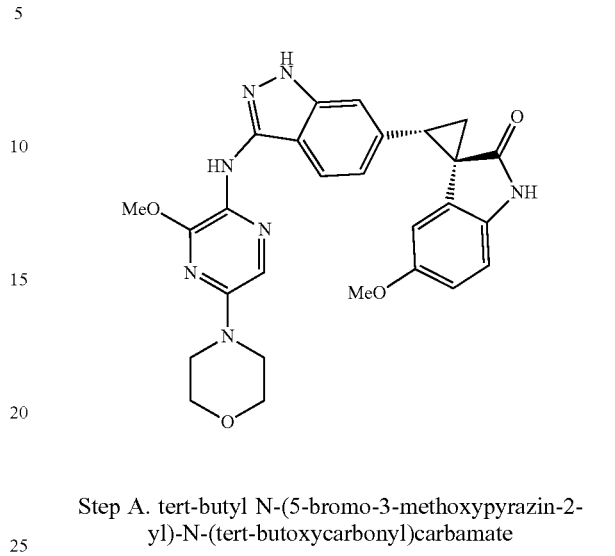

Step A. tert-butyl N-(5-bromo-3-methoxypyrazin-2-yl)-N-(tert-butoxycarbonyl)carbamate To a stirred mixture of 5-bromo-3-methoxypyrazin-2-amine (1 g, 4.901 mmol, 1.00 equiv) and (Boc)2O (2.35 g, 10.782 mmol, 2.2 equiv) in DCM (20 mL) was added TEA (1.09 g, 10.782 mmol, 2.2 equiv) and DMAP (0.06 g, 0.490 mmol, 0.1 equiv) at 25° C. under nitrogen atmosphere. The resulting mixture was warmed up to 50° C. and stirred for 16 hours. The mixture was concentrated under reduced pressure. The residue was purified by silica gel column chromatography, eluted with EA in PE, 1% to 21% gradient in 20 min to afford the title compound (1.4 g, 70.66%) as an off-white solid. m/z (ESI, +ve ion)=403.95 [M+H]+

Step B. tert-butyl N-(tert-butoxycarbonyl)-N-[3-methoxy-5-(morpholin-4-yl)pyrazin-2-yl]carbamate

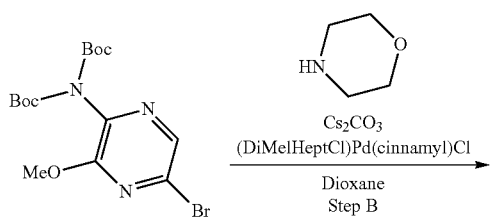

-continued

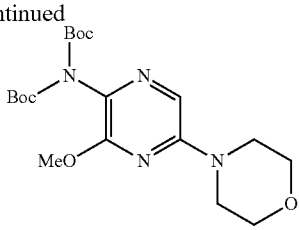

To a stirred mixture of tert-butyl N-(5-bromo-3-methoxy-pyrazin-2-yl)-N-(tert-butoxycarbonyl)carbamate (700 mg, 1.945 mmol, 1.00 equiv) and morpholine (254.24 mg, 2.917 mmol, 1.5 equiv) in 1,4-dioxane (2 mL) were added (DiMeI-HeptCl)Pd(cinnamyl)Cl (CAS: 2138491-47-9, 454.22 mg, 0.389 mmol, 0.2 equiv) and $Cs_2CO_3$ (296.26 mg, 3.890 mmol, 2 equiv) at 25° C. under nitrogen atmosphere. The mixture was warmed up to 100° C. and stirred for 2 h. The mixture was concentrated under reduced pressure. The residue was purified by silica gel column chromatography, eluted with EA in PE, 26% to 46% gradient in 20 min; Detector, UV: 254 nm to afford the title compound (270 mg, 33.81%) as an off-white solid. m/z (ESI, +ve ion)=411.20 $[M+H]^+$. $^1$H NMR (400 MHz, Chloroform-d) δ 7.48 (s, 1H), 3.93 (s, 3H), 3.89-3.82 (m, 4H), 3.58-3.53 (m, 4H), 1.45 (s, 18H).

Step C.
3-methoxy-5-(morpholin-4-yl)pyrazin-2-amine

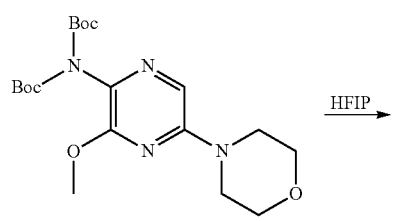

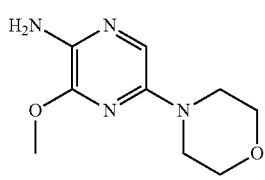

Into a vial were added tert-butyl N-(tert-butoxycarbonyl)-N-[3-methoxy-5-(morpholin-4-yl)pyrazin-2-yl]carbamate (270 mg, 0.658 mmol, 1.00 equiv) and 1,1,1,3,3,3-hexafluoropropan-2-ol (2 mL). The mixture was warmed up to 60° C. and stirred for 16 h. The mixture was concentrated under reduced pressure. The residue was purified by Prep-TLC (PF:EA=1:1) to afford the title compound (90 mg, 64%) as an off-white solid. m/z (ESI, +ve ion)=211.20 $[M+H]^+$.

Step D. tert-butyl (1R,2S)-2-[1-(tert-butoxycarbonyl)-3-{[3-methoxy-5-(morpholin-4-yl)pyrazin-2-yl]amino}indazol-6-yl]-5'-methoxy-2'-oxospiro[cyclopropane-1,3'-indole]-1'-carboxylate

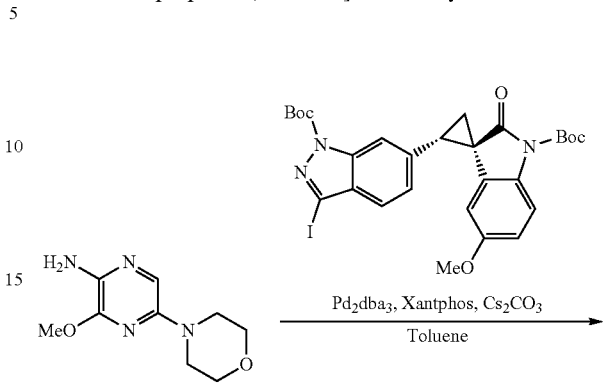

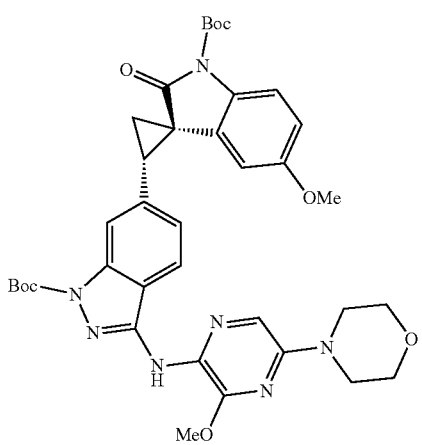

To a stirred mixture of 3-methoxy-5-(morpholin-4-yl)pyrazin-2-amine (10 mg, 0.048 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (30.04 mg, 0.048 mmol, 1 equiv) in 1,4-dioxane (1 mL, 11.350 mmol, 238.62 equiv) were added XantPhos (24 mg, 0.2 equiv), $Cs_2CO_3$ (31.00 mg, 0.096 mmol, 2 equiv) and $Pd_2(dba)_3$ (8.71 mg, 0.010 mmol, 0.2 equiv) under nitrogen atmosphere. The mixture was warmed up to 90° C. The mixture was concentrated under reduced pressure. The crude product was purified by silica gel chromatography, eluted with PE:EA=1:5 to afford the title compound (30 mg, 70%) as an off-white solid. m/z [ESI, +ve ion]=714.60, $[M+H]^+$.

457

Step E. (1R,2S)-5'-methoxy-2-(3-{[3-methoxy-5-(morpholin-4-yl)pyrazin-2-yl]amino}-1H-indazol-6-yl)-1'H-spiro[cyclopropane-1,3'-indol]-2'-one

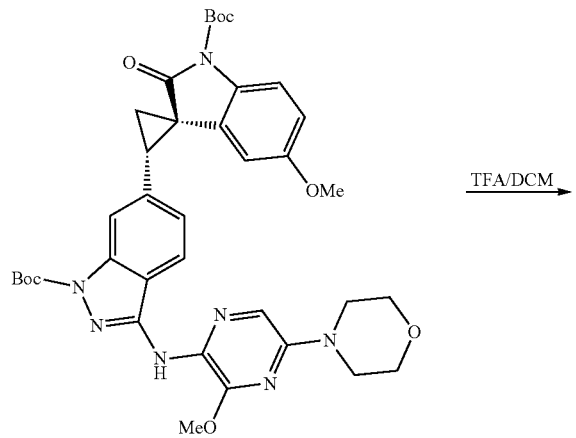

To a stirred solution of tert-butyl (1R,2S)-2-[1-(tert-butoxycarbonyl)-3-{3-methoxy-5-(morpholin-4-yl)pyrazin-2-yl]amino}indazol-6-yl]-5'-methoxy-2'-oxospiro[cyclopropane-1,3'-indole]-1'-carboxylate (20 mg, 0.028 mmol) in DCM (2.5 mL) was added TFA (0.5 mL) at 25° C. The solution was stirred for 30 minutes. The mixture was concentrated under reduced pressure. The residue was purified by prep-HPLC with following conditions: Column: XBridge Shield RP18 OBD Column, 30×150 mm, 5 μm; Mobile Phase A: Water (10 mmol/L NH$_4$HCO) Mobile Phase B: ACN; Flow rate: 60 mL/min; Gradient: 19% B to 29% B in 8 min, 29% B; wavelength: 254 nm; RT1(min): 7.28 to afford Example 94 (10 mg, 69%) as an off-white solid. m/z (ESI, +ve ion) 514.35 [M+H]$^+$. $^1$H NMR (400 MHz, Methanol-d$_4$): δ 7.61 (d, J=8.4 Hz, 1H), 7.37 (s, 1H), 7.12 (s, 1H), 6.89 (d, J=8.5 Hz, 1H), 6.84 (d, J=8.4 Hz, 1H), 6.63 (dd, J=8.4, 2.6 Hz, 1H), 5.65 (d, J=2.5 Hz, 1H), 4.06 (s, 3H), 3.87-3.75 (m, 4H), 3.33 (s, 5H), 3.30 (s, 3H), 2.25-2.16 (m, 2H).

458

Example 95. (1R,2S)-5'-methoxy-2-(3-{[3-methoxy-2-(morpholin-4-yl)pyridin-4-yl]amino}-1H-indazol-6-yl)spiro[cyclopropane-1,3'-indol]-2'(1'H)-one

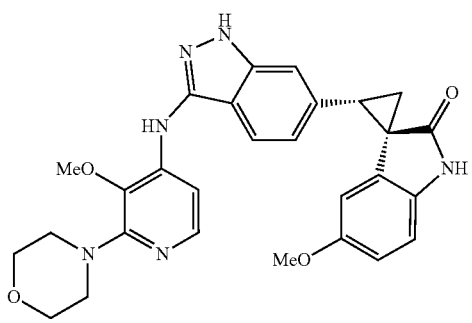 [SMILES: COc1ccc2c(c1)[C@]1(C[C@H]1c1ccc3c(Nc4ccnc(N5CCOCC5)c4OC)n[nH]c3c1)C(=O)N2]

Step A. tert-butyl N-(tert-butoxycarbonyl)-N-(2-chloro-3-methoxypyridin-4-yl)carbamate

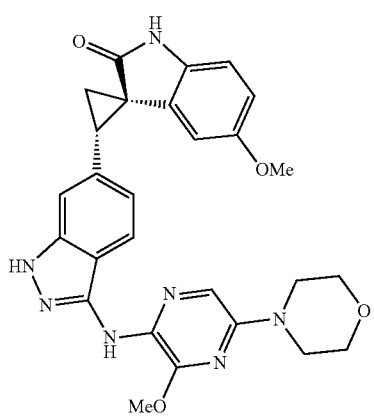

To the mixture of 2-chloro-3-methoxypyridin-4-amine (300 mg, 1.892 mmol, 1.00 equiv) in DCM (10.00 mL) and TEA (574.25 mg, 5.676 mmol, 3 equiv) were added Boc2O (1238.55 mg, 5.676 mmol, 3 equiv) and DMAP (23.11 mg, 0.189 mmol, 0.1 equiv) at 0° C. The mixture was stirred at 25° C. for 12 h. The mixture was diluted with DCM (50 mL) and washed with sat. NaHCO3 (20 mL) and brine (20 mL). The organic layer was dried over anhydrous Na$_2$SO$_4$, filtered and concentrated in vacuo. The residue was purified by silica gel column eluted with 0-50% of EA in PE to give the title compound (420 mg, 61.88%) as a light yellow solid. m/z (ESI=ve ion)=359.25 [M+H]+

Step B. tert-butyl N-[3-methoxy-2-(morpholin-4-yl)pyridin-4-yl]carbamate

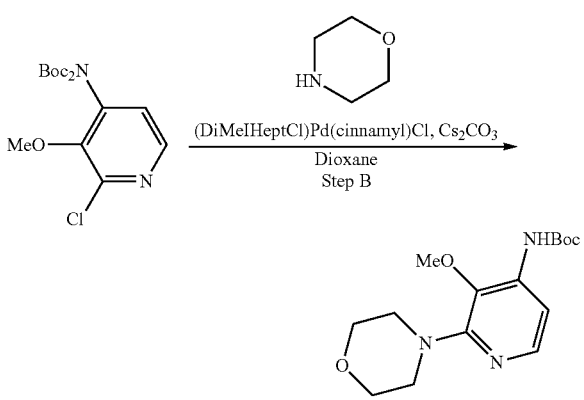

To the mixture of 61a (300 mg, 0.836 mmol, 1.00 equiv) and morpholine (145.68 mg, 1.672 mmol, 2 equiv) in dry dioxane (5 mL, 59.020 mmol, 70.59 equiv) were added Cs$_2$CO$_3$ (544.82 mg, 1.672 mmol, 2 equiv) and (DiMeIHeptCl)Pd(cinnamyl)Cl (195.20 mg, 0.167 mmol, 0.2 equiv) under nitrogen atmosphere. The mixture was stirred at 90° C. for 2 h. The mixture was filtered and washed with EA (5 mL×3). The filtrate was removed under reduced pressure. The residue was purified by silica gel column eluted with 0-100% of EA in PE to give crude the title compound (200 mg, 38.66%) as a yellow solid. m/z (ESI+ve ion)=310.20 [M+H]+

Step C.
3-methoxy-2-(morpholin-4-yl)pyridin-4-amine

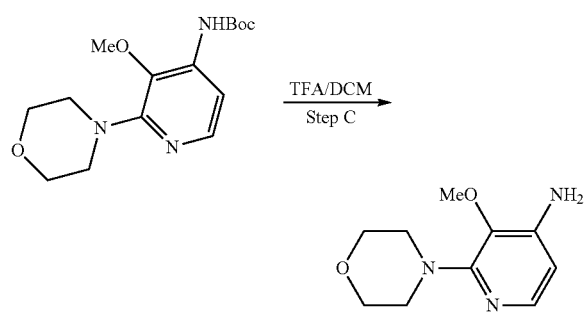

The mixture of tert-butyl N-[3-methoxy-2-(morpholin-4-yl)pyridin-4-yl]carbamate (200 mg, 0.323 mmol, 1.00 equiv) in TFA (0.5 mL, 6.732 mmol, 20.83 equiv) and DCM (3 mL) was stirred at 25° C. for 1 h. The solvent was removed under reduced pressure. The residue was purified by reverse phase flash with the following conditions: Column: AQ-C18 Column, 40 g, 40 g, 60 Å, 40-60 µm; Mobile Phase A: 10 mM aq. NH$_4$HCO$_3$, Mobile Phase B: MeCN; Flow rate: 60 mL/min; Gradient: 0% B to 0% B in 5 min, 0% B to 40% B in 30 min (41% hold 5 min); Detector: UV 254 & 280 nm. The product-containing fractions were concentrated to afford the title compound (60 mg, 88.71%) as a white solid. m/z (ESI+ve ion)=210.15 [M+H]+

Step D. tert-butyl (1R,2S)-2-[1-(tert-butoxycarbonyl)-3-{[3-methoxy-2-(morpholin-4-yl)pyridin-4-yl]amino}indazol-6-yl]-5'-methoxy-2'-oxospiro[cyclopropane-1,3'-indole]-1'-carboxylate

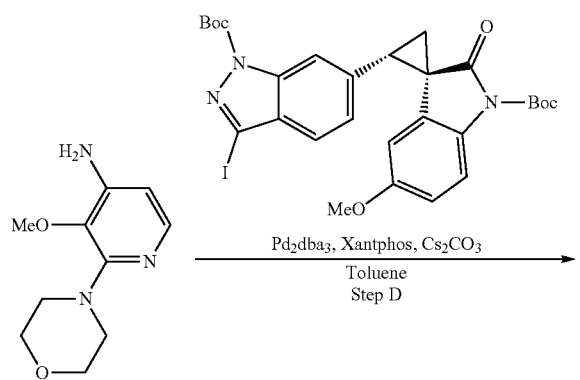

-continued

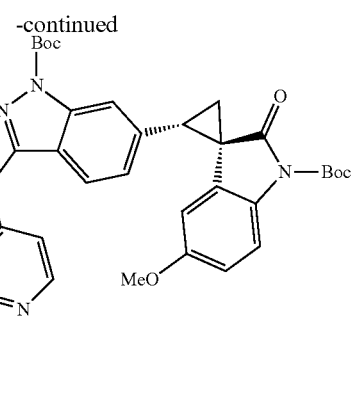

To a stirred solution of 3-methoxy-2-(morpholin-4-yl)pyridin-4-amine (13.25 mg, 0.063 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (40.0 mg, 0.063 mmol, 1.00 equiv) in toluene (2.0 mL) were added Pd$_2$(dba)$_3$ (11.60 mg, 0.013 mmol, 0.2 equiv) and XantPhos (7.33 mg, 0.013 mmol, 0.2 equiv) and Cs$_2$CO$_3$ (41.28 mg, 0.126 mmol, 2.0 equiv) at room temperature under nitrogen atmosphere. The resulting mixture was stirred for 2 h at 90° C. under nitrogen atmosphere. The mixture was cooled down to room temperature. The resulting mixture was filtered, the filter cake was washed with EA (3×10 mL). The filtrate was concentrated under reduced pressure. The residue was purified by silica gel column chromatography, eluted with PE/EA (1/1) to afford the title compound (25.0 mg, 55.37%) as a yellow solid. m/z (ESI, +ve ion)=713.55 [M+H]+.

Step E. (1R,2S)-5'-methoxy-2-(3-{[3-methoxy-2-(morpholin-4-yl)pyridin-4-yl]amino}-1H-indazol-6-yl)-1'H-spiro[cyclopropane-1,3'-indol]-2'-one

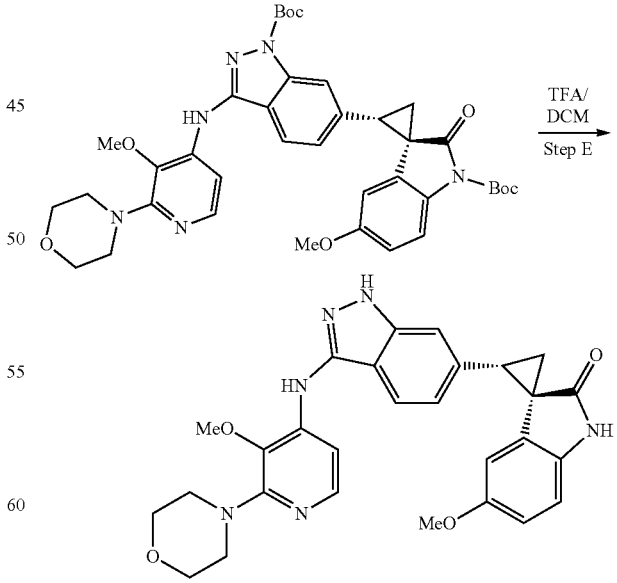

To a stirred solution of tert-butyl (1R,2S)-2-[1-(tert-butoxycarbonyl)-3-{[3-methoxy-24morpholin-4-yl)pyridin-4-yl]amino}indazol-6-yl]-5'-methoxy-2'-oxospiro[cyclopropane-1,3'-indole]-1'-carboxylate (20.0 mg) in DCM (5.0 mL) was added TFA (0.5 mL) dropwise at room temperature under air atmosphere. The resulting mixture was stirred for 2.0 h at room temperature under air atmosphere. The resulting mixture was concentrated under vacuum. The crude product (22 mg) was purified by Prep-HPLC with the following conditions: Column: XBridge Prep OBD C18 Column, 30×150 mm, 5 μm; Mobile Phase A: Water (10 mmol/L NH$_4$HCO$_3$). Mobile Phase B: ACN; Flow rate: 60 mL/min; Gradient: 28% B to 38% B in 8 min, 38% B; wavelength: 254 nm to afford Example 95 (10.8 mg, 75.09%) as a white solid. m/z (ESI, +ve ion)=513.30 [M+H]$^+$. $^1$H NMR (400 MHz, Methanol-d$_4$) δ 7.66 (d, J=8.0 Hz, 2H), 7.42 (s, 1H), 7.13 (d, J=4.0 Hz, 1H), 6.95 (d, J=8.0 Hz, 1H), 6.84 (d, J=8.0 Hz, 1H), 6.68-6.66 (m, 1H), 5.61 (d, J=4.0 Hz, 1H), 4.85 (s, 4H), 3.85-3.93 (m, 7H), 3.31-3.28 (m, 4H), 2.21-2.31 (m, 2H).

Example 96. (1R,2S)-2-{3-[(5-chloro-2-methylpyridin-4-yl)amino]-1H-indazol-6-yl}-5'-methoxyspiro[cyclopropane-1,3'-indol]-2'(1'H)-one

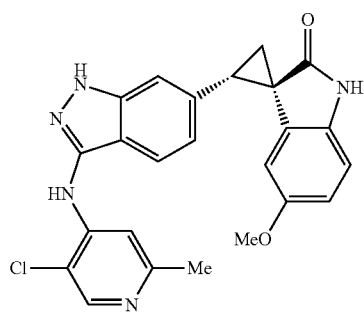 [SMILES: COc1ccc2c(c1)[C@]1(C[C@H]1c1ccc3c(Nc4cc(C)ncc4Cl)n[nH]c3c1)C(=O)N2]

Step A. tert-butyl (1R,2S)-2-[1-(tert-butoxycarbonyl)-3-[(5-chloro-2-methylpyridin-4-yl)amino]indazol-6-yl]-5'-methoxy-2'-oxospiro[cyclopropane-1,3'-indole]-1'-carboxylate

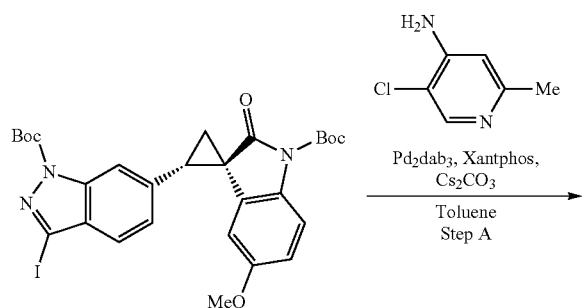

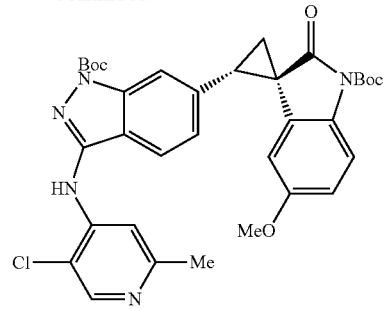

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (135 mg, 0.215 mmol, 1.00 equiv) and 5-chloro-2-methylpyridin-4-amine (30 mg, 0.215 mmol, 1 equiv) and Cs$_2$CO$_3$ (139 mg, 0.430 mmol, 2 equiv) in 1,4-dioxane (5 mL) were added Pd$_2$(dba)$_3$ (39 mg, 0.043 mmol, 0.2 equiv) and XantPhos (4.95 mg, 0.043 mmol, 0.2 equiv) at 25° C. under nitrogen atmosphere. The mixture was allowed to warmed up to 90° C. and stirred for 2 h. The mixture was allowed to cool down to 25° C. The residue was purified by silica gel column chromatography, eluted with EA in PE, 20% to 40% gradient in 20 min to afford the title compound (100 mg, 65%) as an off-white solid. m/z=646.30 [M+H]$^+$.

Step B. (1R,2S)-2-{3-[(5-chloro-2-methylpyridin-4-yl)amino]-1H-indazol-6-yl}-5'-methoxy-1'H-spiro[cyclopropane-1,3'-indol]-2'-one

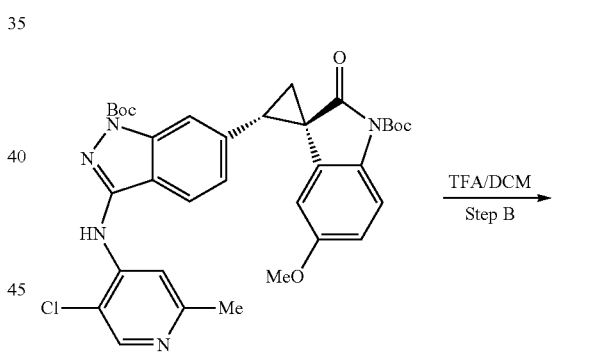

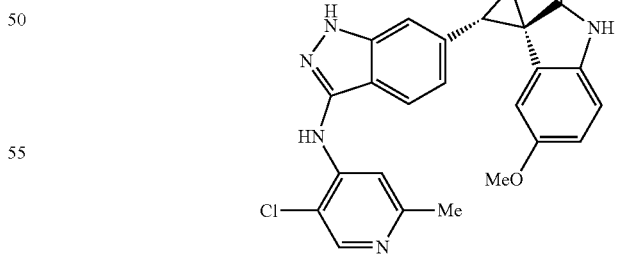

To a stirred mixture of tert-butyl (1R,2S)-2-[1-(tert-butoxycarbonyl)-3-[(5-chloro-2-methylpyridin-4-yl)amino]indazol-6-yl]-5'-methoxy-2'-oxospiro[cyclopropane-1,3'-indole]-1'-carboxylate (100 mg, 0.152 mmol, 1.00 equiv) in DCM (5 mL) was added TFA (1 mL) at 25° C. The solution was stirred for 30 minutes. The residue was purified by RP flash, MeCN in water (5 mM NH$_4$HCO$_3$), 10% to 30% gradient in 20 min to afford Example 96 (37.4 mg, 55.30%) as an off-white solid. m/z (ESI, +ve ion)=446.20 [M+H]+. 1H NMR (400 MHz, DMSO-d6) δ 12.71 (s, 1H), 10.44 (s, 1H), 8.55 (s, 1H), 8.23 (s, 1H), 7.64 (d, J=8.4 Hz, 1H), 7.44 (s, 1H), 7.22 (s, 1H), 6.95 (d, J=8.4 Hz, 1H), 6.75 (d, J=8.4 Hz, 1H), 6.59 (dd, J=8.4, 2.6 Hz, 1H), 5.69 (d, J=2.5 Hz, 1H), 3.30-3.20 (m, 4H), 2.40-2.18 (m, 4H), 1.99-1.97 (m, 1H).

Example 97. (1R,2S)-5'-methoxy-2-(3-{[5-methoxy-2-(morpholin-4-yl)pyrimidin-4-yl]amino}-1H-indazol-6-yl)spiro[cyclopropane-1,3'-indol]-2'(1'H)-one

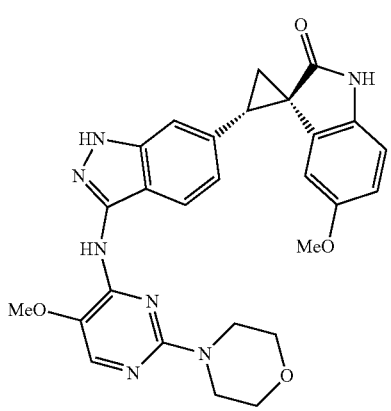 [SMILES: COc1ccc2c(c1)[C@]1(C[C@H]1c1ccc3c(Nc4nc(N5CCOCC5)ncc4OC)n[nH]c3c1)C(=O)N2]

Step A.
5-methoxy-2-(morpholin-4-yl)pyrimidin-4-amine

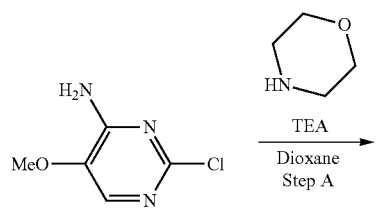

To a stirred solution of 2-chloro-5-methoxypyrimidin-4-amine (200 mg, 1.253 mmol, 1.00 equiv) and morpholine (545.98 mg, 6.265 mmol, 5 equiv) in 1,4-dioxane (5 mL) was added TEA (253.66 mg, 2.506 mmol, 2 equiv) at 25° C. under nitrogen atmosphere. The mixture was allowed to warm up to 120° C. for 2 hours. The residue was purified by silica gel column chromatography, eluted with 50% EA in PE to afford the title compound (54 mg, 20.49%) as an off-white solid. m/z (ESI, +ve ion)=211.10 [M+H]+. 1H NMR (400 MHz, DMSO-d6) δ 7.57 (s, 1H), 6.40 (s, 2H), 3.62-3.59 (m, 4H), 3.49-3.47 (m, 4H), 3.60 (s, 3H).

Step C. tert-butyl (1R,2S)-2-[1-(tert-butoxycarbonyl)-3-{[5-methoxy-2-(morpholin-4-yl)pyrimidin-4-yl]amino}indazol-6-yl]-5'-methoxy-2'-methylidene-spiro[cyclopropane-1,3'-indole]-1'-carboxylate

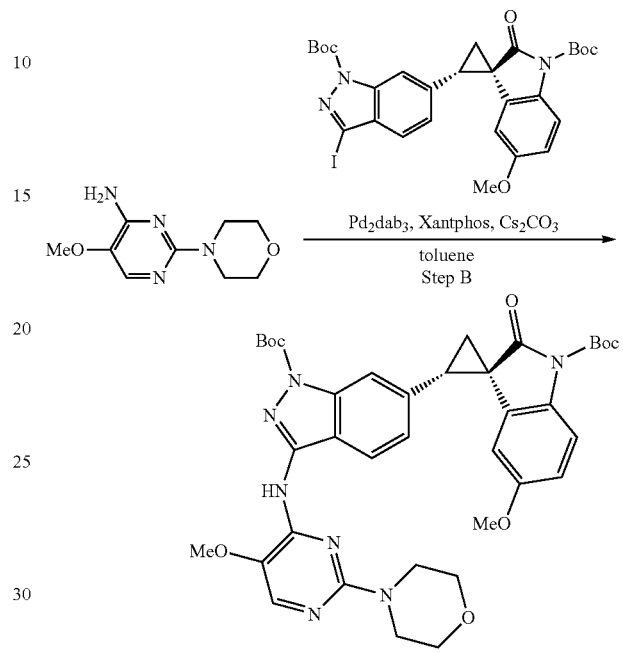

To a stirred mixture of 5-methoxy-2-(morpholin-4-yl)pyrimidin-4-amine (44 mg, 0.209 mmol, 1.00 equiv), tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (132.16 mg, 0.209 mmol, 1 equiv) and Cs2CO3 (136.38 mg, 0.418 mmol, 2 equiv) in 1,4-dioxane (2 mL) were added Pd2(dba)3 (38.33 mg, 0.042 mmol, 0.2 equiv) and XantPhos (24.22 mg, 0.042 mmol, 0.2 equiv) at 25° C. under nitrogen atmosphere. The mixture was allowed to warmed up to 90° C. The mixture was cooled down to 25° C. The residue was purified by silica gel column chromatography, eluted with EA in PE, 80% to 100% gradient in 20 min; Detector. UV 254 nm to afford the title compound (80 mg, 53.70%) as an off-white solid. m/z (ESI, +ve ion)=715.10[M+H]+.

Step C. (1R,2S)-5'-methoxy-2-(3-{[5-methoxy-2-(morpholin-4-yl)pyrimidin-4-yl]amino}-1H-indazol-6-yl)-1'H-spiro[cyclopropane-1,3'-indol]-2'-one

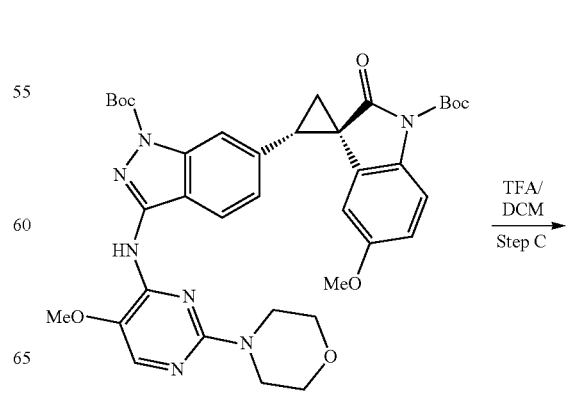

-continued

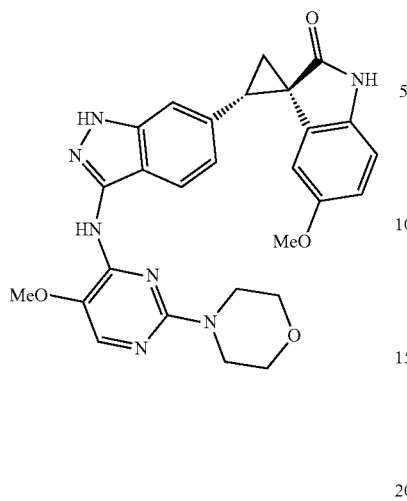

To a stirred mixture of tert-butyl (1R,2S)-2-[1-(tert-butoxycarbonyl)-3-{[5-methoxy-2-(morpholin-4-yl)pyrimidin-4-yl]amino}indazol-6-yl]-5'-methoxy-2'-methylidenespiro[cyclopropane-1,3'-indole]-1'-carboxylate (80 mg, 0.112 mmol, 1.00 equiv) in DCM (5 mL) was added TFA (1 mL) at 25° C. The solution was stirred for 30 minutes. The residue was purified by prep-HPLC with following condition: Column: XBridge Prep OBD C18 Column, 19×250 mm, 5 μm; Mobile Phase A: Water (10 mmoL/L NH₄HCO₃), Mobile Phase B: MeOH-HPLC; Flow rate: 25 mL/min; Gradient: 55% B to 60% B in 10 min, 60% B: wavelength: 254 nm; RT1(min): 9 to afford Example 97 (30 mg, 52.12%) as an off-white solid. m/z (ESI, +ve ion)=514.25 [M+H]⁺. ¹H NMR (400 MHz, Chloroform-d) δ 7.78-7.72 (m, 3H), 7.37 (s, 1H), 6.91 (d, J=8.3 Hz, 1H), 6.83 (d, J=8.4 Hz, 1H), 6.63 (dd, J=8.5, 2.6 Hz, 1H), 5.52 (d, J=2.5 Hz, 1H), 3.92 (s, 3H), 3.57-3.47 (m, 9H), 3.38 (s, 3H), 2.31-2.28 (m, 1H), 2.09-2.06 (m, 1H).

Example 98. (1R,2S)-2-{3-[(5-chloro-2-methylpyrimidin-4-yl)amino]-1H-indazol-6-yl}-5'-methoxyspiro[cyclopropane-1,3'-indol]-2'(1'H)-one

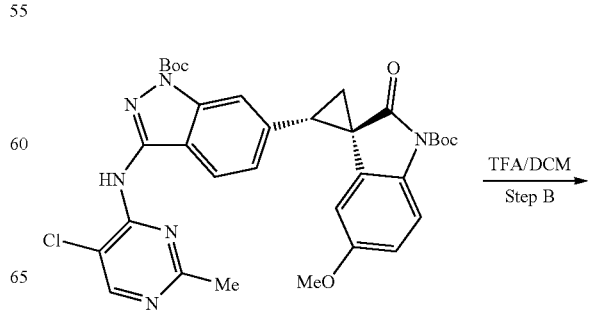

Step A. tert-butyl (1R,2S)-2-[1-tert-butoxycarbonyl)-3-[(5-chloro-2-methylpyrimidin-4-yl)amino]indazol-6-yl]-5'-methoxy-2'-oxospiro[cyclopropane-1,3'-indole]-1'-carboxylate

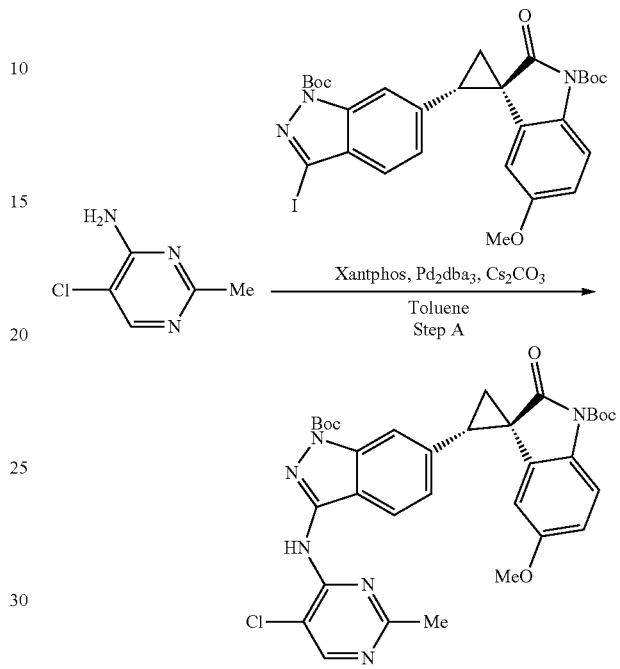

To a stirred mixture of 5-chloro-2-methylpyrimidin-4-amine (21.6 mg, 0.150 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (95.00 mg, 0.150 mmol, 1 equiv) in 1,4-dioxane (2 mL) and Cs₂CO₃ (98.04 mg, 0.300 mmol, 2 equiv) were added Pd₂(dba)₃ (27.55 mg, 0.030 mmol, 0.2 equiv) and XantPhos (17.41 mg, 0.030 mmol, 0.2 equiv) at 25° C. under nitrogen atmosphere. The mixture was warmed up to 90° C. and stirred for 2 h. The mixture was concentrated under reduced pressure. The residue was purified by silica gel column chromatography, eluted with EA in PE, 20% to 40% gradient in 20 min to afford the title compound (91 mg, 90%) as an off-white solid. m/z (ESI, +ve ion)=647.25 [M+H]⁺.

Step B. (1R,2S)-2-{3-[(5-chloro-2-methylpyrimidin-4-yl)amino]-1H-indazol-6-yl}-5'-methoxy-1'H-spiro[cyclopropane-1,3'-indol]-2'-one -continued

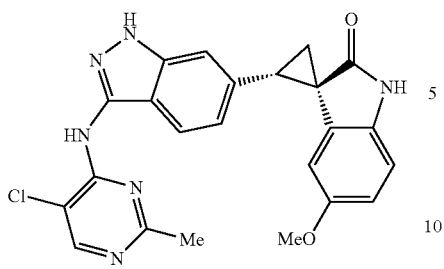

To a stirred mixture of tert-butyl (1R,2S)-2-[1-(tert-butoxycarbonyl)-3-[(5-chloro-2-methylpyrimidin-4-yl)amino]indazol-6-yl]-5'-methoxy-2'-oxospiro[cyclopropane-1,3'-indole]-1'-carboxylate (91 mg) in DCM (5 mL) was added TFA (1 mL) at 25° C. The solution was stirred for 30 minutes. Desired product could be detected by LCMS. The mixture was concentrated under reduced pressure. The residue was purified by prep-HPLC with following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 27% B to 37% B in 8 min, 37% B; wavelength: 254 nm; RT1(min): 7 to afford Example 98 (29 mg) as an off-white solid. m/z (ESI, +ve ion)=447.15 [M+H]$^+$. $^1$H NMR (400 MHz, Methanol-d$_4$) δ 8.27 (s, 1H), 7.60-7.36 (m, 2H), 6.94 (dd, J=8.4, 1.4 Hz, 1H), 6.84 (d, J=8.5 Hz, 1H), 6.63 (dd, J=8.5, 2.5 Hz, 1H), 5.61 (d, J=2.5 Hz, 1H), 3.38 (t, J=8.4 Hz, 1H), 3.30 (s, 3H), 2.32 (s, 3H), 2.47-2.08 (m, 2H).

Example 99. (1R,2S)-5'-methoxy-2-(3-{[3-methoxy-6-(morpholin-4-yl)pyrazin-2-yl]amino}-1H-indazol-6-yl)spiro[cyclopropane-1,3'-indol]-2'(1'H)-one

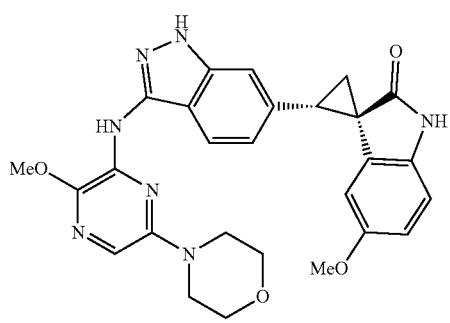 [SMILES: COc1ccc2c(c1)[C@]1(C[C@H]1c1ccc3c(Nc4nc(N5CCOCC5)cnc4OC)n[nH]c3c1)C(=O)N2]

Step A. tert-butyl N-(tert-butoxycarbonyl)-N-[3-methoxy-6-(morpholin-4-yl) pyrazin-2-yl]carbamate

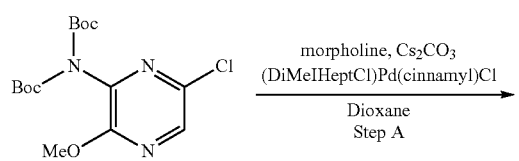

-continued

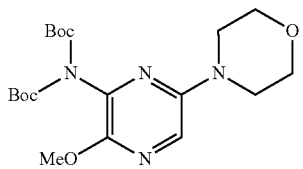

To a stirred solution of tert-butyl (tert-butoxycarbonyl)(6-chloro-3-methoxypyrazin-2-yl)carbamate (100.0 mg, 0.278 mmol, 1.00 equiv) and morpholine (72.64 mg, 0.834 mmol, 3.0 equiv) in dioxane (5.0 mL) were added (DiMeIHeptCl)Pd(cinnamyl)Cl (CAS: 2138491-47-9, 64.89 mg, 0.056 mmol, 0.2 equiv) and Cs$_2$CO$_3$ (181.11 mg, 0.556 mmol, 2.0 equiv) at room temperature under nitrogen atmosphere. The resulting mixture was stirred for 5 h at 100° C. under nitrogen atmosphere. The mixture was cooled down to room temperature. The residue was purified by silica gel column chromatography, eluted with PE/EA (1/3) to afford the title compound (60.0 mg, 27.61%) as a yellow solid. m/z (ESI, +ve ion)=411.22 [M+H]$^+$.

Step B.
3-methoxy-6-(morpholin-4-yl)pyrazin-2-amine

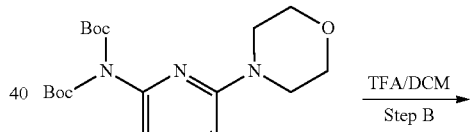

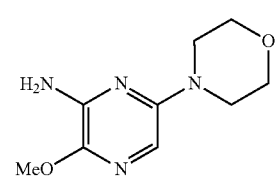

To a stirred solution of tert-butyl N-(tert-butoxycarbonyl)-N-[3-methoxy-6-(morpholin-4-yl)pyrazin-2-yl]carbamate (100.0 mg, 0.244 mmol, 1.00 equiv) in DCM (20.0 mL) was added TFA (2.0 mL) dropwise at room temperature. The resulting mixture was stirred for 5 h at room temperature. The resulting mixture was concentrated under reduced pressure to afford the title compound (40.0 mg, 78.10%) as a light yellow solid. m/z (ESI, +ve ion)=211.10 [M+H]$^+$.

Step C. tert-butyl (1R,2S)-2-[1-(tert-butoxycarbonyl)-3-{[3-methoxy-6-(morpholin-4-yl)pyrazin-2-yl]amino}indazol-6-yl]-5'-methoxy-2'-oxospiro[cyclopropane-1,3'-indole]-1'-carboxylate

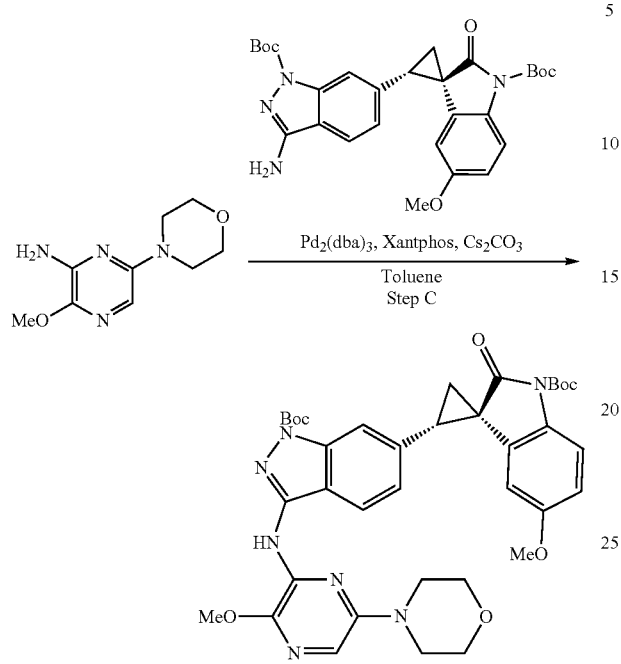

To a stirred solution of 3-methoxy-6-(morpholin-4-yl)pyrazin-2-amine (19.98 mg, 0.095 mmol, 1.0 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (60.0 mg, 0.095 mmol, 1.00 equiv) in toluene (3.0 mL) were added $Cs_2CO_3$ (61.92 mg, 0.190 mmol, 2.0 equiv), XantPhos (11.00 mg, 0.019 mmol, 0.2 equiv) and $Pd_2(dba)_3$ (17.40 mg, 0.019 mmol, 0.2 equiv) at room temperature under nitrogen atmosphere. The resulting mixture was stirred for 2 h at 90° C. under nitrogen atmosphere. The mixture was cooled down to room temperature. The resulting mixture was filtered, the filter cake was washed with EA (3×10 mL). The filtrate was concentrated under reduced pressure. The residue was purified by silica gel column chromatography, eluted with PE/EA (4/1) to afford the title compound (50.0 mg, 73.72%) as a yellow solid. m/z (ESI, +ve ion)=714.35 $[M+H]^+$.

Step D. (1R,2S)-5'-methoxy-2-(3-{[3-methoxy-6-(morpholin-4-yl)pyrazin-2-yl]amino}-1H-indazol-6-yl)-1'H-spiro[cyclopropane-1,3'-indol]-2'-one

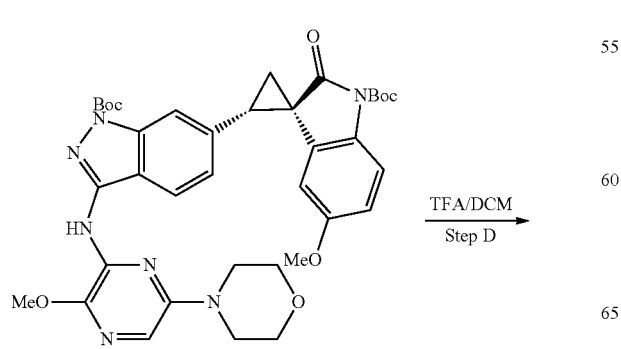

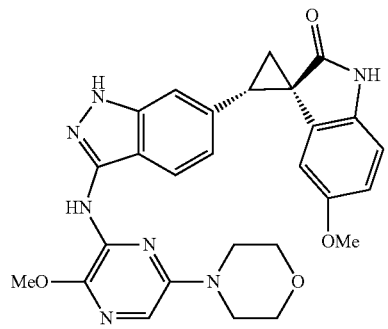

To a stirred solution of tert-butyl (1R,2S)-2-[1-(tert-butoxycarbonyl)-3-{[3-methoxy-6-(morpholin-4-yl)pyrazin-2-yl]amino}indazol-6-yl]-5'-methoxy-2'-oxospiro[cyclopropane-1,3'-indole]-1'-carboxylate (50.0 mg, 0.070 mmol, 1.00 equiv) in DCM (10.0 mL) was added TFA (1.0 mL) dropwise at room temperature. The resulting mixture was stirred for 5 h at room temperature. The reaction was monitored by LCMS. The resulting mixture was concentrated under vacuum. The crude product (30.0 mg) was purified by Prep-HPLC with the following conditions: Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 15% B to 35% B in 8 min, 35% B; wavelength: 254 nm to afford Example 99 (11.7 mg, 32.52%) as a pink solid. m/z (ESI, +ve ion)=514.40 $[M+H]^+$. $^1$H NMR (400 MHz, Methanol-$d_4$) δ 7.60 (d, J=8.0 Hz, 1H), 7.45 (s, 1H), 6.96 (s, 1H), 6.86 (d, J=8.0 Hz, 2H), 6.64 (d, J=8.0 Hz, 1H), 5.61 (d, J=4.0 Hz, 1H), 4.01 (s, 3H), 3.5-3.57 (m, 4H), 3.30 (s, 4H), 3.08 (d, J=8.0 Hz, 4H), 2.28-2.24 (m, 1H), 2.19-2.15 (m, 1H).

Example 100. (1R,2S)-5'-methoxy-2-(3-{[3-methoxy-6-(oxetan-3-yl)pyrazin-2-yl]amino}-1H-indazol-6-yl)spiro[cyclopropane-1,3'-indol]-2'(1'H)-one

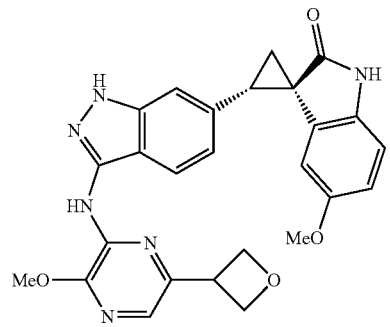 [SMILES: COc1ccc2c(c1)[C@]1(C[C@H]1c1ccc3c(Nc4nc(C5COC5)cnc4OC)n[nH]c3c1)C(=O)N2]

Step A. tert-butyl N-(tert-butoxycarbonyl)-N-[3-methoxy-6-(oxetan-3-yl)pyrazin-2-yl]carbamate

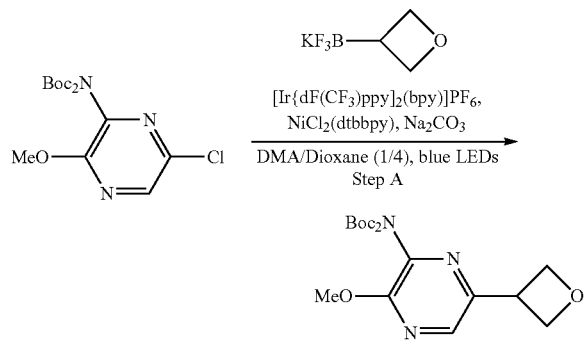

The mixture of tert-butyl (tert-butoxycarbonyl)(6-chloro-3-methoxypyrazin-2-yl)carbamate (160 mg, 0.445 mmol, 1.00 equiv), trifluoro(oxetan-3-yl)-lambda4-borane potassium (145.84 mg, 0.890 mmol, 2 equiv), [Ir{dFCF$_3$ppy}$_2$(bpy)]PF$_6$ (44.90 mg, 0.045 mmol, 0.1 equiv), [4,4'-Bis(1,1-dimethylethyl)-2,2'-bipyridine] nickel (II) dichloride (26.55 mg, 0.067 mmol, 0.15 equiv) and Na$_2$CO$_3$ (94.26 mg, 0.890 mmol, 2 equiv) in DMA (0.4 mL) and dioxane (1.6 mL) was stirred for 16 h at 25° C. under nitrogen atmosphere. The reaction mixture is irradiated under blue LEDs and away from light. The solvent was removed under reduced pressure. The residue was purified by silica gel column chromatography, eluted with 0-50% of EA in PE to afford the title compound (110 mg, 64.85%) as a light yellow solid. m/z (ESI+ve ion)=382.20 [M+H]$^+$. $^1$H NMR (400 MHz, Chloroform-d) δ 7.97 (s, 1H), 5.05-5.02 (m, 2H), 4.95-4.92 (m, 2H), 4.45-4.37 (m, 1H), 4.01 (s, 3H), 1.44 (s, 18H).

Step B. 3-methoxy-6-(oxetan-3-yl)pyrazin-2-amine

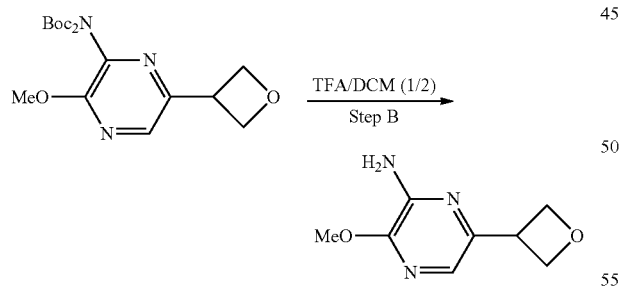

To a stirred solution of tert-butyl N-(tert-butoxycarbonyl)-N-[3-methoxy-6-(oxetan-3-yl)pyrazin-2-yl]carbamate (100 mg, 0.262 mmol, 1.00 equiv) in DCM (2 mL) was added TFA (1 mL). The resulting mixture was stirred for 1 h at room temperature. The resulting mixture was concentrated under reduced pressure to afford the title compound (45 mg, 94.73%) as an off-white solid. m/z (ESI+ve ion)=182.10 [M+H]$^+$. $^1$H NMR (400 MHz, DMSO-d$_6$) δ 7.16 (s, 1H), 6.38 (s, 2H), 4.80-4.70 (m, 4H), 4.20-4.12 (m, 1H), 3.86 (s, 3H).

Step C. tert-butyl (1R,2S)-2-[1-(tert-butoxycarbonyl)-3-{[3-methoxy-6-(oxetan-3-yl)pyrazin-2-yl]amino}indazol-6-yl]-5'-methoxy-2'-oxospiro[cyclopropane-1,3'-indole]-1'-carboxylate

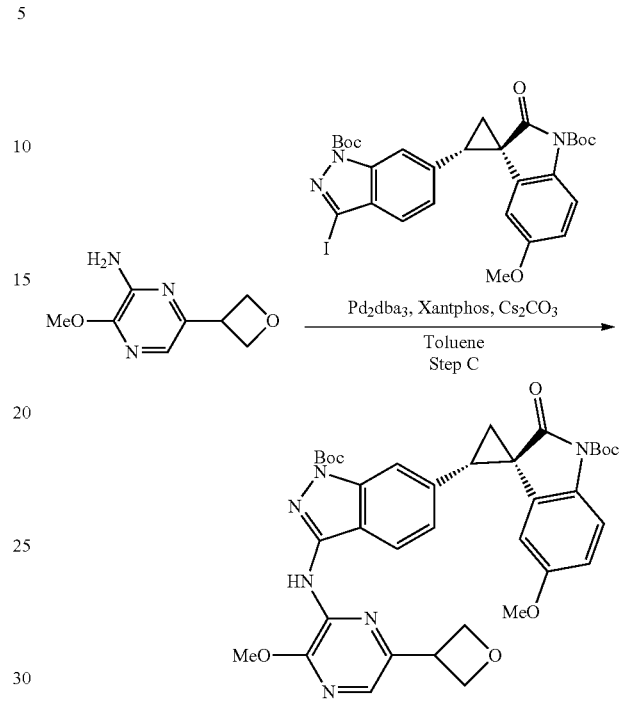

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (90 mg, 0.143 mmol, 1.00 equiv) and 3-methoxy-6-(oxetan-3-yl)pyrazin-2-amine (30.99 mg, 0.172 mmol, 1.2 equiv) in toluene (2.50 mL) were added Cs$_2$CO$_3$ (92.88 mg, 0.286 mmol, 2 equiv), Pd$_2$(dba)$_3$ (26.10 mg, 0.029 mmol, 0.2 equiv) and XantPhos (16.49 mg, 0.029 mmol, 0.2 equiv) under nitrogen atmosphere. The resulting mixture was stirred for 2 h at 90° C. under nitrogen atmosphere. The mixture was filtered and washed with EA (3×5 mL). The filtrate was concentrated in vacuo. The residue was purified by silica gel column chromatography, eluted with 0-50% of EA in PE to afford the title compound (80 mg, 81.97%) as a yellow solid. m/z (ESI+ve ion)=685.30 [M+H]$^+$.

Step D. (1R,2S)-5'-methoxy-2-(3-{[3-methoxy-6-(oxetan-3-yl)pyrazin-2-yl]amino}-1H-indazol-6-yl)-1'H-spiro[cyclopropane-1,3'-indol]-2'-one

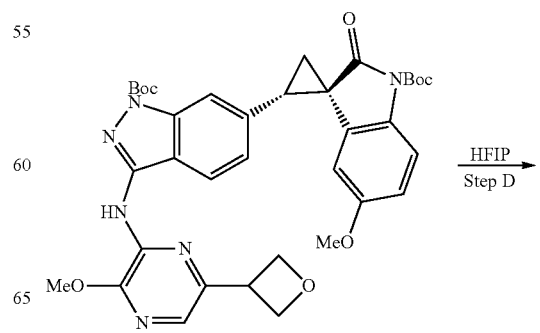

-continued

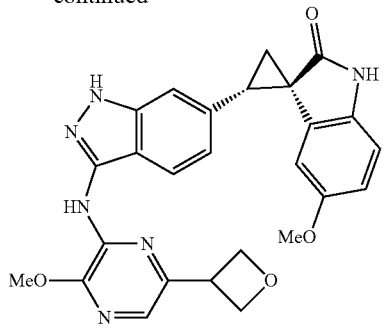

The mixture of tert-butyl (1R,2S)-2-[1-(tert-butoxycarbonyl)-3-{[3-methoxy-6-(oxetan-3-yl)pyrazin-2-yl]amino}indazol-6-yl]-5'-methoxy-2'-oxospiro[cyclopropane-1,3'-indole]-1'-carboxylate (75 mg, 0.110 mmol, 1.00 equiv) in HFIP (5 mL) was stirred at 60° C. for 12 h. The solvent was removed under reduced pressure. The residue was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 23% B to 33% B in 8 min; wavelength: 254 nm; RT1(min): 7. The product-containing fractions were collected and concentrated in vacuo to afford Example 100 (29.8 mg, 56.10%) as a white solid. m/z (ESI+ve ion)=485.25 [M+H]$^+$. $^1$H NMR (400 MHz, Methanol-$d_4$) δ 7.69 (d, J=8.4 Hz, 1H), 7.41-7.40 (m, 2H), 6.92-6.89 (m, 1H), 6.84 (d, J=8.4 Hz, 1H), 6.64-6.62 (m, 1H), 5.63 (d, J=2.4 Hz, 1H), 4.81-4.75 (m, 4H), 4.25-4.19 (m, 1H), 4.08 (s, 3H), 3.37 (d, J=8.4 Hz, 1H), 3.31 (s, 3H), 2.25-2.22 (m, 1H), 2.20-2.16 (m, 1H).

Example 101. (1R,2S)-5'-methoxy-2-(3-{[3-methoxy-6-(propan-2-yl)pyridazin-4-yl]amino}-1H-indazol-6-yl)spiro[cyclopropane-1,3'-indol]-2'(1'H)-one

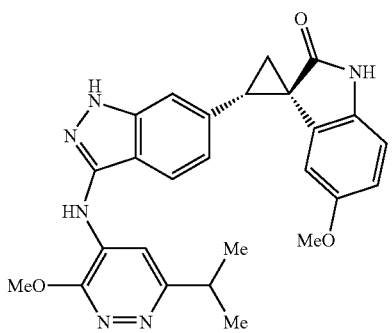 [SMILES: COc1ccc2c(c1)[C@]1(C[C@H]1c1ccc3c(Nc4cc(C(C)C)nnc4OC)n[nH]c3c1)C(=O)N2]

Step A. 6-chloro-3-methoxypridazin-4-amine

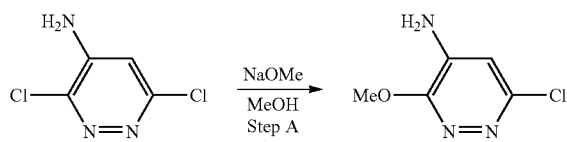 [SMILES: Nc1cc(Cl)nnc1Cl ; COc1nnc(Cl)cc1N ; "NaOMe"]

To a stirred solution of 3,6-dichloropyridazin-4-amine (500.0 mg, 3.049 mmol, 1.00 equiv) in MeOH (10.0 mL) was added NaOMe (658.87 mg, 12.196 mmol, 4.0 equiv) in portions at 0° C. under nitrogen atmosphere. The resulting mixture was stirred for 3 h at 55° C. under nitrogen atmosphere. The resulting mixture was concentrated under reduced pressure. The resulting mixture was extracted with EtOAc (3×50 mL). The combined organic layers were washed with brine (3×10 mL), dried over anhydrous $Na_2SO_4$. After filtration, the filtrate was concentrated under reduced pressure. The residue was purified by silica gel column chromatography, eluted with PE/EA (5/1) to afford the title compound (300.0 mg, 61.66%) as a light yellow solid. m/z (ESI, +ve ion)=160.05 [M+H]$^+$. $^1$H NMR (300 MHz, DMSO-$d_6$) δ 7.18 (s, 1H), 3.98 (d, J=0.8 Hz, 3H).

Step B. 3-methoxy-6-(prop-1-en-2-yl)pyridazin-4-amine

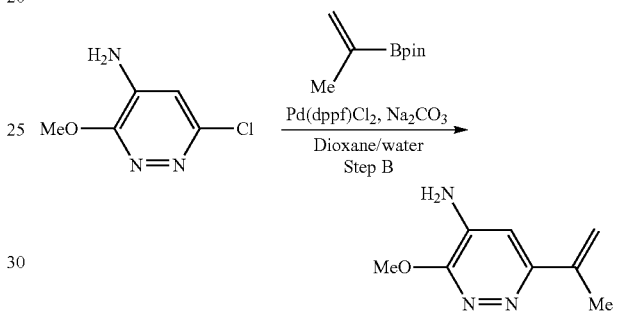

To a stirred solution of 6chloro-3-methoxypyridazin-4-amine (240.0 mg, 1.504 mmol, 1.00 equiv) and 4,4,5,5-tetramethyl-2-(prop-1-en-2-yl)-1,3,2-dioxaborolane (303.29 mg, 1.805 mmol, 1.2 equiv) in dioxane (10.0 mL) and water (1.0 mL) were added Pd(dppf)Cl$_2$·DCM (122.52 mg, 0.150 mmol, 0.1 equiv) and Na$_2$CO$_3$ (318.82 mg, 3.008 mmol, 2.0 equiv) at room temperature under nitrogen atmosphere. The resulting mixture was stirred for 3 h at 110° C. under nitrogen atmosphere. The mixture was cooled down to room temperature. The resulting mixture was filtered, the filter cake was washed with EA (3×10 mL). The filtrate was concentrated under reduced pressure. The residue was purified by silica gel column chromatography, eluted with PE/EA (1/1) to afford the title compound (110.0 mg, 44.27%) as a white solid. m/z. (ESI, +ve ion)=166.15 [M+H]$^+$. $^1$H NMR (400 MHz, Chloroform-d) δ 7.50 (d, J=8.0 Hz, 1H), 5.64 (s, 2H), 5.32 (d, J=4.0 Hz, 2H), 4.17 (s, 3H), 2.30 (d, J=4.0 Hz, 3H).

Step C. 6-isopropyl-3-methoxypyridazin-4-amine

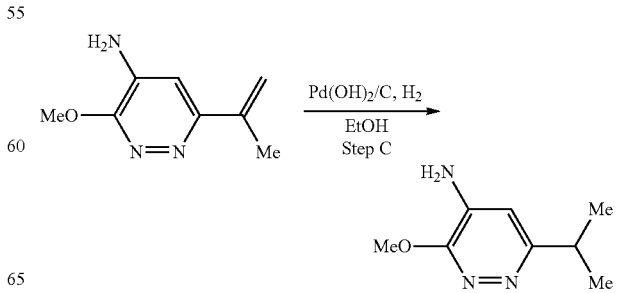

To a solution of 3-methoxy-6-(prop-1-en-2-yl)pyridazin-4-amine (60.0 mg, 0.363 mmol, 1.00 equiv) in 3.0 mL EtOH was added Pd(OH)$_2$/C (20%, 60.0 mg) under nitrogen atmosphere in a 50 mL round-bottom flask. The mixture was hydrogenated at room temperature for 2 h under hydrogen atmosphere using a hydrogen balloon, filtered through a Celite pad, and concentrated under reduced pressure. The residue was purified by silica gel column chromatography, eluted with PE/EA (1/1) to afford the title compound (30.0 mg, 49.40%) as a white solid. m/z (ESI, +ve ion)=168.20 [M+H]$^+$. $^1$H NMR (400 MHz, Chloroform-d) δ 6.56 (s, 1H), 4.13 (s, 3H), 3.17 (d, J=8.0 Hz, 1H), 1.30 (d, J=8.0 Hz, 6H).

Step D. tert-butyl (1R,2S)-2-[1-(tert-butoxycarbonyl)-3-[(6-isopropyl-3-methoxypyridazin-4-yl)amino]indazol-6-yl]-5'-methoxy-2'-oxospiro[cyclopropane-1,3'-indole]-1'-carboxylate

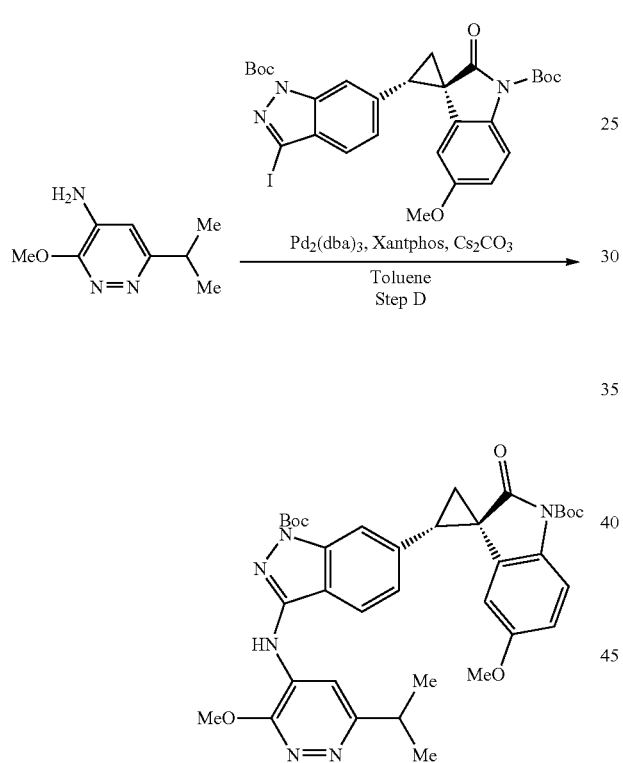

To a stirred solution of 6-isopropyl-3-methoxypyridazin-4-amine (21.18 mg, 0.127 mmol, 1.0 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80.0 mg, 0.127 mmol, 1.00 equiv) in toluene (4.0 mL) were added Cs$_2$CO$_3$ (82.56 mg, 0.254 mmol, 2.0 equiv), XantPhos (14.66 mg, 0.025 mmol, 0.2 equiv) and Pd$_2$(dba)$_3$ (23.20 mg, 0.025 mmol, 0.2 equiv) at room temperature under nitrogen atmosphere. The resulting mixture was stirred for 2 h at 90° C. under nitrogen atmosphere. The resulting mixture was filtered, the filter cake was washed with EA (3×10 mL). The filtrate was concentrated under reduced pressure. The residue was purified by silica gel column chromatography, eluted with PE/EA (1/2) to afford the title compound (60.0 mg, 70.61%) as a yellow solid. m/z (ESI, +ve ion)=671.40 [M+H]$^+$.

Step E. (1R,2S)-2-{3-[(6-isopropyl-3-methoxypyridazin-4-yl)amino]-1H-indazol-6-yl}-5'-methoxy-1'H-spiro[cyclopropane-1,3'-indol]-2'-one

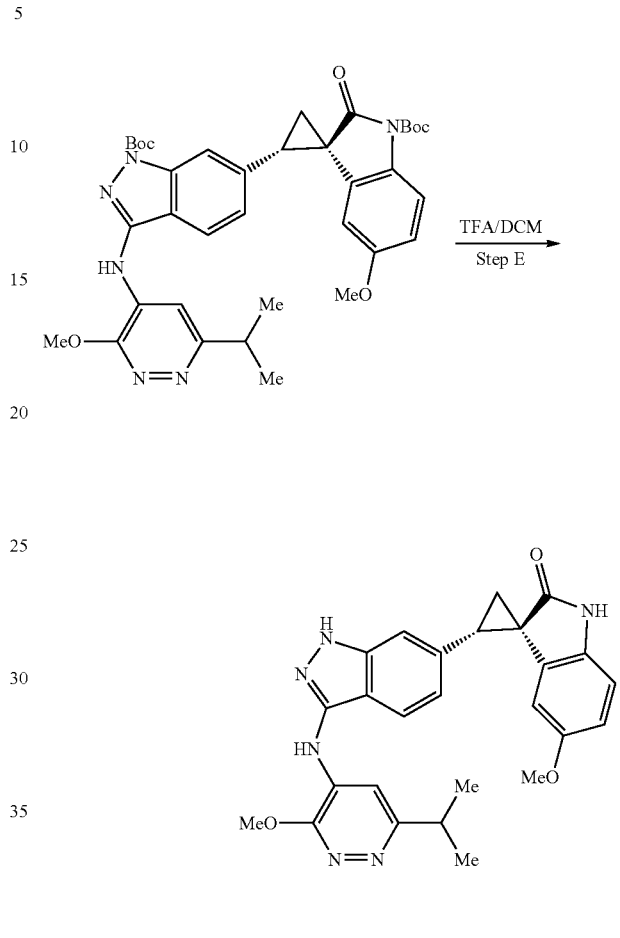

To a stirred solution of tert-butyl (1R,2S)-2-[1-(tert-butoxycarbonyl)-3-[(6-isopropyl-3-methoxypyridazin-4-yl)amino]indazol-6-yl]-5'-methoxy-2'-oxospiro[cyclopropane-1,3'-indole]-1'-carboxylate (60.0 mg, 0.089 mmol, 1.00 equiv) in DCM (10.0 mL) was added TFA (1.0 mL, 13.463 mmol) dropwise at room temperature. The resulting mixture was stirred for 2 h at room temperature. The resulting mixture was concentrated under reduced pressure. The crude product (30.0 mg) was purified by Prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 26% B to 36% B in 8 min, 36% B; wavelength: 254 nm to afford Example 101 (18.6 mg, 44.19%) as a white solid. m/z (ESI, +ve ion)=471.35 [M+H]$^+$. $^1$H NMR (400 MHz, Methanol-d$_4$) δ 7.79 (s, 1H), 7.73 (d, J=8.0 Hz, 1H), 7.44 (s, 1H), 6.96 (d, J=8.0 Hz, 1H), 6.84 (d, J=8.0 Hz, 1H), 6.63 (d, J=8.0 Hz, 1H), 5.61 (d, J=4.0 Hz, 1H), 4.21 (s, 3H), 3.38 (d, J=8.0 Hz, 1H), 3.31 (s, 3H), 3.09-3.06 (m, 1H), 2.27-2.24 (m, 1H), 2.20-2.18 (m, 1H), 1.29 (d, J=8.0 Hz, 6H).

Example 102. (1R,2S)-5'-methoxy-2-(3-{[6-(morpholin-4-yl)-2-(propan-2-yl)pyrimidin-4-yl]amino}-1H-indazol-6-yl)spiro[cyclopropane-1,3'-indol]-2'(1'H)-one

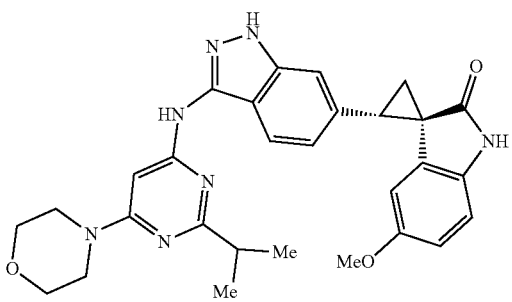 [SMILES: COc1ccc2c(c1)[C@]1(C[C@H]1c1ccc3c(Nc4cc(N5CCOCC5)nc(C(C)C)n4)n[nH]c3c1)C(=O)N2]

Step A. 6-hydroxy-2-isopropyl-3H-pyrimidin-4-one

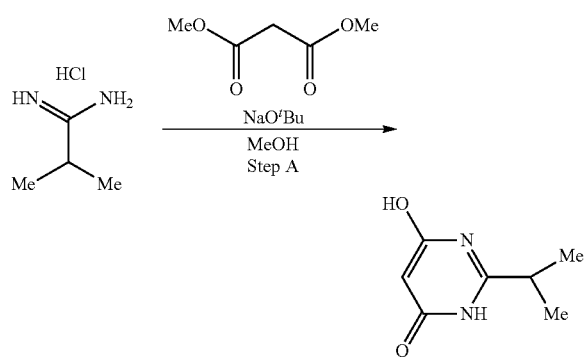

To MeOH (10 mL) was added sodium 2-methylpropan-2-olate (1.96 g, 20.392 mmol, 2.5 equiv) at 0° C. under nitrogen atmosphere. Then 2-methylpropanimidamide hydrochloride (I g, 8.157 mmol, 1.00 equiv) and dimethyl malonate (1.08 g, 8.157 mmol, 1 equiv) were added. The mixture was stirred at 80° C. for 16 h. After cooled to 0° C., the PH value was adjusted to 4 with conc. HCl and filtered. The filter cake was lyophilized overnight to give the title compound (1 g, 79.52%) as a white solid. m/z (ESI, +ve ion)=155.05[M+H]$^+$. $^1$H NMR (400 MHz, DMSO-4) δ 5.12 (s, 1H), 2.82-2.74 (m, 1H), 1.18 (s, 3H), 1.16 (s, 3H).

Step B. 4,6-dichloro-2-isopropylpyrimidine

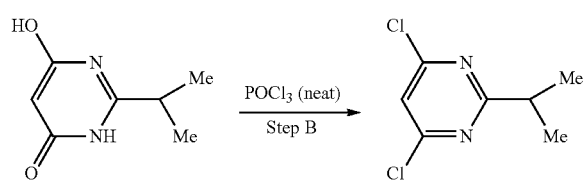 [SMILES: CC(C)c1nc(O)cc(=O)[nH]1 ; CC(C)c1nc(Cl)cc(Cl)n1]

The mixture of 6-hydroxy-2-isopropyl-3H-pyrimidin-4-one (1 g, 6.486 mmol, 1.00 equiv) in POCl$_3$ (10 mL) was stirred at 100° C. for 5 h. After cooled to room temperature, the PH of mixture was adjusted to 8 with sat. aq. NH$_4$HCO$_3$. The resulting mixture was extracted with EA (50 mL×3). The combined organic layers were washed with brine (50 mL), dried over anhydrous Na$_2$SO$_4$ and filtered. After filtration, the filtrate was concentrated under reduced pressure. The residue was purified by silica gel column chromatography, eluted with 0-30% of EA in PE to afford the title compound (330 mg, 26.63%) as a colorless oil. $^1$H NMR (400 MHz, Chloroform-d) δ 7.25 (s, 1H), 3.25-3.15 (m, 1H), 1.37 (s, 3H), 1.35 (s, 3H).

Step C. 6-chloro-2-isopropylpyrimidin-4-amine

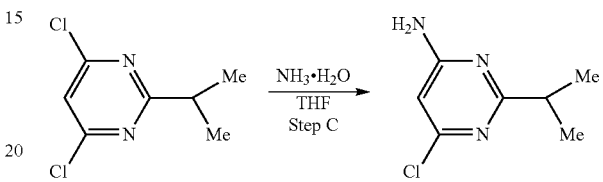

The mixture of 4,6-dichloro-2-isopropylpyrimidine (330 mg, 1.727 mmol, 1.00 equiv) in NH$_4$OH (3 mL) and THF (3 mL) was stirred at 60° C. for 8 h. The solvent was removed under reduced pressure. The residue was purified by silica gel column chromatography, eluted with 0-100% of EA in PE to give the title compound (250 mg, 84.33%) as a white solid. m/z (ESI, +ve ion)=172.05 [M+H]$^+$. $^1$H NMR (400 MHz, DMSO-d$_6$) δ 7.09 (s, 2H), 6.25 (s, 1H), 2.81-2.72 (m, 1H), 1.15 (d, J=6.8 Hz, 6H).

Step D. 2-isopropyl-6-(morpholin-4-yl)pyrimidin-4-amine

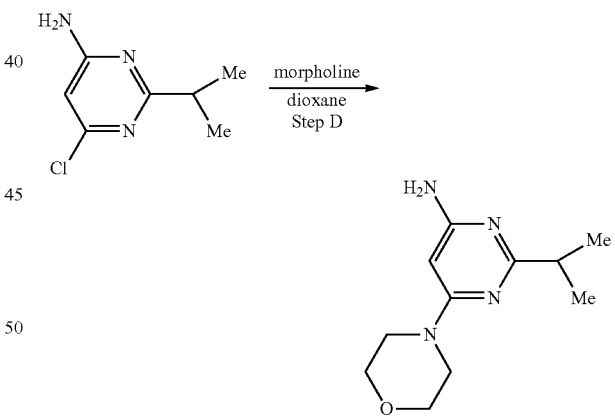

The mixture of 6-chloro-2-isopropylpyrimidin-4-amine (250 mg, 1.457 mmol, 1.00 equiv), morpholine (253.81 mg, 2.914 mmol, 2 equiv) and TEA (442.19 mg, 4.371 mmol, 3 equiv) in dioxane (2 mL, 23.608 mmol, 16.21 equiv) was stirred at 120° C. for 8 h. The solvent was removed under reduced pressure. The residue was purified by silica gel column chromatography, eluted with 0-50% of EA in PE to afford the title compound (200 mg, 61.77%) as a white solid. m/z (ESI, +ve ion)=223.10 [M+H]$^+$. $^1$H NMR (400 MHz, DMSO-d$_6$) δ 6.11 (s, 2H), 5.44 (s, 1H), 3.66-3.64 (m, 4H), 3.40-3.37 (m, 4H), 2.71-2.64 (m, 1H), 1.15 (s, 3H), 1.13 (s, 3H).

Step E. tert-butyl (1R,2S)-2-[1-(tert-butoxycarbo-nyl)-3-{[2-isopropyl-6-(morpholin-4-yl)pyrimidin-4-yl]amino}indazol-6-yl]-5'-methoxy-2'-oxospiro[cyclopropane-1,3'-indole]-1'-carboxylate

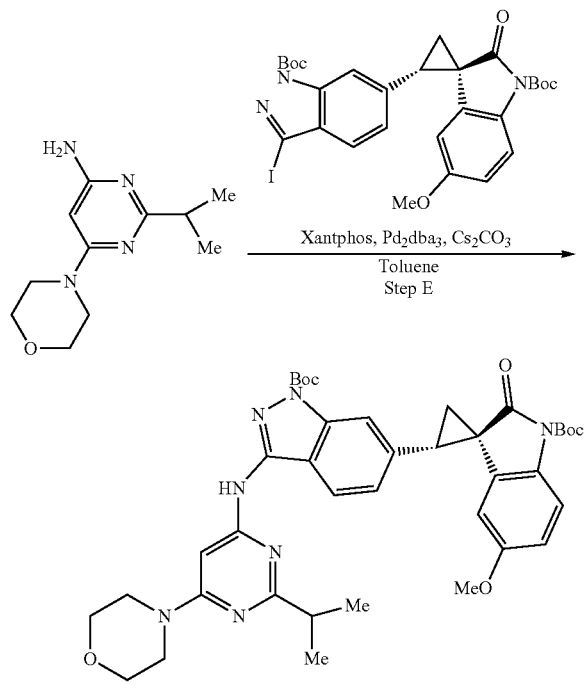

To the mixture of 2-isopropyl-6-(morpholin-4-yl)pyrimidin-4-amine (38.02 mg, 0.172 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (90 mg, 0.143 mmol, 1.00 equiv) in toluene (2.5 mL) were added $Cs_2CO_3$ (92.88 mg, 0.286 mmol, 2 equiv), XantPhos (16.49 mg, 0.029 mmol, 0.2 equiv) and $Pd_2(dba)_3$ (26.10 mg, 0.029 mmol, 0.2 equiv) under nitrogen atmosphere. The mixture was stirred at 90° C. for 2 h. The resulting mixture was filtered and washed with EA (3×5 mL). The filtrate was concentrated in vacuo. The residue was purified by silica gel column eluted with 0-50% EA in PE to give crude the title compound (70 mg, 67.66%) as a light yellow solid. m/z (ESI, +ve ion)=726.45 [M+H]⁺.

Step F. (1R,2S)-2-(3-{[2-isopropyl-6-(morpholin-4-yl)pyrimidin-4-yl]amino}-1H-indazol-6-yl)-5'-methoxy-1'H-spiro[cyclopropane-1,3'-indol]-2'-one

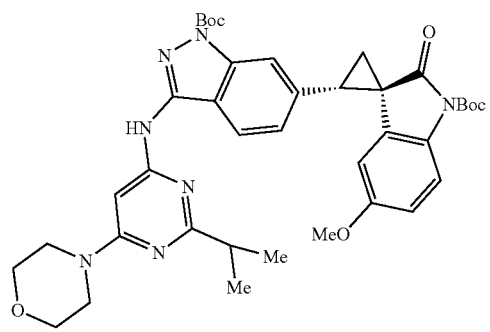

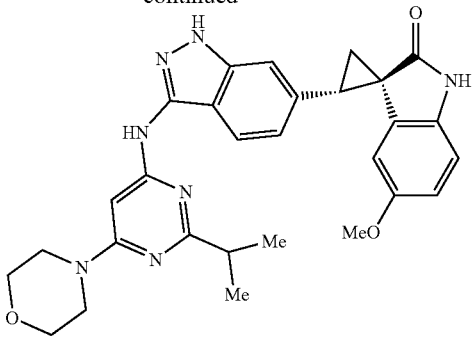

The mixture of tert-butyl (1R,2S)-2-[1-(tert-butoxycarbonyl)-3-{[2-isopropyl-6-(morpholin-4-yl)pyrimidin-4-yl]amino}indazol-6-yl]-5'-methoxy-2'-oxospiro[cyclopropane-1,3'-indole]-1'-carboxylate (70 mg, 0.096 mmol, 1.00 equiv) in TFA (0.5 mL) and DCM (5 mL) was stirred at 25° C. for 6 h. The solvent was removed under reduced pressure. The residue was purified by Prep-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 39% B to 49% B in 8 min; wavelength: 254 nm; RT1(min): 6.6. The product-containing fractions were collected and concentrated in vacuo to give Example 102 (30 mg, 59.18%) as a white solid. m/z (ESI, +ve ion)=526.40 [M+H]⁺. ¹H NMR (400 MHz, DMSO-$d_4$) δ 12.29 (s, 1H), 10.41 (s, 1H), 9.66 (s, 1H), 7.98 (s, 1H), 7.32 (s, 1H), 7.06 (s, 1H), 6.90-6.87 (m, 1H), 6.75 (d, J=8.4 Hz, 1H), 6.60-6.57 (m, 1H), 5.69 (d, J=2.4 Hz, 1H), 3.71-3.68 (m, 4H), 3.52-3.50 (m, 4H), 3.32 (s, 3H), 3.20-3.15 (m, 1H), 2.85-2.78 (m, 1H), 2.34-2.31 (m, 1H), 1.99-1.96 (m, 1H), 1.22 (d, J=6.8 Hz, 6H).

Example 103. (1R,2S)-2-(3-{[5-chloro-2-(morpholin-4-yl)pyrimidin-4-yl]amino}-1H-indazol-6-yl)-5'-methoxyspiro[cyclopropane-1,3'-indol]-2'(1'H)-one

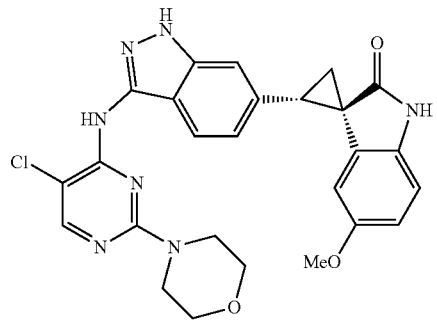 [SMILES: COc1ccc2c(c1)[C@]1(C[C@H]1c1ccc3c(Nc4nc(N5CCOCC5)ncc4Cl)n[nH]c3c1)C(=O)N2]

Step A. 2-(morpholin-4-yl)pyrimidin-4-amine

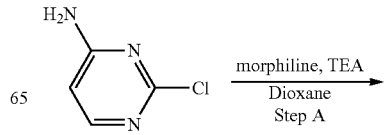

481

-continued

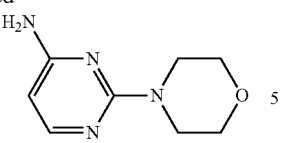

A solution of 2-chloropyrimidin-4-amine (258 mg, 1.992 mmol, 1.00 equiv), TEA (403.04 mg, 3.984 mmol, 2 equiv) and morpholine (208.21 mg, 2.390 mmol, 1.2 equiv) in dioxane (2 mL, 23.608 mmol, 11.85 equiv) was stirred for 16 h at 100° C. under nitrogen atmosphere. The resulting mixture was concentrated under reduced pressure. The residue was purified by reverse flash chromatography, eluted with 50% ACN in water (5 mM NH$_4$HCO$_3$) to afford the title compound (200 mg, 55.73%) as a white solid. m/z (ESI +ve ion)=181.10 [M+H]$^+$. $^1$H NMR (400 MHz, DMSO-d$_6$) δ 7.75 (d, J=5.6 Hz, 1H), 6.40 (s, 2H), 5.76 (d, J=5.6 Hz, 1H), 3.63-3.56 (m, 8H)

Step B.
5-chloro-2-(morpholin-4-yl)pyrimidin-4-amine

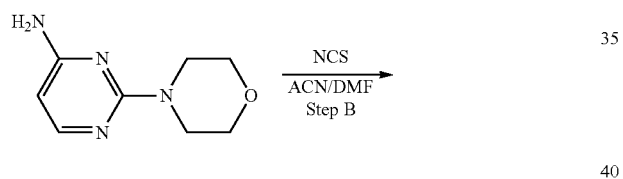

To a stirred mixture of 2-(morpholin-4-yl)pyrimidin-4-amine (108 mg, 0.599 mmol, 1.00 equiv) in ACN (3 mL) and DMF (3 mL) was added NCS (88.03 mg, 0.659 mmol, 1.1 equiv). The resulting mixture was stirred for 16 h at room temperature. The resulting mixture was diluted with water (30 mL). The resulting mixture was extracted with EA (3×20 mL). The combined organic layers were washed with brine (5×5 mL), dried over anhydrous Na$_2$SO$_4$. After filtration, the filtrate was concentrated under reduced pressure. The residue was purified by reverse flash chromatography, eluted with 40% ACN in water (5 mM NH$_4$HCO$_3$) to afford the title compound (100 mg, 77.74%) as a white solid. m/z (ESI, +ve ion)=215.05 [M+H]$^+$. $^1$H NMR (400 MHz, DMSO-d$_6$) δ 8.00-7.84 (m, 1H), 6.87-6.80 (m, 2H), 3.74-3.54 (m, 8H)

482

Step C. tert-butyl (1R,2S)-2-[1-(tert-butoxycarbonyl)-3-{[5-chloro-2-(morpholin-4-yl)pyrimidin-4-yl]amino}indazol-6-yl]-5'-methoxy-2'-oxospiro[cyclopropane-1,3'-indole]-1'-carboxylate

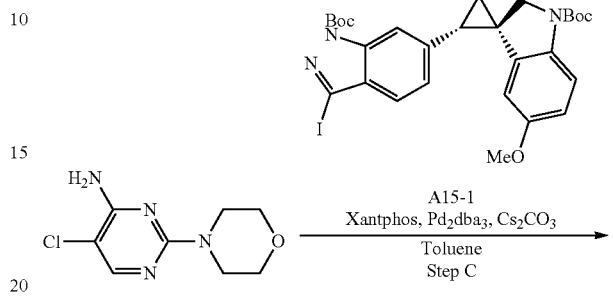

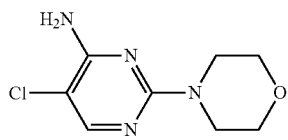

To a stirred mixture of 5-chloro-2-(morpholin-4-yl)pyrimidin-4-amine (25.29 mg, 0.118 mmol, 1.20 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (62 mg, 0.098 mmol, 1.00 equiv) in toluene (2 mL) were added Pd$_2$(dba)$_3$ (8.99 mg, 0.010 mmol, 0.1 equiv) and XantPhos (5.68 mg, 0.010 mmol, 0.1 equiv) at room temperature under nitrogen atmosphere. The resulting mixture was stirred for 2 h at 100° C. under nitrogen atmosphere. The resulting mixture was concentrated under reduced pressure. The residue was purified by silica gel column chromatography, eluted with PE/EA (1/1) to afford crude the title compound (60 mg, 42.54%) as a yellow solid. m/z (ESI, +ve ion)=718.10 [M+H]+

Step D. (1R,2S)-2-(3-{[5-chloro-2-(morpholin-4-yl)pyrimidin-4-yl]amino}-1H-indazol-6-yl)-5'-methoxy-1'H-spiro[cyclopropane-1,3'-indol]-2'-one

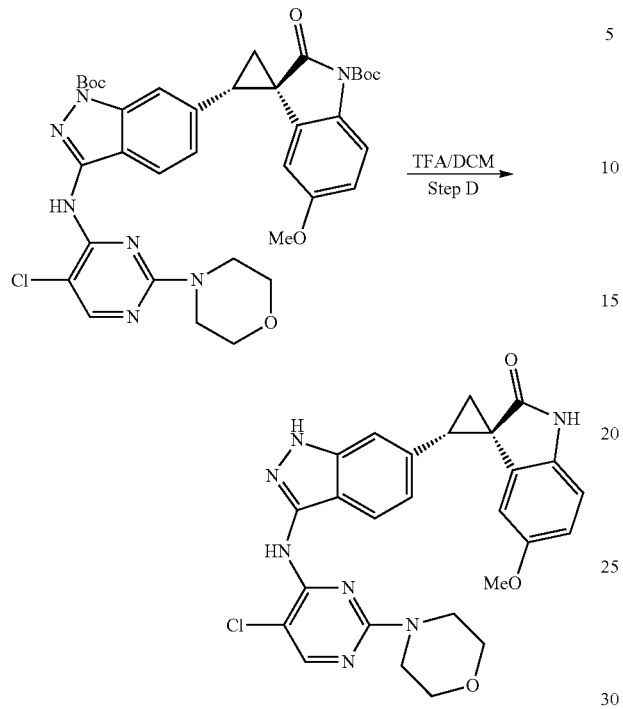

A solution of tert-butyl (1R,2S)-2-[1-(tert-butoxycarbonyl)-3-{[5-chloro-2-(morpholin-4-yl)pyrimidin-4-yl]amino}indazol-6-yl]-5'-methoxy-2'-oxospiro[cyclopropane-1,3'-indole]-1'-carboxylate (60 mg, 0.084 mmol, 1.00 equiv) and TFA (0.5 mL) in DCM (1 mL) was stirred for 1 h at room temperature. The crude product was concentrated under reduced pressure. The residue was purified by Prep-HPLC with the following conditions: Column: XBridge Shield RP18 OBD Column, 19×250 mm, 10 μm; Mobile Phase A: Water (10 mmol/L $NH_4HCO_3$), Mobile Phase B: ACN; Flow rate: 25 mL/min; Gradient: 35% B to 50% B in 8 min, 50% B; wavelength: 254 nm; RT1(min): 7.8 to afford Example 103 (26 mg, 60.03%) as a white solid. m/z (ESI+ve ion)=518.30 [M+H]$^+$. $^1$H-NMR (400 MHz, Methanol-$d_4$) δ 7.98 (s, 1H), 7.51 (d, J=8.6 Hz, 2H), 6.91-6.82 (m, 2H), 6.65 (dd, J=8.5, 2.5 Hz, 1H), 5.64 (d, J=2.5 Hz, 1H), 3.51-3.33 (m, 7H), 3.32-3.19 (m, 5H), 2.32-2.24 (m, 1H), 2.22-2.14 (m, 1H).

Example 104. (1R,2S)-2-(3-{[5-(3-hydroxyazetidin-1-yl)-3-methoxypyridin-2-yl]amino}-1H-indazol-yl)-5'-methoxyspiro[cyclopropane-1,3'-indol]-2'(1'H)-one

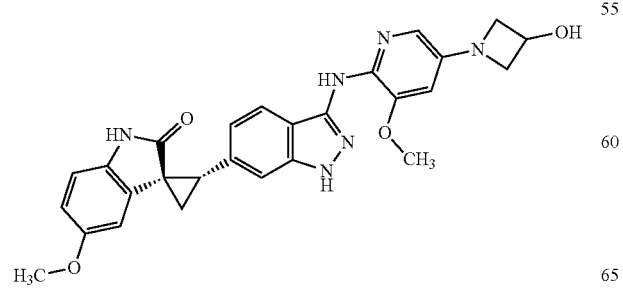

Example 104 was prepared using procedures similar to those of other examples, but using a 5-(3-hydroxyazetidin-1-yl)-3-methoxypyridin-2-yl starting material.

Example 105. (1R,2S)-5'-methoxy-2-(3-{[3-methyl-6-(propan-2-yl)pyrazin-2-yl]amino}-1H-indazol-6-yl)spiro[cyclopropane-1,3'-indol]-2'(1'H)-one

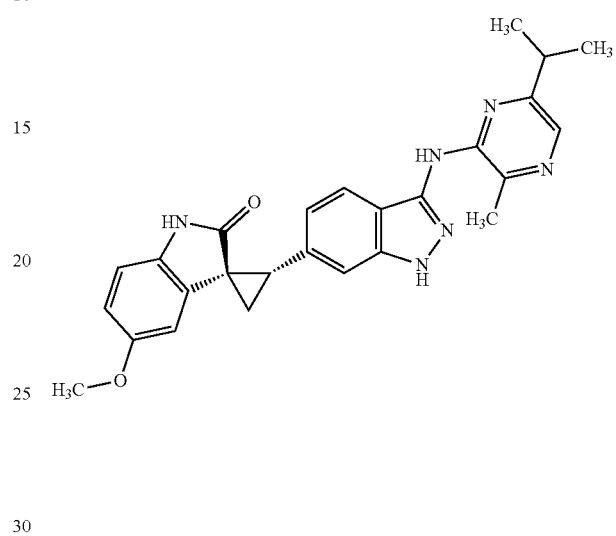

Example 105 was prepared using procedures similar to those of other examples, but using a 3-methyl-6-(propan-2-yl)pyrazin-2-yl starting material.

Example 106. (1R,2S)-5'-methoxy-2-(3-{[6-(propan-2-yl)pyrazin-2-yl]amino}-1H-indazol-6-yl)spiro[cyclopropane-1,3'-indol]-2'(1'H)-one

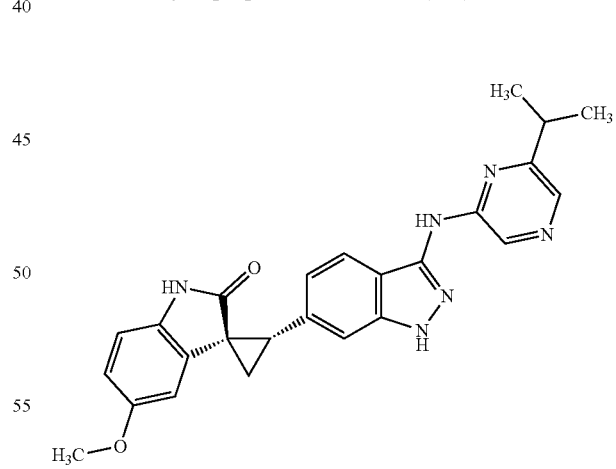

Example 106 was prepared using procedures similar to those of other examples, but using a 6-(propan-2-yl)pyrazin-2-yl starting material.

Example 107. (1R,2S)-2-(3-{[5-chloro-6-(3-hydroxyazetidin-1-yl)pyrimidin-4-yl]amino}-1H-indazol-6-yl)-5'-methoxy-1'-methylspiro[cyclopropane-1,3'-indol]-2'(1'H)-one

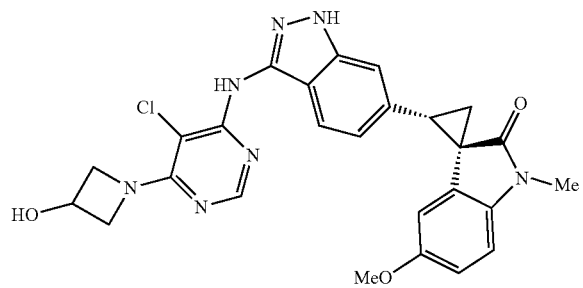 [SMILES: COc1ccc2c(c1)[C@]1(C[C@H]1c1ccc3c(Nc4ncnc(N5CC(O)C5)c4Cl)n[nH]c3c1)C(=O)N2C]

Step A. 5-methoxy-1-methylindole-2,3-dione

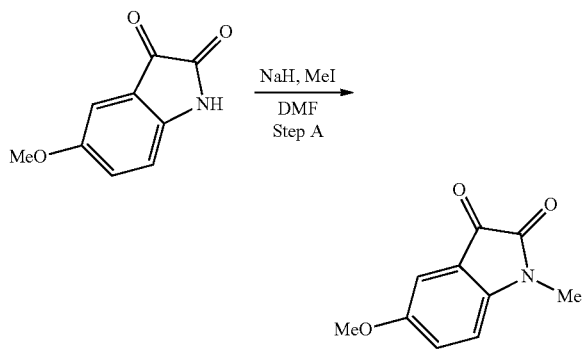

To the mixture of 5-methoxy-1H-indole-2,3-dione (1 g, 5.645 mmol, 1.00 equiv) in DMF (20 mL) was added NaH (0.14 g, 5.927 mmol, 1.05 equiv, 60% in mineral oil) under nitrogen atmosphere at 0° C. After stirred at 0° C. for 30 min, methyl iodide (0.88 g, 6.210 mmol, 1.1 equiv) was added drop-wise. The resulting mixture was stirred at 25° C. for 2 h. The reaction was quenched with sat. aq·NH$_4$Cl (10 mL) and extracted with EA (3×30 mL). The combined organic layers were washed with brine (30 mL×2), dried over anhydrous Na$_2$SO$_4$ and filtered. The filtrate was concentrated in vacuo. The residue was purified by silica gel column chromatography, eluted with 0-50% EA in PE to afford the title compound (900 mg, 83.40%) as a brown solid. m/z (ESI, +ve ion)=192.00 [M+H]$^+$. $^1$H NMR (400 MHz, Chloroform-d) δ 7.19-7.15 (m, 2H), 6.84-6.82 (m, 1H), 3.83 (s, 3H), 3.24 (s, 3H).

Step B. 5-methoxy-1-methyl-3H-indol-2-one

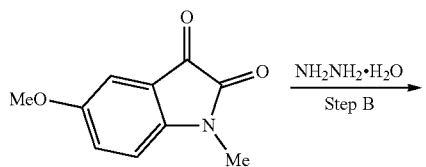

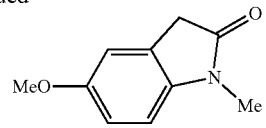

A solution of 5-methoxy-1-methylindole-2,3-dione (900 mg, 4.707 mmol, 1.00 equiv) in hydrazine hydrate (98%) (10 mL) was stirred for 5 h at 150° C. under argon atmosphere. The mixture was diluted with water (50 mL) and extracted with EA (3×50 mL). The combined organic layer was washed with brine (50 mL), dried over anhydrous Na$_2$SO$_4$ and filtered. The filtrate was concentrated in vacuo. The residue was purified by silica gel column chromatography, eluted with 0-50% EA in PE to afford the title compound (700 mg, 83.92%) as a yellow solid. m/z (ESI, +ve ion)=178.05 [M+H]$^+$. $^1$H NMR (400 MHz, Chloroform-d) δ 6.90-6.89 (m, 1H), 6.84-6.82 (m, 1H), 6.73 (d, J=8.4 Hz, 1H), 3.81 (s, 3H), 3.52 (s, 2H), 3.21 (s, 3H).

Step C. (1R,2S)-2-(1-benzylindazol-6-yl)-5'-methoxy-1'-methylspiro[cyclopropane-1,3'-indol]-2'-one

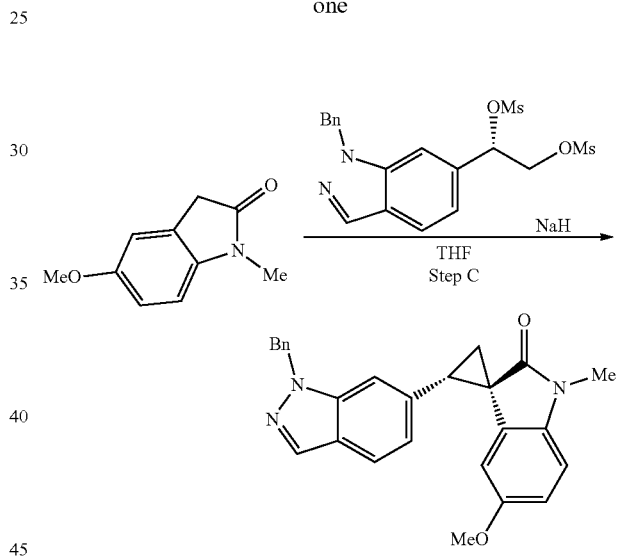

A solution of 5-methoxy-1-methyl-3H-indol-2-one (100 mg, 0.564 mmol, 1.00 equiv) in THF (3.00 mL) was cooled in an ice bath. NaH (28.44 mg, 1.184 mmol, 2.1 equiv, 60% in mineral oil) was added in portions, and the mixture was stirred at 0° C. for 30 min. A solution of (1S)-1-(1-benzylindazol-6-yl)-2-(methanesulfonyloxy)ethyl methanesulfonate (239.55 mg, 0.564 mmol, 1 equiv) in THF (7.14 mL) was added dropwise over 10 min and stirred for 3 h. The reaction was quenched with sat aq. NH$_4$Cl (50 mL) and extracted with EA (50 mL×3). The organic layer was washed with brine (50 mL), dried with Na$_2$SO$_4$, and filtered. The filtrate was concentrated in vacuo. The residue was purified by silica gel column eluted with 0-50% EA in PE to afford the title compound (130 mg, 56.26%) as a light yellow solid. m/z (ESI, +ve ion)=410.15 [M+H]$^+$. $^1$H NMR (400 MHz, Chloroform-d) δ 8.03 (d, J=0.8 Hz, 1H), 7.66 (d, J=8.4 Hz, 1H), 7.29-7.26 (m, 3H), 7.23 (s, 1H), 7.17-7.15 (m, 2H), 6.98-6.96 (m, 1H), 6.77 (d, J=8.4 Hz, 1H), 6.69-6.66 (m, 1H), 5.65-5.54 (m, 2H), 5.40 (d, J=2.4 Hz, 1H), 3.46 (t, J=8.4 Hz, 1H), 3.33 (s, 3H), 3.25 (s, 3H), 2.26-2.22 (m, 1H), 2.00-1.97 (m, 1H).

Step D. (1R,2S)-2-(1H-indazol-6-yl)-5'-methoxy-1'-methylspiro[cyclopropane-1,3'-indol]-2'-one

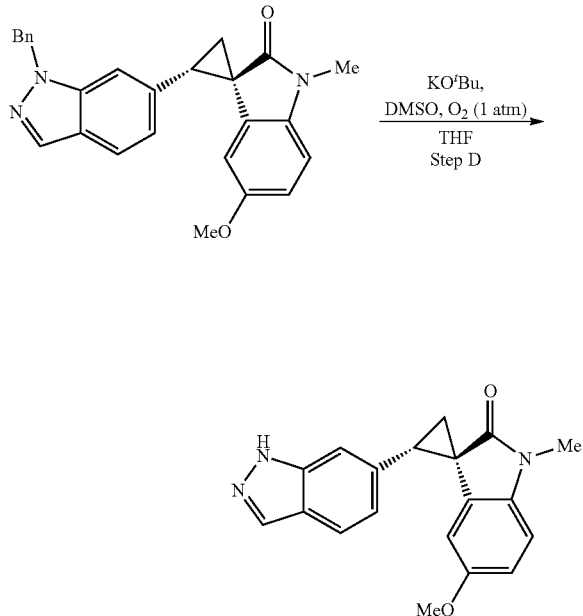

A solution of (1R,2S)-2-(1-benzylindazol-6-yl)-5'-methoxy-1'-methylspiro[cyclopropane-1,3'-indol]-2'-one (330 mg, 0.806 mmol, 1.00 equiv) in THF (2.5 mL) was cooled in ice before addition of Potassium tert-butoxide in THF (1.8 M, 8.95 mL, 16.120 mmol, 20 equiv). DMSO (1196.35 mg, 15.314 mmol, 19 equiv) was added and the mixture was purged gently with oxygen in an ice bath for 3 h. The reaction was quenched by sat. aq. NH$_4$Cl (15 mL) and extracted with EA (20 mL×4). The combined organic layer was dried over anhydrous Na$_2$SO$_4$, filtered and concentrated in vacuo. The residue was purified by silica gel column chromatography, eluted with 0-100% of EA in PE to afford the title compound (220 mg, 85.48%) as a light yellow solid. m/z (ESI, +ve ion)=320.15 [M+H]$^+$. $^1$H NMR (400 MHz, Chloroform-d) δ 8.10 (s, 1H), 7.70 (d, J=8.0 Hz, 1H), 7.44 (s, 1H), 7.03 (d, J=8.4 Hz, 1H), 6.80-6.77 (m, 1H), 6.69-6.67 (m, 1H), 5.55 (t, J=2.4 Hz, 1H), 3.49 (t, J=8.4 Hz, 1H), 3.34 (d, J=3.2 Hz, 6H), 2.30-2.27 (m, 1H), 2.08-2.05 (m, 1H).

Step E. (1R,2S)-2-(3-iodo-1H-indazol-6-yl)-5'-methoxy-1'-methylspiro[cyclopropane-1,3'-indol]-2'-one

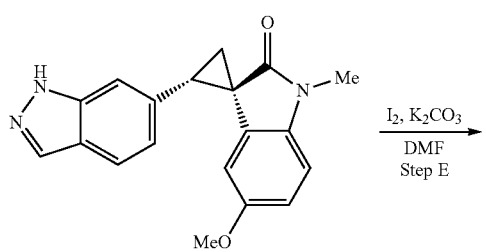

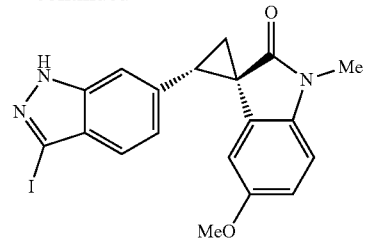

To a stirred mixture of (1R,2S)-2-(1H-indazol-6-yl)-5'-methoxy-1'-methylspiro[cyclopropane-1,3'-indol]-2'-one (90 mg, 0.282 mmol, 1.00 equiv) and K$_2$CO$_3$ (77.90 mg, 0.564 mmol, 2 equiv) in DMF (1.00 mL) was added a solution of I$_2$ (121.59 mg, 0.479 mmol, 1.7 equiv) in DMF (1.00 mL) drop-wise. The resulting mixture was stirred for 3 h at room temperature. The mixture was poured in a mixture of water (5 mL) and sat. aq. Na$_2$S$_2$O$_3$ (5 mL) and the mixture was stirred at 25° C. for 1 h. The mixture was extracted with EA (10 mL×3). The combined organic layer was washed with brine (20 mL), dried over anhydrous Na$_2$SO$_4$, filtered and concentrated in vacuo. The residue was purified by silica gel column eluted with 0-90% of EA in PE to give the title compound (90 mg, 71.73%) as a white solid. m/z (ESI, +ve ion)=446.00 [M+H]$^+$. $^1$H NMR (400 MHz, DMSO-d$_6$) δ 13.48 (s, 1H), 7.52 (s, 1H), 7.33 (d, J=8.4 Hz, 1H), 7.05-7.03 (m, 1H), 6.92 (d, J=8.4 Hz, 1H), 6.70-6.67 (m, 1H), 5.69 (d, J=2.8 Hz, 1H), 3.34 (s, 3H), 3.28-3.24 (m, 1H), 3.22 (s, 3H), 2.42-2.39 (m, 1H), 2.06-2.03 (m, 1H).

Step F. tert-butyl 3-iodo-6-[(1R,2S)-5'-methoxy-1'-methyl-2'-oxospiro[cyclopropane-1,3'-indol]-2-yl]indazole-1-carboxylate

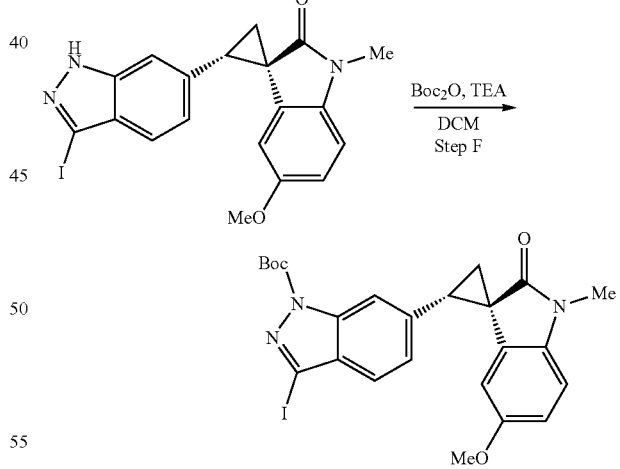

To a stirred mixture of (1R,2S)-2-(3-iodo-1H-indazol-6-yl)-5'-methoxy-1'-methylspiro[cyclopropane-1,3'-indol]-2'-one (90 mg, 0.202 mmol, 1.00 equiv) and TEA (40.91 mg, 0.404 mmol, 2 equiv) in DCM (2 mL, 31.460 mmol, 155.64 equiv) was added Boc$_2$O (66.17 mg, 0.303 mmol, 1.5 equiv) dropwise at 25° C. The mixture was stirred at 25° C. for 4 h. The solvent was removed under reduced pressure. The residue was purified by silica gel column chromatography, eluted with 0-50% of EA in PE to afford the title compound (97 mg, 87.99%) as a white solid. m/z (ESI, +ve ion)=546.05

[M+H]⁺. ¹H NMR (400 MHz, DMSO-d₄) δ 8.11 (s, 1H), 7.27 (d, J=8.0 Hz, 1H), 7.18-7.16 (m, 1H), 6.79 (d, J=8.4 Hz, 1H), 6.71-6.68 (m, 1H), 5.64 (d, J=2.4 Hz, 1H), 3.39-3.43 (m, 4H), 3.38 (s, 3H), 3.32-2.29 (m, 1H), 2.11-2.08 (m, 1H), 1.71 (s, 9H).

Step G. tert-butyl 3-[(6-{3-[(tert-butyldimethylsilyl)oxy]azetidin-1-yl}-5-chloropyrimidin-4-yl)amino]-6-[(1R,2S)-5'-methoxy-1'-methyl-2'-oxospiro[cyclopropane-1,3'-indol]-2-yl]indazole-1-carboxylate

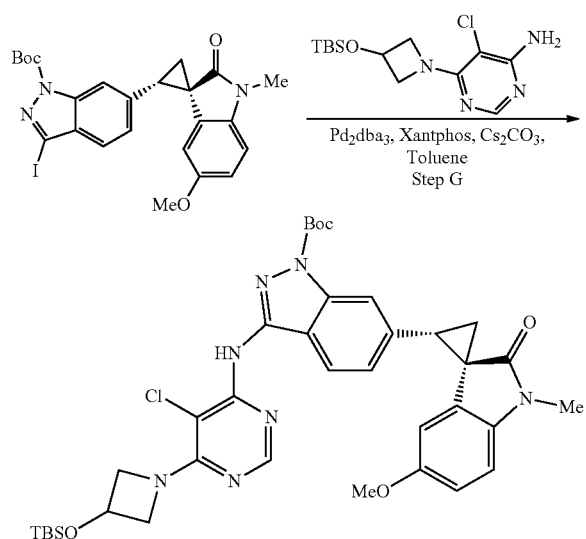

To a stirred mixture of tert-butyl 3-iodo-6-[(1R,2S)-5'-methoxy-1'-methyl-2'-oxospiro[cyclopropane-1,3'-indol]-2-yl]indazole-1-carboxylate (90 mg, 0.165 mmol, 1.00 equiv) and 6-(3-((tert-butyldimethylsilyl)oxy)azetidin-1-yl)-5-chloropyrimidin-4-amine (62.36 mg, 0.198 mmol, 1.2 equiv) in toluene (2.50 mL) were added Cs₂CO₃ (107.54 mg, 0.330 mmol, 2 equiv), Pd₂(dba)₃ (15.11 mg, 0.017 mmol, 0.1 equiv) and XantPhos (9.55 mg, 0.017 mmol, 0.1 equiv) under nitrogen atmosphere. The resulting mixture was stirred for 2 h at 90° C. under nitrogen atmosphere. The mixture was filtered and washed with EA (3×5 mL). The filtrate was concentrated in vacuo. The residue was purified by silica gel column chromatography, eluted with 0-50% of EA in PE to afford the title compound (70 mg, 43.44%) as a yellow solid. m/z (ESI, +ve ion)=732.30 [M+H]⁺.

Step H. (1R,2S)-2-(3-{[5-chloro-6-(3-hydroxyazetidin-1-yl)pyrimidin-4-yl]amino}-1H-indazol-6-yl)-5'-methoxy-1'-methylspiro[cyclopropane-1,3'-indol]-2'-one

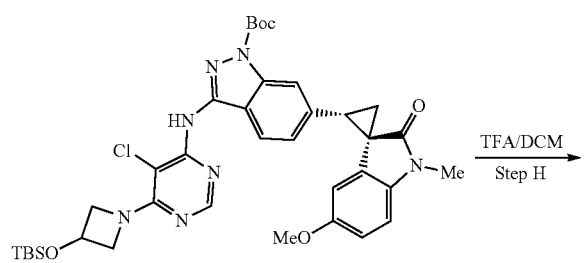

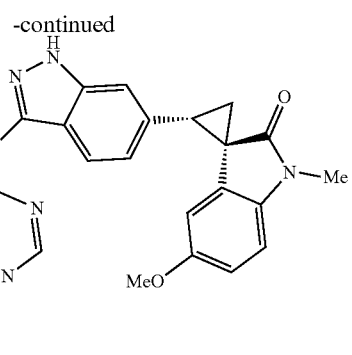

The mixture of tert-butyl 3-[(6-{3-[(tert-butyldimethylsilyl)oxy]azetidin-1-yl}-5-chloropyrimidin-4-yl)amino]-6-[(1R,2S)-5'-methoxy-1'-methyl-2'-oxospiro[cyclopropane-1,3'-indol]-2-yl]indazole-1-carboxylate (65 mg, 0.089 mmol, 1.00 equiv) in TFA (0.5 mL) and DCM (2 mL) was stirred at 40° C. for 24 h. The solvent was removed under reduced pressure. The residue was purified by Prep-HPLC with the following conditions: Column: XBridge Shield RP18 OBD Column, 30×150 mm, 5 μm; Mobile Phase A: Water (10 mmol/L NH₄HCO₃), Mobile Phase B: ACN; Flow rate: 60 mL/min; Gradient: 25% B to 37% B in 8 min; wavelength: 254 nm; RT1(min): 6.8. The product-containing fractions were collected and concentrated in vacuo to Example 107 (22.3 mg, 48.41%) as a white solid. m/z (ESI, +ve ion)=518.30 [M+H]⁺. ¹H NMR (400 MHz, Methanol-d₄) δ 7.83 (s, 1H), 7.51 (d, J=8.4 Hz, 1H), 7.43 (s, 1H), 6.95-6.92 (m, 2H), 6.73-6.70 (m, 1H), 5.70 (d, J=2.4 Hz, 1H), 4.65-4.59 (m, 3H), 4.19-4.113 (m, 2H), 3.41-3.38 (m, 1H), 3.36 (s, 3H), 3.32 (s, 3H), 2.29-2.19 (m, 2H).

Example 108. (1R,2S)-2-(3-{[5-chloro-6-(3-hydroxyazetidin-1-yl)pyrimidin-4-yl]amino}-1H-indazol-6-yl)-1'-ethyl-5'-methoxyspiro[cyclopropane-1,3'-indol]-2'(1'H)-one

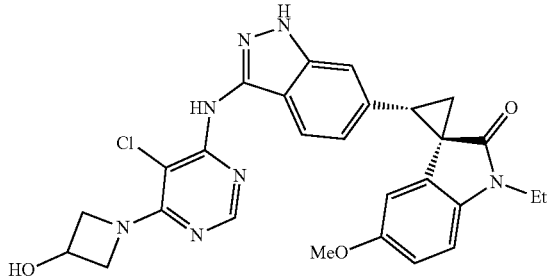 [SMILES: CCN1C(=O)[C@@]2(C[C@H]2c2ccc3c(Nc4ncnc(N5CC(O)C5)c4Cl)n[nH]c3c2)c2cc(OC)ccc21]

Step A. 1-ethyl-5-methoxyindole-2,3-dione

-continued

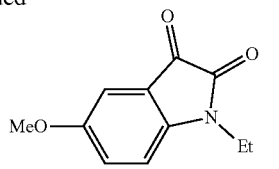

To the mixture of 5-methoxy-1H-indole-2,3-dione (1 g, 5.645 mmol, 1.00 equiv) in DMF (20 mL) was added NaH (0.14 g, 5.927 mmol, 1.05 equiv, 60% in mineral oil) under nitrogen atmosphere at 0° C. After stirred at 0° C. for 30 min, ethyl iodide (0.97 g, 6.210 mmol, 1.1 equiv) was added drop-wise. The resulting mixture was stirred at 25° C. for 2 h. The reaction was quenched with sat.aq. NH$_4$Cl (10 mL) and extracted with EA (30 mL×3). The combined organic layers were washed with brine (30 mL×2), dried over anhydrous Na$_2$SO$_4$ and filtered. The filtrate was concentrated in vacuo. The residue was purified by silica gel column chromatography, eluted with 0-50% EA in PE to afford the title compound (1 g, 86.33%) as a brown solid. m/z (ESI, +ve ion)=206.10 [M+H]$^+$. $^1$H NMR (400 MHz, Chloroform-d) δ 7.17-7.14 (m, 2H), 6.85-6.83 (m, 1H), 3.82 (s, 3H), 3.80-3.75 (m, 2H), 1.32 (t, J=7.2 Hz, 3H).

Step B. 1-ethyl-5-methoxy-3H-indol-2-one

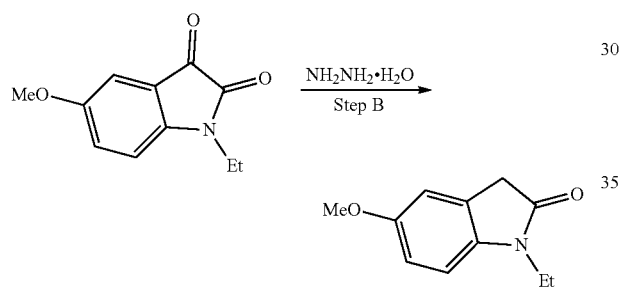

A solution of 1-ethyl-5-methoxyindole-2,3-dione (1 g, 4.873 mmol, 1.00 equiv) in hydrazine hydrate (98%, 10 mL, 205.751 mmol, 43.71 equiv) was stirred for 5 h at 150° C. under argon atmosphere. The mixture was diluted with water (50 mL) and extracted with EA (50 mL×3). The combined organic layer was washed with brine (50 mL), dried over anhydrous Na$_2$SO$_4$ and filtered. The filtrate was concentrated in vacuo. The residue was purified by silica gel column chromatography, eluted with 0-50% EA in PE to afford the title compound (800 mg, 85.85%) as a yellow solid. m/z (ESI, +ve ion)=192.05 [M+H]$^+$. $^1$H NMR (400 MHz, Chloroform-d) δ 6.91-6.90 (m, 1H), 6.84-6.81 (m, 1H), 6.75 (d, J=8.4 Hz, 1H), 3.81 (s, 3H), 3.79-3.74 (m, 2H), 3.51 (s, 2H), 1.28 (t, J=7.2 Hz, 3H).

Step C. (1R,2S)-2-(1-benzylindazol-6-yl)-1'-ethyl-5'-methoxyspiro[cyclopropane-1,3'-indol]-2'-one

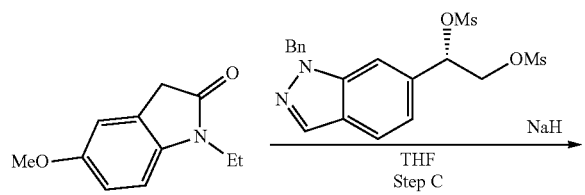

-continued

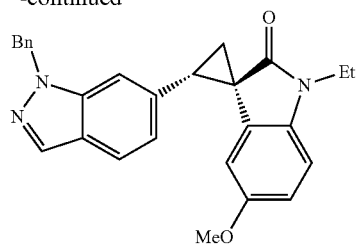

A solution of 1-ethyl-5-methoxy-3H-indol-2-one (180.20 mg, 0.942 mmol, 1 equiv) in THF (6 mL) was cooled in an ice bath. NaH (47.49 mg, 1.978 mmol, 2.1 equiv, 60% in mineral oil) was added in portions, and the mixture was stirred at 0° C. for 15 min. A solution of (1S)-1-(1-benzylindazol-6-yl)-2-(methanesulfonyloxy)ethyl methanesulfonate (400 mg, 0.942 mmol, 1.00 equiv) in THF (12 mL) was added drop-wise over 20 min and stirred for 3 h. The reaction was quenched with sat. aq. NH$_4$Cl (50 mL) and extracted with EA (3×50 mL). The organic layer was washed with brine (50 mL), dried with Na$_2$SO$_4$, and filtered. The filtrate was concentrated in vacuo. The residue was purified by silica gel column eluted with 0-50% EA in PE to afford the title compound (200 mg, 50.11%) as a light yellow solid. m/z (ESI, +ve ion)=424.30 [M+H]$^+$. $^1$H NMR (400 MHz, Chloroform-d) δ 8.03 (d, J=0.8 Hz, 1H), 7.65 (d, J=8.4 Hz, 1H), 7.27-7.25 (m, 3H), 7.22 (d, J=1.6 Hz, 1H), 7.17-7.15 (m, 2H), 6.97-6.94 (m, 1H), 6.79 (d, J=8.4 Hz, 1H), 6.68-6.65 (m, 1H), 5.70-5.49 (m, 2H), 5.40 (d, J=2.8 Hz, 1H), 3.97-3.79 (m, 2H), 3.45 (t, J=8.4 Hz, 1H), 3.24 (s, 3H), 2.25-2.22 (m, 1H), 1.98-1.95 (m, 1H), 1.34 (t, J=7.2 Hz, 3H).

Step D. (1R,2S)-1'-ethyl-2-(1H-indazol-6-yl)-5'-methoxyspiro[cyclopropane-1,3'-indol]-2'-one

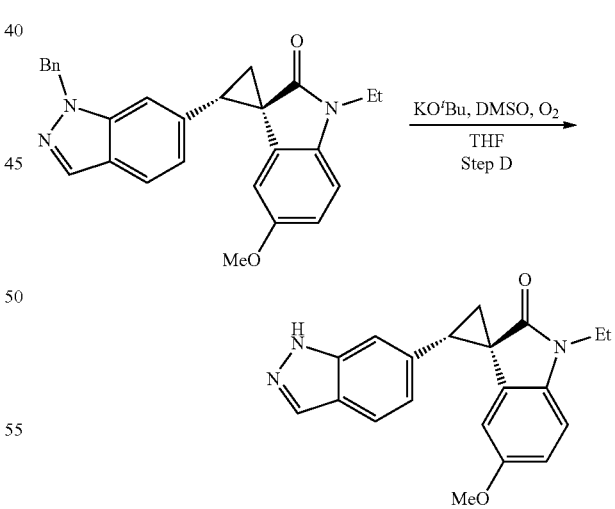

A solution of (1R,2S)-2-(1-benzylindazol-6-yl)-1'-ethyl-5'-methoxyspiro[cyclopropane-1,3'-indol]-2'-one (280 mg, 0.661 mmol, 1.00 equiv) in THF (1.8 mL) was cooled in ice before addition of Potassium tert-butoxide in THF (1.8 M, 7.35 mL, 13.220 mmol, 20 equiv). DMSO (981.47 mg, 12.559 mmol, 19 equiv) was added and the mixture was purged gently with oxygen in an ice bath for 3 h. The reaction was quenched by sat. aq. NH$_4$Cl (15 mL) and extracted with EA (20 mL×4). The combined organic layer was dried over anhydrous Na₂SO₄, filtered and concentrated in vacuo. The residue was purified by silica gel column chromatography, eluted with 0-100% of EA in PE to afford the title compound (220 mg, 99.81%) as a light yellow solid. m/z (ESI, +ve ion)=334.10 [M+H]⁺. ¹H NMR (400 MHz, DMSO-d₄) δ 13.01 (s, 1H), 8.03 (s, 1H), 7.66 (d, J=8.4 Hz, 1H), 7.47 (s, 1H), 6.97-6.93 (m, 2H), 6.68-6.65 (m, 1H), 5.68 (d, J=2.4 Hz, 1H), 3.84-3.74 (m, 2H), 3.30 (s, 3H), 3.26 (t, J=8.4 Hz, 1H), 2.38-2.35 (m, 1H), 2.06-2.02 (m, 1H), 1.22-1.16 (m, 3H).

Step E. (1R,2S)-1'-ethyl-2-(3-iodo-1H-indazol-6-yl)-5'-methoxyspiro[cyclopropane-1,3'-indol]-2'-one

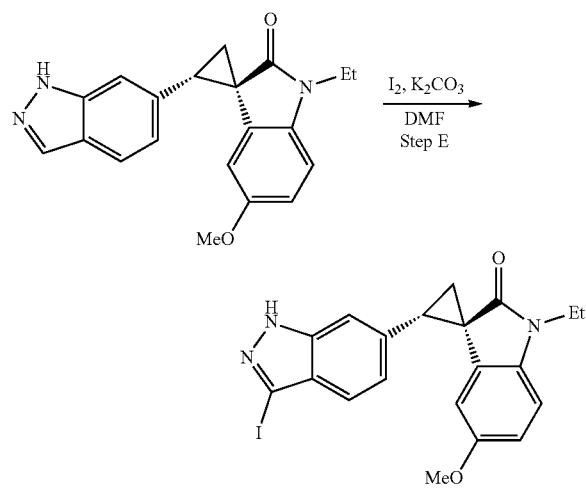

To a stirred mixture of (1R,2S)-1'-ethyl-2-(1H-indazol-6-yl)-5'-methoxyspiro[cyclopropane-1,3'-indol]-2'-one (220 mg, 0.660 mmol, 1.00 equiv) and K₂CO₃ (182.40 mg, 1.320 mmol, 2 equiv) in DMF (3 mL) was added a solution of I₂ (284.72 mg, 1.122 mmol, 1.7 equiv) in DMF (3 mL) dropwise. The mixture was stirred at 25° C. for 4 h. The reaction was quenched by the addition of sat. aq. Na₂S₂O₃ (10 mL). The aqueous layer was extracted with EA (3×20 mL). The combined organic layers were washed with brine (3×20 mL), dried over anhydrous Na₂SO₄ and filtered. After filtration, the filtrate was concentrated under reduced pressure. The residue was purified by silica gel column chromatography, eluted with 0-100% of EA in PE to afford the title compound (245 mg, 80.84%) as a yellow solid. ma (ESI, +ve ion)=460.05 [M+H]⁺.

Step F. tert-butyl 6-[(1R,2S)-1'-ethyl-5'-methoxy-2'-oxospiro[cyclopropane-1,3'-indol]-2-yl]-3-iodoindazole-1-carboxylate

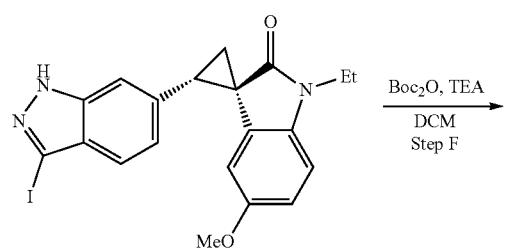

To a stirred mixture of (1R,2S)-1'-ethyl-2-(3-iodo-1H-indazol-6-yl)-5'-methoxyspiro[cyclopropane-1,3'-indol]-2'-one (245 mg, 0.533 mmol, 1.00 equiv) and TEA (107.96 mg, 1.066 mmol, 2 equiv. in DCM (5 mL was added Boc₂O (174.63 mg, 0.800 mmol, 1.5 equiv) at 25° C. The mixture was stirred at 25° C. for 4 h. The solvent was removed under reduced pressure. The residue was purified by silica gel column chromatography, eluted with 0-50% of EA in PE to afford the title compound (268 mg, 89.81%) as a white solid. m/z (ESI, +ve ion)=560.05 [M+H]⁺. ¹H NMR (400 MHz, Chloroform-d) 8.08 (s, 1H), 7.42-7.39 (m, 1H), 7.19-7.17 (m, 1H), 6.81 (d, J=8.4 Hz, 1H), 6.70-6.67 (m, 1H), 5.64 (d, J=2.8 Hz, 1H), 3.94-3.82 (m, 2H), 3.47 (t, J=8.4 Hz, 1H), 3.42 (s, 3H), 2.32-2.28 (m, 1H), 2.09-2.06 (m, 1H), 1.70 (s, 9H), 1.35 (t, J=7.2 Hz, 3H).

Step G. tert-butyl 3-[(6-{3-[(tert-butyldimethylsilyl)oxy]azetidin-1-yl}-5-chloropyrimidin-4-yl)amino]-6-[(1R,2S)-1'-ethyl-5'-methoxy-2'-oxospiro[cyclopropane-1,3'-indol]-2-yl]indazole-1-carboxylate

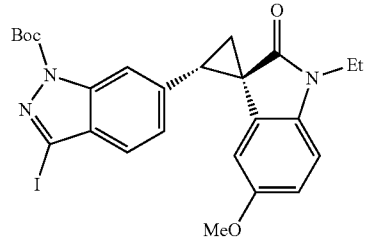

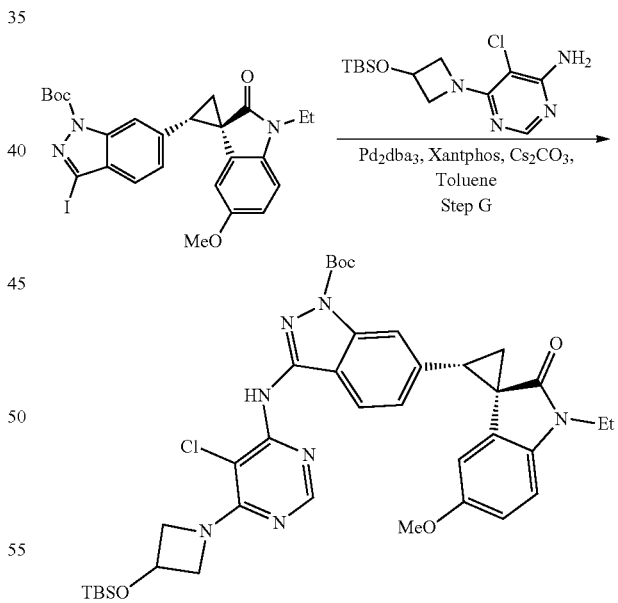

To a stirred mixture of tert-butyl 6-[(1R,2S)-1'-ethyl-5'-methoxy-2'-oxospiro[cyclopropane-1,3'-indol]-2-yl]-3-iodoindazole-1-carboxylate and 6-(3-((tert-butyldimethylsilyl)oxy)azetidin-1-yl)-5-chloropyrimidin-4-amine (74.30 mg, 0.236 mmol, 1.2 equiv) in toluene (3 mL) were added Cs₂CO₃ (128.14 mg, 0.394 mmol, 2 equiv), Pd₂(dba); (36.01 mg, 0.039 mmol, 0.2 equiv) and XantPhos (22.76 mg, 0.039 mmol, 0.2 equiv) under nitrogen atmosphere. The resulting mixture was stirred for 2 h at 90° C. under nitrogen atmosphere. The mixture was filtered and washed with EA (5 mL×3). The filtrate was concentrated in vacuo. The residue was purified by silica gel column chromatography, eluted with 0-50% of EA in PE to afford the title compound (90 mg, 49.06%) as a yellow solid. m/z (ESI, +ve ion) =746.35 [M+H]⁺.

Step H. (1R,2S)-2-(3-{[5-chloro-6-(3-hydroxyazetidin-1-yl)pyrimidin-4-yl]amino}-1H-indazol-6-yl)-1'-ethyl-5'-methoxyspiro[cyclopropane-1,3'-indol]-2'-one

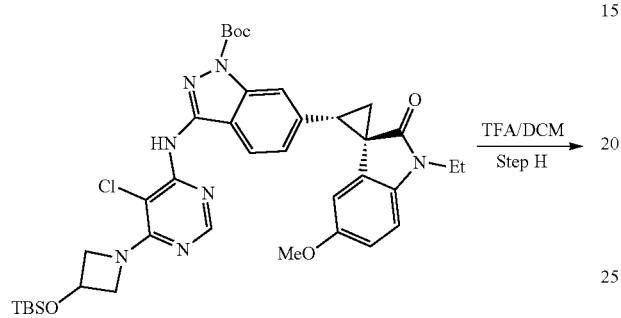

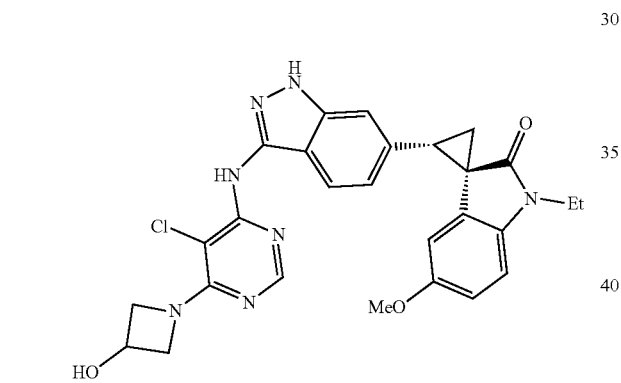

The mixture of tert-butyl 3-[(6-{3-[(tert-butyldimethylsilyl)oxy]azetidin-1-yl}-5-chloropyrimidin-4-yl)amino]-6-[(1R,2S)-1'-ethyl-5'-methoxy-2'-oxospiro[cyclopropane-1,3'-indol]-2-yl]indazole-1-carboxylate (90 mg, 0.121 mmol, 1.00 equiv) in TFA (0.5 mL) and DCM (2.5 mL) was stirred at 40° C. for 12 h. The solvent was removed under reduced pressure. The residue was purified by Prep-HPLC with the following conditions: Column: XBridge Prep OBD C18 Column, 30×150 mm, 5 µm; Mobile Phase A: Water (10 mmol/L NH₄HCO₃), Mobile Phase B: ACN; Flow rate: 60 mL/min; Gradient: 24% B to 34% B in 8 min; wavelength: 254 nm; RT1(min): 7. The product-containing fractions were collected and concentrated in vacuo to give Example 71 (29 mg, 44.80%) as a white solid. m/z (ESI, +ve ion)=532.40 [M+H]⁺. ¹H NMR (400 MHz, DMSO-d₆) δ 12.65 (s, 1H), 8.89 (s, 1H), 7.82 (s, 1H), 7.40 (s, 1H), 7.36 (d, J=8.4 Hz, 1H), 6.96 (d, J=8.8 Hz, 1H), 6.90-6.87 (m, 1H), 6.69-6.66 (m, 1H), 5.76 (d, J=2.4 Hz, 1H), 5.67 (d, J=6.0 Hz, 1H), 4.54-4.44 (m, 3H), 3.99-3.96 (m, 2H), 3.84-3.74 (m, 2H), 3.36 (s, 3H), 3.25 (t, J=8.4 Hz, 1H), 2.39-2.36 (m, 1H), 2.06-2.02 (m, 1H), 1.20 (t, J=6.8 Hz, 3H).

Example 109. (1R,2S)-2-(3-{[5-(difluoromethoxy)-6-(morpholin-4-yl)pyrimidin-4-yl]amino}-1H-indazol-6-yl)-5'-methoxyspiro[cyclopropane-1,3'-indol]-2'(1'H)-one

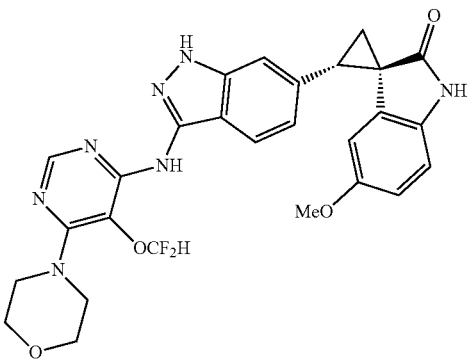

Step A. (1R,2S)-2-(3-iodo-1H-indazol-6-yl)-5'-methoxyspiro[cyclopropane-1,3'-indolin]-2'-one

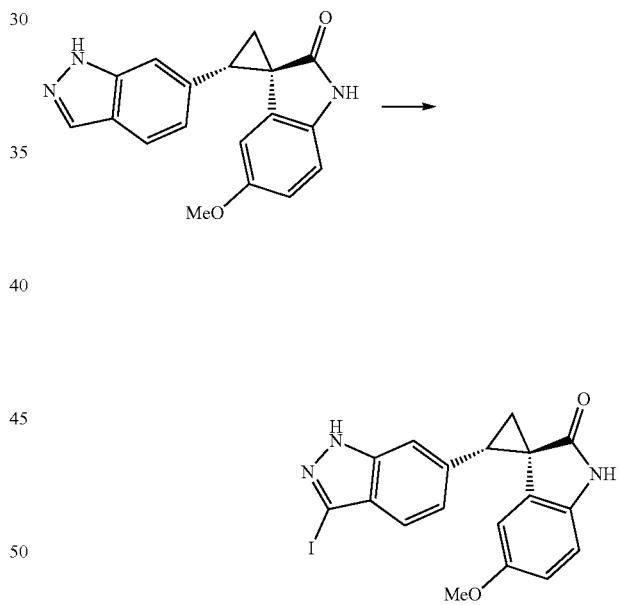

To a vial was added (1R,2S)-2-(1H-indazol-6-yl)-5'-methoxyspiro[cyclopropane-1,3'-indolin]-2'-one (46.0 mg, 151 µmol) followed by DMF (100 µL) and MeOH (100 µL). To this suspension was added potassium carbonate (41.6 mg, 301 µmol). Finally, iodine (48.3 mg, 190 µmol) dissolved in DMF (100 µL) was added dropwise and allowed to stir at rt. After 2 h, another portion of iodine (9.3 mg, 36.58 mmol) in 100 µL of DMF was added to the mixture and stirred for 16 h at it. The mixture was quenched with Na₂S₂O₃ in water and stirred for 2 h. The mixture was diluted with excess water and a solid precipitated. The solid was collected by filtration and washed with water, affording the title compound (50.0 mg, 77%). m/z (ESI, +ve ion)=432.0 [M+H]+.

Step B. tert-butyl 6-((1R,2S)-1'-(tert-butoxycarbonyl)-5'-methoxy-2'-oxospiro[cyclopropane-1,3'-indolin]-2-yl)-3-iodo-1H-indazole-1-carboxylate

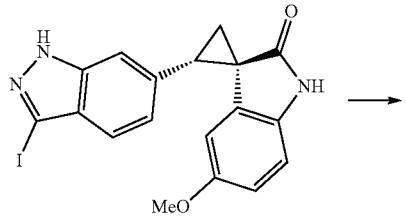

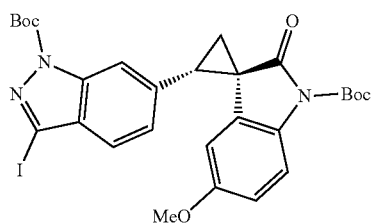

4-Dimethylaminopyridine (1.5 mg, 11.6 µmol) was added to a solution of di-tert-butyl dicarbonate (73.4 µL, 313 µmol), (1R,2S)-2-(3-iodo-1H-indazol-6-yl)-5'-methoxyspiro[cyclopropane-1,3'-indolin]-2'-one (50.0 mg, 116 µmol) and triethylamine (65.3 µL, 464 µmol) in DCM (400 µL). The solution was stirred at room temperature for 16 h and then concentrated to dryness. The product was purified by column chromatography (0 to 10/% EtOAc in hexane), affording the title compound (52.7 mg, 72%) as yellow foamy solid. m/z (ESI, +ve ion)=432.0 [M+H]+−2boc. 1H NMR (400 MHz, CDCl3) δ 8.09 (s, 1H), 7.79 (d, J=8.9 Hz, 1H), 7.38 (d, J=8.3 Hz, 1H), 7.13 (dd, J=8.3, 0.7 Hz, 1H), 6.67 (dd, J=8.9, 2.7 Hz, 1H), 5.51 (d, J=2.6 Hz, 1H), 3.50 (t, J=8.6 Hz, 1H), 3.37 (s, 3H), 2.36 (dd, J=9.2.4.8 Hz, 1H), 2.09 (dd, J=8.1, 4.8 Hz, 1H), 1.68 (d, J=5.0 Hz, 18H).

Step C. 6-chloro-5-(difluoromethoxy)pyrimidin-4-amine

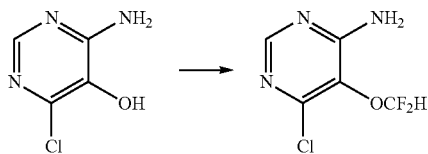

Potassium hydroxide (1.5 g, 26.4 mmol) was added to a solution of 4-amino-6-chloropyrimidin-5-ol (200.0 mg, 1.32 mmol) dissolved in a mixture of MeCN and water (1:1) (13 mL) and the mixture was stirred in an ice-water bath. Diethyl(bromodifluoromethyl)phosphonate (483 µL, 2.64 mmol) was then added dropwise at 0° C. The reaction was then stirred at rt for 24 h. The mixture was directly loaded onto a C18 column chromatography and the product purified (isocratic 50% MeCN in aq. ammonium formate buffer) affording title compound (50.0 mg, 78%). m/z (ESI, +ve ion)=196.0 [M+H]+.

Step D. 5-(difluoromethoxy)-6-morpholinopyrimidin-4-amine

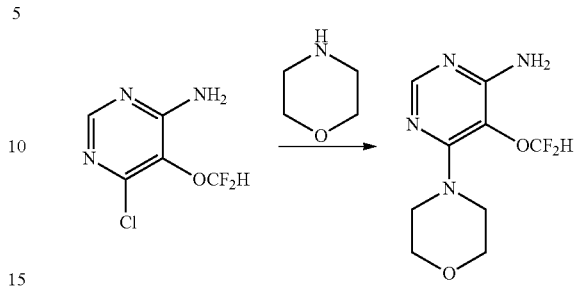

In a flask was dissolved 6-chloro-5-(difluoromethoxy)pyrimidin-4-amine (92.0 mg, 470 µmol) in DMF (2.75 mL) to which were added morpholine (100 µL, 1.13 mmol) and cesium carbonate (300 mg, 903 µmol). The reaction was heated to 90° C. and stirred for 22 h. The reaction was cooled down to room temperature and the mixture was passed through a pad of silica gel, washed successively with heptanes, DCM, and finally EtOAc:MeOH (8:2). The crude product eluted with EtOAc/MeOH and was collected and concentrated. The residue was further purified by C18 column chromatography (15-35% MeCN in aq. ammonium formate buffer) to afford title compound (58.0 mg, 47%) as a yellow solid. m/z (ESI, +ve ion)=246.9 [M+H]+.

Step E. (1R,2S)-2-(3-((5-(difluoromethoxy)-6morpholinopyrimidin-4-yl)amino)-1H-indazol-1-yl)-5'-methoxyspiro[cyclopropane-1,3'-indolin]-2'-one

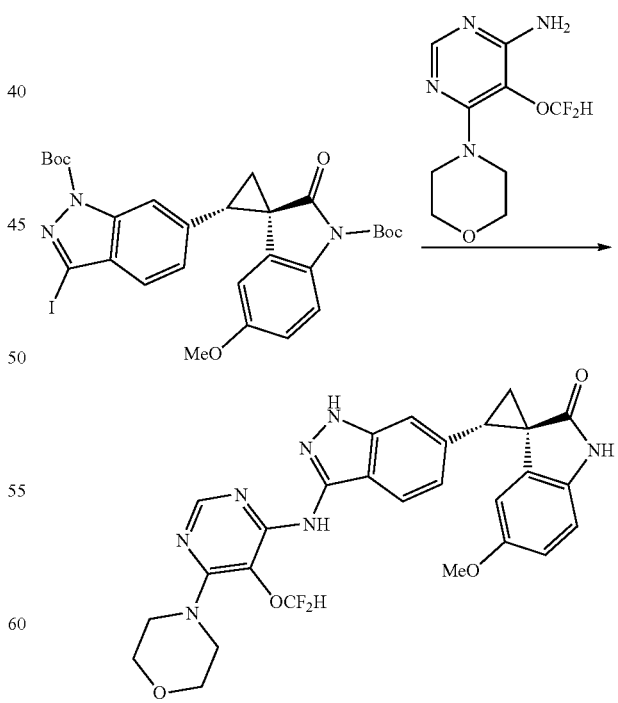

To a microwave vial were added 5-(difluoromethoxy)-6-morpholinopyrimidin-4-amine (25.0 mg, 102 µmol), tert-butyl (1R,2S)-2-(14tert-butoxycarbonyl)-3-iodo-1H-indazol-6-yl)-5'-methoxy-2'-oxospiro[cyclopropane-1,3'-indoline]-1'-carboxylate (64.1 mg, 102 µmol), Pd$_2$(dba)$_3$ (5.83 mg, 10.1 µmol), XantPhos (6.00 mg, 10.2 µmol), and cesium carbonate (67.5 mg, 203 µmol). Degassed toluene (4.00 mL) was then added and the reaction was purged with nitrogen gas for 30 seconds. The vial was then sealed and the reaction was heated to 100° C. for 16 h in an oil bath. The cooled solution was passed through a pad of silica gel washing successively with hexanes, DCM, and then EtOAc: MeOH (8:2) as eluent. The EtOAc/MeOH portion was collected and concentrated. The crude residue was dissolved in DCM (5.00 mL) and TFA (5.00 mL) and stirred at rt for 1 h. The solvents were removed under vacuum and the residue was purified by silica gel chromatography (30% isopropanol in DCM) and then by C18 column chromatography (45% MeCN in aq. ammonium formate buffer) to afford Example 109 (8.0 mg, 14%) as a white solid. m/z (ESI, +ve ion)=550.2 [M+H]+. 1H NMR (500 MHz, DMSO) δ 12.62 (s, 1H), 10.41 (s, 1H), 9.11 (s, 1H), 7.89 (s, 1H), 7.45-7.36 (m, 2H), 6.95 (t, J=73.6 Hz, 1H), 6.90 (d, J=9.5 Hz, 1H), 6.75 (d, J=8.4 Hz, 1H), 6.59 (dd, J=8.5, 2.6 Hz, 1H), 5.72 (d, J=2.6 Hz, 1H), 3.76-3.63 (m, 4H), 3.62-3.48 (m, 4H), 3.33 (s, 3H), 3.18 (t, J=8.5 Hz, 1H), 2.32 (dd, J=7.9, 4.6 Hz, 1H), 2.02-1.95 (m, 1H), 19F NMR (470 MHz, DMSO) δ -82.03 (d, J=73.6 Hz).

Example 110. (1R,2S)-2-(3-{[6-(azetidin-3-yl)-3-methoxypyrazin-2-yl]amino}-1H-indazol-1-yl)-5'-methoxyspiro[cyclopropane-1,3'-indol]-2'(1'H)-one

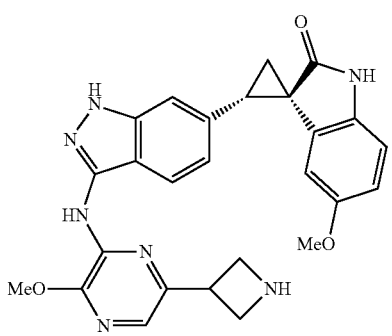 [SMILES: COc1ccc2c(c1)[C@]1(C[C@H]1c1ccc3c(Nc4nc(C5CNC5)cnc4OC)n[nH]c3c1)C(=O)N2]

Step A. tert-butyl 3-{6-[bis(tert-butoxycarbonyl)amino]-5-methoxypyrazin-2-yl}azetidine-1-carboxylate

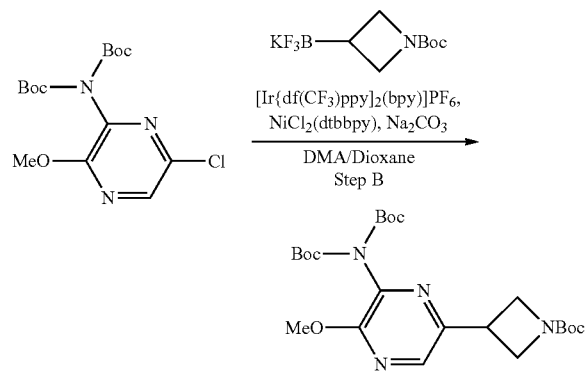

To a stirred mixture of tert-butyl (tert-butoxycarbonyl)(6-chloro-3-methoxypyrazin-2-yl)carbamate (179.91 mg, 0.500 mmol, 1.00 equiv) and tert-butyl 3-(trifluoro-lambda4-boranyl)azetidine-1-carboxylate potassium (263.12 mg, 1.000 mmol, 2 equiv) in DMA (1 mL) and dioxane (4 mL) were added [Ir{dFCF3ppy}$_2$(bpy)]PF$_6$ (50.49 mg, 0.050 mmol, 0.1 equiv), [4,4'-Bis(1,1-dimethylethyl)-2,2'-bipyridine]nickel (II) dichloride (29.85 mg, 0.075 mmol, 0.15 equiv) and Na$_2$CO$_3$ (105.99 mg, 1.000 mmol, 2 equiv) at room temperature under nitrogen atmosphere. The resulting mixture was stirred for 16 h at room temperature under blue LEDs. The resulting mixture was concentrated under reduced pressure. The residue was purified by Prep-TLC (PE/EA 1/1) to afford the title compound (175 mg, 72.83%) as a green solid. m/z (ESI+ve ion)=381.25 [M+H-100]+.

Step B. tert-butyl 3-(6-amino-5-methoxypyrazin-2-yl)azetidine-1-carboxylate

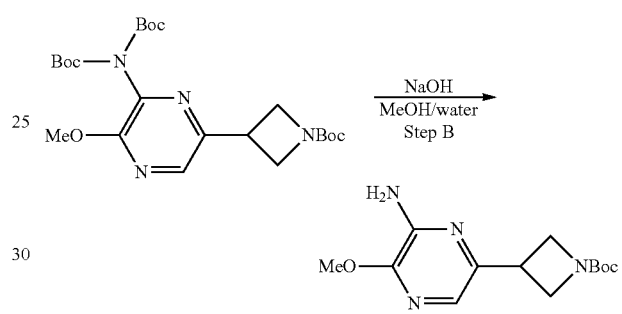

To a stirred mixture of tert-butyl 3-{6-[bis(tert-butoxycarbonyl)amino]-5-methoxypyrazin-2-yl}azetidine-1-carboxylate (120 mg, 0.250 mmol, 1.00 equiv) in MeOH (1 mL) was added NaOH (99.88 mg, 2.500 mmol, 10 equiv) in H$_2$O (0.5 mL) dropwise at room temperature. The resulting mixture was stirred for 16 h at 60° C. The resulting mixture was concentrated under reduced pressure. The residue was purified by reverse flash chromatography with the following conditions: column, C18 silica gel; mobile phase, ACN in water, 10% to 50% gradient in 50 min; detector, UV 254 nm to afford the title compound (68.8 mg, 98.290) as a white solid. m/z (ESI, +ve ion)=281.25 [M+H]+. $^1$H NMR (400 MHz DMSO-d$_6$) δ 7.17 (d, J=1.0 Hz, 1H), 6.39 (s, 2H), 4.07 (s, 3H), 3.86 (d, J=1.0 Hz, 3H), 3.76-3.61 (m, 4H), 3.34 (s, 1H), 1.40 (d, J=1.0 Hz, 9H).

Step D. tert-butyl (1R,2S)-2-[1-(tert-butoxycarbonyl)-3-({6-[1-(tert-butoxycarbonyl)azetidin-3-yl]-3-methoxypyrazin-2-yl}amino)indazol-6-yl]-5'-methoxy-2'-oxospiro[cyclopropane-1,3'-indole]-1'-carboxylate

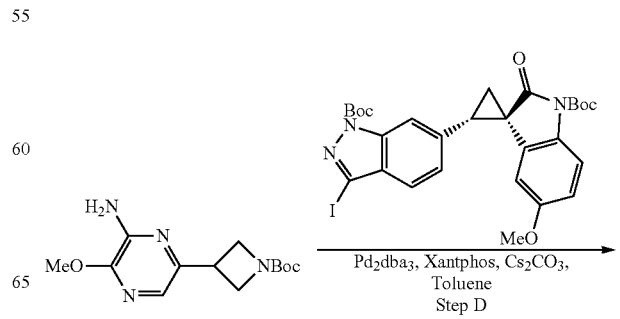

-continued

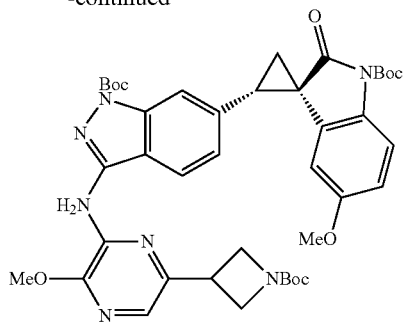

To a stirred mixture of tert-butyl 3-(6-amino-5-methoxypyrazin-2-yl)azetidine-1-carboxylate (31.96 mg, 0.114 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (60 mg, 0.095 mmol, 1.00 equiv) in toluene (1 mL) were added Pd$_2$(dba)$_3$ (8.70 mg, 0.010 mmol, 0.1 equiv), XantPhos (5.50 mg, 0.010 mmol, 0.1 equiv) and Cs$_2$CO$_3$ (61.92 mg, 0.190 mmol, 2 equiv) at room temperature under nitrogen atmosphere. The resulting mixture was stirred for 2 h at 90° C. under nitrogen atmosphere. The resulting mixture was concentrated under reduced pressure. The residue was purified by Prep-TLC (PE/EA 1/1) to afford the title compound (45.3 mg, 60.82%) as a white solid. m/z (ESI+ve ion)=784.50 [M+H]$^+$.

Step E. (1R,2S)-2-(3-{[6-(azetidin-3-yl)-3-methoxypyrazin-2-yl]amino}-1H-indazol-6-yl)-5'-methoxy-1'H-spiro[cyclopropane-1,3'-indol]-2'-one

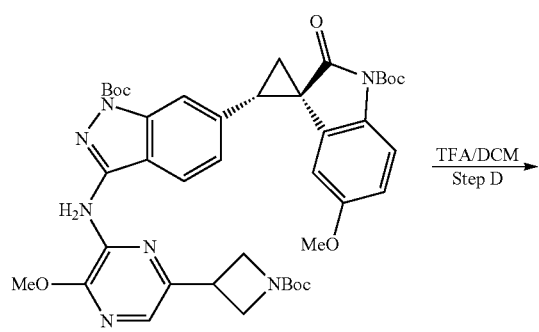

To a stirred mixture of tert-butyl (1R,2S)-2-[1-(tert-butoxycarbonyl)-3-({6-[1-(tert-butoxycarbonyl)azetidin-3-yl]-3-methoxypyrazin-2-yl}amino)indazol-6-yl]-5'-methoxy-2'-oxospiro[cyclopropane-1,3'-indole]-1'-carboxylate (40 mg, 0.051 mmol, 1.00 equiv) in DCM (2 mL) was added TFA (1 mL) dropwise at room temperature. The resulting mixture was stirred for 1 h at 60° C. The mixture was cooled down to room temperature. The resulting mixture was concentrated under reduced pressure. The residue was purified by Prep-HPLC with the following conditions: Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 15% B to 40/o B in 8 min, 40% B; wavelength: 254 nm; RT1(min): 6.2 to afford Example 110 (20 mg, 80.90%) as an off-white solid. m/z (ESI, +ve ion)=484.20 [M+H]+. 1H NMR (400 MHz, Methanol-d$_4$) δ 7.60 (d, J=8.4 Hz, 1H), 7.46 (s, 1H), 7.39 (s, 1H), 6.91 (d, J=8.4 Hz, 1H), 6.85 (d, J=8.0 Hz, 1H), 6.65-6.62 (m, 1H), 5.65 (d, J=2.4 Hz, 1H), 4.09-3.92 (m, 4H), 3.93 (m, 3H), 3.75 (m, 2H), 3.50-3.38 (m, 2H), 3.15 (t, J=1.6 Hz, 1H), 2.26 (m, 1H), 2.19 (m, 1H).

Example 111. (1R,2S)-2-(3-{[6-(3-hydroxyazetidin-1-yl)-2-(propan-2-yl)pyrimidin-4-yl]amino}-1H-indazol-6-yl)-5'-methoxyspiro[cyclopropane-1,3'-indol]-2'(1'H)-one

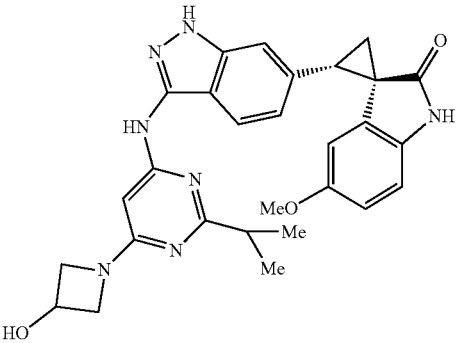 [SMILES: COc1ccc2c(c1)[C@]1(C[C@H]1c1ccc3c(Nc4cc(N5CC(O)C5)nc(C(C)C)n4)n[nH]c3c1)C(=O)N2]

Step A. 6-{3-[(tert-butyldimethylsilyl)oxy]azetidin-1-yl}-2-isopropylpyrimidin-4-amine

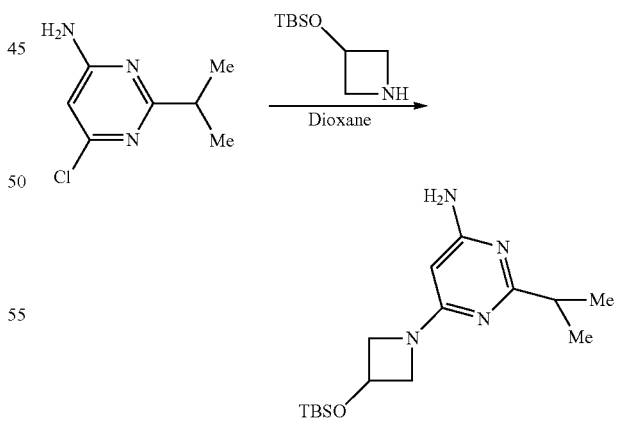

The mixture of 3-((tert-butyldimethylsilyl)oxy)azetidine (120 mg, 0.699 mmol, 1.00 equiv), 6-chloro-2-isopropylpyrimidin-4-amine (131.00 mg, 0.699 mmol, 1 equiv) and TEA (141.50 mg, 1.398 mmol, 2 equiv) in dioxane (2 mL) was stirred at 120° C. for 8 h. The solvent was removed under reduced pressure. The residue was purified by silica gel column chromatography, eluted with 0-50% of EA in PE to afford the title compound (80 mg, 35.48%) as a white solid. m/z (ESI, +ve ion)=323.35[M+H]$^+$. $^1$H NMR (400 MHz, DMSO-d$_6$) δ 6.09 (s, 2H), 5.09 (s, 1H), 4.75-4.70 (m, 1H), 4.14-4.11 (m, 2H), 3.60-3.57 (m, 2H), 2.68-2.59 (m, 1H), 1.13 (s, 3H), 1.11 (s, 3H), 0.88 (s, 9H), 0.07 (s, 6H).

Step B. tert-butyl (1R,2S)-2-[1-(tert-butoxycarbonyl)-3-[(6-{3-[(tert-butyldimethylsilyl)oxy]azetidin-1-yl}-2-isopropylpyrimidin-4-yl)amino]indazol-6-yl]-5'-methoxy-2'-oxospiro[cyclopropane-1,3'-indole]-1'-carboxylate

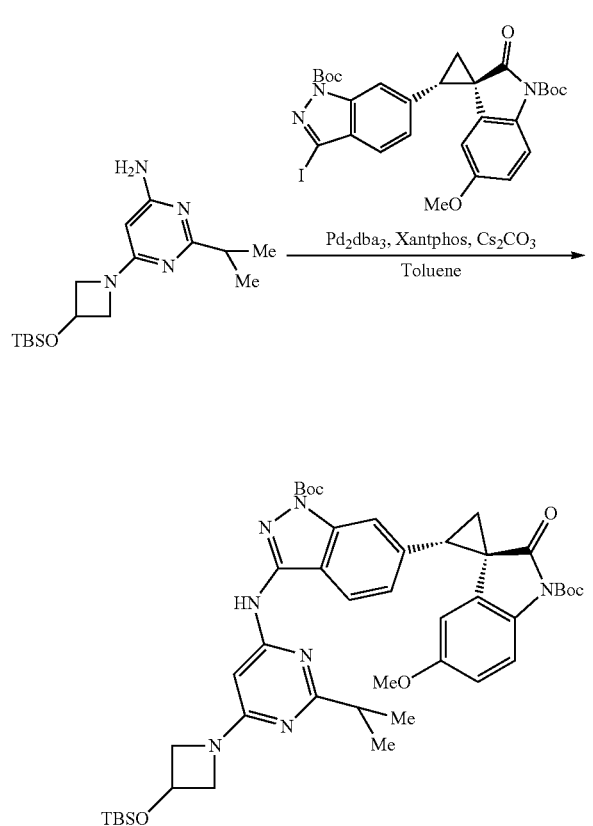

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80 mg, 0.127 mmol, 1.00 equiv) and 6-{3-[(tert-butyldimethylsilyl)oxy]azetidin-1-yl}-2-isopropylpyrimidin-4-amine (49.03 mg, 0.152 mmol, 1.2 equiv) in toluene (2.0 mL) were added Cs$_2$CO$_3$ (82.56 mg, 0.254 mmol, 2 equiv), XantPhos (14.66 mg, 0.025 mmol, 0.2 equiv) and Pd$_2$(dba)$_3$ (23.20 mg, 0.025 mmol, 0.2 equiv) under nitrogen atmosphere. The mixture was stirred at 90° C. for 2 h. The resulting mixture was filtered and washed with EA (3×5 mL). The filtrate was concentrated in vacuo. The residue was purified by silica gel column eluted with 0-50% EA in PE to give crude title compound (70 mg, 66.89%) as a yellow solid. m/z (ESI, +ve ion)=826.50 [M+H]$^+$.

Step C. (1R,2S)-2-(3-{[6-(3-hydroxyazetidin-1-yl)-2-isopropylpyrimidin-4-yl]amino}-1H-indazol-6-yl)-5'-methoxy-1'H-spiro[cyclopropane-1,3'-indol]-2'-one

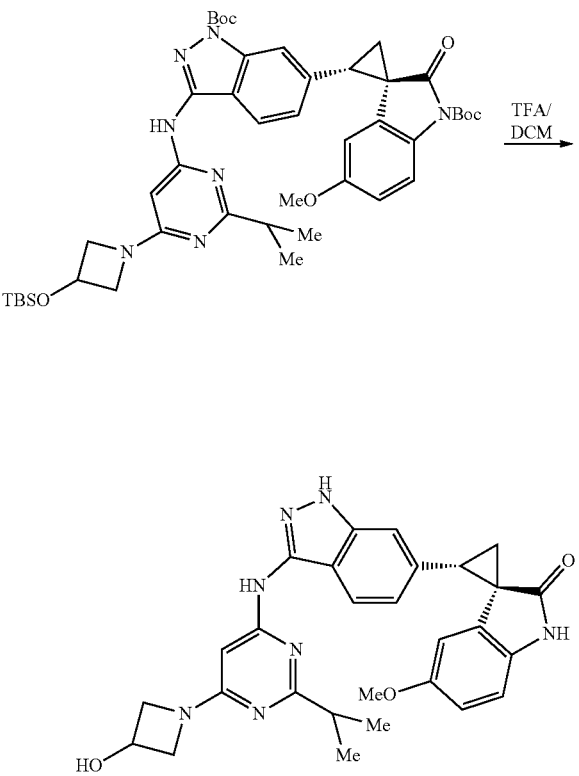

The mixture of tert-butyl (1R,2S)-2-[1-(tert-butoxycarbonyl)-3-[(6-{3-[(tert-butyldimethylsilyl)oxy]azetidin-1-yl}-2-isopropylpyrimidin-4-yl)amino]indazol-6-yl]-5'-methoxy-2'-oxospiro[cyclopropane-1,3'-indole]-1'-carboxylate (70 mg, 0.085 mmol, 1.00 equiv) in TFA (1 mL) and DCM (5 mL) was stirred at 25° C. for 48 h. The solvent was removed under reduced pressure. The residue was purified by prep-HPLC with the following conditions: Column: XBridge Shield RP18 OBD Column, 30×150 mm, 5 µm; Mobile Phase A: Water (10 mmol/L NH$_4$HCO$_3$), Mobile Phase B: ACN; Flow rate: 60 mL/min; Gradient: 25% B to 45% B in 8 min; wavelength: 254 nm; RT1(min): 6.5. The product containing fractions were collected and concentrated in vacuo to give Example 111 (27.8 mg, 63.94%) as a white solid. m/z (ESI, +ve ion)=512.25 [M+H]$^+$. $^1$H NMR (400 MHz, Methanol-d$_4$) δ 7.70-7.68 (m, 1H), 7.40-7.39 (m, 1H), 6.94-6.92 (m, 1H), 6.84 (d, J=8.4 Hz, 1H), 6.64-6.62 (m, 1H), 6.31 (s, 1H), 5.61 (d, J=2.4 Hz, 1H), 4.71-4.65 (m, 1H), 4.29-4.25 (m, 2H), 3.85-3.80 (m, 2H), 3.38-3.36 (m, 1H), 3.30 (s, 3H), 2.90-2.83 (m, 1H), 2.26-2.17 (m, 2H), 1.27 (d, J=6.8 Hz, 6H).

Example 114: (1R,2S)-2-(3-{[2-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one

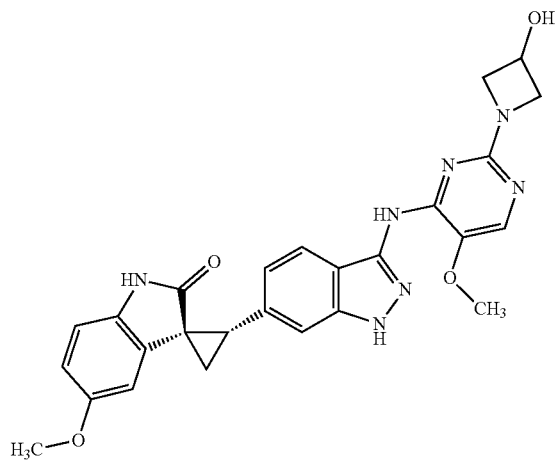 [SMILES: COc1ccc2c(c1)[C@]1(C[C@H]1c1ccc3c(Nc4nc(N5CC(O)C5)ncc4OC)n[nH]c3c1)C(=O)N2]

Step A. 2-{3-[(tert-butyldimethylsilyl)oxy]azetidin-1-yl}-5-methoxypyrimidin-4-amine

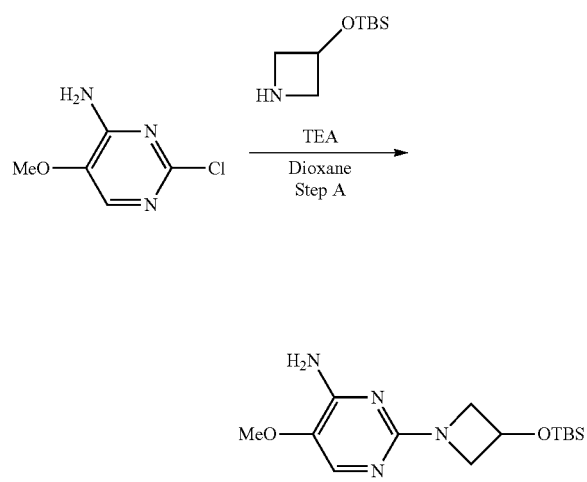

To a stirred solution of 2-chloro-5-methoxypyrimidin-4-amine (160.0 mg, 1.003 mmol, 1.00 equiv) and 3-[(tert-butyldimethylsilyl)oxy]azetidine (375.73 mg, 2.006 mmol, 2.0 equiv) in dioxane (2.0 mL) was added TEA (304.39 mg, 3.009 mmol, 3.0 equiv) dropwise at room temperature under nitrogen atmosphere. The resulting mixture was stirred for 16 h at 100° C. under nitrogen atmosphere. The resulting mixture was cooled down to room temperature and concentrated under reduced pressure. The residue was purified by silica gel column chromatography, eluted with PE:EA (1:1) to afford the title compound (80.0 mg, 25.70%) as a white solid. m/z (ESI, +ve ion)=311.20 [M+H]$^+$. $^1$H NMR (400 MHz, Chloroform-d) δ 7.55 (s, 1H), 4.72-4.67 (m, 1H), 4.32 (s, 2H), 3.94 (s, 2H), 3.81 (s, 3H), 0.91 (s, 9H), 0.09 (s, 6H).

Step B. tert-butyl (1R,2S)-2-[1-(tert-butoxycarbonyl)-3-[(2-{3-[(tert-butyldimethylsilyl)oxy]azetidin-1-yl}-5-methoxypyrimidin-4-yl)amino]indazol-6-yl]-5'-methoxy-2'-oxospiro[cyclopropane-1,3'-indole]-1'-carboxylate

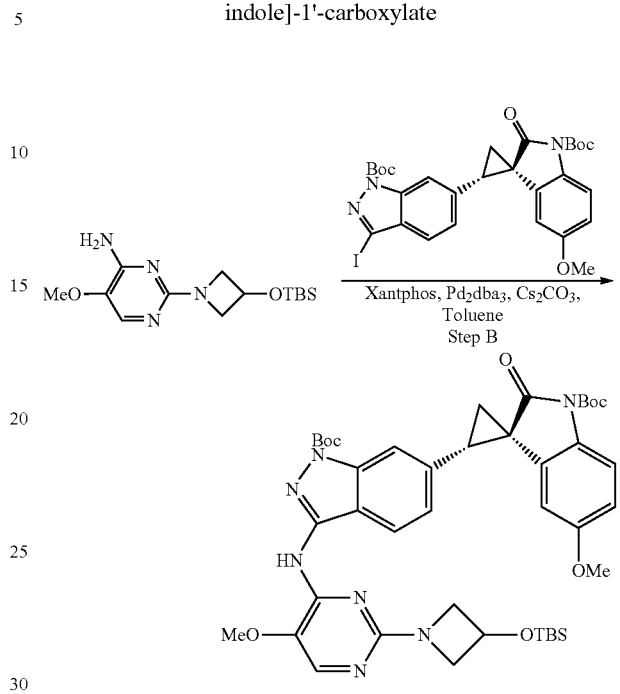

To a stirred solution of 2-{3-[(tert-butyldimethylsilyl)oxy]azetidin-1-yl}-5-methoxypyrimidin-4-amine (34.42 mg, 0.111 mmol, 1.0 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (70.0 mg, 0.111 mmol, 1.00 equiv) in toluene (3.5 mL) were added XantPhos (12.83 mg, 0.022 mmol, 0.2 equiv), Pd$_2$(dba)$_3$ (20.30 mg, 0.022 mmol, 0.2 equiv) and Cs$_2$CO$_3$ (72.24 mg, 0.222 mmol, 2.0 equiv) at room temperature under nitrogen atmosphere. The resulting mixture was stirred for 2 h at 90° C. under nitrogen atmosphere then cooled down to room temperature. The resulting mixture was filtered, the filter cake was washed with EA (3×10 mL). The filtrate was concentrated under reduced pressure. The residue was purified by silica gel column chromatography, eluted with PE:EA (1:1) to afford the title compound (80.0 mg, 88.66%) as a yellow solid. m/z (ESI, +ve ion)=814.60 [M+H]$^+$.

Step C. tert-butyl (1R,2S)-2-[1-(tert-butoxycarbonyl)-3-{[2-(3-hydroxyazetidin-1-yl)-5-methoxypyrimidin-4-yl]amino}indazol-6-yl]-5'-methoxy-2'-oxospiro[cyclopropane-1,3'-indole]-1'-carboxylate

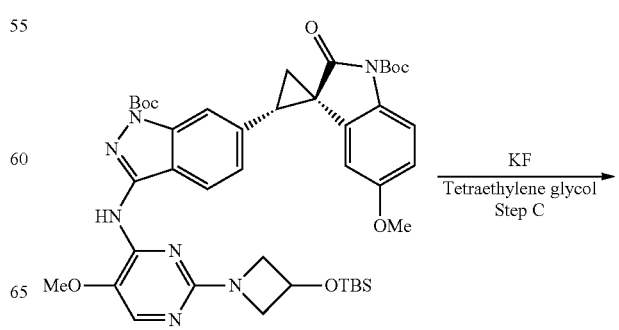

-continued

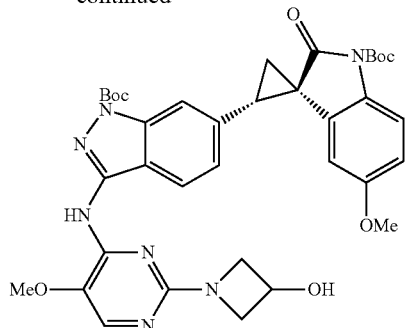

To a stirred solution of tert-butyl (1R,2S)-2-[1-(tert-butoxycarbonyl)-3-[(2-{3-[(tert-butyldimethylsilyl)oxy]azetidin-1-yl}-5-methoxypyrimidin-4-yl)amino]indazol-6-yl]-5'-methoxy-2'-oxospiro[cyclopropane-1,3'-indole]-1'-carboxylate (75.0 mg, 0.092 mmol, 1.00 equiv) in tetraethylene glycol (5.0 mL) was added KF (16.1 mg, 0.28 mmol, 3 equiv) at room temperature under nitrogen atmosphere. The resulting mixture was stirred for 8 h at room temperature under nitrogen atmosphere. The reaction was quenched with water at room temperature. The resulting mixture was extracted with EA (3×30 mL). The combined organic layers were washed with brine (3×10 mL), dried over anhydrous Na$_2$SO$_4$. After filtration, the filtrate was concentrated under reduced pressure to afford the title compound (40.0 mg, 62.04%) as a yellow oil. m/z (ESI, +ve ion)=700.35[M+H]$^+$.

Step D. (1R,2S)-2-(3-{[2-(3-hydroxyazetidin-1-yl)-5-methoxypyrimidin-4-yl]amino}-1H-indazol-6-yl)-5'-methoxy-1'H-spiro[cyclopropane-1,3'-indol]-2'-one

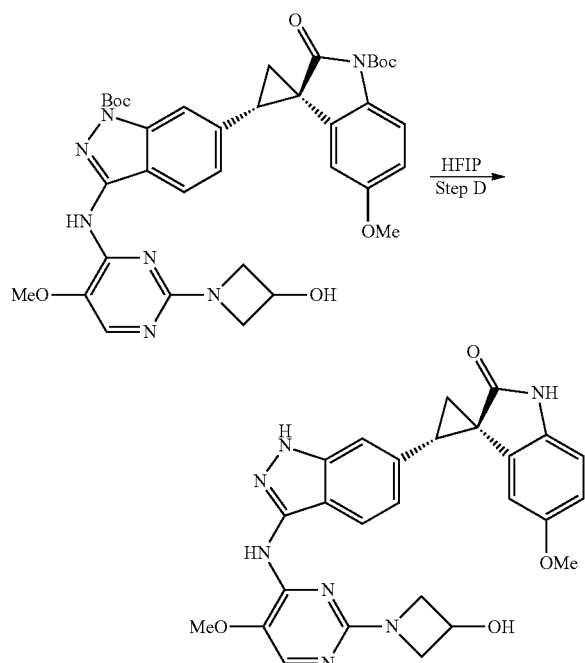

A solution of tert-butyl (1R,2S)-2-[1-(tert-butoxycarbonyl)-3-{[2-(3-hydroxyazetidin-1-yl)-5-methoxypyrimidin-4-yl]amino}indazol-6-yl]-5'-methoxy-2'-oxospiro[cyclopropane-1,3'-indole]-1'-carboxylate (70.0 mg, 0.100 mmol, 1.00 equiv) in HFIP (5.0 mL) was stirred for 6 h at 60° C. The mixture was allowed to cool down to room temperature. The resulting mixture was concentrated under reduced pressure. The crude product (45 mg) was purified by prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 17% B to 27% B in 8 min, 27% B; wavelength: 254 nm; RT1(min): 7.43 to afford Example 114 (18.7 mg, 37.42%) as a white solid. m/z (ESI, +ve ion)=500.35 [M+H]$^+$. $^1$H NMR (400 MHz, Methanol-d$_4$) δ 7.58 (d, J=8.4 Hz, 1H), 7.51 (s, 1H), 7.30 (s, 1H), 6.77-6.71 (m, 2H), 6.53-6.50 (m, 1H), 5.49 (d, J=3.6 Hz, 1H), 4.35-4.30 (m, 1H), 3.88-3.79 (m, 6H), 3.53-3.48 (m, 2H), 3.25 (d, J=8.0 Hz, 2H), 3.19 (s, 3H), 2.14-2.11 (m, 1H), 2.08-2.05 (m, 1H).

Example 116: (1R,2S)-2-(3-((5-chloro-2-cyclopropylpyrimidin-4-yl)amino)-1H-indazol-6-yl)-5'-methoxyspiro[cyclopropane-1,3'-indolin]-2'-one

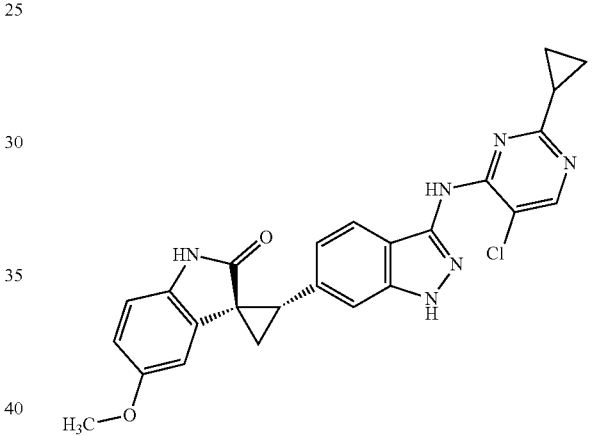

Step A. 6-chloro-2-cyclopropylpyrimidin-4-amine

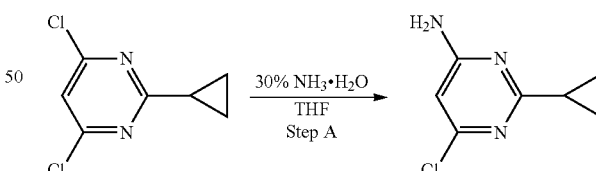

To a stirred solution of 4,6-dichloro-2-cyclopropylpyrimidine (400.0 mg, 2.116 mmol, 1.00 equiv) in THF (1.6 mL) was added NH$_3$·H$_2$O (30%, 0.8 mL) dropwise at room temperature. The resulting mixture was stirred for 16 h at 70° C. then cooled down to room temperature. The resulting mixture was concentrated under reduced pressure. The residue was purified by silica gel column chromatography, eluted with PE:EA (1:1) to afford the title compound (250.0 mg, 69.66%) as a white solid. m/z (ESI, +ve ion)=170.20 [M+H]$^+$. $^1$H NMR (400 MHz, Chloroform-d) δ 6.25 (s, 1H), 4.92 (s, 2H), 2.06-2.00 (m, 1H), 1.13-1.04 (m, 2H), 1.04-0.98 (m, 2H).

Step B. 2-cyclopropylpyrimidin-4-amine

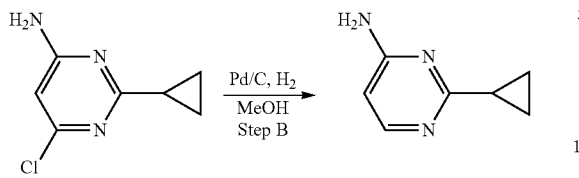

To a solution of 6chloro-2-cyclopropylpyrimidin-4-amine (200.0 mg, 1.179 mmol, 1.00 equiv) in 10.0 mL EtOH was added Pd/C (10%, 100 mg) in a 50 mL round bottom flask at room temperature under nitrogen atmosphere. The resulting mixture was hydrogenated at room temperature under 1 atm of hydrogen pressure for 1 h. then filtered through a Celite pad. The filtrate was concentrated under reduced pressure to afford the title compound (120.0 mg, 75.29%) as a white solid. m/z (ESI, +ve ion)=136.25 [M+H]$^+$.

Step C. 5-chloro-2-cyclopropylpyrimidin-4-amine

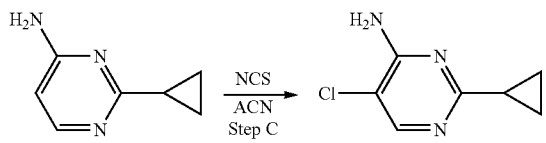

To a stirred solution of 2-cyclopropylpyrimidin-4-amine (110.0 mg, 0.814 mmol, 1.00 equiv) in ACN (5.0 mL) was added NCS (130.40 mg, 0.977 mmol, 1.2 equiv) at room temperature. The resulting mixture was stirred for 2 h at room temperature. The resulting mixture was concentrated under reduced pressure. The residue was purified by silica gel column chromatography, eluted with PE:EA (1:1) to afford the title compound (60.0 mg, 43.47%) as a white solid. m/z (ESI, +ve ion)=170.20 [M+H]$^+$. $^1$H NMR (400 MHz, DMSO-d$_6$) δ 8.05 (s, 1H), 7.09 (s, 2H), 1.90-1.86 (m, 1H), 0.92-0.85 (m, 4H).

Step D. tert-butyl (1R,2S)-2-[1-(tert-butoxycarbonyl)-3-[(5-chloro-2-cyclopropylpyrimidin-4-yl)amino]indazol-6-yl]-5'-methoxy-2'-oxospiro[cyclopropane-1,3'-indole]-1'-carboxylate

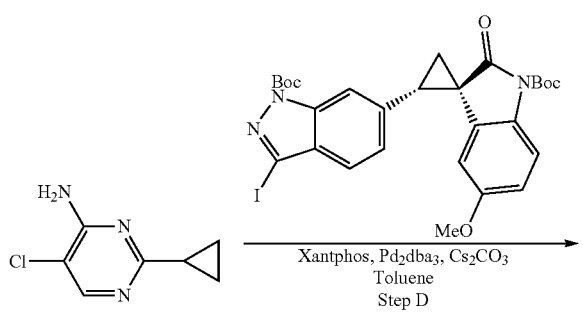

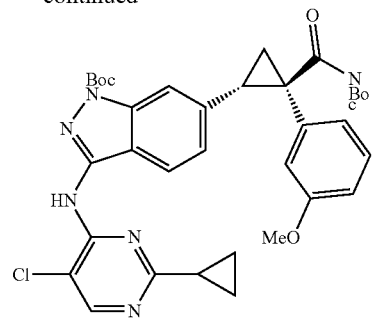

To a stirred solution of 5-chloro-2-cyclopropylpyrimidin-4-amine (21.49 mg, 0.127 mmol, 1.0 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80.00 mg, 0.127 mmol, 1.00 equiv) in toluene (4.00 mL) were added Pd$_2$(dba)$_3$ (23.20 mg, 0.025 mmol, 0.2 equiv), XantPhos (14.66 mg, 0.025 mmol, 0.2 equiv) and Cs$_2$CO$_3$ (82.56 mg, 0.254 mmol, 2.0 equiv) at room temperature under nitrogen atmosphere. The resulting mixture was stirred for 2 h at 90° C. under nitrogen atmosphere then cooled down to room temperature. The resulting mixture was filtered and the filter cake was washed with EA (3×10 mL). The filtrate was concentrated under reduced pressure. The residue was purified by silica gel column chromatography, eluted with PE:EA (1:1) to afford the title compound (60.00 mg, 70.35%) as a yellow solid. m/z (ESI, +ve ion)=673.50 [M+H]$^+$.

Step E. (1R,2S)-2-{3-[(5-chloro-2-cyclopropylpyrimidin-4-yl)amino]-1H-indazol-6-yl}-5'-methoxy-1'H-spiro[cyclopropane-1,3'-indol]-2'-one

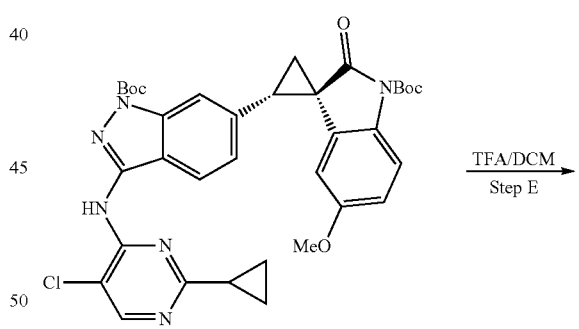

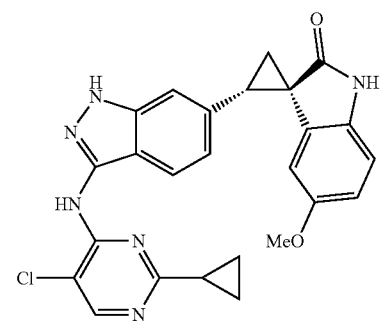

To a stirred solution of tert-butyl (0R,2S)-2-[1-(tert-butoxycarbonyl)-3-[(5-chloro-2-cyclopropylpyrimidin-4-yl)amino]indazol-6-yl]-5'-methoxy-2'-oxospiro[cyclopropane- 1,3'-indole]-1'-carboxylate (55.00 mg, 0.082 mmol, 1.00 equiv) in DCM (5.00 mL) was added TFA (1.00 mL) dropwise at room temperature. The resulting mixture was stirred for 4 h at room temperature then concentrated under reduced pressure. The residue was purified by prep-HPLC with the following conditions: Column: XBridge Prep OBD C18 Column, 30×150 mm, 5 μm; Mobile Phase A: Water (10 mmol/L NH$_4$HCO$_3$). Mobile Phase B: ACN; Flow rate: 60 mL/min; Gradient: 29% B to 39% B in 8 min, 39% B: wavelength: 254 nm; RT1(min): 7.27 to afford Example 116 (20.00 mg, 51.76%) as a white solid. m/z (ESI, +ve ion)=473.20 [M+H]$^+$. $^1$H NMR (400 MHz, Methanol-d$_4$) δ 8.20 (s, 1H), 7.49-7.41 (m, 2H), 6.94 (d, J=8.0 Hz, 1H), 6.84 (d, J=8.4 Hz, 1H), 6.63-6.61 (m, 1H), 5.64 (d, J=2.4 Hz, 1H), 3.39 (d, J=8.4 Hz, 1H), 3.32 (s, 3H), 2.27-2.21 (m, 1H), 2.21-2.17 (m, 1H), 1.85 (d, J=4.4 Hz, 1H), 0.79-0.62 (m, 4H).

Example 117: (1R,2S)-2-(3-{[5-chloro-2-(propan-2-yl)pyrimidin-4-yl]amino}-1H-indazol-6-yl)-5'-methoxyspiro[cyclopropane-1,3'-indol]-2'(1'H)-one

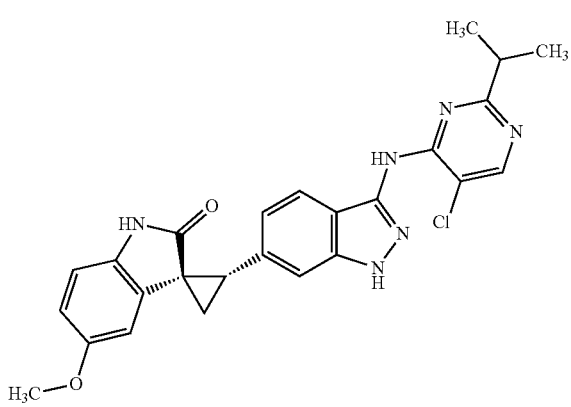 [SMILES: COc1ccc2c(c1)[C@]1(C[C@H]1c1ccc3c(Nc4nc(C(C)C)ncc4Cl)n[nH]c3c1)C(=O)N2]

Step A. N-(2-bromopyrimidin-4-yl)-N-(tert-butoxy-carbonyl)carbamate

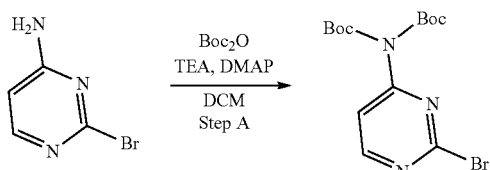

To a stirred mixture of 2-bromopyrimidin-4-amine (500 mg, 2.874 mmol, 1.00 equiv) and Boc$_2$O (1881.43 mg, 8.622 mmol, 3 equiv) in DCM (4 mL) were added TEA (1163.10 mg, 11.496 mmol, 4 equiv) and DMAP (35.11 mg, 0.287 mmol, 0.1 equiv) at 25° C. The resulting mixture was stirred for 16 h at 60° C. then concentrated under reduced pressure. The residue was purified by silica gel column chromatography, eluted with (EA in PE, 2% to 22% gradient in 20 min) to afford the title compound (842 mg, 78.30%) as an off white solid. m/z (ESI, +ve ion)=374.23 [M+H]$^+$. $^1$H NMR (400 MHz, Chloroform-d) δ 8.62 (dd, J=19.3, 5.9 Hz, 1H), 7.73 (dd, J=12.4, 5.9 Hz, 1H), 1.60 (s, 18H).

Step B. tert-butyl N-(tert-butoxycarbonyl)-N-[2-prop-1-en-2-yl)pyrimidin-4-yl]carbamate

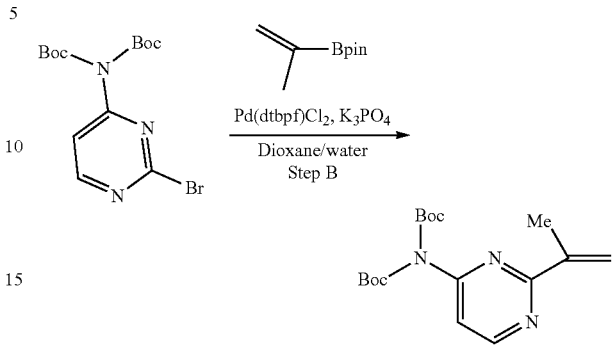

To a stirred solution of tert-butyl N-(2-bromopyrimidin-4-yl)-N-(tert-butoxycarbonyl)carbamate (269 mg, 0.719 mmol, 1.00 equiv) and 4,4,5,5-tetramethyl-2-(prop-1-en-2-yl)-1,3,2-dioxaborolane (120.79 mg, 0.719 mmol, 1 equiv) in H$_2$O (0.2 mL) and 1,4-dioxane (0.4 mL) were added Pd(DtBPF)Cl$_2$ (93.70 mg, 0.144 mmol, 0.2 equiv) and K$_3$PO$_4$ (305.15 mg, 1.438 mmol, 2 equiv) at 25° C. under nitrogen atmosphere. The resulting mixture was stirred for 16 h at 100° C. then concentrated under reduced pressure. The residue was purified by silica gel chromatography, eluted with EA in PE, 1% to 30% gradient in 20 min to afford the title compound (236 mg, 97.89%) as an off white solid. m/z (ESI, +ve ion)=336.40 [M+H]$^+$.

Step C. tert-butyl N-(tert-butoxycarbonyl)-N-(2-isopropylpyrimidin-4-yl)carbamate

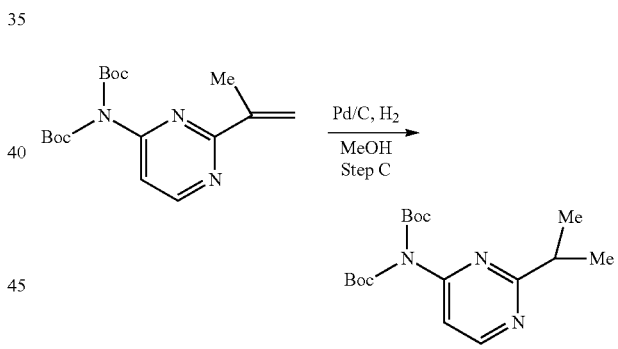

To a stirred solution of tert-butyl N-(tert-butoxycarbonyl)-N-[2-(prop-1-en-2-yl)pyrimidin-4-yl]carbamate (100 mg, 0.298 mmol, 1.00 equiv) and Pd(OH)$_2$/C (25.12 mg) in EtOH (5 mL) at 25° C. under H$_2$ atmosphere. The resulting mixture was stirred for 2 h under 1 atm H$_2$ atmosphere then filtered. The filtrate was concentrated under reduced pressure to afford the title compound (80 mg, 79.52%) as an off white solid. m/z (ESI+ve ion)=138.31 [M+H−200]$^+$.

Step D. 2-isopropylpyrimidin-4-amine

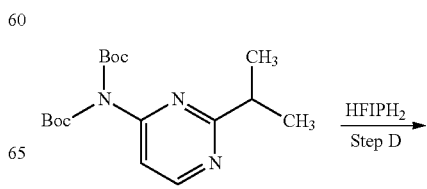

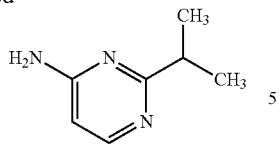

A solution of tert-butyl N-(tert-butoxycarbonyl)-N-(2-isopropylpyrimidin-4-yl)carbamate (236 mg, 0.699 mmol, 1.00 equiv) in 1,1,1,3,3,3-hexafluoropropan-2-ol (0.12 mL, 0.699 mmol, 1 equiv) was stirred for 4 hours at 60° C. then concentrated under reduced pressure. The residue was purified by prep-TLC (PE:EA=1:4) to afford the title compound (74 mg, 77.12%) as an off white solid. m/z (ESI, +ve ion)=138.25 [M+H]$^+$. $^1$H NMR (400 MHz, Chloroform-d) δ 8.22 (d, J=5.8 Hz, 1H), 6.27 (d, J=5.8 Hz, 1H), 4.85 (s, 2H), 2.99 (hept, J=6.9 Hz, 1H), 1.31 (d, J=6.9 Hz, 6H).

Step E. 5-chloro-2-isopropylpyrimidin-4-amine

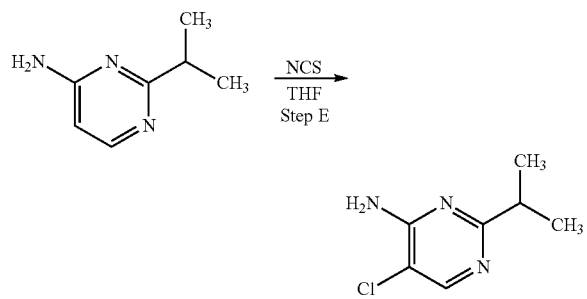

To a stirred solution of 2-isopropylpyrimidin-4-amine (100 mg, 0.729 mmol, 1.00 equiv) in THF (5 mL) was added NCS (107.07 mg, 0.802 mmol, 1.1 equiv) at 25° C. The resulting mixture was stirred for 16 h at 40° C. then concentrated under reduced pressure. The residue was purified by prep-TLC (PE:EA=3:2) to afford the title compound (50 mg, 39.97%) as an off white solid. m/z (ESI, +ve ion)=172.20 [M+H]$^+$. $^1$H NMR (400 MHz, Chloroform-d) δ 8.24 (s, 1H), 5.32 (s, 2H), 3.10-3.02 (m, 1H), 1.30 (d, J=6.9 Hz, 6H).

Step F. tert-butyl (1R,2S)-2-[1-(tert-butoxycarbonyl)-3-[(5-chloro-2-isopropylpyrimidin-4-yl)amino]indazol-6-yl]-5'-methoxy-2'-oxospiro[cyclopropane-1,3'-indole]-1'-carboxylate

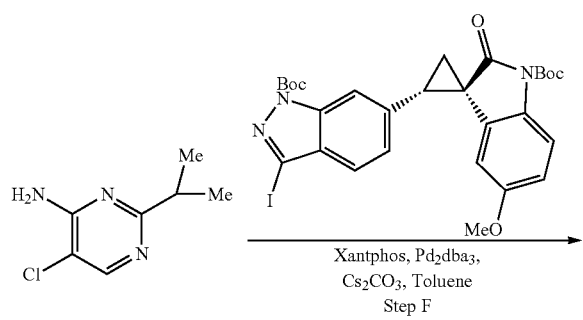

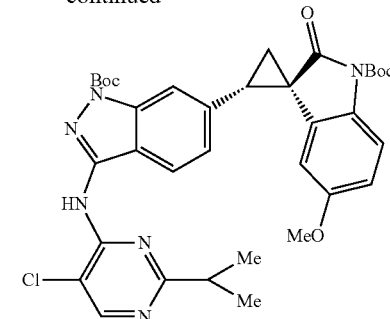

To a stirred solution of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (68.04 mg, 0.108 mmol, 1 equiv) and 5-chloro-2-isopropylpyrimidin-4-amine (20 mg, 0.108 mmol, 1.00 equiv) in toluene (0.2 mL) were added Pd$_2$(dba)$_3$ (19.73 mg, 0.022 mmol, 0.2 equiv), XantPhos (12.47 mg, 0.022 mmol, 0.2 equiv) and Cs$_2$CO$_3$ (70.38 mg, 0.216 mmol, 2 equiv) at 25° C. under nitrogen atmosphere. The resulting mixture was stirred for 2 h at 90° C. then concentrated under reduced pressure. The residue was purified by prep-TLC (PE:EA=1:1) to afford the title compound (60 mg, 80.80%) as an off white solid. m/z (ESI, +ve ion)=675.50 [M+H]$^+$.

Step G. (1R,2S)-2-{3-[(5-chloro-2-isopropylpyrimidin-4-yl)amino]-1H-indazol-6-yl}-5'-methoxy-1'H-spiro[cyclopropane-1,3'-indol]-2'-one

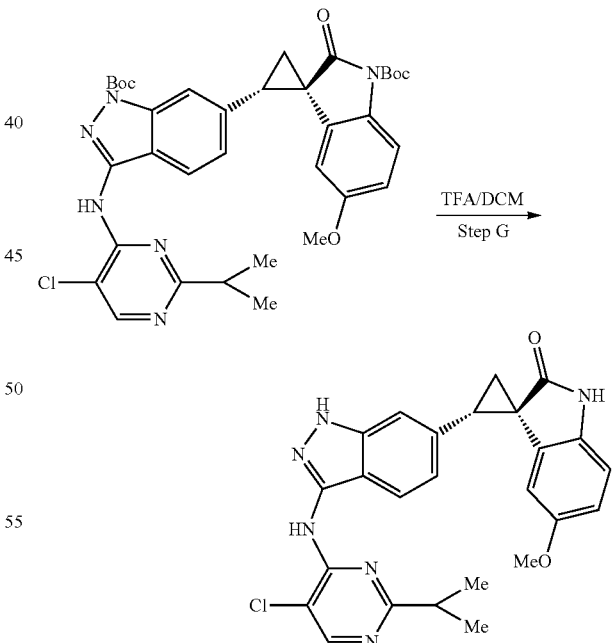

Into a stirred solution of tert-butyl (1R,2S)-2-[1-(tert-butoxycarbonyl)-3-[(5-chloro-2-isopropylpyrimidin-4-yl)amino]indazol-6-yl]-5'-methoxy-2'-oxospiro[cyclopropane-1,3'-indole]-1'-carboxylate (60 mg, 0.089 mmol, 1.00 equiv) in DCM (2 mL) was added TFA (0.5 mL) at 25° C. The resulting mixture was stirred for 1 hours at 25° C. then concentrated under reduced pressure. The crude product (60 mg) was purified by prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 20% B to 40% B in 8 min, 40% B; wavelength: 254 nm; RT1(min): 6.27 to afford Example 117 (20 mg, 47%) as an off-white solid. m/z (ESI, +ve ion)=475.15 [M+H]$^+$. $^1$H NMR (400 MHz, DMSO-d$_6$) δ 12.74 (s, 1H), 10.40 (s, 1H), 9.46 (s, 1H), 8.37 (s, 1H), 7.42 (s, 1H), 7.37 (d, J=8.4 Hz, 1H), 6.88 (dd, J=8.5, 1.4 Hz, 1H), 6.75 (d, J=8.4 Hz, 1H), 6.59 (dd, J=8.4, 2.6 Hz, 1H), 5.67 (d, J=2.6 Hz, 1H), 3.30 (s, 3H), 3.20 (t, J=8.4 Hz, 1H), 2.72-2.68 (m, 1H), 2.31 (dd, J=8.0, 4.7 Hz, 1H), 1.99 (dd. J=9.0.4.6 Hz, 1H), 0.98 (d, J=6.9 Hz, 6H).

Example 119: (1R,2S)-5'-methoxy-2-(3-{[5-methoxy-2-(oxetan-3-yl)pyrimidin-4-yl]amino}-1H-indazol-6-yl)spiro[cyclopropane-1,3'-indol]-2'(1'H)-one

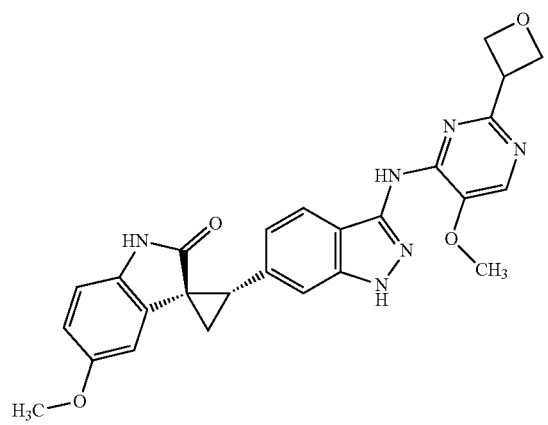 [SMILES: COc1ccc2c(c1)[C@]1(C[C@H]1c1ccc3c(Nc4nc(C5COC5)ncc4OC)n[nH]c3c1)C(=O)N2]

Step A. tert-butyl N-(tert-butoxycarbonyl)-N-(2-chloro-5-methoxypyrimidin-4-yl)carbamate

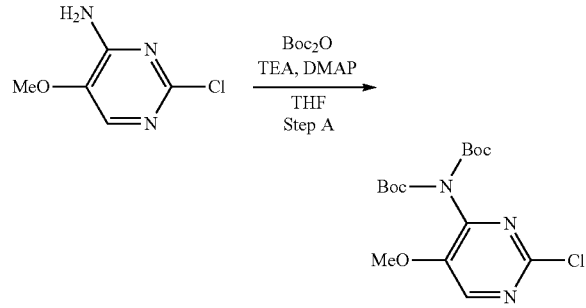

To a stirred mixture of 2-chloro-5-methoxypyrimidin-4-amine (300 mg, 1.880 mmol, 1.00 equiv) and triethylamine (570.74 mg, 5.640 mmol, 3 equiv) in THF (5 mL) were added di-tert-butyl dicarbonate (1025.80 mg, 4.700 mmol, 2.5 equiv) and DMAP (91.87 mg, 0.752 mmol, 0.4 equiv) at 0° C. under nitrogen atmosphere. After stirred for 12 h at 25° C., the solvent was removed under reduced pressure. The residue was purified by silica gel column chromatography, eluted with 0-50% of EA in PE to afford the title compound (500 mg, 73.91%) as a white solid. m/z (ESI, +ve ion)=360.10 [M+H]$^+$. $^1$H NMR (400 MHz, Chloroform-d) δ 8.29 (s, 1H), 3.98 (s, 3H), 1.46 (s, 18H).

Step B. tert-butyl N-(tert-butoxycarbonyl)-N-[5-methoxy-2-(oxetan-3-yl)pyrimidin-4-yl]carbamate

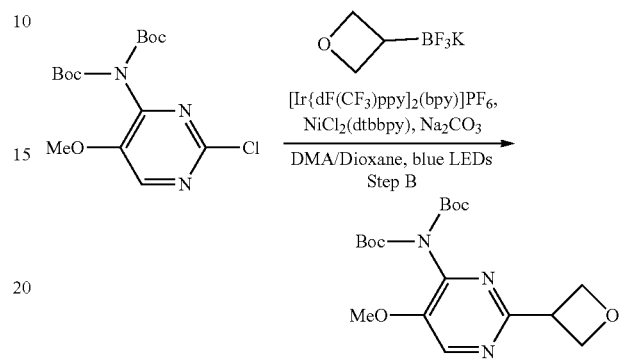

Into a 8 mL sealed tube were added tert-butyl N-(tert-butoxycarbonyl)-N-(2-chloro-5-methoxypyrimidin-4-yl) carbamate (200 mg, 0.556 mmol, 1.00 equiv), trifluoro (oxetan-3-yl)potassio-lambda5-borane (182.30 mg, 1.112 mmol, 2 equiv), [Ir{dFCF$_3$ppy}$_2$(bpy)]PF$_6$ (56.12 mg, 0.056 mmol, 0.1 equiv), [4,4'-Bis(1,1-dimethylethyl)-2,2'-bipyridine] nickel (II) dichloride (33.18 mg, 0.083 mmol, 0.15 equiv) and Na$_2$CO$_3$ (117.83 mg, 1.112 mmol, 2 equiv), DMA (4 mL) under nitrogen atmosphere. The reaction mixture is irradiated under blue LEDs. After stirred at room temperature for 12 h, the solvent was removed under reduced pressure. The residue was purified by silica gel column chromatography, eluted with 0-100% of EA in PE to afford crude the title compound (60 mg, 16.98%) as a yellow solid. m/z (ESI+ve ion)=382.20 [M+H]$^+$.

Step C. 5-methoxy-2-(oxetan-3-yl)pyrimidin-4-amine

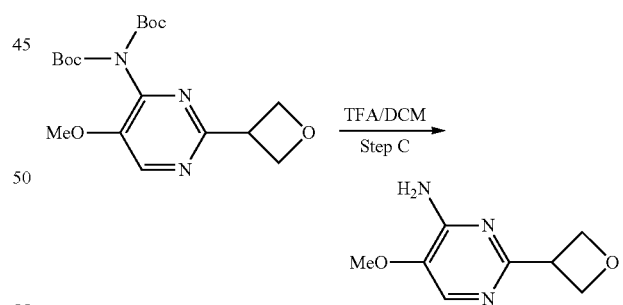

The mixture of crude tert-butyl N-(tert-butoxycarbonyl)-N-[5-methoxy-2-(oxetan-3-yl)pyrimidin-4-yl]carbamate (60 mg, 0.094 mmol, 1.00 equiv, 60%) in TFA (0.5 mL) and DCM (5 mL) was stirred at 25° C. for 8 h. The solvent was removed under reduced pressure. The residue was purified by prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 5% B to 10% B in 8 min; wavelength: 254 nm; RT1(min): 5.78 to afford the title compound (10 mg, 58.47%) as a white solid. m/z (ESI, +ve ion)=182.10 [M+H]$^+$.

Step D. tert-butyl (1R,2S)-2-[1-(tert-butoxycarbonyl)-3-{[5-methoxy-2-(oxetan-3-yl)pyrimidin-4-yl]amino}indazol-6-yl]-5'-methoxy-2'-oxospiro[cyclopropane-1,3'-indole]-1'-carboxylate

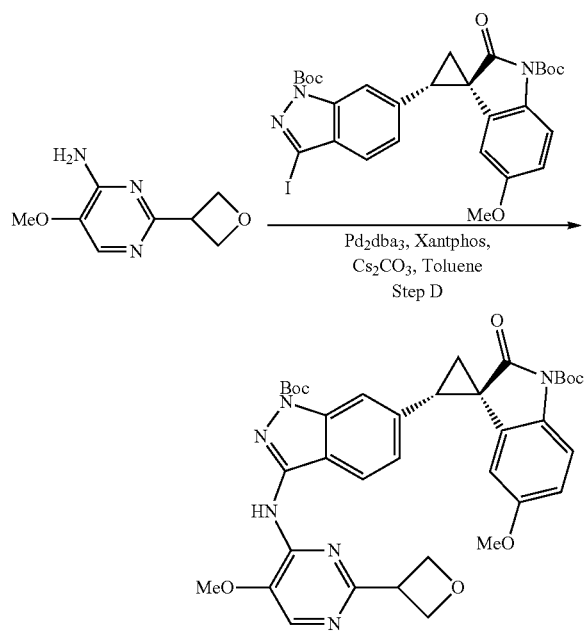

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (41.82 mg, 0.066 mmol, 1.00 equiv) and 5-methoxy-2-(oxetan-3-yl)pyrimidin-4-amine (12 mg, 0.066 mmol, 1.00 equiv) in toluene (1 mL) were added $Cs_2CO_3$ (10.09 mg, 0.132 mmol, 2 equiv), XantPhos (7.66 mg, 0.013 mmol, 0.2 equiv) and $Pd_2(dba)_3$ (12.13 mg, 0.013 mmol, 0.2 equiv) under nitrogen atmosphere. The mixture was stirred at 90° C. for 2 h. The mixture was filtered and washed with EA (10 mL). The filtrate was concentrated under reduced pressure. The residue was purified by prep-TLC (rinsed with EA) to afford the title compound (30 mg, 52.92%) as a yellow solid. m/z (ESI, +ve ion)=685.35 [M+H]$^+$.

Step E. (1R,2S)-5'-methoxy-2-(3-{[5-methoxy-2-(oxetan-3-yl)pyrimidin-4-yl]amino}-1H-indazol-6-yl)-1'H-spiro[cyclopropane-1,3'-indol]-2'-one

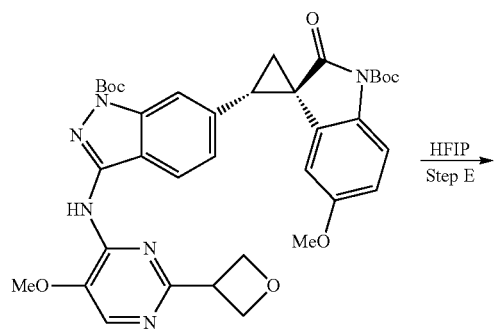

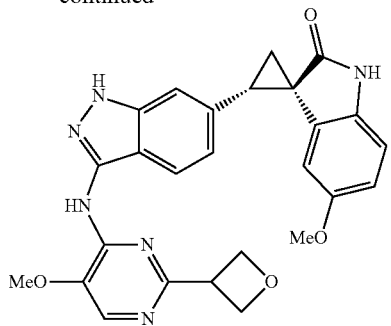

The mixture of tert-butyl (1R,2S)-2-[1-(tert-butoxycarbonyl)-3-{[5-methoxy-2-(oxetan-3-yl)pyrimidin-4-yl]amino}indazol-6-yl]-5'-methoxy-2'-oxospiro[cyclopropane-1,3'-indole]-1'-carboxylate (30 mg, 0.044 mmol, 1.00 equiv) in HFIP (3 mL) was stirred at 60° C. for 12 h. The solvent was removed under reduced pressure. The residue was purified by prep-HPLC with the following conditions: Column: XSelect CSH Prep C18 OBD Column, 19×250 mm, 5 μm; Mobile Phase A: Water (0.1% FA), Mobile Phase B: ACN; Flow rate: 25 mL/min; Gradient: 25% B to 35% B in 10 min; wavelength: 254 nm; RT1 (min): 7 to give Example 119 (8 mg, 37.69%) as a white solid. m/z (ESI, +e ion)=485.25 [M+H]$^+$. $^1$H NMR (400 MHz, Methanol-$d_4$) δ 7.96 (s, 1H), 7.61 (d, J=8.4 Hz, 1H), 7.44 (s, 1H), 6.91 (d, J=8.0 Hz, 1H), 6.84 (d, J=8.4 Hz, 1H), 6.65-6.63 (m, 1H), 5.62 (d, J=2.4 Hz, 1H), 4.81-4.74 (m, 4H), 4.23-4.16 (m, 1H), 4.04 (s, 3H), 3.38-3.36 (m, 1H), 3.32 (s, 3H), 2.26-2.23 (m, 1H), 2.20-2.17 (m, 1H).

Example 121: (1R,2S)-2-(3-{[5-(difluoromethoxy)-2-methylpyrimidin-4-yl]amino}-1H-indazol-6-yl)-5'-methoxyspiro[cyclopropane-1,3'-indol]-2'(1'H)-one

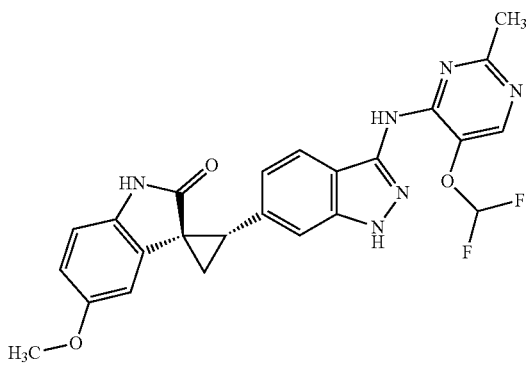 [SMILES: COc1ccc2c(c1)[C@]1(C[C@H]1c1ccc3c(Nc4nc(C)ncc4OC(F)F)n[nH]c3c1)C(=O)N2]

Step A. 4-amino-2-methylpyrimidin-5-ol hydrobromide

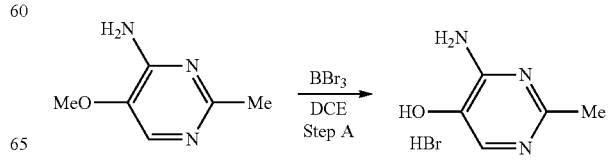

To a stirred mixture of 5-methoxy-2-methylpyrimidin-4-amine (834 mg, 5.993 mmol, 1 equiv) in DCE (30 mL) was added BBr$_3$ (5.67 mL, 59.977 mmol, 10.01 equiv) dropwise at room temperature under nitrogen atmosphere. After the resulting mixture was stirred for 16 h at 50° C. under nitrogen atmosphere, 100 mL of DCE was added. The above clear solution was removed and the precipitate was collected and dissolved in MeOH (100 mL). The resulting mixture was concentrated under reduced pressure to afford the title compound (1.2 g, 97.18%) as an off-white solid. m/z (ESI+ve ion)=126.20 [M+H]$^+$.

Step B.
5-(difluoromethoxy)-2-methylpyrimidin-4-amine

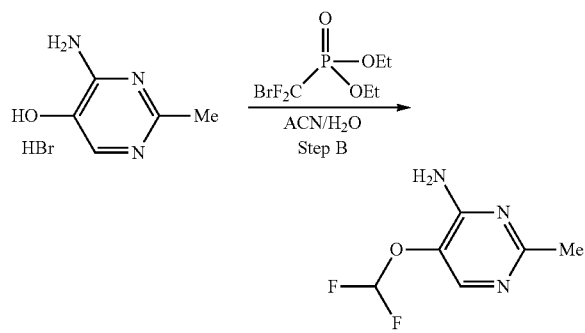

To a stirred mixture of 4-amino-2-methylpyrimidin-5-ol hydrobromide (80 mg, 0.388 mmol, 1 equiv) and 4 M aqueous of KOH (0.97 mL, 3.880 mmol, 10 equiv) in ACN (1 mL) was added diethyl bromodifluoromethylphosphonate (155.51 mg, 0.582 mmol, 1.5 equiv) dropwise at 0° C. under nitrogen atmosphere. The resulting mixture was stirred for 2 h at 0° C. under nitrogen atmosphere then extracted with CHCl$_3$ (4×10 mL). The combined organic layers were dried over anhydrous Na$_2$SO$_4$. After filtration, the filtrate was concentrated under reduced pressure. The residue was purified by silica gel column chromatography, eluted with DCM: MeOH (20:1) to afford the title compound (30 mg, 44.12%) as an off-white solid. m/z (ESI, +ve ion)=176.20 [M+H]$^+$. $^1$H NMR (400 MHz, DMSO-d$_6$) δ 7.91 (d, J=1.3 Hz, 1H), 7.44-6.77 (m, 3H).

Step C. tert-butyl (1R,2S)-2-(1-(tert-butoxycarbonyl)-3-((5-(difluoromethoxy)-2-methylpyrimidin-4-yl)amino)-1H-indazol-6-yl)-5'-methoxy-2'-oxospiro[cyclopropane-1,3'-indoline]-1'-carboxylate

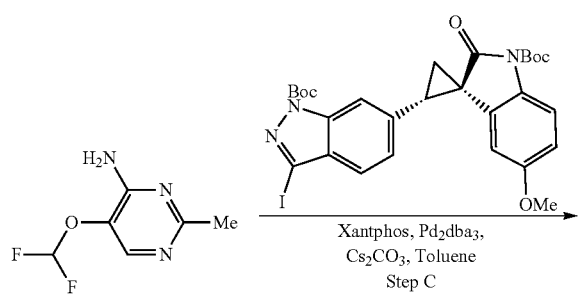

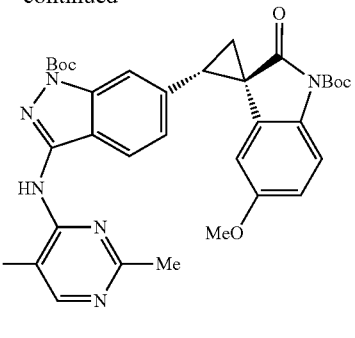

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (65 mg, 0.103 mmol, 1.00 equiv) and 5-(difluoromethoxy)-2-methylpyrimidin-4-amine (21.63 mg, 0.124 mmol, 1.2 equiv) in toluene (2.5 mL) were added Pd$_2$(dba)$_3$ (9.43 mg, 0.010 mmol, 0.1 equiv), Cs$_2$CO$_3$ (67.08 mg, 0.206 mmol, 2 equiv) and XantPhos (5.96 mg, 0.010 mmol, 0.1 equiv) at room temperature under nitrogen atmosphere. The resulting mixture was stirred for 2 h at 90° C. under nitrogen atmosphere. The resulting mixture was concentrated under reduced pressure. The residue was purified by prep-TLC (PE:EA=1:1) to afford the title compound (50 mg, 71.57%) as a yellow solid. m/z (ESI, +ve ion)=679.30 [M+H]$^+$.

Step D. (1R,2S)-2-(3-((5-(difluoromethoxy)-2-methylpyrimidin-4-yl)amino)-1H-indazol-6-yl)-5'-methoxyspiro[cyclopropane-1,3'-indolin]-2'-one

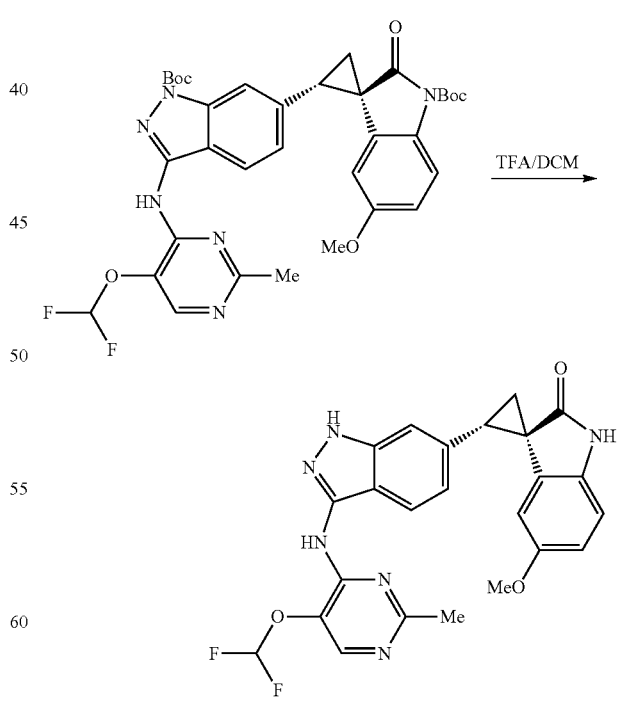

To a stirred solution of tert-butyl (1R,2S)-2-[1-(tert-butoxycarbonyl)-3-{[5-(difluoromethoxy)-2-methylpyrimidin-4-yl]amino}indazol-6-yl]-5'-methoxy-2'-oxospiro[cyclopropane-1,3'-indole]-1'-carboxylate (10 mg, 0.015 mmol, 1 equiv) in DCM (1 mL) was added TFA (0.5 mL) at room temperature under nitrogen atmosphere. The resulting mixture was stirred for 2 h at room temperature under nitrogen atmosphere then concentrated under vacuum. The crude product (10 mg) was purified by prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 23% B to 33% B in 8 min, 33% B; wavelength: 254 nm; RT1(min): 7.67 to afford Example 121 (5 mg, 70.92%) as a white solid. m/z (ESI, +ve ion)=479.15 [M+H]$^+$. $^1$H-NMR (Methanol-d$_4$, ppm) δ 8.09 (s, 1H), 7.54 (d, J=8.4 Hz, 1H), 7.45 (s, 1H), 7.13-6.77 (m, 3H), 6.63 (d, J=8.4 Hz, 1H), 5.61 (s, 1H), 3.39-3.30 (m, 4H), 2.50 (s, 3H), 2.37-2.18 (m, 2H)

Example 122: (1R,2S)-2-{3-[(5-methoxy-2-methylpyrimidin-4-yl)amino]-1H-indazol-6-yl}-1'-methylspiro[cyclopropane-1,3'-indol]-2'(1'H)-one

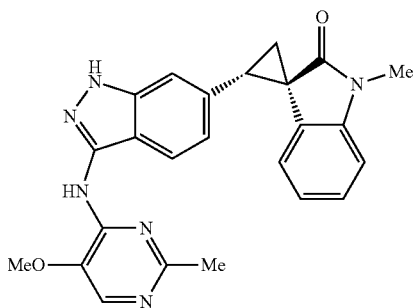 [SMILES: COc1cnc(C)nc1Nc1n[nH]c2cc([C@@H]3C[C@@]34C(=O)N(C)c3ccccc34)ccc12]

tert-butyl (S)-6-(1,2-bis((methylsulfonyl)oxy)ethyl)-3-iodo-1H-indazole-1-carboxylate

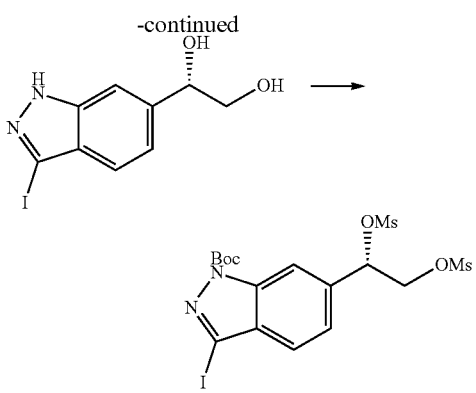

Step A. 3-iodo-1H-indazole-6-carbaldehyde

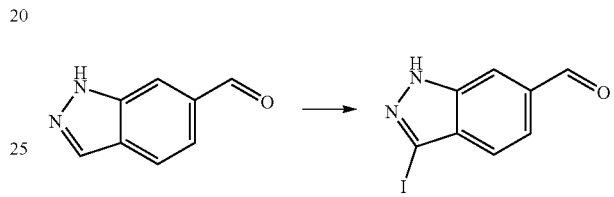

To a flask was added molecular iodine (14.76 g, 58.16 mmol) and DMF (40 mL). This solution was stirred at room temperature and potassium carbonate (9.46 g, 68.42 mmol) was added. To this mixture was added 6-formyl-1H-indazole (5.0 g, 34.21 mmol) in DMF (40 mL) dropwise and the mixture was stirred for 16 h. Sodium thiosulfate (8.5 g) and potassium carbonate (0.5 g) dissolved in 60 mL water were then added and the mixture was stirred for 1 h. The solution was then poured into 300 mL of ice/water mixture and stirred until melted and the precipitate was collected by vacuum filtration, washed with water, and dried under vacuum to give the title compound as a beige solid (8.53 g, 92%). LCMS: m/z (ESI, +ve ion)=279.2 [M+H]$^+$ Step B. 3-iodo-6-vinyl-1H-indazole

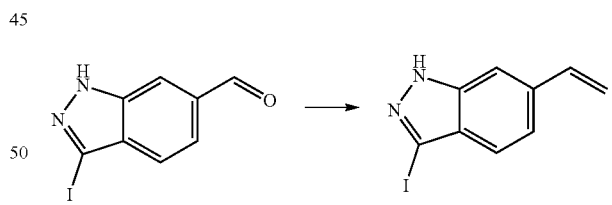

To a solution of potassium tert-butoxide (7.74 g, 68.98 mmol) in THF (100 mL) cooled to 0° C. was added methyltriphenylphosphonium bromide (22.40 g, 62.71 mmol) in 4 portions over 15 minutes. The solution was allowed to warm to room temperature and stirred for 1 h. 3-iodo-1H-indazole-6-carbaldehyde (8.53 g, 31.36 mmol) was then added all at once and the mixture was stirred for 1 h. The mixture was diluted with DCM and washed with water (1×) and brine (1×). The organic layer was dried over sodium sulfate, filtered and the filtrate was concentrated in vacuo. The residue was purified by flash column chromatography (0-30% EtOAc in hexanes) to give the title compound as a white solid (6.51 g, 77%). LCMS: m/z (ESI, +ve ion)=271.0 [M+H]$^+$ $^1$H NMR (400 MHz, CHLOROFORM-d) δ ppm 10.21 (m, J=3.67 Hz, 1H) 7.33-7.52 (m, 3H) 6.76-6.93 (m, 1H) 5.88 (br d, J=17.12 Hz, 1H) 5.39 (br d, J=11.74 Hz, 1H).

Step C. tert-butyl 3-iodo-6-vinyl-1H-indazole-1-carboxylate

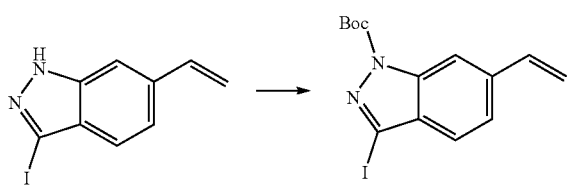 [SMILES: C=Cc1ccc2c(I)n[nH]c2c1 ; C=Cc1ccc2c(I)nn(C(=O)OC(C)(C)C)c2c1]

To a solution of 3-iodo-6-vinyl-1H-indazole (8.45 g, 31.29 mmol). N-ethyl-N-isopropyl-propan-2-amine (10.9 mL, 62.58 mmol) and 4-dimethylaminopyridine (191 mg, 1.56 mmol) in acetonitrile (85 mL) at room temperature was added di-tert-butyl dicarbonate (10.24 g, 46.93 mmol) resulting in a light yellow homogeneous solution. The reaction mixture was stirred for 2 h then concentrated in vacuo and purified by flash column chromatography (0-20% EtOAc in hexanes) to give the title compound as a white solid (10.5 g, 91%). LCMS: m/z (ESI, +ve ion)=315.0 [M−tBu+H]⁺

Step D. tert-butyl (S)-6-(1,2-dihydroxyethyl)-3-iodo-1H-indazole-1-carboxylate

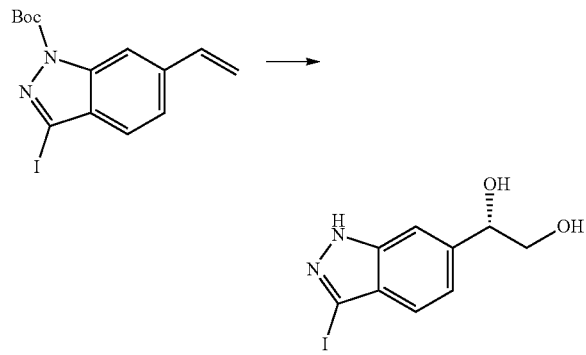

To a solution of (DHQ)₂PHAL (221 mg, 0.28 mmol) in tert-butanol (142 mL) was added potassium osmate (104.5 mg, 0.28 mmol), potassium carbonate (11.76 g, 85.09 mmol) and potassium hexacyanoferrate(III) (28.02 g, 85.09 mmol) as a solution in water (142 mL) and the mixture was stirred until dissolved. The reaction mixture was cooled to 0° C. and tert-butyl 3-iodo-6-vinyl-indazole-1-carboxylate (10.5 g, 28.36 mmol) was added in one portion and the reaction mixture was stirred at 0° C. for 1 h then slowly warmed to room temperature and stirred for 16 h. Sodium sulfite (30 g) was then added and the reaction mixture was stirred for 1 h. The mixture was diluted with DCM and filtered through celite. The filtrate was washed with water and the aqueous layer was extracted with DCM (2×). The combined organic extracts were dried with sodium sulfate, filtered, and the filtrate was concentrated in vacuo. The crude residue was purified by flash column chromatography (0-100% EtOAc in hexanes) to give the title compound as a white foam (8.47 g, 74%). LCMS: m/z (ESI, +ve ion)=349.0 [M−tBu+H]⁺. 1H NMR (400 MHz, CHLOROFORM-d) δ ppm 8.22 (s, 1H) 7.46-7.53 (m, 1H) 7.37-7.44 (m, 1H) 7.29 (s, 1H) 5.04 (m, J=4.16 Hz, 1H) 3.81-3.97 (m, 1H) 3.74 (m, J=3.42 Hz, 1H) 2.79 (s, 1H) 2.10-2.21 (m, 1H) 1.75 (s, 8H). Chiral HPLC (AD-H, 15 min isocratic 7% iPrOH in hexanes, 15 min) showed 98:1 enantiomeric ratio. (97% ee).

Step E. tert-butyl (S)-6-(1,2-bis((methylsulfonyl)oxy)ethyl)-3-iodo-1H-indazole-1-carboxylate

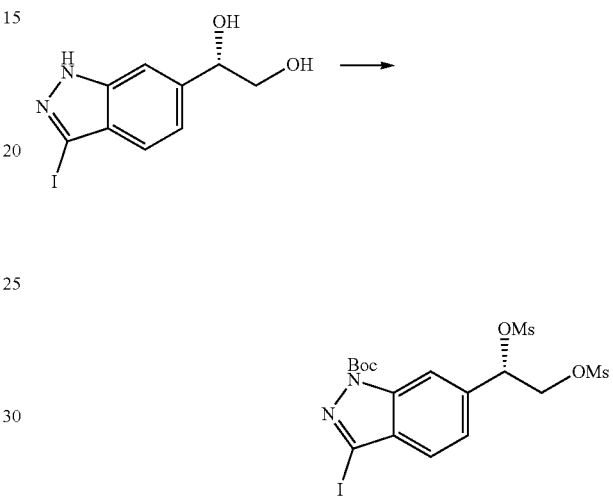

To a solution of tert-butyl 6-[(1S)-1,2-dihydroxyethyl]-3-iodo-indazole-1-carboxylate (2.0 g, 4.95 mmol) and triethylamine (4.14 mL, 29.69 mmol) and in DCM (50 mL) cooled to 0° C. was added ethanesulfonyl chloride (1.53 mL, 19.79 mmol) and the reaction mixture was stirred for 15 min at room temperature. The reaction mixture was concentrated in vacuo and the residue was adsorbed onto silica and purified by flash column chromatography (0-100% EtOAc in hexanes) to give the title compound as a white foam (2.59 g, 93%). LCMS: m/z (ESI, +ve ion)=461.0 [M−Boc+H]⁺.

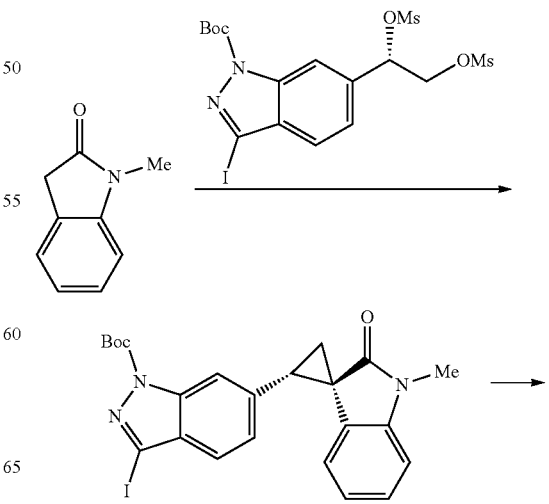

Step F. tert-butyl 3-iodo-6-((1R,2S)-1'-methyl-2'-oxospiro[cyclopropane-1,3'-indolin]-2-yl)-1H-indazole-1-carboxylate

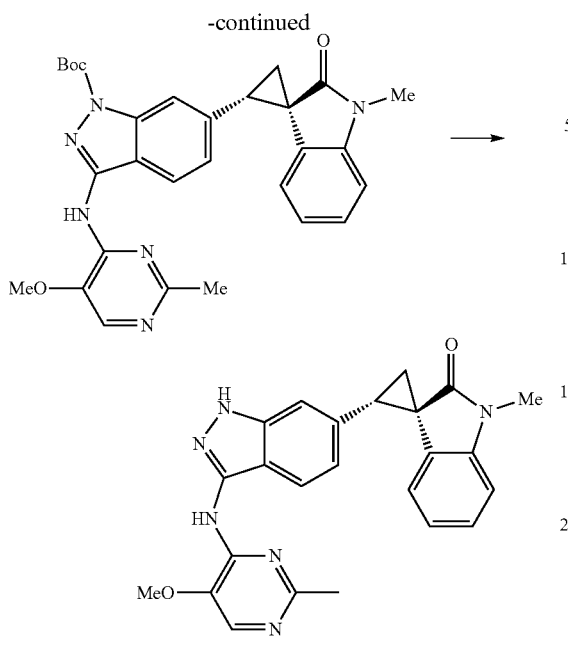

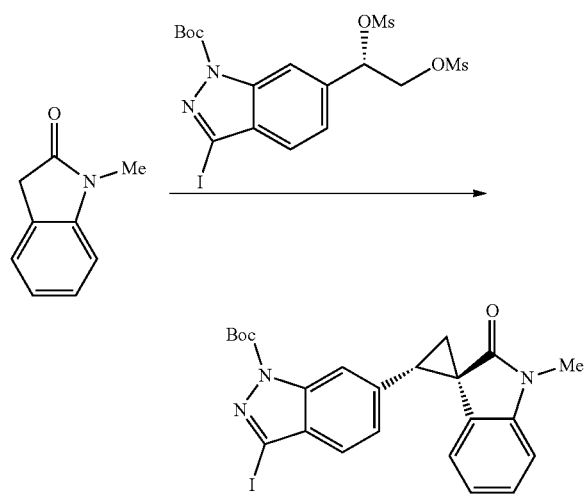

To a vial was added 1-methylindolin-2-one (50.7 mg, 0.34 mmol) followed by THF (6 mL). Sodium hydride (41.3 mg, 1.03 mmol) was added in one portion and the mixture was stirred for 5 min then tert-butyl 6-[(1S)-1,2-bis(methylsulfonyloxy)ethyl]-3-iodo-indazole-1-carboxylate (192.9 mg, 0.34 mmol) was added as a solution in THF (3 mL) dropwise by syringe and the reaction mixture was stirred at room temperature for 1 h. The reaction mixture was quenched with sat. ammonium chloride and extracted with EtOAc (3×). The combined organic extracts were washed with brine, dried over sodium sulfate, filtered and the filtrate was concentrated in vacuo. The crude residue was purified by flash column chromatography (0-50% EtOAc in hexanes) to give the title compound as a brown solid (39.1 mg, 22%) LCMS: m/z (ESI, +ve ion)=416.0 [M-Boc+H]$^+$

Step G. tert-butyl 3-((5-methoxy-2-methylpyrimidin-4-yl)amino)-6-((1R,2S)-1'-methyl-2'-oxospiro[cyclopropane-1,3'-indolin]-2-yl)-1H-indazole-1-carboxylate

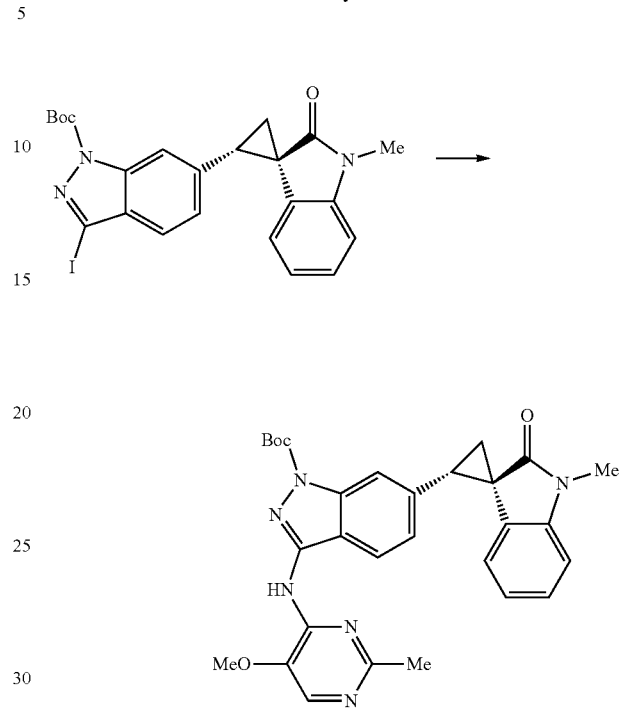

To a solution of tert-butyl 3-iodo-6-[(1S,2R)-1'-methyl-2'-oxo-spiro[cyclopropane-2,3'-indoline]-1-yl]indazole-1-carboxylate (39.1 mg, 0.08 mmol) in dry toluene (0.75 mL) was added Xantphos Pd G4 (7.3 mg, 0.01 mmol), Xantphos (4.4 mg, 0.01 mmol), cesium carbonate (49.4 mg, 0.15 mmol) and 5-methoxy-2-methyl-pyrimidin-4-amine (11.6 mg, 0.08 mmol). Argon was bubbled through the solution for 5 min then the reaction mixture was heated to 90° C. for 2 h. The reaction mixture was diluted with DCM, filtered through celite, eluting with DCM and the filtrate was concentrated in vacuo. The crude residue was purified by flash column chromatography (0-10% DCM in MeOH, 24 g) to afford the product as a brown solid (22.6 mg, 57%). LCMS: m/z (ESI, +ve ion)=527.2 [M+H]$^+$

Step H. (1R,2S)-2-(3-((5-methoxy-2-methylpyrimidin-4-yl)amino)-1H-indazol-6-yl)-1'-methylspiro[cyclopropane-1,3'-indolin]-2'-one

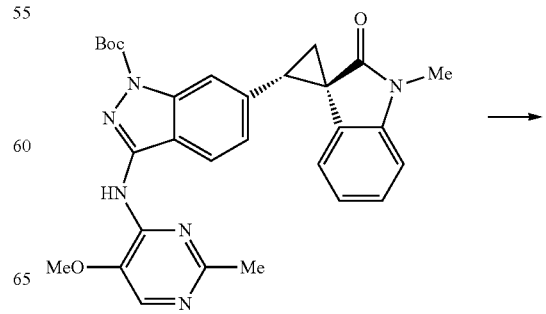

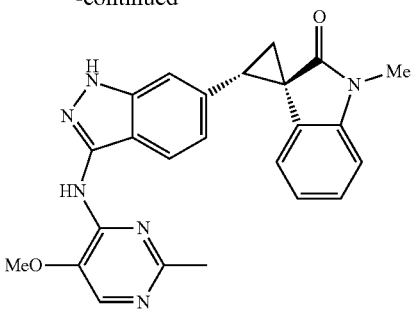

To a solution of tert-butyl 3-[(5-methoxy-2-methyl-pyrimidin-4-yl)amino]-6-[(1S,2R)-1'-methyl-2'-oxo-spiro[cyclopropane-2,3'-indoline]-1-yl]indazole-1-carboxylate (22.6 mg, 0.04 mmol) in DCM (1.0 mL) was added trifluoroacetic acid (164 uL, 2.15 mmol) and the reaction mixture was stirred at room temperature for 2 h. The reaction mixture was concentrated in vacuo and purified by RP-HPLC (20-40% ACN/water, 0.1% FA) to give the title compound as a lyophilized white solid (10.2 mg, 56%). LCMS: m/z (ESI, +ve ion)=427.3 [M+H]$^+$. $^1$H NMR $^1$H NMR (400 MHz, MeOD) δ 7.84 (s, 1H), 7.47-7.38 (m, 1H), 7.34 (s, 1H), 7.09-6.98 (m, 1H), 6.97-6.88 (m, 1H), 6.85-6.76 (m, 1H), 6.58-6.48 (m, 1H), 5.99-5.89 (m, 1H), 3.95 (s, 3H), 3.32-3.25 (m, 1H), 3.24 (s, 3H), 2.28 (s, 3H), 2.21-2.12 (m, 1H), 2.12-2.04 (m, 1H).

Example 125: (1R,2S)-5'-methoxy-2-(3-{[5-methoxy-2-(propan-2-yl)pyrimidin-4-yl]amino}-1H-indazol-6-yl)spiro[cyclopropane-1,3'-indol]-2'(1'H)-one

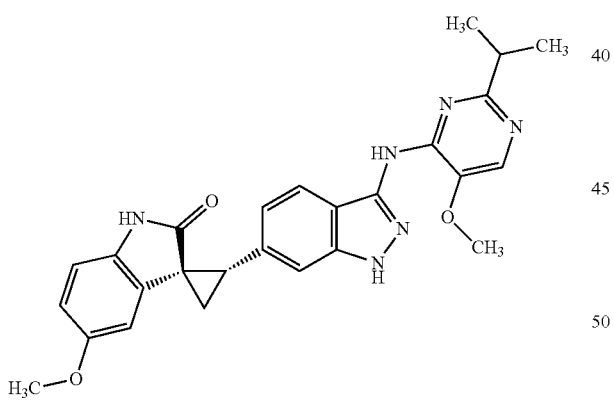

Step A. 2-isopropyl-5-methoxypyrimidine-4,6-diol

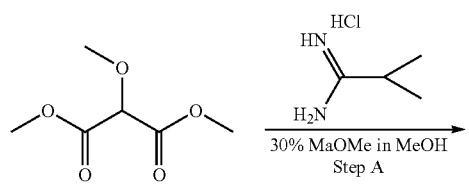

A mixture of 1,3-dimethyl 2-methoxypropanedioate (4 g, 24.670 mmol, 1 equiv) and 2-methylpropanimidamide hydrochloride (3.18 g, 25.904 mmol, 1.05 equiv) in NaOMe (15.55 g, 86.345 mmol, 3.5 equiv, 30% in methanol) was stirred for 1.5 h at 70° C. under nitrogen atmosphere. The mixture was cooled down to room temperature and stirred for 16 h at room temperature under nitrogen atmosphere. The mixture was cooled down to 0° C., 8 mL of conc. HCl was added. The resulting mixture was filtered, the filter cake was washed with Et$_2$O (3×15 mL). The solid was collected and dried to afford the title compound (8 g, 88.03%) as an off-white solid. m/z (ESI, +ve ion)=185.10 [M+H]$^+$. $^1$H NMR (400 MHz, DMSO-d$_6$) δ 11.58 (s, 2H), 3.59 (s, 3H), 2.83-2.73 (m, 1H), 1.15 (d, J=6.8 Hz, 6H).

Step B.
4,6-dichloro-2-isopropyl-5-methoxypyrimidine

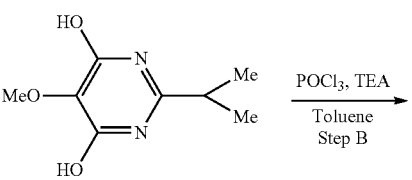

To a stirred mixture of 2-isopropyl-5-methoxypyrimidine-4,6-diol (3.6 g, 19.545 mmol, 1 equiv) and TEA (2.18 g, 21.500 mmol, 1.1 equiv) in toluene (8 mL) was added POCl$_3$ (6.59 g, 42.999 mmol, 2.2 equiv) dropwise at 100° C. under nitrogen atmosphere. The resulting mixture was stirred for 2 h at 110° C. under nitrogen atmosphere. The mixture was cooled down to room temperature and then quenched by the addition of water (10 mL) at room temperature. The resulting mixture was extracted with EtOAc (3×20 mL). The combined organic layers were washed with water (2×6 mL), dried over anhydrous Na$_2$SO$_4$. After filtration, the filtrate was concentrated under reduced pressure. The residue was purified by silica gel column chromatography, eluted with PE/EA (10/1) to afford the title compound (3.2 g, 74.06%) as a colorless oil. m/z (ESI, +ve ion)=221.10 [M+H]$^+$. $^1$H NMR (400 MHz, Chloroform-d S 3.96 (s, 3H), 3.21-3.11 (m, 1H), 1.34 (d, J=6.8 Hz, 6H).

Step C.
6-chloro-2-isopropyl-5-methoxypyrimidin-4-amine

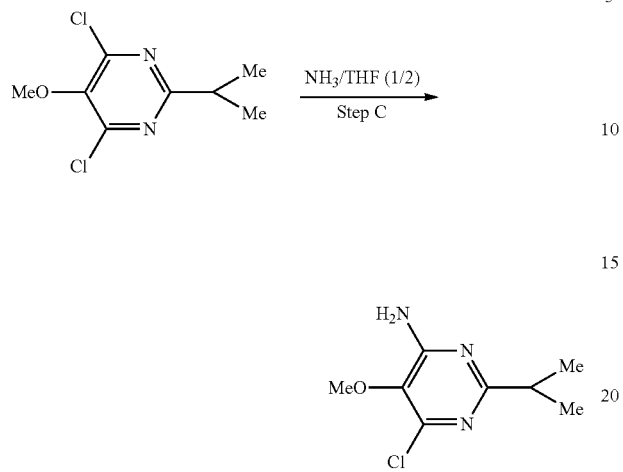

The mixture of 4,6-dichloro-2-isopropyl-5-methoxypyrimidine (1 g, 4.523 mmol, 1 equiv) in NH$_3$H$_2$O (30%, 10 mL) and THF (10 mL) was stirred at 60° C. for 12 h. The solvent was removed under reduced pressure. The residue was purified by silica gel column chromatography, eluted with 0-50% EA in PE to afford the title compound (600 mg, 65.78%) as a white solid. m/z (ESI, +ve ion)=202.05 [M+H]$^+$. $^1$H NMR (400 MHz, DMSO-d$_6$) δ 7.14 (s, 2H), 3.68 (s, 3H), 2.88-2.73 (m, 1H), 1.16 (d, J=6.8 Hz, 6H).

Step D. 2-isopropyl-5-methoxypyrimidin-4-amine

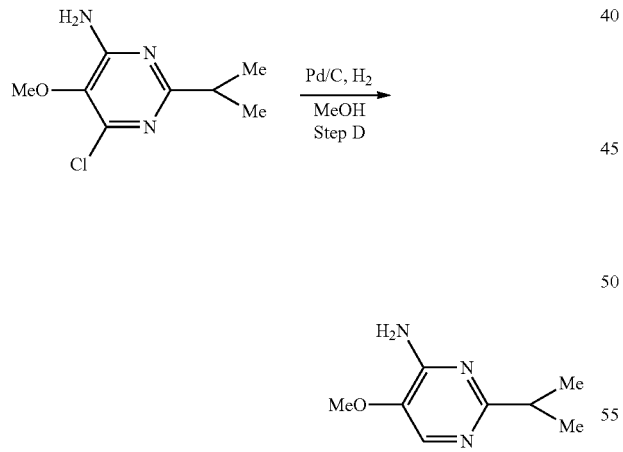

To the mixture of 6-chloro-2-isopropyl-5-methoxypyrimidin-4-amine (100 mg, 0.496 mmol, 1 equiv) in MeOH (5 mL) was added Pd/C (52.77 mg, 10%) under nitrogen atmosphere. The resulting mixture was degassed and purged with H$_2$ for three times then was stirred at 25° C. for 2 h. The mixture was filtered and washed with MeOH (10 mL). The filtrate was concentrated in vacuo to give the title compound (100 mg, 96.48%) as a grey solid. m/z (ESI, +ve ion)=168.05 [M+H]$^+$.

Step E. tert-butyl (1R,2S)-2-[1-(tert-butoxycarbonyl)-3-[(2-isopropyl-5-methoxypyrimidin-4-yl)amino]indazol-6-yl]-5'-methoxy-2'-oxospiro[cyclopropane-1,3'-indole]-1'-carboxylate

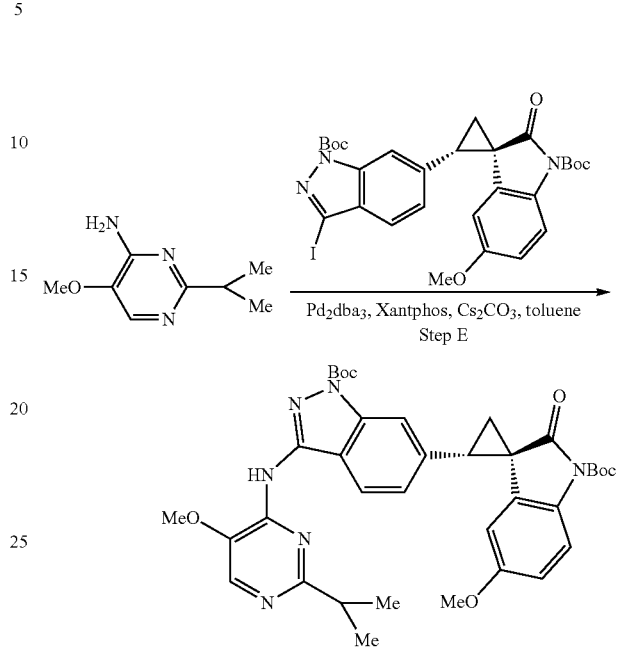

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1 equiv) and 2-isopropyl-5-methoxypyrimidin-4-amine (31.78 mg, 0.190 mmol, 1.2 equiv) in toluene (2.5 mL) were added Cs$_2$CO$_3$ (103.19 mg, 0.316 mmol, 2 equiv), Pd$_2$(dba)$_3$ (29.00 mg, 0.032 mmol, 0.2 equiv) and XantPhos (18.33 mg, 0.032 mmol, 0.2 equiv) at room temperature under nitrogen atmosphere. The resulting mixture was stirred for 2 h at 90° C. under nitrogen atmosphere. The resulting mixture was filtered, the filter cake was washed with EtOAc (10 mL). The filtrate was concentrated under reduced pressure. The residue was purified by silica gel column chromatography, eluted with 0-100% EA in PE to afford the title compound (20 mg, 18.83%) as a yellow solid. m/z (ESI, +ve ion)=671.35 [M+H]$^+$

Step F. (1R,2S)-2-{3-[(2-isopropyl-5-methoxypyrimidin-4-yl)amino]-1H-indazol-6-yl}-5'-methoxy-1'H-spiro[cyclopropane-1,3'-indol]-2'-one

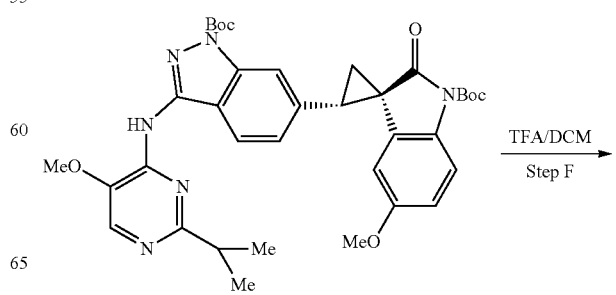

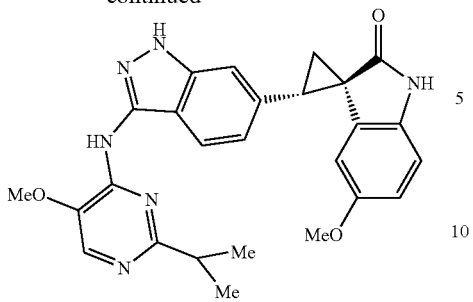

The mixture of tert-butyl (1R,2S)-2-[1-(tert-butoxycarbonyl)-3-[(2-isopropyl-5-methoxypyrimidin-4-yl)amino]indazol-6-yl]-5'-methoxy-2'-oxospiro[cyclopropane-1,3'-indole]-1'-carboxylate (20 mg, 0.030 mmol, 1 equiv) in TFA (0.5 mL) and DCM (3 mL) was stirred for 4 h at 25° C. The solvent was removed under reduced pressure. The residue was purified by prep-HPLC with the following conditions: Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 25% B to 45% B in 8 min, 45% B; wavelength: 254 nm; RT1(min): 7 to give Example 125 (8.1 mg, 57.62%) as a white solid. m/z (ESI, +ve ion)=471.25 $[M+H]^+$. $^1H$ NMR (400 MHz, Methanol-$d_4$) δ 7.86 (s, 1H), 7.59 (d, J=8.4 Hz, 1H), 7.44-7.43 (m, 1H), 6.91-6.83 (m, 2H), 6.64-6.61 (m, 1H), 5.62 (d, J=2.4 Hz, 1H), 4.01 (s, 3H), 3.39-3.37 (m, 1H), 3.30 (s, 3H), 2.86-2.80 (m, 1H), 2.26-2.23 (m, 1H), 2.19-2.17 (m, 1H), 1.06 (t, J=6.8 Hz, 6H).

Example 128: (1R,2S)-2-(3-{[5-(difluoromethoxy)-2-(propan-2-yl)pyrimidin-4-yl]amino}-1H-indazol-6-yl)-5'-methoxyspiro[cyclopropane-1,3'-indol]-2'(1'H)-one

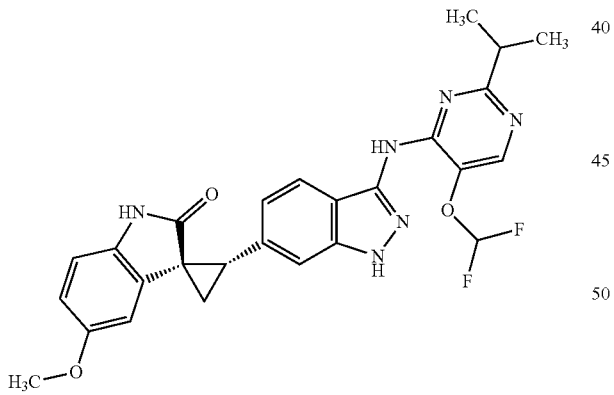

Step A. 4,6-dichloro-2-isopropylpyrimidin-5-ol

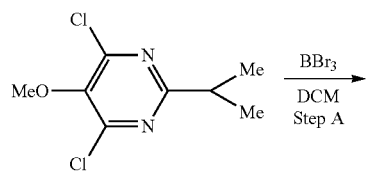

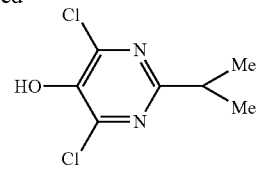

To the mixture of 4,6-dichloro-2-isopropyl-5-methoxypyrimidine (500 mg, 2.262 mmol, 1 equiv) in DCM (5 mL) was added $BBr_3$ (5.67 g, 22.620 mmol, 10 equiv) at 25° C. under nitrogen atmosphere. The mixture was stirred at 40° C. for 12 h then quenched with $H_2O$ (5 mL) at 0° C. The resulting mixture was extracted with EA (5×20 mL) The combined organic layers were washed with brine (20 mL), dried over anhydrous $Na_2SO_4$. After filtration, the filtrate was concentrated under reduced pressure. The residue was purified by silica gel column chromatography, eluted with 0-100% of EA in PE to afford the title compound (450 mg, 96.10%) as a white solid. m/z (ESI, +ve ion)=207.00 $[M+H]^+$. $^1H$ NMR (400 MHz, Chloroform-d) δ 5.69 (s, 1H), 3.20-3.10 (m, 1H), 1.33 (d, J=6.8 Hz, 6H).

Step B. 4,6-dichloro-5-(difluoromethoxy)-2-isopropylpyrimidine

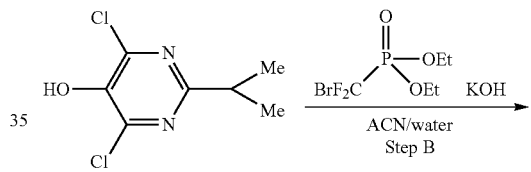

To a stirred mixture of 4,6-dichloro-2-isopropylpyrimidin-5-ol (150 mg, 0.724 mmol, 1 equiv) in ACN (3.75 mL) was added a solution of KOH (812.93 mg, 14.480 mmol, 20 equiv) in $H_2O$ (3.75 mL). The resulting mixture was cooled to 0° C. and diethyl bromodifluoromethylphosphonate (386.87 mg, 1.448 mmol, 2 equiv) was added under nitrogen atmosphere. After the mixture was stirred at 0° C. for 0.5 h, it was diluted with brine (50 mL) and extracted with EA (3×20 mL). The combined organic layers were washed with brine (2×25 mL), dried over anhydrous $Na_2SO_4$. After filtration, the filtrate was concentrated under reduced pressure. The residue was purified by silica gel column chromatography, eluted with 0-20% of EA in PE to afford the title compound (220 mg, 94.51%) as a colorless oil. $^1H$ NMR (400 MHz, DMSO-$d_4$) δ 7.39-7.01 (m, 1H), 3.19-3.0) (m, 1H), 1.28-1.26 (m, 6H). $^{19}F$ NMR (377 MHz, DMSO-$d_6$) δ −79.95 (s, 2F).

Step C. 6-chloro-5-(difluoromethoxy)-2-isopropylpyrimidin-4-amine

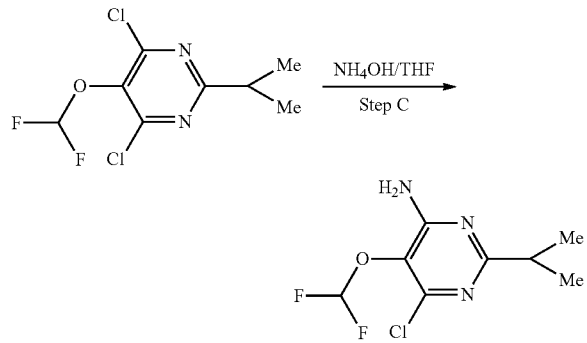

In a 40 mL sealed tube, the mixture of 4,6-dichloro-5-(difluoromethoxy)-2-isopropylpyrimidine (220 mg, 0.685 mmol, 1 equiv, 80%) in NH$_3$·H$_2$O (8 mL, 30%) and THF (2 mL) was stirred for 12 h at 70° C. After SM consumed, the solvent was removed under reduced pressure to give the title compound (200 mg, 98.34%) as a white solid. m/z (ESI, +ve ion)=238.00 [M+H]$^+$.

Step D. 5-(difluoromethoxy)-2-isopropylpyrimidin-4-amine

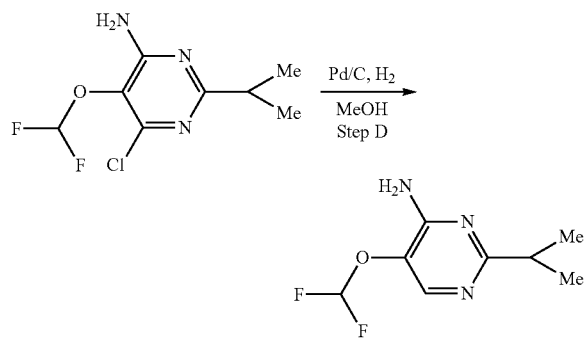

To the mixture of 6-chloro-5-(difluoromethoxy)-2-isopropylpyrimidin-4-amine (200 mg, 0.842 mmol, 1 equiv) in MeOH (4 mL) was added Pd/C (89.57 mg, 10%) under nitrogen atmosphere. The resulting mixture was de-gassed and purged with H$_2$ for three times. After stirred for 3 h at 25° C. under H$_2$ atmosphere, SM was consumed. The mixture was filtered and washed with MeOH (10 mL). The filtrate was concentrated in vacuo. The residue was purified by RP-Flash with the following conditions: Column: AQ-C18 Column, 40 g, 60 Å, 40-60 μm; Mobile Phase A: 10 mM aq. NH$_4$HCO$_3$, Mobile Phase B: MeCN; Flow rate: 60 mL/min; Gradient: 0% B to 0% B in 5 min, 0% B to 30% B in 30 min; Detector: UV 254 & 220 nm to give the title compound (80 mg, 46.78%) as a white solid. m/z (ESI, +ve ion)=204.05 [M+H]$^+$. $^1$H NMR (400 MHz, DMSO-d$_4$) δ 7.97-7.96 (m, 1H), 7.23-6.86 (m, 1H), 6.98-6.97 (m, 2H), 2.88-2.81 (m, 1H), 1.19-1.17 (m, 6H). $^{19}$F NMR (377 MHz, DMSO) δ −81.50 (s, 2F).

Step E. tert-butyl (1R,2S)-2-[1-(tert-butoxycarbonyl)-3-{[5-(difluoromethoxy)-2-isopropylpyrimidin-4-yl]amino}indazol-6-yl]-5′-methoxy-2′-oxospiro[cyclopropane-1,3′-indole]-1′-carboxylate To a stirred mixture of tert-butyl (1R,2S)-2-[1-(tert-butoxycarbonyl)-3-iodoindazol-6-yl]-5′-methoxy-2′-oxospiro[cyclopropane-1,3′-indole]-1′-carboxylate (100 mg, 0.158 mmol, 1 equiv) and 5-(difluoromethoxy)-2-isopropylpyrimidin-4-amine (38.61 mg, 0.190 mmol, 1.2 equiv) in toluene (2.5 mL) were added Cs$_2$CO$_3$ (103.19 mg, 0.316 mmol, 2 equiv), Pd$_2$(dba)$_3$ (29.00 mg, 0.032 mmol, 0.2 equiv) and XantPhos (18.33 mg, 0.032 mmol, 0.2 equiv) at room temperature under nitrogen atmosphere. The resulting mixture was stirred for 2 h at 90° C. under nitrogen atmosphere. The resulting mixture was filtered, the filter cake was washed with EA (10 mL). The filtrate was concentrated under reduced pressure. The residue was purified by silica gel column chromatography, eluted with 0-100% of EA in PE to afford the title compound (50 mg, 40.21%) as a yellow solid. m/z (ESI, +ve ion)=707.35 [M+H]$^+$

Step F. (1R,2S)-2-(3-{[5-4difluoromethoxy)-2-isopropylpyrimidin-4-yl]amino}-1H-indazol-6-yl)-5′-methoxy-1′H-spiro[cyclopropane-1,3′-indol]-2′-one

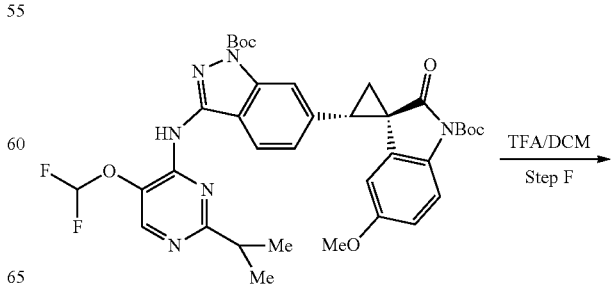

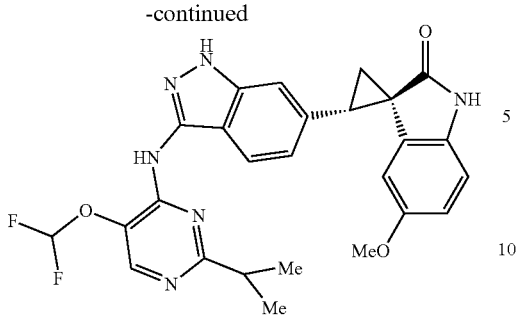

To a stirred mixture of tert-butyl (1R,2S)-2-[I-(tert-butoxycarbonyl)-3-{[5-(difluoromethoxy)-2-isopropylpyrimidin-4-yl]amino}indazol-6-yl]-5'-methoxy-2'-oxospiro[cyclopropane-1,3'-indole]-1'-carboxylate (50 mg, 0.071 mmol, 1 equiv) in DCM (5 mL) was added TFA (0.5 mL) dropwise at room temperature under nitrogen atmosphere. The resulting mixture was stirred for 4 h at room temperature under nitrogen atmosphere. The solvent was removed under reduced pressure. The residue was purified by prep-HPLC with the following conditions: Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 30% B to 40% B in 8 min; wavelength: 254 nm; RT11(min): 7 to give Example 128 (21.7 mg, 60.50%) as a white solid. m/z (ESI, +ve ion)=507.30 $[M+H]^+$. $^1$H NMR (400 MHz, Methanol-$d_4$) δ 8.14-8.13 (m, 1H), 7.52 (d, J=8.4 Hz, 1H), 7.46 (s, 1H), 7.13-6.77 (m, 3H), 6.64-6.61 (m, 1H), 5.62 (d, J=2.4 Hz, 1H), 3.38 (d, J=8.4 Hz, 1H), 3.30 (s, 3H), 2.88-2.81 (m, 1H), 2.27-2.17 (m, 2H), 1.06 (t, J=6.8 Hz, 6H). $^{19}$F NMR (376 MHz, Methanol-$d_4$) δ −83.88 (s, 2F).

Example 132: (1R,2S)-2-(3-{[5-chloro-6-(2-oxa-6-azaspiro[3.3]heptan-6-yl)pyrimidin-4-yl]amino}-1H-indazol-6-yl)-5'-methoxyspiro[cyclopropane-1,3'-indol]-2'(1'H)-one

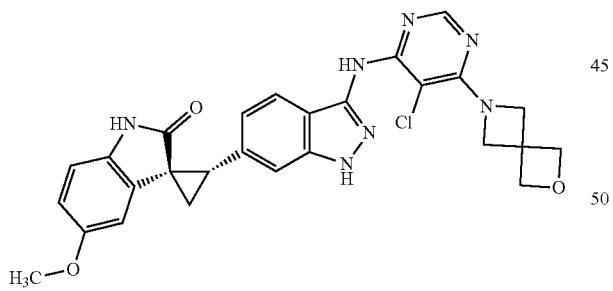

Step A. 5-chloro-6-(2-oxa-6-azaspiro[3.3]heptan-6-yl)pyrimidin-4-amine

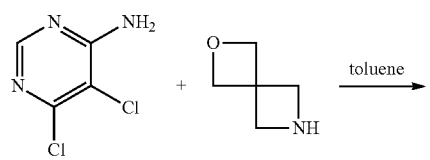

To a 50 ml round bottom flask containing 5,6-Dichloro-4-pyrimidinamine (1000.0 mg, 6.098 mmol) in toluene (9.0 mL) were added 2-Oxa-6-azaspiro[3.3]heptane (1:1) (625.4 mg, 6.308 mmol). The reaction mixture was heated to 100° C. and stirred, monitored by LCMS until the full conversion of the starting materials (approx. 2.5 hrs). Then the reaction mixture was cooled down to rt, diluted with acetone. The organic layer was then concentrated under reduced pressure and the residue was purified by column chromatography (DCM/MeOH=0~4%) to provide the title compound 1a (868.0 mg, 63%) as a pale yellow oil.

Step B. tert-butyl (1R,2S)-2-[1-tert-butoxycarbonyl-3-[[5-chloro-6-(2-oxa-6-azaspiro[3.3]heptan-6-yl)pyrimidin-4-yl]amino]indazol-6-yl]-5'-methoxy-2'-oxo-spiro[cyclopropane-1,3'-indoline]-1'-carboxylate

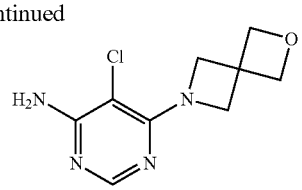

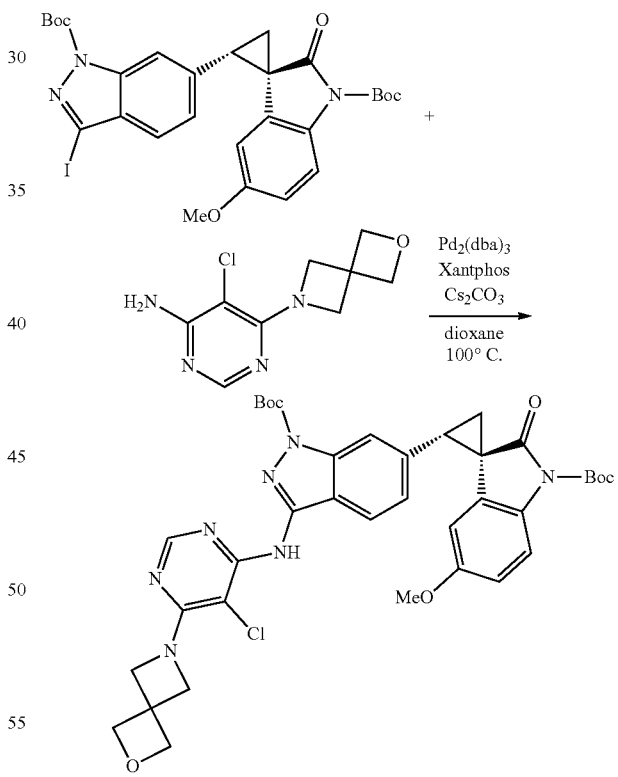

To a 50 ml round bottom flask were added cesium carbonate (60.8 mg, 0.187 mmol), tert-butyl (1R,2S)-2-(1-tert-butoxycarbonyl-3-iodo-indazol-6-yl)-5'-methoxy-2'-oxo-spiro[cyclopropane-1,3'-indoline]-1'-carboxylate (59.0 mg, 0.934 mmol), Tris(dibenzylideneacetone)dipalladium (0) (8.6 mg, 0.0093 mmol), 1a (23.3 mg, 0.103 mmol), Xantphos (5.4 mg, 0.010 mmol) and dioxane (1.0 mL). The reaction mixture was stirred and purged with argon (in balloon) for 10 min to form a green suspension, and then heated to 100° C., resulting in a yellow suspension. The reaction was monitored by LCMS and TLC until the full conversion of the starting materials (approx. 2.5 hrs), cooled down to rt, diluted with EtOAc, washed with sat. aq. NaHCO₃ and dried over Na₂SO₄. The residue was purified by column chromatography (DCM/MeOH=0~6%) to provide the title compound 1b (17.2 mg, 25%) as a yellow solid.

Step C. (1R,2S)-2-[3-[[5-chloro-6-(2-oxa-6-azaspiro[3.3]heptan-6-yl)pyrimidin-4-yl]amino]-1H-indazol-6-yl]-5'-methoxy-spiro[cyclopropane-1,3'-indoline]-2'-one

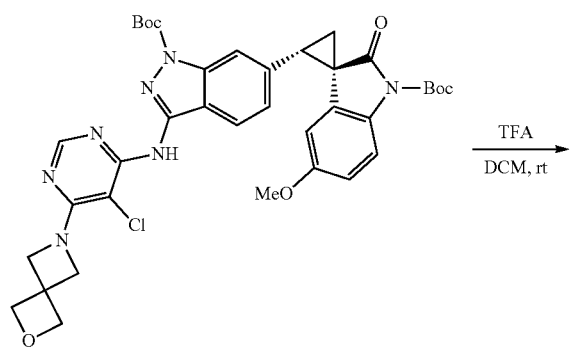

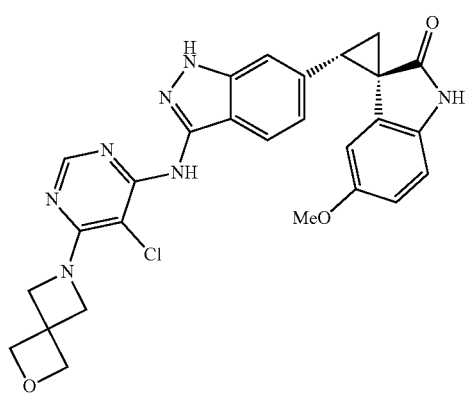

To a 50 mil round bottom flask containing 1b (17.2 mg, 0.0235 mmol) in DCM (0.50 mL) was added trifluoroacetic acid (0.13 mL, 1.6 mmol). The reaction mixture was stirred and monitored by LCMS until the full conversion of the starting materials (approx. 2 hrs), diluted with methanol, quenched with 1N NaOH. The resulting brown solution was purified by Prep. HPLC (Gemini C18, 10 to 40% (0.1% Formic Acid in water)/(0.1% Formic Acid in Acetonitrile)) to provide Example 132 product as a yellow solid. ¹H NMR (400 MHz, DMSO-d₆) δ ppm 1.97 (br dd, J=4.40, 2.93 Hz, 1H) 2.07 (br d, J=0.73 Hz, 1H) 2.28-2.37 (m, 1H) 3.17 (br d, J=2.45 Hz, 1H) 4.42 (br s, 4H) 4.71 (br s, 4H) 5.70 (br s, 1H) 6.58 (br d, J=7.34 Hz, 1H) 6.74 (br d, J=7.09 Hz, 1H) 6.84-6.93 (m, 1H) 7.27-7.36 (m, 1H) 7.40 (br d, J=0.73 Hz, 1H) 7.82 (br s, 1H) 8.93 (br s, 1H) 10.43 (br s, 1H) 12.68 (br s, 1H); m/z (ESI, +ve ion) 530.2 (M+H)+.

Example 134: (1R,2S)-2-{3-[(5-ethoxy-2-methylpyrimidin-4-yl)amino]-1H-indazol-6-yl}-5'-methoxyspiro[cyclopropane-1,3'-indol]-2'(1'H)-one

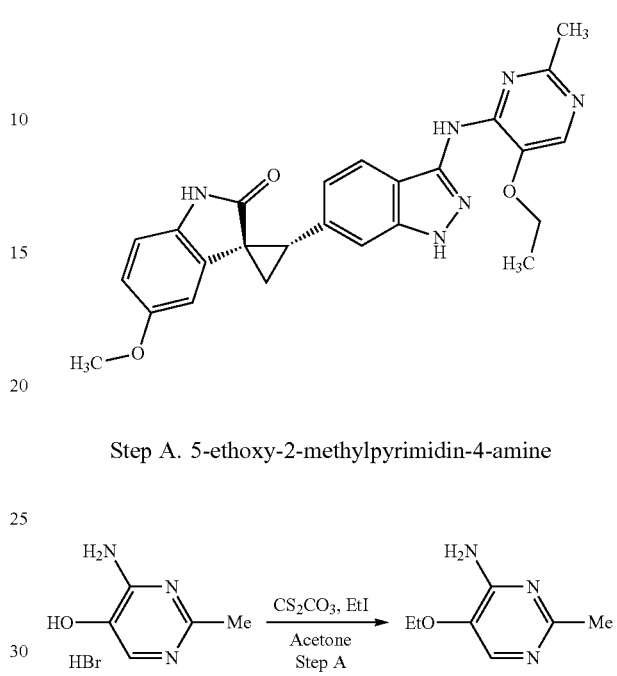

Step A. 5-ethoxy-2-methylpyrimidin-4-amine

To a stirred mixture of 4-amino-2-methylpyrimidin-5-ol hydrobromide (80 mg, 0.388 mmol, 1 equiv) in acetone (2 mL) were added ethyl iodide (72.67 mg, 0.466 mmol, 1.2 equiv) and Cs₂CO₃ (404.82 mg, 1.242 mmol, 3.2 equiv) at room temperature under nitrogen atmosphere. The resulting mixture was stirred for 16 h at 50° C. under nitrogen atmosphere then diluted with water (10 mL). The resulting mixture was extracted with CHCl₃ (4×5 mL). The combined organic layers were washed with brine (2×5 mL), dried over anhydrous Na₂SO₄. After filtration, the filtrate was concentrated under reduced pressure. The residue was purified by prep-TLC (DCM:MeOH, 10:1) to afford the title compound (40 mg, 67.25%) as a yellow solid. m/z (ESI, +ve ion)=154.20 [M+H]⁺. ¹H NMR (400 MHz, DMSO-d₆) δ 7.68 (s, 1H), 6.48 (s, 2H), 4.02 (m, 2H), 2.25 (s, 3H), 1.33 (m, 3H).

Step B. tert-butyl (1R,2S)-2-[1-(tert-butoxycarbonyl)-3-[(5-ethoxy-2-methylpyrimidin-4-yl)amino]indazol-6-yl]-5'-methoxy-2'-oxospiro[cyclopropane-1,3'-indole]-1'-carboxylate

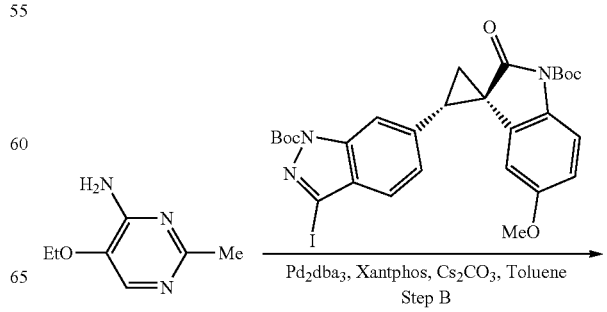

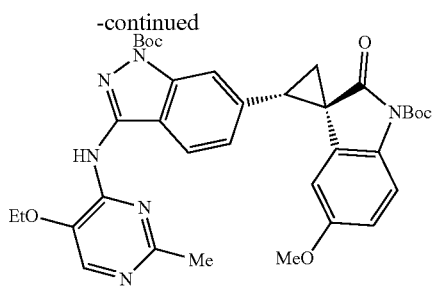

To a stirred mixture of 5-ethoxy-2-methylpyrimidin-4-amine (26.20 mg, 0.172 mmol, 1.20 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.143 mmol, 1.00 equiv) in toluene (0.5 mL) was added Cs$_2$CO$_3$ (92.88 mg, 0.286 mmol, 2 equiv) at room temperature under nitrogen atmosphere. To the above mixture were added XantPhos (16.49 mg, 0.029 mmol, 0.2 equiv) and Pd$_2$(dba)$_3$ (26.10 mg, 0.029 mmol, 0.2 equiv) at room temperature. The resulting mixture was stirred for 2 h at 90° C. under nitrogen atmosphere then filtered. The filter cake was washed with EA (3×10 mL). The filtrate was concentrated under reduced pressure. The residue was purified by silica gel column chromatography, eluted with DCM:MeOH (10:1) to afford the title compound (64 mg, 68.37%) as a white solid. m/z (ESI, +ve ion)=657.50.

Step C. (1R,2S)-2-{3-[(5-ethoxy-2-methylpyrimidin-4-yl)amino]-1H-indazol-6-yl}-5'-methoxy-1'H-spiro[cyclopropane-1,3'-indol]-2'-one

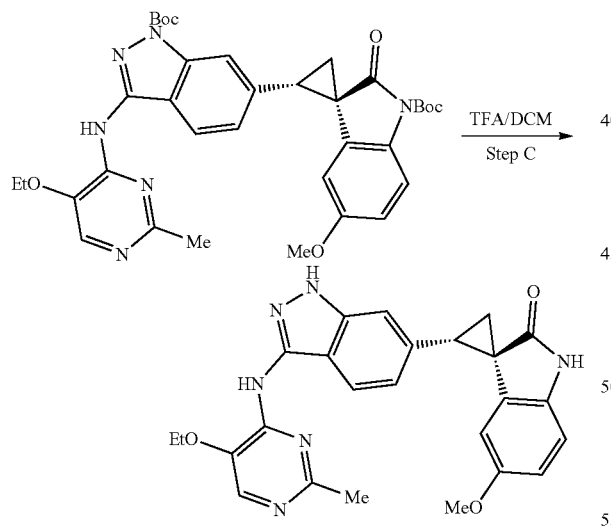

To a stirred solution of tert-butyl (1R,2S)-2-[1-(tert-butoxycarbonyl)-3-[(5-ethoxy-2-methylpyrimidin-4-yl)amino]indazol-6-yl]-5'-methoxy-2'-oxospiro[cyclopropane-1,3'-indole]-1'-carboxylate (70 mg, 0.107 mmol, 1 equiv) and DCM (2 mL, 31.460 mmol, 295.16 equiv) was added TFA (0.2 mL, 2.693 mmol, 25.26 equiv) dropwise at room temperature under nitrogen atmosphere. The resulting mixture was concentrated under reduced pressure. The crude product was purified by prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 22% B to 32% B in 8 min, 32% B: wavelength: 254 nm; RT1(min): 7 to afford Example 134 (32.1 mg, 65.91%) as a white solid. m/z (ESI, +ve ion)=457.20 [M+H]$^+$. $^1$H-NMR (400 MHz, Methanol-d$_4$) δ 7.84 (s, 1H), 7.62 (d, J=8.8 Hz, 1H), 7.44 (s, 1H), 6.93 (d, J=8.4 Hz, 1H), 6.85 (d, J=8.4 Hz, 1H), 6.64 (m, 1H), 5.64 (s, 1H), 4.27-4.21 (m, 2H), 3.36-3.39 (m, 4H), 2.31 (s, 3H), 2.27-2.17 (m, 2H), 1.54-1.50 (m, 3H).

Example 154. (1R,2S)-5'-methoxy-2-(3-{[5-methoxy-2-(oxan-4-yl)pyrimidin-4-yl]amino}-1H-indazol-6-yl)spiro[cyclopropane-1,3'-indol]-2'(1'H)-one

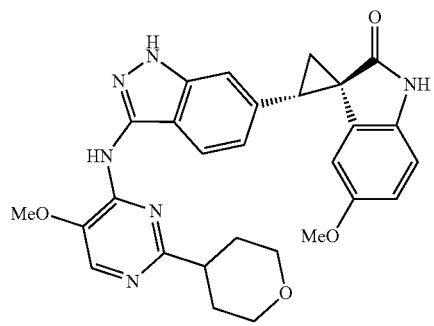 [SMILES: COc1ccc2c(c1)[C@]1(C[C@H]1c1ccc3c(Nc4nc(C5CCOCC5)ncc4OC)n[nH]c3c1)C(=O)N2]

Step A. 2-(3,6-dihydro-2H-pyran-4-yl)-5-methoxy-pyrimidin-4-amine

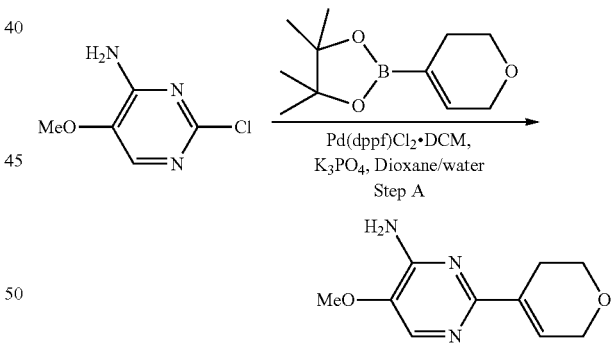

The mixture of 2-chloro-5-methoxypyrimidin-4-amine (159.6 mg, 1.000 mmol, 1 equiv) and 2-(3,6-dihydro-2H-pyran-4-yl)-4,4,5,5-tetramethyl-1,3,2-dioxaborolane (315.1 mg, 1.500 mmol, 1.50 equiv) was dissolved in 1,4-dioxane (8.5 mL) and water (1.75 mL) under the nitrogen atmosphere. To the solution were added K$_3$PO$_4$ (636.8 mg, 3.000 mmol, 3.00 equiv) and Pd(dppf)Cl$_2$·DCM (81.8 mg, 0.100 mmol, 0.10 equiv). The mixture was stirred at 90° C. overnight. After cooled to room temperature, the solvent was removed under reduced pressure. The residue was purified by Prep-TLC (PE/EA=1/10) to afford the title compound (165.7 mg, 79.94%) as a yellow solid. m/z (ESI, +ve ion)=208.30 [M+H]$^+$.

Step B. 5-methoxy-2-(tetrahydro-2H-pyran-4-yl)pyrimidin-4-amine

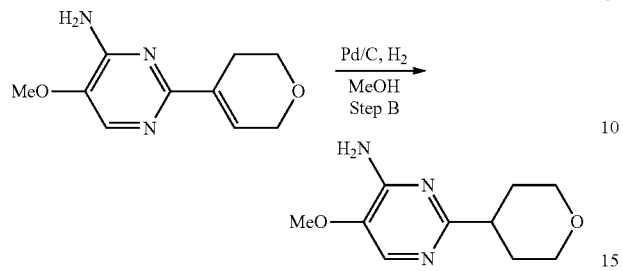

To a solution of 2-(3,6-dihydro-2H-pyran-4-yl)-5-methoxypyrimidin-4-amine (165.7 mg, 0.800 mmol, 1 equiv) in MeOH (12 mL) was added 10% Pd/C (110 mg) under nitrogen atmosphere. The reaction system was degassed and purged with hydrogen three times. The mixture was hydrogenated at room temperature for 3 h under hydrogen atmosphere using a hydrogen balloon. The resulting mixture was filtered through a Celite pad and the filtrate was concentrated under reduced pressure. The residue was purified by Prep-TLC (DCM/MeOH/TEA=100/10/1) to afford the title compound (143.2 mg, 85.59%) as a white solid. m/z (ESI, +ve ion)=210.10 [M+H]$^+$.

Step C. tert-butyl (1R,2S)-2-(1-(tert-butoxycarbonyl)-3-((5-methoxy-2-(tetrahydro-2H-pyran-4-yl)pyrimidin-4-yl)amino)-1H-indazol-6-yl)-5'-methoxy-2'-oxospiro[cyclopropane-1,3'-indoline]-1'-carboxylate

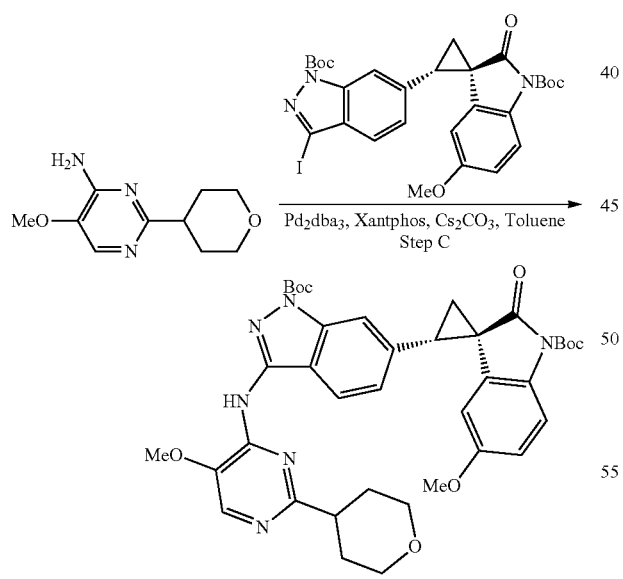

tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 0.83 equiv) and 5-methoxy-2-(tetrahydro-2H-pyran-4-yl)pyrimidin-4-amine (40 mg, 0.191 mmol, 1 equiv) were dissolved in toluene (3 mL) under nitrogen atmosphere. To the solution were added Cs$_2$CO$_3$ (104.4 mg, 0.320 mmol, 1.68 equiv), XantPhos (19 mg, 0.033 mmol, 0.17 equiv) and Pd$_2$(dba)$_3$ (29 mg, 0.032 mmol, 0.17 equiv). The reaction mixture was bubble with nitrogen for 5 minutes. The reaction mixture was then stirred at 90° C. for 2 h. The resulting mixture was filtered, the filter cake was washed with EA (5 mL). The filtrate was concentrated under reduced pressure. The residue was purified by Prep-TLC (PE/EtOAc=1/20) to afford the title compound (75.9 mg, 55.70%) as an orange solid. m/z (ESI, +ve ion)=713.55 [M+H]$^+$.

Step D. (1R,2S)-5'-methoxy-2-(3-{[5-methoxy-2-(oxan-4-yl)pyrimidin-4-yl]amino}-1H-indazol-6-yl)spiro[cyclo propane-1,3'-indol]-2'(1'H)-one

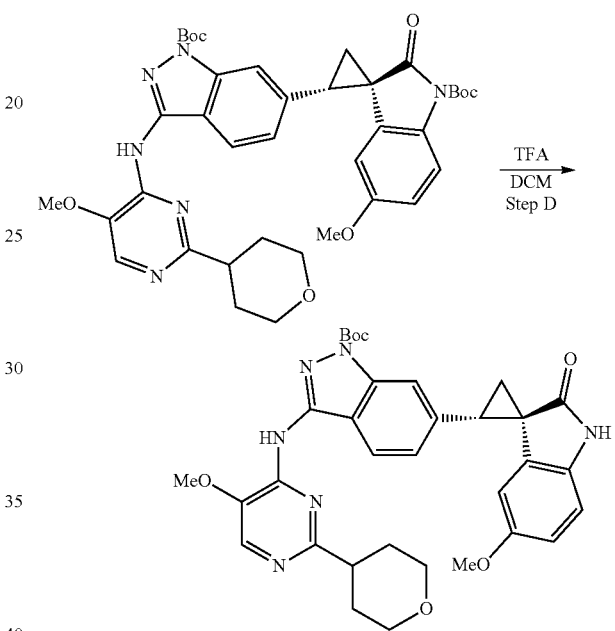

To a solution of tert-butyl (1R,2S)-2-(1-(tert-butoxycarbonyl)-3-((5-methoxy-2-(tetrahydro-2H-pyran-4-yl)pyrimidin-4-yl)amino)-1H-indazol-6-yl)-5'-methoxy-2'-oxospiro[cyclopropane-1,3'-indoline]-1'-carboxylate (75.9 mg, 0.106 mmol, 1 equiv) in DCM (2 mL) was added TFA (164 uL, 2.208 mmol, 20.74 equiv). The reaction mixture was stirred at room temperature overnight. The solvent was removed under reduced pressure. The residual was azeotropic roto-evaporated with toluene to remove TFA. The crude product was purified by Prep-HPLC: Column: XBridge Shield RP18 OBD Column, 30×150 mm, 5 μm; Mobile Phase A: Water (10 mmol/L NH$_4$HCO$_3$). Mobile Phase B: ACN; Flow rate: 60 mL/min; Gradient: 25% B to 35% B in 8 min, 35% B; wavelength: 254 nm; RT1(min): 7.67 to afford Example 154 (18.6 mg, 34.08%) as a white solid. m/z (ESI, +ve ion)=513.25 [M+H]$^+$. $^1$H NMR (400 MHz, DMSO-d$_6$) δ 12.60 (s, 1H), 10.40 (s, 1H), 9.00 (s, 1H), 8.00 (s, 1H), 7.45 (d, J=4.2, 1H), 7.39 (s, 1H), 6.87 (d, J=8.8 Hz, 1H), 6.75 (d, J=8.4 Hz, 1H), 6.59 (dd, J=8.4, 2.8 Hz, 1H), 5.66 (d, J=2.8 Hz, 1H), 3.92 (s, 3H), 3.73 (t, J=13.2 Hz, 2H), 3.31-3.18 (m, 5H), 2.68-2.51 (m, 2H), 2.31-2.28 (m, 1H), 2.00-1.97 (m, 1H), 1.66-1.50 (m, 4H).

Example 157. (1R,2S)-2-(3-{[2-(azetidin-1-yl)-5-methoxypyrimidin-4-yl]amino}-1H-indazol-6-yl)-5'-methoxyspiro[cyclopropane-1,3'-indol]-2'(1'H)-one

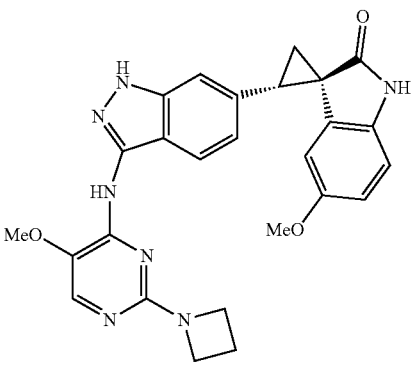 [SMILES: COc1ccc2c(c1)[C@]1(C[C@H]1c1ccc3c(Nc4nc(N5CCC5)ncc4OC)n[nH]c3c1)C(=O)N2]

Step A.
2-(azetidin-1-yl)-5-methoxypyrimidin-4-amine

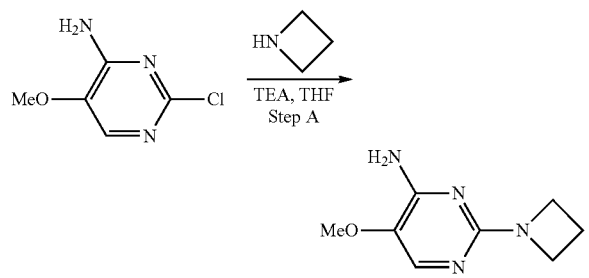

The mixture of 2-chloro-5-methoxypyrimidin-4-amine (200 mg, 1.253 mmol, 1 equiv) and azetidine (214.69 mg, 3.759 mmol, 3 equiv) in THF (4 mL) was stirred at 60° C. for 12 h. The solvent was removed under reduced pressure. The residue was purified by Prep-HPLC with the following conditions (Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 6% B to 15% B in 8 min, 15% B; wavelength: 254 nm; RT1(min): 7) to afford the title compound (60 mg, 21.25%) as a white solid. m/z (ESI, +ve ion)=181.15 [M+H]$^+$.

Step B. tert-butyl (1R,2S)-2-(3-{[2-(azetidin-1-yl)-5-methoxypyrimidin-4-yl]amino}-1-(tert-butoxycarbonyl)indazol-6-yl)-5'-methoxy-2'-oxospiro[cyclopropane-1,3'-indole]-1'-carboxylate

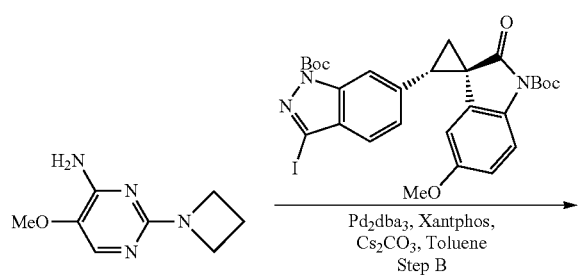

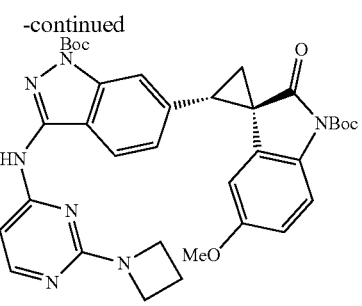

To the mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (110 mg, 0.174 mmol, 1 equiv) and 2-(azetidin-1-yl)-5-methoxypyrimidin-4-amine (31.39 mg, 0.174 mmol, 1 equiv) in toluene (3 mL) were added Cs$_2$CO$_3$ (113.38 mg, 0.348 mmol, 2 equiv). Pd$_2$(dba)$_3$ (31.90 mg, 0.035 mmol, 0.2 equiv) and XantPhos (20.16 mg, 0.035 mmol, 0.2 equiv) under nitrogen atmosphere. The mixture was stirred at 90° C. for 2 h. After cooled to room temperature, the mixture was filtered and washed with EA (20 mL). The solvent was removed under reduced pressure. The residue was purified by silica gel column chromatography, eluted with 0-100% of EtOAc in PE to afford the title compound (90 mg, 75.56%) as a yellow oil. m/z (ESI, +ve ion)=684.35 [M+H]$^+$.

Step C. (1R,2S)-2-(3-{[2-(azetidin-1-yl)-5-methoxypyrimidin-4-yl]amino}-1H-indazol-6-yl)-5'-methoxyspiro[cyclopropane-1,3'-indol]-2'(1'H)-one

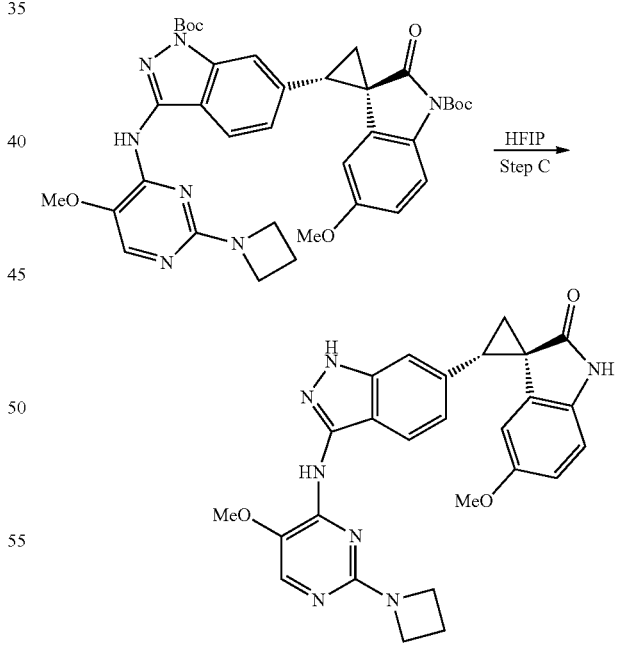

The mixture of tert-butyl (1R,2S)-2-(3-{[2-(azetidin-1-yl)-5-methoxypyrimidin-4-yl]amino}-1-tert-butoxycarbonyl)indazol-6-yl)-5'-methoxy-2'-oxospiro[cyclopropane-1,3'-indole]-1'-carboxylate (90 mg, 0.132 mmol, 1 equiv) in HFIP (5 mL) was stirred at 65° C. for 12 h. The solvent was removed under reduced pressure. The residue was purified by Prep-HPLC with the following conditions (Column:

XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 23% B to 33% B in 8 min; wavelength: 254 nm; RT1(min): 7) to afford Example 157 (40 mg, 62.60%) as a white solid. m/z (ESI, +ve ion)=484.20 [M+H]⁺. ¹H NMR (400 MHz, DMSO-d₆) δ 12.55 (s, 1H), 10.41 (s, 1H), 8.85 (s, 1H), 7.73 (s, 1H), 7.56 (d, J=8.4 Hz, 1H), 7.36 (s, 1H), 6.86-6.84 (m, 1H), 6.74 (d, J=8.4 Hz, 1H), 6.59-6.56 (m, 1H), 5.65 (d, J=2.4 Hz, 1H), 3.79 (s, 3H), 3.67-3.50 (m, 4H), 3.32 (s, 3H), 3.18 (t, J=8.0 Hz, 1H), 2.32-2.29 (m, 1H), 2.08-1.96 (m, 3H).

Example 160. (1R,2S)-2-{3-[(2-ethyl-5-methoxypyrimidin-4-yl)amino]-1H-indazol-6-yl}-5'-methoxyspiro[cyclopropane-1,3'-indol]-2'(1'H)-one

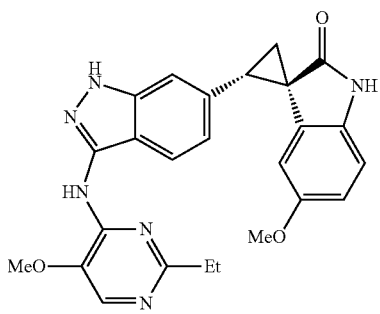 [SMILES: CCc1ncc(OC)c(Nc2n[nH]c3cc([C@@H]4C[C@@]45C(=O)Nc4ccc(OC)cc45)ccc23)n1]

Step A. 2-ethenyl-5-methoxypyrimidin-4-amine

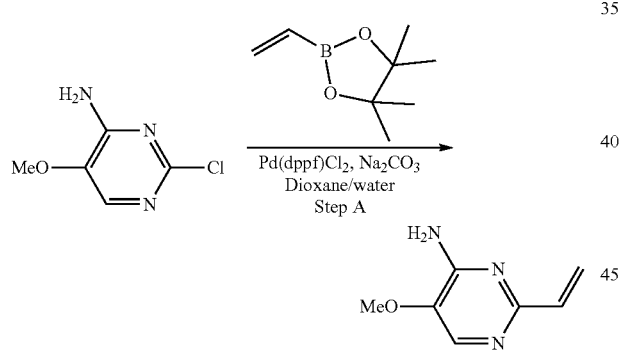

To a stirred solution of 2-chloro-5-methoxypyrimidin-4-amine (958 mg, 6.004 mmol, 1 equiv) and 2-ethenyl-4,4,5,5-tetramethyl-1,3,2-dioxaborolane (1109.62 mg, 7.205 mmol, 1.2 equiv) in dioxane (50 mL) and water (10 mL) were added Pd(dppf)Cl₂·CH₂Cl₂ (489.07 mg, 0.600 mmol, 0.1 equiv) and Na₂CO₃ (1272.63 mg, 12.008 mmol, 2 equiv) at room temperature under nitrogen atmosphere. The resulting mixture was stirred for 16 h at 100° C. under nitrogen atmosphere. The mixture was allowed to cool down to room temperature. The resulting mixture was diluted with water (50 mL). The resulting mixture was extracted with EtOAc (3×50 mL). The combined organic layers were washed with brine (3×150 mL), dried over anhydrous Na₂SO₄. After filtration, the filtrate was concentrated under reduced pressure. The residue was purified by silica gel column chromatography, eluted with PE/EA (1/1) to afford the title compound (350 mg, 38.56%) as a white solid. m/z (ESI, +ve ion)=152.10 [M+H]⁺.

Step B. 2-ethyl-5-methoxypyrimidin-4-amine

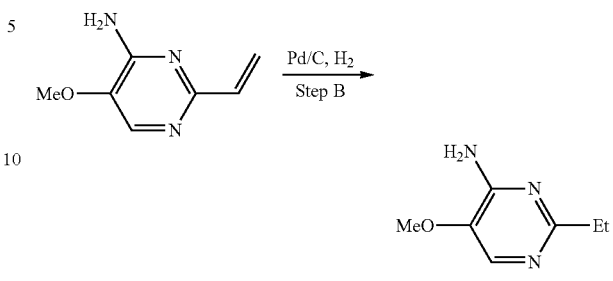

To a solution of 2-ethenyl-5-methoxypyrimidin-4-amine (350 mg, 2.315 mmol, 1 equiv) in 5 mL MeOH was added Pd/C (10%, 35 mg) under nitrogen atmosphere. The mixture was hydrogenated at room temperature under hydrogen atmosphere for 2 h. The mixture was filtered through a Celite pad and the filtrate was concentrated under reduced pressure. The resulting mixture was filtered, the filter cake was washed with MeOH (3×50 mL). The filtrate was concentrated under reduced pressure to afford the title compound (350 mg, 98.68%) as a white solid. m/z (ESI, +ve ion)=154.10 [M+H]⁺.

Step C. tert-butyl (1R,2S)-2-[1-(tert-butoxycarbonyl)-3-[(2-ethyl-5-methoxypyrimidin-4-yl)amino]indazol-6-yl]-5'-methoxy-2'-oxospiro[cyclopropane-1,3'-indole]-1'-carboxylate

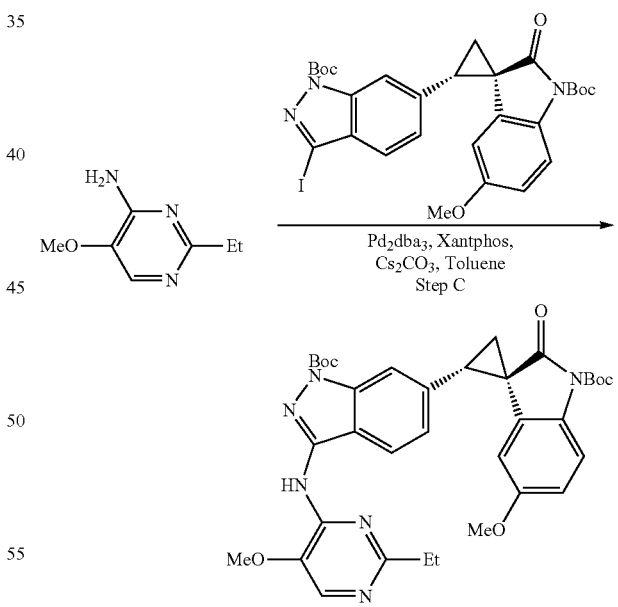

To a stirred solution of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (120 mg, 0.190 mmol, 1 equiv) and 2-ethyl-5-methoxypyrimidin-4-amine (34.93 mg, 0.228 mmol, 1.2 equiv) in toluene (6 mL) were added Pd₂(dba)₃ (17.40 mg, 0.019 mmol, 0.1 equiv), XantPhos (11.00 mg, 0.019 mmol, 0.1 equiv) and Cs₂CO₃ (123.83 mg, 0.380 mmol, 2 equiv) at room temperature under nitrogen atmosphere. The resulting mixture was stirred for 2 h at 90° C. under nitrogen atmosphere. The mixture was allowed to cool down to room temperature. The resulting mixture was diluted with water (20 mL). The resulting mixture was extracted with EA (3×20 mL). The combined organic layers were washed with brine (3×60 mL), dried over anhydrous $Na_2SO_4$. After filtration, the filtrate was concentrated under reduced pressure. The residue was purified by Prep-TLC (PE/EA=1/1) to afford the title compound (90 mg, 72.11%) as a yellow solid. m/z (ESI, +ve ion)=657.25 $[M+H]^+$.

Step D. (1R,2S)-2-{3-[(2-ethyl-5-methoxypyrimidin-4-yl)amino]-1H-indazol-6-yl}-5'-methoxyspiro[cyclopropane-1,3'-indol]-2'(1'H)-one

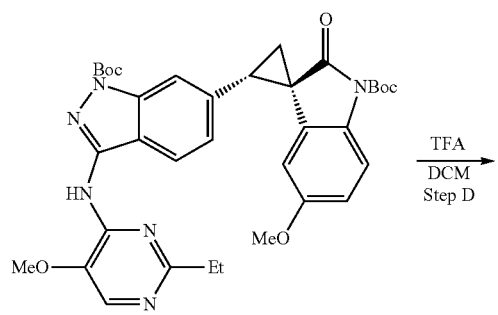

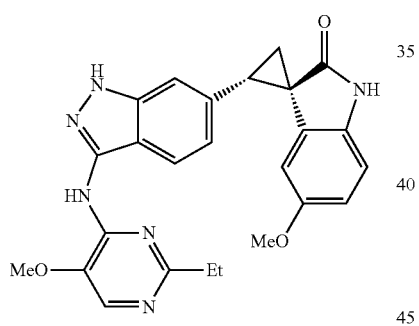

To a stirred mixture of tert-butyl (1R,2S)-2-[1-(tert-butoxycarbonyl)-3-[(2-ethyl-5-methoxypyrimidin-4-yl)amino]indazol-6-yl]-5'-methoxy-2'-oxospiro[cyclopropane-1,3'-indole]-1'-carboxylate (85 mg, 0.129 mmol, 1 equiv) in DCM (4 mL) was added TFA (2 mL) at room temperature under nitrogen atmosphere. The resulting mixture was stirred for 2 h at room temperature. The resulting mixture was concentrated under reduced pressure. The residue was purified by Prep-HPLC with the following conditions (Column: XBridge Prep OBD C18 Column, 30×150 mm, 5 µm; Mobile Phase A: Water (10 mmol/L $NH_4HCO_3$), Mobile Phase B: ACN; Flow rate: 60 mL/min; Gradient: 22% B to 32% B in 8 min, 32% B; wavelength: 254 nm; RT1(min): 7) to afford the title compound (32.8 mg, 54.57%) as a white solid. m/z (ESI+ve ion)=457.20 $[M+H]^+$. $^1H$ NMR (400 MHz, DMSO-$d_6$) δ 12.60 (s, 1H), 10.40 (s, 1H), 8.96 (s, 1H), 7.95 (s, 1H), 7.46 (d, J=8.4 Hz, 1H), 7.39 (s, 1H), 6.88 (d, J=10.4 Hz, 1H), 6.75 (d, J=8.0 Hz, 1H), 6.59 (dd, J=10.8, 2.4 Hz, 1H), 5.69 (d, J=2.4 Hz, 1H), 3.91 (s, 3H), 3.32 (s, 3H), 3.19 (t, J=8.4 Hz, 1H), 2.48-2.42 (m, 2H), 2.34-2.30 (m, 1H), 2.02-1.97 (m, 1H), 1.01 (t, J=7.6 Hz, 3H).

Example 161. (1R,2S)-5'-methoxy-2-{3-[(7-methoxyquinolin-6-yl)amino]-1H-indazol-6-yl}spiro[cyclopropane-1,3'-indol]-2'(1'H)-one

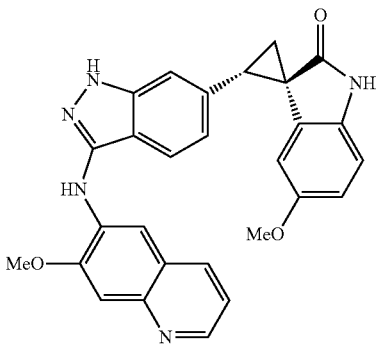 [SMILES: COc1ccc2c(c1)[C@]1(C[C@H]1c1ccc3c(Nc4cc5cccnc5cc4OC)n[nH]c3c1)C(=O)N2]

Step A. tert-butyl (1R,2S)-2-[1-(tert-butoxycarbonyl)-3-[(7-methoxyquinolin-6-yl)amino]indazol-6-yl]-5'-methoxy-2'-oxospiro[cyclopropane-1,3'-indole]-1'-carboxylate

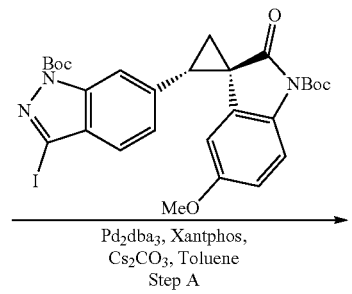

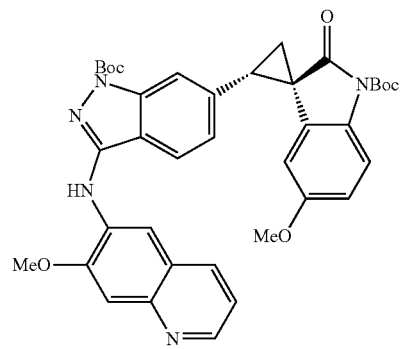

To a stirred solution of 7-methoxyquinolin-6-amine (33.10 mg, 0.190 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (120.00 mg, 0.190 mmol, 1.00 equiv) in toluene (5.00 mL) were added $Pd_2(dba)_3$ (34.80 mg, 0.038 mmol, 0.20 equiv), XantPhos (21.99 mg, 0.038 mmol, 0.20 equiv) and $Cs_2CO_3$ (123.83 mg, 0.380 mmol, 2.00 equiv) at room temperature under nitrogen atmosphere. The resulting mixture was stirred for 2 h at 90° C. under nitrogen atmosphere. The mixture was allowed to cool down to room temperature. The resulting mixture was filtered. The filter cake was washed with EA (3×30 mL). The filtrate was concentrated under reduced pressure. The residue was purified by silica gel column chromatography, eluted with PE/EA (1/1) to afford the title compound (82.00 mg, 63.67%) as a yellow solid. m/z (ESI, +ve ion)=678.30 [M+H]$^+$.

Step B. (1R,2S)-5'-methoxy-2-{3-[(7-methoxyquinolin-6-yl)amino]-1H-indazol-6-yl}spiro[cyclopropane-1,3'-indol]-2'(1'H)-one

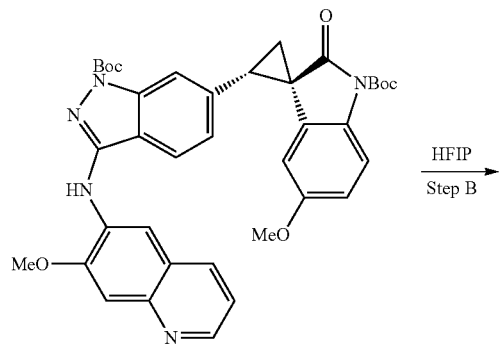

Example 163. (1R,2S)-5'-methoxy-2-{3-[(3-methoxyquinolin-2-yl)amino]-1H-indazol-6-yl}spiro[cyclopropane-1,3'-indol]-2'(1'H)-one

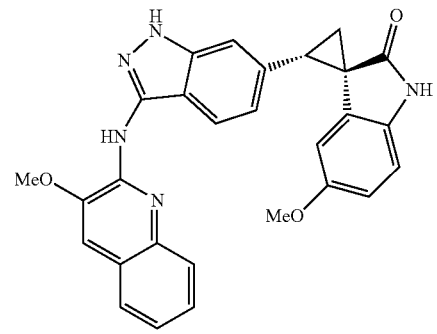 [SMILES: COc1ccc2c(c1)[C@]1(C[C@H]1c1ccc3c(Nc4nc5ccccc5cc4OC)n[nH]c3c1)C(=O)N2]

Step A. 3-methoxyquinolin-2-amine

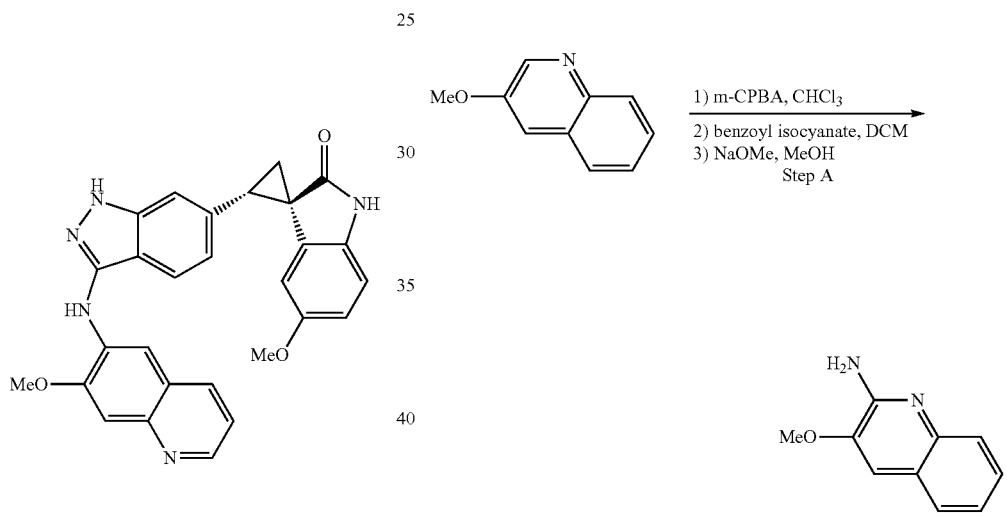

A solution of tert-butyl (1R,2S)-2-[1-(tert-butoxycarbonyl)-3-[(7-methoxyquinolin-6-yl)amino]indazol-6-yl]-5'-methoxy-2'-oxospiro[cyclopropane-1,3'-indole]-1'-carboxylate (80.00 mg, 0.118 mmol, 1.00 equiv) in HFIP (5.00 mL) was stirred for 6 h at 60° C. The mixture was allowed to cool down to room temperature. The resulting mixture was concentrated under reduced pressure. The crude product (48 mg) was purified by Prep-HPLC with the following conditions (Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 37% B to 45% B in 8 min, 45% B: wavelength: 254 nm; RT1(min): 7.82) to afford the title compound (27.20 mg, 48.02%) as a white solid. m/z (ESI+ve ion)=478.20 [M+H]$^+$. $^1$H-NMR (400 MHz, Methanol-d$_4$) δ 8.55-8.54 (m, 1H), 8.23 (s, 1H), 8.09 (d, J=7.6 Hz, 1H), 7.71 (d, J=8.0 Hz, 1H), 7.41-7.34 (m, 2H), 7.34-7.31 (m, 1H), 6.94 (d, J=8.0 Hz, 1H), 6.85 (d, J=8.4 Hz, 1H), 6.65-6.62 (m, 1H), 5.64 (d, J=2.4 Hz, 1H), 4.17 (s, 3H), 3.40-3.36 (m, 1H), 3.31 (s, 3H), 2.27-2.18 (m, 2H).

The mixture of 3-methoxyquinoline (500 mg, 3.141 mmol, 1 equiv) and m-CPBA (2092.12 mg, 12.124 mmol, 3.86 equiv) in CHCl$_3$ (9 mL) was stirred for 5 h at 25° C. under nitrogen atmosphere. The mixture was diluted with EtOAc (30 mL) and washed with water (30 mL), brine (30 mL). The organic layer was dried over anhydrous Na$_2$SO$_4$ and filtered. The filtrate was concentrated in vacuo. The residue was purified by silica gel column eluted with 0-100% of EtOAc in PE to give 840 mg of intermediate. The mixture of intermediate and benzoyl isocyanate (1386.41 mg, 9.423 mmol, 3 equiv) in DCM (9 mL) was stirred for 1 h at 55° C. After cooled to room temperature, the solvent was removed under reduced pressure. The residue was dissolved in MeOH (9 mL) and to this mixture was added sodium methoxide (848.43 mg, 15.705 mmol, 5 equiv) at 25° C. The resulting mixture was stirred at 75° C. for 2 h. After cooled to room temperature, the solvent was removed under reduced pressure. The residue was purified by silica gel column chromatography, eluted with 0-10% of MeOH in DCM to afford the title compound (200 mg, 36.55%) as a white solid. m/z (ESI, +ve ion)=175.10 [M+H]$^+$.

Step B. tert-butyl (1R,2S)-2-[1-(tert-butoxycarbonyl)-3-[(3-methoxyquinolin-2-yl)amino]indazol-4-yl]-5'-methoxy-2'-oxospiro[cyclopropane-1,3'-indole]-1'-carboxylate

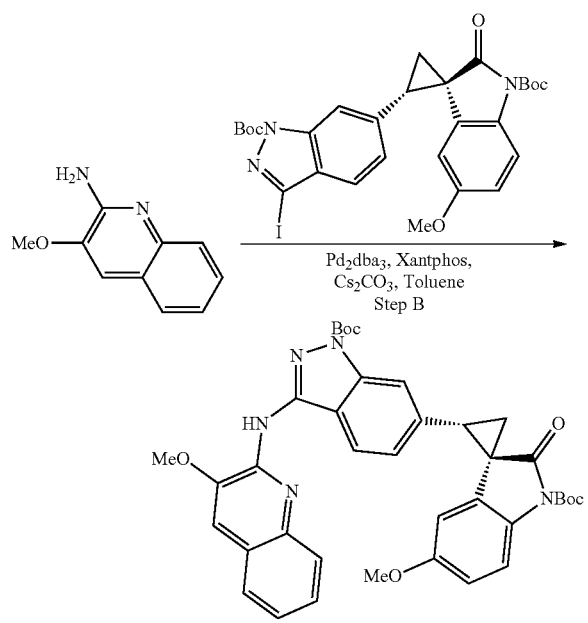

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1 equiv) and 3-methoxyquinolin-2-amine (33.10 mg, 0.19) mmol, 1.2 equiv) in toluene (2.5 mL) were added Cs₂CO₃ (103.19 mg, 0.316 mmol, 2 equiv), XantPhos (18.33 mg, 0.032 mmol, 0.2 equiv) and Pd₂(dba)₃ (29.00 mg, 0.032 mmol, 0.2 equiv) at room temperature under nitrogen atmosphere. The mixture was stirred at 90° C. for 2 h. After cooled to room temperature, the mixture was filtered and washed with EA (20 mL). The filtrate was concentrated in vacuo and the residue was purified by silica gel column, eluted with 0-100% of EtOAc in PE to give the title compound (85 mg, 79.19%) as a yellow solid. m/z (ESI, +ve ion)=678.30 [M+H]⁺.

Step C. (1R,2S)-5'-methoxy-2-{3-[(3-methoxyquinolin-2-yl)amino]-1H-indazol-6-yl}spiro[cyclopropane-1,3'-indol]-2'(1'H)-one

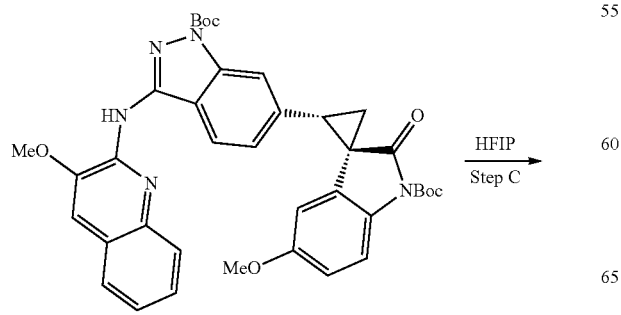

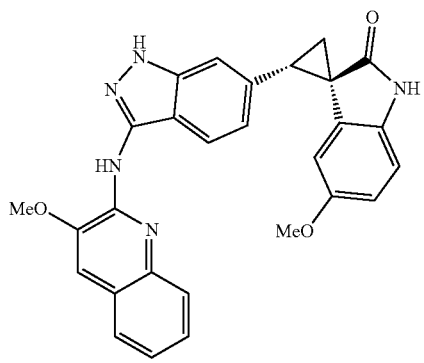

The mixture of tert-butyl (1R,2S)-2-[1-(tert-butoxycarbonyl)-3-[(3-methoxyquinolin-2-yl)amino]indazol-6-yl]-5'-methoxy-2'-oxospiro[cyclopropane-1,3'-indole]-1'-carboxylate (85 mg, 0.125 mmol, 1 equiv) in HFIP (5 mL) was stirred at 60° C. for 12 h. After cooled to 25° C., the solvent was removed under reduced pressure. The residue was purified by Prep-HPLC with the following conditions (Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 35% B to 45% B in 8 min-; wavelength: 254 nm; RT1(min): 7) to afford the title compound (33.6 mg, 56.05%) as a light yellow solid. m/z (ESI, +ve ion)=478.15 [M+H]⁺. ¹H NMR (400 MHz, DMSO-d₆) δ 12.53 (s, 1H), 10.40 (s, 1H), 8.72 (s, 1H), 7.69 (d, J=7.6 Hz, 1H), 7.62 (d, J=8.4 Hz, 1H), 7.54 (s, 1H), 7.39 (s, 1H), 7.36-7.30 (m, 2H), 7.26-7.22 (m, 1H), 6.89 (d, J=8.8 Hz, 1H), 6.76 (d, J=8.4 Hz, 1H), 6.63-6.60 (m, 1H), 5.77 (d, J=2.4 Hz, 1H), 4.02 (s, 3H), 3.38 (s, 3H), 3.20 (t, J=8.0 Hz, 1H), 2.35-2.32 (m, 1H), 2.01-1.98 (m, 1H).

Example 167. (1R,2S)-5'-methoxy-2-(3-{[5-methoxy-2-(pyrrolidin-1-yl)pyrimidin-4-yl]amino}-1H-indazol-6-yl)spiro[cyclopropane-1,3'-indol]-2'(1'H)-one

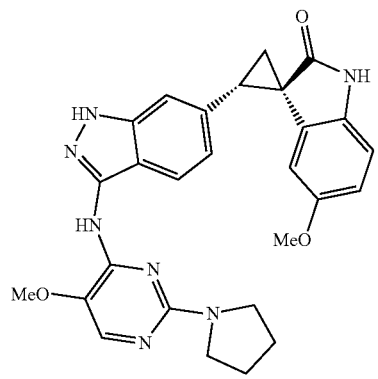 [SMILES: COc1ccc2c(c1)[C@]1(C[C@H]1c1ccc3c(Nc4nc(N5CCCC5)ncc4OC)n[nH]c3c1)C(=O)N2]

Step A.
5-methoxy-2-(pyrrolidin-1-yl)pyrimidin-4-amine

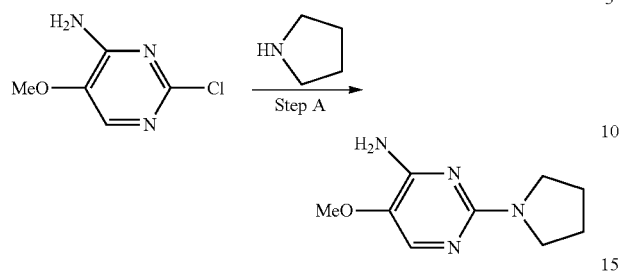

A solution of 2-chloro-5-methoxypyrimidin-4-amine (500 mg, 3.133 mmol, 1 equiv) in pyrrolidine (4.46 g, 62.660 mmol, 20 equiv) in sealed tube was stirred for 4 h at 80° C. The mixture was allowed to cool down to room temperature. The resulting mixture was concentrated under vacuum. The residue was dissolved in DMF (0.5 mL). The residue was purified by reverse flash chromatography with the following conditions: Column: C18 Column, 40 g, 60 Å, 40-60 μm; Mobile Phase A: 10 mM aq. NH$_4$HCO$_3$, Mobile Phase B: MeCN; Flow rate: 60 mL/min; Gradient: 0% B to 0% B in 5 min, 0% B to 50% B in 30 min; Detector: UV 254 & 220 nm. The resulting mixture was concentrated under vacuum. This resulted in the title compound (350 mg, 50.03%) as a white solid. m/z (ESI, +ve ion)=195.10 [M+H]$^+$.

Step B. tert-butyl (1R,2S)-2-(1-(tert-butoxycarbonyl)-3-((5-methoxy-2-(pyrrolidin-1-yl)pyrimidin-4-yl)amino)-1H-indazol-6-yl)-5'-methoxy-2'-oxospiro[cyclopropane-1,3'-indoline]-1'-carboxylate

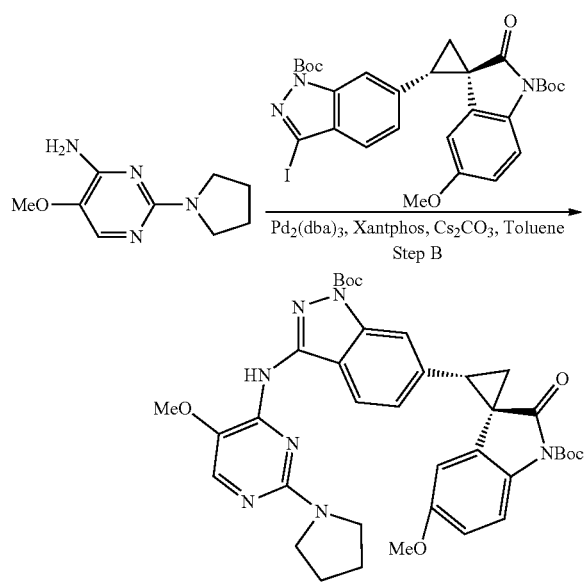

To a stirred mixture of Pd$_2$(dba)$_3$ (34.80 mg, 0.038 mmol, 0.2 equiv) and XantPhos (21.99 mg, 0.038 mmol, 0.2 equiv) in toluene (5 mL) were added Cs$_2$CO$_3$ (123.83 mg, 0.380 mmol, 2 equiv), 5-methoxy-2-(pyrrolidin-1-yl)pyrimidin-4-amine (44.29 mg, 0.228 mmol, 1.20 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (120 mg, 0.190 mmol, 1.00 equiv) at 25° C. The resulting mixture was stirred for additional 2 h at 80° C. under nitrogen atmosphere. The mixture was allowed to cool down to 25° C. The resulting mixture was filtered, the filter cake was washed with DCM (3×10 mL). The filtrate was concentrated under reduced pressure. The residue was purified by Prep-TLC (EA/PE=1/1) to afford the title compound (90 mg, 66.51%) as a grey solid. m/z (ESI, +ve ion)=698.25 [M+H]$^+$.

Step C. (1R,2S)-5'-methoxy-2-(3-{[5-methoxy-2-(pyrrolidin-1-yl)pyrimidin-4-yl]amino}-1H-indazol-6-yl)spiro[cyclopropane-1,3'-indol]-2'(1'H)-one

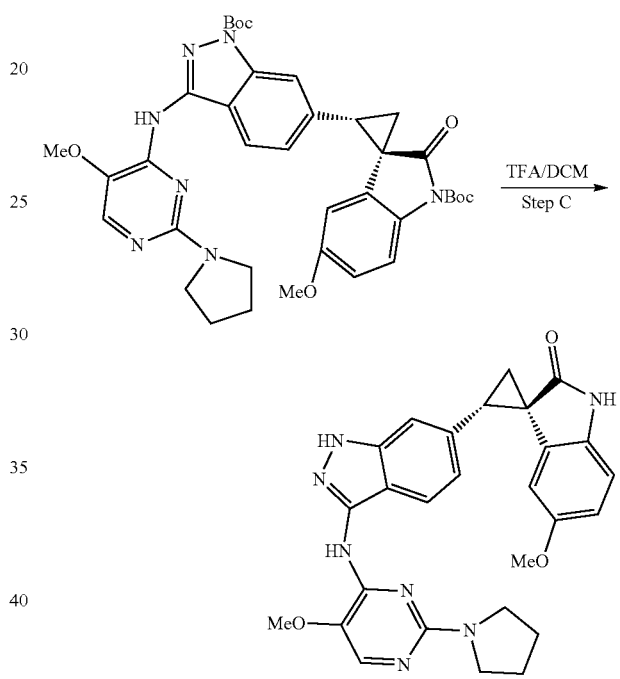

To a stirred solution of tert-butyl 6-{[1-(tert-butoxycarbonyl)-5-methoxy-2-oxo-3H-indol-3-yl]methyl}-3-{[5-methoxy-2-(pyrrolidin-1-yl)pyrimidin-4-yl]amino}indazole-1-carboxylate (90 mg, 0.043 mmol, 1 equiv) in DCM (1 mL) was added TFA (0.2 mL) dropwise at 25° C. under nitrogen atmosphere. The resulting mixture was stirred for 2 h at 25° C. under nitrogen atmosphere. The resulting mixture was diluted with toluene (2 mL). The resulting mixture was concentrated under vacuum. The crude product (80 mg) was purified by Prep-HPLC with the following conditions (Column: XBridge Shield RP18 OBD Column, 30×150 mm, 5 um; Mobile Phase A: Water (10 mmol/L NH$_4$HCO$_3$), Mobile Phase B: ACN; Flow rate: 60 mL/min; Gradient: 30% B to 43% B in 8 min, 43% B: wavelength: 254 nm; RT1(min): 7.3 to afford the title compound (25.5 mg, 39.77%) as a white solid. m/z (ESI, +ve ion)=498.15 [M+H]$^+$. $^1$H NMR (400 MHz, DMSO-d) δ 12.53 (s, 1H), 10.40 (s, 1H), 8.74 (s, 1H), 7.75 (s, 1H), 7.56 (d, J=8.4 Hz, 1H), 7.37 (s, 1H), 6.85 (dd. J=8.5, 1.4 Hz, 1H), 6.75 (d, J=8.4 Hz, 1H), 6.58 (dd, J=8.4, 2.6 Hz, 1H), 5.63 (d, J=2.5 Hz, 1H), 3.78 (s, 3H), 3.29 (s, 3H), 3.19 (t, J=8.4 Hz, 1H), 3.11 (s, 4H), 2.29 (dd. J=7.9, 4.7 Hz, 1H), 1.97 (dd, J=9.0, 4.6 Hz, 1H), 1.68 (s, 4H).

Example 169. (1R,2S)-2-[3-({2-[(3R)-3-fluoropyrrolidin-1-yl]-5-methoxypyrimidin-4-yl}amino)-1H-indazol-6-yl]-5'-methoxyspiro[cyclopropane-1,3'-indol]-2'(1'H)-one

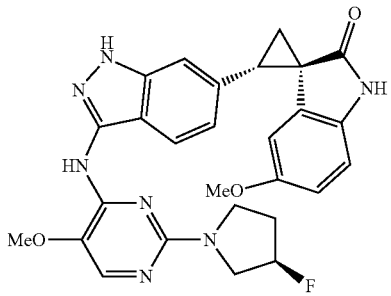 [SMILES: COc1ccc2c(c1)[C@]1(C[C@H]1c1ccc3c(Nc4nc(N5CC[C@@H](F)C5)ncc4OC)n[nH]c3c1)C(=O)N2]

Step A. 2-[(3R)-3-fluoropyrrolidin-1-yl]-5-methoxypyrimidin-4-amine

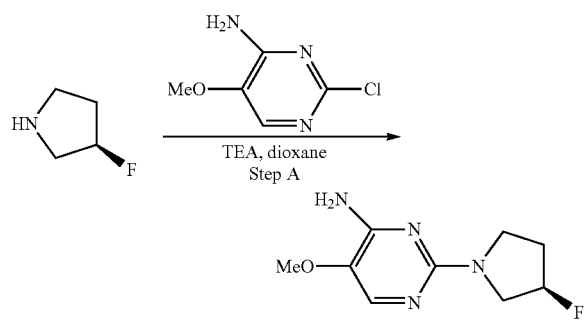

To a stirred mixture of 2-chloro-5-methoxypyrimidin-4-amine (159 mg, 0.996 mmol, 1.00 equiv) and (3R)-3-fluoropyrrolidine (177.59 mg, 1.992 mmol, 2 equiv) in dioxane (0.5 mL) was added TEA (403.33 mg, 3.984 mmol, 4 equiv) dropwise at room temperature under nitrogen atmosphere. The resulting mixture was stirred for 16 h at 100° C. under nitrogen atmosphere. The mixture was allowed to cool down to room temperature and concentrated under reduced pressure. The residue was purified by reverse phase flash with the following conditions (column, C18; mobile phase, water (5 mM in NH₄HCO₃) in MeCN, 2% to 50% gradient in 30 min; detector, UV 254/210 nm.) to afford the title compound (130 mg, 61.47%) as a white solid. m/z (ESI, +ve ion)=213.10 [M+H]⁺.

Step B. tert-butyl (1R,2S)-2-[1-(tert-butoxycarbonyl)-3-({2-[(3R)-3-fluoropyrrolidin-1-yl]-5-methoxypyrimidin-4-yl}amino)indazol-6-yl]-5'-methoxy-2'-oxospiro[cyclopropane-1,3'-indole]-1'-carboxylate

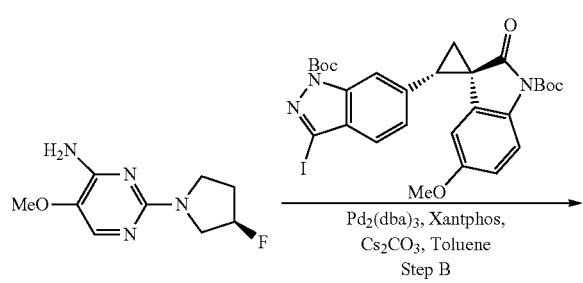

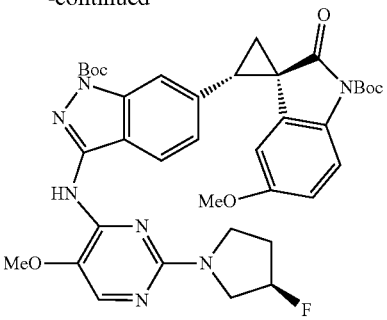

To a stirred solution of tert-butyl (1R,2S)-2-[1-(tert-butoxycarbonyl)-3-iodo-4,5-dihydroindazol-6-yl]-5'-methoxy-2'-oxospiro[cyclopropane-1,3'-indole]-1'-carboxylate (100 mg, 0.158 mmol, 1.00 equiv) and 2-[(3R)-3-fluoropyrrolidin-1-yl]-5-methoxypyrimidin-4-amine (40.20 mg, 0.190 mmol, 1.2 equiv) in toluene (5 mL) were added Cs₂CO₃ (102.87 mg, 0.316 mmol, 2 equiv), XantPhos (18.27 mg, 0.032 mmol, 0.2 equiv) and Pd₂(dba)₃ (28.91 mg, 0.032 mmol, 0.2 equiv) at room temperature. The resulting mixture was stirred for 2 h at 90° C. under nitrogen atmosphere. The mixture was allowed to cool down to room temperature. The resulting mixture was filtered, the filter cake was washed with EtOAc (3×30 mL). The filtrate was concentrated under reduced pressure. The residue was purified by silica gel column chromatography, eluted with PE/EtOAc (1/1) to afford the title compound (102 mg, 90.27%) as a yellow solid. m/z (ESI, +ve ion)=716.20 [M+H]⁺

Step C. (1R,2S)-2-[3-({2-[(3R)-3-fluoropyrrolidin-1-yl]-5-methoxypyrimidin-4-yl}amino)-1H-indazol-6-yl]-5'-methoxyspiro[cyclopropane-1,3'-indol]-2'(1'H)-one

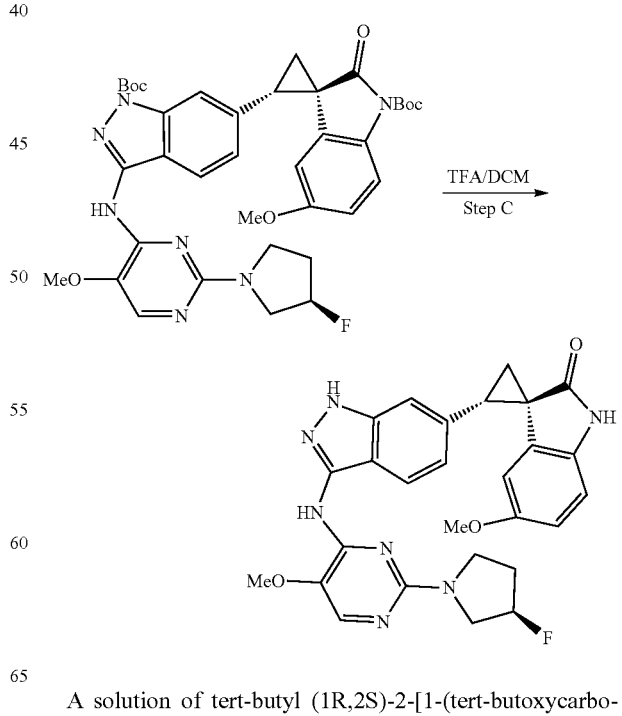

A solution of tert-butyl (1R,2S)-2-[1-(tert-butoxycarbonyl)-3-({2-[(3R)-3-fluoropyrrolidin-1-yl]-5-methoxypyrimidin-4-yl}amino)indazol-6-yl]-5'-methoxy-2'-oxospiro[cyclopropane-1,3'-indole]-1'-carboxylate (92 mg, 0.129 mmol, 1 equiv) in TFA (1 mL) and DCM (5 mL) was stirred at room temperature for 1 h. The resulting mixture was concentrated under reduced pressure. The crude product (110 mg) was purified by Prep-HPLC with the following conditions (Column: XBridge Prep OBD C18 Column, 30×150 mm, 5 µm; Mobile Phase A: Water (10 mmoL/L NH$_4$HCO$_3$), Mobile Phase B: ACN; Flow rate: 60 mL/min; Gradient: 25% B to 35% B in 8 min, 35% B; wavelength: 254 nm; RT1(min): 7) to afford Example 169 (33.2 mg, 50.10%) as a white solid. m/z (ESI, +ve ion)=516.20 [M+H]$^+$. $^1$H NMR (400 MHz, DMSO-d) δ 12.56 (s, 1H), 10.40 (s, 1H), 8.85 (s, 1H), 7.77 (s, 1H), 7.54 (d, J=8.4 Hz, 1H), 7.38 (s, 1H), 6.85 (d, J=8.4 Hz, 1H), 6.75 (d, J=8.4 Hz, 1H), 6.58-6.60 (m, 1H), 5.63 (d, J=2.5 Hz, 1H), 5.16 (d, J=53.9 Hz, 1H), 3.80 (s, 3H), 3.30-3.48 (m, 6H), 3.23-3.05 (m, 2H), 2.29-2.31 (m, 1H), 1.87-1.92 (m, 3H).

Example 170. (1R,2S)-2-(3-{[2-(3,3-difluoropyrrolidin-1-yl)-5-methoxypyrimidin-4-yl]amino}-1H-indazol-6-yl)-5'-methoxyspiro[cyclopropane-1,3'-indol]-2'(1'H)-one

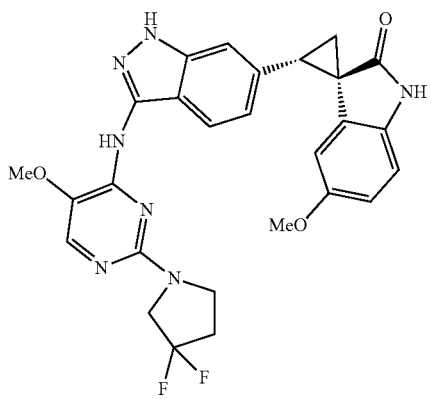 [SMILES: COc1ccc2c(c1)[C@]1(C[C@H]1c1ccc3c(Nc4nc(N5CCC(F)(F)C5)ncc4OC)n[nH]c3c1)C(=O)N2]

Step A. 2-(3,3-difluoropyrrolidin-1-yl)-5-methoxypyrimidin-4-amine

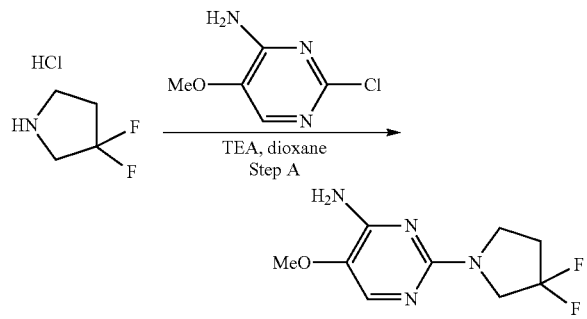

To a stirred mixture of 2-chloro-5-methoxypyrimidin-4-amine (159 mg, 0.996 mmol, 1.00 equiv) and 3,3-difluoropyrrolidine hydrochloride (286.09 mg, 1.992 mmol, 2 equiv) in dioxane (0.5 mL) was added TEA (403.33 mg, 3.984 mmol, 4 equiv) at room temperature under nitrogen atmosphere. The resulting mixture was stirred for 16 h at 100° C. under nitrogen atmosphere. The mixture was allowed to cool down to room temperature and concentrated under reduced pressure. The residue was purified by reverse phase flash with the following conditions (column, C18; mobile phase, water (5 mM NH$_4$HCO$_3$) in MeCN, 2% to 50% gradient in 30 min; detector, UV 254/210 nm.) to afford the title compound (184 mg, 80.21%) as a white solid. m/z (ESI, +ve ion)=231.05 [M+H]$^+$.

Step B. tert-butyl (1R,2S)-2-[1-(tert-butoxycarbonyl)-3-{[2-(3,3-difluoropyrrolidin-1-yl)-5-methoxypyrimidin-4-yl]amino}indazol-6-yl]-5'-methoxy-2'-oxospiro[cyclopropane-1,3'-indole]-1'-carboxylate

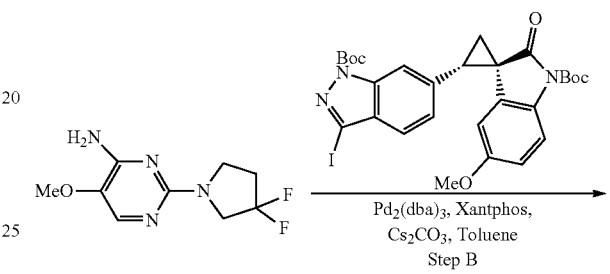

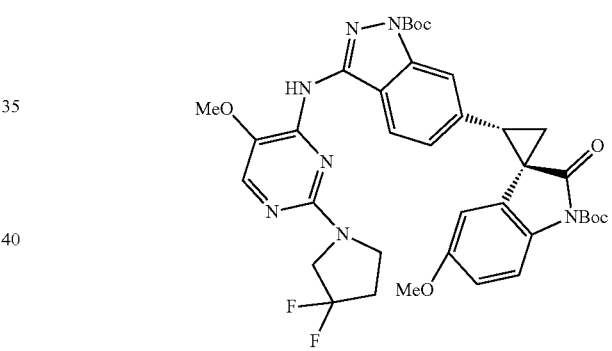

To a stirred solution of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and 2-(3,3-difluoropyrrolidin-1-yl)-5-methoxypyrimidin-4-amine (43.75 mg, 0.190 mmol, 1.2 equiv) in toluene (5 mL) were added Cs$_2$CO$_3$ (103.19 mg, 0.316 mmol, 2 equiv), XantPhos (18.33 mg, 0.032 mmol, 0.2 equiv) and Pd(dba)$_3$ (29.00 mg, 0.032 mmol, 0.2 equiv) at room temperature under nitrogen atmosphere. The resulting mixture was stirred for 2 h at 90° C. under nitrogen atmosphere. The mixture was allowed to cool down to room temperature. The resulting mixture was filtered, the filter cake was washed with EA (3×30 mL). The filtrate was concentrated under reduced pressure. The residue was purified by silica gel column chromatography, eluted with PE/EA (1/1) to afford the title compound (130 mg, 78.31%) as a yellow solid. m/z (ESI, +ve ion)=734.25 [M+H]$^+$.

559

Step C. (1R,2S)-2-(3-{[2-(3,3-difluoropyrrolidin-1-yl)-5-methoxypyrimidin-4-yl]amino}-1H-indazol-6-yl)-5'-methoxyspiro[cyclopropane-1,3'-indol]-2'(1'H)-one

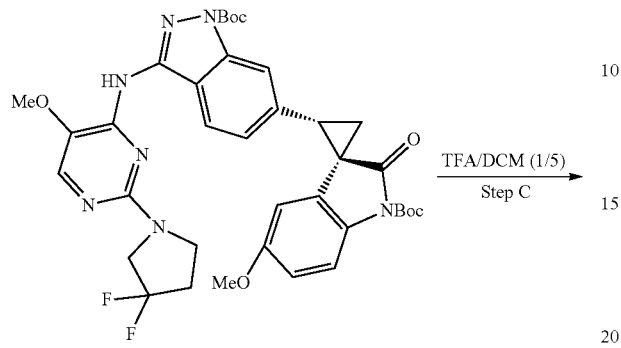

A solution of tert-butyl (1R,2S)-2-[1-(tert-butoxycarbonyl)-3-{[2-(3,3-difluoropyrrolidin-1-yl)-5-methoxypyrimidin-4-yl]amino}indazol-6-yl]-5'-methoxy-2'-oxospiro[cyclopropane-1,3'-indole]-1'-carboxylate (120 mg, 0.114 mmol, 1 equiv, 70%) in TFA (1 mL) and DCM (5 mL) was stirred for 1 h at room temperature. The resulting mixture was concentrated under reduced pressure. The crude product (130 mg) was purified by Prep-HPLC with the following conditions (Column: XBridge Shield RP18 OBD Column, 30×150 mm, 5 μm; Mobile Phase A: Water (10 mmol/L NH$_4$HCO), Mobile Phase B: ACN; Flow rate: 60 mL/min; Gradient: 32% B to 45% B in 8 min, 45% B; wavelength: 254 nm; RT1(min): 7.2) to afford the title compound (38.3 mg, 62.71%) as a white solid. m/z (ESI, +ve ion)=534.30 [M+H]$^+$. $^1$H NMR (400 MHz, DMSO-d$_6$) δ 12.59 (s, 1H), 10.41 (s, 1H), 8.97 (s, 1H), 7.79 (s, 1H), 7.53 (d, J=8.4 Hz, 1H), 7.38 (s, 1H), 6.87 (d, J=8.8 Hz, 1H), 6.75 (d, J=8.4 Hz, 1H), 6.57-6.60 (m, 1H), 5.62 (d, J=2.5 Hz, 1H), 3.81 (s, 3H), 3.57 (t, J=13.4 Hz, 2H), 3.32-3.30 (m, 5H), 3.20 (t, J=8.4 Hz, 1H), 2.33-2.17 (m, 3H), 1.96-2.00 (m, 1H).

560

Example 173. (1R,2S)-2-(3-{[2-(3,3-difluoroazetidin-1-yl)-5-methoxypyrimidin-4-yl]amino}-1H-indazol-6-yl)-5'-methoxyspiro[cyclopropane-1,3'-indol]-2'(1'H)-one

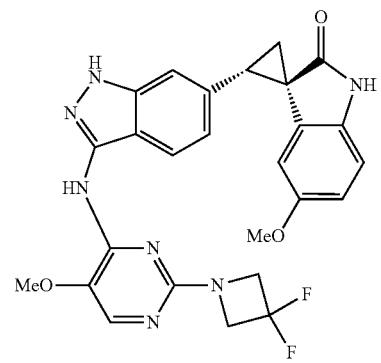 [SMILES: COc1ccc2c(c1)[C@]1(C[C@H]1c1ccc3c(Nc4nc(N5CC(F)(F)C5)ncc4OC)n[nH]c3c1)C(=O)N2]

Step A. 2-(3,3-difluoroazetidin-1-yl)-5-methoxypyrimidin-4-amine

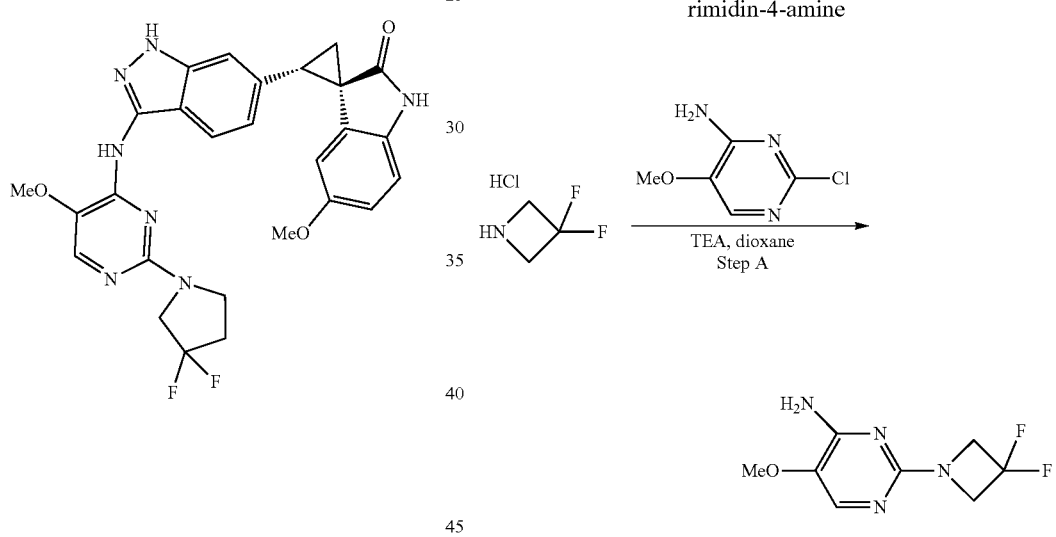

To a stirred mixture of 3,3-difluoroazetidine hydrochloride (258.13 mg, 1.992 mmol, 2 equiv) and 2-chloro-5-methoxypyrimidin-4-amine (159 mg, 0.996 mmol, 1.00 equiv) in dioxane (1 mL) was added TEA (604.99 mg, 5.976 mmol, 6 equiv) under nitrogen atmosphere. The resulting mixture was stirred for 16 h at 25° C. under nitrogen atmosphere. The resulting mixture was concentrated under vacuum. The resulting mixture was extracted with EA (3×30 mL). The combined organic layers were washed with brine (3×10 mL), dried over anhydrous sodium sulfate. After filtration, the filtrate was concentrated under reduced pressure. The residue was purified by silica gel column chromatography, eluted with EA/PE (1/2) to afford the title compound (100 mg, 46.42%) as a grey solid. m/z (ESI, +ve ion)=217.10 [M+H]$^+$.

Step B. tert-butyl (1R,2S)-2-[1-(tert-butoxycarbonyl)-3-{[2-(3,3-difluoroazetidin-1-yl)-5-methoxypyrimidin-4-yl]amino}indazol-6-yl]-5'-methoxy-2'-oxospiro[cyclopropane-1,3'-indole]-1'-carboxylate

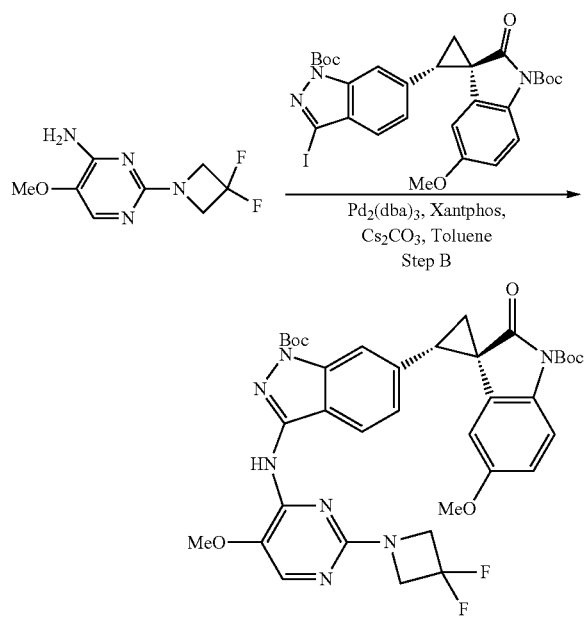

To a stirred solution of 2-(3,3-difluoroazetidin-1-yl)-5-methoxypyrimidin-4-amine (41.08 mg, 0.190 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) in toluene (5.0 mL) were added XantPhos (18.33 mg, 0.032 mmol, 0.2 equiv), $Cs_2CO_3$ (103.19 mg, 0.316 mmol, 2 equiv) and $Pd_2(dba)_3$ (29.00 mg, 0.032 mmol, 0.2 equiv) at room temperature under nitrogen atmosphere. The resulting mixture was stirred for 2 h at 90° C. under nitrogen atmosphere. The mixture was allowed to cool down to room temperature. The resulting mixture was filtered. The filtrate was concentrated under reduced pressure. The residue was purified by silica gel column chromatography, eluted with PE/EA (1/1) to afford the title compound (78 mg, 68.43%) as a yellow oil. m/z (ESI, +ve ion)=720.20 [M+H]$^+$.

Step C. (1R,2S)-2-(3-{[2-(3,3-difluoroazetidin-1-yl)-5-methoxypyrimidin-4-yl]amino}-1H-indazol-6-yl)-5'-methoxyspiro[cyclopropane-1,3'-indol]-2'(1'H)-one

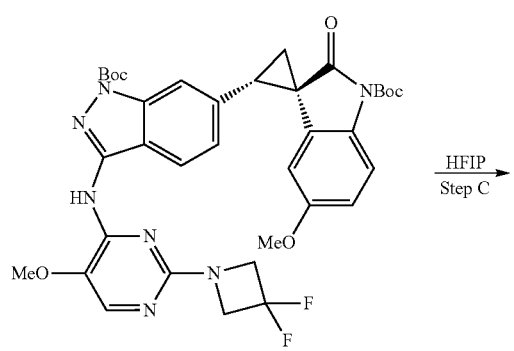

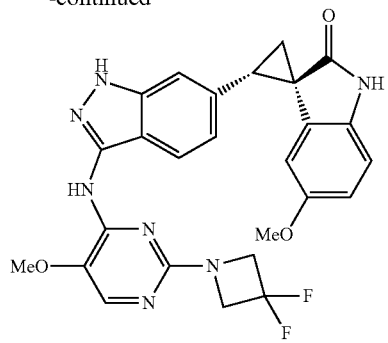

The mixture of tert-butyl (1R,2S)-2-[1-(tert-butoxycarbonyl)-3-{[2-(3,3-difluoroazetidin-1-yl)-5-methoxypyrimidin-4-yl]amino}indazol-6-yl]-5'-methoxy-2'-oxospiro[cyclopropane-1,3'-indole]-1'-carboxylate (78 mg, 0.106 mmol, 1 equiv) in HFIP (5 mL) was stirred at 60° C. for 12 h. The solvent was removed in vacuo. The residue was purified by Prep-HPLC with the following conditions: Column: XBridge Shield RP18 OBD Column, 19×250 mm, 10 μm; Mobile Phase A: Water (10 mmol/L $NH_4HCO_3$), Mobile Phase B: ACN; Flow rate: 25 mL/min; Gradient: 35% B to 50% B in 8 min, 50% B; wavelength: 254 nm; RT1(min): 7.8 to afford Example 173 (27.6 mg, 50.13%) as a white solid. m/z (ESI, +ve ion)=520.30 [M+H]$^+$. $^1$H NMR (400 MHz, Methanol-$d_4$) δ 7.69 (s, 1H), 7.59 (d, J=8.8 Hz, 1H), 7.47 (s, 1H), 6.88-6.83 (m, 2H), 6.63-6.61 (m, 1H), 5.60 (s, 1H), 4.12-3.94 (m, 4H), 3.75 (s, 3H), 3.51-3.49 (m, 1H), 3.39-3.13 (m, 3H), 2.29-2.25 (m, 11H), 2.21-2.17 (m, 1H).

Example 174. (1R,2S)-2-(3-{[2-(3-fluoroazetidin-1-yl)-5-methoxypyrimidin-4-yl]amino}-1H-indazol-6-yl)-5'-methoxyspiro[cyclopropane-1,3'-indol]-2'(1'H)-one

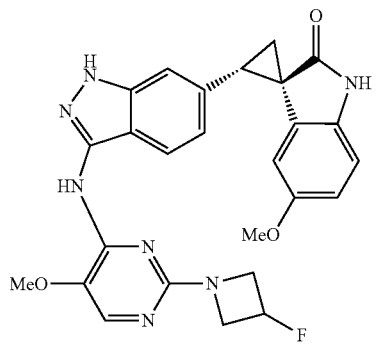 [SMILES: COc1ccc2c(c1)[C@]1(C[C@H]1c1ccc3c(Nc4nc(N5CC(F)C5)ncc4OC)n[nH]c3c1)C(=O)N2]

Step A. 2-(3-fluoroazetidin-1-yl)-5-methoxypyrimidin-4-amine

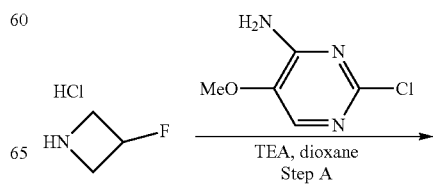

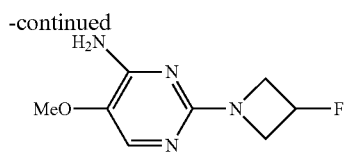

To a stirred mixture of 3-fluoroazetidine hydrochloride (223.68 mg, 2.006 mmol, 2 equiv) and 2-chloro-5-methoxypyrimidin-4-amine (160 mg, 1.003 mmol, 1.00 equiv) in dioxane (1 mL) was added TEA (608.79 mg, 6.018 mmol, 6 equiv) under nitrogen atmosphere. The resulting mixture was stirred for 16 h at 100° C. The resulting mixture was cool down to room temperature and then concentrated under vacuum. The resulting mixture was extracted with EA (3×30 mL). The combined organic layers were washed with brine (3×10 mL), dried over anhydrous sodium sulfate. After filtration, the filtrate was concentrated under reduced pressure. The residue was purified by silica gel column chromatography, eluted with EA/PE (1/2) to afford the title compound (110 mg, 50.92%) as a grey solid. m/z (ESI, +ve ion)=199.10 [M+H]$^+$.

Step B. tert-butyl (1R,2S)-2-[1-(tert-butoxycarbonyl)-3-{[2-(3-fluoroazetidin-1-yl)-5-methoxypyrimidin-4-yl]amino}indazol-6-yl]-5'-methoxy-2'-oxospiro[cyclopropane-1,3'-indole]-1'-carboxylate

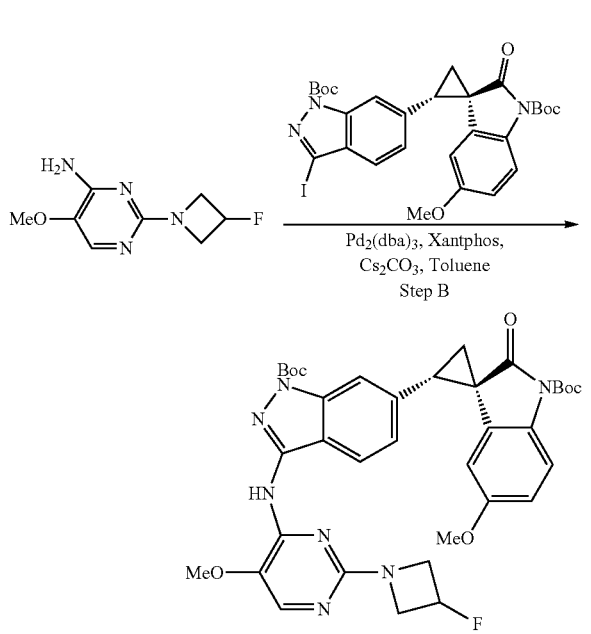

To a stirred solution of 2-(3-fluoroazetidin-1-yl)-5-methoxypyrimidin-4-amine (31.39 mg, 0.158 mmol, 1 equiv) and tert-butyl (1R,2S)-2-[1-(tert-butoxycarbonyl)-3-iodoindazol-6-yl]-5'-methoxy-2'-oxospiro[cyclopropane-1, 3'-indole]-1'-carboxylate (100 mg, 0.158 mmol, 1.00 equiv) in toluene (5.0 mL) were added XantPhos (18.33 mg, 0.032 mmol, 0.2 equiv), Cs$_2$CO$_3$ (103.19 mg, 0.316 mmol, 2 equiv) and Pd$_2$(dba)$_3$ (29.00 mg, 0.032 mmol, 0.2 equiv) at room temperature under nitrogen atmosphere. The resulting mixture was stirred for 2 h at 90° C. under nitrogen atmosphere. The mixture was allowed to cool down to room temperature. The resulting mixture was concentrated under reduced pressure. The residue was purified by silica gel column chromatography, eluted with PE/EA (1/1) to afford the title compound (72.0 mg, 64.79%) as a yellow oil. m/z (ESI, +ve ion)=702.20 [M+H]$^+$.

Step C. (1R,2S)-2-(3-{[2-(3-fluoroazetidin-1-yl)-5-methoxypyrimidin-4-yl]amino}-1H-indazol-6-yl)-5'-methoxyspiro[cyclopropane-1,3'-indol]-2'(1'H)-one

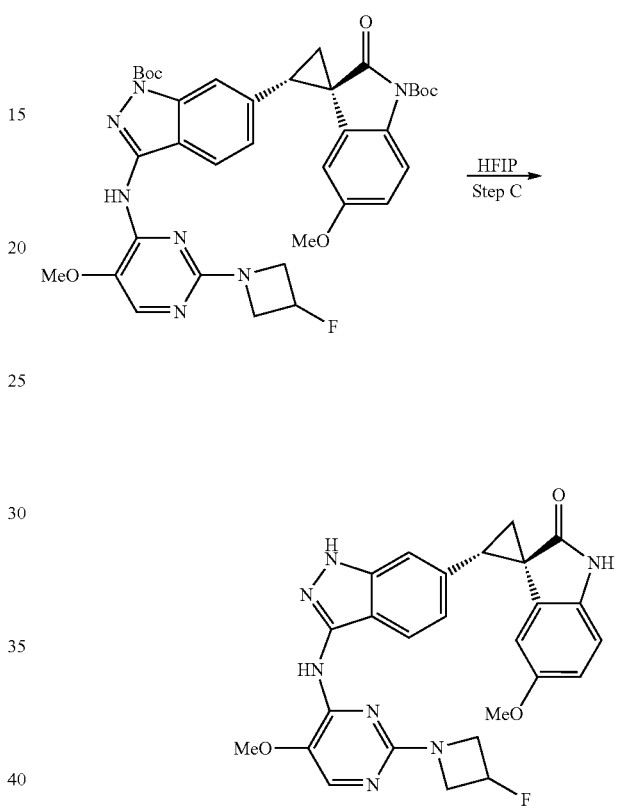

The mixture of tert-butyl (1R,2S)-2-[1-(tert-butoxycarbonyl)-3-{[2-(3-fluoroazetidin-1-yl)-5-methoxypyrimidin-4-yl]amino}indazol-6-yl]-5'-methoxy-2'-oxospiro[cyclopropane-1,3'-indole]-1'-carboxylate (72 mg, 0.104 mmol, 1 equiv) in HFIP (5 mL) was stirred at 60° C. for 12 h. The solvent was removed in vacuo. The residue was purified by Prep-HPLC with the following conditions: Column: XBridge Shield RP18 OBD Column, 19×250 mm, 10 μm; Mobile Phase A: Water (10 mmol/L NH$_4$HCO$_3$), Mobile Phase B: ACN; Flow rate: 25 mL/min; Gradient: 35% B to 50% B in 8 min, 50% B; wavelength: 254 nm; RT1(min): 7.8 to afford Example 174 (22 mg, 42.00%) as a white solid. m/z (ESI, +ve ion)=502.30 [M+H]$^+$. $^1$H NMR (400 MHz, Methanol-d$_4$) δ 7.64 (d, J=8.8 Hz, 2H), 7.45 (s, 1H), 6.87-6.83 (m, 2H), 6.64-6.61 (m, 1H), 5.61 (d, J=2.4 Hz, 1H), 5.27-5.11 (m, 1H), 4.08-3.95 (m, 2H), 3.92 (s, 3H), 3.85-3.73 (m, 2H), 3.39-3.37 (m, 1H), 3.34 (s, 3H), 2.28-2.25 (m, 1H), 2.21-2.17 (m, 1H).

Example 183: (1R,2S)-5'-methoxy-2-(3-{[2-methoxy-6-(morpholine-4-carbonyl)pyridin-3-yl]amino}-1H-indazol-6-yl)spiro[cyclopropane-1,3'-indol]-2'(1'H)-one

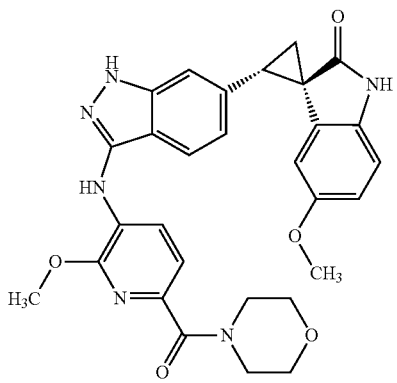 [SMILES: COc1ccc2c(c1)[C@]1(C[C@H]1c1ccc3c(Nc4ccc(C(=O)N5CCOCC5)nc4OC)n[nH]c3c1)C(=O)N2]

Step A:
(6-methoxy-5-nitro-2-pyridyl)-morpholino-methanone

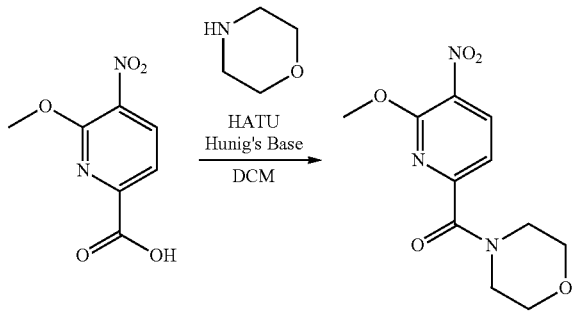 [SMILES: COc1nc(C(=O)O)ccc1[N+](=O)[O-] ; C1COCCN1 ; COc1nc(C(=O)N2CCOCC2)ccc1[N+](=O)[O-]]

To a solution of 6-methoxy-5-nitro-2-pyridinecarboxylic acid (100 mg, 0.5 mmol) and HATU (230 mg, 0.61 mmol) in DCM (3 mL) was added morpholine (0.07 mL, 0.76 mmol) and N,N-diisopropylethylamine (0.22 mL, 1.26 mmol) and the reaction mixture was stirred at room temperature for 16 h. The reaction mixture was quenched by the addition of saturated, aq. sodium bicarbonate and extracted with DCM (3×). The combined organic layers were dried over sodium sulfate, filtered and the filtrate was concentrated in vacuo. The crude residue was purified by column chromatography (0-100% EA in hexanes) to afford the product as a yellow solid (134 mg, 99%). m/z (ESI, +ve ion)=268.1 [M+H]+.

Step B:
(5-amino-6-methoxy-2-pyridyl)-morpholino-methanone

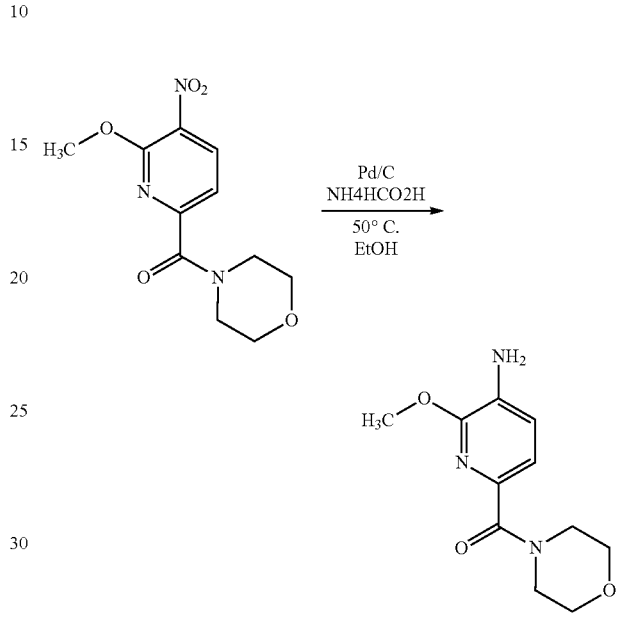

To a solution of (6-methoxy-5-nitro-2-pyridyl)-morpholino-methanone (134 mg, 0.50 mmol) and ammonium formate (316 mg, 5.0 mmol) in ethanol (3.3 mL) under argon was added 10% palladium on carbon (107 mg, 0.1 mmol) and the reaction mixture was heated to 50° C. for 16 h. The reaction mixture was filtered through celite and concentrated in vacuo to give the desired product as a white foam (118 mg, 99%). m/z (ESI, +ve ion)=238.1 [M+H]+.

Step C: tert-butyl (1R,2S)-2-[1-tert-butoxycarbonyl-3-[[2-methoxy-6-(morpholine-4-carbonyl)-3-pyridyl]amino]indazol-6-yl]-5'-methoxy-2'-oxo-spiro[cyclopropane-1,3'-indoline]-1'-carboxylate

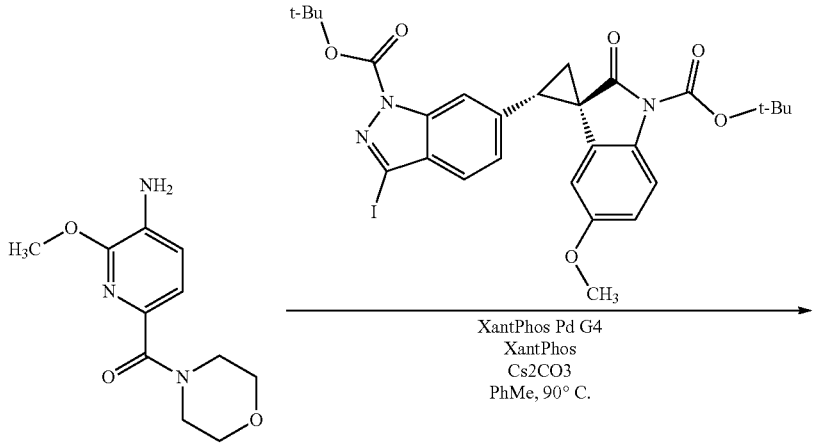

-continued

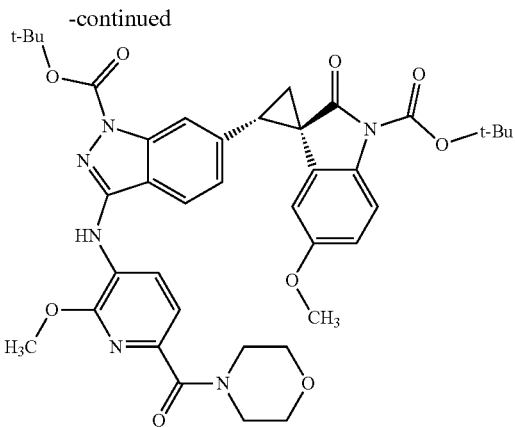

To a solution of (5-amino-6-methoxy-2-pyridyl)-morpholino-methanone (41 mg, 0.17 mmol) in dry toluene (1.6 mL) was added tert-butyl (1R,2S)-2-(1-tert-butoxycarbonyl-3-iodo-indazol-6-yl)-5'-methoxy-2'-oxo-spiro[cyclopropane-1,3'-indoline]-1'-carboxylate (100 mg, 0.16 mmol), Xantphos Pd G4 (15 mg, 0.02 mmol), Xantphos (9.2 mg, 0.02 mmol), and cesium carbonate (155 mg, 0.48 mmol). Argon was bubbled through the solution for 3 min then the reaction mixture was heated to 90° C. for 75 min. The reaction mixture was diluted with DCM, filtered through celite, eluting with DCM and the filtrate was concentrated in vacuo. The crude residue was purified by column chromatography (0-100% hexanes in acetone) to afford the product as a yellow foam (83.5 mg, 71%). m/z (ESI, +ve ion)=741.2 [M+H]+.

Step D: (1R,2S)-5'-methoxy-2-(3-{[2-methoxy-6-(morpholine-4-carbonyl)pyridin-3-yl]amino}-1H-indazol-6-yl)spiro[cyclopropane-1,3'-indol]-2'(1'H)-one

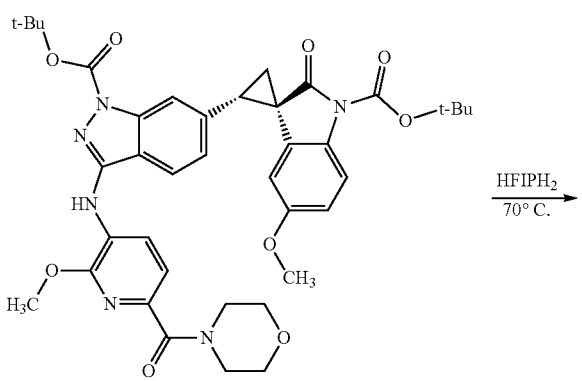

-continued

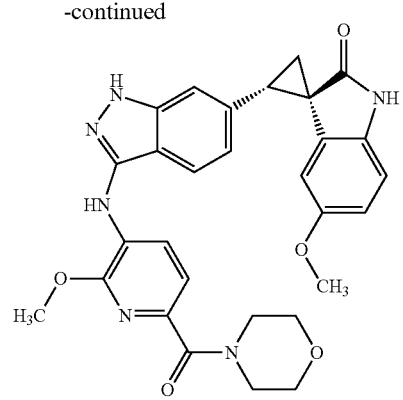

A solution of tert-butyl (1R,2S)-2-[1-tert-butoxycarbonyl-3-[[2-methoxy-6-(morpholine-4-carbonyl)-3-pyridyl]amino]indazol-6-yl]-5'-methoxy-2'-oxo-spiro[cyclopropane-1,3'-indoline]-1'-carboxylate (83.5 mg, 0.11 mmol) in hexafluoroisopropanol (3 mL) was heated to 70° C. for 16 h. The reaction mixture was concentrated in vacuo and the crude residue was purified by RP-HPLC using 10-70% ACN/water (10 mmol/L ammonium bicarbonate) to give the title compound as a white lyophilized solid (40.7 mg, 67%). m/z (ESI, +ve ion)=541.3 [M+H]+. 1H NMR (400 MHz, DMSO) δ 12.31 (s, 1H), 10.44 (s, 1H), 8.51-8.34 (m, 2H), 7.99-7.87 (m, 1H), 7.43-7.26 (m, 2H), 6.98-6.85 (m, 1H), 6.82-6.69 (m, 1H), 6.65-6.52 (m, 1H), 5.70 (s, 1H), 3.99 (s, 3H), 3.82-3.58 (m, 8H), 3.32 (s, 3H), 3.25-3.13 (m, 1H), 2.41-2.27 (m, 1H), 2.05-1.92 (m, 1H).

Example 185: (1R,2S)-2-(3-{[6-(4,4-difluoropiperi-dine-1-carbonyl)-2-methoxypyridin-3-yl]amino}-1H-indazol-6-yl)-5'-methoxyspiro[cyclopropane-1,3'-indol]-2'(1'H)-one

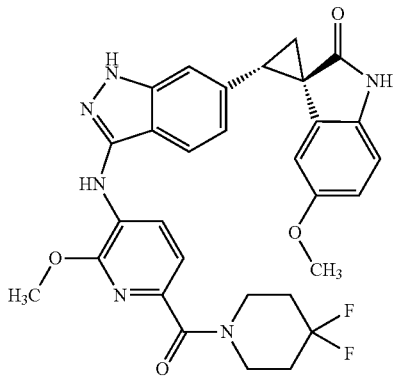 [SMILES: COc1ccc2c(c1)[C@]1(C[C@H]1c1ccc3c(Nc4ccc(C(=O)N5CCC(F)(F)CC5)nc4OC)n[nH]c3c1)C(=O)N2]

The title compound was prepared using the procedure for Example 183 starting from 6-methoxy-5-nitro-2-pyridinecarboxylic acid and 4,4-difluoropiperidine hydrochloride. m/z (ESI, +ve ion)=575.2 [M+H]⁺. 1H NMR (400 MHz, DMSO) δ 12.32 (s, 1H), 10.44 (d, J=3.4 Hz, 1H), 8.50-8.37 (m, 2H), 7.99-7.86 (m, 1H), 7.41-7.30 (m, 2H), 6.96-6.87 (m, 1H), 6.81-6.70 (m, 1H), 6.64-6.55 (m, 1H), 5.71 (s, 1H), 4.01 (s, 3H), 3.92-3.66 (m, 4H), 3.32 (s, 3H), 3.24-3.12 (m, 1H), 2.40-2.30 (m, 1H), 2.22-2.02 (m, 4H), 2.02-1.93 (m, 1H).

Example 189. (1R,2S)-2-(3-{[2-(4,4-difluoropiperidin-1-yl)-5-methoxypyrimidin-4-yl]amino}-1H-indazol-6-yl)-5'-methoxyspiro[cyclopropane-1,3'-indol]-2'(1'H)-one

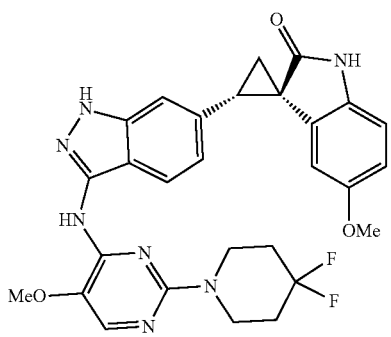 [SMILES: COc1ccc2c(c1)[C@]1(C[C@H]1c1ccc3c(Nc4nc(N5CCC(F)(F)CC5)ncc4OC)n[nH]c3c1)C(=O)N2]

Step A. 2-(4,4-difluoropiperidin-1-yl)-5-methoxypyrimidin-4-amine

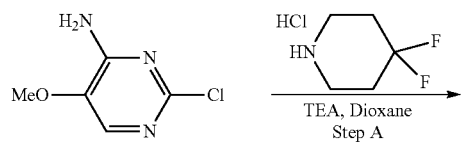

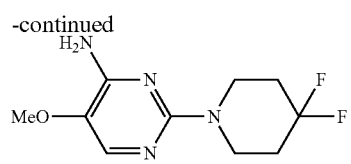

To a stirred solution of 2-chloro-5-methoxypyrimidin-4-amine (159 mg, 0.996 mmol, 1 equiv) in dioxane (0.5 mL) was added TEA (0.83 mL, 5.976 mmol, 6 equiv) and 4,4-difluoropiperidine hydrochloride (314.05 mg, 1.992 mmol, 2 equiv) under nitrogen atmosphere. The resulting mixture was stirred for 16 hours at 100° C. The reaction was quenched by the addition of water (5 mL) at 25° C. The resulting mixture was extracted with DCM (3×5 mL). The combined organic layers were washed with brine (3×5 mL), dried over anhydrous Na₂SO₄. After filtration, the filtrate was concentrated under reduced pressure. The residue was purified by Prep-TLC (DCM/MeOH=10/1) to afford the title compound (116 mg, 47.66%) as white solid. m/z (ESI, +ve ion)=245.10 [M+H]⁺.

Step B. tert-butyl (1R,2S)-2-(1-tert-butoxycarbonyl)-3-((2-(4,4-difluoropiperidin-1-yl)-5-methoxypyrimidin-4-yl)amino)-1H-indazol-6-yl)-5'-methoxy-2'-oxospiro[cyclopropane-1,3'-indoline]-1'-carboxylate

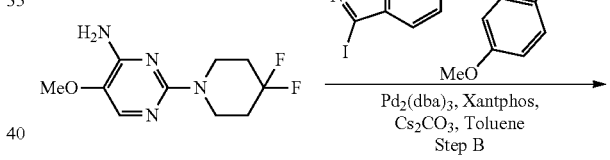

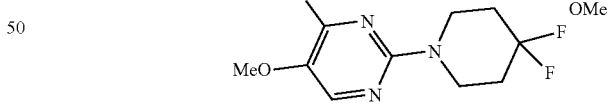

To a stirred solution of 2-(4,4-difluoropiperidin-1-yl)-5-methoxypyrimidin-4-amine (46.41 mg, 0.190 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) in toluene (1 mL) were added Pd₂(dba)₃ (14.50 mg, 0.016 mmol, 0.1 equiv), XantPhos (9.16 mg, 0.016 mmol, 0.1 equiv) and Cs₂CO₃ (103.19 mg, 0.316 mmol, 2 equiv) under nitrogen atmosphere. The final reaction mixture was reacted for 2 hours at 90° C. The reaction was quenched by the addition of water (10 mL) at 25° C. The resulting mixture was extracted with DCM (3×10 mL). The combined organic layers were washed with brine (3×10 mL), dried over anhydrous Na₂SO₄. After filtration, the filtrate was concentrated under reduced pressure. The residue was purified by Prep-TLC (EtOAc/PE=1/1) to afford the title compound (77 mg, 65.02%) as a yellow solid. m/z (ESI, +ve ion)=748.30 [M+H]⁺.

Step C. (1R,2S)-2-(3-{[2-(4,4-difluoropiperidin-1-yl)-5-methoxypyrimidin-4-yl]amino}-1H-indazol-6-yl)-5'-methoxyspiro[cyclopropane-1,3'-indol]-2'(1'H)-one

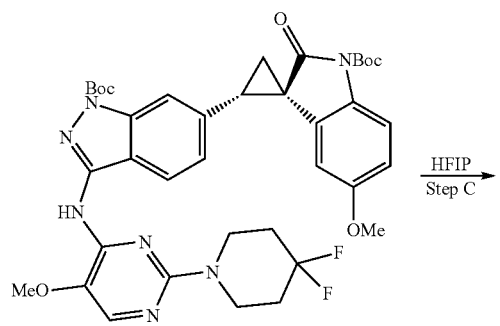

A solution of tert-butyl (1R,2S)-2-[1-(tert-butoxycarbonyl)-3-{[2-(4,4-difluoropiperidin-1-yl)-5-methoxypyrimidin-4-yl]amino}indazol-6-yl]-5'-methoxy-2'-oxospiro[cyclopropane-1,3'-indole]-1'-carboxylate (77 mg, 0.103 mmol, 1 equiv) in HFIP (2 mL) was stirred for 16 hours at 60° C. The resulting mixture was concentrated under reduced pressure. The crude product (55.8 mg) was purified by Prep-HPLC with the following conditions (Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 31% B to 41% B in 8 min, 41% B; wavelength: 254 nm; RT1(min): 7) to afford the title compound (11.2 mg, 19.86%) as a white solid. m/z (ESI, +ve ion)=548.10 [M+H]⁺. ¹H-NMR (400 MHz, DMSO-d₆) δ 12.60 (s, 1H), 10.40 (s, 1H), 9.01 (s, 1H), 7.77 (s, 1H), 7.44-7.43 (d, J=4 Hz, 2H), 6.81-6.74 (m, 2H), 6.59-6.56 (m, 1H), 5.63 (d, J=4 Hz, 1H), 3.81 (s, 3H), 3.44-3.37 (m, 4H), 3.34 (s, 3H), 3.20 (t, J=8 Hz, 1H), 2.33-2.30 (m, 1H), 1.99-1.96 (m, 1H), 1.72-1.68 (m, 2H), 1.53-1.50 (m, 2H).

Example 193. (1R,2S)-2-(3-{[5-(methanesulfonyl)-3-methoxypyridin-2-yl]amino}-1H-indazol-6-yl)-5'-methoxyspiro[cyclopropane-1,3'-indol]-2'(1'H)-one

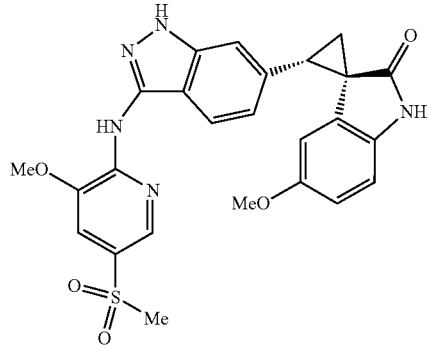 [SMILES: COc1ccc2c(c1)[C@]1(C[C@H]1c1ccc3c(Nc4ncc(S(C)(=O)=O)cc4OC)n[nH]c3c1)C(=O)N2]

Step A.
3-methoxy-5-(methylsulfonyl)pyridin-2-amine

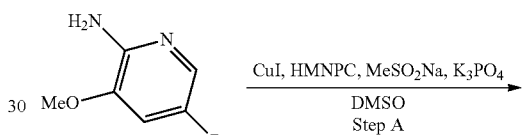

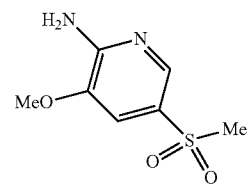

To a stirred solution of 5-bromo-3-methoxypyridin-2-amine (203 mg, 1.000 mmol, 1 equiv) and (2S,4R)-4-hydroxy-N-(2-methylnaphthalen-1-yl)pyrrolidine-2-carboxamide (HMNPC, 27.03 mg, 0.100 mmol, 0.1 equiv) in DMSO (3 mL) were added CuI (19.04 mg, 0.100 mmol, 0.1 equiv), sodium methanesulfinate (132.69 mg, 1.300 mmol, 1.3 equiv) and K₃PO₄ (212.22 mg, 1.000 mmol, 1 equiv) at 25° C. under nitrogen atmosphere. The resulting mixture was stirred for additional 24 h at 120° C. The mixture was allowed to cool down to 25° C. The residue was purified by reverse flash chromatography with the following conditions: column, C18 Column; mobile phase, water (5 mM NH₄HCO₃) in ACN, 20% to 60% gradient in 30 min; detector, UV 254 nm. The resulting mixture was concentrated under reduced pressure to afford the title compound (198.4 mg, 98.12%) as a yellow solid. m/z (ESI, +ve ion)=203.10 [M+H]⁺.

Step B. tert-butyl (1R,2S)-2-[1-(tert-butoxycarbonyl)-3-[(5-methanesulfonyl-3-methoxypyridin-2-yl)amino]indazol-6-yl]-5'-methoxy-2'-oxospiro[cyclopropane-1,3'-indole]-1'-carboxylate

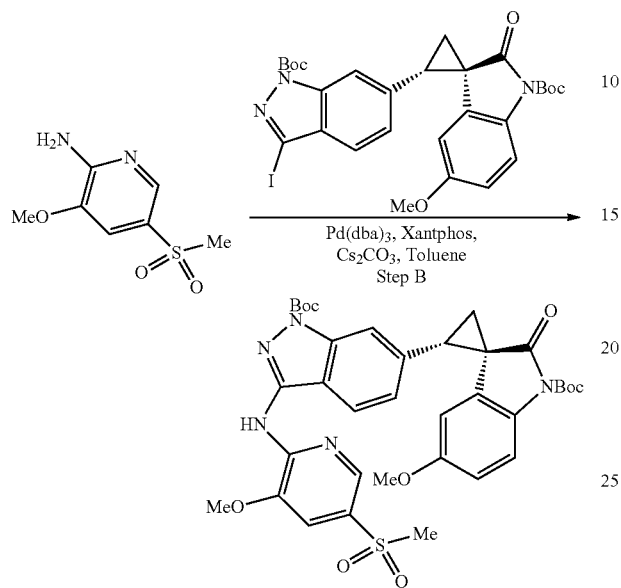

To a stirred solution of 5-methanesulfonyl-3-methoxypyridin-2-amine (38.43 mg, 0.190 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) in toluene (3 mL) were added $Pd_2(dba)_3$ (14.50 mg, 0.016 mmol, 0.1 equiv), XantPhos (9.16 mg, 0.016 mmol, 0.1 equiv) and $Cs_2CO_3$ (103.19 mg, 0.316 mmol, 2 equiv) under nitrogen atmosphere. The final reaction mixture was stirred at 90° C. for 2 hours. The mixture was allowed to cool down to 25° C. The reaction was quenched by the addition of water (10 mL) at 25° C. The resulting mixture was extracted with DCM (3×10 mL). The combined organic layers were washed with brine (3×10 mL), dried over anhydrous $Na_2SO_4$. After filtration, the filtrate was concentrated under reduced pressure. The residue was purified by Prep-TLC (EA/PE=1/1) to afford the title compound (108.6 mg, 97.17%) as a yellow solid. m/z (ESI, +ve ion)=706.10 [M+H]$^+$.

Step C. (1R,2S)-2-(3-{[5-(methanesulfonyl)-3-methoxypyridin-2-yl]amino}-1H-indazol-6-yl)-5'-methoxyspiro[cyclopropane-1,3'-indol]-2'(1'H)-one

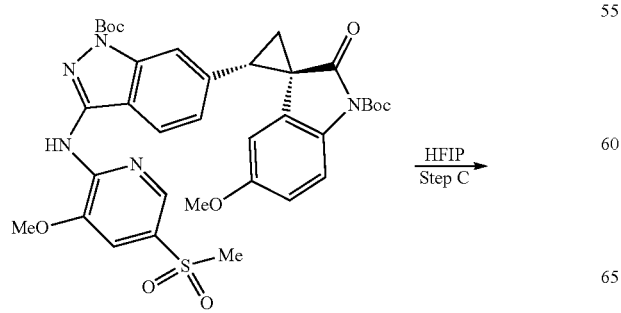

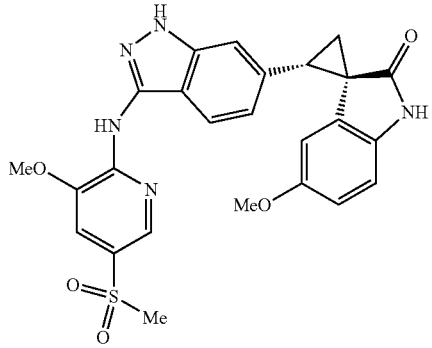

A solution of tert-butyl (1R,2S)-2-[1-(tert-butoxycarbonyl)-3-[(5-methanesulfonyl-3-methoxypyridin-2-yl)amino]indazol-6-yl]-5'-methoxy-2'-oxospiro[cyclopropane-1,3'-indole]-1'-carboxylate (130 mg, 0.184 mmol, 1 equiv) in HFIP (2 mL, 18.996 mmol) was stirred for 16 hours at 60° C. The resulting mixture was concentrated under reduced pressure. The crude product (96.8 mg) was purified by Prep-HPLC with the following conditions (Column: XBridge Prep Phenyl OBD Column, 19×250 mm, 5 μm; Mobile Phase A: Water (10 mmol/L $NH_4HCO_3$), Mobile Phase B: ACN; Flow rate: 25 mL/min; Gradient: 35% B to 40% B in 10 min, 40% B; wavelength: 254 nm; RT1(min): 9) to afford the title compound (25.7 mg, 27.60%) as a white solid. m/z (ESI, +ve ion)=506.20 [M+H]$^+$. $^1$H-NMR (4 (0) MHz, DMSO-$d_6$) δ 12.67 (s, 1H), 10.42 (s, 1H), 9.14 (s, 1H), 7.96 (s, 1H), 7.50 (s, 1H), 7.41-7.38 (m, 2H), 6.89 (d, J=16 Hz, 1H), 6.75 (d, J=8 Hz, 1H), 6.60-6.57 (m, 1H), 5.72 (d, J=4 Hz, 1H), 3.99 (s, 3H), 3.33 (s, 3H), 3.21 (s, 3H), 3.19-3.17 (t, J=8 Hz, 1H), 2.34-2.31 (m, 1H), 2.08-1.97 (m, 1H).

Example 194. 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methyl-N-(propan-2-yl)pyridine-2-carboxamide

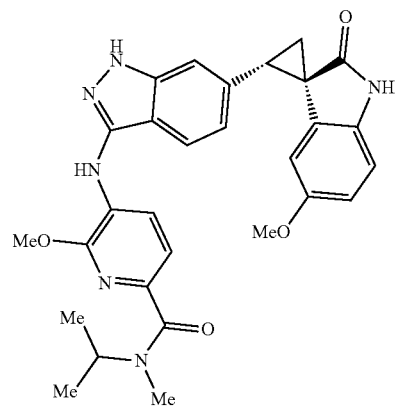 [SMILES: COc1ccc2c(c1)[C@]1(C[C@H]1c1ccc3c(Nc4ccc(C(=O)N(C)C(C)C)nc4OC)n[nH]c3c1)C(=O)N2]

Step A. N-isopropyl-6-methoxy-N-methyl-5-nitropyridine-2-carboxamide

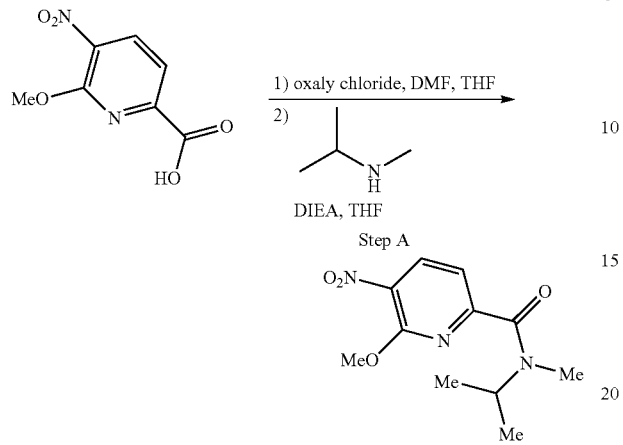

To a solution of 6-methoxy-5-nitropyridine-2-carboxylic acid (50 mg, 0.252 mmol, 1 equiv) in THF (4 mL) at 0° C. was added dropwise oxalyl chloride (39 mg, 0.307 mmol, 1.22 equiv) followed by one drop of DMF. The mixture was stirred for 2 h at 25° C. under nitrogen atmosphere. The resulting mixture was concentrated in vacuo under nitrogen atmosphere to afford the acid chloride which was used for next step without further purification. To a stirred solution of N-methylpropan-2-amine (25 mg, 0.342 mmol, 1.35 equiv) and DIEA (100 mg, 0.774 mmol, 3.07 equiv) in THF (1 mL) at 0° C. was added dropwise the solution of acid chloride in THF (1 mL) under nitrogen atmosphere. The mixture was stirred for 2 h at room temperature under nitrogen atmosphere. The resulting mixture was diluted with water (10 mL) and extracted with EA (2×30 mL). The combined organic layers were washed with brine (10 mL), dried over anhydrous $Na_2SO_4$. After filtration, the filtrate was concentrated under reduced pressure to afford the title compound (45 mg, 70.41%) as a light yellow oil. m/z (ESI, +ve ion)=254.05 $[M+H]^+$.

Step B. 5-amino-N-isopropyl-6-methoxy-N-methylpyridine-2-carboxamide

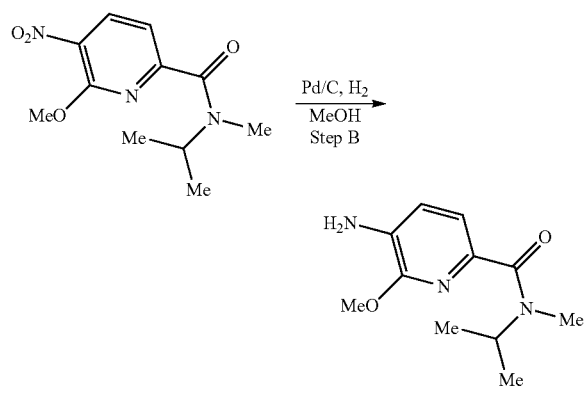

Into a 25 mL round-bottom flask were added N-isopropyl-6-methoxy-N-methyl-5-nitropyridine-2-carboxamide (50 mg, 0.197 mmol, 1 equiv) and MeOH (2 mL) at 25° C. To the above mixture was added Pd/C (25 mg) at 25° C. under nitrogen atmosphere. The resulting mixture was degassed and purged with hydrogen for three times. The resulting mixture was stirred for 4 h at 25° C. under hydrogen atmosphere. The resulting mixture was filtered and the filter cake was washed with MeOH (3×10 mL). The filtrate was concentrated under reduced pressure to afford the title compound (37 mg, 83.94%) as a grey solid. m/z (ESI, +ve ion)=224.15 $[M+H]^+$.

Step C. tert-butyl (1R,2S)-2-[1-(tert-butoxycarbonyl)-3-({6-[isopropyl(methyl)carbamoyl]-2-methoxypyridin-3-yl}amino)indazol-6-yl]-5'-methoxy-2'-oxospiro[cyclopropane-1,3'-indole]-1'-carboxylate

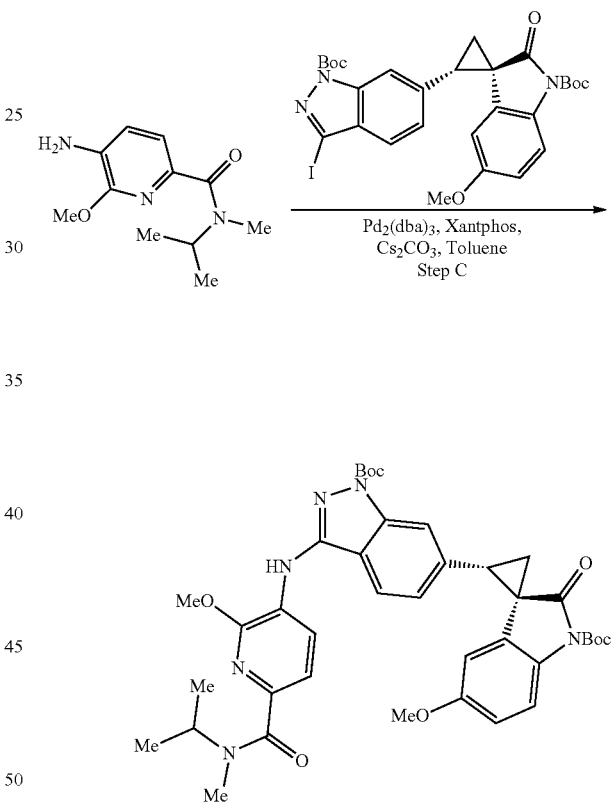

To a solution of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (80 mg, 0.127 mmol, 1 equiv) and 5-amino-N-isopropyl-6-methoxy-N-methylpyridine-2-carboxamide (31 mg, 0.139 mmol, 1.10 equiv) in toluene (2.5 mL) were added $Cs_2CO_3$ (80 mg, 0.246 mmol, 1.94 equiv), $Pd_2(dba)_3$ (24 mg, 0.026 mmol, 0.21 equiv) and XantPhos (16 mg, 0.028 mmol, 0.22 equiv). After stirring for 2 h at 90° C. under a nitrogen atmosphere. The resulting mixture was filtered and the filter cake was washed with EA (3×50 mL). The filtrate was concentrated under reduced pressure. The residue was purified by Prep-TLC (PE/EA=1/1) to afford the title compound (60 mg, 65.16%) as a light yellow solid. m/z (ESI, +ve ion)=727.40 $[M+H]^+$ Step D. 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methyl-N-(propan-2-yl)pyridine-2-carboxamide

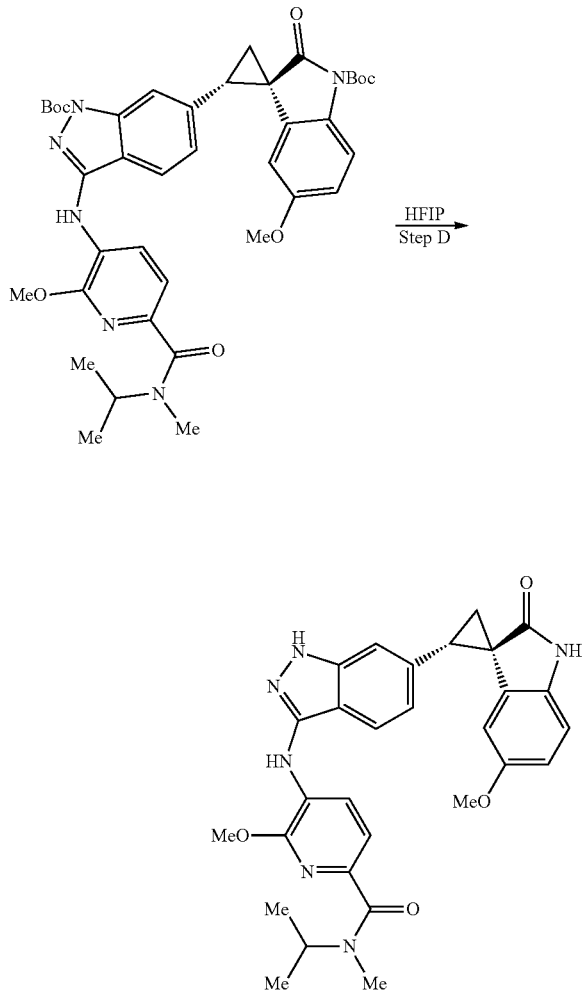 [SMILES: COc1ccc2c(c1)[C@]1(C[C@H]1c1ccc3c(Nc4ccc(C(=O)N(C)C(C)C)nc4OC)nn(C(=O)OC(C)(C)C)c3c1)C(=O)N2C(=O)OC(C)(C)C ; "HFIP" ; "Step D" ; COc1ccc2c(c1)[C@]1(C[C@H]1c1ccc3c(Nc4ccc(C(=O)N(C)C(C)C)nc4OC)n[nH]c3c1)C(=O)N2]

Into a 8 mL vial were added tert-butyl (1R,2S)-2-[1-(tert-butoxycarbonyl)-3-({6-[isopropyl(methyl)carbamoyl]-2-methoxypyridin-3-yl}amino)indazol-6-yl]-5'-methoxy-2'-oxospiro[cyclopropane-1,3'-indole]-1'-carboxylate (60 mg, 0.083 mmol, 1 equiv) and HFIP (1 mL, 9.498 mmol) at 25° C. The mixture was stirred for 12 h at 60° C. under nitrogen atmosphere. The resulting mixture was concentrated under reduced pressure. The crude product was purified by Prep-HPLC with the following conditions (Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 34% B to 32% B in 8 min, 32% B; wavelength: 254 nm; RT1 (min): 7) to afford the title compound (25 mg, 57.51%) as a white solid. m/z (ESI, +ve ion)=527.15 [M+H]$^+$. $^1$H NMR (400 MHz, DMSO-d$_6$) δ 12.27 (s, 1H), 10.43 (s, 1H), 8.40 (d, J=8.0 Hz, 1H), 8.31 (s, 1H), 7.94 (d, J=8.0 Hz, 1H), 7.35 (s, 1H), 7.20 (s, 1H), 6.92 (d, J=8.0 Hz, 1H), 6.75 (d, J=8.4 Hz, 1H), 6.60-6.57 (m, 1H), 5.71 (d, J=2.4 Hz, 1H), 4.70-4.31 (m, 1H), 4.01 (s, 3H), 3.20 (s, 3H), 3.18 (t, J=8.4 Hz, 1H), 2.94-2.91 (m, 1H), 2.88-2.86 (m, 2H), 2.33-2.28 (m, 1H), 2.00-1.97 (m, 1H), 1.18 (s, 6H).

Example 195. (1R,2S)-2-(3-{[5-ethoxy-2-(methylsulfanyl)pyrimidin-4-yl]amino}-1H-indazol-6-yl)-5'-methoxyspiro[cyclopropane-1,3'-indol]-2'(1'H)-one

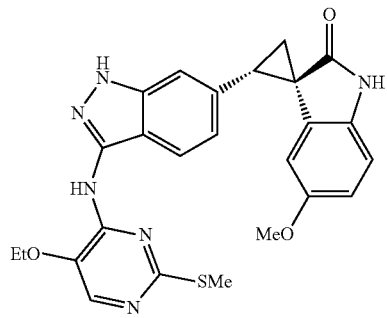 [SMILES: CCOc1cnc(SC)nc1Nc1n[nH]c2cc([C@@H]3C[C@@]34C(=O)Nc3ccc(OC)cc34)ccc12]

Step A. 4-amino-2-chloropyrimidin-5-ol

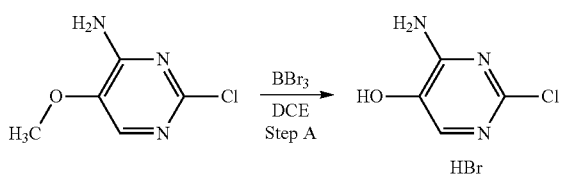

To a stirred mixture of 2-chloro-5-methoxypyrimidin-4-amine (318 mg, 1.993 mmol, 1 equiv) in DCE (10 mL) was added BBr$_3$ (1.88 mL, 19.930 mmol, 10 equiv) dropwise at room temperature under nitrogen atmosphere. After the resulting mixture was stirred for 16 h at room temperature under nitrogen atmosphere, 20 mL of DCE was added into the mixture and then stand for hours. Then the upper solution was removed. The deposited semi-solid was dissolved in MeOH (10 mL) and concentrated under reduced pressure to afford the title compound (480 mg, 63.82%) as a yellow solid. m/z (ESI, +ve ion)=145.95 [M+H]$^+$ Step B. 2-chloro-5-ethoxypyrimidin-4-amine

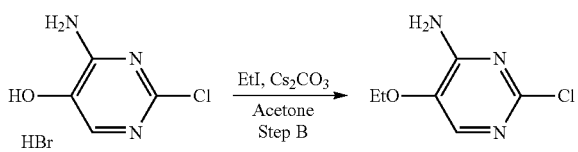

To a stirred mixture of 4-amino-2-chloropyrimidin-5-ol (500 mg, 1.374 mmol, 1 equiv, 40%) and Cs$_2$CO$_3$ (1343.12 mg, 4.122 mmol, 3 equiv) in acetone (10 mL) was added iodoethane (171.45 mg, 1.099 mmol, 0.8 equiv) at room temperature under nitrogen atmosphere. The resulting mixture was stirred for additional 16 h at 60° C. The resulting mixture was diluted with water (10 mL). The resulting mixture was extracted with EA (3×10 mL). The combined organic layers were dried over anhydrous Na$_2$SO$_4$. After filtration, the filtrate was concentrated under reduced pressure. The residue was purified by silica gel column chromatography, eluted with PE/EA (1/1) to afford the title compound (146 mg, 61.20%) as a light yellow solid. m/z (ESI, +ve ion)=174.00 [M+H]⁺.

Step C.
5-ethoxy-2-(methylsulfanyl)pyrimidin-4-amine

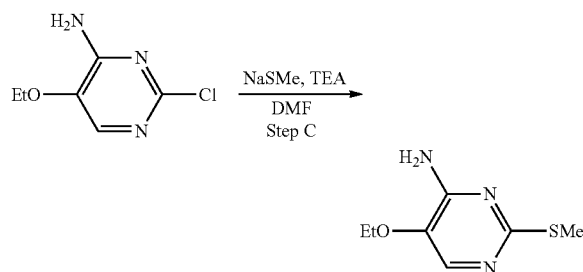

To a stirred mixture of 2-chloro-5-ethoxypyrimidin-4-amine (120 mg, 0.691 mmol, 1 equiv) in DMF (2 mL) were added sodium thiomethoxide (290.65 mg, 4.146 mmol, 6 equiv) and TEA (629.54 mg, 6.219 mmol, 9 equiv) at room temperature under nitrogen atmosphere. The resulting mixture was stirred for additional 4 h at 60° C. The resulting mixture was diluted with water (5 mL). The resulting mixture was extracted with EA (3×10 mL). The combined organic layers were dried over anhydrous $Na_2SO_4$. After filtration, the filtrate was concentrated under reduced pressure. The residue was purified by silica gel column chromatography, eluted with PE/EA (1/1) to afford the title compound (52 mg, 39.39%) as a light yellow solid. m/z (ESI, +ve ion)=186.00 [M+H]⁺.

Step D. tert-butyl (1R,2S)-2-[1-(tert-butoxycarbonyl)-3-{[5-ethoxy-2-(methylsulfanyl)pyrimidin-4-yl]amino}indazol-6-yl]-5'-methoxy-2'-oxospiro[cyclopropane-1,3'-indole]-1'-carboxylate

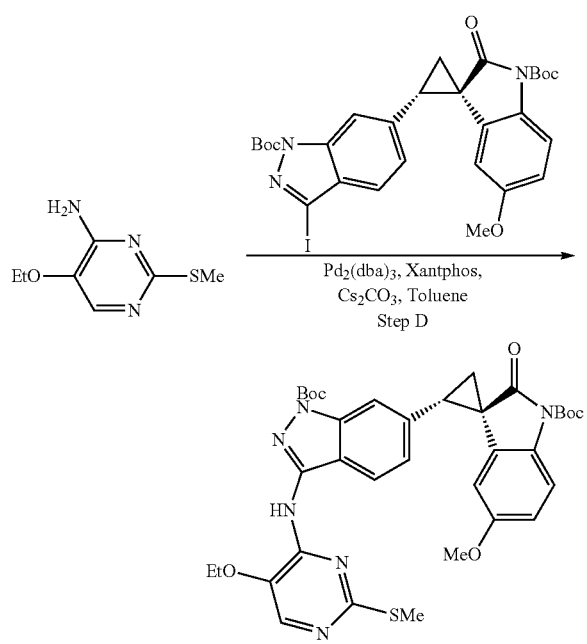

To a stirred mixture of 5-ethoxy-2-(methylsulfanyl)pyrimidin-4-amine (35.20 mg, 0.190 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) in toluene (2.5 mL) were added $Pd_2(dba)_3$ (14.50 mg, 0.016 mmol, 0.1 equiv), $Cs_2CO_3$ (154.79 mg, 0.474 mmol, 3 equiv) and XantPhos (9.16 mg, 0.016 mmol, 0.1 equiv) at room temperature under nitrogen atmosphere. The resulting mixture was stirred for additional 2 h at 60° C. The resulting mixture was concentrated under reduced pressure. The residue was purified by silica gel column chromatography, eluted with PE/EA (1/1) to afford the title compound (100 mg, 90.76%) as a yellow solid. m/z (ESI, +ve ion)=689.35 [M+H]⁺.

Step E. (1R,2S)-2-(3-{[5-ethoxy-2-(methylsulfanyl)pyrimidin-4-yl]amino}-1H-indazol-6-yl)-5'-methoxyspiro[cyclopropane-1,3'-indol]-2'(1'H)-one

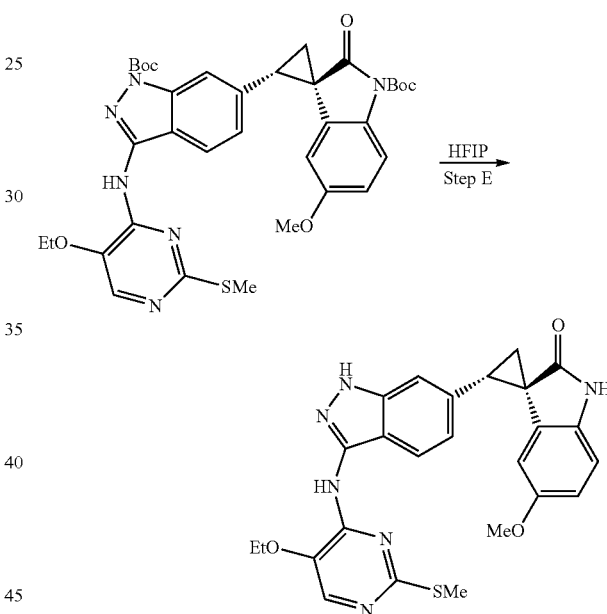

A solution of tert-butyl (1R,2S)-2-[1-(tert-butoxycarbonyl)-3-{[5-ethoxy-2-(methylsulfanyl)pyrimidin-4-yl]amino}indazol-6-yl]-5'-methoxy-2'-oxospiro[cyclopropane-1,3'-indole]-1'-carboxylate (100 mg, 0.145 mmol, 1 equiv) in HFIP (5 mL) was stirred for 12 h at 60° C. under nitrogen atmosphere. The resulting mixture was concentrated under reduced pressure. The crude product was purified by Prep-HPLC with the following conditions (Column: YMC-Actus Triart C18 ExRS, 30×150 mm, 5 μm; Mobile Phase A: Water (10 mmol/L $NH_4HCO_3$), Mobile Phase B: ACN; Flow rate: 60 mL/min; Gradient: 36% B to 36% B in 10 min, 36% B: wavelength: 254 nm; RT1(min): 10.2) to afford the title compound (18.5 mg, 26.03%) as a white solid. m/z (ESI, +ve ion)=489.15 [M+H]⁺. ¹H NMR (400 MHz, DMSO-$d_6$) δ 12.69 (s, 1H), 10.40 (s, 1H), 9.17 (s, 1H), 7.93 (s, 1H), 7.42 (d, J=8.4 Hz, 2H), 6.91 (d, J=8.8 Hz, 1H), 6.75 (d, J=8.4 Hz, 1H), 6.60-6.57 (m, 1H), 5.69 (d, J=2.0 Hz, 1H), 4.17-4.12 (m, 2H), 3.32 (s, 3H) 3.20 (t, J=8.8 Hz, 1H), 2.34-2.30 (m, 1H), 2.08 (s, 3H), 1.99 (t, J=4.8 Hz, 1H), 1.39 (t, J=8.0, 7.5 Hz, 3H).

Example 203. 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide

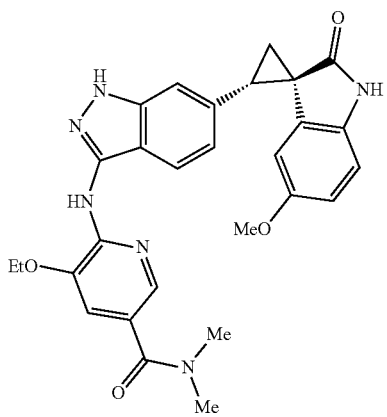 [SMILES: CCOc1cc(C(=O)N(C)C)cnc1Nc1n[nH]c2cc([C@@H]3C[C@@]34C(=O)Nc3ccc(OC)cc34)ccc12]

Step A. ethyl 5-ethoxy-6-nitropyridine-3-carboxylate

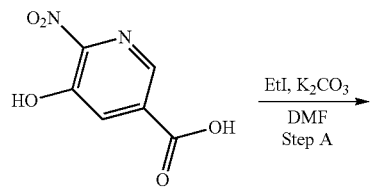

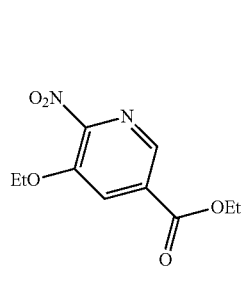

To a stirred solution of 5-hydroxy-6-nitropyridine-3-carboxylic acid (200.00 mg, 1.086 mmol, 1.00 equiv) and $K_2CO_3$ (375.34 mg, 2.715 mmol, 2.50 equiv) in DMF (2.00 mL) was added iodoethane (423.57 mg, 2.715 mmol, 2.50 equiv) dropwise at room temperature under nitrogen atmosphere. The resulting mixture was stirred for 24 h at 60° C. under nitrogen atmosphere. The mixture was allowed to cool down to room temperature. The resulting mixture was diluted with water (50 mL) and extracted with EA (3×60 mL). The combined organic layers were washed with brine (3×30 mL), dried over anhydrous $Na_2SO_4$. After filtration, the filtrate was concentrated under reduced pressure. The residue was purified by silica gel column chromatography, eluted with PE/EA (1/1) to afford the title compound (140.00 mg, 53.65%) as a yellow solid. m/z (ESI, +ve ion)=241.10 [M+H]$^+$.

Step B. 5-ethoxy-6-nitropyridine-3-carboxylic acid

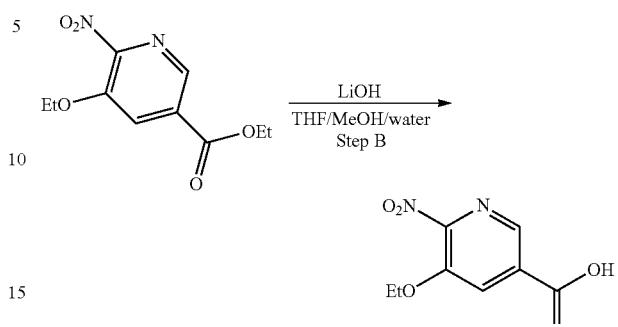

To a stirred mixture of ethyl 5-ethoxy-6-nitropyridine-3-carboxylate (140.00 mg, 0.583 mmol, 1.00 equiv) in THF (2.00 mL), MeOH (2.00 mL) and water (1.00 mL) was added LiOH (27.92 mg, 1.166 mmol, 2.00 equiv) at room temperature under nitrogen atmosphere. The resulting mixture was stirred for 0.5 h at room temperature under nitrogen atmosphere. The mixture was acidified to pH 5 with 2 M aqueous of HCl. The resulting mixture was extracted with EA (3×50 mL). The combined organic layers were washed with brine (3×30 mL), dried over anhydrous $Na_2SO_4$. After filtration, the filtrate was concentrated under reduced pressure. The residue was purified by silica gel column chromatography, eluted with DCM/MeOH (5/1) to afford the title compound (85.00 mg, 68.74%) as a yellow solid. m/z (ESI, +ve ion)=213.10 [M+H]$^+$.

Step C. 5-ethoxy-N,N-dimethyl-6-nitropyridine-3-carboxamide

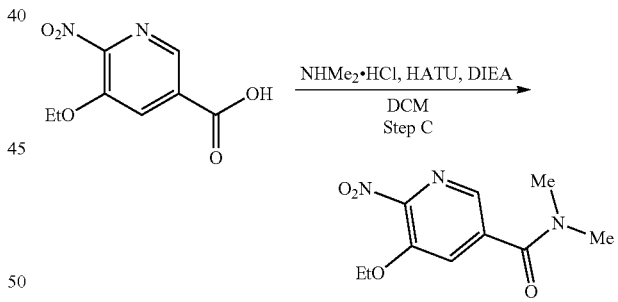

To a stirred solution of 5-ethoxy-6-nitropyridine-3-carboxylic acid (75.00 mg, 0.354 mmol, 1.00 equiv) and dimethylamine hydrochloride (28.83 mg, 0.354 mmol, 1.00 equiv) in DMF (4.00 mL) were added HATU (268.83 mg, 0.708 mmol, 2.00 equiv) and DIEA (182.76 mg, 1.416 mmol, 4.00 equiv) at room temperature under nitrogen atmosphere. The resulting mixture was stirred for 16 h at room temperature under nitrogen atmosphere. The mixture was purified by reverse flash chromatography with the following conditions: C18 Column, 40 g, 60 Å, 40-60 µm; Mobile Phase A: 10 mM aq. $NH_4HCO_3$, Mobile Phase B: MeCN; Flow rate: 60 mL/min; Gradient: 0% B to 0% B in 5 min, 0% B to 40% B in 30 min; Detector: UV 254 & 220 nm to afford the title compound (60.00 mg, 70.95%) as a yellow solid. m/z (ESI, +ve ion)=240.15 [M+H]$^+$.

Step D. 6-amino-5-ethoxy-N,N-dimethylpyridine-3-carboxamide

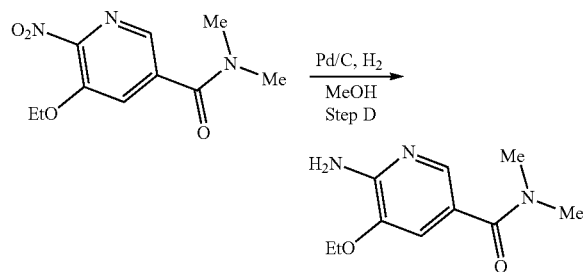

To a solution of 5-ethoxy-N,N-dimethyl-6-nitropyridine-3-carboxamide (55.00 mg, 0.230 mmol, 1.00 equiv) in MeOH (5.00 mL) was added Pd/C (10%, 24.47 mg) under nitrogen atmosphere. The mixture was degassed and purged with H₂ for three times. The mixture was hydrogenated at room temperature for 2 h under hydrogen atmosphere. The resulting mixture was filtered through a Celite pad and the filtrate was concentrated under reduced pressure. The residue was purified by silica gel column chromatography, eluted with DCM/MeOH (5/1) to afford the title compound (40.00 mg, 83.15%) as a yellow solid. m/z (ESI, +ve ion)=210.15 [M+H]⁺.

Step E. tert-butyl (1R,2S)-2-[1-(tert-butoxycarbonyl)-3-{[5-(dimethylcarbamoyl)-3-ethoxypyridin-2-yl]amino}indazol-6-yl]-5'-methoxy-2'-oxospiro[cyclopropane-1,3'-indole]-1'-carboxylate

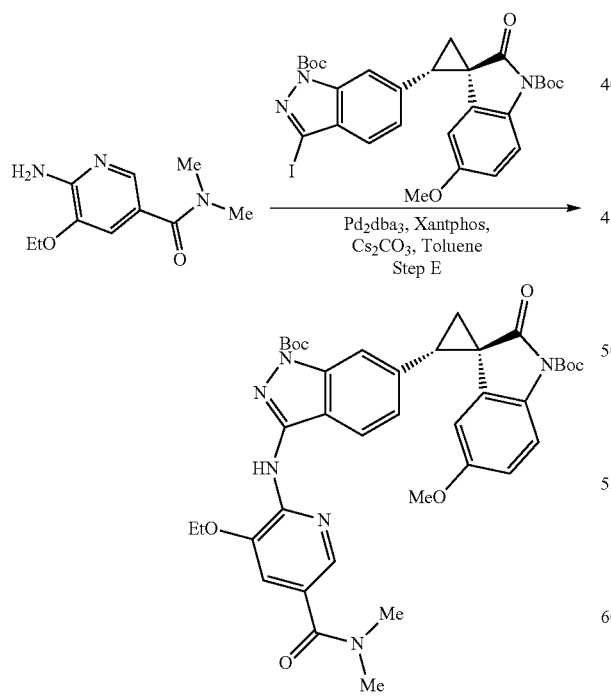

To a stirred solution of 6-amino-5-ethoxy-N,N-dimethylpyridine-3-carboxamide (33.14 mg, 0.158 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100.00 mg, 0.158 mmol, 1.00 equiv) in toluene (5.00 mL) were added Pd₂(dba)₃ (29.00 mg, 0.032 mmol, 0.20 equiv), XantPhos (18.33 mg, 0.032 mmol, 0.20 equiv) and Cs₂CO₃ (103.19 mg, 0.316 mmol, 2.00 equiv) at room temperature under nitrogen atmosphere. The resulting mixture was stirred for 2 h at 90° C. under nitrogen atmosphere. The mixture was allowed to cool down to room temperature. The resulting mixture was filtered, the filter cake was washed with EA (3×30 mL). The filtrate was concentrated under reduced pressure. The residue was purified by silica gel column chromatography, eluted with PE/EA (1/1) to afford the title compound (80.00 mg, 70.87%) as a yellow solid. m/z (ESI, +ve ion)=713.40 [M+H]⁺.

Step F. 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide

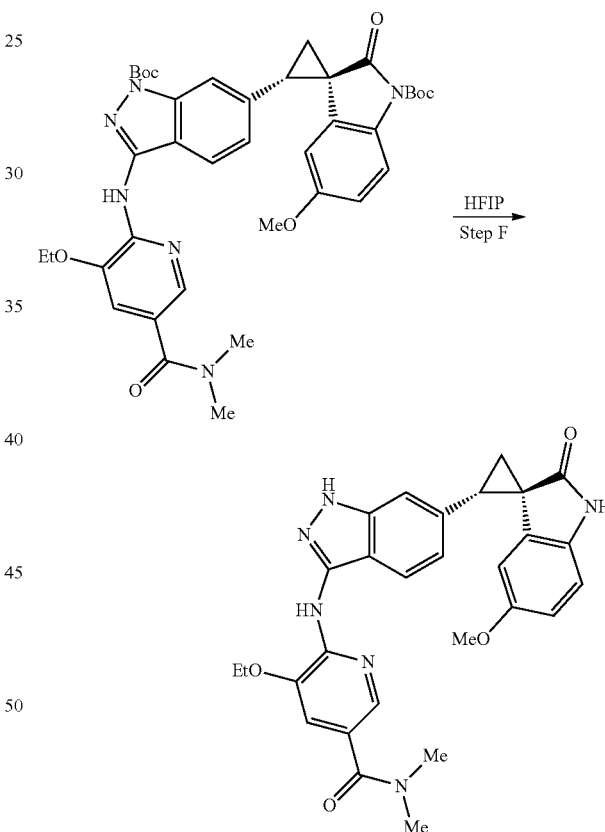

A solution of tert-butyl (1R,2S)-2-[I-(tert-butoxycarbonyl)-3-{[5-(dimethylcarbamoyl)-3-ethoxypyridin-2-yl]amino}indazol-6-yl]-5'-methoxy-2'-oxospiro[cyclopropane-1,3'-indole]-1'-carboxylate (76.00 mg, 0.107 mmol, 1.00 equiv) in HFIP (5.00 mL) was stirred for 16 h at 60° C. under nitrogen atmosphere. The mixture was allowed to cool down to room temperature. The resulting mixture was concentrated under reduced pressure. The residue was purified by Prep-HPLC with the following conditions (Column: XBridge Shield RP18 OBD Column, 30×150 mm, 5 μm; Mobile Phase A: Water (10 mmol/L NH₄HCO₃), Mobile Phase B: ACN; Flow rate: 60 mL/min; Gradient: 30% B to 50% B in 8 min, 50% B; wavelength: 254 nm; RT1(min): 7.2) to afford the title compound (25.90 mg, 47.39%) as a white solid. m/z (ESI, +ve ion)=513.30 [M+H]⁺. ¹H-NMR (400 MHz, Methanol-d₄) δ 7.70 (s, 1H), 7.61 (d, J=8.4 Hz, 1H), 7.42 (s, 1H), 7.27 (d, J=1.2 Hz, 1H), 6.93 (d, J=8.4 Hz, 1H), 6.84 (d, J=8.4 Hz, 1H), 6.64-6.61 (m, 1H), 5.67 (d, J=2.4 Hz, 1H), 4.27-4.24 (m, 2H), 3.37 (d, J=8.0 Hz, 1H), 3.34 (s, 3H), 3.12 (s, 6H), 2.25-2.17 (m, 2H), 1.56-1.53 (m, 3H).

Example 204. 5-methoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-sulfonamide

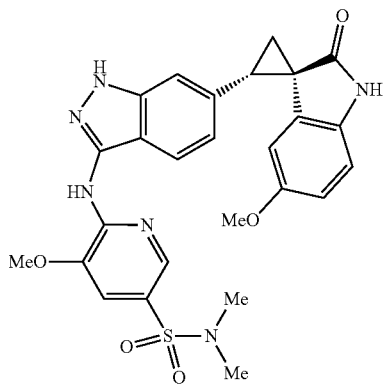 [SMILES: COc1ccc2c(c1)[C@]1(C[C@H]1c1ccc3c(Nc4ncc(S(=O)(=O)N(C)C)cc4OC)n[nH]c3c1)C(=O)N2]

Step A.
5-(benzylsulfanyl)-3-methoxy-2-nitropyridine

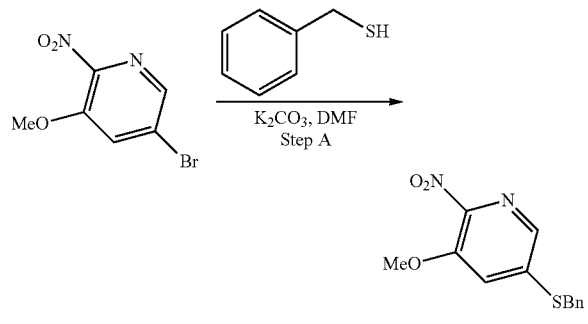

To the mixture of 5-bromo-3-methoxy-2-nitropyridine (500 mg, 2.146 mmol, 1 equiv) and K₂CO₃ (355.86 mg, 2.575 mmol, 1.2 equiv) in DMF (5 mL) was added benzyl mercaptan (293.15 mg, 2.361 mmol, 1.1 equiv) at room temperature under nitrogen atmosphere. The mixture was stirred for 4 h at room temperature. The resulting mixture was diluted with water (50 mL). The resulting mixture was extracted with EtOAc (20 mL×3). The combined organic layers were washed with brine (20 mL×3), dried over anhydrous Na₂SO₄. After filtration, the filtrate was concentrated under reduced pressure. The residue was purified by silica gel column chromatography, eluted with 0-100% of EA in PE to afford the title compound (450 mg, 75.90%) as a yellow solid. m/z (ESI, +ve ion)=277.05 [M+H]⁺.

Step B. 5-methoxy-N,N-dimethyl-6-nitropyridine-3-sulfonamide

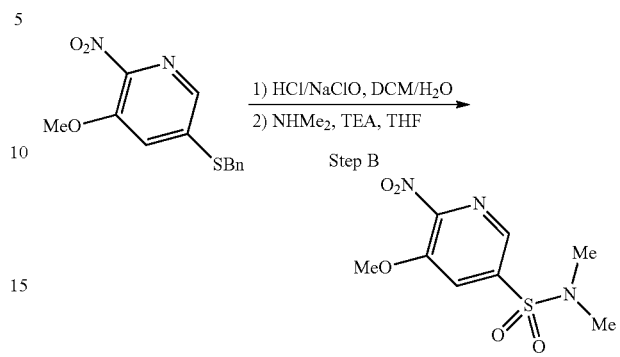

To the mixture of 5-(benzylsulfanyl)-3-methoxy-2-nitropyridine (390 mg, 1.411 mmol, 1 equiv) in H₂O (5 mL) and DCM (10 mL) was added conc. HCl (2.02 mL) and NaClO (5.85 mL, 8.645 mmol, 6.12 equiv, 8%-10% active chlorine aqueous solution) at 0° C. under nitrogen atmosphere. The mixture was stirred at 0° C. for 15 min. The organic phase was separated quickly and injected into the mixture of dimethylamine (0.64 mL, 1.270 mmol, 0.9 equiv, 2 M in THF) and TEA (428.49 mg, 4.233 mmol, 3 equiv) in THF (3 mL) at 0° C. under nitrogen atmosphere. The mixture was stirred at 0° C. for 10 min and 25° C. for 1 h. The resulting mixture diluted with brine (20 mL). The mixture was extracted with DCM (30 mL×3). The combined organic layers were dried over anhydrous Na₂SO₄. After filtration, the filtrate was concentrated under reduced pressure. The residue was purified by silica gel column chromatography, eluted with 0-100% of EA in PE to afford the title compound (240 mg, 65.09%) as a light yellow solid. m/z (ESI, +ve ion)=260.15 [M–H]⁺. ¹H NMR (400 MHz, Chloroform-d) δ 8.43 (d, J=1.7 Hz, 1H), 7.84 (d, J=1.7 Hz, 1H), 4.07 (s, 3H), 2.87 (s, 6H).

Step C. 6-amino-5-methoxy-N,N-dimethylpyridine-3-sulfonamide

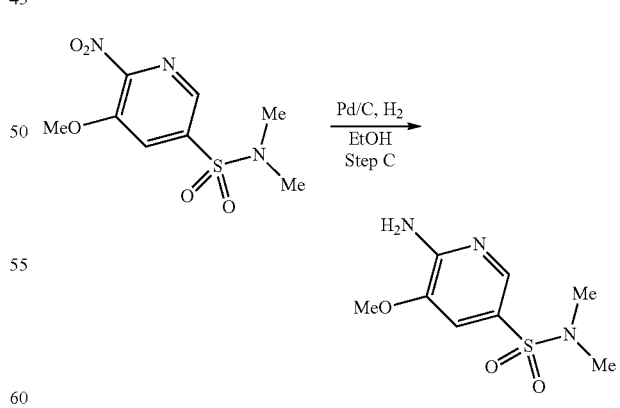

To a stirred mixture of 5-methoxy-N,N-dimethyl-6-nitropyridine-3-sulfonamide (240 mg, 0.367 mmol, 1 equiv) in EtOH (10 mL) was added Pd/C (101.67 mg, 10%) at room temperature under nitrogen atmosphere. The reaction mixture was degassed and purged for H₂ for three times. Then the resulting mixture was stirred at 25° C. for 4 h under H₂

(about 2 atm) atmosphere. The mixture was filtered and washed with EA (20 mL). The filtrate was concentrated in vacuo. The residue was purified by silica gel column chromatography, eluted with 0-20% of MeOH in DCM to afford the title compound (150 mg, 70.40/6) as a grey solid. m/z (ESI, +ve ion)=232.10 [M+H]⁺.

Step D. tert-butyl (1R,2S)-2-[1-(tert-butoxycarbonyl)-3-{[5-(dimethylsulfamoyl)-3-methoxypyridin-2-yl]amino}indazol-6-yl]-5'-methoxy-2'-oxospiro[cyclopropane-1,3'-indole]-1'-carboxylate Step E. 5-methoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-sulfonamide

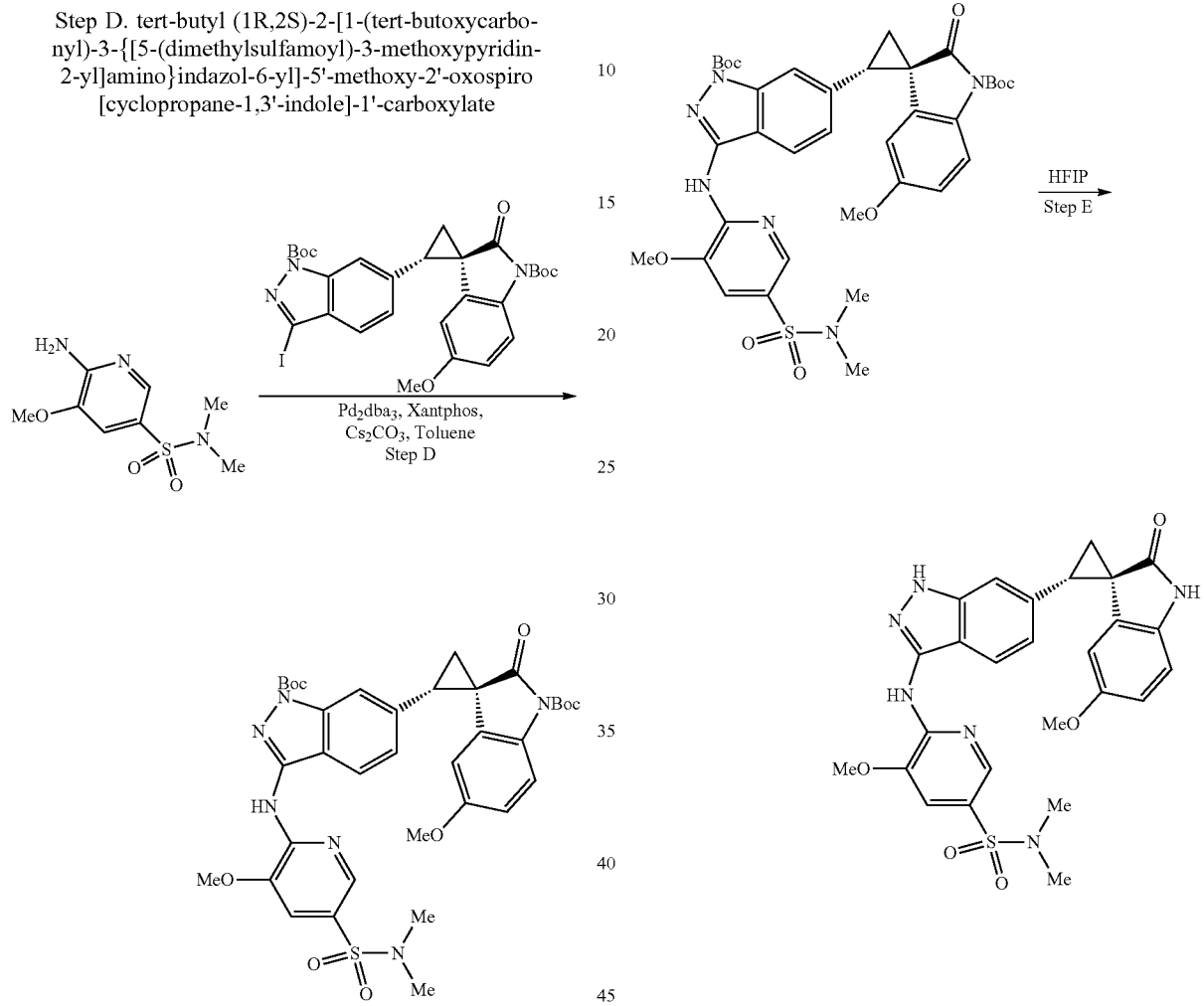

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (130 mg, 0.206 mmol, 1 equiv) and 6-amino-5-methoxy-N,N-dimethylpyridine-3-sulfonamide (57.13 mg, 0.247 mmol, 1.2 equiv) in toluene (6.50 mL) were added Cs₂CO₃ (134.15 mg, 0.412 mmol, 2 equiv), XantPhos (23.82 mg, 0.041 mmol, 0.2 equiv) and Pd₂(dba)₃ (37.70 mg, 0.041 mmol, 0.2 equiv) at room temperature under nitrogen atmosphere. The mixture was stirred at 90° C. for 2 h. After cooled to room temperature, the mixture was filtered and washed with EtOAc (20 mL). The filtrate was concentrated in vacuo. The residue was purified by silica gel column eluted with 0-00% of EtOAc in PE to give the title compound (100 mg, 66.10%) as a yellow oil. m/z (ESI, +ve ion)=735.30 [M+H]⁺.

The mixture of tert-butyl (1R,2S)-2-[1-(tert-butoxycarbonyl)-3-{[5-(dimethylsulfamoyl)-3-methoxypyridin-2-yl]amino}indazol-6-yl]-5'-methoxy-2'-oxospiro[cyclopropane-1,3'-indole]-1'-carboxylate (100 mg, 0.136 mmol, 1 equiv) in HFIP (5 mL) was stirred at 60° C. for 16 h under nitrogen atmosphere. After cooled to room temperature, the solvent was removed under reduced pressure. The residue was purified by Prep-HPLC with the following conditions (Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 28% B to 36% B in 8 min, 36% B; wavelength: 254 nm; RT1(min): 7) to afford the title compound (52.3 mg, 71.82%) as a white solid. m/z (ESI, +ve ion)=535.15 [M+H]⁺. ¹H NMR (400 MHz, DMSO-4) δ 12.65 (s, 1H), 10.41 (s, 1H), 9.11 (s, 1H), 7.85 (s, 1H), 7.42 (d, J=8.0 Hz, 2H), 7.28 (s, 1H), 6.90 (d, J=8.4 Hz, 1H), 6.75 (d, J=8.4 Hz, 1H), 6.60-6.58 (m, 1H), 5.74 (d, J=2.0 Hz, 1H), 3.99 (s, 3H), 3.34 (s, 3H), 3.19 (t, J=8.4 Hz, 1H), 2.62 (s, 6H), 2.35-2.31 (m, 1H), 2.01-1.97 (m, 1H).

Example 208. (1R,2S)-2-(3-{[3-ethoxy-5-(methanesulfonyl)pyridin-2-yl]amino}-1H-indazol-6-yl)-5'-methoxyspiro[cyclopropane-1,3'-indol]-2'(1'H)-one

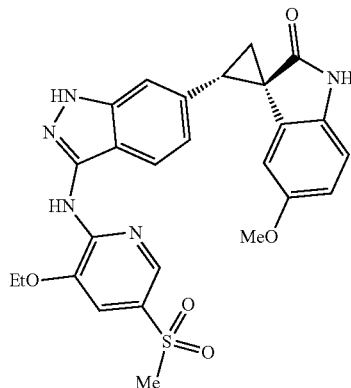 [SMILES: CCOc1cc(S(C)(=O)=O)cnc1Nc1n[nH]c2cc([C@@H]3C[C@@]34C(=O)Nc3ccc(OC)cc34)ccc12]

Step A. 5-bromo-3-ethoxy-2-nitropyridine

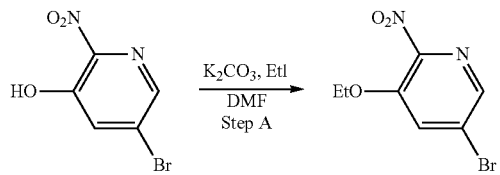 [SMILES: O=[N+]([O-])c1ncc(Br)cc1O ; CCOc1cc(Br)cnc1[N+](=O)[O-]]

To a stirred solution of 5-bromo-2-nitropyridin-3-ol (657 mg, 3.000 mmol, 1 equiv) and K$_2$CO$_3$ (829.25 mg, 6.000 mmol, 2 equiv) in DMF (7 mL) were added iodoethane (561.49 mg, 3.600 mmol, 1.2 equiv) dropwise at 25° C. under nitrogen atmosphere. The reaction mixture was stirred for 2 h at 25° C. The reaction was quenched by the addition of Water (15 mL). The resulting mixture was extracted with DCM (3×15 mL). The combined organic layers were washed with brine (3×15 mL), dried over anhydrous Na$_2$SO$_4$. After filtration, the filtrate was concentrated under reduced pressure. The residue was purified by Prep-TLC (PE/EA=5/1) to afford the title compound (278 mg, 37.51%) as a yellow solid. m/z (ESI, +ve ion)=246.90, 248.90 [M+H]$^+$.

Step B. 5-bromo-3-ethoxypyridin-2-amine

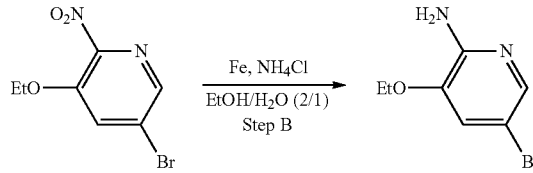

To a stirred solution of 5-bromo-3-ethoxy-2-nitropyridine (600 mg, 2.429 mmol, 1 equiv) and NH$_4$Cl (649.55 mg, 12.145 mmol, 5 equiv) in EtOH (2 mL) and H$_2$O (1 mL) was added Fe (678.15 mg, 12.145 mmol, 5 equiv) at 25° C. under nitrogen atmosphere. The mixture was stirred for 2 h at 25° C. The resulting mixture was filtered, the filter cake was washed with EA (3×20 mL). The filtrate was concentrated under reduced pressure. The residue was purified by silica gel column chromatography, eluted with PE/EA (5/1) to afford the title compound (147 mg, 27.88%) as a yellow solid. m/z (ESI, +ve ion)=216.95, 218.95 [M+H]$^+$.

Step C. 3-ethoxy-5-(methylsulfonyl)pyridin-2-amine

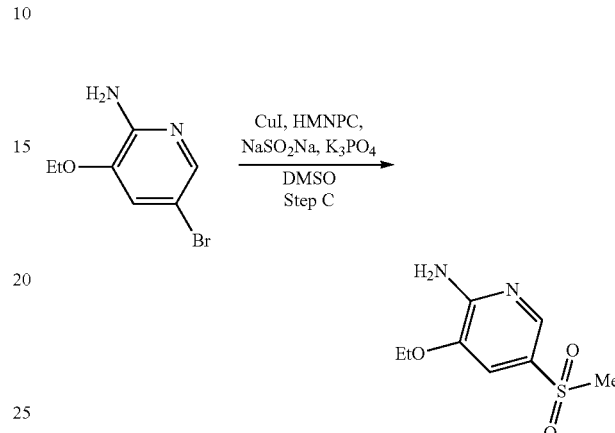

To a stirred solution of 5-bromo-3-ethoxypyridin-2-amine (137 mg, 0.631 mmol, 1 equiv) and (2S,4R)-4-hydroxy-N-(2-methylnaphthalen-1-yl)pyrrolidine-2-carboxamide (HMNPC, 17.06 mg, 0.063 mmol, 0.1 equiv) in DMSO (1.5 mL) were added sodium methanesulfinate (83.76 mg, 0.820 mmol, 1.3 equiv), CuI (12.02 mg, 0.063 mmol, 0.1 equiv) and K$_3$PO$_4$ (133.97 mg, 0.631 mmol, 1 equiv) at 25° C. under nitrogen atmosphere. The resulting mixture was stirred for 16 h at 80° C. under nitrogen atmosphere. The mixture was allowed to cool down to 25° C. The residue was purified by reverse flash chromatography with the following conditions: column, C18 silica gel; mobile phase, water (5 mM NH$_4$HCO$_3$) in ACN, 20% to 60% gradient in 30 min; detector, UV 254 nm. The resulting mixture was concentrated under reduced pressure to afford the title compound (76 mg, 55.68%) as a yellow solid. m/z (ESI, +ve ion)=217.10 [M+H]$^+$.

Step D. tert-butyl (1R,2S)-2-(1-(tert-butoxycarbonyl)-3-((3-ethoxy-5-(methylsulfonyl)pyridin-2-yl)amino)-1H-indazol-6-yl)-5'-methoxy-2'-oxospiro[cyclopropane-1,3'-indoline]-1'-carboxylate

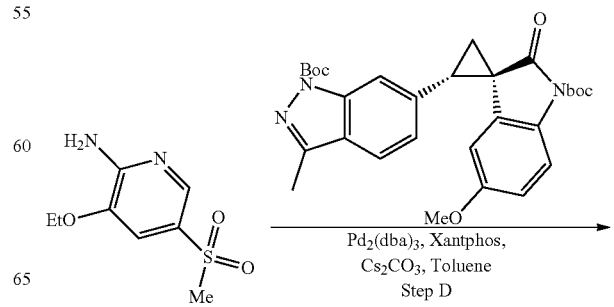

591

-continued

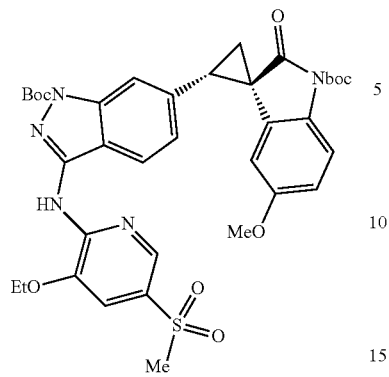

To a stirred solution of 3-ethoxy-5-methanesulfonylpyridin-2-amine (61.65 mg, 0.286 mmol, 1.2 equiv) and Cs$_2$CO$_3$ (36.17 mg, 0.476 mmol, 2 equiv) in toluene (2 mL) were added tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (150 mg, 0.238 mmol, 1.00 equiv), Pd$_2$(dba)$_3$ (43.50 mg, 0.048 mmol, 0.2 equiv) and XantPhos (27.49 mg, 0.048 mmol, 0.2 equiv) at 25° C. under nitrogen atmosphere. The resulting mixture was stirred for 2 h at 90° C. under nitrogen atmosphere. The mixture was allowed to cool down to 25° C. The reaction was quenched by the addition of water (15 mL). The resulting mixture was extracted with DCM (3×15 mL). The combined organic layers were washed with brine (3×15 mL), dried over anhydrous Na$_2$SO$_4$. After filtration, the filtrate was concentrated under reduced pressure. The residue was purified by silica gel column chromatography, eluted with PE/EA (1/1) to afford the title compound (99 mg, 57.90%) as a yellow solid. m/z (ESI, +ve ion)=720.25 [M+H]$^+$.

Step E. (1R,2S)-2-(3-{[3-ethoxy-5-(methanesulfonyl)pyridin-2-yl]amino}-1H-indazol-6-yl)-5'-methoxyspiro[cyclopropane-1,3'-indol]-2'(1'H)-one

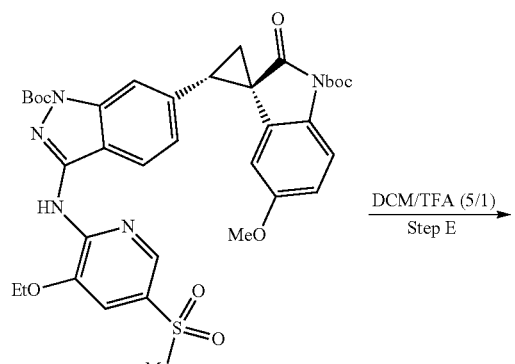

592

-continued

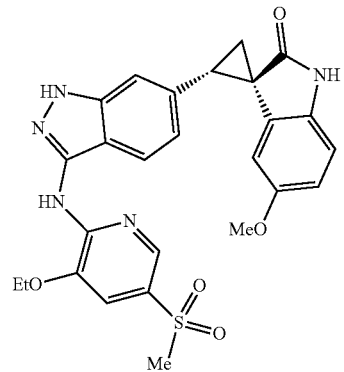

A solution of tert-butyl (1R,2S)-2-[1-(tert-butoxycarbonyl)-3-[(3-ethoxy-5-methanesulfonylpyridin-2-yl)amino]indazol-6-yl]-5'-methoxy-2'-oxospiro[cyclopropane-1,3'-indole]-1'-carboxylate (99 mg, 0.138 mmol, 1 equiv) in TFA (0.2 mL) and DCM (1 mL) was stirred for 2 h at 25° C. under nitrogen atmosphere. The resulting mixture was concentrated under reduced pressure. The crude product (69 mg) was purified by Prep-HPLC with the following conditions (Column: XBridge Prep OBD C18 Column, 30×150 mm, 5 μm; Mobile Phase A: Water (10 mmol/L NH$_4$HCO$_3$). Mobile Phase B: ACN; Flow rate: 60 mL/min; Gradient: 28% B to 32% B in 8 min, 32% B; wavelength: 254 nm; RT1(min): 7) to afford the title compound (31.6 mg, 44.18%) as a white solid. m/z (ESI, +ve ion)=520.20 [M+H]$^+$. $^1$H-NMR (400 MHz, DMSO-d$_6$) δ 12.67 (s, 1H), 10.41 (s, 1H), 9.05 (s, 1H), 7.96 (d, J=4 Hz, 1H), 7.48 (d, J=4 Hz, 1H), 7.40 (t, J=12 Hz, 2H), 6.89 (d, J=8 Hz, 1H), 6.75 (d, J=8 Hz, 1H), 6.60-6.57 (m, 1H), 5.71 (d, J=4 Hz, 1H), 4.28-4.23 (m, 2H), 3.31 (s, 3H), 3.21-3.17 (m, 4H), 2.34-2.31 (m, 1H), 2.00-1.97 (m, 1H), 1.46 (t, J=8 Hz, 3H).

Example 212. 2,5-Dimethoxy-4-({6-[(1R,2S)-5'-methoxy-2'-oxo-1',2'-dihydrospiro[cyclopropane-1,3'-indol]-2-yl]-1H-indazol-3-yl}amino)benzene-1-sulfonamide

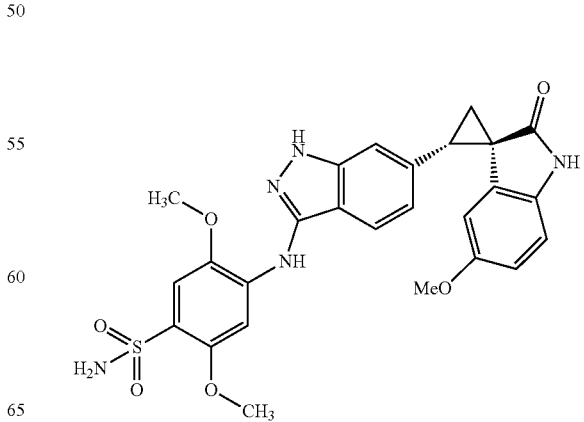

Step A: Tert-butyl 6-((1R,2S)-1'-(tert-butoxycarbonyl)-5'-methoxy-2'-oxospiro[cyclopropane-1,3'-indolin]-2-yl)-3-((2,5-dimethoxy-4-sulfamoylphenyl)amino)-1H-indazole-1-carboxylate

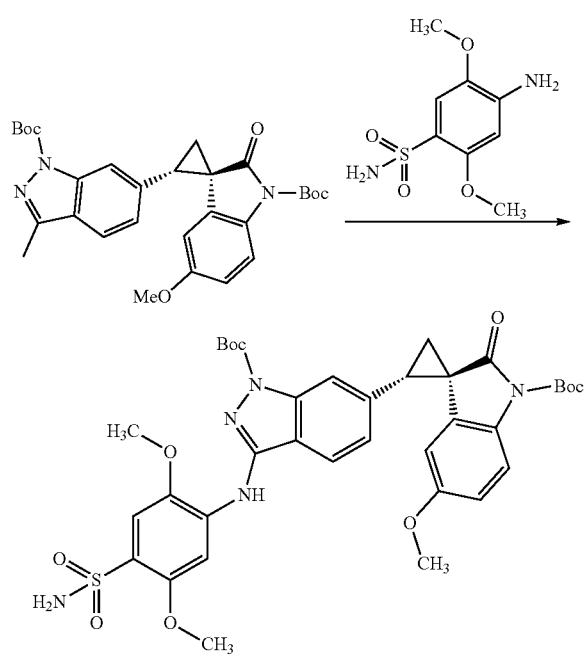

A microwave vial was charged with tert-butyl 6-((1R,2S)-1'-(tert-butoxycarbonyl)-5'-methoxy-2'-oxospiro[cyclopropane-1,3'-indolin]-2-yl)-3-iodo-1H-indazole-1-carboxylate (100 mg, 158 μmol), 2,5-dimethoxysulfanilamide (38.7 mg, 158 μmol), tris(dibenzylideneacetone)-dipalladium(0) (14.8 mg, 15.8 μmol), 4,4-bis(diphenylphosphino)-9,9-dimethyl-xanthene (9.65 mg, 15.8 μmol), cesium carbonate (105 mg, 317 μmol) and dioxane (2.00 mL). The vial was sealed, and the mixture was bubbled with nitrogen for 5 minutes at room temperature and stirred at 100° C. overnight. The reaction mixture was cooled to room temperature and diluted with 10 mL of water and was extracted with ethyl acetate. The combined organic layers were washed with brine, dried over Na$_2$SO$_4$, filtered, and concentrated under reduced pressure to obtain the crude product (167 mg) as a brown color gum. m/z (ESI, +ve ion)=736.5 [M+H]+.

Step B: 2,5-Dimethoxy-4-((6-((1R,2S)-5'-methoxy-2'-oxospiro[cyclopropane-1,3'-indolin]-2-yl)-1H-indazol-3-yl)amino)benzenesulfonamide

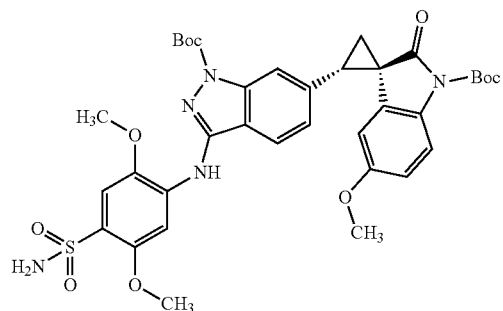

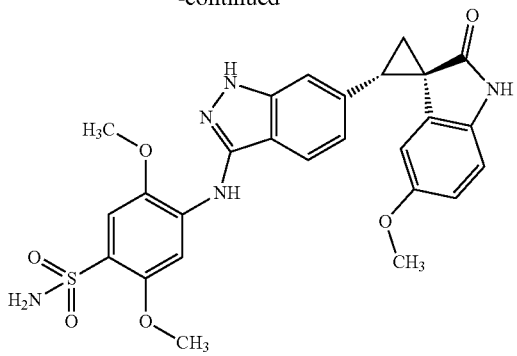

The crude material prepared above (167 mg) was dissolved in anhydrous dichloromethane (1.0 mL), cooled to 0° C., and trifluoroacetic acid (0.3 mL) was added dropwise. The reaction mixture was stirred at room temperature for 45 minutes, and concentrated under reduced pressure to obtain a crude product. The crude product was purified using reverse phase chromatography (2 to 50% MeCN in ammonium formate) to furnish the title compound (13.8 mg, 16%, 2 steps) as a white solid after lyophilization. m/z (ESI, +ve ion)=536.3 [M+H]+. 1H NMR (400 MHz, DMSO-d$_6$) δ 12.39 (s, 1H), 10.43 (s, 1H), 8.26 (s, 1H), 7.96 (s, 1H), 7.84 (d, J=8.4 Hz, 1H), 7.35 (s, 1H), 7.25 (s, 1H), 6.91 (d, J=8.2 Hz, 1H), 6.85 (s, 2H), 6.74 (d, J=8.4 Hz, 1H), 6.58 (dd, J=8.5, 2.6 Hz, 1H), 5.69 (d, J=2.5 Hz, 1H), 3.88 (s, 3H), 3.79 (s, 3H), 3.32 (s, 3H), 3.22-3.13 (m, 1H), 2.33 (dd, J=7.8, 4.8 Hz, 1H), 1.97 (dd, J=8.9, 4.6 Hz, 1H).

Example 228. (1R,2S)-2-(3-{[5-(Ethanesulfonyl)-3-methoxypyridin-2-yl]amino}-1H-indazol-6-yl)-5'-methoxyspiro[cyclopropane-1,3'-indol]-2'(1'H)-one

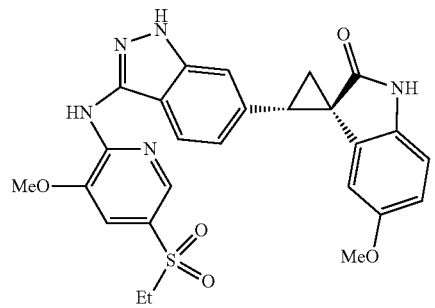 [SMILES: CCS(=O)(=O)c1cnc(Nc2n[nH]c3cc([C@@H]4C[C@@]45C(=O)Nc4ccc(OC)cc45)ccc23)c(OC)c1]

Step A.
5-(Ethanesulfonyl)-3-methoxypyridin-2-amine

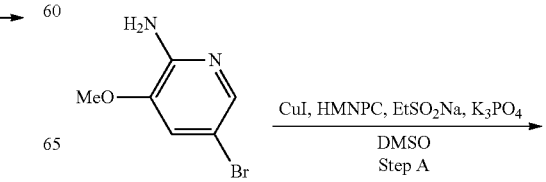

-continued

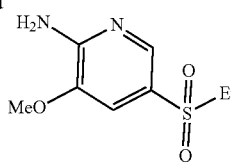

To a solution of 5-bromo-3-methoxypyridin-2-amine (7.0 g, 34 mmol, 1 equiv) and sodium ethanesulfinate (5.20 g, 44.8 mmol, 1.30 equiv) in DMSO (40 mL) was added CuI (0.66 g, 3.5 mmol, 0.1 equiv), (4R)-4-hydroxy-N-(2-methylnaphthalen-1-yl)pyrrolidine-2-carboxamide (0.93 g, 3.5 mmol, 0.1 equiv) and K₃PO₄ (7.32 g, 34.5 mmol, 1 equiv). After stirring for 16 h at 120° C. under a nitrogen atmosphere, the resulting mixture was diluted with water (200 mL). The resulting mixture was extracted with EtOAc (100 mL×3). The combined organic layers were washed with brine (100 mL×3), dried over anhydrous Na₂SO₄ and filtered. The filtrate was concentrated in vacuo. The residue was purified on silica gel column chromatography and eluted with 0-20% MeOH in DCM to afford the title compound (7.2 g, 97%) as a black solid. m/z (ESI +ve ion)=217.00 [M+H]⁺.

Step B. Tert-butyl (1R,2S)-2-[1-(tert-butoxycarbonyl)-3-{[5-(ethanesulfonyl)-3-methoxypyridin-2-yl]amino}indazol-6-yl]-5'-methoxy-2'-oxospiro[cyclopropane-1,3'-indole]-1'-carboxylate

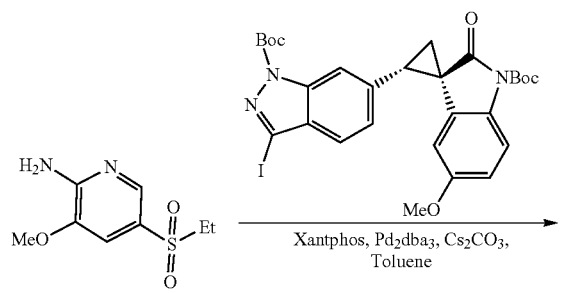

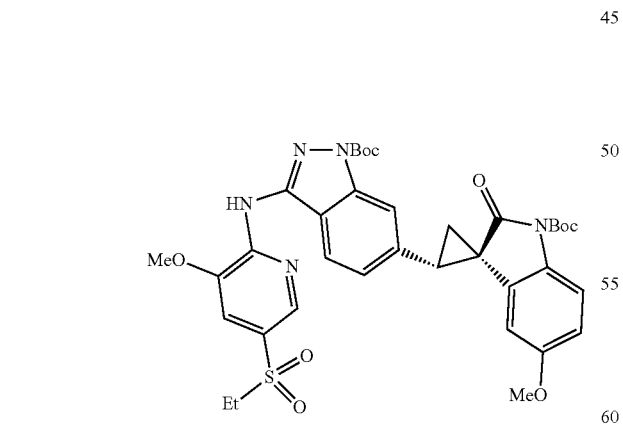

To a solution of 5-(ethanesulfonyl)-3-methoxypyridin-2-amine (2.71 g, 12.5 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (6.60 g, 10.5 mmol, 1.00 equiv) in toluene (130 mL) under a nitrogen atmosphere was added Pd₂(dba)₃ (1.91 g, 2.09 mmol, 0.2 equiv), XantPhos (1.21 g, 2.09 mmol, 0.2 equiv) and Cs₂CO₃ (6.81 g, 20.90 mmol, 2 equiv). After stirring for 1 h at 90° C. under a nitrogen atmosphere, the resulting mixture was cooled down to room temperature, filtered and washed with EtOAc (50 mL). The filtrate was concentrated under reduced pressure. The residue was purified on silica gel column chromatography and eluted with 0-100% EtOAc in PE to afford the title compound (6.2 g, 82%) as a yellow solid. m/z (ESI, +ve ion)=720.20 [M+H]⁺.

Step C. (1R,2S)-2-(3-{[5-(Ethanesulfonyl)-3-methoxypyridin-2-yl]amino}-1H-indazol-6-yl)-5'-methoxy-1'H-spiro[cyclopropane-1,3'-indol]-2'-one

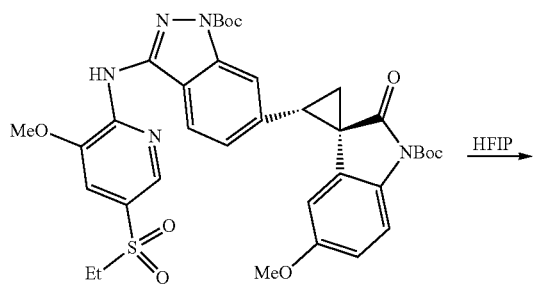

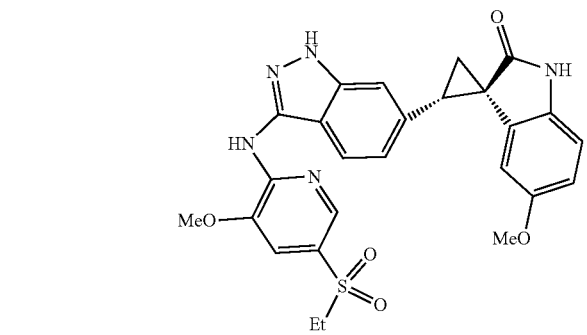

A solution of tert-butyl (1R,2S)-2-[1-(tert-butoxycarbonyl)-3-{[5-(ethanesulfonyl)-3-methoxypyridin-2-yl]amino}indazol-6-yl]-5'-methoxy-2'-oxospiro[cyclopropane-1,3'-indole]-1'-carboxylate (8.30 g, 11.5 mmol, 1 equiv) in 1,1,1,3,3,3-hexafluoropropan-2-ol (80 mL) was stirred for 16 h at 60° C. The resulting mixture was concentrated under reduced pressure. The residue was purified on silica gel column chromatography and eluted with 0-20% MeOH in DCM to afford the title compound (5.3 g, 88%) as a white solid. m/z (ESI, +ve ion)=520.20 [M+H]⁺. ¹H-NMR (400 MHz, DMSO-d) δ 12.67 (s, 1H), 10.41 (s, 1H), 9.16 (s, 1H), 7.92 (d, J=2.0 Hz, 1H), 7.44-7.39 (m, 3H), 6.91-6.89 (m, 1H), 6.75 (d, J=8.4 Hz, 1H), 6.61-6.58 (m, 1H), 5.72 (d, J=2.0 Hz, 1H), 3.99 (s, 3H), 3.34 (s, 3H), 3.32-3.29 (m, 2H), 3.21-3.18 (m, 1H), 2.34-2.31 (m, 1H), 2.01-1.97 (m, 1H), 1.13 (t, J=7.2 Hz, 3H).

Example 234. (1R,2S)-5'-Methoxy-2-(3-{[2-methoxy-5-(1,3-oxazol-2-yl)pyridin-3-yl]amino}-1H-indazol-6-yl)spiro[cyclopropane-1,3'-indol]-2'(1'H)-one

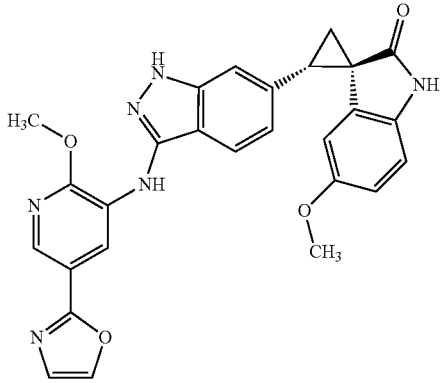 [SMILES: COc1ccc2c(c1)[C@]1(C[C@H]1c1ccc3c(Nc4cc(-c5ncco5)cnc4OC)n[nH]c3c1)C(=O)N2]

Step A: 5-Bromo-N-(2,2-dimethoxyethyl)-6-methoxynicotinamide

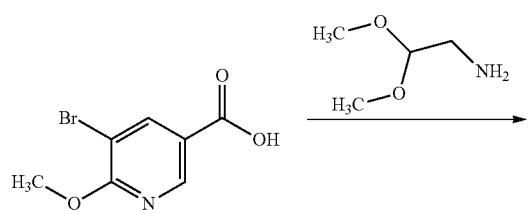

To an ice-cold solution of 5-bromo-6-methoxynicotinic acid (1.00 g, 4.18 mmol) in anhydrous tetrahydrofuran (10.0 mL) was added 4-methylmorpholine (693 µL, 6.27 mmol), isopropyl chloroformate solution (1M in toluene, 6.27 mL, 6.27 mmol) and aminoacetaldehyde dimethyl acetal (680 mg, 6.27 mmol). The reaction mixture was stirred at room temperature overnight. The mixture was diluted with water and the aqueous phase was extracted with ethyl acetate twice. The combined organic layers were washed with brine, dried over Na$_2$SO$_4$, filtered, and concentrated under reduced pressure to provide the title compound (1.36 g, 97%) as a white solid. The residue was used in the next step without further purification. m/z (ESI, +ve ion)=319.1 [M+H]+. 1H NMR (400 MHz, CDCl3) δ 8.49 (d, J=2.2 Hz, 1H), 8.23 (d, J=2.2 Hz, 1H), 6.54-5.97 (m, 1H), 4.42 (dt, J=43.0, 5.2 Hz, 1H), 4.05 (s, 3H), 3.59 (t, J=5.4 Hz, 2H), 3.43 (s, 6H).

Step B: 5-Bromo-6-methoxy-N-(2-oxoethyl)nicotinamide

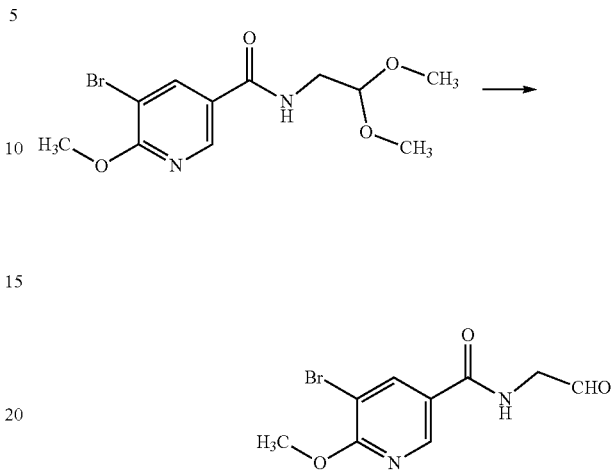

To an ice-cold solution of 5-bromo-N-(2,2-dimethoxyethyl)-6-methoxynicotinamide (500 mg, 1.57 mmol) in acetone (3.00 mL) was added water (0.75 mL) and hydrochloric acid (37%) (0.75 mL, 24.8 mmol). The reaction mixture was stirred at room temperature overnight. Then the reaction mixture was diluted with water and neutralized with saturated NaHCO$_3$ solution. The mixture was extracted with ethyl acetate. The combined organic layers were washed with brine, dried over Na$_2$SO$_4$, filtered, and concentrated under reduced pressure to obtain the title compound (383 mg, 48%) as a white solid. The residue was not purified further and used in the next step. m/z (ESI, +ve ion)=273.1 [M+H]+.

Step C: 2-(5-Bromo-6-methoxypyridin-3-yl)oxazole

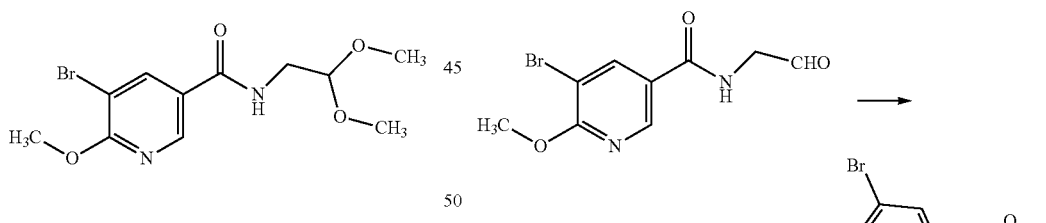

A mixture of 5-bromo-6-methoxy-N-(2-oxoethyl)nicotinamide (200 mg, 732 µmol), Burgess reagent (358 mg, 1.46 mmol), and tetrahydrofuran (5.00 mL) was stirred at 70° C. for 30 minutes. The reaction mixture was diluted with water (10 mL). The mixture was extracted with ethyl acetate. The combined organic layers were washed with brine, dried over Na$_2$SO$_4$, filtered, and concentrated to obtain a crude product. The crude product was purified by column chromatography (0 to 50% ethyl acetate in hexane) to afford the title compound (32.0 mg, 17%) as a white solid. 1H NMR (400 MHz, CDCl3) δ 8.76 (m, J=3.6 Hz, 1H), 8.46 (t, J=3.2 Hz, 1H), 7.72 (s, 1H), 7.25-7.20 (m, 1H), 4.08 (s, 3H).

Step D: Tert-butyl 6-((1R,2S)-1'-(tert-butoxycarbonyl)-5'-methoxy-2'-oxospiro[cyclopropane-1,3'-indolin]-2-yl)-3-((2-methoxy-5-(oxazol-2-yl)pyridin-3-yl)amino)-1H-indazole-1-carboxylate

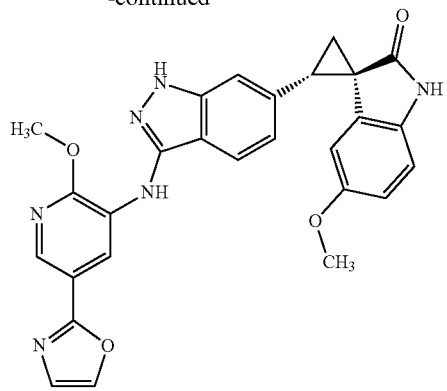

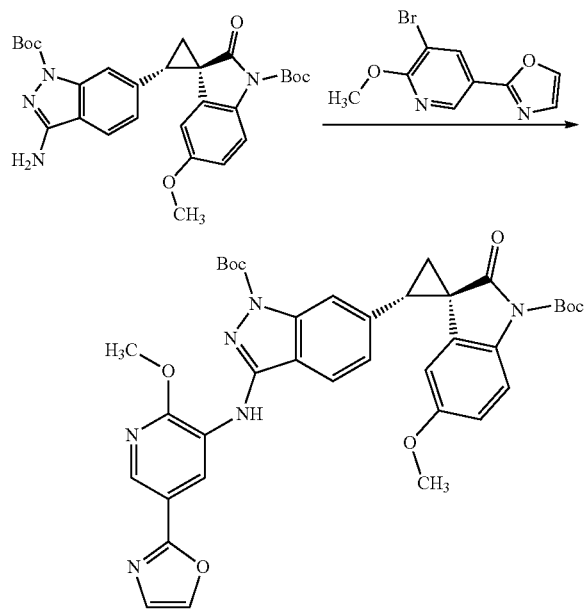

A 10-mL vial was charged with 2-(5-bromo-6-methoxypyridin-3-yl)oxazole (27.0 mg, 106 μmol), aminoindazole (intermediate 5) (32.4 mg, 62.3 μmol), 4,4-bis(diphenylphosphino)-9,9-dimethylxanthene (7.4 mg, 13 μmol), tris(dibenzylideneacetone)-dipalladium(0) (11.4 mg, 13 μmol), cesium carbonate (61.5 mg, 187 μmol) and dioxane (3.00 mL). The vial was bubbled with nitrogen for 5 minutes, sealed and the reaction mixture was stirred at 100° C. for 30 minutes. Then the mixture was cooled to room temperature and diluted with water. The mixture was extracted with ethyl acetate and the combined organic layers were washed with brine, dried over Na$_2$SO$_4$, filtered, and concentrated by rotary evaporation to obtain a crude product (60.0 mg). m/z (ESI, +ve ion)=695.5 [M+H]+.

Step E: Tert-butyl 6-((1R,2S)-1'-(tert-butoxycarbonyl)-5'-methoxy-2'-oxospiro[cyclopropane-1,3'-indolin]-2-yl)-3-((2-methoxy-5-(oxazol-2-yl)pyridin-3-yl)amino)-1H-indazole-1-carboxylate

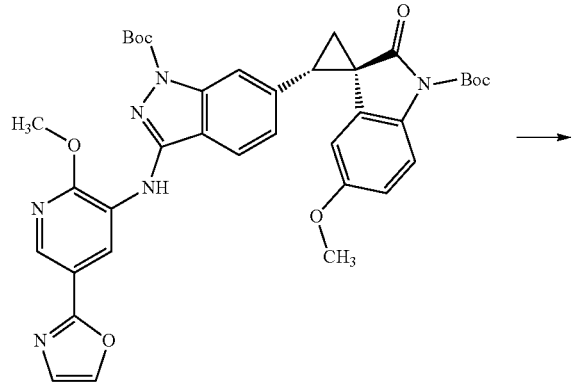

Tert-butyl 6-((1R,2S)-1'-(tert-butoxycarbonyl)-5'-methoxy-2'-oxospiro[cyclopropane-1,3'-indolin]-2-yl)-3-((2-methoxy-5-(oxazol-2-yl)pyridin-3-yl)amino)-1H-indazole-1-carboxylate (60.0 mg) was dissolved in anhydrous DCM (1.00 mL), cooled to 0° C., and trifluoroacetic acid (500 uL) was added dropwise. The reaction mixture was stirred at room temperature for 15 minutes. The reaction mixture was concentrated under reduced pressure. The product was purified by reverse phase chromatography (5 to 50% MeCN in ammonium formate buffer) to afford the title compound (16.8 mg, 54%, 2 steps) as a white solid. m/z (ESI, +ve ion)=495.3 [M+H]+. 1H NMR (400 MHz, DMSO-d$_6$) δ 12.34 (s, 1H), 10.43 (s, 1H), 9.07 (d, J 2.0, 1H), 8.37 (s, 1H), 8.25 (d, J 2.0, 1H), 8.21 (s, 1H), 7.97 (d, J 8.4, 1H), 7.36 (s, 2H), 6.91 (d, J 8.4, 1H), 6.74 (d, J 8.4, 1H), 6.58 (dd, J 8.4, 2.5, 1H), 5.71 (d, J 2.4, 1H), 4.07 (s, 3H), 3.31 (s, 3H), 3.23-3.09 (m, 1H), 2.35 (dd, J 8.0, 4.8, 1H), 2.07-1.93 (m, 1H).

Example 248. (1R,2S)-5'-Methoxy-2-(3-{[3-methoxy-5-(propane-2-sulfonyl)pyridin-2-yl]amino}-1H-indazol-6-yl)spiro[cyclopropane-1,3'-indol]-2'(1'H)-one

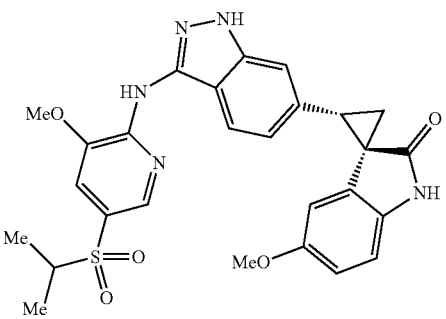 [SMILES: COc1ccc2c(c1)[C@]1(C[C@H]1c1ccc3c(Nc4ncc(S(=O)(=O)C(C)C)cc4OC)n[nH]c3c1)C(=O)N2]

Step A.
3-Methoxy-5-(propane-2-sulfonyl)pyridin-2-amine

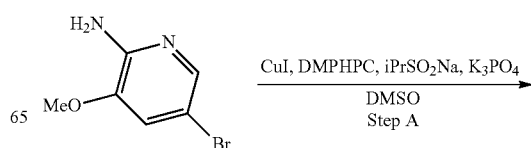

-continued

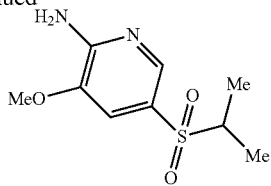

To a stirred mixture of 5-bromo-3-methoxypyridin-2-amine (200 mg, 0.985 mmol, 1 equiv) and (2S,4R)—N-(2,6-dimethylphenyl)-4-hydroxypyrrolidine-2-carboxamide (46.16 mg, 0.197 mmol, 0.2 equiv) in DMSO (4 mL) was added CuI (37.52 mg, 0.197 mmol, 0.2 equiv), sodium propane-2-sulfinate (166.65 mg, 1.280 mmol, 1.3 equiv) and K₃PO₄ (209.09 mg, 0.985 mmol, 1 equiv) at room temperature under nitrogen atmosphere. The mixture was stirred at 120° C. for 16 h. After cooling to room temperature, the mixture was diluted with water (20 mL). The resulting mixture solution was extracted with EtOAc (20 mL×3). The combined organic layers were washed with brine (50 mL×2), dried over anhydrous Na₂SO₄. After filtration, the filtrate was concentrated under reduced pressure. The residue was purified by silica gel column chromatography and eluted with 0-10% of MeOH in DCM to afford the title compound (120 mg, 53%) as a light yellow solid. m/z (ESI, +ve ion)=231.05 [M+H]⁺.

Step B. Tert-butyl (1R,2S)-2-[1-(tert-butoxycarbonyl)-3-{[3-methoxy-5-(propane-2-sulfonyl)pyridin-2-yl]amino}indazol-6-yl]-5'-methoxy-2'-oxospiro[cyclopropane-1,3'-indole]-1'-carboxylate

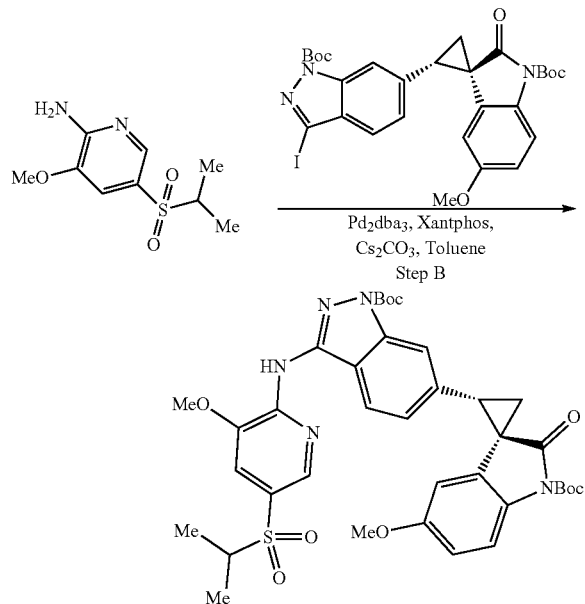

To a stirred solution of 3-methoxy-5-(propane-2-sulfonyl)pyridin-2-amine (43.76 mg, 0.190 mmol, 1.00 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (120.00 mg, 0.190 mmol, 1.00 equiv) in toluene (5.00 mL) was added Pd₂(dba)₃ (17.40 mg, 0.019 mmol, 0.10 equiv) and XantPhos (11.00 mg, 0.019 mmol, 0.10 equiv) and Cs₂CO₃ (123.83 mg, 0.380 mmol, 2.00 equiv) at room temperature under nitrogen atmosphere. The resulting mixture was stirred for 2 h at 90° C. under nitrogen atmosphere. The mixture was allowed to cool down to room temperature. The resulting mixture was filtered and the filter cake was washed with EtOAc (3×30 mL). The filtrate was concentrated under reduced pressure. The residue was purified by silica gel column chromatography and eluted with PE:EtOAc (1:1) to afford the title compound (82.00 mg, 59%) as a yellow solid. m/z (ESI+ve ion)=734.25 [M+H]⁺.

Step C. (1R,2S)-5'-Methoxy-2-(3-{[3-methoxy-5-(propane-2-sulfonyl)pyridin-2-yl]amino}-1H-indazol-6-yl)-1'H-spiro[cyclopropane-1,3'-indol]-2'-one

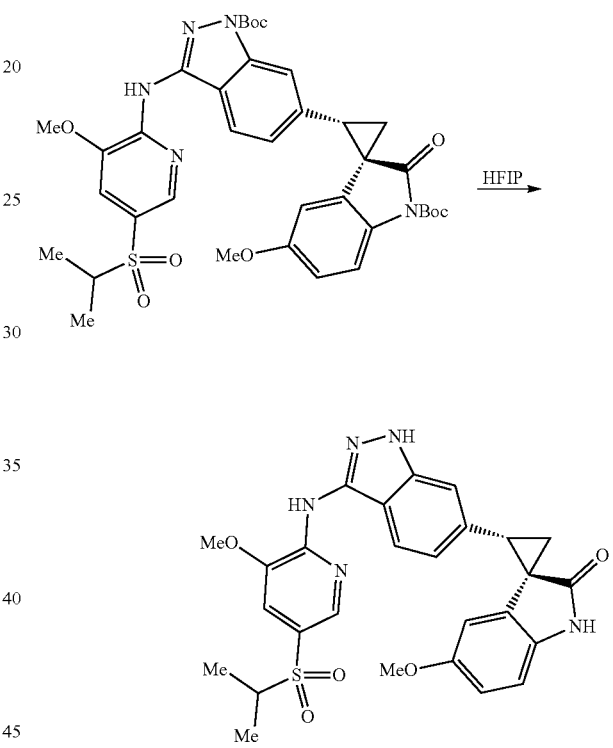

A solution of tert-butyl (1R,2S)-2-[1-(tert-butoxycarbonyl)-3-{[3-methoxy-5-(propane-2-sulfonyl)pyridin-2-yl]amino}indazol-6-yl]-5'-methoxy-2'-oxospiro[cyclopropane-1,3'-indole]-1'-carboxylate (80.00 mg, 0.109 mmol, 1.00 equiv) in HFIP (5.00 mL) was stirred for 16 h at 60° C. under nitrogen atmosphere. The mixture was allowed to cool to room temperature. The resulting mixture was concentrated under reduced pressure. The crude product (40 mg) was purified by prep-HPLC with the following conditions (Column: XBridge Shield RP18 OBD Column, 30×150 mm, 5 μm; Mobile Phase A: water (10 mmol/L NH₄HCO₃), Mobile Phase B: ACN; Flow rate: 60 mL/min; Gradient: 31% B to 41% B in 10 min, 41% B; Wavelength: 254 nm; RT1(min): 7.98 to afford the title compound (28.50 mg, 49%) as a white solid. m/z (ESI, +ve ion)=534.15 [M+H]⁺. ¹H-NMR (400 MHz, Methanol-d₄) δ 8.02 (d, J=2.0 Hz, 1H), 7.59 (d, J=8.4 Hz, 1H), 7.44 (d, J=2.0 Hz, 2H), 6.96 (d, J=8.8 Hz, 1H), 6.84 (d, J=8.4 Hz, 1H), 6.65-6.62 (m, 1H), 5.65 (d, J=2.4 Hz, 1H), 4.07 (s, 3H), 3.38 (d, J=7.6 Hz, 5H), 2.27-2.24 (m, 1H), 2.21-2.17 (m, 1H), 1.31 (d, J=6.8 Hz, 6H).

Example 258. (1R,2S)-2-(3-{[5-(Cyclopropane-sulfonyl)-3-methoxypyridin-2-yl]amino}-1H-indazol-6-yl)-5'-methoxyspiro[cyclopropane-1,3'-indol]-2'(1'H)-one

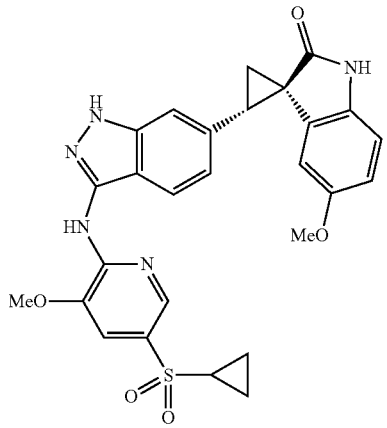 [SMILES: COc1ccc2c(c1)[C@]1(C[C@H]1c1ccc3c(Nc4ncc(S(=O)(=O)C5CC5)cc4OC)n[nH]c3c1)C(=O)N2]

Step A.
5-(Cyclopropanesulfonyl)-3-methoxypyridin-2-amine

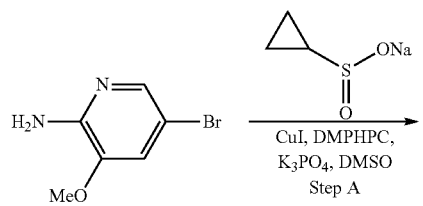

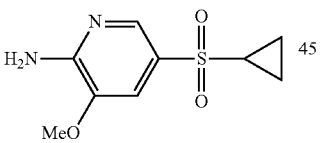

To a stirred mixture of 5-bromo-3-methoxypyridin-2-amine (200 mg, 0.985 mmol, 1 equiv) and sodium cyclopropanesulfinate (151 mg, 1.18 mmol, 1.2 equiv) in DMSO (5 mL) was added 4-hydroxy-L-proline-derived 2,6-dimethyl-aniline amide DMPHPC (CAS: 2227488-62-0, 10.1 mg, 0.099 mmol, 0.1 equiv), CuI (18.8 mg, 0.10 mmol, 0.1 equiv) and K₃PO₄ (209 mg, 0.99 mmol, 1 equiv) at room temperature under nitrogen atmosphere. The resulting mixture was stirred for 16 h at 120° C. under nitrogen atmosphere. The mixture was allowed to cool to room temperature. Water (50 mL) was added and the resulting mixture was extracted with EtOAc (20 mL×3). The combined organic layers were washed with brine (20 mL×3), dried over anhydrous Na₂SO₄ and concentrated under reduced pressure. The residue was purified by prep-TLC (PE:EtOAc 1:1) to afford the title compound (180 mg, 80%) as a yellow solid. m/z (ESI, +ve ion)=229.00 [M+H]⁺.

Step B. Tert-butyl (1R,2S)-2-[1-(tert-butoxycarbonyl)-3-{[5-(cyclopropanesulfonyl)-3-methoxypyridin-2-yl]amino}indazol-6-yl]-5'-methoxy-2'-oxospiro[cyclopropane-1,3'-indole]-1'-carboxylate

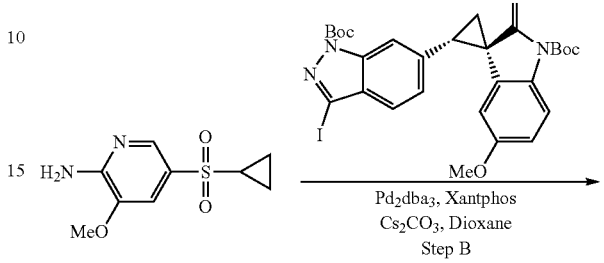

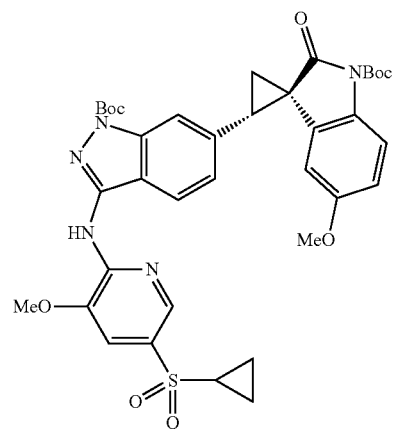

To a mixture of 5-(cyclopropanesulfonyl)-3-methoxypyridin-2-amine (43.4 mg, 0.190 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) in toluene (5 mL) was added Pd₂(dba)₃ (29.0 mg, 0.032 mmol, 0.2 equiv), XantPhos (18.3 mg, 0.032 mmol, 0.2 equiv) and Cs₂CO₃ (103 mg, 0.316 mmol, 2 equiv) at room temperature under nitrogen atmosphere. The resulting mixture was stirred for 2 h at 90° C. under nitrogen atmosphere. The mixture was allowed to cool to room temperature. The resulting mixture was concentrated under reduced pressure. The residue was purified by Prep-TLC (PE/EA 1:1) to afford the title compound (95 mg, 82%) as a yellow solid. m/z (ESI, +ve ion)=732.30 [M+H]⁺.

Step C. (1R,2S)-2-(3-{[5-cyclopropanesulfonyl)-3-methoxypyridin-2-yl]amino}-1H-indazol-6-yl)-5'-methoxy-1'H-spiro[cyclopropane-1,3'-indol]-2'-one

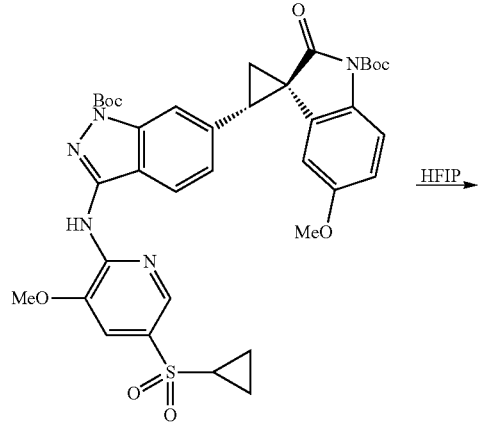

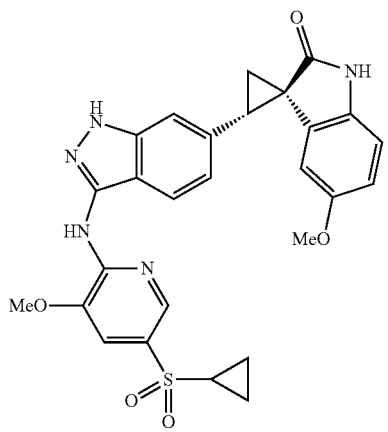

Into an 8 mL vial was added tert-butyl (1R,2S)-2-[1-(tert-butoxycarbonyl)-3-{[5-(cyclopropanesulfonyl)-3-methoxypyridin-2-yl]amino}indazol-6-yl]-5'-methoxy-2'-oxospiro[cyclopropane-1,3'-indole]-1'-carboxylate (95 mg, 0.130 mmol, 1 equiv) and HFIP (5 mL) at room temperature. The resulting mixture was stirred for 16 h at 60° C. under nitrogen atmosphere. The mixture was allowed to cool to mom temperature. The solvent was removed under reduced pressure. The crude product was purified by prep-HPLC with the following conditions: Column: XBridge Shield RP18 OBD Column, 19×250 mm, 10 μm; Mobile Phase A: water (10 mmol/L NH$_4$HCO$_3$), Mobile Phase B: ACN; Flow rate: 25 mL/min; Gradient: 35% B to 50% B in 8 min, 50% B; Wavelength: 254 nm; RT1(min): 7.8 to afford the title compound (30.2 mg, 43.76%) as a white solid. m/z (ESI, +ve ion)=532.20 [M+H]$^+$. $^1$H NMR (400 MHz, DMSO-d$_6$) δ 12.67 (s, 1H), 10.42 (s, 1H), 9.14 (s, 1H), 7.94 (s, 1H), 7.45-7.40 (m, 3H), 6.90 (d, J=8.4 Hz, 1H), 6.75 (d, J=8.4 Hz, 1H), 6.61-6.58 (m, 1H), 5.73 (d, J=2.0 Hz, 1H), 4.00 (s, 3H), 3.34-3.30 (m, 3H), 3.21-3.17 (m, 1H), 2.89-2.85 (m, 1H), 2.35-2.32 (m, 1H), 2.0)-1.97 (m, 1H), 1.12-1.11 (m, 2H), 1.11-1.04 (m, 2H).

Example 272. (1R,2S)-2-{3-[2-Ethoxy-4-(methanesulfonyl)anilino]-1H-indazol-6-yl}-5'-methoxyspiro[cyclopropane-1,3'-indol]-2'(1'H)-one

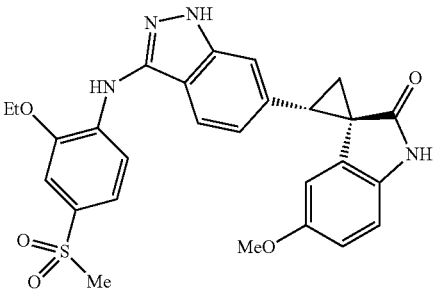 [SMILES: CCOc1cc(S(C)(=O)=O)ccc1Nc1n[nH]c2cc([C@@H]3C[C@@]34C(=O)Nc3ccc(OC)cc34)ccc12]

Step A. 4-Bromo-2-ethoxyaniline

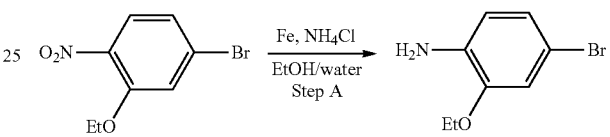

Into a 40 mL vial was added 4-bromo-2-ethoxy-1-nitrobenzene (500 mg, 2.032 mmol, 1 equiv), iron (567 mg, 10.2 mmol, 5 equiv) and NH$_4$Cl (544 mg, 10.2 mmol, 5 equiv) at 25° C. To the mixture was added water (2 mL) and ethyl alcohol (8 mL) at 25° C. under nitrogen atmosphere. The resulting mixture was stirred for additional 2 hours at 25° C. The mixture was filtered and the filter cake was washed with EtOAc (3×10 mL). The solvents were removed under reduced pressure. Water (10 mL) was added and the resulting mixture was extracted with EtOAc (3×10 mL). The combined organic layers were washed with brine (10 mL) and dried over anhydrous Na$_2$SO$_4$. After filtration, the filtrate was concentrated under reduced pressure. The residue was purified by silica gel column chromatography that was eluted with PE:EtOAc (3:1) to afford the title compound (411 mg, 94%) as a brown oil. m/z (ESI+ve ion)=216.00, 218.00 [M+H]$^+$.

Step B. 2-Ethoxy-4-methanesulfonylaniline

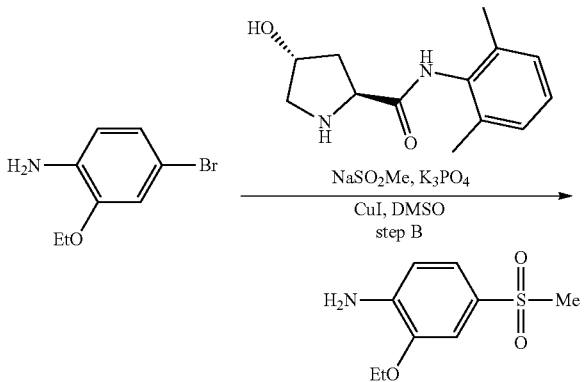

Into a 20 mL vial was added 4-bromo-2-ethoxyaniline (200 mg, 0.926 mmol, 1 equiv) and sodium methanesulfinate (122.84 mg, 1.204 mmol, 1.3 equiv), K$_3$PO$_4$ (295 mg, 1.39 mmol, 1.5 equiv), CuI (35.26 mg, 0.185 mmol, 0.2 equiv), (2S,4R)—N-(2,6-dimethylphenyl)-4-hydroxypyrrolidine-2-carboxamide (21.66 mg, 0.093 mmol, 0.10 equiv), and DMSO (5 mL) at 25° C. The resulting mixture was stirred for 16 h at 120° C. under nitrogen atmosphere. The mixture was filtered and the filter cake was washed with EtOAc (3×10 mL). The filtrate was concentrated under reduced pressure. The residue was purified by silica gel column chromatography that eluted with 0-100% EtOAc in PE to afford the title compound (120 mg, 60%) as a light yellow solid. m/z (ESI, +ve ion)=214.00 [M−H]

Step C. Tert-butyl (1R,2S)-2-[1-(tert-butoxycarbonyl)-3-[(2-ethoxy-4-methanesulfonylphenyl)amino]indazol-6-yl]-5'-methoxy-2'-oxospiro[cyclopropane-1,3'-indole]-1'-carboxylate

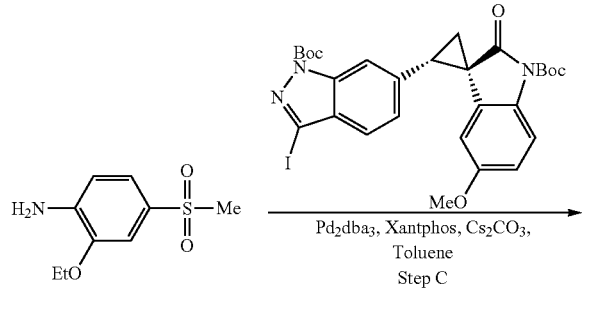

Into a 20 mL vial was added tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1 equiv), 2-ethoxy-4-methanesulfonylaniline (40.91 mg, 0.190 mmol, 1.2 equiv), Pd$_2$(dba)$_3$ (29.00 mg, 0.032 mmol, 0.2 equiv), XantPhos (18.33 mg, 0.032 mmol, 0.2 equiv), Cs$_2$CO$_3$ (103.19 mg, 0.316 mmol, 2 equiv) and toluene (2.5 mL) at 25° C. The resulting mixture was stirred for an additional 2 h at 90° C. under nitrogen atmosphere. The mixture was filtered and washed with EtOAc (3×10 mL). The filtrate was concentrated in vacuo. The residue was purified by silica gel column chromatography that eluted with PE:EtOAc (1:1) to afford the title compound (73 mg, 64%) as a light yellow solid. m/z (ESI, +ve ion)=717.25 [M−H]$^-$.

Step D. (1R,2S)-2-{3-[(2-Ethoxy-4-methanesulfonylphenyl)amino]-1H-indazol-6-yl}-5'-methoxy-1'H-spiro[cyclopropane-1,3'-indol]-2'-one

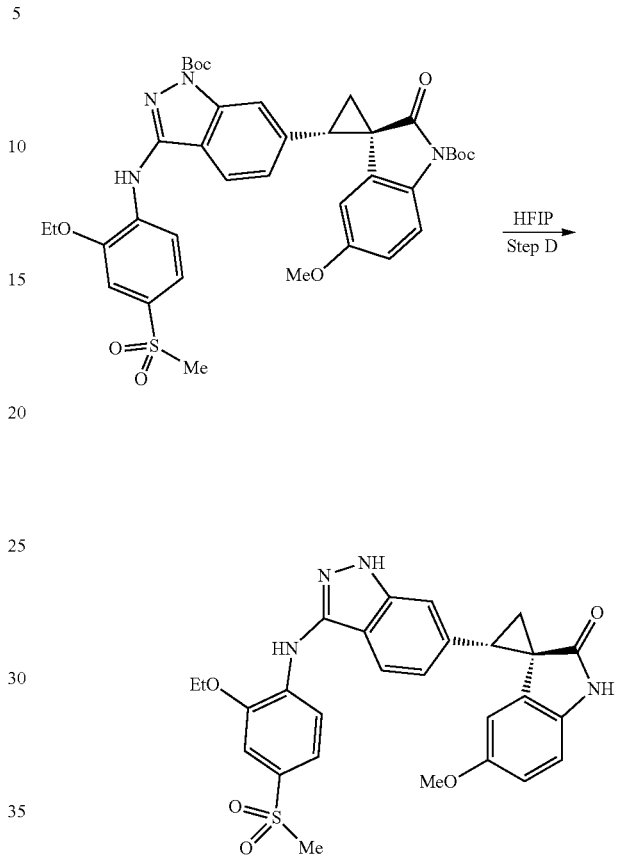

A mixture of tert-butyl (1R,2S)-2-[1-(tert-butoxycarbonyl)-3-[(2-ethoxy-4-methanesulfonylphenyl)amino]indazol-6-yl]-5'-methoxy-2'-oxospiro[cyclopropane-1,3'-indole]-1'-carboxylate (100 mg, 0.139 mmol, 1 equiv) in HFIP (5 mL) was stirred at 60° C. for 16 h. The mixture was allowed to cool to room temperature. The resulting mixture was concentrated under reduced pressure. The crude product was purified by prep-HPLC with the following conditions (Column: XBridge Prep OBD C18 Column, 30×150 mm, 5 μm; Mobile Phase A: water (10 mmol/L NH$_4$HCO$_3$), Mobile Phase B: ACN; Flow rate: 60 mL/min; Gradient: 36% B to 44% B in 8 min, 44% B; Wavelength: 254 nm; RT1(min): 7.70) to afford the title compound (30.5 mg, 42.23%) as a white solid. m/z (ESI, +ve ion)=519.15 [M+H]$^+$. $^1$H NMR (400 MHz, DMSO-d$_6$) δ 12.42 (s, 1H), 10.43 (s, 1H), 8.18 (s, 1H), 7.99 (d, J=8.4 Hz, 1H), 7.73 (d, J=8.4 Hz, 1H), 7.43-7.39 (m, 3H), 6.93 (d, J=8.4 Hz, 1H), 6.76 (d, J=8.4 Hz, 1H), 6.60-6.58 (m, 1H), 5.69 (d, J=2.4 Hz, 1H), 4.29-4.24 (m, 2H), 3.325 (s, 3H), 3.20 (t, J=8.5 Hz, 1H), 3.15 (s, 3H), 2.35-2.32 (m, 1H), 2.01-1.99 (m, 1H), 1.48 (t, J=7.2 Hz, 3H).

Example 274. (1R,2S)-2-(3-{[5-(Ethanesulfonyl)-3-ethoxypyridin-2-yl]amino}-1H-indazol-4-yl)-5'-methoxyspiro[cyclopropane-1,3'-indol]-2'(1'H)-one

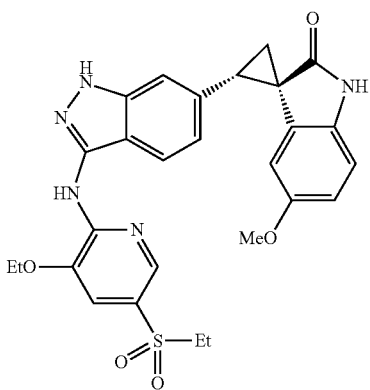 [SMILES: CCOc1cc(S(=O)(=O)CC)cnc1Nc1n[nH]c2cc([C@@H]3C[C@@]34C(=O)Nc3ccc(OC)cc34)ccc12]

Step A. 5-(Ethanesulfonyl)-3-ethoxypyridin-2-amine

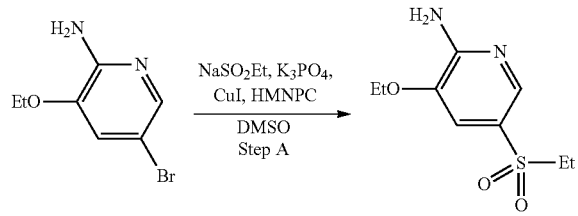 [SMILES: CCOc1cc(Br)cnc1N ; CCOc1cc(S(=O)(=O)CC)cnc1N]

To a stirred solution of 5-bromo-3-ethoxypyridin-2-amine (163 mg, 0.751 mmol, 1 equiv) and (2S,4R)-4-hydroxy-N-(2-methylnaphthalen-1-yl)pyrrolidine-2-carboxamide (20.30 mg, 0.075 mmol, 0.1 equiv) in DMSO (2 mL) was added sodium ethanesulfinate (113.35 mg, 0.976 mmol, 1.3 equiv), CuI (14.30 mg, 0.075 mmol, 0.1 equiv) and K$_3$PO$_4$ (159.39 mg, 0.751 mmol, 1 equiv) at 20° C. under nitrogen atmosphere. The resulting mixture was stirred for 16 h at 120° C. under nitrogen atmosphere. The mixture was allowed to cool to room temperature. The residue was purified by reverse flash chromatography with the following conditions: column, C18 silica gel; mobile phase, MeCN in Water (10 mmol/L NH$_4$HCO$_3$), 10% to 50% gradient in 10 min; detector, UV 254 nm. The mixture was concentrated under reduced pressure to afford the title compound (150 mg, 87%) as a yellow solid. m/z (ESI+ve ion)=231.10 [M+H]$^+$ Step B. Tert-butyl (1R,2S)-2-[1-(tert-butoxycarbonyl)-3-{[5-(ethanesulfonyl)-3-ethoxypyridin-2-yl]amino}indazol-6-yl]-5'-methoxy-2'-oxospiro[cyclopropane-1,3'-indole]-1'-carboxylate

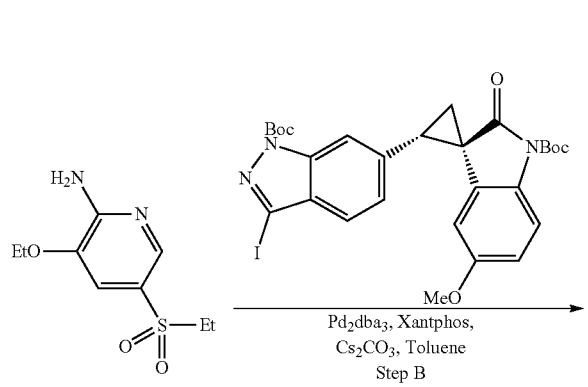

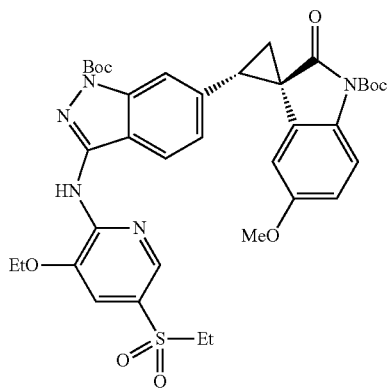

To a stirred mixture of 5-(ethanesulfonyl)-3-ethoxypyridin-2-amine (40.11 mg, 0.174 mmol, 1.1 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) and Cs$_2$CO$_3$ (103.19 mg, 0.316 mmol, 2.0 equiv) was added Pd$_2$(dba)$_3$ (29.00 mg, 0.032 mmol, 0.2 equiv) and XantPhos (18.33 mg, 0.032 mmol, 0.2 equiv) in toluene (4 mL) at room temperature under nitrogen atmosphere. The resulting mixture was stirred for 2 h at 90° C. under nitrogen atmosphere. The reaction mixture was concentrated under reduced pressure. The residue was purified by prep-TLC (PE:EtOAc 1:2) to afford the title compound (100 mg, 81%) as a light yellow oil. m/z (ESI+ve ion)=734.30 [M+H]$^+$ Step C. (1R,2S)-2-(3-{[5-(Ethansulfonyl)-3-ethoxypyridin-2-yl]amino}-1H-indazol-6-yl)-5'-methoxy-1'H-spiro[cyclopropane-1,3'-indol]-2'-one

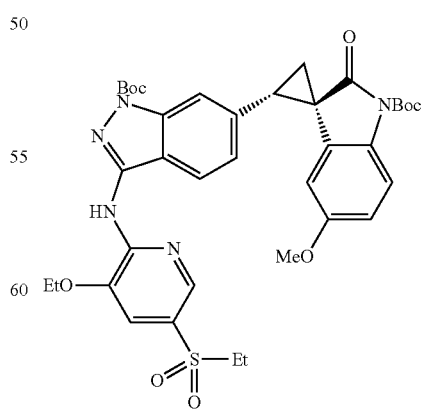

611
-continued

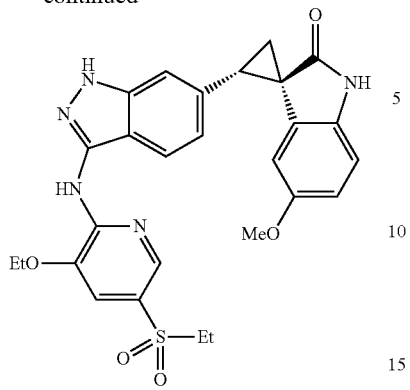

A solution of tert-butyl (1R,2S)-2-[1-(tert-butoxycarbonyl)-3-{[5-(ethanesulfonyl)-3-ethoxypyridin-2-yl]amino}indazol-6-yl]-5'-methoxy-2'-oxospiro[cyclopropane-1,3'-indole]-1'-carboxylate (100 mg, 0.136 mmol, 1 equiv) in HFIP (3 mL) was stirred overnight at 60° C. under nitrogen atmosphere. The resulting mixture was concentrated under reduced pressure. The crude product (70 mg) was purified by prep-HPLC with the following conditions (Column: XBridge Prep OBD C18 Column, 30×150 mm, 5 μm; Mobile Phase A: water (10 mmol/L NH$_4$HCO$_3$), Mobile Phase B: ACN; Flow rate: 60 mL/min; Gradient: 32% B to 40% B in 10 min, 40% B; Wavelength: 254 nm. RT1(min): 6.78) to afford the title compound (23.2 mg, 32%) as a light yellow solid. m/z (ESI, +ve ion)=534.25 [M+H]$^1$H NMR (400 MHz, DMSO-d$_6$) δ 12.68 (s, 1H), 10.41 (s, 1H), 9.07 (s, 1H), 7.91 (d, J=1.9 Hz, 1H), 7.41 (dd, J=5.0, 2.9 Hz, 3H), 6.90 (d, J=8.4 Hz, 1H), 6.75 (d, J=8.4 Hz, 1H), 6.59 (dd, J=8.4, 2.6 Hz, 1H), 5.73 (d, J=2.6 Hz, 1H), 4.25 (q, J=6.9 Hz, 2H), 3.34 (s, 3H), 3.27 (d, J=7.2 Hz, 2H), 3.20 (t, J=8.4 Hz, 1H), 2.33 (dd. J=8.0, 4.6 Hz, 1H), 1.99 (dd, J=9.0, 4.7 Hz, 1H), 1.45 (t, J=6.9 Hz, 3H), 1.13 (t, J=7.3 Hz, 3H).

Example 276. (1R,2S)-5'-chloro-2-(3-{[3-ethoxy-5-(methanesulfonyl)pyridin-2-yl]amino}-1H-indazol-6-yl)spiro[cyclopropane-1,3'-indol]-2'(1'H)-one

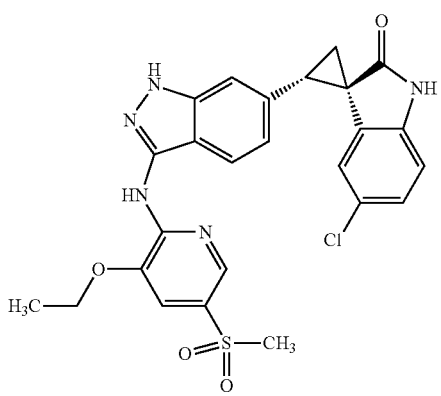 [SMILES: CCOc1cc(S(C)(=O)=O)cnc1Nc1n[nH]c2cc([C@@H]3C[C@@]34C(=O)Nc3ccc(Cl)cc34)ccc12]

612
Step A. tert-butyl 5-chloro-2-oxoindoline-1-carboxylate

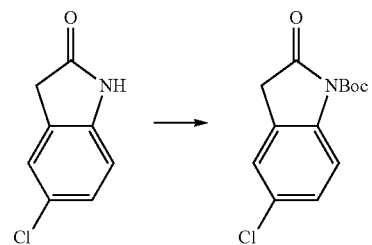 [SMILES: O=C1Cc2cc(Cl)ccc2N1 ; CC(C)(C)OC(=O)N1C(=O)Cc2cc(Cl)ccc21]

To a 100 mL round-bottom flask was added 5-chloro-2-oxindole (500 mg, 2.98 mmol) in THF (15 mL). Next, sodium carbonate (2.85 g, 26.85 mmol) followed by di-tert-butyl dicarbonate (1.71 mL, 7.46 mmol) were added. The flask was equipped with a Findenser™, heated to 70° C. and stirred for 1 h. The reaction was allowed to cool to room temperature. The reaction mixture was filtered through a plug of Celite eluting with EtOAc (×3) and then the filtrate was concentrated in vacuo. The crude residue was purified by flash column chromatography (0-25% EtOAc in hexanes) to give the title compound as a light brown-orange solid (449.5 mg, 56.3%). $^1$H NMR (400 MHz, CDCl$_3$) δ 7.75 (d, J=8.3 Hz, 1H), 7.28 (s, 1H), 7.23 (s, 1H), 3.64 (s, 2H), 1.63 (s, 9H).

Step B. tert-butyl (1R,2S)-2-(1-(tert-butoxycarbonyl)-3-iodo-1H-indazol-6-yl)-5'-chloro-2'-oxospiro[cyclopropane-1,3'-indoline]-1'-carboxylate

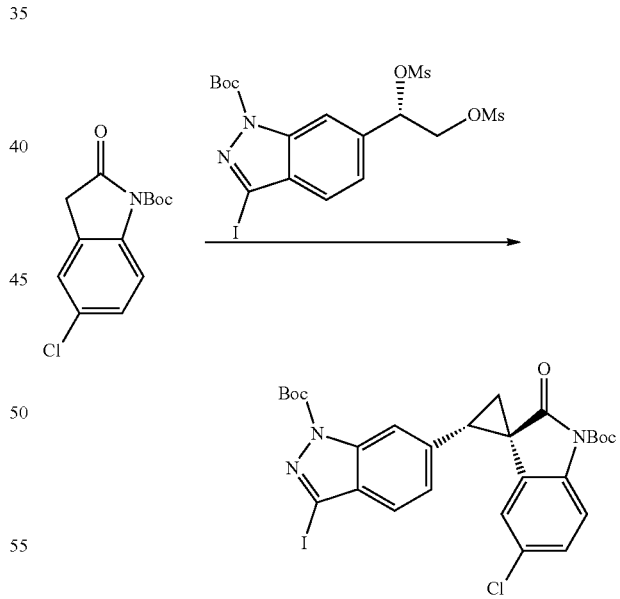

To a 20 mL vial, was added tert-butyl 5-chloro-2-oxoindoline-1-carboxylate (159.4 mg, 0.6 mmol) and tert-butyl (S)-6-(1,2-bis((methylsulfonyl)oxy)ethyl)-3-iodo-1H-indazole-1-carboxylate (333.7 mg, 0.6 mmol) in THF (6 mL). Next, cesium carbonate (582 mg, 1.79 mmol) was added. The reaction was stirred at room temperature for 3 h. The reaction mixture was quenched with sat. ammonium chloride and extracted with EtOAc (×3). The combined organic extracts were washed with brine, dried over sodium sulfate, filtered and the filtrate was concentrated in vacuo. The crude residue was purified by flash column chromatography (0-40% EtOAc in hexanes) to give a diastereomeric mixture of the title compound as a clear film (42.5 mg, 11.2%). LCMS: m/z (ESI, +ve ion)=435.9 [M−2Boc+H]⁺

Step C. tert-butyl (1R,2S)-2-(1-(tert-butoxycarbonyl)-3-((3-ethoxy-5-(methylsulfonyl)pyridin-2-yl)amino)-1H-indazol-6-yl)-5'-chloro-2'-oxospiro[cyclopropane-1,3'-indoline]-1'-carboxylate

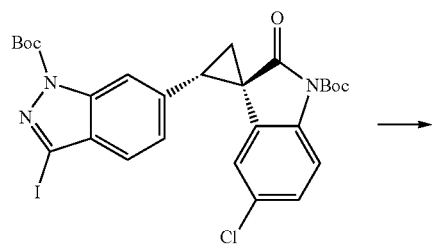

To a 4 mL vial was added a diastereomeric mixture of tert-butyl (1R,2S)-2-(1-tert-butoxycarbonyl-3-iodo-indazol-6-yl)-5'-chloro-2'-oxo-spiro[cyclopropane-1,3'-indoline]-1'-carboxylate (59.9 mg, 0.09 mmol), 3-ethoxy-5-methylsulfonyl-pyridin-2-amine (24.5 mg, 0.11 mmol), Xantphos (10.9 mg, 0.02 mmol), cesium carbonate (61.4 mg, 0.19 mmol) and tris(dibenzylideneacetone)dipalladium(0) (17.3 mg, 0.02 mmol) in dry toluene (1.9 mL). Argon was bubbled through the solution for 5 min then the reaction mixture was heated to 90° C. for 2 h. The reaction mixture was allowed to cool to room temperature. The reaction mixture was diluted with DCM, filtered through a plug of Celite eluting with DCM (3×), and then the filtrate was concentrated in vacuo. The crude residue was purified by flash column chromatography (0-100% acetone in hexanes) to give a diastereomeric mixture of the title compound as a brown solid (30.3 mg, 44.4%). LCMS: m/z (ESI, +ve ion)=624.2 [M−Boc+H]⁺

Step D. (1R,2S)-5'-chloro-2-(3-((3-ethoxy-5-(methylsulfonyl)pyridin-2-yl)amino)-1H-indazol-6-yl)spiro[cyclopropane-1,3'-indolin]-2'-one

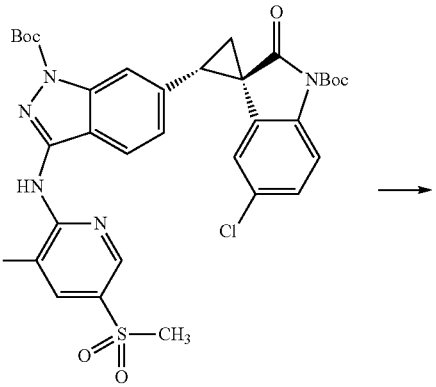

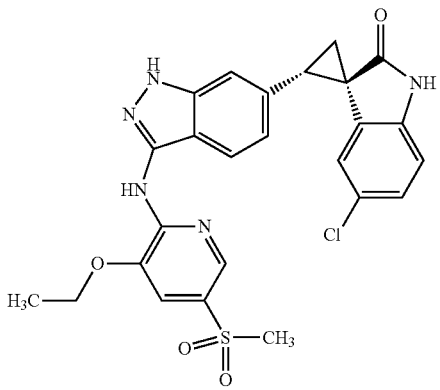

To a 20 ml vial, was added a diastereomeric mixture of tert-butyl (1R,2S)-2-[1-tert-butoxycarbonyl-3-[(3-ethoxy-5-methylsulfonyl-2-pyridyl)amino]indazol-6-yl]-5'-chloro-2'-oxo-spiro[cyclopropane-1,3'-indoline]-1'-carboxylate (30.3 mg, 0.04 mmol) in hexafluoro-2-propanol (3 mL, 0.04 mmol). The reaction was heated to 60° C. and stirred overnight. The reaction was allowed to cool to room temperature. The solvent was removed under reduced pressure. The crude residue was dissolved in MeCN:H₂O and then purified by RP-HPLC (Interchim) using water (00 mM ammonium bicarbonate):acetonitrile (20% to 65% MeCN over 30 min) to afford the title compound as a lyophilized white solid (1.9 mg, 8.5%). LCMS: m/z (ESI, +ve ion)=524.1 [M+H]⁺. ¹H NMR (400 MHz, DMSO) δ 12.74 (s, 1H), 10.77 (s, 1H), 9.08 (s, 1H), 7.96 (s, 1H), 7.46 (d, J=8.9 Hz, 2H), 7.40 (d, J=8.4 Hz, 1H), 7.07 (d, J=8.3 Hz, 1H), 6.87 (t, J=9.9 Hz, 2H), 6.13 (s, 1H), 4.24 (q, J=7.0 Hz, 2H), 3.23 (t, J=8.8 Hz, 1H), 3.19 (s, 3H), 2.05-2.00 (m, 1H), 1.66 (s, 1H), 1.44 (t, J=7.0 Hz, 3H).

Example 278. (1R,2S)-2-(3-{[6-(2-hydroxypropan-2-yl)-3-methoxypyridin-2-yl]amino}-1H-indazol-4-yl)-5'-methoxy-1'H-spiro[cyclopropane-1,3'-indol]-2'-one

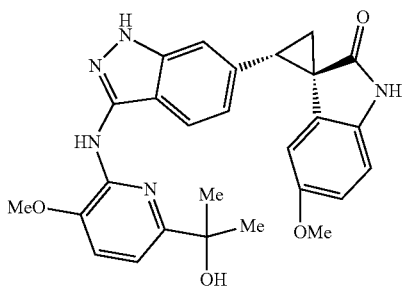 [SMILES: COc1ccc2c(c1)[C@]1(C[C@H]1c1ccc3c(Nc4nc(C(C)(C)O)ccc4OC)n[nH]c3c1)C(=O)N2]

Step A.
2-(6-bromo-5-methoxypyridin-2-yl)propan-2-ol

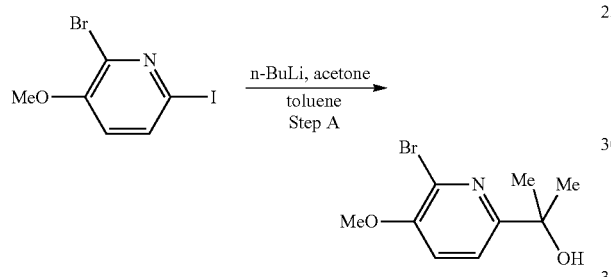

To a stirred solution of 2-bromo-6-iodo-3-methoxypyridine (600 mg, 1.911 mmol, 1 equiv) in toluene (6 mL) was added 2.5 M n-BuLi in hexane (0.76 mL, 1.911 mmol, 1 equiv) dropwise at −78° C. under nitrogen atmosphere. The resulting mixture was stirred for 1 h at −78° C. under nitrogen atmosphere. To the above mixture was added acetone (0.28 mL, 3.822 mmol, 2 equiv) at −78° C. The resulting mixture was stirred for additional 16 h at room temperature. The reaction was quenched by the addition of sat. NH₄Cl (aq., 20 mL) at room temperature. The resulting mixture was extracted with EtOAc (3×20 mL). The combined organic layers were washed with brine (3×20 mL) and dried over anhydrous Na₂SO₄. After filtration, the filtrate was concentrated under reduced pressure. The residue was purified by silica gel column chromatography that eluted with PE:EtOAc (1:1) to afford the title compound (280 mg, 60%) as a colorless oil. m/z (ESI, +ve ion)=246.05, 248.05 [M+H]⁺.

Step B.
2-(6-amino-5-methoxypyridin-2-yl)propan-2-ol

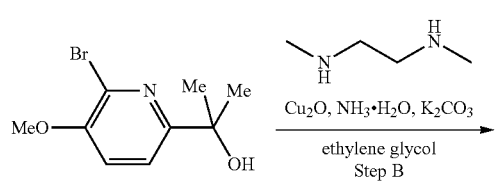

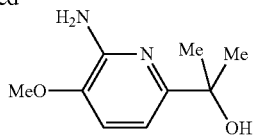

To a stirred mixture of 2-(6-bromo-5-methoxypyridin-2-yl)propan-2-ol (246 mg, 1.000 mmol, 1 equiv), Cu₂O (7.15 mg, 0.050 mmol, 0.05 equiv) and K₂CO₃ (276.29 mg, 2.000 mmol, 2 equiv) in ethane-1,2-diol (6 mL) was added 1,2-bis(methylamino)ethane (8.81 mg, 0.100 mmol, 0.1 equiv) and 28% NH₃·H₂O (2.570 g, 20.000 mmol, 20 equiv) at room temperature under nitrogen atmosphere. The resulting mixture was stirred for 6 h at 60° C. under nitrogen atmosphere in a sealed tube. The mixture was allowed to cool to room temperature. The resulting mixture was diluted with water (15 mL). The mixture was extracted with EtOAc (3×15 mL). The combined organic layers were washed with brine (3×20 mL) and dried over anhydrous Na₂SO₄. After filtration, the filtrate was concentrated under reduced pressure. The residue was purified by silica gel column chromatography that eluted with PE:EtOAc (1:2) to afford the title compound (60 mg, 33%) as a colorless oil. m/z (ESI, +ve ion)=183.15 [M+H]⁺.

Step C. tert-butyl (1R,2S)-2-[1-(tert-butoxycarbonyl)-3-{[6-(2-hydroxypropan-2-yl)-3-methoxypyridin-2-yl]amino}indazol-6-yl]-5'-methoxy-2'-oxospiro[cyclopropane-1,3'-indole]-1'-carboxylate

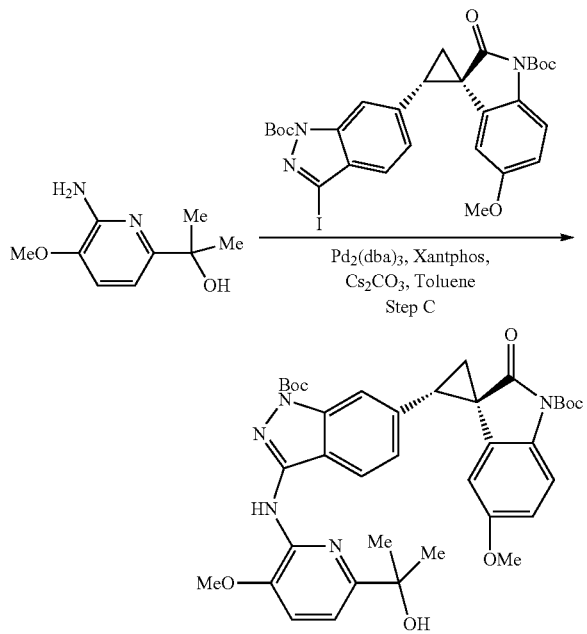

To a stirred mixture of tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1 equiv) and 2-(6-amino-5-methoxypyridin-2-yl)propan-2-ol (37.51 mg, 0.205 mmol, 1.3 equiv) in toluene (6 mL, 56.392 mmol) was added Pd₂(dba)₃ (29.00 mg, 0.032 mmol, 0.2 equiv), XantPhos (18.33 mg, 0.032 mmol, 0.2 equiv) and Cs₂CO₃ (103.19 mg, 0.316 mmol, 2 equiv) at room temperature under nitrogen atmosphere. The resulting mixture was stirred for 2 h at 90° C. under nitrogen atmosphere. The mixture was allowed to cool to room temperature. The resulting mixture was diluted with water (15 mL). The mixture was extracted with EtOAc (3×15 mL). The combined organic layers were washed with brine (3×20 mL) and dried over anhydrous Na$_2$SO$_4$. After filtration, the filtrate was concentrated under reduced pressure. The residue was purified by prep-TLC (DCM:MeOH=10:1) to afford the title compound (76 mg, 70%) as a yellow solid. m/z (ESI, +ve ion)=686.35 [M+H]$^+$.

Step D. (1R,2S)-2-(3-{[6-(2-hydroxypropan-2-yl)-3-methoxypyridin-2-yl]amino}-1H-indazol-6-yl)-5'-methoxy-1'H-spiro[cyclopropane-1,3'-indol]-2'-one

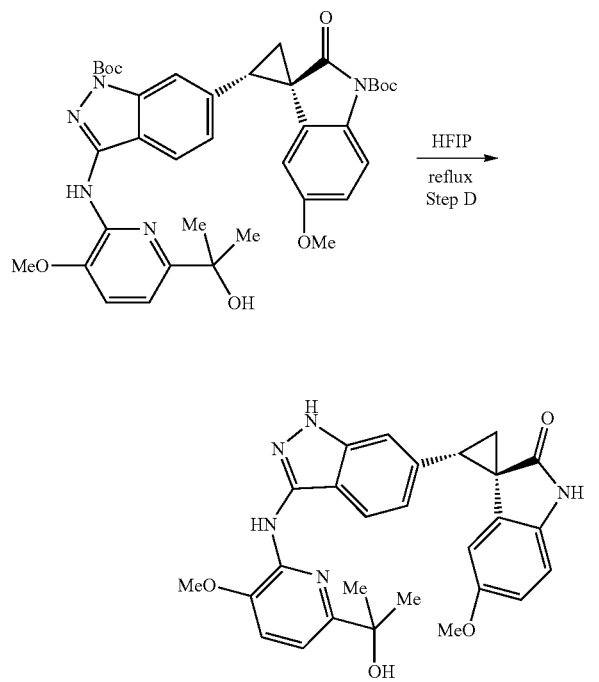 [SMILES: COc1ccc2c(c1)[C@]1(C[C@H]1c1ccc3c(Nc4nc(C(C)(C)O)ccc4OC)nn(C(=O)OC(C)(C)C)c3c1)C(=O)N2C(=O)OC(C)(C)C ; "HFIP" ; COc1ccc2c(c1)[C@]1(C[C@H]1c1ccc3c(Nc4nc(C(C)(C)O)ccc4OC)n[nH]c3c1)C(=O)N2]

A solution of tert-butyl (1R,2S)-2-[1-(tert-butoxycarbonyl)-3-{[6-(2-hydroxypropan-2-yl)-3-methoxypyridin-2-yl]amino}indazol-6-yl]-5'-methoxy-2'-oxospiro[cyclopropane-1,3'-indole]-1'-carboxylate (69 mg, 0.101 mmol, 1 equiv) in HFIP (6 mL) was stirred for 16 h at 60° C. The mixture was allowed to cool to room temperature. The resulting mixture was concentrated under reduced pressure. The crude product (80 mg) was purified by prep-HPLC with the following conditions: (Column: XBridge Prep OBD C18 Column, 30×150 mm, 5 μm; Mobile Phase A: water 10 mmol/L NH$_4$HCO), Mobile Phase B: ACN; Flow rate: 60 mL/min; Gradient: 31% B to 39% B in 10 min. 39% B: wavelength: 254 nm; RT1(min): 7.22) to afford the title compound (28.7 mg, 58%) as a white solid. m/z (ESI, +ve ion)=486.20 [M+H]$^+$. $^1$H NMR (400 MHz, DMSO-d$_6$) δ 12.34 (s, 1H), 10.40 (s, 1H), 8.09 (s, 1H), 7.50 (d, J=8.4 Hz, 1H), 7.32 (s, 1H), 7.19 (d, J=8.0 Hz, 1H), 6.95 (d, J=8.0 Hz, 1H), 6.81 (d, J=10.8 Hz, 1H), 6.75 (d, J=8.4 Hz, 1H), 6.62-6.55 (m, 1H), 5.67 (d, J=2.4 Hz, 1H), 4.77 (s, 1H), 3.87 (s, 3H), 3.31 (s, 3H), 3.22-3.13 (m, 1H), 2.32-2.25 (m, 1H), 2.02-1.94 (m, 1H), 1.16 (d, J=16.0 Hz, 6H).

Example 279. (1R,2S)-2-{3-[(4-ethoxy-6-methanesulfonylpyridin-3-yl)amino]-1H-indazol-6-yl}-5'-methoxy-1'H-spiro[cyclopropane-1,3'-indol]-2'-one

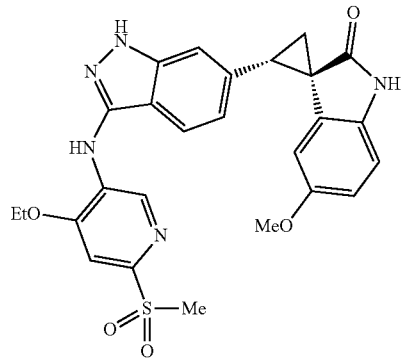 [SMILES: CCOc1cc(S(C)(=O)=O)ncc1Nc1n[nH]c2cc([C@@H]3C[C@@]34C(=O)Nc3ccc(OC)cc34)ccc12]

Step A. 2-bromo-4-ethoxy-5-nitropyridine

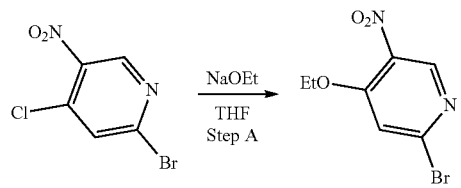 [SMILES: O=[N+]([O-])c1cnc(Br)cc1Cl ; CCOc1cc(Br)ncc1[N+](=O)[O-] ; "NaOEt"]

Into a 20 mL vial was added 2-bromo-4-chloro-5-nitropyridine (500 mg, 2.106 mmol, 1 equiv), EtONa (530 mg, 2.336 mmol, 1.11 equiv, 30/in EtOH) and THF (2 mL) at room temperature. The mixture was stirred for 12 h at 25° C. under nitrogen atmosphere. The resulting mixture was concentrated under reduced pressure. The residue was purified by prep-TLC (PE:EtOAc=2:1) to afford the title compound (320 mg, 62%) as a yellow solid. m/z (ESI, +ve ion)=246.90 [M+H]$^+$.

Step B. 6-bromo-4-ethoxypyridin-3-amine

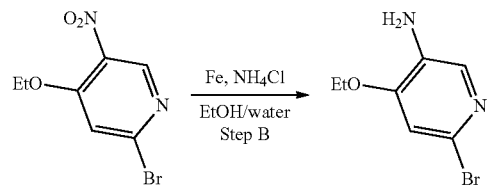

Into a 20 mL vial was added 2-bromo-4-ethoxy-5-nitropyridine (250 mg, 1.012 mmol, 1 equiv), Fe (250 mg, 4.477 mmol, 4.42 equiv), NH$_4$Cl (250 mg, 4.674 mmol, 4.62 equiv), EtOH (5 mL) and water (1 mL) at room temperature. The resulting mixture was stirred for 4 h at 30° C. under nitrogen atmosphere. The resulting mixture was filtered and the filter cake was washed with MeOH (3×10 mL). The filtrate was concentrated under reduced pressure. The residue was purified by silica gel column chromatography that eluted with PE:EtOAc (1:1) to afford the title compound (180 mg, 82%) as a light yellow solid. m/z (ESI, +ve ion)=216.90 [M+H]+.

Step C. 4-ethoxy-6-methanesulfonylpyridin-3-amine

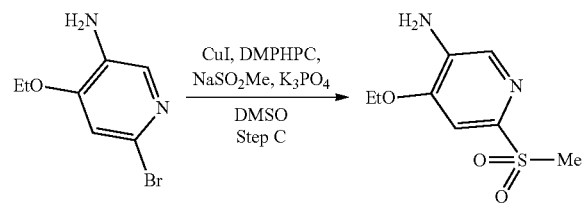

To a stirred mixture of 6-bromo-4-ethoxypyridin-3-amine (200 mg, 0.921 mmol, 1 equiv) and (2S,4R)—N-(2,6-dimethylphenyl)-4-hydroxypyrrolidine-2-carboxamide (30.22 mg, 0.129 mmol, 0.14 equiv), sodium methanesulfinate (129.81 mg, 1.271 mmol, 1.38 equiv) and K₃PO₄ (199.49 mg, 0.939 mmol, 1.02 equiv) in DMSO (3 mL) was added CuI (19.30 mg, 0.101 mmol, 0.11 equiv) at room temperature under nitrogen atmosphere. The mixture was stirred for 4 h at 120° C. under nitrogen atmosphere. The mixture was allowed to cool to room temperature. The resulting mixture was diluted with water (10 mL). The mixture was extracted with EtOAc (3×10 mL). The combined organic layers were washed with brine (10 mL) and dried over anhydrous Na₂SO₄. After filtration, the filtrate was concentrated under reduced pressure. The residue was purified by silica gel column chromatography that eluted with PE:EtOAc (1:1) to afford the title compound (180 mg, 90%) as a light yellow solid. m/z (ESI, +ve ion)=217.05 [M+H]+

Step D. tert-butyl (1R,2S)-2-[1-(tert-butoxycarbonyl)-3-[(4-ethoxy-6-methanesulfonylpyridin-3-yl)amino]indazol-6-yl]-5'-methoxy-2'-oxospiro[cyclopropane-1,3'-indole]-1'-carboxylate

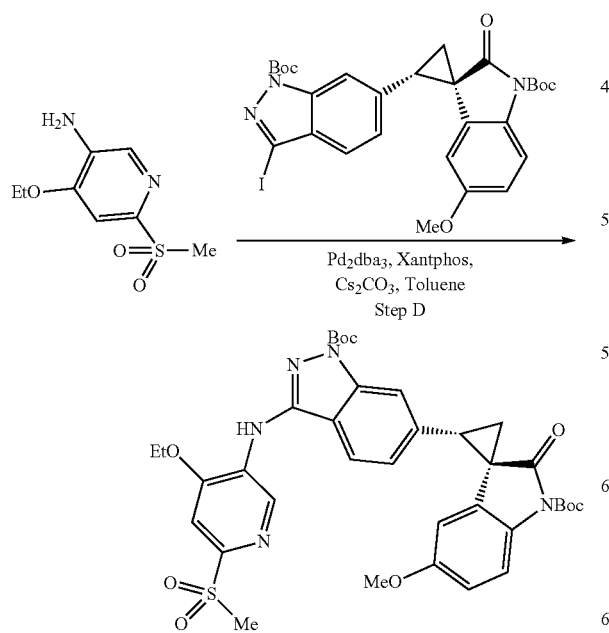

To a solution of 4-ethoxy-6-methanesulfonylpyridin-3-amine (50.00 mg, 0.231 mmol, 1.46 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) in toluene (3 mL) was added Cs₂CO₃ (100 mg, 0.307 mmol, 1.94 equiv), Pd₂(dba)₃ (30 mg, 0.033 mmol, 0.21 equiv) and XantPhos (25 mg, 0.043 mmol, 0.27 equiv) under nitrogen atmosphere. After stirring for 2 h at 90° C., the mixture was allowed to cool to room temperature. The resulting mixture was filtered and the filtrate was concentrated under reduced pressure. The residue was purified by prep-TLC (PE:EtOAc=1:1) to afford the title compound (75 mg, 66%) as a light yellow solid. m/z (ESI, +ve ion)=720.25 [M+H]+.

Step E. (1R,2S)-2-{3-[(4-ethoxy-6-methanesulfonylpyridin-3-yl)amino]-1H-indazol-6-yl}-5'-methoxy-1'H-spiro[cyclopropane-1,3'-indol]-2'-one

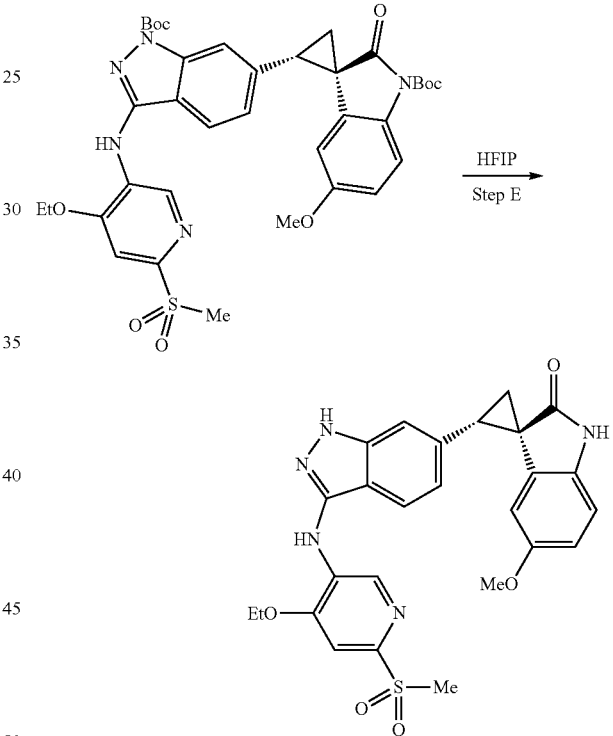

Into a 8 mL vial was added tert-butyl (1R, 2S)-2-[1-(tert-butoxycarbonyl)-3-[(4-ethoxy-6-methanesulfonylpyridin-3-yl)amino]indazol-6-yl]-5'-methoxy-2'-oxospiro[cyclopropane-1,3'-indole]-1'-carboxylate (80 mg, 0.111 mmol, 1 equiv) and HFIP (0.5 mL) at room temperature. The resulting mixture was stirred for 12 h at 60° C. under nitrogen atmosphere. The mixture was allowed to cool to room temperature. The mixture was concentrated under reduced pressure. The crude product was purified by prep-HPLC with the following conditions (Column: XBridge Prep OBD C18 Column, 30×150 mm, 5 μm; Mobile Phase A: water (10 mmol/L NH₄HCO₃), Mobile Phase B: ACN; Flow rate: 60 mL/min; Gradient: 31% B to 39% B in 8 min, 39% B: wavelength: 254 nm; RT1(min): 7.7) to afford the title compound (30.3 mg, 53%) as a white solid. m/z (ESI, +ve ion)=520.25 [M+H]+. ¹H NMR (400 MHz, DMSO-d₆) δ

12.46 (s, 1H), 10.42 (s, 1H), 9.18 (s, 1H), 8.37 (s, 1H), 7.83 (d, J=8.0 Hz, 1H), 7.54 (s, 1H), 7.39 (s, 1H), 6.94 (d, J=8.8 Hz, 1H), 6.76 (d, J=8.4 Hz, 1H), 6.60-6.57 (m, 1H), 5.70 (d, J=2.8 Hz, 1H), 4.39-4.35 (m, 2H), 3.33-3.28 (m, 3H), 3.21-3.17 (m, 4H), 2.35-2.32 (m, 1H), 2.01-1.97 (m, 1H), 1.48 (t, J=6.8 Hz, 3H).

Example 280. (1R,2S)-2-{3-[(5-difluoromethanesulfonyl-3-methoxypyridin-2-yl)amino]-1H-indazol-6-yl}-5'-methoxy-1'H-spiro[cyclopropane-1,3'-indol]-2'-one

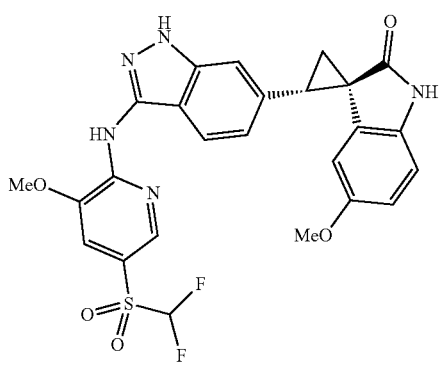 [SMILES: COc1ccc2c(c1)[C@]1(C[C@H]1c1ccc3c(Nc4ncc(S(=O)(=O)C(F)F)cc4OC)n[nH]c3c1)C(=O)N2]

Step A. 2-ethylhexyl 3-[(5-methoxy-6-nitropyridin-3-yl)sulfanyl]propanoate

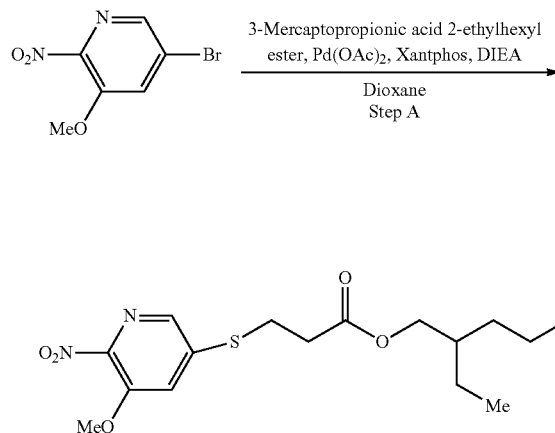

To a stirred mixture of 5-bromo-3-methoxy-2-nitropyridine (500 mg, 2.146 mmol, 1 equiv) and 2-ethylhexyl 3-sulfanylpropanoate (562.24 mg, 2.575 mmol, 1.2 equiv) in dioxane (10 mL) was added Pd(OAc)₂ (96.35 mg, 0.429 mmol, 0.2 equiv), XantPhos (248.32 mg, 0.429 mmol, 0.2 equiv) and DIEA (554.66 mg, 4.292 mmol, 2 equiv) at room temperature under nitrogen atmosphere. The resulting mixture was stirred for 12 h at 100° C. under nitrogen atmosphere. The mixture was concentrated under reduced pressure. The residue was purified by silica gel column chromatography that eluted with PE:EtOAc (1:1) to afford the title compound (490 mg, 62%) as a yellow solid. m/z (ESI, +ve ion)=371.20 [M+H]⁺.

Step B. 5-methoxy-6-nitropyridine-3-thiol

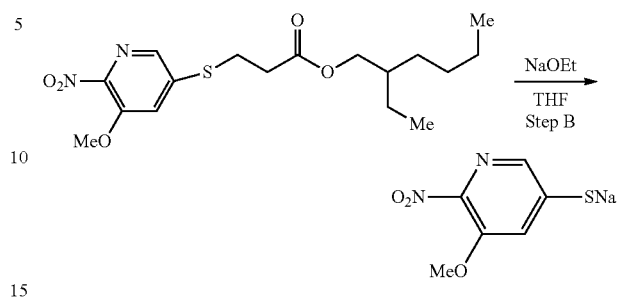

To a stirred mixture of 2-ethylhexyl 3-[(5-methoxy-6-nitropyridin-3-yl)sulfanyl]propanoate (450 mg, 1.215 mmol, 1 equiv) and THF (10 mL) was added EtONa (99.19 mg, 1.458 mmol, 1.2 equiv) at room temperature under nitrogen atmosphere. The resulting mixture was stirred for 16 h at room temperature under nitrogen atmosphere. 10 mL of water was added into the mixture and the mixture was extracted with MTBE (2×10 mL) The aqueous layer was used directly for the next step. m/z (ESI, +ve ion)=187.05 [M+H]⁺.

Step C. difluoromethyl)thio)-3-methoxy-2-nitropyridine

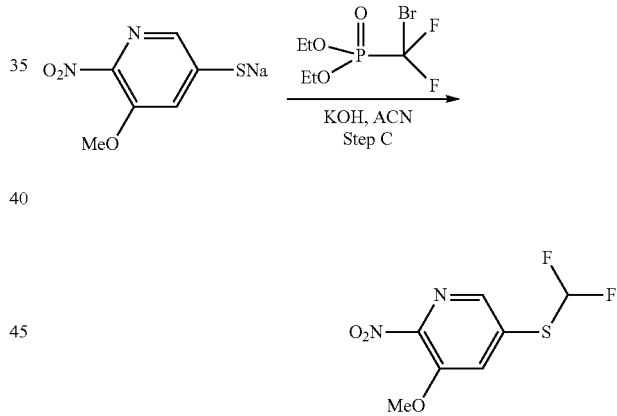

To a stirred mixture of 5-methoxy-6-nitropyridine-3-thiol Na salt (10 mL crude aqueous solution from previous step) and diethyl (bromodifluoromethyl)phosphonate (286.81 mg, 1.070 mmol, 10 equiv) in CH₃CN (10 mL) was added KOH (1145 mg, 20.409 mmol, 20.00 equiv) at room temperature under nitrogen atmosphere. The resulting mixture was stirred for 16 h at room temperature under nitrogen atmosphere. The mixture was extracted with EtOAc (3×10 mL) and the combined organic layer was dried over Na₂SO₄. After filtration, the filtrate was concentrated under reduced pressure. The residue was purified by silica gel column chromatography that eluted with PE:EtOAc (1:1) to afford 200 mg crude (contained phosphors impurity on H-NMR). The crude product was repurified by RP flash that eluted with 40% MeCN in water (10 mM NH₄HCO₃) to give the title compound (140 mg, 58%) as a yellow oil. m/z (ESI, +ve ion)=237.10 [M+H]⁺.

Step D. 5-[(difluoromethyl)sulfanyl]-3-methoxy-pyridin-2-amine

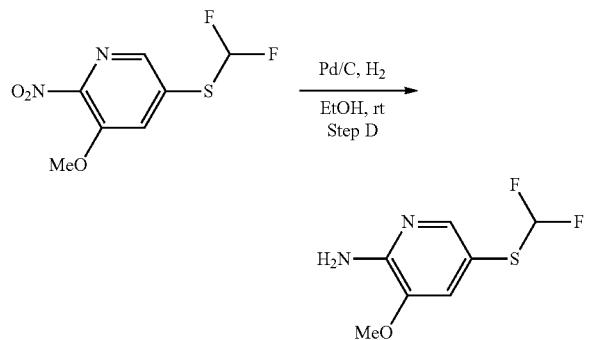

A solution of 5-[(difluoromethyl)sulfanyl]-3-methoxy-2-nitropyridine (60 mg, 0.254 mmol, 1 equiv) and 10% Pd/C (13.52 mg) in EtOH (5 mL) was stirred for 16 h at room temperature under hydrogen atmosphere. The resulting mixture was filtered and the filtrate was concentrated under reduced pressure. The residue was purified by prep-TLC (DCM:MeOH=10:1) to afford the title compound (48 mg, 91.63%). m/z (ESI, +ve ion)=206.85 [M+H]⁺

Step E. tert-butyl (1R,2S)-2-[1-(tert-butoxycarbonyl)-3-({5-[(difluoromethyl)sulfanyl]-3-methoxy-pyridin-2-yl}amino)indazol-6-yl]-5'-methoxy-2'-oxospiro[cyclopropane-1,3'-indole]-1'-carboxylate

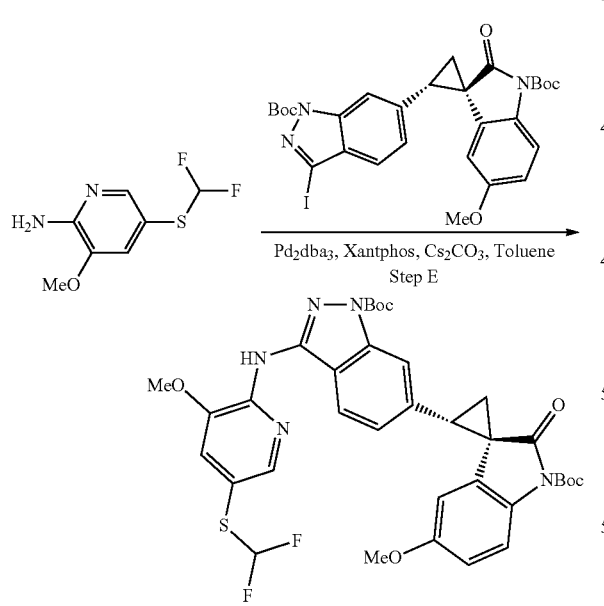

To a stirred mixture of 5-[(difluoromethyl)sulfanyl]-3-methoxypyridin-2-amine (39.19 mg, 0.190 mmol, 1.2 equiv) and tert-butyl (1R,2S)-2-[1-(tert-butoxycarbonyl)-3-iodoindazol-6-yl]-5'-methoxy-2'-oxospiro[cyclopropane-1,3'-indole]-1'-carboxylate (100 mg, 0.158 mmol, 1.00 equiv) in toluene (5 mL) was added Pd₂(dba)₃. (29.00 mg, 0.032 mmol, 0.2 equiv), XantPhos (18.33 mg, 0.032 mmol, 0.2 equiv) and Cs₂CO₃ (103.19 mg, 0.316 mmol, 2 equiv) at room temperature under nitrogen atmosphere. The resulting mixture was stirred for 2 h at 90° C. under nitrogen atmosphere. The mixture was concentrated under reduced pressure. The residue was purified by prep-TLC (PE:EtOAc 1:1) to afford the title compound (85 mg, 76%) as a yellow solid. m/z (ESI, +ve ion)=710.30 [M+H]⁺

Step F. tert-butyl (1R,2S)-2-[1-(tert-butoxycarbonyl)-3-[(5-difluoromethanesulfonyl-3-methoxypyridin-2-yl)amino]indazol-6-yl]-5'-methoxy-2'-oxospiro[cyclopropane-1,3'-indole]-1'-carboxylate

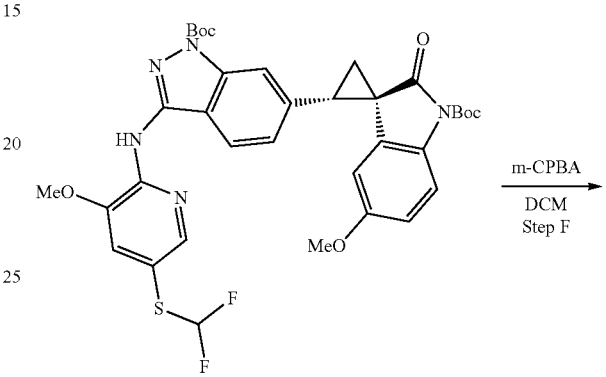

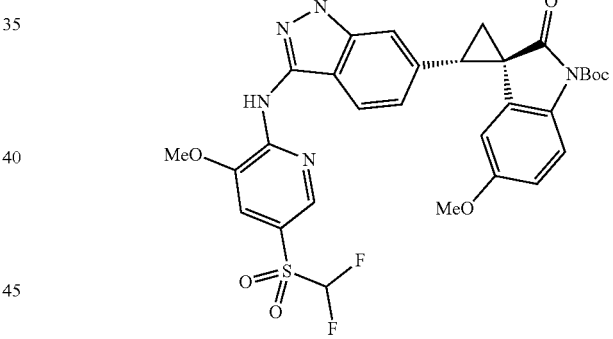

A mixture of tert-butyl (1R,2S)-2-[1-(tert-butoxycarbonyl)-3-({5-[(difluoromethyl)sulfanyl]-3-methoxypyridin-2-yl}amino)indazol-6-yl]-5'-methoxy-2'-oxospiro[cyclopropane-1,3'-indole]-1'-carboxylate (50 mg, 0.070 mmol, 1 equiv) and mCPBA (24.31 mg, 0.140 mmol, 2 equiv) in DCM (3 mL) was stirred for 2 h at room temperature under nitrogen atmosphere. The resulting mixture was quenched with aq. NaHCO₃ (10 mL), extracted with EtOAc (3×10 mL) and the combined organic layer was dried with Na₂SO₄. After filtration, the filtrate was concentrated under reduced pressure. The residue was purified by prep-TLC (PE:EtOAc=1:1) to afford the title compound (45 mg, 86%) as a yellow solid. m/z (ESI, +ve ion)=742.15 [M+H]⁺

Step H. (1R,2S)-2-{3-[(5-difluoromethanesulfonyl-3-methoxypyridin-2-yl)amino]-1H-indazol-6-yl}-5'-methoxy-1'H-spiro[cyclopropane-1,3'-indol]-2'-one

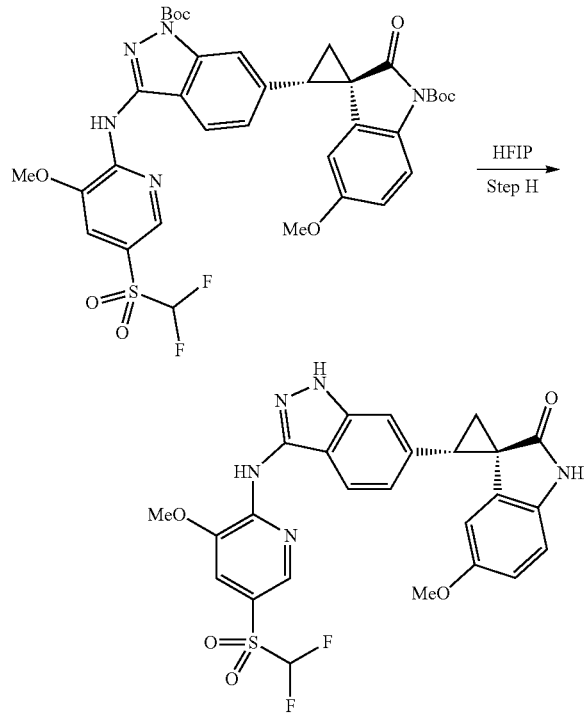

Into an 8 mL vial was added tert-butyl (1R,2S)-2-[1-(tert-butoxycarbonyl)-3-[(5-difluoromethanesulfonyl-3-methoxypyridin-2-yl)amino]indazol-6-yl]-5'-methoxy-2'-oxospiro[cyclopropane-1,3'-indole]-1'-carboxylate (45 mg, 0.061 mmol, 1 equiv) and HFIP (5 mL) at room temperature. The resulting mixture was stirred for 16 h at 60° C. under nitrogen atmosphere. The resulting mixture was concentrated under reduced pressure. The crude product was purified by prep-HPLC with the following conditions: Column: XBridge Shield RP18 OBD Column, 19×250 mm, 10 µm; Mobile Phase A: water (10 mmol/L NH$_4$HCO$_3$), Mobile Phase B: ACN; Flow rate: 25 mL/min; Gradient: 35% B to 50% B in 8 min, 50% B; wavelength: 254 nm; RT1(min): 7.8 to afford the title compound (8.6 mg, 26%) as a white solid. m/z (ESI, +ve ion)=542.15 [M+H]$^+$. $^1$H NMR (400 MHz, DMSO-d$_6$) δ 12.78 (s, 1H), 10.42 (s, 1H), 9.60 (s, 1H), 8.01 (d, J=2.0 Hz, 1H), 7.44-7.34 (m, 3H), 7.33-7.08 (m, 1H), 6.92 (d, J=8.4 Hz, 1H), 6.75 (d, J=8.4 Hz, 1H), 6.61 (d, J=2.4 Hz, 1H), 5.72 (d, J=2.4 Hz, 1H), 4.01 (s, 3H), 3.33-3.22 (m, 3H), 3.18 (t, J=8.0 Hz, 1H), 2.35-2.32 (m, 1H), 2.01-1.99 (m, 1H).

The compounds in Table 1B were prepared using materials and methods analogous to those disclosed herein and methods known to those having ordinary skill in the art.

TABLE 1B

| Example No. | MS/$^1$H NMR |
|---|---|
| 112 | m/z (ESI + ve ion) = 465.20 [M + H]$^+$. $^1$H NMR (400 MHz, Methanol-d$_4$) δ 7.58 (d, J = 8.4 Hz, 1H), 7.34 (s, 1H), 6.88-6.83 (m, 2H), 6.32 (d, J = 4.4 Hz, 1H), 6.19-6.05 (m, 1H), 6.01 (s, 1H), 5.59 (s, 1H), 4.52-4.47 (m, 2H), 3.34-3.32 (m, 4H), 2.25-2.16 (m, 5H). $^{19}$F NMR (376 MHz, Methanol-d$_4$) δ-123.83. |
| 113 | m/z (ESI, +ve ion) = 528.30 [M + H]$^+$. $^1$H NMR (400 MHz, Methanol-d$_4$) δ 7.85 (s, 1H), 7.57 (d, J = 8.4 Hz, 1H), 7.43 (s, 1H), 6.94-6.61 (m, 2H), 6.73-6.70 (m, 1H), 5.71 (d, J = 2.4 Hz, 1H), 3.84-3.80 (m, 7H), 3.71-3.68 (m, 4H), 3.38-3.36 (m, 4H), 3.34 (s, 3H), 2.29-2.25 (m, 1H), 2.22-2.19 (m, 1H). |
| 115 | m/z (ESI, +ve ion) = 455.20 [M + H]$^+$. $^1$H NMR (400 MHz, DMSO-d$_6$) δ 12.36 (s, 1H), 10.41 (s, 1H), 10.03 (s, 1H), 9.08 (s, 1H), 8.02-7.94 (m, 2H), 7.36 (s, 1H), 6.91 (dd, J = 8.5, 1.4 Hz, 1H), 6.76 (d, J = 8.4 Hz, 1H), 6.59 (dd, J = 8.5, 2.6 Hz, 1H), 5.71 (d, J = 2.6 Hz, 1H), 4.91-4.79 (m, 4H), 4.40-4.36 (m, 1H), 3.19 (t, J = 8.4 Hz, 1H), 2.33 (dd, J = 8.0, 4.7 Hz, 1H), 1.99 (dd, J = 9.0, 4.7 Hz, 1H). |
| 118 | m/z (ESI + ve ion) = 489.15 [M + H]$^+$. $^1$H NMR (400 MHz, Methanol-d$_4$) δ 8.38 (s, 1H), 7.55-7.45 (m, 2H), 6.92 (dd, J = 8.5, 1.4 Hz, 1H), 6.85 (d, J = 8.4 Hz, 1H), 6.65 (dd, J = 8.5, 2.5 Hz, 1H), 5.62 (d, J = 2.5 Hz, 1H), 4.81-4.69 (m, 4H), 4.20-4.16 (m, 1H), 3.38 (d, J = 8.4 Hz, 1H), 3.34-3.32(m, 3H), 2.25 (dd, J = 7.9, 4.8 Hz, 1H), 2.19 (dd, J = 9.1, 4.8 Hz, 1H) |
| 120 | m/z (ESI, +ve ion) = 504.15 [M + H]$^+$. $^1$H NMR (400 MHz, Methanol-d$_4$) δ 7.94 (s, 1H), 7.59 (d, J = 8.4 Hz, 1H), 7.44 (s, 1H), 6.91-6.85 (m, 1H), 6.84 (d, J = 8.8 Hz, 1H), 6.65-6.62 (m, 1H), 5.61 (d, J = 1.6 Hz, 1H), 4.46-4.41 (m, 1H), 3.97 (s, 2H), 3.60 (s, 2H), 3.37 (d, J = 8.8 Hz, 1H), 3.33-3.16 (m, 3H), 2.27-2.24 (m, 1H), 2.19-2.17 (m, 1H) |
| 123 | m/z (ESI, +ve ion) = 461.15 [M + H]$^+$. $^1$H NMR (400 MHz, Methanol-d$_4$) δ 7.89 (s, 1H), 7.54 (d, J = 8.4 Hz, 1H), 7.18-7.15 (m, 1H), 6.85 (d, J = 8.4 Hz, 1H), 6.65-6.63 (m, 1H), 5.56 (d, J = 2.4 Hz, 1H), 4.02 (s, 3H), 3.31 (s, 3H), 3.25 (t, J = 8.8 Hz, 1H), 2.35 (s, 3H), 2.25-2.20 (m, 2H). $^{19}$F NMR (376 MHz, Methanol-d$_4$) δ-136.60 (s, 1F) |
| 124 | m/z (ESI, +ve ion) = 413.1 [M + H]$^+$. 1H NMR (400 MHz, METHANOL-d4) δ ppm 7.75 (s, 1H) 7.46 (d, J = 8.10 Hz, 1H) 7.31 (s, 1H) 6.89-7.02 (m, 1H) 6.77-6.87 (m, 2H) 6.40-6.55 (m, 1H) 5.92 (d, J = 7.60 Hz, 1H) 3.90 (s, 3H) 3.23-3.28 (m, 1 H) 2.21 (s, 3H) 1.99-2.15 (m, 2H) |

TABLE 1B-continued

| Example No. | MS/¹H NMR |
|---|---|
| 126 | m/z (ESI, +ve ion) = 427.1 [M + H]⁺. 1H NMR (400 MHz, MeOD) δ 7.85-7.68 (m, 1H), 7.56-7.42 (m, 1H), 7.31 (d, J = 2.5 Hz, 1H), 6.87-6.67 (m, 3H), 5.78 (s, 1H), 3.91 (s, 3H), 3.60-3.43 (m, 1H), 2.22 (s, 3H), 2.14-2.00 (m, 2H), 1.82 (s, 3H) |
| 127 | m/z (ESI, +ve ion) = 427.1 [M + H]⁺. 1H NMR (400 MHz, MeOD) δ 7.82-7.69 (m, 1H), 7.49-7.41 (m, 1H), 7.33 (s, 1H), 6.97-6.87 (m, 2H), 6.84 (s, 1H), 6.77-6.69 (m, 1H), 3.90 (s, 3H), 3.56-3.45 (m, 1H), 2.32-2.27 (m, 1H), 2.26 (s, 3H), 2.22 (s, 3H), 2.15-2.06 (m, 1H) |
| 129 | m/z (ESI, +ve ion) = 431.2 [M + H]⁺. 1H NMR (400 MHz, MeOD) δ 7.74 (s, 1H), 7.42 (d, J = 8.5 Hz, 1H), 7.26 (s, 1H), 7.04-6.94 (m, 1H), 6.80 (d, J = 8.5 Hz, 1H), 6.70 (d, J = 7.4 Hz, 1H), 6.26 (t, J = 9.5 Hz, 1H), 3.89 (s, 3H), 3.18-3.08 (m, 1H), 2.50-2.43 (m, 1H), 2.21 (s, 3H), 2.08-1.99 (m, 1H) |
| 130 | m/z (ESI, +ve ion) = 431.2 [M + H]⁺. 1H NMR (400 MHz, MeOD) δ 7.86 (s, 1H), 7.58 (d, J = 8.7 Hz, 1H), 7.46 (s, 1H), 7.28-7.18 (m, 1H), 7.03 (d, J = 8.5 Hz, 1H), 6.85-6.77 (m, 2H), 4.02 (s, 3H), 3.82-3.71 (m, 1H), 2.59-2.48 (m, 1H), 2.43-2.36 (m, 1H), 2.34 (s, 3H) |
| 131 | m/z (ESI, +ve ion) = 431.2 [M + H]⁺. 1H NMR (400 MHz, MeOD) δ 7.80-7.69 (m, 1H), 7.51-7.43 (m, 1H), 7.34-7.29 (m, 1H), 6.84-6.76 (m, 1H), 6.64-6.56 (m, 1H), 6.21 (t, J = 9.4 Hz, 1H), 5.93-5.80 (m, 1H), 3.90 (s, 3H), 3.60-3.44 (m, 1H), 2.21 (s, 3H), 2.18-2.10 (m, 1H), 2.10-2.00 (m, 1H) |
| 133 | m/z (ESI, +ve ion) = 431.15 [M + H]⁺. ¹H NMR (400 MHz, DMSO-d₆) δ 12.64 (s, 1H), 10.63 (s, 1H), 8.98 (s, 1H), 7.92 (s, 1H), 7.49-7.39 (m, 2H), 6.93-6.79 (m, 3H), 5.93-5.86 (m, 1H), 3.90 (s, 3H), 3.24 (t, J = 8.4 Hz, 1H), 2.56-2.38 (m, 1H), 2.17 (s, 3H), 2.11-2.01 (m, 1H) |
| 135 | m/z (ESI, +ve ion) = 467.15 [M + H]⁺. ¹H NMR (400 MHz, DMSO-d₆) δ 12.76 (s, 1H), 10.65 (s, 1H), 9.60 (s, 1H), 8.13 (d, J = 1.2 Hz, 1H), 7.46-7.39 (m, 2H), 7.16 (s, 1H), 6.93-6.90 (m, 1H), 6.90-6.79 (m, 2H), 5.92-5.86 (m, 1H), 3.25 (t, J = 8.4 Hz, 1H), 2.46-2.41 (m, 1H), 2.22 (s, 3H), 2.10-2.00 (m, 1H) |
| 136 | m/z (ESI, +ve ion) = 471.35 [M + H]⁺. ¹H NMR (400 MHz, Methanol-d₄) δ 7.87 (s, 1H), 7.63 (d, J = 8.4 Hz, 1H), 7.44 (s, 1H), 6.95 (d, J = 8.4 Hz, 1H), 6.85 (d, J = 8.4 Hz, 1H), 6.64-6.61 (m, 1H), 5.64 (s, 1H), 4.78-4.72 (m, 1H), 3.50-3.15 (m, 4H), 2.31 (s, 3H), 2.27-2.17 (m, 2H), 1.46 (m, 6H). |
| 137 | m/z (ESI, +ve ion) = 481.0 [M + H]⁺. 1H NMR (400 MHz, DMSO) δ 12.74-12.58 (m, 1H), 11.02 (d, J = 3.3 Hz, 1H), 9.01 (s, 1H), 7.92 (d, J = 2.8 Hz, 1H), 7.51-7.32 (m, 3H), 7.02 (q, J = 3.1 Hz, 1H), 6.99-6.87 (m, 1H), 6.40 (s, 1H), 3.89 (d, J = 3.0 Hz, 3H), 3.29 (s, 1H), 2.16 (d, J = 3.2 Hz, 3H), 2.10-2.04 (m, 2H) |
| 138 | m/z (ESI, +ve ion) = 497.2 [M + H]⁺. ¹H NMR (400 MHz, DMSO) δ 12.62 (s, 1H), 10.82 (s, 1H), 9.01 (s, 1H), 7.91 (s, 1H), 7.45 (d, J = 8.4 Hz, 1H), 7.40 (s, 1H), 7.08-6.99 (m, 1H), 6.96-6.84 (m, 2H), 6.03 (s, 1H), 3.89 (s, 3H), 3.31-3.20 (m, 1H), 2.16 (s, 3H), 2.11-2.01 (m, 2H) |
| 139 | m/z (ESI, +ve ion) = 497.2 [M + H]⁺. ¹H NMR (400 MHz, DMSO) δ 12.60 (s, 1H), 10.55 (s, 1H), 8.97 (s, 1H), 7.91 (s, 1H), 7.41 (d, J = 8.6 Hz, 1H), 7.36 (s, 1H), 7.27 (s, 1H), 7.23-7.11 (m, 1H), 6.92 (t, J = 8.3 Hz, 2H), 3.90 (s, 3H), 3.42 (s, 1H), 2.36-2.26 (m, 2H), 2.19 (s, 3H) |
| 140 | m/z (ESI + ve ion) = 453.20 [M + H]⁺. ¹H NMR (400 MHz, DMSO-d₆) δ 8.98 (s, 1H), 7.92 (s, 1H), 7.41 (d, J = 7.6 Hz, 2H), 6.89 (d, J = 8.8 Hz, 1H), 6.77 (d, J = 8.4 Hz, 1H), 6.59-6.56 (m, 1H), 6.02 (s, 1H), 5.70 (d, J = 2.8 Hz, 1H), 3.33(s, 3H), 3.21 (t, J = 8.4 Hz, 1H), 2.31 (dd, J = 4.8, 4.8 Hz, 1H), 2.172 (s, 3H), 1.991 (dd, J = 4.8, 4.4 Hz, 1H), 1.85-1.81 (m, 1H), 0.96-0.91 (m, 2H), 0.67-0.63 (m, 2H) |
| 141 | m/z (ESI, +ve ion) = 521.20 [M + H]⁺. ¹H-NMR (400 MHz, Methanol-d₄) δ 8.23(s, 1H), 7.54 (d, J = 8.6 Hz, 1H), 7.46(s, 1H), 7.17-6.80 (m, 3H), 6.66-6.63 (m, 1H), 5.61 (d, J = 2.4 Hz, 1H), 4.48-4.47 (m, 4H), 4.22-4.18 (m, 1H), 3.33-3.32 (m, 4H), 2.27-2.17 (m, 2H). ¹⁹F NMR (376 MHz, Methanol-d₄) δ-83.99 |
| 142 | m/z (ESI, +ve ion) = 449.15 [M + H]+. ¹H-NMR (400 MHz, Methanol-d4) δ 7.89 (s, 1H), 7.54 (d, J = 8.4 Hz, 1H), 7.17-7.13 (m, 1H), 6.93-6.90 (m, 1H), 6.85-6.80 (m, 1H), 5.78-5.75 (m, 1H), 4.03 (s, 3H), 3.28 (t, J = 8.8 Hz, 1H), 2.35 (s, 3H), 2.28-2.26 (m, 2H). 19F NMR (376 MHz, Methanol-d₄) δ −123.62 (s, 1F), −136.88 (s, 1F) |
| 143 | m/z (ESI, +ve ion) = 485.10 [M + H]+. 1H NMR (400 MHz, Methanol-d4) δ 8.15 (s, 1H), 7.48 (d, J = 8.4 Hz, 1H), 7.20-7.14 (m, 1H), 6.97-6.79 (m, 3H), 5.75-5.73 (m, 1H), 3.32-3.27 (m, 1H), 2.39 (s, 3H), 2.30-2.22 (m, 2H) |
| 144 | m/z (ESI, +ve ion) = 461.20 [M + H]+. ¹H-NMR (400 MHz, Methanol-d4) δ 7.85 (s, 1H), 7.64 (d, J = 6.0 Hz, 1H), 7.23 (d, J = 10.0 Hz, 1H), 6.85 (d, J = 8.4 Hz, 1H), 6.65-6.62 (m, 1H), 5.59 (d, J = 2.4 Hz, 1H), 4.00 (s, 3H), 3.29 (s, 3H), 3.22-3.18 (m, 1H), 2, 29 (s, 3H), 2.23 (d, J = 8, 4 Hz, 2H) |
| 145 | m/z (ESI, +ve ion) = 443.4 [M + H]+. ¹HNMR (500 MHz, DMSO) δ 12.52 (s, 1H), 10.41 (s, 1H), 8.86 (s, 1H), 7.91 (d, J = 8.4 Hz, 1H), 7.80 (s, 1H), 7.38 (s, 1H), 6.93 (dd, J = 8.6, 1.1 Hz, 1H), 6.74 (d, J = 8.4 Hz, 1H), 6.58 (dd, J = 8.5, 2.6 Hz, 1H), 5.69 (d, J = 2.6 Hz, 1H), 4.09 (s, 3H), 3.31 (s, 3H), 3.18 (t, J = 8.4 Hz, 1H), 2.40 (s, 3H), 2.33 (dd, J = 7.9, 4.8 Hz, 1H), 1.98 (dd, J = 9.0, 4.7 Hz, 1H). |
| 146 | m/z (ESI, +ve ion) = 483.20 [M + H]+. ¹H-NMR (400 MHz, DMSO-d6) δ 12.63 (s, 1H), 10.40 (s, 1H), 8.82 (s, 1H), 7.92 (s, 1H), 7.49 (d, J = 8.4 Hz, 1H), 7.40 (s, 1H), 6.92 (d, J = 8.4 Hz, 1H), 6.76 (d, J = 8.4 Hz, 1H), 6.57-6.54 (m, 1H), 5.72 (d, J = 2.4 Hz, 1H), 3.97 (d, J = 6.8 Hz, 2H), 3.32-3.31 (m, 3H), 3.22 (t, J = 8.8 Hz, 1H), 2.32-2.30 (m, 1H), 2.19 (s, 3H), 2.01-1.97 (m, 1H), 1.31-1.29 (m, 1H), 0.60-0.57 (m, 2H), 0.38-0.37 (m, 2H) |
| 147 | m/z (ESI, +ve ion) = 493.20 [M + H]+. ¹H-NMR (400 MHz, Methanol-d4) δ 7.96 (s, 1H), 7.59 (d, J = 8.4 Hz, 1H), 7.45 (s, 1H), 6.94-6.92 (m, 1H), 6.84 (d, J = 7.6 Hz, 1H), 6.64-6.61 (m, 1H), 6.33-6.31 (m, 1H), 5.62 (d, J = 2.4 Hz, 1H), 4.49-4.41 |

TABLE 1B-continued

| Example No. | MS/¹H NMR |
|---|---|
| | (m, 2H), 3.38 (d, J = 8.4 Hz, 1H), 3.31 (s, 3H), 2.32 (s, 3H), 2.27-2.24 (m, 1H), 2.20-2.19 (m, 1H) |
| 148 | m/z (ESI + ve ion) = 441.20 [M + H]+. ¹H NMR (400 MHz, Methanol-d4) δ 7.61-7.57 (m, 2H), 7.35 (s, 1H), 6.90-6.83 (m, 3H), 6.67-6.61 (m, 2H), 5.62 (d, J = 2.4 Hz, 1H), 3.93 (s, 3H), 3.38-3.36 (m, 1H), 3.30 (s, 3H), 2.25-2.17 (m, 5H) |
| 149 | m/z (ESI, +ve ion) = 511.20 [M + H]+. ¹H-NMR (400 MHz, Methanol-d4) δ 8.02 (s, 1H), 7.58 (d, J = 8.4 Hz, 1H), 7.46 (s, 1H), 6.95-6.93 (d, J = 8 Hz, 1H), 6.85 (d, J = 8.4 Hz, 1H), 6.64-6.62 (m, 1H), 5.63 (d, J = 2.4 Hz, 1H), 4.82-4.76 (m, 2H), 3.39-3.37 (m, 1H), 3.31 (s, 3H), 2.32 (s, 3H), 2.28-2.24 (m, 1H), 2.21-2.17 (m, 1H) |
| 150 | m/z (ESI, +ve ion) = 442.20 [M + H]⁺. ¹H-NMR (400 MHz, Methanol-$d_4$) δ 8.07 (d, J = 8.0 Hz, 1H), 7.68 (d, J = 8.4 Hz, 1H), 7.34 (s, 1H), 6.91-6.89 (m, 1H), 6.84 (d, J = 8.4 Hz, 1H), 6.73 (d, J = 8, 0 Hz, 1H), 6.64-6.61 (m, 1H), 5.62 (d, J = 2.4 Hz, 1H), 4.06 (s, 3H), 3.37 (d, J = 8.4 Hz, 1H), 3.30 (s, 3H), 2.39 (s, 3H), 2.25-2.22 (m, 1H). 2.19-2.16 (m, 1H) |
| 151 | m/z (ESI, +ve ion) = 455.2 [M + H]⁺. ¹H NMR (400 MHz, DMSO) δ 12.42 (s, 1H), 10.43 (s, 1H), 9.98 (s, 1H), 7.91 (d, J = 8.5 Hz, 1H), 7.41 (s, 1H), 7.36 (s, 1H), 6.90 (d, J = 8.5 Hz, 1H), 6.75 (d, J = 8.5 Hz, 1H), 6.58 (d, J = 8.4 Hz, 1H), 5.69 (s, 1H), 3.21-3.14 (m, 1H), 2.98-2.85 (m, 1H), 2.37-2.27 (m, 4H), 2.02-1.94 (m, 1H), 1.22 (d, J = 6.6 Hz, 6H) |
| 152 | m/z (ESI, +ve ion) = 441.20 [M + H]⁺. ¹H NMR (400 MHz, DMSO-$d_6$) δ 12.60 (s, 1H), 10.41 (s, 1H), 8.93 (s, 1H), 8.03 (s, 1H), 7.39-7.35 (m, 2H), 6.89 (d, J = 8.0 Hz, 1H), 6.75 (d, J = 8.4 Hz, 1H), 6.59 (dd, J = 8.4, 2.4 Hz, 1H), 5.70 (d, J = 2.4 Hz, 1H), 3.33 (s, 3H), 3.20 (t, J = 8.4 Hz, 1H), 2.68-2.59 (m, 2H), 2.33-2.31 (m, 1H), 2.17 (s, 3H), 1.99 (dd, J = 9.6, 4.4 Hz, 1H), 1.20 (t, J = 7.2 Hz, 3H) |
| 153 | m/z (ESI, +ve ion) = 455.1 [M + H]+. ¹H NMR (500 MHz, DMSO) δ 12.52 (s, 1H), 10.40 (s, 1H), 9.15 (s, 1H), 7.42 (d, J = 8.4 Hz, 1H), 7.36 (s, 1H), 6.88 (d, J = 8.5 Hz, 1H), 6.74 (d, J = 8.4 Hz, 1H), 6.58 (dd, J = 8.5, 2.6 Hz, 1H), 5.70 (d, J = 2.5 Hz, 1H), 4.55 (t, J = 9.2 Hz, 2H), 3.31 (s, 3H), 3.22-3.10 (m, 3H), 2.31 (dd, J = 7.9, 4.7 Hz, 1H), 2.22 (s, 3H), 1.97 (dd, J = 9.0, 4.7 Hz, 1H) |
| 155 | m/z (ESI, +ve ion) = 475.1 [M + H]⁺. ¹H NMR (400 MHz, DMSO) δ 12.70 (s, 1H), 10.43 (s, 1H), 9.30 (s, 1H), 7.94 (d, J = 2.8 Hz, 1H), 7.48-7.34 (m, 2H), 6.90 (d, J = 8.4 Hz, 1H), 6.74 (d, J = 8.1 Hz, 1H), 6.58 (d, J = 8.3 Hz, 1H), 5.69 (s, 1H), 3.89 (s, 3H), 3.23-3.10 (m, 1H), 2.38-2.28 (m, 1H), 2.06 (s, 3H), 2.01-1.92 (m, 1H) |
| 156 | m/z (ESI, +ve ion) = 459.4 [M + H]+. ¹H NMR (500 MHz, DMSO) δ 12.67 (s, 1H), 10.41 (s, 1H), 9.18 (s, 1H), 7.81 (s, 1H), 7.44 (d, J = 8.4 Hz, 1H), 7.39 (s, 1H), 6.90 (d, J = 8.4 Hz, 1H), 6.74 (d, J = 8.4 Hz, 1H), 6.58 (dd, J = 8.5, 2.6 Hz, 1H), 5.68 (d, J = 2.5 Hz, 1H), 3.89-3.82 (m, 3H), 3.52 (s, 3H), 3.32 (s, 3H), 3.20-3.15 (m, 1H), 2.31 (dd, J = 7.9, 4.8 Hz, 1H), 1.97 (dd, J = 9.1, 4.6 Hz, 1H) |
| 158 | m/z (ESI, +ve ion) = 496.15 [M + H]⁺. ¹H-NMR (400 MHz, Methanol-$d_4$) δ 7.86 (s, 1H), 7.58 (d, J = 8.4 Hz, 1H), 7.43 (s, 1H), 7.36 (d, J = 1.6 Hz, 1H), 6.95 (d, J = 8.8 Hz, 1H), 6.84 (d, J = 8.4 Hz, 1H), 6.65-6.62 (m, 1H), 5.66 (d, J = 2.4 Hz, 1H), 4.05 (s, 3H), 3.38-3.32 (m, 4H), 2.27-2.23 (m, 1H), 2.20-2.18 (m, 1H) |
| 159 | m/z (ESI, +ve ion) = 453.4 [M + H]+. ¹H NMR (500 MHz, MeOD) δ = 7.52 (d, J = 8.5, 1H), 7.43 (s, 1H), 6.92 (dd, J = 8.5, 1.0, 1H), 6.82 (d, J = 8.5, 1H), 6.61 (dd, J = 8.5, 2.6, 1H), 5.60 (d, J = 2.5, 1H), 3.37-3.33 (m, 1H), 3.30 (s, 3H), 2.88 (t, J = 7.8, 2H), 2.70 (t, J = 7.4, 2H), 2.23 (dd, J = 7.9, 4.8, 1H), 2.17 (dd, J = 9.1, 4.8, 1H), 2.14-2.07 (m, 2H) |
| 162 | m/z (ESI, +ve ion) = 459.15 [M + H]⁺. ¹H NMR (400 MHz, Methanol-$d_6$) δ 8.34 (s, 1H), 7.56 (d, J = 8.8 Hz, 1H), 7.47 (s, 1H), 6.94 (d, J = 8.4 Hz, 1H), 6.84 (d, J = 8.4 Hz, 1H), 6.64-6.62 (m, 1H), 5.62 (d, J = 2.0 Hz, 1H), 3.80-3.60 (m, 1H), 3.31 (s, 3H), 2.46 (s, 3H), 2.33 (s, 3H), 2.27-2.25 (m, 1H), 2.21-2.17 (m, 1H) |
| 164 | m/z (ESI, +ve ion) = 458.05 [M + H]⁺. ¹H NMR (400 MHz, DMSO-$d_6$) δ 12.21 (s, 1H), 10.42 (s, 1H), 8.15 (d, J = 2.4 Hz, 1H), 8.07 (s, 1H), 7.92 (d, J = 8.4 Hz, 1H), 7.33 (s, 1H), 7.30 (d, J = 2.4 Hz, 1H), 6.90 (d, J = 7.6 Hz, 1H), 6.75 (d, J = 8.4 Hz, 1H), 6.58 (dd, J = 10.8, 2.4 Hz, 1H), 5.70 (d, J = 2.4 Hz, 1H), 3.95 (s, 3H), 3.76 (s, 3H), 3.32 (s, 3H), 3.18 (t, J = 8.4 Hz, 1H), 2.34-2.31 (m, 1H), 2.00-1.96 (m, 1H) |
| 165 | m/z (ESI, +ve ion) = 473.3 [M + H]+. ¹H NMR (400 MHz, DMSO-d6) δ 12.87 (s, 1H), 10.43 (s, 1H), 8.41 (s, 1H), 8.29 (d, J = 2.0 Hz, 1H), 7.52 (d, J = 8.5 Hz, 1H), 7.45 (s, 1H), 7.03 (d, J = 2.2 Hz, 1H), 6.95 (d, J = 7.9 Hz, 1H), 6.74 (d, J = 8.4 Hz, 1H), 6.58 (dd, J = 8.4, 2.6 Hz, 1H), 5.70 (d, J = 2.5 Hz, 1H), 3.32 (s, 3H), 3.20 (t, J = 8.3 Hz, 1H), 2.37-2.31 (m, 1H), 1.98 (dd, J = 9.1, 4.7 Hz, 1H) |
| 166 | m/z (ESI, +ve ion) = 499.3 [M + H]⁺. ¹H NMR (400 MHz, DMSO) δ 12.30 (s, 1H), 10.45 (s, 1H), 8.56-8.24 (m, 2H), 7.94 (s, 1H), 7.51-7.15 (m, 2H), 7.08-6.43 (m, 3H), 5.71 (s, 1H), 4.01 (s, 3H), 3.21-3.11 (m, 4H), 2.99 (s, 3H), 2.51 (s, 3H), 2.42-2.26 (m, 1H), 2.07-1.89 (m, 1H) |
| 168 | m/z (ESI, +ve ion) = 506.2 [M + H]⁺. ¹H NMR (400 MHz, DMSO) δ 12.47 (s, 1H), 10.44 (s, 1H), 8.79 (s, 1H), 8.52-8.36 (m, 1H), 7.99-7.86 (m, 1H), 7.71-7.54 (m, 1H), 7.38 (s, 1H), 7.01-6.87 (m, 1H), 6.82-6.68 (m, 1H), 6.68-6.50 (m, 1H), 5.70 (s, 1H), 4.09 (s, 3H), 3.19 (s, 4H), 2.39-2.28 (m, 1H), 2.08-1.93 (m, 1H) |
| 171 | m/z (ESI, +ve ion) = 486.3 [M + H]⁺. ¹H NMR (400 MHz, DMSO-d6) δ 12.74 (s, 1H), 10.42 (d, J = 8.5 Hz, 1H), 9.31 (s, 1H), 8.39 (s, 1H), 7.64 (d, J = 11.1 Hz, 1H), 7.43 (d, J = 6.1 Hz, 1H), 6.92 (d, J = 8.6 Hz, 1H), 6.74 (d, J = 8.4 Hz, 1H), 6.58 (dd, J = 8.5, 2.5 Hz, 1H), 6.38 (t, J = 6.6 Hz, 1H), 5.72 (d, J = 2.5 Hz, 1H), 4.07 (s, 3H), 3.31-3.26 (m, 3H), 3.19 (t, J = 8.4 Hz, 1H), 2.37-2.29 (m, 1H), 1.96 (dt, J = 30.4, 15.2 Hz, 1H) |

TABLE 1B-continued

| Example No. | MS/$^1$H NMR |
|---|---|
| 172 | m/z (ESI, +ve ion) = 454.3 [M + H]$^+$. $^1$H NMR (500 MHz, DMSO) δ = 12.83 (s, 1H), 10.42 (s, 1H), 9.77 (s, 1H), 8.17 (s, 1H), 7.44 (d, J = 8.7, 2H), 6.97-6.94 (m, 1H), 6.74 (d, J = 8.4, 1H), 6.58 (dd, J = 8.4, 2.6, 1H), 5.68 (d, J = 2.5, 1H), 4.03 (s, 3H), 3.30 (s, 3H), 3.20 (t, J = 8.5, 1H), 2.33 (dd, J = 7.9, 4.7, 1H), 1.99 (dd, J = 9.0, 4.7, 1H) |
| 175 | m/z (ESI, +ve ion) = 519.10 [M + H]$^+$. $^1$H-NMR (400 MHz, DMSO-d$_6$) δ 12.28 (s, 1H), 10.40 (s, 1H), 8.66 (s, 1H), 8.14 (s, 1H), 7.88 (d, J = 8 Hz, 1H), 7.34 (t, J = 8 Hz, 2H), 7.21 (d, J = 8 Hz, 1H), 6.89 (d, J = 8 Hz, 1H), 6.75 (d, J = 8 Hz, 1H), 6.59-6.57 (m, 1H), 5.70 (s, 1H), 4.01 (s, 3H), 3.32-3.28 (m, 3H), 3.18-3.12 (m, 3H), 2.34-2.31 (m, 1H), 2.00-1.96 (m, 1H), 1.12-1.11 (d, J = 4 Hz, 3H) |
| 176 | m/z (ESI, +ve ion) = 498.10 [M + H]$^+$. $^1$H NMR (400 MHz, DMSO-d$_6$) δ 12.10 (s, 1H), 10.42 (s, 1H), 8.19 (d, J = 2.0 Hz, 1H), 7.86-7.83 (m, 2H), 7.33 (s, 1H), 7.02 (d, J = 8.4 Hz, 1H), 6, 88-6.86 (m, 2H), 6.76 (d, J = 8.4 Hz, 1H), 6.58-6.57 (m, 1H), 5.70 (d, J = 2.4 Hz, 1H), 3.94 (s, 3H), 3.44-3.31 (m, 3H), 3.20-3.16 (m, 1H), 2.96 (s, 6H), 2.34-2.31 (m, 1H), 1.98-1.96 (m, 1H) |
| 177 | m/z (ESI + ve ion) = 484.10 [M + H]$^+$. $^1$H NMR (400 MHz, DMSO-d$_6$) δ 12.14 (s, 1H), 10.42 (s, 1H), 8.52 (d, J = 2.0 Hz, 1H), 8.15 (d, J = 4.4 Hz, 1H), 7.81 (d, J = 8.4 Hz, 1H), 7.74 (s, 1H), 7.33-7.29 (m, 2H), 7.03 (d, J = 8.4 Hz, 1H), 6.88 (d, J = 8.4 Hz, 1H), 6.76 (d, J = 8.4 Hz, 1H), 6.58-6.57(m, 1H), 5.71 (d, J = 2.4 Hz, 1H), 3.94 (s, 3H), 3.33 (s, 3H), 3.20-3.16 (m, 1H), 2.74 (d, J = 4.4 Hz, 3H), 2.34-2.31 (m, 1H), 2.00-1.96 (m, 1H) |
| 178 | m/z (ESI, +ve ion) = 533.30 [M + H]$^+$. $^1$H NMR (400 MHz, Methanol-d$_4$) δ 8.43 (t, J = 1.9 Hz, 1H), 7.67 (d, J = 8.5 Hz, 1H), 7.41-7.34 (m, 2H), 7.20-7.17 (m, 1H), 6.91 (d, J = 8.4 Hz, 1H), 6.84 (d, J = 8.5 Hz, 1H), 6.64-6.61 (m, 1H), 5.62 (d, J = 2.5 Hz, 1H), 4.08 (d, J = 1.8 Hz, 3H), 3.39-3.37 (m, 1H), 3.32-3.29 (s, 4H), 2.26-2.22 (m, 1H), 2.20-2.17 (m, 1H), 1.26 (d, J = 6.8 Hz, 6H) |
| 179 | m/z (ESI, +ve ion) = 534.20 [M + H]$^+$. $^1$H NMR (400 MHz, Methanol-d$_4$) δ 8.33 (d, J = 2.0 Hz, 1H), 7.67 (d, J = 8.8 Hz, 1H), 7.39 (s, 1H), 7.31-7, 28 (m, 1H), 7.16 (d, J = 8.4 Hz, 1H), 6.91 (d, J = 9.2, 1H), 6.84 (d, J = 8.4 Hz, 1H), 6.64-6.61 (m, 1H), 5.63 (d, J = 2.8 Hz, 1H), 4.07 (s, 3H), 3.33-3.30 (m, 4H), 2.66 (s, 6H), 2.25-2.18 (m, 2H) |
| 180 | m/z (ESI, +ve ion) = 540.10 [M + H]$^+$. $^1$H NMR (400 MHz, DMSO-d$_6$) δ 12.13 (s, 1H), 10.42 (s, 1H), 8.24 (d, J = 2.0 Hz, 1H), 7.87 (d, J = 8.0 Hz, 2H), 7.33 (s, 1H), 7.04 (d, J = 8.4 Hz, 1H), 6.90-6.87 (m, 2H), 6, 75 (d, J = 8.4 Hz, 1H), 6.58-6.57 (m, 1H), 5.70 (d, J = 2.8 Hz, 1H), 3.94 (s, 3H), 3.60-3.58 (m, 4 H), 3.52-3.49 (m, 4H), 3.32 (s, 3H), 3.20-3.16 (m, 1H), 2.34-2.31 (m, 1H), 2.00-1.96 (m, 1H) |
| 181 | m/z (ESI, +ve ion) = 499.60 [M + H]$^+$. $^1$H NMR (400 MHz, Methanol-d$_4$) δ 8.33 (d, J = 2.4 Hz, 1H), 7.73 (t, J = 5.2 Hz, 2H), 7.37 (s, 1H), 6.92 (d, J = 7.6 Hz, 1H), 6.84 (d, J = 8.4 Hz, 1H), 6.64-6.61 (m, 1H), 5.62 (d, J = 2.4 Hz, 1H), 4.13 (s, 3H), 3.38-3.36 (m, 1H), 3.29 (s, 3H), 3.10 (s, 6H), 2.25-2.17 (m, 2H) |
| 182 | m/z (ESI, +ve ion) = 456.10 [M + H]$^+$. $^1$H-NMR (400 MHz, DMSO-d$_6$) δ 12.52 (s, 1H), 10.41 (s, 1H), 8.73 (s, 1H), 7.76 (s, 1H), 7.43-7.34 (m, 2H), 6.84 (d, J = 8.4 Hz, 1H), 6.75 (d, J = 8.4 Hz, 1H), 6.57-6.60 (m, 1H), 5.64 (d, J = 2.6 Hz, 1H), 3.33 (s, 3H), 3.18 (t, J = 8.4 Hz, 1H), 2.70 (s, 6H), 2.28-2.31 (m, 1H), 2.06 (s, 3H), 1.96-1.99 (m, 1H) |
| 184 | m/z (ESI, +ve ion) = 547.1 [M + H]+. $^1$H NMR (400 MHz, DMSO) δ 12.39 (s, 1H), 10.44 (s, 1H), 8.58 (s, 1H), 8.46-8.35 (m, 1H), 7.97-7.87 (m, 1H), 7.73-7.64 (m, 1H), 7.36 (s, 1H), 6.97-6.87 (m, 1H), 6.79-6.71 (m, 1H), 6.64-6.53 (m, 1H), 5.70 (s, 1H), 5.16 (t, J = 12.8 Hz, 2H), 4.46 (t, J = 12.7 Hz, 2H), 4.05 (s, 3H), 3.32 (s, 3H), 3.23-3.11 (m, 1H), 2.40-2.27 (m, 1H), 2.04-1.92 (m, 1H) |
| 186 | m/z (ESI, +ve ion) = 493.05 [M + H]$^+$. $^1$H NMR (400 MHz, Methanol-d$_6$) δ 7.82 (s, 1H), 7.28 (s, 1H), 6.87 (d, J = 8.4 Hz, 1H), 6.76-6.60 (m, 2H), 5.76 (d, J = 2.4 Hz, 1H), 3.98 (s, 3H), 3.40 (s, 3H), 3.35-3.34 (m, 1H), 2.27-2.24 (m, 1H), 2.17-2.10 (m, 1H), 1.93 (s, 3H) |
| 187 | m/z (ESI, +ve ion) = 443.05 [M + H]$^+$. $^1$H-NMR (400 MHz, DMSO-d$_6$) δ 12.68 (s, 1H), 10.42 (s, 1H), 9.07 (s, 1H), 7.92 (s, 1H), 7.39 (d, J = 7.7 Hz, 2H), 6.89 (d, J = 8.4 Hz, 1H), 6.75 (d, J = 8.4 Hz, 1H), 6.57-6.60 (m, 1H), 5.67 (d, J = 2.5 Hz, 1H), 3.48 (s, 3H), 3.33 (s, 3H), 3.19 (t, J = 8.4 Hz, 1H), 2.30-2.33 (m, 1H), 2.14 (s, 3H), 1.97-2.00 (m, 1H) |
| 188 | m/z (ESI, +ve ion) = 553.25 [M + H]$^+$. $^1$H NMR (400 MHz, DMSO-d$_6$) δ 12.34 (s, 1H), 10.43 (s, 1H), 8.47 (s, 1H), 8.39 (d, J = 8.0 Hz, 1H), 7.92 (d, J = 8.4 Hz, 1H), 7.60 (d, J = 8.2 Hz, 1H), 7.36 (s, 1H), 6.92 (d, J = 8.5 Hz, 1H), 6.75 (d, J = 8.4 Hz, 1H), 6.60-6.57 (m, 1H), 5.70 (d, J = 2.0 Hz, 1H), 4.92 (s, 2H), 4.75-4.71 (m, 4H), 4.20 (s, 2H), 4.08 (s, 3H), 3.30 (s, 3H), 3.19 (t, J = 8.4 Hz, 1H), 2.35-2.32 (m, 1H), 2.00-1.97 (m, 1H |
| 190 | m/z (ESI, +ve ion) = 562.05 [M + H]$^+$. $^1$H-NMR (400 MHz, DMSO-d$_6$) δ 12.62 (s, 1H), 10.42 (s, 1H), 9.11 (s, 1H), 7.79 (s, 1H), 7.47-7.44 (m, 2H), 6.76 (t, J = 16 Hz, 2H), 6.59-6.57 (m, 1H), 5.62 (d, J = 4 Hz, 1H), 3.82 (s, 3H), 3, 75-3.72 (m, 2H), 3.69-3.64 (m, 2H), 3.34 (s, 3H), 3.20 (t, J = 16 Hz, 1H), 2.93-2.89 (m, 2H), 2.51-2.50 (m, 2H), 2.36-2.32 (m, 1H), 2.00-1.98 (m, 1H) |
| 191 | m/z (ESI, +ve ion) = 485.10 [M + H]$^+$. $^1$H NMR (400 MHz, DMSO-d$_6$) δ 12.32 (s, 1H), 10.43 (s, 1H), 8.46-8.40 (m, 2H), 8.30 (d, J = 4.8 Hz, 1H), 7.93 (d, J = 8.4 Hz, 1H), 7.61 (d, J = 8.0 Hz, 1H), 7.35 (s, 1H), 6.92 (d, J = 8.4 Hz, 1H), 6.76 (d, J = 8.4 Hz, 1H), 6.59-6.57(m, 1H), 5.70 (d, J = 2.0 Hz, 1H), 4.12 (s, 3H), 3.33 (s, 3H), 3.20-3.14 (m, 1H), 2.83 (d, J = 4.4 Hz, 3H), 2.35-2.32 (m, 1H), 2.00-1.97 (m, 1H) |
| 192 | m/z (ESI, +ve ion) = 526.15 [M + H]$^+$. $^1$H-NMR (400 MHz, DMSO-d$_6$) δ 12.55 (s, 1H), 10.40 (s, 1H), 8.87 (s, 1H), 7.73 (s, 1H), 7.54 (d, J = 8 Hz, 1H), 7.39 (s, 1H), 6.84 (d, J = 12 Hz, 1H), 6.76 (d, J = 8 Hz, 1H), 6.63-6.60 (m, 1H), 5, 66 (s, 1H), |

TABLE 1B-continued

| Example No. | MS/$^1$H NMR |
|---|---|
| | 4.60-4.53 (m, 4H), 3.81-3.74 (m, 6H), 3.31(s, 4H), 3.22-3.18 (t, J = 16 Hz, 1H), 2.33-2.30 (m, 1H), 2.01-1.98 (m, 1H) |
| 196 | m/z (ESI, +ve ion) = 506.05 [M + H]$^+$. $^1$H NMR (400 MHz, DMSO-d$_6$) δ 12.60 (s, 1H), 10.41 (s, 1H), 8.98 (s, 1H), 7.49 (d, J = 8.5 Hz, 1H), 7.42-7.32 (m, 3H), 6.81 (dd, J = 8.2, 1.3 Hz, 1H), 6.76 (d, J = 8.4 Hz, 1H), 6.60 (dd, J = 8.4, 2.6 Hz, 1H), 5.65 (d, J = 2.5 Hz, 1H), 3.98 (s, 3H), 3.33 (s, 3H), 3.18 (t, J = 8.5 Hz, 1H), 2.74 (s, 3H), 2.34-2.28 (m, 1H), 1.99-1.96 (m, 1H) |
| 197 | m/z (ESI, +ve ion) = 499.20 [M + H]$^+$. $^1$H-NMR. (400 MHz, Methanol-d$_4$) δ 7.71 (d, J = 1.2 Hz, 1H), 7.60 (d, J = 8.4 Hz, 1H), 7.42 (s, 1H), 7.30 (d, J = 1.6 Hz, 1H), 6.93 (d, J = 8.4 Hz, 1H), 6.84 (d, J = 8.4 Hz, 1H), 6.64-6.61 (m, 1H), 5.67 (d, J = 2.4 Hz, 1H), 4.03 (s, 3H), 3.37-3.33 (m, 1H), 3.32 (s, 3H), 3.12 (s, 6H), 2.24-2.17 (m, 2H) |
| 198 | m/z (ESI, +ve ion) = 499.10 [M + H]$^+$. $^1$H-NMR (400 MHz, DMSO-d$_6$) δ 12.43 (s, 1H), 10.42 (s, 1H), 8.56 (s, 1H), 8.12 (s, 1H), 8.07 (s, 1H), 7.86 (d, J = 8.4 Hz, 1H), 7.39 (s, 1H), 6.92 (d, J = 8.4 Hz, 1H), 6.75 (d, J = 8.4 Hz, 1H), 6.57-6.60 (m, 1H), 5.70 (d, J = 2.5 Hz, 1H), 4.03 (s, 3H), 3.31 (s, 3H), 3.19 (t, J = 8.4 Hz, 1H), 2.97 (d, J = 5.4 Hz, 6H), 2.32-2.35 (m, 1H), 1.97-2.00 (m, 1H) |
| 199 | m/z (ESI, +ve ion) = 540.15 [M + H]$^+$. $^1$H NMR (400 MHz, DMSO-d$_6$) δ 12.19 (s, 1H), 10.43 (s, 1H), 8.07 (d, J = 8.0 Hz, 1H), 7.95 (s, 1H), 7.84 (d, J = 8.4 Hz, 1H), 7.34 (s, 1H), 7.04 (s, 1H), 7.00 (d, J = 8.0 Hz, 1H), 6.90 (d, J = 8.8 Hz, 1H), 6.76 (d, J = 8.0 Hz, 1H), 6.60-6.57 (m, 1H), 5.70 (d, J = 2.4 Hz, 1H), 3.93 (s, 3H), 3.61 (s, 4H), 3.54 (s, 4H), 3.30 (s, 3H), 3.20-3.16 (m, 1H), 2.34-2.31 (m, 1H), 2.00-1.97 (m, 1H) |
| 200 | m/z (ESI, +ve ion) = 499.20 [M + H]$^+$. $^1$H NMR (400 MHz, DMSO-d$_6$) δ 12.61 (s, 1H), 10.42 (s, 1H), 9.09 (s, 1H), 7.99 (s, 1H), 7.44 (d, J = 8.4 Hz, 1H), 7.39 (s, 1H), 6.88 (d, J = 8.4 Hz, 1H), 6.75 (d, J = 8.4 Hz, 1H), 6.60 (d, J = 8.4 Hz, 1H), 5.68 (s, 1H), 3.92 (s, 3H), 3.83-3.79 (m, 1H), 3.63-3.57 (m, 3H), 3.34-3.24 (m, 3H), 3.22-3.17 (m, 2H), 2.33-2.30 (m, 1H), 2.09-1.92 (m, 3H) |
| 201 | m/z (ESI, +ve ion) = 499.20 [M + H]$^+$. $^1$H NMR (400 MHz, DMSO-d$_6$) δ 12.61 (s, 1H), 10.42 (s, 1H), 9.10 (s, 1H), 7.99 (s, 1H), 7.42-7.38 (m, 2H), 6.86 (d, J = 8.4 Hz, 1H), 6.75 (d, J = 8.4 Hz, 1H), 6.60-6.57 (m, 1H), 5.67 (d, J = 2.4 Hz, 1H), 3.92 (s, 3H), 3.87-3.83 (m, 1H), 3.65-3.61 (m, 1H), 3.53-3.49 (m, 2H), 3.34-3.24 (m, 3H), 3.22-3.17 (m, 2H), 2.33-2.30 (m, 1H), 2.05-1.92 (m, 2H), 1.90-1.87 (m, 1H) |
| 202 | m/z (ESI, +ve ion) = 520.15 [M + H]$^+$. $^1$H NMR (400 MHz, DMSO-d$_6$) δ 12.47 (s, 1H), 10.42 (s, 1H), 8.60 (s, 1H), 8.36 (d, J = 8.2 Hz, 1H), 7.87 (d, J = 8.4 Hz, 1H), 7.59 (d, J = 8.1 Hz, 1H), 7.39 (s, 1H), 6.98-6.91 (m, 1H), 6.76 (d, J = 8.4 Hz, 1H), 6.59 (dd, J = 8.4, 2.6 Hz, 1H), 5.69 (d, J = 2.6 Hz, 1H), 4.58-4.52 (m, 2H), 3.32 (s, 3H), 3.22-3.20 (m, 1H), 3.18 (s, 3H), 2.35-2.32 (m, 1H), 2.01-1.98 (m, 1H), 1.47 (t, J = 7.0 Hz, 3H) |
| 205 | m/z (ESI, +ve ion) = 504.15 [M + H]$^+$. $^1$H NMR (400 MHz, DMSO-d$_6$) δ 12.32 (s, 1H), 10.41 (s, 1H), 8.40-8.37 (m, 2H), 7.92 (d, J = 8.8 Hz, 1H), 7.49-7.46 (m, 1H), 7.36 (s, 1H), 6.92 (d, J = 8.4 Hz, 1H), 6.76 (d, J = 8.0 Hz, 1H), 6.60-6.58 (m, 1H), 5.71 (d, J = 2.0 Hz, 1H), 4.04 (s, 3H), 3.32 (s, 3H), 3.19 (t, J = 8.4 Hz, 1H), 2.35-2.31 (m, 1H), 2.01-1.97 (m, 1H), 1.63 (d, J = 13.2 Hz, 6H) |
| 206 | m/z (ESI, +ve ion) = 516.20 [M + H]$^+$. $^1$H NMR (400 MHz, DMSO-d$_6$) δ 12.26 (s, 1H), 10.41 (s, 1H), 8.20 (s, 1H), 8.01 (d, J = 12.4 Hz, 1H), 7.89 (d, J = 8.4 Hz, 1H), 7.35 (s, 1H), 6.91 (t, J = 6 Hz, 2H), 6.75 (d, J = 8.4 Hz, 1H), 6.60-6.57 (m, 1H), 5.70 (d, J = 2.0 Hz, 1H), 4.03 (s, 3H), 3.35 (s, 3H), 3.19-3.12 (m, 1H), 3.14 (s, 3H), 2.92 (s, 3H), 2.34-2.31 (m, 1H), 2.08-1.98 (m, 1H) |
| 207 | m/z (ESI, +ve ion) = 558.25 [M + H]$^+$. $^1$H-NMR (400 MHz, Methanol-d$_4$) δ 7.77 (d, J = 12.0 Hz, 1H), 7.69 (d, J = 8.4 Hz, 1H), 7.39 (s, 1H), 6.96-6.92 (m, 2H), 6.84 (d, J = 8.8 Hz, 1H), 6.64-6.61 (m, 1H), 5.61 (d, J = 2.8 Hz, 1H), 3.99 (s, 3H), 3.77-3.68 (m, 6H), 3.48 (s, 2H), 3.38-3.32 (m, 1H), 3.30 (s, 3H), 2.26-2.23 (m, 2H) |
| 209 | m/z (ESI, +ve ion) = 520.1 [M + H]+. $^1$H NMR (400 MHz, DMSO) δ 12.42 (s, 1H), 10.38 (s, 1H), 8.74 (s, 1H), 8.46-8.27 (m, 1H), 7.95-7.79 (m, 1H), 7.63-7.50 (m, 1H), 7.32 (s, 1H), 6.94-6.82 (m, 1H), 6, 74-6.64 (m, 1H), 6.58-6.47 (m, 1H), 5.76-5.57 (m, 2H), 4.00 (s, 3H), 3.26 (s, 3H), 3.18-3.04 (m, 2H), 2.35-2.23 (m, 1H), 1.99-1.88 (m, 1H), 1.16-0.99 (m, 3H) |
| 210 | m/z (ESI, +ve ion) = 534.4 [M + H]+. $^1$HNMR (400 MHz, DMSO-d6) δ 12.33 (s, 1H), 10.43 (s, 1H), 8.17 (s, 1H), 7.92 (s, 1H), 7.81 (d, J = 8.4 Hz, 1H), 7.34 (d, J = 17.1 Hz, 2H), 7.18 (q, J = 5.0 Hz, 1H), 6.90 (d, J = 8.5 Hz, 1H), 6.74 (d, J = 8.4 Hz, 1H), 6.58 (dd, J = 8.5, 2.5 Hz, 1H), 5, 69 (d, J = 2.5 Hz, 1H), 3.92 (s, 3H), 3.31 (s, 3H), 3.18 (t, J = 8.4 Hz, 1H), 2.43 (s, 3H), 2.39 (d, J = 5.0 Hz, 3H), 2.33 (dd, J = 7.9, 4, 7 Hz, 1H), 1.98 (dd, J = 9.0, 4.6 Hz, 1H) |
| 211 | m/z (ESI, +ve ion) = 485.4 [M + H]+. $^1$H NMR: (400 MHz, DMSO-d6) δ 12.67 (s, 1H), 10.43 (s, 1H), 9.33 (s, 1H), 7.41 (d, J = 7.9 Hz, 2H), 6.90 (d, J = 9.1 Hz, 1H), 6.74 (d, J = 8.4 Hz, 1H), 6.58 (dd, J = 8.5, 2.5 Hz, 1H), 5.71 (d, J = 2.5 Hz, 1H), 4.74 (dd, J = 6.4, 2.5 Hz, 1H), 4.26 (d, J = 15.7, 2.8 Hz, 1H), 3.97 (d, J = 15.7 Hz, 1H), 3.32 (s, 3H), 3.24-3.10 (m, 1H), 2.33 (dd, J = 7.8, 4.6 Hz, 1H), 2.23 (s, 3H), 1.98 (dd, J = 9.1, 4.7 Hz, 1H), 1.47 (d, J = 6, 5 Hz, 3H) |
| 213 | m/z (ESI, +ve ion) = 482.2 [M + H]$^+$. $^1$H NMR (500 MHz, DMSO) δ = 12.87 (s, 1H), 10.43 (s, 1H), 10.18 (s, 1H), 7.47-7.43 (m, 2H), 6.88 (d, J = 8.5, 0.9, 1H), 6.75 (d, J = 8.4, 1H), 6.58 (dd, J = 8.5, 2.6, 1H), 5.60 (d, J = 2.6, 1H), 3.31 (s, 3H), 3.19 (t, J = 8.4, 1H), 2.94-2.67 (m, 10H), 2.30 (dd, J = 7.9, 4.7, 1H), 2.13-2.04 (m, 2H), 1.98 (dd, J = 9.0, 4.7, 1H) |
| 214 | m/z (ESI, +ve ion) = 513.15 [M + H]$^+$. $^1$H NMR (400 MHz, DMSO-d$_6$) δ 12.29 (s, 1H), 10.41 (s, 1H), 8.34 (d, J = 8.1 Hz, 1H), 8.15 (s, 1H), 7.86 (d, J = 8.3 Hz, 1H), |

TABLE 1B-continued

| Example No. | MS/$^1$H NMR |
|---|---|
| | 7.36 (s, 1H), 7.25 (d, J = 8.0 Hz, 1H), 6.92 (d, J = 8.3 Hz, 1H), 6.76 (d, J = 8.4 Hz, 1H), 6.59 (dd, J = 8.4, 2.6 Hz, 1H), 5.69 (d, J = 2.6 Hz, 1H), 4.49-4.44 (m, 2H), 3.32 (s, 3H), 3.19 (t, J = 8.4 Hz, 1H), 3.15 (s, 3H), 2.99 (s, 3H), 2.32-2.30 (m, 1H), 2.00-1.97 (m, 1H). 1.44 (t, J = 7.0 Hz, 3H) |
| 215 | m/z (ESI, +ve ion) = 511.25 [M + H]$^+$. $^1$H NMR (400 MHz, DMSO-d$_6$) δ 12.05 (s, 1H), 10.42 (s, 1H), 8.43 (d, J = 8.8 Hz, 1H), 7.94-7.90 (m, 2H), 7.78 (d, J = 8.4 Hz, 1H), 7.30 (s, 1H), 6.87 (d, J = 8.4 Hz, 1H), 6.75 (d, J = 8.4 Hz, 1H), 6.59 (d, J = 7.6 Hz, 1H), 5.71 (s, 1H), 4.05-3.99 (m, 5H), 3.33 (s, 3H), 3.20-3.16 (m, 1H), 2.56-2.51 (m, 2H), 2.33 (d, J = 4.8 Hz, 1H), 2.07-2.03 (m, 2H), 2.00-1.98 (m, 1H) |
| 216 | m/z (ESI + ve ion) = 576.20 [M + H]$^+$. $^1$H-NMR (400 MHz, Methanol-d$_4$) δ 8.15 (s, 1H), 7.64 (d, J = 8.4 Hz, 1H), 7.42 (s, 1H), 7.29-7.26 (m, 1H), 7.17 (d, J = 8.4 Hz, 1H), 6.90 (d, J = 8, 4 Hz, 1H), 6.84 (d, J = 8.4 Hz, 1H), 6.64-6.62 (m, 1H), 5.64 (d, J = 2.4 Hz, 1H), 4.08 (s, 3H), 3.65-3.61 (m, 4H), 3.37 (d, J = 8.4 Hz, 1H), 3.31 (s, 3H), 3.01-2.88 (m, 4H), 2.27-2.24 (m, 1H), 2.20-2.17 (m, 1H) |
| 217 | m/z (ESI, +ve ion) = 479.1 [M + H]+. $^1$H NMR (400 MHz, DMSO) δ: 12.64 (s, 1H), 10.44 (s, 1H), 9.08 (s, 1H), 8.55 (s, 1H), 7.64 (d, J = 7.3 Hz, 1H), 7.49-7.55 (m, 2H), 7.41 (s, 1H), 7.35 (br. s., 1H), 6.89 (d, J = 7.1 Hz, 1H), 6.75 (d, J = 8.8 Hz, 1H), 6.60 (d, J = 8.5 Hz, 1H), 5.75 (s, 1H), 4.07 (s, 3H), 3.36 (s, 3H), 3.21 (t, J = 9.7 Hz, 1H), 2.33 (s, 1H), 1.99 (s, 1H) |
| 218 | m/z (ESI, +ve ion) = 515.2 [M + H]+. $^1$H NMR (400 MHz, DMSO) δ 12.26 (s, 1H), 10.37 (s, 1H), 8.44-8.25 (m, 2H), 7.94-7.77 (m, 1H), 7.41-7.19 (m, 2H), 6.97-6.79 (m, 1H), 6.78-6.62 (m, 1H), 6.62-6.45 (m, 1H), 5.64 (s, 1H), 3.97 (s, 3H), 3.72 (s, 3H), 3.15-3.06 (m, 1H), 2.34-2.20 (m, 1H), 2.02-1.83 (m, 1H) |
| 219 | m/z (ESI, +ve ion) = 528.2 [M + H]+. $^1$H NMR (400 MHz, DMSO) δ 12.27 (s, 1H), 10.37 (s, 1H), 9.60-9.49 (m, 1H), 8.48-8.28 (m, 2H), 7.94-7.80 (m, 1H), 7.59-7.46 (m, 1H), 7.36-7.23 (m, 1H), 6.93-6.79 (m, 1H), 6.76-6.63 (m, 1H), 6.58-6.45 (m, 1H), 5.63 (s, 1H), 4.80 (s, 1H), 4.05 (s, 3H), 3.15-3.07 (m, 1H), 3.07-2.99 (m, 1H), 2.33-2.20 (m, 1H), 1.97-1.86 (m, 1H), 0.96 (s, 6H) |
| 220 | m/z (ESI, +ve ion) = 511.4 [M + H]+. NMR (400 MHz, DMSO-d6) δ 12.22 (s, 1H), 10.43 (s, 1H), 8.78 (d, J = 2.2 Hz, 1H), 8.10 (s, 1H), 7.92 (d, J = 8.4 Hz, 1H), 7.79 (d, J = 2.2 Hz, 1H), 7.32 (s, 1H), 6.88 (d, J = 8.5 Hz, 1H), 6.74 (d, J = 8.4 Hz, 1H), 6.58 (dd, J = 8.4, 2.4 Hz, 1H), 5.70 (d, J = 2.2 Hz, 1H), 3.98 (s, 3H), 3.79 (t, J = 7.0 Hz, 2H), 3.31 (s, 3H), 3.17 (t, J = 8.4 Hz, 1H), 2.46 (t, J = 8.0 Hz, 2H), 2.33 (dd, J = 7.7, 4.7 Hz, 1H), 2.12-2.03 (m, 2H), 1.97 (dd, J = 8.9, 4.7 Hz, 1H) |
| 221 | m/z (ESI, +ve ion) = 534.4 [M + H]+. $^1$H NMR (400 MHz, DMSO-d6) δ 12.33 (s, 1H), 10.43 (s, 1H), 8.17 (s, 1H), 7.92 (s, 1H), 7.81 (d, J = 8.4 Hz, 1H), 7.34 (d, J = 17.1 Hz, 2H), 7.18 (q, J = 5.0 Hz, 1H), 6.90 (d, J = 8.5 Hz, 1H), 6.74 (d, J = 8.4 Hz, 1H), 6.58 (dd, J = 8.5, 2.5 Hz, 1H), 5.69 (d, J = 2.5 Hz, 1H), 3.92 (s, 3H), 3.31 (s, 3H), 3.18 (t, J = 8.4 Hz, 1H), 2.43 (s, 3H), 2.39 (d, J = 5.0 Hz, 3H), 2.33 (dd, J = 7.9, 4.7 Hz, 1H), 1.98 (dd, J = 9.0, 4.6 Hz, 1H) |
| 222 | m/z (ESI + ve ion) = 535.15 [M + H]+. $^1$H-NMR (400 MHz, DMSO-d6) δ 12.43 (s, 1H), 10.42 (s, 1H), 8.69 (s, 1H), 8.43 (d, J = 8.0 Hz, 1H), 7.94 (d, J = 8.4 Hz, 1H), 7.50 (d, J = 8.4 Hz, 1H), 7.38 (s, 1H), 6.95 (d, J = 8.4 Hz, 1H), 6.76 (d, J = 8.4 Hz, 1H), 6.60-6.58 (m, 1H), 5.71 (d, J = 2.4 Hz, 1H), 4.06 (s, 3H), 3.32 (s, 3H), 3.21-3.17 (m, 1H), 2.81 (s, 6H), 2.35-2.32 (m, 1H), 2.01-1.96 (m, 1H). |
| 223 | m/z (ESI, +ve ion) = 549.10 [M + H]$^+$. $^1$H NMR (400 MHz, DMSO-d$_6$) δ 12.45 (s, 1H), 10.42 (s, 1H), 8.53 (s, 1H), 8.36 (d, J = 8.2 Hz, 1H), 7.87 (d, J = 8.4 Hz, 1H), 7.47 (d, J = 8.1 Hz, 1H), 7.39 (s, 1H), 6.97-6.90 (m, 1H), 6.76 (d, J = 8.4 Hz, 1H), 6.59 (dd, J = 8.4, 2.6 Hz, 1H), 5.69 (d, J = 2.6 Hz, 1H), 4.51 (q, J = 7.0 Hz, 2H), 3.32 (s, 3H), 3.20 (t, J = 8.5 Hz, 1H), 2.81 (s, 6H), 2.34-2.32 (m, 1H), 2.00-1.98 (m, 1H), 1.46 (t, J = 7.0 Hz, 3H) |
| 224 | m/z (ESI, +ve ion) = 549.10 [M + H]+. $^1$H NMR (400 MHz, DMSO-d6) δ 12.45 (s, 1H), 10.42 (s, 1H), 8.53 (s, 1H), 8.36 (d, J = 8.2 Hz, 1H), 7.87 (d, J = 8.4 Hz, 1H), 7.47 (d, J = 8.1 Hz, 1H), 7.39 (s, 1H), 6.97-6.90 (m, 1H), 6.76 (d, J = 8.4 Hz, 1H), 6.59 (dd, J = 8.4, 2.6 Hz, 1H), 5.69 (d, J = 2.6 Hz, 1H), 4.51 (q, J = 7.0 Hz, 2H), 3.32 (s, 3H), 3.20 (t, J = 8.5 Hz, 1H), 2.81 (s, 6H), 2.34-2.32 (m, 1H), 2.00-1.98 (m, 1H), 1.46 (t, J = 7.0 Hz, 3H |
| 225 | m/z (ESI, +ve ion) = 504.20 [M + H]+. $^1$H NMR (400 MHz, Chloroform-d) δ 7.93-7.90 (m, 1H), 7.58 (d, J = 8.4 Hz, 1H), 7.45 (d, J = 12 Hz, 2H), 6.93 (d, J = 8 Hz, 1H), 6.84 (d, J = 4.4 Hz, 1H), 6.64-6.61 (m, 1H), 5.66 (d, J = 2.4 Hz, 1H), 4.06 (s, 3H), 3.42 (s, 1H), 3.36 (d, J = 8.8 3H), 2.26-2.20 (m, 1H), 2.19-2.16 (m, 1H), 1.81 (s, 3H), 1.79 (s, 3H). |
| 226 | m/z (ESI, +ve ion) = 486.4 [M + H]+. $^1$H NMR (400 MHz, DMSO) δ 12.17 (s, 1H), 10.41 (s, 1H), 8.53 (d, J = 2.1 Hz, 1H), 7.92-7.84 (m, 2H), 7.68 (d, J = 2.2 Hz, 1H), 7.31 (s, 1H), 6.89-6.84 (m, 1H), 6.74 (d, J = 8.4 Hz, 1H), 6.58 (dd, J = 8.4, 2.5 Hz, 1H), 5.70 (d, J = 2.5 Hz, 1H), 4.96 (s, 1H), 3.96 (s, 3H), 3.17 (t, J = 8.4 Hz, 1H), 2.37-2.27 (m, 1H), 2.01-1.92 (m, 1H), 1.43 (s, 6H). 3 protons are under water peak at 3.30 ppm |
| 227 | m/z (ESI, +ve ion) = 520.25 [M + H]+. $^1$H NMR (400 MHz, DMSO-d6) δ 12.40 (s, 1H), 10.41 (s, 1H), 8.64 (s, 1H), 8.27 (s, 1H), 7.92 (d, J = 8.4 Hz, 1H), 7.38 (s, 1H), 6.93 (d, J = 8.4 Hz, 1H), 6.75 (d, J = 8.4 Hz, 1H), 6.60-6.58 (m, 1H), 5.71 (d, J = 2.4 Hz, 1H), 4.04 (s, 3H), 3.33 (s, 3H), 3.31 (s, 3H), 3.19 (t, J = 8.4 Hz, 1H), 2.51 (s, 3H), 2.34-2.33 (m, 1H), 2.00-1.97 (m, 1H). |
| 229 | m/z (ESI, +ve ion) = 505.10 [M + H]+. $^1$H-NMR (400 MHz, Methanol-d4) δ 8.02 (d, J = 2.8 Hz, 1H), 7.59 (d, J = 8.4 Hz, 1H), 7.44 (s, 1H), 6.95 (d, J = 8.8 Hz, 1H), 6.84 (d, J = 8.4 Hz, 1H), 6.64-6.61 (m, 1H), 5.62 (d, J = 2.4 Hz, 1H), 4.16 (s, 3H), 3.38 (d, J = 8.4 Hz, 1H), 3.31 (s, 3H), 2.26-2.17 (m, 2H), 1.82 (s, 3H), 1.78 (s, 3H). |

TABLE 1B-continued

| Example No. | MS/¹H NMR |
|---|---|
| 230 | m/z (ESI, +ve ion) = 525.25 [M + H]+. ¹H-NMR (400 MHz, Methanol-d4) δ 8.24 (d, J = 8.4 Hz, 1H), 7.73-7.67 (m, 2H), 7.40 (s, 1H), 6.94 (d, J = 8.4 Hz, 1H), 6.84 (d, J = 8.4 Hz, 1H), 6.64-6.61 (m, 1H), 5.62 (d, J = 2.4 Hz, 1H), 4.20 (s, 3H), 3.38 (d, J = 8.4 Hz, 2H), 3.33-3.31 (s, 4H), 2.26-2.05 (m, 2H), 1.19-1.12 (m, 1H), 0.58-0.54 (m, 2H), 0.36-0.32 (m, 2H) |
| 231 | m/z (ESI + ve ion) = 513.25 [M + H]+. 1H-NMR (400 MHz, Methanol-d4) δ 8.23 (d, J = 8.4 Hz, 1H), 7.73-7.66 (m, 2H), 7.40 (s, 1H), 6.94 (d, J = 8.4 Hz, 1H), 6.84 (d, J = 8.4 Hz, 1H), 6.64-6.61 (m, 1H), 5.62 (d, J = 2.4 Hz, 1H), 4.18 (s, 4H), 3.38 (d, J = 8.4 Hz, 1H), 3.30 (s, 3H), 2.26-2.17 (m, 2H), 1.31 (d, J = 6.4 Hz, 6H) |
| 232 | m/z (ESI + ve ion) = 567.25 [M + H]+. ¹H NMR (400 MHz, DMSO-d₆) δ 12.31 (s, 1H), 10.41 (s, 1H), 8.48-8.32 (m, 2H), 7.93 (d, J = 8.4 Hz, 1H), 7.51 (d, J = 8.2 Hz, 1H), 7.36 (s, 1H), 6.92 (d, J = 8.8 Hz, 1H), 6.76 (d, J = 8.4 Hz, 1H), 6.59 (dd, J = 8.4, 2.6 Hz, 1H), 5.71 (d, J = 2.6 Hz, 1H), 5.13 (s, 1H), 4.59 (d, J = 6.6 Hz, 1H), 4.00 (s, 3H), 3.82 (s, 1H), 3.67 (d, J = 11.8 Hz, 3H), 3.32 (s, 3H), 3.21-3.17 (m, 1H). 2.33 (m, 1H), 2.04-1.75 (m, 5H) |
| 233 | m/z (ESI, +ve ion) = 459.4 [M + H]+. NMR (400 MHz,) δ 12.45 (s, 1H), 10.42 (s, 1H), 8.41 (s, 1H), 7.48 (d, J = 8.4 Hz, 1H), 7.35 (s, 1H), 6.87 (d, J = 8.5 Hz, 1H), 6.74 (d, J = 8.4 Hz, 1H), 6.58 (dd, J = 8.5, 2.4 Hz, 1H), 6.29 (s, 1H), 5.67 (d, J = 2.4 Hz, 1H), 3.88 (s, 3H), 3.31 (s, 3H), 3.27 (s, 3H), 3.18 (t, J = 8.4 Hz, 1H), 2.30 (dd, J = 7.8. 4.8 Hz, 1H), 1.97 (dd, J = 9.0, 4.6 Hz, 1H) |
| 235 | m/z (ESI, +ve ion) = 541.3 [M + H]+. ¹H NMR (400 MHz, DMSO) δ 12.58 (s, 1H), 10.44 (s, 1H), 8.75 (s, 1H), 7.83 (s, 1H), 7.47-7.37 (m, 2H), 7.34 (s, 1H), 6.87 (d, J = 8.4 Hz, 1H), 6.75 (d, J = 8.5 Hz, 1H), 6.59 (d, J = 8.3 Hz, 1H), 5.75 (s, 1H), 4.59-4.37 (m, 1H), 4.31-4.08 (m, 5H), 3.93 (s, 3H), 3.88-3.74 (m, 2H), 3.26-3.11 (m, 5H), 2.40-2.28 (m, 1H), 2.04-1.94 (m, 1H) |
| 236 | m/z (ESI, +ve ion) = 500.2 [M + H]+. ¹H NMR (400 MHz, DMSO) δ 12.71 (s, 1H), 10.47 (s, 1H), 9.31 (s, 1H), 7.78 (s, 1H), 7.54-7.34 (m, 2H), 6.90 (d, J = 8.5 Hz, 1H), 6.77 (d, J = 8.5 Hz, 1H), 6.65-6.55 (m, 1H), 5.72 (s, 1H), 4.01 (s, 3H), 3.33 (s, 3H), 3.25-3.10 (m, 4H), 2.98 (s, 3H), 2.38-2.29 (m, 1H), 2.05-1.96 (m, 1H) |
| 237 | m/z (ESI, +ve ion) = 514.3 [M + H]+. ¹H NMR (400 MHz, DMSO) δ 12.69 (s, 1H), 10.43 (s, 1H), 9.21 (s, 1H), 7.77 (s, 1H), 7.48-7.37 (m, 2H), 6.89 (d, J = 8.5 Hz, 1H), 6.74 (d, J = 8.8 Hz, 1H), 6.67-6.52 (m, 1H), 5.71 (s, 1H), 4.52-4.38 (m, 2H), 3.23-3.06 (m, 4H), 2.97 (s, 3H), 2.33 (s, 1H), 1.76 (s, 1H), 1.43 (s, 3H) |
| 238 | m/z (ESI, +ve ion) = 513.25 [M + H]+. ¹H NMR (400 MHz, Methanol-d4) δ 8.08 (s, 1H), 7.70 (d, J = 8.4 Hz, 1H), 7.39 (s, 1H), 6.94-6.91 (m, 1H), 6.84 (d, J = 8.4 Hz, 1H), 6.64-6.61 (m, 1H), 5.62 (d, J = 2.4 Hz, 1H), 4.06 (s, 3H), 3.38-3.36 (m, 1H), 3.30 (s, 3H), 3.14 (s, 3H), 2.97 (s, 3H), 2.26-2.18 (m, 5H) |
| 239 | m/z (ESI, +ve ion) = 490.20 [M + H]⁺. ¹H NMR (400 MHz, DMSO-d₆) δ 12.32 (s, 1H), 10.42 (s, 1H), 8.53 (d, J = 8.4 Hz, 1H), 8.43 (s, 1H), 7.93 (d, J = 8.4 Hz, 1H), 7.42 (d, J = 8.0 Hz, 1H), 7.36 (s, 1H), 6.93-6.91 (m, 1H), 6.75 (d, J = 8.4 Hz, 1H), 6.60-6.57 (m, 1H), 5.71 (d, J = 2.4 Hz, 1H), 4.05 (s, 3H), 3.32 (s, 3H), 3.21-3.17 (m, 1H), 2.78 (s, 3H), 2.34-2.37 (m, 1H), 2.00-1.97 (m, 1H) |
| 240 | m/z (ESI, +ve ion) = 490.20 [M + H]⁺. ¹H NMR (400 MHz, DMSO-d₆) δ 12.32 (s, 1H), 10.42 (s, 1H), 8.54 (d, J = 8.0 Hz, 1H), 8.43 (s, 1H), 7.94 (d, J = 8.4 Hz, 1H), 7.42 (d, J = 8.4 Hz, 1H), 7.36 (s, 1H), 6.92 (d, J = 8.8 Hz, 1H), 6.75 (d, J = 8.4 Hz, 1H), 6.60-6.57 (m, 1H), 5.71 (d, J = 2.4 Hz, 1H), 4.05 (s, 3H), 3.33 (s, 3H), 3.21-3.17 (m, 1H), 2.78 (s, 3H), 2.35-2.32 (m, 1H), 2.08-1.97 (m, 1H) |
| 241 | m/z (ESI, +ve ion) = 506.15 [M + H]+. ¹H NMR (400 MHz, DMSO-d6) δ 12.43 (s, 1H), 10.42 (s, 1H), 9.28 (s, 1H), 8.54 (s, 1H), 7.90 (d, J = 8.4 Hz, 1H), 7.58 (s, 1H), 7.37 (s, 1H), 6.95-6.92 (m, 1H), 6.76 (d, J = 8.4 Hz, 1H), 6.60-6.58 (m, 1H), 5.71 (d, J = 2.4 Hz, 1H), 4.09 (s, 3H), 3.33 (s, 3H), 3.32-3.21 (s, 4H), 2.35-2.32 (m, 1H), 2.01-1.98 (m, 1H). |
| 242 | m/z (ESI, +ve ion) = 507.20 [M + H]⁺. ¹H-NMR (400 MHz, DMSO-d₆) δ 12.80 (s, 1H), 10.42 (s, 1H), 9.76 (s, 1H), 8.03 (s, 1H), 7.44-7.41 (m, 2H), 6.92-6.90 (m, 1H), 6.75 (d, J = 8.4 Hz, 1H), 6.60-6.57 (m, 1H), 5.71 (d, J = 2.4 Hz, 1H), 4.09 (s, 3H). 3.33 (s, 3H), 3.21-3.15 (m, 4H), 2.35-2.31 (m, 1H), 2.00-1.97 (m, 1H). |
| 243 | m/z (ESI, +ve ion) = 551.20 [M + H]+. ¹H NMR (400 MHz, DMSO-d6) δ 12.27 (s, 1H), 10.42 (s, 1H), 8.40 (d, J = 8.0 Hz, 1H), 8.32 (s, 1H), 7.93 (d, J = 8.8 Hz, 1H), 7.35 (s, 1H), 7.27 (d, J = 8.4 Hz, 1H), 6.92 (d, J = 8.4 Hz, 1H), 6.76 (d, J = 8.4 Hz, 1H), 6.60-6.57 (m, 1H), 5.71 (d, J = 2.4 Hz, 1H), 3.98 (s, 3H), 3.32-3.21 (m, 3H), 3.19 (t, J = 8.0 Hz, 1H), 2.87 (s, 2H), 2.34-2.31 (m, 1H), 2.05-1.97 (m, 1H), 0.69 (s, 4H), 0.59 (s, 4H). |
| 244 | m/z (ESI, +ve ion) = 535.15 [M + H]+. ¹H NMR (400 MHz, DMSO-d6) δ 12.35 (s, 1H), 10.42 (s, 1H), 8.60-8.57 (m, 1H), 8.52 (s, 1H), 8.42 (d, J = 8.0 Hz, 1H), 7.93 (d, J = 8.4 Hz, 1H), 7.65 (d, J = 8.0 Hz, 1H), 7.36 (s, 1H), 6.92 (d, J = 8.4 Hz, 1H), 6.75 (d, J = 8.4 Hz, 1H), 6.60-6.52 (m, 1H), 6.29-6.01 (m, 1H), 5.71 (d, J = 2.8 Hz, 1H), 4.14 (s, 3H), 3.78-3.66 (m, 2H), 3.30 (s, 3H), 3.21-3.17 (m, 1H), 2.34-2.31 (m, 1H), 2.00-1.97 (m, 1H) |
| 245 | m/z (ESI, +ve ion) = 567.30 [M + H]+. ¹H NMR (400 MHz, DMSO-d6) δ 12.23 (s, 1H), 10.41 (s, 1H), 8.40 (d, J = δ 0 Hz, 1H), 8.24 (s, 1H), 7.93 (d, J = 8.4 Hz, 1H), 7.34 (s, 1H), 7.13 (d, J = 8.0 Hz, 1H), 6.92-6.90 (m, 1H), 6.76 (d, J = 8.4 Hz, 1H), 6.60-6.57 (m, 1H), 5.71 (d, J = 2.4 Hz, 1H), 4.53 (s, 2H), 4.01 (s, 3H), 3.32 (d, J = 5.6 Hz, 3H), 3.20 (t, J = 8.4 Hz, 1H), 2.34-2.31 (m, 1H), 2.01-1.97 (m, 1H), 1.86 (d, J = 12 Hz, 1H), 1.61 (d, J = 5.2 Hz, 4H), 1.49 (d, J = 2.8 Hz, 1H), 1.29 (d, J = 6.8 Hz, 6H) |
| 246 | m/z (ESI, +ve ion) = 567.20 [M + H]+. ¹H NMR (400 MHz, DMSO-d6) δ 12.29 (s, 1H), 10.42 (s, 1H), 8.41-8.37 (m, 2H), 7.93 (d, J = 8.4 Hz, 1H), 7.35 (s, 1H), 7.30 (d, J = 8.1 Hz, 1H), 6.92 (d, J = 8.0 Hz, 1H), 6.75 (d, J = 8.4 Hz, 1H), 6.59 (d, J = |

TABLE 1B-continued

| Example No. | MS/$^1$H NMR |
|---|---|
|  | 2.4 Hz, 1H), 5.71 (d, J = 2.6 Hz, 1H), 4.39-4.36 (m, 1H), 4.28-4.26 (m, 1H), 4.13-4.09 (m, 1H), 4.01 (s, 4H), 3.32-3.29 (m, 5H), 3.19 (t, J = 8.4 Hz, 1H), 3.00-2.98 (m, 1H). 2.34-2.31(m, 1H), 2.00-1.93(m, 1H), 1.83-1.80 (m, 3H). |
| 247 | m/z (ESI, +ve ion) = 510.10 [M + H]+. $^1$H NMR (400 MHz, DMSO-d6) δ 12.82 (s, 1H), 10.42 (s, 1H), 9.55 (s, 1H), 8.29 (d, J = 2.1 Hz, 1H), 8.19 (d, J = 2.2 Hz, 1H), 7.45 (s, 1H), 7.36 (d, J = 8.4 Hz, 1H), 6.91 (d, J = 8.3 Hz, 1H), 6.75 (d, J = 8.4 Hz, 1H), 6.60 (dd, J = 8.4, 2.6 Hz, 1H), 5.71 (d, J = 2.6 Hz, 1H), 3.34 (s, 3H), 3.25 (s, 3H), 3.20 (t, J = 8.4 Hz, 1H), 2.34-2.32 (m, 1H), 2.08-1.94 (m, 1H) |
| 249 | m/z (ESI, +ve ion) = 504.15 [M + H]+. $^1$H NMR (400 MHz, DMSO-d6) δ 12.29 (s, 1H), 10.42 (s, 1H), 9.32 (s, 1H), 8.23 (s, 1H), 7.90 (d, J = 8.3 Hz, 1H), 7.51 (d, J = 5.9 Hz, 1H), 7.34 (s, 1H), 6.91 (d, J = 8.4 Hz, 1H), 6.76 (d, J = 8.4 Hz, 1H), 6.59 (dd, J = 8.5, 2.6 Hz, 1H), 5.71 (d, J = 2.6 Hz, 1H), 4.04 (s, 3H), 3.33 (s, 3H), 3.19 (t, J = 8.5 Hz, 1H), 2.35-2.32 (m, 1H), 2.01-1.97 (m, 1H), 1.63 (d, J = 13.5 Hz, 6H) |
| 250 | m/z (ESI, +ve ion) = 549.20 [M + H]+. $^1$H NMR (400 MHz, Methanol-d4) δ 8.25 (d, J = 8.1 Hz, 1H), 7.73-7.70 (m, 2H), 7.40 (s, 1H), 6.95-6.93 (m, 1H), 6.84 (d, J = 8.4 Hz, 1H), 6.64-6.61 (m, 1H), 5.62 (d, J = 2.4 Hz, 1H), 4.78-4.76 (m, 1H), 4.73-4.69 (m, 1H), 4.66-4.63 (m, 1H), 4.60-4.52 (m, 2H), 4.18 (s, 3H), 3.39-3.34 (m, 1H), 3.31 (s, 3H), 2.27-2.23 (m, 1H), 2.21-2.17 (m, 1H) |
| 251 | m/z (ESI, +ve ion) = 503.20 [M + H]+. $^1$H NMR (400 MHz, DMSO-d$_6$) δ 12.56 (s, 1H), 10.43 (s, 1H), 8.47 (s, 1H), 8.17 (d, J = 8.4 Hz, 1H), 7.64 (d, J = 8.4 Hz, 1H), 7.56 (d, J = 8.4 Hz, 1H), 7.41 (s, 1H), 6.96 (d, J = 8.8 Hz, 1H), 6.77 (d, J = 8.4 Hz, 1H), 6.61-6.53 (m, 1H), 5.71 (d, J = 2.4 Hz, 1H), 3.35 (s, 3H), 3.22-3.18 (m, 1H), 3.07 (s, 3H), 2.99 (s, 3H), 2.35-2.32 (m, 1H), 2.08-1.91 (m, 1H) |
| 252 | m/z (ESI, +ve ion) = 486.20 [M + H]+. $^1$H NMR (400 MHz, DMSO-d6) δ 12.33 (s, 1H), 10.41 (s, 1H), 8.17 (s, 1H), 8.05 (s, 1H), 7.77-7.75 (m, 2H), 7.38 (s, 1H), 6.93-6.91 (m, 1H), 6.76 (d, J = 8.0 Hz, 1H), 6.61-6.58 (m, 1H). 5.71 (d, J = 2.4 Hz, 1H), 3.34 (s, 3H), 3.25 (t, J = 8.4 Hz, 1H), 2.57 (s, 3H), 2.34-2.31 (m, 1H), 2.00-1.98 (m, 1H) |
| 253 | m/z (ESI, +ve ion) = 499.25 [M + H]+. $^1$H NMR (400 MHz, DMSO-d6) δ 12.24 (s, 1H), 10.42 (s, 1H), 9.18 (s, 1H), 8.14 (s, 1H), 7.91 (d, J = 8.4 Hz, 1H), 7.34 (s, 1H), 7.26 (s, 1H), 6.91 (d, J = 8.4 Hz, 1H), 6.76 (d, J = 8.4 Hz, 1H), 6.62-6.55 (m, 1H), 5.71 (d, J = 2.4 Hz, 1H), 4.00 (s, 3H), 3.33 (s, 3H), 3.19 (t, J = 8.4 Hz, 1H), 3.07 (s, 3H), 3.00 (s, 3H), 2.37-2.29 (m, 1H), 2.03-1.95 (m, 1H) |
| 254 | m/z (ESI + ve ion) = 533.20 [M + H]+. $^1$H-NMR (400 MHz, DMSO-d6) δ 12.57 (s, 1H), 10.41 (s, 1H), 8.93 (s, 1H), 7.52 (s, 1H), 7.38 (d, J = 6.6 Hz, 2H), 6.87 (d, J = 8.5 Hz, 1H), 6.75 (d, J = 8.4 Hz, 1H), 6.62-6.55 (m, 1H), 5.71 (d, J = 2.4 Hz, 1H), 4.42 (t, J = 8.7 Hz, 4H), 4.06 (s, 3H), 3.88-3.79 (m, 1H), 3.33 (s, 3H), 3.18 (t, J = 8.5 Hz, 1H), 2.33-2.30 (m, 1H), 2.00-1.97 (m, 1H) |
| 255 | m/z (ESI, +ve ion) = 577.15 [M + H]+. $^1$H-NMR (400 MHz, Methanol-d4) δ 7.96 (d, J = 2.0 Hz, 1H), 7.60 (d, J = 8.4 Hz, 1H), 7.44 (s, 1H), 7.35 (d, J = 1.6 Hz, 1H), 6.96 (d, J = 8.4 Hz, 1H), 6.84 (d, J = 8.4 Hz, 1H), 6.64-6.62 (m, 1H), 5.65 (d, J = 2.4 Hz, 1H), 4.07 (s, 3H), 3.75-3.73 (m, 4H), 3.37 (d, J = 8.4 Hz, 1H), 3.32 (s, 3H), 3.04-3.01 (m, 4H), 2.27-2.25 (m, 1H). 2.19-2.14 (m, 1H) |
| 256 | m/z (ESI, +ve ion) = 603.20 [M + H]+. $^1$H-NMR (400 MHz, Methanol-d4) δ 7.94 (d, J = 1.9 Hz, 1H), 7.59 (d, J = 8.4 Hz, 1H), 7.44 (s, 1H), 7.33 (d, J = 2.0 Hz, 1H), 6.95 (d, J = 7.6 Hz, 1H), 6.84 (d, J = 8.4 Hz, 1H), 6.65-6.62 (m, 1H), 5.65 (d, J = 2.8 Hz, 1H), 4.39 (s, 2H), 4.07 (s, 3H), 3.51-3.50 (m, 3H), 3.38 (d, J = 11.2 Hz, 3H), 2.67 (d, J = 10.8 Hz, 2H), 2.27-2.24 (m, 1H), 2.21-2.17 (m, 1H), 2.00-1.93 (m, 4H) |
| 257 | m/z (ESI, +ve ion) = 532.60 [M + H]+. $^1$H NMR (400 MHz, DMSO-d6) δ 12.35 (s, 1H), 10.43 (s, 1H), 8.42-8.40 (m, 2H), 7.92 (d, J = 8.4 Hz, 1H), 7.49-7.47 (m, 1H), 7.36 (s, 1H), 6.93-6.91 (m, 1H), 6.75 (d, J = 8.4 Hz, 1H), 6.60-6.58 (m, 1H), 5.71 (d, J = 2.4 Hz, 1H), 4.02 (s, 3H), 3.32 (d, J = 2.0 Hz, 3H), 3.19 (t, J = 8.4 Hz, 1H), 2.35-2.32 (m, 1H), 2.01-1.87 (m, 5H), 1.03-0.95 (m, 6H) |
| 259 | m/z (ESI, +ve ion) = 576.15 [M + H]+. $^1$H-NMR (400 MHz, Methanol-d4) δ 8.02 (d, J = 1.9 Hz, 1H), 7.59 (d, J = 8.4 Hz, 1H), 7.44 (d, J = 2.0 Hz, 2H), 6.95 (d, J = 8.8 Hz, 1H), 6.84 (d, J = 8.8 Hz, 1H), 6.65-6.62 (m, 1H), 5.65 (d, J = 2.4 Hz, 1H), 4.08 (s, 3H), 4.04-4.02 (m, 2H), 3.46-3.42 (m, 4H), 3, 40-3.37 (m, 3H), 2.27-2.24 (m, 1H), 2.20-2.17 (m, 1H), 1.91-1.81 (m, 2H), 1.80-1.70 (m, 2H) |
| 260 | m/z (ESI, +ve ion) = 453.2 [M + H]+. $^1$H NMR (400 MHz, DMSO δ 12.52 (s, 1H), 10.44 (s, 1H), 8.89 (s, 1H), 8.41-8.29 (m, 1H), 7.96-7.88 (m, 1H), 7.63-7.54 (m, 1H), 7.38 (s, 1H), 6.95-6.91 (m, 1H), 6.80-6.70 (m, 1H), 6.58 (s, 1H), 5, 69 (s, 1H), 4.04 (s, 3H), 3.32 (s, 3H), 3.21-3.15 (m, 1H), 2.33 (s, 1H), 2.00 (s, 1H). |
| 261 | [0059] m/z (ESI, +ve ion) = 531.20 [M + H]+. $^1$H NMR (400 MHz, Methanol-d4) δ 8.17-8.13 (m, 1H), 7.61 (d, J = 8.4 Hz, 1H), 7.37 (s, 1H), 7.29-7.25 (m, 1H), 7.16-7.13 (m, 1H), 6.89-6.82 (m, 2H), 6.63-6.60 (m, 1H), 5.62 (d, J = 2.4 Hz, 1H), 4.03 (s, 3H), 3.37-3.29 (m, 4H), 2.24-2.19 (m, 1H), 2.18-2.15 (m, 1H), 2.00-1.88 (m, 4H), 1.12-1.01 (m, 6H) |
| 262 | m/z (ESI, +ve ion) = 520.25 [M + H]$^+$. $^1$H NMR (400 MHz, DMSO-d$_6$) δ 12, 43 (s, 1H), 10.41 (s, 1H), 9.29 (s, 1H), 8.55 (s, 1H), 7.90 (d, J = 8.4 Hz, 1H), 7.57 (s, 1H), 7.37 (s, 1H), 6.93 (dd, J = 8.4, 1, 4 Hz, 1H), 6.76 (d, J = 8.4 Hz, 1H), 6.59 (dd, J = 8.5, 2.6 Hz, 1H), 5.71 (d, J = 2.6 Hz, 1H), 4.09 (s, 3H), 3.37-3.34 (m, 2H), 3.33 (s, 3H), 3.19 (t, J = 8.5 Hz, 1H), 2.34 (dd, J = 7.9, 4.7 Hz, 1H), 1.99 (dd, J = 9.0, 4.7 Hz, 1H), 1.14 (t, J = 7.4 Hz, 3H) |

TABLE 1B-continued

| Example No. | MS/$^1$H NMR |
|---|---|
| 263 | m/z (ESI, +ve ion) = 511.3 [M + H]+. $^1$H NMR (400 MHz, DMSO) δ 12.57 (s, 1H), 10.43 (s, 1H), 8.72 (s, 1H), 7.88-7.76 (m, 1H), 7.44-7.37 (m, 2H), 7.37-7.28 (m, 1H), 6.96-6.82 (m, 1H), 6.81-6.70 (m, 1H), 6.66-6.53 (m, 1H), 5.75 (s, 1H), 4.43-4.27 (m, 2H), 4.10-3.96 (m, 2H), 3.92 (s, 3H), 3.22-3.10 (m, 1H), 2.39-2.30 (m, 1H), 2.30-2.17 (m, 2H), 2.05-1.91 (m, 1H) |
| 264 | m/z (ESI, +ve ion) = 541.3 [M + H]+. $^1$H NMR (400 MHz, DMSO) δ 12.54 (s, 1H), 10.43 (s, 1H), 8.61 (s, 1H), 7.61 (s, 1H), 7.46-7.40 (m, 1H), 7.39 (s, 1H), 7.21 (s, 1H), 6.96-6.79 (m, 1H), 6.81-6.69 (m, 1H), 6.68-6.52 (m, 1H), 5.74 (s, 1H), 3.91 (s, 3H), 3.65-3.56 (m, 4H), 3.56-3.49 (m, 4H), 3.22-3.13 (m, 1H), 2.39-2.28 (m, 1H), 2.03-1.93 (m, 1H) |
| 265 | m/z (ESI, +ve ion) = 496.25 [M + H]+. $^1$H NMR (400 MHz, DMSO-d6) δ 12.24 (s, 1H), 10.42 (s, 1H), 8.26 (s, 1H), 8.07 (s, 1H), 7.85 (d, J = 8.0 Hz, 1H), 7.34 (s, 1H), 7.19 (s, 1H), 6.92 (d, J = 8.4 Hz, 1H), 6.76 (d, J = 8.4 Hz, 1H), 6.60-6.58 (m, 1H), 5.71 (d, J = 2.4 Hz, 1H), 4.34 (s, 2H), 3.98 (s, 3H), 3.35 (s, 3H), 3.19-3.14 (m, 1H), 3.04 (s, 3H), 2.34-2.31 (m, 1H), 2.01-1.97 (m, 1H) |
| 266 | m/z (ESI, +ve ion) = 496.20 [M + H]+. $^1$H-NMR (400 MHz, DMSO-d6) δ 12.27 (s, 1H), 10.41 (s, 1H), 8.16 (s, 1H), 8.04 (d, J = 8.4 Hz, 1H), 7.80 (d, J = 8.4 Hz, 1H), 7.36 (s, 1H), 7.28 (d, J = 8.4 Hz, 1H), 6.91-6.89 (m, 1H), 6.76 (d, J = 8.4 Hz, 1H), 6.60-6.57 (m, 1H), 5.70 (d, J = 2.8 Hz, 1H), 4.64 (s, 2H), 3.99 (s, 3H), 3.33 (s, 3H), 3.19 (t, J = 8.0 Hz, 1H), 3.06 (s, 3H), 2.34-2.30 (m, 1H), 2.00-1.97 (m, 1H) |
| 267 | m/z (ESI, +ve ion) = 563.25 [M + H]+. $^1$H NMR (400 MHz, Methanol-d4) δ 8.08 (s, 1H), 7.59 (d, J = 8.4 Hz, 1H), 7.47-7.44 (m, 2H), 6.97 (d, J = 8.4 Hz, 1H), 6.85 (d, J = 8.4 Hz, 1H), 6.64-6.62 (m, 1H), 5.65 (d, J = 2.4 Hz, 1H), 4.01 (s, 3H), 3.94-3.88 (m, 2H), 3.69-3.66 (m, 2H), 3.38-3.33 (m, 4H), 2.27-2.14 (m, 4H) |
| 268 | m/z (ESI, +ve ion) = 547.25 [M + H]+. $^1$H NMR (400 MHz, DMSO-d6) δ 12.66 (s, 1H), 10.41 (s, 1H), 9.16 (s, 1H), 7.90 (d, J = 2.0 Hz, 1H), 7.46-7.42 (m, 2H), 7.33 (d, J = 1.6 Hz, 1H), 6.92 (d, J = 8.4 Hz, 1H), 6.76 (d, J = 8.4 Hz, 1H), 6.61-6.58 (m, 1H), 5.74 (d, J = 2.8 Hz, 1H), 4.01 (s, 3H), 3, 70-3.67 (m, 4H), 3.34-3.285 (m, 3H), 3.21-3.19 (m, 1H), 2.35-2.33 (m, 1H), 2.04-1.99 (m, 3H) |
| 269 | m/z (ESI, +ve ion) = 577.25 [M + H]+. $^1$H NMR (400 MHz, DMSO-d6) δ 12.64 (s, 1H), 10.41 (s, 1H), 9.07 (s, 1H), 7.88 (d, J = 2.0 Hz, 1H), 7.40-7.36 (m, 3H), 6.90 (d, J = 8.4 Hz, 1H), 6.75 (d, J = 8.4 Hz, 1H), 6.59 (dd, J = 8.5, 2.6 Hz, 1H), 5.72 (d, J = 2.5 Hz, 1H), 4.56 (d, J = 6.0 Hz, 2H), 4.12 (d, J = 6.0 Hz, 2H), 3.97 (s, 3H), 3.34 (s, 3H), 3.19 (t, J = 8.4 Hz, 1H), 2.34-2.31 (m, 1H), 2.00-1.97 (m, 1H), 1.46 (s, 3H) |
| 270 | m/z (ESI, +ve ion) = 591.30 [M + H]+. $^1$H NMR (400 MHz, DMSO-d6) δ 12.67 (s, 1H), 10.42 (s, 1H), 9.15 (s, 1H), 7.95 (d, J = 1.9 Hz, 1H), 7.41 (d, J = 7.8 Hz, 2H), 7.33 (d, J = 2.0 Hz, 1H), 6.90 (d, J = 8.5 Hz, 1H), 6.75 (d, J = 8.4 Hz, 1H), 6.59 (dd, J = 8.4, 2.6 Hz, 1H), 5.74 (d, J = 2.6 Hz, 1H), 4.77 (d, J = 6.0 Hz, 2H), 4.13 (d, J = 6.0 Hz, 2H), 3.82 (s, 3H), 3.35 (s, 3H), 3.19 (t, J = 8.5 Hz, 1H), 2.50 (s, 3H), 2.34-2.32 (m, 1H), 2.00-1.97 (m, 1H), 1.56 (s, 3H) |
| 271 | m/z (ESI, +ve ion) = 472.3 [M + H]+. $^1$H NMR (400 MHz, DMSO) δ 12.19 (s, 1H), 10.43 (s, 1H), 8.44 (s, 1H), 7.97 (s, 1H), 7.94-7.86 (m, 1H), 7.55 (s, 1H), 7.33 (s, 1H), 6.94-6.83 (m, 1H), 6.79-6.71 (m, 1H), 6.64-6.52 (m, 1H), 5.70 (s, 1H), 5.12 (s, 1H), 4.76-4.59 (m, 1H), 3.97 (s, 3H), 3.34-3.27 (m, 6H), 3.23-3.11 (m, 1H), 2.38-2.29 (m, 1H), 2.02-1.92 (m, 1H) |
| 273 | m/z (ESI, I've ion) = 604.25 [M + H]+. $^1$H NMR (400 MHz, DMSO-d6) δ 12.69 (s, 1H), 10.42 (s, 1H), 9.06 (s, 1H), 7.83 (s, 1H), 7.42 (d, J = 4.8 Hz, 2H), 7.23 (s, 1H), 6.90 (d, J = 8.4 Hz, 1H), 6.75 (d, J = 8.4 Hz, 1H), 6.63-6.56 (m, 1H), 5.74 (d, J = 1.6 Hz, 1H), 4.29-4.19 (m, 2H), 3.34 (s, 3H), 3.19 (t, J = 8.4 Hz, 1H), 2.95-2.92 (m, 4H), 2.50 (s, 1H), 2.38-2.31 (s, 4H), 2.17 (s, 3H), 2.03-1.95 (m, 1H), 1.44 (t, J = 6.8 Hz, 3H) |
| 275 | m/z (ESI, +ve ion) = 535.15 [M + H]+. $^1$H-NMR (400 MHz, Methanol-d4) δ 8.01 (d, J = 2.0 Hz, 1H), 7.59 (d, J = 8.4 Hz, 1H), 7.43-7.41 (m, 2H), 6.96-6.94 (m, 1H), 6.84 (d, J = 8.4 Hz, 1H), 6.64-6.61 (m, 1H), 5.66 (d, J = 2.8 Hz, 1H), 4.32-4.27 (m, 2H), 3.39-3.36 (m, 1H), 3.32 (s, 3H), 2.56 (s, 3H), 2.26-2.23 (m, 1H), 2.20-2.17 (m, 1H), 1.56 (t, J = 6, 8 Hz, 3H) |
| 277 | m/z (ESI, +ve ion) = 473.25 [M + H]+. $^1$H NMR (400 MHz, DMSO-d6) δ 12.45 (s, 1H), 10.41 (s, 1H), 8.33 (s, 1H), 7.49 (d, J = 8.8 Hz, 1H), 7.36 (s, 1H), 6.88 (d, J = 8.4 Hz, 1H), 6.75 (d, J = 8.4 Hz, 1H), 6.59-6.57 (m, 1H), 6.25 (s, 1H), 5.68 (d, J = 2.4 Hz, 1H), 4.14 (d, J = 7.2 Hz, 2H), 3.33 (s, 3H), 3.27 (s, 3H), 3.20-3.19 (m, 1H), 2, 32-2.29 (m, 1H), 2.00-1.96 (m, 1H), 1.39 (t, J = 6.8 Hz, 3H) |

Biological Activity Examples

Biological Activity Example No. 1: PLK4 Biochemical Assay

Activity of human recombinant PLK4 (ThermoFisher, cat #PV6396) was measured by quantification of adenosine diphosphate (ADP) using the ADP-Glo Kinase Assay Kit (Promega, cat #V9102). Test compounds were solubilized in dimethyl sulfoxide (DMSO) and dispensed into 384-well white polystyrene nonbinding plates (Greiner, cat #781094) using the Echo acoustic dispenser (Labcyte Inc.) in a 11-point 3-fold titration in duplicates. 5 μL of 1.0 nM PLK4 protein in assay buffer (50 mM HEPES. pH 7.5, 0.01% Brij-35, 0.01% BSA, 10 mM MgCl$_2$, 1 mM EGTA, 1 mM DTT) was added to the plates. Test compounds and PLK4 were incubated for 15 minutes at room temperature (RT). Then 5 μL of a 16 μM adenosine triphosphate (ATP) (Promega, cat #V915B) and 9.3 μM Myelin Basic Protein (MBP) (SignalChem, cat #M42-51N) substrate solution in assay buffer was added and the reaction mixture was incubated for 6 hours at RT. The final concentration of PLK4. ATP and MBP in the reactions were 0.5 nM, 8.0 μM and 4.7 μM, respectively. Reactions were stopped and the remaining ATP depleted by adding 10 μL of ADP-Glo reagent (Promega, cat #V912B) and incubating for 40 minutes at RT. The simultaneous conversion of the remaining ADP to ATP and measurement of the newly synthesized ATP was achieved by addition of 20 μL Kinase Detection reagent (Promega, eat #V914B), incubation for 30 min at RT, and luminescence detection using the EnVision plate reader (PerkinElmer). Reactions lacking PLK4 were used as 100% inhibition controls. Reactions containing DMSO alone were used as 0% inhibition controls. The $IC_{50}$ values reported in Table 2 were determined using four parameter non-linear regression curve fit.

Biological Activity Example No. 2: CHP134 CellTiter-Glo (CTG) assay

CHP-134 cells (DSMZ-German Collection of Microorganisms and Cell Cultures, Braunschweig Germany) were cultured in RPMI 1640 supplemented with 10% fetal bovine serum, penicillin (100 U/ml), 1% L-Glutamine and streptomycin (100 mg/ml). Cells were seeded (200 cells/well) in 384-well plates for 16 hours. On day two, nine serial 1:3 compound dilutions were made in DMSO in a 96-well plate. The compounds were then further diluted into growth media using a BRAVO robot (Agilent, Santa Clara, CA). The diluted compounds were then added to quadruplicate wells in the 384-well cell plate and incubated at 37° C. and 5% $CO_2$. After 5 days, relative numbers of viable cells were measured by luminescence using CellTiter-Glo® (Promega) according to the manufacturer's instructions and read on a SPARK Multimode Microplate Reader (Tecan, Mannedorf Switzerland). The $IC_{50}$ calculations for the values reported in Table 2 were carried out using Prism 6.0 software (GraphPad, San Diego).

Biological Activity Example No. 3: Aurora a Kinase Biochemical Assay

Activity of human recombinant Aurora A (ThermoFisher, cat #PR5935A) was measured by quantification of adenosine diphosphate (ADP) using the ADP-Glo Kinase Assay Kit (Promega, cat #V9102). Test compounds were solubilized in dimethyl sulfoxide (DMSO) and dispensed into 384-well white polystyrene nonbinding plates (Greiner, cat #781094) using the Echo acoustic dispenser (Labcyte Inc.) in a 1-point 3-fold titration in duplicates. 5 μL of 5.0 nM Aurora A in assay buffer (50 mM HEPES, pH 7.5, 0.01% Brij-35, 0.01% BSA, 10 mM $MgCl_2$, 1 mM EGTA, 1 mM DTT) was added to the plates. Test compounds and Aurora A were incubated for 15 minutes at room temperature (RT). Then 5 μL of a 40 μM adenosine triphosphate (ATP) (Promega, cat #V915B) and 9.3 uM Myelin Basic Protein (MBP) (SignalChem, cat #M42-51N) substrate solution in assay buffer was added and the reaction mixture was incubated for 2 hours at RT. The final concentration of Aurora A, ATP and MBP in the reactions were 2.5 nM, 20 μM and 4.7 μM, respectively. Reactions were stopped and the remaining ATP depleted by adding 10 uL of ADP-Glo reagent (Promega, cat #V912B) and incubating for 40 minutes at RT. The simultaneous conversion of the remaining ADP to ATP and measurement of the newly synthesized ATP was achieved by addition of 20 μL Kinase Detection reagent (Promega, cat #V914B), incubation for 30 min at RT, and luminescence detection using the EnVision plate reader (PerkinElmer). Reactions lacking Aurora A were used as 100% inhibition controls. Reactions containing DMSO alone were used as 0% inhibition controls. The $IC_{50}$ values reported in Table 2 were determined using four parameter non-linear regression curve fit.

Biological Activity Example No. 4: Aurora B Kinase Biochemical Assay

Activity of human recombinant Aurora B (ThermoFisher, cat #PR9210B) was measured by quantification of adenosine diphosphate (ADP) using the ADP-Glo Kinase Assay Kit (Promega, cat #V9102). Test compounds were solubilized in dimethyl sulfoxide (DMSO) and dispensed into 384-well white polystyrene nonbinding plates (Greiner, cat #781094) using the Echo acoustic dispenser (Labcyte Inc.) in a 1-point 3-fold titration in duplicates. 5 μL of 20 nM Aurora B in assay buffer (50 mM HEPES, pH 7.5, 0.01% Brij-35, 0.01% BSA, 10 mM $MgCl_2$. 1 mM EGTA, 1 mM DTT) was added to the plates. Test compounds and Aurora B were incubated for 15 minutes at room temperature (RT). Then 5 μL of a 228 μM adenosine triphosphate (ATP) (Promega, cat #V915B) and 9.3 M Myelin Basic Protein (MBP) (SignalChem, cat #M42-51N) substrate solution in assay buffer was added and the reaction mixture was incubated for 2 hours at RT. The final concentration of Aurora b, ATP and MBP in the reactions were 10 nM, 114 μM and 4.7 μM, respectively. Reactions were stopped and the remaining ATP depleted by adding 10 uL of ADP-Glo reagent (Promega, cat #V912B) and incubating for 40 minutes at RT. The simultaneous conversion of the remaining ADP to ATP and measurement of the newly synthesized ATP was achieved by addition of 20 μL Kinase Detection reagent (Promega, cat #V914B), incubation for 30 min at RT, and luminescence detection using the EnVision plate reader (PerkinElmer). Reactions lacking Aurora B were used as 100% inhibition controls. Reactions containing DMSO alone were used as 0% inhibition controls. The $IC_{50}$ values reported in Table 2 were determined using four parameter non-linear regression curve fit.

As shown in Table 2, many of the compounds of Formula (I), (Ia), (Ib), (II), and (III) demonstrated potent inhibition of PLK4 and less potent inhibition of Aurora A kinase and Aurora B kinase. As such, the compounds of Formula (I), (Ia), (Ib), (II), and (III) demonstrated selective inhibition of PLK4. As also set forth in Table 2, many of the compounds of Formula (I), (Ia), (Ib), (II), and (III) demonstrated, surprisingly and unexpectedly, greater selectivity in the inhibition of PLK4 versus inhibition of Aurora A kinase and/or Aurora B kinase than the CFI-400495compound. In Table 2, ND means not determined.

TABLE 2

| Ex. No. | PLK4 $IC_{50}$ (nM) | CTG $IC_{50}$ (nM) | [Aurora A $IC_{50}$ (nM)]/ [PLK4 $IC_{50}$ (nM)] | [Aurora B $IC_{50}$ (nM)]/ [PLK4 $IC_{50}$ (nM)] |
|---|---|---|---|---|
| 1 | 3.495 | | | |
| 2 | 29.34 | | 318.03 | 15.6544 |
| 3 | 9.948 | | | |
| 4 | 3.955 | | 465.4867 | 11.45133 |

TABLE 2-continued

| Ex. No. | PLK4 IC$_{50}$ (nM) | CTG IC$_{50}$ (nM) | [Aurora A IC$_{50}$ (nM)]/ [PLK4 IC$_{50}$ (nM)] | [Aurora B IC$_{50}$ (nM)]/ [PLK4 IC$_{50}$ (nM)] |
|---|---|---|---|---|
| 5 | 2.178 | | | |
| 6 | 18.18 | | | |
| 7 | 4.559 | | 693.5732 | 47.26914 |
| 8 | 492.3 | | 17.60918 | 32.98802 |
| 9 | 0.6944 | 99.73 | 4791.187 | 240.6394 |
| 10 | 1.587 | 438.1 | 954.6314 | 103.0876 |
| 11 | 4.876 | 2952.3 | 3277.276 | 77.87121 |
| 12 | 4.959 | 2025.5 | | |
| 13 | 2.99 | | 667.5585 | 10.30435 |
| 14 | 36.03 | | 74.16042 | 3.866223 |
| 15 | 45.66 | | | |
| 16 | 2.181 | | 605.6855 | 11.76066 |
| 17 | 4.304 | | 1145.911 | 34.89777 |
| 18 | 22.9 | | | |
| 19 | 24.81 | | | |
| 20 | 2.254 | 262.7 | 4489.796 | 306.8323 |
| 21 | 41.73 | | | |
| 22 | 39.8 | | | |
| 23 | 5.048 | 45.9 | 215.5309 | 170.7409 |
| 24 | 2.255 | | | |
| 25 | 34.18 | | 249.6489 | 28.10123 |
| 26 | 3.853 | | | |
| 27 | 2.083 | | | |
| 28 | 0.375 | | | |
| 29 | 5.967 | | | |
| 30 | 31.24 | | 36.20359 | 6.18758 |
| 31 | 3.02 | | 207.053 | 22.16887 |
| 32 | 3.938 | | 911.8842 | 17.5546 |
| 33 | 5.911 | | 355.9465 | 8.474031 |
| 34 | 3.215 | | 893.3126 | 19.95956 |
| 35 | 7.525 | | 67.29568 | 2.162126 |
| 36 | 6.173 | | 218.2083 | 5.700632 |
| 37 | 12.46 | | 1799.358 | 49.51043 |
| 38 | 14.09 | | 43.69056 | 2.760823 |
| 39 | 26.43 | | 30.38214 | 1.018161 |
| 40 | 15.21 | | 67.06114 | 2.783037 |
| 41 | 2.711 | 844.1 | 2257.47 | 471.4128 |
| 42 | 36.24 | | 1053.808 | 42.30132 |
| 43 | 14.49 | | 1347.136 | 21.90476 |
| 44 | 20.66 | | 1269.119 | 45.11133 |
| 45 | 15.49 | | 137.8309 | 4.60297 |
| 46 | 2.521 | 1428.99 | 2542.642 | 135.8985 |
| 47 | 1.302 | 610.5 | 1879.416 | 104.3011 |
| 18 | 3.277 | 741.5 | 1948.123 | 292.3406 |
| 49 | 19.1 | | 253.4031 | 53.19372 |
| 50 | 61.69 | | 361.809 | 27.4923 |
| 51 | 1.232 | 143.3 | 3031.656 | 1241.883 |
| 52 | 7.011 | 2260 | 2009.699 | 55.0706 |
| 53 | 1.251 | | 4028.777 | 251.7986 |
| 54 | 33.24 | 10000 | 1504.212 | 117.2684 |
| 55 | 1.247 | | 3251.804 | 17.89896 |
| 56 | 3.837 | 2683 | 1047.694 | 423.7686 |
| 57 | 5.08 | 3959.798 | 3527.559 | 831.2992 |
| 58 | 2.316 | 157.4 | 1393.782 | 140.6736 |
| 59 | 8.442 | | 108.4696 | 39.23241 |
| 60 | 7.355 | | 69.69409 | 7.854521 |
| 61 | 9.745 | 2385 | 588.8148 | 955.0539 |
| 62 | 16.91 | 10000 | 540.9225 | 946.7771 |
| 63 | 72.22 | | 56.84021 | 16.68513 |
| 64 | 86.96 | | 210.2116 | 98.83855 |
| 65 | 44.19 | | 82.48473 | 5.356415 |
| 66 | 2340 | | 21.36752 | 7.606838 |
| 67 | 1.342 | 4394.315 | 4976.155 | 499.9255 |
| 68 | 7.38 | 2476 | 4761.518 | 1347.967 |
| 69 | 2.981 | 686.1 | 1785.978 | 480.7112 |
| 70 | 1.101 | 80.33505 | 1376.93 | 512.7157 |
| 71 | 3.062 | 988.6843 | 420.9667 | 38.66754 |
| 72 | 0.997 | 42.71 | 2006.018 | 405.2156 |
| 73 | 7.045 | 10000 | 3290.277 | 346.7708 |
| 74 | 3.312 | | 293.0556 | 37.13768 |
| 75 | 157.2 | | 173.4097 | 23.27608 |
| 76 | 0.434 | 93.46214 | 3304.147 | 535.4839 |
| 77 | 1.757 | 725.1 | 6738.759 | 1577.689 |
| 78 | 0.35 | 61.37396 | 5660 | 1778.857 |
| 79 | 91.86 | | 210.5378 | 6.98563 |
| 80 | 2.365 | 293.5 | 346.5116 | 54.12262 |
| 81 | 3.633 | 965 | 1478.393 | 220.4239 |

TABLE 2-continued

| Ex. No. | PLK4 IC$_{50}$ (nM) | CTG IC$_{50}$ (nM) | [Aurora A IC$_{50}$ (nM)]/ [PLK4 IC$_{50}$ (nM)] | [Aurora B IC$_{50}$ (nM)]/ [PLK4 IC$_{50}$ (nM)] |
|---|---|---|---|---|
| 82 | 6.207 | | 187.8524 | 38.55325 |
| 83 | 2.238 | 277.2 | 908.4004 | 333.3333 |
| 84 | 1.278 | 394.8 | 39123.63 | 3151.017 |
| 85 | 1.91 | 107.2 | 5554.974 | 3067.539 |
| 86 | 21.2 | 459.3 | 1414.623 | 669.3396 |
| 87 | 1.58 | 235.2 | 973.4177 | 133.9241 |
| 88 | 2.672 | 1813.308 | 1997.754 | 44.7979 |
| 89 | 2.317 | 10000 | 1736.729 | 314.3289 |
| 90 | 17.81 | | 1505.334 | 44.32903 |
| 91 | 4.019 | 3202.9 | 436.427 | 79.87061 |
| 92 | 8.838 | | 132.8355 | 76.36343 |
| 93 | 24.34 | | 1733.361 | 1055.053 |
| 94 | 5.612 | 4602 | 533.856 | 41.732 |
| 95 | 1.306 | 319 | 2386.677 | 54.26493 |
| 96 | 11.35 | 56.55534 | 511.3656 | 351.8943 |
| 97 | 1.139 | 221.649 | 309.2186 | 520.2809 |
| 98 | 7.554 | 65.76947 | 787.0003 | 305.5335 |
| 99 | 5.802 | 565.24 | 155.05 | 129.9724 |
| 100 | 1.734 | 566.93 | 382.0069 | 230.4498 |
| 101 | 11.33 | 2288.9 | 1271.845 | 1002.648 |
| 102 | 6.162 | | 114.7355 | 74.69977 |
| 103 | 2.796 | | 416.6667 | 977.1102 |
| 107 | 5.704 | 729.7 | 1455.295 | 174.4215 |
| 108 | 4.366 | 1091 | 3889.143 | 230.6459 |
| 109 | 6.759 | 1871 | 50000 | 11070 |
| 110 | 3.908 | | 679.6315 | 232.1904 |
| 111 | 1.535 | | 234.7231 | 144.4951 |
| 112 | 23.7 | | 197.5105 | 121.8987 |
| 113 | 10.65 | 2517 | 1888.2629 | 231.7370 |
| 114 | 2.091 | 10000 | 590.1482 | 811.5734 |
| 115 | 8.039 | 3462 | 132.6035 | 186.3415 |
| 116 | 2.89 | 133.5 | 788.5813 | 483.7370 |
| 117 | 2.321 | 108.7 | 1388.1947 | 906.5058 |
| 118 | 7.321 | 2359 | 457.0413 | 902.3357 |
| 119 | 1.588 | 2664 | 870.2770 | 973.5516 |
| 120 | 3.815 | 10000 | 444.0366 | 684.6657 |
| 121 | 1.794 | 5324 | 875.6967 | 230.8807 |
| 122 | 73.1 | | 11.1709 | 11.86593 |
| 123 | 4.798 | 2110 | 667.5698 | 84.09754 |
| 124 | 13.57 | | 38.03242 | 35.89535 |
| 125 | 0.8331 | 159.6 | 1323.9707 | 495.7388 |
| 126 | 9.014 | 459.3 | 66.2192 | 92.0568 |
| 127 | 2196 | | 22.76867 | 22.7686 |
| 128 | 2.887 | 1492 | 2750.2597 | 1337.0280 |
| 129 | 34.52 | | 18.1054 | 17.1349 |
| 130 | 603.1 | | 58.4811 | 60.1890 |
| 131 | 53.78 | | 105.7084 | 40.8516 |
| 132 | 2.149 | 618 | 5290.8329 | 249.5114 |
| 133 | 8.322 | 192.8 | 43.3910 | 45.1453 |
| 134 | 1.79 | 782.4 | 8849.1620 | 969.2737 |
| 135 | 70.77 | | 28.3312 | 62.6112 |
| 136 | 19.43 | | 2573.3401 | 979.4132 |
| 137 | 97.2 | | 62 | 72 |
| 138 | 27.33 | | 70 | 36 |
| 139 | 3175 | | 7.4 | 9.6 |
| 140 | 16.56 | 7758 | 814 | 537 |
| 141 | 13.13 | | 327.4181 | 891.0891 |
| 142 | 21.48 | | 13.818 | 26.308 |
| 143 | 84.74 | | 14.621 | 40.607 |
| 144 | 1.413 | 750.1 | 852.7955 | 61.4367 |
| 145 | 5.819 | 2915 | 1001.5467 | 280.8043 |
| 146 | 1.491 | 655.1 | 3512.4078 | 745.8082 |
| 147 | 4.223 | 1303 | 2292.2093 | 483.0689 |
| 148 | 6.87 | 3569 | 397.3799 | 338.8646 |
| 149 | 3.153 | 844.2 | 3193.7837 | 879.4799 |
| 150 | 8.128 | 3156 | 720.7185 | 366.7569 |
| 151 | 9.743 | | 61.2440 | 96.3153 |
| 152 | 7.156 | | 502.7949 | 107.8116 |
| 153 | 1.906 | 875.6 | 1254.4596 | 123.6097 |
| 154 | 0.976 | 260.1 | 1373.9754 | 655.2254 |
| 155 | 1.035 | 192.2 | 305.4106 | 68.0773 |
| 156 | | 493.8 | | |
| 157 | 1.947 | 287.9 | 510.6317 | 303.9548 |
| 158 | 8.591 | | 704.9238 | 51.7286 |
| 159 | 1.962 | 1298 | 309.7350 | 58.0530 |
| 160 | 1.932 | 310.2 | 545.5487 | 149.5859 |
| 161 | 2.21 | 351.7 | 291.4932 | 258.4163 |

TABLE 2-continued

| Ex. No. | PLK4 IC$_{50}$ (nM) | CTG IC$_{50}$ (nM) | [Aurora A IC$_{50}$ (nM)]/ [PLK4 IC$_{50}$ (nM)] | [Aurora B IC$_{50}$ (nM)]/ [PLK4 IC$_{50}$ (nM)] |
|---|---|---|---|---|
| 162 | 8.394 | | 648.6776 | 105.2895 |
| 163 | 1.524 | 226.3 | 2164.0420 | 389.4357 |
| 164 | 6.277 | 1637 | 397.0049 | 161.2235 |
| 165 | 4.682 | 1063 | 111.2559 | 76.9329 |
| 166 | 0.802 | 80.6 | 1151.3716 | 68.4539 |
| 167 | 1.18 | 212.3 | 295.5932 | 916.9492 |
| 168 | 1.966 | 1620 | 946.5921 | 265.0051 |
| 169 | 0.995 | 188.5 | 666.9347 | 431.4573 |
| 170 | 1.358 | 325.7 | 694.1090 | 587.9234 |
| 171 | 5.871 | 1517 | 1176.6309 | 259.2403 |
| 172 | 4.09 | 1263 | 324.94 | 202.96 |
| 173 | 2.666 | 331.7 | 301.0878 | 314.9287 |
| 174 | 1.921 | 392.3 | 365.8511 | 353.7741 |
| 175 | 3.569 | 2209 | 14009.5265 | 8627.0664 |
| 176 | 2.843 | 1552 | 1725.2902 | 1300.3869 |
| 177 | 4.255 | 3675 | 11750.8813 | 11750.8813 |
| 178 | 3.294 | 630.8 | 15179.1135 | 15179.1135 |
| 179 | 3.811 | 948 | 13119.9160 | 5384.4135 |
| 180 | 2.854 | 740.8 | 5455.5011 | 1996.8465 |
| 181 | 7.576 | | 2415.5227 | 3693.2418 |
| 182 | 4.454 | | 53.6821 | 198.8774 |
| 183 | 1.245 | 125 | 534.2169 | 322.5703 |
| 184 | 6.998 | 882 | 7144.8985 | 7144.8985 |
| 185 | 1.956 | 134 | 3240.7975 | 180.1636 |
| 186 | 1.779 | 537 | 641.9337 | 232.5464 |
| 187 | 6.116 | 563 | 109.5814 | 112.2793 |
| 188 | 6.27 | 760 | 7974.4817 | 191.7065 |
| 189 | 1.045 | 112 | 383.7321 | 514.5455 |
| 190 | 2.661 | 5115 | 129.5378 | 279.1432 |
| 191 | 2.266 | 494 | 2416.5931 | 84.9956 |
| 192 | 1.639 | 1180 | 2835.2654 | 678.4625 |
| 193 | 1.134 | 390 | 1463.8448 | 138.8889 |
| 194 | 0.965 | 126 | 805.6995 | 103.7306 |
| 195 | 1.56 | 160 | 3459.6154 | 740.3846 |
| 196 | 3.318 | 1673 | 732.3689 | 100.8137 |
| 197 | 1.076 | 1082 | 1243.4944 | 73.8197 |
| 198 | 8.692 | 10000 | 5752.4160 | 5752.4160 |
| 199 | 0.716 | 108 | 439.9441 | 57.7095 |
| 200 | 3.256 | | 906.0197 | 523.3415 |
| 201 | 1.706 | 455 | 485.6389 | 229.0739 |
| 202 | 2.68 | 422 | 1031.3433 | 321.4179 |
| 203 | 1.042 | 324 | 2922.2649 | 333.7812 |
| 204 | 0.81 | 122 | 342.9630 | 222.8395 |
| 205 | 1.642 | 3445 | 737.5152 | 235.7491 |
| 206 | 0.806 | | 618.8586 | 80.2233 |
| 207 | 0.952 | | 497.3739 | 111.6597 |
| 208 | 0.8967 | 402 | 7904 | 2471 |
| 209 | 1.537 | 605.8 | 273.2595 | 254.6519 |
| 210 | 1.348 | 65.47 | 462.3887 | 316.5430 |
| 211 | 8.658 | | 531.9935 | 218.4107 |
| 212 | 1.585 | 161 | 353.1230 | 280 |
| 213 | 2.131 | 189.7 | 92.2102 | 225.3871 |
| 214 | 1.011 | 32.23 | 953.01681 | 59.0999 |
| 215 | 2.098 | 191.6 | 986.6539 | 53.57483 |
| 216 | 2.688 | 766.4 | 7712.05357 | 18601.19048 |
| 217 | 1.189 | 450.2 | 416.7367 | 170.9840 |
| 218 | 0.955 | 73.81 | 806.5968 | 70.8586 |
| 219 | 2.504 | 510.1 | 763.5782 | 64.2571 |
| 220 | 6.013 | | 1042.4081 | 498.7527 |
| 221 | 2.802 | 848.9 | 511.06352 | 1463.5974 |
| 222 | 1.359 | 456 | 446.1368 | 546.4311 |
| 223 | 2.304 | 163.1 | 1004.7743 | 445.3125 |
| 224 | 4.016 | 2023 | 12450.1992 | 12450.1992 |
| 225 | 6.118 | | 1884.6028 | 381.4972 |
| 226 | 4.747 | 2146 | 2759.6376 | 474.6155 |
| 227 | 2.209 | 532.3 | 917.1570 | 478.9497 |
| 228 | 1.347 | 180.4 | 813.6599 | 340.4602 |
| 229 | 7.847 | | 1669.4278 | 130.8780 |
| 230 | 2.434 | 394.6 | 12432.2103 | 213.4346 |
| 231 | 1.56 | 397.3 | 4955.7692 | 316.7307 |
| 232 | 1.033 | 141 | 651.7909 | 105.5179 |
| 233 | 3.572 | 4799 | 332.3068 | 107.2788 |
| 234 | 2.294 | 276.3 | 608.9799 | 831.7349 |
| 235 | 2.169 | | 2053.4808 | 260.3503 |
| 236 | 2.262 | | 949.6021 | 114.8983 |
| 237 | 2.943 | | 3385.3211 | 369.01121 |
| 238 | 1.361 | 133.4 | 536.07641 | 582.2189 |

TABLE 2-continued

| Ex. No. | PLK4 IC$_{50}$ (nM) | CTG IC$_{50}$ (nM) | [Aurora A IC$_{50}$ (nM)]/ [PLK4 IC$_{50}$ (nM)] | [Aurora B IC$_{50}$ (nM)]/ [PLK4 IC$_{50}$ (nM)] |
|---|---|---|---|---|
| 239 | 1.69 | 948.6 | 1429.5857 | 466.8047 |
| 240 | 2.179 | 421.9 | 735.1996 | 102.4323 |
| 241 | 2.493 | 1105 | 2066.9875 | 253.4697 |
| 242 | 6.519 | 5509 | 307.7159 | 129.0381 |
| 243 | 1.149 | 187.9 | 479.1122 | 164.5778 |
| 244 | 2.91 | 545.3 | 1578.3505 | 312.26804 |
| 245 | 0.738 | 131 | 1730.3523 | 319.6476 |
| 246 | 0.843 | 68.38 | 426.8090 | 176.8683 |
| 247 | 3.734 | 1013 | 1434.9223 | 423.6743 |
| 248 | 1.239 | 119.6 | 683.4543 | 206.5375 |
| 249 | 6.563 | | 2585.7077 | 451.7751 |
| 250 | 6.188 | | 819.6509 | 110.6011 |
| 251 | 1.332 | 287 | 1734.2342 | 268.6936 |
| 252 | 9.282 | | 518.4227 | 365.8694 |
| 253 | 5.982 | | 709.6288 | 88.7161 |
| 254 | 5.19 | 2164 | 297.6878 | 96.18497 |
| 255 | 1.164 | 380.3 | 840.1202 | 566.4948 |
| 256 | 0.6498 | 309.7 | 1143.4287 | 1152.50846 |
| 257 | 3.91 | 1592 | 1259.8465 | 324.5524 |
| 258 | 1.413 | 167.6 | 1100.4954 | 464.7558 |
| 259 | 0.9708 | 899.9 | 1294.8084 | 835.2904 |
| 260 | 9.327 | | 1330.5457 | 294.8429 |
| 261 | 7.91 | | 5824.2730 | 2807.8381 |
| 262 | 1.389 | 507.4 | 3488.1209 | 526.70986 |
| 263 | 0.65 | 599.4 | 1133.6923 | 181.6923 |
| 264 | 0.785 | 859.9 | 307.8980 | 66.6751 |
| 265 | 1.981 | 1067 | 686.01716 | 725.3912 |
| 266 | 2.344 | 791.6 | 723.9761 | 154.9914 |
| 267 | 1.569 | 325.1 | 789.0376 | 406.8833 |
| 268 | 0.874 | 123.5 | 1159.03890 | 769.9084 |
| 269 | 0.89 | 1346 | 191.7977 | 138.7640 |
| 270 | 0.564 | 268.9 | 473.58156 | 1790.7801 |
| 271 | 6.042 | | 825.7199 | 492.8831 |
| 272 | 0.833 | 77.83 | 3273.7094 | 448.8595 |
| 273 | 1.453 | 1703 | 3483.1383 | 2831.3833 |
| 274 | 0.763 | 72.26 | 2560.9436 | 961.3368 |
| 275 | 0.59 | | 2162.7118 | 230 |
| 276 | 2.614 | 4085 | 377.9648 | 2173.2976 |
| 277 | 2.198 | | 1120.5641 | 1049.1355 |
| 278 | 0.804 | | 1269.9004 | 423.6318 |
| 279 | 1.336 | | 37425.1497 | 2792.6646 |
| 280 | 1.932 | | 727.2256 | 309.1097 |
| CFI-400495 | 0.4962 | 9.082 | 86.3160 | 12.0435 |

EMBODIMENTS

Embodiment 1: A compound of Formula (I), or a pharmaceutically acceptable salt, solvate, or stereoisomer thereof:

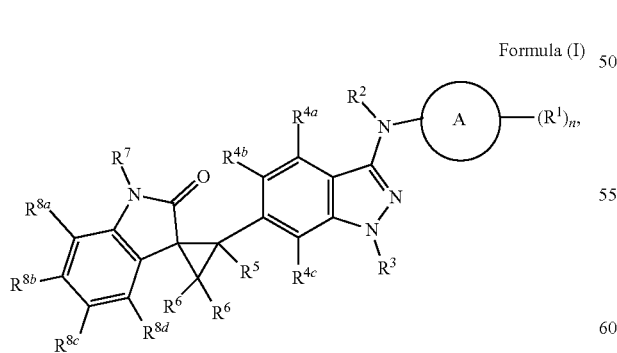

Formula (I)

wherein:
Ring A is $C_6$-$C_{10}$aryl, heteroaryl, $C_3$-$C_{10}$cycloalkyl, or heterocycloalkyl;
each $R^1$ is independently deuterium, halogen, —CN, oxo, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, —OC$_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is optionally and independently substituted with one or more $R^{1a}$;

or two $R^1$ on adjacent atoms are taken together to form a $C_3$-$C_{10}$cycloalkyl or heterocycloalkyl; each optionally substituted with one or more $R^{1b}$;

each $R^{1a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_1$-$C_{10}$cycloalkyl, heterocycloalkyl, $C_6$-$C_{10}$aryl, or heteroaryl;

or two $R^{1a}$ on the same atom are taken together to form an oxo;

each $R^{1b}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

or two $R^{1b}$ on the same atom are taken together to form an oxo;

n is 0, 1, 2, 3, 4, 5, 6, 7, or 8;

$R^2$ is hydrogen, C$_1$-C$_6$alkyl, C$_1$-C$_6$haloalkyl, or C$_1$-C$_6$deuteroalkyl;

$R^3$ is hydrogen, C$_1$-C$_6$alkyl, C$_1$-C$_6$haloalkyl, or C$_1$-C$_6$deuteroalkyl;

each of $R^{4a}$, $R^{4b}$, and $R^{4c}$ is independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

$R^5$ is hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each $R^6$ is independently hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

$R^7$ is hydrogen, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;

each of $R^{8a}$, $R^{8b}$, $R^{8c}$, and $R^{8d}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$—NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each $R^b$ is independently hydrogen, C$_1$-C$_6$alkyl, C$_1$-C$_6$haloalkyl, C$_1$-C$_6$deuteroalkyl, C$_1$-C$_6$ hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_1$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$ hydroxyalkyl, C$_1$-C$_6$aminoalkyl, or C$_1$-C$_6$heteroalkyl; and each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)NH$_2$, —S(=O)$_2$NHCH$_3$, —S(=O)$_2$N(CH$_3$ h), —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$), —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

Embodiment 2: A compound of Formula (Ia), or a pharmaceutically acceptable salt, solvate, or stereoisomer thereof:

Formula (Ia)

wherein:

Ring A is C$_6$-C$_{10}$aryl, heteroaryl, C$_3$-C$_{10}$cycloalkyl, or heterocycloalkyl;

each $R^1$ is independently deuterium, halogen, —CN, oxo, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C (=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, —OC$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_1$-C$_{10}$cycloalkyl, heterocycloalkyl, C$_6$-C$_{10}$aryl, or heteroaryl; wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is optionally and independently substituted with one or more R$^{1a}$;

or two R$^1$ on adjacent atoms are taken together to form a C$_3$-C$_{10}$cycloalkyl or heterocycloalkyl; each optionally substituted with one or more R$^{1b}$;

each R$^{1a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

or two R$^{1a}$ on the same atom are taken together to form an oxo;

each R$^{1b}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

or two R$^{1b}$ on the same atom are taken together to form an oxo;

n is 0, 1, 2, 3, 4, 5, 6, 7, or 8;

R$^2$ is hydrogen, C$_1$-C$_6$alkyl, C$_1$-C$_6$haloalkyl, or C$_1$-C$_6$deuteroalkyl;

R$^3$ is hydrogen, C$_1$-C$_6$alkyl, C$_1$-C$_6$haloalkyl, or C$_1$-C$_6$deuteroalkyl;

each of R$^{4a}$, R$^{4b}$, and R$^{4c}$ is independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

R$^5$ is hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^6$ is independently hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

R$^7$ is hydrogen, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;

each of R$^{8a}$, R$^{8b}$, R$^{8c}$, and R$^{8d}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_1$-C$_6$alkynyl, C$_3$-C$_{10}$cycloalkyl, heterocycloalkyl, C$_6$-C$_{10}$aryl, or heteroaryl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CHs, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$), —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)NH$_2$, —S(=O)?NHCH$_3$, —S(=O)N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_1$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$), —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or R$^c$ and R$^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)?N(CH$_3$)$_2$, —NH$_2$, —NHCH$_3$, —N(CH$_3$), —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

Embodiment 3: A compound of Formula (Ib), or a pharmaceutically acceptable salt, solvate, or stereoisomer thereof:

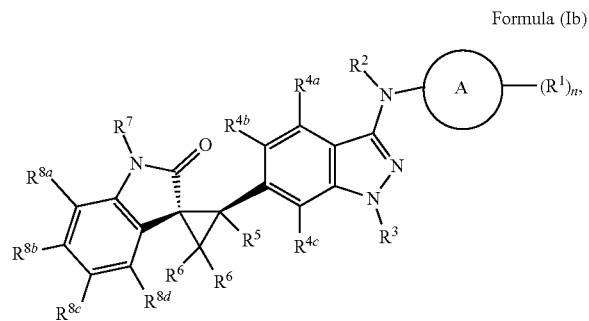

Formula (Ib)

wherein:

Ring A is $C_6$-$C_{10}$aryl, heteroaryl, $C_3$-$C_{10}$cycloalkyl, or heterocycloalkyl;

each $R^1$ is independently deuterium, halogen, —CN, oxo, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, —$OC_1$-$C_6$haloalkyl, $C_1$-$C_6$deuteroalkyl, $C_1$-$C_6$hydroxyalkyl, $C_1$-$C_6$aminoalkyl, $C_1$-$C_1$heteroalkyl, $C_2$-$C_6$alkenyl, $C_2$-$C_6$alkynyl, $C_1$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is optionally and independently substituted with one or more $R^{1a}$;

or two $R^1$ on adjacent atoms are taken together to form a $C_3$-$C_{10}$cycloalkyl or heterocycloalkyl; each optionally substituted with one or more $R^{1b}$;

each $R^{1a}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

or two $R^{1a}$ on the same atom are taken together to form an oxo;

each $R^{1b}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

or two $R^{1b}$ on the same atom are taken together to form an oxo;

n is 0, 1, 2, 3, 4, 5, 6, 7, or 8;

$R^2$ is hydrogen, $C_1$-$C_6$alkyl, $C_1$-$C_6$haloalkyl, or $C_1$-$C_6$deuteroalkyl;

$R^3$ is hydrogen, $C_1$-$C_6$alkyl, $C_1$-$C_6$haloalkyl, or $C_1$-$C_6$deuteroalkyl;

each of $R^{4a}$, $R^{4b}$, and $R^{4c}$ is independently hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^5$ is hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^6$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^7$ is hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

each of $R^{8a}$, $R^{8b}$, $R^{8c}$, and $R^{8d}$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_1$-$C_6$alkynyl, $C_3$-$C_{10}$cycloalkyl, heterocycloalkyl, $C_6$-$C_{10}$aryl, or heteroaryl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_1$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$NH_2$, —S(=O)?$NHCH_3$, —S(=O)$N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_1$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)?N(CH$_3$)$_2$, —NH$_2$, —NHCH$_3$, —N(CH$_3$), —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Embodiment 4: The compound according to any one of embodiments 1 to 3, or a pharmaceutically acceptable salt, solvate, or stereoisomer thereof, wherein Ring A is $C_6$-$C_{10}$aryl or heteroaryl.

Embodiment 5: The compound according to embodiment 4, or a pharmaceutically acceptable salt, solvate, or stereoisomer thereof, wherein Ring A is $C_6$-$C_{10}$aryl.

Embodiment 6: The compound according to embodiment 5, or a pharmaceutically acceptable salt, solvate, or stereoisomer thereof, wherein Ring A is phenyl.

Embodiment 7: The compound according to embodiment 4, or a pharmaceutically acceptable salt, solvate, or stereoisomer thereof, wherein Ring A is heteroaryl.

Embodiment 8: The compound according to embodiment 7, or a pharmaceutically acceptable salt, solvate, or stereoisomer thereof, wherein Ring A is furanyl, pyrrolyl, thiophenyl, oxazolyl, imidazolyl, thiazolyl, pyrazolyl, isoxazolyl, isothiazolyl, triazolyl, pyridinyl, pyrazinyl, pyrimidinyl, or pyridazinyl.

Embodiment 9: The compound according to embodiment 8, or a pharmaceutically acceptable salt, solvate, or stereoisomer thereof, wherein Ring A is pyrazolyl, pyridinyl, pyrazinyl, pyrimidinyl, or pyridazinyl.

Embodiment 10: The compound according to embodiment 9, or a pharmaceutically acceptable salt, solvate, or stereoisomer thereof, wherein Ring A is pyrazolyl, pyridinyl, pyrazinyl, or pyrimidinyl.

Embodiment 11: The compound according to embodiment 10, or a pharmaceutically acceptable salt, solvate, or stereoisomer thereof, wherein Ring A is pyrazolyl.

Embodiment 12: The compound according to embodiment 11, or a pharmaceutically acceptable salt, solvate, or stereoisomer thereof, wherein Ring A is 1-pyrazolyl, 3-pyrazolyl, 4-pyrazolyl, or 5-pyrazolyl.

Embodiment 13: The compound according to embodiment 12, or a pharmaceutically acceptable salt, solvate, or stereoisomer thereof, wherein Ring A is 1-pyrazolyl.

Embodiment 14: The compound according to embodiment 12, or a pharmaceutically acceptable salt, solvate, or stereoisomer thereof, wherein Ring A is 3-pyrazolyl.

Embodiment 15: The compound according to embodiment 12, or a pharmaceutically acceptable salt, solvate, or stereoisomer thereof, wherein Ring A is 4-pyrazolyl.

Embodiment 16: The compound according to embodiment 12, or a pharmaceutically acceptable salt, solvate, or stereoisomer thereof, wherein Ring A is 5-pyrazolyl.

Embodiment 17: The compound according to embodiment 10, or a pharmaceutically acceptable salt, solvate, or stereoisomer thereof, wherein Ring A is pyridinyl.

Embodiment 18: The compound according to embodiment 17, or a pharmaceutically acceptable salt, solvate, or stereoisomer thereof, wherein Ring A is 2-pyridinyl, 3-pyridinyl, 4-pyridinyl, 5-pyridinyl, or 6-pyridinyl.

Embodiment 19: The compound according to embodiment 18, or a pharmaceutically acceptable salt, solvate, or stereoisomer thereof, wherein Ring A is 2-pyridinyl.

Embodiment 20: The compound according to embodiment 18, or a pharmaceutically acceptable salt, solvate, or stereoisomer thereof, wherein Ring A is 3-pyridinyl.

Embodiment 21: The compound according to embodiment 18, or a pharmaceutically acceptable salt, solvate, or stereoisomer thereof, wherein Ring A is 4-pyridinyl.

Embodiment 22: The compound according to embodiment 18, or a pharmaceutically acceptable salt, solvate, or stereoisomer thereof, wherein Ring A is 5-pyridinyl.

Embodiment 23: The compound according to embodiment 18, or a pharmaceutically acceptable salt, solvate, or stereoisomer thereof, wherein Ring A is 6-pyridinyl.

Embodiment 24: The compound according to embodiment 10, or a pharmaceutically acceptable salt, solvate, or stereoisomer thereof, wherein Ring A is pyrazinyl.

Embodiment 25: The compound according to embodiment 24, or a pharmaceutically acceptable salt, solvate, or stereoisomer thereof, wherein Ring A is 2-pyrazinyl, 3-pyrazinyl, 5-pyrazinyl, or 6-pyrazinyl.

Embodiment 26: The compound according to embodiment 25, or a pharmaceutically acceptable salt, solvate, or stereoisomer thereof, wherein Ring A is 2-pyrazinyl.

Embodiment 27: The compound according to embodiment 25, or a pharmaceutically acceptable salt, solvate, or stereoisomer thereof, wherein Ring A is 3-pyrazinyl.

Embodiment 28: The compound according to embodiment 25, or a pharmaceutically acceptable salt, solvate, or stereoisomer thereof, wherein Ring A is 5-pyrazinyl.

Embodiment 29: The compound according to embodiment 25, or a pharmaceutically acceptable salt, solvate, or stereoisomer thereof, wherein Ring A is 6-pyrazinyl.

Embodiment 30: The compound according to embodiment 10, or a pharmaceutically acceptable salt, solvate, or stereoisomer thereof, wherein Ring A is pyrimidinyl.

Embodiment 31: The compound according to embodiment 30, or a pharmaceutically acceptable salt, solvate, or stereoisomer thereof, wherein Ring A is 2-pyrimidinyl, 4-pyrimidinyl, 5-pyrimidinyl, or 6-pyrimidinyl.

Embodiment 32: The compound according to embodiment 31, or a pharmaceutically acceptable salt, solvate, or stereoisomer thereof, wherein Ring A is 2-pyrimidinyl.

Embodiment 33: The compound according to embodiment 31, or a pharmaceutically acceptable salt, solvate, or stereoisomer thereof, wherein Ring A is 4-pyrimidinyl.

Embodiment 34: The compound according to embodiment 31, or a pharmaceutically acceptable salt, solvate, or stereoisomer thereof, wherein Ring A is 5-pyrimidinyl.

Embodiment 35: The compound according to embodiment 31, or a pharmaceutically acceptable salt, solvate, or stereoisomer thereof, wherein Ring A is 6-pyrimidinyl.

Embodiment 36: The compound according to embodiment 9, or a pharmaceutically acceptable salt, solvate, or stereoisomer thereof, wherein Ring A is pyridazinyl.

Embodiment 37: The compound according to embodiment 36, or a pharmaceutically acceptable salt, solvate, or stereoisomer thereof, wherein Ring A is 3-pyridazinyl, 4-pyridazinyl, 5-pyridazinyl, or 6-pyridazinyl.

Embodiment 38: The compound according to embodiment 37, or a pharmaceutically acceptable salt, solvate, or stereoisomer thereof, wherein Ring A is 3-pyridazinyl.

Embodiment 39: The compound according to embodiment 37, or a pharmaceutically acceptable salt, solvate, or stereoisomer thereof, wherein Ring A is 4-pyridazinyl.

Embodiment 40: The compound according to embodiment 37, or a pharmaceutically acceptable salt, solvate, or stereoisomer thereof, wherein Ring A is 5-pyridazinyl.

Embodiment 41: The compound according to embodiment 37, or a pharmaceutically acceptable salt, solvate, or stereoisomer thereof, wherein Ring A is 6-pyridazinyl.

Embodiment 42: The compound according to any one of embodiments 1 to 3, or a pharmaceutically acceptable salt, solvate, or stereoisomer thereof, wherein Ring A is $C_3$-$C_{10}$cycloalkyl or heterocycloalkyl.

Embodiment 43: The compound according to embodiment 42, or a pharmaceutically acceptable salt, solvate, or stereoisomer thereof, wherein Ring A is $C_3$-$C_{10}$cycloalkyl.

Embodiment 44: The compound according to embodiment 42, or a pharmaceutically acceptable salt, solvate, or stereoisomer thereof, wherein Ring A is heterocycloalkyl.

Embodiment 45: Embodiment 40: The compound according to any one of embodiments 1 to 44, or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$haloalkyl, —$OC_1$-$C_6$haloalkyl, $C_1$-$C_6$hydroxyalkyl, $C_1$-$C_6$aminoalkyl, $C_1$-$C_6$heteroalkyl, $C_3$-$C_{10}$cycloalkyl, heterocycloalkyl, $C_6$-$C_{10}$aryl, or heteroaryl; wherein each of the $C_1$-$C_6$alkyl, $C_3$-$C_{10}$cycloalkyl, heterocycloalkyl, $C_6$-$C_{10}$aryl, and heteroaryl is optionally and independently substituted with one or more $R^{1a}$.

Embodiment 46: The compound according to embodiment 45, or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$haloalkyl, —$OC_1$-$C_6$haloalkyl, $C_1$-$C_6$hydroxyalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 47: The compound according to embodiment 46, or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$haloalkyl, —$OC_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 48: The compound according to embodiment 47, or a pharmaceutically acceptable salt, solvate, or stereoisomer thereof, wherein each $R^1$ is independently halogen, —CN, —OH, —$OR^a$, $C_1$-$C_6$alkyl, —$OC_1$-$C_6$haloalkyl, —$CF_3$, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 49: The compound according to embodiment 48, or a pharmaceutically acceptable salt, solvate, or stereoisomer thereof, wherein each $R^1$ is independently fluoro, chloro, bromo, iodo, —CN, —OH, —$OR^a$, $C_1$-$C_6$alkyl, —$OC_1$-$C_6$haloalkyl, —$CF_3$, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 50: The compound according to embodiment 49, or a pharmaceutically acceptable salt, solvate, or stereoisomer thereof, wherein each $R^1$ is independently fluoro, chloro, bromo, —CN, —OH, —$OC_1$-$C_6$alkyl, —$OC_1$-$C_6$haloalkyl, $C_1$-$C_6$alkyl, —$CF_3$, $C_3$-$C_{10}$cycloalkyl, or heterocycloalkyl; wherein each of the —$OC_1$-$C_6$alkyl, $C_1$-$C_6$alkyl, $C_3$-$C_{10}$cycloalkyl, and heterocycloalkyl is optionally and independently substituted with one or more $R^{1a}$.

Embodiment 51: The compound according to embodiment 50, or a pharmaceutically acceptable salt, solvate, or stereoisomer thereof, wherein each $R^1$ is independently fluoro, chloro, —CN, —OH, —$OCH_3$, —$OCH_2CH_3$, —$C_1$-$C_6$alkyl($OR^{1a}$), —$CH_3$, —$CH_2CH_3$, iso-propyl, n-propyl, n-butyl, i-butyl, t-butyl, —$OCHF_2$, —$OC_1$-$C_6$hydroxyalkyl, —$CF_3$, cyclopropyl, azetidinyl, oxetanyl, piperidinyl, piperazinyl, morpholinyl, 1,4-oxazepanyl, or thiazinyl; wherein each of the azetidinyl, oxetanyl, piperidinyl, piperazinyl, morpholinyl, thiazinyl, and 1,4-oxazepanyl is optionally and independently substituted with one or more $R^{1a}$.

Embodiment 52: The compound according to embodiment 51, or a pharmaceutically acceptable salt, solvate, or stereoisomer thereof, wherein each $R^1$ is independently chloro, —CN, —OH, —$OCH_3$, —$OCH_2CH_3$, —$CH_3$, iso-propyl, —$OCHF_2$, —$CF_3$, cyclopropyl, azetidinyl, oxetanyl, piperidinyl, piperazinyl, morpholinyl, or 1,4-oxazepanyl; wherein each of the azetidinyl, oxetanyl, piperidinyl, piperazinyl, morpholinyl, and 1,4-oxazepanyl is optionally and independently substituted with one or more $R^{1a}$.

Embodiment 53: The compound according to embodiment 52, or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, azetidinyl, piperidinyl, piperazinyl, or morpholinyl; wherein each of the azetidinyl, piperidinyl, piperazinyl, and morpholinyl, is optionally and independently substituted with one or more $R^{1a}$.

Embodiment 54: The compound according to embodiment 53, or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, azetidinyl, piperidinyl, piperazinyl, or morpholinyl; wherein each of the azetidinyl, piperidinyl, piperazinyl, and morpholinyl, is optionally and independently substituted with one or more $R^{1a}$.

Embodiment 55: The compound according to embodiment 54, or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, piperidinyl, piperazinyl, or morpholinyl; wherein piperidinyl, piperazinyl, and morpholinyl are optionally substituted with one or more $R^1$.

Embodiment 56: The compound according to embodiment 55, or a pharmaceutically acceptable salt, solvate, or stereoisomer thereof, wherein each $R^1$ is independently chloro, —CN, —$OCH_3$—$CH_3$, iso-propyl, —$OCHF_2$, —$CF_3$, cyclopropyl, piperidinyl, piperazinyl, or morpholinyl; wherein piperidinyl, piperazinyl, and morpholinyl are optionally substituted with one or more —$CH_3$, —$CH_2CH_3$, —$CH_2CH_2CH_3$, —OH, and —$OCH_3$.

Embodiment 57: The compound according to embodiment 56, or a pharmaceutically acceptable salt, solvate, or stereoisomer thereof, wherein each $R^1$ is independently chloro, —CN, —$OCH_3$—$CH_3$, —$OCHF_2$, cyclopropyl, piperidinyl, piperazinyl, or morpholinyl; wherein piperidinyl, piperazinyl, and morpholinyl are optionally substituted with one or more —$CH_3$, —$CH_2CH_3$, —$CH_2CH_2CH_3$, —OH, and —$OCH_3$.

Embodiment 58: The compound according to embodiment 57, or a pharmaceutically acceptable salt, solvate, or stereoisomer thereof, wherein each $R^1$ is independently chloro, —CN, —$OCH_3$—$CH_3$, —$OCHF_2$, cyclopropyl, or morpholinyl; wherein morpholinyl is optionally substituted with one or more —$CH_3$, —$CH_2CH_3$, —$CH_2CH_2CH_3$, —OH, and —$OCH_3$.

Embodiment 59: The compound according to embodiment 58, or a pharmaceutically acceptable salt, solvate, or stereoisomer thereof, wherein each $R^1$ is independently chloro, —$OCH_3$—$CH_3$, —$OCHF_2$, cyclopropyl, or morpholinyl; wherein morpholinyl is optionally substituted with one or more —$CH_3$.

Embodiment 60: The compound according to any one of embodiments 1 to 59, or a pharmaceutically acceptable salt, solvate, or stereoisomer thereof, wherein n is 1, 2, or 3.

Embodiment 61: The compound according to embodiment 60, or a pharmaceutically acceptable salt, solvate, or stereoisomer thereof, wherein n is 1.

Embodiment 62: The compound according to embodiment 60, or a pharmaceutically acceptable salt, solvate, or stereoisomer thereof, wherein n is 2.

Embodiment 63: The compound according to embodiment 60, or a pharmaceutically acceptable salt, solvate, or stereoisomer thereof, wherein n is 3.

Embodiment 64: The compound according to any one of embodiments 1 to 63, or a pharmaceutically acceptable salt, solvate, or stereoisomer thereof, wherein $R^2$ is hydrogen.

Embodiment 65: The compound according to any one of embodiments 1 to 64, or a pharmaceutically acceptable salt, solvate, or stereoisomer thereof, wherein $R^3$ is hydrogen.

Embodiment 66: The compound according to any one of embodiments 1 to 65, or a pharmaceutically acceptable salt, solvate, or stereoisomer thereof, wherein $R^{4a}$, $R^{4b}$, and $R^{4c}$ are independently hydrogen or halogen.

Embodiment 67: The compound according to embodiment 66, or a pharmaceutically acceptable salt, solvate, or stereoisomer thereof, wherein $R^{4a}$ is halogen and $R^{4b}$, and $R^{4c}$ are hydrogen.

Embodiment 68: The compound according to embodiment 66, or a pharmaceutically acceptable salt, solvate, or stereoisomer thereof, wherein $R^{4a}$ and $R^{4c}$ are hydrogen and $R^{4b}$ is halogen.

Embodiment 69: The compound according to embodiment 66, or a pharmaceutically acceptable salt, solvate, or stereoisomer thereof, wherein $R^{4a}$ and $R^{4b}$ are hydrogen and $R^{4c}$ is halogen.

Embodiment 70: The compound according to embodiment 66, or a pharmaceutically acceptable salt, solvate, or stereoisomer thereof, wherein $R^{4a}$ and $R^{4b}$ are halogen and $R^{4c}$ is hydrogen.

Embodiment 71: The compound according to embodiment 66, or a pharmaceutically acceptable salt, solvate, or stereoisomer thereof, wherein $R^{4a}$ and $R^{4b}$ are halogen and $R^{4c}$ is hydrogen.

Embodiment 72: The compound according to embodiment 66, or a pharmaceutically acceptable salt, solvate, or stereoisomer thereof, wherein $R^{4a}$, $R^{4b}$ and $R^{4c}$ are halogen.

Embodiment 73: The compound according to embodiment 66, or a pharmaceutically acceptable salt, solvate, or stereoisomer thereof, wherein $R^{4a}$, $R^{4b}$, and $R^{4c}$ are hydrogen.

Embodiment 74: The compound according to any one of embodiments 1 to 73, or a pharmaceutically acceptable salt, solvate, or stereoisomer thereof, wherein $R^5$ is hydrogen.

Embodiment 75: The compound according to any one of embodiments 1 to 74, or a pharmaceutically acceptable salt, solvate, or stereoisomer thereof, wherein each $R^6$ is hydrogen.

Embodiment 76: The compound according to any one of embodiments 1 to 75, or a pharmaceutically acceptable salt, solvate, or stereoisomer thereof, wherein $R^7$ is hydrogen or $C_1$-$C_6$alkyl.

Embodiment 77: The compound according to embodiment 76, or a pharmaceutically acceptable salt, solvate, or stereoisomer thereof, wherein $R^7$ is hydrogen.

Embodiment 78: The compound according to embodiment 76, or a pharmaceutically acceptable salt, solvate, or stereoisomer thereof, wherein $R^7$ is $C_1$-$C_6$alkyl.

Embodiment 79: The compound according to any one of embodiments 1 to 78, or a pharmaceutically acceptable salt, solvate, or stereoisomer thereof, wherein each of $R^{8a}$, $R^{8b}$, $R^{8c}$, and $R^{8d}$ is independently hydrogen, halogen, or —$OR^a$.

Embodiment 80: The compound according to embodiment 79, or a pharmaceutically acceptable salt, solvate, or stereoisomer thereof, wherein each of $R^{8a}$, $R^{8b}$, and $R^{8d}$ are hydrogen and $R^{8c}$ is hydrogen, halogen, or —$OR^{1a}$.

Embodiment 81: The compound according to embodiment 80, or a pharmaceutically acceptable salt, solvate, or stereoisomer thereof, wherein $R^{8c}$ is halogen or —$OR^a$.

Embodiment 82: The compound according to embodiment 81, or a pharmaceutically acceptable salt, solvate, or stereoisomer thereof, wherein $R^{8c}$ is halogen.

Embodiment 83: The compound according to embodiment 82, or a pharmaceutically acceptable salt, solvate, or stereoisomer thereof, wherein $R^{8c}$ is fluoro, chloro, bromo, or iodo.

Embodiment 84: The compound according to embodiment 81, or a pharmaceutically acceptable salt, solvate, or stereoisomer thereof, wherein $R^{8c}$ is —$OR^a$.

Embodiment 85: The compound according to embodiment 84, or a pharmaceutically acceptable salt, solvate, or stereoisomer thereof, wherein $R^a$ is $C_1$-$C_6$alkyl.

Embodiment 86: The compound according to embodiment 85, or a pharmaceutically acceptable salt, solvate, or stereoisomer thereof, wherein $R^a$ is —$CH_3$.

Embodiment 87: A compound of Formula (11), or a pharmaceutically acceptable salt, solvate, or stereoisomer thereof:

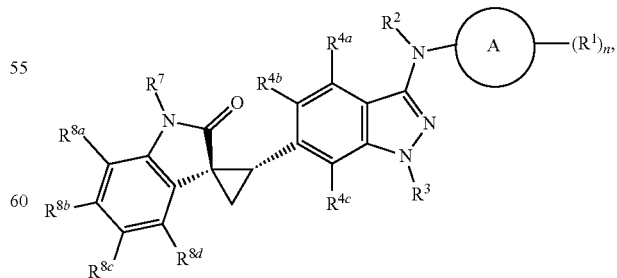

Formula (II)

wherein:
Ring A is $C_6$-$C_{10}$aryl or heteroaryl, $C_3$-$C_{10}$cycloalkyl, and heterocycloalkyl;

each $R^1$ is independently halogen, —CN, —OH, —$OR^a$, $C_1$-$C_6$alkyl, $C_1$-$C_6$haloalkyl, —$OC_1$-$C_6$haloalkyl, $C_1$-$C_6$hydroxyalkyl, $C_1$-$C_6$aminoalkyl, $C_1$-$C_6$heteroalkyl, $C_3$-$C_{10}$cycloalkyl, heterocycloalkyl, $C_6$-$C_{10}$aryl, or heteroaryl; wherein each of the $C_1$-$C_6$alkyl, $C_3$-$C_{10}$cycloalkyl, heterocycloalkyl, $C_6$-$C_{10}$aryl, and heteroaryl is optionally and independently substituted with one or more $R^{1a}$;

each $R^{1a}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^a$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

n is 1, 2, 3, 4, 5, 6, 7, or 8;

$R^2$ is hydrogen or $C_1$-$C_6$alkyl;

$R^3$ is hydrogen or $C_1$-$C_6$alkyl;

$R^{4a}$, $R^{4b}$, and $R^{4c}$ are each independently hydrogen, deuterium, or halogen;

$R^7$ is hydrogen or $C_1$-$C_6$alkyl;

each of $R^{8a}$, $R^{8b}$, $R^{8c}$, and $R^{8d}$ is independently hydrogen, deuterium, halogen, or —$OR^a$; each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Embodiment 88: The compound according to embodiment 87, or a pharmaceutically acceptable salt, solvate, or stereoisomer thereof, wherein Ring A is $C_6$-$C_{10}$aryl.

Embodiment 89: The compound according to embodiment 88, or a pharmaceutically acceptable salt, solvate, or stereoisomer thereof, wherein Ring A is phenyl.

Embodiment 90: The compound according to embodiment 87, or a pharmaceutically acceptable salt, solvate, or stereoisomer thereof, wherein Ring A is heteroaryl.

Embodiment 91: The compound according to embodiment 90, or a pharmaceutically acceptable salt, solvate, or stereoisomer thereof, wherein Ring A is pyrazolyl, pyridinyl, pyrazinyl, pyrimidinyl, or pyridazinyl.

Embodiment 92: The compound according to embodiment 91, or a pharmaceutically acceptable salt, solvate, or stereoisomer thereof, wherein Ring A is pyrazolyl.

Embodiment 93: The compound according to embodiment 92, or a pharmaceutically acceptable salt, solvate, or stereoisomer thereof, wherein Ring A is 1-pyrazolyl, 3-pyrazolyl, 4-pyrazolyl, or 5-pyrazolyl.

Embodiment 94: The compound according to embodiment 93, or a pharmaceutically acceptable salt, solvate, or stereoisomer thereof, wherein Ring A is 1-pyrazolyl.

Embodiment 95: The compound according to embodiment 93, or a pharmaceutically acceptable salt, solvate, or stereoisomer thereof, wherein Ring A is 3-pyrazolyl.

Embodiment 96: The compound according to embodiment 93, or a pharmaceutically acceptable salt, solvate, or stereoisomer thereof, wherein Ring A is 4-pyrazolyl.

Embodiment 97: The compound according to embodiment 93, or a pharmaceutically acceptable salt, solvate, or stereoisomer thereof, wherein Ring A is 5-pyrazolyl.

Embodiment 98: The compound according to embodiment 91, or a pharmaceutically acceptable salt, solvate, or stereoisomer thereof, wherein Ring A is pyridinyl.

Embodiment 99: The compound according to embodiment 98, or a pharmaceutically acceptable salt, solvate, or stereoisomer thereof, wherein Ring A is 2-pyridinyl, 3-pyridinyl, 4-pyridinyl, 5-pyridinyl, or 6-pyridinyl.

Embodiment 100: The compound according to embodiment 99, or a pharmaceutically acceptable salt, solvate, or stereoisomer thereof, wherein Ring A is 2-pyridinyl.

Embodiment 101: The compound according to embodiment 99, or a pharmaceutically acceptable salt, solvate, or stereoisomer thereof, wherein Ring A is 3-pyridinyl.

Embodiment 102: The compound according to embodiment 99, or a pharmaceutically acceptable salt, solvate, or stereoisomer thereof, wherein Ring A is 4-pyridinyl.

Embodiment 103: The compound according to embodiment 99, or a pharmaceutically acceptable salt, solvate, or stereoisomer thereof, wherein Ring A is 5-pyridinyl.

Embodiment 104: The compound according to embodiment 99, or a pharmaceutically acceptable salt, solvate, or stereoisomer thereof, wherein Ring A is 6-pyridinyl.

Embodiment 105: The compound according to embodiment 91, or a pharmaceutically acceptable salt, solvate, or stereoisomer thereof, wherein Ring A is pyrazinyl.

Embodiment 106: The compound according to embodiment 105, or a pharmaceutically acceptable salt, solvate, or stereoisomer thereof, wherein Ring A is 2-pyrazinyl, 3-pyrazinyl, 5-pyrazinyl, or 6-pyrazinyl.

Embodiment 107: The compound according to embodiment 106, or a pharmaceutically acceptable salt, solvate, or stereoisomer thereof, wherein Ring A is 2-pyrazinyl.

Embodiment 108: The compound according to embodiment 106, or a pharmaceutically acceptable salt, solvate, or stereoisomer thereof, wherein Ring A is 3-pyrazinyl.

Embodiment 109: The compound according to embodiment 106, or a pharmaceutically acceptable salt, solvate, or stereoisomer thereof, wherein Ring A is 5-pyrazinyl.

Embodiment 110: The compound according to embodiment 106, or a pharmaceutically acceptable salt, solvate, or stereoisomer thereof, wherein Ring A is 6-pyrazinyl.

Embodiment 111: The compound according to embodiment 91, or a pharmaceutically acceptable salt, solvate, or stereoisomer thereof, wherein Ring A is pyrimidinyl.

Embodiment 112: The compound according to embodiment 111, or a pharmaceutically acceptable salt, solvate, or stereoisomer thereof, wherein Ring A is 2-pyrimidinyl, 4-pyrimidinyl, 5-pyrimidinyl, or 6-pyrimidinyl.

Embodiment 113: The compound according to embodiment 112, or a pharmaceutically acceptable salt, solvate, or stereoisomer thereof, wherein Ring A is 2-pyrimidinyl.

Embodiment 114: The compound according to embodiment 112, or a pharmaceutically acceptable salt, solvate, or stereoisomer thereof, wherein Ring A is 4-pyrimidinyl.

Embodiment 115: The compound according to embodiment 112, or a pharmaceutically acceptable salt, solvate, or stereoisomer thereof, wherein Ring A is 5-pyrimidinyl.

Embodiment 116: The compound according to embodiment 112, or a pharmaceutically acceptable salt, solvate, or stereoisomer thereof, wherein Ring A is 6-pyrimidinyl.

Embodiment 117: The compound according to embodiment 91, or a pharmaceutically acceptable salt, solvate, or stereoisomer thereof, wherein Ring A is pyridazinyl.

Embodiment 118: The compound according to embodiment 117, or a pharmaceutically acceptable salt, solvate, or stereoisomer thereof, wherein Ring A is 3-pyridazinyl, 4-pyridazinyl, 5-pyridazinyl, or 6-pyridazinyl.

Embodiment 119: The compound according to embodiment 118, or a pharmaceutically acceptable salt, solvate, or stereoisomer thereof, wherein Ring A is 3-pyridazinyl.

Embodiment 120: The compound according to embodiment 118, or a pharmaceutically acceptable salt, solvate, or stereoisomer thereof, wherein Ring A is 4-pyridazinyl.

Embodiment 121: The compound according to embodiment 118, or a pharmaceutically acceptable salt, solvate, or stereoisomer thereof, wherein Ring A is 5-pyridazinyl.

Embodiment 122: The compound according to embodiment 118, or a pharmaceutically acceptable salt, solvate, or stereoisomer thereof, wherein Ring A is 6-pyridazinyl.

Embodiment 123: The compound according to embodiment 87, or a pharmaceutically acceptable salt, solvate, or stereoisomer thereof, wherein Ring A is $C_3$-$C_{10}$cycloalkyl or heterocycloalkyl.

Embodiment 124: The compound according to embodiment 123, or a pharmaceutically acceptable salt, solvate, or stereoisomer thereof, wherein Ring A is $C_3$-$C_{10}$cycloalkyl.

Embodiment 125: The compound according to embodiment 123, or a pharmaceutically acceptable salt, solvate, or stereoisomer thereof, wherein Ring A is heterocycloalkyl.

Embodiment 126: The compound according to any one of embodiments 87 to 125, or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$ haloalkyl, $OC_1$-$C_6$haloalkyl, $C_1$-$C_6$hydroxyalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 127: The compound according to embodiment 126, or a pharmaceutically acceptable salt, solvate, or stereoisomer thereof, wherein each $R^1$ is independently halogen, —CN, —OH, —$OR^a$, $C_1$-$C_6$alkyl, $C_1$-$C_6$haloalkyl, —$OC_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 128: The compound according to embodiment 127, or a pharmaceutically acceptable salt, solvate, or stereoisomer thereof, wherein each $R^1$ is independently fluoro, chloro, bromo, iodo, —CN, —OH, —$OR^a$, $C_1$-$C_6$alkyl, —$CF_3$, —$OC_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 129: The compound according to embodiment 128, or a pharmaceutically acceptable salt, solvate, or stereoisomer thereof, wherein each $R^1$ is independently fluoro, chloro, bromo, —CN, —OH, —$OR^a$, $C_1$-$C_6$alkyl, —$CF_3$, —$OC_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$.

Embodiment 130: The compound according to embodiment 129, or a pharmaceutically acceptable salt, solvate, or stereoisomer thereof, wherein each $R^1$ is independently fluoro, chloro, —CN, —OH, —$OC_1$-$C_6$alkyl, $C_1$-$C_6$alkyl, —$CF_3$, —$OC_1$-$C_6$haloalkyl, $C_3$-$C_{10}$cycloalkyl, or heterocycloalkyl; wherein each of the —$OC_1$-$C_6$alkyl, $C_1$-$C_6$alkyl, $C_3$-$C_{10}$cycloalkyl, and heterocycloalkyl is optionally and independently substituted with one or more $R^{1a}$.

Embodiment 131: The compound according to embodiment 130, or a pharmaceutically acceptable salt, solvate, or stereoisomer thereof, wherein each $R^1$ is independently fluoro, chloro, —CN, —OH, —$OCH_3$, —$OCH_2CH_3$, —$C_1$-$C_6$alkyl($OR^{1a}$), —$CH_3$, —$CH_2CH_3$, iso-propyl, n-propyl, n-butyl, i-butyl, t-butyl, —$OC_1$-$C_6$hydroxyalkyl, —$CF_3$, —$OCHF_2$, cyclopropyl, azetidinyl, oxetanyl, piperidinyl, piperazinyl, morpholinyl, 1,4-oxazepanyl, or thiazinyl; wherein each of the azetidinyl, oxetanyl, piperidinyl, piperazinyl, morpholinyl, thiazinyl, and 1,4-oxazepanyl is optionally and independently substituted with one or more $R^{1a}$.

Embodiment 132: The compound according to embodiment 131, or a pharmaceutically acceptable salt, solvate, or stereoisomer thereof, wherein each $R^1$ is independently chloro, —CN, —OH, —$OCH_3$, —$OCH_2CH_3$, —$CH_3$, iso-propyl, —$CF_3$, —$OCHF_2$, cyclopropyl, azetidinyl, oxetanyl, piperidinyl, piperazinyl, morpholinyl, or 1,4-oxazepanyl; wherein each of the azetidinyl, oxetanyl, piperidinyl, piperazinyl, morpholinyl, and 1,4-oxazepanyl is optionally and independently substituted with one or more $R^{1a}$.

Embodiment 133: The compound according to embodiment 132, or a pharmaceutically acceptable salt, solvate, or stereoisomer thereof, wherein each $R^1$ is independently chloro, —CN, —OCH$_3$, —CH$_3$, iso-propyl, —CF$_3$, —OCHF$_2$, cyclopropyl, azetidinyl, piperidinyl, piperazinyl, or morpholinyl; wherein each of the azetidinyl, piperidinyl, piperazinyl, and morpholinyl, is optionally and independently substituted with one or more $R^{1a}$.

Embodiment 134: The compound according to embodiment 133, or a pharmaceutically acceptable salt, solvate, or stereoisomer thereof, wherein each $R^1$ is independently chloro, —CN, —OCH$_3$, —CH$_3$, iso-propyl, —CF$_3$, —OCHF$_2$, cyclopropyl, piperidinyl, piperazinyl, or morpholinyl; wherein each of the azetidinyl, piperidinyl, piperazinyl, and morpholinyl, is optionally and independently substituted with one or more $R^{1a}$.

Embodiment 135: The compound according to embodiment 134, or a pharmaceutically acceptable salt, solvate, or stereoisomer thereof, wherein each $R^1$ is independently chloro, —OCH$_3$, —CH$_3$, iso-propyl, —CF$_3$, —OCHF$_2$, cyclopropyl, piperidinyl, piperazinyl, or morpholinyl; wherein piperidinyl, piperazinyl, and morpholinyl are optionally substituted with one or more $R^{1a}$.

Embodiment 136: The compound according to embodiment 135, or a pharmaceutically acceptable salt, solvate, or stereoisomer thereof, wherein each $R^1$ is independently chloro, —OCH$_3$, —CH$_3$, iso-propyl, —CF$_3$, —OCHF$_2$, cyclopropyl, piperidinyl, piperazinyl, or morpholinyl; wherein piperidinyl, piperazinyl, and morpholinyl are optionally substituted with one or more —CH$_3$, —CH$_2$CH$_3$, —CH$_2$CH$_2$CH$_3$, —OH, and —OCH$_3$.

Embodiment 137: The compound according to embodiment 136, or a pharmaceutically acceptable salt, solvate, or stereoisomer thereof, wherein each $R^1$ is independently chloro, —OCH$_3$, —CH$_3$, —OCHF$_2$, cyclopropyl, piperidinyl, piperazinyl, or morpholinyl; wherein piperidinyl, piperazinyl, and morpholinyl are optionally substituted with one or more —CH$_3$, —CH$_2$CH$_3$, —CH$_2$CH$_2$CH$_3$, —OH, and —OCH$_3$.

Embodiment 138: The compound according to embodiment 137, or a pharmaceutically acceptable salt, solvate, or stereoisomer thereof, wherein each $R^1$ is independently chloro, —OCH$_3$—CH$_3$, —OCHF$_2$, cyclopropyl, or morpholinyl; wherein morpholinyl is optionally substituted with one or more —CH$_3$, —CH$_2$CH$_3$, —CH$_2$CH$_2$CH$_3$, —OH, and —OCH$_3$.

Embodiment 139: The compound according to embodiment 138, or a pharmaceutically acceptable salt, solvate, or stereoisomer thereof, wherein each $R^1$ is independently chloro, —OCH$_3$, —CH$_3$, cyclopropyl, or morpholinyl; wherein morpholinyl is optionally substituted with one or more —CH$_3$.

Embodiment 140: The compound according to any one of embodiments 87 to 139, or a pharmaceutically acceptable salt, solvate, or stereoisomer thereof, wherein n is 1, 2, or 3.

Embodiment 141: The compound according to embodiment 140, or a pharmaceutically acceptable salt, solvate, or stereoisomer thereof, wherein n is 1.

Embodiment 142: The compound according to embodiment 140, or a pharmaceutically acceptable salt, solvate, or stereoisomer thereof, wherein n is 2.

Embodiment 143: The compound according to embodiment 140, or a pharmaceutically acceptable salt, solvate, or stereoisomer thereof, wherein n is 3.

Embodiment 144: The compound according to any one of embodiments 87 to 143, or a pharmaceutically acceptable salt, solvate, or stereoisomer thereof, wherein $R^2$ is hydrogen.

Embodiment 145: The compound according to any one of embodiments 87 to 144, or a pharmaceutically acceptable salt, solvate, or stereoisomer thereof, wherein $R^3$ is hydrogen.

Embodiment 146: The compound according to any one of embodiments 87 to 145, or a pharmaceutically acceptable salt, solvate, or stereoisomer thereof, wherein $R^{4a}$, $R^{4b}$, and $R^{4c}$ are independently hydrogen or halogen.

Embodiment 147: The compound according to embodiment 146, or a pharmaceutically acceptable salt, solvate, or stereoisomer thereof, wherein $R^{4a}$ is halogen and $R^{4b}$, and $R^{4c}$ are hydrogen.

Embodiment 148: The compound according to embodiment 146, or a pharmaceutically acceptable salt, solvate, or stereoisomer thereof, wherein $R^{4a}$ and $R^{4c}$ are hydrogen and $R^{4b}$ is halogen.

Embodiment 149: The compound according to embodiment 146, or a pharmaceutically acceptable salt, solvate, or stereoisomer thereof, wherein $R^{4a}$ and $R^{4b}$ are hydrogen and $R^{4c}$ is halogen.

Embodiment 150: The compound according to embodiment 146, or a pharmaceutically acceptable salt, solvate, or stereoisomer thereof, wherein $R^{4a}$ and $R^{4b}$ are halogen and $R^{4c}$ is hydrogen.

Embodiment 151: The compound according to embodiment 146, or a pharmaceutically acceptable salt, solvate, or stereoisomer thereof, wherein $R^{4a}$ and $R^{4c}$ are halogen and $R^{4b}$ is hydrogen.

Embodiment 152: The compound according to embodiment 146, or a pharmaceutically acceptable salt, solvate, or stereoisomer thereof, wherein $R^{4a}$ is halogen and $R^{4b}$ and $R^{4c}$ are hydrogen.

Embodiment 153: The compound according to embodiment 146, or a pharmaceutically acceptable salt, solvate, or stereoisomer thereof, wherein $R^{4a}$, $R^{4b}$, and $R^{4c}$ are hydrogen.

Embodiment 154: The compound according to embodiment 146, or a pharmaceutically acceptable salt, solvate, or stereoisomer thereof, wherein $R^{4a}$, $R^{4b}$, and $R^{4c}$ are halogen.

Embodiment 155: The compound according to embodiment 146, or a pharmaceutically acceptable salt, solvate, or stereoisomer thereof, wherein $R^{4a}$, $R^{4b}$, and $R^{4c}$ are fluoro.

Embodiment 156: The compound according to any one of embodiments 87 to 155, or a pharmaceutically acceptable salt, solvate, or stereoisomer thereof, wherein $R^7$ is hydrogen or $C_1$-$C_6$alkyl.

Embodiment 157: The compound according to embodiment 156, or a pharmaceutically acceptable salt, solvate, or stereoisomer thereof, wherein $R^7$ is hydrogen.

Embodiment 158: The compound according to embodiment 156, or a pharmaceutically acceptable salt, solvate, or stereoisomer thereof, wherein $R^7$ is $C_1$-$C_6$alkyl.

Embodiment 159: The compound according to any one of embodiments 87 to 158, or a pharmaceutically acceptable salt, solvate, or stereoisomer thereof, wherein each of $R^{8a}$, $R^{8b}$, $R^{8c}$, and $R^{8d}$ is independently hydrogen, deuterium, halogen, or —OR$^a$.

Embodiment 160: The compound according to embodiment 159, or a pharmaceutically acceptable salt, solvate, or stereoisomer thereof, wherein each of $R^{8a}$, $R^{8b}$ and $R^{8d}$ are hydrogen and $R^{8c}$ is hydrogen, halogen, or —OR$^a$.

Embodiment 161: The compound according to embodiment 160, or a pharmaceutically acceptable salt, solvate, or stereoisomer thereof, wherein $R^{8c}$ is halogen or —$OR^a$.

Embodiment 162: The compound according to embodiment 161, or a pharmaceutically acceptable salt, solvate, or stereoisomer thereof, wherein $R^{8c}$ is halogen.

Embodiment 163: The compound according to embodiment 162, or a pharmaceutically acceptable salt, solvate, or stereoisomer thereof, wherein $R^{8c}$ is fluoro, chloro, bromo, or iodo.

Embodiment 164: The compound according to embodiment 161, or a pharmaceutically acceptable salt, solvate, or stereoisomer thereof, wherein $R^{8c}$ is —$OR^a$.

Embodiment 165: The compound according to embodiment 164, or a pharmaceutically acceptable salt, solvate, or stereoisomer thereof, wherein $R^a$ is $C_1$-$C_6$alkyl.

Embodiment 166: The compound according to embodiment 165, or a pharmaceutically acceptable salt, solvate, or stereoisomer thereof, wherein $R^a$ is —$CH_3$.

Embodiment 167: A compound of Formula (III), or a pharmaceutically acceptable salt, solvate, or stereoisomer thereof:

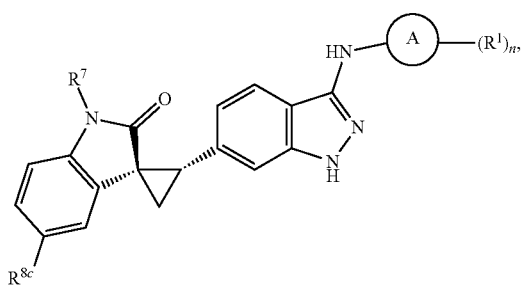

Formula (III)

wherein:
Ring A is heteroaryl;
each $R^1$ is independently halogen, —CN, —OH, —$OR^a$, $C_1$-$C_6$alkyl, $C_1$-$C_6$haloalkyl, —$OC_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;
each $R^{1a}$ is independently deuterium, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$—C(alkynyl, $C_3$-$C_{10}$cycloalkyl, heterocycloalkyl, $C_6$-$C_{10}$aryl, or heteroaryl;
n is 1, 2, 3, 4, 5, 6, 7, or 8;
$R^7$ is hydrogen or $C_1$-$C_6$alkyl;
$R^{8c}$ is halogen or —$OR^a$; and
each $R^3$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_1$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)?NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Embodiment 168: The compound according to embodiment 167, or a pharmaceutically acceptable salt, solvate, or stereoisomer thereof, wherein Ring A is pyrazolyl, pyridinyl, pyrazinyl, pyrimidinyl, or pyridazinyl.

Embodiment 169: The compound according to embodiment 168, or a pharmaceutically acceptable salt, solvate, or stereoisomer thereof, wherein Ring A is pyrazolyl.

Embodiment 170: The compound according to embodiment 169, or a pharmaceutically acceptable salt, solvate, or stereoisomer thereof, wherein Ring A is 1-pyrazolyl, 3-pyrazolyl, 4-pyrazolyl, or 5-pyrazolyl.

Embodiment 171: The compound according to embodiment 170, or a pharmaceutically acceptable salt, solvate, or stereoisomer thereof, wherein Ring A is 1-pyrazolyl.

Embodiment 172: The compound according to embodiment 170, or a pharmaceutically acceptable salt, solvate, or stereoisomer thereof, wherein Ring A is 3-pyrazolyl.

Embodiment 173: The compound according to embodiment 170, or a pharmaceutically acceptable salt, solvate, or stereoisomer thereof, wherein Ring A is 4-pyrazolyl.

Embodiment 174: The compound according to embodiment 170, or a pharmaceutically acceptable salt, solvate, or stereoisomer thereof, wherein Ring A is 5-pyrazolyl.

Embodiment 175: The compound according to embodiment 168, or a pharmaceutically acceptable salt, solvate, or stereoisomer thereof, wherein Ring A is pyridinyl.

Embodiment 176: The compound according to embodiment 175, or a pharmaceutically acceptable salt, solvate, or stereoisomer thereof, wherein Ring A is 2-pyridinyl, 3-pyridinyl, 4-pyridinyl, 5-pyridinyl, or 6-pyridinyl.

Embodiment 177: The compound according to embodiment 176, or a pharmaceutically acceptable salt, solvate, or stereoisomer thereof, wherein Ring A is 2-pyridinyl.

Embodiment 178: The compound according to embodiment 176, or a pharmaceutically acceptable salt, solvate, or stereoisomer thereof, wherein Ring A is 3-pyridinyl.

Embodiment 179: The compound according to embodiment 176, or a pharmaceutically acceptable salt, solvate, or stereoisomer thereof, wherein Ring A is 4-pyridinyl.

Embodiment 180: The compound according to embodiment 176, or a pharmaceutically acceptable salt, solvate, or stereoisomer thereof, wherein Ring A is 5-pyridinyl.

Embodiment 181: The compound according to embodiment 176, or a pharmaceutically acceptable salt, solvate, or stereoisomer thereof, wherein Ring A is 6-pyridinyl.

Embodiment 182: The compound according to embodiment 168, or a pharmaceutically acceptable salt, solvate, or stereoisomer thereof, wherein Ring A is pyrazinyl.

Embodiment 183: The compound according to embodiment 182, or a pharmaceutically acceptable salt, solvate, or stereoisomer thereof, wherein Ring A is 2-pyrazinyl, 3-pyrazinyl, 5-pyrazinyl, or 6-pyrazinyl.

Embodiment 184: The compound according to embodiment 183, or a pharmaceutically acceptable salt, solvate, or stereoisomer thereof, wherein Ring A is 2-pyrazinyl.

Embodiment 185: The compound according to embodiment 183, or a pharmaceutically acceptable salt, solvate, or stereoisomer thereof, wherein Ring A is 3-pyrazinyl.

Embodiment 186: The compound according to embodiment 183, or a pharmaceutically acceptable salt, solvate, or stereoisomer thereof, wherein Ring A is 5-pyrazinyl.

Embodiment 187: The compound according to embodiment 183, or a pharmaceutically acceptable salt, solvate, or stereoisomer thereof, wherein Ring A is 6-pyrazinyl.

Embodiment 188: The compound according to embodiment 168, or a pharmaceutically acceptable salt, solvate, or stereoisomer thereof, wherein Ring A is pyrimidinyl.

Embodiment 189: The compound according to embodiment 188, or a pharmaceutically acceptable salt, solvate, or stereoisomer thereof, wherein Ring A is 2-pyrimidinyl, 4-pyrimidinyl, 5-pyrimidinyl, or 6-pyrimidinyl.

Embodiment 190: The compound according to embodiment 189, or a pharmaceutically acceptable salt, solvate, or stereoisomer thereof, wherein Ring A is 2-pyrimidinyl.

Embodiment 191: The compound according to embodiment 189, or a pharmaceutically acceptable salt, solvate, or stereoisomer thereof, wherein Ring A is 4-pyrimidinyl.

Embodiment 192: The compound according to embodiment 189, or a pharmaceutically acceptable salt, solvate, or stereoisomer thereof, wherein Ring A is 5-pyrimidinyl.

Embodiment 193: The compound according to embodiment 189, or a pharmaceutically acceptable salt, solvate, or stereoisomer thereof, wherein Ring A is 6-pyrimidinyl.

Embodiment 194: The compound according to embodiment 168, or a pharmaceutically acceptable salt, solvate, or stereoisomer thereof, wherein Ring A is pyridazinyl.

Embodiment 195: The compound according to embodiment 194, or a pharmaceutically acceptable salt, solvate, or stereoisomer thereof, wherein Ring A is 3-pyridazinyl, 4-pyridazinyl, 5-pyridazinyl, or 6-pyridazinyl.

Embodiment 196: The compound according to embodiment 195, or a pharmaceutically acceptable salt, solvate, or stereoisomer thereof, wherein Ring A is 3-pyridazinyl.

Embodiment 197: The compound according to embodiment 195, or a pharmaceutically acceptable salt, solvate, or stereoisomer thereof, wherein Ring A is 4-pyridazinyl.

Embodiment 198: The compound according to embodiment 195, or a pharmaceutically acceptable salt, solvate, or stereoisomer thereof, wherein Ring A is 5-pyridazinyl.

Embodiment 199: The compound according to embodiment 195, or a pharmaceutically acceptable salt, solvate, or stereoisomer thereof, wherein Ring A is 6-pyridazinyl.

Embodiment 200: A compound according to embodiment 167, or a pharmaceutically acceptable salt, solvate, or stereoisomer thereof, wherein:
Ring A is pyrazolyl, pyridinyl, pyrazinyl, pyrimidinyl, or pyridazinyl;
each $R^1$ is independently halogen, —CN, —OH, —OR$^a$, $C_1$-$C_6$alkyl, $C_1$-$C_6$haloalkyl, —OC$_1$-$C_6$haloalkyl, $C_1$-$C_{10}$cycloalkyl, or heterocycloalkyl; wherein each of the $C_1$-$C_6$alkyl, $C_1$-$C_{10}$cycloalkyl, and heterocycloalkyl is optionally and independently substituted with one or more $R^{1a}$;
each $R^1$ is independently —OH, —OR$^a$, $C_1$-$C_6$alkyl, $C_1$-$C_6$haloalkyl, $C_1$-$C_6$hydroxyalkyl, or $C_1$-$C_6$heteroalkyl;
n is 1, 2, or 3;
$R^7$ is hydrogen;
$R^{8c}$ is —OR$^a$; and
each $R^a$ is $C_1$-$C_6$alkyl.

Embodiment 201: The compound of embodiment 200, or a pharmaceutically acceptable salt, solvate, or stereoisomer thereof, wherein Ring A is pyrimidinyl.

Embodiment 202: The compound according to embodiment 201, or a pharmaceutically acceptable salt, solvate, or stereoisomer thereof, wherein Ring A is 2-pyrimidinyl, 4-pyrimidinyl, 5-pyrimidinyl, or 6-pyrimidinyl.

Embodiment 203: The compound according to embodiment 202, or a pharmaceutically acceptable salt, solvate, or stereoisomer thereof, wherein Ring A is 2-pyrimidinyl.

Embodiment 204: The compound according to embodiment 202, or a pharmaceutically acceptable salt, solvate, or stereoisomer thereof, wherein Ring A is 4-pyrimidinyl.

Embodiment 205: The compound according to embodiment 202, or a pharmaceutically acceptable salt, solvate, or stereoisomer thereof, wherein Ring A is 5-pyrimidinyl.

Embodiment 206: The compound according to embodiment 202, or a pharmaceutically acceptable salt, solvate, or stereoisomer thereof, wherein Ring A is 6-pyrimidinyl.

Embodiment 207: A compound according to embodiment 167, or a pharmaceutically acceptable salt, solvate, or stereoisomer thereof, wherein:
Ring A is pyridinyl or pyrimidinyl;
each $R^1$ is independently fluoro, chloro, —CN, —OH, —OR$^a$, $C_1$-$C_6$alkyl, $C_1$-$C_6$haloalkyl, —OC$_1$-$C_6$haloalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;
each $R^{1a}$ is independently —OH, —OR$^a$, $C_1$-$C_6$alkyl, $C_1$-$C_6$haloalkyl, $C_1$-$C_6$hydroxyalkyl, or $C_1$-$C_6$heteroalkyl;
n is 1, 2, or 3;
$R^7$ is hydrogen;
$R^{8c}$ is —OCH$_3$; and
each $R^a$ is $C_1$-$C_6$alkyl.

Embodiment 208: The compound according to embodiment 207, or a pharmaceutically acceptable salt, solvate, or stereoisomer thereof, wherein Ring A is pyridinyl.

Embodiment 209: The compound according to embodiment 208, or a pharmaceutically acceptable salt, solvate, or stereoisomer thereof, wherein Ring A is 2-pyridinyl, 3-pyridinyl, 4-pyridinyl, 5-pyridinyl, or 6-pyridinyl.

Embodiment 210: The compound according to embodiment 209, or a pharmaceutically acceptable salt, solvate, or stereoisomer thereof, wherein Ring A is 2-pyridinyl.

Embodiment 211: The compound according to embodiment 209, or a pharmaceutically acceptable salt, solvate, or stereoisomer thereof, wherein Ring A is 3-pyridinyl.

Embodiment 212: The compound according to embodiment 209, or a pharmaceutically acceptable salt, solvate, or stereoisomer thereof, wherein Ring A is 4-pyridinyl.

Embodiment 213: The compound according to embodiment 20), or a pharmaceutically acceptable salt, solvate, or stereoisomer thereof, wherein Ring A is 5-pyridinyl.

Embodiment 214: The compound according to embodiment 209, or a pharmaceutically acceptable salt, solvate, or stereoisomer thereof, wherein Ring A is 6-pyridinyl.

Embodiment 215: The compound according to embodiment 207, or a pharmaceutically acceptable salt, solvate, or stereoisomer thereof, wherein Ring A is pyrimidinyl.

Embodiment 216: The compound according to embodiment 215, or a pharmaceutically acceptable salt, solvate, or stereoisomer thereof, wherein Ring A is 2-pyrimidinyl, 4-pyrimidinyl, 5-pyrimidinyl, or 6-pyrimidinyl.

Embodiment 217: The compound according to embodiment 216, or a pharmaceutically acceptable salt, solvate, or stereoisomer thereof, wherein Ring A is 2-pyrimidinyl.

Embodiment 218: The compound according to embodiment 216, or a pharmaceutically acceptable salt, solvate, or stereoisomer thereof, wherein Ring A is 4-pyrimidinyl.

Embodiment 219: The compound according to embodiment 216, or a pharmaceutically acceptable salt, solvate, or stereoisomer thereof, wherein Ring A is 5-pyrimidinyl.

Embodiment 220: The compound according to embodiment 216, or a pharmaceutically acceptable salt, solvate, or stereoisomer thereof, wherein Ring A is 6-pyrimidinyl.

Embodiment 221: A compound according to embodiment 167, or a pharmaceutically acceptable salt, solvate, or stereoisomer thereof, wherein:

Ring A is pyridinyl or pyrimidinyl;
each $R^1$ is independently chloro, —CN, —OH, —OCH$_3$, —OCH$_2$CH$_3$, —CHI, —CH$_2$CH$_3$, —CH(CH$_3$)$_2$, —CF$_3$, —OCHF$_2$, cyclopropyl, morpholinyl, piperidinyl, piperazinyl, azetidinyl, 1,1-dioxidothiomorpholinyl, or oxetanyl; wherein morpholinyl, piperidinyl, piperazinyl, azetidinyl, 1,1-dioxidothiomorpholinyl, or oxetanyl are each optionally and independently substituted with one or more $R^{1a}$; each $R^{1a}$ is independently —OH, —OR$^a$, C$_1$-C$_6$alkyl, C$_1$-C$_6$haloalkyl, C$_1$-C$_6$hydroxyalkyl, or C$_1$-C$_6$heteroalkyl;
n is 1, 2, or 3;
$R^7$ is hydrogen;
$R^{8c}$ is —OCH$_3$; and
each $R^a$ is C$_1$-C$_6$alkyl.

Embodiment 222: A compound of Formula (III), or a pharmaceutically acceptable salt, solvate, or stereoisomer thereof:

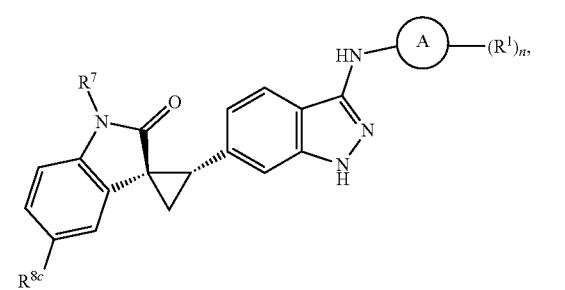

Formula (III)

wherein:
Ring A is heteroaryl;
each $R^1$ is independently halogen, —CN, —OR$^a$, —OC(=O)R$^a$, —OC(=O)OR$^b$, —OC(=O)NR$^c$R$^d$, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, —OC$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_1$-C$_{10}$aryl, or heteroaryl; wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is optionally and independently substituted with one or more $R^{1a}$;
each $R^{1a}$ is independently deuterium, —OH, —OR$^a$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;
n is 1, 2, or 3;
$R^7$ is hydrogen or C$_1$-C$_6$alkyl;
$R^{8c}$ is halogen or —OR$^a$;

each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl. C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CHI)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)NHCH$_3$, —S(=O)$_2$N(CH$_3$)$_2$, —NH$_2$, —NHCH$_3$, —N(CH$_3$)?, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_4$heteroalkyl.

Embodiment 223: The compound according to embodiment 222, or a pharmaceutically acceptable salt, solvate, or stereoisomer thereof, wherein Ring A is pyrazolyl, pyridinyl, pyrazinyl, pyrimidinyl, or pyridazinyl.

Embodiment 224: A compound of Formula (III), or a pharmaceutically acceptable salt, solvate, or stereoisomer thereof:

Formula (III)

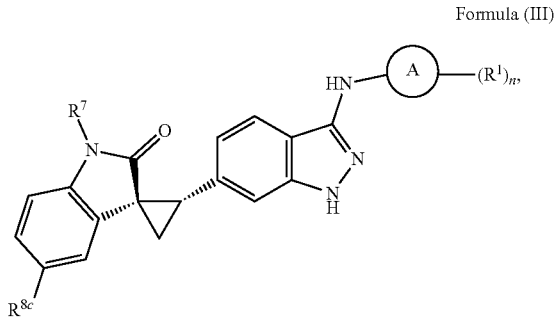

wherein:

Ring A is heteroaryl;

each $R^1$ is independently halogen, —$OR^a$, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bS(=O)_2R^a$, —C(=O)$R^a$, —C(=O)$NR^cR^d$, $C_1$-$C_6$alkyl, $C_1$-$C_6$haloalkyl, —O$C_1$-$C_6$haloalkyl, $C_1$-$C_6$hydroxyalkyl, $C_1$-$C_6$aminoalkyl, $C_1$-$C_6$ heteroalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;

each $R^{1a}$ is independently deuterium, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_1$-$C_6$alkenyl, $C_2$-$C_6$alkynyl, $C_3$-$C_{10}$cycloalkyl, heterocycloalkyl, $C_6$-$C_{10}$aryl, or heteroaryl;

n is 1, 2, or 3;

$R^7$ is hydrogen or $C_1$-$C_6$alkyl;

$R^{8c}$ is halogen or —$OR^a$;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$ alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Embodiment 225: The compound according to embodiment 222, or a pharmaceutically acceptable salt, solvate, or stereoisomer thereof, wherein Ring A is pyrazolyl, pyridinyl, pyrazinyl, pyrimidinyl, or pyridazinyl.

Embodiment 226: A compound of Formula (III), or a pharmaceutically acceptable salt, solvate, or stereoisomer thereof:

Formula (III)

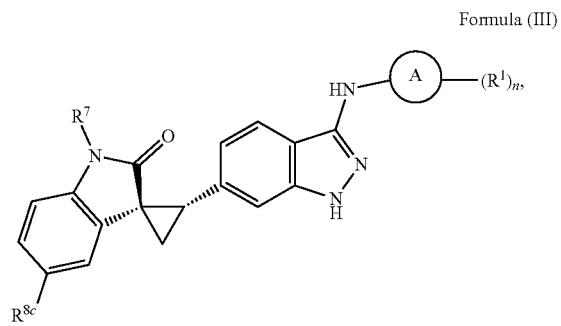

wherein:

Ring A is heteroaryl;

each $R^1$ is independently halogen, —$OR^a$, —$SR^a$, —S(=O)$R^3$, —S(=O)$_2R^a$, —S(=O)$_2NR^cR^d$, —$NR^cR^d$, —$NR^bC(=O)NR^cR^d$, —$NR^bC(=O)R^a$, —$NR^bS(=O)_2R^a$, —C(=O)$R^a$, —C(=O)$NR^cR^d$, $C_1$-$C_6$alkyl, $C_1$-$C_6$haloalkyl, —O$C_1$-$C_6$haloalkyl, $C_1$-$C_6$hydroxyalkyl, $C_1$-$C_6$aminoalkyl, $C_1$-$C_6$heteroalkyl, $C_3$-$C_{10}$cycloalkyl, or heterocycloalkyl; wherein each of the $C_1$-$C_6$alkyl, $C_3$-$C_{10}$cycloalkyl, and heterocycloalkyl is optionally and independently substituted with one or more $R^{1a}$;

each $R^{1a}$ is independently deuterium, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;

n is 1, 2, or 3;

$R^7$ is hydrogen or $C_1$-$C_6$alkyl;

$R^{8c}$ is halogen or —$OR^a$;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$ h, —C(=O)CH$_3$, —C(=O) OH, —C(=O)OCH$_3$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, or $C_1$-$C_6$heteroalkyl;

each R$^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$ alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each R$^c$ and R$^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O) CH$_3$, —S(=O)$_2$NH$_2$, —S(=O)$_2$NHCH$_3$, —S(=O)$_2$N (CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Embodiment 227: The compound according to embodiment 226, or a pharmaceutically acceptable salt, solvate, or stereoisomer thereof, wherein Ring A is pyrazolyl, pyridinyl, pyrazinyl, pyrimidinyl, or pyridazinyl.

Embodiment 228: A compound of Formula (III), or a pharmaceutically acceptable salt, solvate, or stereoisomer thereof:

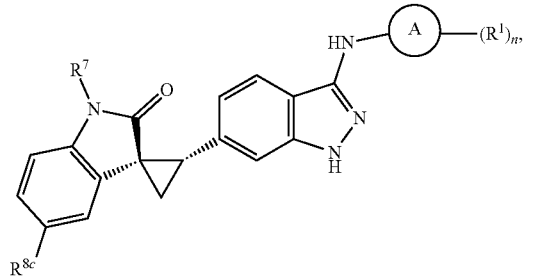

Formula (III)

wherein:
Ring A is phenyl, pyrazolyl, pyridinyl, pyrazinyl, pyrimidinyl, or pyridazinyl;

each R$^1$ is independently halogen, —S(=O)$_2$($C_1$-$C_6$ alkyl), —S(=O)$_2$N($C_1$-$C_6$ alkyl)$_2$, —O$C_1$-$C_6$ alkyl, —C(=O)N ($C_1$-$C_6$ alkyl)$_2$, —C(=O)N(H)($C_1$-$C_6$ alkyl), —O$C_1$-$C_6$haloalkyl, $C_1$-$C_6$alkyl, —S($C_1$-$C_6$ alkyl), heterocycloalkyl, or —C(=O)(heterocycloalkyl);
n is 1, 2, or 3;
R$^7$ is hydrogen; and
R$^{8c}$ is hydrogen, halogen, CH$_3$, or —OCH$_3$.

Embodiment 229: A compound of Formula (III), or a pharmaceutically acceptable salt, solvate, or stereoisomer thereof:

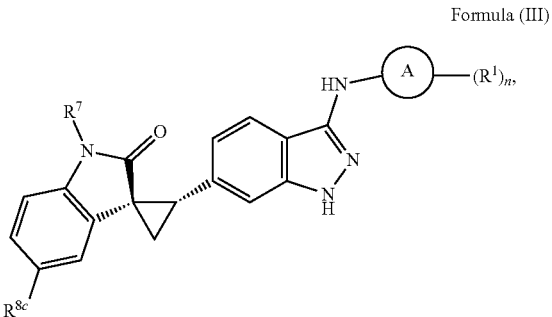

Formula (III)

wherein:
Ring A is phenyl, pyrazolyl, pyridinyl, pyrazinyl, pyrimidinyl, or pyridazinyl;
each R$^1$ is independently halogen, —CF$_3$, —CN, —S(=O)$_2$(CH$_3$), —S(=O)$_2$(CH$_2$CH)—S(=O)$_2$N(CH$_3$)$_2$, —OCH$_3$, —CH$_2$CHF$_2$, —C(=O)N(CH$_3$)$_2$, —C(=O)N(H) (CH$_3$), —O$C_1$$C_6$haloalkyl, —CH$_3$, —CH$_2$CH$_3$, iso-propyl, n-propyl, —SCH$_3$, azetidinyl, pyrrolidinyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;
n is 1, 2, or 3:
R$^7$ is hydrogen; and
R$^{8c}$ is hydrogen, halogen, CH$_3$, or —OCH$_3$.

Embodiment 230: A compound of Formula (III), or a pharmaceutically acceptable salt, solvate, or stereoisomer thereof:

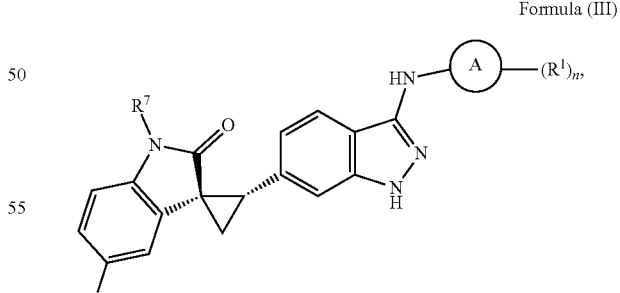

Formula (III)

wherein:
Ring A is aryl;
each R$^1$ is independently halogen, —CN, —OR$^a$, —OC (=O)R$^a$, —OC(=O)OR$^b$, —OC(=O)NR$^c$R$^d$, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O) OR$^a$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, —OC$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_1$-C$_{10}$aryl, or heteroaryl; wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is optionally and independently substituted with one or more R$^{1a}$;

each R$^{1a}$ is independently deuterium, —OH, —OR$^a$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, or heteroaryl;

n is 1, 2, or 3:

R$^7$ is hydrogen or C$_1$-C$_6$alkyl;

R$^{8c}$ is hydrogen, C$_1$-C$_6$alkyl, halogen or —OR$^a$;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(C$_6$-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, C$_3$-C$_{10}$cycloalkyl, heterocycloalkyl, C$_6$-C$_{10}$aryl, heteroaryl, C$_1$-C$_6$alkyl(C$_3$-C$_{10}$cycloalkyl), C$_1$-C$_6$alkyl(heterocycloalkyl), C$_1$-C$_6$alkyl(G-C$_{10}$aryl), or C$_1$-C$_6$alkyl(heteroaryl); wherein each of the C$_1$-C$_6$alkyl, C$_2$-C$_6$alkenyl, C$_2$-C$_6$alkynyl, C$_3$-C$_{10}$cycloalkyl, heterocycloalkyl, C$_6$-C$_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; or R$^c$ and R$^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)?, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

Embodiment 231: A compound selected from (1R,2S)-5'-methoxy-2-{3-[(5-methoxypyrimidin-4-yl)amino]-1H-indazol-6-yl}spiro[cyclopropane-1,3'-indol]-2'(1'H)-one; (1R,2S)-5'-methoxy-2-{3-[(5-methylpyrimidin-4-yl)amino]-1H-indazol-6-yl}spiro[cyclopropane-1,3'-indol]-2'(1'H)-one; (1R,2S)-2-{3-[(5-chloropyrimidin-4-yl)amino]-1H-indazol-6-yl}-5'-methoxyspiro[cyclopropane-1,3'-indol]-2'(1'H)-one; (1R,2S)-5'-methoxy-2-{3-[(5-methoxypyrimidin-4-yl)amino]-1H-indazol-6-yl}spiro[cyclopropane-1,3'-indol]-2'(1'H)-one; (1R,2S)-2-{3-[(5-ethoxypyrimidin-4-yl)amino]-1H-indazol-6-yl}-5'-methoxyspiro[cyclopropane-1,3'-indol]-2'($^1$H)-one; (1R,2S)-2-{3-[(5-cyclopropylpyrimidin-4-yl)amino]-1H-indazol-6-yl}-5'-methoxyspiro[cyclopropane-1,3'-indol]-2'(1'H)-one; (1R,2S)-2-{3-[(5-chloropyrimidin-4-yl)amino]-1H-indazol-6-yl}-5'-methoxyspiro[cyclopropane-1,3'-indol]-2'(1'H)-one; (1S,2R)-5'-methoxy-2-{3-[(5-methoxypyrimidin-4-yl)amino]-1H-indazol-6-yl}spiro[cyclopropane-1,3'-indol]-2'(1'H)-one; (1R,2S)-2-(3-{[5-chloro-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-{3-[(2-chloro-5-methoxypyrimidin-4-yl)amino]-1H-indazol-6-yl}-5'-methoxyspiro[cyclopropane-1,3'-indol]-2'(1'H)-one; (1R,2S)-5'-methoxy-2-(3-{[5-methoxy-6-(morpholin-4-yl)pyrimidin-4-yl]amino}-1H-indazol-6-yl)spiro[cyclopropane-1,3'-indol]-2'(1'H)-one; (1R,2S)-5'-methoxy-2-(3-{[5-methoxy-6-(piperidin-1-yl)pyrimidin-4-yl]amino}-1H-indazol-6-yl)spiro[cyclopropane-1,3'-indol]-2'(1'H)-one; (1R,2S)-5'-methoxy-2-{3-[(3-methoxypyrazin-2-yl)amino]-1H-indazol-6-yl}spiro[cyclopropane-1,3'-indol]-2'(1'H)-one; (1R,2S)-5'-methoxy-2-{3-[(6-methoxypyrimidin-4-yl)amino]-1H-indazol-6-yl}spiro[cyclopropane-1,3'-indol]-2'(1'H)-one; (1R,2S)-2-{3-[(6,7-dihydro-5H-cyclopenta[d]pyrimidin-4-yl)amino]-1H-indazol-6-yl}-5'-methoxyspiro[cyclopropane-1,3'-indol]-2'(1'H)-one; (1R,2S)-2-{3-[(2,3-dihydro-1-benzofuran-7-yl)amino]-1H-indazol-6-yl}-5'-methoxyspiro[cyclopropane-1,3'-indol]-2'($^1$H)-one; (1R,2S)-5'-methoxy-2-{3-[(3-methoxypyridin-2-yl)amino]-1H-indazol-6-yl}spiro[cyclopropane-1,3'-indol]-2'(1'H)-one; (1R,2S)-5'-methoxy-2-{3-[(4-methoxypyridin-3-yl)amino]-1H-indazol-6-yl}spiro[cyclopropane-1,3'-indol]-2'(1'H)-one; (1R,2S)-5'-methoxy-2-{3-[(3-methoxypyridin-4-yl)amino]-1H-indazol-6-yl}spiro[cyclopropane-1,3'-indol]-2'(1'H)-one; (1R,2S)-2-(3-{[5-chloro-6-(4-methylpiperazin-1-yl)pyrimidin-4-yl]amino}-1H-indazol-6-yl)-5'-methoxyspiro[cyclopropane-1,3'-indol]-2'(1'H)-one; (1R,2S)-5'-methoxy-2-{3-[(1,3,5-trimethyl-1H-pyrazol-4-yl)amino]-1H-indazol-6-yl}spiro[cyclopropane-1,3'-indol]-2'(1'H)-one; (1R,2S)-5'-methoxy-2-(3-{[5-(trifluoromethyl)pyrimidin-4-yl]amino}-1H-indazol-6-yl)spiro[cyclopropane-1,3'-indol]-2'(1'H)-one; (1R,2S)-2-{3-[(5-chloro-2-methoxypyrimidin-4-yl)amino]-1H-indazol-6-yl}-5'-methoxyspiro[cyclopropane-1,3'-indol]-2'(1'H)-one; (1R,2S)-5'-methoxy-2-{3-[(2-methoxypyridin-3-yl)amino]-1H-indazol-6-yl}spiro[cyclopropane-1,3'-indol]-2'(1'H)-one; (1R,2S)-2-{3-[(1-benzofuran-7-yl)amino]-1H-indazol-6-yl}-5'-methoxyspiro[cyclopropane-1,3'-indol]-2'(1'H)-one; (1R,2S)-5'-methoxy-2-{3-[(3-methoxy-1-methyl-1H-pyrazol-4-yl)amino]-1H-indazol-6-yl}spiro[cyclopropane-1,3'-indol]-2'(1'H)-one;

(1R,2S)-2-{3-[(3-hydroxy-2,3-dihydro-1-benzofuran-7-yl)amino]-1H-indazol-6-yl}-5'-methoxyspiro[cyclopropane-1,3'-indol]-2'(1'H)-one; (1R,2S)-2-(3-{[(3S)-3-hydroxy-2,3-dihydro-1-benzofuran-7-yl]amino}-1H-indazol-6-yl)-5'-methoxyspiro[cyclopropane-1,3'-indol]-2'(1'H)-one; (1R,2S)-2-(3-{[(3R)-3-hydroxy-2,3-dihydro-1-benzofuran-7-yl]amino}-1H-indazol-6-yl)-5'-methoxyspiro[cyclopropane-1,3'-indol]-2'(1'H)-one; (1R,2S)-2-{3-[(2,3-dihydropyrazolo[5,1-b][1,3]oxazol-7-yl)amino]-1H-indazol-6-yl}-5'-methoxyspiro[cyclopropane-1,3'-indol]-2'(1'H)-one; (1R,2S)-5'-methoxy-2-{3-[(3-oxo-2,3-dihydro-1-benzofuran-7-yl)amino]-1H-indazol-6-yl}spiro[cyclopropane-1,3'-indol]-2'(1'H)-one; (1R,2S)-2-{3-[(2,3-dihydrofuro[2,3-c]pyridin-7-yl)amino]-1H-indazol-6-yl}-5'-methoxyspiro[cyclopropane-1,3'-indol]-2'(1'H)-one; (1R,2S)-2-(3-{[(3S)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one; (1R,2S)-2-(3-{[(3R)-3-(hydroxymethyl)-2,3-dihydrofuro[2,3-c]pyridin-7-yl]amino}-1H-indazol-6-yl)-5'-methoxyspiro[cyclopropane-1,3'-indol]-2'(1'H)-one; (1R,2S)-5'-methoxy-2-(3-{[6-(3-methoxyazetidin-1-yl)pyrimidin-4-yl]amino}-1H-indazol-6-yl)spiro[cyclopropane-1,3'-indol]-2'(1'H)-one; (1R,2S)-2-(3-{[6-(3-hydroxyazetidin-1-yl)pyrimidin-4-yl]amino}-1H-indazol-6-yl)-5'-methoxyspiro[cyclopropane-1,3'-indol]-2'(1'H)-one; (1R,2S)-2-(3-((6-(3-oxa-8-azabicyclo[3.2.1]octan-8-yl)-5-methoxypyrimidin-4-yl)amino)-1H-indazol-6-yl)-5'-methoxyspiro[cyclopropane-1,3'-indolin]-2'-one; (1R,2S)-2-(3-{[6-(2-hydroxyethoxy)pyrimidin-4-yl]amino}-1H-indazol-6-yl)-5'-methoxyspiro[cyclopropane-1,3'-indol]-2'(1'H)-one; (1R,2S)-2-(3-((6-(1,1-dioxidothiomorpholino)pyrimidin-4-yl)amino)-1H-indazol-6-yl)-5'-methoxyspiro[cyclopropane-1,3'-indolin]-2-one); (1R,2S)-5'-methoxy-2-(3-{[6-(1,4-oxazepan-4-yl)pyrimidin-4-yl]amino}-1H-indazol-6-yl)spiro[cyclopropane-1,3'-indol]-2'(1'H)-one; (1R,2S)-5'-methoxy-2-(3-{[5-methoxy-2-methyl-6-(morpholin-4-yl)pyrimidin-4-yl]amino}-1H-indazol-6-yl)spiro[cyclopropane-1,3'-indol]-2'(1'H)-one; (1R,2S)-2-(3-{[6-(azetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-(3-{[6-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-5'-methoxy-2-(3-{[5-methoxy-6-(1,4-oxazepan-4-yl)pyrimidin-4-yl]amino}-1H-indazol-6-yl)spiro[cyclopropane-1,3'-indol]-2'(1'H)-one; (1R,2S)-2-(3-{[6-(azetidin-1-yl)pyrimidin-4-yl]amino}-1H-indazol-6-yl)-5'-methoxyspiro[cyclopropane-1,3'-indol]-2'(1'H)-one; (1R,2S)-2-(3-{[5-chloro-6-(3-hydroxyazetidin-1-yl)pyrimidin-4-yl]amino}-1H-indazol-6-yl)-5'-methoxyspiro[cyclopropane-1,3'-indol]-2'(1'H)-one; (1R,2S)-2-(3-{[5-chloro-6-(3-methoxyazetidin-1-yl)pyrimidin-4-yl]amino}-1H-indazol-6-yl)-5'-methoxyspiro[cyclopropane-1,3'-indol]-2'(1'H)-one; (1R,2S)-2-(3-{[2-chloro-5-methoxy-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-{[4-chloro-5-methoxy-6-(morpholin-4-yl)pyrimidin-2-yl]amino}-1H-indazol-6-yl)-5'-methoxyspiro[cyclopropane-1,3'-indol]-2'(1'H)-one; (1R,2S)-2-(3-{[1-(2-hydroxyethyl)-3-methoxy-1H-pyrazol-4-yl]amino}-1H-indazol-6-yl)-5'-methoxyspiro[cyclopropane-1,3'-indol]-2'(1'H)-one; (1R,2S)-2-(3-{[2-cyclopropyl-5-methoxy-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-[3-({6-[(2R,6S)-2,6-dimethylmorpholin-4-yl]-5-methoxypyrimidin-4-yl}amino)-1H-indazol-6-yl]-5'-methoxyspiro[cyclopropane-1,3'-indol]-2'(1'H)-one; (1R,2S)-2-(3-((5-chloro-6-(1,1-dioxidothiomorpholino)pyrimidin-4-yl)amino)-1H-indazol-6-yl)-5'-methoxyspiro[cyclopropane-1,3'-indolin]-2'-one; (1R,2S)-2-(3-((6-(1,1-dioxidothiomorpholino)-5-methoxypyrimidin-4-yl)amino)-1H-indazol-6-yl)-5'-methoxyspiro[cyclopropane-1,3'-indolin]-2'-one; (1R,2S)-2-(3-{[5-(2-hydroxyethyl)-3-methoxypyrazin-2-yl]amino}-1H-indazol-6-yl)-5'-methoxyspiro[cyclopropane-1,3'-indol]-2'(1'H)-one; (1R,2S)-2-(3-{[6-(2-hydroxyethyl)-3-methoxypyrazin-2-yl]amino}-1H-indazol-6-yl)-5'-methoxyspiro[cyclopropane-1,3'-indol]-2'(1'H)-one; (1R,2S)-2-(3-((6-(1,1-dioxidothiomorpholino)-5-methoxy-2-methylpyrimidin-4-yl)amino)-1H-indazol-6-yl)-5'-methoxyspiro[cyclopropane-1,3'-indol]-2'-one; (1R,2S)-2-(3-((5-chloro-6-(1,1-dioxidothiomorpholino)-2-methylpyrimidin-4-yl)amino)-1H-indazol-6-yl)-5'-methoxyspiro[cyclopropane-1,3'-indolin]-2'-one; (1R,2S)-2-(34 (2-cyclopropyl-6-(1,1-dioxidothiomorpholino)pyrimidin-4-yl)amino)-1H-indazol-6-yl)-5'-methoxyspiro[cyclopropane-1,3'-indolin]-2'-one; (1R,2S)-2-(3-((6-(1,1-dioxidothiomorpholino)-2-methylpyrimidin-4-yl)amino)-1H-indazol-6-yl)-5'-methoxyspiro[cyclopropane-1,3'-indolin]-2'-one; 5-methoxy-4-({6-[(1R,2S)-5'-methoxy-2'-oxo-1',2'-dihydrospiro[cyclopropane-1,3'-indol]-2-yl]-1H-indazol-3-yl}amino)-6-(morpholin-4-yl)pyrimidine-2-carbonitrile; 4-(1,1-dioxidothiomorpholino)-5-methoxy-6-((6-((1R,2S)-5'-methoxy-2'-oxospiro[cyclopropane-1,3'-indolin]-2-yl)-1H-indazol-3-yl)amino)pyrimidine-2-carbonitrile; (1R,2S)-2-{3-[(1,3-dimethyl-1H-pyrazol-4-yl)amino]-1H-indazol-6-yl}-5'-methoxyspiro[cyclopropane-1,3'-indol]-2'(1'H)-one; (1R,2S)-5'-methoxy-2-(3-{[1-methyl-3-(trifluoromethyl)-1H-pyrazol-4-yl]amino}-1H-indazol-6-yl)spiro[cyclopropane-1,3'-indol]-2'(1'H)-one; (1R,2S)-5'-methoxy-2-{3-[(1-methyl-1H-pyrazol-4-yl)amino]-1H-indazol-6-yl}spiro[cyclopropane-1,3'-indol]-2'(1'H)-one; 4-({6-[(1R,2S)-5'-methoxy-2'-oxo-1',2'-dihydrospiro[cyclopropane-1,3'-indol]-2-yl]-1H-indazol-3-yl})amino)-1-methyl-1H-pyrazole-3-carbonitrile; (1R,2S)-2-[3-({6-[(2R,6S)-2,6-dimethylmorpholin-4-yl]-5-methoxy-2-methylpyrimidin-4-yl}amino)-1H-indazol-6-yl]-5'-methoxyspiro[cyclopropane-1,3'-indol]-2'(1'H)-one; (1R,2S)-2-(3-{[2-(2-hydroxyethyl)-5-methoxy-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-((2-cyclopropyl-6-(1,1-dioxidothiomorpholino)-5-methoxypyrimidin-4-yl)amino)-1H-indazol-6-yl)-5'-methoxyspiro[cyclopropane-1,3'-indolin]-2'-one; (1R,2S)-2-(3-((5-chloro-2-cyclopropyl-6-(1,1-dioxidothiomorpholino)pyrimidin-4-yl)amino)-1H-indazol-6-yl)-5'-methoxyspiro[cyclopropane-1,3'-indolin]-2'-one; (1R,2S)-5'-methoxy-2-{3-[(3-methoxy-6-methylpyrazin-2-yl)amino]-1H-indazol-6-yl}spiro[cyclopropane-1,3'-indol]-2'(1'H)-one; (1R,2S)-2-(3-{[5-chloro-6-(3-hydroxyazetidin-1-yl)-2-methylpyrimidin-4-yl]amino}-1H-indazol-6-yl)-5'-methoxyspiro[cyclopropane-1,3'-indol]-2'(1'H)-one; (1R,2S)-2-(3-{[6-(3-hydroxyazetidin-1-yl)-5-methoxy-2-methylpyrimidin-4-yl]amino}-1H-indazol-6-yl)-5'-methoxyspiro[cyclopropane-1,3'-indol]-2'(1'H)-one; (1R,2S)-2-{3-[(1,3-dimethyl-1H-pyrazol-5-yl)amino]-1H-indazol-6-yl}-5'-methoxyspiro[cyclopropane-1,3'-indol]-2'(1'H)-one; (1R,2S)-5'-methoxy-2-{3-[(4-methoxy-1-methyl-1H-pyrazol-5-yl)amino]-1H-indazol-6-yl}spiro[cyclopropane-1,3'-indol]-2'(1'H)-one; (1R,2S)-2-(3-{[5-chloro-2-cyclopropyl-6-(3-hydroxyazetidin-1-yl)pyrimidin-4-yl]amino}-1H-indazol-6-yl)-5'-methoxyspiro[cyclopropane-1,3'-indol]-2'(1'H)-one; (1R,2S)-2-[3-({2-cyclopropyl-6-[(2R,6S)-2,6-dimethylmorpholin-4-yl]-5-methoxypyrimidin-4-yl}amino)-1H-indazol-6-yl]-5'- methoxyspiro[cyclopropane-1,3'-indol]-2'(1'H)-one; (1R,2S)-2-(3-((5-chloro-6-(1,1-dioxidothiomorpholino)-2-isopropylpyrimidin-4-yl)amino)-1H-indazol-6-yl)-5'-methoxyspiro[cyclopropane-1,3'-indolin]-2'-one; (1R,2S)-5'-methoxy-2-{3-[(4-methoxy-1-methyl-1H-pyrazol-3-yl)amino]-1H-indazol-6-yl}spiro[cyclopropane-1,3'-indol]-2'(1'H)-one; (1R,2S)-2-{3-[(6-cyclopropyl-3-methoxypyrazin-2-yl)amino]-1H-indazol-6-yl}-5'-methoxyspiro[cyclopropane-1,3'-indol]-2'(1'H)-one; (1R,2S)-2-(3-{[2-cyclopropyl-6-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-{3-[(3,6-dimethylpyrazin-2-yl)amino]-1H-indazol-6-yl}-5'-methoxyspiro[cyclopropane-1,3'-indol]-2'(1'H)-one; (1R,2S)-5'-methoxy-2-(3-{[3-methoxy-6-(propan-2-yl)pyrazin-2-yl]amino}-1H-indazol-6-yl)spiro[cyclopropane-1,3'-indol]-2'(1'H)-one; (1R,2S)-2-(3-((6-(1,1-dioxidothiomorpholino)-2-isopropyl-5-methoxypyrimidin-4-yl)amino)-1H-indazol-6-yl)-5'-methoxyspiro[cyclopropane-1,3'-indolin]-2'-one; (1R,2S)-5'-methoxy-2-(3-{[5-methoxy-6-(morpholin-4-yl)-2-(propan-2-yl)pyrimidin-4-yl]amino}-1H-indazol-6-yl)spiro[cyclopropane-1,3'-indol]-2'(1'H)-one; (1R,2S)-5'-methoxy-2-{3-[(5-methoxy-2-methylpyridin-4-yl)amino]-1H-indazol-6-yl}spiro[cyclopropane-1,3'-indol]-2'(1'H)-one; (1R,2S)-5'-methoxy-2-{3-[(5-methoxy-2-methylpyrimidin-4-yl)amino]-1H-indazol-6-yl}spiro[cyclopropane-1,3'-indol]-2'(1'H)-one; (1R,2S)-5'-methoxy-2-{3-[(3-methoxy-6-methylpyridin-2-yl)amino]-1H-indazol-6-yl}spiro[cyclopropane-1,3'-indol]-2'(1'H)-one; (1R,2S)-5'-methoxy-2-{3-[(2-methoxy-5-methylpyridin-3-yl)amino]-1H-indazol-6-yl}spiro[cyclopropane-1,3'-indol]-2'(1'H)-one; (1R,2S)-5'-methoxy-2-{3-[(4-methoxypyridazin-3-yl)amino]-1H-indazol-6-yl}spiro[cyclopropane-1,3'-indol]-2'(1'H)-one; (1R,2S)-2-{3-[(3-cyclopropyl-1-methyl-1H-pyrazol-5-yl)amino]-1H-indazol-6-yl}-5'-methoxyspiro[cyclopropane-1,3'-indol]-2'(1'H)-one; (1R,2S)-2-{3-[(3-cyclopropyl-1-ethyl-1H-pyrazol-5-yl)amino]-1H-indazol-6-yl}-5'-methoxyspiro[cyclopropane-1,3'-indol]-2'(1'H)-one; (1R,2S)-2-(3-{[2-(2-hydroxy-2-methylpropyl)-5-methoxy-6-(morpholin-4-yl)pyrimidin-4-yl]amino}-1H-indazol-6-yl)-5'-methoxyspiro[cyclopropane-1,3'-indol]-2'($^1$H)-one; (1R,2S)-5'-methoxy-2-(3-{[3-methoxy-5-(morpholin-4-yl)pyrazin-2-yl]amino}-1H-indazol-6-yl)spiro[cyclopropane-1,3'-indol]-2'(1'H)-one; (0R,2S)-5'-methoxy-2-(3-{[3-methoxy-6-(morpholin-4-yl)pyridin-4-yl]amino}-1H-indazol-6-yl)spiro[cyclopropane-1,3'-indol]-2'(1'H)-one; (1R,2S)-2-{3-[(5-chloro-2-methylpyridin-4-yl)amino]-1H-indazol-6-yl}-5'-methoxyspiro[cyclopropane-1,3'-indol]-2'(1'H)-one; (1R,2S)-5'-methoxy-2-(3-{[5-methoxy-2-(morpholin-4-yl)pyrimidin-4-yl]amino}-1H-indazol-6-yl)spiro[cyclopropane-1,3'-indol]-2'(1'H)-one; (1R,2S)-2-{3-[(5-chloro-2-methylpyrimidin-4-yl)amino]-1H-indazol-6-yl}-5'-methoxyspiro[cyclopropane-1,3'-indol]-2'(1'H)-one; (1R,2S)-5'-methoxy-2-(3-{[3-methoxy-6-(morpholin-4-yl)pyrazin-2-yl]amino}-1H-indazol-6-yl)spiro[cyclopropane-1,3'-indol]-2'(1'H)-one; (0R,2S)-5'-methoxy-2-(3-{[3-methoxy-6-(oxetan-3-yl)pyrazin-2-yl]amino}-1H-indazol-6-yl)spiro[cyclopropane-1,3'-indol]-2'(1'H)-one; (1R,2S)-5'-methoxy-2-(3-{[3-methoxy-6-(propan-2-yl)pyridazin-4-yl]amino}-1H-indazol-6-yl)spiro[cyclopropane-1,3'-indol]-2'(1'H)-one; (1R,2S)-5'-methoxy-2-(3-{[6-(morpholin-4-yl)-2-(propan-2-yl)pyrimidin-4-yl]amino}-1H-indazol-6-yl)spiro[cyclopropane-1,3'-indol]-2'(1'H)-one; (1R,2S)-2-(3-{[5-chloro-2-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-{[5-(3-hydroxyazetidin-1-yl)-3-methoxypyridin-2-yl]amino}-1H-indazol-6-yl)-5'-methoxyspiro[cyclopropane-1,3'-indol]-2'(1'H)-one; (1R,2S)-5'-methoxy-2-(3-{[3-methyl-6-(propan-2-yl)pyrazin-2-yl]amino}-1H-indazol-6-yl)spiro[cyclopropane-1,3'-indol]-2'($^1$H)-one; (1R,2S)-5'-methoxy-2-(3-{[6-(propan-2-yl)pyrazin-2-yl]amino}-1H-indazol-6-yl)spiro[cyclopropane-1,3'-indol]-2'(1'H)-one; (1R,2S)-2-(3-{[5-chloro-6-(3-hydroxyazetidin-1-yl)pyrimidin-4-yl]amino}-1H-indazol-6-yl)-5'-methoxy-1'-methylspiro[cyclopropane-1,3'-indol]-2'(1'H)-one; (1R,2S)-2-(3-{[5-chloro-6-(3-hydroxyazetidin-1-yl)pyrimidin-4-yl]amino}-1H-indazol-6-yl)-1'-ethyl-5'-methoxyspiro[cyclopropane-1,3'-indol]-2'(1'H)-one; (1R,2S)-2-(3-{[5-(difluoromethoxy)-6-(morpholin-4-yl)pyrimidin-4-yl]amino}-1H-indazol-6-yl)-5'-methoxyspiro[cyclopropane-1,3'-indol]-2'(1'H)-one; (1R,2S)-2-(3-{[6-(azetidin-3-yl)-3-methoxypyrazin-2-yl]amino}-1H-indazol-6-yl)-5'-methoxyspiro[cyclopropane-1,3'-indol]-2'(1'H)-one; (1R,2S)-2-(3-{[6-(3-hydroxyazetidin-1-yl)-2-(propan-2-yl)pyrimidin-4-yl]amino}-1H-indazol-6-yl)-5'-methoxyspiro[cyclopropane-1,3'-indol]-2'(1'H)-one, (1R,2S)-2-(3-{[1-(2,2-difluoroethyl)-3-methyl-1H-pyrazol-5-yl]amino}-1H-indazol-6-yl)-5'-methoxyspiro[cyclopropane-1,3'-indol]-2'(1'H)-one; (1R,2S)-5'-methoxy-2-(3-{[5-methoxy-6-(morpholin-4-yl)pyrimidin-4-yl]amino}-1H-indazol-6-yl)-1'-methylspiro[cyclopropane-1,3'-indol]-2'(1'H)-one; (1R,2S)-2-(3-{[2-(3-hydroxyazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-5'-methoxy-2-(3-{[6-(oxetan-3-yl)pyrazin-2-yl]amino}-1H-indazol-6-yl)spiro[cyclopropane-1,3'-indol]-2'(1'H)-one; (1R,2S)-2-(3-{[5-chloro-2-(propan-2-yl)pyrimidin-4-yl]amino}-1H-indazol-6-yl)-5'-methoxyspiro[cyclopropane-1,3'-indol]-2'(1'H)-one; (1R,2S)-2-(3-{[5-chloro-2-(oxetan-3-yl)pyrimidin-4-yl]amino}-1H-indazol-6-yl)-5'-methoxyspiro[cyclopropane-1,3'-indol]-2'(1'H)-one; (1R,2S)-5'-methoxy-2-(3-{[5-methoxy-2-(oxetan-3-yl)pyrimidin-4-yl]amino}-1H-indazol-6-yl)spiro[cyclopropane-1,3'-indol]-2'(1'H)-one; (1R,2S)-2-(3-{[5-chloro-2-(3-hydroxyazetidin-1-yl)pyrimidin-4-yl]amino}-1H-indazol-6-yl)-5'-methoxyspiro[cyclopropane-1,3'-indol]-2'(1'H)-one; (1R,2S)-2-(3-{[5-(difluoromethoxy)-2-methylpyrimidin-4-yl]amino}-1H-indazol-6-yl)-5'-methoxyspiro[cyclopropane-1,3'-indol]-2'(1'H)-one; (1R,2S)-2-{3-[(5-methoxy-2-methylpyrimidin-4-yl)amino]-1H-indazol-6-yl}-1'-methylspiro[cyclopropane-1,3'-indol]-2'(1'H)-one; (1R,2R)-2-{7-fluoro-3-[(5-methoxy-2-methylpyrimidin-4-yl)amino]-1H-indazol-6-yl}-5'-methoxyspiro[cyclopropane-1,3'-indol]-2'(1'H)-one; (1R,2S)-2-{3-[(5-methoxy-2-methylpyrimidin-4-yl)amino]-1H-indazol-6-yl}spiro[cyclopropane-1,3'-indol]-2'(1'H)-one; (1R,2S)-5'-methoxy-2-(3-{[5-methoxy-2-(propan-2-yl)pyrimidin-4-yl]amino}-1H-indazol-6-yl)spiro[cyclopropane-1,3'-indol]-2'(1'H)-one; (1R,2S)-2-{3-[(5-methoxy-2-methylpyrimidin-4-yl)amino]-1H-indazol-6-yl}-5'-methylspiro[cyclopropane-1,3'-indol]-2'(1'H)-one; (1S,2S)-2-{3-[(5-methoxy-2-methylpyrimidin-4-yl)amino]-1H-indazol-6-yl}-5'-methylspiro[cyclopropane-1,3'-indol]-2'(1'H)-one; (1R,2S)-2-(3-{[5-(difluoromethoxy)-2-(propan-2-yl)pyrimidin-4-yl]amino}-1H-indazol-6-yl)-5'-methoxyspiro[cyclopropane-1,3'-indol]-2'(1'H)-one; (1R,2S)-4'-fluoro-2-{3-[(5-methoxy-2-methylpyrimidin-4-yl)amino]-1H-indazol-6-yl}spiro[cyclopropane-1,3'-indol]-2'(1'H)-one; (1S,2S)-4'-fluoro-2-{3-[(5-methoxy-2-methylpyrimidin-4-yl)amino]-1H-indazol-6-yl}spiro[cyclopropane-1,3'-indol]-2'($^1$H)-one; (1R,2S)-6'-fluoro-2-{3-[(5-methoxy-2-methylpyrimidin-4-yl)amino]-1H-indazol-6-yl}spiro[cyclopropane-1,3'-indol]-2'(1'H)-one; (1R,2S)-2-(3-{[5-chloro-6-(2-oxa-6-azaspiro

[3.3]heptan-6-yl)pyrimidin-4-yl]amino}-1H-indazol-6-yl)-5'-methoxyspiro[cyclopropane-1,3'-indol]-2'(1'H)-one; (1R,2S)-5'-fluoro-2-{3-[(5-methoxy-2-methylpyrimidin-4-yl)amino]-1H-indazol-6-yl}spiro[cyclopropane-1,3'-indol]-2'(1'H)-one; (1R,2S)-2-{3-[(5-ethoxy-2-methylpyrimidin-4-yl)amino]-1H-indazol-6-yl}-5'-methoxyspiro[cyclopropane-1,3'-indol]-2'($^1$H)-one; (1R,2S)-2-(3-{[5-(difluoromethoxy)-2-methylpyrimidin-4-yl]amino}-1H-indazol-6-yl)-5'-fluorospiro[cyclopropane-1,3'-indol]-2'(1'H)-one; (1R,2S)-5'-methoxy-2-[3-({2-methyl-5-[(propan-2-yl)oxy]pyrimidin-4-yl}amino)-1H-indazol-6-yl]spiro[cyclopropane-1,3'-indol]-2'(1'H)-one; (1R,2S)-2-{3-[(5-methoxy-2-methylpyrimidin-4-yl)amino]-1H-indazol-6-yl}-5'-(trifluoromethyl)spiro[cyclopropane-1,3'-indol]-2'(1'H)-one; (1R,2S)-2-{3-[(5-methoxy-2-methylpyrimidin-4-yl)amino]-1H-indazol-6-yl}-5'-(trifluoromethoxy)spiro[cyclopropane-1,3'-indol]-2'(1'H)-one; (1S,2S)-2-{3-[(5-methoxy-2-methylpyrimidin-4-yl)amino]-1H-indazol-6-yl}-5'-(trifluoromethoxy)spiro[cyclopropane-1,3'-indol]-2'(1'H)-one; (1R,2S)-2-{3-[(5-cyclopropyl-2-methylpyrimidin-4-yl)amino]-1H-indazol-6-yl}-5'-methoxyspiro[cyclopropane-1,3'-indol]-2'(1'H)-one; and (1R,2S)-2-(3-{[5-(difluoromethoxy)-2-(oxetan-3-yl)pyrimidin-4-yl]amino}-1H-indazol-6-yl)-5'-methoxyspiro[cyclopropane-1,3'-indol]-2'(1'H)-one; (1R,2R)-5'-fluoro-2-{7-fluoro-3-[(5-methoxy-2-methylpyrimidin-4-yl)amino]-1H-indazol-6-yl}spiro[cyclopropane-1,3'-indol]-2'(1'H)-one; and (1R,2R)-2-(3-{[5-(difluoromethoxy)-2-methylpyrimidin-4-yl]amino}-7-fluoro-1H-indazol-6-yl)-5'-fluorospiro[cyclopropane-1,3'-indol]-2'(1'H)-one or a pharmaceutically acceptable salt, solvate, or stereoisomer thereof.

Embodiment 232: A compound selected from (1R,2R)-2-{5-fluoro-3-[(5-methoxy-2-methylpyrimidin-4-yl)amino]-1H-indazol-6-yl}-5'-methoxyspiro[cyclopropane-1,3'-indol]-2'(1'H)-one; (1R,2S)-5'-methoxy-2-{3-[(3-methoxy-6-methylpyridazin-4-yl)amino]-1H-indazol-6-yl}spiro[cyclopropane-1,3'-indol]-2'(1'H)-one; (1R,2S)-2-(3-{[5-(cyclopropylmethoxy)-2-methylpyrimidin-4-yl]amino}-1H-indazol-6-yl)-5'-methoxyspiro[cyclopropane-1,3'-indol]-2'(1'H)-one; (1R,2S)-2-(3-{[5-(2,2-difluoroethoxy)-2-methylpyrimidin-4-yl]amino}-1H-indazol-6-yl)-5'-methoxyspiro[cyclopropane-1,3'-indol]-2'(1'H)-one; (1R,2S)-5'-methoxy-2-[3-(2-methoxy-5-methylanilino)-1H-indazol-6-yl]spiro[cyclopropane-1,3'-indol]-2'(1'H)-one; (1R,2S)-5'-methoxy-2-(3-{[2-methyl-5-(2,2,2-trifluoroethoxy)pyrimidin-4-yl]amino}-1H-indazol-6-yl)spiro[cyclopropane-1,3'-indol]-2'(1'H)-one; (1R,2S)-5'-methoxy-2-{3-[(2-methoxy-6-methylpyridin-3-yl)amino]-1H-indazol-6-yl}spiro[cyclopropane-1,3'-indol]-2'(1'H)-one; (1R,2S)-5'-methoxy-2-(3-{[2-methyl-6-(propan-2-yl)pyrimidin-4-yl]amino}-1H-indazol-6-yl)spiro[cyclopropane-1,3'-indol]-2'(1'H)-one; (1R,2S)-2-{3-[(5-ethyl-2-methylpyrimidin-4-yl)amino]-1H-indazol-6-yl}-5'-methoxyspiro[cyclopropane-1,3'-indol]-2'($^1$H)-one; (1R,2S)-5'-methoxy-2-{3-[(2-methyl-6,7-dihydrofuro[3,2-d]pyrimidin-4-yl)amino]-1H-indazol-6-yl}spiro[cyclopropane-1,3'-indol]-2'(1'H)-one; (1R,2S)-5'-methoxy-2-(3-{[5-methoxy-2-(oxan-4-yl)pyrimidin-4-yl]amino}-1H-indazol-6-yl)spiro[cyclopropane-1,3'-indol]-2'(1'H)-one; (1R,2S)-5'-methoxy-2-(3-{[5-methoxy-2-(methylsulfanyl)pyrimidin-4-yl]amino}-1H-indazol-6-yl)spiro[cyclopropane-1,3'-indol]-2'(1'H)-one; (1R,2S)-2-{3-[(2,5-dimethoxypyrimidin-4-yl)amino]-1H-indazol-6-yl}-5'-methoxyspiro[cyclopropane-1,3'-indol]-2'(1'H)-one; (1R,2S)-2-(3-{[2-(azetidin-1-yl)-5-methoxypyrimidin-4-yl]amino}-1H-indazol-6-yl)-5'-methoxyspiro[cyclopropane-1,3'-indol]-2'($^1$H)-one; (1R,2S)-5'-methoxy-2-(3-{[3-methoxy-5-(trifluoromethyl)pyridin-2-yl]amino}-1H-indazol-6-yl)spiro[cyclopropane-1,3'-indol]-2'(1'H)-one; (1R,2S)-5'-methoxy-2-{3-[(2-methyl-6,7-dihydro-5H-cyclopenta[d]pyrimidin-4-yl)amino]-1H-indazol-6-yl}spiro[cyclopropane-1,3'-indol]-2'(1'H)-one; (1R,2S)-2-{3-[(2-ethyl-5-methoxypyrimidin-4-yl)amino]-1H-indazol-6-yl}-5'-methoxyspiro[cyclopropane-1,3'-indol]-2'(1'H)-one; (1R,2S)-5'-methoxy-2-{3-[(7-methoxyquinolin-6-yl)amino]-1H-indazol-6-yl}spiro[cyclopropane-1,3'-indol]-2'(1'H)-one; (1R,2S)-5'-methoxy-2-(3-{[2-methyl-54methylsulfanyl)pyrimidin-4-yl]amino}-1H-indazol-6-yl)spiro[cyclopropane-1,3'-indol]-2'(1'H)-one; (1R,2S)-5'-methoxy-2-{3-[(3-methoxyquinolin-2-yl)amino]-1H-indazol-6-yl}spiro[cyclopropane-1,3'-indol]-2'(1'H)-one; (1R,2S)-2-{3-[(2,5-dimethoxypyridin-3-yl)amino]-1H-indazol-6-yl}-5'-methoxyspiro[cyclopropane-1,3'-indol]-2'(1'H)-one; (1R,2S)-2-{3-[(2-chlorofuro[3,2-d]pyrimidin-4-yl)amino]-1H-indazol-6-yl}-5'-methoxyspiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-5'-methoxy-2-(3-{[5-methoxy-2-(pyrrolidin-1-yl)pyrimidin-4-yl]amino}-1H-indazol-6-yl)spiro[cyclopropane-1,3'-indol]-2'(1'H)-one; (1R,2S)-2-(3-{[6-(methanesulfonyl)-2-methoxypyridin-3-yl]amino}-1H-indazol-6-yl)-5'-methoxyspiro[cyclopropane-1,3'-indol]-2'($^1$H)-one; (1R,2S)-2-[3-({2-[(3R)-3-fluoropyrrolidin-1-yl]-5-methoxypyrimidin-4-yl}amino)-1H-indazol-6-yl]-5'-methoxyspiro[cyclopropane-1,3'-indol]-2'(1'H)-one; (1R,2S)-2-(3-{[2-(3,3-difluoropyrrolidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-{3-[(2-chloro-5-methyl-5H-pyrrolo[3,2-d]pyrimidin-4-yl)amino]-1H-indazol-6-yl}-5'-methoxyspiro[cyclopropane-1,3'-indol]-2'(1'H)-one; 5-methoxy-4-({6-[(1R,2S)-5'-methoxy-2'-oxo-1',2'-dihydrospiro[cyclopropane-1,3'-indol]-2-yl]-1H-indazol-3-yl}amino)pyrimidine-2-carbonitrile; (1R,2S)-2-(3-{[2-(3,3-difluoroazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-(3-{[2-(3-fluoroazetidin-1-yl)-5-methoxypyrimidin-4-yl]amino}-1H-indazol-6-yl)-5'-methoxyspiro[cyclopropane-1,3'-indol]-2'(1'H)-one; (1R,2S)-2-{3-[(2-(ethanesulfonyl)-2-methoxyanilino]-1H-indazol-6-yl}-5'-methoxyspiro[cyclopropane-1,3'-indol]-2'(1'H)-one; 4-methoxy-3-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzamide; 4-methoxy-3-({6-[(1R,2S)-5'-methoxy-2'-oxo-1',2'-dihydrospiro[cyclopropane-1,3'-indol]-2-yl]-1H-indazol-3-yl}amino)-N-methylbenzamide; (1R,2S)-5'-methoxy-2-{3-[2-methoxy-5-(propane-2-sulfonyl)anilino]-1H-indazol-6-yl}spiro[cyclopropane-1,3'-indol]-2'(1'H)-one; 4-methoxy-3-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzene-1-sulfonamide; (1R,2S)-5'-methoxy-2-{3-[2-methoxy-5-(morpholine-4-carbonyl)anilino]-1H-indazol-6-yl}spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide; (1R,2S)-2-(3-{[2-(dimethylamino)-5-methylpyrimidin-4-yl]amino}-1H-indazol-6-yl)-5'-methoxyspiro[cyclopropane-1,3'-indol]-2'($^1$H)-one; (1R,2S)-5'-methoxy-2-(3-{[2-methoxy-6-(morpholine-4-carbonyl)pyridin-3-yl]amino}-1H-indazol-6-yl)spiro[cyclopropane-1,3'-indol]-2'(1'H)-one; (1R,2S)-2-(3-{[6-(3,3-difluoroazetidine-1-carbonyl)-2- methoxypyridin-3-yl]amino}-1H-indazol-6-yl)-5'-methoxyspiro[cyclopropane-1,3'-indol]-2'(1'H)-one; (1R,2S)-2-(3-{[6-(4,4-difluoropiperidine-1-carbonyl)-2-methoxypyridin-3-yl]amino}-1H-indazol-6-yl)-5'-methoxyspiro[cyclopropane-1,3'-indol]-2'(1'H)-one; (1R,2S)-2-(4-fluoro-3-{[5-methoxy-2-(methylsulfanyl)pyrimidin-4-yl]amino}-1H-indazol-6-yl)-5'-methoxyspiro[cyclopropane-1,3'-indol]-2'(1'H)-one; (1R,2S)-5'-methoxy-2-{3-[(2-methoxy-5-methylpyrimidin-4-yl)amino]-1H-indazol-6-yl}spiro[cyclopropane-1,3'-indol]-2'(1'H)-one; (1R,2S)-5'-methoxy-2-(3-{[2-methoxy-6-(2-oxa-6-azaspiro[3.3]heptane-6-carbonyl)pyridin-3-yl]amino}-1H-indazol-6-yl)spiro[cyclopropane-1,3'-indol]-2'(1'H)-one; (1R,2S)-2-(3-{[2-(4,4-difluoropiperidin-1-yl)-5-methoxypyrimidin-4-yl]amino}-1H-indazol-6-yl)-5'-methoxyspiro[cyclopropane-1,3'-indol]-2'(1'H)-one; 4-[5-methoxy-4-({6-[(1R,2S)-5'-methoxy-2'-oxo-1',2'-dihydrospiro[cyclopropane-1,3'-indol]-2-yl]-1H-indazol-3-yl}amino)pyrimidin-2-yl]-1λ6-thiomorpholine-1,1-dione; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methylpyridine-2-carboxamide; (1R,2S)-5'-methoxy-2-(3-{[5-methoxy-2-(2-oxa-6-azaspiro[3.3]heptan-6-yl)pyrimidin-4-yl]amino}-1H-indazol-6-yl)spiro[cyclopropane-1,3'-indol]-2'(1'H)-one; (1R,2S)-2-(3-{[5-(methanesulfonyl)-3-methoxypyridin-2-yl]amino}-1H-indazol-6-yl)-5'-methoxyspiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-methyl-N-(propan-2-yl)pyridine-2-carboxamide; (1R,2S)-2-(3-{[5-ethoxy-2-(methylsulfanyl)pyrimidin-4-yl]amino}-1H-indazol-6-yl)-5'-methoxyspiro[cyclopropane-1,3'-indol]-2'(1'H)-one; (R,2S)-2-(3-{[6-(methanesulfonyl)-3-methoxypyridin-2-yl]amino}-1H-indazol-6-yl)-5'-methoxyspiro[cyclopropane-1,3'-indol]-2'(1'H)-one; 5-methoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide; 5-methoxy-4-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-5'-methoxy-2-{3-[2-methoxy-4-(morpholine-4-carbonyl)anilino]-1H-indazol-6-yl}spiro[cyclopropane-1,3'-indol]-2'(1'H)-one; Diastereomer 1: (1R,2S)-5'-methoxy-2-(3-{[5-methoxy-2-(oxolan-3-yl)pyrimidin-4-yl]amino}-1H-indazol-6-yl)spiro[cyclopropane-1,3'-indol]-2'(1'H)-one; Diastereomer 2: (1R,2S)-5'-methoxy-2-(3-{[5-methoxy-2-(oxolan-3-yl)pyrimidin-4-yl]amino}-1H-indazol-6-yl)spiro[cyclopropane-1,3'-indol]-2'(1'H)-one; (1R,2S)-2-(3-{[2-ethoxy-6-(methanesulfonyl)pyridin-3-yl]amino}-1H-indazol-6-yl)-5'-methoxyspiro[cyclopropane-1,3'-indol]-2'(1'H)-one; 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-carboxamide; 5-methoxy-6-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-3-sulfonamide; (1R,2S)-2-(3-{[6-(dimethylphosphoryl)-2-methoxypyridin-3-yl]amino}-1H-indazol-6-yl)-5'-methoxyspiro[cyclopropane-1,3'-indol]-2'(1'H)-one; 2-fluoro-5-methoxy-4-({6-[(1R,2S)-5'-methoxy-2'-oxo-1',2'-dihydrospiro[cyclopropane-1,3'-indol]-2-yl]-1H-indazol-3-yl}amino)-N,N-dimethylbenzamide; (1R,2S)-2-(3-[5-fluoro-2-methoxy-4-(morpholine-4-carbonyl)anilino]-1H-indazol-6-yl)-5'-methoxyspiro[cyclopropane-1,3'-indol]-2'(1'H)-one; and (1R,2S)-2-(3-{[3-ethoxy-5-(methanesulfonyl)pyridin-2-yl]amino}-1H-indazol-6-yl)-5'-methoxyspiro[cyclopropane-1,3'-indol]-2'(1'H)-one, or a pharmaceutically acceptable salt thereof.

Embodiment 233: A compound selected from (1R,2S)-2-(3-{[6-(ethanesulfonyl)-2-methoxypyridin-3-yl]amino}-1H-indazol-6-yl)-5'-methoxyspiro[cyclopropane-1,3'-indol]-2'(1'H)-one; 5-methoxy-4-({6-[(1R,2S)-5'-methoxy-2'-oxo-1',2'-dihydrospiro[cyclopropane-1,3'-indol]-2-yl]-1H-indazol-3-yl}amino)-N,2-dimethylbenzene-1-sulfonamide; (1R,2S)-2-{3-[(2,5-dimethyl-5,7-dihydrothieno[3,4-d]pyrimidin-4-yl)amino]-1H-indazol-6-yl}-5'-methoxyspiro[cyclopropane-1,3'-indol]-2'(1'H)-one; 2,5-dimethoxy-4-({6-[(1R,2S)-5'-methoxy-2'-oxo-1',2'-dihydrospiro[cyclopropane-1,3'-indol]-2-yl]-1H-indazol-3-yl}amino)benzene-1-sulfonamide; (1R,2S)-2-(3-{[2-(dimethylamino)-6,7-dihydro-5H-cyclopenta[d]pyrimidin-4-yl]amino}-1H-indazol-6-yl)-5'-methoxyspiro[cyclopropane-1,3'-indol]-2'($^1$H)-one; 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-5'-methoxy-2-(3-{[2-methoxy-6-(2-oxopyrrolidin-1-yl)pyridin-3-yl]amino}-1H-indazol-6-yl)spiro[cyclopropane-1,3'-indol]-2'(1'H)-one; (1R,2S)-5'-methoxy-2-(3-[2-methoxy-5-(morpholine-4-sulfonyl)anilino]-1H-indazol-6-yl)spiro[cyclopropane-1,3'-indol]-2'(1'H)-one; (1R,2S)-5'-methoxy-2-{3-[(3-methoxy-1,5-naphthyridin-2-yl)amino]-1H-indazol-6-yl}spiro[cyclopropane-1,3'-indol]-2'(1'H)-one; N,6-dimethoxy-5-({6-[(1R,2S)-5'-methoxy-2'-oxo-1',2'-dihydrospiro[cyclopropane-1,3'-indol]-2-yl]-1H-indazol-3-yl}amino)-N-methylpyridine-2-carboxamide; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N'-(propan-2-yl)pyridine-2-carbohydrazide; (1R,2S)-5'-methoxy-2-(3-{[2-methoxy-5-(2-oxopyrrolidin-1-yl)pyridin-3-yl]amino}-1H-indazol-6-yl)spiro[cyclopropane-1,3'-indol]-2'(1'H)-one; (1R,2S)-5'-methoxy-2-(3-{[2-methoxy-5-(3-methyl-2-oxoimidazolidin-1-yl)pyridin-3-yl]amino}-1H-indazol-6-yl)spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-sulfonamide; 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-sulfonamide; (1R,2S)-5'-methoxy-2-{3-[2-methoxy-5-(oxane-4-sulfonyl)anilino]-1H-indazol-6-yl}spiro[cyclopropane-1,3'-indol]-2'(1'H)-one; (1R,2S)-2-(3-{[5-(dimethylphosphoryl)-3-methoxypyridin-2-yl]amino}-1H-indazol-6-yl)-5'-methoxyspiro[cyclopropane-1,3'-indol]-2'(1'H)-one; (1R,2S)-2-(3-{[5-(2-hydroxypropan-2-yl)-2-methoxypyridin-3-yl]amino}-1H-indazol-6-yl)-5'-methoxyspiro[cyclopropane-1,3'-indol]-2'(1'H)-one; (1R,2S)-2-(3-{[6-(methanesulfonyl)-2-methoxy-5-methylpyridin-3-yl]amino}-1H-indazol-6-yl)-5'-methoxyspiro[cyclopropane-1,3'-indol]-2'(1'H)-one; (1R,2S)-2-(3-{[5-(ethanesulfonyl)-3-methoxypyridin-2-yl]amino}-1H-indazol-6-yl)-5'-methoxyspiro[cyclopropane-1,3'-indol]-2'(1'H)-one; (1R,2S)-2-(3-{[5-(dimethylphosphoryl)-3-methoxypyrazin-2-yl]amino}-1H-indazol-6-yl)-5'-methoxyspiro[cyclopropane-1,3'-indol]-2'(1'H)-one; N-(cyclopropylmethyl)-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N-(propan-2-yl)pyridine-2-carboxamide; (1R, 2S)-5'-methoxy-2-(3-{[2-methoxy-6-(3-oxa-8-azabicyclo[3.2.1]octane-8-carbonyl)pyridin-3-yl]amino}-1H-indazol-6-yl)spiro[cyclopropane-1,3'-indol]-2'(1'H)-one; (1R,2S)-5'-methoxy-2-{3-[(4-methoxy-1-methyl-6-oxo-1,6-dihydropyridazin-3-yl)amino]-1H-indazol-6-yl}spiro[cyclopropane-1,3'-indol]-2'(1'H)-one; (1R,2S)-5'-methoxy-2-(3-{[2-methoxy-5-(1,3-oxazol-2-yl)pyridin-3-yl]amino}-1H-indazol-6-yl)spiro[cyclopropane-1,3'-indol]-2'($^1$H)-one; (1R,2S)-5'-methoxy-2-(3-{[3-methoxy-5-(3-methoxyazetidine-1-carbonyl)pyridin-2-yl]amino}-1H-indazol-6-yl)spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyrazine-2-carboxamide; 6-ethoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyrazine-2-carboxamide; 6-methoxy-5-({6-[(1R,2S)-5'-methoxy-2'-oxo-1',2'-dihydrospiro[cyclopropane-1,3'-indol]-2-yl]-1H-indazol-3-yl}amino)-N,N,3-trimethylpyridine-2-carboxamide; (1R,2S)-2-(3-{[6-(methanesulfinyl)-2-methoxypyridin-3-yl]amino}-1H-indazol-6-yl)-5'-methoxyspiro[cyclopropane-1,3'-indol]-2'(1'H)-one; (1R,2S)-2-(3-{[6-(methanesulfinyl)-2-methoxypyridin-3-yl]amino}-1H-indazol-6-yl)-5'-methoxyspiro[cyclopropane-1,3'-indol]-2'($^1$H)-one; (1R,2S)-2-(3-{[6-(methanesulfonyl)-4-methoxypyridin-3-yl]amino}-1H-indazol-6-yl)-5'-methoxyspiro[cyclopropane-1,3'-indol]-2'(1'H)-one; (1R,2S)-2-(3-{[5-(methanesulfonyl)-3-methoxypyrazin-2-yl]amino}-1H-indazol-6-yl)-5'-methoxyspiro[cyclopropane-1,3'-indol]-2'(1'H)-one; N,N-dicyclopropyl-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide; N-(2,2-difluoroethyl)-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide; (1R,2S)-2-[3-({6-[(2R,6S)-2,6-dimethylpiperidine-1-carbonyl]-2-methoxypyridin-3-yl}amino)-1H-indazol-6-yl]-5'-methoxyspiro[cyclopropane-1,3'-indol]-2'($^1$H)-one; (1R,2S)-5'-methoxy-2-(3-{[2-methoxy-6-(8-oxa-3-azabicyclo[3.2.1]octane-3-carbonyl)pyridin-3-yl]amino}-1H-indazol-6-yl)spiro[cyclopropane-1,3'-indol]-2'(1'H)-one; (1R,2S)-2-(3-{[3-chloro-5-(methanesulfonyl)pyridin-2-yl]amino}-1H-indazol-6-yl)-5'-methoxyspiro[cyclopropane-1,3'-indol]-2'(1'H)-one; (1R,2S)-5'-methoxy-2-(3-{[3-methoxy-5-(propane-2-sulfonyl)pyridin-2-yl]amino}-1H-indazol-6-yl)spiro[cyclopropane-1,3'-indol]-2'(1'H)-one; (1R,2S)-2-(3-{[6-(dimethylphosphoryl)-4-methoxypyridin-3-yl]amino}-1H-indazol-6-yl)-5'-methoxyspiro[cyclopropane-1,3'-indol]-2'(1'H)-one; N-(1,3-difluoropropan-2-yl)-6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carboxamide; 6-chloro-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; (1R,2S)-2-{3-[(5-chloro-2-methyl-1,3-benzoxazol-6-yl)amino]-1H-indazol-6-yl}-5'-methoxyspiro[cyclopropane-1,3'-indol]-2'(1'H)-one; 4-methoxy-5-({6-[(1R,2S)-5'-methoxy-2'-oxo-1',2'-dihydrospiro[cyclopropane-1,3'-indol]-2-yl]-1H-indazol-3-yl}amino)-N,N-dimethylpyridine-2-carboxamide; 3-[6-methoxy-5-({6-[(1R,2S)-5'-methoxy-2'-oxo-1',2'-dihydrospiro[cyclopropane-1,3'-indol]-2-yl]-1H-indazol-3-yl}amino)pyrazin-2-yl]-1λ6-thietane-1,1-dione; (1R,2S)-5'-methoxy-2-(3-{[3-methoxy-5-(morpholine-4-sulfonyl)pyridin-2-yl]amino}-1H-indazol-6-yl)spiro[cyclopropane-1,3'-indol]-2'(1'H)-one; (1R,2S)-5'-methoxy-2-(3-{[3-methoxy-5-(8-oxa-3-azabicyclo[3.2.1]octane-3-sulfonyl)pyridin-2-yl]amino}-1H-indazol-6-yl)spiro[cyclopropane-1,3'-indol]-2'(1'H)-one; (1R,2S)-2-(3-{[6-(diethylphosphoryl)-2-methoxypyridin-3-yl]amino}-1H-indazol-6-yl)-5'-methoxyspiro[cyclopropane-1,3'-indol]-2'($^1$H)-one; (1R,2S)-2-(3-{[5-(cyclopropanesulfonyl)-3-methoxypyridin-2-yl]amino}-1H-indazol-6-yl)-5'-methoxyspiro[cyclopropane-1,3'-indol]-2'($^1$H)-one; (1R,2S)-5'-methoxy-2-(3-{[3-methoxy-5-(oxane-4-sulfonyl)pyridin-2-yl]amino}-1H-indazol-6-yl)spiro[cyclopropane-1,3'-indol]-2'(1'H)-one; 6-methoxy-5-({6-[(1R,2S)-5'-methoxy-2'-oxo-1',2'-dihydrospiro[cyclopropane-1,3'-indol]-2-yl]-1H-indazol-3-yl}amino)pyridine-2-carbonitrile; (1R,2S)-2-{3-[5-(diethylphosphoryl)-2-methoxyanilino]-1H-indazol-6-yl}-5'-methoxyspiro[cyclopropane-1,3'-indol]-2'(1'H)-one; (1R,2S)-2-(3-{[6-(ethanesulfonyl)-4-methoxypyridin-3-yl]amino}-1H-indazol-6-yl)-5'-methoxyspiro[cyclopropane-1,3'-indol]-2'(1'H)-one; (1R,2S)-2-(3-{[5-(azetidine-1-carbonyl)-3-methoxypyridin-2-yl]amino}-1H-indazol-6-yl)-5'-methoxyspiro[cyclopropane-1,3'-indol]-2'(1'H)-one; (1R,2S)-5'-methoxy-2-(3-{[3-methoxy-5-(morpholine-4-carbonyl)pyridin-2-yl]amino}-1H-indazol-6-yl)spiro[cyclopropane-1,3'-indol]-2'(1'H)-one; (1R,2S)-5'-methoxy-2-{3-[(6-methoxy-2-methyl-1-oxo-2,3-dihydro-1H-isoindol-5-yl)amino]-1H-indazol-6-yl}spiro[cyclopropane-1,3'-indol]-2'(1'H)-one; (1R,2S)-5'-methoxy-2-{3-[(4-methoxy-2-methyl-1-oxo-2,3-dihydro-1H-isoindol-5-yl)amino]-1H-indazol-6-yl}spiro[cyclopropane-1,3'-indol]-2'(1'H)-one; (1R,2S)-5'-methoxy-2-(3-{[3-methoxy-5-(1,2-oxazolidine-2-sulfonyl)pyridin-2-yl]amino}-1H-indazol-6-yl)spiro[cyclopropane-1,3'-indol]-2'(1'H)-one; (1R,2S)-2-(3-{[5-(azetidine-1-sulfonyl)-3-methoxypyridin-2-yl]amino}-1H-indazol-6-yl)-5'-methoxyspiro[cyclopropane-1,3'-indol]-2'(1'H)-one; 5-methoxy-6-({6-[(1R,2S)-5'-methoxy-2'-oxo-1',2'-dihydrospiro[cyclopropane-1,3'-indol]-2-yl]-1H-indazol-3-yl}amino)-N-(3-methyloxetan-3-yl)pyridine-3-sulfonamide; 5-methoxy-6-({6-[(1R,2S)-5'-methoxy-2'-oxo-1',2'-dihydrospiro[cyclopropane-1,3'-indol]-2-yl]-1H-indazol-3-yl}amino)-N-methyl-N-(3-methyloxetan-3-yl)pyridine-3-sulfonamide; (1R,2S)-2-(3-{[5-(1-hydroxyethyl)-2-methoxypyridin-3-yl]amino}-1H-indazol-6-yl)-5'-methoxyspiro[cyclopropane-1,3'-indol]-2'(1'H)-one; (1R,2S)-2-{3-[2-ethoxy-4-(methanesulfonyl)anilino]-1H-indazol-6-yl}-5'-methoxyspiro[cyclopropane-1,3'-indol]-2'(1'H)-one; (1R,2S)-2-(3-{[3-ethoxy-5-(4-methylpiperazine-1-sulfonyl)pyridin-2-yl]amino}-1H-indazol-6-yl)-5'-methoxyspiro[cyclopropane-1,3'-indol]-2'(1'H)-one; (1R,2S)-2-(3-{[5-(ethanesulfonyl)-3-ethoxypyridin-2-yl]amino}-1H-indazol-6-yl)-5'-methoxyspiro[cyclopropane-1,3'-indol]-2'(1'H)-one; 5-ethoxy-6-({6-[(1R,2S)-5'-methoxy-2'-oxo-1',2'-dihydrospiro[cyclopropane-1,3'-indol]-2-yl]-1H-indazol-3-yl}amino)-N-methylpyridine-3-sulfonamide; (1R,2S)-5'-chloro-2-(3-{[3-ethoxy-5-(methanesulfonyl)pyridin-2-yl]amino}-1H-indazol-6-yl)spiro[cyclopropane-1,3'-indol]-2'(1'H)-one; (1R,2S)-2-{3-[(4-ethoxy-1-methyl-6-oxo-1,6-dihydropyridazin-3-yl)amino]-1H-indazol-6-yl}-5'-methoxyspiro[cyclopropane-1,3'-indol]-2'(1'H)-one; (1R,2S)-2-(3-{[6-(2-hydroxypropan-2-yl)-3-methoxypyridin-2-yl]amino}-1H-indazol-6-yl)-5'-methoxyspiro[cyclopropane-1,3'-indol]-2'(1'H)-one; (1R,2S)-2-(3-{[4-ethoxy-6-(methanesulfonyl)pyridin-3-yl]amino}-1H-indazol-6-yl)-5'-methoxyspiro[cyclopropane-1,3'-indol]-2'(1'H)-one; and (1R,2S)-2-(3-{[5-(difluoromethanesulfonyl)-3-methoxypyridin-2-yl]amino}-1H-indazol-6-yl)-5'- methoxyspiro[cyclopropane-1,3'-indol]-2'(1'H)-one, or a pharmaceutically acceptable salt thereof.

Embodiment 234: A compound of Formula (I), or a pharmaceutically acceptable salt, solvate, or stereoisomer thereof:

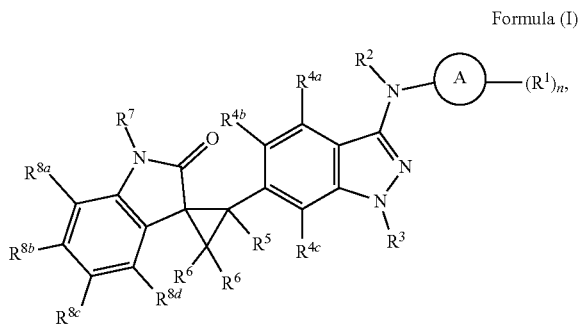

Formula (I)

wherein:
Ring A is $C_6$-$C_{10}$aryl, heteroaryl, $C_3$-$C_{10}$cycloalkyl, or heterocycloalkyl;
each $R^1$ is independently deuterium, halogen, —CN, oxo, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^a$, —$NR^b$S(=O)$_2R^a$, —C(=O)$R^a$, —C(=O)$OR^b$, —C(=O)$NR^cR^d$, —P(O)$(R^3)_2$, —P(O)$_2(R^a)_2$, $C_1$-$C_6$alkyl, $C_1$-$C_6$haloalkyl, —O$C_1$-$C_{10}$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl; wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is optionally and independently substituted with one or more $R^{1a}$;
or two $R^1$ on adjacent atoms are taken together to form a $C_3$-$C_{10}$cycloalkyl or heterocycloalkyl; each optionally substituted with one or more $R^{1b}$;
each $R^{1a}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^a$, —$NR^b$S(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_6$-$C_{10}$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_1$-$C_{10}$cycloalkyl, heterocycloalkyl, $C_6$-$C_{10}$aryl, or heteroaryl;
or two $R^{1a}$ on the same atom are taken together to form an oxo;
each $R^{1b}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^3$, —S(=O)$_2R$*, —S(=O)$_2NR^cR^d$, —$NR^cR^d$, —$NR^b$C(=O)$NR^cR^d$, —$NR^b$C(=O)$R^a$, —$NR^b$C(=O)$OR^a$, —$NR^b$S(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_1$-$C_{10}$cycloalkyl, heterocycloalkyl, $C_6$-$C_{10}$aryl, or heteroaryl;

or two $R^{1b}$ on the same atom are taken together to form an oxo;
n is 0, 1, 2, 3, 4, 5, 6, 7, or 8;
$R^2$ is hydrogen, $C_1$-$C_6$alkyl, $C_1$-$C_6$haloalkyl, or $C_1$-$C_6$deuteroalkyl;
$R^3$ is hydrogen, $C_1$-$C_6$alkyl, $C_1$-$C_6$haloalkyl, or $C_1$-$C_6$deuteroalkyl;
each of $R^{4a}$, $R^{4b}$, and $R^{4c}$ is independently hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
$R^5$ is hydrogen, deuterium, halogen, —CN, —OH, —$OR^a$, —$NR^cR^d$, $C_1$-$C_6$alkyl, $C_1$-$C_6$ haloalkyl, $C_1$-$C_6$ deuteroalkyl, $C_1$-$C_6$hydroxyalkyl, $C_1$-$C_6$aminoalkyl, or $C_1$-$C_6$heteroalkyl;
each $R^6$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
$R^7$ is hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;
each of $R^{8a}$, $R^{8b}$, $R^{8c}$, and $R^{8d}$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^a$, —$NR^b$S(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, or heteroaryl;
each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —N(CH$_3$)$_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_6$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_6$cycloalkyl), $C_1$-$C_6$alkyl(heterocycloalkyl), $C_1$-$C_6$alkyl($C_6$-$C_{10}$aryl), or $C_1$-$C_6$alkyl(heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —N(CH$_3$)$_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$alkoxy, $C_1$-$C_6$aminoalkyl, $C_1$-$C_6$ alkylamino, $C_1$-$C_6$heteroalkyl, $C_2$-$C_6$alkenyl, $C_2$-$C_6$alkynyl, $C_3$-$C_{10}$cycloalkyl, heterocycloalkyl, $C_6$-$C_{10}$aryl, heteroaryl, $C_1$-$C_6$alkyl($C_3$-$C_{10}$cycloalkyl), $C_1$-$C_6$alkyl(heterocycloalkyl), $C_1$-$C_6$alkyl($C_6$-$C_{10}$aryl), or $C_1$-$C_6$alkyl (heteroaryl); wherein each of the $C_1$-$C_6$alkyl, $C_2$-$C_6$alkenyl, $C_2$-$C_6$alkynyl, $C_3$-$C_{10}$cycloalkyl, heterocycloalkyl, $C_6$-$C_{10}$aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$), —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl.

Embodiment 235: A compound of Formula (III), or a pharmaceutically acceptable salt, solvate, or stereoisomer thereof:

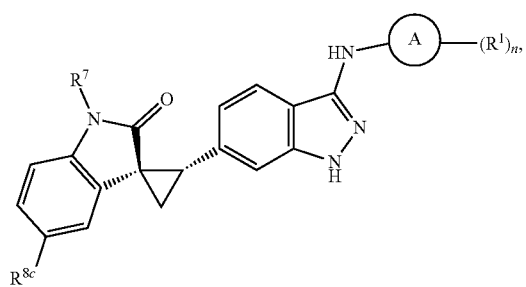

Formula (III)

wherein:
Ring A is phenyl, pyrazolyl, pyridinyl, pyrazinyl, pyrimidinyl, or pyridazinyl;
each $R^1$ is independently halogen, —CF$_3$, —CN, —S(=O)$_2$(CH$_3$), —S(=O)$_2$(CH$_2$CH$_3$), —S(=O)$_2$(i-Pr), —S(=O)$_2$(cyclopropyl), —S(=O)$_2$($C_1C_6$haloalkyl), —S(=O)$_2$N(CH$_3$)$_2$, —S(=O)$_2$NH$_2$, —S(=O)$_2$N(CH$_3$)(H), —OCH$_3$, —OCH$_3$, —OCH$_2$CH$_3$, —CH$_2$CHF$_2$, —C(=O)N(CH$_3$), —C(=O)N(H)(CH$_3$), —OC$_1C_6$haloalkyl, —CH$_3$, —CH$_2$CH$_3$, iso-propyl, n-propyl, —SCH$_3$, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;
n is 1, 2, or 3;
$R^7$ is hydrogen; and
$R^{8c}$ is hydrogen, halogen, CH$_3$, or —OCH$_3$.

Embodiment 236: A compound of Formula (III), or a pharmaceutically acceptable salt, solvate, or stereoisomer thereof:

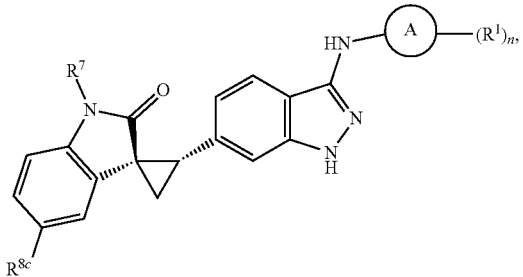

Formula (III)

wherein:
Ring A is phenyl, pyrazolyl, pyridinyl, pyrazinyl, pyrimidinyl, or pyridazinyl;
each $R^1$ is independently halogen, —CF$_3$, —CN, —S(=O)($C_1$-$C_6$alkyl), —S(=O)$_2$($C_3$-$C_{10}$cycloalkyl), —S(=O)$_2$N($C_1$-$C_6$alkyl)$_2$, —S(=O)$_2$NH$_2$, —S(=O)$_2$N($C_1$-$C_6$alkyl)(H), —OC$_1$-$C_6$alkyl, —CH$_2$CHF$_2$, —C(=O)N($C_1$-$C_6$alkyl)$_2$, —C(=O)N(H)($C_1$-$C_6$alkyl), —OC$_1C_6$haloalkyl, —$C_1$-$C_6$alkyl, —S$C_1$-$C_6$alkyl, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;
n is 1, 2, or 3;
$R^7$ is hydrogen; and
$R^{8c}$ is hydrogen, halogen, CH$_3$, or —OCH$_3$.

Embodiment 237: A compound of Formula (III), or a pharmaceutically acceptable salt, solvate, or stereoisomer thereof:

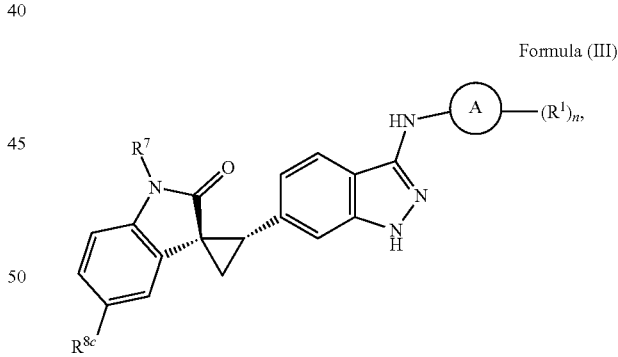

Formula (III)

wherein:
Ring A is phenyl, pyrazolyl, pyridinyl, pyrazinyl, pyrimidinyl, or pyridazinyl;
each $R^1$ is independently halogen, —CF$_3$, —CN, —S(=O)$_2$($C_1$-$C_6$alkyl), —S(=O)$_2$($C_3$-$C_{10}$cycloalkyl), —S(=O)$_2$N($C_1$-$C_6$alkyl)$_2$, —S(=O)$_2$NH$_2$, —S(=O)$_2$N($C_1$-$C_6$alkyl)(H), —OC$_1$-$C_6$alkyl, —CH$_2$CHF$_2$, —C(=O)N($C_1$-$C_6$alkyl)$_2$, —C(=O)N(H)($C_1$-$C_6$alkyl), —OC$_1C_6$haloalkyl, —$C_1$-$C_6$alkyl, —S$C_1$-$C_6$alkyl, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl, and wherein at least one of $R^1$ is —S(=O)$_2$(C$_1$-C$_6$alkyl), —S(=O)$_2$(C$_3$-C$_{10}$cycloalkyl), —S(=O)$_2$N(C$_1$-C$_6$alkyl)$_2$, —S(=O)$_2$NH$_2$, or —S(=O)$_2$N(C$_1$-C$_6$alkyl)(H);
n is 1, 2, or 3;
$R^7$ is hydrogen; and
$R^{8c}$ is hydrogen, halogen, CH$_3$, or —OCH$_3$.

Embodiment 238: A compound of Formula (III), or a pharmaceutically acceptable salt, solvate, or stereoisomer thereof, wherein:
Ring A is heterocycloalkyl;
each $R^1$ is independently halogen, —CF$_3$, —CN, —S(=O)$_2$(C$_1$-C$_6$alkyl), —S(=O)$_2$(C$_2$-C$_{10}$cycloalkyl), —S(=O)$_2$N(C$_1$-C$_6$alkyl)$_2$, —S(=O)$_2$NH$_2$, —S(=O)$_2$N(C$_1$-C$_6$alkyl)(H), —OC$_1$-C$_6$alkyl, —CH$_2$CHF$_2$, —C(=O)N(C$_1$-C$_6$alkyl)$_2$, —C(=O)N(H)(C$_1$-C$_6$alkyl), —OC$_1$C$_6$haloalkyl, —C$_1$-C$_6$alkyl, —SC$_1$-C$_6$alkyl, azetidinyl, pyrrolidinyl, oxazolyl, fluoropyrrolidinyl, difluoropiperidinyl, difluoroazetidinyl, fluoroazetidinyl, morpholinyl, dioxidothiomorpholinyl, —C(=O)(morpholinyl), —C(=O)(azetidinyl), —C(=O)(difluoroazetidinyl), or —C(=O)difluoropiperidinyl;
n is 1, 2, or 3;
$R^7$ is hydrogen; and
$R^{8c}$ is hydrogen, halogen, CH$_3$, or —OCH$_3$.

Embodiment 239: A pharmaceutical composition comprising an amount of a compound according to any one of embodiments 1 to 238, or a pharmaceutically acceptable salt, solvate, or stereoisomer thereof, and one or more pharmaceutically acceptable excipients.

Embodiment 240: A method of treating cancer in a subject in need thereof, comprising administering to the subject a therapeutically effective amount of a compound according to any one of embodiments 1 to 238, or a pharmaceutically acceptable salt, solvate, or stereoisomer thereof.

Embodiment 241: A method of treating cancer in a subject in need thereof, comprising administering to the subject a therapeutically effective amount of a pharmaceutical composition according to embodiment 239.

Embodiment 242: The method according to embodiment 240 or 241, wherein the cancer in the subject is a solid tumor.

Embodiment 243: The method according to embodiment 240 to 242, wherein the cancer is neuroblastoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

Embodiment 244: The method according to any one of embodiments 240 to 243, wherein the cancer in the subject expresses polo-like kinase 4 (PLK4).

Embodiment 245: The method according to any one of embodiments 240 to 244, wherein the cancer in the subject has been determined to express polo-like kinase 4 (PLK4) prior to administering the compound according to any one of embodiments 1 to 238, or a pharmaceutically acceptable salt, solvate, or stereoisomer thereof, or the pharmaceutical composition according to embodiment 233, to the subject.

Embodiment 246: The method according to any one of embodiments 240 to 245, wherein the cancer in the subject exhibits an overexpression of the E3 ubiquitin-protein ligase (TRIM37) protein.

Embodiment 247: The method according to embodiment 246, wherein the cancer in the subject exhibits an overexpression of the gene that encodes the tripartite motif-containing protein 37 (TRIM37).

Embodiment 248: The method according to embodiment 246, wherein the cancer in the subject exhibits an amplification of the gene that encodes the tripartite motif-containing protein 37 (TRIM37).

Embodiment 249: A method of treating cancer in a subject comprising administering to the subject a therapeutically effective amount of a compound according to any one of embodiments 1 to 238, or a pharmaceutically acceptable salt, solvate, or stereoisomer thereof, wherein the cancer in the subject has been determined to overexpress the gene that encodes the tripartite motif-containing protein 37 (TRIM37) prior to administration of the compound to the subject.

Embodiment 250: A method of treating cancer in a subject, wherein the cancer in the subject has been determined to overexpress the gene that encodes the tripartite motif-containing protein 37 (TRIM37), comprising administering to the subject a therapeutically effective amount of a compound according to any one of embodiments 1 to 238, or a pharmaceutically acceptable salt, solvate, or stereoisomer thereof.

Embodiment 251: A method of treating cancer in a subject, comprising:
a. obtaining a biological sample of the cancer from the subject;
b. determining whether the biological sample of the cancer overexpresses the gene that encodes the tripartite motif-containing protein 37 (TRIM37); and
c. administering to the subject a therapeutically effective amount of a compound according to any one of embodiments 1 to 238, or a pharmaceutically acceptable salt, solvate, or stereoisomer thereof, if the biological sample of the cancer is determined to overexpress the gene that encodes the tripartite motif-containing protein 37 (TRIM37).

Embodiment 252: The method according to any one of embodiments 240 to 251, wherein the cancer is neuroblastoma or breast cancer.

Embodiment 253: The method of embodiment 252, wherein the cancer is neuroblastoma.

Embodiment 254: The method of embodiment 252, wherein the cancer is breast cancer.

Embodiment 255: The method according to any one of embodiments 240 to 254, wherein the compound according to any one of embodiments 1 to 238, or a pharmaceutically acceptable salt, solvate, or stereoisomer thereof, or the pharmaceutical composition according to embodiment 239 is administered to the subject with one or more additional therapeutic agents.

Embodiment 256: The method according to embodiment 255, wherein the one or more additional therapeutic agents is selected from one or more mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, and immuno-oncology agents.

Embodiment 257: A method of inhibiting polo-like kinase 4 (PLK4) in a subject in need thereof, comprising administering to the subject a therapeutically effective amount of a compound according to any one of embodiments 1 to 238, or a pharmaceutically acceptable salt, solvate, or stereoisomer thereof.

Embodiment 258: A method of inhibiting polo-like kinase 4 (PLK4) in a subject in need thereof, comprising administering to the subject a therapeutically effective amount of a pharmaceutical composition according to embodiment 239.

Embodiment 259: A method of inhibiting polo-like kinase 4 (PLK4) in a subject having cancer, comprising administering to the subject a therapeutically effective amount of a compound according to any one of embodiments 1 to 238, or a pharmaceutically acceptable salt, solvate, or stereoisomer thereof, wherein the cancer in the subject has been determined to express polo-like kinase 4 (PLK4) prior to administering the compound, or a pharmaceutically acceptable salt, solvate, or stereoisomer thereof, to the subject.

Embodiment 260: A method of inhibiting polo-like kinase 4 (PLK4) in a subject having cancer, comprising administering to the subject a therapeutically effective amount of a pharmaceutical composition according to embodiment 239, wherein the cancer in the subject has been determined to express polo-like kinase 4 (PLK4) prior to administering the pharmaceutical composition to the subject.

Embodiment 261: A compound according to any one of embodiments 1 to 238, or a pharmaceutically acceptable salt, solvate, or stereoisomer thereof, for use in a method of treating cancer in a subject in need thereof.

Embodiment 262: A pharmaceutical composition according to embodiment 239 for use in a method of treating cancer in a subject in need thereof.

Embodiment 263: A compound for use according to embodiment 261, wherein the cancer in the subject is a solid tumor.

Embodiment 264: A compound for use according to embodiment 261 or 262, wherein the cancer is neuroblastoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

Embodiment 265: A compound for use according to any one of embodiments 261, 263, or 264 wherein the cancer in the subject expresses polo-like kinase 4 (PLK4).

Embodiment 266: A compound for use according to any one of embodiments 261, 263, or 264, wherein the cancer in the subject has been determined to express polo-like kinase 4 (PLK4) prior to administering the compound to the subject.

Embodiment 267: A compound for use according to any one of embodiments 261, 263, or 264, wherein the cancer in the subject exhibits an overexpression of the E3 ubiquitin-protein ligase (TRIM37) protein.

Embodiment 268: A compound for use according to any one of embodiments 261, 263, or 264, wherein the cancer in the subject exhibits an overexpression of the gene that encodes the tripartite motif-containing protein 37 (TRIM37).

Embodiment 269: A compound for use according to any one of embodiments 261, 263, or 264, wherein the cancer in the subject exhibits an amplification of the gene that encodes the tripartite motif-containing protein 37 (TRIM37).

Embodiment 270: A compound for use according to any one of embodiments 261, 263, or 264, wherein the cancer in the subject has been determined to overexpress the gene that encodes the tripartite motif-containing protein 37 (TRIM37) prior to administration of the compound to the subject.

Embodiment 271: A compound for use according to any one of embodiments 261, 263, or 264, wherein the cancer is neuroblastoma or breast cancer.

Embodiment 272: A compound for use according to 271, wherein the cancer is neuroblastoma.

Embodiment 273: A compound for use according to 271, wherein the cancer is breast cancer.

Embodiment 274: A compound according to any one of embodiments 1 to 238, or a pharmaceutically acceptable salt, solvate, or stereoisomer thereof, for use in inhibiting polo-like kinase 4 (PLK4) in a subject having cancer.

Embodiment 275: Use of a compound according to any one of embodiments 1 to 238, or a pharmaceutically acceptable salt, solvate, or stereoisomer thereof, in the manufacture of a medicament for the treatment of cancer in a subject in need thereof.

Embodiment 276: Use according to embodiment 275, wherein the cancer is neuroblastoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

Embodiment 277: Use according to embodiment 275 or 276, wherein the cancer in the subject expresses polo-like kinase 4 (PLK4).

Embodiment 278: Use according to embodiment 275 or 276, wherein the cancer in the subject has been determined to express polo-like kinase 4 (PLK4) prior to administering the compound to the subject.

Embodiment 279: Use according to any one of embodiments 274 to 278, wherein the cancer in the subject exhibits an overexpression of the E3 ubiquitin-protein ligase (TRIM37) protein.

Embodiment 280: Use according to any one of embodiments 274 to 279, wherein the cancer in the subject exhibits an overexpression of the gene that encodes the tripartite motif-containing protein 37 (TRIM37).

Embodiment 281: Use according to any one of embodiments 274 to 279, wherein the cancer in the subject exhibits an amplification of the gene that encodes the tripartite motif-containing protein 37 (TRIM37).

Embodiment 282: Use according to any one of embodiments 274 to 279, wherein the cancer in the subject has been determined to overexpress the gene that encodes the tripartite motif-containing protein 37 (TRIM37) prior to administration of the compound to the subject.

Embodiment 283: Use according to any one of embodiments 274 to 282, wherein the cancer is neuroblastoma or breast cancer.

Embodiment 284: Use according to embodiment 283, wherein the cancer is neuroblastoma.

Embodiment 285: Use according to embodiment 283, wherein the cancer is breast cancer.

What is claimed is:

1. A compound selected from the group consisting of:

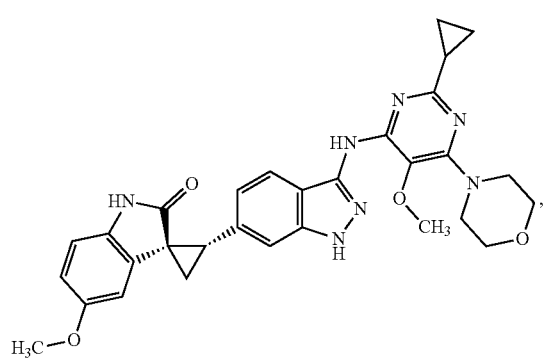 [SMILES: COc1ccc2c(c1)[C@]1(C[C@H]1c1ccc3c(Nc4nc(C5CC5)nc(N5CCOCC5)c4OC)n[nH]c3c1)C(=O)N2]

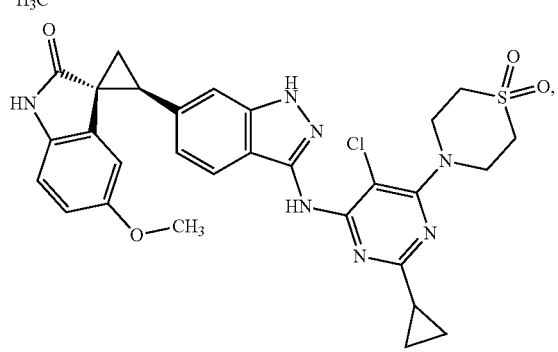

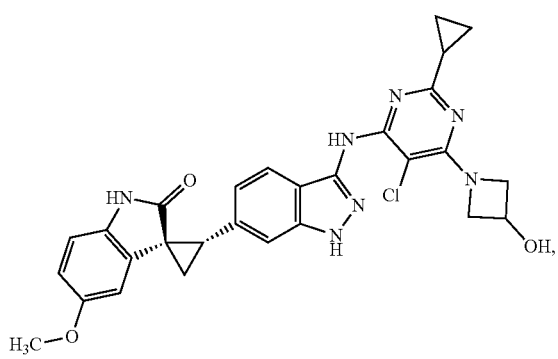 [SMILES: COc1ccc2c(c1)[C@]1(C[C@H]1c1ccc3c(Nc4nc(C5CC5)nc(N5CC(O)C5)c4Cl)n[nH]c3c1)C(=O)N2]

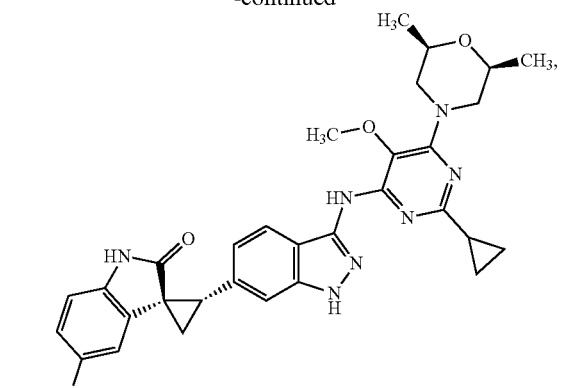

-continued

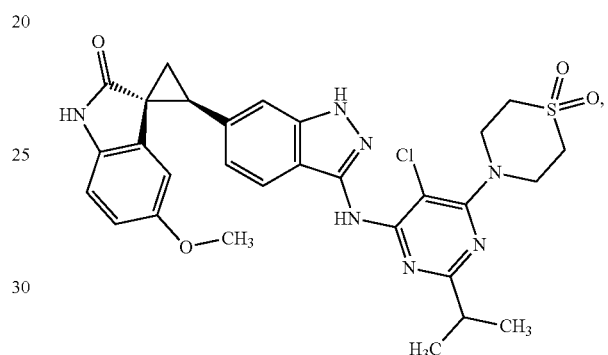

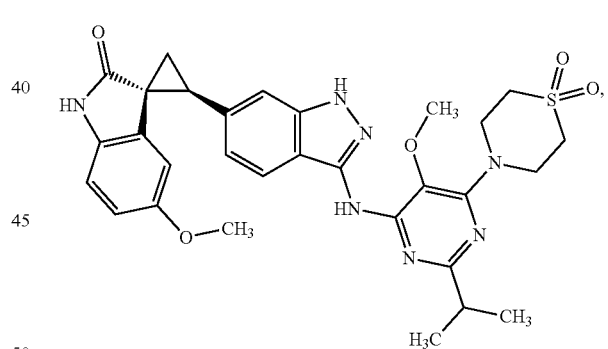

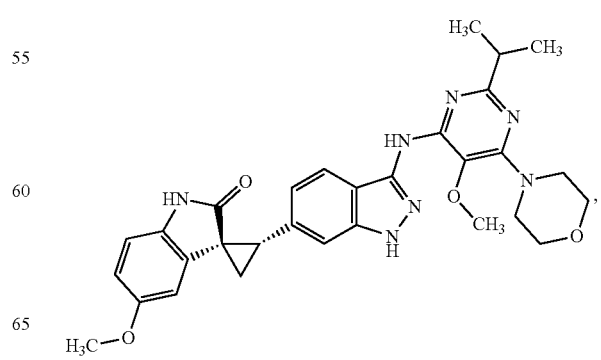

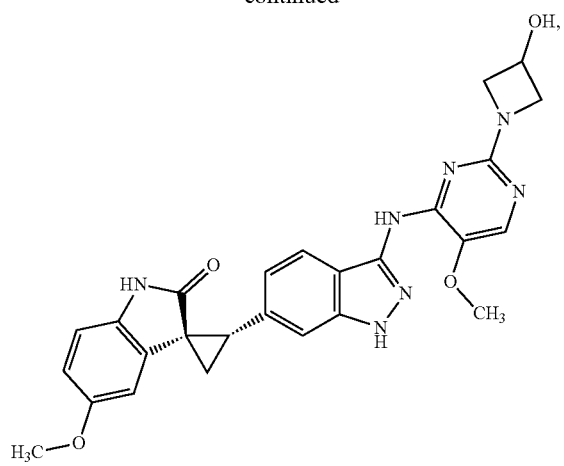
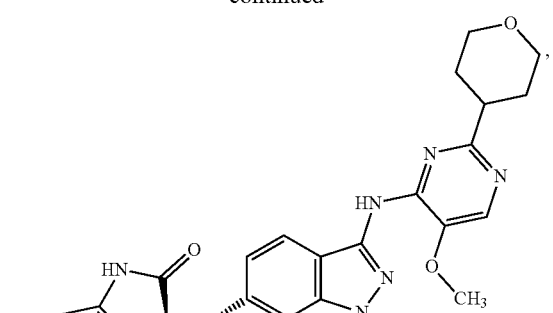

-continued
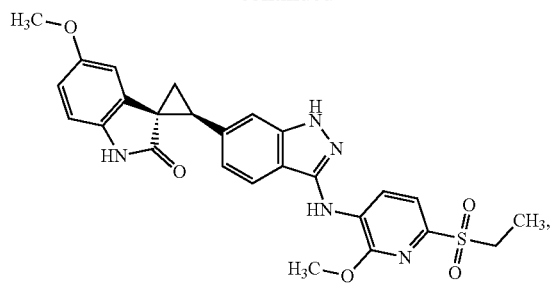
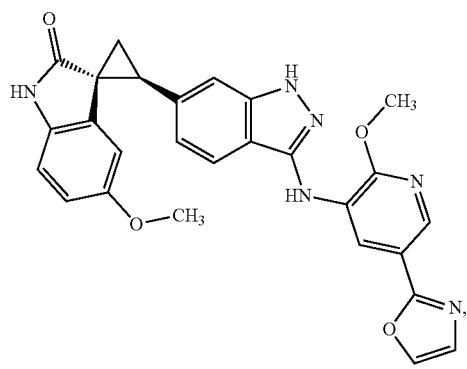
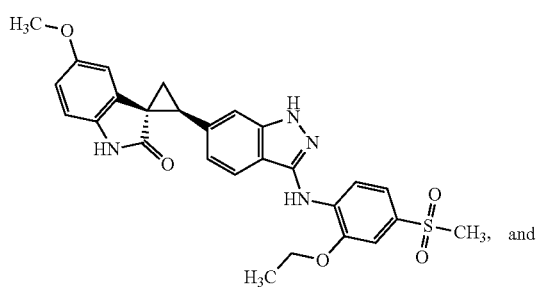 and
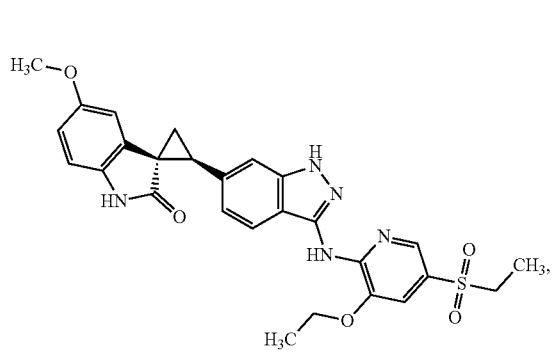
or a pharmaceutically acceptable salt thereof.
2. The compound of claim 1, wherein the compound is
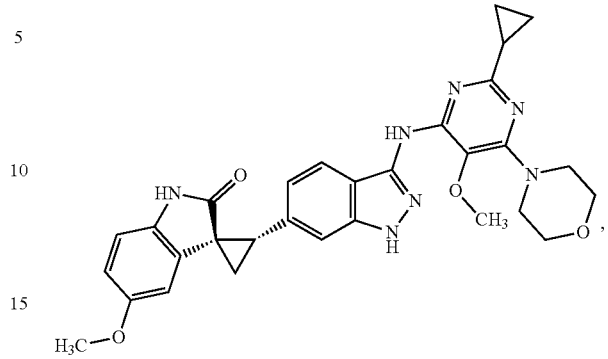
or a pharmaceutically acceptable salt thereof.
3. The compound of claim 1, wherein the compound is
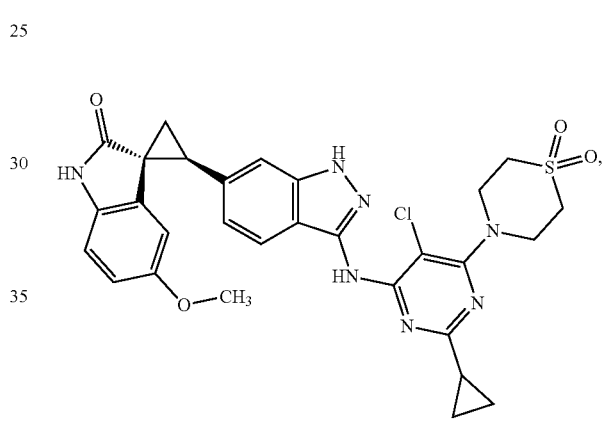
or a pharmaceutically acceptable salt thereof.
4. The compound of claim 1, wherein the compound is
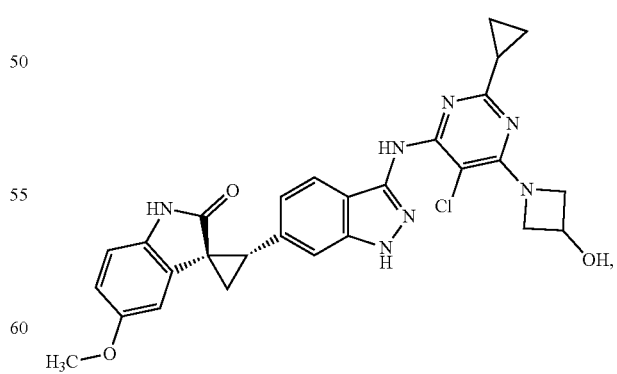
or a pharmaceutically acceptable salt thereof.

5. The compound of claim 1, wherein the compound is

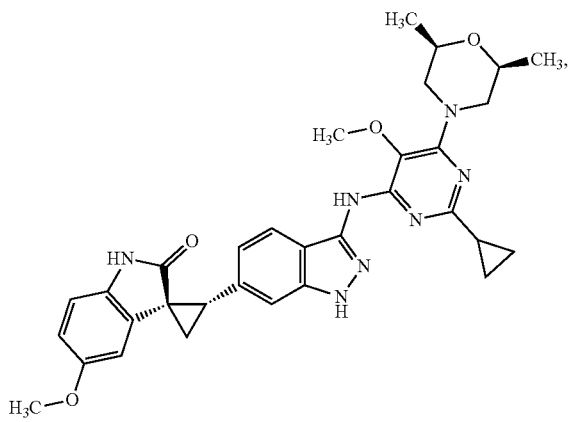 [SMILES: COc1ccc2c(c1)[C@]1(C[C@H]1c1ccc3c(Nc4nc(C5CC5)nc(N5C[C@@H](C)O[C@@H](C)C5)c4OC)n[nH]c3c1)C(=O)N2]

or a pharmaceutically acceptable salt thereof.

6. The compound of claim 1, wherein the compound is

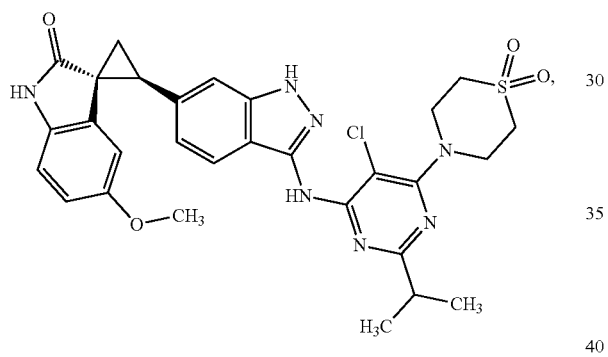

or a pharmaceutically acceptable salt thereof.

7. The compound of claim 1, wherein the compound is

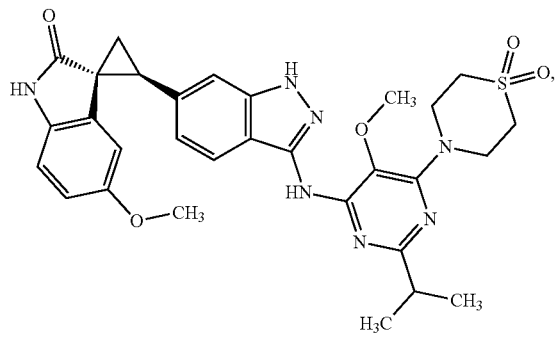 [SMILES: COc1ccc2c(c1)[C@]1(C[C@H]1c1ccc3c(Nc4nc(C(C)C)nc(N5CCS(=O)(=O)CC5)c4OC)n[nH]c3c1)C(=O)N2]

or a pharmaceutically acceptable salt thereof.

8. The compound of claim 1, wherein the compound is

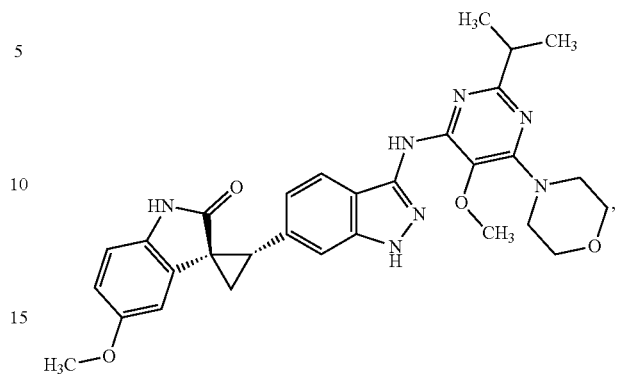

or a pharmaceutically acceptable salt thereof.

9. The compound of claim 1, wherein the compound is or a pharmaceutically acceptable salt thereof.

10. The compound of claim 1, wherein the compound is or a pharmaceutically acceptable salt thereof.

11. The compound of claim 1, wherein the compound is

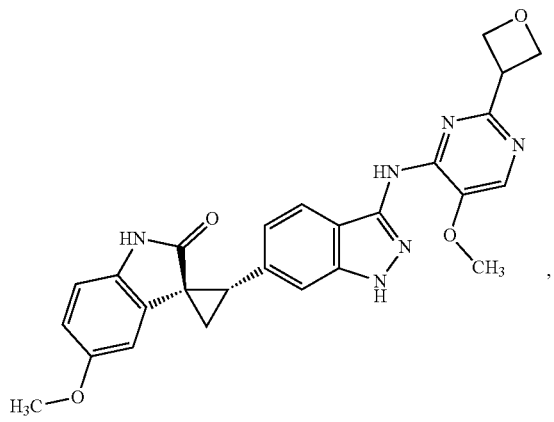 [SMILES: COc1ccc2c(c1)[C@]1(C[C@H]1c1ccc3c(Nc4nc(C5COC5)ncc4OC)n[nH]c3c1)C(=O)N2]

a pharmaceutically acceptable salt thereof.

12. The compound of claim 1, wherein the compound is

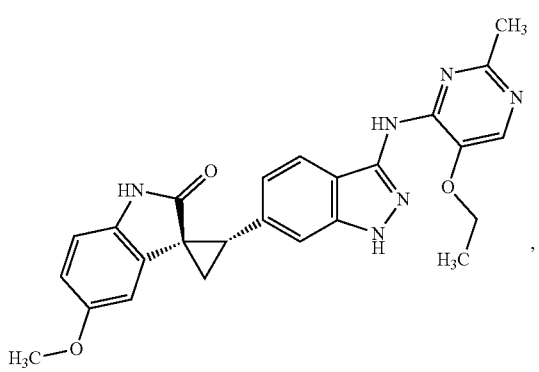 [SMILES: CCOc1cnc(C)nc1Nc1n[nH]c2cc([C@@H]3C[C@@]34C(=O)Nc3ccc(OC)cc34)ccc12]

or a pharmaceutically acceptable salt thereof.

13. The compound of claim 1, wherein the compound is

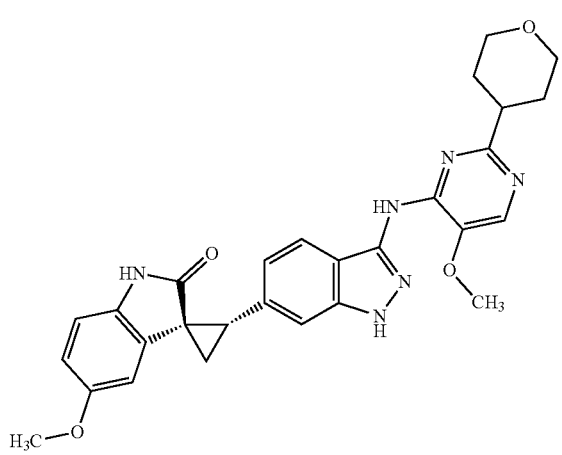

or a pharmaceutically acceptable salt thereof.

14. The compound of claim 1, wherein the compound is

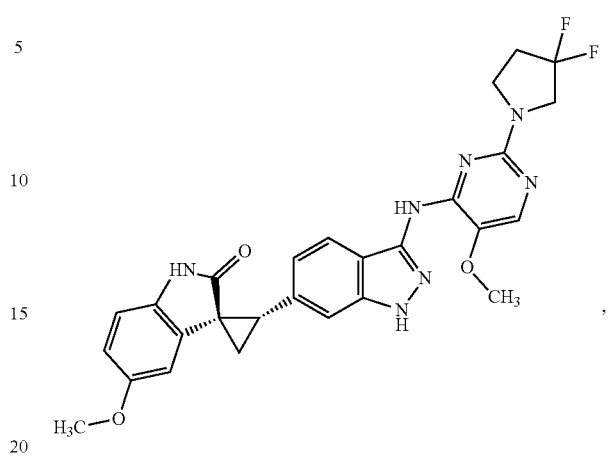

or a pharmaceutically acceptable salt thereof.

15. The compound of claim 1, wherein the compound is

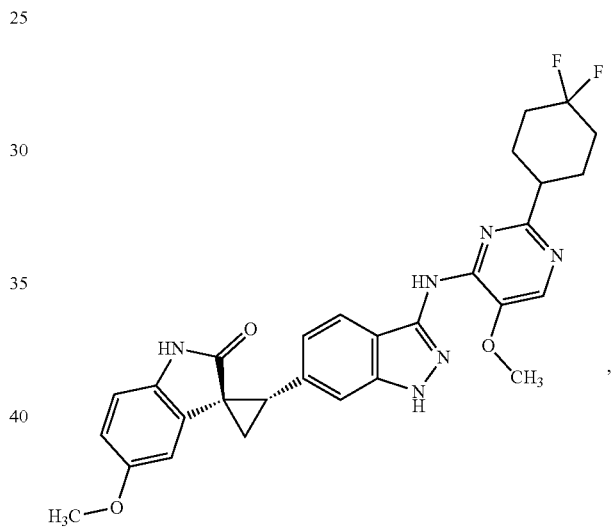

or a pharmaceutically acceptable salt thereof.

16. The compound of claim 1, wherein the compound is

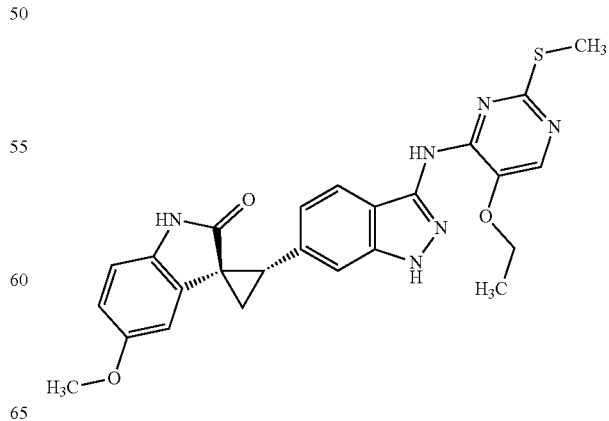

or a pharmaceutically acceptable salt thereof.

17. The compound of claim 1, wherein the compound is

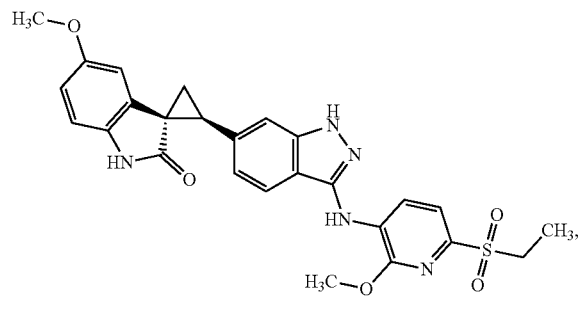 [SMILES: CCS(=O)(=O)c1ccc(Nc2n[nH]c3cc([C@@H]4C[C@@]45C(=O)Nc4ccc(OC)cc45)ccc23)c(OC)n1]

or a pharmaceutically acceptable salt thereof.

18. The compound of claim 1, wherein the compound is

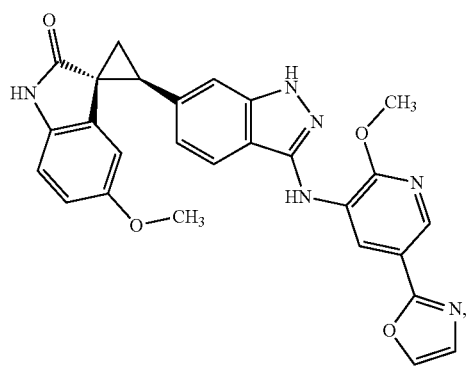 [SMILES: COc1ccc2c(c1)[C@]1(C[C@H]1c1ccc3c(Nc4cc(-c5ncco5)cnc4OC)n[nH]c3c1)C(=O)N2]

or a pharmaceutically acceptable salt thereof.

19. The compound of claim 1, wherein the compound is

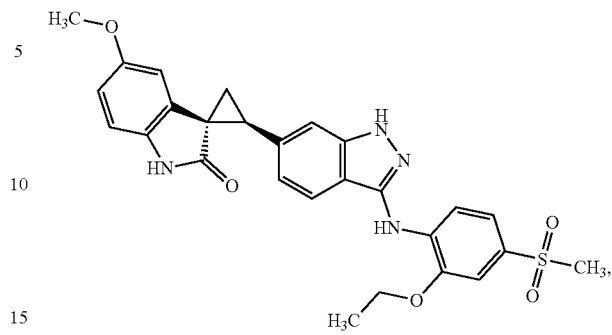

or a pharmaceutically acceptable salt thereof.

20. The compound of claim 1, wherein the compound is

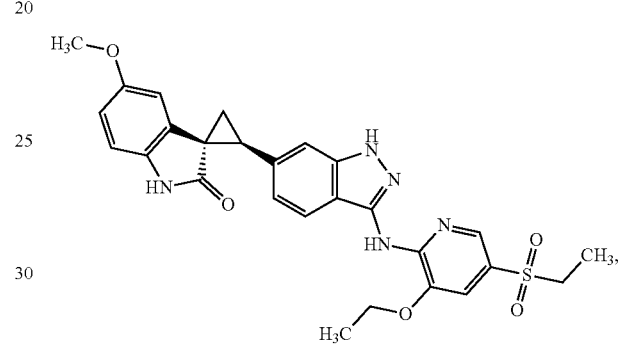

or a pharmaceutically acceptable salt thereof.

21. A pharmaceutical composition, comprising an amount of a compound of claim 1, or a pharmaceutically acceptable salt thereof, and one or more pharmaceutically acceptable excipients.

* * * * *